United States Patent
Palmgren et al.

(10) Patent No.: US 8,577,624 B2
(45) Date of Patent: Nov. 5, 2013

(54) CRYSTAL STRUCTURE OF A PLASMA MEMBRANE PROTON PUMP

(75) Inventors: Michael G. Palmgren, Gentorfte (DK);
Morten Buch-Pedersen, Copenhagen (DK); Bjørn Pañella Pedersen, Aarhus (DK); Poul Nissen, Risskov (DK)

(73) Assignees: Aarhus Universitet, Aarhus C (DK);
Kobenhavns Universitet, Kobenhaven K (DK)

( * ) Notice: Subject to any disclaimer, the term of this patent is extended or adjusted under 35 U.S.C. 154(b) by 0 days.

(21) Appl. No.: 12/747,598

(22) PCT Filed: Dec. 12, 2008

(86) PCT No.: PCT/DK2008/050305
§ 371 (c)(1),
(2), (4) Date: Jul. 28, 2010

(87) PCT Pub. No.: WO2009/074156
PCT Pub. Date: Jun. 18, 2009

(65) Prior Publication Data
US 2010/0296963 A1    Nov. 25, 2010

Related U.S. Application Data

(60) Provisional application No. 60/013,282, filed on Dec. 12, 2007.

(30) Foreign Application Priority Data

Dec. 12, 2007  (DK) ................................ 2007 01778

(51) Int. Cl.
*G01N 31/00* (2006.01)
*C12Q 1/34* (2006.01)

(52) U.S. Cl.
USPC .............................................. 702/27; 435/18

(58) Field of Classification Search
None
See application file for complete search history.

(56) References Cited

U.S. PATENT DOCUMENTS

| 4,588,580 | A | 5/1986 | Gale et al. |
| 4,788,062 | A | 11/1988 | Gale et al. |
| 4,816,258 | A | 3/1989 | Nedberge et al. |
| 4,904,475 | A | 2/1990 | Gale et al. |
| 4,927,408 | A | 5/1990 | Haak et al. |
| 2005/0143402 | A1* | 6/2005 | Cheetham et al. ....... 514/266.21 |

FOREIGN PATENT DOCUMENTS

WO    WO2004/075835    9/2004

OTHER PUBLICATIONS

Afonine PV et al. (2005): A robust bulk-solvent correction and anisotropic scaling procedure; Acta Crystallogr. D Biol. Crystallogr.; 61.

Amory A et al. (Nov. 1982): Exchange of oxygen between phosphate and water catalyzed by the plasma membrane ATPase from the yeast *Schizosaccharomyces pombe*; J Biol Chem, 257 (21), 12509-12516.

(Continued)

*Primary Examiner* — Nashaat Nashed
(74) *Attorney, Agent, or Firm* — Merchant & Gould P.C.

(57) ABSTRACT

The present invention relates to a crystal structure of a plasma membrane proton pump type ATPase. The invention further describes method for identification of modulators of ATPases as well as uses of such modulators. Based on the provided three dimensional structure of the ATPase, various method, such as computer implemented methods may be used for identification of modulators, such putative modulators may be further analysed using in vitro and in vivo experiments to confirm there functionality. Several modulator interaction regions are described as target of regulation by ATPase modulators.

10 Claims, 417 Drawing Sheets

(56) References Cited

OTHER PUBLICATIONS

Auer M et al. (1998): Three-dimensional map of the plasma membrane H+-ATPase in the open conformation; Nature 392 (6678), 840-843.

Axelsen KB (1998): Evolution of substrate specificities in the P-type ATPase superfamily; J Mol Evol; 46 (1), 84-101.

Baginsky ES et al. (1967): Determination of phosphate: Study of labile organic phosphate interference; Clin Chim Acta, 15, 155-158.

Bagshaw CR (2001): ATP analogues at a glance; J Cell Sci, 114 (3), 459-460.

Blatt MR et al. (1987): Potassium-proton symport in *Neurospora*: Kinetic control by pH and membrane potential; J Membr. Biol, 98 (2), 169-189.

Bowman BJ et al. (1981): Purification and characterization of the plasma membrane ATPase of *Neurospora crassa*; J Bio Chem, 256 (23), 12343-9.

Briskin DP et al. (1991): Determination of H/ATP stoichiometry for the plasma membrane H-ATPase from red beet (*Beta Vulgaris* L.) storage tissue; Plant Physiol, 95 (1), 242-250.

Brunger AT et al (1998): A new software suite for macromolecular structure determination; Acta Crystallogr D Biol., 54, 905-921.

Buch-Pedersen M J et al, Protons and how they are transported by proton pumps, Pfluegers Archiv European J of Physiology, vol. 457, No. 3, Jan. 2009, pp. 573-579.

Buch-Pedersen MJ et al. (May 16, 2003): Conserved Asp684 in transmembrane segment M6 of the plant plasma membrane P-type proton pump AHA2 is a molecular determinant of proton translocation; J Biol Chem; 278 (20), 17845-17851.

Buch-Pedersen MJ et al. (Dec. 15, 2000): Abolishment of proton pumping and accumulation in the E1P conformational state of a plant plasma membrane H+-ATPase by substitution of a conserved aspartyl residue in transmembrane segment 6; J Biol Chem, 275 (50), 39167-73.

Bukrinsky Jens T et al: A putative proton binding site of plasma membrane H+-ATPase identified through homology modelling, FEBS Letters, Elsevier, 494, 1-2, Apr. 6, 2001, pp. 6-10.

Chernoff J et al. (1983): Multiple forms of phosphotyrosyl- and phosphoseryl-protein phosphatase from cardiac muscle: partial purification and characterization of an EDTA-stimulated phosphotyrosyl-protein phosphatase; Arch. Biochem. Biophys., 226 (2), 517-530.

Cowtan K et al (1998): Miscellaneous Algorithms for Density Modification; Acta Crystallogr Sec D, vol. 54, pp. 487-493.

De La Fortelle E et al. (1997): Maximum-likelihood heavy-atom parameter refinement for multiple isomorphous replacement and multiwavelength anomalous diffraction methods; Macromol Crystallogr., Pt A 276, 472-494 (Book).

DeLano WL (2002): The PyMOL User's Manual. DeLano Scientific, CA, USA, San Carlos.

Dutra MB et al. (Jul. 10, 1998): Structure-function relationships in membrane segment 5 of the yeast Pma1 H+-ATPase; J Biol Chem, 273 (28), 17411-17417.

Edgar RC (2004): MUSCLE: Multiple sequence alignment with high accuracy and high throughput; Nucleic Acids Research, 32 (5), 1792-97.

Eraso P et al. (Apr. 8, 1994): Molecular mechanism of regulation of yeast plasma membrane H+-ATPase by glucose. Interaction between domains and Identification of new regulatory sites; J Biol Chem., 269, 10393-10399.

Fersht A; Freeman & Co (1985): Enzyme structure and mechanism (book), 2nd edition, New York, p. 6.

Fillingame RH et al. (2002): Structural model of the transmembrane Fo rotary sector of H+-transporting ATP synthase derived by solution NMR and intersubunit vross-linking in situ; Biochim. Biophys. Acta; 1565, 232-245.

Golenser J et al (2006): Current Perspectives on the mechanism of action of artemisinins; Int J Parasitol; 36(14), 1427-41.

Guerra G et al. (1995): Reactivity of the H+-ATPase from *Kluyveromyces lactis* to sulfhydryl reagents; Arch Biochem Biophys, 321 (1), 101-107.

Gupta P et al (1991): Isolation, purification and kinetic characterization of plasma membrane H+-ATPase of *Candida albicans*; Biochem Int, 24, 907-915.

Harper JF et al. (1990): The *Arabidopsis thaliana* plasma membrane H+-ATPase multigene family. Genomic sequence and expression of a third isoform; J. Biol. Chem.; 265, 13601-13608.

Hartmut Michel: Membrane proteins of known structure, Mar. 30, 2006, XP002518031, retrieved from the Internet on Jun. 3, 2009.

Hirsch RE et al. (1998): A role for the AKT1 potassium channel in plant nutrition; Science 280 (5365), 918-921.

Huang LS et al (1990): Purification and characterization of the proton translocating plasma membrane ATPase of red beet storage tissue: Biochim Biophys Acta, 1039(2), 241-252.

Hutcheon ML et al. (2001): Energy-driven subunit rotation at the interface between subunit a and the c oligomer in the FO sector of *Escherichia coli* ATP synthase; Proc Natl Acad Sci USA, 98 (15), 8519-8524.

Jain AN (2006): Scoring functions for protein-ligand docking: Curr Protein Pept Sci, 7 (5), 407-420.

Jensen AM et al. (2006): Modulatory and catalytic modes of ATP binding by the calcium pump; EMBO Journal, 25 (11), 2305-2314.

Jones TA et al. (1991): Improved methods for building protein models in electron-density maps and the location of errors in these models; Acta Crystallogr., A 47, 110-119.

Kabsch W. (1993): Automatic processing of rotation diffraction data from crystals of initially unknown symmetry and cell constants; J Appl Crystallogr., 26 (6), 795-800.

Kleywegt GJ et al. (1994): Detection, delineation, measurement and display of cavities in macromolecular structures; Acta Crystallogr. D Biol. Crystallogr., 50, 178-185.

Kühlbrand W et al. (2002): Structure, mechanism, and regulation of the *Neurospora* plasma membrane H+-ATPase; Science, 297 (5587), 1692-1696.

Lanfermeijer FC et al. (1998): Purification of a histidine-tagged plant plasma membrane H+-ATPase expressed in yeast, Protein Expr. Purif., 12(1), 29-37.

Laskowski RA et al. (1993): Procheck—a program to check the stereochemical quality of protein structures; J Appl Crystallogr., 26 (part 2).

Luecke H et al. (1998): Proton transfer pathways in bacteriorhodopsin at 2.3 angstrom resolution; Science, 280 (5371), 1934-1937.

Luo S et al. (2002): *Trypanosoma cruzi* H+-ATPase 1 (TcHA1) and 2 (TcHA2) genes complement yeast mutants defective in H+ pumps and encode plasma membrane P-type H+-ATPases with different enzymatic properties, J Biol Chem, 277.

MacLennan DH et al. (Aug. 2002): Structure-function relationships in Ca2+ cycling proteins; J Mol Cell Cardiol; 34 (8), 897-918.

Monk BC et al. (1991): Cloning and characterization of the plasma membrane H+-ATPase from *Candida albicans*, Journal of Bacteriol, 173(21), 6826-36.

Morsomme et al. (2000): Mutagenic study of the structure, function and biogenesis of the yeast plasma membrane H+-ATPase.

Morsomme P et al. (Dec. 25, 1998): Single point mutations distributed in 10 soluble and membrane regions of the *Nicotiana plumbaginifolla* plasma membrane PMA2 H+-ATPase activate the enzyme and modify the structure of the C-terminal region; J Biol Chem; 273 (52), 34837-34842.

Morth JP et al. (Dec. 13, 2007): Crystal structure of the sodium-potassium pump; Nature, 450 (7172), 1043-9.

Needleman & Wunsch (1970): A general method applicable to the search for similarities in the amino acid sequence of two proteins; J Mol Biol; 48(3). 443-53.

Olesen C et al. (Dec. 13, 2007): The structural basis of calcium transport by the calcium pump; Nature, 450 (7172), 1036-42.

Palmgren MG (1990): An H-ATPase assay: Proton pumping and ATPase activity determines simultaneously in the same sample. Plant Physiol, 94(3), 882-6.

(56) References Cited

OTHER PUBLICATIONS

Palmgren MG (1991): Acridine orange as a probe for measuring pH gradients across membranes: meshanism and limitations, Anal. Blochem, 192(2), 316-21.

Palmgren MG (2001): Plant plasma membrane H+-ATPases: Powerhouses for nutrient uptake; Annu. Rev. Plant Physiol. Plant Mol. Biol.

Pearson & Lipman (1988): Improved tools for biological sequence comparison; Proc Natl Acad Sci USA, 85(8), 2444-8.

Pebay-Peyroula E et al. (1997): X-Ray structure of bacteriorhodopsin at 2.5 angstroms from microcrystals grown in lipidic cubic phases; Science, 277 (5332), 1676-1681.

Pedersen BP et al (2007): Crystal structure of the plasma membrane proton pump; Nature, 450(7172), 1111-4.

Pedersen P et al. (1987): Ion motive ATPases. 1. Ubiquity, properties, and significance to cell function; Trends Biochem Sci; 12, 146-150.

Pedersen, Bjørn P et al, Crystal structure of the plasma membrane proton pump, Nature, vol. 450, No. 7172, Dec. 2007, p. 1111.

Perlin DS et al (1984): Electrogenlc H+ translocation by the plasma membrane ATPase of *Neurospora*. Studies on plasma membrane vesicles and reconstituted enzyme, J Biol. Chem., 259(12), 7884-92.

Regenberg B et al. (1995): C-terminal deletion analysis of plant plasma membrane H+-ATPase: yeast as a model system for solute transport across the plant plasma membrane, Plant Cell, 7(10), 1655-66.

Robinson JD et al (1983): A model for the reaction pathways of the K+-dependent phosphatase activity of the (Na+/K+)- dependent ATPase., Biochim. Biophys. Acta, 731(3), 406-14.

Sampedro JG et al (2007): Fluorescence quenching by nucleotides of the plasma membrane H+-ATPase from *Kluveromyces lactis*, Biochemistry, 46(18), 5616-22.

Sazinsky MH et al. (Feb. 22, 2006): Structure of the ATP binding domain from the *Archaeoglobus fulgidus* Cu+-ATPase; J Biol Chem, 281, 11161-11166.

Seifert MH et al (2007): Virtual high-throughput screening of molecular databases, Curr. Opn. Drug Disc. Dev., 10(3), 298-307.

Serrano R (1984): Purification of the proton pumping ATPase from plasma membranes., Biochem. Biophys. Res. Commun., 121(2), 735-40.

Serrano R (1988): H+-ATPase from plasma membranes of *Saccharomyces cerevisiae* and *Avena sativa* roots: Purification and reconstruction., Methods Enzymol, 157, 533-44.

Serrano R. et al. (1986): Yeast plasma membrane ATPase is essential for growth and has homology with (Na++K+), K+- and Ca2+-ATPases; Nature; 319 (6055), 689-93.

Skou JC et al. (1992): The Na, K-ATPase; J. Bioenerg. Biomembr.; 24 (3), 249-261.

Smith and Waterman (1981): Comparison of biosequences; Adv Appl Math, 2, 482-489.

Sorensen TL et al. (2004): Phosphoryl transfer and calcium ion occlusion in the calcium pump; Science, 304 (5677), 1672-1675.

Storoni LC et al. (2004): Likelihood-enhanced fast rotation functions; Acta Crystallogr. D Biol. Crystallogr., 60, 432-438.

Strong M et al. (2006): Toward the structural genomics of complexes: Crystal structure of a PE/PPE protein complex from *Mycobacterium tuberculosis*; Proc Natl Acad Sci USA, 103 (21), 8060-8065.

Toyoshima C et al. (2000): Crystal structure of the calcium pump of sarcoplasmic reticulum at 2.6 A resolution. Nature, 405 (6787), 647-655.

Toyoshima C et al. (2004): Crystal structure of the calcium pump with a bound ATP analogue; Nature, 430 (6999), 529-535.

Toyoshima C et al. (Aug. 8, 2002): Structural changes in the calcium pump accompanying the dissociation of calcium; Nature, 418 (6898), 605-611.

Warren GL et al (2006): A critical assessment of docking programs and scoring functions; J Med Chem; 49(20), 5912-5931.

Zhang Zy et al. (1994): Protein tyrosine phosphatases: mechanism of catalysis and substrate specificity; Adv. Enzymol. Relat. Areas Mol. Biol., 68, 1-36.

International Search Report for PCT/DK2008/050305 mailed Apr. 2, 2009 (Form PCT/ISA/210).

\* cited by examiner

```
H+-ATPase AHA2      ENKTAFTMKKDYGKEEREAQWALAQRTLHGLQPKEAVNIFPEKGSYRELSEIAEQAKRRAEIARLRE  921
H+-ATPase PMA1      NGKP..........MKEKKSTRSVED...................................... 902
Ca2+-ATPase SERCA1a ................................................................

H+-ATPase AHA2      LHTLKGHVESVVKLKGLDIETPS.HYTV  948
H+-ATPase PMA1      ........FMAAMQRVSTQHEKET.... 918
Ca2+-ATPase SERCA1a ............................
```

Fig. 9

```
P19456|PMA2_ARATH          --------------------------------------------------
P20649|PMA1_ARATH          --------------------------------------------------
Q43178|Q43178_SOLTU        --------------------------------------------------
Q96578|Q96578_SOLLC        --------------------------------------------------
Q43131|Q43131_VICFA        --------------------------------------------------
Q43271|Q43271_MAIZE        --------------------------------------------------
Q9SH76|PMA6_ARATH          --------------------------------------------------
Q08435|PMA1_NICPL          --------------------------------------------------
Q42932|Q42932_NICPL        --------------------------------------------------
Q43002|Q43002_ORYSJ        --------------------------------------------------
O74242|O74242_CRYNE        MSDHEKVGHTEEIPTKESSLENKVQGEEVPAAAAADEEPRKKREYKEMEH 50
O14437|O14437_UROFA        ------------MSLKE------------------GSDPVHKKNFDKTFED 21
P05030|PMA1_YEAST          ---------MTDTSSSSSSSSASSVSAHQPTQEKPAKTYDDAAS----ES 37
Q00002|PMA1_Candida        ---------MSDVESNN--------------EKPPQDVYEDE------EM 21
P24545|PMA1_ZYGRO          ----MSDERITEKPPHQQPESEGEPVPEEEVEEETEEEVPDE------QS 40
P49380|PMA1_KLULA          ---------MSAATEPT--------------KEKPVNNQDSD-------- 19
P28877|PMA1_CANAL          ---------MSATEPTN---------------EKVDKIVSDD-------- 18
P07038|PMA1_NEUCR          ---------MADHSASGAPALSTNIESGKFDEKAAEAAAYQPKP--KVED 39
Q07421|PMA1_AJECA          ---------MAHSAASGAASAAH------FEKKTPEVAHEEKKPPLPEEE 35
Q92446|Q92446_PNECA        ---------MSEEGKALIHETVYYKHTSTFEISETTKDLEKGGEEECLLD 41
P09627|PMA1_SCHPO          ---------MADNAGEYHDAEKHAPEQQAPPPQQPAHAAAPAQD-----D 36
Q00001|PMA1_Aspergillus    ---------MAERRISYAPDVENGDHSRHAENEGNLDEYTALNRYISTAR 41

P19456|PMA2_ARATH          ----------------MSSLEDIKNETVDLEKIPIEEVFQQLKCSRE--G 32
P20649|PMA1_ARATH          ----------------MSGLEDIKNETVDLEKIPIEEVFQQLKCTRE--G 32
Q43178|Q43178_SOLTU        --------------MAKAISLEEIKNETVDLEKIPIEEVFEQLKCSRE--G 35
Q96578|Q96578_SOLLC        --------------MAKAISLEEIKNETVDLEKIPIEEVFEQLKCSRE--G 35
Q43131|Q43131_VICFA        ---------------MAAISLEQIKNESVDLEKIPIEEVFAQLKCTRE--G 34
Q43271|Q43271_MAIZE        ----------------MGGLEEIKNEAVDLENIPIEEVFEQLKCTRE--G 32
Q9SH76|PMA6_ARATH          -------------MAADISWDEIKKENVDLEKIPVDEVFQQLKCSRE--G 35
Q08435|PMA1_NICPL          -----------MGEEKPEVLDAVLKEAVDLENIPIEEVFENLRCTKE--G 37
Q42932|Q42932_NICPL        -----------MGE-KPEVLDAVLKETVDLENIPIEEVFENLRCTKE--G 36
Q43002|Q43002_ORYSJ        -----------MAE-KGDNLEAVLNESVDLENIPLEEVFEHLRCNRE--G 36
O74242|O74242_CRYNE        KTEGDLHAKVDMNTIQFTAADLYDKDKVDIEHVVMEEVYQLLQCTDA--G 98
O14437|O14437_UROFA        EIKG-TSALVDIGTIQLTAEDLYDKDKVDLEQVHLEDVWKLLQTTEE--G 68
P05030|PMA1_YEAST          SDDDDIDALIEELQSNHGVDDEDSDNDGPVAAGEARPVPEEYLQTDPSYG 87
Q00002|PMA1_Candida        SEDDDIDALIEELQSHHGMGDDDDSEDEGHHTGSARVVPEEYLQTDPSYG 71
P24545|PMA1_ZYGRO          SEDDDIDGLIDELQSQE-AHEEAEEDDGPAAAGEARKIPEELLQTDPSVG 89
P49380|PMA1_KLULA          DEDEDIDQLIEDLQSHHGLDDE-SEDDEHVAAGSARPVPEELLQTDPSYG 68
P28877|PMA1_CANAL          -EDEDIDQLVADLQSNPGAGDEEEEEEN---DSSFKAVPEELLQTDPRVG 64
P07038|PMA1_NEUCR          DEDEDIDALIEDLESHDGHDAEEEEEEA--TPGGGRVVPEDMLQTDTRVG 87
Q07421|PMA1_AJECA          DEDEDMDALIEELESQDGHIDIEDDEDG--EPGGARPVPDELLTTDTRHG 83
Q92446|Q92446_PNECA        DEDNDIEALIDELESQGGDQEDNIEDTE---FQSQRQVPEELLATDTRIG 88
P09627|PMA1_SCHPO          EPDDDIDALIEELFSEDVQEEQEDNDDAP-AAGEAKAVPEELLQTDMNTG 85
Q00001|PMA1_Aspergillus    DGRRGSTSSAGARSLQQKKKPWYAFWRKDAETGGAFVCPDEWLETDLRTG 91
                                                                              *
```

Fig. 9 (continued)

```
P19456|PMA2_ARATH         LTTQEGEDRIQIFGPNKLEEKKESKLLKFLGFMWNPLSWVMEMAAIMAIA  82
P20649|PMA1_ARATH         LTTQEGEDRIVIFGPNKLEEKKESKILKFLGFMWNPLSWVMEAAALMAIA  82
Q43178|Q43178_SOLTU       LTSDEGANRLQIFGPNKLEEKKESKILKFLGFMWNPLSWVMEAAAIMAIA  85
Q96578|Q96578_SOLLC       LTSDEGANRLQIFGPNKLEEKKESKILKFLGFMWNPLSWVMEAAAIMAIA  85
Q43131|Q43131_VICFA       LSSTEGESRIQIFGPNKLEEKKESKFLKFLGFMWNPLSWVMEAAAVMAIA  84
Q43271|Q43271_MAIZE       LSSSEGQQRLEIFGPNRLEEKKESKVLKFLGFMWNPLSWVMEMAAIMAIA  82
Q9SH76|PMA6_ARATH         LSSEEGRNRLQIFGANKLEEKVENKFLKFLGFMWNPLSWVMEAAAIMAIV  85
Q08435|PMA1_NICPL         LTATAAQERLAIFGYNKLEEKKDSKLLKFLGFMWNPLSWVMEAAAIMAIA  87
Q42932|Q42932_NICPL       LSGPAAQERLAIFGYNKLEEKKESKFLKFLGFMWNPLSWVMEAAAIMAIA  86
Q43002|Q43002_ORYSJ       LTSANAEQRLNLFGLNRLEEKKESKFLKFLGFMWNPLSWVMEAAAIMAIV  86
O74242|O74242_CRYNE       LTEAEATDRIGIFGPNKLEEKSENVLLQFLSFMWNPLSWVMEGAALVAIA 148
O14437|O14437_UROFA       LTAEEVQRRLEIFGPNKLESKEVNPLLLFLSFMWNPLSWVMEGAAIVAIG 118
P05030|PMA1_YEAST         LTSDEVLKRRKKYGLNQMADEKESLVVKFVMFFVGPIQFVMEAAAILAAG 137
Q00002|PMA1_Candida       LTSDEVAHRRKKYGLNQMADERESMIVKFVMFFVGPIQFVMEAAAILAAG 121
P24545|PMA1_ZYGRO         LSSDEVVNRRKKYGLNQMREESENLLVKFLMFFIGPIQFVMEAAAVLAAG 139
P49380|PMA1_KLULA         LTSDEVTKRRKKYGLNQMSEETENLFVKFLMFFIGPIQFVMEAAAILAAG 118
P28877|PMA1_CANAL         LTDDEVTKRRKRYGLNQMAEEQENLVLKFVMFFVGPIQFVMEAAAVLAAG 114
P07038|PMA1_NEUCR         LTSEEVVQRRRKYGLNQMKEEKENHFLKFLGFFVGPIQFVMEGAAVLAAG 137
Q07421|PMA1_AJECA         LTDAEVVARRKKYGLNQMKEEKENLVLKFLSYFVGPIQFVMEAAAILAAG 133
Q92446|Q92446_PNECA       LTSQEVVNRRKKYGLNKMKEEKENMIIKFLMYFVGPIQFVMEAAAILAAS 138
P09627|PMA1_SCHPO         LTMSEVEERRKKYGLNQMKEELENPFLKFIMFFVGPIQFVMEMAAALAAG 135
Q00001|PMA1_Aspergillus   LASSQIETRRKKGGWNELTTEKTNFFVQFIGYFRGPILYVMELAVFLAAG 141
                          *:        *      * *.:   :     ..:   *: ::  .*: :***  *. :*

P19456|PMA2_ARATH         LANGDGRPPDWQDFVGIICLLVINSTISFIEENNAGNAAAALMAGLAPKT 132
P20649|PMA1_ARATH         LANGDNRPPDWQDFVGIICLLVINSTISFIEENNAGNAAAALMAGLAPKT 132
Q43178|Q43178_SOLTU       LANGNGKPPDWQDFVGIVCLLVINSTISFIEENNAGNAAAALMAGLAPKT 135
Q96578|Q96578_SOLLC       LANGDGKPPDWQDFVGIVCLLVINSTISFIEENNAGNAAAALMAGLAPKT 135
Q43131|Q43131_VICFA       LANGGGQPPDWQDFVGIVCLLVINSTISFIEENNAGNAAAALMAGLAPKT 134
Q43271|Q43271_MAIZE       LANSGGKPPDWQDFVGIIVLLVINSTISFIEENNAGNAAAALMANLAPKT 132
Q9SH76|PMA6_ARATH         LANGGGRPPDWQDFVGITCLLIINSTISFIEENNAGNAAAALMANLAPKT 135
Q08435|PMA1_NICPL         LANGGGKPPDWQDFVGIITLLIINSTISFIEENNAGNAAAALMARLAPKA 137
Q42932|Q42932_NICPL       LANGGGKPPDWQDFVGIITLLVINSTISFIEENNAGNAAAALMARLAPKA 136
Q43002|Q43002_ORYSJ       LANGGGKPPDWQDFVGIITLLIINSTISFIEENNAGNAAAALMARLAPKA 136
O74242|O74242_CRYNE       LSNGGGTPPDWQDFVGIILLFVNSTIGFVEERNAGNAVKALMDSLAPKA 198
O14437|O14437_UROFA       LSNGQGRPPDWQDFLGIMLLLFINAGIGFYEERSAGNAVKALMDSLAPKA 168
P05030|PMA1_YEAST         LS-------DWVDFGVICGLLMLNAGVGFVQEFQAGSIVDELKKTLANTA 180
Q00002|PMA1_Candida       LS-------DWVDFGVICGLLMLNACVGFIQEFQAGSIVDELKKTLANVA 164
P24545|PMA1_ZYGRO         LE-------DWVDFGVICGLLFLNAGVGFIQEFQAGSIVEELKKTLANTA 182
P49380|PMA1_KLULA         LE-------DWVDFGVICGLLFLNAAVGFIQEYQAGSIVDELKKTLANSA 161
P28877|PMA1_CANAL         LE-------DWVDFGVICALLLLNAFVGFIQEYQAGSIVDELKKTLANSA 157
P07038|PMA1_NEUCR         LE-------DWVDFGVICALLLLNACVGFVQEFQAGSIVDELKKTLALKA 180
Q07421|PMA1_AJECA         LE-------DWVDFGVICALLLLNACVGFVQEFQAGSIVDELKKTLALKA 176
Q92446|Q92446_PNECA       LQ-------DWVDFGVICALLLLNAFVGFIQEFQAGSIVDELKKTLALKA 181
P09627|PMA1_SCHPO         LR-------DWVDFGVICALLMLNAVVGFVQEYQAGSIVDELKKSLALKA 178
Q00001|PMA1_Aspergillus   LR-------DWIDLGVICGILLLNAVVGWYQEKQAADVVASLKGDIAMKA 184
                          *         ** *:   *   :*.:*: :.: :*  .*.. .  *   :*  :
```

Fig. 9 (continued)

```
P19456|PMA2_ARATH          KVLRDGKWSEQEAAILVPGDIVSIKLGDIIPADARLLEGD---------- 172
P20649|PMA1_ARATH          KVLRDGKWSEQEAAILVPGDIVSIKLGDIIPADARLLEGD---------- 172
Q43178|Q43178_SOLTU        KVLRDGRWSEQEAAILVPGDIISVKLGDIVPADARLLEGD---------- 175
Q96578|Q96578_SOLLC        KVLRDGRWSEQEAAILVPGDIISVKLGDIVPADARLLEGD---------- 175
Q43131|Q43131_VICFA        KVLRDGKWSEQEAAILVPGDIISIKLGDIIPADARLLEGD---------- 174
Q43271|Q43271_MAIZE        KVLRDGRWGEQEAAILVPGDIISIKLGDIIPADARLLEGD---------- 172
Q9SH76|PMA6_ARATH          KVLRDGRWGEQEAAILVPGDLISIKLGDIVPADARLLEGD---------- 175
Q08435|PMA1_NICPL          KVLRDGRWKEEDAAVLVPGDIISIKLGDIIPADARLLEGD---------- 177
Q42932|Q42932_NICPL        KVLRDGKWDEQDAAILVPGDIISIKLGDIIPADARLLEGD---------- 176
Q43002|Q43002_ORYSJ        KVLRNGRWSEEEAAILVPGDIISVKRGDIIPADARLLEGD---------- 176
O74242|O74242_CRYNE        RVKRDGQWKEIESSELVPGDLIAFKHGDVCPSDCRLVEAI---------- 238
O14437|O14437_UROFA        KVRRAGVWSEIDSADLVPGDIVAFKIGDVVPSDCRLYDAI---------- 208
P05030|PMA1_YEAST          VVIRDGQLVEIPANEVVPGDILQLEDGTVIPTDGRIVTED---------- 220
Q00002|PMA1_Candida        VVIRDGQLVEVPANEVVPGDILQLEDGTIIPADGRLVTEN---------- 204
P24545|PMA1_ZYGRO          TVIRDGSVQEAPANEIVPGDILKLEDGTVIPADGRLVTEE---------- 222
P49380|PMA1_KLULA          VVIRDGNLVEVPSNEVVPGDILQLEDGVVIPADGRLVTED---------- 201
P28877|PMA1_CANAL          LVVRNGQLVEIPANEVVPGDILQLEDGTVIPTDGRIVSED---------- 197
P07038|PMA1_NEUCR          VVLRDGTLKEIEAPEVVPGDILQVEEGTIIPADGRIVTDD---------- 220
Q07421|PMA1_AJECA          VVLRNGRLTEVEAPEVVPGDILQVEEGTIIPADGRIVTEE---------- 216
Q92446|Q92446_PNECA        TVLRDGRLIDIEAEEVVPGDILQLEEGSIVPADGRIVTEE---------- 221
P09627|PMA1_SCHPO          VVIREGQVHELEANEVVPGDILKLDEGTIICADGRVVTPD---------- 218
Q00001|PMA1_Aspergillus    VVIRDGQEQEILARELVTGDIIVVEEGTVIPADIRLICDYDKPEMFETYK 234
                             *  *      :    : :*.**::  .. *  :   :* *:

P19456|PMA2_ARATH          ------------------------------PLKVDQSALTGESLPVTKHP 192
P20649|PMA1_ARATH          ------------------------------PLKVDQSALTGESLPVTKHP 192
Q43178|Q43178_SOLTU        ------------------------------PLKIDQSALTGESLPVTKNP 195
Q96578|Q96578_SOLLC        ------------------------------PLKIDQSALTGESLPVTKNP 195
Q43131|Q43131_VICFA        ------------------------------PLKVDQAALTGESLPVTRHP 194
Q43271|Q43271_MAIZE        ------------------------------PLKVDQSALTGESLPVTKGP 192
Q9SH76|PMA6_ARATH          ------------------------------PLKIDQSALTGESLPATKHQ 195
Q08435|PMA1_NICPL          ------------------------------PLKIDQSALTGESLPVTKGP 197
Q42932|Q42932_NICPL        ------------------------------PLKIDQSALTGESLPVTKGP 196
Q43002|Q43002_ORYSJ        ------------------------------PLKIDQSALTGESLPVTKGP 196
O74242|O74242_CRYNE        ------------------------------DVSMDQAALTGESLPVGKHE 258
O14437|O14437_UROFA        ------------------------------NVSIDQAALTGESLPSTKHV 228
P05030|PMA1_YEAST          ------------------------------CFLQIDQSAITGESLAVDKHY 241
Q00002|PMA1_Candida        ------------------------------CFLQVDQSAITGESLAVDKGY 225
P24545|PMA1_ZYGRO          ------------------------------CFLQVDQSSITGESLAVDKHY 243
P49380|PMA1_KLULA          ------------------------------CFIQIDQSAITGESLAVDKRF 222
P28877|PMA1_CANAL          ------------------------------CLLQVDQSAITGESLAVDKRS 218
P07038|PMA1_NEUCR          ------------------------------AFLQVDQSALTGESLAVDKHK 241
Q07421|PMA1_AJECA          ------------------------------AFLQVDQSAITGESLAVDKHK 237
Q92446|Q92446_PNECA        ------------------------------AYIQVDQSSITGESLAVDKHK 242
P09627|PMA1_SCHPO          ------------------------------VHLQVDQSAITGESLAVDKHY 239
Q00001|PMA1_Aspergillus    EYLATANDDTLKEKDDDDEDGGIEARVGVSLIAVDQSAITGESLAVDKYM 284
                                                         : :**:::*****. :
```

Fig. 9 (continued)

```
P19456|PMA2_ARATH        GQEVFSGSTCKQGEIEAVVIATGVHTFFGKAAHLVDSTN-QVGHFQKVLT 241
P20649|PMA1_ARATH        GQEVFSGSTCKQGEIEAVVIATGVHTFFGKAAHLVDSTN-QVGHFQKVLT 241
Q43178|Q43178_SOLTU      GDEVFSGSTCKQGELEAVVIATGVHTFFGKAAHLVDSTN-NVGHFQKVLT 244
Q96578|Q96578_SOLLC      GDEVFSGSTCKQGELEAVVIATGVHTFFGKAAHLVDSTN-NVGHFQKVLT 244
Q43131|Q43131_VICFA      GQEVFSGSTCKQGEIEAVVIATGVHTFFGKAAHLVDNTN-NVGHFQMVLK 243
Q43271|Q43271_MAIZE      GDEVFSGSTCKQGEIEAVVIATGVHTFFGKAAHLVDSTN-QVGHFQQVLT 241
Q9SH76|PMA6_ARATH        GDEVFSGSTCKQGEIEAVVIATGVHTFFGKAAHLVDSTN-NVGHFQKVLT 244
Q08435|PMA1_NICPL        GDGVYSGSTCKQGEIEAIVIATGVHTFFGKAAHLVDSTN-QVGHFQKVLT 246
Q42932|Q42932_NICPL      GDGVYSGSTCKQGEIEAVVIATGVHTFFGKAAHLVDSTN-QVGHFQKVLT 245
Q43002|Q43002_ORYSJ      GDGVYSGSTCKQGEIEAVVIATGVHTFFGKAAHLVDSTN-QVGHFQKVLT 245
O74242|O74242_CRYNE      GDECFSGSTCKQGEAEGIVIATGPNTFFGRAATLVGQDNDQVGHLQQVLA 308
O14437|O14437_UROFA      GDQCFSGSTCKQGEAEGVVIATGPNTFFGRAATLVGADNDSTGHMQAVLA 278
P05030|PMA1_YEAST        GDQTFSSSTVKRGEGFMVVTATGDNTFVGRAAALVNKAAGGQGHFTEVLN 291
Q00002|PMA1_Candida      GDQTFSSSTVKRGEAFMVVTATGDNTFVGRAAALVNKASGGQGHFTEVLN 275
P24545|PMA1_ZYGRO        GDEVFSSSTVKRGEGFMIVTATGDNTFVGRAASLVNAAAGGQGHFTEVLN 293
P49380|PMA1_KLULA        GDSTFSSSTVKRGEAFMIVTATGDSTFVGRAAALVNKAAAGSGHFTEVLN 272
P28877|PMA1_CANAL        GDSCYSSSTVKTGEAFMIVTATGDSTFVGRAAALVNKASAGTGHFTEVLN 268
P07038|PMA1_NEUCR        GDQVFASSAVKRGEAFVVITATGDNTFVGRAAALVNASGDHFTEVLN 291
Q07421|PMA1_AJECA        GDTCYASSAVKRGEAFMVITATGDNTFVGRGPALVNAASAGTGHFTEVLN 287
Q92446|Q92446_PNECA      GDNIYSSSVVKRGETFMVVTATGDGTFVGHAASLVNKASCGTGHFTDVLN 292
P09627|PMA1_SCHPO        GDPTFASSGVKRGEGLMVVTATGDSTFVGRAASLVNAAAGGTGHFTEVLN 289
Q00001|PMA1_Aspergillus  ADTCYYTTGCKRGKAYAIVTATAKQSFVGKTAALVQGAK-DQGHFKAVMD 333
                         .:    :    :  * *:    ::  **. :*.*:  . **       **:  *:

P19456|PMA2_ARATH        AIGNFCICSIAIGMVIEIIVMYPIQRRKYRDG------IDNLLVLLIGGI 285
P20649|PMA1_ARATH        SIGNFCICSIAIGIAIEIVVMYPIQHRKYRDG------IDNLLVLLIGGI 285
Q43178|Q43178_SOLTU      AIGNFCICSIAVGMLIEIIVMYPIQHRKYRDG------IDNLLVLLIGGI 288
Q96578|Q96578_SOLLC      AIGNFCICSIAIGMLVEIIVMYPIQHRKYRDG------IDNLLVLLIGGI 288
Q43131|Q43131_VICFA      SIGNFCICSIAIGMLAEIIVVMYPIQHRKYRDG------IDNLLVLLIGGI 287
Q43271|Q43271_MAIZE      AIGNFCICSIGVGILVEIIVMFPIQHRRYRSG------IENLLVLLIGGI 285
Q9SH76|PMA6_ARATH        AIGNFCICSIGIGMLIEIIIMYPIQHRKYRDG------IDNLLVLLIGGI 288
Q08435|PMA1_NICPL        AIGNFCICSIAVGMIIEIIVMYPIQHRAYRPG------IDNLLVLLIGGI 290
Q42932|Q42932_NICPL      AIGNFCICSIAVGMIIEIIVMYPIQHRKYRPG------IDNLLVLLIGGI 289
Q43002|Q43002_ORYSJ      AIGNFCICSIAIGMVVEIIVMYPIQHRDYRPG------IDNLLVLLIGGI 289
O74242|O74242_CRYNE      RIGTFCLVSIGIFVLLEILILYADFRYPYRRG------LDNILVLLIGGI 352
O14437|O14437_UROFA      KIGTFCLVSIGIFVVLEIIILYGGFRYQYRRG------IDNILVLLIGGI 322
P05030|PMA1_YEAST        GIGIILLVLVIATLLLVWTACFYRTNGIVR-------ILRYTLGITIIGV 334
Q00002|PMA1_Candida      GIGILLLVLVIVTLLGVWAACFYRTDNIVK-------ILRFTLGITIIGV 318
P24545|PMA1_ZYGRO        GIGVILLVLVVITLLLIWTACFYRTVRIVP-------ILRYTLGITIVGV 336
P49380|PMA1_KLULA        GITILLILVTLLLVWVASFYRTNKIVR-------ILRYTLAITIVGV 315
P28877|PMA1_CANAL        GIGTTLLVFVIVTLLVWVACFYRTVRIVP-------ILRYTLAITIIGV 311
P07038|PMA1_NEUCR        GIGTILLILVIFTLLIVWVSSFYRSNPIVQ-------ILEFTLAITIIGV 334
Q07421|PMA1_AJECA        GIGTVLLILVILTLLVWVSSFYRSNSIVT-------ILEFTLAITIIGV 330
Q92446|Q92446_PNECA      RIGTILLVLVVFTLFVVYISAFYRSSTTIT-------ILKYTLAITIIGV 335
P09627|PMA1_SCHPO        GIGTILLVLVLLTLFCIYTAAFYRSVRLAR-------LLEYTLAITIIGV 332
Q00001|PMA1_Aspergillus  NIGTTLLVLVMFWILAAWIGGFYRHLKIATPEHEDNNLLHYTLILLIIGV 383
                         **    :   :   :           :               :  * : * *:
```

Fig. 9 (continued)

```
P19456|PMA2_ARATH         PIAMPTVLSVTMAIGSHRLSQQGAITKRMTAIEEMAGMDVLCSDKTGTLT 335
P20649|PMA1_ARATH         PIAMPTVLSVTMAIGSHRLSQQGAITKRMTAIEEMAGMDVLCSDKTGTLT 335
Q43178|Q43178_SOLTU       PIAMPTVLSVTMAIGSHRLSQQGAITKRMTAIEEMAGMDVLCSDKTGTLT 338
Q96578|Q96578_SOLLC       PIAMPTVLSVTMAIGSHRLSQQGAITKRMTAIEEMAGMDVLCSDKTGTLT 338
Q43131|Q43131_VICFA       PIAMPTVLSVTMAIGSHKLSQQGAITKRMTAIEEMAGMDVLCSDKTGTLT 337
Q43271|Q43271_MAIZE       PIAMPTVLSVTMPIGSHKLSQQGAITKRMTAIEEMAGMDVLCSDKTGTLT 335
Q9SH76|PMA6_ARATH         PIAMPTVLSVTMAIGSHRLSQQGAITKRMTAIEEMAGMDVLCSDKTGTLT 338
Q08435|PMA1_NICPL         PIAMPTVLSVTMAIGSHRLQQGAITKRMTAIEEMAGMDVLCSDKTGTLT 340
Q42932|Q42932_NICPL       PIAMPTVLSVTMAIGSHRLAQQGAITKRMTAIEEMAGMDVLCSDKTGTLT 339
Q43002|Q43002_ORYSJ       PIAMPTVLSVTMAIGSHRLAQQGAITKRMTAIEEMAGMDVLCSDKTGTLT 339
O74242|O74242_CRYNE       PIAMPTVLSVTLAVGAQQLAKHKAIVTRITAIEELAGVTILCSDKTGTLT 402
O14437|O14437_UROFA       PIAMPTVLSVTLAVGAQQLAKYKAIVTRITAIEELAGVTILCSDKTGTLT 372
P05030|PMA1_YEAST         PVGLPAVVTTTMAVGAAYLAKKQAIVQKLSAIESLAGVEILCSDKTGTLT 384
Q00002|PMA1_Candida       PVGLPAVVTTTMAVGAAYLAKKQAIVQKLSAIESLAGVEILCSDKTGTLT 368
P24545|PMA1_ZYGRO         PVGLPAVVTTTMAGGAAYLAKKQAIVQKLSAIESLAGVEILCSDKTGTLT 386
P49380|PMA1_KLULA         PVGLPAVVTTTMAVGAAYLAKKQAIVQKLSAIESLAGVEILCSDKTGTLT 365
P28877|PMA1_CANAL         PVGLPAVVTTTMAVGAAYLAKKQAIVQKLSAIESLAGVEILCSDKTGTLT 361
P07038|PMA1_NEUCR         PVGLPAVVTTTMAVGAAYLAKKKAIVQKLSAIESLAGVEILCSDKTGTLT 384
Q07421|PMA1_AJECA         PVGLPAVVTTTMAVGAAYLAKKKAIVQKLSAIESLAGVEILCSDKTGTLT 380
Q92446|Q92446_PNECA       PVGLPAVVTTTMAVGAAYLAKKKAIVQKLSAIESLAGVEILCSDKTGTLT 385
P09627|PMA1_SCHPO         PVGLPAVVTTTMAVGAAYLAEKQAIVQKLSAIESLAGVEVLCSDKTGTLT 382
Q00001|PMA1_Aspergillus   PVGLPVVTTTTLAVGAAYLAEQKAIVQKLTAIESLAGVDILCSDKTGTLT 433
                          *:.:*.*  :.*:. *:  *::  **. ::***:**:  :**********

P19456|PMA2_ARATH         LNKLSVDKNLVEVFCKGVEKDQVLLFAAMASRVENQDAIDAAMVGMLADP 385
P20649|PMA1_ARATH         LNKLSVDKNLVEVFCKGVEKDQVLLFAAMASRVENQDAIDAAMVGMLADP 385
Q43178|Q43178_SOLTU       LNKLSVDKTLVEVFVKGVDKEYVLLLPARASRVENQDAIDACMVGMLADP 388
Q96578|Q96578_SOLLC       LNKLSVDRSLVEVFTKGVDKEYVLLLAARASRVENQDAIDACMVGMLADP 388
Q43131|Q43131_VICFA       LNKLSVDRNLIEVFIKGMDKEHVILLAARAARTENQDAIDAAIVGMLADP 387
Q43271|Q43271_MAIZE       LNKLSVDKNLVEVFCKGVDKDHVLLLAARASRTENLDAIDAAMVGMLADP 385
Q9SH76|PMA6_ARATH         LNKLTVDKNLIEVFSKDVDKDYVILLSARASRVENQDAIDTSIVNMLGDP 388
Q08435|PMA1_NICPL         LTVDKNLIEVFAKGVDADMVVLMAARASRTENQDAIDAAIVGMLADP 390
Q42932|Q42932_NICPL       LNKLTVDKNLVEVFAKGVDADTVVLMAARASRTENQDAIDTAIVGMLSDP 389
Q43002|Q43002_ORYSJ       LNKLTVDKSLIEVFQRGVDQDTVILMAARASRTENQDAIDATIVGMLADP 389
O74242|O74242_CRYNE       TNKLTIDKENVKCYSK-WDVEGVCLLAAYASRTENQDAIDGCVVGTLPDP 451
O14437|O14437_UROFA       TNKLTIDKSTVKTYAD-FSADEVCVLAAYASRTENQDAIDTCVVGNVG-A 420
P05030|PMA1_YEAST         KNKLSLHEPYTVEGVSPDDLMLTACLAASR-KKKGLDAIDKAFLKSLKQY 433
Q00002|PMA1_Candida       KNKLSLHEPYTVEGVSADDLMLTACLAASR-KKKGLDAIDKAFLKSLINY 417
P24545|PMA1_ZYGRO         KNKLSLHEPYTVEGVSSDDLMLTACLAASR-KKKGLDAIDKAFLKSLAQY 435
P49380|PMA1_KLULA         KNKLSLHEPYTVEGVDPDDLMLTACLAASR-KKKGLDAIDKAFLKSLISY 414
P28877|PMA1_CANAL         KNKLSLHEPYTVEGVEPDDLMLTACLAASR-KKKGLDAIDKAFLKSLINY 410
P07038|PMA1_NEUCR         KNKLSLHDPYTVAGVDPEDLMLTACLAASR-KKKGIDAIDKAFLKSLKYY 433
Q07421|PMA1_AJECA         KNKLSLAEPYCVSGVDPEDLMLTACLAASR-KKKGIDAIDKAFLKSLRYY 429
Q92446|Q92446_PNECA       KNDLSLAEPYTVEGISCDELMLTACLAASR-KKKGLDAIDKAFLKALRNY 434
P09627|PMA1_SCHPO         KNKLSLGEPFTVSGVSGDDLVLTACLAASR-KRKGLDAIDKAFLKALKNY 431
Q00001|PMA1_Aspergillus   ANQLSIREPYVNEGVDVNWMMAVAAIASNH-NVKNLDPIDKVTILTLRRY 482
                              *.*::                        .  :.:   . :. *.**   :   :
```

Fig. 9 (continued)

```
P19456|PMA2_ARATH         KEARAGIRE----VHFLPFNPVDKRTALTYIDG-SG-NWHRVSKGAPEQI 429
P20649|PMA1_ARATH         KEARAGIRE----VHFLPFNPVDKRTALTYIDS-DG-NWHRVSKGAPEQI 429
Q43178|Q43178_SOLTU       KEARAGIRE----VHFLPFNPVDKRTALTYIDN-NG-NWHRASKGAPEQI 432
Q96578|Q96578_SOLLC       KEARAGIRE----VHFLPFNPVDKRTALTYIDS-NG-NWHRASKGAPEQI 432
Q43131|Q43131_VICFA       KEARAEITE----VHFLPFNPNDKRTALTYIDNKDG-TWHRASKGAPEQI 432
Q43271|Q43271_MAIZE       KEARAGIRE----IHFLPFNPVDKRTALTYIDA-DG-NWHRVSKGAPEQI 429
Q9SH76|PMA6_ARATH         KEARAGITE----VHFLPFNPVEKRTAITYIDT-NG-EWHRCSKGAPEQI 432
Q08435|PMA1_NICPL         KEARAGIRE----IHFLPFNPTDKRTALTYLDG-EG-KMHRVSKGAPEQI 434
Q42932|Q42932_NICPL       KEARAGIRE----IHFLPFNPTDKRTALTYLDG-EG-KMHRVSKGAPEQI 433
Q43002|Q43002_ORYSJ       KEARAGIQE----VHFLPFNPTDKRTALTYIDG-EG-KMHRVSKGAPEQI 433
O74242|O74242_CRYNE       QQARAGIKL----LDFKPFNPVDKRTEITYRDEMDGGKLKRATKGMTGII 497
O14437|O14437_UROFA       DVARRGIQL----LDFKPFNPVDKRTEITYIDTESG-QMRRVTKGMTGVI 465
P05030|PMA1_YEAST         PKAKDALTK-YKVLEFHPFDPVSKKVTAVVESP--EGERIVCVKGAPLFV 480
Q00002|PMA1_Candida       PKAKDALTK-YKVIEFHPFDPVSKKVTAVVESP--EGERIVCVKGAPLFV 464
P24545|PMA1_ZYGRO         PKAKGALTK-YKVLEFHPFDPVSKKVTAVVESP--EGERIICVKGAPLFV 482
P49380|PMA1_KLULA         PRAKAALTK-YKLLEFHPFDPVSKKVTAIVESP--EGERIICVKGAPLFV 461
P28877|PMA1_CANAL         PRAKAALPK-YKVIEFQPFDPVSKKVTAIVESP--EGERIICVKGAPLFV 457
P07038|PMA1_NEUCR         PRAKSVLSK-YKVLQFHPFDPVSKKVVAVVESP--QGERITCVKGAPLFV 480
Q07421|PMA1_AJECA         PRAKSVLTQ-YKVLEFHPFDPVSKKVSAVVLSP--QGERITCVKGAPLSV 476
Q92446|Q92446_PNECA       PVVRSAISK-YNLVEFHPFDPVSKKVTAIVESP--SGERIACVKGAPLFV 481
P09627|PMA1_SCHPO         PGPRSMLTK-YKVIEFQPFDPVSKKVTAYVQAP--DGTRITCVKGAPLWV 478
Q00001|PMA1_Aspergillus   PKAREILSRNWVTEKYTPFDPVSKRITTVCTC---DGVRYVCAKGAPKAI 529
                             :    :       .: **:* .*:              **  . :

P19456|PMA2_ARATH         LELAKA----SNDLSKKVLSIIDKYAERGLRSLAVARQVVPEKTKESPGA 475
P20649|PMA1_ARATH         LDLANA----RPDLRKKVLSCIDKYAERGLRSLAVARQVVPEKTKESPGG 475
Q43178|Q43178_SOLTU       LDLCNC----KEDVRRKVHSMIDKYAEAGLRSLAVARQEVPEKSKESAGG 478
Q96578|Q96578_SOLLC       LDLCNC----KEDVRRKVHSMIDKYAEAGLRSLAVARQEVPEKSKESTGG 478
Q43131|Q43131_VICFA       IELCNM----REDAQKKIHSMIEKFAERGLRSLGVARQEVPEKTKESAGA 478
Q43271|Q43271_MAIZE       LDLCHC----KEDLRRKVHSIIDKYAERGLRSLAVARQEVPEKNKESPGG 475
Q9SH76|PMA6_ARATH         IELCDL----KGETKRRAHEIIDKFAERGLRSLGVARQRVPEKDKESAGT 478
Q08435|PMA1_NICPL         LNLAHN----KSDIERRVHAVIDKFAERGLRSLGVAYQEVPEGRKESAGG 480
Q42932|Q42932_NICPL       LNLAHN----KSDIERRVHSVIDKFAERGLRSLGVAYQEVPEGRKESTGG 479
Q43002|Q43002_ORYSJ       LNLAHN----KTEIERRVRAVIDKFAERGLRSLAVQYHQVPDGRKESPGG 479
O74242|O74242_CRYNE       IEICTRNK--TNELEDQLEADVEEFARRGLRALAVAFEDVAGDDPSAEGN 545
O14437|O14437_UROFA       IELCTHNK--TEALEQRLESDVEEFARRGLRALAVAYEDVPNAQVDAPGS 513
P05030|PMA1_YEAST         LKTVEEDHPIPEDVHENYENKVAELASRGFRALGVARKRG--------EG 522
Q00002|PMA1_Candida       LKTVEEDHPIPEDVHENYENKVAELASRGFRALGVARKRG--------EG 506
P24545|PMA1_ZYGRO         LKTVEEDHPIPEDVHENYENKVAELASRGFRALGVARKRG--------EG 524
P49380|PMA1_KLULA         LKTVEEEHPIPEDVRENYENKVAELASRGFRALGVARKRG--------EG 503
P28877|PMA1_CANAL         LKTVEDDHPIPEDVHENYQNTVAEFASRGFRSLGVARKRG--------EG 499
P07038|PMA1_NEUCR         LKTVEEDHPIPEEVDQAYKNKVAEFATRGFRSLGVARKRG--------EG 522
Q07421|PMA1_AJECA         LKTVEEDHPIPDEVDSAYKNKVAEFATRGFRSLGVARKRG--------EG 518
Q92446|Q92446_PNECA       LRTVEEDQPVPEDIQNAYKDKVAEFASRGYRSLGIARKTG--------NS 523
P09627|PMA1_SCHPO         LKTVEEDHPIPEDVLSAYKDKVGDLASRGYRSLGVARKIE--------GQ 520
Q00001|PMA1_Aspergillus   LNMSQCS----EEEAAKFREKAAEFARRGFRSLGVAVQKE--------GE 567
                          :               .  *   * *:*.:  .
```

Fig. 9 (continued)

```
P19456|PMA2_ARATH         PWEFVGLLPLFDPPRHDSAETIRRALNLGVNVKMITGDQLAIGKETGRRL 525
P20649|PMA1_ARATH         PWEFVGLLPLFDPPRHDSAETIRRALNLGVNVKMITGDQLAIGKETGRRL 525
Q43178|Q43178_SOLTU       PWQFVGLLPLFDPPRHDSAETIRRALNLGVNVKMITGDQLAIAKETGRRL 528
Q96578|Q96578_SOLLC       PWQFVGLLPLFDPPRHDSAETIRRALNLGVNVKMITGDQLAIAKETGRRL 528
Q43131|Q43131_VICFA       PWQFVGLLSVFDPPRHDSAETIRQALNLGVNVKMITGDQLAIAKETGRRL 528
Q43271|Q43271_MAIZE       PWQFVGLLRVFDPPRHDSAETIRKALVLGVNVKMITGDQLAIGKETGRRL 525
Q9SH76|PMA6_ARATH         PWEFVGLLPLFDPPRHDSAETIRRALDLGVNVKMITGDQLAIGKETGRRL 528
Q08435|PMA1_NICPL         PWQFIGLLPLFDPPRHDSAETIRRALNLGVNVKMVTGDQLAIGKETGRRL 530
Q42932|Q42932_NICPL       PWQFIGLLPLFDPPRHDSAETIRRALNLGVNVKMVTGDQLAIGKETGRRL 529
Q43002|Q43002_ORYSJ       PWQFVGLLPLFDPPRHDSAETIRRALNLGVNVKMITGDQLAIGKETARRL 529
O74242|O74242_CRYNE       GFELVGLLSIFDPPRSDTKKTIDDAMALGVKVKMVTGDQLAIAKETGRRL 595
O14437|O14437_UROFA       GFELIGLLSIFDPPRDDTKQTIDDAQALGVKVKMVTGDQLAIAKETGRRL 563
P05030|PMA1_YEAST         HWEILGVMPCMDPPRDDTAQTVSEARHLGLRVKMLTGDAVGIAKETCRQL 572
Q00002|PMA1_Candida       HWEILGVMPCMDPPRDDTAETVNEARRLGLRVKMLTGDAVGIAKETCRQL 556
P24545|PMA1_ZYGRO         HWEILGVMPCMDPPRDDTAATVNEAKRLGLSVKMLTGDAVGIAKETCRQL 574
P49380|PMA1_KLULA         HWEILGVMPCMDPPRDDTAQTVNEARHLGLRVKMLTGDAVGIAKETCRQL 553
P28877|PMA1_CANAL         HWEILGIMPCMDPPRDDTAATVNEARRLGLRVKMLTGDAVGIAKETCRQL 549
P07038|PMA1_NEUCR         SWEILGIMPCMDPPRHDTYKTVCEAKTLGLSIKMLTGDAVGIARETSRQL 572
Q07421|PMA1_AJECA         SWEILGIMPCSDPPRHDTAKTINEAKTLGLSIKMLTGDAVGIARETSRQL 568
Q92446|Q92446_PNECA       NWEILGIMPCSDPPRCDTARTISEAIRLGLRIKMLTGDAVGIAKETARQL 573
P09627|PMA1_SCHPO         HWEIMGIMPCSDPPRHDTARTISEAKRLGLRVKMLTGDAVDIAKETARQL 570
Q00001|PMA1_Aspergillus   PWQLLGMYPMFDPPREDTAHTIAEAQHLGLSVKMLTGDALAIAKETCKML 617
                          :::::*:     **** *:  *:   * **::**:***  : *.:** : *

P19456|PMA2_ARATH         GMGTNMYPSSALLGTHKDANLASIPVEELIEKADGFAGVFPEHKYEIVKK 575
P20649|PMA1_ARATH         GMGTNMYPSAALLGTDKDSNIASIPVEELIEKADGFAGVFPEHKYEIVKK 575
Q43178|Q43178_SOLTU       GMGTNMYPSASLLGQDKDSSIASLPVEELIEKADGFAGVFPEHKYEIVKK 578
Q96578|Q96578_SOLLC       GMGTNMYPSASLLGQDKDSSIASLPVEELIEKADGFAGVFPEHKYEIVKK 578
Q43131|Q43131_VICFA       GMGTNMYPSATLLGLDKDSSVASMPVEELIEKADGFAGVFPEHKYEIVKK 578
Q43271|Q43271_MAIZE       GMGTNMYPSSALLGQNKDRTLSALPVDELIEKADGFAGVFPEHKYEIVKR 575
Q9SH76|PMA6_ARATH         GMGTNMYPSSSLLE-NKDDTTGGVPVDELIEKADGFAGVFPEHKYEIVRK 577
Q08435|PMA1_NICPL         GMGTNMYPSSALLGQTKDESISALPIDELIEKADGFAGVFPEHKYEIVKR 580
Q42932|Q42932_NICPL       GMGTNMYPSSALLGQTKDESIASLPIDELIEKADGFAGVFPEHKYEIVKR 579
Q43002|Q43002_ORYSJ       GMGTNMYPSSALLGQDKDESIVALPVDELIEKADGFAGVFPEHKYEIVKR 579
O74242|O74242_CRYNE       GLGDHMYPAKVLKEGPEAGSKHAN-LDEMIMDADGFAGVFPEHKFEIVKR 644
O14437|O14437_UROFA       GMGDHMYPSKVLKDGPEPGGKFSS-LDEMILDADGFAGVFPEHKYEIVKR 612
P05030|PMA1_YEAST         GLGTNIYNAE-RLGLGGGGDMPGSELADFVENADGFAEVFPQHKYRVVEI 621
Q00002|PMA1_Candida       GLGTNIYNAE-RLGLGGGGDMPGSELADFVENADGFAEVFPQHKYKVVEI 605
P24545|PMA1_ZYGRO         GLGTNIYDAE-RLGLGGGGSMPGSEMYDFVENADGFAEVFPQHKFAVVDI 623
P49380|PMA1_KLULA         GLGTNIYNAE-RLGLGGGGDMPGSELADFVENADGFAEVFPQHKYNVVEI 602
P28877|PMA1_CANAL         GLGTNIYDAD-RLGLSGGGDMAGSEIADFVENADGFAEGFPTNKYNAVEI 598
P07038|PMA1_NEUCR         GLGTNIYNAE-RLGLGGGGDMPGSEVYDFVEAADGFAEVFPQHKYNVVEI 621
Q07421|PMA1_AJECA         GLGTNVYNAE-RLGLGGGGTMPGSEVYDFVEAADGFAEVFPQHKYNVVEI 617
Q92446|Q92446_PNECA       GMGTNVYNAE-RLGLGGGGDMPGSEVYDFVEAADGFAEVFPQHKYNVVEI 622
P09627|PMA1_SCHPO         GMGTNIYNAE-RLGLTGGGNMPGSEVYDFVEAADGFEVFPQHKYAVVDI 619
Q00001|PMA1_Aspergillus   ALSTKVYDSE-RLIHGG---LAGSAQHDLVEKADGFAEVFPEHKYQVVEM 663
                          .:. ::* :           .   ::: ****. ** :*:  *
```

Fig. 9 (continued)

```
P19456|PMA2_ARATH            LQERKHIVGMTGDGVNDAPALKKADIGIAVADATDAARGASDIVLTEPGL 625
P20649|PMA1_ARATH            LQERKHIVGMTGDGVNDAPALKKADIGIAVADATDAARGASDIVLTEPGL 625
Q43178|Q43178_SOLTU          LQERKHIVGMTGDGVNDAPALKKADIGIAVADATDAARGASDIVLTEPGL 628
Q96578|Q96578_SOLLC          LQERKHIVGMTGDGVNDAPALKKADIGIAVADATDAARGRSDIVLTEPGL 628
Q43131|Q43131_VICFA          LQERKHICGMTGDGVNDAPALKKADIGIAVADATDAARGASDIVLTEPGL 628
Q43271|Q43271_MAIZE          LQEKKHIVGMTGDGVNDAPALKKADIGIAVADATDAARSASDIVLTEPGL 625
Q9SH76|PMA6_ARATH            LQERKHIVGMTGDGVNDAPALKKADIGIAVDDATDAARSASDIVLTEPGL 627
Q08435|PMA1_NICPL            LQARKHICGMTGDGVNDAPALKKADIGIAVDDATDAARSASDIVLTEPGL 630
Q42932|Q42932_NICPL          LQARKHICGMTGDGVNDAPALKKADIGIAVDDATDAARSASDIVLTEPGL 629
Q43002|Q43002_ORYSJ          LQARKHICGMTGDGVNDAPALKKADIGIAVDDSTDAARSASDIVLTEPGL 629
O74242|O74242_CRYNE          IQNLGHLCAMTGDGANDAPALSRANVGIAVEGATDAARGAADIVLTEPGL 694
O14437|O14437_UROFA          LQGLGHLCAMTGDGANDAPALARANVGIAVEGATDAARGAADIVLTEPGL 662
P05030|PMA1_YEAST            LQNRGYLVAMTGDGVNDAPSLKKADTGIAVEGATDAARSAADIVFLAPGL 671
Q00002|PMA1_Candida          LQNRGYLVAMTGDGVNDAPSLKKADTGIAVEGASDAARSAADIVFLAPGL 655
P24545|PMA1_ZYGRO            LQQRGYLVAMTGDGVNDAPSLKKADTGIAVEGATDAARSAADIVFLAPGL 673
P49380|PMA1_KLULA            LQQRGYLVAMTGDGVNDAPSLKKADTGIAVEGATDAARSAADIVFLAPGL 652
P28877|PMA1_CANAL            LQSRGYLVAMTGDGVNDAPSLKKADTGIAVEGATDAARSAADIVFLAPGL 648
P07038|PMA1_NEUCR            LQQRGYLVAMTGDGVNDAPSLKKADTGIAVEGSSDAARSAADIVFLAPGL 671
Q07421|PMA1_AJECA            LQQRGYLVAMTGDGVNDAPSLKKADTGIAVEGASDAARSAADIVFLAPGL 667
Q92446|Q92446_PNECA          LQQRGYLVAMTGDGVNDAPSLKKADTGIAVEGASDAARSAADIVFLAPGL 672
P09627|PMA1_SCHPO            LQQRGYLVAMTGDGVNDAPSLKKADTGIAVEGATDAARSAADIVFLAPGL 669
Q00001|PMA1_Aspergillus      LQQRGHLTAMTGDGVNDAPSLKKADCGIAVEGSTEAAQAAADIVFLAPGL 713
                             :*    ::  .*****.****:* :*: ****  .:::**:. :***: ***

P19456|PMA2_ARATH            SVIISAVLTSRAIFQRMKNYTIYAVSITIRIVFGFMLIALIWEFDFSAFM 675
P20649|PMA1_ARATH            SVIISAVLTSRAIFQRMKNYTIYAVSITIRIVFGFMLIALIWEFDFSAFM 675
Q43178|Q43178_SOLTU          SVIISAVLTSRAIFQRMKNYTIYAVSITIRIVFGFMLIALIWKYDFSAFM 678
Q96578|Q96578_SOLLC          SVIISAVLTSRAIFQRMKNYTIYAVSITIRIVFGFMLIALIWKYDFSAFM 678
Q43131|Q43131_VICFA          SVIISAVLTSRAIFQRMKNYTIYAVSITIRIVFGFMFIALIWKFDFSPFM 678
Q43271|Q43271_MAIZE          SVIISAVLTSRAIFQRMKNYTIYAVSITIRIVLGFMLIALIWQYDFSPFM 675
Q9SH76|PMA6_ARATH            SVIVSAVLTSRAIFQRMKNYTIYAVSITIRIVLGFMLVALIWEFDFSPFM 677
Q08435|PMA1_NICPL            SVIISAVLTSRAIFQRMKNYTIYAVSITIRIVLGFMLLALIWKFDFPPFM 680
Q42932|Q42932_NICPL          SVIISAVLTSRAIFQRMKNYTIYAVSITIRIVLGFMLLALIWKFDFPPFM 679
Q43002|Q43002_ORYSJ          SVIISAVLTSRAIFQRMKNYTIYAVSITIRIVLGFMLLALIWKFDFPPFM 679
O74242|O74242_CRYNE          STIVHAIYGSRVIFQRMRNYAIYACAVTIRIVLCFAIMAFAWRFDFPPFM 744
O14437|O14437_UROFA          STIVHAIRQSRIVFQRMRNYSIYACAVTIRIVVGFAVMAFAFKFDFPPFM 712
P05030|PMA1_YEAST            SAIIDALKTSRQIFHRMYSYVVYRIALSLHLEIFLGLWIAILDNSLDIDL 721
Q00002|PMA1_Candida          SAIIDALKTSRQIFHRMYSYVVYRIALSLHLELFLGLWIIILNHSLDIEL 705
P24545|PMA1_ZYGRO            SAIIDALKTSRQIFHRMYAYVVYRIALSLHLEIFLGLWIAILNHSLDIDL 723
P49380|PMA1_KLULA            SAIIDALKTSRQIFHRMYSYVVYRIALSLHLEIFLGLWIAILNRSLNIDL 702
P28877|PMA1_CANAL            SAIIDALKTSRQIFHRMYSYVVYRIALSLHLELFLGLWIAILNRSLDINL 698
P07038|PMA1_NEUCR            GAIIDALKTSRQIFHRMYSYVVYRIALSIHLEIFLGLWIAILNRSLNIEL 721
Q07421|PMA1_AJECA            SAIIDALKTSRQIFHRMYAYVVYRIALSLHLEIFLGLWIAILNTSLNLQL 717
Q92446|Q92446_PNECA          SAIIDALKTSRQIFHRMYAYVVYRIALSLHLEIFLGLWIVIFNHLMILEL 722
P09627|PMA1_SCHPO            SAIIDALKTSRQIFHRMYSYVVYRIALSLHLEIFLGLWLIIRNQLLNLEL 719
Q00001|PMA1_Aspergillus      STIVDAIKLARQIFQRMKAYIQYRIALCLHLEIYLVTSMIIIDETLRSDL 763
                             ..*: *:   :*  :*:**  *   *  ::  :::  . :          :    :
```

Fig. 9 (continued)

```
P19456|PMA2_ARATH        VLIIAILNDGTIMTISKDRVKPSPTPDSWKLKEIFATGVVLGGYQAIMTV 725
P20649|PMA1_ARATH        VLIIAILNDGTIMTISKDRVKPSPTPDSWKLKEIFATGIVLGGYQAIMSV 725
Q43178|Q43178_SOLTU      VLIIAILNDGTIMTISKDRVKPSPMPDSWKLNEIFATGVVLGGYQALMTV 728
Q96578|Q96578_SOLLC      VLIIAILNDGTIMTISKDRVKPSPMPDSWKLNEIFATGVVLGGYQALMTV 728
Q43131|Q43131_VICFA      ILIIAILNDGTIMTISKDRVKPSPLPDSWKLKEIFATGVMLGGYQALMTV 728
Q43271|Q43271_MAIZE      VLIIAILNDGTIMTISKDRVKPSPLPDSWKLKEIFATGIVLGGYLALMTV 725
Q9SH76|PMA6_ARATH        VLIIAILNDGTIMTISKDRVKPSPIPDSWKLKEIFATGVVLGTYMALVTV 727
Q08435|PMA1_NICPL        VLIIAILNDGTIMTISKDRVKPSPLPDSWKLAEIFTTGIVLGGYLAMMTV 730
Q42932|Q42932_NICPL      VLIIAILNDGTIMTISKDRVKPSPLPDSWKLAEIFTTGVVLGGYLAMMTV 729
Q43002|Q43002_ORYSJ      VLIIAILNDGTIMTISKDRVKPSPQPDSWKLSEIFATGVVLGSYLAMMTV 729
O74242|O74242_CRYNE      VLIIAVLNDGTIMTLSLDRVLPSTTPDSWDLAEVFSFGVAYGVYLSASTI 794
O14437|O14437_UROFA      VLVIALLNDGTIMTLSLDRVLPSSNPDHWDLTEIFTYAIGYGLCLALSTI 762
P05030|PMA1_YEAST        IVFIAIFADVATLAIAYDNAPYSPKPVKWNLPRLWGMSIILGIVLAIG-- 769
Q00002|PMA1_Candida      IVFIAIFADVATLAIAYDNAPFSQTPVKWNLPRLWGMSIILGIVLAIG-- 753
P24545|PMA1_ZYGRO        IVFIAIFADVATLAIAYDNAPFSPSPVKWNLPRLWGMSIMMGIILAAG-- 771
P49380|PMA1_KLULA        VVFIAIFADVATLAIAYDNAPYSPKPVKWNLRRLWGMSVILGIILAIG-- 750
P28877|PMA1_CANAL        IVFIAIFADVATLAIAYDNAPYDPKPVKWNLPRLWGMSIVLGIILAIG-- 746
P07038|PMA1_NEUCR        VVFIAIFADVATLAIAYDNAPYSQTPVKWNLPKLWGMSVLLGVVLAVG-- 769
Q07421|PMA1_AJECA        VVFIAIFADIATLAIAYDNAPFSKTPVKWNLPKLWGMSVLLGIVLAVG-- 765
Q92446|Q92446_PNECA      VVFIAIFADIATLAIAYDNAPYSLLPTKWNLPKLWGISLLLGAALAIG-- 770
P09627|PMA1_SCHPO        VVFIAIFADVATLAIAYDNAPYSMKPVKWNLPRLWGLSTVIGIVLAIG-- 767
Q00001|PMA1_Aspergillus  VVFIALFADLATIAVAYDNAHYEMRPVEWQLPKIWVISIVLGVLLAGA-- 811
                         ::.**:: * : :::: *..  . * *.* .::  .    *   :

P19456|PMA2_ARATH        IFFWAAHKTDFFSDTFGVRSIRDNNHE----LMGAVYLQVSIISQALIFV 771
P20649|PMA1_ARATH        IFFWAAHKTDFFSDKFGVRSIRDNNDE----LMGAVYLQVSIISQALIFV 771
Q43178|Q43178_SOLTU      LFFWAMHDTKFFSDKFGVKDIRESDEE----MMSALYLQVSIISQALIFV 774
Q96578|Q96578_SOLLC      IFFWAMHDTSFFTDKFGVKDIRESDEE----MMSALYLQVSIISQALIFV 774
Q43131|Q43131_VICFA      IFFWIVQGTKFFPDRFGVRHIHDNPDE----LTAALYLQVSIVSQALIFV 774
Q43271|Q43271_MAIZE      IFFWAMHKTDFFSDKFGVRSIRDSEHE----MMSALYLQVSIVSQALIFV 771
Q9SH76|PMA6_ARATH        VFFWLAHDTTFFSDKFGVRSLQGKDEE----LIAVLYLQVSIISQALIFV 773
Q08435|PMA1_NICPL        IFFWAAYKTNFFPHVFGVSTLEKTATDDFRKLASAIYLQVSIISQALIFV 780
Q42932|Q42932_NICPL      IFFWAAYETDFFPRVFGVSTLQKTATDDFRKLASAIYLQVSTISQALIFV 779
Q43002|Q43002_ORYSJ      IFFWVAYKTDFFPRVFHVESLQKTAQDDFQKLASAVYLQVSIISQALIFV 779
O74242|O74242_CRYNE      ALYATMENTTFFFEDRFGVEPLK-GNSYG---GHMVIYLQVAIISQALIFV 840
O14437|O14437_UROFA      VLLAVIIHTQFFEDRFGVQPLKDANDPH---VHMIIYLQVAIISQALIFV 809
P05030|PMA1_YEAST        --SWITLTTMFLP--KGGIIQNFGAMN------GIMFLQISLTENWLIFI 809
Q00002|PMA1_Candida      --TWICLTTMFLP--RGGIIQNFGSID------GVLFLQISLTENWLIFV 793
P24545|PMA1_ZYGRO        --TWITLTTMFLP--KGGIIQNFGSID------GILFLEISLTENWLIFI 811
P49380|PMA1_KLULA        --TWITLTTMFVP--KGGIIQNFGSID------GVLFLQISLTENWLIFI 790
P28877|PMA1_CANAL        --TWITLTTMLLP--KGGIIQNFGGLD------GILFLQISLTENWLIFV 786
P07038|PMA1_NEUCR        --TWITVTTMYAQGENGGIVQNFGNMD------EVLFLQISLTENWLIFI 811
Q07421|PMA1_AJECA        --TWITLTTMLVGSENGGIVQNFGRTH------PVLFLEISLTENWLIFI 807
Q92446|Q92446_PNECA      --SWIALTTIYINDNTFGIVQGYGNVD------AVMFLEISLTENWLIFI 812
P09627|PMA1_SCHPO        --TWITNTTMIAQGQNRGIVQNFGVQD------EVLFLEISLTENWLIFV 809
Q00001|PMA1_Aspergillus  --TWIMRASLFLN--DGGLIQNFGSPQ------EMIFLEVALTENWLIFV 851
                           :                            ::*:::  .: ***:
```

Fig. 9 (continued)

```
P19456|PMA2_ARATH         TRSRSWSFVERPGALLMIAFLIAQLIATLIAVYANWEFAKIRGIGWGWAG 821
P20649|PMA1_ARATH         TRSRSWSFVERPGALLMIAFVIAQLVATLIAVYADWTFAKVKGIGWGWAG 821
Q43178|Q43178_SOLTU       TRSRSWSFVERPGALLMIAFLIAQLVATLIAVYADWTFARVKGCGWGWAG 824
Q96578|Q96578_SOLLC       TRSRSWSFVERPGALLMIAFLIAQLVATLIAVYADWTFARVKGCGWGWAG 824
Q43131|Q43131_VICFA       TRSRSGLMLNAPGLLLLGAFLIAQLIATLIAVYANWAFARIQGIGWGWAG 824
Q43271|Q43271_MAIZE       TRSRSWSFVERPGLLLVTAF-VAQLVATLIAVYANWRFARIKGIGWGWAG 820
Q9SH76|PMA6_ARATH         TRSRSWSFVERPGLLLLIAFFVAQLIATLIATYAHWEFARIKGCGWGWCG 823
Q08435|PMA1_NICPL         TRSRSWSFVERPGFLLVIAFVIAQLVATLIAVYANWSFAAIEGIGWGWAG 830
Q42932|Q42932_NICPL       TRSRSWSFVERPGLLLVVAFLIAQLVATLIAVYANWAFAAIEGIGWGWAG 829
Q43002|Q43002_ORYSJ       TRSRSWSFVERPGFLLVFAFFVAQLIATLIAVYANWGFASIKGIGWGWAG 829
O74242|O74242_CRYNE       TRSHGPSWTERPSVALMLAFCLAQLVSSIIAAYADWSFSQVHSVSGGWIG 890
O14437|O14437_UROFA       TRSHGWFFMERPSVALFGAFVIAQLISSLIAAYGDWAFTDVRGISATWIA 859
P05030|PMA1_YEAST         TRAAGPFWSSIPSWQLAGAVFAVDIIATMFTLFGWWSEN---------- 848
Q00002|PMA1_Candida       TRAVGPFWSSIPSWQLAGAVFAVDIIATMFTLFGWFSQN---------- 832
P24545|PMA1_ZYGRO         TRAVGPFWSSIPSWQLAGAVFVVDVVATMFTLFGWWSQN---------- 850
P49380|PMA1_KLULA         TRAAGPFWSSIPSWQLSGAVLIVDIIATMFCLFGWWSQN---------- 829
P28877|PMA1_CANAL         TRAQGPFWSSIPSWQLSGAVLIVDIIATCFTLFGWWSQN---------- 825
P07038|PMA1_NEUCR         TRANGPFWSSIPSWQLSGAIFLVDILATCFTIWGWFEHS---------- 850
Q07421|PMA1_AJECA         TRANGPFWSSIPSWQLSGAILLVDIIATLFTIFGWFVGG---------- 846
Q92446|Q92446_PNECA       TRANGPFWSSLPSWQLFGAVFLVDVIATIFCIFGWFTGTKEHGL------ 856
P09627|PMA1_SCHPO         TRCNGPFWSSIPSWQLSGAVLAVDILATMFCIFGWFKGG---------- 848
Q00001|PMA1_Aspergillus   TRGG----KTWPSWQLVGAIFVVDVLATLFCVFGWLSGDYRQTSPPSHAE 897
                           **         *.  * *.  .:::::  :  :.

P19456|PMA2_ARATH         VIWLYSIVTYFPLDVFKFAIRYILSGKAWLNLFENKTAFTMKKDYGKEER 871
P20649|PMA1_ARATH         VIWIYSIVTYFPQDILKFAIRYILSGKAWASLFDNRTAFTTKKDYGIGER 871
Q43178|Q43178_SOLTU       VIWIFSIVTYFPLDIMKFAIRYILSGKAWNNLLDNKTAFTTKKDYGKEER 874
Q96578|Q96578_SOLLC       VIWIFSIVTYFPLDIMKFAIRYILSGKAWNNLLDNKTAFTTKKDYGKEER 874
Q43131|Q43131_VICFA       VIWLYSIIFYIPLDIIKFATRYFLSGKAWSN-LENKTAFTTKKDYGKGER 873
Q43271|Q43271_MAIZE       VVWLYSIVFYFPLDLLKFFIRFVLSGRAWDNLLDTRIAFTRKKDLRKGER 870
Q9SH76|PMA6_ARATH         VIWIYSIVTYIPLDILKFITRYTLSGKAWNNMIENRTAFTTKKDYGRGER 873
Q08435|PMA1_NICPL         VIWIYNLVFYIPLDIIKFFIRYALSGRAWDLVFERRIAFTRKKDFGKEQR 880
Q42932|Q42932_NICPL       VIWLYNLVFYFPLDIIKFLIRYALSGRAWDLVLEQRIAFTRKKDFGKEQR 879
Q43002|Q43002_ORYSJ       VIWLYNIVFYLPLDIIKFLIRYALSGRAWDLVLEQRIAFTRKKDFGTQEN 879
O74242|O74242_CRYNE       IVWIWNIVWYFPLDGIKFIMKKTVI------AALQRRKARKAGPA-VADA 933
O14437|O14437_UROFA       IVWIWNVIWFLPLDLVKFGMRAVIR------MFKPPVALNKPIPANQLTR 903
P05030|PMA1_YEAST         -----WTDIVTVVRVWISIGIFCVLGGFYYEMSTSEAFDRLMNGKPMKE 893
Q00002|PMA1_Candida       -----WTDIVTVVKIYIWSIGVFCVLGGFYYIMSESVVFDRLMNGKPLKE 877
P24545|PMA1_ZYGRO         -----WTDIVTVVRIYIWSIGIFCCLGGAYYLMSESETFDRLMNGKPLKE 895
P49380|PMA1_KLULA         -----WNDIVTVVRVWIFSFGVFCVMGGAYYMMSESEAFDRFMNGKSRRD 874
P28877|PMA1_CANAL         -----WTDIVTVVRTWIFSFGVFCVMGGAYYLMSTSEAFDNFCNGRKPQQ 870
P07038|PMA1_NEUCR         -----DTSIVAVVRIWIFSFGIFCIMGGVYYILQDSVGFDNLMHGKSPKG 895
Q07421|PMA1_AJECA         -----QTSIVAVVRIWVFSFGCFCVLGGLYYLLQGSAGFDNMMHGKSPKK 891
Q92446|Q92446_PNECA       ----ERTSIITVVRVWLFSLGVFCIMAGIYYLLSDSVAFDNIMHGKSVKK 902
P09627|PMA1_SCHPO         ----HQTSIVAVLRIWMYSFGIFCIMAGTYYILSESAGFDRMMNGKP-KE 893
Q00001|PMA1_Aspergillus   FSVNGDVDIVTVVVIWGYSIGVTIIIAVVYYILTIIPALDNLG---RKTR 944
                                                  :
```

Fig. 9 (continued)

```
P19456|PMA2_ARATH        EAQWALAQRTLHGLQPKEAVNIFPEKGSYRELSEIAEQAKRRAEIARLRE 921
P20649|PMA1_ARATH        EAQWAQAQRTLHGLQPKEDVNIFPEKGSYRELSEIAEQAKRRAEIARLRE 921
Q43178|Q43178_SOLTU      EAQWALAQRTLHGLQPPEASNLFNEKNSYRELSEIAEQAKRRAEMARLRE 924
Q96578|Q96578_SOLLC      EAQWALAQRTLHGLQPPEASNLFNEKNSYRELSEIAEQAKRRAEMARLRE 924
Q43131|Q43131_VICFA      EAQWAHAQRTLHGLEPPESSGIFHEKNSYRELSEIAEQAKRRAEVARLRE 923
Q43271|Q43271_MAIZE      EAQWATAQRTLHGLQPPESNTLFNDKSSYRELSEIAEQAKRRAEIARLRE 920
Q9SH76|PMA6_ARATH        EAQWALAQRTLHGLKPPES--MFEDTATYTELSEIAEQAKKRAEVARLRE 921
Q08435|PMA1_NICPL        ELQWAHAQRTLHGLQ-VPDTKLFSEATNFNELNQLAEEAKRRAEIARLRE 929
Q42932|Q42932_NICPL      ELQWAHAQRTLHGLQ-VPDTKLFSEATNFNELNQLAEEAKRRAEIARQRE 928
Q43002|Q43002_ORYSJ      QLKWATAQRTIHGLQPAATAAVFRDMTSYNDLNQLAEEARRRAEIARLRE 929
O74242|O74242_CRYNE      ALHRAPSRH---------ESLYSNRTNFLTRAANRLRGGAKISMSQ-NE  972
O14437|O14437_UROFA      TTSRPASIN---------ESLYSNRASFIQRASRRSVLGGRVHADD-RE  942
P05030|PMA1_YEAST        KKS---------------------TRSVEDFMAAMQRVSTQHEKET---  918
Q00002|PMA1_Candida      EKS---------------------TRSVEDFLAAMQRVSTQHEKEN---  902
P24545|PMA1_ZYGRO        NKS---------------------TRSVEDFLASMRRVSTQHEKGN---  920
P49380|PMA1_KLULA        KPS---------------------GRSVEDFLMAMQRVSTQHEKEN---  899
P28877|PMA1_CANAL        HTD---------------------KRSLEDFLVSMQRVSTQHEKST---  895
P07038|PMA1_NEUCR        NQK---------------------QRSLEDFVVSLQRVSTQHEKSQ---  920
Q07421|PMA1_AJECA        NQK---------------------QRSLEDFVVSLQRVSTQHEKSS---  916
Q92446|Q92446_PNECA      NSK---------------------QRSLEDFVVALQRMSTKHEKGE---  927
P09627|PMA1_SCHPO        SRN---------------------QRSIEDLVVALQRTSTRHEKGDA-  919
Q00001|PMA1_Aspergillus  SKA---------------------DTKIENMIAHLSKLAIEHETDNNGK 972

P19456|PMA2_ARATH        LHTLKGHVESVVKLKGLDIETP-SHYTV----- 948
P20649|PMA1_ARATH        LHTLKGHVESVAKLKGLDIDTAGHHYTV----- 949
Q43178|Q43178_SOLTU      LHTLKGHVESVVKLKGLDIETIQQHYTV----- 952
Q96578|Q96578_SOLLC      LHTLKGHVESVVKLKGLDIETIQQHYTV----- 952
Q43131|Q43131_VICFA      LHTLKGHVESVVKLKGLDIDTIQQHYTVYKGNT 956
Q43271|Q43271_MAIZE      LNTLKGHVESVAKLKGLDIDTIQQNYTV----- 948
Q9SH76|PMA6_ARATH        VHTLKGHVESVVKLKGLDIDNLNQHYTV----- 949
Q08435|PMA1_NICPL        LHTLKGHVESVVKLKGLDIETIQQAYTV----- 957
Q42932|Q42932_NICPL      LHTLKGHVESVVKLKGLDIETIQQSYTV----- 956
Q43002|Q43002_ORYSJ      LTTLKGRMESVVKQKGLDLETIQQSYTV----- 957
O74242|O74242_CRYNE      LQRFS---SIQAQQSGAALTRAHSRPAA----- 997
O14437|O14437_UROFA      LRRFS---SAQAVSSGAALSRAQ---------- 962
P05030|PMA1_YEAST        ---------------------------------
Q00002|PMA1_Candida      ---------------------------------
P24545|PMA1_ZYGRO        ---------------------------------
P49380|PMA1_KLULA        ---------------------------------
P28877|PMA1_CANAL        ---------------------------------
P07038|PMA1_NEUCR        ---------------------------------
Q07421|PMA1_AJECA        ---------------------------------
Q92446|Q92446_PNECA      ---------------------------------
P09627|PMA1_SCHPO        ---------------------------------
Q00001|PMA1_Aspergillus  SYYTLGARAEVEEDDE---------------- 988
```

FIG. 13

```
HEADER    HYDROLASE                               01-NOV-07   3B8C
TITLE     CRYSTAL STRUCTURE OF A PLASMA MEMBRANE PROTON PUMP
COMPND    MOL_ID: 1;
COMPND   2 MOLECULE: ATPASE 2, PLASMA MEMBRANE-TYPE;
COMPND   3 CHAIN: A, B;
COMPND   4 FRAGMENT: AHA2DELTA73 C-TERMINAL TRUNCATED;
COMPND   5 SYNONYM: PROTON PUMP 2, AHA2;
COMPND   6 EC: 3.6.3.6;
COMPND   7 ENGINEERED: YES
SOURCE    MOL_ID: 1;
SOURCE   2 ORGANISM_SCIENTIFIC: ARABIDOPSIS THALIANA;
SOURCE   3 ORGANISM_COMMON: MOUSE-EAR CRESS;
SOURCE   4 GENE: AHA2;
SOURCE   5 EXPRESSION_SYSTEM: SACCHAROMYCES CEREVISIAE;
SOURCE   6 EXPRESSION_SYSTEM_COMMON: YEAST;
SOURCE   7 EXPRESSION_SYSTEM_STRAIN: RS-72;
SOURCE   8 EXPRESSION_SYSTEM_VECTOR_TYPE: PLASMID;
SOURCE   9 EXPRESSION_SYSTEM_PLASMID: PMP-652
KEYWDS    PLASMA MEMBRANE, P-TYPE ATPASE, PROTON PUMP, ATP-BINDING,
KEYWDS   2 HYDROGEN ION TRANSPORT, HYDROLASE, ION TRANSPORT, MAGNESIUM,
KEYWDS   3 MEMBRANE, METAL-BINDING, NUCLEOTIDE-BINDING,
KEYWDS   4 PHOSPHORYLATION, TRANSMEMBRANE, TRANSPORT, ACETYLATION
EXPDTA    X-RAY DIFFRACTION
AUTHOR    B.P.PEDERSEN,M.BUCH-PEDERSEN,J.P.MORTH,M.G.PALMGREN,P.NISSEN
JRNL        AUTH   B.P.PEDERSEN,M.BUCH-PEDERSEN,J.P.MORTH,
JRNL        AUTH 2 M.G.PALMGREN,P.NISSEN
JRNL        TITL   CRYSTAL STRUCTURE OF A PLASMA MEMBRANE PROTON PUMP
JRNL        REF    TO BE PUBLISHED
JRNL        REFN
REMARK   1
REMARK   2
REMARK   2 RESOLUTION. 3.60 ANGSTROMS.
REMARK   3
REMARK   3 REFINEMENT.
REMARK   3   PROGRAM     : PHENIX
REMARK   3
REMARK   3   DATA USED IN REFINEMENT.
REMARK   3   RESOLUTION RANGE HIGH (ANGSTROMS) : 3.60
REMARK   3   RESOLUTION RANGE LOW  (ANGSTROMS) : 20.00
REMARK   3   DATA CUTOFF            (SIGMA(F)) : NULL
REMARK   3   DATA CUTOFF HIGH         (ABS(F)) : NULL
REMARK   3   DATA CUTOFF LOW          (ABS(F)) : NULL
REMARK   3   COMPLETENESS (WORKING+TEST)   (%) : 94.8
REMARK   3   NUMBER OF REFLECTIONS             : 40804
REMARK   3
REMARK   3   FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE            (WORKING SET) : 0.350
REMARK   3   FREE R VALUE                     : 0.366
REMARK   3   FREE R VALUE TEST SET SIZE   (%) : 5.030
REMARK   3   FREE R VALUE TEST SET COUNT      : 2159
REMARK   3   ESTIMATED ERROR OF FREE R VALUE  : NULL
REMARK   3
REMARK   3   FIT IN THE HIGHEST RESOLUTION BIN.
REMARK   3   TOTAL NUMBER OF BINS USED             : 15
REMARK   3   BIN RESOLUTION RANGE HIGH       (A)   : 3.60
REMARK   3   BIN RESOLUTION RANGE LOW        (A)   : 3.68
REMARK   3   BIN COMPLETENESS (WORKING+TEST) (%)   : 58.01
REMARK   3   REFLECTIONS IN BIN    (WORKING SET)   : 1637
REMARK   3   BIN R VALUE           (WORKING SET)   : 0.4280
REMARK   3   BIN FREE R VALUE                      : 0.4690
REMARK   3   BIN FREE R VALUE TEST SET SIZE  (%)   : 5.43
REMARK   3   BIN FREE R VALUE TEST SET COUNT       : 94
```

FIG. 13 Continued

```
REMARK   3    ESTIMATED ERROR OF BIN FREE R VALUE : NULL
REMARK   3
REMARK   3   NUMBER OF NON-HYDROGEN ATOMS USED IN REFINEMENT.
REMARK   3    PROTEIN ATOMS            : 12832
REMARK   3    NUCLEIC ACID ATOMS       : 0
REMARK   3    HETEROGEN ATOMS          : 64
REMARK   3    SOLVENT ATOMS            : 0
REMARK   3
REMARK   3   B VALUES.
REMARK   3    FROM WILSON PLOT           (A**2) : 110.61
REMARK   3    MEAN B VALUE      (OVERALL, A**2) : 174.93
REMARK   3    OVERALL ANISOTROPIC B VALUE.
REMARK   3     B11 (A**2) : -10.51000
REMARK   3     B22 (A**2) : -8.06000
REMARK   3     B33 (A**2) : 18.30000
REMARK   3     B12 (A**2) : 0.00000
REMARK   3     B13 (A**2) : 0.00000
REMARK   3     B23 (A**2) : 0.00000
REMARK   3
REMARK   3   ESTIMATED COORDINATE ERROR.
REMARK   3    ESD FROM LUZZATI PLOT      (A) : NULL
REMARK   3    ESD FROM SIGMAA            (A) : NULL
REMARK   3    LOW RESOLUTION CUTOFF      (A) : NULL
REMARK   3
REMARK   3   CROSS-VALIDATED ESTIMATED COORDINATE ERROR.
REMARK   3    ESD FROM C-V LUZZATI PLOT  (A) : NULL
REMARK   3    ESD FROM C-V SIGMAA        (A) : NULL
REMARK   3
REMARK   3   RMS DEVIATIONS FROM IDEAL VALUES.
REMARK   3    BOND LENGTHS              (A) : 0.009
REMARK   3    BOND ANGLES         (DEGREES) : 1.78
REMARK   3    DIHEDRAL ANGLES     (DEGREES) : 26.87
REMARK   3    IMPROPER ANGLES     (DEGREES) : NULL
REMARK   3
REMARK   3   ISOTROPIC THERMAL MODEL : ANISOTROPIC GROUP ADPS (TLS)
REMARK   3
REMARK   3   ISOTROPIC THERMAL FACTOR RESTRAINTS.    RMS    SIGMA
REMARK   3    MAIN-CHAIN BOND           (A**2) : NULL ; NULL
REMARK   3    MAIN-CHAIN ANGLE          (A**2) : NULL ; NULL
REMARK   3    SIDE-CHAIN BOND           (A**2) : NULL ; NULL
REMARK   3    SIDE-CHAIN ANGLE          (A**2) : NULL ; NULL
REMARK   3
REMARK   3   NCS MODEL : CHAIN A & B
REMARK   3
REMARK   3   NCS RESTRAINTS.                        RMS   SIGMA/WEIGHT
REMARK   3    GROUP  1  POSITIONAL        (A) : 0.018 ; NULL
REMARK   3    GROUP  1  B-FACTOR       (A**2) : NULL  ; NULL
REMARK   3
REMARK   3   PARAMETER FILE  1  : NULL
REMARK   3   PARAMETER FILE  2  : NULL
REMARK   3   TOPOLOGY  FILE  1  : NULL
REMARK   3   TOPOLOGY  FILE  2  : NULL
REMARK   3
REMARK   3   OTHER REFINEMENT REMARKS: USED PHENIX.REFINE (VERSION: 2007_
REMARK   3   08_18_1856). TARGET: MLHL. MAXIMUM LIKELIHOOD ESTIMATE FOR
REMARK   3   COORDINATE ERROR: 0.98 A. USED 8 TLS GROUPS IN REFINEMENT.
REMARK   3   USED FLAT BULK SOLVENT MODEL (K_SOL 0.229, B_SOL 54.662).
REMARK   4
REMARK   4 3B8C COMPLIES WITH FORMAT V. 3.1, 1-AUG-2007
REMARK 100
REMARK 100 THIS ENTRY HAS BEEN PROCESSED BY PDBJ.
REMARK 100 THE RCSB ID CODE IS RCSB045205.
REMARK 200
REMARK 200 EXPERIMENTAL DETAILS
REMARK 200  EXPERIMENT TYPE               : X-RAY DIFFRACTION
REMARK 200  DATE OF DATA COLLECTION       : 03-DEC-2006
REMARK 200  TEMPERATURE          (KELVIN) : 100.0
REMARK 200  PH                            : 6.00
REMARK 200  NUMBER OF CRYSTALS USED       : 1
```

FIG. 13 Continued

```
REMARK 200
REMARK 200  SYNCHROTRON              (Y/N) : Y
REMARK 200  RADIATION SOURCE               : SLS
REMARK 200  BEAMLINE                       : X06SA
REMARK 200  X-RAY GENERATOR MODEL          : NULL
REMARK 200  MONOCHROMATIC OR LAUE    (M/L) : M
REMARK 200  WAVELENGTH OR RANGE        (A) : 1.007829
REMARK 200  MONOCHROMATOR                  : SI(111) MONOCHROMATOR
REMARK 200  OPTICS                         : NULL
REMARK 200
REMARK 200  DETECTOR TYPE                  : CCD
REMARK 200  DETECTOR MANUFACTURER          : MARMOSAIC 225 MM CCD
REMARK 200  INTENSITY-INTEGRATION SOFTWARE : XDS
REMARK 200  DATA SCALING SOFTWARE          : XSCALE
REMARK 200
REMARK 200  NUMBER OF UNIQUE REFLECTIONS   : 45423
REMARK 200  RESOLUTION RANGE HIGH      (A) : 3.600
REMARK 200  RESOLUTION RANGE LOW       (A) : 84.000
REMARK 200  REJECTION CRITERIA  (SIGMA(I)) : -3.000
REMARK 200
REMARK 200 OVERALL.
REMARK 200  COMPLETENESS FOR RANGE     (%) : 99.5
REMARK 200  DATA REDUNDANCY                : 7.900
REMARK 200  R MERGE                    (I) : 0.13600
REMARK 200  R SYM                      (I) : 0.13600
REMARK 200  <I/SIGMA(I)> FOR THE DATA SET  : 9.4300
REMARK 200
REMARK 200 IN THE HIGHEST RESOLUTION SHELL.
REMARK 200  HIGHEST RESOLUTION SHELL, RANGE HIGH (A) : 3.60
REMARK 200  HIGHEST RESOLUTION SHELL, RANGE LOW  (A) : 3.70
REMARK 200  COMPLETENESS FOR SHELL     (%) : 100.0
REMARK 200  DATA REDUNDANCY IN SHELL       : 6.70
REMARK 200  R MERGE FOR SHELL          (I) : 0.83100
REMARK 200  R SYM FOR SHELL            (I) : 0.83100
REMARK 200  <I/SIGMA(I)> FOR SHELL         : 2.200
REMARK 200
REMARK 200 DIFFRACTION PROTOCOL: SINGLE WAVELENGTH
REMARK 200 METHOD USED TO DETERMINE THE STRUCTURE: MIRAS/SIRAS
REMARK 200 SOFTWARE USED: SHARP/DMMULTI
REMARK 200 STARTING MODEL: PDB ENTRY 1T5T
REMARK 200
REMARK 200 REMARK: NULL
REMARK 280
REMARK 280 CRYSTAL
REMARK 280 SOLVENT CONTENT, VS   (%): 75.04
REMARK 280 MATTHEWS COEFFICIENT, VM (ANGSTROMS**3/DA): 4.93
REMARK 280
REMARK 280 CRYSTALLIZATION CONDITIONS: PEG 400, SUCROSE, KCL, C12E8, CYMAL
REMARK 280  -5, DDM, PH 6.0, VAPOR DIFFUSION
REMARK 290
REMARK 290 CRYSTALLOGRAPHIC SYMMETRY
REMARK 290 SYMMETRY OPERATORS FOR SPACE GROUP: P 21 21 21
REMARK 290
REMARK 290     SYMOP    SYMMETRY
REMARK 290     NNNMMM   OPERATOR
REMARK 290      1555    X,Y,Z
REMARK 290      2555    1/2-X,-Y,1/2+Z
REMARK 290      3555    -X,1/2+Y,1/2-Z
REMARK 290      4555    1/2+X,1/2-Y,-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290   SMTRY1   1  1.000000  0.000000  0.000000        0.00000
REMARK 290   SMTRY2   1  0.000000  1.000000  0.000000        0.00000
```

FIG. 13 Continued

```
REMARK 290   SMTRY3   1  0.000000  0.000000  1.000000        0.00000
REMARK 290   SMTRY1   2 -1.000000  0.000000  0.000000       42.64500
REMARK 290   SMTRY2   2  0.000000 -1.000000  0.000000        0.00000
REMARK 290   SMTRY3   2  0.000000  0.000000  1.000000      156.05500
REMARK 290   SMTRY1   3 -1.000000  0.000000  0.000000        0.00000
REMARK 290   SMTRY2   3  0.000000  1.000000  0.000000       72.21000
REMARK 290   SMTRY3   3  0.000000  0.000000 -1.000000      156.05500
REMARK 290   SMTRY1   4  1.000000  0.000000  0.000000       42.64500
REMARK 290   SMTRY2   4  0.000000 -1.000000  0.000000       72.21000
REMARK 290   SMTRY3   4  0.000000  0.000000 -1.000000        0.00000
REMARK 290
REMARK 290 REMARK: NULL
REMARK 300
REMARK 300 BIOMOLECULE: 1, 2
REMARK 300 SEE REMARK 350 FOR THE AUTHOR PROVIDED AND PROGRAM
REMARK 300 GENERATED ASSEMBLY INFORMATION FOR THE STRUCTURE IN
REMARK 300 THIS ENTRY. THE REMARK MAY ALSO PROVIDE INFORMATION ON
REMARK 300 BURIED SURFACE AREA.
REMARK 350
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 AUTHOR DETERMINED BIOLOGICAL UNIT: MONOMER
REMARK 350 APPLY THE FOLLOWING TO CHAINS: A
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 350
REMARK 350 BIOMOLECULE: 2
REMARK 350 AUTHOR DETERMINED BIOLOGICAL UNIT: MONOMER
REMARK 350 APPLY THE FOLLOWING TO CHAINS: B
REMARK 350   BIOMT1   1  1.000000  0.000000  0.000000        0.00000
REMARK 350   BIOMT2   1  0.000000  1.000000  0.000000        0.00000
REMARK 350   BIOMT3   1  0.000000  0.000000  1.000000        0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSEQ=SEQUENCE NUMBER; I=INSERTION CODE.)
REMARK 465
REMARK 465   M RES C  SSEQI
REMARK 465     MET A    1
REMARK 465     SER A    2
REMARK 465     SER A    3
REMARK 465     LEU A    4
REMARK 465     GLU A    5
REMARK 465     ASP A    6
REMARK 465     ILE A    7
REMARK 465     LYS A    8
REMARK 465     ASN A    9
REMARK 465     GLU A   10
REMARK 465     THR A   11
REMARK 465     LEU A  845
REMARK 465     SER A  846
REMARK 465     GLY A  847
REMARK 465     LYS A  848
REMARK 465     ALA A  849
REMARK 465     TRP A  850
REMARK 465     LEU A  851
REMARK 465     ASN A  852
REMARK 465     LEU A  853
REMARK 465     PHE A  854
REMARK 465     GLU A  855
REMARK 465     ASN A  856
REMARK 465     LYS A  857
```

FIG. 13 Continued

```
REMARK 465     THR A   858
REMARK 465     ALA A   859
REMARK 465     PHE A   860
REMARK 465     THR A   861
REMARK 465     MET A   862
REMARK 465     LYS A   863
REMARK 465     LYS A   864
REMARK 465     ASP A   865
REMARK 465     TYR A   866
REMARK 465     GLY A   867
REMARK 465     LYS A   868
REMARK 465     GLU A   869
REMARK 465     GLU A   870
REMARK 465     ARG A   871
REMARK 465     GLU A   872
REMARK 465     ALA A   873
REMARK 465     GLN A   874
REMARK 465     TRP A   875
REMARK 465     MET A   876
REMARK 465     ARG A   877
REMARK 465     GLY A   878
REMARK 465     SER A   879
REMARK 465     HIS A   880
REMARK 465     HIS A   881
REMARK 465     HIS A   882
REMARK 465     HIS A   883
REMARK 465     HIS A   884
REMARK 465     HIS A   885
REMARK 465     MET B     1
REMARK 465     SER B     2
REMARK 465     SER B     3
REMARK 465     LEU B     4
REMARK 465     GLU B     5
REMARK 465     ASP B     6
REMARK 465     ILE B     7
REMARK 465     LYS B     8
REMARK 465     ASN B     9
REMARK 465     GLU B    10
REMARK 465     THR B    11
REMARK 465     LEU B   845
REMARK 465     SER B   846
REMARK 465     GLY B   847
REMARK 465     LYS B   848
REMARK 465     ALA B   849
REMARK 465     TRP B   850
REMARK 465     LEU B   851
REMARK 465     ASN B   852
REMARK 465     LEU B   853
REMARK 465     PHE B   854
REMARK 465     GLU B   855
REMARK 465     ASN B   856
REMARK 465     LYS B   857
REMARK 465     THR B   858
REMARK 465     ALA B   859
REMARK 465     PHE B   860
REMARK 465     THR B   861
REMARK 465     MET B   862
REMARK 465     LYS B   863
REMARK 465     LYS B   864
REMARK 465     ASP B   865
REMARK 465     TYR B   866
REMARK 465     GLY B   867
REMARK 465     LYS B   868
REMARK 465     GLU B   869
REMARK 465     GLU B   870
REMARK 465     ARG B   871
REMARK 465     GLU B   872
REMARK 465     ALA B   873
REMARK 465     GLN B   874
```

FIG. 13 Continued

```
REMARK 465     TRP B   875
REMARK 465     MET B   876
REMARK 465     ARG B   877
REMARK 465     GLY B   878
REMARK 465     SER B   879
REMARK 465     HIS B   880
REMARK 465     HIS B   881
REMARK 465     HIS B   882
REMARK 465     HIS B   883
REMARK 465     HIS B   884
REMARK 465     HIS B   885
REMARK 500
REMARK 500 GEOMETRY AND STEREOCHEMISTRY
REMARK 500 SUBTOPIC: CLOSE CONTACTS IN SAME ASYMMETRIC UNIT
REMARK 500
REMARK 500 THE FOLLOWING ATOMS ARE IN CLOSE CONTACT.
REMARK 500
REMARK 500   ATM1  RES C  SSEQI    ATM2  RES C  SSEQI
REMARK 500   O     ASN A   67      N     LEU A   69             2.07
REMARK 500   O     ASN B   67      N     LEU B   69             2.11
REMARK 500   OE1   GLU A  752      O     ALA A  810             2.16
REMARK 500   O     VAL A  803      N     ALA A  805             2.17
REMARK 500   OE1   GLU B  752      O     ALA B  810             2.17
REMARK 500   O     VAL B  803      N     ALA B  805             2.19
REMARK 500
REMARK 500 REMARK: NULL
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES PROTEIN: ENGH AND HUBER, 1999
REMARK 500 EXPECTED VALUES NUCELIC ACID: CLOWNEY ET AL 1996
REMARK 500
REMARK 500   M RES CSSEQI ATM1   ATM2   ATM3
REMARK 500     PRO A 783   C  -  N  -  CA   ANGL. DEV. = -11.1 DEGREES
REMARK 500     PRO B 783   C  -  N  -  CA   ANGL. DEV. = -11.2 DEGREES
REMARK 500
REMARK 500 REMARK: NULL
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M=MODEL NUMBER; RES=RESIDUE NAME; C=CHAIN IDENTIFIER;
REMARK 500 SSEQ=SEQUENCE NUMBER; I=INSERTION CODE).
REMARK 500
REMARK 500 STANDARD TABLE:
REMARK 500 FORMAT:(10X,I3,1X,A3,1X,A1,I4,A1,4X,F7.2,3X,F7.2)
REMARK 500
REMARK 500 EXPECTED VALUES: GJ KLEYWEGT AND TA JONES (1996). PHI/PSI-
REMARK 500 CHOLOGY: RAMACHANDRAN REVISITED. STRUCTURE 4, 1395 - 1400
REMARK 500
REMARK 500   M RES CSSEQI        PSI        PHI
REMARK 500     ASP A  13      -172.43     -174.11
REMARK 500     LYS A  16        21.58       91.53
REMARK 500     ILE A  17      -147.13      -81.76
REMARK 500     GLU A  20         7.11      -56.78
REMARK 500     PHE A  23       -88.18      -53.50
REMARK 500     LEU A  26        92.07     -164.86
REMARK 500     LYS A  27        90.11      -11.40
REMARK 500     CYS A  28       103.42       13.47
```

FIG. 13 Continued

```
REMARK 500     SER A   29       81.68   -161.55
REMARK 500     GLU A   31      -60.93   -140.55
REMARK 500     LEU A   33       87.72    -63.28
REMARK 500     THR A   34      100.69     51.08
REMARK 500     PHE A   45      140.57    178.63
REMARK 500     PRO A   47       23.56    -67.80
REMARK 500     ASN A   48     -144.24    -61.12
REMARK 500     GLU A   51      -34.16   -168.92
REMARK 500     LYS A   54       48.35    -51.43
REMARK 500     GLU A   55     -174.31    -62.24
REMARK 500     LYS A   57       27.30     49.39
REMARK 500     LYS A   60      -22.49    152.85
REMARK 500     LEU A   62       -5.11     60.00
REMARK 500     PHE A   64       -5.26   -153.63
REMARK 500     MET A   65       85.92    -49.96
REMARK 500     ASN A   67      108.44     51.29
REMARK 500     PRO A   68       36.54    -45.64
REMARK 500     SER A   70       44.48   -149.54
REMARK 500     ALA A   76        5.34    -63.22
REMARK 500     MET A   79        9.63    -66.61
REMARK 500     ILE A   81       35.89    -92.19
REMARK 500     ALA A   82       12.98   -141.83
REMARK 500     LEU A   83       15.78   -150.42
REMARK 500     ALA A   84       39.91    170.47
REMARK 500     PRO A   91     -122.44    -54.30
REMARK 500     GLN A   94       32.80    -51.28
REMARK 500     THR A  108      -93.09   -139.51
REMARK 500     ILE A  109        8.17    -57.04
REMARK 500     SER A  110      -86.82   -110.70
REMARK 500     PHE A  111       22.06    -64.67
REMARK 500     GLU A  113       42.57    -70.35
REMARK 500     GLU A  114      -23.00   -140.87
REMARK 500     ALA A  121       -7.51    -53.76
REMARK 500     ALA A  122      -87.44    -73.61
REMARK 500     LEU A  124      -86.93    -76.64
REMARK 500     MET A  125        6.09    -56.20
REMARK 500     LEU A  128      -18.12   -149.41
REMARK 500     ALA A  129      102.58    -46.59
REMARK 500     PRO A  130       41.41    -18.49
REMARK 500     LYS A  131      140.57    -30.39
REMARK 500     LYS A  133       54.04     72.40
REMARK 500     ARG A  136      -80.09     46.00
REMARK 500     ASP A  137      -52.23    159.04
REMARK 500     SER A  141      151.17    -40.90
REMARK 500     ILE A  147      -19.23    -40.88
REMARK 500     LEU A  148      -81.91    -39.77
REMARK 500     VAL A  149      100.29     35.58
REMARK 500     PRO A  150      131.50    -31.05
REMARK 500     VAL A  154     -151.65   -114.99
REMARK 500     SER A  155     -164.17   -169.73
REMARK 500     LYS A  157     -153.35   -137.18
REMARK 500     ILE A  162      143.27    -24.21
REMARK 500     ASP A  165      146.27    -36.04
REMARK 500     ALA A  166     -155.93   -161.08
REMARK 500     ARG A  167        5.57   -152.20
REMARK 500     LEU A  168      104.90     32.94
REMARK 500     GLU A  170     -166.69    172.81
REMARK 500     ASP A  172       90.48    178.04
REMARK 500     PRO A  173      150.01    -27.66
REMARK 500     VAL A  176       46.66    -97.64
REMARK 500     ASP A  177       97.03    -40.31
REMARK 500     ALA A  180      -72.18   -133.18
REMARK 500     THR A  182       55.01   -150.97
REMARK 500     SER A  185       33.59    -55.84
REMARK 500     PRO A  187     -173.26    -35.28
REMARK 500     VAL A  188      -41.04   -153.94
REMARK 500     THR A  189      120.54     26.29
REMARK 500     PRO A  192       70.33    -56.49
REMARK 500     VAL A  196       53.95    -65.36
```

FIG. 13 Continued

```
REMARK 500     SER A 198      -32.46    -37.46
REMARK 500     LYS A 203     -120.17    -82.99
REMARK 500     VAL A 211      109.89    -56.07
REMARK 500     ALA A 213     -174.41     46.84
REMARK 500     THR A 218      -49.30   -171.98
REMARK 500     LYS A 222       45.33   -141.58
REMARK 500     ALA A 224     -105.09    -79.12
REMARK 500     VAL A 227      146.76    173.00
REMARK 500     GLN A 232       38.10    172.01
REMARK 500     VAL A 233        1.63    -49.64
REMARK 500     HIS A 235       83.90    -55.22
REMARK 500     PHE A 236      -62.97   -149.07
REMARK 500     LYS A 238       33.86    -70.19
REMARK 500     PHE A 246       38.63    -95.99
REMARK 500     CYS A 247      -45.86   -134.00
REMARK 500     SER A 250      -37.23   -152.10
REMARK 500     ILE A 259      -74.08    -70.66
REMARK 500     ILE A 260        6.52    -61.68
REMARK 500     MET A 262      -61.70   -137.75
REMARK 500     ILE A 265      -95.62    -66.00
REMARK 500     GLN A 266        9.44    -65.46
REMARK 500     ARG A 267     -136.47     29.71
REMARK 500     ARG A 268       57.59     21.15
REMARK 500     TYR A 270      -83.66    174.91
REMARK 500     LEU A 281       20.46    -70.52
REMARK 500     ILE A 282      -27.78   -158.11
REMARK 500     ILE A 287       33.96     55.30
REMARK 500     VAL A 292      -71.83    -54.40
REMARK 500     LEU A 304      -75.59    -71.47
REMARK 500     SER A 305       18.18    -53.46
REMARK 500     MET A 314      -15.51    -42.81
REMARK 500     ALA A 316        1.47    -69.47
REMARK 500     MET A 323       79.15    -28.42
REMARK 500     LYS A 330      -84.95    -61.38
REMARK 500     THR A 333      -95.19   -161.12
REMARK 500     LEU A 334      -15.63    -47.60
REMARK 500     LYS A 343       57.31    -95.73
REMARK 500     PHE A 349     -133.04    -85.82
REMARK 500     CYS A 350       88.03    179.41
REMARK 500     LYS A 351      134.31    156.22
REMARK 500     GLU A 354      -93.04     24.40
REMARK 500     LYS A 355      -38.43    -35.32
REMARK 500     ASP A 356      -73.29    -67.18
REMARK 500     GLN A 357      -46.68    -28.68
REMARK 500     PHE A 361      -70.49    -48.43
REMARK 500     SER A 366      155.08    161.37
REMARK 500     ARG A 367     -166.39    -73.01
REMARK 500     VAL A 368      -70.54    -80.09
REMARK 500     ASP A 372      150.50    -44.03
REMARK 500     MET A 381     -150.88     44.18
REMARK 500     ALA A 383       89.46    -56.63
REMARK 500     ASP A 384      150.84    -44.01
REMARK 500     PRO A 385     -128.91    -13.24
REMARK 500     LYS A 386       46.39    -95.70
REMARK 500     GLU A 387       43.90   -107.66
REMARK 500     ALA A 388       32.87   -150.29
REMARK 500     ALA A 390       80.93     48.23
REMARK 500     ARG A 393      144.72    157.78
REMARK 500     GLU A 394       22.54   -150.68
REMARK 500     PHE A 397       35.84   -147.92
REMARK 500     PRO A 399      125.50    -29.30
REMARK 500     ASN A 401      148.73    171.88
REMARK 500     PRO A 402      170.71    -55.91
REMARK 500     VAL A 403       -2.57     59.60
REMARK 500     ALA A 408       56.40   -151.07
REMARK 500     LEU A 409      175.64    -54.16
REMARK 500     ASP A 413      -19.28   -174.49
REMARK 500     SER A 415      -87.21    -39.75
REMARK 500     SER A 422      137.34    178.15
```

FIG. 13 Continued

```
REMARK 500     ALA A 425      -87.17     -56.24
REMARK 500     GLU A 427       20.21     -59.96
REMARK 500     LEU A 432       -8.04      47.44
REMARK 500     LYS A 434       87.48      62.92
REMARK 500     ALA A 435       87.72     -56.02
REMARK 500     SER A 436     -149.21     -84.74
REMARK 500     ASN A 437      -58.87    -138.56
REMARK 500     VAL A 465       79.53      36.64
REMARK 500     PRO A 466      -78.08     -90.47
REMARK 500     GLU A 467      -61.07    -151.02
REMARK 500     LYS A 470      -73.94      63.23
REMARK 500     SER A 472      160.50     -46.23
REMARK 500     PRO A 473      -88.37    -106.17
REMARK 500     ALA A 475     -177.55     -57.28
REMARK 500     PHE A 479      124.53      53.00
REMARK 500     GLN A 514      132.78     -25.88
REMARK 500     LYS A 519        5.53     -65.44
REMARK 500     THR A 521       23.18     -78.10
REMARK 500     MET A 527       73.98     -43.92
REMARK 500     MET A 531      -60.83     -95.18
REMARK 500     SER A 535     -118.80     -51.41
REMARK 500     LYS A 542       27.52     -75.44
REMARK 500     ASP A 543       46.35    -149.11
REMARK 500     ALA A 544      -21.78    -170.17
REMARK 500     ASN A 545      -37.26    -158.09
REMARK 500     LEU A 546      -76.70     -83.54
REMARK 500     SER A 548     -144.33     -79.35
REMARK 500     ILE A 549      167.60      61.55
REMARK 500     LYS A 557       39.03     -57.23
REMARK 500     ALA A 558     -131.43    -146.39
REMARK 500     PRO A 566      -67.98     -28.51
REMARK 500     GLU A 567      -32.80     -39.19
REMARK 500     LYS A 569      -70.65     -39.62
REMARK 500     ASP A 588      -42.86    -168.85
REMARK 500     ALA A 599      143.13     -39.54
REMARK 500     ILE A 601     -148.89     -86.05
REMARK 500     ALA A 606      162.68     -44.26
REMARK 500     THR A 609      148.44      70.27
REMARK 500     ILE A 618     -147.84    -156.82
REMARK 500     VAL A 619      113.59     160.96
REMARK 500     PRO A 623     -101.31     -38.76
REMARK 500     ALA A 631       -4.34     -57.01
REMARK 500     LYS A 643      -89.50     -60.20
REMARK 500     ILE A 656       34.97     -53.11
REMARK 500     MET A 661      -61.57     -90.49
REMARK 500     LEU A 662       46.20     -68.40
REMARK 500     ILE A 663      -74.38    -145.67
REMARK 500     LEU A 665     -104.46     -94.92
REMARK 500     ILE A 666     -122.08     -85.20
REMARK 500     GLU A 668     -117.64     -89.54
REMARK 500     PHE A 669      110.04     -32.46
REMARK 500     PHE A 671     -149.35      37.25
REMARK 500     ALA A 673      -84.92     -81.40
REMARK 500     PHE A 674        4.95     -57.69
REMARK 500     ILE A 678       40.71     -76.53
REMARK 500     ILE A 679      -42.01    -144.75
REMARK 500     ASP A 684      -70.37     -77.32
REMARK 500     MET A 688       28.21     -71.00
REMARK 500     SER A 691       34.42    -160.80
REMARK 500     LYS A 692     -178.96     -57.74
REMARK 500     VAL A 695     -153.35     -56.88
REMARK 500     PRO A 697     -121.79     -79.78
REMARK 500     SER A 698      -68.23    -171.72
REMARK 500     SER A 703      -77.51    -160.84
REMARK 500     THR A 712      -72.98     -84.57
REMARK 500     TYR A 719      -36.43    -141.03
REMARK 500     ILE A 722       37.25     -79.00
REMARK 500     VAL A 725       12.35     -59.11
REMARK 500     PHE A 728      -46.47    -136.70
```

FIG. 13 Continued

```
REMARK 500    ALA A 730      32.57    -160.64
REMARK 500    ALA A 731      89.46     -62.52
REMARK 500    HIS A 732       3.62      89.47
REMARK 500    THR A 734      15.34    -154.25
REMARK 500    ASP A 735      26.83     -68.46
REMARK 500    SER A 738       5.03    -163.67
REMARK 500    ASP A 739    -159.57     -71.58
REMARK 500    PHE A 741     -73.73     -36.27
REMARK 500    VAL A 743     -98.57     -43.01
REMARK 500    ARG A 744     -76.84     -25.48
REMARK 500    ILE A 746    -151.17     -83.48
REMARK 500    ARG A 747    -162.42      55.52
REMARK 500    ASN A 750     -59.27    -159.31
REMARK 500    HIS A 751     -77.74     -62.44
REMARK 500    GLU A 752       1.53     -56.68
REMARK 500    LEU A 753     -72.63     -75.97
REMARK 500    VAL A 757     -26.57    -150.15
REMARK 500    GLN A 760      58.76    -172.04
REMARK 500    VAL A 761     -56.13    -164.44
REMARK 500    ILE A 764      54.88     -93.34
REMARK 500    ILE A 769      56.35     -96.20
REMARK 500    ARG A 773       3.83     162.80
REMARK 500    PHE A 779      20.27     -62.44
REMARK 500    GLU A 781     -27.27      64.61
REMARK 500    ARG A 782     -78.48     -74.70
REMARK 500    ALA A 785     103.58     -46.74
REMARK 500    LEU A 786      11.85      44.69
REMARK 500    PHE A 791      42.18    -143.95
REMARK 500    LEU A 792      29.34    -160.67
REMARK 500    ILE A 793     -44.98    -139.23
REMARK 500    LEU A 796     -75.58     -83.24
REMARK 500    THR A 799     -36.80    -136.81
REMARK 500    VAL A 803    -163.01     171.05
REMARK 500    TYR A 804     -15.77      44.54
REMARK 500    ASN A 806     119.00     170.66
REMARK 500    LYS A 811    -177.98     178.15
REMARK 500    ILE A 812      77.28     160.62
REMARK 500    ARG A 813     179.13     -49.67
REMARK 500    ILE A 815      66.43      78.65
REMARK 500    TRP A 817     -17.34      81.20
REMARK 500    SER A 827     -70.48     -70.83
REMARK 500    PHE A 839      -3.50     -56.79
REMARK 500    TYR A 843      16.67     -59.25
REMARK 500    ASP B  13    -172.38    -175.06
REMARK 500    LYS B  16      21.97      91.17
REMARK 500    ILE B  17    -147.68     -82.44
REMARK 500    GLU B  20       7.06     -56.95
REMARK 500    PHE B  23     -88.35     -53.78
REMARK 500    LEU B  26      93.26    -164.63
REMARK 500    LYS B  27      89.97     -12.20
REMARK 500    CYS B  28     103.07      13.74
REMARK 500    SER B  29      81.99    -161.38
REMARK 500    GLU B  31     -61.01    -140.41
REMARK 500    LEU B  33      87.72     -63.28
REMARK 500    THR B  34     100.52      50.89
REMARK 500    PHE B  45     140.50     178.67
REMARK 500    PRO B  47      24.04     -68.19
REMARK 500    ASN B  48    -144.22     -61.17
REMARK 500    GLU B  51     -34.60    -168.91
REMARK 500    LYS B  54      48.35     -51.73
REMARK 500    GLU B  55    -174.41     -62.27
REMARK 500    LYS B  57      27.07      49.34
REMARK 500    LYS B  60     -21.88     151.28
REMARK 500    LEU B  62      -5.17      60.30
REMARK 500    PHE B  64      -4.85    -152.77
REMARK 500    MET B  65      85.76     -50.10
REMARK 500    ASN B  67     109.43      51.81
REMARK 500    PRO B  68      35.65     -46.01
REMARK 500    SER B  70      44.49    -149.11
```

FIG. 13 Continued

```
REMARK 500     ALA B  76       5.40    -63.94
REMARK 500     MET B  79       9.57    -66.62
REMARK 500     ILE B  81      35.80    -92.17
REMARK 500     ALA B  82      13.16   -142.20
REMARK 500     LEU B  83      16.12   -150.18
REMARK 500     ALA B  84      39.50    170.00
REMARK 500     PRO B  91    -121.93    -54.52
REMARK 500     GLN B  94      33.07    -50.74
REMARK 500     THR B 108     -93.58   -140.02
REMARK 500     ILE B 109       7.69    -56.81
REMARK 500     SER B 110     -87.45   -110.21
REMARK 500     PHE B 111      22.08    -64.26
REMARK 500     GLU B 113      43.75    -72.43
REMARK 500     GLU B 114     -23.16   -141.04
REMARK 500     ALA B 117     -68.67    -90.54
REMARK 500     ALA B 121      -7.66    -54.04
REMARK 500     ALA B 122     -87.52    -73.57
REMARK 500     LEU B 124     -86.59    -76.96
REMARK 500     MET B 125       5.65    -56.04
REMARK 500     LEU B 128     -18.29   -148.85
REMARK 500     ALA B 129     102.67    -46.60
REMARK 500     PRO B 130      42.06    -18.73
REMARK 500     LYS B 131     140.45    -31.43
REMARK 500     LYS B 133      54.29     72.55
REMARK 500     ARG B 136     -81.34     46.50
REMARK 500     ASP B 137     -51.59    160.14
REMARK 500     SER B 141     150.63    -40.33
REMARK 500     ILE B 147     -19.45    -41.35
REMARK 500     LEU B 148     -82.34    -39.04
REMARK 500     VAL B 149     100.04     35.49
REMARK 500     PRO B 150     131.59    -31.22
REMARK 500     VAL B 154    -151.40   -115.52
REMARK 500     SER B 155    -164.18   -170.25
REMARK 500     ILE B 156     162.98    179.93
REMARK 500     LYS B 157    -152.81   -137.54
REMARK 500     ILE B 162     141.85    -26.07
REMARK 500     ASP B 165     146.44    -36.05
REMARK 500     ALA B 166    -156.21   -161.16
REMARK 500     ARG B 167       4.89   -151.74
REMARK 500     LEU B 168     104.87     33.72
REMARK 500     GLU B 170    -166.89    173.53
REMARK 500     ASP B 172      90.60    176.75
REMARK 500     PRO B 173     149.94    -27.62
REMARK 500     VAL B 176      46.40    -97.12
REMARK 500     ASP B 177      96.68    -40.31
REMARK 500     ALA B 180     -72.35   -133.18
REMARK 500     THR B 182      55.17   -150.28
REMARK 500     SER B 185      33.80    -55.95
REMARK 500     PRO B 187    -173.32    -36.34
REMARK 500     VAL B 188     -41.36   -154.17
REMARK 500     THR B 189     119.79     26.87
REMARK 500     PRO B 192      72.00    -56.47
REMARK 500     VAL B 196      54.11    -65.19
REMARK 500     SER B 198     -32.91    -37.53
REMARK 500     LYS B 203    -121.32    -82.69
REMARK 500     VAL B 211     109.85    -57.35
REMARK 500     ALA B 213    -174.18     46.66
REMARK 500     THR B 218     -49.27   -171.73
REMARK 500     LYS B 222      45.31   -141.57
REMARK 500     ALA B 224    -105.24    -79.10
REMARK 500     VAL B 227     146.62    172.92
REMARK 500     THR B 230     138.49    -39.64
REMARK 500     GLN B 232      38.10    171.55
REMARK 500     VAL B 233       1.93    -50.03
REMARK 500     HIS B 235      83.78    -55.17
REMARK 500     PHE B 236     -62.34   -149.09
REMARK 500     LYS B 238      35.52    -69.79
REMARK 500     PHE B 246      38.93    -95.97
REMARK 500     CYS B 247     -46.06   -134.14
```

FIG. 13 Continued

```
REMARK 500     SER B 250      -36.88    -152.66
REMARK 500     ILE B 259      -73.74     -71.03
REMARK 500     ILE B 260        6.47     -61.90
REMARK 500     MET B 262      -61.40    -138.49
REMARK 500     ILE B 265      -96.19     -65.45
REMARK 500     GLN B 266        9.75     -64.69
REMARK 500     ARG B 267     -136.46      28.78
REMARK 500     ARG B 268       57.94      21.73
REMARK 500     TYR B 270      -83.57     174.45
REMARK 500     LEU B 281       19.49     -69.54
REMARK 500     ILE B 282      -25.57    -158.47
REMARK 500     ILE B 287      -34.21      55.01
REMARK 500     VAL B 292      -70.67     -55.38
REMARK 500     LEU B 304      -75.04     -73.48
REMARK 500     SER B 305       19.37     -54.86
REMARK 500     MET B 314      -15.33     -41.97
REMARK 500     MET B 323       79.67     -28.98
REMARK 500     LYS B 330      -85.43     -60.59
REMARK 500     THR B 333      -95.01    -161.40
REMARK 500     LEU B 334      -16.31     -47.71
REMARK 500     LYS B 343       57.87     -95.21
REMARK 500     PHE B 349     -132.25     -85.98
REMARK 500     CYS B 350       87.72     178.59
REMARK 500     LYS B 351      134.55     156.84
REMARK 500     GLU B 354      -93.09      24.52
REMARK 500     LYS B 355      -38.11     -35.27
REMARK 500     ASP B 356      -73.28     -67.74
REMARK 500     GLN B 357      -47.43     -28.62
REMARK 500     PHE B 361      -70.91     -48.61
REMARK 500     SER B 366      155.24     161.66
REMARK 500     ARG B 367     -166.38     -73.79
REMARK 500     VAL B 368      -72.15     -79.30
REMARK 500     ASP B 372      150.70     -43.54
REMARK 500     MET B 381     -151.41      43.67
REMARK 500     ALA B 383       89.53     -56.94
REMARK 500     ASP B 384      150.05     -44.00
REMARK 500     PRO B 385     -129.24     -12.59
REMARK 500     LYS B 386       46.37     -95.29
REMARK 500     GLU B 387       43.52    -108.01
REMARK 500     ALA B 388       32.90    -150.40
REMARK 500     ALA B 390       80.72      48.55
REMARK 500     ARG B 393      144.85     158.31
REMARK 500     GLU B 394       22.49    -150.61
REMARK 500     PHE B 397       35.53    -148.44
REMARK 500     PRO B 399      125.36     -29.47
REMARK 500     ASN B 401      149.13     172.01
REMARK 500     PRO B 402      170.90     -56.45
REMARK 500     VAL B 403       -2.62      59.79
REMARK 500     ALA B 408       56.27    -150.98
REMARK 500     LEU B 409      175.97     -53.97
REMARK 500     ASP B 413      -19.11    -174.88
REMARK 500     SER B 415      -86.84     -40.30
REMARK 500     SER B 422      137.75     177.96
REMARK 500     ALA B 425      -87.22     -56.76
REMARK 500     GLU B 427       20.38     -60.77
REMARK 500     LEU B 432       -7.90      47.08
REMARK 500     LYS B 434       87.63      62.70
REMARK 500     ALA B 435       88.75     -56.44
REMARK 500     SER B 436     -149.53     -85.61
REMARK 500     ASN B 437      -59.11    -137.99
REMARK 500     VAL B 465       79.80      36.06
REMARK 500     PRO B 466      -78.08     -90.38
REMARK 500     GLU B 467      -60.64    -151.02
REMARK 500     LYS B 470      -73.27      62.81
REMARK 500     SER B 472      160.30     -45.95
REMARK 500     PRO B 473      -88.62    -106.30
REMARK 500     ALA B 475     -177.30     -56.95
REMARK 500     PHE B 479      123.99      53.57
REMARK 500     GLN B 514      133.22     -26.12
```

FIG. 13 Continued

```
REMARK 500     LYS B 519        6.12    -65.76
REMARK 500     THR B 521       23.50    -79.11
REMARK 500     MET B 527       74.85    -43.93
REMARK 500     MET B 531      -61.30    -95.64
REMARK 500     SER B 535     -118.37    -50.46
REMARK 500     LYS B 542       27.35    -76.11
REMARK 500     ASP B 543       46.66   -148.68
REMARK 500     ALA B 544      -22.32   -170.55
REMARK 500     ASN B 545      -38.68   -157.32
REMARK 500     LEU B 546      -77.37    -82.00
REMARK 500     SER B 548     -144.55    -79.07
REMARK 500     ILE B 549      167.56     61.84
REMARK 500     LYS B 557       39.07    -57.00
REMARK 500     ALA B 558     -131.39   -146.68
REMARK 500     PRO B 566      -67.95    -28.36
REMARK 500     GLU B 567      -32.10    -39.50
REMARK 500     LYS B 569      -70.58    -39.51
REMARK 500     ASP B 588      -43.10   -169.01
REMARK 500     ALA B 599      142.20    -39.46
REMARK 500     ILE B 601     -149.91    -86.48
REMARK 500     ALA B 606      161.66    -44.15
REMARK 500     THR B 609      148.26     70.49
REMARK 500     ILE B 618     -147.60   -158.34
REMARK 500     VAL B 619      113.66    160.43
REMARK 500     PRO B 623     -101.31    -39.56
REMARK 500     ALA B 631       -4.23    -57.26
REMARK 500     LYS B 643      -90.02    -60.23
REMARK 500     ILE B 656       34.68    -53.94
REMARK 500     MET B 661      -61.77    -90.11
REMARK 500     LEU B 662       46.30    -67.93
REMARK 500     ILE B 663      -73.45   -145.45
REMARK 500     LEU B 665     -104.52    -95.06
REMARK 500     ILE B 666     -121.60    -84.74
REMARK 500     GLU B 668     -117.50    -90.04
REMARK 500     PHE B 669      110.01    -32.35
REMARK 500     PHE B 671     -149.60     36.98
REMARK 500     ALA B 673      -84.05    -81.11
REMARK 500     PHE B 674        4.03    -57.69
REMARK 500     ILE B 678       41.33    -78.07
REMARK 500     ILE B 679      -41.58   -145.01
REMARK 500     ASP B 684      -70.09    -78.26
REMARK 500     MET B 688       28.63    -69.99
REMARK 500     SER B 691       35.45   -159.59
REMARK 500     LYS B 692     -179.22    -59.23
REMARK 500     VAL B 695     -152.37    -57.37
REMARK 500     PRO B 697     -123.43    -80.09
REMARK 500     SER B 698      -67.20   -170.43
REMARK 500     SER B 703      -75.85   -161.37
REMARK 500     THR B 712      -72.65    -85.27
REMARK 500     TYR B 719      -35.93   -141.67
REMARK 500     ILE B 722       38.33    -79.58
REMARK 500     VAL B 725       14.02    -60.26
REMARK 500     PHE B 728      -45.77   -136.92
REMARK 500     ALA B 730       32.35   -161.69
REMARK 500     ALA B 731       69.29    -62.00
REMARK 500     HIS B 732        4.13     89.40
REMARK 500     THR B 734       15.42   -153.30
REMARK 500     ASP B 735       26.58    -67.97
REMARK 500     SER B 738        5.11   -163.08
REMARK 500     ASP B 739     -159.22    -72.18
REMARK 500     PHE B 741      -73.67    -36.61
REMARK 500     VAL B 743      -99.44    -43.37
REMARK 500     ARG B 744      -76.16    -24.69
REMARK 500     ILE B 746     -151.46    -83.35
REMARK 500     ARG B 747     -161.32     55.49
REMARK 500     ASN B 750      -58.89   -158.67
REMARK 500     HIS B 751      -77.67    -62.67
REMARK 500     GLU B 752        1.94    -59.10
REMARK 500     LEU B 753      -72.09    -76.20
```

FIG. 13 Continued

```
REMARK 500     VAL B 757       -26.44    148.65
REMARK 500     GLN B 760        58.43   -169.80
REMARK 500     VAL B 761       -56.10   -163.75
REMARK 500     ILE B 764        55.10    -93.59
REMARK 500     ILE B 769        56.91    -97.24
REMARK 500     ARG B 773         3.57    162.78
REMARK 500     PHE B 779        20.27    -63.13
REMARK 500     GLU B 781       -27.58     65.33
REMARK 500     ARG B 782       -78.85    -74.20
REMARK 500     ALA B 785       103.01    -48.02
REMARK 500     LEU B 786        11.24     45.50
REMARK 500     PHE B 791        40.65   -144.44
REMARK 500     LEU B 792        30.11   -158.63
REMARK 500     ILE B 793       -45.31   -139.82
REMARK 500     LEU B 796       -75.00    -83.40
REMARK 500     THR B 799       -36.21   -136.10
REMARK 500     VAL B 803      -163.64    170.03
REMARK 500     TYR B 804       -15.90     44.96
REMARK 500     ASN B 806       118.93    171.05
REMARK 500     LYS B 811      -177.63    179.60
REMARK 500     ILE B 812        77.13    160.54
REMARK 500     ARG B 813       178.79    -49.18
REMARK 500     ILE B 815        66.42     79.70
REMARK 500     TRP B 817       -17.67     81.22
REMARK 500     SER B 827       -71.29    -71.77
REMARK 500     PHE B 839        -2.63    -59.18
REMARK 500     TYR B 843        16.89    -57.89
REMARK 500
REMARK 500 REMARK: NULL
DBREF  3B8C A    1   875  UNP    P19456   PMA2_ARATH       1    875
DBREF  3B8C B    1   875  UNP    P19456   PMA2_ARATH       1    875
SEQADV 3B8C MET A  876  UNP  P19456              EXPRESSION TAG
SEQADV 3B8C ARG A  877  UNP  P19456              EXPRESSION TAG
SEQADV 3B8C GLY A  878  UNP  P19456              EXPRESSION TAG
SEQADV 3B8C SER A  879  UNP  P19456              EXPRESSION TAG
SEQADV 3B8C HIS A  880  UNP  P19456              EXPRESSION TAG
SEQADV 3B8C HIS A  881  UNP  P19456              EXPRESSION TAG
SEQADV 3B8C HIS A  882  UNP  P19456              EXPRESSION TAG
SEQADV 3B8C HIS A  883  UNP  P19456              EXPRESSION TAG
SEQADV 3B8C HIS A  884  UNP  P19456              EXPRESSION TAG
SEQADV 3B8C HIS A  885  UNP  P19456              EXPRESSION TAG
SEQADV 3B8C MET B  876  UNP  P19456              EXPRESSION TAG
SEQADV 3B8C ARG B  877  UNP  P19456              EXPRESSION TAG
SEQADV 3B8C GLY B  878  UNP  P19456              EXPRESSION TAG
SEQADV 3B8C SER B  879  UNP  P19456              EXPRESSION TAG
SEQADV 3B8C HIS B  880  UNP  P19456              EXPRESSION TAG
SEQADV 3B8C HIS B  881  UNP  P19456              EXPRESSION TAG
SEQADV 3B8C HIS B  882  UNP  P19456              EXPRESSION TAG
SEQADV 3B8C HIS B  883  UNP  P19456              EXPRESSION TAG
SEQADV 3B8C HIS B  884  UNP  P19456              EXPRESSION TAG
SEQADV 3B8C HIS B  885  UNP  P19456              EXPRESSION TAG
SEQRES   1 A  885  MET SER SER LEU GLU ASP ILE LYS ASN GLU THR VAL ASP
SEQRES   2 A  885  LEU GLU LYS ILE PRO ILE GLU GLU VAL PHE GLN GLN LEU
SEQRES   3 A  885  LYS CYS SER ARG GLU GLY LEU THR THR GLN GLU GLY GLU
SEQRES   4 A  885  ASP ARG ILE GLN ILE PHE GLY PRO ASN LYS LEU GLU GLU
SEQRES   5 A  885  LYS LYS GLU SER LYS LEU LYS PHE LEU GLY PHE MET
SEQRES   6 A  885  TRP ASN PRO LEU SER TRP VAL MET GLU MET ALA ALA ILE
SEQRES   7 A  885  MET ALA ILE ALA LEU ALA ASN GLY ASP GLY ARG PRO PRO
SEQRES   8 A  885  ASP TRP GLN ASP PHE VAL GLY ILE ILE CYS LEU LEU VAL
SEQRES   9 A  885  ILE ASN SER THR ILE SER PHE ILE GLU GLU ASN ASN ALA
SEQRES  10 A  885  GLY ASN ALA ALA ALA ALA LEU MET ALA GLY LEU ALA PRO
SEQRES  11 A  885  LYS THR LYS VAL LEU ARG ASP GLY LYS TRP SER GLU GLN
SEQRES  12 A  885  GLU ALA ALA ILE LEU VAL PRO GLY ASP ILE VAL SER ILE
SEQRES  13 A  885  LYS LEU GLY ASP ILE ILE PRO ALA ASP ALA ARG LEU LEU
SEQRES  14 A  885  GLU GLY ASP PRO LEU LYS VAL ASP GLN SER ALA LEU THR
SEQRES  15 A  885  GLY GLU SER LEU PRO VAL THR LYS HIS PRO GLY GLN GLU
SEQRES  16 A  885  VAL PHE SER GLY SER THR CYS LYS GLN GLY GLU ILE GLU
SEQRES  17 A  885  ALA VAL VAL ILE ALA THR GLY VAL HIS THR PHE PHE GLY
SEQRES  18 A  885  LYS ALA ALA HIS LEU VAL ASP SER THR ASN GLN VAL GLY
```

FIG. 13 Continued

```
SEQRES  19 A  885  HIS PHE GLN LYS VAL LEU THR ALA ILE GLY ASN PHE CYS
SEQRES  20 A  885  ILE CYS SER ILE ALA ILE GLY MET VAL ILE GLU ILE ILE
SEQRES  21 A  885  VAL MET TYR PRO ILE GLN ARG ARG LYS TYR ARG ASP GLY
SEQRES  22 A  885  ILE ASP ASN LEU LEU VAL LEU LEU ILE GLY GLY ILE PRO
SEQRES  23 A  885  ILE ALA MET PRO THR VAL LEU SER VAL THR MET ALA ILE
SEQRES  24 A  885  GLY SER HIS ARG LEU SER GLN GLY GLY ALA ILE THR LYS
SEQRES  25 A  885  ARG MET THR ALA ILE GLU GLU MET ALA GLY MET ASP VAL
SEQRES  26 A  885  LEU CYS SER ASP LYS THR GLY THR LEU THR LEU ASN LYS
SEQRES  27 A  885  LEU SER VAL ASP LYS ASN LEU VAL GLU VAL PHE CYS LYS
SEQRES  28 A  885  GLY VAL GLU LYS ASP GLN VAL LEU LEU PHE ALA ALA MET
SEQRES  29 A  885  ALA SER ARG VAL GLU ASN GLN ASP ALA ILE ASP ALA ALA
SEQRES  30 A  885  MET VAL GLY MET LEU ALA ASP PRO LYS GLU ALA ARG ALA
SEQRES  31 A  885  GLY ILE ARG GLU VAL HIS PHE LEU PRO PHE ASN PRO VAL
SEQRES  32 A  885  ASP LYS ARG THR ALA LEU THR TYR ILE ASP GLY SER GLY
SEQRES  33 A  885  ASN TRP HIS ARG VAL SER LYS GLY ALA PRO GLU GLN ILE
SEQRES  34 A  885  LEU GLU LEU ALA LYS ALA SER ASN ASP LEU SER LYS LYS
SEQRES  35 A  885  VAL LEU SER ILE ILE ASP LYS TYR ALA GLU ARG GLY LEU
SEQRES  36 A  885  ARG SER LEU ALA VAL ALA ARG GLN VAL VAL PRO GLU LYS
SEQRES  37 A  885  THR LYS GLU SER PRO GLY ALA PRO TRP GLU PHE VAL GLY
SEQRES  38 A  885  LEU LEU PRO LEU PHE ASP PRO PRO ARG HIS ASP SER ALA
SEQRES  39 A  885  GLU THR ILE ARG ARG ALA LEU ASN LEU GLY VAL ASN VAL
SEQRES  40 A  885  LYS MET ILE THR GLY ASP GLN LEU ALA ILE GLY LYS GLU
SEQRES  41 A  885  THR GLY ARG ARG LEU GLY MET GLY THR ASN MET TYR PRO
SEQRES  42 A  885  SER SER ALA LEU LEU GLY THR HIS LYS ASP ALA ASN LEU
SEQRES  43 A  885  ALA SER ILE PRO VAL GLU GLU ILE GLU LYS ALA ASP
SEQRES  44 A  885  GLY PHE ALA GLY VAL PHE PRO GLU HIS LYS TYR GLU ILE
SEQRES  45 A  885  VAL LYS LYS LEU GLN GLU ARG LYS HIS ILE VAL GLY MET
SEQRES  46 A  885  THR GLY ASP GLY VAL ASN ASP ALA PRO ALA LEU LYS LYS
SEQRES  47 A  885  ALA ASP ILE GLY ILE ALA VAL ALA ASP ALA THR ASP ALA
SEQRES  48 A  885  ALA ARG GLY ALA SER ASP ILE VAL LEU THR GLU PRO GLY
SEQRES  49 A  885  LEU SER VAL ILE ILE SER ALA VAL LEU THR SER ARG ALA
SEQRES  50 A  885  ILE PHE GLN ARG MET LYS ASN TYR THR ILE TYR ALA VAL
SEQRES  51 A  885  SER ILE THR ILE ARG ILE VAL PHE GLY PHE MET LEU ILE
SEQRES  52 A  885  ALA LEU ILE TRP GLU PHE ASP PHE SER ALA PHE MET VAL
SEQRES  53 A  885  LEU ILE ILE ALA ILE LEU ASN ASP GLY THR ILE MET THR
SEQRES  54 A  885  ILE SER LYS ASP ARG VAL LYS PRO SER PRO THR PRO ASP
SEQRES  55 A  885  SER TRP LYS LEU LYS GLU ILE PHE ALA THR GLY VAL VAL
SEQRES  56 A  885  LEU GLY GLY TYR GLN ALA ILE MET THR VAL ILE PHE PHE
SEQRES  57 A  885  TRP ALA ALA HIS LYS THR ASP PHE PHE SER ASP THR PHE
SEQRES  58 A  885  GLY VAL ARG SER ILE ARG ASP ASN ASN HIS GLU LEU MET
SEQRES  59 A  885  GLY ALA VAL TYR LEU GLN VAL SER ILE ILE SER GLN ALA
SEQRES  60 A  885  LEU ILE PHE VAL THR ARG SER ARG SER TRP SER PHE VAL
SEQRES  61 A  885  GLU ARG PRO GLY ALA LEU LEU MET ILE ALA PHE LEU ILE
SEQRES  62 A  885  ALA GLN LEU ILE ALA THR LEU ILE ALA VAL TYR ALA ASN
SEQRES  63 A  885  TRP GLU PHE ALA LYS ILE ARG GLY ILE GLY TRP GLY TRP
SEQRES  64 A  885  ALA GLY VAL ILE TRP LEU TYR SER ILE VAL THR TYR PHE
SEQRES  65 A  885  PRO LEU ASP VAL PHE LYS PHE ALA ILE ARG TYR ILE LEU
SEQRES  66 A  885  SER GLY LYS ALA TRP LEU ASN LEU PHE GLU ASN LYS THR
SEQRES  67 A  885  ALA PHE THR MET LYS LYS ASP TYR GLY LYS GLU GLU ARG
SEQRES  68 A  885  GLU ALA GLN TRP MET ARG GLY SER HIS HIS HIS HIS HIS
SEQRES  69 A  885  HIS
SEQRES   1 B  885  MET SER SER LEU GLU ASP ILE LYS ASN GLU THR VAL ASP
SEQRES   2 B  885  LEU GLU LYS ILE PRO ILE GLU GLU VAL PHE GLN GLN LEU
SEQRES   3 B  885  LYS CYS SER ARG GLU GLY LEU THR THR GLN GLU GLY GLU
SEQRES   4 B  885  ASP ARG ILE GLN ILE PHE GLY PRO ASN LYS LEU GLU GLU
SEQRES   5 B  885  LYS LYS GLU SER LYS LEU LEU LYS PHE LEU GLY PHE MET
SEQRES   6 B  885  TRP ASN PRO LEU SER TRP VAL MET GLU MET ALA ALA ILE
SEQRES   7 B  885  MET ALA ILE ALA LEU ALA ASN GLY ASP GLY ARG PRO PRO
SEQRES   8 B  885  ASP TRP GLN ASP PHE VAL GLY ILE ILE CYS LEU LEU VAL
SEQRES   9 B  885  ILE ASN SER THR ILE SER PHE ILE GLU GLU ASN ASN ALA
SEQRES  10 B  885  GLY ASN ALA ALA ALA ALA LEU MET ALA GLY LEU ALA PRO
SEQRES  11 B  885  LYS THR LYS VAL LEU ARG ASP GLY LYS TRP SER GLU GLN
SEQRES  12 B  885  GLU ALA ALA ILE LEU VAL PRO GLY ASP ILE VAL SER ILE
SEQRES  13 B  885  LYS LEU GLY ASP ILE ILE PRO ALA ASP ALA ARG LEU LEU
SEQRES  14 B  885  GLU GLY ASP PRO LEU LYS VAL ASP GLN SER ALA LEU THR
SEQRES  15 B  885  GLY GLU SER LEU PRO VAL THR LYS HIS PRO GLY GLN GLU
SEQRES  16 B  885  VAL PHE SER GLY SER THR CYS LYS GLN GLY GLU ILE GLU
SEQRES  17 B  885  ALA VAL VAL ILE ALA THR GLY VAL HIS THR PHE PHE GLY
SEQRES  18 B  885  LYS ALA ALA HIS LEU VAL ASP SER THR ASN GLN VAL GLY
```

FIG. 13 Continued

```
SEQRES  19 B  885  HIS PHE GLN LYS VAL LEU THR ALA ILE GLY ASN PHE CYS
SEQRES  20 B  885  ILE CYS SER ILE ALA ILE GLY MET VAL ILE GLU ILE ILE
SEQRES  21 B  885  VAL MET TYR PRO ILE GLN ARG ARG LYS TYR ARG ASP GLY
SEQRES  22 B  885  ILE ASP ASN LEU LEU VAL LEU LEU ILE GLY GLY ILE PRO
SEQRES  23 B  885  ILE ALA MET PRO THR VAL LEU SER VAL THR MET ALA ILE
SEQRES  24 B  885  GLY SER HIS ARG LEU SER GLN GLN GLY ALA ILE THR LYS
SEQRES  25 B  885  ARG MET THR ALA ILE GLU GLU MET ALA GLY MET ASP VAL
SEQRES  26 B  885  LEU CYS SER ASP LYS THR GLY THR LEU THR LEU ASN LYS
SEQRES  27 B  885  LEU SER VAL ASP LYS ASN LEU VAL GLU VAL PHE CYS LYS
SEQRES  28 B  885  GLY VAL GLU LYS ASP GLN VAL LEU LEU PHE ALA ALA MET
SEQRES  29 B  885  ALA SER ARG VAL GLU ASN GLN ASP ALA ILE ASP ALA ALA
SEQRES  30 B  885  MET VAL GLY MET LEU ALA ASP PRO LYS GLU ALA ARG ALA
SEQRES  31 B  885  GLY ILE ARG GLU VAL HIS PHE LEU PRO PHE ASN PRO VAL
SEQRES  32 B  885  ASP LYS ARG THR ALA LEU THR TYR ILE ASP GLY SER GLY
SEQRES  33 B  885  ASN TRP HIS ARG VAL SER LYS GLY ALA PRO GLU GLN ILE
SEQRES  34 B  885  LEU GLU LEU ALA LYS ALA SER ASN ASP LEU SER LYS LYS
SEQRES  35 B  885  VAL LEU SER ILE ILE ASP LYS TYR ALA GLU ARG GLY LEU
SEQRES  36 B  885  ARG SER LEU ALA VAL ALA ARG GLN VAL VAL PRO GLU LYS
SEQRES  37 B  885  THR LYS GLU SER PRO GLY ALA PRO TRP GLU PHE VAL GLY
SEQRES  38 B  885  LEU LEU PRO LEU PHE ASP PRO PRO ARG HIS ASP SER ALA
SEQRES  39 B  885  GLU THR ILE ARG ARG ALA LEU ASN LEU GLY VAL ASN VAL
SEQRES  40 B  885  LYS MET ILE THR GLY ASP GLN LEU ALA ILE GLY LYS GLU
SEQRES  41 B  885  THR GLY ARG ARG LEU GLY MET GLY THR ASN MET TYR PRO
SEQRES  42 B  885  SER SER ALA LEU LEU GLY THR HIS LYS ASP ALA ASN LEU
SEQRES  43 B  885  ALA SER ILE PRO VAL GLU GLU LEU ILE GLU LYS ALA ASP
SEQRES  44 B  885  GLY PHE ALA GLY VAL PHE PRO GLU HIS LYS TYR GLU ILE
SEQRES  45 B  885  VAL LYS LYS LEU GLN GLU ARG LYS HIS ILE VAL GLY MET
SEQRES  46 B  885  THR GLY ASP GLY VAL ASN ASP ALA PRO ALA LEU LYS LYS
SEQRES  47 B  885  ALA ASP ILE GLY ILE ALA VAL ALA ASP ALA THR ASP ALA
SEQRES  48 B  885  ALA ARG GLY ALA SER ASP ILE VAL LEU THR GLU PRO GLY
SEQRES  49 B  885  LEU SER VAL ILE ILE SER ALA VAL LEU THR SER ARG ALA
SEQRES  50 B  885  ILE PHE GLN ARG MET LYS ASN TYR THR ILE TYR ALA VAL
SEQRES  51 B  885  SER ILE THR ILE ARG ILE VAL PHE GLY PHE MET LEU ILE
SEQRES  52 B  885  ALA LEU ILE TRP GLU PHE ASP PHE SER ALA PHE MET VAL
SEQRES  53 B  885  LEU ILE ILE ALA THR LEU ASN ASP GLY THR ILE MET THR
SEQRES  54 B  885  ILE SER LYS ASP ARG VAL LYS PRO SER PRO THR PRO ASP
SEQRES  55 B  885  SER TRP LYS LEU LYS GLU ILE PHE ALA THR GLY VAL VAL
SEQRES  56 B  885  LEU GLY GLY TYR GLN ALA ILE MET THR VAL ILE PHE PHE
SEQRES  57 B  885  TRP ALA ALA HIS LYS THR ASP PHE PHE SER ASP THR PHE
SEQRES  58 B  885  GLY VAL ARG SER ILE ARG ASP ASN ASN HIS GLU LEU MET
SEQRES  59 B  885  GLY ALA VAL TYR LEU GLN VAL SER ILE ILE SER GLN ALA
SEQRES  60 B  885  LEU ILE PHE VAL THR ARG SER ARG SER TRP SER PHE VAL
SEQRES  61 B  885  GLU ARG PRO GLY ALA LEU LEU MET ILE ALA PHE LEU ILE
SEQRES  62 B  885  ALA GLN LEU ILE ALA THR LEU ILE ALA VAL TYR ALA ASN
SEQRES  63 B  885  TRP GLU PHE ALA LYS ILE ARG GLY ILE GLY TRP GLY TRP
SEQRES  64 B  885  ALA GLY VAL ILE TRP LEU TYR SER ILE VAL THR TYR PHE
SEQRES  65 B  885  PRO LEU ASP VAL PHE LYS PHE ALA ILE ARG TYR ILE LEU
SEQRES  66 B  885  SER GLY LYS ALA TRP LEU ASN LEU PHE GLU ASN LYS THR
SEQRES  67 B  885  ALA PHE THR MET LYS LYS ASP TYR GLY LYS GLU GLU ARG
SEQRES  68 B  885  GLU ALA GLN TRP MET ARG GLY SER HIS HIS HIS HIS HIS
SEQRES  69 B  885  HIS
HET     MG  A1002       1
HET     MG  B1004       1
HET    ACP  A1001      31
HET    ACP  B1003      31
HETNAM      MG MAGNESIUM ION
HETNAM     ACP PHOSPHOMETHYLPHOSPHONIC ACID ADENYLATE ESTER
HETSYN     ACP ADENOSINE-5'-[BETA, GAMMA-METHYLENE]TRIPHOSPHATE
FORMUL   3  MG    2(MG 2+)
FORMUL   5 ACP    2(C11 H18 N5 O12 P3)
HELIX    1   1 THR A   34  ILE A   42  1                                9
HELIX    2   2 TRP A   66  SER A   70  5                                5
HELIX    3   3 TRP A   71  MET A   79  1                                9
HELIX    4   4 ALA A   80  LEU A   83  5                                4
HELIX    5   5 ASP A   95  LEU A  103  1                                9
HELIX    6   6 LEU A  240  ILE A  259  1                               20
HELIX    7   7 ASP A  272  LEU A  281  1                               10
HELIX    8   8 THR A  291  THR A  296  1                                6
HELIX    9   9 ALA A  298  SER A  305  1                                8
```

FIG. 13 Continued

```
HELIX    10   10 ARG A   313  THR A   315  5                          3
HELIX    11   11 ALA A   316  ALA A   321  1                          6
HELIX    12   12 GLU A   354  SER A   366  1                         13
HELIX    13   13 ALA A   373  MET A   381  1                          9
HELIX    14   14 ALA A   425  ILE A   429  5                          5
HELIX    15   15 LYS A   442  ALA A   451  1                         10
HELIX    16   16 ARG A   490  LEU A   503  1                         14
HELIX    17   17 GLN A   514  LYS A   519  1                          6
HELIX    18   18 LYS A   519  ARG A   524  1                          6
HELIX    19   19 GLY A   539  ASP A   543  5                          5
HELIX    20   20 PRO A   550  LYS A   557  1                          8
HELIX    21   21 PHE A   565  ARG A   579  1                         15
HELIX    22   22 ASP A   592  ALA A   599  1                          8
HELIX    23   23 ALA A   608  ARG A   613  1                          6
HELIX    24   24 GLY A   614  SER A   616  5                          3
HELIX    25   25 GLY A   624  ILE A   629  1                          6
HELIX    26   26 ILE A   629  THR A   634  1                          6
HELIX    27   27 THR A   634  THR A   653  1                         20
HELIX    28   28 PHE A   660  LEU A   665  1                          6
HELIX    29   29 SER A   672  GLY A   685  1                         14
HELIX    30   30 THR A   712  GLY A   718  1                          7
HELIX    31   31 GLN A   720  VAL A   725  1                          6
HELIX    32   32 ILE A   746  ASN A   749  5                          4
HELIX    33   33 ASN A   750  GLY A   755  1                          6
HELIX    34   34 SER A   765  ILE A   769  5                          5
HELIX    35   35 MET A   788  LEU A   792  5                          5
HELIX    36   36 TRP A   819  SER A   827  1                          9
HELIX    37   37 ILE A   828  THR A   830  5                          3
HELIX    38   38 TYR A   831  ARG A   842  1                         12
HELIX    39   39 THR B    34  ILE B    42  1                          9
HELIX    40   40 TRP B    66  SER B    70  5                          5
HELIX    41   41 TRP B    71  MET B    79  1                          9
HELIX    42   42 ALA B    80  LEU B    83  5                          4
HELIX    43   43 ASP B    95  LEU B   103  1                          9
HELIX    44   44 LEU B   240  ILE B   259  1                         20
HELIX    45   45 ASP B   272  LEU B   281  1                         10
HELIX    46   46 THR B   291  THR B   296  1                          6
HELIX    47   47 ALA B   298  SER B   305  1                          8
HELIX    48   48 ARG B   313  THR B   315  5                          3
HELIX    49   49 ALA B   316  ALA B   321  1                          6
HELIX    50   50 GLU B   354  SER B   366  1                         13
HELIX    51   51 ALA B   373  MET B   381  1                          9
HELIX    52   52 ALA B   425  ILE B   429  5                          5
HELIX    53   53 LYS B   442  ALA B   451  1                         10
HELIX    54   54 ARG B   490  LEU B   503  1                         14
HELIX    55   55 GLN B   514  LYS B   519  1                          6
HELIX    56   56 LYS B   519  ARG B   524  1                          6
HELIX    57   57 GLY B   539  ASP B   543  5                          5
HELIX    58   58 PRO B   550  LYS B   557  1                          8
HELIX    59   59 PHE B   565  ARG B   579  1                         15
HELIX    60   60 ASP B   592  ALA B   599  1                          8
HELIX    61   61 ALA B   608  ARG B   613  1                          6
HELIX    62   62 GLY B   614  SER B   616  5                          3
HELIX    63   63 GLY B   624  ILE B   629  1                          6
HELIX    64   64 ILE B   629  THR B   634  1                          6
HELIX    65   65 THR B   634  THR B   653  1                         20
HELIX    66   66 PHE B   660  LEU B   665  1                          6
HELIX    67   67 SER B   672  GLY B   685  1                         14
HELIX    68   68 THR B   712  GLY B   718  1                          7
HELIX    69   69 GLN B   720  VAL B   725  1                          6
HELIX    70   70 ILE B   746  ASN B   749  5                          4
HELIX    71   71 ASN B   750  GLY B   755  1                          6
HELIX    72   72 SER B   765  ILE B   769  5                          5
HELIX    73   73 MET B   788  LEU B   792  5                          5
HELIX    74   74 TRP B   819  SER B   827  1                          9
HELIX    75   75 ILE B   828  THR B   830  5                          3
HELIX    76   76 TYR B   831  ARG B   842  1                         12
SHEET     1       A 3 CYS A   327  ASP A   329  0
SHEET     2       A 3 LYS A   508  THR A   511  1  O  LYS A  508   N  SER A  328
```

FIG. 13 Continued

```
SHEET    3   A 3 PHE A 561  ALA A 562  1  O  PHE A 561   N  MET A 509
SHEET    1   B 2 ARG A 456  VAL A 460  0
SHEET    2   B 2 GLY A 481  LEU A 485 -1  O  LEU A 485   N  ARG A 456
SHEET    1   C 3 CYS B 327  ASP B 329  0
SHEET    2   C 3 LYS B 508  THR B 511  1  O  LYS B 508   N  SER B 328
SHEET    3   C 3 PHE B 561  ALA B 562  1  O  PHE B 561   N  MET B 509
SHEET    1   D 2 ARG B 456  VAL B 460  0
SHEET    2   D 2 GLY B 481  LEU B 485 -1  O  LEU B 485   N  ARG B 456
CISPEP   1 PHE A   45    GLY A   46          0       -0.67
CISPEP   2 PHE B   45    GLY B   46          0       -0.57
CRYST1   85.290  144.420  312.110  90.00  90.00  90.00 P 21 21 21    8
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.011725 -0.000000 -0.000000        0.00000
SCALE2      0.000000  0.006924  0.000000        0.00000
SCALE3      0.000000  0.000000  0.003204        0.00000
MTRIX1   1 -0.344376  0.938440  0.027112       25.46390
MTRIX2   1  0.938813  0.344408  0.003614      -19.12910
MTRIX3   1 -0.005946  0.026698 -0.999626      109.95300
ATOM     1  N   VAL A  12     -42.183 -29.656  28.192  1.00224.44           N
ANISOU   1  N   VAL A  12     23271  35753  26253 -17530  -7067   6153       N
ATOM     2  CA  VAL A  12     -43.460 -30.308  27.933  1.00230.29           C
ANISOU   2  CA  VAL A  12     24086  36501  26912 -18279  -7931   6531       C
ATOM     3  C   VAL A  12     -44.117 -30.787  29.217  1.00227.32           C
ANISOU   3  C   VAL A  12     23197  35915  27260 -18339  -7979   6613       C
ATOM     4  O   VAL A  12     -44.679 -31.881  29.260  1.00231.03           O
ANISOU   4  O   VAL A  12     24106  36157  27519 -18836  -8478   6503       O
ATOM     5  CB  VAL A  12     -43.314 -31.509  26.979  1.00236.82           C
ANISOU   5  CB  VAL A  12     26146  37114  26720 -18743  -8383   6076       C
ATOM     6  CG1 VAL A  12     -42.968 -31.036  25.578  1.00241.60           C
ANISOU   6  CG1 VAL A  12     27255  37982  26558 -18843  -8503   6146       C
ATOM     7  CG2 VAL A  12     -42.269 -32.482  27.504  1.00233.73           C
ANISOU   7  CG2 VAL A  12     26473  36270  26063 -18347  -7863   5234       C
ATOM     8  N   ASP A  13     -44.032 -29.971  30.264  1.00222.76           N
ANISOU   8  N   ASP A  13     21728  35393  27516 -17842  -7441   6796       N
ATOM     9  CA  ASP A  13     -44.661 -30.295  31.544  1.00219.82           C
ANISOU   9  CA  ASP A  13     20802  34846  27873 -17844  -7408   6925       C
ATOM    10  C   ASP A  13     -44.527 -29.120  32.517  1.00213.45           C
ANISOU  10  C   ASP A  13     19018  34163  27921 -17269  -6775   7179       C
ATOM    11  O   ASP A  13     -44.079 -28.034  32.136  1.00211.92           O
ANISOU  11  O   ASP A  13     18533  34199  27788 -16948  -6445   7330       O
ATOM    12  CB  ASP A  13     -44.083 -31.589  32.149  1.00218.22           C
ANISOU  12  CB  ASP A  13     21321  34193  27399 -17747  -7239   6209       C
ATOM    13  CG  ASP A  13     -45.077 -32.323  33.072  1.00218.87           C
ANISOU  13  CG  ASP A  13     21118  34073  27968 -18094  -7549   6417       C
ATOM    14  OD1 ASP A  13     -46.278 -31.970  33.088  1.00221.72           O
ANISOU  14  OD1 ASP A  13     20805  34653  28787 -18511  -7996   7111       O
ATOM    15  OD2 ASP A  13     -44.651 -33.267  33.778  1.00216.87           O
ANISOU  15  OD2 ASP A  13     21311  33443  27646 -17942  -7334   5906       O
ATOM    16  N   LEU A  14     -44.924 -29.355  33.768  1.00221.12           N
ANISOU  16  N   LEU A  14     19527  34959  29529 -17157  -6600   7223       N
ATOM    17  CA  LEU A  14     -44.926 -28.339  34.820  1.00215.65           C
ANISOU  17  CA  LEU A  14     17943  34331  29663 -16661  -6021   7460       C
ATOM    18  C   LEU A  14     -43.585 -28.206  35.553  1.00209.15           C
ANISOU  18  C   LEU A  14     17291  33329  28849 -15983  -5251   6800       C
ATOM    19  O   LEU A  14     -42.721 -29.080  35.469  1.00208.55           O
ANISOU  19  O   LEU A  14     17976  33033  28231 -15869  -5150   6157       O
ATOM    20  CB  LEU A  14     -46.048 -28.648  35.823  1.00215.90           C
ANISOU  20  CB  LEU A  14     17400  34271  30362 -16880  -6192   7858       C
ATOM    21  CG  LEU A  14     -47.455 -28.847  35.232  1.00222.76           C
ANISOU  21  CG  LEU A  14     17988  35328  31324 -17585  -6981   8556       C
ATOM    22  CD1 LEU A  14     -48.244 -29.949  35.938  1.00224.65           C
ANISOU  22  CD1 LEU A  14     18257  35330  31769 -17980  -7301   8598       C
ATOM    23  CD2 LEU A  14     -48.233 -27.540  35.230  1.00223.48           C
ANISOU  23  CD2 LEU A  14     17074  35748  32091 -17505  -6934   9362       C
ATOM    24  N   GLU A  15     -43.418 -27.102  36.271  1.00204.80           N
ANISOU  24  N   GLU A  15     16026  32867  28921 -15535  -4711   6975       N
ATOM    25  CA  GLU A  15     -42.206 -26.866  37.049  1.00198.94           C
```

FIG. 13 Continued

```
ANISOU   25  CA  GLU A  15    15331  31992  28263 -14923  -4008   6409       C
ATOM     26  C   GLU A  15   -42.507 -25.935  38.220  1.00194.96           C
ANISOU   26  C   GLU A  15    13988  31496  28591 -14593  -3552   6687       C
ATOM     27  O   GLU A  15   -43.010 -24.828  38.030  1.00195.63           O
ANISOU   27  O   GLU A  15    13465  31776  29092 -14578  -3483   7225       O
ATOM     28  CB  GLU A  15   -41.091 -26.313  36.168  1.00198.51           C
ANISOU   28  CB  GLU A  15    15591  32076  27757 -14665  -3727   6121       C
ATOM     29  CG  GLU A  15   -40.039 -25.536  36.930  1.00192.94           C
ANISOU   29  CG  GLU A  15    14588  31350  27368 -14061  -2991   5789       C
ATOM     30  CD  GLU A  15   -40.209 -24.029  36.804  1.00192.17           C
ANISOU   30  CD  GLU A  15    13801  31465  27750 -13913  -2714   6263       C
ATOM     31  OE1 GLU A  15   -40.616 -23.393  37.799  1.00189.50           O
ANISOU   31  OE1 GLU A  15    12825  31084  28093 -13731  -2434   6499       O
ATOM     32  OE2 GLU A  15   -39.933 -23.484  35.711  1.00194.55           O
ANISOU   32  OE2 GLU A  15    14230  31955  27733 -13971  -2752   6401       O
ATOM     33  N   LYS A  16   -42.178 -26.409  39.421  1.00209.25           N
ANISOU   33  N   LYS A  16    15819  33076  30610 -14317  -3232   6313       N
ATOM     34  CA  LYS A  16   -42.484 -25.748  40.696  1.00205.78           C
ANISOU   34  CA  LYS A  16    14708  32580  30899 -14021  -2799   6496       C
ATOM     35  C   LYS A  16   -43.826 -26.236  41.247  1.00208.15           C
ANISOU   35  C   LYS A  16    14685  32803  31598 -14365  -3124   6968       C
ATOM     36  O   LYS A  16   -44.472 -25.571  42.055  1.00207.14           O
ANISOU   36  O   LYS A  16    13901  32681  32122 -14238  -2865   7358       O
ATOM     37  CB  LYS A  16   -42.413 -24.221  40.610  1.00204.48           C
ANISOU   37  CB  LYS A  16    13934  32596  31161 -13763  -2410   6823       C
ATOM     38  CG  LYS A  16   -40.991 -23.671  40.696  1.00200.63           C
ANISOU   38  CG  LYS A  16    13611  32111  30509 -13300  -1869   6280       C
ATOM     39  CD  LYS A  16   -40.208 -24.314  41.838  1.00196.68           C
ANISOU   39  CD  LYS A  16    13355  31400  29976 -12972  -1546   5668       C
ATOM     40  CE  LYS A  16   -40.853 -24.043  43.189  1.00194.67           C
ANISOU   40  CE  LYS A  16    12592  31017  30357 -12836  -1289   5869       C
ATOM     41  NZ  LYS A  16   -40.165 -24.757  44.294  1.00191.45           N
ANISOU   41  NZ  LYS A  16    12463  30415  29865 -12551  -1045   5312       N
ATOM     42  N   ILE A  17   -44.223 -27.413  40.775  1.00181.91           N
ANISOU   42  N   ILE A  17    11856  29394  27867 -14812  -3677   6924       N
ATOM     43  CA  ILE A  17   -45.410 -28.117  41.229  1.00184.80           C
ANISOU   43  CA  ILE A  17    12035  29659  28521 -15213  -4042   7302       C
ATOM     44  C   ILE A  17   -44.976 -28.839  42.528  1.00181.10           C
ANISOU   44  C   ILE A  17    11784  28887  28139 -14915  -3681   6836       C
ATOM     45  O   ILE A  17   -44.185 -28.272  43.267  1.00176.44           O
ANISOU   45  O   ILE A  17    11059  28264  27717 -14391  -3108   6531       O
ATOM     46  CB  ILE A  17   -45.911 -29.038  40.094  1.00190.67           C
ANISOU   46  CB  ILE A  17    13290  30425  28730 -15850  -4797   7404       C
ATOM     47  CG1 ILE A  17   -47.444 -29.229  40.171  1.00195.42           C
ANISOU   47  CG1 ILE A  17    13371  31101  29778 -16387  -5283   8124       C
ATOM     48  CG2 ILE A  17   -45.059 -30.313  40.009  1.00190.38           C
ANISOU   48  CG2 ILE A  17    14216  30099  28022 -15855  -4868   6678       C
ATOM     49  CD1 ILE A  17   -48.043 -30.221  39.175  1.00201.87           C
ANISOU   49  CD1 ILE A  17    14684  31918  30101 -17104  -6089   8235       C
ATOM     50  N   PRO A  18   -45.513 -30.034  42.864  1.00304.74           N
ANISOU   50  N   PRO A  18    27747  44324  43715 -15248  -4003   6811       N
ATOM     51  CA  PRO A  18   -44.857 -30.623  44.042  1.00300.89           C
ANISOU   51  CA  PRO A  18    27533  43560  43230 -14862  -3592   6310       C
ATOM     52  C   PRO A  18   -43.378 -30.937  43.804  1.00298.15           C
ANISOU   52  C   PRO A  18    27863  43125  42297 -14480  -3365   5572       C
ATOM     53  O   PRO A  18   -43.050 -31.845  43.041  1.00300.72           O
ANISOU   53  O   PRO A  18    28895  43330  42034 -14698  -3696   5266       O
ATOM     54  CB  PRO A  18   -45.635 -31.917  44.258  1.00304.53           C
ANISOU   54  CB  PRO A  18    28307  43776  43625 -15327  -4014   6402       C
ATOM     55  CG  PRO A  18   -47.003 -31.582  43.811  1.00309.08           C
ANISOU   55  CG  PRO A  18    28301  44548  44586 -15847  -4438   7158       C
ATOM     56  CD  PRO A  18   -46.846 -30.629  42.651  1.00310.08           C
ANISOU   56  CD  PRO A  18    28260  44994  44562 -15877  -4576   7344       C
ATOM     57  N   ILE A  19   -42.511 -30.188  44.485  1.00174.64           N
ANISOU   57  N   ILE A  19    11993  27532  26830 -13917  -2792   5299       N
ATOM     58  CA  ILE A  19   -41.051 -30.290  44.369  1.00171.89           C
ANISOU   58  CA  ILE A  19    12114  27158  26039 -13484  -2496   4648       C
ATOM     59  C   ILE A  19   -40.500 -31.685  44.689  1.00172.22           C
ANISOU   59  C   ILE A  19    12891  26898  25648 -13410  -2567   4143       C
```

FIG. 13 Continued

```
ATOM     60  O   ILE A  19     -39.642 -32.198  43.970  1.00173.13           O
ANISOU   60  O   ILE A  19    13612  26963  25208 -13325  -2621   3720       O
ATOM     61  CB  ILE A  19     -40.382 -29.249  45.284  1.00167.15           C
ANISOU   61  CB  ILE A  19    11041  26653  25815 -12951  -1891   4508       C
ATOM     62  CG1 ILE A  19     -40.725 -27.836  44.811  1.00167.10           C
ANISOU   62  CG1 ILE A  19    10416  26909  26166 -12975  -1770   4940       C
ATOM     63  CG2 ILE A  19     -38.898 -29.473  45.350  1.00164.65           C
ANISOU   63  CG2 ILE A  19    11148  26311  25101 -12509  -1599   3854       C
ATOM     64  CD1 ILE A  19     -40.817 -27.706  43.312  1.00170.46           C
ANISOU   64  CD1 ILE A  19    11029  27506  26231 -13291  -2139   5112       C
ATOM     65  N   GLU A  20     -41.015 -32.301  45.753  1.00274.50           N
ANISOU   65  N   GLU A  20    25805  39635  38857 -13431  -2546   4212       N
ATOM     66  CA  GLU A  20     -40.577 -33.636  46.170  1.00275.09           C
ANISOU   66  CA  GLU A  20    26560  39383  38579 -13347  -2595   3790       C
ATOM     67  C   GLU A  20     -40.741 -34.661  45.053  1.00279.83           C
ANISOU   67  C   GLU A  20    27872  39817  38635 -13786  -3093   3689       C
ATOM     68  O   GLU A  20     -40.543 -35.859  45.259  1.00281.45           O
ANISOU   68  O   GLU A  20    28710  39693  38535 -13808  -3197   3393       O
ATOM     69  CB  GLU A  20     -41.339 -34.098  47.420  1.00274.87           C
ANISOU   69  CB  GLU A  20    26339  39153  38947 -13399  -2537   4007       C
ATOM     70  CG  GLU A  20     -40.885 -33.440  48.724  1.00270.37           C
ANISOU   70  CG  GLU A  20    25352  38640  38738 -12869  -1992   3902       C
ATOM     71  CD  GLU A  20     -39.566 -33.993  49.248  1.00268.07           C
ANISOU   71  CD  GLU A  20    25542  38220  38091 -12355  -1725   3288       C
ATOM     72  OE1 GLU A  20     -39.307 -35.201  49.068  1.00270.19           O
ANISOU   72  OE1 GLU A  20    26477  38223  37959 -12409  -1924   3022       O
ATOM     73  OE2 GLU A  20     -38.790 -33.220  49.850  1.00264.52           O
ANISOU   73  OE2 GLU A  20    24803  37928  37773 -11899  -1319   3083       O
ATOM     74  N   GLU A  21     -41.099 -34.180  43.869  1.00176.90           N
ANISOU   74  N   GLU A  21    14763  26992  25459 -14134  -3398   3937       N
ATOM     75  CA  GLU A  21     -41.311 -35.052  42.724  1.00182.05           C
ANISOU   75  CA  GLU A  21    16107  27509  25553 -14608  -3904   3859       C
ATOM     76  C   GLU A  21     -40.027 -35.344  41.933  1.00182.25           C
ANISOU   76  C   GLU A  21    16830  27491  24924 -14307  -3756   3280       C
ATOM     77  O   GLU A  21     -39.295 -34.440  41.520  1.00180.10           O
ANISOU   77  O   GLU A  21    16347  27485  24597 -13991  -3471   3183       O
ATOM     78  CB  GLU A  21     -42.401 -34.484  41.820  1.00185.71           C
ANISOU   78  CB  GLU A  21    16196  28226  26139 -15181  -4372   4445       C
ATOM     79  CG  GLU A  21     -43.364 -35.515  41.299  1.00191.69           C
ANISOU   79  CG  GLU A  21    17377  28788  26670 -15885  -5014   4635       C
ATOM     80  CD  GLU A  21     -44.559 -34.863  40.684  1.00195.15           C
ANISOU   80  CD  GLU A  21    17233  29525  27392 -16420  -5465   5324       C
ATOM     81  OE1 GLU A  21     -44.766 -33.663  40.953  1.00192.44           O
ANISOU   81  OE1 GLU A  21    16083  29481  27555 -16194  -5209   5699       O
ATOM     82  OE2 GLU A  21     -45.284 -35.538  39.935  1.00200.93           O
ANISOU   82  OE2 GLU A  21    18313  30188  27842 -17065  -6079   5497       O
ATOM     83  N   VAL A  22     -39.795 -36.638  41.729  1.00203.37           N
ANISOU   83  N   VAL A  22    20347  29804  27119 -14418  -3933   2918       N
ATOM     84  CA  VAL A  22     -38.621 -37.160  41.053  1.00204.48           C
ANISOU   84  CA  VAL A  22    21257  29815  26621 -14118  -3769   2351       C
ATOM     85  C   VAL A  22     -38.934 -37.794  39.708  1.00210.64           C
ANISOU   85  C   VAL A  22    22782  30473  26780 -14650  -4250   2302       C
ATOM     86  O   VAL A  22     -38.379 -37.415  38.682  1.00211.96           O
ANISOU   86  O   VAL A  22    23193  30812  26531 -14590  -4207   2158       O
ATOM     87  CB  VAL A  22     -38.007 -38.281  41.892  1.00203.92           C
ANISOU   87  CB  VAL A  22    21713  29343  26424 -13760  -3543   1915       C
ATOM     88  CG1 VAL A  22     -37.009 -39.075  41.060  1.00206.93           C
ANISOU   88  CG1 VAL A  22    23023  29499  26100 -13557  -3457   1375       C
ATOM     89  CG2 VAL A  22     -37.384 -37.716  43.156  1.00198.16           C
ANISOU   89  CG2 VAL A  22    20396  28741  26154 -13141  -3027   1836       C
ATOM     90  N   PHE A  23     -39.821 -38.781  39.740  1.00237.44           N
ANISOU   90  N   PHE A  23    26565  33552  30098 -15186  -4703   2414       N
ATOM     91  CA  PHE A  23     -40.169 -39.577  38.567  1.00244.13           C
ANISOU   91  CA  PHE A  23    28243  34197  30316 -15761  -5211   2319       C
ATOM     92  C   PHE A  23     -40.607 -38.760  37.341  1.00246.91           C
ANISOU   92  C   PHE A  23    28419  34932  30465 -16173  -5569   2648       C
ATOM     93  O   PHE A  23     -39.788 -38.409  36.496  1.00247.29           O
ANISOU   93  O   PHE A  23    28775  35122  30061 -15930  -5378   2393       O
ATOM     94  CB  PHE A  23     -41.241 -40.620  38.936  1.00248.12           C
```

FIG. 13 Continued

```
ANISOU   94  CB  PHE A  23      29008  34339  30925 -16363  -5679   2501         C
ATOM     95  CG  PHE A  23     -40.824 -41.572  40.041  1.00 246.47              C
ANISOU   95  CG  PHE A  23      29132  33694  30821 -15999  -5363   2174         C
ATOM     96  CD1 PHE A  23     -40.548 -41.104  41.321  1.00 240.51              C
ANISOU   96  CD1 PHE A  23      27702  33046  30637 -15456  -4897   2244         C
ATOM     97  CD2 PHE A  23     -40.729 -42.936  39.802  1.00 251.33              C
ANISOU   97  CD2 PHE A  23      30767  33776  30950 -16211  -5538   1809         C
ATOM     98  CE1 PHE A  23     -40.173 -41.974  42.337  1.00 239.37              C
ANISOU   98  CE1 PHE A  23      27870  32519  30561 -15117  -4629   1978         C
ATOM     99  CE2 PHE A  23     -40.355 -43.810  40.814  1.00 250.16              C
ANISOU   99  CE2 PHE A  23      30932  33214  30905 -15857  -5244   1548         C
ATOM    100  CZ  PHE A  23     -40.077 -43.326  42.083  1.00 244.15              C
ANISOU  100  CZ  PHE A  23      29464  32599  30703 -15305  -4800   1647         C
ATOM    101  N   GLN A  24     -41.899 -38.461  37.252  1.00 216.91              N
ANISOU  101  N   GLN A  24      24104  31306  27004 -16784  -6079   3242         N
ATOM    102  CA  GLN A  24     -42.455 -37.747  36.101  1.00 220.42              C
ANISOU  102  CA  GLN A  24      24365  32118  27267 -17234  -6510   3636         C
ATOM    103  C   GLN A  24     -41.807 -36.380  35.857  1.00 216.24              C
ANISOU  103  C   GLN A  24      23265  32016  26881 -16740  -6085   3732         C
ATOM    104  O   GLN A  24     -41.800 -35.878  34.731  1.00 219.15              O
ANISOU  104  O   GLN A  24      23758  32638  26871 -16937  -6296   3862         O
ATOM    105  CB  GLN A  24     -43.984 -37.623  36.234  1.00 223.48              C
ANISOU  105  CB  GLN A  24      24132  32646  28134 -17917  -7100   4333         C
ATOM    106  CG  GLN A  24     -44.494 -37.437  37.672  1.00 219.21              C
ANISOU  106  CG  GLN A  24      22777  32079  28436 -17726  -6842   4635         C
ATOM    107  CD  GLN A  24     -44.704 -38.752  38.424  1.00 220.67              C
ANISOU  107  CD  GLN A  24      23448  31773  28624 -17895  -6915   4400         C
ATOM    108  OE1 GLN A  24     -45.132 -39.754  37.845  1.00 226.68              O
ANISOU  108  OE1 GLN A  24      24909  32261  28957 -18487  -7428   4308         O
ATOM    109  NE2 GLN A  24     -44.419 -38.742  39.726  1.00 215.53              N
ANISOU  109  NE2 GLN A  24      22445  30997  28448 -17392  -6405   4313         N
ATOM    110  N   GLN A  25     -41.266 -35.789  36.919  1.00 233.31              N
ANISOU  110  N   GLN A  25      24829  34245  29574 -16120  -5493   3670         N
ATOM    111  CA  GLN A  25     -40.595 -34.494  36.831  1.00 229.16              C
ANISOU  111  CA  GLN A  25      23748  34076  29247 -15637  -5033   3729         C
ATOM    112  C   GLN A  25     -39.319 -34.640  35.993  1.00 229.85              C
ANISOU  112  C   GLN A  25      24546  34137  28649 -15298  -4742   3183         C
ATOM    113  O   GLN A  25     -38.919 -33.717  35.273  1.00 229.58              O
ANISOU  113  O   GLN A  25      24330  34407  28492 -15164  -4587   3276         O
ATOM    114  CB  GLN A  25     -40.276 -33.960  38.237  1.00 222.67              C
ANISOU  114  CB  GLN A  25      22227  33274  29104 -15086  -4481   3718         C
ATOM    115  CG  GLN A  25     -39.771 -32.521  38.273  1.00 218.62              C
ANISOU  115  CG  GLN A  25      21030  33114  28923 -14669  -4035   3861         C
ATOM    116  CD  GLN A  25     -40.886 -31.497  38.340  1.00 218.76              C
ANISOU  116  CD  GLN A  25      20188  33406  29526 -14939  -4219   4572         C
ATOM    117  OE1 GLN A  25     -41.666 -31.473  39.292  1.00 217.50              O
ANISOU  117  OE1 GLN A  25      19522  33190  29005 -15009  -4234   4877         O
ATOM    118  NE2 GLN A  25     -40.954 -30.628  37.334  1.00 220.57              N
ANISOU  118  NE2 GLN A  25      20245  33930  29632 -15058  -4324   4860         N
ATOM    119  N   LEU A  26     -38.692 -35.812  36.103  1.00 210.34              N
ANISOU  119  N   LEU A  26      22885  31284  25750 -15147  -4641   2635         N
ATOM    120  CA  LEU A  26     -37.498 -36.176  35.333  1.00 211.97              C
ANISOU  120  CA  LEU A  26      23869  31392  25275 -14818  -4346   2088         C
ATOM    121  C   LEU A  26     -37.286 -37.687  35.431  1.00 215.22              C
ANISOU  121  C   LEU A  26      25235  31294  25247 -14863  -4432   1620         C
ATOM    122  O   LEU A  26     -36.619 -38.170  36.349  1.00 212.25              O
ANISOU  122  O   LEU A  26      24922  30690  25032 -14371  -4037   1287         O
ATOM    123  CB  LEU A  26     -36.262 -35.433  35.827  1.00 206.52              C
ANISOU  123  CB  LEU A  26      22767  30882  24818 -14058  -3635   1836         C
ATOM    124  CG  LEU A  26     -35.136 -35.368  34.800  1.00 208.54              C
ANISOU  124  CG  LEU A  26      23577  31206  24453 -13759  -3316   1457         C
ATOM    125  CD1 LEU A  26     -34.133 -34.310  35.211  1.00 203.42              C
ANISOU  125  CD1 LEU A  26      22273  30852  24165 -13144  -2694   1386         C
ATOM    126  CD2 LEU A  26     -34.466 -36.719  34.615  1.00 211.86              C
ANISOU  126  CD2 LEU A  26      25011  31198  24287 -13586  -3211    885         C
ATOM    127  N   LYS A  27     -37.853 -38.407  34.461  1.00 227.54              N
ANISOU  127  N   LYS A  27      27552  32671  26234 -15462  -4957   1608         N
ATOM    128  CA  LYS A  27     -37.845 -39.874  34.402  1.00 232.05              C
ANISOU  128  CA  LYS A  27      29129  32701  26340 -15653  -5133   1206         C
```

FIG. 13 Continued

```
ATOM    129  C   LYS A  27     -36.895 -40.535  35.403  1.00228.75           C
ANISOU  129  C   LYS A  27    28910  31955  26051 -14977  -4579    747       C
ATOM    130  O   LYS A  27     -35.726 -40.767  35.100  1.00228.99           O
ANISOU  130  O   LYS A  27    29437  31884  25684 -14445  -4117    280       O
ATOM    131  CB  LYS A  27     -37.533 -40.345  32.973  1.00238.68           C
ANISOU  131  CB  LYS A  27    31008  33414  26265 -15901  -5306    898       C
ATOM    132  CG  LYS A  27     -38.463 -39.776  31.897  1.00242.99           C
ANISOU  132  CG  LYS A  27    31465  34285  26577 -16605  -5921   1349       C
ATOM    133  CD  LYS A  27     -39.453 -40.810  31.380  1.00250.37           C
ANISOU  133  CD  LYS A  27    33142  34894  27095 -17444  -6655   1382       C
ATOM    134  CE  LYS A  27     -38.800 -41.729  30.359  1.00256.67           C
ANISOU  134  CE  LYS A  27    35285  35320  26919 -17487  -6620    799       C
ATOM    135  NZ  LYS A  27     -39.764 -42.705  29.790  1.00264.57           N
ANISOU  135  NZ  LYS A  27    37072  35992  27462 -18371  -7370    809       N
ATOM    136  N   CYS A  28     -37.423 -40.823  36.593  1.00245.96           N
ANISOU  136  N   CYS A  28    30677  33984  28791 -14997  -4626    919       N
ATOM    137  CA  CYS A  28     -36.687 -41.467  37.688  1.00243.00           C
ANISOU  137  CA  CYS A  28    30423  33306  28600 -14403  -4176    574       C
ATOM    138  C   CYS A  28     -35.176 -41.505  37.500  1.00241.84           C
ANISOU  138  C   CYS A  28    30622  33145  28120 -13643  -3570     63       C
ATOM    139  O   CYS A  28     -34.652 -42.327  36.749  1.00246.53           O
ANISOU  139  O   CYS A  28    32169  33424  28078 -13591  -3514   -341       O
ATOM    140  CB  CYS A  28     -37.209 -42.885  37.937  1.00247.44           C
ANISOU  140  CB  CYS A  28    31753  33290  28974 -14762  -4479    432       C
ATOM    141  SG  CYS A  28     -36.371 -43.749  39.293  1.00244.55           S
ANISOU  141  SG  CYS A  28    31579  32522  28817 -14038  -3962     67       S
ATOM    142  N   SER A  29     -34.478 -40.628  38.209  1.00266.47           N
ANISOU  142  N   SER A  29    32970  36595  31681 -13057  -3105     85       N
ATOM    143  CA  SER A  29     -33.027 -40.566  38.122  1.00265.25           C
ANISOU  143  CA  SER A  29    32977  36495  31312 -12322  -2519   -343       C
ATOM    144  C   SER A  29     -32.470 -39.828  39.328  1.00258.82           C
ANISOU  144  C   SER A  29    31271  35955  31115 -11762  -2109   -287       C
ATOM    145  O   SER A  29     -32.166 -38.635  39.251  1.00255.52           O
ANISOU  145  O   SER A  29    30161  35973  30951 -11603  -1902   -135       O
ATOM    146  CB  SER A  29     -32.598 -39.860  36.833  1.00267.16           C
ANISOU  146  CB  SER A  29    33324  37037  31145 -12351  -2426   -377       C
ATOM    147  OG  SER A  29     -33.044 -40.564  35.685  1.00273.70           O
ANISOU  147  OG  SER A  29    35066  37611  31315 -12861  -2801   -470       O
ATOM    148  N   ARG A  30     -32.337 -40.544  40.442  1.00200.88           N
ANISOU  148  N   ARG A  30    23984  28343  23997 -11480  -2000   -409       N
ATOM    149  CA  ARG A  30     -31.825 -39.950  41.673  1.00195.35           C
ANISOU  149  CA  ARG A  30    22516  27874  23835 -10970  -1652   -377       C
ATOM    150  C   ARG A  30     -30.317 -39.782  41.619  1.00194.43           C
ANISOU  150  C   ARG A  30    22390  27912  23575 -10250  -1123   -752       C
ATOM    151  O   ARG A  30     -29.695 -39.288  42.563  1.00190.44           O
ANISOU  151  O   ARG A  30    21285  27624  23450  -9790   -821   -783       O
ATOM    152  CB  ARG A  30     -32.236 -40.771  42.895  1.00194.62           C
ANISOU  152  CB  ARG A  30    22491  27453  24002 -10929  -1735   -340       C
ATOM    153  CG  ARG A  30     -33.729 -40.719  43.172  1.00194.76           C
ANISOU  153  CG  ARG A  30    22259  27410  24330 -11601  -2190    112       C
ATOM    154  CD  ARG A  30     -34.327 -39.391  42.703  1.00192.81           C
ANISOU  154  CD  ARG A  30    21290  27614  24355 -11944  -2325    504       C
ATOM    155  NE  ARG A  30     -33.967 -38.260  43.555  1.00187.34           N
ANISOU  155  NE  ARG A  30    19714  27292  24175 -11562  -1984    621       N
ATOM    156  CZ  ARG A  30     -34.126 -36.985  43.211  1.00185.21           C
ANISOU  156  CZ  ARG A  30    18800  27421  24150 -11661  -1938    881       C
ATOM    157  NH1 ARG A  30     -34.631 -36.670  42.024  1.00187.99           N
ANISOU  157  NH1 ARG A  30    19263  27888  24278 -12107  -2222   1077       N
ATOM    158  NH2 ARG A  30     -33.772 -36.025  44.053  1.00180.65           N
ANISOU  158  NH2 ARG A  30    17498  27116  24027 -11319  -1611    945       N
ATOM    159  N   GLU A  31     -29.739 -40.189  40.496  1.00192.73           N
ANISOU  159  N   GLU A  31    22843  27588  22798 -10172  -1015  -1030       N
ATOM    160  CA  GLU A  31     -28.309 -40.086  40.282  1.00192.94           C
ANISOU  160  CA  GLU A  31    22899  27756  22655  -9505   -492  -1368       C
ATOM    161  C   GLU A  31     -28.095 -39.669  38.830  1.00196.06           C
ANISOU  161  C   GLU A  31    23588  28311  22597  -9677   -437  -1416       C
ATOM    162  O   GLU A  31     -27.548 -38.604  38.552  1.00193.95           O
ANISOU  162  O   GLU A  31    22756  28465  22471  -9502   -171  -1352       O
ATOM    163  CB  GLU A  31     -27.636 -41.431  40.574  1.00196.18           C
```

FIG. 13 Continued

```
ANISOU  163  CB   GLU A  31     24042  27718  22780  -9047   -295  -1739       C
ATOM    164  CG   GLU A  31     -28.369 -42.304  41.612  1.00195.87            C
ANISOU  164  CG   GLU A  31     24185  27292  22945   9192    568   1651       C
ATOM    165  CD   GLU A  31     -28.470 -41.667  42.999  1.00190.20            C
ANISOU  165  CD   GLU A  31     22567  26839  22860  -9018   -530  -1427       C
ATOM    166  OE1  GLU A  31     -27.470 -41.086  43.477  1.00187.43            O
ANISOU  166  OE1  GLU A  31     21675  26813  22728  -8469   -163  -1530       O
ATOM    167  OE2  GLU A  31     -29.558 -41.760  43.616  1.00188.92            O
ANISOU  167  OE2  GLU A  31     22254  26556  22971  -9445   -864  -1145       O
ATOM    168  N    GLY A  32     -28.557 -40.506  37.909  1.00196.91            N
ANISOU  168  N    GLY A  32     24606  28067  22146 -10052   -697  -1522       N
ATOM    169  CA   GLY A  32     -28.459 -40.220  36.491  1.00200.75            C
ANISOU  169  CA   GLY A  32     25507  28663  22106 -10275   -695  -1566       C
ATOM    170  C    GLY A  32     -28.137 -41.467  35.693  1.00207.43            C
ANISOU  170  C    GLY A  32     27549  29027  22237 -10222   -632  -1962       C
ATOM    171  O    GLY A  32     -26.995 -41.919  35.691  1.00209.00            O
ANISOU  171  O    GLY A  32     28047  29109  22253  -9579   -125  -2313       O
ATOM    172  N    LEU A  33     -29.140 -42.025  35.017  1.00212.22            N
ANISOU  172  N    LEU A  33     28843  29348  22444 -10899  -1143  -1899       N
ATOM    173  CA   LEU A  33     -28.949 -43.226  34.198  1.00219.36            C
ANISOU  173  CA   LEU A  33     30997  29736  22612 -10946  -1127  -2289       C
ATOM    174  C    LEU A  33     -27.980 -42.951  33.041  1.00222.81            C
ANISOU  174  C    LEU A  33     31834  30323  22500 -10621   -676  -2540       C
ATOM    175  O    LEU A  33     -28.398 -42.605  31.928  1.00226.13            O
ANISOU  175  O    LEU A  33     32578  30870  22471 -11096   -917  -2446       O
ATOM    176  CB   LEU A  33     -30.291 -43.745  33.667  1.00223.66            C
ANISOU  176  CB   LEU A  33     32135  30000  22844 -11847  -1837  -2137       C
ATOM    177  CG   LEU A  33     -31.267 -44.325  34.691  1.00222.21            C
ANISOU  177  CG   LEU A  33     31808  29533  23089 -12211  -2266  -1941       C
ATOM    178  CD1  LEU A  33     -32.590 -44.644  34.030  1.00226.84            C
ANISOU  178  CD1  LEU A  33     32846  29954  23389 -13167  -2994  -1729       C
ATOM    179  CD2  LEU A  33      30.681  45.561  35.346  1.00223.97            C
ANISOU  179  CD2  LEU A  33     32658  29200  23242 -11734  -1965  -2319       C
ATOM    180  N    THR A  34     -26.688 -43.130  33.317  1.00221.11            N
ANISOU  180  N    THR A  34     31595  30097  22321  -9805    -20  -2838       N
ATOM    181  CA   THR A  34     -25.616 -42.852  32.362  1.00224.20            C
ANISOU  181  CA   THR A  34     32248  30653  22283  -9371    535  -3066       C
ATOM    182  C    THR A  34     -25.767 -41.458  31.784  1.00221.68            C
ANISOU  182  C    THR A  34     31235  30922  22070  -9634    482  -2738       C
ATOM    183  O    THR A  34     -26.572 -41.230  30.880  1.00224.45            O
ANISOU  183  O    THR A  34     31927  31317  22035 -10271     65  -2573       O
ATOM    184  CB   THR A  34     -25.560 -43.869  31.212  1.00232.60            C
ANISOU  184  CB   THR A  34     34689  31228  22462  -9504    578  -3429       C
ATOM    185  OG1  THR A  34     -25.219 -45.159  31.731  1.00235.42            O
ANISOU  185  OG1  THR A  34     35717  31004  22727  -9127    763  -3763       O
ATOM    186  CG2  THR A  34     -24.504 -43.456  30.204  1.00235.79            C
ANISOU  186  CG2  THR A  34     35296  31858  22436  -9074   1182  -3610       C
ATOM    187  N    THR A  35     -24.981 -40.528  32.310  1.00218.36            N
ANISOU  187  N    THR A  35     29849  30948  22171  -9149    896  -2633       N
ATOM    188  CA   THR A  35     -25.026 -39.151  31.851  1.00215.81            C
ANISOU  188  CA   THR A  35     28814  31165  22019  -9335    920  -2315       C
ATOM    189  C    THR A  35     -24.883 -39.108  30.329  1.00221.90            C
ANISOU  189  C    THR A  35     30341  31948  22021  -9520   1027  -2405       C
ATOM    190  O    THR A  35     -25.265 -38.129  29.688  1.00221.44            O
ANISOU  190  O    THR A  35     29968  32246  21923  -9885    870  -2097       O
ATOM    191  CB   THR A  35     -23.932 -38.307  32.533  1.00211.19            C
ANISOU  191  CB   THR A  35     27247  30988  22006  -8704   1471  -2297       C
ATOM    192  OG1  THR A  35     -23.893 -38.619  33.932  1.00206.94            O
ANISOU  192  OG1  THR A  35     26235  30357  22036  -8438   1427  -2316       O
ATOM    193  CG2  THR A  35     -24.212 -36.824  32.357  1.00207.46            C
ANISOU  193  CG2  THR A  35     25912  31028  21887  -8985   1399  -1899       C
ATOM    194  N    GLN A  36     -24.345 -40.184  29.759  1.00226.69            N
ANISOU  194  N    GLN A  36     31986  32145  22003  -9258   1305  -2822       N
ATOM    195  CA   GLN A  36     -24.170 -40.296  28.313  1.00233.44            C
ANISOU  195  CA   GLN A  36     33728  32942  22027  -9404   1449  -2970       C
ATOM    196  C    GLN A  36     -25.461 -40.772  27.642  1.00237.59            C
ANISOU  196  C    GLN A  36     35055  33197  22023 -10251    711  -2889       C
ATOM    197  O    GLN A  36     -25.813 -40.307  26.557  1.00240.99            O
ANISOU  197  O    GLN A  36     35796  33809  21959 -10675    524  -2746       O
```

FIG. 13 Continued

```
ATOM    198  CB  GLN A  36      -23.014 -41.243  27.979  1.00238.84           C
ANISOU  198  CB  GLN A  36    35216  33277  22253   -8726   2123  -3460       C
ATOM    199  CG  GLN A  36      -22.169 -40.802  26.790  1.00243.36           C
ANISOU  199  CG  GLN A  36    36100  34068  22298   -8461   2695  -3561       C
ATOM    200  CD  GLN A  36      -22.969 -40.661  25.510  1.00248.35           C
ANISOU  200  CD  GLN A  36    37492  34690  22180   -9165   2287  -3466       C
ATOM    201  OE1 GLN A  36      -23.904 -41.420  25.261  1.00251.73           O
ANISOU  201  OE1 GLN A  36    38720  34732  22193   -9731   1713  -3542       O
ATOM    202  NE2 GLN A  36      -22.597 -39.689  24.685  1.00249.27           N
ANISOU  202  NE2 GLN A  36    37369  35234  22108   -9150   2571  -3290       N
ATOM    203  N   GLU A  37      -26.162 -41.701  28.288  1.00239.72           N
ANISOU  203  N   GLU A  37    35654  33039  22389  -10513    281  -2965       N
ATOM    204  CA  GLU A  37      -27.434 -42.189  27.766  1.00243.78           C
ANISOU  204  CA  GLU A  37    36852  33295  22479  -11373   -477  -2868       C
ATOM    205  C   GLU A  37      -28.397 -41.019  27.656  1.00240.33           C
ANISOU  205  C   GLU A  37    35582  33361  22370  -11970  -1015  -2306       C
ATOM    206  O   GLU A  37      -28.850 -40.669  26.565  1.00244.41           O
ANISOU  206  O   GLU A  37    36466  34035  22363  -12458  -1313  -2156       O
ATOM    207  CB  GLU A  37      -28.030 -43.265  28.678  1.00243.54           C
ANISOU  207  CB  GLU A  37    37096  32762  22677  -11544   -827  -2972       C
ATOM    208  CG  GLU A  37      -27.459 -44.661  28.472  1.00249.72           C
ANISOU  208  CG  GLU A  37    39091  32886  22906  -11221   -508  -3516       C
ATOM    209  CD  GLU A  37      -27.870 -45.283  27.149  1.00258.48           C
ANISOU  209  CD  GLU A  37    41506  33658  23047  -11771   -784  -3742       C
ATOM    210  OE1 GLU A  37      -28.347 -44.547  26.262  1.00260.00           O
ANISOU  210  OE1 GLU A  37    41656  34207  22926  -12273  -1106  -3500       O
ATOM    211  OE2 GLU A  37      -27.712 -46.513  26.996  1.00264.23           O
ANISOU  211  OE2 GLU A  37    43337  33750  23308  -11701   -681  -4162       O
ATOM    212  N   GLY A  38      -28.690 -40.406  28.798  1.00232.69           N
ANISOU  212  N   GLY A  38    33503  32643  22265  -11903  -1116  -1988       N
ATOM    213  CA  GLY A  38      -29.578 -39.263  28.845  1.00229.07           C
ANISOU  213  CA  GLY A  38    32160  32642  22234  -12378  -1553  -1429       C
ATOM    214  C   GLY A  38      -29.153 -38.145  27.910  1.00229.63           C
ANISOU  214  C   GLY A  38    31976  33175  22099  -12310  -1297  -1249       C
ATOM    215  O   GLY A  38      -29.990 -37.386  27.435  1.00229.88           O
ANISOU  215  O   GLY A  38    31692  33504  22148  -12838  -1746   -811       O
ATOM    216  N   GLU A  39      -27.854 -38.034  27.643  1.00229.35           N
ANISOU  216  N   GLU A  39    32052  33205  21884  -11653   -566  -1554       N
ATOM    217  CA  GLU A  39      -27.361 -36.979  26.759  1.00230.17           C
ANISOU  217  CA  GLU A  39    31923  33734  21795  -11555   -246  -1387       C
ATOM    218  C   GLU A  39      -27.923 -37.152  25.356  1.00237.40           C
ANISOU  218  C   GLU A  39    33761  34606  21833  -12122   -623  -1338       C
ATOM    219  O   GLU A  39      -28.718 -36.334  24.887  1.00237.47           O
ANISOU  219  O   GLU A  39    33440  34933  21856  -12629  -1065   -881       O
ATOM    220  CB  GLU A  39      -25.825 -36.960  26.706  1.00230.41           C
ANISOU  220  CB  GLU A  39    31964  33813  21769  -10743    640  -1743       C
ATOM    221  CG  GLU A  39      -25.242 -35.776  25.922  1.00230.73           C
ANISOU  221  CG  GLU A  39    31623  34317  21728  -10605   1047  -1537       C
ATOM    222  CD  GLU A  39      -23.758 -35.924  25.610  1.00233.14           C
ANISOU  222  CD  GLU A  39    32143  34631  21810   -9872   1917  -1903       C
ATOM    223  OE1 GLU A  39      -23.248 -37.063  25.647  1.00236.59           O
ANISOU  223  OE1 GLU A  39    33316  34667  21909   -9528   2174  -2343       O
ATOM    224  OE2 GLU A  39      -23.104 -34.898  25.319  1.00231.96           O
ANISOU  224  OE2 GLU A  39    31419  34880  21837   -9637   2361  -1733       O
ATOM    225  N   ASP A  40      -27.501 -38.317  24.695  1.00311.21           N
ANISOU  225  N   ASP A  40    44290  43549  30408  -12023   -442  -1807       N
ATOM    226  CA  ASP A  40      -27.951 -38.524  23.343  1.00319.08           C
ANISOU  226  CA  ASP A  40    46335  44449  30454  -12550   -775  -1846       C
ATOM    227  C   ASP A  40      -29.470 -38.598  23.289  1.00320.18           C
ANISOU  227  C   ASP A  40    46490  44575  30588  -13444  -1759  -1482       C
ATOM    228  O   ASP A  40      -30.088 -38.078  22.360  1.00323.72           O
ANISOU  228  O   ASP A  40    47095  45280  30625  -13974  -2185  -1167       O
ATOM    229  CB  ASP A  40      -27.339 -39.836  22.832  1.00326.01           C
ANISOU  229  CB  ASP A  40    48549  44776  30545  -12310   -444  -2460       C
ATOM    230  CG  ASP A  40      -25.959 -39.645  22.221  1.00328.51           C
ANISOU  230  CG  ASP A  40    49130  45185  30506  -11600    474  -2742       C
ATOM    231  OD1 ASP A  40      -25.222 -38.744  22.672  1.00323.19           O
ANISOU  231  OD1 ASP A  40    47461  44902  30435  -11088    982  -2578       O
ATOM    232  OD2 ASP A  40      -25.610 -40.401  21.290  1.00336.20           O
```

FIG. 13 Continued

```
ANISOU  232  OD2  ASP A  40      51319  45828  30595 -11561    701  -3128           O
ATOM    233  N    ARG A  41     -30.072 -39.238  24.289  1.00 250.82                N
ANISOU  233  N    ARG A  41      37519  35508  22273 -13611  -2119  -1495           N
ATOM    234  CA   ARG A  41     -31.526 -39.375  24.325  1.00 252.11                C
ANISOU  234  CA   ARG A  41      37633  35649  22508 -14461  -3043  -1132           C
ATOM    235  C    ARG A  41     -32.232 -38.032  24.540  1.00 247.30                C
ANISOU  235  C    ARG A  41      35819  35605  22539 -14721  -3367   -457           C
ATOM    236  O    ARG A  41     -33.177 -37.708  23.819  1.00 250.95                O
ANISOU  236  O    ARG A  41      36355  36267  22727 -15389  -4009    -74           O
ATOM    237  CB   ARG A  41     -31.967 -40.416  25.361  1.00 250.73                C
ANISOU  237  CB   ARG A  41      37564  35012  22691 -14558  -3289  -1304           C
ATOM    238  CG   ARG A  41     -31.494 -41.831  25.054  1.00 256.87                C
ANISOU  238  CG   ARG A  41      39666  35153  22778 -14438  -3097  -1928           C
ATOM    239  CD   ARG A  41     -31.693 -42.183  23.588  1.00 265.95                C
ANISOU  239  CD   ARG A  41      42006  36180  22862 -14929  -3369  -2095           C
ATOM    240  NE   ARG A  41     -33.101 -42.332  23.237  1.00 269.75                N
ANISOU  240  NE   ARG A  41      42661  36665  23167 -15920  -4348  -1765           N
ATOM    241  CZ   ARG A  41     -33.716 -43.501  23.105  1.00 275.62                C
ANISOU  241  CZ   ARG A  41      44349  36883  23490 -16468  -4834  -2010           C
ATOM    242  NH1  ARG A  41     -33.047 -44.629  23.295  1.00 278.28                N
ANISOU  242  NH1  ARG A  41      45587  36614  23532 -16089  -4402  -2595           N
ATOM    243  NH2  ARG A  41     -35.000 -43.544  22.783  1.00 279.24                N
ANISOU  243  NH2  ARG A  41      44845  37414  23838 -17400  -5753  -1655           N
ATOM    244  N    ILE A  42     -31.785 -37.254  25.526  1.00 263.38                N
ANISOU  244  N    ILE A  42      36766  37889  25419 -14201  -2934   -303           N
ATOM    245  CA   ILE A  42     -32.361 -35.930  25.744  1.00 258.98                C
ANISOU  245  CA   ILE A  42      35088  37826  25486 -14369  -3133    314           C
ATOM    246  C    ILE A  42     -31.863 -35.025  24.632  1.00 261.43                C
ANISOU  246  C    ILE A  42      35462  38498  25370 -14278  -2861    454           C
ATOM    247  O    ILE A  42     -30.827 -34.377  24.766  1.00 258.18                O
ANISOU  247  O    ILE A  42      34637  38276  25184 -13677  -2166    357           O
ATOM    248  CB   ILE A  42     -31.979 -35.325  27.115  1.00 250.49                C
ANISOU  248  CB   ILE A  42      32893  36887  25396 -13842  -2713    404           C
ATOM    249  CG1  ILE A  42     -32.666 -36.088  28.251  1.00 248.03                C
ANISOU  249  CG1  ILE A  42      32414  36269  25555 -14006  -3051    390           C
ATOM    250  CG2  ILE A  42     -32.369 -33.858  27.179  1.00 246.72                C
ANISOU  250  CG2  ILE A  42      31365  36898  25479 -13925  -2764    991           C
ATOM    251  CD1  ILE A  42     -34.183 -35.992  28.227  1.00 249.50                C
ANISOU  251  CD1  ILE A  42      32343  36529  25926 -14779  -3870    908           C
ATOM    252  N    GLN A  43     -32.607 -35.000  23.530  1.00 270.54                N
ANISOU  252  N    GLN A  43      37148  39749  25897 -14897  -3425    693           N
ATOM    253  CA   GLN A  43     -32.243 -34.201  22.371  1.00 273.97                C
ANISOU  253  CA   GLN A  43      37761  40514  25820 -14885  -3237    863           C
ATOM    254  C    GLN A  43     -31.859 -32.808  22.818  1.00 267.63                C
ANISOU  254  C    GLN A  43      35786  40130  25771 -14482  -2795   1235           C
ATOM    255  O    GLN A  43      31.037  32.147  22.187  1.00 268.51                O
ANISOU  255  O    GLN A  43      35915  40460  25645 -14154  -2269   1224           O
ATOM    256  CB   GLN A  43     -33.398 -34.132  21.370  1.00 280.38                C
ANISOU  256  CB   GLN A  43      38970  41475  26085 -15698  -4084   1272           C
ATOM    257  CG   GLN A  43     -33.728 -35.459  20.702  1.00 288.19                C
ANISOU  257  CG   GLN A  43      41276  42055  26169 -16173  -4532    879           C
ATOM    258  CD   GLN A  43     -32.594 -35.984  19.841  1.00 293.21                C
ANISOU  258  CD   GLN A  43      43025  42473  25909 -15793  -3920    298           C
ATOM    259  OE1  GLN A  43     -31.518 -35.386  19.773  1.00 290.71                O
ANISOU  259  OE1  GLN A  43      42450  42326  25681 -15152  -3135    190           O
ATOM    260  NE2  GLN A  43     -32.831 -37.111  19.177  1.00 300.78                N
ANISOU  260  NE2  GLN A  43      45240  43042  26000 -16198  -4260    -78           N
ATOM    261  N    ILE A  44     -32.460 -32.365  23.915  1.00 247.22                N
ANISOU  261  N    ILE A  44      32204  37634  24094 -14518  -2991   1565           N
ATOM    262  CA   ILE A  44     -32.137 -31.063  24.465  1.00 241.17                C
ANISOU  262  CA   ILE A  44      30331  37204  24097 -14153  -2574   1892           C
ATOM    263  C    ILE A  44     -30.776 -31.166  25.159  1.00 236.94                C
ANISOU  263  C    ILE A  44      29631  36561  23834 -13402  -1744   1400           C
ATOM    264  O    ILE A  44     -30.677 -31.713  26.259  1.00 232.99                O
ANISOU  264  O    ILE A  44      28903  35837  23786 -13180  -1666   1160           O
ATOM    265  CB   ILE A  44     -33.216 -30.583  25.461  1.00 236.48                C
ANISOU  265  CB   ILE A  44      28764  36706  24379 -14407  -3005   2381           C
ATOM    266  CG1  ILE A  44     -34.494 -31.418  25.333  1.00 240.48                C
ANISOU  266  CG1  ILE A  44      29665  37044  24663 -15095  -3861   2549           C
```

FIG. 13 Continued

```
ATOM    267  CG2 ILE A  44     -33.521 -29.111  25.234  1.00234.87           C
ANISOU  267  CG2 ILE A  44    27731  36916  24593 -14450  -2981   2996       C
ATOM    268  CD1 ILE A  44     -35.392 -30.998  24.188  1.00246.38           C
ANISOU  268  CD1 ILE A  44    30591  38055  24966 -15703  -4468   3061       C
ATOM    269  N   PHE A  45     -29.734 -30.656  24.500  1.00235.00           N
ANISOU  269  N   PHE A  45    29504  36487  23299 -13024  -1136   1273       N
ATOM    270  CA  PHE A  45     -28.367 -30.679  25.030  1.00231.95           C
ANISOU  270  CA  PHE A  45    28921  36061  23149 -12313   -331    849       C
ATOM    271  C   PHE A  45     -27.375 -30.056  24.048  1.00234.98           C
ANISOU  271  C   PHE A  45    29484  36674  23125 -12022    272    812       C
ATOM    272  O   PHE A  45     -27.475 -30.262  22.844  1.00241.29           O
ANISOU  272  O   PHE A  45    31087  37478  23115 -12267    157    817       O
ATOM    273  CB  PHE A  45     -27.936 -32.113  25.364  1.00233.55           C
ANISOU  273  CB  PHE A  45    29864  35836  23037 -12078   -226    263       C
ATOM    274  CG  PHE A  45     -27.675 -32.970  24.156  1.00241.33           C
ANISOU  274  CG  PHE A  45    32093  36608  22992 -12170   -195    -64       C
ATOM    275  CD1 PHE A  45     -26.383 -33.186  23.712  1.00243.90           C
ANISOU  275  CD1 PHE A  45    32839  36894  22939 -11609    552   -462       C
ATOM    276  CD2 PHE A  45     -28.720 -33.560  23.466  1.00246.55           C
ANISOU  276  CD2 PHE A  45    33510  37109  23060 -12826   -904     30       C
ATOM    277  CE1 PHE A  45     -26.140 -33.975  22.600  1.00251.52           C
ANISOU  277  CE1 PHE A  45    35004  37634  22928 -11670    636   -777       C
ATOM    278  CE2 PHE A  45     -28.485 -34.349  22.356  1.00254.21           C
ANISOU  278  CE2 PHE A  45    35700  37856  23033 -12936   -876   -300       C
ATOM    279  CZ  PHE A  45     -27.194 -34.556  21.921  1.00256.69           C
ANISOU  279  CZ  PHE A  45    36472  38103  22954 -12342    -83   -713       C
ATOM    280  N   GLY A  46     -26.414 -29.300  24.564  1.00220.60           N
ANISOU  280  N   GLY A  46    26926  35042  21850 -11519    915    776       N
ATOM    281  CA  GLY A  46     -26.311 -29.059  25.986  1.00213.65           C
ANISOU  281  CA  GLY A  46    25149  34158  21870 -11264   1014    758       C
ATOM    282  C   GLY A  46     -26.877 -27.709  26.368  1.00209.45           C
ANISOU  282  C   GLY A  46    23637  33910  22034 -11457    882   1299       C
ATOM    283  O   GLY A  46     -27.419 -27.000  25.517  1.00212.03           O
ANISOU  283  O   GLY A  46    23977  34431  22153 -11800    667   1724       O
ATOM    284  N   PRO A  47     -26.744 -27.344  27.656  1.00220.95           N
ANISOU  284  N   PRO A  47    24263  35381  24308 -11224   1023   1291       N
ATOM    285  CA  PRO A  47     -27.230 -26.081  28.226  1.00216.62           C
ANISOU  285  CA  PRO A  47    22759  35038  24508 -11344    970   1751       C
ATOM    286  C   PRO A  47     -26.452 -24.899  27.680  1.00217.11           C
ANISOU  286  C   PRO A  47    22447  35379  24667 -11160   1508   1918       C
ATOM    287  O   PRO A  47     -26.393 -23.861  28.332  1.00213.15           O
ANISOU  287  O   PRO A  47    21123  35008  24855 -11081   1704   2139       O
ATOM    288  CB  PRO A  47     -26.938 -26.230  29.726  1.00210.90           C
ANISOU  288  CB  PRO A  47    21452  34209  24470 -11031   1125   1514       C
ATOM    289  CG  PRO A  47     -26.696 -27.685  29.938  1.00212.36           C
ANISOU  289  CG  PRO A  47    22319  34105  24263 -10878   1043   1040       C
ATOM    290  CD  PRO A  47     -26.079 -28.174  28.674  1.00218.25           C
ANISOU  290  CD  PRO A  47    23900  34833  24191 -10804   1260    816       C
ATOM    291  N   ASN A  48     -25.855 -25.068  26.505  1.00290.27           N
ANISOU  291  N   ASN A  48    32343  44710  33238 -11098   1767   1805       N
ATOM    292  CA  ASN A  48     -25.064 -24.017  25.874  1.00291.63           C
ANISOU  292  CA  ASN A  48    32244  45135  33426 -10931   2319   1964       C
ATOM    293  C   ASN A  48     -25.861 -22.751  25.561  1.00291.27           C
ANISOU  293  C   ASN A  48    31706  45280  33681 -11274   2107   2598       C
ATOM    294  O   ASN A  48     -26.747 -22.354  26.320  1.00287.60           O
ANISOU  294  O   ASN A  48    30691  44788  33794 -11474   1741   2892       O
ATOM    295  CB  ASN A  48     -24.384 -24.536  24.600  1.00298.08           C
ANISOU  295  CB  ASN A  48    33942  45966  33348 -10825   2618   1743       C
ATOM    296  CG  ASN A  48     -23.200 -25.441  24.891  1.00298.63           C
ANISOU  296  CG  ASN A  48    34296  45905  33264 -10310   3126   1148       C
ATOM    297  OD1 ASN A  48     -23.073 -25.981  25.989  1.00294.77           O
ANISOU  297  OD1 ASN A  48    33541  45267  33192 -10101   3085    874       O
ATOM    298  ND2 ASN A  48     -22.325 -25.612  23.902  1.00303.83           N
ANISOU  298  ND2 ASN A  48    35501  46621  33319 -10082   3628    970       N
ATOM    299  N   LYS A  49     -25.527 -22.117  24.441  1.00233.01           N
ANISOU  299  N   LYS A  49    24537  38088  25910 -11313   2375   2824       N
ATOM    300  CA  LYS A  49     -26.175 -20.876  24.034  1.00233.48           C
ANISOU  300  CA  LYS A  49    24170  38326  26215 -11590   2242   3455       C
ATOM    301  C   LYS A  49     -27.181 -21.082  22.910  1.00238.89           C
```

FIG. 13 Continued

```
ANISOU  301  C    LYS A  49      25493  39064  26210 -12046   1646   3828           C
ATOM    302  O    LYS A  49     -26.965 -21.895  22.011  1.00243.97                  O
ANISOU  302  O    LYS A  49      27020  39674  26003 -12098   1597   3593           O
ATOM    303  CB   LYS A  49     -25.125 -19.852  23.594  1.00234.55                  C
ANISOU  303  CB   LYS A  49      24005  38648  26466 -11339   2965   3538           C
ATOM    304  CG   LYS A  49     -24.094 -19.524  24.663  1.00229.87                  C
ANISOU  304  CG   LYS A  49      22719  38046  26576 -10937   3538   3211           C
ATOM    305  CD   LYS A  49     -24.757 -19.024  25.935  1.00223.99                  C
ANISOU  305  CD   LYS A  49      21194  37216  26696 -11015   3286   3371           C
ATOM    306  CE   LYS A  49     -25.519 -17.734  25.682  1.00224.10                  C
ANISOU  306  CE   LYS A  49      20757  37317  27074 -11284   3167   4018           C
ATOM    307  NZ   LYS A  49     -26.351 -17.326  26.851  1.00219.16                  N
ANISOU  307  NZ   LYS A  49      19474  36575  27223 -11361   2879   4210           N
ATOM    308  N    LEU A  50     -28.278 -20.333  22.973  1.00233.14                  N
ANISOU  308  N    LEU A  50      24314  38418  25850 -12372   1196   4420           N
ATOM    309  CA   LEU A  50     -29.318 -20.387  21.949  1.00238.50                  C
ANISOU  309  CA   LEU A  50      25461  39201  25957 -12838    560   4878           C
ATOM    310  C    LEU A  50     -28.842 -19.631  20.715  1.00243.49                  C
ANISOU  310  C    LEU A  50      26368  40046  26101 -12827    897   5157           C
ATOM    311  O    LEU A  50     -29.289 -18.516  20.437  1.00244.16                  O
ANISOU  311  O    LEU A  50      26003  40290  26478 -12951    853   5756           O
ATOM    312  CB   LEU A  50     -30.633 -19.795  22.469  1.00236.39                  C
ANISOU  312  CB   LEU A  50      24525  38970  26324 -13141      2   5473           C
ATOM    313  CG   LEU A  50     -31.936 -20.137  21.731  1.00241.42                  C
ANISOU  313  CG   LEU A  50      25544  39691  26491 -13680   -857   5923           C
ATOM    314  CD1  LEU A  50     -33.123 -19.947  22.657  1.00238.13                  C
ANISOU  314  CD1  LEU A  50      24415  39233  26831 -13884  -1352   6313           C
ATOM    315  CD2  LEU A  50     -32.120 -19.329  20.445  1.00247.21                  C
ANISOU  315  CD2  LEU A  50      26488  40683  26759 -13868   -931   6473           C
ATOM    316  N    GLU A  51     -27.929 -20.257  19.984  1.00274.83                  N
ANISOU  316  N    GLU A  51      31099  44002  29323 -12656   1265   4726           N
ATOM    317  CA   GLU A  51     -27.343 -19.685  18.778  1.00280.16                  C
ANISOU  317  CA   GLU A  51      32154  44865  29430 -12609   1672   4914           C
ATOM    318  C    GLU A  51     -26.562 -20.783  18.072  1.00284.82                  C
ANISOU  318  C    GLU A  51      33755  45365  29099 -12463   1931   4349           C
ATOM    319  O    GLU A  51     -26.508 -20.835  16.843  1.00291.45                  O
ANISOU  319  O    GLU A  51      35341  46311  29084 -12607   1931   4466           O
ATOM    320  CB   GLU A  51     -26.399 -18.527  19.133  1.00277.07                  C
ANISOU  320  CB   GLU A  51      31001  44565  29706 -12244   2461   5000           C
ATOM    321  CG   GLU A  51     -27.009 -17.131  19.033  1.00276.65                  C
ANISOU  321  CG   GLU A  51      30291  44659  30166 -12415   2377   5726           C
ATOM    322  CD   GLU A  51     -26.637 -16.416  17.745  1.00282.66                  C
ANISOU  322  CD   GLU A  51      31403  45618  30378 -12444   2707   6087           C
ATOM    323  OE1  GLU A  51     -25.919 -17.013  16.915  1.00287.26                  O
ANISOU  323  OE1  GLU A  51      32756  46235  30155 -12341   3005   5765           O
ATOM    324  OE2  GLU A  51     -27.055 -15.253  17.566  1.00283.07                  O
ANISOU  324  OE2  GLU A  51      30975  45775  30804 -12553   2699   6702           O
ATOM    325  N    GLU A  52     -25.970 -21.670  18.869  1.00236.50                  N
ANISOU  325  N    GLU A  52      27678  39035  23147 -12161   2159   3743           N
ATOM    326  CA   GLU A  52     -25.149 -22.755  18.346  1.00240.66                  C
ANISOU  326  CA   GLU A  52      29117  39421  22900  11930   2497   3164           C
ATOM    327  C    GLU A  52     -23.986 -22.211  17.513  1.00244.47                  C
ANISOU  327  C    GLU A  52      29766  40071  23049 -11607   3324   3141           C
ATOM    328  O    GLU A  52     -23.419 -22.933  16.693  1.00250.08                  O
ANISOU  328  O    GLU A  52      31375  40716  22927 -11476   3614   2806           O
ATOM    329  CB   GLU A  52     -25.992 -23.724  17.509  1.00246.60                  C
ANISOU  329  CB   GLU A  52      30929  40059  22707 -12370   1815   3121           C
ATOM    330  CG   GLU A  52     -27.278 -24.199  18.175  1.00244.02                  C
ANISOU  330  CG   GLU A  52      30448  39600  22666 -12792    930   3252           C
ATOM    331  CD   GLU A  52     -27.036 -25.058  19.404  1.00238.83                  C
ANISOU  331  CD   GLU A  52      29581  38665  22498 -12533    991   2747           C
ATOM    332  OE1  GLU A  52     -26.060 -24.797  20.135  1.00234.48                  O
ANISOU  332  OE1  GLU A  52      28471  38112  22510 -12037   1643   2499           O
ATOM    333  OE2  GLU A  52     -27.831 -25.990  19.647  1.00239.40                  O
ANISOU  333  OE2  GLU A  52      30040  38526  22396 -12845    368   2617           O
ATOM    334  N    LYS A  53     -23.637 -20.941  17.725  1.00241.02                  N
ANISOU  334  N    LYS A  53      28482  39830  23263 -11484   3729   3497           N
ATOM    335  CA   LYS A  53     -22.579 -20.305  16.951  1.00244.74                  C
ANISOU  335  CA   LYS A  53      29015  40474  23499 -11220   4522   3554           C
```

FIG. 13 Continued

```
ATOM    336  C   LYS A  53     -22.939 -20.474  15.481  1.00252.77           C
ANISOU  336  C   LYS A  53    31039  41576  23426 -11501   4325   3768       C
ATOM    337  O   LYS A  53     -22.066 -20.511  14.618  1.00258.00           O
ANISOU  337  O   LYS A  53    32220  42309  23498 -11279   4943   3637       O
ATOM    338  CB  LYS A  53     -21.232 -20.970  17.246  1.00244.71           C
ANISOU  338  CB  LYS A  53    29106  40385  23488 -10685   5265   2938       C
ATOM    339  CG  LYS A  53     -20.575 -20.548  18.556  1.00237.92           C
ANISOU  339  CG  LYS A  53    27182  39530  23686  10359   5636   2778       C
ATOM    340  CD  LYS A  53     -19.366 -19.653  18.304  1.00239.30           C
ANISOU  340  CD  LYS A  53    26891  39906  24127 -10050   6517   2854       C
ATOM    341  CE  LYS A  53     -18.285 -20.393  17.519  1.00245.29           C
ANISOU  341  CE  LYS A  53    28359  40669  24172  -9677   7173   2465       C
ATOM    342  NZ  LYS A  53     -17.075 -19.559  17.262  1.00247.20           N
ANISOU  342  NZ  LYS A  53    28115  41122  24688  -9380   8066   2553       N
ATOM    343  N   LYS A  54     -24.243 -20.573  15.224  1.00254.34           N
ANISOU  343  N   LYS A  54    31492  41778  23368 -11998   3452   4113       N
ATOM    344  CA  LYS A  54     -24.803 -20.868  13.902  1.00262.22           C
ANISOU  344  CA  LYS A  54    33501  42849  23280 -12368   3042   4316       C
ATOM    345  C   LYS A  54     -24.318 -20.004  12.738  1.00267.95           C
ANISOU  345  C   LYS A  54    34484  43815  23512 -12328   3532   4687       C
ATOM    346  O   LYS A  54     -25.121 -19.502  11.954  1.00272.03           O
ANISOU  346  O   LYS A  54    35226  44503  23632 -12715   3052   5238       O
ATOM    347  CB  LYS A  54     -26.337 -20.852  13.962  1.00262.04           C
ANISOU  347  CB  LYS A  54    33408  42858  23298 -12933   1988   4767       C
ATOM    348  CG  LYS A  54     -27.039 -21.437  12.740  1.00270.30           C
ANISOU  348  CG  LYS A  54    35567  43949  23187 -13395   1371   4684       C
ATOM    349  CD  LYS A  54     -27.035 -22.958  12.744  1.00272.58           C
ANISOU  349  CD  LYS A  54    36781  43945  22844 -13462   1130   4226       C
ATOM    350  CE  LYS A  54     -25.824 -23.522  12.024  1.00277.59           C
ANISOU  350  CE  LYS A  54    38306  44478  22687 -13083   1918   3695       C
ATOM    351  NZ  LYS A  54     -25.923 -25.000  11.878  1.00281.19           N
ANISOU  351  NZ  LYS A  54    39814  44610  22416 -13194   1641   3094       N
ATOM    352  N   GLU A  55     -23.009 -19.833  12.620  1.00269.04           N
ANISOU  352  N   GLU A  55    34573  43975  23675 -11862   4484   4413       N
ATOM    353  CA  GLU A  55     -22.461 -19.130  11.477  1.00275.17           C
ANISOU  353  CA  GLU A  55    35687  44956  23910 -11801   5031   4718       C
ATOM    354  C   GLU A  55     -22.825 -19.926  10.235  1.00283.68           C
ANISOU  354  C   GLU A  55    38099  46021  23665 -12067   4697   4637       C
ATOM    355  O   GLU A  55     -23.560 -20.913  10.310  1.00284.44           O
ANISOU  355  O   GLU A  55    38757  45952  23364 -12343   3998   4391       O
ATOM    356  CB  GLU A  55     -20.938 -19.024  11.571  1.00275.19           C
ANISOU  356  CB  GLU A  55    35474  44967  24118 -11243   6135   4362       C
ATOM    357  CG  GLU A  55     -20.403 -17.626  11.834  1.00272.46           C
ANISOU  357  CG  GLU A  55    34123  44797  24601 -11095   6705   4776       C
ATOM    358  CD  GLU A  55     -19.051 -17.403  11.185  1.00277.14           C
ANISOU  358  CD  GLU A  55    34893  45496  24912 -10706   7755   4647       C
ATOM    359  OE1 GLU A  55     -18.844 -17.916  10.065  1.00284.61           O
ANISOU  359  OE1 GLU A  55    36871  46466  24803 -10693   7948   4551       O
ATOM    360  OE2 GLU A  55     -18.201 -16.717  11.789  1.00273.77           O
ANISOU  360  OE2 GLU A  55    33584  45128  25308  10429   8391   4645       O
ATOM    361  N   SER A  56     -22.303 -19.492   9.093  1.00337.40           N
ANISOU  361  N   SER A  56    45434  52991  29773 -12004   5206   4842       N
ATOM    362  CA  SER A  56     -22.535 -20.183   7.833  1.00346.43           C
ANISOU  362  CA  SER A  56    47927  54132  29570 -12237   4985   4755       C
ATOM    363  C   SER A  56     -21.493 -21.276   7.633  1.00349.77           C
ANISOU  363  C   SER A  56    49142  54337  29417 -11822   5672   4011       C
ATOM    364  O   SER A  56      21.410  21.867   6.555  1.00357.99           O
ANISOU  364  O   SER A  56    51388  55339  29293 -11906   5735   3840       O
ATOM    365  CB  SER A  56     -22.476 -19.197   6.664  1.00352.82           C
ANISOU  365  CB  SER A  56    48999  55221  29837 -12354   5231   5353       C
ATOM    366  OG  SER A  56     -23.400 -18.139   6.838  1.00350.16           O
ANISOU  366  OG  SER A  56    47905  55070  30068 -12682   4655   6083       O
ATOM    367  N   LYS A  57     -20.704 -21.543   8.673  1.00296.29           N
ANISOU  367  N   LYS A  57    41707  47421  23450 -11365   6188   3580       N
ATOM    368  CA  LYS A  57     -19.608 -22.504   8.581  1.00299.23           C
ANISOU  368  CA  LYS A  57    42668  47595  23432 -10870   6945   2915       C
ATOM    369  C   LYS A  57     -18.811 -22.144   7.330  1.00307.46           C
ANISOU  369  C   LYS A  57    44352  48796  23672 -10679   7748   3036       C
ATOM    370  O   LYS A  57     -18.175 -22.991   6.697  1.00313.78           O
```

FIG. 13 Continued

```
ANISOU  370  O    LYS A  57    46134  49445  23645 -10413   8256   2588       O
ATOM    371  CB   LYS A  57   -20.122 -23.946   8.531  1.00301.80             C
ANISOU  371  CB   LYS A  57    44023  47592  23056 -11038   6391   2393       C
ATOM    372  CG   LYS A  57   -20.876 -24.380   9.786  1.00294.03             C
ANISOU  372  CG   LYS A  57    42435  46429  22854 -11211   5648   2258       C
ATOM    373  CD   LYS A  57   -19.950 -24.567  10.978  1.00287.49             C
ANISOU  373  CD   LYS A  57    40764  45490  22979 -10644   6242   1872       C
ATOM    374  CE   LYS A  57   -19.240 -25.907  10.926  1.00291.08             C
ANISOU  374  CE   LYS A  57    42071  45617  22910 -10246   6672   1168       C
ATOM    375  NZ   LYS A  57   -18.523 -26.199  12.195  1.00284.55             N
ANISOU  375  NZ   LYS A  57    40412  44677  23028  -9746   7053    821       N
ATOM    376  N    LEU A  58   -16.880 -20.860   6.991  1.00245.16             N
ANISOU  376  N    LEU A  58    27935  28167  37047 -17056   2328 -10910       N
ATOM    377  CA   LEU A  58   -18.212 -20.278   5.830  1.00240.98             C
ANISOU  377  CA   LEU A  58    27503  28086  35971 -16471   1748 -11114       C
ATOM    378  C    LEU A  58   -18.490 -20.992   4.506  1.00248.49             C
ANISOU  378  C    LEU A  58    28150  29360  36904 -17088   1365 -11865       C
ATOM    379  O    LEU A  58   -17.570 -21.516   3.876  1.00248.09             O
ANISOU  379  O    LEU A  58    28732  28891  36640 -16927   1324 -12098       O
ATOM    380  CB   LEU A  58   -16.699 -20.101   6.064  1.00232.79             C
ANISOU  380  CB   LEU A  58    27480  26407  34563 -15584   1860 -10711       C
ATOM    381  CG   LEU A  58    15.985  18.935   5.356  1.00225.33             C
ANISOU  381  CG   LEU A  58    26623  25956  33035 -14711   1394 -10563       C
ATOM    382  CD1  LEU A  58   -14.731 -18.489   6.112  1.00216.98             C
ANISOU  382  CD1  LEU A  58    26377  24333  31732 -13866   1600  -9944       C
ATOM    383  CD2  LEU A  58   -15.630 -19.286   3.930  1.00228.13             C
ANISOU  383  CD2  LEU A  58    26985  26556  33136 -14801   1010 -11102       C
ATOM    384  N    LEU A  59   -19.761 -21.042   4.104  1.00241.47             N
ANISOU  384  N    LEU A  59    26268  29220  36260 -17840   1096 -12250       N
ATOM    385  CA   LEU A  59   -20.084 -21.459   2.745  1.00248.60             C
ANISOU  385  CA   LEU A  59    26795  30663  36996 -18386    562 -12977       C
ATOM    386  C    LEU A  59   -19.452 -20.303   1.983  1.00241.16             C
ANISOU  386  C    LEU A  59    25951  30299  35380 -17466     39 -12823       C
ATOM    387  O    LEU A  59   -19.307 -20.332   0.760  1.00243.88             O
ANISOU  387  O    LEU A  59    26249  31091  35322 -17542   -459 -13292       O
ATOM    388  CB   LEU A  59   -21.598 -21.531   2.501  1.00258.09             C
ANISOU  388  CB   LEU A  59    26754  32749  38559 -19299    264 -13322       C
ATOM    389  CG   LEU A  59   -22.315 -22.885   2.619  1.00269.42             C
ANISOU  389  CG   LEU A  59    27965  33805  40597 -20527    563 -13813       C
ATOM    390  CD1  LEU A  59   -23.826 -22.721   2.523  1.00278.12             C
ANISOU  390  CD1  LEU A  59    27652  35924  42097 -21321    265 -13989       C
ATOM    391  CD2  LEU A  59   -21.627 -23.861   1.560  1.00275.01             C
ANISOU  391  CD2  LEU A  59    29220  34172  41099 -20987    374 -14547       C
ATOM    392  N    LYS A  60   -19.101 -19.283   2.775  1.00177.54             N
ANISOU  392  N    LYS A  60    18054  22193  27208 -16643    193 -12153       N
ATOM    393  CA   LYS A  60   -18.354 -18.089   2.385  1.00169.01             C
ANISOU  393  CA   LYS A  60    17224  21429  25563 -15665   -135 -11828       C
ATOM    394  C    LYS A  60   -18.669 -16.862   3.267  1.00162.88             C
ANISOU  394  C    LYS A  60    16136  20926  24826 -15121    -64 -11227       C
ATOM    395  O    LYS A  60   -17.861 -15.936   3.369  1.00154.73             O
ANISOU  395  O    LYS A  60    15565  19802  23422 -14276   -114 -10824       O
ATOM    396  CB   LYS A  60   -18.443 -17.792   0.877  1.00171.94             C
ANISOU  396  CB   LYS A  60    17253  22624  25450 -15685   -839 -12289       C
ATOM    397  CG   LYS A  60   -17.261 -18.371   0.067  1.00171.09             C
ANISOU  397  CG   LYS A  60    18001  22017  24988 -15503   -817 -12569       C
ATOM    398  CD   LYS A  60   -15.907 -18.380   0.867  1.00162.70             C
ANISOU  398  CD   LYS A  60    17918  19970  23932 -14770   -276 -12029       C
ATOM    399  CE   LYS A  60   -15.305 -16.970   1.178  1.00152.87             C
ANISOU  399  CE   LYS A  60    16843  18899  22344 -13771   -372 -11385       C
ATOM    400  NZ   LYS A  60   -13.932 -16.984   1.773  1.00145.94             N
ANISOU  400  NZ   LYS A  60    16835  17200  21415 -13115     26 -10909       N
ATOM    401  N    PHE A  61   -19.828 -16.862   3.915  1.00259.32             N
ANISOU  401  N    PHE A  61    27560  33445  37523 -15639     96 -11169       N
ATOM    402  CA   PHE A  61   -20.188 -15.742   4.775  1.00254.44             C
ANISOU  402  CA   PHE A  61    26610  33058  37009 -15196    245 -10634       C
ATOM    403  C    PHE A  61   -19.034 -15.411   5.697  1.00245.53             C
ANISOU  403  C    PHE A  61    26573  31054  35664 -14477    675 -10128       C
ATOM    404  O    PHE A  61   -18.365 -16.316   6.190  1.00245.38             O
ANISOU  404  O    PHE A  61    27324  30191  35718 -14584   1081 -10085       O
```

FIG. 13 Continued

```
ATOM    405  CB   PHE A  61      -21.428 -16.056   5.600  1.00260.78           C
ANISOU  405  CB   PHE A  61    26569  34038  38480 -15914    635 -10568        C
ATOM    406  CG   PHE A  61      -22.647 -15.299   5.166  1.00266.99           C
ANISOU  406  CG   PHE A  61    26091  36057  39295 -15776    333 -10495        C
ATOM    407  CD1  PHE A  61      -22.698 -13.917   5.296  1.00263.00           C
ANISOU  407  CD1  PHE A  61    25424  36045  38457 -14750    288  -9986        C
ATOM    408  CD2  PHE A  61      -23.748 -15.966   4.637  1.00277.81           C
ANISOU  408  CD2  PHE A  61    26434  38091  41029 -16630    109 -10906        C
ATOM    409  CE1  PHE A  61      -23.821 -13.212   4.901  1.00269.64           C
ANISOU  409  CE1  PHE A  61    25090  38018  39342 -14498     40  -9845        C
ATOM    410  CE2  PHE A  61      -24.879 -15.269   4.240  1.00284.62           C
ANISOU  410  CE2  PHE A  61    26054  40158  41929 -16431   -195 -10774        C
ATOM    411  CZ   PHE A  61      -24.916 -13.891   4.371  1.00280.53           C
ANISOU  411  CZ   PHE A  61    25374  40120  41093 -15324   -221 -10220        C
ATOM    412  N    LEU A  62      -18.814 -14.117   5.927  1.00166.42           N
ANISOU  412  N    LEU A  62    16587  21255  25390 -13767    558  -9741        N
ATOM    413  CA   LEU A  62      -17.706 -13.623   6.761  1.00158.17           C
ANISOU  413  CA   LEU A  62    16542  19486  24071 -13062    867  -9260        C
ATOM    414  C    LEU A  62      -16.361 -14.058   6.189  1.00155.03           C
ANISOU  414  C    LEU A  62    16999  18625  23282 -12669    756  -9303        C
ATOM    415  O    LEU A  62      -15.306 -13.690   6.702  1.00148.80           O
ANISOU  415  O    LEU A  62    16975  17327  22233 -12068    913  -8907        O
ATOM    416  CB   LEU A  62      -17.852 -14.039   8.233  1.00158.50           C
ANISOU  416  CB   LEU A  62    16921  18853  24449 -13321   1546  -8938        C
ATOM    417  CG   LEU A  62      -18.868 -13.279   9.103  1.00160.38           C
ANISOU  417  CG   LEU A  62    16600  19453  24885 -13239   1924  -8598        C
ATOM    418  CD1  LEU A  62      -19.862 -14.236   9.786  1.00168.53           C
ANISOU  418  CD1  LEU A  62    17181  20398  26456 -14014   2470  -8632        C
ATOM    419  CD2  LEU A  62      -18.186 -12.373  10.126  1.00153.75           C
ANISOU  419  CD2  LEU A  62    16559  18155  23705 -12509   2242  -8074        C
ATOM    420  N    GLY A  63      -16.423 -14.870   5.137  1.00191.88           N
ANISOU  420  N    GLY A  63    21476  23491  27941 -13066    502  -9789        N
ATOM    421  CA   GLY A  63      -15.256 -15.276   4.381  1.00190.09           C
ANISOU  421  CA   GLY A  63    21880  22947  27397 -12763    394  -9898        C
ATOM    422  C    GLY A  63      -15.224 -14.251   3.275  1.00187.93           C
ANISOU  422  C    GLY A  63    21299  23419  26688 -12350   -167  -9985        C
ATOM    423  O    GLY A  63      -14.802 -14.524   2.154  1.00189.64           O
ANISOU  423  O    GLY A  63    21611  23810  26633 -12354   -447 -10307        O
ATOM    424  N    PHE A  64      -15.695 -13.056   3.625  1.00178.35           N
ANISOU  424  N    PHE A  64    19728  22619  25418 -12013   -307  -9693        N
ATOM    425  CA   PHE A  64      -15.820 -11.940   2.703  1.00176.60           C
ANISOU  425  CA   PHE A  64    19140  23137  24822 -11610   -854  -9704        C
ATOM    426  C    PHE A  64      -15.753 -10.604   3.420  1.00170.26           C
ANISOU  426  C    PHE A  64    18415  22325  23951 -11011   -800  -9219        C
ATOM    427  O    PHE A  64      -15.774  -9.559   2.781  1.00168.15           O
ANISOU  427  O    PHE A  64    17933  22571  23385 -10597  -1218  -9147        O
ATOM    428  CB   PHE A  64      -17.163 -12.011   1.983  1.00184.17           C
ANISOU  428  CB   PHE A  64    19021  25046  25910 -12186  -1321 -10112        C
ATOM    429  CG   PHE A  64      -17.193 -12.979   0.848  1.00190.70           C
ANISOU  429  CG   PHE A  64    19761  26111  26585 -12697  -1609 -10680        C
ATOM    430  CD1  PHE A  64      -16.069 -13.188   0.069  1.00188.47           C
ANISOU  430  CD1  PHE A  64    20193  25532  25887 -12392  -1659 -10786        C
ATOM    431  CD2  PHE A  64      -18.359 -13.657   0.535  1.00199.72           C
ANISOU  431  CD2  PHE A  64    20064  27807  28013 -13523  -1828 -11124        C
ATOM    432  CE1  PHE A  64      -16.093 -14.074  -0.990  1.00194.97           C
ANISOU  432  CE1  PHE A  64    20987  26545  26549 -12905  -1893 -11366        C
ATOM    433  CE2  PHE A  64      -18.403 -14.549  -0.532  1.00206.57           C
ANISOU  433  CE2  PHE A  64    20902  28886  28700 -14073  -2120 -11723        C
ATOM    434  CZ   PHE A  64      -17.265 -14.758  -1.297  1.00204.13           C
ANISOU  434  CZ   PHE A  64    21396  28224  27938 -13761  -2141 -11864        C
ATOM    435  N    MET A  65      -15.704 -10.637   4.747  1.00206.81           N
ANISOU  435  N    MET A  65    23370  26365  28843 -11003   -291  -8906        N
ATOM    436  CA   MET A  65      -15.674  -9.405   5.531  1.00201.56           C
ANISOU  436  CA   MET A  65    22855  25602  28127 -10516   -172  -8501        C
ATOM    437  C    MET A  65      -14.599  -8.449   5.012  1.00195.51           C
ANISOU  437  C    MET A  65    22653  24757  26874  -9777   -421  -8282        C
ATOM    438  O    MET A  65      -13.466  -8.425   5.502  1.00191.05           O
ANISOU  438  O    MET A  65    22901  23562  26127  -9395   -168  -7970        O
ATOM    439  CB   MET A  65      -15.457  -9.703   7.024  1.00199.73           C
```

FIG. 13 Continued

```
ANISOU  439  CB   MET A  65     23183  24601  28105 -10596    439  -8197       C
ATOM    440  CG   MET A  65     -16.626 -10.418   7.729  1.00 206.49           C
ANISOU  440  CG   MET A  65     23481  25557  29418  11180    862   8244       C
ATOM    441  SD   MET A  65     -17.732  -9.385   8.734  1.00 209.89           S
ANISOU  441  SD   MET A  65     23470  26391  29887 -10680   1404  -7764       S
ATOM    442  CE   MET A  65     -16.661  -8.938  10.104  1.00 202.85           C
ANISOU  442  CE   MET A  65     23802  24539  28734 -10291   1834  -7341       C
ATOM    443  N    TRP A  66     -14.963  -7.653   4.016  1.00 171.59           N
ANISOU  443  N    TRP A  66     19150  22462  23584  -9452   -855  -8317       N
ATOM    444  CA   TRP A  66     -14.011  -6.726   3.444  1.00 166.35           C
ANISOU  444  CA   TRP A  66     18975  21733  22496  -8853  -1106  -8139       C
ATOM    445  C    TRP A  66     -13.912  -5.464   4.268  1.00 163.15           C
ANISOU  445  C    TRP A  66     18884  21130  21973  -8152   -807  -7614       C
ATOM    446  O    TRP A  66     -12.921  -4.756   4.169  1.00 157.89           O
ANISOU  446  O    TRP A  66     18831  20119  21040  -7738   -876  -7423       O
ATOM    447  CB   TRP A  66     -14.321  -6.432   1.978  1.00 169.97           C
ANISOU  447  CB   TRP A  66     18935  23029  22616  -8714  -1654  -8320       C
ATOM    448  CG   TRP A  66     -13.512  -7.289   1.047  1.00 170.13           C
ANISOU  448  CG   TRP A  66     19282  22915  22446  -8987  -1840  -8665       C
ATOM    449  CD1  TRP A  66     -12.153  -7.394   1.018  1.00 165.97           C
ANISOU  449  CD1  TRP A  66     19536  21779  21746  -8634  -1583  -8437       C
ATOM    450  CD2  TRP A  66     -14.003  -8.165   0.013  1.00 176.75           C
ANISOU  450  CD2  TRP A  66     19664  24286  23206  -9492  -2160  -9152       C
ATOM    451  NE1  TRP A  66     -11.764  -8.275   0.035  1.00 169.28           N
ANISOU  451  NE1  TRP A  66     20014  22285  22019  -8872  -1681  -8760       N
ATOM    452  CE2  TRP A  66     -12.878  -8.761  -0.598  1.00 175.94           C
ANISOU  452  CE2  TRP A  66     20176  23793  22880  -9409  -2029  -9232       C
ATOM    453  CE3  TRP A  66     -15.279  -8.498  -0.457  1.00 183.89           C
ANISOU  453  CE3  TRP A  66     19658  25992  24222 -10037  -2559  -9530       C
ATOM    454  CZ2  TRP A  66     -12.989  -9.671  -1.651  1.00 181.87           C
ANISOU  454  CZ2  TRP A  66     20778  24848  23475  -9862  -2245  -9738       C
ATOM    455  CZ3  TRP A  66     -15.388  -9.404  -1.507  1.00 190.07           C
ANISOU  455  CZ3  TRP A  66     20289  27113  24815 -10504  -2825 -10021       C
ATOM    456  CH2  TRP A  66     -14.248  -9.979  -2.090  1.00 188.93           C
ANISOU  456  CH2  TRP A  66     20884  26489  24410 -10419  -2649 -10149       C
ATOM    457  N    ASN A  67     -14.931  -5.186   5.081  1.00 144.61           N
ANISOU  457  N    ASN A  67     16130  18979  19836  -8040   -439  -7399       N
ATOM    458  CA   ASN A  67     -14.894  -4.031   5.993  1.00 142.49           C
ANISOU  458  CA   ASN A  67     16238  18438  19464  -7405    -50  -6947       C
ATOM    459  C    ASN A  67     -14.528   2.694   5.327  1.00 140.53           C
ANISOU  459  C    ASN A  67     16162  18390  18843  -6646   -281  -6676       C
ATOM    460  O    ASN A  67     -13.363  -2.504   4.981  1.00 135.18           O
ANISOU  460  O    ASN A  67     16121  17312  17931  -6566   -490  -6684       O
ATOM    461  CB   ASN A  67     -13.862  -4.272   7.121  1.00 136.77           C
ANISOU  461  CB   ASN A  67     16475  16749  18745  -7566    263  -6858       C
ATOM    462  CG   ASN A  67     -14.343  -5.261   8.194  1.00 139.35           C
ANISOU  462  CG   ASN A  67     16770  16769  19406  -8123    700  -6920       C
ATOM    463  OD1  ASN A  67     -15.089  -6.201   7.901  1.00 144.11           O
ANISOU  463  OD1  ASN A  67     16746  17707  20303  -8647    673  -7183       O
ATOM    464  ND2  ASN A  67     -13.894  -5.054   9.445  1.00 136.72           N
ANISOU  464  ND2  ASN A  67     17157  15784  19005  -8043   1102  -6674       N
ATOM    465  N    PRO A  68     -15.499  -1.757   5.173  1.00 140.80           N
ANISOU  465  N    PRO A  68     15638  19006  18855  -6072   -205  -6400       N
ATOM    466  CA   PRO A  68     -15.186  -0.465   4.547  1.00 139.76           C
ANISOU  466  CA   PRO A  68     15705  19008  18388  -5320   -382  -6089       C
ATOM    467  C    PRO A  68     -13.912   0.258   5.005  1.00 132.94           C
ANISOU  467  C    PRO A  68     15900  17318  17295  -5046   -235  -5907       C
ATOM    468  O    PRO A  68     -13.901   1.491   5.083  1.00 133.22           O
ANISOU  468  O    PRO A  68     16181  17263  17173  -4381    -78  -5563       O
ATOM    469  CB   PRO A  68     -16.464   0.349   4.767  1.00 146.43           C
ANISOU  469  CB   PRO A  68     15878  20386  19373  -4740   -113  -5764       C
ATOM    470  CG   PRO A  68     -17.525  -0.674   4.598  1.00 152.49           C
ANISOU  470  CG   PRO A  68     15682  21798  20458  -5276   -212  -6020       C
ATOM    471  CD   PRO A  68     -16.960  -1.956   5.235  1.00 148.68           C
ANISOU  471  CD   PRO A  68     15630  20711  20153  -6123    -74  -6388       C
ATOM    472  N    LEU A  69     -12.864  -0.517   5.287  1.00 142.59           N
ANISOU  472  N    LEU A  69     17707  17943  18528  -5564   -291  -6131       N
ATOM    473  CA   LEU A  69     -11.514  -0.024   5.535  1.00 136.47           C
ANISOU  473  CA   LEU A  69     17836  16461  17556  -5445   -294  -6014       C
```

FIG. 13 Continued

```
ATOM    474  C   LEU A  69      -10.785  -0.285   4.222  1.00134.65           C
ANISOU  474  C   LEU A  69      17581  16437  17143  -5549   -778  -6184      C
ATOM    475  O   LEU A  69       -9.843   0.418   3.856  1.00131.36           O
ANISOU  475  O   LEU A  69      17658  15750  16505  -5275   -887  -6028      O
ATOM    476  CB  LEU A  69      -10.866  -0.801   6.689  1.00133.00           C
ANISOU  476  CB  LEU A  69      17959  15302  17273  -5943    -68  -6117      C
ATOM    477  CG  LEU A  69      -11.286  -0.469   8.142  1.00134.17           C
ANISOU  477  CG  LEU A  69      18425  15078  17477  -5855    460  -5929      C
ATOM    478  CD1 LEU A  69      -11.510  -1.728   9.028  1.00135.04           C
ANISOU  478  CD1 LEU A  69      18525  14947  17839  -6478    687  -6091      C
ATOM    479  CD2 LEU A  69      -10.321   0.548   8.822  1.00130.51           C
ANISOU  479  CD2 LEU A  69      18869  13958  16760  -5554    586  -5697      C
ATOM    480  N   SER A  70      -11.270  -1.325   3.538  1.00 93.42           N
ANISOU  480  N   SER A  70      11781  11696  12019  -5985  -1028  -6524      N
ATOM    481  CA  SER A  70      -10.838  -1.771   2.202  1.00 93.65           C
ANISOU  481  CA  SER A  70      11675  12062  11844  -6162  -1468  -6789      C
ATOM    482  C   SER A  70      -12.033  -2.412   1.489  1.00100.30           C
ANISOU  482  C   SER A  70      11644  13737  12726  -6430  -1722  -7061      C
ATOM    483  O   SER A  70      -11.941  -3.502   0.914  1.00101.64           O
ANISOU  483  O   SER A  70      11660  14025  12933  -6991  -1942  -7497      O
ATOM    484  CB  SER A  70       -9.670  -2.764   2.251  1.00 90.36           C
ANISOU  484  CB  SER A  70      11722  11095  11515  -6537  -1395  -6935      C
ATOM    485  OG  SER A  70       -8.420  -2.119   2.047  1.00 86.75           O
ANISOU  485  OG  SER A  70      11826  10282  10854  -6134  -1334  -6590      O
ATOM    486  N   TRP A  71      -13.163  -1.721   1.612  1.00125.48           N
ANISOU  486  N   TRP A  71      14268  17465  15943  -6031  -1658  -6800      N
ATOM    487  CA  TRP A  71      -14.443  -2.035   0.986  1.00133.12           C
ANISOU  487  CA  TRP A  71      14269  19355  16954  -6154  -1927  -6933      C
ATOM    488  C   TRP A  71      -14.522  -0.869   0.016  1.00135.24           C
ANISOU  488  C   TRP A  71      14418  20159  16807  -5438  -2232  -6589      C
ATOM    489  O   TRP A  71      -14.896  -1.010  -1.148  1.00139.97           O
ANISOU  489  O   TRP A  71      14540  21515  17125  -5479  -2724  -6719      O
ATOM    490  CB  TRP A  71      -15.568  -1.857   2.030  1.00136.96           C
ANISOU  490  CB  TRP A  71      14257  19960  17821  -6039  -1510  -6725      C
ATOM    491  CG  TRP A  71      -16.614  -2.961   2.217  1.00142.85           C
ANISOU  491  CG  TRP A  71      14211  21118  18946  -6699  -1494  -7044      C
ATOM    492  CD1 TRP A  71      -16.403  -4.252   2.637  1.00141.81           C
ANISOU  492  CD1 TRP A  71      14228  20565  19089  -7505  -1369  -7444      C
ATOM    493  CD2 TRP A  71      -18.031  -2.821   2.070  1.00151.25           C
ANISOU  493  CD2 TRP A  71      14214  23046  20207  -6593  -1551  -6939      C
ATOM    494  NE1 TRP A  71      -17.595  -4.928   2.712  1.00149.04           N
ANISOU  494  NE1 TRP A  71      14264  22020  20346  -7963  -1350  -7625      N
ATOM    495  CE2 TRP A  71      -18.609  -4.074   2.366  1.00154.98           C
ANISOU  495  CE2 TRP A  71      14219  23601  21065  -7428  -1477  -7326      C
ATOM    496  CE3 TRP A  71      -18.864  -1.766   1.688  1.00156.64           C
ANISOU  496  CE3 TRP A  71      14264  24445  20808  -5864  -1664  -6533      C
ATOM    497  CZ2 TRP A  71      -19.983  -4.298   2.289  1.00163.91           C
ANISOU  497  CZ2 TRP A  71      14227  25544  22506  -7607  -1526  -7340      C
ATOM    498  CZ3 TRP A  71      -20.223  -1.991   1.614  1.00165.52           C
ANISOU  498  CZ3 TRP A  71      14251  26398  22242  -5977  -1729  -6521      C
ATOM    499  CH2 TRP A  71      -20.770  -3.246   1.914  1.00169.08           C
ANISOU  499  CH2 TRP A  71      14209  26952  23082  -6869  -1667  -6932      C
ATOM    500  N   VAL A  72      -14.138   0.296   0.543  1.00170.58           N
ANISOU  500  N   VAL A  72      19399  24190  21225  -4794  -1921  -6141      N
ATOM    501  CA  VAL A  72      -14.155   1.567  -0.172  1.00172.47           C
ANISOU  501  CA  VAL A  72      19670  24739  21124  -4018  -2073  -5702      C
ATOM    502  C   VAL A  72      -13.096   1.599  -1.258  1.00169.65           C
ANISOU  502  C   VAL A  72      19786  24342  20332  -4055  -2421  -5786      C
ATOM    503  O   VAL A  72      -13.392   1.797  -2.434  1.00174.17           O
ANISOU  503  O   VAL A  72      20009  25631  20535  -3858  -2851  -5728      O
ATOM    504  CB  VAL A  72      -13.917   2.765   0.798  1.00169.88           C
ANISOU  504  CB  VAL A  72      19909  23750  20889   3401   1557   5257      C
ATOM    505  CG1 VAL A  72      -13.980   4.084   0.048  1.00172.73           C
ANISOU  505  CG1 VAL A  72      20319  24369  20942  -2580  -1669  -4771      C
ATOM    506  CG2 VAL A  72      -14.927   2.753   1.941  1.00173.00           C
ANISOU  506  CG2 VAL A  72      19919  24129  21686  -3337  -1102  -5180      C
ATOM    507  N   MET A  73      -11.854   1.389  -0.860  1.00145.42           N
ANISOU  507  N   MET A  73      17499  20458  17294  -4312  -2230  -5909      N
ATOM    508  CA  MET A  73      -10.763   1.462  -1.813  1.00142.81           C
```

FIG. 13 Continued

```
ANISOU  508  CA  MET A  73    17640  20018  16601   -4325  -2451  -5960         C
ATOM    509  C   MET A  73    -10.459   0.094  -2.436  1.00142.90               C
ANISOU  509  C   MET A  73    17543  20184  16568   -5031  -2713  -6532         C
ATOM    510  O   MET A  73     -9.337  -0.251  -2.838  1.00139.34               O
ANISOU  510  O   MET A  73    17590  19357  15995   -5250  -2727  -6714         O
ATOM    511  CB  MET A  73     -9.602   2.210  -1.185  1.00136.76               C
ANISOU  511  CB  MET A  73    17707  18373  15881   -4103  -2122  -5695         C
ATOM    512  CG  MET A  73    -10.174   3.322  -0.289  1.00137.84               C
ANISOU  512  CG  MET A  73    17908  18301  16165   -3544  -1779  -5265         C
ATOM    513  SD  MET A  73     -9.582   5.011  -0.565  1.00137.48               S
ANISOU  513  SD  MET A  73    18468  17911  15859   -2784  -1625  -4697         S
ATOM    514  CE  MET A  73    -10.968   6.010   0.011  1.00143.36               C
ANISOU  514  CE  MET A  73    18824  18894  16750   -2072  -1339  -4289         C
ATOM    515  N   GLU A  74    -11.530  -0.681  -2.467  1.00167.23               N
ANISOU  515  N   GLU A  74    19934  23811  19795   -5389  -2879  -6817         N
ATOM    516  CA  GLU A  74    -11.614  -1.902  -3.218  1.00170.11               C
ANISOU  516  CA  GLU A  74    20045  24516  20072   -6036  -3186  -7382         C
ATOM    517  C   GLU A  74    -12.625  -1.460  -4.271  1.00177.84               C
ANISOU  517  C   GLU A  74    20350  26569  20652   -5752  -3655  -7270         C
ATOM    518  O   GLU A  74    -12.575  -1.883  -5.424  1.00181.56               O
ANISOU  518  O   GLU A  74    20727  27557  20700   -5986  -4059  -7575         O
ATOM    519  CB  GLU A  74    -12.238  -3.019  -2.364  1.00171.34               C
ANISOU  519  CB  GLU A  74    19847  24527  20728   -6673  -3027  -7736         C
ATOM    520  CG  GLU A  74    -13.716  -3.269  -2.742  1.00179.74               C
ANISOU  520  CG  GLU A  74    19938  26534  21820   -6837  -3331  -7855         C
ATOM    521  CD  GLU A  74    -14.398  -4.338  -1.904  1.00181.83               C
ANISOU  521  CD  GLU A  74    19811  26656  22618   -7500  -3119  -8172         C
ATOM    522  OE1 GLU A  74    -15.316  -5.000  -2.438  1.00188.90               O
ANISOU  522  OE1 GLU A  74    19997  28241  23536   -7960  -3442  -8509         O
ATOM    523  OE2 GLU A  74    -14.029  -4.511  -0.721  1.00177.05               O
ANISOU  523  OE2 GLU A  74    19610  25272  22390   -7587  -2643  -8075         O
ATOM    524  N   MET A  75    -13.548  -0.589  -3.852  1.00205.39               N
ANISOU  524  N   MET A  75    23379  30396  24265   -5220  -3590  -6814         N
ATOM    525  CA  MET A  75    -14.613  -0.080  -4.721  1.00213.66               C
ANISOU  525  CA  MET A  75    23677  32499  25006   -4846  -4041  -6588         C
ATOM    526  C   MET A  75    -14.089   0.908  -5.760  1.00214.37               C
ANISOU  526  C   MET A  75    24133  32825  24492   -4232  -4277  -6208         C
ATOM    527  O   MET A  75    -14.157   0.645  -6.965  1.00219.07               O
ANISOU  527  O   MET A  75    24569  34099  24569   -4371  -4774  -6391         O
ATOM    528  CB  MET A  75    -15.742   0.573  -3.901  1.00217.28               C
ANISOU  528  CB  MET A  75    23510  33190  25856   -4380  -3815  -6165         C
ATOM    529  CG  MET A  75    -16.862  -0.377  -3.442  1.00222.35               C
ANISOU  529  CG  MET A  75    23288  34253  26941   -4956  -3844  -6492         C
ATOM    530  SD  MET A  75    -18.461   0.418  -3.063  1.00230.95               S
ANISOU  530  SD  MET A  75    23283  36112  28354   -4324  -3784  -5971         S
ATOM    531  CE  MET A  75    -18.129   1.176  -1.473  1.00224.51               C
ANISOU  531  CE  MET A  75    23104  34229  27970   -3845  -2897  -5599         C
ATOM    532  N   ALA A  76    -13.575   2.042  -5.286  1.00177.68               N
ANISOU  532  N   ALA A  76    20016  27604  19892   -3582  -3903  -5685         N
ATOM    533  CA  ALA A  76     13.035   3.076   6.165  1.00178.37               C
ANISOU  533  CA  ALA A  76    20525  27782  19464   -2973  -4022  -5245         C
ATOM    534  C   ALA A  76    -11.823   2.558  -6.949  1.00174.90               C
ANISOU  534  C   ALA A  76    20715  27099  18641   -3375  -4118  -5585         C
ATOM    535  O   ALA A  76    -11.164   3.307  -7.676  1.00174.81               O
ANISOU  535  O   ALA A  76    21172  27050  18198   -2977  -4138  -5264         O
ATOM    536  CB  ALA A  76    -12.677   4.323  -5.364  1.00174.74               C
ANISOU  536  CB  ALA A  76    20575  26595  19222   -2309  -3523  -4686         C
ATOM    537  N   ALA A  77    -11.542   1.266  -6.792  1.00161.89               N
ANISOU  537  N   ALA A  77    19079  25258  17175   -4154  -4125  -6222         N
ATOM    538  CA  ALA A  77    -10.436   0.615  -7.480  1.00159.30               C
ANISOU  538  CA  ALA A  77    19295  24670  16562   -4566  -4148  -6617         C
ATOM    539  C   ALA A  77    -10.869  -0.081  -8.772  1.00166.40               C
ANISOU  539  C   ALA A  77    19860  26458  16908   -4913  -4676  -7033         C
ATOM    540  O   ALA A  77    -10.078  -0.190  -9.705  1.00166.71               O
ANISOU  540  O   ALA A  77    20356  26526  16462   -4978  -4741  -7182         O
ATOM    541  CB  ALA A  77     -9.742  -0.365  -6.549  1.00153.04               C
ANISOU  541  CB  ALA A  77    18820  23026  16302   -5157  -3792  -7040         C
ATOM    542  N   ILE A  78    -12.111  -0.566  -8.820  1.00220.04               N
ANISOU  542  N   ILE A  78    25865  33976  23766   -5170  -5038  -7242         N
```

FIG. 13 Continued

```
ATOM    543  CA  ILE A  78     -12.640  -1.196 -10.033  1.00228.15           C
ANISOU  543  CA  ILE A  78    26527  35934  24227   5550   5623   7658       C
ATOM    544  C   ILE A  78     -12.874  -0.104 -11.057  1.00233.63           C
ANISOU  544  C   ILE A  78    27164  37382  24221  -4857  -5995  -7111       C
ATOM    545  O   ILE A  78     -12.951  -0.348 -12.264  1.00239.92           O
ANISOU  545  O   ILE A  78    27953  38895  24309  -5015  -6458  -7333       O
ATOM    546  CB  ILE A  78     -13.956  -1.946  -9.773  1.00234.33           C
ANISOU  546  CB  ILE A  78    26391  37331  25313  -6042  -5942  -7989       C
ATOM    547  CG1 ILE A  78     -13.719  -3.088  -8.786  1.00229.61           C
ANISOU  547  CG1 ILE A  78    25907  35944  25389  -6762  -5543  -8514       C
ATOM    548  CG2 ILE A  78     -14.530  -2.485 -11.076  1.00243.89           C
ANISOU  548  CG2 ILE A  78    27222  39584  25863  -6440  -6634  -8404       C
ATOM    549  CD1 ILE A  78     -12.471  -3.899  -9.094  1.00225.26           C
ANISOU  549  CD1 ILE A  78    26158  34705  24726  -7214  -5317  -9024       C
ATOM    550  N   MET A  79     -12.976   1.113 -10.536  1.00219.59           N
ANISOU  550  N   MET A  79    25403  35397  22635  -4081  -5760  -6384       N
ATOM    551  CA  MET A  79     -13.127   2.309 -11.341  1.00224.27           C
ANISOU  551  CA  MET A  79    26034  36512  22667  -3291  -5993  -5715       C
ATOM    552  C   MET A  79     -11.843   2.509 -12.129  1.00221.44           C
ANISOU  552  C   MET A  79    26567  35800  21771  -3241  -5836  -5706       C
ATOM    553  O   MET A  79     -11.629   3.550 -12.745  1.00223.78           O
ANISOU  553  O   MET A  79    27153  36262  21611  -2595  -5866  -5112       O
ATOM    554  CB  MET A  79     -13.400   3.513 -10.436  1.00222.08           C
ANISOU  554  CB  MET A  79    25708  35828  22845  -2510  -5617  -4995       C
ATOM    555  CG  MET A  79     -14.821   3.561  -9.874  1.00227.46           C
ANISOU  555  CG  MET A  79    25407  37070  23948  -2345  -5786  -4841       C
ATOM    556  SD  MET A  79     -15.468   1.962  -9.332  1.00228.14           S
ANISOU  556  SD  MET A  79    24834  37341  24509  -3384  -5913  -5675       S
ATOM    557  CE  MET A  79     -17.190   2.376  -9.046  1.00237.41           C
ANISOU  557  CE  MET A  79    24750  39443  26011  -2962  -6186  -5267       C
ATOM    558  N   ALA A  80     -10.983   1.497 -12.082  1.00181.85           N
ANISOU  558  N   ALA A  80    21982  30260  16852  -3916  -5618  -6346       N
ATOM    559  CA  ALA A  80      -9.724   1.499 -12.811  1.00179.54           C
ANISOU  559  CA  ALA A  80    22480  29618  16118  -3961  -5401  -6435       C
ATOM    560  C   ALA A  80     -10.009   1.191 -14.269  1.00188.27           C
ANISOU  560  C   ALA A  80    23531  31697  16305  -4106  -5932  -6672       C
ATOM    561  O   ALA A  80      -9.507   1.862 -15.164  1.00190.75           O
ANISOU  561  O   ALA A  80    24295  32210  15972  -3714  -5939  -6317       O
ATOM    562  CB  ALA A  80      -8.774   0.466 -12.231  1.00172.66           C
ANISOU  562  CB  ALA A  80    22004  27874  15726  -4594  -4978  -7032       C
ATOM    563  N   ILE A  81     -10.799   0.152 -14.504  1.00259.57           N
ANISOU  563  N   ILE A  81    32046  41322  25257  -4719  -6366  -7291       N
ATOM    564  CA  ILE A  81     -11.212  -0.167 -15.861  1.00269.23           C
ANISOU  564  CA  ILE A  81    33172  43571  25553  -4923  -6965  -7567       C
ATOM    565  C   ILE A  81     -12.552   0.552 -16.110  1.00277.35           C
ANISOU  565  C   ILE A  81    33393  45648  26339   4451   7593   7032       C
ATOM    566  O   ILE A  81     -13.445   0.035 -16.790  1.00286.39           O
ANISOU  566  O   ILE A  81    33995  47785  27034  -4809  -8261  -7360       O
ATOM    567  CB  ILE A  81     -11.253  -1.704 -16.128  1.00271.84           C
ANISOU  567  CB  ILE A  81    33474  43972  25840  -5908  -7111  -8594       C
ATOM    568  CG1 ILE A  81      -9.862  -2.324 -15.935  1.00264.54           C
ANISOU  568  CG1 ILE A  81    33361  41989  25164  -6225  -6443  -9019       C
ATOM    569  CG2 ILE A  81     -11.731  -2.009 -17.539  1.00282.94           C
ANISOU  569  CG2 ILE A  81    34813  46491  26202  -6164  -7781  -8924       C
ATOM    570  CD1 ILE A  81      -8.882  -2.028 -17.058  1.00266.39           C
ANISOU  570  CD1 ILE A  81    34357  42275  24586  -6015  -6288  -8971       C
ATOM    571  N   ALA A  82     -12.670   1.752 -15.534  1.00216.15           N
ANISOU  571  N   ALA A  82    25565  37644  18917  -3643  -7364  -6204       N
ATOM    572  CA  ALA A  82     -13.844   2.615 -15.710  1.00223.74           C
ANISOU  572  CA  ALA A  82    25800  39477  19733  -2995  -7844  -5538       C
ATOM    573  C   ALA A  82     -13.421   4.084 -15.811  1.00222.53           C
ANISOU  573  C   ALA A  82    26109  39028  19416  -2012  -7554  -4598       C
ATOM    574  O   ALA A  82     -14.256   4.987 -15.734  1.00227.44           O
ANISOU  574  O   ALA A  82    26232  40086  20096  -1298  -7757  -3906       O
ATOM    575  CB  ALA A  82     -14.838   2.422 -14.573  1.00223.04           C
ANISOU  575  CB  ALA A  82    24858  39369  20518  -3073  -7818  -5556       C
ATOM    576  N   LEU A  83     -12.118   4.304 -15.996  1.00273.64           N
ANISOU  576  N   LEU A  83    33522  44739  25712  -1985  -7054  -4572       N
ATOM    577  CA  LEU A  83     -11.540   5.649 -16.092  1.00272.18           C
```

FIG. 13 Continued

```
ANISOU  577  CA   LEU A  83     33905  44112  25400   -1171  -6686  -3735           C
ATOM    578  C    LEU A  83       10.275    5.728   16.973  1.00270.98             C
ANISOU  578  C    LEU A  83     34672  43673  24616   -1251  -6414  -3763           C
ATOM    579  O    LEU A  83       -9.533    6.713  -16.901  1.00268.00             O
ANISOU  579  O    LEU A  83     34880  42666  24283    -750  -5946  -3178           O
ATOM    580  CB   LEU A  83      -11.217    6.194  -14.695  1.00263.42             C
ANISOU  580  CB   LEU A  83     32948  41900  25240    -921  -6032  -3477           C
ATOM    581  CG   LEU A  83      -12.369    6.450  -13.719  1.00264.52             C
ANISOU  581  CG   LEU A  83     32315  42150  26039    -626  -6088  -3255           C
ATOM    582  CD1  LEU A  83      -11.834    6.609  -12.303  1.00254.95             C
ANISOU  582  CD1  LEU A  83     31421  39757  25690    -678  -5400  -3294           C
ATOM    583  CD2  LEU A  83      -13.180    7.668  -14.135  1.00272.54             C
ANISOU  583  CD2  LEU A  83     33022  43739  26792     332  -6334  -2372           C
ATOM    584  N    ALA A  84      -10.033    4.698  -17.790  1.00194.10             N
ANISOU  584  N    ALA A  84     25070  34369  14312   -1894  -6662  -4452           N
ATOM    585  CA   ALA A  84       -8.869    4.649  -18.687  1.00194.08             C
ANISOU  585  CA   ALA A  84     25906  34166  13670   -2012  -6365  -4556           C
ATOM    586  C    ALA A  84       -8.703    3.274  -19.334  1.00196.79             C
ANISOU  586  C    ALA A  84     26333  34864  13576   -2842  -6568  -5518           C
ATOM    587  O    ALA A  84       -7.583    2.774  -19.468  1.00192.64             O
ANISOU  587  O    ALA A  84     26415  33723  13056   -3196  -6067  -5927           O
ATOM    588  CB   ALA A  84       -7.589    5.032  -17.943  1.00184.22             C
ANISOU  588  CB   ALA A  84     25279  31658  13059   -1940  -5540  -4394           C
ATOM    589  N    ASN A  85       -9.819    2.665  -19.723  1.00255.11             N
ANISOU  589  N    ASN A  85     33093  43221  20617   -3156  -7285  -5885           N
ATOM    590  CA   ASN A  85       -9.804    1.336  -20.328  1.00259.05             C
ANISOU  590  CA   ASN A  85     33657  44075  20694   -4001  -7526  -6863           C
ATOM    591  C    ASN A  85       -9.722    1.327  -21.863  1.00269.12             C
ANISOU  591  C    ASN A  85     35363  46242  20649   -4021  -7906  -6943           C
ATOM    592  O    ASN A  85      -10.702    1.647  -22.540  1.00278.76             O
ANISOU  592  O    ASN A  85     36157  48572  21187   -3812  -8656  -6664           O
ATOM    593  CB   ASN A  85      -11.029    0.534  -19.862  1.00262.23             C
ANISOU  593  CB   ASN A  85     33155  44990  21492   -4513  -8081  -7351           C
ATOM    594  CG   ASN A  85      -12.350    1.264  -20.113  1.00270.69             C
ANISOU  594  CG   ASN A  85     33426  47149  22274   -4019  -8825  -6737           C
ATOM    595  OD1  ASN A  85      -12.375    2.475  -20.339  1.00272.29             O
ANISOU  595  OD1  ASN A  85     33723  47518  22218   -3180  -8832  -5843           O
ATOM    596  ND2  ASN A  85      -13.454    0.523  -20.070  1.00276.73             N
ANISOU  596  ND2  ASN A  85     33376  48645  23125   -4539  -9440  -7200           N
ATOM    597  N    GLY A  86       -8.563    0.961  -22.412  1.00185.93             N
ANISOU  597  N    GLY A  86     25658  35253   9735   -4259  -7389  -7307           N
ATOM    598  CA   GLY A  86       -8.433    0.853  -23.853  1.00195.82             C
ANISOU  598  CA   GLY A  86     27413  37308   9683   -4344  -7666  -7475           C
ATOM    599  C    GLY A  86       -9.336   -0.281  -24.303  1.00204.02             C
ANISOU  599  C    GLY A  86     28049  39181  10290   -5111  -8379  -8359           C
ATOM    600  O    GLY A  86       -8.959   -1.446  -24.211  1.00202.40             O
ANISOU  600  O    GLY A  86     28060  38544  10300   -5845  -8122  -9293           O
ATOM    601  N    ASP A  87      -10.534    0.055  -24.773  1.00267.84             N
ANISOU  601  N    ASP A  87     35523  48441  17802   -4948  -9278  -8058           N
ATOM    602  CA   ASP A  87      -11.520   -0.949  -25.183  1.00276.92             C
ANISOU  602  CA   ASP A  87     36163  50496  18556   -5715 -10075  -8855           C
ATOM    603  C    ASP A  87      -11.404   -1.349  -26.664  1.00288.55             C
ANISOU  603  C    ASP A  87     38251  52831  18554   -6069 -10465  -9331           C
ATOM    604  O    ASP A  87      -11.142   -0.503  -27.518  1.00293.54             O
ANISOU  604  O    ASP A  87     39353  53930  18248   -5486 -10533  -8689           O
ATOM    605  CB   ASP A  87      -12.931   -0.440  -24.871  1.00281.98             C
ANISOU  605  CB   ASP A  87     35694  52028  19418   -5408 -10893  -8309           C
ATOM    606  CG   ASP A  87      -13.995   -1.498  -25.079  1.00290.70             C
ANISOU  606  CG   ASP A  87     36099  53986  20368   -6283 -11698  -9132           C
ATOM    607  OD1  ASP A  87      -14.253   -1.881  -26.242  1.00302.06             O
ANISOU  607  OD1  ASP A  87     37747  56385  20636   -6677 -12321  -9551           O
ATOM    608  OD2  ASP A  87      -14.586   -1.937  -24.071  1.00286.76             O
ANISOU  608  OD2  ASP A  87     34846  53205  20903   -6604 -11706  -9359           O
ATOM    609  N    GLY A  88      -11.619   -2.632  -26.964  1.00268.96             N
ANISOU  609  N    GLY A  88     35801  50545  15845   -7036 -10708 -10456           N
ATOM    610  CA   GLY A  88      -11.513   -3.148  -28.326  1.00280.59             C
ANISOU  610  CA   GLY A  88     37926  52781  15904   -7496 -11049 -11080           C
ATOM    611  C    GLY A  88      -10.139   -3.723  -28.659  1.00276.94             C
ANISOU  611  C    GLY A  88     38584  51392  15247   -7753 -10086 -11695           C
```

FIG. 13 Continued

```
ATOM    612  O   GLY A  88      -9.937  -4.294 -29.740  1.00286.31           O
ANISOU  612  O   GLY A  88    40439  53043  15302   8211  10201  12370       O
ATOM    613  N   ARG A  89      -9.199  -3.556 -27.721  1.00370.70           N
ANISOU  613  N   ARG A  89    50650  61975  28225  -7445  -9136 -11448       N
ATOM    614  CA  ARG A  89      -7.812  -4.038 -27.835  1.00365.82           C
ANISOU  614  CA  ARG A  89    50953  60333  27707  -7581  -8111 -11905       C
ATOM    615  C   ARG A  89      -7.522  -5.194 -26.866  1.00358.37           C
ANISOU  615  C   ARG A  89    49883  58326  27955   8213   7621  12725       C
ATOM    616  O   ARG A  89      -8.099  -5.255 -25.777  1.00352.26           O
ANISOU  616  O   ARG A  89    48350  57264  28227  -8274  -7792 -12588       O
ATOM    617  CB  ARG A  89      -6.824  -2.893 -27.577  1.00357.65           C
ANISOU  617  CB  ARG A  89    50274  58640  26977  -6711  -7377 -10911       C
ATOM    618  CG  ARG A  89      -7.062  -1.658 -28.430  1.00364.40           C
ANISOU  618  CG  ARG A  89    51284  60390  26780  -5999  -7760  -9956       C
ATOM    619  CD  ARG A  89      -6.418  -1.785 -29.802  1.00373.55           C
ANISOU  619  CD  ARG A  89    53414  61963  26555  -6081  -7533 -10229       C
ATOM    620  NE  ARG A  89      -5.072  -1.220 -29.824  1.00367.58           N
ANISOU  620  NE  ARG A  89    53343  60347  25972  -5608  -6496  -9760       N
ATOM    621  CZ  ARG A  89      -4.787   0.007 -30.248  1.00369.09           C
ANISOU  621  CZ  ARG A  89    53827  60748  25664  -4868  -6357  -8730       C
ATOM    622  NH1 ARG A  89      -5.754   0.799 -30.692  1.00376.42           N
ANISOU  622  NH1 ARG A  89    54445  62709  25870  -4450  -7196  -8034       N
ATOM    623  NH2 ARG A  89      -3.535   0.441 -30.234  1.00363.93           N
ANISOU  623  NH2 ARG A  89    53755  59265  25258  -4544  -5373  -8371       N
ATOM    624  N   PRO A  90      -6.605  -6.102 -27.249  1.00280.71           N
ANISOU  624  N   PRO A  90    40816  47871  17972  -8645  -6955 -13545       N
ATOM    625  CA  PRO A  90      -6.293  -7.292 -26.442  1.00275.32           C
ANISOU  625  CA  PRO A  90    40110  46160  18341  -9248  -6469 -14357       C
ATOM    626  C   PRO A  90      -5.168  -7.225 -25.388  1.00262.35           C
ANISOU  626  C   PRO A  90    38581  43151  17948  -8898  -5504 -14040       C
ATOM    627  O   PRO A  90      -4.611  -8.283 -25.101  1.00260.51           O
ANISOU  627  O   PRO A  90    38640  42076  18267  -9351  -4955 -14779       O
ATOM    628  CB  PRO A  90      -5.925  -8.349 -27.509  1.00285.12           C
ANISOU  628  CB  PRO A  90    42167  47475  18690  -9887  -6259 -15455       C
ATOM    629  CG  PRO A  90      -6.238  -7.715 -28.865  1.00296.41           C
ANISOU  629  CG  PRO A  90    43960  50156  18506  -9691  -6805 -15238       C
ATOM    630  CD  PRO A  90      -6.107  -6.242 -28.628  1.00290.54           C
ANISOU  630  CD  PRO A  90    42958  49586  17847  -8735  -6813 -13921       C
ATOM    631  N   PRO A  91      -4.834  -6.043 -24.831  1.00234.50           N
ANISOU  631  N   PRO A  91    34850  39392  14857  -8135  -5307 -12991       N
ATOM    632  CA  PRO A  91      -3.783  -6.037 -23.795  1.00222.99           C
ANISOU  632  CA  PRO A  91    33466  36678  14584  -7896  -4473 -12746       C
ATOM    633  C   PRO A  91      -4.043  -6.998 -22.627  1.00217.34           C
ANISOU  633  C   PRO A  91    32313  35228  15036  -8390  -4409 -13229       C
ATOM    634  O   PRO A  91      -4.192  -8.206 -22.825  1.00221.98           O
ANISOU  634  O   PRO A  91    33055  35675  15613  -9066  -4395 -14162       O
ATOM    635  CB  PRO A  91      -3.792  -4.586 -23.287  1.00216.76           C
ANISOU  635  CB  PRO A  91    32364  35933  14061  -7117  -4534 -11577       C
ATOM    636  CG  PRO A  91      -4.255  -3.792 -24.444  1.00225.66           C
ANISOU  636  CG  PRO A  91    33657  38161  13924  -6795  -5028 -11178       C
ATOM    637  CD  PRO A  91      -5.227  -4.674 -25.213  1.00236.45           C
ANISOU  637  CD  PRO A  91    34928  40431  14482  -7447  -5737 -12002       C
ATOM    638  N   ASP A  92      -4.083  -6.454 -21.413  1.00278.08           N
ANISOU  638  N   ASP A  92    39521  42425  23713  -8058  -4338 -12590       N
ATOM    639  CA  ASP A  92      -4.300  -7.261 -20.212  1.00272.38           C
ANISOU  639  CA  ASP A  92    38406  40980  24105  -8457  -4238 -12910       C
ATOM    640  C   ASP A  92      -5.398  -6.673 -19.314  1.00269.16           C
ANISOU  640  C   ASP A  92    37197  40904  24167  -8305  -4779 -12375       C
ATOM    641  O   ASP A  92      -5.227  -5.618 -18.700  1.00262.72           O
ANISOU  641  O   ASP A  92    36213  39903  23705  -7701  -4675 -11544       O
ATOM    642  CB  ASP A  92      -2.993  -7.415 -19.416  1.00263.72           C
ANISOU  642  CB  ASP A  92    37581  38658  23963  -8239  -3371 -12706       C
ATOM    643  CG  ASP A  92      -1.888  -8.113 -20.209  1.00267.29           C
ANISOU  643  CG  ASP A  92    38745  38688  24127  -2728 -13255              C
ATOM    644  OD1 ASP A  92      -2.115  -8.476 -21.384  1.00276.28           O
ANISOU  644  OD1 ASP A  92    40273  40453  24248  -8667  -2925 -13857       O
ATOM    645  OD2 ASP A  92      -0.782  -8.300 -19.651  1.00261.60           O
ANISOU  645  OD2 ASP A  92    38195  37023  24180  -8195  -2024 -13089       O
ATOM    646  N   TRP A  93      -6.521  -7.382 -19.242  1.00232.09           N
```

FIG. 13 Continued

```
ANISOU  646  N    TRP A  93    32013  36671  19498   -8879  -5312 -12878       N
ATOM    647  CA   TRP A  93     -7.685  -6.984 -18.448  1.00 230.81            C
ANISOU  647  CA   TRP A  93    31018  36905  19776   -8822  -5821 -12487       C
ATOM    648  C    TRP A  93     -7.264  -6.608 -17.021  1.00 219.80            C
ANISOU  648  C    TRP A  93    29459  34563  19491   -8459  -5320 -11911       C
ATOM    649  O    TRP A  93     -7.913  -5.791 -16.358  1.00 216.89            O
ANISOU  649  O    TRP A  93    28575  34423  19410   -8084  -5566 -11304       O
ATOM    650  CB   TRP A  93     -8.685  -8.166 -18.445  1.00 238.15            C
ANISOU  650  CB   TRP A  93    31491  38129  20867   -9651  -6173 -13228       C
ATOM    651  CG   TRP A  93    -10.104  -7.931 -17.901  1.00 240.15            C
ANISOU  651  CG   TRP A  93    30799  39080  21366   -9784  -6858 -13046       C
ATOM    652  CD1  TRP A  93    -10.533  -8.116 -16.614  1.00 235.14            C
ANISOU  652  CD1  TRP A  93    29623  37934  21786   -9850  -6638 -12823       C
ATOM    653  CD2  TRP A  93    -11.268  -7.541 -18.654  1.00 249.70            C
ANISOU  653  CD2  TRP A  93    31433  41609  21833   -9814  -7729 -12962       C
ATOM    654  NE1  TRP A  93    -11.877  -7.836 -16.515  1.00 239.95            N
ANISOU  654  NE1  TRP A  93    29371  39470  22330   -9968  -7362 -12710       N
ATOM    655  CE2  TRP A  93    -12.350  -7.480 -17.750  1.00 249.34            C
ANISOU  655  CE2  TRP A  93    30468  41786  22483   -9904  -8016 -12726       C
ATOM    656  CE3  TRP A  93    -11.494  -7.220 -19.996  1.00 259.15            C
ANISOU  656  CE3  TRP A  93    32791  43839  21836   -9740  -8280 -13008       C
ATOM    657  CZ2  TRP A  93    -13.634  -7.113 -18.145  1.00 258.13            C
ANISOU  657  CZ2  TRP A  93    30746  44121  23211   -9905  -8833 -12528       C
ATOM    658  CZ3  TRP A  93    -12.769  -6.856 -20.386  1.00 267.90            C
ANISOU  658  CZ3  TRP A  93    33104  46176  22510   -9748  -9155 -12799       C
ATOM    659  CH2  TRP A  93    -13.823  -6.806 -19.464  1.00 267.36            C
ANISOU  659  CH2  TRP A  93    32050  46308  23228   -9821  -9427 -12557       C
ATOM    660  N    GLN A  94     -6.127  -7.165 -16.605  1.00 252.24            N
ANISOU  660  N    GLN A  94    33994  37616  24231   -8477  -4527 -11975       N
ATOM    661  CA   GLN A  94     -5.627  -7.128 -15.221  1.00 243.36            C
ANISOU  661  CA   GLN A  94    32748  35506  24213   -8252  -3978 -11502       C
ATOM    662  C    GLN A  94     -5.497  -5.834 -14.409  1.00 235.41            C
ANISOU  662  C    GLN A  94    31627  34326  23491   -7629  -3973 -10692       C
ATOM    663  O    GLN A  94     -4.588  -5.728 -13.584  1.00 228.61            O
ANISOU  663  O    GLN A  94    30956  32595  23311   -7397  -3420 -10327       O
ATOM    664  CB   GLN A  94     -4.328  -7.943 -15.091  1.00 241.13            C
ANISOU  664  CB   GLN A  94    32953  34244  24421   -8338  -3203 -11689       C
ATOM    665  CG   GLN A  94     -3.219  -7.549 -16.050  1.00 241.43            C
ANISOU  665  CG   GLN A  94    33632  34246  23856   -8070  -2939 -11714       C
ATOM    666  CD   GLN A  94     -2.080  -8.552 -16.057  1.00 241.42            C
ANISOU  666  CD   GLN A  94    34034  33392  24305   -8242  -2227 -12057       C
ATOM    667  OE1  GLN A  94     -1.260  -8.572 -16.975  1.00 243.98            O
ANISOU  667  OE1  GLN A  94    34892  33702  24106   -8177  -1952 -12317       O
ATOM    668  NE2  GLN A  94     -2.029  -9.396 -15.032  1.00 239.05            N
ANISOU  668  NE2  GLN A  94    33494  32391  24942   -8435  -1906 -12053       N
ATOM    669  N    ASP A  95     -6.372  -4.857 -14.614  1.00 154.30            N
ANISOU  669  N    ASP A  95    21048  24863  12717   -7346  -4578 -10386       N
ATOM    670  CA   ASP A  95     -6.365  -3.725 -13.690  1.00 147.97            C
ANISOU  670  CA   ASP A  95    20088  23776  12358   -6753  -4448  -9579       C
ATOM    671  C    ASP A  95     -7.572  -3.777 -12.746  1.00 147.86            C
ANISOU  671  C    ASP A  95    19373  23955  12853   -6863  -4721  -9493       C
ATOM    672  O    ASP A  95     -7.476  -3.369 -11.584  1.00 141.47            O
ANISOU  672  O    ASP A  95    18492  22565  12697   -6638  -4447  -9101       O
ATOM    673  CB   ASP A  95     -6.225  -2.373 -14.383  1.00 149.64            C
ANISOU  673  CB   ASP A  95    20474  24438  11946   -6055  -4545  -8884       C
ATOM    674  CG   ASP A  95     -5.397  -1.412 -13.562  1.00 141.77            C
ANISOU  674  CG   ASP A  95    19760  22665  11442   -5553  -4081  -8227       C
ATOM    675  OD1  ASP A  95     -5.123  -0.289 -14.026  1.00 142.55            O
ANISOU  675  OD1  ASP A  95    20092  22927  11143   -4996  -4040  -7629       O
ATOM    676  OD2  ASP A  95     -5.004  -1.799 -12.443  1.00 135.30            O
ANISOU  676  OD2  ASP A  95    18955  21051  11401   -5747  -3758  -8313       O
ATOM    677  N    PHE A  96     -8.699  -4.275 -13.261  1.00 204.06            N
ANISOU  677  N    PHE A  96    25976  31910  19647   -7232  -5253  -9869       N
ATOM    678  CA   PHE A  96     -9.883  -4.524 -12.444  1.00 205.40            C
ANISOU  678  CA   PHE A  96    25404  32310  20327   -7461  -5484  -9891       C
ATOM    679  C    PHE A  96     -9.574  -5.748 -11.614  1.00 202.25            C
ANISOU  679  C    PHE A  96    25105  31067  20673   -8060  -5044 -10372       C
ATOM    680  O    PHE A  96     -9.792  -5.756 -10.402  1.00 197.88            O
ANISOU  680  O    PHE A  96    24324  30021  20842   -8022  -4757 -10118       O
```

FIG. 13 Continued

```
ATOM    681  CB  PHE A  96     -11.114   -4.816  -13.294  1.00215.84           C
ANISOU  681  CB  PHE A  96     26101  34787  21120   -7775  -6185 -10191       C
ATOM    682  CG  PHE A  96     -12.033   -5.852  -12.689  1.00218.74           C
ANISOU  682  CG  PHE A  96     25865  35207  22037   -8499  -6321 -10703       C
ATOM    683  CD1 PHE A  96     -13.040   -5.483  -11.815  1.00218.91           C
ANISOU  683  CD1 PHE A  96     25139  35458  22581   -8342  -6409 -10320       C
ATOM    684  CD2 PHE A  96     -11.889   -7.197  -13.002  1.00222.13           C
ANISOU  684  CD2 PHE A  96     26492  35418  22490    9326   6279  11547       C
ATOM    685  CE1 PHE A  96     -13.878   -6.434  -11.263  1.00222.13           C
ANISOU  685  CE1 PHE A  96     24976  35910  23513   -9040  -6480 -10766       C
ATOM    686  CE2 PHE A  96     -12.724   -8.153  -12.453  1.00226.05           C
ANISOU  686  CE2 PHE A  96     26453  35890  23546   -9969  -6275 -11921       C
ATOM    687  CZ  PHE A  96     -13.718   -7.772  -11.583  1.00225.25           C
ANISOU  687  CZ  PHE A  96     25586  36074  23925   -9921  -6484 -11616       C
ATOM    688  N   VAL A  97      -9.084   -6.794  -12.278  1.00211.83           N
ANISOU  688  N   VAL A  97     26650  32092  21742   -8494   4832  10908       N
ATOM    689  CA  VAL A  97      -8.642   -7.981  -11.563  1.00210.57           C
ANISOU  689  CA  VAL A  97     26639  31040  22326   -8866  -4207 -11141       C
ATOM    690  C   VAL A  97      -7.304   -7.655  -10.905  1.00202.28           C
ANISOU  690  C   VAL A  97     26106  29035  21719   -8390  -3557 -10641       C
ATOM    691  O   VAL A  97      -6.729   -8.490  -10.210  1.00200.21           O
ANISOU  691  O   VAL A  97     26014  27985  22073   -8532  -3018 -10660       O
ATOM    692  CB  VAL A  97      -8.521   -9.248  -12.446  1.00218.07           C
ANISOU  692  CB  VAL A  97     27818  32018  23022   -9491  -4155 -11914       C
ATOM    693  CG1 VAL A  97      -9.746   -9.419  -13.322  1.00227.39           C
ANISOU  693  CG1 VAL A  97     28536  34291  23570   -9968  -4919 -12416       C
ATOM    694  CG2 VAL A  97       7.257    9.208   13.273  1.00217.30           C
ANISOU  694  CG2 VAL A  97     28423  31622  22520   -9274  -3842 -11995       C
ATOM    695  N   GLY A  98      -6.805   -6.439  -11.140  1.00123.66           N
ANISOU  695  N   GLY A  98     16386  19181  11417   -7834  -3643 -10184       N
ATOM    696  CA  GLY A  98      -5.604   -5.974  -10.475  1.00116.21           C
ANISOU  696  CA  GLY A  98     15847  17413  10895   -7410  -3115  -9671       C
ATOM    697  C   GLY A  98      -5.972   -5.873   -9.014  1.00111.63           C
ANISOU  697  C   GLY A  98     14988  16399  11026   -7321  -2931  -9290       C
ATOM    698  O   GLY A  98      -5.206   -6.233   -8.128  1.00107.52           O
ANISOU  698  O   GLY A  98     14660  15109  11085   -7253  -2436  -9041       O
ATOM    699  N   ILE A  99      -7.192   -5.412   -8.775  1.00165.25           N
ANISOU  699  N   ILE A  99     21302  23761  17725   -7331  -3366  -9261       N
ATOM    700  CA  ILE A  99      -7.696   -5.235   -7.427  1.00161.68           C
ANISOU  700  CA  ILE A  99     20584  22992  17855   -7262  -3216  -8954       C
ATOM    701  C   ILE A  99      -8.484   -6.439   -6.905  1.00165.46           C
ANISOU  701  C   ILE A  99     20673  23441  18753   -7813  -3130  -9319       C
ATOM    702  O   ILE A  99      -8.333   -6.811   -5.749  1.00162.37           O
ANISOU  702  O   ILE A  99     20333  22431  18928   -7836  -2714  -9112       O
ATOM    703  CB  ILE A  99      -8.521   -3.945   -7.312  1.00160.68           C
ANISOU  703  CB  ILE A  99     20164  23414  17472   -6907  -3672  -8674       C
ATOM    704  CG1 ILE A  99      -7.789   -2.784   -8.008  1.00158.49           C
ANISOU  704  CG1 ILE A  99     20322  23224  16671   -6377  -3770  -8335       C
ATOM    705  CG2 ILE A  99      -8.783   -3.615   -5.848  1.00156.08           C
ANISOU  705  CG2 ILE A  99     19487  22336  17481   -6769  -3392  -8329       C
ATOM    706  CD1 ILE A  99      -6.462   -2.362   -7.351  1.00151.57           C
ANISOU  706  CD1 ILE A  99     20036  21413  16141   -6089  -3238  -7935       C
ATOM    707  N   ILE A 100      -9.318   -7.051   -7.740  1.00205.79           N
ANISOU  707  N   ILE A 100     25412  29225  23552   -8282  -3535  -9859       N
ATOM    708  CA  ILE A 100     -10.046   -8.240   -7.295  1.00210.18           C
ANISOU  708  CA  ILE A 100     25623  29713  24522   -8892  -3434 -10253       C
ATOM    709  C   ILE A 100      -9.047   -9.339   -6.939  1.00208.98           C
ANISOU  709  C   ILE A 100     25966  28662  24774   -9058  -2808 -10351       C
ATOM    710  O   ILE A 100      -9.336  -10.196   -6.106  1.00209.92           O
ANISOU  710  O   ILE A 100     25982  28378  25400   -9388  -2515 -10440       O
ATOM    711  CB  ILE A 100     -11.076   -8.770   -8.340  1.00219.44           C
ANISOU  711  CB  ILE A 100     26314  31793  25269   -9470  -4022 -10881       C
ATOM    712  CG1 ILE A 100     -12.136   -9.655   -7.669  1.00223.87           C
ANISOU  712  CG1 ILE A 100     26322  32403  26334  -10090  -4010 -11178       C
ATOM    713  CG2 ILE A 100     -10.391   -9.573   -9.430  1.00223.76           C
ANISOU  713  CG2 ILE A 100     27320  32267  25431   -9764  -3953 -11390       C
ATOM    714  CD1 ILE A 100     -12.929   -8.978   -6.565  1.00220.72           C
ANISOU  714  CD1 ILE A 100     25411  32104  26351   -9898  -4042 -10759       C
ATOM    715  N   CYS A 101      -7.870   -9.308   -7.562  1.00169.75           N
```

FIG. 13 Continued

```
ANISOU  715  N    CYS A 101      21518  23395  19583   -8822  -2608 -10321        N
ATOM    716  CA   CYS A 101       -6.837 -10.294  -7.269  1.00168.82              C
ANISOU  716  CA   CYS A 101      21825  22463  19855   -8909  -2051 -10380        C
ATOM    717  C    CYS A 101       -6.316 -10.004  -5.878  1.00162.03              C
ANISOU  717  C    CYS A 101      21085  20948  19530   -8525  -1667  -9743        C
ATOM    718  O    CYS A 101       -6.248 -10.893  -5.032  1.00162.25              O
ANISOU  718  O    CYS A 101      21156  20455  20034   -8722  -1333  -9739        O
ATOM    719  CB   CYS A 101       -5.698 -10.226  -8.281  1.00168.79              C
ANISOU  719  CB   CYS A 101      22288  22350  19495   -8730  -1937 -10491        C
ATOM    720  SG   CYS A 101       -4.994 -11.838  -8.684  1.00173.74              S
ANISOU  720  SG   CYS A 101      23280  22392  20342   -9183  -1500 -11091        S
ATOM    721  N    LEU A 102       -5.964  -8.743  -5.648  1.00112.15              N
ANISOU  721  N    LEU A 102      14854  14670  13089   -7998  -1741  -9218        N
ATOM    722  CA   LEU A 102       -5.526  -8.277  -4.333  1.00106.16              C
ANISOU  722  CA   LEU A 102      14228  13383  12726   -7639  -1461  -8614        C
ATOM    723  C    LEU A 102       -6.443  -8.756  -3.200  1.00106.94              C
ANISOU  723  C    LEU A 102      14057  13369  13206   -7889  -1365  -8603        C
ATOM    724  O    LEU A 102       -5.998  -9.034  -2.089  1.00104.13              O
ANISOU  724  O    LEU A 102      13893  12457  13216   -7789  -1036  -8274        O
ATOM    725  CB   LEU A 102       -5.526  -6.752  -4.332  1.00102.08              C
ANISOU  725  CB   LEU A 102      13741  13098  11946   -7176  -1685  -8203        C
ATOM    726  CG   LEU A 102       -5.884  -6.063  -3.015  1.00 98.08              C
ANISOU  726  CG   LEU A 102      13187  12370  11708   -6949  -1601  -7761        C
ATOM    727  CD1  LEU A 102       -4.627  -5.842  -2.205  1.00 93.22              C
ANISOU  727  CD1  LEU A 102      12993  11092  11335   -6634  -1254  -7258        C
ATOM    728  CD2  LEU A 102       -6.583  -4.738  -3.261  1.00 97.15              C
ANISOU  728  CD2  LEU A 102      12910  12729  11274   -6689  -1974  -7651        C
ATOM    729  N    LEU A 103       -7.729  -8.860  -3.504  1.00118.11              N
ANISOU  729  N    LEU A 103      15010  15359  14506   -8244  -1684  -8975        N
ATOM    730  CA   LEU A 103       -8.739  -9.184  -2.509  1.00119.39              C
ANISOU  730  CA   LEU A 103      14836  15510  15017   -8527  -1620  -8996        C
ATOM    731  C    LEU A 103       -9.247 -10.623  -2.531  1.00125.45              C
ANISOU  731  C    LEU A 103      15437  16188  16040   -9183  -1499  -9499        C
ATOM    732  O    LEU A 103      -10.399 -10.896  -2.177  1.00129.03              O
ANISOU  732  O    LEU A 103      15427  16923  16675   -9593  -1608  -9710        O
ATOM    733  CB   LEU A 103       -9.878  -8.177  -2.622  1.00120.07              C
ANISOU  733  CB   LEU A 103      14417  16294  14909   -8466  -2060  -8991        C
ATOM    734  CG   LEU A 103        9.199   6.802   2.634  1.00114.27              C
ANISOU  734  CG   LEU A 103      13995  15494  13930   -7820  -2120  -8513        C
ATOM    735  CD1  LEU A 103      -10.154  -5.667  -2.966  1.00114.98              C
ANISOU  735  CD1  LEU A 103      13656  16294  13736   -7646  -2621  -8497        C
ATOM    736  CD2  LEU A 103       -8.508  -6.556  -1.307  1.00108.72              C
ANISOU  736  CD2  LEU A 103      13698  14051  13558   -7521  -1672  -8008        C
ATOM    737  N    VAL A 104       -8.382 -11.532  -2.959  1.00179.12              N
ANISOU  737  N    VAL A 104      22601  22574  22880   -9308  -1265  -9708        N
ATOM    738  CA   VAL A 104       -8.665 -12.960  -2.893  1.00184.79              C
ANISOU  738  CA   VAL A 104      23312  23001  23899   -9916  -1059 -10173        C
ATOM    739  C    VAL A 104       -7.415 -13.538  -2.257  1.00181.66              C
ANISOU  739  C    VAL A 104      23442  21761  23820   -9673   -585  -9874        C
ATOM    740  O    VAL A 104       -7.222 -14.751  -2.160  1.00185.45              O
ANISOU  740  O    VAL A 104      24104  21764  24594  -10040   -312 -10167        O
ATOM    741  CB   VAL A 104       -9.011 -13.592  -4.264  1.00192.08              C
ANISOU  741  CB   VAL A 104      24119  24352  24511  -10430  -1333 -10902        C
ATOM    742  CG1  VAL A 104       -9.030 -15.126  -4.184  1.00197.92              C
ANISOU  742  CG1  VAL A 104      25021  24570  25609  -11046  -1017 -11392        C
ATOM    743  CG2  VAL A 104      -10.369 -13.087  -4.742  1.00196.18              C
ANISOU  743  CG2  VAL A 104      23997  25794  24749  -10727  -1892 -11168        C
ATOM    744  N    ILE A 105       -6.550 -12.623  -1.844  1.00160.90              N
ANISOU  744  N    ILE A 105      21046  18960  21128   -9056   -523  -9289        N
ATOM    745  CA   ILE A 105       -5.402 -12.980  -1.037  1.00157.59              C
ANISOU  745  CA   ILE A 105      21028  17840  21010   -8773   -172  -8887        C
ATOM    746  C    ILE A 105       -5.760 -12.513   0.393  1.00154.05              C
ANISOU  746  C    ILE A 105      20556  17242  20732   -8605    -92  -8389        C
ATOM    747  O    ILE A 105       -5.281 -13.072   1.384  1.00153.17              O
ANISOU  747  O    ILE A 105      20698  16588  20913   -8573    167  -8123        O
ATOM    748  CB   ILE A 105        4.078  12.394   1.593  1.00153.87              C
ANISOU  748  CB   ILE A 105      20835  17263  20365   -8295   -165  -8635        C
ATOM    749  CG1  ILE A 105       -3.980 -12.659  -3.086  1.00157.86              C
ANISOU  749  CG1  ILE A 105      21346  18056  20576   -8501   -280  -9188        C
```

FIG. 13 Continued

```
ATOM    750  CG2 ILE A 105      -2.883 -13.086  -0.988  1.00152.62           C
ANISOU  750  CG2 ILE A 105    21009  16412  20566  -8136    149   -8392      C
ATOM    751  CD1 ILE A 105      -3.680 -14.097  -3.404  1.00163.08           C
ANISOU  751  CD1 ILE A 105    22194  18276  21493  -8902    -10   -9683      C
ATOM    752  N   ASN A 106      -6.631 -11.506   0.496  1.00113.13           N
ANISOU  752  N   ASN A 106    15086  12542  15357  -8521   -322   -8295      N
ATOM    753  CA  ASN A 106      -7.121 -11.070   1.803  1.00110.70           C
ANISOU  753  CA  ASN A 106    14761  12111  15188  -8440   -217   -7933      C
ATOM    754  C   ASN A 106      -8.276 -11.933   2.252  1.00115.53           C
ANISOU  754  C   ASN A 106    15082  12740  16072  -9021   -110   -8262      C
ATOM    755  O   ASN A 106      -8.575 -11.989   3.425  1.00114.69           O
ANISOU  755  O   ASN A 106    15053  12366  16159  -9078    101   -8020      O
ATOM    756  CB  ASN A 106      -7.507  -9.602   1.808  1.00107.22           C
ANISOU  756  CB  ASN A 106    14177  12073  14490  -8092   -452   -7697      C
ATOM    757  CG  ASN A 106      -6.295  -8.704   1.870  1.00102.00           C
ANISOU  757  CG  ASN A 106    13904  11194  13656  -7537   -449   -7225      C
ATOM    758  OD1 ASN A 106      -6.409  -7.499   2.122  1.00 98.81           O
ANISOU  758  OD1 ASN A 106    13536  10919  13091  -7223   -560   -6955      O
ATOM    759  ND2 ASN A 106      -5.110  -9.292   1.652  1.00101.52           N
ANISOU  759  ND2 ASN A 106    14133  10775  13665  -7442   -318   -7144      N
ATOM    760  N   SER A 107      -8.941 -12.585   1.303  1.00147.51           N
ANISOU  760  N   SER A 107    18802  17125  20119  -9577   -264   -8834      N
ATOM    761  CA  SER A 107      -9.951 -13.588   1.621  1.00153.35           C
ANISOU  761  CA  SER A 107    19258  17830  21178 -10173   -146   -9212      C
ATOM    762  C   SER A 107      -9.147 -14.861   1.868  1.00155.28           C
ANISOU  762  C   SER A 107    19953  17347  21701 -10347    210   -9273      C
ATOM    763  O   SER A 107      -9.631 -15.983   1.687  1.00161.44           O
ANISOU  763  O   SER A 107    20643  17967  22730 -10958    326   -9730      O
ATOM    764  CB  SER A 107     -10.936 -13.771   0.459  1.00159.47           C
ANISOU  764  CB  SER A 107    19489  19291  21812 -10672   -522   -9829      C
ATOM    765  OG  SER A 107     -11.630 -15.016   0.517  1.00166.47           O
ANISOU  765  OG  SER A 107    20189  20034  23028 -11427   -385  -10299      O
ATOM    766  N   THR A 108      -7.896 -14.655   2.276  1.00178.82           N
ANISOU  766  N   THR A 108    23402  19885  24656  -9819    358   -8810      N
ATOM    767  CA  THR A 108      -6.952 -15.731   2.546  1.00180.07           C
ANISOU  767  CA  THR A 108    23986  19339  25092  -9855    651   -8776      C
ATOM    768  C   THR A 108      -6.148 -15.396   3.794  1.00175.10           C
ANISOU  768  C   THR A 108    23719  18282  24528  -9405    791   -8110      C
ATOM    769  O   THR A 108      -6.582 -15.658   4.909  1.00175.66           O
ANISOU  769  O   THR A 108    23872  18094  24776  -9577    966   -7912      O
ATOM    770  CB  THR A 108      -5.995 -15.949   1.348  1.00180.64           C
ANISOU  770  CB  THR A 108    24222  19373  25041  -9704    596   -9024      C
ATOM    771  OG1 THR A 108      -6.665 -16.709   0.332  1.00187.27           O
ANISOU  771  OG1 THR A 108    24872  20407  25874 -10287    540   -9738      O
ATOM    772  CG2 THR A 108      -4.721 -16.683   1.771  1.00179.94           C
ANISOU  772  CG2 THR A 108    24578  18545  25247   9494    868    8793      C
ATOM    773  N   ILE A 109      -4.993 -14.778   3.614  1.00179.31           N
ANISOU  773  N   ILE A 109    24464  18768  24896  -8869    694   -7773      N
ATOM    774  CA  ILE A 109      -4.152 -14.451   4.748  1.00175.29           C
ANISOU  774  CA  ILE A 109    24287  17900  24413   8486    740    7172      C
ATOM    775  C   ILE A 109      -4.903 -13.581   5.771  1.00172.80           C
ANISOU  775  C   ILE A 109    23937  17784  23935  -8431    709   -6863      C
ATOM    776  O   ILE A 109      -4.319 -13.077   6.730  1.00169.50           O
ANISOU  776  O   ILE A 109    23811  17169  23423  -8135    690   -6381      O
ATOM    777  CB  ILE A 109      -2.779 -13.891   4.284  1.00171.57           C
ANISOU  777  CB  ILE A 109    23973  17393  23822  -7985    607   -6908      C
ATOM    778  CG1 ILE A 109      -1.923 -15.044   3.737  1.00174.72           C
ANISOU  778  CG1 ILE A 109    24518  17334  24533  -8078    763   -7154      C
ATOM    779  CG2 ILE A 109      -2.042 -13.174   5.400  1.00167.26           C
ANISOU  779  CG2 ILE A 109    23688  16675  23187  -7602    519   -6292      C
ATOM    780  CD1 ILE A 109      -1.946 -16.306   4.599  1.00178.40           C
ANISOU  780  CD1 ILE A 109    25207  17173  25402  -8371   1000   -7154      C
ATOM    781  N   SER A 110      -6.207 -13.411   5.559  1.00162.98           N
ANISOU  781  N   SER A 110    22328  16933  22665  -8756    692   -7180      N
ATOM    782  CA  SER A 110      -7.062 -12.744   6.546  1.00161.75           C
ANISOU  782  CA  SER A 110    22110  16901  22446  -8799    747   -6985      C
ATOM    783  C   SER A 110      -8.017 -13.765   7.175  1.00166.69           C
ANISOU  783  C   SER A 110    22637  17303  23395  -9398   1016   -7211      C
ATOM    784  O   SER A 110      -7.705 -14.359   8.200  1.00167.33           O
```

FIG. 13 Continued

```
ANISOU  784  O    SER A 110    23088  16869  23622  -9486   1241  -6954        O
ATOM    785  CB   SER A 110     -7.834 -11.562   5.941  1.00160.24             C
ANISOU  785  CB   SER A 110    21525  17330  22027  -8674    513  -7112        C
ATOM    786  OG   SER A 110     -8.557 -10.831   6.924  1.00158.87             O
ANISOU  786  OG   SER A 110    21331  17209  21825  -8669    604  -6923        O
ATOM    787  N    PHE A 111     -9.165 -13.991   6.545  1.00163.56             N
ANISOU  787  N    PHE A 111    21733  17293  23118  -9851    970  -7690        N
ATOM    788  CA   PHE A 111    -10.151 -14.949   7.056  1.00169.11             C
ANISOU  788  CA   PHE A 111    22255  17814  24183 -10518   1233  -7942        C
ATOM    789  C    PHE A 111     -9.623 -16.402   7.052  1.00173.22             C
ANISOU  789  C    PHE A 111    23095  17717  25003 -10833   1461  -8087        C
ATOM    790  O    PHE A 111    -10.393 -17.375   7.019  1.00179.33             O
ANISOU  790  O    PHE A 111    23678  18348  26111 -11486   1645  -8459        O
ATOM    791  CB   PHE A 111    -11.491 -14.829   6.304  1.00173.30             C
ANISOU  791  CB   PHE A 111    22062  18985  24800 -10987   1052  -8443        C
ATOM    792  CG   PHE A 111    -11.842 -13.410   5.876  1.00169.68             C
ANISOU  792  CG   PHE A 111    21251  19178  24043 -10604    714  -8377        C
ATOM    793  CD1  PHE A 111    -11.572 -12.320   6.702  1.00164.20             C
ANISOU  793  CD1  PHE A 111    20815  18406  23169 -10113    770  -7908        C
ATOM    794  CD2  PHE A 111    -12.458 -13.178   4.646  1.00172.46             C
ANISOU  794  CD2  PHE A 111    21036  20206  24285 -10771    322  -8803        C
ATOM    795  CE1  PHE A 111    -11.894 -11.026   6.301  1.00161.36             C
ANISOU  795  CE1  PHE A 111    20171  18556  22583  -9775    483  -7867        C
ATOM    796  CE2  PHE A 111    -12.786 -11.897   4.242  1.00169.66             C
ANISOU  796  CE2  PHE A 111    20359  20429  23676 -10417    -17  -8724        C
ATOM    797  CZ   PHE A 111    -12.502 -10.819   5.070  1.00164.01             C
ANISOU  797  CZ   PHE A 111    19919  19554  22842  -9910     85  -8256        C
ATOM    798  N    ILE A 112     -8.296 -16.521   7.047  1.00168.17             N
ANISOU  798  N    ILE A 112    22913  16705  24280 -10386   1441  -7805        N
ATOM    799  CA   ILE A 112     -7.616 -17.799   7.199  1.00171.49             C
ANISOU  799  CA   ILE A 112    23708  16434  25010 -10565   1666  -7839        C
ATOM    800  C    ILE A 112     -6.986 -17.778   8.591  1.00168.95             C
ANISOU  800  C    ILE A 112    23672  15615  24705 -10309   1799  -7230        C
ATOM    801  O    ILE A 112     -6.931 -18.814   9.262  1.00172.71             O
ANISOU  801  O    ILE A 112    24645  15473  25502 -10618   2067  -7163        O
ATOM    802  CB   ILE A 112     -6.534 -18.037   6.115  1.00170.99             C
ANISOU  802  CB   ILE A 112    23759  16288  24921 -10284   1538  -8004        C
ATOM    803  CG1  ILE A 112     -6.537 -19.501   5.643  1.00177.76             C
ANISOU  803  CG1  ILE A 112    24731  16629  26180 -10797   1779  -8485        C
ATOM    804  CG2  ILE A 112     -5.144 -17.535   6.579  1.00165.58             C
ANISOU  804  CG2  ILE A 112    23441  15367  24105  -9629   1436  -7432        C
ATOM    805  CD1  ILE A 112     -6.639 -20.525   6.749  1.00181.41             C
ANISOU  805  CD1  ILE A 112    25523  16357  27050 -11132   2124  -8312        C
ATOM    806  N    GLU A 113     -6.524 -16.594   9.021  1.00111.43             N
ANISOU  806  N    GLU A 113    16696   8582  17060  -9785   1599  -6797        N
ATOM    807  CA   GLU A 113     -5.972 -16.401  10.376  1.00109.20             C
ANISOU  807  CA   GLU A 113    16891   7927  16674  -9575   1643  -6235        C
ATOM    808  C    GLU A 113     -7.118 -16.487  11.411  1.00111.63             C
ANISOU  808  C    GLU A 113    17220   8151  17041 -10014   1930  -6198        C
ATOM    809  O    GLU A 113     -7.214  15.696  12.348  1.00109.00             O
ANISOU  809  O    GLU A 113    17104   7868  16442  -9865   1938  -5864        O
ATOM    810  CB   GLU A 113      5.148  15.089  10.497  1.00103.11             C
ANISOU  810  CB   GLU A 113    16248   7438  15492  -3969   1338  -5844        C
ATOM    811  CG   GLU A 113     -3.897 -15.126  11.455  1.00101.32             C
ANISOU  811  CG   GLU A 113    16546   6765  15186  -8672   1207  -5309        C
ATOM    812  CD   GLU A 113     -2.540 -15.460  10.767  1.00100.51             C
ANISOU  812  CD   GLU A 113    16481   6472  15238  -8349   1007  -5248        C
ATOM    813  OE1  GLU A 113     -2.460 -16.423   9.973  1.00103.71             O
ANISOU  813  OE1  GLU A 113    16751   6672  15983  -8518   1137  -5586        O
ATOM    814  OE2  GLU A 113     -1.533 -14.778  11.042  1.00 97.17             O
ANISOU  814  OE2  GLU A 113    16231   6065  14624  -7963    734  -4882        O
ATOM    815  N    GLU A 114     -7.990 -17.465  11.188  1.00187.98             N
ANISOU  815  N    GLU A 114    26666  17676  27083 -10607   2189  -6584        N
ATOM    816  CA   GLU A 114     -9.116 -17.761  12.056  1.00191.66             C
ANISOU  816  CA   GLU A 114    27082  18006  27734 -11150   2538  -6602        C
ATOM    817  C    GLU A 114     -9.263 -19.277  12.141  1.00198.30             C
ANISOU  817  C    GLU A 114    28066  18224  29055 -11711   2853  -6779        C
ATOM    818  O    GLU A 114     -9.863 -19.795  13.075  1.00202.04             O
ANISOU  818  O    GLU A 114    28705  18319  29741 -12162   3218  -6644        O
```

FIG. 13 Continued

```
ATOM    819  CB  GLU A 114     -10.394 -17.102  11.553  1.00192.33           C
ANISOU  819  CB  GLU A 114    26505  18748  27824 -11406   2515  -6972       C
ATOM    820  CG  GLU A 114     -10.442 -15.613  11.821  1.00186.73           C
ANISOU  820  CG  GLU A 114    25749  18481  26718 -10938   2340  -6733       C
ATOM    821  CD  GLU A 114     -11.845 -15.129  12.109  1.00188.67           C
ANISOU  821  CD  GLU A 114    25502  19080  27102 -11325   2529  -6905       C
ATOM    822  OE1 GLU A 114     -11.984 -13.954  12.509  1.00184.85           O
ANISOU  822  OE1 GLU A 114    25043  18828  26363 -11008   2487  -6713       O
ATOM    823  OE2 GLU A 114     -12.805 -15.924  11.948  1.00194.47           O
ANISOU  823  OE2 GLU A 114    25808  19837  28245 -11979   2736  -7236       O
ATOM    824  N   ASN A 115      -8.745 -19.981  11.136  1.00162.83           N
ANISOU  824  N   ASN A 115    23527  13591  24752 -11718   2757  -7100       N
ATOM    825  CA  ASN A 115      -8.585 -21.427  11.222  1.00169.01           C
ANISOU  825  CA  ASN A 115    24596  13617  26005 -12149   3057  -7226       C
ATOM    826  C   ASN A 115      -7.176 -21.479  11.812  1.00165.79           C
ANISOU  826  C   ASN A 115    24766  12721  25507 -11585   2944  -6678       C
ATOM    827  O   ASN A 115      -6.718 -22.483  12.361  1.00169.49           O
ANISOU  827  O   ASN A 115    25676  12417  26305 -11725   3162  -6474       O
ATOM    828  CB  ASN A 115      -8.653 -22.093   9.835  1.00172.97           C
ANISOU  828  CB  ASN A 115    24817  14174  26731 -12425   3011  -7879       C
ATOM    829  CG  ASN A 115      -9.421 -23.442   9.836  1.00181.81           C
ANISOU  829  CG  ASN A 115    25941  14748  28389 -13273   3412  -8280       C
ATOM    830  OD1 ASN A 115     -10.325 -23.673  10.645  1.00185.12           O
ANISOU  830  OD1 ASN A 115    26301  15033  29003 -13769   3703  -8188       O
ATOM    831  ND2 ASN A 115      -9.068 -24.317   8.899  1.00186.09           N
ANISOU  831  ND2 ASN A 115    26561  14959  29186 -13478   3458  -8748       N
ATOM    832  N   ASN A 116      -6.507 -20.337  11.689  1.00126.50           N
ANISOU  832  N   ASN A 116    19754   8212  20099 -10960   2578  -6430       N
ATOM    833  CA  ASN A 116      -5.190 -20.088  12.245  1.00122.85           C
ANISOU  833  CA  ASN A 116    19720   7476  19483 -10414   2352  -5898       C
ATOM    834  C   ASN A 116      -5.393 -19.356  13.588  1.00120.40           C
ANISOU  834  C   ASN A 116    19707   7212  18829  10344   2339   5407       C
ATOM    835  O   ASN A 116      -4.553 -19.417  14.474  1.00119.61           O
ANISOU  835  O   ASN A 116    20083   6717  18645 -10128   2222  -4919       O
ATOM    836  CB  ASN A 116      -4.389 -19.239  11.231  1.00117.88           C
ANISOU  836  CB  ASN A 116    18846   7343  18602  -9868   1984  -5971       C
ATOM    837  CG  ASN A 116      -2.862 -19.211  11.485  1.00115.39           C
ANISOU  837  CG  ASN A 116    18855   6694  18293  -9365   1733  -5538       C
ATOM    838  OD1 ASN A 116      -2.067 -19.365  10.545  1.00114.92           O
ANISOU  838  OD1 ASN A 116    18672   6616  18375  -9124   1629  -5706       O
ATOM    839  ND2 ASN A 116      -2.456 -18.952  12.731  1.00114.02           N
ANISOU  839  ND2 ASN A 116    19080   6288  17956  -9233   1618  -4999       N
ATOM    840  N   ALA A 117      -6.521 -18.675  13.750  1.00289.05           N
ANISOU  840  N   ALA A 117    32247  47786  29793  -6114  15817   1964       N
ATOM    841  CA  ALA A 117      -6.761 -17.957  14.999  1.00280.97           C
ANISOU  841  CA  ALA A 117    30104  46815  29835   6361  15316   2057       C
ATOM    842  C   ALA A 117      -7.459 -18.800  16.061  1.00274.29           C
ANISOU  842  C   ALA A 117    29281  45748  29190  -6382  14487   1690       C
ATOM    843  O   ALA A 117      -6.863 -19.147  17.079  1.00271.34           O
ANISOU  843  O   ALA A 117    28219  45417  29462  -6088  14536   1409       O
ATOM    844  CB  ALA A 117      -7.540 -16.683  14.748  1.00278.82           C
ANISOU  844  CB  ALA A 117    29629  46578  29730   6958  14981   2580       C
ATOM    845  N   GLY A 118      -8.725 -19.124  15.812  1.00272.14           N
ANISOU  845  N   GLY A 118    29790  45252  28358  -6725  13720   1719       N
ATOM    846  CA  GLY A 118      -9.547 -19.876  16.746  1.00266.03           C
ANISOU  846  CA  GLY A 118    29101  44248  27730  -6808  12887   1432       C
ATOM    847  C   GLY A 118      -8.864 -21.054  17.406  1.00265.97           C
ANISOU  847  C   GLY A 118    29084  44148  27827  -6274  13065    916       C
ATOM    848  O   GLY A 118      -9.283 -21.486  18.476  1.00260.12           O
ANISOU  848  O   GLY A 118    28053  43273  27508  -6292  12488    701       O
ATOM    849  N   ASN A 119      -7.821 -21.583  16.771  1.00273.19           N
ANISOU  849  N   ASN A 119    30325  45123  28353  -5778  13884    736       N
ATOM    850  CA  ASN A 119      -7.074 -22.696  17.344  1.00274.13           C
ANISOU  850  CA  ASN A 119    30416  45156  28583  -5195  14148    284       C
ATOM    851  C   ASN A 119      -6.629 -22.365  18.763  1.00268.03           C
ANISOU  851  C   ASN A 119    28379  44540  28920  -5100  14002    230       C
ATOM    852  O   ASN A 119      -6.558 -23.239  19.624  1.00265.43           O
ANISOU  852  O   ASN A 119    27968  44077  28807  -4813  13745   -107       O
ATOM    853  CB  ASN A 119      -5.875 -23.064  16.470  1.00282.89           C
```

FIG. 13 Continued

```
ANISOU  853  CB   ASN A 119   31840  46371  28275  -4644  15195    192       C
ATOM    854  CG   ASN A 119    -6.257 -23.954  15.308  1.00 289.25           C
ANISOU  854  CG   ASN A 119   34118  46903  28879  -4567  15293     18       C
ATOM    855  OD1  ASN A 119    -7.335 -24.549  15.296  1.00 287.09           O
ANISOU  855  OD1  ASN A 119   34629  46335  28116  -4857  14544   -128       O
ATOM    856  ND2  ASN A 119    -5.373 -24.055  14.323  1.00 297.57           N
ANISOU  856  ND2  ASN A 119   35569  48049  29444  -4191  16229     31       N
ATOM    857  N    ALA A 120    -6.332 -21.093  19.002  1.00 287.00           N
ANISOU  857  N    ALA A 120   29825  47213  32007  -5356  14160    566       N
ATOM    858  CA   ALA A 120    -5.971 -20.648  20.338  1.00 281.44           C
ANISOU  858  CA   ALA A 120   27938  46661  32335  -5363  13967    532       C
ATOM    859  C    ALA A 120    -7.239 -20.598  21.167  1.00 273.64           C
ANISOU  859  C    ALA A 120   26953  45462  31555  -5791  12984    521       C
ATOM    860  O    ALA A 120    -7.236 -20.935  22.350  1.00 268.87           O
ANISOU  860  O    ALA A 120   25852  44823  31482  -5689  12610    300       O
ATOM    861  CB   ALA A 120    -5.319 -19.281  20.289  1.00 282.35           C
ANISOU  861  CB   ALA A 120   27119  47084  33079  -5569  14428    890       C
ATOM    862  N    ALA A 121    -8.327 -20.185  20.525  1.00 250.37           N
ANISOU  862  N    ALA A 121   24577  42384  28169  -6261  12575    785       N
ATOM    863  CA   ALA A 121    -9.623 -20.077  21.178  1.00 243.72           C
ANISOU  863  CA   ALA A 121   23764  41347  27490  -6694  11667    849       C
ATOM    864  C    ALA A 121   -10.013 -21.393  21.854  1.00 241.14           C
ANISOU  864  C    ALA A 121   23858  40772  26993  -6483  11180    436       C
ATOM    865  O    ALA A 121   -11.010 -21.470  22.579  1.00 235.50           O
ANISOU  865  O    ALA A 121   23105  39892  26483  -6775  10442    435       O
ATOM    866  CB   ALA A 121   -10.680 -19.650  20.173  1.00 245.11           C
ANISOU  866  CB   ALA A 121   24640  41431  27060  -7151  11352   1201       C
ATOM    867  N    ALA A 122    -9.215 -22.426  21.610  1.00 260.72           N
ANISOU  867  N    ALA A 122   26743  43212  29107  -5959  11632    104       N
ATOM    868  CA   ALA A 122    -9.450 -23.734  22.204  1.00 259.26           C
ANISOU  868  CA   ALA A 122   26998  42762  28746  -5694  11272   -294       C
ATOM    869  C    ALA A 122    -9.087 -23.731  23.681  1.00 253.85           C
ANISOU  869  C    ALA A 122   25351  42160  28942  -5525  11075   -444       C
ATOM    870  O    ALA A 122    -9.936 -23.476  24.535  1.00 247.58           O
ANISOU  870  O    ALA A 122   24256  41278  28534  -5867  10406   -387       O
ATOM    871  CB   ALA A 122    -8.651 -24.798  21.470  1.00 266.47           C
ANISOU  871  CB   ALA A 122   28647  43582  29016  -5140  11893   -586       C
ATOM    872  N    ALA A 123    -7.818 -24.003  23.972  1.00 242.58           N
ANISOU  872  N    ALA A 123   23433  40914  27821  -4991  11671   -615       N
ATOM    873  CA   ALA A 123    -7.347 -24.056  25.345  1.00 238.52           C
ANISOU  873  CA   ALA A 123   22015  40517  28093  -4789  11510   -760       C
ATOM    874  C    ALA A 123    -7.948 -22.907  26.126  1.00 232.05           C
ANISOU  874  C    ALA A 123   20441  39794  27931  -5323  11018   -526       C
ATOM    875  O    ALA A 123    -8.386 -23.080  27.261  1.00 226.64           O
ANISOU  875  O    ALA A 123   19442  39022  27648  -5404  10969   -641       O
ATOM    876  CB   ALA A 123    -5.835 -23.995  25.392  1.00 243.21           C
ANISOU  876  CB   ALA A 123   21923  41429  29055  -4279  12280   -803       C
ATOM    877  N    LEU A 124    -8.007 -21.740  25.498  1.00 233.12           N
ANISOU  877  N    LEU A 124   20345  40083  28148  -5686  11231   -187       N
ATOM    878  CA   LEU A 124    -8.531 -20.551  26.161  1.00 227.78           C
ANISOU  878  CA   LEU A 124   18971  39470  28105  -6181  10858     59       C
ATOM    879  C    LEU A 124   -10.051 -20.486  26.284  1.00 222.94           C
ANISOU  879  C    LEU A 124   18814  38584  27308  -6642  10097    185       C
ATOM    880  O    LEU A 124   -10.622 -20.896  27.298  1.00 218.01           O
ANISOU  880  O    LEU A 124   18091  37811  26930  -6686   9540     28       O
ATOM    881  CB   LEU A 124    -8.034 -19.291  25.460  1.00 230.82           C
ANISOU  881  CB   LEU A 124   18931  40085  28686  -6400  11387    404       C
ATOM    882  CG   LEU A 124    -6.529 -19.104  25.528  1.00 235.16           C
ANISOU  882  CG   LEU A 124   18762  40954  29633  -6040  12111    345       C
ATOM    883  CD1  LEU A 124    -6.224 -17.631  25.674  1.00 234.60           C
ANISOU  883  CD1  LEU A 124   17846  41079  30214  -6423  12318    650       C
ATOM    884  CD2  LEU A 124    -5.996 -19.888  26.704  1.00 233.23           C
ANISOU  884  CD2  LEU A 124   18073  40761  29781  -5660  11945     -1       C
ATOM    885  N    MET A 125   -10.687 -19.955  25.241  1.00 225.30           N
ANISOU  885  N    MET A 125   19588  38836  27180  -6977  10089    500       N
ATOM    886  CA   MET A 125   -12.133 -19.727  25.223  1.00 221.62           C
ANISOU  886  CA   MET A 125   19474  38162  26568  -7448   9400    723       C
ATOM    887  C    MET A 125   -12.955 -20.981  25.492  1.00 219.84           C
ANISOU  887  C    MET A 125   19946  37660  25922  -7406   8816    470       C
```

FIG. 13 Continued

| | | | | | | | | | | | |
|---|---|---|---|---|---|---|---|---|---|---|---|
| ATOM | 888 | O | MET | A | 125 | -14.178 | -20.955 | 25.388 | 1.00 | 217.65 | O |
| ANISOU | 888 | O | MET | A | 125 | 20034 | 37213 | 25448 | -7786 | 8230 | 654 | O |
| ATOM | 889 | CB | MET | A | 125 | -12.576 | -19.061 | 23.910 | 1.00 | 225.35 | C |
| ANISOU | 889 | CB | MET | A | 125 | 20414 | 38660 | 26547 | -7755 | 9526 | 1122 | C |
| ATOM | 890 | CG | MET | A | 125 | -12.422 | -17.523 | 23.866 | 1.00 | 224.77 | C |
| ANISOU | 890 | CG | MET | A | 125 | 19618 | 38750 | 27035 | -8045 | 9781 | 1524 | C |
| ATOM | 891 | SD | MET | A | 125 | -10.914 | -16.849 | 23.074 | 1.00 | 231.20 | S |
| ANISOU | 891 | SD | MET | A | 125 | 20073 | 39862 | 27910 | -7818 | 10799 | 1632 | S |
| ATOM | 892 | CE | MET | A | 125 | -9.848 | -16.542 | 24.478 | 1.00 | 228.16 | C |
| ANISOU | 892 | CE | MET | A | 125 | 18518 | 39647 | 28527 | -7621 | 11019 | 1381 | C |
| ATOM | 893 | N | ALA | A | 126 | -12.279 | -22.074 | 25.828 | 1.00 | 245.52 | N |
| ANISOU | 893 | N | ALA | A | 126 | 23369 | 40865 | 29053 | -6944 | 8987 | 74 | N |
| ATOM | 894 | CA | ALA | A | 126 | -12.952 | -23.319 | 26.176 | 1.00 | 244.11 | C |
| ANISOU | 894 | CA | ALA | A | 126 | 23833 | 40392 | 28526 | -6874 | 8481 | -195 | C |
| ATOM | 895 | C | ALA | A | 126 | -12.673 | -23.692 | 27.627 | 1.00 | 239.62 | C |
| ANISOU | 895 | C | ALA | A | 126 | 22660 | 39808 | 28578 | -6638 | 8285 | -447 | C |
| ATOM | 896 | O | ALA | A | 126 | -13.369 | -24.525 | 28.211 | 1.00 | 236.96 | O |
| ANISOU | 896 | O | ALA | A | 126 | 22662 | 39223 | 28150 | -6660 | 7773 | -612 | O |
| ATOM | 897 | CB | ALA | A | 126 | -12.515 | -24.434 | 25.251 | 1.00 | 250.36 | C |
| ANISOU | 897 | CB | ALA | A | 126 | 25549 | 41055 | 28521 | -6520 | 8824 | -449 | C |
| ATOM | 898 | N | GLY | A | 127 | -11.644 | -23.071 | 28.198 | 1.00 | 241.92 | N |
| ANISOU | 898 | N | GLY | A | 127 | 22062 | 40371 | 29487 | -6431 | 8686 | -463 | N |
| ATOM | 899 | CA | GLY | A | 127 | -11.246 | -23.334 | 29.568 | 1.00 | 238.38 | C |
| ANISOU | 899 | CA | GLY | A | 127 | 20982 | 39966 | 29625 | -6201 | 8531 | -683 | C |
| ATOM | 900 | C | GLY | A | 127 | -11.935 | -22.486 | 30.623 | 1.00 | 232.13 | C |
| ANISOU | 900 | C | GLY | A | 127 | 19556 | 39176 | 29466 | -6597 | 8051 | -536 | C |
| ATOM | 901 | O | GLY | A | 127 | -11.339 | -22.197 | 31.658 | 1.00 | 230.03 | O |
| ANISOU | 901 | O | GLY | A | 127 | 18537 | 39068 | 29796 | -6476 | 8081 | -641 | O |
| ATOM | 902 | N | LEU | A | 128 | -13.184 | -22.093 | 30.382 | 1.00 | 200.89 | N |
| ANISOU | 902 | N | LEU | A | 128 | 15900 | 35049 | 25381 | -7062 | 7609 | -288 | N |
| ATOM | 903 | CA | LEU | A | 128 | -13.897 | -21.267 | 31.351 | 1.00 | 195.38 | C |
| ANISOU | 903 | CA | LEU | A | 128 | 14639 | 34319 | 25276 | -7418 | 7203 | -128 | C |
| ATOM | 904 | C | LEU | A | 128 | -15.413 | -21.448 | 31.405 | 1.00 | 192.24 | C |
| ANISOU | 904 | C | LEU | A | 128 | 14694 | 33654 | 24696 | -7790 | 6566 | 44 | C |
| ATOM | 905 | O | LEU | A | 128 | -16.037 | -21.065 | 32.392 | 1.00 | 187.64 | O |
| ANISOU | 905 | O | LEU | A | 128 | 13716 | 32996 | 24582 | -7991 | 6206 | 110 | O |
| ATOM | 906 | CB | LEU | A | 128 | -13.560 | -19.783 | 31.166 | 1.00 | 195.59 | C |
| ANISOU | 906 | CB | LEU | A | 128 | 14013 | 34548 | 25755 | -7670 | 7529 | 156 | C |
| ATOM | 907 | CG | LEU | A | 128 | -13.273 | -19.233 | 29.770 | 1.00 | 200.41 | C |
| ANISOU | 907 | CG | LEU | A | 128 | 14868 | 35272 | 26008 | -7756 | 7982 | 411 | C |
| ATOM | 908 | CD1 | LEU | A | 128 | -13.759 | -17.800 | 29.663 | 1.00 | 198.92 | C |
| ANISOU | 908 | CD1 | LEU | A | 128 | 14268 | 35103 | 26209 | -8194 | 7972 | 810 | C |
| ATOM | 909 | CD2 | LEU | A | 128 | -11.785 | -19.324 | 29.450 | 1.00 | 205.06 | C |
| ANISOU | 909 | CD2 | LEU | A | 128 | 15182 | 36117 | 26615 | -7365 | 8662 | 247 | C |
| ATOM | 910 | N | ALA | A | 129 | -16.009 | -22.030 | 30.368 | 1.00 | 201.34 | N |
| ANISOU | 910 | N | ALA | A | 129 | 16665 | 34665 | 25169 | -7892 | 6425 | 120 | N |
| ATOM | 911 | CA | ALA | A | 129 | -17.468 | -22.202 | 30.333 | 1.00 | 199.16 | C |
| ANISOU | 911 | CA | ALA | A | 129 | 16795 | 34165 | 24712 | -8287 | 5793 | 327 | C |
| ATOM | 912 | C | ALA | A | 129 | -18.009 | -22.755 | 31.645 | 1.00 | 194.46 | C |
| ANISOU | 912 | C | ALA | A | 129 | 16028 | 33397 | 24460 | -8273 | 5337 | 164 | C |
| ATOM | 913 | O | ALA | A | 129 | -17.953 | -23.958 | 31.879 | 1.00 | 195.07 | O |
| ANISOU | 913 | O | ALA | A | 129 | 16559 | 33313 | 24247 | -8044 | 5198 | -131 | O |
| ATOM | 914 | CB | ALA | A | 129 | -17.881 | -23.094 | 29.175 | 1.00 | 203.58 | C |
| ANISOU | 914 | CB | ALA | A | 129 | 18344 | 34579 | 24426 | -8342 | 5662 | 306 | C |
| ATOM | 915 | N | PRO | A | 130 | -18.601 | -21.871 | 32.461 | 1.00 | 184.54 | N |
| ANISOU | 915 | N | PRO | A | 130 | 14174 | 32145 | 23797 | -8531 | 5113 | 379 | N |
| ATOM | 916 | CA | PRO | A | 130 | -19.104 | -22.000 | 33.836 | 1.00 | 179.72 | C |
| ANISOU | 916 | CA | PRO | A | 130 | 13212 | 31413 | 23659 | -8560 | 4759 | 299 | C |
| ATOM | 917 | C | PRO | A | 130 | -19.351 | -23.422 | 34.333 | 1.00 | 179.21 | C |
| ANISOU | 917 | C | PRO | A | 130 | 13633 | 31137 | 23320 | -8376 | 4439 | 9 | C |
| ATOM | 918 | O | PRO | A | 130 | -20.337 | -23.657 | 35.030 | 1.00 | 176.14 | O |
| ANISOU | 918 | O | PRO | A | 130 | 13265 | 30571 | 23091 | 8571 | 3991 | 90 | O |
| ATOM | 919 | CB | PRO | A | 130 | -20.411 | -21.214 | 33.791 | 1.00 | 177.60 | C |
| ANISOU | 919 | CB | PRO | A | 130 | 12835 | 31053 | 23592 | -9017 | 4397 | 731 | C |
| ATOM | 920 | CG | PRO | A | 130 | -20.133 | -20.128 | 32.812 | 1.00 | 180.16 | C |
| ANISOU | 920 | CG | PRO | A | 130 | 13006 | 31545 | 23903 | -9160 | 4740 | 1022 | C |
| ATOM | 921 | CD | PRO | A | 130 | -19.112 | -20.646 | 31.823 | 1.00 | 184.90 | C |
| ANISOU | 921 | CD | PRO | A | 130 | 14018 | 32268 | 23968 | -8892 | 5146 | 819 | C |
| ATOM | 922 | N | LYS | A | 131 | -18.439 | -24.334 | 34.007 | 1.00 | 188.94 | N |

FIG. 13 Continued

```
ANISOU  922  N    LYS A 131   15231  32381  24178  -7986   4709   -310       N
ATOM    923  CA   LYS A 131   -18.519 -25.738  34.400  1.00189.34            C
ANISOU  923  CA   LYS A 131   15804  32199  23937  -7751   4489   -605       C
ATOM    924  C    LYS A 131   -19.246 -25.922  35.745  1.00184.57            C
ANISOU  924  C    LYS A 131   14931  31448  23749  -7850   4054   -610       C
ATOM    925  O    LYS A 131   -19.082 -25.121  36.669  1.00181.27            O
ANISOU  925  O    LYS A 131   13803  31167  23904  -7863   4096   -563       O
ATOM    926  CB   LYS A 131   -17.104 -26.335  34.407  1.00192.39            C
ANISOU  926  CB   LYS A 131   16185  32696  24220  -7188   4971   -948       C
ATOM    927  CG   LYS A 131   -16.326 -26.016  33.117  1.00197.32            C
ANISOU  927  CG   LYS A 131   16985  33494  24493  -7076   5493   -914       C
ATOM    928  CD   LYS A 131   -14.807 -26.073  33.290  1.00199.83            C
ANISOU  928  CD   LYS A 131   16885  34050  24992  -6551   6068  -1140       C
ATOM    929  CE   LYS A 131   -14.065 -25.574  32.039  1.00204.70            C
ANISOU  929  CE   LYS A 131   17574  34868  25335  -6479   6637  -1046       C
ATOM    930  NZ   LYS A 131   -12.576 -25.716  32.129  1.00208.04            N
ANISOU  930  NZ   LYS A 131   17593  35531  25923  -5948   7229  -1242       N
ATOM    931  N    THR A 132   -20.064 -26.968  35.839  1.00235.93            N
ANISOU  931  N    THR A 132   22035  37662  29948  -7943   3646   -664       N
ATOM    932  CA   THR A 132   -20.906 -27.189  37.018  1.00231.89            C
ANISOU  932  CA   THR A 132   21348  36984  29776  -8083   3225   -618       C
ATOM    933  C    THR A 132   -20.325 -28.060  38.117  1.00230.88            C
ANISOU  933  C    THR A 132   21176  36771  29775  -7668   3243   -941       C
ATOM    934  O    THR A 132   -20.477 -27.755  39.304  1.00227.24            O
ANISOU  934  O    THR A 132   20220  36338  29781  -7661   3120   -927       O
ATOM    935  CB   THR A 132   -22.237 -27.842  36.636  1.00232.52            C
ANISOU  935  CB   THR A 132   22045  36781  29520  -8474   2718   -450       C
ATOM    936  OG1  THR A 132   -22.941 -26.991  35.728  1.00233.34            O
ANISOU  936  OG1  THR A 132   22130  36977  29551  -8897   2606    -79       O
ATOM    937  CG2  THR A 132   -23.083 -28.092  37.883  1.00228.67            C
ANISOU  937  CG2  THR A 132   21353  36124  29408  -8600   2337   -386       C
ATOM    938  N    LYS A 133    19.696  29.162  37.731  1.00176.86            N
ANISOU  938  N    LYS A 133   14894  29807  22499  -7315   3395  -1219       N
ATOM    939  CA   LYS A 133   -19.164 -30.076  38.724  1.00176.52            C
ANISOU  939  CA   LYS A 133   14866  29660  22543  -6887   3401  -1492       C
ATOM    940  C    LYS A 133   -20.319 -30.827  39.406  1.00174.46            C
ANISOU  940  C    LYS A 133   14957  29064  22267  -7116   2897  -1441       C
ATOM    941  O    LYS A 133   -20.455 -30.825  40.634  1.00171.26            O
ANISOU  941  O    LYS A 133   14179  28651  22242  -7048   2743  -1449       O
ATOM    942  CB   LYS A 133    18.312  29.298  39.728  1.00174.07            C
ANISOU  942  CB   LYS A 133   13678  29665  22798  -6649   3615  -1542       C
ATOM    943  CG   LYS A 133   -17.368 -28.276  39.057  1.00175.76            C
ANISOU  943  CG   LYS A 133   13418  30230  23134  -6583   4075  -1502       C
ATOM    944  CD   LYS A 133   -16.655 -27.401  40.088  1.00173.44            C
ANISOU  944  CD   LYS A 133   12233  30235  23430  -6473   4210  -1531       C
ATOM    945  CE   LYS A 133   -15.815 -26.306  39.448  1.00175.17            C
ANISOU  945  CE   LYS A 133   11949  30781  23825  -6496   4645  -1455       C
ATOM    946  NZ   LYS A 133   -15.361 -25.330  40.485  1.00172.72            N
ANISOU  946  NZ   LYS A 133   10800  30716  24111  -6544   4683  -1456       N
ATOM    947  N    VAL A 134   -21.146 -31.451  38.565  1.00177.90            N
ANISOU  947  N    VAL A 134   16126  29228  22239  -7414   2645  -1378       N
ATOM    948  CA   VAL A 134   -22.302 -32.248  38.965  1.00177.12            C
ANISOU  948  CA   VAL A 134   16462  28783  22052  -7705   2162  -1305       C
ATOM    949  C    VAL A 134   -21.889 -33.603  39.531  1.00178.80            C
ANISOU  949  C    VAL A 134   17148  28706  22082  -7298   2175  -1608       C
ATOM    950  O    VAL A 134   -20.722 -33.978  39.453  1.00181.17            O
ANISOU  950  O    VAL A 134   17507  29066  22263  -6778   2561  -1867       O
ATOM    951  CB   VAL A 134   -23.180 -32.535  37.748  1.00180.29            C
ANISOU  951  CB   VAL A 134   17549  29002  21952  -8162   1893  -1168       C
ATOM    952  CG1  VAL A 134   -23.314 -31.295  36.900  1.00180.22            C
ANISOU  952  CG1  VAL A 134   17199  29290  21986  -8450   1982   -894       C
ATOM    953  CG2  VAL A 134   -22.576 -33.661  36.926  1.00185.63            C
ANISOU  953  CG2  VAL A 134   19091  29442  21997  -7890   2082  -1488       C
ATOM    954  N    LEU A 135   -22.850 -34.343  40.086  1.00176.73            N
ANISOU  954  N    LEU A 135   17217  28122  21811  -7528   1769  -1550       N
ATOM    955  CA   LEU A 135   -22.577 -35.666  40.661  1.00178.50            C
ANISOU  955  CA   LEU A 135   17942  28011  21870  -7175   1754  -1800       C
ATOM    956  C    LEU A 135   -22.542 -36.778  39.618  1.00184.02            C
ANISOU  956  C    LEU A 135   19646  28349  21924  -7153   1776  -2005       C
```

FIG. 13 Continued

```
ATOM    957  O   LEU A 135     -22.691 -37.959  39.943  1.00186.04           O
ANISOU  957  O   LEU A 135    20495  28207  21985  -7029   1659  -2159       O
ATOM    958  CB  LEU A 135     -23.536 -35.998  41.806  1.00175.53           C
ANISOU  958  CB  LEU A 135    17476  27430  21787  -7395   1366  -1653       C
ATOM    959  CG  LEU A 135     -23.014 -35.578  43.185  1.00171.81           C
ANISOU  959  CG  LEU A 135    16280  27181  21820  -7051   1486  -1667       C
ATOM    960  CD1 LEU A 135     -24.146 -35.203  44.129  1.00167.94           C
ANISOU  960  CD1 LEU A 135    15440  26653  21718  -7437   1149  -1392       C
ATOM    961  CD2 LEU A 135     -22.142 -36.665  43.788  1.00173.91           C
ANISOU  961  CD2 LEU A 135    16836  27273  21968  -6460   1651  -1943       C
ATOM    962  N   ARG A 136     -22.365 -36.365  38.365  1.00187.21           N
ANISOU  962  N   ARG A 136    20262  28878  21989  -7290   1934   -999       N
ATOM    963  CA  ARG A 136     -22.158 -37.259  37.225  1.00193.14           C
ANISOU  963  CA  ARG A 136    21981  29336  22066  -7237   2054  -2226       C
ATOM    964  C   ARG A 136     -23.098 -38.472  37.117  1.00195.94           C
ANISOU  964  C   ARG A 136    23241  29160  22048  -7567   1639  -2293       C
ATOM    965  O   ARG A 136     -24.065 -38.455  36.355  1.00197.62           O
ANISOU  965  O   ARG A 136    23862  29263  21963  -8161   1267  -2145       O
ATOM    966  CB  ARG A 136     -20.676 -37.700  37.193  1.00196.08           C
ANISOU  966  CB  ARG A 136    22428  29743  22330  -6476   2644  -2543       C
ATOM    967  CG  ARG A 136     -20.328 -38.826  36.211  1.00202.79           C
ANISOU  967  CG  ARG A 136    24356  30201  22493  -6269   2866  -2841       C
ATOM    968  CD  ARG A 136     -18.894 -39.355  36.389  1.00205.78           C
ANISOU  968  CD  ARG A 136    24739  30586  22863  -5437   3461  -3117       C
ATOM    969  NE  ARG A 136     -18.802 -40.778  36.060  1.00211.36           N
ANISOU  969  NE  ARG A 136    26512  30736  23061  -5192   3556  -3404       N
ATOM    970  CZ  ARG A 136     -18.621 -41.259  34.833  1.00217.34           C
ANISOU  970  CZ  ARG A 136    28151  31254  23174  -5176   3803  -3601       C
ATOM    971  NH1 ARG A 136     -18.500 -40.434  33.803  1.00218.50           N
ANISOU  971  NH1 ARG A 136    28229  31699  23092  -5382   3977  -3524       N
ATOM    972  NH2 ARG A 136     -18.560 -42.568  34.637  1.00222.52           N
ANISOU  972  NH2 ARG A 136    29799  31350  23397  -4951   3892  -3876       N
ATOM    973  N   ASP A 137     -22.794 -39.510  37.888  1.00196.10           N
ANISOU  973  N   ASP A 137    23557  28858  22094  -7186   1695  -2499       N
ATOM    974  CA  ASP A 137     -23.493 -40.786  37.639  1.00199.49           C
ANISOU  974  CA  ASP A 137    24905  28722  22172  -7411   1388  -2614       C
ATOM    975  C   ASP A 137     -22.532 -41.794  38.449  1.00201.62           C
ANISOU  975  C   ASP A 137    25466  28722  22418  -6695   1743  -2909       C
ATOM    976  O   ASP A 137     -22.881 -42.530  39.372  1.00200.87           O
ANISOU  976  O   ASP A 137    25507  28325  22491  -6650   1545  -2907       O
ATOM    977  CB  ASP A 137     -23.808 -41.162  36.385  1.00205.17           C
ANISOU  977  CB  ASP A 137    26548  29213  22194  -7773   1312  -2727       C
ATOM    978  CG  ASP A 137     -24.007 -42.656  36.187  1.00210.61           C
ANISOU  978  CG  ASP A 137    28365  29255  22401  -7777   1219  -3005       C
ATOM    979  OD1 ASP A 137     -23.922 -43.114  35.029  1.00216.33           O
ANISOU  979  OD1 ASP A 137    29963  29746  22485  -7887   1306  -3211       O
ATOM    980  OD2 ASP A 137     -24.247 -43.374  37.178  1.00209.54           O
ANISOU  980  OD2 ASP A 137    28286  28823  22505  -7677   1074  -3020       O
ATOM    981  N   GLY A 138     -21.308 -41.800  37.919  1.00243.79           N
ANISOU  981  N   GLY A 138    30877  34188  27564  -6119   2290  -3131       N
ATOM    982  CA  GLY A 138      20.241  42.671  38.378  1.00246.57           C
ANISOU  982  CA  GLY A 138    31438  34345  27902  -5346   2706  -3383       C
ATOM    983  C   GLY A 138     -19.380 -42.039  39.458  1.00242.53           C
ANISOU  983  C   GLY A 138    29877  34285  27986  -4837   2926  -3297       C
ATOM    984  O   GLY A 138     -19.004 -42.709  40.416  1.00242.58           O
ANISOU  984  O   GLY A 138    29844  34138  28187  -4390   2973  -3357       O
ATOM    985  N   LYS A 139     -19.068 -40.751  39.311  1.00200.74           N
ANISOU  985  N   LYS A 139    23754  29543  22975  -4917   3046  -3148       N
ATOM    986  CA  LYS A 139     -18.257 -40.046  40.308  1.00197.20           C
ANISOU  986  CA  LYS A 139    22285  29553  23089  -4517   3220  -3071       C
ATOM    987  C   LYS A 139     -18.571 -38.557  40.461  1.00192.04           C
ANISOU  987  C   LYS A 139    20732  29390  22844  -4935   3081  -2820       C
ATOM    988  O   LYS A 139     -18.636 -37.816  39.479  1.00192.55           O
ANISOU  988  O   LYS A 139    20748  29649  22763  -5214   3186  -2749       O
ATOM    989  CB  LYS A 139     -16.762 -40.223  40.027  1.00201.22           C
ANISOU  989  CB  LYS A 139    22671  30237  23548  -3768   3820  -3260       C
ATOM    990  CG  LYS A 139     -16.105 -41.336  40.836  1.00203.79           C
ANISOU  990  CG  LYS A 139    23196  30315  23920  -3103   3961  -3402       C
ATOM    991  CD  LYS A 139     -16.327 -41.157  42.338  1.00199.02           C
```

FIG. 13 Continued

```
ANISOU  991  CD   LYS A 139      21947  29854  23818  -3095   3624  -3252        C
ATOM    992  CE   LYS A 139       15.458  40.049  42.918  1.00196.29             C
ANISOU  992  CE   LYS A 139      20475  30140  23966  -2873   3783  -3156        C
ATOM    993  NZ   LYS A 139      -15.735 -39.824  44.366  1.00191.91             N
ANISOU  993  NZ   LYS A 139      19357  29721  23840  -2922   3435  -3023        N
ATOM    994  N    TRP A 140      -18.733 -38.143  41.718  1.00201.42             N
ANISOU  994  N    TRP A 140      21243  30757  24531  -4948   2871  -2688        N
ATOM    995  CA   TRP A 140      -19.018 -36.762  42.120  1.00196.48             C
ANISOU  995  CA   TRP A 140      19746  30547  24359  -5294   2750  -2463        C
ATOM    996  C    TRP A 140      -18.217 -35.735  41.322  1.00197.23             C
ANISOU  996  C    TRP A 140      19376  31059  24505  -5229   3130  -2453        C
ATOM    997  O    TRP A 140      -18.652 -34.594  41.152  1.00194.31             O
ANISOU  997  O    TRP A 140      18533  30936  24359  -5648   3045  -2250        O
ATOM    998  CB   TRP A 140      -18.724 -36.623  43.627  1.00193.27             C
ANISOU  998  CB   TRP A 140      18706  30306  24422  -5037   2662  -2439        C
ATOM    999  CG   TRP A 140      -18.759 -35.218  44.232  1.00188.76             C
ANISOU  999  CG   TRP A 140      17208  30162  24349  -5272   2617  -2270        C
ATOM   1000  CD1  TRP A 140      -19.875 -34.463  44.510  1.00184.82             C
ANISOU 1000  CD1  TRP A 140      16466  29674  24082  -5828   2317  -2033        C
ATOM   1001  CD2  TRP A 140      -17.623 -34.438  44.692  1.00188.24             C
ANISOU 1001  CD2  TRP A 140      16350  30546  24625  -4949   2887  -2326        C
ATOM   1002  NE1  TRP A 140      -19.501 -33.261  45.084  1.00181.92             N
ANISOU 1002  NE1  TRP A 140      15270  29697  24154  -5860   2413  -1963        N
ATOM   1003  CE2  TRP A 140      -18.130 -33.220  45.206  1.00183.94             C
ANISOU 1003  CE2  TRP A 140      15180  30230  24479  -5359   2738  -2146        C
ATOM   1004  CE3  TRP A 140      -16.230 -34.646  44.704  1.00191.44             C
ANISOU 1004  CE3  TRP A 140      16505  31183  25050  -4362   3243  -2496        C
ATOM   1005  CZ2  TRP A 140      -17.285 -32.213  45.724  1.00182.80             C
ANISOU 1005  CZ2  TRP A 140      14221  30511  24723  -5242   2915  -2166        C
ATOM   1006  CZ3  TRP A 140      -15.403 -33.645  45.219  1.00190.29             C
ANISOU 1006  CZ3  TRP A 140      15485  31503  25313  -4260   3391  -2485        C
ATOM   1007  CH2  TRP A 140      -15.935 -32.446  45.717  1.00186.02             C
ANISOU 1007  CH2  TRP A 140      14387  31155  25135  -4718   3217  -2337        C
ATOM   1008  N    SER A 141      -17.065 -36.163  40.811  1.00187.76             N
ANISOU 1008  N    SER A 141      18330  29913  23098  -4695   3575  -2654        N
ATOM   1009  CA   SER A 141      -16.130 -35.286  40.103  1.00189.27             C
ANISOU 1009  CA   SER A 141      18057  30507  23352  -4548   4016  -2651        C
ATOM   1010  C    SER A 141      -16.754 -34.266  39.150  1.00188.14             C
ANISOU 1010  C    SER A 141      17860  30500  23125  -5115   3970  -2457        C
ATOM   1011  O    SER A 141      -17.823 -34.485  38.578  1.00188.21             O
ANISOU 1011  O    SER A 141      18453  30240  22820  -5572   3665  -2368        O
ATOM   1012  CB   SER A 141      -15.045 -36.103  39.389  1.00195.38             C
ANISOU 1012  CB   SER A 141      19268  31198  23768  -3949   4516  -2876        C
ATOM   1013  OG   SER A 141      -13.961 -36.383  40.264  1.00196.36             O
ANISOU 1013  OG   SER A 141      18897  31507  24203  -3331   4731  -2969        O
ATOM   1014  N    GLU A 142       16.050  33.150  38.992  1.00199.95             N
ANISOU 1014  N    GLU A 142      18633  32424  24916  -5081   4271  -2374        N
ATOM   1015  CA   GLU A 142      -16.492 -32.044  38.158  1.00199.01             C
ANISOU 1015  CA   GLU A 142      18345  32480  24788  -5560   4287  -2155        C
ATOM   1016  C    GLU A 142      -16.618 -32.431  36.698  1.00203.61             C
ANISOU 1016  C    GLU A 142      19727  32895  24741  -5649   4453  -2187        C
ATOM   1017  O    GLU A 142      -16.182 -33.504  36.284  1.00207.98             O
ANISOU 1017  O    GLU A 142      20937  33213  24873  -5283   4656  -2416        O
ATOM   1018  CB   GLU A 142      -15.498 -30.894  38.255  1.00198.55             C
ANISOU 1018  CB   GLU A 142      17401  32885  25153  -5425   4666  -2097        C
ATOM   1019  CG   GLU A 142      -14.248 -31.129  37.446  1.00203.87             C
ANISOU 1019  CG   GLU A 142      18150  33711  25599  -4953   5247  -2244        C
ATOM   1020  CD   GLU A 142      -13.565 -29.841  37.056  1.00204.15             C
ANISOU 1020  CD   GLU A 142      17473  34165  25932  -5038   5615  -2102        C
ATOM   1021  OE1  GLU A 142      -13.638 -28.866  37.835  1.00200.30             O
ANISOU 1021  OE1  GLU A 142      16238  33897  25970  -5269   5472  -1978        O
ATOM   1022  OE2  GLU A 142      -12.955 -29.802  35.967  1.00208.57             O
ANISOU 1022  OE2  GLU A 142      18247  34812  26189  -4882   6068  -2117        O
ATOM   1023  N    GLN A 143      -17.205 -31.528  35.921  1.00221.70             N
ANISOU 1023  N    GLN A 143      21975  35302  26960  -6127   4379  -1949        N
ATOM   1024  CA   GLN A 143      -17.365 -31.711  34.483  1.00226.22             C
ANISOU 1024  CA   GLN A 143      23276  35769  26908  -6282   4512  -1938        C
ATOM   1025  C    GLN A 143      -17.749 -30.388  33.826  1.00225.06             C
ANISOU 1025  C    GLN A 143      22764  35887  26861  -6731   4509  -1613        C
```

FIG. 13 Continued

```
ATOM   1026  O   GLN A 143     -18.318 -29.504  34.476  1.00220.46           O
ANISOU 1026  O   GLN A 143    21556  35437  26772  -7044   4248  -1376       O
ATOM   1027  CB  GLN A 143     -18.414 -32.786  34.172  1.00227.83           C
ANISOU 1027  CB  GLN A 143    24434  35524  26606  -6561   4066  -1998       C
ATOM   1028  CG  GLN A 143     -17.884 -34.208  34.192  1.00231.87           C
ANISOU 1028  CG  GLN A 143    25657  35696  26745  -6085   4242  -2350       C
ATOM   1029  CD  GLN A 143     -16.592 -34.356  33.418  1.00237.05           C
ANISOU 1029  CD  GLN A 143    26474  36472  27124  -5553   4922  -2544       C
ATOM   1030  OE1 GLN A 143     -16.331 -33.616  32.471  1.00239.02           O
ANISOU 1030  OE1 GLN A 143    26666  36954  27196  -5666   5205  -2431       O
ATOM   1031  NE2 GLN A 143     -15.774 -35.318  33.818  1.00239.66           N
ANISOU 1031  NE2 GLN A 143    26999  36640  27420  -4949   5211  -2812       N
ATOM   1032  N   GLU A 144     -17.428 -30.255  32.542  1.00197.99           N
ANISOU 1032  N   GLU A 144    19755  32520  22953  -6739   4829  -1595       N
ATOM   1033  CA  GLU A 144     -17.742 -29.042  31.794  1.00197.78           C
ANISOU 1033  CA  GLU A 144    19462  32731  22953  -7134   4865  -1264       C
ATOM   1034  C   GLU A 144     -19.259 -28.794  31.692  1.00195.49           C
ANISOU 1034  C   GLU A 144    19364  32304  22610  -7763   4224   -961       C
ATOM   1035  O   GLU A 144     -20.070 -29.718  31.825  1.00195.69           O
ANISOU 1035  O   GLU A 144    19962  32019  22371  -7936   3780  -1034       O
ATOM   1036  CB  GLU A 144     -17.085 -29.075  30.403  1.00203.86           C
ANISOU 1036  CB  GLU A 144    20752  33573  23133  -6991   5354  -1312       C
ATOM   1037  CG  GLU A 144     -15.549 -29.002  30.416  1.00206.43           C
ANISOU 1037  CG  GLU A 144    20683  34130  23620  -6399   6070  -1501       C
ATOM   1038  CD  GLU A 144     -14.942 -28.717  29.039  1.00212.17           C
ANISOU 1038  CD  GLU A 144    21768  34994  23855  -6316   6614  -1454       C
ATOM   1039  OE1 GLU A 144     -15.340 -29.372  28.054  1.00216.47           O
ANISOU 1039  OE1 GLU A 144    23276  35309  23664  -6423   6560  -1524       O
ATOM   1040  OE2 GLU A 144     -14.056 -27.841  28.941  1.00212.78           O
ANISOU 1040  OE2 GLU A 144    21178  35403  24265  -6156   7104  -1350       O
ATOM   1041  N   ALA A 145     -19.623 -27.536  31.453  1.00194.16           N
ANISOU 1041  N   ALA A 145    18691  32364  22717  -8098   4192   -601       N
ATOM   1042  CA  ALA A 145     -21.018 -27.115  31.345  1.00192.29           C
ANISOU 1042  CA  ALA A 145    18481  32059  22520  -8666   3630   -233       C
ATOM   1043  C   ALA A 145     -21.822 -27.941  30.336  1.00196.54           C
ANISOU 1043  C   ALA A 145    19995  32369  22310  -8977   3258   -210       C
ATOM   1044  O   ALA A 145     -23.052 -27.864  30.278  1.00195.68           O
ANISOU 1044  O   ALA A 145    19990  32174  22187  -9454   2703     77       O
ATOM   1045  CB  ALA A 145     -21.075 -25.634  30.985  1.00191.32           C
ANISOU 1045  CB  ALA A 145    17763  32216  22714  -8892   3788    152       C
ATOM   1046  N   ALA A 146     -21.116 -28.732  29.540  1.00206.68           N
ANISOU 1046  N   ALA A 146    21996  33559  22975  -8709   3572   -509       N
ATOM   1047  CA  ALA A 146     -21.744 -29.529  28.497  1.00211.72           C
ANISOU 1047  CA  ALA A 146    23660  33969  22816  -9000   3271   -544       C
ATOM   1048  C   ALA A 146     -22.446 -30.772  29.031  1.00211.55           C
ANISOU 1048  C   ALA A 146    24171  33561  22646  -9117   2787   -746       C
ATOM   1049  O   ALA A 146     -23.675 -30.869  28.980  1.00211.16           O
ANTSOU 1049  O   ALA A 146    24304  33399  22528  -9643   2167   -509       O
ATOM   1050  CB  ALA A 146     -20.710 -29.915  27.433  1.00217.80           C
ANISOU 1050  CB  ALA A 146    25069  34743  22943  -8652   3849   -809       C
ATOM   1051  N   ILE A 147     -21.653 -31.712  29.543  1.00206.04           N
ANISOU 1051  N   ILE A 147    23696  32667  21922  -8622   3081  -1157       N
ATOM   1052  CA  ILE A 147     -22.160 -32.992  30.036  1.00206.58           C
ANISOU 1052  CA  ILE A 147    24350  32320  21821  -8661   2715  -1390       C
ATOM   1053  C   ILE A 147     -23.454 -32.804  30.806  1.00202.21           C
ANISOU 1053  C   ILE A 147    23426  31712  21691  -9157   2055  -1091       C
ATOM   1054  O   ILE A 147     -24.225 -33.744  30.984  1.00203.30           O
ANISOU 1054  O   ILE A 147    24107  31511  21626  -9413   1610  -1163       O
ATOM   1055  CB  ILE A 147     -21.126 -33.702  30.948  1.00205.69           C
ANISOU 1055  CB  ILE A 147    24103  32089  21963  -7997   3119  -1757       C
ATOM   1056  CG1 ILE A 147     -19.742 -33.728  30.291  1.00209.84           C
ANISOU 1056  CG1 ILE A 147    24772  32742  22217  -7436   3857  -1994       C
ATOM   1057  CG2 ILE A 147     -21.575 -35.118  31.278  1.00207.54           C
ANISOU 1057  CG2 ILE A 147    25110  31833  21913  -8008   2810  -2012       C
ATOM   1058  CD1 ILE A 147     -19.627 -34.696  29.127  1.00217.05           C
ANISOU 1058  CD1 ILE A 147    26877  33340  22253  -7396   4004  -2256       C
ATOM   1059  N   LEU A 148     -23.682 -31.568  31.240  1.00200.14           N
ANISOU 1059  N   LEU A 148    22246  31773  22024  -9294   2024   -744       N
ATOM   1060  CA  LEU A 148     -24.844 -31.205  32.044  1.00195.82           C
```

FIG. 13 Continued

```
ANISOU 1060  CA  LEU A 148    21202  31220  21981  -9698   1501   -416       C
ATOM   1061  C   LEU A 148   -26.111 -31.904  31.586  1.00198.60             C
ANISOU 1061  C   LEU A 148    22212  31315  21933 -10262    858   -277       C
ATOM   1062  O   LEU A 148   -26.495 -32.924  32.152  1.00198.66             O
ANISOU 1062  O   LEU A 148    22574  31002  21906 -10303    590   -447       O
ATOM   1063  CB  LEU A 148   -25.041 -29.683  32.044  1.00192.78             C
ANISOU 1063  CB  LEU A 148    19973  31196  22078  -9870   1564      0       C
ATOM   1064  CG  LEU A 148   -25.844 -29.056  33.191  1.00187.36             C
ANISOU 1064  CG  LEU A 148    18503  30558  22126 -10060   1283    296       C
ATOM   1065  CD1 LEU A 148   -25.370 -29.542  34.559  1.00183.76             C
ANISOU 1065  CD1 LEU A 148    17748  29989  22084  -9673   1419      7       C
ATOM   1066  CD2 LEU A 148   -25.770 -27.541  33.105  1.00185.19             C
ANISOU 1066  CD2 LEU A 148    17468  30606  22291 -10123   1499    639       C
ATOM   1067  N   VAL A 149   -26.747 -31.362  30.555  1.00213.70             N
ANISOU 1067  N   VAL A 149    24286  33371  23541 -10709    602     46       N
ATOM   1068  CA  VAL A 149   -27.987 -31.930  30.042  1.00217.01             C
ANISOU 1068  CA  VAL A 149    25274  33602  23576 -11317    -70    231       C
ATOM   1069  C   VAL A 149   -28.852 -32.501  31.161  1.00214.02             C
ANISOU 1069  C   VAL A 149    24698  32994  23627 -11509   -499    290       C
ATOM   1070  O   VAL A 149   -28.627 -33.616  31.630  1.00214.70             O
ANISOU 1070  O   VAL A 149    25250  32747  23579 -11327   -485    -71       O
ATOM   1071  CB  VAL A 149   -27.737 -33.010  28.965  1.00223.86             C
ANISOU 1071  CB  VAL A 149    27328  34205  23523 -11375    -88   -117       C
ATOM   1072  CG1 VAL A 149   -26.695 -34.024  29.432  1.00224.34             C
ANISOU 1072  CG1 VAL A 149    27796  33977  23465 -10794    369   -667       C
ATOM   1073  CG2 VAL A 149   -29.052 -33.700  28.580  1.00227.47             C
ANISOU 1073  CG2 VAL A 149    28375  34436  23619 -12060   -853     42       C
ATOM   1074  N   PRO A 150   -29.863 -31.733  31.572  1.00232.50             N
ANISOU 1074  N   PRO A 150    26354  35498  26486 -11870   -862    773       N
ATOM   1075  CA  PRO A 150   -30.816 -32.044  32.643  1.00229.58             C
ANISOU 1075  CA  PRO A 150    25644  34973  26614 -12095  -1253    948       C
ATOM   1076  C   PRO A 150   -31.111 -33.536  32.816  1.00232.39             C
ANISOU 1076  C   PRO A 150    26786  34899  26614 -12231  -1550    646       C
ATOM   1077  O   PRO A 150   -31.391 -34.244  31.844  1.00237.96             O
ANISOU 1077  O   PRO A 150    28328  35431  26655 -12564  -1845    549       O
ATOM   1078  CB  PRO A 150   -32.066 -31.297  32.194  1.00230.57             C
ANISOU 1078  CB  PRO A 150    25419  35298  26888 -12674  -1758   1546       C
ATOM   1079  CG  PRO A 150   -31.500 -30.064  31.526  1.00230.27             C
ANISOU 1079  CG  PRO A 150    25015  35612  26866 -12511  -1397   1724       C
ATOM   1080  CD  PRO A 150   -30.172 -30.448  30.921  1.00232.54             C
ANISOU 1080  CD  PRO A 150    25883  35861  26611 -12087   -890   1232       C
ATOM   1081  N   GLY A 151   -31.039 -33.990  34.066  1.00222.32             N
ANISOU 1081  N   GLY A 151    25258  33441  25774 -11980  -1462    500       N
ATOM   1082  CA  GLY A 151   -31.268 -35.380  34.420  1.00224.51             C
ANISOU 1082  CA  GLY A 151    26209  33277  25816 -12051  -1680    226       C
ATOM   1083  C   GLY A 151   -30.515 -35.772  35.681  1.00220.67             C
ANISOU 1083  C   GLY A 151    25489  32652  25701 -11473  -1294    -71       C
ATOM   1084  O   GLY A 151   -31.112 -36.158  36.689  1.00218.52             O
ANISOU 1084  O   GLY A 151    25014  32209  25807 -11564  -1497     24       O
ATOM   1085  N   ASP A 152   -29.191 -35.656  35.613  1.00228.72             N
ANISOU 1085  N   ASP A 152    26522  33769  26612 -10876   -732   -407       N
ATOM   1086  CA  ASP A 152   -28.294 -36.001  36.712  1.00225.81             C
ANISOU 1086  CA  ASP A 152    25933  33323  26540 -10267   -342   -699       C
ATOM   1087  C   ASP A 152   -28.377 -35.018  37.876  1.00219.78             C
ANISOU 1087  C   ASP A 152    24144  32837  26525 -10139   -246   -462       C
ATOM   1088  O   ASP A 152   -29.118 -34.037  37.822  1.00217.80             O
ANISOU 1088  O   ASP A 152    23344  32820  26591 -10491   -432    -69       O
ATOM   1089  CB  ASP A 152   -26.855 -36.065  36.204  1.00227.72             C
ANISOU 1089  CB  ASP A 152    26407  33648  26469  -9688    228  -1070       C
ATOM   1090  CG  ASP A 152   -26.445 -34.806  35.460  1.00227.18             C
ANISOU 1090  CG  ASP A 152    25879  34007  26431  -9683    484   -905       C
ATOM   1091  OD1 ASP A 152   -27.135 -33.774  35.601  1.00224.20             O
ANISOU 1091  OD1 ASP A 152    24855  33882  26448 -10012    287   -515       O
ATOM   1092  OD2 ASP A 152   -25.431 -34.850  34.734  1.00230.05             O
ANISOU 1092  OD2 ASP A 152    26533  34441  26433  -9335    911  -1151       O
ATOM   1093  N   ILE A 153   -27.602 -35.287  38.924  1.00186.22             N
ANISOU 1093  N   ILE A 153    19664  28552  22540  -9622     53   -699       N
ATOM   1094  CA  ILE A 153   -27.603 -34.455  40.128  1.00180.97             C
ANISOU 1094  CA  ILE A 153    18117  28111  22531  -9474    158   -540       C
```

FIG. 13 Continued

```
ATOM   1095  C   ILE A 153     -26.420 -33.481  40.174  1.00179.04           C
ANISOU 1095  C   ILE A 153     17296  28240  22493  -9047    643   -654      C
ATOM   1096  O   ILE A 153     -25.327 -33.800  39.712  1.00181.40           O
ANISOU 1096  O   ILE A 153     17862  28568  22492  -8647    982   -956      O
ATOM   1097  CB  ILE A 153     -27.634 -35.323  41.409  1.00179.51           C
ANISOU 1097  CB  ILE A 153     17996  27669  22543  -9241    105   -673      C
ATOM   1098  CG1 ILE A 153     -29.019 -35.949  41.607  1.00180.38           C
ANISOU 1098  CG1 ILE A 153     18398  27474  22664  -9765   -387   -430      C
ATOM   1099  CG2 ILE A 153     -27.257 -34.496  42.632  1.00174.78           C
ANISOU 1099  CG2 ILE A 153     16566  27327  22514  -8952    325   -625      C
ATOM   1100  CD1 ILE A 153     -29.423 -36.901  40.519  1.00185.62           C
ANISOU 1100  CD1 ILE A 153     19957  27829  22743 -10098   -663   -513      C
ATOM   1101  N   VAL A 154     -26.646 -32.301  40.747  1.00194.90           N
ANISOU 1101  N   VAL A 154     18513  30515  25027  -9135    691   -407      N
ATOM   1102  CA  VAL A 154     -25.635 -31.244  40.790  1.00193.25           C
ANISOU 1102  CA  VAL A 154     17705  30655  25064  -8837   1114   -473      C
ATOM   1103  C   VAL A 154     -25.116 -30.855  42.178  1.00189.57           C
ANISOU 1103  C   VAL A 154     16616  30316  25094  -8515   1297   -571      C
ATOM   1104  O   VAL A 154     -25.093 -31.673  43.097  1.00188.95           O
ANISOU 1104  O   VAL A 154     16683  30056  25051  -8313   1208   -718      O
ATOM   1105  CB  VAL A 154     -26.174 -29.983  40.106  1.00192.61           C
ANISOU 1105  CB  VAL A 154     17234  30800  25149  -9215   1086   -110      C
ATOM   1106  CG1 VAL A 154     -25.675 -29.905  38.676  1.00196.42           C
ANISOU 1106  CG1 VAL A 154     18098  31382  25152  -9228   1251   -161      C
ATOM   1107  CG2 VAL A 154     -27.702 -29.974  40.149  1.00192.15           C
ANISOU 1107  CG2 VAL A 154     17201  30595  25210  -9739    616    280      C
ATOM   1108  N   SER A 155     -24.695 -29.595  42.302  1.00161.13           N
ANISOU 1108  N   SER A 155     12353  27019  21850  -8485   1548   -486      N
ATOM   1109  CA  SER A 155     -24.170 -29.038  43.549  1.00158.08           C
ANISOU 1109  CA  SER A 155     11353  26789  21921  -8242   1721   -581      C
ATOM   1110  C   SER A 155     -24.010 -27.519  43.447  1.00156.43           C
ANISOU 1110  C   SER A 155     10491  26853  22092  -8383   1944   -410      C
ATOM   1111  O   SER A 155     -24.559 -26.894  42.546  1.00157.11           O
ANISOU 1111  O   SER A 155     10572  26977  22147  -8702   1911   -141      O
ATOM   1112  CB  SER A 155     -22.816 -29.662  43.886  1.00159.49           C
ANISOU 1112  CB  SER A 155     11581  27048  21969  -7701   1973   -961      C
ATOM   1113  OG  SER A 155     -22.917 -31.064  44.050  1.00161.25           O
ANISOU 1113  OG  SER A 155     12420  26980  21867   7524   1804   1119      O
ATOM   1114  N   ILE A 156     -23.251 -26.929  44.370  1.00155.72           N
ANISOU 1114  N   ILE A 156      9870  26945  22350  -8155   2162   -562      N
ATOM   1115  CA  ILE A 156     -22.991 -25.488  44.332  1.00154.57           C
ANISOU 1115  CA  ILE A 156      9126  27025  22578  -8285   2408   -442      C
ATOM   1116  C   ILE A 156     -22.078 -24.959  45.466  1.00153.19           C
ANISOU 1116  C   ILE A 156      8414  27036  22754  -8048   2605   -670      C
ATOM   1117  O   ILE A 156     -21.860 -25.630  46.477  1.00152.50           O
ANISOU 1117  O   ILE A 156      8367  26902  22674  -7814   2496   -863      O
ATOM   1118  CB  ILE A 156     -24.311 -24.689  44.297  1.00152.84           C
ANISOU 1118  CB  ILE A 156      8747  26697  22628  -8716   2247    -39      C
ATOM   1119  CG1 ILE A 156     -24.211 -23.546  43.297  1.00153.84           C
ANISOU 1119  CG1 ILE A 156      8630  26980  22844  -8913   2464    178      C
ATOM   1120  CG2 ILE A 156      24.678  24.188  45.674  1.00149.93           C
ANISOU 1120  CG2 ILE A 156      7980  26281  22706  -8739   2230    -13      C
ATOM   1121  CD1 ILE A 156     -25.364 -22.608  43.361  1.00152.42           C
ANISOU 1121  CD1 ILE A 156      8184  26717  23012  -9265   2372    590      C
ATOM   1122  N   LYS A 157     -21.541 -23.755  45.270  1.00151.72           N
ANISOU 1122  N   LYS A 157      7745  27059  22843  -8130   2883   -637      N
ATOM   1123  CA  LYS A 157     -20.686 -23.090  46.248  1.00151.00           C
ANISOU 1123  CA  LYS A 157      7120  27157  23095  -8001   3055   -839      C
ATOM   1124  C   LYS A 157     -21.098 -21.629  46.316  1.00149.69           C
ANISOU 1124  C   LYS A 157      6532  26999  23344  -8335   3201   -626      C
ATOM   1125  O   LYS A 157     -22.240 -21.292  46.046  1.00148.57           O
ANISOU 1125  O   LYS A 157      6493  26676  23281  -8612   3095   -314      O
ATOM   1126  CB  LYS A 157     -19.215 -23.159  45.830  1.00153.78           C
ANISOU 1126  CB  LYS A 157      7289  27791  23350  -7705   3331  -1083      C
ATOM   1127  CG  LYS A 157     -18.572 -24.553  45.837  1.00155.78           C
ANISOU 1127  CG  LYS A 157      7898  28053  23238  -7279   3270  -1321      C
ATOM   1128  CD  LYS A 157     -17.021 -24.463  45.831  1.00158.57           C
ANISOU 1128  CD  LYS A 157      7859  28739  23651  -6945   3560  -1556      C
ATOM   1129  CE  LYS A 157     -16.322 -25.790  45.469  1.00161.63           C
```

FIG. 13 Continued

```
ANISOU 1129  CE  LYS A 157     8629  29130  23654  -6477   3611  -1738       C
ATOM   1130  NZ  LYS A 157     -16.318 -26.819  46.558  1.00161.14           N
ANISOU 1130  NZ  LYS A 157     8744  28961  23520  -6179   3352  -1890       N
ATOM   1131  N   LEU A 158     -20.170 -20.758  46.689  1.00159.97           N
ANISOU 1131  N   LEU A 158     7351  28503  24928  -8311   3445   -781       N
ATOM   1132  CA  LEU A 158     -20.445 -19.320  46.699  1.00159.35           C
ANISOU 1132  CA  LEU A 158     6897  28398  25249  -8622   3640   -600       C
ATOM   1133  C   LEU A 158     -19.780 -18.657  45.488  1.00161.76           C
ANISOU 1133  C   LEU A 158     7047  28871  25544  -8696   3949   -510       C
ATOM   1134  O   LEU A 158     -19.324 -17.506  45.534  1.00162.45           O
ANISOU 1134  O   LEU A 158     6723  29038  25964  -8856   4209   -500       O
ATOM   1135  CB  LEU A 158     -20.016 -18.667  48.022  1.00158.57           C
ANISOU 1135  CB  LEU A 158     6402  28347  25499  -8639   3693   -817       C
ATOM   1136  CG  LEU A 158     -20.215 -17.152  48.202  1.00158.36           C
ANISOU 1136  CG  LEU A 158     6014  28243  25912  -8952   3930   -691       C
ATOM   1137  CD1 LEU A 158     -20.869 -16.792  49.553  1.00156.48           C
ANISOU 1137  CD1 LEU A 158     5722  27810  25924  -9046   3841   -735       C
ATOM   1138  CD2 LEU A 158     -18.883 -16.399  47.983  1.00160.85           C
ANISOU 1138  CD2 LEU A 158     5905  28816  26396  -8978   4214   -879       C
ATOM   1139  N   GLY A 159     -19.734 -19.404  44.391  1.00154.47           N
ANISOU 1139  N   GLY A 159     6495  27980  24217  -8591   3933   -446       N
ATOM   1140  CA  GLY A 159     -19.132 -18.909  43.168  1.00157.18           C
ANISOU 1140  CA  GLY A 159     6777  28479  24467  -8833   4240   -346       C
ATOM   1141  C   GLY A 159     -19.615 -19.667  41.950  1.00158.70           C
ANISOU 1141  C   GLY A 159     7529  28599  24169  -8625   4141   -180       C
ATOM   1142  O   GLY A 159     -19.407 -19.254  40.809  1.00161.03           O
ANISOU 1142  O   GLY A 159     7887  28980  24319  -8711   4361    -15       O
ATOM   1143  N   ASP A 160     -20.263 -20.796  42.189  1.00159.49           N
ANISOU 1143  N   ASP A 160     8072  28533  23993  -8589   3804   -224       N
ATOM   1144  CA  ASP A 160     -20.780 -21.574  41.084  1.00161.31           C
ANISOU 1144  CA  ASP A 160     8898  28664  23728  -8580   3657    -93       C
ATOM   1145  C   ASP A 160     -22.122 -20.991  40.579  1.00160.56           C
ANISOU 1145  C   ASP A 160     8896  28418  23690  -8983   3454    346       C
ATOM   1146  O   ASP A 160     -23.198 -21.547  40.862  1.00159.26           O
ANISOU 1146  O   ASP A 160     8994  28056  23463  -9120   3087    481       O
ATOM   1147  CB  ASP A 160     -20.964 -23.049  41.485  1.00161.19           C
ANISOU 1147  CB  ASP A 160     9367  28494  23386  -8364   3369   -304       C
ATOM   1148  CG  ASP A 160     -19.781 -23.618  42.242  1.00161.69           C
ANISOU 1148  CG  ASP A 160     9274  28687  23475  -7942   3511   -687       C
ATOM   1149  OD1 ASP A 160     -19.050 -22.841  42.879  1.00161.07           O
ANISOU 1149  OD1 ASP A 160     8628  28799  23772  -7881   3713   -788       O
ATOM   1150  OD2 ASP A 160     -19.606 -24.856  42.212  1.00163.05           O
ANISOU 1150  OD2 ASP A 160     9901  28757  23292  -7680   3404   -873       O
ATOM   1151  N   ILE A 161     -22.069 -19.884  39.832  1.00170.92           N
ANISOU 1151  N   ILE A 161     9980  29827  25135  -9170   3690    599       N
ATOM   1152  CA  ILE A 161     -23.295 -19.327  39.260  1.00170.92           C
ANISOU 1152  CA  ILE A 161     10053 29711  25179  -9517   3501   1064       C
ATOM   1153  C   ILE A 161     -24.003 -20.500  38.636  1.00172.31           C
ANISOU 1153  C   ILE A 161     10862 29776  24833  -9583   3120   1123       C
ATOM   1154  O   ILE A 161     -23.541 -21.060  37.653  1.00175.32           O
ANISOU 1154  O   ILE A 161     11670 30226  24718  -9503   3181   1026       O
ATOM   1155  CB  ILE A 161     -23.040 -18.296  38.138  1.00173.44           C
ANISOU 1155  CB  ILE A 161     10256 30158  25488  -9662   3795   1337       C
ATOM   1156  CG1 ILE A 161     -22.265 -17.076  38.659  1.00172.77           C
ANISOU 1156  CG1 ILE A 161     9560  30161  25922  -9641   4207   1277       C
ATOM   1157  CG2 ILE A 161     -24.366 -17.900  37.476  1.00174.09           C
ANISOU 1157  CG2 ILE A 161     10473 30132  25540  -9992   3525   1856       C
ATOM   1158  CD1 ILE A 161     -21.824 -16.107  37.569  1.00175.68           C
ANISOU 1158  CD1 ILE A 161     9017  30654  26279  -9754   4564   1513       C
ATOM   1159  N   ILE A 162     -25.110 -20.891  39.228  1.00158.94           N
ANISOU 1159  N   ILE A 162     9247  27898  23245  -9735   2743   1270       N
ATOM   1160  CA  ILE A 162     -25.847 -22.032  38.731  1.00160.48           C
ANISOU 1160  CA  ILE A 162     10037 27960  22978  -9857   2336   1323       C
ATOM   1161  C   ILE A 162     -25.554 -22.267  37.247  1.00164.54           C
ANISOU 1161  C   ILE A 162     11029 28566  22922  -9915   2374   1365       C
ATOM   1162  O   ILE A 162     -25.366 -21.322  36.484  1.00166.02           O
ANISOU 1162  O   ILE A 162     11044 28897  23139  -10011  2595   1591       O
ATOM   1163  CB  ILE A 162     -27.383 -21.841  38.951  1.00159.49           C
ANISOU 1163  CB  ILE A 162     9824  27688  23086  -10206  1945   1768       C
```

FIG. 13 Continued

```
ATOM   1164  CG1 ILE A 162      -27.789 -22.150  40.403  1.00156.22           C
ANISOU 1164  CG1 ILE A 162       9190  27120  23046 -10128   1832   1665      C
ATOM   1165  CG2 ILE A 162      -28.197 -22.686  37.968  1.00162.55           C
ANISOU 1165  CG2 ILE A 162      10800  27999  22962 -10476   1513   1957      C
ATOM   1166  CD1 ILE A 162      -27.888 -20.931  41.299  1.00153.64           C
ANISOU 1166  CD1 ILE A 162       8227  26803  23345 -10118   2081   1796      C
ATOM   1167  N   PRO A 163      -25.487 -23.540  36.844  1.00220.82           N
ANISOU 1167  N   PRO A 163      18801  35590  29511  -9848   2184   1138      N
ATOM   1168  CA  PRO A 163      -25.309 -23.958  35.449  1.00225.27           C
ANISOU 1168  CA  PRO A 163      19973  36190  29430  -9917   2179   1140      C
ATOM   1169  C   PRO A 163      -26.546 -23.607  34.632  1.00227.07           C
ANISOU 1169  C   PRO A 163      20353  36404  29518 -10381   1789   1630      C
ATOM   1170  O   PRO A 163      -26.445 -23.011  33.557  1.00229.89           O
ANISOU 1170  O   PRO A 163      20805  36907  29635 -10502   1906   1848      O
ATOM   1171  CB  PRO A 163      -25.218 -25.479  35.553  1.00226.67           C
ANISOU 1171  CB  PRO A 163      20802  36159  29164  -9773   1985    785      C
ATOM   1172  CG  PRO A 163      -24.922 -25.767  36.974  1.00223.03           C
ANISOU 1172  CG  PRO A 163      19993  35624  29123  -9503   2036    540      C
ATOM   1173  CD  PRO A 163      -25.496 -24.677  37.775  1.00219.39           C
ANISOU 1173  CD  PRO A 163      18834  35225  29298  -9669   2004    831      C
ATOM   1174  N   ALA A 164      -27.702 -24.000  35.166  1.00171.98           N
ANISOU 1174  N   ALA A 164      13386  29264  22695 -10633   1325   1820      N
ATOM   1175  CA  ALA A 164      -29.010 -23.766  34.565  1.00173.80           C
ANISOU 1175  CA  ALA A 164      13682  29486  22867 -11091    867   2325      C
ATOM   1176  C   ALA A 164      -30.052 -24.241  35.566  1.00171.53           C
ANISOU 1176  C   ALA A 164      13243  29014  22916 -11256    478   2445      C
ATOM   1177  O   ALA A 164      -29.736 -25.016  36.460  1.00169.55           O
ANISOU 1177  O   ALA A 164      13080  28614  22727 -11039    514   2089      O
ATOM   1178  CB  ALA A 164      -29.145 -24.513  33.260  1.00178.67           C
ANISOU 1178  CB  ALA A 164      15110  30115  22740 -11302    607   2312      C
ATOM   1179  N   ASP A 165      -31.291 -23.794  35.409  1.00173.94           N
ANISOU 1179  N   ASP A 165      13316  29335  23439 -11628    116   2972      N
ATOM   1180  CA  ASP A 165      -32.364 -24.110  36.360  1.00172.12           C
ANISOU 1180  CA  ASP A 165      12843  28950  23603 -11800   -212   3170      C
ATOM   1181  C   ASP A 165      -32.345 -25.519  36.997  1.00171.69           C
ANISOU 1181  C   ASP A 165      13237  28659  23339 -11743   -405   2784      C
ATOM   1182  O   ASP A 165      -31.943 -26.508  36.371  1.00174.46           O
ANISOU 1182  O   ASP A 165      14276  28920  23090 -11745   -517   2474      O
ATOM   1183  CB  ASP A 165      -33.735 -23.813  35.733  1.00174.98           C
ANISOU 1183  CB  ASP A 165      13102  29371  24011 -12270   -697   3795      C
ATOM   1184  CG  ASP A 165      -34.094 -24.777  34.608  1.00179.92           C
ANISOU 1184  CG  ASP A 165      14468  29973  23922 -12617  -1182   3799      C
ATOM   1185  OD1 ASP A 165      -34.195 -25.993  34.873  1.00180.59           O
ANISOU 1185  OD1 ASP A 165      15028  29852  23735 -12685  -1422   3505      O
ATOM   1186  OD2 ASP A 165      -34.297 -24.317  33.461  1.00183.50           O
ANISOU 1186  OD2 ASP A 165      15053  30598  24069 -12838  -1331   4104      O
ATOM   1187  N   ALA A 166      -32.791 -25.579  38.254  1.00167.32           N
ANISOU 1187  N   ALA A 166      12309  27984  23282 -11681   -413   2816      N
ATOM   1188  CA  ALA A 166      -32.879 -26.819  39.026  1.00166.70           C
ANISOU 1188  CA  ALA A 166      12572  27663  23105 -11626   -578   2523      C
ATOM   1189  C   ALA A 166      -33.833 -26.640  40.205  1.00164.21           C
ANISOU 1189  C   ALA A 166      11763  27249  23379 -11716   -676   2803      C
ATOM   1190  O   ALA A 166      -34.702 -25.769  40.178  1.00164.20           O
ANISOU 1190  O   ALA A 166      11273  27342  23773 -11931   -755   3295      O
ATOM   1191  CB  ALA A 166      -31.512 -27.259  39.508  1.00165.03           C
ANISOU 1191  CB  ALA A 166      12548  27412  22742 -11138   -186   1944      C
ATOM   1192  N   ARG A 167      -33.662 -27.447  41.248  1.00245.99           N
ANISOU 1192  N   ARG A 167      22246  37416  33802 -11525   -638   2509      N
ATOM   1193  CA  ARG A 167      -34.598 -27.412  42.369  1.00244.17           C
ANISOU 1193  CA  ARG A 167      21631  37070  34073 -11617   -720   2768      C
ATOM   1194  C   ARG A 167      -34.043 -27.821  43.744  1.00241.08           C
ANISOU 1194  C   ARG A 167      21195  36546  33856 -11243   -462   2407      C
ATOM   1195  O   ARG A 167      -34.811 -27.913  44.703  1.00239.93           O
ANISOU 1195  O   ARG A 167      20812  36281  34069 -11310   -514   2601      O
ATOM   1196  CB  ARG A 167      -35.806 -28.288  42.035  1.00247.40           C
ANISOU 1196  CB  ARG A 167      22334  37325  34342 -12086  -1257   3068      C
ATOM   1197  CG  ARG A 167      -35.432 -29.599  41.356  1.00250.46           C
ANISOU 1197  CG  ARG A 167      23551  37541  34070 -12170  -1509   2715      C
ATOM   1198  CD  ARG A 167      -34.769 -30.567  42.326  1.00248.81           C
```

FIG. 13 Continued

```
ANISOU 1198  CD  ARG A 167    23659  37102  33775 -11821  -1340   2251       C
ATOM   1199  NE  ARG A 167   -35.749 -31.340  43.084  1.00249.33             N
ANISOU 1199  NE  ARG A 167    23779  36928  34027 -12060  -1617   2428       N
ATOM   1200  CZ  ARG A 167   -35.927 -32.653  42.960  1.00252.12             C
ANISOU 1200  CZ  ARG A 167    24789  36994  34013 -12226  -1902   2256       C
ATOM   1201  NH1 ARG A 167   -35.176 -33.350  42.118  1.00254.67             N
ANISOU 1201  NH1 ARG A 167    25799  37220  33746 -12148  -1929   1880       N
ATOM   1202  NH2 ARG A 167    36.850  33.274  43.684  1.00252.71             N
ANISOU 1202  NH2 ARG A 167    24852  36855  34312 -12467  -2129   2461       N
ATOM   1203  N   LEU A 168   -32.732 -28.065  43.834  1.00184.52             N
ANISOU 1203  N   LEU A 168    14251  29418  26442 -10849   -186   1915       N
ATOM   1204  CA  LEU A 168   -32.056 -28.473  45.085  1.00182.10             C
ANISOU 1204  CA  LEU A 168    13925  29026  26241 -10460     36   1556       C
ATOM   1205  C   LEU A 168   -32.868 -29.342  46.064  1.00181.86             C
ANISOU 1205  C   LEU A 168    14025  28741  26330 -10548   -172   1639       C
ATOM   1206  O   LEU A 168   -33.726 -28.831  46.780  1.00180.54             O
ANISOU 1206  O   LEU A 168    13441  28555  26602 -10682   -163   1959       O
ATOM   1207  CB  LEU A 168   -31.428 -27.267  45.807  1.00179.09             C
ANISOU 1207  CB  LEU A 168    12946  28832  26266 -10190    448   1482       C
ATOM   1208  CG  LEU A 168   -32.221 -25.995  46.117  1.00177.70             C
ANISOU 1208  CG  LEU A 168    12166  28728  26622 -10367    562   1893       C
ATOM   1209  CD1 LEU A 168   -31.469 -25.127  47.124  1.00175.00             C
ANISOU 1209  CD1 LEU A 168    11401  28481  26611 -10062    965   1676       C
ATOM   1210  CD2 LEU A 168   -32.507 -25.210  44.849  1.00179.45             C
ANISOU 1210  CD2 LEU A 168    12266  29096  26821 -10618    515   2211       C
ATOM   1211  N   LEU A 169   -32.565 -30.641  46.126  1.00229.11             N
ANISOU 1211  N   LEU A 169    20597  34517  31938 -10446   -313   1356       N
ATOM   1212  CA  LEU A 169   -33.338 -31.572  46.968  1.00229.49             C
ANISOU 1212  CA  LEU A 169    20847  34290  32059 -10561   -519   1447       C
ATOM   1213  C   LEU A 169   -33.524 -31.081  48.402  1.00226.46             C
ANISOU 1213  C   LEU A 169    19984  33922  32138 -10378   -295   1524       C
ATOM   1214  O   LEU A 169   -34.655 -30.983  48.885  1.00226.46             O
ANISOU 1214  O   LEU A 169    19755  33831  32458 -10646   -408   1896       O
ATOM   1215  CB  LEU A 169   -32.735 -32.990  46.968  1.00231.45             C
ANISOU 1215  CB  LEU A 169    21806  34286  31850 -10361   -603   1066       C
ATOM   1216  CG  LEU A 169   -33.685 -34.191  47.183  1.00233.88             C
ANISOU 1216  CG  LEU A 169    22571  34238  32055 -10668   -948   1201       C
ATOM   1217  CD1 LEU A 169   -32.950 -35.524  47.065  1.00236.25             C
ANISOU 1217  CD1 LEU A 169    23625  34260  31877 -10422   -972    795       C
ATOM   1218  CD2 LEU A 169   -34.449 -34.134  48.504  1.00232.04             C
ANISOU 1218  CD2 LEU A 169    21984  33917  32262 -10704   -919   1446       C
ATOM   1219  N   GLU A 170   -32.417 -30.776  49.075  1.00237.68             N
ANISOU 1219  N   GLU A 170    21257  35466  33586  -9932     24   1182       N
ATOM   1220  CA  GLU A 170   -32.463 -30.318  50.460  1.00235.21             C
ANISOU 1220  CA  GLU A 170    20566  35173  33632  -9741    244   1191       C
ATOM   1221  C   GLU A 170   -31.075 -30.205  51.054  1.00233.85             C
ANISOU 1221  C   GLU A 170    20344  35147  33363  -9262    507    753       C
ATOM   1222  O   GLU A 170   -30.072 -30.257  50.342  1.00234.59             O
ANISOU 1222  O   GLU A 170    20564  35372  33198  -9074    577    485       O
ATOM   1223  CB  GLU A 170   -33.281 -31.286  51.318  1.00235.91             C
ANISOU 1223  CB  GLU A 170    20900  34982  33754  -9831     79   1325       C
ATOM   1224  CG  GLU A 170    32.969  32.751  51.055  1.00238.23             C
ANISOU 1224  CG  GLU A 170    21874  35040  33603  -9759   -136   1095       C
ATOM   1225  CD  GLU A 170   -31.509 -32.979  50.707  1.00238.41             C
ANISOU 1225  CD  GLU A 170    22124  35176  33287  -9339     11    639       C
ATOM   1226  OE1 GLU A 170   -30.653 -32.849  51.608  1.00236.91             O
ANISOU 1226  OE1 GLU A 170    21781  35092  33142  -8932    229    391       O
ATOM   1227  OE2 GLU A 170   -31.217 -33.280  49.530  1.00240.44             O
ANISOU 1227  OE2 GLU A 170    22705  35428  33225  -9416    -89    541       O
ATOM   1228  N   GLY A 171   -31.029 -30.065  52.373  1.00190.60             N
ANISOU 1228  N   GLY A 171    14678  29655  28087  -9071    650    696       N
ATOM   1229  CA  GLY A 171   -29.771 -30.007  53.087  1.00189.77             C
ANISOU 1229  CA  GLY A 171    14505  29704  27897  -8640    840    308       C
ATOM   1230  C   GLY A 171   -29.732 -28.871  54.086  1.00187.80             C
ANISOU 1230  C   GLY A 171    13765  29591  27998  -8586   1086    318       C
ATOM   1231  O   GLY A 171   -29.637 -29.099  55.293  1.00187.34             O
ANISOU 1231  O   GLY A 171    13730  29488  27962  -8397   1135    218       O
ATOM   1232  N   ASP A 172   -29.814 -27.645  53.570  1.00191.85             N
ANISOU 1232  N   ASP A 172    13875  30252  28766  -8757   1246    441       N
```

FIG. 13 Continued

```
ATOM   1233  CA   ASP A 172     -29.769 -26.434  54.385  1.00190.42           C
ANISOU 1233  CA   ASP A 172     13254  30168  28928  -8740   1516    439      C
ATOM   1234  C    ASP A 172     -29.838 -25.188  53.492  1.00190.16           C
ANISOU 1234  C    ASP A 172     12855  30258  29140  -8944   1677    602      C
ATOM   1235  O    ASP A 172     -28.793 -24.681  53.065  1.00190.24           O
ANISOU 1235  O    ASP A 172     12714  30472  29097  -8832   1805    364      O
ATOM   1236  CB   ASP A 172     -28.485 -26.410  55.211  1.00190.20           C
ANISOU 1236  CB   ASP A 172     13175  30314  28780  -8393   1623     14      C
ATOM   1237  CG   ASP A 172     -28.593 -25.528  56.435  1.00189.31           C
ANISOU 1237  CG   ASP A 172     12788  30210  28929  -8376   1837    -23      C
ATOM   1238  OD1  ASP A 172     -29.444 -25.807  57.312  1.00189.15           O
ANISOU 1238  OD1  ASP A 172     12883  30002  28982  -8411   1834    140      O
ATOM   1239  OD2  ASP A 172     -27.809 -24.559  56.524  1.00189.12           O
ANISOU 1239  OD2  ASP A 172     12457  30372  29027  -8337   2020   -222      O
ATOM   1240  N    PRO A 173     -31.072 -24.691  53.222  1.00155.07           N
ANISOU 1240  N    PRO A 173      6247  25691  24980  -9238   1681   1038      N
ATOM   1241  CA   PRO A 173     -31.375 -23.528  52.369  1.00155.25           C
ANISOU 1241  CA   PRO A 173      7933  25786  25267  -9446   1818   1303      C
ATOM   1242  C    PRO A 173     -30.258 -22.477  52.292  1.00154.75           C
ANISOU 1242  C    PRO A 173      7594  25912  25293  -9323   2101   1033      C
ATOM   1243  O    PRO A 173     -29.492 -22.314  53.244  1.00154.09           O
ANISOU 1243  O    PRO A 173      7447  25886  25215  -9120   2246    698      O
ATOM   1244  CB   PRO A 173     -32.630 -22.961  53.024  1.00155.10           C
ANISOU 1244  CB   PRO A 173      7668  25598  25664  -9599   1941   1696      C
ATOM   1245  CG   PRO A 173     -33.357 -24.219  53.511  1.00155.60           C
ANISOU 1245  CG   PRO A 173      8044  25493  25584  -9633   1689   1801      C
ATOM   1246  CD   PRO A 173     -32.313 -25.290  53.763  1.00155.42           C
ANISOU 1246  CD   PRO A 173      8413  25512  25128  -9380   1548   1349      C
ATOM   1247  N    LEU A 174     -30.168 -21.779  51.160  1.00231.13           N
ANISOU 1247  N    LEU A 174     17110  35685  35025  -9468   2164   1190      N
ATOM   1248  CA   LEU A 174     -29.094 -20.798  50.962  1.00231.12           C
ANISOU 1248  CA   LEU A 174     16848  35855  35113  -9391   2439    959      C
ATOM   1249  C    LEU A 174     -29.466 -19.529  50.187  1.00231.77           C
ANISOU 1249  C    LEU A 174     16621  35938  35501  -9598   2640   1288      C
ATOM   1250  O    LEU A 174     -30.529 -19.440  49.561  1.00232.49           O
ANISOU 1250  O    LEU A 174     16700  35942  35695  -9800   2525   1731      O
ATOM   1251  CB   LEU A 174     -27.864 -21.445  50.310  1.00231.93           C
ANISOU 1251  CB   LEU A 174     17143  36158  34823  -9216   2366    618      C
ATOM   1252  CG   LEU A 174     -27.978 -22.112  48.933  1.00233.44           C
ANISOU 1252  CG   LEU A 174     17636  36385  34676  -9306   2163    753      C
ATOM   1253  CD1  LEU A 174     -29.326 -21.874  48.243  1.00234.07           C
ANISOU 1253  CD1  LEU A 174     17716  36340  34879  -9625   2013   1262      C
ATOM   1254  CD2  LEU A 174     -26.813 -21.705  48.035  1.00234.67           C
ANISOU 1254  CD2  LEU A 174     17709  36765  34691  -9221   2350    564      C
ATOM   1255  N    LYS A 175     -28.547 -18.564  50.241  1.00204.92           N
ANISOU 1255  N    LYS A 175     13016  32625  32219   9519   2918   1071      N
ATOM   1256  CA   LYS A 175     -28.690 -17.266  49.593  1.00206.67           C
ANISOU 1256  CA   LYS A 175     13116  32767  32643  -9569   3131   1314      C
ATOM   1257  C    LYS A 175     -28.234 -17.311  48.140  1.00207.52           C
ANISOU 1257  C    LYS A 175     13184  33089  32574  -9710   3106   1409      C
ATOM   1258  O    LYS A 175     -27.043 -17.233  47.848  1.00207.74           O
ANISOU 1258  O    LYS A 175     13110  33325  32496  -9657   3247   1106      O
ATOM   1259  CB   LYS A 175     -27.915 -16.206  50.382  1.00207.30           C
ANISOU 1259  CB   LYS A 175     13061  32786  32917  -9440   3338   1017      C
ATOM   1260  CG   LYS A 175     -28.640 -15.765  51.656  1.00207.21           C
ANISOU 1260  CG   LYS A 175     13082  32497  33151  -9363   3554   1050      C
ATOM   1261  CD   LYS A 175      27.699  15.518  52.828  1.00206.96           C
ANISOU 1261  CD   LYS A 175     12991  32505  33139  -9270   3698    566      C
ATOM   1262  CE   LYS A 175     -28.477 -15.397  54.138  1.00206.62           C
ANISOU 1262  CE   LYS A 175     13025  32220  33262  -9220   3791    582      C
ATOM   1263  NZ   LYS A 175     -27.601 -15.494  55.340  1.00206.19           N
ANISOU 1263  NZ   LYS A 175     12935  32271  33135  -9172   3833    104      N
ATOM   1264  N    VAL A 176     -29.203 -17.439  47.238  1.00353.62           N
ANISOU 1264  N    VAL A 176     31744  51561  51054  -9908   2930   1853      N
ATOM   1265  CA   VAL A 176     -28.944 -17.541  45.805  1.00355.10           C
ANISOU 1265  CA   VAL A 176     32014  51922  50985 -10044   2862   1990      C
ATOM   1266  C    VAL A 176     -29.101 -16.209  45.080  1.00356.70           C
ANISOU 1266  C    VAL A 176     31972  52111  51445 -10164   3101   2333      C
ATOM   1267  O    VAL A 176     -29.730 -16.141  44.026  1.00358.21           O
```

FIG. 13 Continued

```
ANISOU 1267  O   VAL A 176    32201  52347  51557 -10360   2960   2739       O
ATOM   1268  CB  VAL A 176    -29.891 -18.565  45.152  1.00356.08           C
ANISOU 1268  CB  VAL A 176    32479  52011  50805 -10186   2438   2264       C
ATOM   1269  CG1 VAL A 176    -29.345 -19.972  45.313  1.00355.83           C
ANISOU 1269  CG1 VAL A 176    32863  52012  50325 -10027   2218   1870       C
ATOM   1270  CG2 VAL A 176    -31.286 -18.454  45.755  1.00355.63           C
ANISOU 1270  CG2 VAL A 176    32269  51765  51089 -10324   2311   2664       C
ATOM   1271  N   ASP A 177    -28.519 -15.158  45.643  1.00259.48           N
ANISOU 1271  N   ASP A 177    19529  39694  39368  -9993   3422   2160       N
ATOM   1272  CA  ASP A 177    -28.646 -13.808  45.096  1.00261.64           C
ANISOU 1272  CA  ASP A 177    19655  39861  39895 -10034   3676   2464       C
ATOM   1273  C   ASP A 177    -28.581 -13.701  43.576  1.00263.15           C
ANISOU 1273  C   ASP A 177    19809  40257  39920 -10249   3665   2769       C
ATOM   1274  O   ASP A 177    -27.502 -13.652  42.985  1.00263.64           O
ANISOU 1274  O   ASP A 177    19820  40528  39822 -10274   3845   2548       O
ATOM   1275  CB  ASP A 177    -27.610 -12.877  45.724  1.00262.23           C
ANISOU 1275  CB  ASP A 177    19609  39866  40161  -9898   4029   2101       C
ATOM   1276  CG  ASP A 177    -27.823 -12.697  47.210  1.00261.35           C
ANISOU 1276  CG  ASP A 177    19524  39517  40260  -9744   4086   1877       C
ATOM   1277  OD1 ASP A 177    -28.641 -13.454  47.783  1.00259.99           O
ANISOU 1277  OD1 ASP A 177    19469  39270  40045  -9705   3862   1954       O
ATOM   1278  OD2 ASP A 177    -27.178 -11.802  47.802  1.00262.25           O
ANISOU 1278  OD2 ASP A 177    19542  39521  40582  -9697   4364   1627       O
ATOM   1279  N   GLN A 178    -29.755 -13.651  42.958  1.00184.15           N
ANISOU 1279  N   GLN A 178     9800  30204  29963 -10416   3463   3304       N
ATOM   1280  CA  GLN A 178    -29.867 -13.472  41.520  1.00185.95           C
ANISOU 1280  CA  GLN A 178     9988  30624  30041 -10670   3428   3677       C
ATOM   1281  C   GLN A 178    -29.778 -11.982  41.261  1.00188.15           C
ANISOU 1281  C   GLN A 178    10080  30764  30645 -10615   3781   3936       C
ATOM   1282  O   GLN A 178    -30.786 -11.337  40.961  1.00189.88           O
ANISOU 1282  O   GLN A 178    10181  30857  31107 -10680   3740   4476       O
ATOM   1283  CB  GLN A 178    -31.210 -13.996  41.014  1.00187.21           C
ANISOU 1283  CB  GLN A 178    10274  30769  30087 -10842   2986   4169       C
ATOM   1284  CG  GLN A 178    -31.892 -14.946  41.971  1.00185.33           C
ANISOU 1284  CG  GLN A 178    10113  30428  29877 -10820   2704   4071       C
ATOM   1285  CD  GLN A 178    -32.545 -16.101  41.258  1.00186.83           C
ANISOU 1285  CD  GLN A 178    10669  30701  29619 -10989   2182   4235       C
ATOM   1286  OE1 GLN A 178    -32.052 -16.557  40.228  1.00188.59           O
ANISOU 1286  OE1 GLN A 178    11236  31076  29343 -11044   2044   4141       O
ATOM   1287  NE2 GLN A 178    -33.656 -16.592  41.803  1.00186.55           N
ANISOU 1287  NE2 GLN A 178    10582  30553  29746 -11086   1901   4476       N
ATOM   1288  N   SER A 179    -28.568 -11.443  41.384  1.00180.61           N
ANISOU 1288  N   SER A 179     9070  29833  29720 -10508   4131   3567       N
ATOM   1289  CA  SER A 179    -28.331 -10.012  41.236  1.00182.85           C
ANISOU 1289  CA  SER A 179     9192  29944  30338 -10474   4510   3737       C
ATOM   1290  C   SER A 179    -28.174  -9.543  39.783  1.00185.19           C
ANISOU 1290  C   SER A 179     9415  30425  30524 -10686   4643   4122       C
ATOM   1291  O   SER A 179    -27.795  -8.398  39.538  1.00187.29           O
ANISOU 1291  O   SER A 179     9552  30572  31036 -10682   4998   4242       O
ATOM   1292  CB  SER A 179    -27.109  -9.614  42.063  1.00182.55           C
ANISOU 1292  CB  SER A 179     9106  29843  30411 -10325   4810   3176       C
ATOM   1293  OG  SER A 179    -27.080 -10.348  43.274  1.00180.22           O
ANISOU 1293  OG  SER A 179     8906  29494  30077 -10173   4642   2775       O
ATOM   1294  N   ALA A 180    -28.481 -10.414  38.823  1.00187.30           N
ANISOU 1294  N   ALA A 180     9829  30948  30389 -10863   4349   4316       N
ATOM   1295  CA  ALA A 180    -28.337 -10.063  37.410  1.00190.70           C
ANISOU 1295  CA  ALA A 180    10405  31520  30530 -10963   4394   4655       C
ATOM   1296  C   ALA A 180    -29.553 -10.438  36.562  1.00192.72           C
ANISOU 1296  C   ALA A 180    10862  31832  30529 -11105   3939   5204       C
ATOM   1297  O   ALA A 180    -30.304  -9.562  36.141  1.00194.81           O
ANISOU 1297  O   ALA A 180    10946  32014  31060 -11195   3973   5775       O
ATOM   1298  CB  ALA A 180    -27.069 -10.679  36.831  1.00191.49           C
ANISOU 1298  CB  ALA A 180    10768  31858  30131 -10886   4497   4223       C
ATOM   1299  N   LEU A 181    -29.745 -11.731  36.315  1.00172.59           N
ANISOU 1299  N   LEU A 181     8690  29416  27472 -11132   3506   5044       N
ATOM   1300  CA  LEU A 181    -30.862 -12.197  35.500  1.00175.01           C
ANISOU 1300  CA  LEU A 181     9222  29796  27477 -11325   3004   5524       C
ATOM   1301  C   LEU A 181    -32.128 -11.365  35.735  1.00175.77           C
ANISOU 1301  C   LEU A 181     8924  29746  28113 -11412   2926   6157       C
```

FIG. 13 Continued

```
ATOM   1302  O   LEU A 181     -32.797 -10.938  34.792  1.00179.19           O
ANISOU 1302  O   LEU A 181      9357  30254  28472 -11555   2751   6737      O
ATOM   1303  CB  LEU A 181     -31.130 -13.684  35.771  1.00173.80           C
ANISOU 1303  CB  LEU A 181      9427  29679  26929 -11353   2547   5223      C
ATOM   1304  CG  LEU A 181     -32.574 -14.223  35.761  1.00174.74           C
ANISOU 1304  CG  LEU A 181      9578  29766  27051 -11563   1992   5650      C
ATOM   1305  CD1 LEU A 181     -33.299 -13.994  34.431  1.00179.27           C
ANISOU 1305  CD1 LEU A 181     10295  30486  27333 -11810   1666   6251      C
ATOM   1306  CD2 LEU A 181     -32.590 -15.701  36.120  1.00173.49           C
ANISOU 1306  CD2 LEU A 181      9811  29598  26508 -11581   1634   5242      C
ATOM   1307  N   THR A 182     -32.439 -11.138  37.003  1.00178.56           N
ANISOU 1307  N   THR A 182      8948  29893  29002 -11305   3072   6055      N
ATOM   1308  CA  THR A 182     -33.590 -10.348  37.414  1.00179.24           C
ANISOU 1308  CA  THR A 182      8631  29800  29672 -11321   3097   6610      C
ATOM   1309  C   THR A 182     -33.116  -9.784  38.738  1.00176.44           C
ANISOU 1309  C   THR A 182      8044  29194  29801 -11107   3553   6224      C
ATOM   1310  O   THR A 182     -33.747  -9.955  39.782  1.00175.48           O
ANISOU 1310  O   THR A 182      7897  28861  29916 -10930   3468   6180      O
ATOM   1311  CB  THR A 182     -34.859 -11.225  37.576  1.00179.59           C
ANISOU 1311  CB  THR A 182      8689  29871  29675 -11449   2551   6910      C
ATOM   1312  OG1 THR A 182     -35.230 -11.774  36.303  1.00182.92           O
ANISOU 1312  OG1 THR A 182      9416  30524  29560 -11671   2071   7219      O
ATOM   1313  CG2 THR A 182     -36.033 -10.417  38.128  1.00180.46           C
ANISOU 1313  CG2 THR A 182      8318  29792  30457 -11413   2642   7483      C
ATOM   1314  N   GLY A 183     -31.964  -9.122  38.669  1.00184.82           N
ANISOU 1314  N   GLY A 183      9130  30224  30869 -11007   3970   5903      N
ATOM   1315  CA  GLY A 183     -31.262  -8.649  39.846  1.00183.61           C
ANISOU 1315  CA  GLY A 183      9000  29807  30957 -10720   4302   5398      C
ATOM   1316  C   GLY A 183     -31.402  -7.246  40.410  1.00185.34           C
ANISOU 1316  C   GLY A 183      9058  29652  31710 -10540   4709   5545      C
ATOM   1317  O   GLY A 183     -30.798  -6.285  39.918  1.00187.25           O
ANISOU 1317  O   GLY A 183      9221  29840  32085 -10574   5061   5613      O
ATOM   1318  N   GLU A 184     -32.199  -7.146  41.469  1.00203.41           N
ANISOU 1318  N   GLU A 184     11305  31666  34316 -10364   4693   5589      N
ATOM   1319  CA  GLU A 184     -32.297  -5.938  42.265  1.00204.75           C
ANISOU 1319  CA  GLU A 184     11367  31430  34999 -10185   5119   5604      C
ATOM   1320  C   GLU A 184     -31.241  -6.180  43.338  1.00202.59           C
ANISOU 1320  C   GLU A 184     11262  31092  34623 -10083   5253   4835      C
ATOM   1321  O   GLU A 184     -31.079  -7.314  43.782  1.00200.08           O
ANISOU 1321  O   GLU A 184     11090  30946  33987 -10061   4965   4485      O
ATOM   1322  CB  GLU A 184     -33.682  -5.827  42.896  1.00205.42           C
ANISOU 1322  CB  GLU A 184     11315  31282  35454 -10053   5059   6025      C
ATOM   1323  CG  GLU A 184     -34.768  -6.588  42.150  1.00205.96           C
ANISOU 1323  CG  GLU A 184     11275  31600  35379 -10195   4593   6585      C
ATOM   1324  CD  GLU A 184     -34.715  -8.082  42.415  1.00203.14           C
ANISOU 1324  CD  GLU A 184     11123  31482  34577 -10272   4157   6232      C
ATOM   1325  OE1 GLU A 184     -35.464  -8.841  41.760  1.00203.57           O
ANISOU 1325  OE1 GLU A 184     11130  31769  34446 -10471   3732   6604      O
ATOM   1326  OE2 GLU A 184     -33.921  -8.498  43.283  1.00200.73           O
ANISOU 1326  OE2 GLU A 184     11019  31131  34119 -10160   4235   5593      O
ATOM   1327  N   SER A 185     -30.522  -5.145  43.756  1.00190.62           N
ANISOU 1327  N   SER A 185      9714  29338  33377 -10050   5677   4582      N
ATOM   1328  CA  SER A 185     -29.426  -5.315  44.722  1.00189.12           C
ANISOU 1328  CA  SER A 185      9634  29135  33087 -10015   5784   3865      C
ATOM   1329  C   SER A 185     -29.782  -5.996  46.064  1.00186.84           C
ANISOU 1329  C   SER A 185      9461  28751  32778  -9875   5638   3542      C
ATOM   1330  O   SER A 185     -29.190  -5.686  47.098  1.00186.55           O
ANISOU 1330  O   SER A 185      9468  28563  32852  -9848   5838   3075      O
ATOM   1331  CB  SER A 185     -28.727  -3.973  44.976  1.00191.45           C
ANISOU 1331  CB  SER A 185      9850  29151  33743 -10073   6267   3701      C
ATOM   1332  OG  SER A 185     -28.261  -3.400  43.766  1.00193.62           O
ANISOU 1332  OG  SER A 185     10027  29530  34010 -10213   6425   3959      O
ATOM   1333  N   LEU A 186     -30.717  -6.939  46.049  1.00196.55           N
ANISOU 1333  N   LEU A 186     10737  30086  33857  -9825   5289   3789      N
ATOM   1334  CA  LEU A 186     -31.114  -7.625  47.275  1.00194.60           C
ANISOU 1334  CA  LEU A 186     10599  29754  33586  -9701   5168   3541      C
ATOM   1335  C   LEU A 186     -31.351  -9.128  47.088  1.00192.34           C
ANISOU 1335  C   LEU A 186     10433  29764  32884  -9726   4698   3511      C
ATOM   1336  O   LEU A 186     -32.081  -9.539  46.185  1.00192.84           O
```

FIG. 13 Continued

```
ANISOU 1336  O   LEU A 186   10452  29965  32853  -9823   4437   3965       O
ATOM   1337  CB  LEU A 186    -32.372  -6.984  47.866  1.00196.02           C
ANISOU 1337  CB  LEU A 186   10675  29580  34224  -9587   5364   3952       C
ATOM   1338  CG  LEU A 186    -32.285  -5.559  48.417  1.00198.21           C
ANISOU 1338  CG  LEU A 186   10872  29464  34975  -9545   5893   3924       C
ATOM   1339  CD1 LEU A 186    -33.588  -5.214  49.138  1.00199.36           C
ANISOU 1339  CD1 LEU A 186   10922  29287  35538  -9395   6086   4303       C
ATOM   1340  CD2 LEU A 186    -31.086  -5.387  49.346  1.00197.35           C
ANISOU 1340  CD2 LEU A 186   10889  29314  34782  -9591   6079   3211       C
ATOM   1341  N   PRO A 187    -30.734  -9.944  47.966  1.00180.00           N
ANISOU 1341  N   PRO A 187    9014  28294  31083  -9666   4591   2982       N
ATOM   1342  CA  PRO A 187    -30.761 -11.410  48.073  1.00177.73           C
ANISOU 1342  CA  PRO A 187    8871  28238  30418  -9674   4208   2821       C
ATOM   1343  C   PRO A 187    -32.070 -12.052  47.724  1.00177.82           C
ANISOU 1343  C   PRO A 187    8886  28251  30425  -9737   3910   3316       C
ATOM   1344  O   PRO A 187    -32.989 -11.385  47.274  1.00179.78           O
ANISOU 1344  O   PRO A 187    8984  28371  30955  -9768   3965   3844       O
ATOM   1345  CB  PRO A 187    -30.475 -11.639  49.551  1.00176.31           C
ANISOU 1345  CB  PRO A 187    8778  27946  30265  -9544   4293   2373       C
ATOM   1346  CG  PRO A 187    -29.464 -10.543  49.859  1.00177.47           C
ANISOU 1346  CG  PRO A 187    8843  28007  30579  -9545   4647   2039       C
ATOM   1347  CD  PRO A 187    -29.764  -9.372  48.920  1.00179.95           C
ANISOU 1347  CD  PRO A 187    9017  28179  31176  -9617   4878   2460       C
ATOM   1348  N   VAL A 188    -32.146 -13.353  47.950  1.00206.40           N
ANISOU 1348  N   VAL A 188   12653  32019  33751  -9769   3593   3158       N
ATOM   1349  CA  VAL A 188    -33.343 -14.100  47.611  1.00206.71           C
ANISOU 1349  CA  VAL A 188   12697  32082  33763  -9896   3260   3599       C
ATOM   1350  C   VAL A 188    -33.474 -15.337  48.488  1.00204.72           C
ANISOU 1350  C   VAL A 188   12615  31843  33327  -9869   3047   3343       C
ATOM   1351  O   VAL A 188    -34.575 -15.683  48.935  1.00205.14           O
ANISOU 1351  O   VAL A 188   12642  31769  33533  -9886   2925   3648       O
ATOM   1352  CB  VAL A 188    -33.303 -14.524  46.142  1.00207.42           C
ANISOU 1352  CB  VAL A 188   12795  32438  33579 -10150   2987   3829       C
ATOM   1353  CG1 VAL A 188    -33.775 -13.389  45.245  1.00210.05           C
ANISOU 1353  CG1 VAL A 188   12914  32734  34163 -10224   3113   4348       C
ATOM   1354  CG2 VAL A 188    -31.897 -14.946  45.770  1.00206.09           C
ANISOU 1354  CG2 VAL A 188   12747  32501  33057 -10165   3026   3322       C
ATOM   1355  N   THR A 189    -32.337 -15.995  48.709  1.00227.30           N
ANISOU 1355  N   THR A 189   15616  34864  35882  -9828   3017   2812       N
ATOM   1356  CA  THR A 189    -32.225 -17.171  49.573  1.00225.36           C
ANISOU 1356  CA  THR A 189   15532  34645  35450  -9783   2850   2509       C
ATOM   1357  C   THR A 189    -33.494 -18.008  49.740  1.00225.54           C
ANISOU 1357  C   THR A 189   15613  34575  35505  -9909   2572   2865       C
ATOM   1358  O   THR A 189    -34.510 -17.521  50.237  1.00226.70           O
ANISOU 1358  O   THR A 189   15651  34518  35967  -9862   2670   3210       O
ATOM   1359  CB  THR A 189    -31.703 -16.777  50.970  1.00224.50           C
ANISOU 1359  CB  THR A 189   15421  34413  35465  -9564   3121   2120       C
ATOM   1360  OG1 THR A 189    -32.305 -17.622  51.957  1.00223.47           O
ANISOU 1360  OG1 THR A 189   15397  34189  35323  -9530   3006   2107       O
ATOM   1361  CG2 THR A 189    -32.036 -15.319  51.286  1.00226.71           C
ANISOU 1361  CG2 THR A 189   15485  34386  36061  -9481   3476   2291       C
ATOM   1362  N   LYS A 190    -33.427 -19.281  49.363  1.00179.46           N
ANISOU 1362  N   LYS A 190    9938  28878  29371 -10079   2250   2777       N
ATOM   1363  CA  LYS A 190    -34.608 -20.133  49.507  1.00179.99           C
ANISOU 1363  CA  LYS A 190   10063  28850  29473 -10260   1961   3108       C
ATOM   1364  C   LYS A 190    -34.392 -21.598  49.883  1.00178.91           C
ANISOU 1364  C   LYS A 190   10240  28719  29018 -10287   1703   2822       C
ATOM   1365  O   LYS A 190    -33.318 -22.179  49.685  1.00178.44           O
ANISOU 1365  O   LYS A 190   10471  28754  28573 -10138   1643   2390       O
ATOM   1366  CB  LYS A 190    -35.515 -20.052  48.271  1.00182.24           C
ANISOU 1366  CB  LYS A 190   10256  29197  29791 -10565   1693   3643       C
ATOM   1367  CG  LYS A 190    -36.705 -19.119  48.420  1.00184.51           C
ANISOU 1367  CG  LYS A 190   10279  29328  30500 -10525   1793   4203       C
ATOM   1368  CD  LYS A 190    -37.826 -19.744  49.237  1.00185.16           C
ANISOU 1368  CD  LYS A 190   10332  29254  30767 -10572   1669   4465       C
ATOM   1369  CE  LYS A 190    -37.463 -19.876  50.711  1.00183.26           C
ANISOU 1369  CE  LYS A 190   10193  28857  30581 -10291   1955   4079       C
ATOM   1370  NZ  LYS A 190    -36.823 -18.653  51.276  1.00182.80           N
ANISOU 1370  NZ  LYS A 190   10051  28707  30697  -9986   2404   3849       N
```

FIG. 13 Continued

```
ATOM   1371  N   HIS A 191      -35.462 -22.163  50.439  1.00202.24           N
ANISOU 1371  N   HIS A 191     13211  31523  32110 -10397   1557   3096       N
ATOM   1372  CA  HIS A 191      -35.545 -23.559  50.826  1.00202.37           C
ANISOU 1372  CA  HIS A 191     13628  31442  31822 -10392   1281   2931       C
ATOM   1373  C   HIS A 191      -35.371 -24.393  49.564  1.00204.04           C
ANISOU 1373  C   HIS A 191     14213  31719  31592 -10565    897   2901       C
ATOM   1374  O   HIS A 191      -35.313 -23.845  48.463  1.00205.12           O
ANISOU 1374  O   HIS A 191     14264  31988  31684 -10700    848   3058       O
ATOM   1375  CB  HIS A 191      -36.936 -23.862  51.421  1.00203.46           C
ANISOU 1375  CB  HIS A 191     13637  31410  32259 -10569   1196   3373       C
ATOM   1376  CG  HIS A 191      -37.141 -23.388  52.834  1.00202.28           C
ANISOU 1376  CG  HIS A 191     13274  31142  32440 -10371   1571   3350       C
ATOM   1377  ND1 HIS A 191      -37.210 -22.054  53.179  1.00202.50           N
ANISOU 1377  ND1 HIS A 191     13033  31128  32781 -10177   1942   3448       N
ATOM   1378  CD2 HIS A 191      -37.352 -24.080  53.981  1.00201.93           C
ANISOU 1378  CD2 HIS A 191     13398  30952  32375 -10261   1617   3249       C
ATOM   1379  CE1 HIS A 191      -37.422 -21.945  54.479  1.00202.12           C
ANISOU 1379  CE1 HIS A 191     12973  30931  32894  -9992   2214   3379       C
ATOM   1380  NE2 HIS A 191      -37.512 -23.160  54.989  1.00201.29           N
ANISOU 1380  NE2 HIS A 191     13040  30803  32638 -10099   2042   3279       N
ATOM   1381  N   PRO A 192      -35.278 -25.722  49.723  1.00254.29           N
ANISOU 1381  N   PRO A 192     21038  37971  37611 -10556    642   2695       N
ATOM   1382  CA  PRO A 192      -35.202 -26.706  48.634  1.00256.48           C
ANISOU 1382  CA  PRO A 192     21791  38233  37425 -10735    269   2636       C
ATOM   1383  C   PRO A 192      -36.367 -26.653  47.628  1.00259.24           C
ANISOU 1383  C   PRO A 192     22076  38594  37830 -11184    -71   3154       C
ATOM   1384  O   PRO A 192      -37.203 -27.553  47.577  1.00261.25           O
ANISOU 1384  O   PRO A 192     22556  38702  38007 -11458   -410   3350       O
ATOM   1385  CB  PRO A 192      -35.202 -28.036  49.386  1.00256.68           C
ANISOU 1385  CB  PRO A 192     22243  38047  37237 -10651    122   2419       C
ATOM   1386  CG  PRO A 192      -34.479 -27.715  50.655  1.00254.09           C
ANISOU 1386  CG  PRO A 192     21749  37736  37057 -10261    474   2115       C
ATOM   1387  CD  PRO A 192      -34.895 -26.316  51.018  1.00252.85           C
ANISOU 1387  CD  PRO A 192     21009  37671  37390 -10286    765   2382       C
ATOM   1388  N   GLY A 193      -36.394 -25.591  46.830  1.00176.95           N
ANISOU 1388  N   GLY A 193     11344  28348  27538 -11268     10   3385       N
ATOM   1389  CA  GLY A 193      -37.380 -25.377  45.785  1.00179.92           C
ANISOU 1389  CA  GLY A 193     11614  28797  27951 -11667   -315   3898       C
ATOM   1390  C   GLY A 193      -37.103 -24.003  45.197  1.00179.63           C
ANISOU 1390  C   GLY A 193     11190  28951  28110 -11603    -61   4071       C
ATOM   1391  O   GLY A 193      -37.488 -22.990  45.782  1.00178.55           O
ANISOU 1391  O   GLY A 193     10543  28813  28483 -11517    231   4329       O
ATOM   1392  N   GLN A 194      -36.434 -23.957  44.044  1.00292.95           N
ANISOU 1392  N   GLN A 194     25811  43442  42056 -11636   -136   3932       N
ATOM   1393  CA  GLN A 194      -36.017 -22.679  43.461  1.00292.83           C
ANISOU 1393  CA  GLN A 194     25480  43595  42186 -11555    145   4058       C
ATOM   1394  C   GLN A 194      -35.862 -22.651  41.941  1.00295.86           C
ANISOU 1394  C   GLN A 194     26137  44139  42137 -11757    -81   4177       C
ATOM   1395  O   GLN A 194      -35.315 -23.575  41.337  1.00297.18           O
ANISOU 1395  O   GLN A 194     26862  44306  41747 -11781   -265   3853       O
ATOM   1396  CB  GLN A 194      -34.690 -22.236  44.085  1.00289.87           C
ANISOU 1396  CB  GLN A 194     25041  43247  41848 -11159    620   3549       C
ATOM   1397  CG  GLN A 194      -34.819 -21.257  45.242  1.00287.53           C
ANISOU 1397  CG  GLN A 194     24238  42881  42129 -10982   1012   3614       C
ATOM   1398  CD  GLN A 194      -34.601 -19.816  44.814  1.00287.74           C
ANISOU 1398  CD  GLN A 194     23879  43002  42449 -10952   1338   3817       C
ATOM   1399  OE1 GLN A 194      -34.689 -18.894  45.626  1.00286.44           O
ANISOU 1399  OE1 GLN A 194     23335  42753  42745 -10828   1688   3877       O
ATOM   1400  NE2 GLN A 194      -34.308 -19.616  43.533  1.00289.74           N
ANISOU 1400  NE2 GLN A 194     24267  43406  42415 -11067   1244   3919       N
ATOM   1401  N   GLU A 195      -36.338 -21.561  41.344  1.00209.92           N
ANISOU 1401  N   GLU A 195     14877  33376  31509 -11880    -37   4653       N
ATOM   1402  CA  GLU A 195      -36.200 -21.309  39.912  1.00213.04           C
ANISOU 1402  CA  GLU A 195     15477  33945  31522 -12057   -202   4831       C
ATOM   1403  C   GLU A 195      -34.819 -20.731  39.688  1.00211.61           C
ANISOU 1403  C   GLU A 195     15344  33853  31203 -11756    259   4434       C
ATOM   1404  O   GLU A 195      -34.657 -19.637  39.149  1.00212.38           O
ANISOU 1404  O   GLU A 195     15177  34063  31454 -11738    485   4677       O
ATOM   1405  CB  GLU A 195      -37.266 -20.332  39.397  1.00215.48           C
```

FIG. 13 Continued

```
ANISOU 1405  CB  GLU A 195    15329  34352  32190 -12281   -329   5553       C
ATOM   1406  CG  GLU A 195    -38.657 -20.933  39.213  1.00218.51            C
ANISOU 1406  CG  GLU A 195    15681  34730  32614 -12670   -894   6040       C
ATOM   1407  CD  GLU A 195    -39.556 -20.058  38.360  1.00222.13            C
ANISOU 1407  CD  GLU A 195    15773  35355  33271 -12901  -1099   6763       C
ATOM   1408  OE1 GLU A 195    -39.043 -19.406  37.422  1.00223.52            O
ANISOU 1408  OE1 GLU A 195    16032  35677  33220 -12873   -993   6827       O
ATOM   1409  OE2 GLU A 195    -40.776 -20.029  38.626  1.00223.91            O
ANISOU 1409  OE2 GLU A 195    15615  35573  33886 -13103  -1359   7293       O
ATOM   1410  N   VAL A 196    -33.828 -21.478  40.146  1.00247.88            N
ANISOU 1410  N   VAL A 196    20254  38392  35538 -11513    406   3844       N
ATOM   1411  CA  VAL A 196    -32.440 -21.090  40.019  1.00246.83            C
ANISOU 1411  CA  VAL A 196    20151  38357  35274 -11218    832   3429       C
ATOM   1412  C   VAL A 196    -31.983 -21.046  38.563  1.00250.09            C
ANISOU 1412  C   VAL A 196    20911  38930  35180 -11311    797   3461       C
ATOM   1413  O   VAL A 196    -31.000 -21.683  38.198  1.00250.78            O
ANISOU 1413  O   VAL A 196    21410  39057  34820 -11142    902   3032       O
ATOM   1414  CB  VAL A 196    -31.557 -22.057  40.806  1.00244.91            C
ANISOU 1414  CB  VAL A 196    20178  38034  34841 -10933    930   2837       C
ATOM   1415  CG1 VAL A 196    -31.403 -21.577  42.237  1.00241.46            C
ANISOU 1415  CG1 VAL A 196    19299  37521  34925 -10717   1216   2699       C
ATOM   1416  CG2 VAL A 196    -32.161 -23.456  40.768  1.00246.27            C
ANISOU 1416  CG2 VAL A 196    20853  38059  34659 -11092    481   2787       C
ATOM   1417  N   PHE A 197    -32.706 -20.301  37.733  1.00189.47            N
ANISOU 1417  N   PHE A 197    13077  31346  27568 -11561    662   3990       N
ATOM   1418  CA  PHE A 197    -32.337 -20.153  36.328  1.00192.99            C
ANISOU 1418  CA  PHE A 197    13855  31954  27519 -11665    637   4079       C
ATOM   1419  C   PHE A 197    -30.826 -19.908  36.205  1.00192.21            C
ANISOU 1419  C   PHE A 197    13823  31943  27267 -11340   1150   3616       C
ATOM   1420  O   PHE A 197    -30.238 -19.198  37.015  1.00189.42            O
ANISOU 1420  O   PHE A 197    13030  31577  27363 -11114   1557   3458       O
ATOM   1421  CB  PHE A 197    -33.128 -19.005  35.682  1.00195.09            C
ANISOU 1421  CB  PHE A 197    13761  32322  28042 -11877    579   4735       C
ATOM   1422  CG  PHE A 197    -34.477 -19.415  35.112  1.00198.37            C
ANISOU 1422  CG  PHE A 197    14304  32761  28308 -12272    -36   5238       C
ATOM   1423  CD1 PHE A 197    -35.462 -19.956  35.926  1.00197.39            C
ANISOU 1423  CD1 PHE A 197    14019  32505  28473 -12408   -354   5380       C
ATOM   1424  CD2 PHE A 197    -34.765 -19.223  33.762  1.00202.88            C
ANISOU 1424  CD2 PHE A 197    15130  33501  28454 -12523   -297   5599       C
ATOM   1425  CE1 PHE A 197    -36.698 -20.316  35.400  1.00200.91            C
ANISOU 1425  CE1 PHE A 197    14521  32998  28819 -12806   -938   5871       C
ATOM   1426  CE2 PHE A 197    -35.991 -19.586  33.230  1.00206.45            C
ANISOU 1426  CE2 PHE A 197    15672  34007  28764 -12920   -911   6077       C
ATOM   1427  CZ  PHE A 197    -36.960 -20.129  34.051  1.00205.51            C
ANISOU 1427  CZ  PHE A 197    15347  33765  28972 -13071  -1239   6218       C
ATOM   1428  N   SER A 198    -30.209 -20.506  35.192  1.00194.46            N
ANISOU 1428  N   SER A 198    14662  32312  26913 -11331   1130   3404       N
ATOM   1429  CA  SER A 198    -28.774 -20.393  34.983  1.00194.52            C
ANISOU 1429  CA  SER A 198    14748  32421  26741 -11019   1618   2987       C
ATOM   1430  C   SER A 198    -28.248 -19.005  35.320  1.00192.81            C
ANISOU 1430  C   SER A 198    13905  32288  27065 -10890   2097   3089       C
ATOM   1431  O   SER A 198    -27.102 -18.850  35.749  1.00191.49            O
ANISOU 1431  O   SER A 198    13569  32175  27015 -10611   2510   2705       O
ATOM   1432  CB  SER A 198    -28.420 -20.725  33.539  1.00199.09            C
ANISOU 1432  CB  SER A 198    15914  33114  26616 -11097   1595   2983       C
ATOM   1433  OG  SER A 198    -28.642 -19.606  32.704  1.00201.17            O
ANISOU 1433  OG  SER A 198    15979  33520  26938  11260   1695   3441       O
ATOM   1434  N   GLY A 199    -29.071 -17.988  35.097  1.00359.55            N
ANISOU 1434  N   GLY A 199    34682  53414  48515 -11101   2042   3621       N
ATOM   1435  CA  GLY A 199    -28.684 -16.636  35.439  1.00358.28            C
ANISOU 1435  CA  GLY A 199    33963  53269  48899 -11012   2493   3745       C
ATOM   1436  C   GLY A 199    -28.821 -16.430  36.935  1.00354.30            C
ANISOU 1436  C   GLY A 199    33023  52610  48985 -10892   2592   3586       C
ATOM   1437  O   GLY A 199    -29.791 -15.831  37.398  1.00353.44            O
ANISOU 1437  O   GLY A 199    32581  52384  49327 -11008   2505   3964       O
ATOM   1438  N   SER A 200    -27.851 -16.931  37.696  1.00163.43            N
ANISOU 1438  N   SER A 200     8858  28439  24799 -10644   2782   3040       N
ATOM   1439  CA  SER A 200    -27.888 -16.783  39.146  1.00160.00            C
ANISOU 1439  CA  SER A 200     8068  27873  24851 -10525   2873   2844       C
```

FIG. 13 Continued

```
ATOM   1440  C   SER A 200     -26.510 -16.891  39.796  1.00158.71           C
ANISOU 1440  C   SER A 200      7793  27790  24720 -10251   3199   2291      C
ATOM   1441  O   SER A 200     -25.868 -17.941  39.781  1.00158.94           O
ANISOU 1441  O   SER A 200      8137  27887  24368 -10073   3126   1921      O
ATOM   1442  CB  SER A 200     -28.904 -17.747  39.785  1.00158.65           C
ANISOU 1442  CB  SER A 200      8070  27558  24653 -10591   2442   2890      C
ATOM   1443  OG  SER A 200     -28.984 -18.980  39.093  1.00160.43           O
ANISOU 1443  OG  SER A 200      8850  27814  24293 -10639   2103   2787      O
ATOM   1444  N   THR A 201     -26.070 -15.771  40.351  1.00197.24           N
ANISOU 1444  N   THR A 201     12217  32654  30070 -10226   3560   2260      N
ATOM   1445  CA  THR A 201     -24.605 -15.693  41.049  1.00196.41           C
ANISOU 1445  CA  THR A 201     11902  32645  30081 -10021   3848   1785      C
ATOM   1446  C   THR A 201     -25.095 -15.944  42.511  1.00193.55           C
ANISOU 1446  C   THR A 201     11400  32145  29994  -9940   3734   1579      C
ATOM   1447  O   THR A 201     -25.183 -15.001  43.293  1.00192.52           O
ANISOU 1447  O   THR A 201     10919  31906  30323  -9997   3932   1602      O
ATOM   1448  CB  THR A 201     -24.233 -14.285  40.936  1.00197.41           C
ANISOU 1448  CB  THR A 201     11618  32797  30593 -10104   4279   1865      C
ATOM   1449  OG1 THR A 201     -24.801 -13.634  39.792  1.00199.59           O
ANISOU 1449  OG1 THR A 201     11951  33057  30828 -10292   4321   2349      O
ATOM   1450  CG2 THR A 201     -22.725 -14.328  40.813  1.00198.75           C
ANISOU 1450  CG2 THR A 201     11676  33187  30653  -9943   4572   1471      C
ATOM   1451  N   CYS A 202     -25.247 -17.210  42.886  1.00199.90           N
ANISOU 1451  N   CYS A 202     12517  32933  30504  -9811   3432   1379      N
ATOM   1452  CA  CYS A 202     -25.600 -17.543  44.264  1.00197.45           C
ANISOU 1452  CA  CYS A 202     12131  32487  30404  -9731   3307   1217      C
ATOM   1453  C   CYS A 202     -24.515 -17.128  45.253  1.00196.70           C
ANISOU 1453  C   CYS A 202     11722  32477  30537  -9572   3559    813      C
ATOM   1454  O   CYS A 202     -23.323 -17.190  44.951  1.00198.02           O
ANISOU 1454  O   CYS A 202     11826  32848  30565  -9434   3727    541      O
ATOM   1455  CB  CYS A 202     -25.911 -19.036  44.419  1.00197.04           C
ANISOU 1455  CB  CYS A 202     12514  32387  29967  -9622   2945   1087      C
ATOM   1456  SG  CYS A 202     -24.616 -20.006  45.226  1.00196.65           S
ANISOU 1456  SG  CYS A 202     12559  32459  29701  -9251   2970    506      S
ATOM   1457  N   LYS A 203     -24.945 -16.686  46.430  1.00199.75           N
ANISOU 1457  N   LYS A 203     11911  32712  31274  -9604   3590    752      N
ATOM   1458  CA  LYS A 203     -24.029 -16.313  47.499  1.00199.36           C
ANISOU 1458  CA  LYS A 203     11607  32727  31415  -9495   3759    405      C
ATOM   1459  C   LYS A 203     -23.604 -17.578  48.262  1.00198.56           C
ANISOU 1459  C   LYS A 203     11708  32706  31030  -9241   3521     60      C
ATOM   1460  O   LYS A 203     -23.032 -18.495  47.670  1.00199.55           O
ANISOU 1460  O   LYS A 203     12049  32977  30793  -9069   3417    -74      O
ATOM   1461  CB  LYS A 203     -24.673 -15.277  48.425  1.00199.72           C
ANISOU 1461  CB  LYS A 203     11671  32448  31765  -9485   3853    491      C
ATOM   1462  CG  LYS A 203     -24.626 -13.846  47.895  1.00201.94           C
ANISOU 1462  CG  LYS A 203     11834  32597  32297  -9584   4142    683      C
ATOM   1463  CD  LYS A 203     -23.336 -13.179  48.298  1.00203.40           C
ANISOU 1463  CD  LYS A 203     11799  32888  32598  -9566   4371    305      C
ATOM   1464  CE  LYS A 203     -23.097 -13.339  49.791  1.00202.57           C
ANISOU 1464  CE  LYS A 203     11683  32735  32548  -9475   4304    -59      C
ATOM   1465  NZ  LYS A 203     -21.659 -13.295  50.150  1.00203.76           N
ANISOU 1465  NZ  LYS A 203     11578  33158  32685  -9456   4373   -484      N
ATOM   1466  N   GLN A 204     -23.886 -17.636  49.563  1.00205.61           N
ANISOU 1466  N   GLN A 204     12568  33487  32069  -9196   3455    -72      N
ATOM   1467  CA  GLN A 204     -23.497 -18.791  50.379  1.00205.13           C
ANISOU 1467  CA  GLN A 204     12704  33488  31748  -8941   3230   -370      C
ATOM   1468  C   GLN A 204     -24.479 -19.967  50.345  1.00204.22           C
ANISOU 1468  C   GLN A 204     13000  33207  31386  -8893   2932   -198      C
ATOM   1469  O   GLN A 204     -25.643 -19.822  49.960  1.00203.71           O
ANISOU 1469  O   GLN A 204     13022  32963  31417  -9092   2870    169      O
ATOM   1470  CB  GLN A 204     -23.265 -18.371  51.829  1.00204.58           C
ANISOU 1470  CB  GLN A 204     12454  33393  31883  -8911   3282   -611      C
ATOM   1471  CG  GLN A 204     -24.526 -17.990  52.564  1.00203.19           C
ANISOU 1471  CG  GLN A 204     12331  32930  31941  -9052   3301   -385      C
ATOM   1472  CD  GLN A 204     -24.764 -16.497  52.605  1.00204.60           C
ANISOU 1472  CD  GLN A 204     12420  32904  32414  -9165   3571   -270      C
ATOM   1473  OE1 GLN A 204     -24.966 -15.908  53.663  1.00204.86           O
ANISOU 1473  OE1 GLN A 204     12458  32768  32612  -9167   3681   -372      O
ATOM   1474  NE2 GLN A 204     -24.734 -15.876  51.436  1.00205.83           N
```

FIG. 13 Continued

```
ANISOU 1474  NE2 GLN A 204    12523  33059  32626  -9256   3696    -57       N
ATOM   1475  N   GLY A 205    -23.989 -21.129  50.768  1.00200.31            N
ANISOU 1475  N   GLY A 205    12743  32772  30592   8632   2745    451       N
ATOM   1476  CA  GLY A 205    -24.798 -22.332  50.844  1.00199.84            C
ANISOU 1476  CA  GLY A 205    13107  32533  30290  -8583   2465   -338       C
ATOM   1477  C   GLY A 205    -24.378 -23.457  49.920  1.00201.40            C
ANISOU 1477  C   GLY A 205    13678  32776  30067  -8424   2325   -423       C
ATOM   1478  O   GLY A 205     24.521  23.355  48.706  1.00202.47            O
ANISOU 1478  O   GLY A 205    13918  32930  30082  -8558   2346   -260       O
ATOM   1479  N   GLU A 206    -23.855 -24.534  50.505  1.00146.76            N
ANISOU 1479  N   GLU A 206     6993  25864  22907  -8124   2195   -675       N
ATOM   1480  CA  GLU A 206    -23.454 -25.724  49.753  1.00148.67            C
ANISOU 1480  CA  GLU A 206     7665  26086  22736  -7919   2088   -784       C
ATOM   1481  C   GLU A 206    -24.662 -26.666  49.706  1.00148.43            C
ANISOU 1481  C   GLU A 206     8110  25750  22538  -8066   1805   -577       C
ATOM   1482  O   GLU A 206    -25.013 -27.279  50.713  1.00147.69            O
ANISOU 1482  O   GLU A 206     8156  25512  22448  -7976   1663   -606       O
ATOM   1483  CB  GLU A 206    -22.237 -26.422  50.403  1.00149.93            C
ANISOU 1483  CB  GLU A 206     7826  26395  22745  -7481   2109  -1134       C
ATOM   1484  CG  GLU A 206    -20.954 -25.566  50.605  1.00150.75            C
ANISOU 1484  CG  GLU A 206     7401  26839  23039  -7339   2348  -1350       C
ATOM   1485  CD  GLU A 206    -19.941 -26.221  51.561  1.00152.03            C
ANISOU 1485  CD  GLU A 206     7492  27158  23116  -6931   2289  -1634       C
ATOM   1486  OE1 GLU A 206    -19.497 -25.574  52.542  1.00151.68            O
ANISOU 1486  OE1 GLU A 206     7053  27281  23296  -6925   2307  -1757       O
ATOM   1487  OE2 GLU A 206    -19.600 -27.396  51.335  1.00153.78            O
ANISOU 1487  OE2 GLU A 206     8074  27321  23033   6616   2215   1724       O
ATOM   1488  N   ILE A 207    -25.274 -26.797  48.529  1.00153.09            N
ANISOU 1488  N   ILE A 207     8957  26247  23308  -8308   1714   -363       N
ATOM   1489  CA  ILE A 207    -26.544 -27.512  48.405  1.00153.26            C
ANISOU 1489  CA  ILE A 207     9355  25991  22883  -8562   1417   -108       C
ATOM   1490  C   ILE A 207    -26.656 -28.517  47.267  1.00155.94            C
ANISOU 1490  C   ILE A 207    10279  26200  22771  -8621   1238   -116       C
ATOM   1491  O   ILE A 207    -26.133 -28.295  46.176  1.00157.62            O
ANISOU 1491  O   ILE A 207    10567  26541  22782  -8618   1354   -162       O
ATOM   1492  CB  ILE A 207    -27.683 -26.510  48.170  1.00152.21            C
ANISOU 1492  CB  ILE A 207     8925  25831  23076  -8965   1388    305       C
ATOM   1493  CG1 ILE A 207    -27.349 -25.172  48.833  1.00150.38            C
ANISOU 1493  CG1 ILE A 207     8113  25757  23265  -8931   1677    294       C
ATOM   1494  CG2 ILE A 207    -29.013 -27.084  48.636  1.00151.93            C
ANISOU 1494  CG2 ILE A 207     9068  25541  23117  -9198   1115    583       C
ATOM   1495  CD1 ILE A 207    -27.258 -25.225  50.353  1.00148.77            C
ANISOU 1495  CD1 ILE A 207     7767  25509  23251  -8753   1725    136       C
ATOM   1496  N   GLU A 208    -27.379 -29.606  47.534  1.00177.76            N
ANISOU 1496  N   GLU A 208    13482  28688  25371  -8700    965    -62       N
ATOM   1497  CA  GLU A 208    -27.644 -30.654  46.546  1.00180.76            C
ANISOU 1497  CA  GLU A 208    14506  28867  25306  -8822    748    -73       C
ATOM   1498  C   GLU A 208    -28.832 -30.250  45.681  1.00181.54            C
ANISOU 1498  C   GLU A 208    14618  28925  25433  -9339    513    323       C
ATOM   1499  O   GLU A 208    -29.672 -29.473  46.120  1.00179.70            O
ANISOU 1499  O   GLU A 208    13953  28728  25597  -9576    471    639       O
ATOM   1500  CB  GLU A 208    -27.932 -31.990  47.236  1.00181.62            C
ANISOU 1500  CB  GLU A 208    15091  28666  25251  -8723    548   -171       C
ATOM   1501  CG  GLU A 208    -26.759 -32.555  48.024  1.00181.67            C
ANISOU 1501  CG  GLU A 208    15155  28698  25172  -8179    736   -534       C
ATOM   1502  CD  GLU A 208    -25.591 -32.970  47.143  1.00184.40            C
ANISOU 1502  CD  GLU A 208    15795  29116  25150  -7849    926   -831       C
ATOM   1503  OE1 GLU A 208    -25.795 -33.209  45.932  1.00186.82            O
ANISOU 1503  OE1 GLU A 208    16501  29339  25144  -8050    862   -801       O
ATOM   1504  OE2 GLU A 208    -24.464 -33.065  47.669  1.00184.51            O
ANISOU 1504  OE2 GLU A 208    15643  29280  25181  -7384   1142  -1086       O
ATOM   1505  N   ALA A 209    -28.913 -30.790  44.466  1.00213.37            N
ANISOU 1505  N   ALA A 209    19159  32878  29034  -9506    359    315       N
ATOM   1506  CA  ALA A 209    -29.971 -30.399  43.535  1.00214.82            C
ANISOU 1506  CA  ALA A 209    19362  33070  29191 -10007     93    704       C
ATOM   1507  C   ALA A 209    -30.058 -31.261  42.281  1.00219.07            C
ANISOU 1507  C   ALA A 209    20623  33468  29144 -10203   -136    633       C
ATOM   1508  O   ALA A 209    -29.068 -31.848  41.851  1.00220.95            O
ANISOU 1508  O   ALA A 209    21290  33671  28989  -9896     45    270       O
```

FIG. 13 Continued

```
ATOM   1509  CB   ALA A 209     -29.769 -28.950  43.125  1.00213.55           C
ANISOU 1509  CB   ALA A 209    18637  33210  29293 -10046    327     890      C
ATOM   1510  N    VAL A 210     -31.252 -31.328  41.697  1.00178.02           N
ANISOU 1510  N    VAL A 210    15561  28191  23888 -10718   -535     991      N
ATOM   1511  CA   VAL A 210     -31.435 -32.014  40.419  1.00182.61           C
ANISOU 1511  CA   VAL A 210    16840  28658  23884 -10996   -802     956      C
ATOM   1512  C    VAL A 210     -31.847 -31.016  39.339  1.00183.99           C
ANISOU 1512  C    VAL A 210    16797  29088  24022 -11322   -901    1309      C
ATOM   1513  O    VAL A 210     -32.924 -30.422  39.403  1.00183.54           O
ANISOU 1513  O    VAL A 210    16325  29110  24303 -11688  -1156    1773      O
ATOM   1514  CB   VAL A 210     -32.457 -33.161  40.494  1.00185.21           C
ANISOU 1514  CB   VAL A 210    17671  28653  24047 -11389  -1274    1050      C
ATOM   1515  CG1  VAL A 210     -32.555 -33.863  39.140  1.00190.54           C
ANISOU 1515  CG1  VAL A 210    19146  29197  24053 -11690  -1547     956      C
ATOM   1516  CG2  VAL A 210     -32.062 -34.146  41.580  1.00184.09           C
ANISOU 1516  CG2  VAL A 210    17763  28237  23945 -11052  -1160     735      C
ATOM   1517  N    VAL A 211     -30.972 -30.833  38.354  1.00193.87           N
ANISOU 1517  N    VAL A 211    18323  30471  24870 -11162   -673    1111      N
ATOM   1518  CA   VAL A 211     -31.220 -29.899  37.265  1.00195.62           C
ANISOU 1518  CA   VAL A 211    18401  30938  24987 -11423   -722    1428      C
ATOM   1519  C    VAL A 211     -32.526 -30.208  36.552  1.00199.22           C
ANISOU 1519  C    VAL A 211    19146  31321  25227 -12032  -1316    1807      C
ATOM   1520  O    VAL A 211     -32.651 -31.223  35.861  1.00203.39           O
ANISOU 1520  O    VAL A 211    20445  31652  25180 -12240  -1592    1636      O
ATOM   1521  CB   VAL A 211     -30.068 -29.912  36.251  1.00198.24           C
ANISOU 1521  CB   VAL A 211    19151  31371  24798 -11165   -387    1119      C
ATOM   1522  CG1  VAL A 211     -28.901 -29.128  36.789  1.00194.95           C
ANISOU 1522  CG1  VAL A 211    18188  31159  24724 -10668    183     925      C
ATOM   1523  CG2  VAL A 211     -29.648 -31.340  35.949  1.00201.65           C
ANISOU 1523  CG2  VAL A 211    20470  31508  24638 -11050   -436     688      C
ATOM   1524  N    ILE A 212     -33.504 -29.328  36.741  1.00207.86           N
ANISOU 1524  N    ILE A 212    19616  32566  26796 -12318  -1511    2328      N
ATOM   1525  CA   ILE A 212     -34.794 -29.471  36.085  1.00211.55           C
ANISOU 1525  CA   ILE A 212    20201  33033  27145 -12912  -2102    2779      C
ATOM   1526  C    ILE A 212     -34.754 -28.750  34.743  1.00214.79           C
ANISOU 1526  C    ILE A 212    20705  33696  27211 -13095  -2164    3017      C
ATOM   1527  O    ILE A 212     -33.713 -28.234  34.339  1.00214.20           O
ANISOU 1527  O    ILE A 212    20651  33759  26975 -12759  -1722    2802      O
ATOM   1528  CB   ILE A 212     -35.949 -28.906  36.949  1.00209.35           C
ANISOU 1528  CB   ILE A 212    19168  32797  27578 -13118  -2283    3232      C
ATOM   1529  CG1  ILE A 212     -37.307 -29.475  36.490  1.00213.70           C
ANISOU 1529  CG1  ILE A 212    19904  33281  28010 -13746  -2963    3697      C
ATOM   1530  CG2  ILE A 212     -35.924 -27.380  36.936  1.00207.15           C
ANISOU 1530  CG2  ILE A 212    18142  32798  27765 -12982  -1987    3649      C
ATOM   1531  CD1  ILE A 212     -38.527 -28.814  37.121  1.00212.69           C
ANISOU 1531  CD1  ILE A 212    18982  33249  28582 -13974  -3144    4312      C
ATOM   1532  N    ALA A 213     -35.892 -28.731  34.056  1.00286.19           N
ANISOU 1532  N    ALA A 213    29794  42807  36137 -13637  -2723    3483      N
ATOM   1533  CA   ALA A 213     -36.020 -28.074  32.758  1.00290.00           C
ANISOU 1533  CA   ALA A 213    30384  43540  36262 -13872  -2877    3790      C
ATOM   1534  C    ALA A 213     -34.875 -28.426  31.816  1.00292.53           C
ANISOU 1534  C    ALA A 213    31452  43851  35844 -13663  -2603    3322      C
ATOM   1535  O    ALA A 213     -34.048 -29.279  32.128  1.00291.81           O
ANISOU 1535  O    ALA A 213    31827  43540  35506 -13359  -2341    2767      O
ATOM   1536  CB   ALA A 213     -36.137 -26.568  32.925  1.00287.34           C
ANISOU 1536  CB   ALA A 213    29184  43471  36520 -13726  -2604    4242      C
ATOM   1537  N    THR A 214     -34.848 -27.783  30.652  1.00229.69           N
ANISOU 1537  N    THR A 214    23617  36127 -13815 -2655    3572               N
ATOM   1538  CA   THR A 214     -33.798 -28.030  29.672  1.00232.73           C
ANISOU 1538  CA   THR A 214    24711  36526  27191 -13624  -2354    3181      C
ATOM   1539  C    THR A 214     -32.708 -26.971  29.796  1.00229.38           C
ANISOU 1539  C    THR A 214    23801  36294  27057 -13116  -1647    3102      C
ATOM   1540  O    THR A 214     -32.970 -25.839  30.207  1.00226.36           O
ANISOU 1540  O    THR A 214    22620  36088  27297 -13065  -1515    3493      O
ATOM   1541  CB   THR A 214     -34.342 -28.074  28.218  1.00239.51           C
ANISOU 1541  CB   THR A 214    26152  37515  27338 -14112  -2829    3455      C
ATOM   1542  OG1  THR A 214     -34.154 -26.802  27.589  1.00239.86           O
ANISOU 1542  OG1  THR A 214    25798  37878  27460 -14038  -2600    3834      O
ATOM   1543  CG2  THR A 214     -35.825 -28.466  28.177  1.00242.43           C
```

FIG. 13 Continued

```
ANISOU 1543  CG2 THR A 214    26501  37854  27755 -14748  -3642   3867          C
ATOM   1544  N   GLY A 215     -31.487 -27.346  29.437  1.00 198.33           N
ANISOU 1544  N   GLY A 215    20359  32312  22684 -12747  -1179   2604          N
ATOM   1545  CA  GLY A 215     -30.358 -26.449  29.547  1.00 195.73           C
ANISOU 1545  CA  GLY A 215    19597  32161  22613 -12281   -496   2489          C
ATOM   1546  C   GLY A 215     -30.621 -25.052  29.018  1.00 196.02           C
ANISOU 1546  C   GLY A 215    19107  32485  22686 -12410   -427   3023          C
ATOM   1547  O   GLY A 215     -30.901 -24.130  29.783  1.00 192.04           O
ANISOU 1547  O   GLY A 215    17798  32062  23107 -12351   -322   3312          O
ATOM   1548  N   VAL A 216     -30.548 -24.897  27.702  1.00 270.33           N
ANISOU 1548  N   VAL A 216    29015  42033  31667 -12583   -477   3163          N
ATOM   1549  CA  VAL A 216     -30.718 -23.591  27.071  1.00 271.41           C
ANISOU 1549  CA  VAL A 216    28739  42436  31948 -12683   -380   3683          C
ATOM   1550  C   VAL A 216     -32.078 -22.950  27.343  1.00 270.63           C
ANISOU 1550  C   VAL A 216    28057  42415  32355 -13050   -887   4327          C
ATOM   1551  O   VAL A 216     -32.332 -21.830  26.904  1.00 271.54           O
ANISOU 1551  O   VAL A 216    27774  42727  32670 -13124   -831   4824          O
ATOM   1552  CB  VAL A 216     -30.487 -23.662  25.546  1.00 277.91           C
ANISOU 1552  CB  VAL A 216    30312  43386  31693 -12843   -409   3739          C
ATOM   1553  CG1 VAL A 216     -31.726 -24.195  24.840  1.00 282.76           C
ANISOU 1553  CG1 VAL A 216    31419  43997  32021 -13420  -1218   4057          C
ATOM   1554  CG2 VAL A 216     -30.114 -22.295  25.003  1.00 278.43           C
ANISOU 1554  CG2 VAL A 216    29954  43707  32128 -12738     -8   4119          C
ATOM   1555  N   HIS A 217     -32.953 -23.657  28.053  1.00 199.50           N
ANISOU 1555  N   HIS A 217    18993  33244  23563 -13268  -1358   4346          N
ATOM   1556  CA  HIS A 217     -34.271 -23.110  28.371  1.00 199.11           C
ANISOU 1556  CA  HIS A 217    18345  33267  24040 -13593  -1818   4975          C
ATOM   1557  C   HIS A 217     -34.287 -22.436  29.736  1.00 193.00           C
ANISOU 1557  C   HIS A 217    16704  32432  24197 -13306  -1479   5054          C
ATOM   1558  O   HIS A 217     -34.778 -22.979  30.722  1.00 190.39           O
ANISOU 1558  O   HIS A 217    16182  31934  24223 -13336  -1657   4949          O
ATOM   1559  CB  HIS A 217     -35.349 -24.180  28.244  1.00 202.33           C
ANISOU 1559  CB  HIS A 217    19159  33565  24151 -14075  -2567   5068          C
ATOM   1560  CG  HIS A 217     -35.567 -24.642  26.834  1.00 209.25           C
ANISOU 1560  CG  HIS A 217    20841  34533  24132 -14463  -3003   5142          C
ATOM   1561  ND1 HIS A 217     -34.593 -24.541  25.862  1.00 212.02           N
ANISOU 1561  ND1 HIS A 217    21753  34965  23840 -14289  -2646   4892          N
ATOM   1562  CD2 HIS A 217     -36.633 -25.228  26.239  1.00 214.41           C
ANISOU 1562  CD2 HIS A 217    21859  35207  24399 -15032  -3767   5427          C
ATOM   1563  CE1 HIS A 217     -35.055 -25.032  24.727  1.00 218.56           C
ANISOU 1563  CE1 HIS A 217    23298  35852  23891 -14724  -3163   5009          C
ATOM   1564  NE2 HIS A 217     -36.291 -25.457  24.928  1.00 220.17           N
ANISOU 1564  NE2 HIS A 217    23398  36026  24232 -15197  -3874   5329          N
ATOM   1565  N   THR A 218     -33.754 -21.220  29.747  1.00 233.57           N
ANISOU 1565  N   THR A 218    21350  37696  29700 -13048   -979   5192          N
ATOM   1566  CA  THR A 218     -33.612 -20.423  30.949  1.00 228.35           C
ANISOU 1566  CA  THR A 218    19921  36971  29869 -12761   -570   5213          C
ATOM   1567  C   THR A 218     -33.150 -19.015  30.573  1.00 228.39           C
ANISOU 1567  C   THR A 218    19514  37122  30141 -12602   -107   5494          C
ATOM   1568  O   THR A 218     -33.717 -18.024  31.037  1.00 226.93           O
ANISOU 1568  O   THR A 218    18687  36936  30599 -12597    -24   5928          O
ATOM   1569  CB  THR A 218     -32.617 -21.077  31.893  1.00 224.42           C
ANISOU 1569  CB  THR A 218    19516  36315  29438 -12400   -200   4533          C
ATOM   1570  OG1 THR A 218     -33.328 -21.956  32.775  1.00 222.73           O
ANISOU 1570  OG1 THR A 218    19306  35919  29401 -12509   -554   4448          O
ATOM   1571  CG2 THR A 218     -31.870 -20.027  32.695  1.00 220.36           C
ANISOU 1571  CG2 THR A 218    18370  35813  29543 -12046    411   4437          C
ATOM   1572  N   PHE A 219     -32.106 -18.936  29.748  1.00 224.48           N
ANISOU 1572  N   PHE A 219    19403  36728  29162 -12459    234   5245          N
ATOM   1573  CA  PHE A 219     -31.683 -17.669  29.159  1.00 225.74           C
ANISOU 1573  CA  PHE A 219    19287  37029  29455 -12371    641   5551          C
ATOM   1574  C   PHE A 219     -32.686 -17.454  28.024  1.00 230.95           C
ANISOU 1574  C   PHE A 219    20149  37840  29760 -12747    134   6178          C
ATOM   1575  O   PHE A 219     -32.779 -16.371  27.436  1.00 233.01           O
ANISOU 1575  O   PHE A 219    20165  38222  30145 -12771    289   6651          O
ATOM   1576  CB  PHE A 219     -30.256 -17.749  28.588  1.00 226.88           C
ANISOU 1576  CB  PHE A 219    19804  37248  29153 -12115   1167   5101          C
ATOM   1577  CG  PHE A 219     -29.169 -17.248  29.521  1.00 222.67           C
ANISOU 1577  CG  PHE A 219    18798  36659  29147 -11743   1804   4721          C
```

FIG. 13 Continued

```
ATOM   1578  CD1 PHE A 219     -29.088 -15.910  29.868  1.00221.08           C
ANISOU 1578  CD1 PHE A 219    17955  36462  29583 -11672   2168   5011       C
ATOM   1579  CD2 PHE A 219     -28.198 -18.115  30.010  1.00220.91           C
ANISOU 1579  CD2 PHE A 219    18796  36379  28761 -11471   2035   4080       C
ATOM   1580  CE1 PHE A 219     -28.078 -15.453  30.712  1.00217.80           C
ANISOU 1580  CE1 PHE A 219    17130  36000  29624 -11388   2713   4646       C
ATOM   1581  CE2 PHE A 219     -27.187 -17.664  30.853  1.00217.64           C
ANISOU 1581  CE2 PHE A 219    17925  35953  28814 -11158   2567   3749       C
ATOM   1582  CZ  PHE A 219     -27.128 -16.334  31.204  1.00216.12           C
ANISOU 1582  CZ  PHE A 219    17102  35773  29240 -11142   2885   4020       C
ATOM   1583  N   PHE A 220     -33.418 -18.525  27.716  1.00306.00           N
ANISOU 1583  N   PHE A 220    30129  47333  38805 -13052   -487   6174       N
ATOM   1584  CA  PHE A 220     -34.478 -18.521  26.711  1.00311.44           C
ANISOU 1584  CA  PHE A 220    31038  48179  39115 -13477  -1114   6750       C
ATOM   1585  C   PHE A 220     -35.833 -18.320  27.402  1.00310.46           C
ANISOU 1585  C   PHE A 220    30307  48026  39628 -13689  -1565   7269       C
ATOM   1586  O   PHE A 220     -36.860 -18.135  26.744  1.00314.80           O
ANISOU 1586  O   PHE A 220    30810  48730  40069 -14035  -2105   7875       O
ATOM   1587  CB  PHE A 220     -34.454 -19.827  25.904  1.00315.68           C
ANISOU 1587  CB  PHE A 220    32509  48712  38724 -13736  -1542   6424       C
ATOM   1588  CG  PHE A 220     -35.640 -20.011  24.990  1.00321.59           C
ANISOU 1588  CG  PHE A 220    33513  49616  39059 -14253  -2318   6972       C
ATOM   1589  CD1 PHE A 220     -35.875 -19.132  23.943  1.00326.04           C
ANISOU 1589  CD1 PHE A 220    34064  50421  39396 -14387  -2405   7534       C
ATOM   1590  CD2 PHE A 220     -36.511 -21.076  25.169  1.00323.14           C
ANISOU 1590  CD2 PHE A 220    33971  49721  39084 -14623  -2977   6938       C
ATOM   1591  CE1 PHE A 220     -36.959 -19.306  23.100  1.00331.99           C
ANISOU 1591  CE1 PHE A 220    35040  51352  39749 -14876  -3169   8060       C
ATOM   1592  CE2 PHE A 220     -37.597 -21.253  24.329  1.00329.11           C
ANISOU 1592  CE2 PHE A 220    34939  50645  39463 -15144  -3739   7449       C
ATOM   1593  CZ  PHE A 220     -37.821 -20.368  23.295  1.00333.59           C
ANISOU 1593  CZ  PHE A 220    35473  51482  39794 -15268  -3852   8013       C
ATOM   1594  N   GLY A 221     -35.822 -18.375  28.734  1.00299.52           N
ANISOU 1594  N   GLY A 221    28457  46454  38895 -13475  -1337   7039       N
ATOM   1595  CA  GLY A 221     -37.006 -18.120  29.537  1.00298.24           C
ANISOU 1595  CA  GLY A 221    27661  46238  39420 -13596  -1617   7499       C
ATOM   1596  C   GLY A 221     -37.109 -16.626  29.785  1.00297.04           C
ANISOU 1596  C   GLY A 221    26793  46110  39957 -13384  -1200   7970       C
ATOM   1597  O   GLY A 221     -38.023 -16.146  30.457  1.00296.13           O
ANISOU 1597  O   GLY A 221    26069  45941  40506 -13397  -1280   8410       O
ATOM   1598  N   LYS A 222     -36.139 -15.901  29.231  1.00297.73           N
ANISOU 1598  N   LYS A 222    26981  46260  39884 -13180   -714   7868       N
ATOM   1599  CA  LYS A 222     -36.049 -14.447  29.315  1.00297.22           C
ANISOU 1599  CA  LYS A 222    26353  46187  40392 -12980   -249   8267       C
ATOM   1600  C   LYS A 222     -35.552 -13.923  27.970  1.00301.58           C
ANISOU 1600  C   LYS A 222    27244  46925  40417 -13026   -140   8479       C
ATOM   1601  O   LYS A 222     -34.652 -13.084  27.912  1.00300.60           O
ANISOU 1601  O   LYS A 222    26995  46769  40449 -12786    463   8372       O
ATOM   1602  CB  LYS A 222     -35.081 -14.014  30.424  1.00291.82           C
ANISOU 1602  CB  LYS A 222    25354  45306  40218 -12607    442   7765       C
ATOM   1603  CG  LYS A 222     -35.648 -14.069  31.836  1.00287.78           C
ANISOU 1603  CG  LYS A 222    24356  44594  40393 -12509    467   7715       C
ATOM   1604  CD  LYS A 222     -35.723 -15.490  32.358  1.00286.01           C
ANISOU 1604  CD  LYS A 222    24474  44313  39882 -12590    125   7246       C
ATOM   1605  CE  LYS A 222     -36.450 -15.540  33.682  1.00282.82           C
ANISOU 1605  CE  LYS A 222    23599  43729  40131 -12529    109   7303       C
ATOM   1606  NZ  LYS A 222     -36.933 -16.912  33.963  1.00282.72           N
ANISOU 1606  NZ  LYS A 222    23908  43680  39834 -12722   -385   7091       N
ATOM   1607  N   ALA A 223     -36.131 -14.445  26.891  1.00242.69           N
ANISOU 1607  N   ALA A 223    20242  39660  32311 -13358   -731   8771       N
ATOM   1608  CA  ALA A 223     -35.749 -14.054  25.541  1.00247.63           C
ANISOU 1608  CA  ALA A 223    21283  40482  32323 -13437   -695   8998       C
ATOM   1609  C   ALA A 223     -36.293 -12.669  25.189  1.00250.11           C
ANISOU 1609  C   ALA A 223    21074  40869  33086 -13412   -597   9794       C
ATOM   1610  O   ALA A 223     -37.491 -12.413  25.338  1.00251.69           O
ANISOU 1610  O   ALA A 223    20849  41110  33674 -13566  -1026  10402       O
ATOM   1611  CB  ALA A 223     -36.236 -15.091  24.536  1.00252.86           C
ANISOU 1611  CB  ALA A 223    22653  41316  32105 -13832  -1402   9041       C
ATOM   1612  N   ALA A 224     -35.408 -11.785  24.724  1.00211.56           N
```

FIG. 13 Continued

```
ANISOU 1612  N   ALA A 224     16215  35997  28171 -13209    -15   9808           N
ATOM   1613  CA  ALA A 224     -35.789 -10.425  24.347  1.00214.22                C
ANISOU 1613  CA  ALA A 224     16116  36362  28917 -13149    166  10546           C
ATOM   1614  C   ALA A 224     -36.443 -10.381  22.968  1.00221.37                C
ANISOU 1614  C   ALA A 224     17375  37550  29184 -13441   -383  11179           C
ATOM   1615  O   ALA A 224     -37.593 -10.780  22.808  1.00224.12                O
ANISOU 1615  O   ALA A 224     17658  38027  29469 -13715  -1090  11607           O
ATOM   1616  CB  ALA A 224     -34.577  -9.502  24.394  1.00212.57                C
ANISOU 1616  CB  ALA A 224     15805  36033  28928 -12854   1007  10318           C
ATOM   1617  N   HIS A 225     -35.698  -9.902  21.976  1.00300.50                N
ANISOU 1617  N   HIS A 225     27772  47680  38725 -13394    -60  11248           N
ATOM   1618  CA  HIS A 225     -36.188  -9.816  20.599  1.00307.80                C
ANISOU 1618  CA  HIS A 225     29115  48886  38949 -13657   -533  11832           C
ATOM   1619  C   HIS A 225     -35.020  -9.718  19.607  1.00310.60                C
ANISOU 1619  C   HIS A 225     30108  49333  38573 -13586    -78  11570           C
ATOM   1620  O   HIS A 225     -33.859  -9.623  20.010  1.00306.91                O
ANISOU 1620  O   HIS A 225     29655  48716  38242 -13322    622  10997           O
ATOM   1621  CB  HIS A 225     -37.153  -8.632  20.425  1.00310.97                C
ANISOU 1621  CB  HIS A 225     28915  49331  39906 -13647   -669  12799           C
ATOM   1622  CG  HIS A 225     -38.585  -8.948  20.761  1.00312.20                C
ANISOU 1622  CG  HIS A 225     28674  49570  40378 -13869  -1422  13290           C
ATOM   1623  ND1 HIS A 225     -39.457  -9.506  19.851  1.00318.33                N
ANISOU 1623  ND1 HIS A 225     29780  50651  40521 -14264  -2274  13723           N
ATOM   1624  CD2 HIS A 225     -39.297  -8.758  21.897  1.00308.59                C
ANISOU 1624  CD2 HIS A 225     27502  48937  40810 -13760  -1437  13442           C
ATOM   1625  CE1 HIS A 225     -40.644  -9.659  20.417  1.00318.42                C
ANISOU 1625  CE1 HIS A 225     29248  50685  41053 -14398  -2795  14133           C
ATOM   1626  NE2 HIS A 225     -40.572  -9.213  21.657  1.00312.53                N
ANISOU 1626  NE2 HIS A 225     27869  49647  41232 -14080  -2275  13975           N
ATOM   1627  N   LEU A 226     -35.338  -9.739  18.314  1.00241.35                N
ANISOU 1627  N   LEU A 226     21854  40824  29026 -13826   -479  12011           N
ATOM   1628  CA  LEU A 226     -34.326  -9.713  17.256  1.00245.11                C
ANISOU 1628  CA  LEU A 226     23020  41414  28698 -13786    -87  11816           C
ATOM   1629  C   LEU A 226     -33.604  -8.371  17.087  1.00245.35                C
ANISOU 1629  C   LEU A 226     22735  41364  29124 -13504    708  12097           C
ATOM   1630  O   LEU A 226     -33.537  -7.830  15.981  1.00251.24                O
ANISOU 1630  O   LEU A 226     23806  42279  29375 -13565    751  12572           O
ATOM   1631  CB  LEU A 226     -34.927 -10.166  15.919  1.00253.04                C
ANISOU 1631  CB  LEU A 226     24737  42724  28684 -14157   -792  12205           C
ATOM   1632  CG  LEU A 226     -35.513 -11.581  15.850  1.00254.33                C
ANISOU 1632  CG  LEU A 226     25420  42966  28249 -14512  -1579  11871           C
ATOM   1633  CD1 LEU A 226     -36.047 -11.883  14.458  1.00263.06                C
ANISOU 1633  CD1 LEU A 226     27262  44377  28312 -14906  -2250  12285           C
ATOM   1634  CD2 LEU A 226     -34.484 -12.620  16.258  1.00250.47                C
ANISOU 1634  CD2 LEU A 226     25407  42302  27457 -14371  -1196  10879           C
ATOM   1635  N   VAL A 227     -33.071  -7.845  18.188  1.00326.26                N
ANISOU 1635  N   VAL A 227     32373  51345  40247 -13218   1323  11805           N
ATOM   1636  CA  VAL A 227     -32.282  -6.608  18.185  1.00326.02                C
ANISOU 1636  CA  VAL A 227     32023  51177  40673 -12971   2134  11962           C
ATOM   1637  C   VAL A 227     -31.953  -6.166  19.615  1.00319.11                C
ANISOU 1637  C   VAL A 227     30435  49986  40825 -12731   2624  11616           C
ATOM   1638  O   VAL A 227     -32.742  -6.387  20.536  1.00315.61                O
ANISOU 1638  O   VAL A 227     29574  49432  40911 -12745   2281  11625           O
ATOM   1639  CB  VAL A 227     -32.984  -5.453  17.428  1.00331.52                C
ANISOU 1639  CB  VAL A 227     32533  51945  41483 -13019   2034  12941           C
ATOM   1640  CG1 VAL A 227     -34.214  -4.978  18.188  1.00329.95                C
ANISOU 1640  CG1 VAL A 227     31622  51627  42117 -13015   1661  13481           C
ATOM   1641  CG2 VAL A 227     -32.011  -4.301  17.186  1.00332.48                C
ANISOU 1641  CG2 VAL A 227     32529  51931  41868 -12809   2903  13053           C
ATOM   1642  N   ASP A 228     -30.782  -5.555  19.797  1.00241.55                N
ANISOU 1642  N   ASP A 228     20489  40026  31262 -12529   3425  11309           N
ATOM   1643  CA  ASP A 228     -30.373  -5.045  21.109  1.00235.74                C
ANISOU 1643  CA  ASP A 228     19119  38991  31460 -12332   3918  10972           C
ATOM   1644  C   ASP A 228     -29.229  -4.030  21.015  1.00236.33                C
ANISOU 1644  C   ASP A 228     19034  38934  31827 -12187   4771  10905           C
ATOM   1645  O   ASP A 228     -28.601  -3.882  19.964  1.00240.75                O
ANISOU 1645  O   ASP A 228     20007  39650  31819 -12211   5038  11010           O
ATOM   1646  CB  ASP A 228     -30.045  -6.182  22.096  1.00230.14                C
ANISOU 1646  CB  ASP A 228     18421  38240  30782 -12278   3804  10161           C
```

FIG. 13 Continued

```
ATOM   1647 CG  ASP A 228      -28.957  -7.113  21.591  1.00230.87           C
ANISOU 1647 CG  ASP A 228    19102  38497  30120 -12245   3990   9534        C
ATOM   1648 OD1 ASP A 228      -28.846  -8.236  22.126  1.00227.74           O
ANISOU 1648 OD1 ASP A 228    18879  38110  29541 -12226   3753   8961        O
ATOM   1649 OD2 ASP A 228      -28.216  -6.728  20.663  1.00234.85           O
ANISOU 1649 OD2 ASP A 228    19904  39110  30220 -12221   4400   9629        O
ATOM   1650 N   SER A 229      -28.988  -3.322  22.116  1.00284.98           N
ANISOU 1650 N   SER A 229    24608  44801  38871 -12058   5195  10744        N
ATOM   1651 CA  SER A 229      -27.938  -2.313  22.176  1.00285.49           C
ANISOU 1651 CA  SER A 229    24450  44696  39326 -11968   5990  10665        C
ATOM   1652 C   SER A 229      -26.599  -2.933  21.818  1.00285.74           C
ANISOU 1652 C   SER A 229    24828  44908  38832 -11929   6365  10049        C
ATOM   1653 O   SER A 229      -26.341  -4.091  22.148  1.00282.96           O
ANISOU 1653 O   SER A 229    24682  44682  38149 -11895   6133   9462        O
ATOM   1654 CB  SER A 229      -27.860  -1.691  23.574  1.00280.72           C
ANISOU 1654 CB  SER A 229    23225  43742  39694 -11871   6311  10424        C
ATOM   1655 OG  SER A 229      -28.954  -0.825  23.820  1.00281.61           O
ANISOU 1655 OG  SER A 229    22991  43628  40379 -11858   6180  11072        O
ATOM   1656 N   THR A 230      -25.752  -2.159  21.146  1.00225.85           N
ANISOU 1656 N   THR A 230    17298  37325  31189 -11921   6969  10206        N
ATOM   1657 CA  THR A 230      -24.428  -2.630  20.756  1.00226.92           C
ANISOU 1657 CA  THR A 230    17705  37636  30879 -11860   7424   9668        C
ATOM   1658 C   THR A 230      -23.804  -3.459  21.880  1.00221.34           C
ANISOU 1658 C   THR A 230    16784  36912  30405 -11749   7455   8869        C
ATOM   1659 O   THR A 230      -23.929  -3.121  23.060  1.00216.96           O
ANISOU 1659 O   THR A 230    15713  36126  30597 -11723   7489   8683        O
ATOM   1660 CB  THR A 230      -23.500  -1.453  20.355  1.00230.35           C
ANISOU 1660 CB  THR A 230    17955  37972  31596 -11865   8212   9899        C
ATOM   1661 OG1 THR A 230      -23.357  -1.420  18.930  1.00236.63           O
ANISOU 1661 OG1 THR A 230    19299  38989  31621 -11907   8312  10297        O
ATOM   1662 CG2 THR A 230      -22.128  -1.609  20.979  1.00228.06           C
ANISOU 1662 CG2 THR A 230    17399  37679  31573 -11781   8775   9205        C
ATOM   1663 N   ASN A 231      -23.155  -4.558  21.505  1.00349.68           N
ANISOU 1663 N   ASN A 231    33469  53400  45994 -11670   7442   8395        N
ATOM   1664 CA  ASN A 231      -22.517  -5.446  22.471  1.00345.10           C
ANISOU 1664 CA  ASN A 231    32742  52833  45549 -11529   7461   7640        C
ATOM   1665 C   ASN A 231      -21.471  -4.711  23.316  1.00343.07           C
ANISOU 1665 C   ASN A 231    31876  52442  46034 -11466   8085   7328        C
ATOM   1666 O   ASN A 231      -21.497  -4.769  24.549  1.00338.27           O
ANISOU 1666 O   ASN A 231    30844  51684  46000 -11429   7996   6983        O
ATOM   1667 CB  ASN A 231      -21.886  -6.642  21.750  1.00347.43           C
ANISOU 1667 CB  ASN A 231    33647  53382  44977 -11419   7466   7248        C
ATOM   1668 CG  ASN A 231      -22.829  -7.261  20.743  1.00350.83           C
ANISOU 1668 CG  ASN A 231    34769  53946  44584 -11542   6887   7573        C
ATOM   1669 OD1 ASN A 231      -24.048  -7.235  20.900  1.00349.78           O
ANISOU 1669 OD1 ASN A 231    34603  53741  44557 -11690   6300   7933        O
ATOM   1670 ND2 ASN A 231      -22.265  -7.882  19.701  1.00355.37           N
ANISOU 1670 ND2 ASN A 231    35977  54721  44328 -11488   7056   7451        N
ATOM   1671 N   GLN A 232      -20.559  -4.019  22.635  1.00282.61           N
ANISOU 1671 N   GLN A 232    24194  44844  38343 -11477   8708   7464        N
ATOM   1672 CA  GLN A 232      -19.518  -3.232  23.279  1.00281.97           C
ANISOU 1672 CA  GLN A 232    23544  44651  38939 -11482   9320   7230        C
ATOM   1673 C   GLN A 232      -18.566  -2.762  22.190  1.00287.80           C
ANISOU 1673 C   GLN A 232    24434  45535  39380 -11494   9954   7424        C
ATOM   1674 O   GLN A 232      -17.360  -2.714  22.401  1.00288.52           O
ANISOU 1674 O   GLN A 232    24246  45713  39667 -11439  10470   7061        O
ATOM   1675 CB  GLN A 232       18.763   4.070  24.317  1.00277.88           C
ANISOU 1675 CB  GLN A 232    22771  44208  38604 -11334   9322   6483        C
ATOM   1676 CG  GLN A 232      -16.503  -3.372  25.660  1.00274.21           C
ANISOU 1676 CG  GLN A 232    21634  43510  39044 -11405   9477   6238        C
ATOM   1677 CD  GLN A 232      -17.453  -2.267  25.588  1.00277.32           C
ANISOU 1677 CD  GLN A 232    21621  43844  39905 -11527  10177   6291        C
ATOM   1678 OE1 GLN A 232      -17.651  -1.248  24.927  1.00280.84           O
ANISOU 1678 OE1 GLN A 232    22090  44154  40465 -11671  10452   6822        O
ATOM   1679 NE2 GLN A 232      -16.337  -2.458  26.289  1.00276.34           N
ANISOU 1679 NE2 GLN A 232    21106  43818  40073 -11482  10456   5759        N
ATOM   1680 N   VAL A 233      -19.117  -2.411  21.029  1.00229.71           N
ANISOU 1680 N   VAL A 233    17507  38220  31552 -11570   9910   8023        N
ATOM   1681 CA  VAL A 233      -18.319  -2.015  19.855  1.00235.95           C
```

FIG. 13 Continued

```
ANISOU 1681  CA  VAL A 233    18553  39162  31935 -11577  10498   8277           C
ATOM   1682  C   VAL A 233    -17.214  -0.953  20.056  1.00237.87                C
ANISOU 1682  C   VAL A 233    18267  39298  32815 -11655  11279   8271           C
ATOM   1683  O   VAL A 233    -16.531  -0.581  19.105  1.00243.31                O
ANISOU 1683  O   VAL A 233    19132  40105  33212 -11670  11817   8507           O
ATOM   1684  CB  VAL A 233    -19.228  -1.562  18.694  1.00240.60                C
ANISOU 1684  CB  VAL A 233    19621  39761  32035 -11682  10293   9030           C
ATOM   1685  CG1 VAL A 233    -20.300  -2.607  18.424  1.00239.60                C
ANISOU 1685  CG1 VAL A 233    20021  39765  31252 -11665   9496   9056           C
ATOM   1686  CG2 VAL A 233    -19.846  -0.212  19.000  1.00240.57                C
ANISOU 1686  CG2 VAL A 233    19206  39437  32764 -11829  10353   9583           C
ATOM   1687  N   GLY A 234    -17.033  -0.488  21.289  1.00223.46                N
ANISOU 1687  N   GLY A 234    32917  24096  27892  -6262   7337  -4879           N
ATOM   1688  CA  GLY A 234    -16.058   0.548  21.609  1.00220.12                C
ANISOU 1688  CA  GLY A 234    33561  23164  26910  -5949   7136  -4906           C
ATOM   1689  C   GLY A 234    -14.586   0.306  21.301  1.00212.41                C
ANISOU 1689  C   GLY A 234    33176  21809  25720  -6274   6251  -4953           C
ATOM   1690  O   GLY A 234    -14.237  -0.294  20.283  1.00207.95                O
ANISOU 1690  O   GLY A 234    32023  21466  25524  -6484   5617  -5010           O
ATOM   1691  N   HIS A 235    -13.726   0.799  22.195  1.00160.05                N
ANISOU 1691  N   HIS A 235    27714  14616  18481  -6313   6227  -4938           N
ATOM   1692  CA  HIS A 235    -12.263   0.716  22.076  1.00153.84                C
ANISOU 1692  CA  HIS A 235    27562  13441  17449  -6593   5426  -4948           C
ATOM   1693  C   HIS A 235    -11.748  -0.710  21.897  1.00150.69                C
ANISOU 1693  C   HIS A 235    26923  13033  17298  -7190   4947  -4872           C
ATOM   1694  O   HIS A 235    -11.332  -1.344  22.860  1.00151.96                O
ANISOU 1694  O   HIS A 235    27728  12866  17144  -7589   4979  -4737           O
ATOM   1695  CB  HIS A 235    -11.618   1.333  23.329  1.00155.87                C
ANISOU 1695  CB  HIS A 235    29112  13147  16966  -6649   5579  -4933           C
ATOM   1696  CG  HIS A 235    -10.118   1.278  23.348  1.00150.81                C
ANISOU 1696  CG  HIS A 235    29112  12132  16059  -6965   4763  -4911           C
ATOM   1697  ND1 HIS A 235     -9.341   2.358  23.711  1.00150.64                N
ANISOU 1697  ND1 HIS A 235    29962  11722  15552  -6844   4578  -4998           N
ATOM   1698  CD2 HIS A 235     -9.253   0.275  23.065  1.00146.51                C
ANISOU 1698  CD2 HIS A 235    28439  11533  15696  -7399   4104  -4807           C
ATOM   1699  CE1 HIS A 235     -8.064   2.024  23.645  1.00146.45                C
ANISOU 1699  CE1 HIS A 235    29743  10972  14929  -7208   3807  -4933           C
ATOM   1700  NE2 HIS A 235     -7.984   0.765  23.254  1.00143.86                N
ANISOU 1700  NE2 HIS A 235    28815  10838  15009  -7510   3523  -4803           N
ATOM   1701  N   PHE A 236    -11.750  -1.204  20.665  1.00164.20                N
ANISOU 1701  N   PHE A 236    27762  15082  19546  -7238   4505  -4954           N
ATOM   1702  CA  PHE A 236    -11.325  -2.570  20.383  1.00161.86                C
ANISOU 1702  CA  PHE A 236    27198  14743  19559  -7769   4111  -4926           C
ATOM   1703  C   PHE A 236    -10.725  -2.575  18.998  1.00156.40                C
ANISOU 1703  C   PHE A 236    25987  14237  19199  -7692   3432  -5068           C
ATOM   1704  O   PHE A 236     -9.545  -2.875  18.800  1.00152.06                O
ANISOU 1704  O   PHE A 236    25771  13393  18613  -7880   2868  -5043           O
ATOM   1705  CB  PHE A 236    -12.538  -3.510  20.386  1.00166.59                C
ANISOU 1705  CB  PHE A 236    27041  15679  20575  -8029   4600  -4933           C
ATOM   1706  CG  PHE A 236    -13.146  -3.732  21.748  1.00172.64                C
ANISOU 1706  CG  PHE A 236    28279  16263  21053  -8191   5339  -4759           C
ATOM   1707  CD1 PHE A 236    -13.097  -4.983  22.348  1.00174.70                C
ANISOU 1707  CD1 PHE A 236    28710  16285  21385  -8745   5459  -4605           C
ATOM   1708  CD2 PHE A 236    -13.777  -2.696  22.425  1.00176.92                C
ANISOU 1708  CD2 PHE A 236    29129  16845  21249  -7774   5968  -4738           C
ATOM   1709  CE1 PHE A 236    -13.656  -5.194  23.606  1.00180.85                C
ANISOU 1709  CE1 PHE A 236    29965  16900  21850  -8903   6180  -4409           C
ATOM   1710  CE2 PHE A 236    -14.334  -2.895  23.686  1.00183.12                C
ANISOU 1710  CE2 PHE A 236    30397  17467  21714  -7919   6714  -4587           C
ATOM   1711  CZ  PHE A 236    -14.276  -4.147  24.276  1.00185.06                C
ANISOU 1711  CZ  PHE A 236    30810  17512  21992  -8495   6815  -4411           C
ATOM   1712  N   GLN A 237    -11.590  -2.251  18.044  1.00205.79                N
ANISOU 1712  N   GLN A 237    31391  21023  25776  -7400   3516  -5200           N
ATOM   1713  CA  GLN A 237    -11.248  -2.115  16.643  1.00201.88                C
ANISOU 1713  CA  GLN A 237    30350  20822  25533  -7251   2959  -5341           C
ATOM   1714  C   GLN A 237    -11.297  -0.629  16.317  1.00201.61                C
ANISOU 1714  C   GLN A 237    30429  20888  25286  -6621   2994  -5312           C
ATOM   1715  O   GLN A 237    -10.454  -0.119  15.584  1.00197.48                O
ANISOU 1715  O   GLN A 237    30040  20292  24701  -6453   2522  -5335           O
```

FIG. 13 Continued

```
ATOM   1716  CB   GLN A 237     -12.260   -2.871   15.789  1.00204.56           C
ANISOU 1716  CB   GLN A 237    29631  21741  26352   -7411   2993  -5494        C
ATOM   1717  CG   GLN A 237     -12.609   -4.257   16.325  1.00207.34           C
ANISOU 1717  CG   GLN A 237    29848  21979  26953   -8025   3221  -5509        C
ATOM   1718  CD   GLN A 237     -11.740   -5.357   15.735  1.00203.80           C
ANISOU 1718  CD   GLN A 237    29394  21309  26732   -8476   2702  -5635        C
ATOM   1719  OE1  GLN A 237     -10.671   -5.090   15.182  1.00199.79           O
ANISOU 1719  OE1  GLN A 237    29111  20761  26037   -8220   2247  -5569        O
ATOM   1720  NE2  GLN A 237     -12.204   -6.605   15.842  1.00206.95           N
ANISOU 1720  NE2  GLN A 237    29470  21686  27475   -9008   2870  -5708        N
ATOM   1721  N    LYS A 238     -12.294    0.064   16.871  1.00170.22           N
ANISOU 1721  N    LYS A 238    26409  17047  21220   -6261   3610  -5246        N
ATOM   1722  CA   LYS A 238     -12.435    1.512   16.691  1.00171.27           C
ANISOU 1722  CA   LYS A 238    26726  17181  21169   -5609   3770  -5192        C
ATOM   1723  C    LYS A 238     -11.317    2.192   17.460  1.00168.91           C
ANISOU 1723  C    LYS A 238    27574  16216  20389   -5624   3676  -5159        C
ATOM   1724  O    LYS A 238     -11.452    3.291   18.006  1.00171.65           O
ANISOU 1724  O    LYS A 238    28474  16303  20441   -5235   4062  -5130        O
ATOM   1725  CB   LYS A 238     -13.816    2.016   17.128  1.00178.26           C
ANISOU 1725  CB   LYS A 238    27244  18352  22133   -5188   4529  -5123        C
ATOM   1726  CG   LYS A 238     -14.946    1.735   16.112  1.00181.45           C
ANISOU 1726  CG   LYS A 238    26371  19536  23034   -5009   4520  -5127        C
ATOM   1727  CD   LYS A 238     -14.607    2.227   14.690  1.00178.29           C
ANISOU 1727  CD   LYS A 238    25552  19452  22738   -4687   3900  -5132        C
ATOM   1728  CE   LYS A 238     -15.733    1.935   13.694  1.00182.40           C
ANISOU 1728  CE   LYS A 238    24811  20814  23678   -4543   3809  -5133        C
ATOM   1729  NZ   LYS A 238     -15.336    2.203   12.281  1.00179.50           N
ANISOU 1729  NZ   LYS A 238    24081  20789  23332   -4344   3137  -5146        N
ATOM   1730  N    VAL A 239     -10.197    1.493   17.470  1.00145.93           N
ANISOU 1730  N    VAL A 239    24992  13030  17426   -6097   3142  -5175        N
ATOM   1731  CA   VAL A 239      -8.987    1.935   18.101  1.00143.63           C
ANISOU 1731  CA   VAL A 239    25668  12175  16731   -6243   2874  -5139        C
ATOM   1732  C    VAL A 239      -7.940    1.940   16.999  1.00139.34           C
ANISOU 1732  C    VAL A 239    24811  11831  16301   -6188   2232  -4992        C
ATOM   1733  O    VAL A 239      -7.092    2.839   16.926  1.00138.76           O
ANISOU 1733  O    VAL A 239    25127  11637  15958   -5975   2038  -4805        O
ATOM   1734  CB   VAL A 239      -8.602    0.955   19.203  1.00144.35           C
ANISOU 1734  CB   VAL A 239    26258  11966  16624   -6779   2876  -5064        C
ATOM   1735  CG1  VAL A 239      -9.711    0.883   20.206  1.00150.32           C
ANISOU 1735  CG1  VAL A 239    27140  12764  17210   -6743   3631  -5032        C
ATOM   1736  CG2  VAL A 239      -8.356   -0.429   18.613  1.00142.64           C
ANISOU 1736  CG2  VAL A 239    25361  12085  16750   -7080   2540  -4924        C
ATOM   1737  N    LEU A 240      -8.032    0.933   16.124  1.00 82.51           N
ANISOU 1737  N    LEU A 240    16834   5050   9466   -6330   1982  -4988        N
ATOM   1738  CA   LEU A 240      -7.136    0.805   14.977  1.00 79.82           C
ANISOU 1738  CA   LEU A 240    16064   5055   9209   -6178   1496  -4779        C
ATOM   1739  C    LEU A 240      -7.704    1.521   13.749  1.00 78.65           C
ANISOU 1739  C    LEU A 240    15445   5142   9298   -5855   1412  -5007        C
ATOM   1740  O    LEU A 240      -6.985    2.188   13.005  1.00 76.96           O
ANISOU 1740  O    LEU A 240    15245   4994   9002   -5587   1145  -4850        O
ATOM   1741  CB   LEU A 240      -6.844   -0.676   14.676  1.00 79.51           C
ANISOU 1741  CB   LEU A 240    15562   5275   9375   -6461   1303  -4687        C
ATOM   1742  CG   LEU A 240      -7.960   -1.739   14.551  1.00 81.22           C
ANISOU 1742  CG   LEU A 240    15233   5658   9968   -6791   1506  -4977        C
ATOM   1743  CD1  LEU A 240      -8.518   -1.903   13.106  1.00 80.57           C
ANISOU 1743  CD1  LEU A 240    14338   6041  10236   -6727   1302  -5243        C
ATOM   1744  CD2  LEU A 240      -7.469   -3.096   15.073  1.00 82.38           C
ANISOU 1744  CD2  LEU A 240    15458   5713  10131   -7120   1480  -4796        C
ATOM   1745  N    THR A 241      -9.006    1.359   13.539  1.00147.65           N
ANISOU 1745  N    THR A 241    23730  14051  18321   -5879   1638  -5343        N
ATOM   1746  CA   THR A 241      -9.671    2.055   12.460  1.00149.26           C
ANISOU 1746  CA   THR A 241    23330  14756  18622   -5384   1619  -5323        C
ATOM   1747  C    THR A 241      -9.436    3.505   12.786  1.00150.02           C
ANISOU 1747  C    THR A 241    24050  14508  18442   -4903   1825  -5173        C
ATOM   1748  O    THR A 241      -9.420    4.343   11.895  1.00150.07           O
ANISOU 1748  O    THR A 241    23898  14683  18440   -4468   1697  -5082        O
ATOM   1749  CB   THR A 241     -11.175    1.751   12.404  1.00154.57           C
ANISOU 1749  CB   THR A 241    23200  16002  19527   -5257   1983  -5344        C
ATOM   1750  OG1  THR A 241     -11.366    0.463   11.813  1.00154.22           O
```

FIG. 13 Continued

```
ANISOU 1750  OG1 THR A 241    22516  16313  19766  -5728   1709  -5528        O
ATOM   1751  CG2 THR A 241    -11.902   2.772  11.562  1.00157.64             C
ANISOU 1751  CG2 THR A 241    23098  16854  19945  -4598   2034  -5219        C
ATOM   1752  N   ALA A 242     -9.222   3.792  14.072  1.00101.77             N
ANISOU 1752  N   ALA A 242    18711   7881  12075  -5004   2147  -5149        N
ATOM   1753  CA  ALA A 242     -8.918   5.154  14.515  1.00103.13             C
ANISOU 1753  CA  ALA A 242    19633   7601  11951  -4638   2370  -5070        C
ATOM   1754  C   ALA A 242     -7.766   5.738  13.676  1.00 99.18             C
ANISOU 1754  C   ALA A 242    19369   6901  11414  -4599   1874  -5023        C
ATOM   1755  O   ALA A 242     -7.771   6.928  13.345  1.00100.73             O
ANISOU 1755  O   ALA A 242    19797   6951  11526  -4140   2003  -4924        O
ATOM   1756  CB  ALA A 242     -8.608   5.193  16.019  1.00104.69             C
ANISOU 1756  CB  ALA A 242    20736   7248  11792  -4926   2654  -5112        C
ATOM   1757  N   ILE A 243     -6.792   4.897  13.318  1.00135.93             N
ANISOU 1757  N   ILE A 243    23786  11770  16093  -4948   1417  -4839        N
ATOM   1758  CA  ILE A 243     -5.703   5.319  12.432  1.00134.00             C
ANISOU 1758  CA  ILE A 243    23487  11628  15800  -4827   1041  -4567        C
ATOM   1759  C   ILE A 243     -6.161   5.189  10.988  1.00132.39             C
ANISOU 1759  C   ILE A 243    22615  11815  15873  -4637    826  -4733        C
ATOM   1760  O   ILE A 243     -6.054   6.126  10.195  1.00132.00             O
ANISOU 1760  O   ILE A 243    22654  11683  15815  -4315    747  -4736        O
ATOM   1761  CB  ILE A 243     -4.438   4.437  12.566  1.00132.73             C
ANISOU 1761  CB  ILE A 243    23247  11642  15544  -5128    708  -4231        C
ATOM   1762  CG1 ILE A 243     -4.055   4.205  14.029  1.00134.62             C
ANISOU 1762  CG1 ILE A 243    24072  11596  15483  -5410    811  -4110        C
ATOM   1763  CG2 ILE A 243     -3.281   5.026  11.757  1.00131.33             C
ANISOU 1763  CG2 ILE A 243    23097  11480  15322  -4997    405  -3989        C
ATOM   1764  CD1 ILE A 243     -4.463   2.841  14.552  1.00135.01             C
ANISOU 1764  CD1 ILE A 243    23875  11798  15626  -5706    879  -4161        C
ATOM   1765  N   GLY A 244     -6.662   3.999  10.661  1.00115.34             N
ANISOU 1765  N   GLY A 244    19831  10065  13928  -4874    725  -4886        N
ATOM   1766  CA  GLY A 244     -7.156   3.701   9.332  1.00114.62             C
ANISOU 1766  CA  GLY A 244    19086  10430  14035  -4809    462  -5111        C
ATOM   1767  C   GLY A 244     -8.038   4.816   8.820  1.00118.07             C
ANISOU 1767  C   GLY A 244    19319  11129  14413  -4191    651  -4996        C
ATOM   1768  O   GLY A 244     -8.097   5.063   7.623  1.00118.49             O
ANISOU 1768  O   GLY A 244    18982  11589  14452  -3932    409  -4927        O
ATOM   1769  N   ASN A 245     -8.718   5.494   9.740  1.00178.37             N
ANISOU 1769  N   ASN A 245    27215  18570  21987  -3896   1126  -4899        N
ATOM   1770  CA  ASN A 245     -9.595   6.610   9.404  1.00183.05             C
ANISOU 1770  CA  ASN A 245    27614  19380  22557  -3186   1418  -4681        C
ATOM   1771  C   ASN A 245     -8.791   7.868   9.087  1.00182.32             C
ANISOU 1771  C   ASN A 245    28158  18831  22285  -2850   1388  -4492        C
ATOM   1772  O   ASN A 245     -8.969   8.468   8.028  1.00183.94             O
ANISOU 1772  O   ASN A 245    28068  19340  22480  -2400   1260  -4292        O
ATOM   1773  CB  ASN A 245    -10.593   6.882  10.543  1.00187.75             C
ANISOU 1773  CB  ASN A 245    28295  19866  23176  -2964   2038  -4659        C
ATOM   1774  CG  ASN A 245    -11.846   7.627  10.078  1.00193.95             C
ANISOU 1774  CG  ASN A 245    28477  21124  24089  -2223   2342  -4436        C
ATOM   1775  OD1 ASN A 245    -11.998   7.942   8.896  1.00194.88             O
ANISOU 1775  OD1 ASN A 245    28118  21685  24243  -1874   2039  -4274        O
ATOM   1776  ND2 ASN A 245    -12.751   7.904  11.015  1.00198.85             N
ANISOU 1776  ND2 ASN A 245    29115  21669  24768  -1960   2959  -4403        N
ATOM   1777  N   PHE A 246     -7.906   8.267   9.999  1.00142.20             N
ANISOU 1777  N   PHE A 246    23958  13024  17047  -3094   1492  -4542        N
ATOM   1778  CA  PHE A 246     -7.095   9.473   9.782  1.00142.11             C
ANISOU 1778  CA  PHE A 246    24605  12496  16895  -2875   1489  -4389        C
ATOM   1779  C   PHE A 246     -5.685   9.159   9.193  1.00137.06             C
ANISOU 1779  C   PHE A 246    24128  11700  16249  -3333    972  -4421        C
ATOM   1780  O   PHE A 246     -4.656   9.767   9.534  1.00136.20             O
ANISOU 1780  O   PHE A 246    24682  11041  16028  -3522    923  -4364        O
ATOM   1781  CB  PHE A 246     -7.100  10.399  11.026  1.00145.22             C
ANISOU 1781  CB  PHE A 246    25878  12190  17107  -2767   1972  -4414        C
ATOM   1782  CG  PHE A 246     -8.446  11.114  11.279  1.00151.55             C
ANISOU 1782  CG  PHE A 246    26536  13098  17949  -2071   2581  -4292        C
ATOM   1783  CD1 PHE A 246     -8.971  12.014  10.351  1.00155.11             C
ANISOU 1783  CD1 PHE A 246    26701  13739  18495  -1361   2702  -4004        C
ATOM   1784  CD2 PHE A 246     -9.162  10.905  12.458  1.00154.62             C
ANISOU 1784  CD2 PHE A 246    27092  13380  18278  -2098   3063  -4431        C
```

FIG. 13 Continued

```
ATOM   1785  CE1 PHE A 246     -10.189  12.672  10.586  1.00161.66           C
ANISOU 1785  CE1 PHE A 246    27347  14659  19419    -658   3276  -3849      C
ATOM   1786  CE2 PHE A 246     -10.382  11.566  12.695  1.00161.12           C
ANISOU 1786  CE2 PHE A 246    27742  14293  19184   -1420   3689  -4308      C
ATOM   1787  CZ  PHE A 246     -10.889  12.447  11.758  1.00164.66           C
ANISOU 1787  CZ  PHE A 246    27846  14932  19784    -684   3787  -4014      C
ATOM   1788  N   CYS A 247      -5.696   8.184   8.289  1.00143.85           N
ANISOU 1788  N   CYS A 247    24302  13120  17233   -3501    619  -4484      N
ATOM   1789  CA  CYS A 247      -4.546   7.764   7.499  1.00140.43           C
ANISOU 1789  CA  CYS A 247    23774  12765  16819   -3801    210  -4433      C
ATOM   1790  C   CYS A 247      -5.051   7.633   6.057  1.00141.11           C
ANISOU 1790  C   CYS A 247    23230  13463  16922   -3517     11  -4431      C
ATOM   1791  O   CYS A 247      -4.401   8.094   5.110  1.00140.58           O
ANISOU 1791  O   CYS A 247    23229  13409  16775   -3396   -151  -4284      O
ATOM   1792  CB  CYS A 247      -4.004   6.426   7.988  1.00139.43           C
ANISOU 1792  CB  CYS A 247    23312  12943  16722   -4225     86  -4293      C
ATOM   1793  SG  CYS A 247      -3.199   5.457   6.689  1.00137.49           S
ANISOU 1793  SG  CYS A 247    22482  13190  16568   -4361   -268  -4201      S
ATOM   1794  N   ILE A 248      -6.213   6.986   5.905  1.00 87.05           N
ANISOU 1794  N   ILE A 248    15726   7205  10145   -3419     39  -4527      N
ATOM   1795  CA  ILE A 248      -6.916   6.921   4.624  1.00 89.76           C
ANISOU 1795  CA  ILE A 248    15385   8291  10430   -3093   -153  -4451      C
ATOM   1796  C   ILE A 248      -7.246   8.358   4.255  1.00 93.59           C
ANISOU 1796  C   ILE A 248    16058   8725  10777   -2392     49  -4072      C
ATOM   1797  O   ILE A 248      -7.014   8.773   3.131  1.00 94.59           O
ANISOU 1797  O   ILE A 248    16091   9105  10745   -2133   -146  -3880      O
ATOM   1798  CB  ILE A 248       8.238   6.129   4.705  1.00 92.92           C
ANISOU 1798  CB  ILE A 248    15028   9315  10963   -3110   -124  -4600      C
ATOM   1799  CG1 ILE A 248      -8.158   4.836   3.904  1.00 91.66           C
ANISOU 1799  CG1 ILE A 248    14339   9646  10843   -3576   -516  -4898      C
ATOM   1800  CG2 ILE A 248      -9.367   6.937   4.126  1.00 98.73           C
ANISOU 1800  CG2 ILE A 248    15295  10581  11638   -2425    -32  -4319      C
ATOM   1801  CD1 ILE A 248      -9.513   4.149   3.748  1.00 96.06           C
ANISOU 1801  CD1 ILE A 248    14060  10912  11527   -3608   -548  -5036      C
ATOM   1802  N   CYS A 249      -7.790   9.121   5.202  1.00133.80           N
ANISOU 1802  N   CYS A 249    21459  13462  15917   -2067    479  -3953      N
ATOM   1803  CA  CYS A 249      -8.042  10.536   4.955  1.00137.97           C
ANISOU 1803  CA  CYS A 249    22282  13781  16360   -1375    749  -3583      C
ATOM   1804  C   CYS A 249      -6.695  11.266   4.958  1.00135.31           C
ANISOU 1804  C   CYS A 249    22776  12714  15923   -1541    739  -3500      C
ATOM   1805  O   CYS A 249      -6.461  12.209   5.730  1.00136.79           O
ANISOU 1805  O   CYS A 249    23670  12205  16098   -1405   1092  -3423      O
ATOM   1806  CB  CYS A 249      -9.031  11.144   5.962  1.00142.56           C
ANISOU 1806  CB  CYS A 249    22978  14147  17041    -946   1292  -3508      C
ATOM   1807  SG  CYS A 249      -9.804  12.736   5.456  1.00150.06           S
ANISOU 1807  SG  CYS A 249    23983  15055  17978    113   1662  -2996       S
ATOM   1808  N   SER A 250      -5.807  10.766   4.103  1.00100.27           N
ANISOU 1808  N   SER A 250    18231   8443  11422   -1886    347  -3550      N
ATOM   1809  CA  SER A 250      -4.516  11.363   3.810  1.00 98.32           C
ANISOU 1809  CA  SER A 250    18571   7669  11116   -2061    286  -3433      C
ATOM   1810  C   SER A 250      -4.201  10.922   2.384  1.00 97.59           C
ANISOU 1810  C   SER A 250    18036   8146  10899   -2075    -61  -3365      C
ATOM   1811  O   SER A 250      -3.654  11.682   1.576  1.00 98.93           O
ANISOU 1811  O   SER A 250    18450   8197  10940   -1863    -54  -3081      O
ATOM   1812  CB  SER A 250      -3.457  10.931   4.817  1.00 94.07           C
ANISOU 1812  CB  SER A 250    18508   6548  10684   -2737    225  -3697      C
ATOM   1813  OG  SER A 250      -3.504  11.777   5.959  1.00 96.02           O
ANISOU 1813  OG  SER A 250    19424   6137  10924   -2673    572  -3685      O
ATOM   1814  N   ILE A 251      -4.585   9.681   2.089  1.00171.52           N
ANISOU 1814  N   ILE A 251    26774  18114  20281   -2338   -331  -3638      N
ATOM   1815  CA  ILE A 251      -4.538   9.141   0.740  1.00172.00           C
ANISOU 1815  CA  ILE A 251    26367  18824  20159   -2342   -650  -3655      C
ATOM   1816  C   ILE A 251      -5.327  10.124  -0.101  1.00177.58           C
ANISOU 1816  C   ILE A 251    26919  19919  20634   -2123   -603  -3241      C
ATOM   1817  O   ILE A 251      -4.831  10.659  -1.096  1.00179.02           O
ANISOU 1817  O   ILE A 251    27262  20170  20586   -1420   -668  -2978      O
ATOM   1818  CB  ILE A 251      -5.262   7.775   0.673  1.00171.67           C
ANISOU 1818  CB  ILE A 251    25646  19399  20180   -2648   -883  -4026      C
ATOM   1819  CG1 ILE A 251      -4.344   6.646   1.134  1.00166.70           C
```

FIG. 13 Continued

```
ANISOU 1819  CG1 ILE A 251    25126  18462  19748  -3339   -991  -4396       C
ATOM   1820  CG2 ILE A 251     -5.752   7.488  -0.727  1.00175.02           C
ANISOU 1820  CG2 ILE A 251    25530  20651  20320  -2462  -1188  -4006       C
ATOM   1821  CD1 ILE A 251     -3.268   6.325   0.146  1.00164.98           C
ANISOU 1821  CD1 ILE A 251    24979  19281  19424  -3557  -1175  -4453       C
ATOM   1822  N   ALA A 252     -6.564  10.365   0.339  1.00107.61           N
ANISOU 1822  N   ALA A 252    17740  11300  11848  -1219   -460  -3152       N
ATOM   1823  CA  ALA A 252     -7.487  11.299   0.300  1.00114.01           C
ANISOU 1823  CA  ALA A 252    18319  12492  12508   -439   -398  -2707       C
ATOM   1824  C   ALA A 252     -7.185  12.755   0.045  1.00116.16           C
ANISOU 1824  C   ALA A 252    19318  12006  12812     34     18  -2310       C
ATOM   1825  O   ALA A 252     -7.925  13.641  -0.359  1.00122.02           O
ANISOU 1825  O   ALA A 252    19960  12919  13483    758    150  -1882       O
ATOM   1826  CB  ALA A 252     -8.947  10.956   0.051  1.00118.01           C
ANISOU 1826  CB  ALA A 252    18102  13579  13158   -177   -378  -2753       C
ATOM   1827  N   ILE A 253     -6.114  12.995   0.798  1.00 92.73           N
ANISOU 1827  N   ILE A 253    17072   8197   9965   -379    214  -2446       N
ATOM   1828  CA  ILE A 253     -5.722  14.360   1.153  1.00 95.10           C
ANISOU 1828  CA  ILE A 253    18149   7681  10303    -57    613  -2140       C
ATOM   1829  C   ILE A 253     -4.638  14.875   0.210  1.00 94.79           C
ANISOU 1829  C   ILE A 253    18491   7420  10105   -127    529  -1885       C
ATOM   1830  O   ILE A 253     -4.531  16.075  -0.063  1.00 98.89           O
ANISOU 1830  O   ILE A 253    19486   7506  10581    321    805  -1474       O
ATOM   1831  CB  ILE A 253     -5.196  14.463   2.602  1.00 92.29           C
ANISOU 1831  CB  ILE A 253    18430   6494  10141   -499    883  -2435       C
ATOM   1832  CG1 ILE A 253     -5.680  15.761   3.274  1.00 97.48           C
ANISOU 1832  CG1 ILE A 253    19663   6508  10869     51   1416  -2207       C
ATOM   1833  CG2 ILE A 253     -3.667  14.344   2.629  1.00 87.76           C
ANISOU 1833  CG2 ILE A 253    18337   5424   9583  -1168    724  -2573       C
ATOM   1834  CD1 ILE A 253     -5.186  17.050   2.619  1.00101.21           C
ANISOU 1834  CD1 ILE A 253    20700   6478  11277    432   1615  -1772       C
ATOM   1835  N   GLY A 254     -3.809  13.965  -0.268  1.00118.34           N
ANISOU 1835  N   GLY A 254    21289  10650  13023   -696    204  -2125       N
ATOM   1836  CA  GLY A 254     -2.781  14.351  -1.202  1.00118.39           C
ANISOU 1836  CA  GLY A 254    21584  10515  12883   -790    166  -1895       C
ATOM   1837  C   GLY A 254     -3.386  14.367  -2.580  1.00122.53           C
ANISOU 1837  C   GLY A 254    21667  11840  13051   -300    -29  -1589       C
ATOM   1838  O   GLY A 254     -3.020  15.196  -3.400  1.00125.88           O
ANISOU 1838  O   GLY A 254    22400  12150  13279      3     84  -1162       O
ATOM   1839  N   MET A 255     -4.331  13.461   2.820  1.00113.02           N
ANISOU 1839  N   MET A 255    19750  11447  11744   -242   -328  -1797       N
ATOM   1840  CA  MET A 255     -4.984  13.352  -4.124  1.00117.66           C
ANISOU 1840  CA  MET A 255    19851  12927  11929    161   -622  -1562       C
ATOM   1841  C   MET A 255     -5.905  14.532  -4.498  1.00125.00           C
ANISOU 1841  C   MET A 255    20782  13991  12721   1054   -484   -954       C
ATOM   1842  O   MET A 255     -6.029  14.859  -5.676  1.00129.60           O
ANISOU 1842  O   MET A 255    21274  15064  12904   1434   -656   -571       O
ATOM   1843  CB  MET A 255     -5.680  11.995  -4.284  1.00116.69           C
ANISOU 1843  CB  MET A 255    18960  13630  11748   -144  -1020  -2011       C
ATOM   1844  CG  MET A 255     -6.890  11.806  -3.416  1.00118.17           C
ANISOU 1844  CG  MET A 255    18692  14010  12197     39   -982  -2123       C
ATOM   1845  SD  MET A 255     -8.434  11.912  -4.337  1.00126.55           S
ANISOU 1845  SD  MET A 255    18917  16188  12979    712  -1314  -1807       S
ATOM   1846  CE  MET A 255     -9.630  12.099  -2.999  1.00128.48           C
ANISOU 1846  CE  MET A 255    18826  16292  13699   1016   -995  -1821       C
ATOM   1847  N   VAL A 256     -6.545  15.176  -3.521  1.00161.99           N
ANISOU 1847  N   VAL A 256    25592  18243  17714   1423   -157   -840       N
ATOM   1848  CA  VAL A 256     -7.310  16.384  -3.842  1.00169.54           C
ANISOU 1848  CA  VAL A 256    26628  19180  18608   2334     57   -214       C
ATOM   1849  C   VAL A 256     -6.291  17.478  -4.125  1.00170.51           C
ANISOU 1849  C   VAL A 256    27621  18489  18676   2430    382    168       C
ATOM   1850  O   VAL A 256     -6.640  18.585  -4.534  1.00176.98           O
ANISOU 1850  O   VAL A 256    28698  19125  19420   3157    609    761       O
ATOM   1851  CB  VAL A 256     -8.278  16.850  -2.727  1.00172.28           C
ANISOU 1851  CB  VAL A 256    26920  19215  19326   2777    430   -183       C
ATOM   1852  CG1 VAL A 256     -9.141  15.697  -2.238  1.00170.63           C
ANISOU 1852  CG1 VAL A 256    25901  19672  19258   2509    196   -628       C
ATOM   1853  CG2 VAL A 256     -7.518  17.517  -1.583  1.00169.54           C
ANISOU 1853  CG2 VAL A 256    27475  17673  19270   2534    944   -321       C
```

FIG. 13 Continued

```
ATOM   1854  N   ILE A 257      -5.024  17.160  -3.868  1.00143.86           N
ANISOU 1854  N   ILE A 257    24682  14598  15381   1684    423   -159       N
ATOM   1855  CA  ILE A 257      -3.925  18.056  -4.194  1.00144.66           C
ANISOU 1855  CA  ILE A 257    25534  13979  15455   1604    701    150       C
ATOM   1856  C   ILE A 257      -3.274  17.577  -5.488  1.00144.25           C
ANISOU 1856  C   ILE A 257    25316  14481  15011   1379    418    233       C
ATOM   1857  O   ILE A 257      -2.641  18.381  -6.298  1.00148.26           O
ANISOU 1857  O   ILE A 257    26220  14807  15306   1643    587    724       O
ATOM   1858  CB  ILE A 257      -2.892  18.167  -3.057  1.00139.79           C
ANISOU 1858  CB  ILE A 257    25518  12390  15207    935    957   -207       C
ATOM   1859  CG1 ILE A 257      -3.550  18.785  -1.821  1.00141.60           C
ANISOU 1859  CG1 ILE A 257    26057  12018  15728   1210   1310   -267       C
ATOM   1860  CG2 ILE A 257      -1.698  19.008  -3.498  1.00141.10           C
ANISOU 1860  CG2 ILE A 257    26358  11884  15369    744   1207     97       C
ATOM   1861  CD1 ILE A 257      -4.295  20.086  -2.101  1.00149.60           C
ANISOU 1861  CD1 ILE A 257    27368  12755  16720   2123   1680    331       C
ATOM   1862  N   GLU A 258      -3.223  16.266  -5.697  1.00151.65           N
ANISOU 1862  N   GLU A 258    25703  16078  15838    899     31   -245       N
ATOM   1863  CA  GLU A 258      -2.668  15.740  -6.938  1.00151.94           C
ANISOU 1863  CA  GLU A 258    25593  16677  15458    698   -201   -231       C
ATOM   1864  C   GLU A 258      -3.627  16.064  -8.067  1.00159.18           C
ANISOU 1864  C   GLU A 258    26207  18408  15864   1402   -424    238       C
ATOM   1865  O   GLU A 258      -3.212  16.504  -9.143  1.00163.06           O
ANISOU 1865  O   GLU A 258    26956  19055  15944   1598   -389    646       O
ATOM   1866  CB  GLU A 258      -2.469  14.228  -6.865  1.00146.57           C
ANISOU 1866  CB  GLU A 258    24423  16467  14801     46   -530   -894       C
ATOM   1867  CG  GLU A 258      -1.909  13.619  -8.144  1.00147.44           C
ANISOU 1867  CG  GLU A 258    24418  17147  14457   -168   -716   -958       C
ATOM   1868  CD  GLU A 258      -2.195  12.125  -8.269  1.00144.75           C
ANISOU 1868  CD  GLU A 258    23490  17469  14038   -610  -1094  -1579       C
ATOM   1869  OE1 GLU A 258      -1.230  11.339  -8.398  1.00141.03           O
ANISOU 1869  OE1 GLU A 258    23070  16880  13637  -1167  -1066  -1948       O
ATOM   1870  OE2 GLU A 258      -3.382  11.733  -8.241  1.00146.92           O
ANISOU 1870  OE2 GLU A 258    23241  18366  14216   -405  -1397  -1694       O
ATOM   1871  N   ILE A 259      -4.916  15.840  -7.815  1.00139.51           N
ANISOU 1871  N   ILE A 259    23147  16465  13395   1779   -658    204       N
ATOM   1872  CA  ILE A 259      -5.950  16.109  -8.812  1.00147.27           C
ANISOU 1872  CA  ILE A 259    23714  18324  13918   2471   -964    663       C
ATOM   1873  C   ILE A 259      -6.139  17.600  -9.025  1.00153.85           C
ANISOU 1873  C   ILE A 259    25029  18705  14721   3280   -623   1457       C
ATOM   1874  O   ILE A 259      -5.703  18.157 -10.033  1.00158.01           O
ANISOU 1874  O   ILE A 259    25915  19291  14830   3523   -583   1940       O
ATOM   1875  CB  ILE A 259      -7.319  15.534  -8.390  1.00148.99           C
ANISOU 1875  CB  ILE A 259    23107  19227  14273   2666  -1278    450       C
ATOM   1876  CG1 ILE A 259      -7.200  14.057  -8.024  1.00142.78           C
ANISOU 1876  CG1 ILE A 259    21882  18761  13609   1845  -1551   -344       C
ATOM   1877  CG2 ILE A 259      -8.349  15.736  -9.495  1.00157.78           C
ANISOU 1877  CG2 ILE A 259    23693  21371  14885   3329  -1703    925       C
ATOM   1878  CD1 ILE A 259      -8.444  13.501  -7.376  1.00143.93           C
ANISOU 1878  CD1 ILE A 259    21272  19391  14023   1913  -1739   -593       C
ATOM   1879  N   ILE A 260      -6.777  18.231  -8.041  1.00154.79           N
ANISOU 1879  N   ILE A 260    25196  18325  15294   3692   -325   1582       N
ATOM   1880  CA  ILE A 260      -7.136  19.647  -8.092  1.00161.90           C
ANISOU 1880  CA  ILE A 260    26529  18719  16267   4550     56   2316       C
ATOM   1881  C   ILE A 260      -5.946  20.611  -8.204  1.00161.92           C
ANISOU 1881  C   ILE A 260    27513  17699  16311   4442    538   2632       C
ATOM   1882  O   ILE A 260      -6.118  21.830  -8.131  1.00167.70           O
ANISOU 1882  O   ILE A 260    28751  17789  17179   5079    952   3205       O
ATOM   1883  CB  ILE A 260      -8.076  20.038  -6.921  1.00163.48           C
ANISOU 1883  CB  ILE A 260    26581  18551  16983   4987    353   2288       C
ATOM   1884  CG1 ILE A 260      -9.127  18.946  -6.686  1.00162.63           C
ANISOU 1884  CG1 ILE A 260    25467  19406  16921   4896    -79   1879       C
ATOM   1885  CG2 ILE A 260      -8.767  21.369  -7.199  1.00173.01           C
ANISOU 1885  CG2 ILE A 260    28008  19511  18215   6068    658   3110       C
ATOM   1886  CD1 ILE A 260     -10.158  18.825  -7.792  1.00170.30           C
ANISOU 1886  CD1 ILE A 260    25660  21569  17478   5499   -598   2306       C
ATOM   1887  N   VAL A 261      -4.742  20.070  -8.377  1.00141.10           N
ANISOU 1887  N   VAL A 261    25131  14885  13597   3637    514   2268       N
ATOM   1888  CA  VAL A 261      -3.584  20.917  -8.680  1.00142.09           C
```

FIG. 13 Continued

```
ANISOU 1888  CA   VAL A 261    26076  14188  13724   3477    930   2603       C
ATOM   1889  C    VAL A 261    -2.742  20.299  -9.801  1.00140.85             C
ANISOU 1889  C    VAL A 261    25865  14555  13096   3034    717   2557       C
ATOM   1890  O    VAL A 261    -1.530  20.505  -9.894  1.00138.81             O
ANISOU 1890  O    VAL A 261    26103  13710  12928   2537   1009   2545       O
ATOM   1891  CB   VAL A 261    -2.753  21.363  -7.437  1.00137.78             C
ANISOU 1891  CB   VAL A 261    26164  12424  13763   2963   1386   2301       C
ATOM   1892  CG1  VAL A 261    -3.625  21.377  -6.162  1.00136.69             C
ANISOU 1892  CG1  VAL A 261    25881  12024  14031   3152   1478   2004       C
ATOM   1893  CG2  VAL A 261    -1.498  20.516  -7.269  1.00130.38             C
ANISOU 1893  CG2  VAL A 261    25249  11362  12928   1971   1295   1748       C
ATOM   1894  N    MET A 262    -3.428  19.551 -10.660  1.00178.07             N
ANISOU 1894  N    MET A 262    29956  20401  17300   3223    218   2529       N
ATOM   1895  CA   MET A 262    -2.824  19.016 -11.872  1.00178.92             C
ANISOU 1895  CA   MET A 262    30038  21121  16824   2947     25   2532       C
ATOM   1896  C    MET A 262    -3.763  19.136 -13.083  1.00187.32             C
ANISOU 1896  C    MET A 262    30793  23213  17168   3638   -368   3045       C
ATOM   1897  O    MET A 262    -3.437  19.823 -14.054  1.00193.29             O
ANISOU 1897  O    MET A 262    31985  23994  17462   3968   -215   3663       O
ATOM   1898  CB   MET A 262    -2.342  17.580 -11.694  1.00171.56             C
ANISOU 1898  CB   MET A 262    28699  20545  15943   2117   -237   1700       C
ATOM   1899  CG   MET A 262    -1.511  17.091 -12.883  1.00172.57             C
ANISOU 1899  CG   MET A 262    28940  21109  15521   1787   -274   1662       C
ATOM   1900  SD   MET A 262    -0.437  18.363 -13.625  1.00177.57             S
ANISOU 1900  SD   MET A 262    30430  21068  15970   1960    314   2422       S
ATOM   1901  CE   MET A 262     0.421  18.948 -12.164  1.00171.73             C
ANISOU 1901  CE   MET A 262    30126  18952  16170   1518    810   2258       C
ATOM   1902  N    TYR A 263    -4.925  18.489 -13.032  1.00176.81             N
ANISOU 1902  N    TYR A 263    28710  22741  15727   3845   -880   2823       N
ATOM   1903  CA   TYR A 263    -5.878  18.589 -14.141  1.00185.65             C
ANISOU 1903  CA   TYR A 263    29455  24925  16159   4486  -1353   3310       C
ATOM   1904  C    TYR A 263     6.055  20.033  14.587  1.00194.02             C
ANISOU 1904  C    TYR A 263    31025  25625  17069   5368  -1057   4309       C
ATOM   1905  O    TYR A 263    -6.119  20.300 -15.780  1.00201.19             O
ANISOU 1905  O    TYR A 263    32058  27127  17260   5734  -1253   4844       O
ATOM   1906  CB   TYR A 263    -7.239  17.995 -13.774  1.00187.08             C
ANISOU 1906  CB   TYR A 263    28724  25904  16454   4702  -1864   3058       C
ATOM   1907  CG   TYR A 263    -7.338  16.499 -13.965  1.00183.23             C
ANISOU 1907  CG   TYR A 263    27640  26232  15748   3973  -2367   2245       C
ATOM   1908  CD1  TYR A 263    -6.442  15.638 -13.338  1.00174.01             C
ANISOU 1908  CD1  TYR A 263    26605  24572  14939   3100  -2175   1489       C
ATOM   1909  CD2  TYR A 263    -8.338  15.945 -14.756  1.00189.53             C
ANISOU 1909  CD2  TYR A 263    27738  28276  15998   4150  -3045   2236       C
ATOM   1910  CE1  TYR A 263    -6.529  14.267 -13.504  1.00171.08             C
ANISOU 1910  CE1  TYR A 263    25743  24850  14409   2452  -2578    750       C
ATOM   1911  CE2  TYR A 263    -8.437  14.574 -14.925  1.00186.71             C
ANISOU 1911  CE2  TYR A 263    26888  28594  15457   3431   -3478  1448       C
ATOM   1912  CZ   TYR A 263    -7.527  13.741 -14.297  1.00177.42             C
ANISOU 1912  CZ   TYR A 263    25913  26828  14669   2599  -3209    708       C
ATOM   1913  OH   TYR A 263     7.610  12.377  14.457  1.00175.12             O
ANISOU 1913  OH   TYR A 263    25191  27108  14236   1901  -3580    -69       O
ATOM   1914  N    PRO A 264    -6.140  20.973 -13.628  1.00205.11             N
ANISOU 1914  N    PRO A 264    32774  26032  19126   5720   -566   4569       N
ATOM   1915  CA   PRO A 264    -6.288  22.378 -14.008  1.00213.60             C
ANISOU 1915  CA   PRO A 264    34408  26619  20132   6576   -208   5530       C
ATOM   1916  C    PRO A 264    -4.953  23.012 -14.373  1.00213.24             C
ANISOU 1916  C    PRO A 264    35289  25717  20016   6260    335   5803       C
ATOM   1917  O    PRO A 264    -4.876  23.774 -15.341  1.00221.14             O
ANISOU 1917  O    PRO A 264    36704  26778  20541   6778    447   6590       O
ATOM   1918  CB   PRO A 264    -6.816  23.039 -12.723  1.00213.04             C
ANISOU 1918  CB   PRO A 264    34404  25694  20847   6950    188   5544       C
ATOM   1919  CG   PRO A 264    -7.129  21.925 -11.778  1.00205.15             C
ANISOU 1919  CG   PRO A 264    32760  24971  20219   6365    -64   4652       C
ATOM   1920  CD   PRO A 264    -6.243  20.801 -12.172  1.00198.41             C
ANISOU 1920  CD   PRO A 264    31820  24506  19063   5423   -328   4025       C
ATOM   1921  N    ILE A 265    -3.915  22.696 -13.605  1.00164.69             N
ANISOU 1921  N    ILE A 265    29435  18799  14340   5411    662   5188       N
ATOM   1922  CA   ILE A 265    -2.606  23.319 -13.788  1.00164.33             C
ANISOU 1922  CA   ILE A 265    30204  17852  14381   5023   1221   5403       C
```

FIG. 13 Continued

```
ATOM   1923  C   ILE A 265      -1.931  22.967 -15.119  1.00166.73           C
ANISOU 1923  C   ILE A 265    30623  18771  13957   4789   1129   5582       C
ATOM   1924  O   ILE A 265      -2.187  23.605 -16.145  1.00175.36           O
ANISOU 1924  O   ILE A 265    31974  20180  14477   5407   1140   6356       O
ATOM   1925  CB  ILE A 265      -1.675  22.988 -12.609  1.00155.16           C
ANISOU 1925  CB  ILE A 265    29215  15828  13912   4135   1502   4678       C
ATOM   1926  CG1 ILE A 265      -2.465  22.985 -11.298  1.00152.16           C
ANISOU 1926  CG1 ILE A 265    28589  15120  14105   4279   1475   4322       C
ATOM   1927  CG2 ILE A 265      -0.512  23.968 -12.551  1.00156.67           C
ANISOU 1927  CG2 ILE A 265    30263  14881  14384   3857   2145   5009       C
ATOM   1928  CD1 ILE A 265      -3.298  24.223 -11.064  1.00159.73           C
ANISOU 1928  CD1 ILE A 265    29870  15571  15250   5203   1780   4979       C
ATOM   1929  N   GLN A 266      -1.061  21.959 -15.092  1.00168.85           N
ANISOU 1929  N   GLN A 266    30726  19188  14241   3922   1071   4888       N
ATOM   1930  CA  GLN A 266      -0.375  21.483 -16.298  1.00170.80           C
ANISOU 1930  CA  GLN A 266    31063  20023  13811   3633   1043   4925       C
ATOM   1931  C   GLN A 266      -1.393  20.883 -17.264  1.00175.83           C
ANISOU 1931  C   GLN A 266    31193  21999  13617   4061    397   4997       C
ATOM   1932  O   GLN A 266      -1.031  20.260 -18.261  1.00177.61           O
ANISOU 1932  O   GLN A 266    31398  22918  13167   3811    253   4874       O
ATOM   1933  CB  GLN A 266       0.732  20.470 -15.942  1.00162.30           C
ANISOU 1933  CB  GLN A 266    29847  18778  13041   2652   1144   4115       C
ATOM   1934  CG  GLN A 266       2.144  21.074 -15.920  1.00161.83           C
ANISOU 1934  CG  GLN A 266    30404  17769  13315   2189   1812   4311       C
ATOM   1935  CD  GLN A 266       2.867  20.891 -14.590  1.00153.76           C
ANISOU 1935  CD  GLN A 266    29356  15873  13193   1505   2003   3742       C
ATOM   1936  OE1 GLN A 266       4.019  21.298 -14.436  1.00153.12           O
ANISOU 1936  OE1 GLN A 266    29657  15041  13481   1030   2477   3815       O
ATOM   1937  NE2 GLN A 266       2.189  20.296 -13.624  1.00148.30           N
ANISOU 1937  NE2 GLN A 266    28206  15294  12846   1442   1631   3202       N
ATOM   1938  N   ARG A 267      -2.668  21.083 -16.933  1.00168.53           N
ANISOU 1938  N   ARG A 267    29850  21424  12761   4691     23   5179       N
ATOM   1939  CA  ARG A 267      -3.812  20.619 -17.717  1.00174.45           C
ANISOU 1939  CA  ARG A 267    30009  23463  12810   5150   -674   5295       C
ATOM   1940  C   ARG A 267      -3.517  19.342 -18.499  1.00172.74           C
ANISOU 1940  C   ARG A 267    29499  24177  11957   4534  -1065   4672       C
ATOM   1941  O   ARG A 267      -2.921  18.396 -17.965  1.00164.40           O
ANISOU 1941  O   ARG A 267    28266  22934  11263   3753  -1012   3847       O
ATOM   1942  CB  ARG A 267      -4.340  21.733 -18.649  1.00186.06           C
ANISOU 1942  CB  ARG A 267    31809  25180  13705   6107   -685   6390       C
ATOM   1943  CG  ARG A 267      -5.874  21.792 -18.727  1.00192.52           C
ANISOU 1943  CG  ARG A 267    31930  26872  14348   6894  -1309   6707       C
ATOM   1944  CD  ARG A 267      -6.410  22.691 -19.833  1.00205.07           C
ANISOU 1944  CD  ARG A 267    33750  28961  15206   7834  -1473   7793       C
ATOM   1945  NE  ARG A 267      -7.872  22.696 -19.831  1.00211.39           N
ANISOU 1945  NE  ARG A 267    33753  30632  15936   8569  -2104   8074       N
ATOM   1946  CZ  ARG A 267      -8.623  21.755 -20.393  1.00214.12           C
ANISOU 1946  CZ  ARG A 267    33330  32333  15694   8459  -2922   7748       C
ATOM   1947  NH1 ARG A 267      -8.057  20.732 -21.012  1.00211.08           N
ANISOU 1947  NH1 ARG A 267    32952  32540  14707   7665  -3176   7105       N
ATOM   1948  NH2 ARG A 267      -9.943  21.836 -20.336  1.00220.55           N
ANISOU 1948  NH2 ARG A 267    33357  33902  16541   9132  -3472   8054       N
ATOM   1949  N   ARG A 268      -3.968  19.341 -19.754  1.00229.48           N
ANISOU 1949  N   ARG A 268    36660  32354  18180   4923  -1459   5091       N
ATOM   1950  CA  ARG A 268      -3.770  18.255 -20.720  1.00230.67           C
ANISOU 1950  CA  ARG A 268    36658  33469  17518   4440  -1829   4592       C
ATOM   1951  C   ARG A 268      -3.450  16.889 -20.079  1.00221.14           C
ANISOU 1951  C   ARG A 268    35013  32278  16732   3550  -1940   3459       C
ATOM   1952  O   ARG A 268      -2.414  16.273 -20.360  1.00217.56           O
ANISOU 1952  O   ARG A 268    34834  31662  16168   2920  -1643   2996       O
ATOM   1953  CB  ARG A 268      -2.717  18.654 -21.775  1.00235.09           C
ANISOU 1953  CB  ARG A 268    38002  33895  17427   4371  -1361   5017       C
ATOM   1954  CG  ARG A 268      -2.634  20.166 -22.083  1.00242.36           C
ANISOU 1954  CG  ARG A 268    39572  34248  18267   5119   -931   6158       C
ATOM   1955  CD  ARG A 268      -3.474  20.604 -23.287  1.00254.75           C
ANISOU 1955  CD  ARG A 268    41192  36826  18774   5891  -1405   6960       C
ATOM   1956  NE  ARG A 268      -3.186  21.990 -23.662  1.00261.90           N
ANISOU 1956  NE  ARG A 268    42847  37083  19579   6530   -878   8059       N
ATOM   1957  CZ  ARG A 268      -3.697  22.613 -24.723  1.00273.63           C
```

FIG. 13 Continued

```
ATOM   1957  CZ  ARG A 268      -4.533  21.983 -25.536  1.00 279.82           C
ANISOU 1957  CZ  ARG A 268    44590  39211  20164   7269  -1119   8974        C
ATOM   1958  NH1 ARG A 268      -4.533  21.983 -25.536  1.00 279.82           N
ANISOU 1958  NH1 ARG A 268    44919  41379  20022   7446  -1939   8906        N
ATOM   1959  NH2 ARG A 268      -3.372  23.875 -24.974  1.00 279.85           N
ANISOU 1959  NH2 ARG A 268    46111  39253  20967   7817   -551   9974        N
ATOM   1960  N   LYS A 269      -4.355  16.430 -19.217  1.00 186.36           N
ANISOU 1960  N   LYS A 269    29925  28053  12831   3535  -2331   3055        N
ATOM   1961  CA  LYS A 269       4.208  15.152  18.533  1.00 178.08           C
ANISOU 1961  CA  LYS A 269    28435  27006  12221   2756  -2463   2048        C
ATOM   1962  C   LYS A 269      -5.592  14.649 -18.132  1.00 179.41           C
ANISOU 1962  C   LYS A 269    27759  27897  12513   2906  -3103   1791        C
ATOM   1963  O   LYS A 269      -6.514  15.449 -17.972  1.00 184.40           O
ANISOU 1963  O   LYS A 269    28158  28673  13231   3623  -3267   2394        O
ATOM   1964  CB  LYS A 269      -3.318  15.313 -17.298  1.00 168.73           C
ANISOU 1964  CB  LYS A 269    27512  24579  12018   2372  -1865   1802        C
ATOM   1965  CG  LYS A 269      -1.833  15.384 -17.606  1.00 166.10           C
ANISOU 1965  CG  LYS A 269    27810  23619  11682   1936  -1284   1772        C
ATOM   1966  CD  LYS A 269      -1.405  14.177 -18.430  1.00 166.11           C
ANISOU 1966  CD  LYS A 269    27715  24273  11126   1365  -1446   1148        C
ATOM   1967  CE  LYS A 269       0.003  13.733 -18.077  1.00 159.40           C
ANISOU 1967  CE  LYS A 269    27137  22669  10759    720   -900    714        C
ATOM   1968  NZ  LYS A 269       0.268  12.322 -18.477  1.00 157.67           N
ANISOU 1968  NZ  LYS A 269    26676  22951  10281    138  -1064   -103        N
ATOM   1969  N   TYR A 270      -5.739  13.332 -17.988  1.00 192.33           N
ANISOU 1969  N   TYR A 270    28925  29968  14182   2243  -3430    921        N
ATOM   1970  CA  TYR A 270      -7.008  12.724 -17.577  1.00 193.55           C
ANISOU 1970  CA  TYR A 270    28225  30802  14515   2239  -4010    592        C
ATOM   1971  C   TYR A 270      -6.912  11.209 -17.619  1.00 190.07           C
ANISOU 1971  C   TYR A 270    27456  30751  14011   1380  -4280   -402        C
ATOM   1972  O   TYR A 270      -6.663  10.557 -16.603  1.00 182.12           O
ANISOU 1972  O   TYR A 270    26292  29174  13732    875  -4073   -978        O
ATOM   1973  CB  TYR A 270      -8.152  13.193 -18.478  1.00 204.78           C
ANISOU 1973  CB  TYR A 270    29270  33306  15230   2921  -4620   1195        C
ATOM   1974  CG  TYR A 270      -9.519  12.634 -18.123  1.00 207.63           C
ANISOU 1974  CG  TYR A 270    28641  34464  15785   2942  -5244    930        C
ATOM   1975  CD1 TYR A 270     -10.516  13.454 -17.600  1.00 211.46           C
ANISOU 1975  CD1 TYR A 270    28669  34996  16680   3696  -5324   1535        C
ATOM   1976  CD2 TYR A 270      -9.817  11.292 -18.329  1.00 207.32           C
ANISOU 1976  CD2 TYR A 270    28117  35116  15540   2206  -5717     80        C
ATOM   1977  CE1 TYR A 270     -11.768  12.949 -17.288  1.00 214.84           C
ANISOU 1977  CE1 TYR A 270    28113  36191  17325   3710  -5859   1321        C
ATOM   1978  CE2 TYR A 270     -11.062  10.778 -18.017  1.00 210.63           C
ANISOU 1978  CE2 TYR A 270    27593  36269  16168   2158  -6273   -157        C
ATOM   1979  CZ  TYR A 270     -12.035  11.608 -17.500  1.00 214.39           C
ANISOU 1979  CZ  TYR A 270    27556  36835  17065   2910  -6346    476        C
ATOM   1980  OH  TYR A 270     -13.274  11.085 -17.198  1.00 218.34           O
ANISOU 1980  OH  TYR A 270    27039  38105  17815   2847  -6870    255        O
ATOM   1981  N   ARG A 271      -7.120  10.652 -18.805  1.00 193.00           N
ANISOU 1981  N   ARG A 271    27765  32085  13481   1219  -4742   -595        N
ATOM   1982  CA  ARG A 271      -6.990   9.222 -18.992  1.00 191.12           C
ANISOU 1982  CA  ARG A 271    27327  32192  13098    398  -4963  -1557        C
ATOM   1983  C   ARG A 271      -5.596   8.800 -18.514  1.00 182.13           C
ANISOU 1983  C   ARG A 271    26720  30030  12450   -136  -4280  -1997        C
ATOM   1984  O   ARG A 271      -5.396   7.662 -18.086  1.00 177.34           O
ANISOU 1984  O   ARG A 271    25924  29259  12198   -797  -4266  -2790        O
ATOM   1985  CB  ARG A 271      -7.206   8.854 -20.461  1.00 200.63           C
ANISOU 1985  CB  ARG A 271    28625  34480  13124    323   5453   1652        C
ATOM   1986  CG  ARG A 271      -6.746   9.931 -21.442  1.00 206.75           C
ANISOU 1986  CG  ARG A 271    30057  35355  13142    918  -5265   -821        C
ATOM   1987  CD  ARG A 271      -6.831   9.472 -22.902  1.00 216.26           C
ANISOU 1987  CD  ARG A 271    31476  37613  13079    759  -5701   -994        C
ATOM   1988  NE  ARG A 271      -8.201   9.176 -23.318  1.00 224.79           N
ANISOU 1988  NE  ARG A 271    31844  39905  13662    850  -6627  -1040        N
ATOM   1989  CZ  ARG A 271      -8.911   9.924 -24.154  1.00 235.31           C
ANISOU 1989  CZ  ARG A 271    33100  42112  14195   1496  -7142   -285        C
ATOM   1990  NH1 ARG A 271      -8.378  11.019 -24.675  1.00 238.49           N
ANISOU 1990  NH1 ARG A 271    34168  42258  14189   2117  -6772    587        N
ATOM   1991  NH2 ARG A 271     -10.152   9.574 -24.469  1.00 243.25           N
ANISOU 1991  NH2 ARG A 271    33347  44255  14823   1509  -8034   -377        N
```

FIG. 13 Continued

```
ATOM    1992  N   ASP A 272      -4.639   9.728 -18.582  1.00150.22           N
ANISOU  1992  N   ASP A 272    23319  25295   8461    159  -3713  -1448       N
ATOM    1993  CA  ASP A 272      -3.263   9.482 -18.134  1.00142.62           C
ANISOU  1993  CA  ASP A 272    22810  23371   8006   -287  -3061  -1740       C
ATOM    1994  C   ASP A 272      -3.074   9.898 -16.678  1.00134.66           C
ANISOU  1994  C   ASP A 272    21739  21384   8043   -271  -2732  -1640       C
ATOM    1995  O   ASP A 272      -2.279   9.304 -15.963  1.00127.56           O
ANISOU  1995  O   ASP A 272    20906  19822   7741   -779  -2417  -2106       O
ATOM    1996  CB  ASP A 272      -2.239  10.233 -19.006  1.00145.78           C
ANISOU  1996  CB  ASP A 272    23928  23540   7922    -76  -2584  -1224       C
ATOM    1997  CG  ASP A 272      -2.325   9.866 -20.479  1.00154.29           C
ANISOU  1997  CG  ASP A 272    25202  25562   7862    -92  -2837  -1303       C
ATOM    1998  OD1 ASP A 272      -2.752   8.735 -20.795  1.00155.89           O
ANISOU  1998  OD1 ASP A 272    25091  26395   7745   -520  -3244  -2019       O
ATOM    1999  OD2 ASP A 272      -1.953  10.717 -21.318  1.00159.91           O
ANISOU  1999  OD2 ASP A 272    26426  26356   7975    302  -2606   -652       O
ATOM    2000  N   GLY A 273      -3.797  10.931 -16.254  1.00137.41           N
ANISOU  2000  N   GLY A 273    21985  21643   8581    335  -2797  -1019       N
ATOM    2001  CA  GLY A 273      -3.674  11.458 -14.906  1.00131.22           C
ANISOU  2001  CA  GLY A 273    21238  19934   8684    401  -2462   -892       C
ATOM    2002  C   GLY A 273      -4.270  10.520 -13.885  1.00126.29           C
ANISOU  2002  C   GLY A 273    20043  19317   8623     10  -2684  -1518       C
ATOM    2003  O   GLY A 273      -3.810  10.446 -12.735  1.00119.38           O
ANISOU  2003  O   GLY A 273    19260  17632   8467   -265  -2374  -1724       O
ATOM    2004  N   ILE A 274      -5.305   9.808 -14.324  1.00163.90           N
ANISOU  2004  N   ILE A 274    24222  25024  13027    -38  -3236  -1806       N
ATOM    2005  CA  ILE A 274      -5.998   8.835 -13.496  1.00160.75           C
ANISOU  2005  CA  ILE A 274    23223  24760  13095   -443  -3475  -2399       C
ATOM    2006  C   ILE A 274      -5.044   7.732 -13.071  1.00153.76           C
ANISOU  2006  C   ILE A 274    22499  23352  12570  -1209  -3240  -3108       C
ATOM    2007  O   ILE A 274      -5.006   7.359 -11.903  1.00147.85           O
ANISOU  2007  O   ILE A 274    21621  22049  12508  -1493  -3080  -3387       O
ATOM    2008  CB  ILE A 274      -7.204   8.223 -14.236  1.00168.04           C
ANISOU  2008  CB  ILE A 274    23487  26864  13498   -453  -4142  -2605       C
ATOM    2009  CG1 ILE A 274      -8.379   9.190 -14.184  1.00174.16           C
ANISOU  2009  CG1 ILE A 274    23847  28086  14240    312  -4391  -1937       C
ATOM    2010  CG2 ILE A 274      -7.607   6.901 -13.612  1.00164.85           C
ANISOU  2010  CG2 ILE A 274    22570  26563  13500  -1133  -4330  -3396       C
ATOM    2011  CD1 ILE A 274      -8.635   9.724 -12.793  1.00169.46           C
ANISOU  2011  CD1 ILE A 274    23162  26738  14487    553  -4022  -1748       C
ATOM    2012  N   ASP A 275      -4.260   7.224 -14.018  1.00137.15           N
ANISOU  2012  N   ASP A 275    20704  21414   9993  -1509  -3190  -3368       N
ATOM    2013  CA  ASP A 275      -3.323   6.150 -13.720  1.00131.63           C
ANISOU  2013  CA  ASP A 275    20147  20233   9634  -2170  -2939  -4014       C
ATOM    2014  C   ASP A 275      -2.420   6.536 -12.556  1.00124.08           C
ANISOU  2014  C   ASP A 275    19481  18208   9457  -2245  -2459  -3870       C
ATOM    2015  O   ASP A 275      -2.190   5.726 -11.665  1.00118.78           O
ANISOU  2015  O   ASP A 275    18671  17104   9357  -2689  -2381  -4320       O
ATOM    2016  CB  ASP A 275      -2.521   5.773 -14.963  1.00135.05           C
ANISOU  2016  CB  ASP A 275    20958  20930   9426  -2351  -2824  -4204       C
ATOM    2017  CG  ASP A 275      -3.416   5.312 -16.107  1.00143.26           C
ANISOU  2017  CG  ASP A 275    21756  23066   9612  -2363  -3356  -4429       C
ATOM    2018  OD1 ASP A 275      -4.585   4.958 -15.835  1.00145.34           O
ANISOU  2018  OD1 ASP A 275    21449  23845   9928  -2410  -3832  -4615       O
ATOM    2019  OD2 ASP A 275      -2.965   5.300 -17.276  1.00148.27           O
ANISOU  2019  OD2 ASP A 275    22759  24075   9502  -2346  -3304  -4424       O
ATOM    2020  N   ASN A 276      -1.938   7.779 -12.543  1.00149.70           N
ANISOU  2020  N   ASN A 276    23137  21028  12715  -1827  -2159  -3231       N
ATOM    2021  CA  ASN A 276      -1.072   8.270 -11.463  1.00143.64           C
ANISOU  2021  CA  ASN A 276    22679  19261  12637  -1926  -1744  -3072       C
ATOM    2022  C   ASN A 276      -1.870   8.667 -10.228  1.00141.26           C
ANISOU  2022  C   ASN A 276    22178  18666  12831  -1746  -1804  -2957       C
ATOM    2023  O   ASN A 276      -1.319   8.910  -9.155  1.00136.34           O
ANISOU  2023  O   ASN A 276    21769  17259  12774  -1910  -1542  -2944       O
ATOM    2024  CB  ASN A 276      -0.237   9.464 -11.927  1.00145.58           C
ANISOU  2024  CB  ASN A 276    23475  19112  12726  -1619  -1367  -2458       C
ATOM    2025  CG  ASN A 276       0.781   9.097 -13.002  1.00147.47           C
ANISOU  2025  CG  ASN A 276    23973  19482  12576  -1846  -1149  -2563       C
ATOM    2026  OD1 ASN A 276       0.773   7.987 -13.553  1.00148.31           O
```

FIG. 13 Continued

```
ANISOU 2026  OD1 ASN A 276   23882 20055 12413 -2162 -1304 -3094       O
ATOM   2027  ND2 ASN A 276    1.663  10.043 -13.309  1.00148.78        N
ANISOU 2027  ND2 ASN A 276   24606 19208 12717 -1695  -739 -2063       N
ATOM   2028  N   LEU A 277   -3.179   8.749 -10.411  1.00196.93        N
ANISOU 2028  N   LEU A 277   28809 26383 19633 -1402 -2150 -2861       N
ATOM   2029  CA  LEU A 277   -4.103   9.074  -9.343  1.00196.09        C
ANISOU 2029  CA  LEU A 277   28432 26127 19946 -1174 -2180 -2760       C
ATOM   2030  C   LEU A 277   -4.562   7.781  -8.677  1.00193.00        C
ANISOU 2030  C   LEU A 277   27558 25893 19880 -1700 -2376 -3404       C
ATOM   2031  O   LEU A 277   -4.689   7.710  -7.457  1.00189.04        O
ANISOU 2031  O   LEU A 277   27025 24889 19911 -1832 -2216 -3514       O
ATOM   2032  CB  LEU A 277   -5.299   9.808  -9.935  1.00203.49        C
ANISOU 2032  CB  LEU A 277   29069 27760 20488  -494 -2441 -2280       C
ATOM   2033  CG  LEU A 277   -6.226  10.602  -9.024  1.00204.81        C
ANISOU 2033  CG  LEU A 277   29061 27727 21030    13 -2334 -1932       C
ATOM   2034  CD1 LEU A 277   -7.312  11.241  -9.875  1.00213.47        C
ANISOU 2034  CD1 LEU A 277   29801 29635 21674   722 -2642 -1413       C
ATOM   2035  CD2 LEU A 277   -6.831   9.721  -7.945  1.00201.35        C
ANISOU 2035  CD2 LEU A 277   28152 27272 21081  -370 -2395 -2435       C
ATOM   2036  N   LEU A 278   -4.809   6.765  -9.502  1.00115.38        N
ANISOU 2036  N   LEU A 278   17401 16747  9693 -2015 -2704 -3830       N
ATOM   2037  CA  LEU A 278   -5.246   5.441  -9.067  1.00113.71        C
ANISOU 2037  CA  LEU A 278   16746 16718  9740 -2572 -2894 -4470       C
ATOM   2038  C   LEU A 278   -4.146   4.754  -8.281  1.00106.78        C
ANISOU 2038  C   LEU A 278   16179 15025  9369 -3097 -2585 -4828       C
ATOM   2039  O   LEU A 278   -4.378   3.748  -7.608  1.00104.41        O
ANISOU 2039  O   LEU A 278   15623 14613  9435  3544  2629  5280       O
ATOM   2040  CB  LEU A 278   -5.589   4.596 -10.287  1.00118.97        C
ANISOU 2040  CB  LEU A 278   17138 18233  9831 -2818 -3284 -4855       C
ATOM   2041  CG  LEU A 278   -6.596   3.452 -10.165  1.00121.31        C
ANISOU 2041  CG  LEU A 278   16806 19073 10215 -3257 -3643 -5409       C
ATOM   2042  CD1 LEU A 278   -8.006   3.958  -9.820  1.00125.54        C
ANISOU 2042  CD1 LEU A 278   16730 20140 10830 -2867 -3903 -5100       C
ATOM   2043  CD2 LEU A 278   -6.613   2.671 -11.471  1.00126.69        C
ANISOU 2043  CD2 LEU A 278   17433 20454 10249 -3572 -3972 -5839       C
ATOM   2044  N   VAL A 279   -2.935   5.291  -8.396  1.00131.16        N
ANISOU 2044  N   VAL A 279   19797 17556 12481 -3046 -2276 -4594       N
ATOM   2045  CA  VAL A 279   -1.818   4.786  -7.622  1.00125.26        C
ANISOU 2045  CA  VAL A 279   19313 16035 12245 -3476 -2004 -4824       C
ATOM   2046  C   VAL A 279    1.955   5.332   6.220  1.00121.60        C
ANISOU 2046  C   VAL A 279   18949 14973 12282 -3401 -1855 -4615       C
ATOM   2047  O   VAL A 279   -1.956   4.569  -5.260  1.00118.15        O
ANISOU 2047  O   VAL A 279   18403 14220 12267 -3768 -1841 -4925       O
ATOM   2048  CB  VAL A 279   -0.453   5.183  -8.206  1.00124.56        C
ANISOU 2048  CB  VAL A 279   19680 15584 12063 -3480 -1717 -4631       C
ATOM   2049  CG1 VAL A 279   -0.286   4.595  -9.609  1.00128.78        C
ANISOU 2049  CG1 VAL A 279   20186 16707 12039 -3563 -1796 -4878       C
ATOM   2050  CG2 VAL A 279   -0.265   6.703  -8.193  1.00125.69        C
ANISOU 2050  CG2 VAL A 279   20185 15448 12123 -3008 -1526 -3981       C
ATOM   2051  N   LEU A 280   -2.099   6.650  -6.104  1.00 97.19        N
ANISOU 2051  N   LEU A 280   16105 11709  9115 -2920 -1724 -4091       N
ATOM   2052  CA  LEU A 280   -2.279   7.255  -4.797  1.00 94.75        C
ANISOU 2052  CA  LEU A 280   15972 10820  9209 -2825 -1544 -3918       C
ATOM   2053  C   LEU A 280   -3.242   6.411  -3.982  1.00 93.91        C
ANISOU 2053  C   LEU A 280   15432 10905  9346 -3028 -1676 -4262       C
ATOM   2054  O   LEU A 280   -2.893   5.924  -2.907  1.00 89.87        O
ANISOU 2054  O   LEU A 280   15032  9887  9229 -3395 -1572 -4476       O
ATOM   2055  CB  LEU A 280   -2.844   8.660  -4.912  1.00 98.67        C
ANISOU 2055  CB  LEU A 280   16652 11311  9528 -2171 -1424 -3360       C
ATOM   2056  CG  LEU A 280   -1.894   9.860  -4.638  1.00 97.84        C
ANISOU 2056  CG  LEU A 280   17197 10435  9543 -2037 -1091 -2963       C
ATOM   2057  CD1 LEU A 280   -1.030  10.165  -5.877  1.00 99.83        C
ANISOU 2057  CD1 LEU A 280   17679 10795  9458 -1992 -1037 -2737       C
ATOM   2058  CD2 LEU A 280   -2.605  11.135  -4.124  1.00100.97        C
ANISOU 2058  CD2 LEU A 280   17826 10550  9990 -1466  -880 -2530       C
ATOM   2059  N   LEU A 281   -4.443   6.225  -4.534  1.00143.54        N
ANISOU 2059  N   LEU A 281   21204 17955 15379 -2805 -1917 -4294       N
ATOM   2060  CA  LEU A 281   -5.553   5.522  -3.876  1.00144.35        C
ANISOU 2060  CA  LEU A 281   20790 18355 15702 -2957 -2027 -4563       C
```

FIG. 13 Continued

```
ATOM   2061  C   LEU A 281      -5.419   3.999  -3.700  1.00142.09           C
ANISOU 2061  C   LEU A 281    20264  18109  15616   -3630  -2148  -5148      C
ATOM   2062  O   LEU A 281       6.429   3.314   3.527  1.00144.43           O
ANISOU 2062  O   LEU A 281    20039  18836  16001   -3799  -2297  -5397      O
ATOM   2063  CB  LEU A 281      -6.893   5.830  -4.578  1.00151.06           C
ANISOU 2063  CB  LEU A 281    21069  20081  16248   -2515  -2287  -4380      C
ATOM   2064  CG  LEU A 281      -7.398   7.256  -4.869  1.00155.55           C
ANISOU 2064  CG  LEU A 281    21704  20785  16611   -1730  -2213  -3757      C
ATOM   2065  CD1 LEU A 281      -8.904   7.242  -5.142  1.00162.14           C
ANISOU 2065  CD1 LEU A 281    21771  22483  17353   -1392  -2483  -3656      C
ATOM   2066  CD2 LEU A 281      -7.083   8.238  -3.751  1.00152.90           C
ANISOU 2066  CD2 LEU A 281    21894  19592  16611   -1468  -1768  -3458      C
ATOM   2067  N   ILE A 282      -4.201   3.465  -3.753  1.00 81.87           N
ANISOU 2067  N   ILE A 282    12985  10027   8094   -4006  -2065  -5352      N
ATOM   2068  CA  ILE A 282      -3.993   2.031  -3.498  1.00 79.99           C
ANISOU 2068  CA  ILE A 282    12597   9679   8116   -4602  -2112  -5870      C
ATOM   2069  C   ILE A 282      -2.552   1.716  -3.080  1.00 77.01           C
ANISOU 2069  C   ILE A 282    12535   8652   8073   -4719  -1762  -5639      C
ATOM   2070  O   ILE A 282      -2.289   0.762  -2.361  1.00 76.61           O
ANISOU 2070  O   ILE A 282    12344   8376   8389   -4913  -1540  -5594      O
ATOM   2071  CB  ILE A 282      -4.470   1.130  -4.671  1.00 84.31           C
ANISOU 2071  CB  ILE A 282    12756  10938   8339   -4824  -2393  -6277      C
ATOM   2072  CG1 ILE A 282      -4.716  -0.314  -4.176  1.00 85.19           C
ANISOU 2072  CG1 ILE A 282    12540  10980   8850   -5273  -2266  -6576      C
ATOM   2073  CG2 ILE A 282      -3.512   1.230  -5.869  1.00 85.21           C
ANISOU 2073  CG2 ILE A 282    13166  11139   8072   -4771  -2390  -6287      C
ATOM   2074  CD1 ILE A 282      -5.926  -0.493  -3.214  1.00 85.84           C
ANISOU 2074  CD1 ILE A 282    12244  11177   9196   -5394  -2321  -6667      C
ATOM   2075  N   GLY A 283      -1.613   2.529  -3.522  1.00 98.92           N
ANISOU 2075  N   GLY A 283    15706  11177  10701   -4558  -1701  -5429      N
ATOM   2076  CA  GLY A 283      -0.248   2.360  -3.076  1.00 96.93           C
ANISOU 2076  CA  GLY A 283    15653  10399  10776   -4628  -1395  -5124      C
ATOM   2077  C   GLY A 283      -0.139   3.015  -1.716  1.00 94.76           C
ANISOU 2077  C   GLY A 283    15595   9648  10762   -4531  -1256  -4769      C
ATOM   2078  O   GLY A 283       0.887   3.640  -1.395  1.00 93.41           O
ANISOU 2078  O   GLY A 283    15739   9061  10693   -4492  -1120  -4456      O
ATOM   2079  N   GLY A 284      -1.215   2.881  -0.932  1.00131.83           N
ANISOU 2079  N   GLY A 284    20126  14429  15533   -4527  -1293  -4854      N
ATOM   2080  CA  GLY A 284      -1.317   3.461   0.403  1.00130.55           C
ANISOU 2080  CA  GLY A 284    20209  13861  15533   -4452  -1148  -4603      C
ATOM   2081  C   GLY A 284      -2.500   2.984   1.246  1.00131.31           C
ANISOU 2081  C   GLY A 284    20063  14086  15742   -4528  -1125  -4775      C
ATOM   2082  O   GLY A 284      -3.160   3.774   1.932  1.00131.22           O
ANISOU 2082  O   GLY A 284    20254  13888  15714   -4389  -1070  -4767      O
ATOM   2083  N   ILE A 285      -2.772   1.683   1.190  1.00113.78           N
ANISOU 2083  N   ILE A 285    17446  12137  13650   -4765  -1123  -4969      N
ATOM   2084  CA  ILE A 285      -3.854   1.091   1.977  1.00114.94           C
ANISOU 2084  CA  ILE A 285    17335  12395  13941   -4924  -1066  -5154      C
ATOM   2085  C   ILE A 285      -3.339  -0.081   2.818  1.00114.96           C
ANISOU 2085  C   ILE A 285    17313  12194  14172   -5142   -861  -5034      C
ATOM   2086  O   ILE A 285      -2.973  -1.141   2.271  1.00116.07           O
ANISOU 2086  O   ILE A 285    17248  12460  14395   -5305   -861  -5168      O
ATOM   2087  CB  ILE A 285      -5.084   0.677   1.118  1.00117.66           C
ANISOU 2087  CB  ILE A 285    17178  13337  14190   -5055  -1321  -5613      C
ATOM   2088  CG1 ILE A 285      -6.131   1.796   1.114  1.00118.09           C
ANISOU 2088  CG1 ILE A 285    17226  13564  14077   -4840  -1504  -5762      C
ATOM   2089  CG2 ILE A 285       5.743   0.570   1.678  1.00119.59           C
ANISOU 2089  CG2 ILE A 285    17065  13695  14681   -5401  -1210  -5820      C
ATOM   2090  CD1 ILE A 285      -5.616   3.177   0.696  1.00117.78           C
ANISOU 2090  CD1 ILE A 285    17577  13383  13790   -4341  -1469  -5384      C
ATOM   2091  N   PRO A 286      -3.294   0.143   4.158  1.00158.47           N
ANISOU 2091  N   PRO A 286    23105  17364  19743   -5139   -689  -4807      N
ATOM   2092  CA  PRO A 286      -2.876  -0.716   5.277  1.00158.63           C
ANISOU 2092  CA  PRO A 286    23247  17139  19885   -5307   -530  -4644      C
ATOM   2093  C   PRO A 286      -3.267  -2.202   5.169  1.00160.64           C
ANISOU 2093  C   PRO A 286    23155  17549  20331   -5587   -472  -4894      C
ATOM   2094  O   PRO A 286      -2.420  -3.032   5.500  1.00160.77           O
ANISOU 2094  O   PRO A 286    23267  17368  20450   -5663   -422  -4759      O
ATOM   2095  CB  PRO A 286      -3.532  -0.034   6.475  1.00158.64           C
```

FIG. 13 Continued

```
ANISOU 2095  CB  PRO A 286     23530  16925  19819  -5294   -387  -4578       C
ATOM   2096  CG  PRO A 286     -3.407   1.421   6.138  1.00157.56             C
ANISOU 2096  CG  PRO A 286     23666  16679  19520  -5020   -451  -4486       C
ATOM   2097  CD  PRO A 286     -3.569   1.517   4.632  1.00157.62             C
ANISOU 2097  CD  PRO A 286     23347  17034  19505  -4924   -656  -4691       C
ATOM   2098  N   ILE A 287     -4.497  -2.522   4.753  1.00123.15             N
ANISOU 2098  N   ILE A 287     18024  13123  15643  -5758   -500  -5267       N
ATOM   2099  CA  ILE A 287     -4.914  -3.916   4.459  1.00125.97             C
ANISOU 2099  CA  ILE A 287     18042  13636  16183  -6091   -457  -5580       C
ATOM   2100  C   ILE A 287     -4.717  -4.935   5.593  1.00126.84             C
ANISOU 2100  C   ILE A 287     18315  13405  16474  -6306   -233  -5469       C
ATOM   2101  O   ILE A 287     -5.491  -5.886   5.749  1.00129.65             O
ANISOU 2101  O   ILE A 287     18435  13818  17008  -6644   -128  -5741       O
ATOM   2102  CB  ILE A 287     -4.198  -4.451   3.166  1.00126.77             C
ANISOU 2102  CB  ILE A 287     18024  13885  16259  -6092   -572  -5731       C
ATOM   2103  CG1 ILE A 287     -4.730  -3.750   1.917  1.00127.49             C
ANISOU 2103  CG1 ILE A 287     17880  14434  16126  -6014   -836  -5979       C
ATOM   2104  CG2 ILE A 287     -4.365  -5.955   3.021  1.00130.02             C
ANISOU 2104  CG2 ILE A 287     18243  14280  16879  -6446   -466  -6034       C
ATOM   2105  CD1 ILE A 287     -6.150  -4.106   1.611  1.00130.90             C
ANISOU 2105  CD1 ILE A 287     17844  15316  16574  -6305   -982  -6412       C
ATOM   2106  N   ALA A 288     -3.655  -4.728   6.361  1.00188.85             N
ANISOU 2106  N   ALA A 288     26579  20908  24269  -6139   -195  -5077       N
ATOM   2107  CA  ALA A 288     -3.306  -5.588   7.474  1.00189.72             C
ANISOU 2107  CA  ALA A 288     26928  20678  24479  -6302    -64  -4916       C
ATOM   2108  C   ALA A 288     -3.740  -4.962   8.802  1.00189.26             C
ANISOU 2108  C   ALA A 288     27198  20437  24274  -6327     52  -4732       C
ATOM   2109  O   ALA A 288     -4.174  -5.670   9.703  1.00191.04             O
ANISOU 2109  O   ALA A 288     27528  20483  24574  -6587    222  -4755       O
ATOM   2110  CB  ALA A 288     -1.820  -5.859   7.464  1.00188.70             C
ANISOU 2110  CB  ALA A 288     27014  20307  24376  -6149   -174  -4646       C
ATOM   2111  N   MET A 289     -3.626  -3.637   8.924  1.00103.48             N
ANISOU 2111  N   MET A 289     16551   9571  13195  -6087     -9  -4574       N
ATOM   2112  CA  MET A 289     -4.086  -2.949  10.129  1.00103.58             C
ANISOU 2112  CA  MET A 289     16943   9376  13038  -6119    144  -4474       C
ATOM   2113  C   MET A 289     -5.452  -3.482  10.537  1.00105.81             C
ANISOU 2113  C   MET A 289     17007   9717  13478  -6415    391  -4775       C
ATOM   2114  O   MET A 289     -5.836  -3.352  11.689  1.00106.74             O
ANISOU 2114  O   MET A 289     17465   9593  13501  -6552    605  -4728       O
ATOM   2115  CB  MET A 289     -4.132  -1.444   9.930  1.00102.09             C
ANISOU 2115  CB  MET A 289     16938   9184  12666  -5844    100  -4422       C
ATOM   2116  CG  MET A 289     -5.326  -0.798  10.575  1.00103.11             C
ANISOU 2116  CG  MET A 289     17184   9232  12761  -5883    340  -4614       C
ATOM   2117  SD  MET A 289     -5.091   0.979  10.731  1.00102.10             S
ANISOU 2117  SD  MET A 289     17564   8852  12378  -5545    353  -4492       S
ATOM   2118  CE  MET A 289     -3.635   1.034  11.788  1.00102.00             C
ANISOU 2118  CE  MET A 289     18183   8501  12073  -5619    257  -4074       C
ATOM   2119  N   PRO A 290     -6.214  -4.038   9.578  1.00177.25             N
ANISOU 2119  N   PRO A 290     25494  19093  22759  -6554    359  -5117       N
ATOM   2120  CA  PRO A 290     -7.402  -4.778  10.000  1.00180.14             C
ANISOU 2120  CA  PRO A 290     25594  19502  23350  -6950    582  -5405       C
ATOM   2121  C   PRO A 290     -6.995  -6.168  10.469  1.00182.01             C
ANISOU 2121  C   PRO A 290     25939  19500  23717  -7231    690  -5336       C
ATOM   2122  O   PRO A 290     -7.516  -6.647  11.471  1.00183.98             O
ANISOU 2122  O   PRO A 290     26345  19520  24039  -7536    949  -5342       O
ATOM   2123  CB  PRO A 290     -8.228  -4.899   8.714  1.00181.59             C
ANISOU 2123  CB  PRO A 290     25118  20169  23710  -7047    405  -5805       C
ATOM   2124  CG  PRO A 290     -7.752  -3.812   7.846  1.00179.08             C
ANISOU 2124  CG  PRO A 290     24829  20023  23190  -6638    146  -5723       C
ATOM   2125  CD  PRO A 290     -6.299  -3.650   8.160  1.00176.63             C
ANISOU 2125  CD  PRO A 290     25027  19385  22698  -6384    123  -5302       C
ATOM   2126  N   THR A 291     -6.076  -6.814   9.756  1.00137.24             N
ANISOU 2126  N   THR A 291     20217  13830  18096  -7150    520  -5284       N
ATOM   2127  CA  THR A 291     -5.669  -8.161  10.150  1.00139.43             C
ANISOU 2127  CA  THR A 291     20620  13806  18551  -7399    617  -5249       C
ATOM   2128  C   THR A 291     -4.354  -8.295  10.941  1.00138.15             C
ANISOU 2128  C   THR A 291     20974  13261  18257  -7231    520  -4825       C
ATOM   2129  O   THR A 291     -4.309  -9.053  11.898  1.00140.05             O
ANISOU 2129  O   THR A 291     21498  13162  18553  -7462    644  -4708       O
```

FIG. 13 Continued

```
ATOM   2130  CB  THR A 291      -5.743  -9.184   8.983  1.00141.83           C
ANISOU 2130  CB  THR A 291    20523  14255  19113   -7578    574  -5598      C
ATOM   2131  OG1 THR A 291      -6.994  -9.044   8.301  1.00143.73           O
ANISOU 2131  OG1 THR A 291    20262  14906  19444   -7801    573  -6008      O
ATOM   2132  CG2 THR A 291      -5.641 -10.616   9.516  1.00145.18           C
ANISOU 2132  CG2 THR A 291    21086  14277  19798   -7925    760  -5636      C
ATOM   2133  N   VAL A 292      -3.286  -7.599  10.575  1.00112.42           N
ANISOU 2133  N   VAL A 292    17836  10037  14842   -6879    280  -4594      N
ATOM   2134  CA  VAL A 292      -2.070  -7.731  11.387  1.00111.89           C
ANISOU 2134  CA  VAL A 292    18199   9632  14681   -6786    117  -4217      C
ATOM   2135  C   VAL A 292      -2.380  -7.426  12.842  1.00112.54           C
ANISOU 2135  C   VAL A 292    18759   9486  14517   -6941    206  -4024      C
ATOM   2136  O   VAL A 292      -2.405  -8.317  13.689  1.00114.81           O
ANISOU 2136  O   VAL A 292    19291   9465  14866   -7194    289  -3947      O
ATOM   2137  CB  VAL A 292      -0.933  -6.761  10.997  1.00109.19           C
ANISOU 2137  CB  VAL A 292    17948   9356  14182   -6444   -157  -3979      C
ATOM   2138  CG1 VAL A 292      -0.190  -7.245   9.762  1.00108.94           C
ANISOU 2138  CG1 VAL A 292    17594   9403  14395   -6308   -252  -4089      C
ATOM   2139  CG2 VAL A 292      -1.467  -5.350  10.850  1.00107.37           C
ANISOU 2139  CG2 VAL A 292    17742   9348  13705   -6289   -132  -3995      C
ATOM   2140  N   LEU A 293      -2.614  -6.152  13.118  1.00 84.93           N
ANISOU 2140  N   LEU A 293    15445   6091  10734   -6804    208  -3963      N
ATOM   2141  CA  LEU A 293      -2.886  -5.702  14.460  1.00 85.83           C
ANISOU 2141  CA  LEU A 293    16096   5967  10548   -6951    322  -3830      C
ATOM   2142  C   LEU A 293      -3.839  -6.627  15.196  1.00 88.68           C
ANISOU 2142  C   LEU A 293    16522   6149  11026   -7333    643  -3967      C
ATOM   2143  O   LEU A 293      -3.750  -6.755  16.411  1.00 90.27           O
ANISOU 2143  O   LEU A 293    17265   6031  11003   -7532    706  -3795      O
ATOM   2144  CB  LEU A 293      -3.429  -4.288  14.425  1.00 84.53           C
ANISOU 2144  CB  LEU A 293    16020   5927  10171   -6787    424  -3914      C
ATOM   2145  CG  LEU A 293      -2.341  -3.305  14.035  1.00 82.45           C
ANISOU 2145  CG  LEU A 293    15895   5698   9735    6489    121   3701      C
ATOM   2146  CD1 LEU A 293      -2.921  -1.904  13.951  1.00 81.69           C
ANISOU 2146  CD1 LEU A 293    15928   5641   9471   -6322    256  -3807      C
ATOM   2147  CD2 LEU A 293      -1.220  -3.389  15.058  1.00 83.29           C
ANISOU 2147  CD2 LEU A 293    16545   5507   9595   -6583   -137  -3382      C
ATOM   2148  N   SER A 294      -4.752  -7.264  14.471  1.00106.53           N
ANISOU 2148  N   SER A 294    18256   8595  13627   -7486    842  -4286      N
ATOM   2149  CA  SER A 294      -5.650  -8.229  15.093  1.00109.87           C
ANISOU 2149  CA  SER A 294    18681   8820  14243   -7920   1173  -4428      C
ATOM   2150  C   SER A 294      -4.860  -9.470  15.502  1.00111.79           C
ANISOU 2150  C   SER A 294    19172   8700  14604   -8073   1083  -4222      C
ATOM   2151  O   SER A 294      -4.831  -9.831  16.674  1.00113.78           O
ANISOU 2151  O   SER A 294    19927   8579  14725   -8309   1197  -4023      O
ATOM   2152  CB  SER A 294      -6.798  -8.605  14.135  1.00111.32           C
ANISOU 2152  CB  SER A 294    18180   9316  14801   -8114   1345  -4857      C
ATOM   2153  OG  SER A 294      -7.459  -9.841  14.453  1.00115.28           O
ANISOU 2153  OG  SER A 294    18571   9613  15616   -8594   1622  -5007      O
ATOM   2154  N   VAL A 295      -4.196 -10.100  14.534  1.00144.01           N
ANISOU 2154  N   VAL A 295    22942  12841  18934   -7938    885  -4272      N
ATOM   2155  CA  VAL A 295      -3.475 -11.352  14.769  1.00146.31           C
ANISOU 2155  CA  VAL A 295    23407  12728  19456   -8064    821  -4132      C
ATOM   2156  C   VAL A 295      -2.364 -11.225  15.790  1.00145.92           C
ANISOU 2156  C   VAL A 295    23934  12346  19161   -7960    538  -3689      C
ATOM   2157  O   VAL A 295      -2.281 -12.007  16.726  1.00148.73           O
ANISOU 2157  O   VAL A 295    24682  12270  19559   -8217    598  -3502      O
ATOM   2158  CB  VAL A 295      -2.907 -11.937  13.467  1.00146.19           C
ANISOU 2158  CB  VAL A 295    22979  12804  19763   -7907    691  -4317      C
ATOM   2159  CG1 VAL A 295      -4.033 -12.137  12.454  1.00147.50           C
ANISOU 2159  CG1 VAL A 295    22608  13297  20137   -8099    908  -4795      C
ATOM   2160  CG2 VAL A 295      -1.815 -11.044  12.914  1.00142.60           C
ANISOU 2160  CG2 VAL A 295    22489  12553  19138   -7465    348  -4143      C
ATOM   2161  N   THR A 296      -1.499 -10.245  15.619  1.00109.39           N
ANISOU 2161  N   THR A 296    19374   7897  14292   -7624    207  -3513      N
ATOM   2162  CA  THR A 296      -0.461 -10.045  16.601  1.00109.54           C
ANISOU 2162  CA  THR A 296    19921   7633  14066   -7593   -138  -3124      C
ATOM   2163  C   THR A 296      -1.080  -9.911  18.003  1.00111.57           C
ANISOU 2163  C   THR A 296    20776   7641  13974   -7912     35  -3006      C
ATOM   2164  O   THR A 296      -0.397 -10.117  18.999  1.00113.19           O
```

FIG. 13 Continued

```
ANISOU 2164  O    THR A 296      21514   7498  13997  -8038   -219  -2694       O
ATOM   2165  CB   THR A 296       0.406  -8.807  16.245  1.00106.47             C
ANISOU 2165  CB   THR A 296      19517   7492  13444  -7264   -480  -2997       C
ATOM   2166  OG1  THR A 296       1.151  -8.362  17.389  1.00107.20             O
ANISOU 2166  OG1  THR A 296      20197   7345  13189  -7347   -810  -2675       O
ATOM   2167  CG2  THR A 296      -0.465  -7.668  15.753  1.00104.36             C
ANISOU 2167  CG2  THR A 296      19063   7605  12986  -7144   -255  -3220       C
ATOM   2168  N    MET A 297      -2.378  -9.605  18.075  1.00 95.12             N
ANISOU 2168  N    MET A 297      18610   5704  11826  -8074    468  -3264       N
ATOM   2169  CA   MET A 297      -3.075  -9.351  19.358  1.00 97.19             C
ANISOU 2169  CA   MET A 297      19453   5720  11753  -8385    746  -3211       C
ATOM   2170  C    MET A 297      -4.036 -10.442  19.853  1.00100.93             C
ANISOU 2170  C    MET A 297      19975   5897  12477  -8822   1200  -3292       C
ATOM   2171  O    MET A 297      -4.638 -10.322  20.927  1.00103.15             O
ANISOU 2171  O    MET A 297      20762   5916  12515  -9124   1510  -3235       O
ATOM   2172  CB   MET A 297      -3.844  -8.053  19.248  1.00 95.42             C
ANISOU 2172  CB   MET A 297      19179   5779  11296  -8270    967  -3433       C
ATOM   2173  CG   MET A 297      -4.122  -7.317  20.515  1.00 96.83             C
ANISOU 2173  CG   MET A 297      20101   5700  10991  -8445   1139  -3365       C
ATOM   2174  SD   MET A 297      -4.796  -5.816  19.805  1.00 94.17             S
ANISOU 2174  SD   MET A 297      19456   5728  10596  -8130   1317  -3670       S
ATOM   2175  CE   MET A 297      -4.429  -4.547  21.010  1.00 95.10             C
ANISOU 2175  CE   MET A 297      20539   5552  10041  -8133   1288  -3566       C
ATOM   2176  N    ALA A 298      -4.228 -11.460  19.028  1.00104.30             N
ANISOU 2176  N    ALA A 298      14003  14974  10653  -5669  -2224    365       N
ATOM   2177  CA   ALA A 298      -4.954 -12.654  19.424  1.00105.08             C
ANISOU 2177  CA   ALA A 298      13836  15314  10778  -5809  -2296    590       C
ATOM   2178  C    ALA A 298      -3.840 -13.699  19.579  1.00103.13             C
ANISOU 2178  C    ALA A 298      13715  14861  10610  -6064  -2344    371       C
ATOM   2179  O    ALA A 298      -4.003 -14.766  20.199  1.00103.29             O
ANISOU 2179  O    ALA A 298      13596  14986  10665  -6174  -2377    468       O
ATOM   2180  CB   ALA A 298      -5.949 -13.052  18.353  1.00106.48             C
ANISOU 2180  CB   ALA A 298      13835  15661  10961  -6014  -2443    840       C
ATOM   2181  N    ILE A 299      -2.695 -13.346  18.994  1.00106.64             N
ANISOU 2181  N    ILE A 299      14427  15006  11085  -6149  -2340     78       N
ATOM   2182  CA   ILE A 299      -1.489 -14.191  19.052  1.00104.84             C
ANISOU 2182  CA   ILE A 299      14344  14551  10940  -6353  -2371   -173       C
ATOM   2183  C    ILE A 299      -0.722 -13.715  20.276  1.00104.14             C
ANISOU 2183  C    ILE A 299      14346  14384  10837  -6114  -2252   -359       C
ATOM   2184  O    ILE A 299       0.220 -14.371  20.695  1.00102.96             O
ANISOU 2184  O    ILE A 299      14273  14097  10749  -6208  -2266   -541       O
ATOM   2185  CB   ILE A 299      -0.610 -13.975  17.803  1.00103.66             C
ANISOU 2185  CB   ILE A 299      14422  14133  10830  -6565  -2412   -402       C
ATOM   2186  CG1  ILE A 299       0.015 -15.323  17.419  1.00102.70             C
ANISOU 2186  CG1  ILE A 299      14332  13885  10803  -6891  -2512   -507       C
ATOM   2187  CG2  ILE A 299       0.420 -12.880  18.006  1.00102.68             C
ANISOU 2187  CG2  ILE A 299      14526  13787  10699  -6395  -2291   -682       C
ATOM   2188  CD1  ILE A 299      -1.021 -16.433  17.017  1.00103.93             C
ANISOU 2188  CD1  ILE A 299      14286  14228  10971  -7120  -2650   -238       C
ATOM   2189  N    GLY A 300      -1.113 -12.576  20.830  1.00142.79             N
ANISOU 2189  N    GLY A 300      19244  19363  15647  -5797  -2138   -321       N
ATOM   2190  CA   GLY A 300      -0.542 -12.120  22.078  1.00142.56             C
ANISOU 2190  CA   GLY A 300      19292  19298  15577  -5551  -2029   -478       C
ATOM   2191  C    GLY A 300      -1.143 -13.050  23.103  1.00143.39             C
ANISOU 2191  C    GLY A 300      19185  19642  15656  -5515  -2035   -274       C
ATOM   2192  O    GLY A 300      -0.468 -13.486  24.029  1.00142.82             O
ANISOU 2192  O    GLY A 300      19153  19527  15584  -5482  -2020   -396       O
ATOM   2193  N    SER A 301      -2.417 -13.379  22.901  1.00119.77             N
ANISOU 2193  N    SER A 301      15959  16907  12642  -5537  -2065     47       N
ATOM   2194  CA   SER A 301      -3.143 -14.292  23.777  1.00120.94             C
ANISOU 2194  CA   SER A 301      15878  17306  12767  -5534  -2065    290       C
ATOM   2195  C    SER A 301      -2.443 -15.636  23.961  1.00119.85             C
ANISOU 2195  C    SER A 301      15765  17059  12714  -5796  -2158    220       C
ATOM   2196  O    SER A 301      -2.347 -16.149  25.080  1.00120.20             O
ANISOU 2196  O    SER A 301      15761  17186  12724  -5715  -2119    260       O
ATOM   2197  CB   SER A 301      -4.550 -14.546  23.236  1.00122.77             C
ANISOU 2197  CB   SER A 301      15844  17807  12997  -5607  -2114    635       C
ATOM   2198  OG   SER A 301      -4.958 -15.880  23.508  1.00123.36             O
ANISOU 2198  OG   SER A 301      15739  18014  13117  -5827  -2188    825       O
```

FIG. 13 Continued

```
ATOM   2199  N   HIS A 302      -1.953 -16.219  22.873  1.00119.29           N
ANISOU 2199  N   HIS A 302    15780  16799  12746   6101   2278    118       N
ATOM   2200  CA  HIS A 302      -1.334 -17.521  23.023  1.00118.54           C
ANISOU 2200  CA  HIS A 302    15710  16588  12739  -6336  -2365     61       C
ATOM   2201  C   HIS A 302      -0.108 -17.476  23.919  1.00117.36           C
ANISOU 2201  C   HIS A 302    15724  16273  12593  -6210  -2317   -200       C
ATOM   2202  O   HIS A 302      -0.095 -18.104  24.961  1.00117.86           O
ANISOU 2202  O   HIS A 302    15725  16421  12634  -6149  -2305   -122       O
ATOM   2203  CB  HIS A 302      -1.045 -18.212  21.695  1.00117.80           C
ANISOU 2203  CB  HIS A 302    15687  16320  12751  -6683  -2495     -9       C
ATOM   2204  CG  HIS A 302      -1.599 -19.599  21.637  1.00118.72           C
ANISOU 2204  CG  HIS A 302    15660  16517  12930  -6942  -2600    198       C
ATOM   2205  ND1 HIS A 302      -1.830 -20.348  22.772  1.00119.54           N
ANISOU 2205  ND1 HIS A 302    15650  16740  13028  -6895  -2580    349       N
ATOM   2206  CD2 HIS A 302      -1.994 -20.366  20.593  1.00119.18           C
ANISOU 2206  CD2 HIS A 302    15681  16552  13052  -7257  -2727    284       C
ATOM   2207  CE1 HIS A 302      -2.334 -21.521  22.430  1.00120.46           C
ANISOU 2207  CE1 HIS A 302    15665  16888  13216  -7177  -2685    522       C
ATOM   2208  NE2 HIS A 302      -2.446 -21.557  21.114  1.00120.28           N
ANISOU 2208  NE2 HIS A 302    15685  16780  13236  -7402  -2780    479       N
ATOM   2209  N   ARG A 303       0.916 -16.723  23.553  1.00136.92           N
ANISOU 2209  N   ARG A 303    18405  18525  15093  -6168  -2292   -502       N
ATOM   2210  CA  ARG A 303       2.092 -16.678  24.411  1.00136.03           C
ANISOU 2210  CA  ARG A 303    18426  18271  14988  -6057  -2263   -754       C
ATOM   2211  C   ARG A 303       1.738 -16.259  25.845  1.00137.14           C
ANISOU 2211  C   ARG A 303    18505  18605  14995  -5750  -2169   -667       C
ATOM   2212  O   ARG A 303       2.530 -16.438  26.768  1.00136.86           O
ANISOU 2212  O   ARG A 303    18541  18517  14942  -5655  -2166   -812       O
ATOM   2213  CB  ARG A 303       3.209 -15.820  23.798  1.00134.70           C
ANISOU 2213  CB  ARG A 303    18469  17847  14865  -6063  -2238  -1088       C
ATOM   2214  CG  ARG A 303       2.769 -14.953  22.622  1.00134.76           C
ANISOU 2214  CG  ARG A 303    18523  17818  14861  -6106  -2214  -1068       C
ATOM   2215  CD  ARG A 303       3.858 -14.823  21.538  1.00133.42           C
ANISOU 2215  CD  ARG A 303    18536  17369  14788  -6306  -2238  -1345       C
ATOM   2216  NE  ARG A 303       5.076 -14.176  22.035  1.00132.65           N
ANISOU 2216  NE  ARG A 303    18593  17096  14711  -6195  -2178  -1655       N
ATOM   2217  CZ  ARG A 303       5.908 -13.456  21.282  1.00131.94           C
ANISOU 2217  CZ  ARG A 303    18672  16793  14667  -6264  -2138  -1895       C
ATOM   2218  NH1 ARG A 303       5.646 -13.281  19.987  1.00131.88           N
ANISOU 2218  NH1 ARG A 303    18716  16720  14672  -6432  -2148  -1855       N
ATOM   2219  NH2 ARG A 303       6.991 -12.904  21.827  1.00131.50           N
ANISOU 2219  NH2 ARG A 303    18730  16597  14635  -6174  -2089  -2169       N
ATOM   2220  N   LEU A 304       0.535 -15.726  26.036  1.00103.86           N
ANISOU 2220  N   LEU A 304    14153  14627  10682  -5589  -2094   -427       N
ATOM   2221  CA  LEU A 304       0.082 -15.336  27.374  1.00105.24           C
ANISOU 2221  CA  LEU A 304    14263  15010  10713  -5288  -1984   -328       C
ATOM   2222  C   LEU A 304      -0.267 -16.578  28.166  1.00106.09           C
ANISOU 2222  C   LEU A 304    14227  15276  10808  -5360  -2017   -114       C
ATOM   2223  O   LEU A 304       0.467 -17.014  29.046  1.00105.86           O
ANISOU 2223  O   LEU A 304    14271  15197  10754  -5314  -2031   -218       O
ATOM   2224  CB  LEU A 304      -1.179 -14.474  27.283  1.00106.85           C
ANISOU 2224  CB  LEU A 304    14336  15437  10827  -5094  -1884   -110       C
ATOM   2225  CG  LEU A 304      -1.290 -13.364  28.323  1.00107.95           C
ANISOU 2225  CG  LEU A 304    14534  15667  10815  -4719  -1734   -174       C
ATOM   2226  CD1 LEU A 304      -0.492 -13.767  29.536  1.00107.77           C
ANISOU 2226  CD1 LEU A 304    14597  15622  10728  -4640  -1728   -310       C
ATOM   2227  CD2 LEU A 304      -0.760 -12.054  27.774  1.00107.31           C
ANISOU 2227  CD2 LEU A 304    14659  15375  10738  -4607  -1691   -424       C
ATOM   2228  N   SER A 305      -1.420 -17.123  27.814  1.00102.19           N
ANISOU 2228  N   SER A 305    13523  14975  10331  -5479  -2034    198       N
ATOM   2229  CA  SER A 305      -1.980 -18.337  28.388  1.00103.38           C
ANISOU 2229  CA  SER A 305    13509  15289  10484  -5596  -2063    461       C
ATOM   2230  C   SER A 305      -1.079 -19.587  28.388  1.00102.39           C
ANISOU 2230  C   SER A 305    13475  14959  10468  -5837  -2185    369       C
ATOM   2231  O   SER A 305      -1.561 -20.721  28.502  1.00103.34           O
ANISOU 2231  O   SER A 305    13475  15156  10635  -6022  -2239    595       O
ATOM   2232  CB  SER A 305      -3.282 -18.630  27.653  1.00104.72           C
ANISOU 2232  CB  SER A 305    13446  15653  10690  -5751  -2089    768       C
ATOM   2233  OG  SER A 305      -3.314 -17.961  26.393  1.00103.93           O
```

FIG. 13 Continued

```
ANISOU 2233  OG  SER A 305    13395  15447  10647  -5825  -2135    672           O
ATOM   2234  N   GLN A 306     0.220 -19.373  28.221  1.00 137.41                N
ANISOU 2234  N   GLN A 306    18121  19130  14958  -5839  -2228     39           N
ATOM   2235  CA  GLN A 306     1.196 -20.450  28.319  1.00 136.60                C
ANISOU 2235  CA  GLN A 306    18116  18827  14959  -6006  -2333    -81           C
ATOM   2236  C   GLN A 306     2.080 -20.121  29.512  1.00 136.47                C
ANISOU 2236  C   GLN A 306    18216  18785  14852  -5763  -2296   -260           C
ATOM   2237  O   GLN A 306     2.865 -20.950  29.992  1.00 136.28                O
ANISOU 2237  O   GLN A 306    18258  18649  14874  -5810  -2370   -331           O
ATOM   2238  CB  GLN A 306     2.009 -20.591  27.029  1.00 134.93                C
ANISOU 2238  CB  GLN A 306    18032  18333  14903  -6238  -2425   -317           C
ATOM   2239  CG  GLN A 306     1.332 -21.493  25.995  1.00 135.31                C
ANISOU 2239  CG  GLN A 306    17989  18369  15053  -6552  -2513   -138           C
ATOM   2240  CD  GLN A 306     2.283 -22.010  24.929  1.00 133.95                C
ANISOU 2240  CD  GLN A 306    17963  17901  15031  -6796  -2609   -374           C
ATOM   2241  OE1 GLN A 306     2.060 -23.075  24.345  1.00 134.35                O
ANISOU 2241  OE1 GLN A 306    17988  17882  15176  -7059  -2700   -278           O
ATOM   2242  NE2 GLN A 306     3.346 -21.257  24.668  1.00 132.54                N
ANISOU 2242  NE2 GLN A 306    17941  17545  14874  -6715  -2582   -689           N
ATOM   2243  N   GLN A 307     1.900 -18.888  29.979  1.00 154.11                N
ANISOU 2243  N   GLN A 307    20475  21128  16952  -5495  -2185   -327           N
ATOM   2244  CA  GLN A 307     2.602 -18.296  31.114  1.00 154.31                C
ANISOU 2244  CA  GLN A 307    20616  21161  16853  -5234  -2138   -510           C
ATOM   2245  C   GLN A 307     1.874 -18.625  32.414  1.00 156.27                C
ANISOU 2245  C   GLN A 307    20761  21681  16934  -5059  -2065   -256           C
ATOM   2246  O   GLN A 307     2.462 -18.647  33.500  1.00 156.77                O
ANISOU 2246  O   GLN A 307    20910  21767  16889  -4897  -2064   -348           O
ATOM   2247  CB  GLN A 307     2.588 -16.785  30.922  1.00 154.11                C
ANISOU 2247  CB  GLN A 307    20675  21123  16758  -5040  -2040   -680           C
ATOM   2248  CG  GLN A 307     3.831 -16.044  31.338  1.00 153.37                C
ANISOU 2248  CG  GLN A 307    20776  20859  16640  -4912  -2047  -1039           C
ATOM   2249  CD  GLN A 307     3.912 -14.709  30.642  1.00 152.85                C
ANISOU 2249  CD  GLN A 307    20814  20681  16583  -4842  -1979  -1219           C
ATOM   2250  OE1 GLN A 307     3.607 -14.600  29.449  1.00 152.15                O
ANISOU 2250  OE1 GLN A 307    20701  20514  16597  -5002  -1989  -1179           O
ATOM   2251  NE2 GLN A 307     4.305 -13.681  31.379  1.00 153.40                N
ANISOU 2251  NE2 GLN A 307    21011  20738  16535  -4606  -1910  -1414           N
ATOM   2252  N   GLY A 308     0.570 -18.843  32.276  1.00 106.02                N
ANISOU 2252  N   GLY A 308    14206  15534  10540  -5093  -2002     66           N
ATOM   2253  CA  GLY A 308    -0.313 -19.196  33.374  1.00 108.17                C
ANISOU 2253  CA  GLY A 308    14344  16095  10662  -4959  -1909    358           C
ATOM   2254  C   GLY A 308    -1.665 -18.518  33.218  1.00 109.63                C
ANISOU 2254  C   GLY A 308    14345  16536  10772  -4841  -1775    586           C
ATOM   2255  O   GLY A 308    -2.727 -19.120  33.448  1.00 111.35                O
ANISOU 2255  O   GLY A 308    14357  16989  10964  -4897  -1727    919           O
ATOM   2256  N   ALA A 309    -1.589 -17.254  32.795  1.00 124.02                N
ANISOU 2256  N   ALA A 309    16246  18303  12573  -4682  -1718    401           N
ATOM   2257  CA  ALA A 309    -2.733 -16.361  32.644  1.00 125.43                C
ANISOU 2257  CA  ALA A 309    16286  18694  12678  -4502  -1586    560           C
ATOM   2258  C   ALA A 309    -3.513 -16.426  31.301  1.00 125.27                C
ANISOU 2258  C   ALA A 309    16111  18691  12797  -4707  -1641    719           C
ATOM   2259  O   ALA A 309    -2.969 -16.221  30.204  1.00 123.57                O
ANISOU 2259  O   ALA A 309    16004  18241  12706  -4867  -1738    540           O
ATOM   2260  CB  ALA A 309    -2.289 -14.927  32.950  1.00 125.29                C
ANISOU 2260  CB  ALA A 309    16452  18599  12555  -4199  -1491    291           C
ATOM   2261  N   ILE A 310    -4.806 -16.698  31.420  1.00 114.81                N
ANISOU 2261  N   ILE A 310    14523  17661  11439  -4698  -1574   1060           N
ATOM   2262  CA  ILE A 310    -5.723 -16.733  30.297  1.00 115.30                C
ANISOU 2262  CA  ILE A 310    14395  17809  11603  -4861  -1625   1253           C
ATOM   2263  C   ILE A 310    -6.189 -15.292  30.047  1.00 115.97                C
ANISOU 2263  C   ILE A 310    14481  17961  11622  -4570  -1516   1210           C
ATOM   2264  O   ILE A 310    -5.585 -14.355  30.548  1.00 115.55                O
ANISOU 2264  O   ILE A 310    14625  17802  11478  -4312  -1431    975           O
ATOM   2265  CB  ILE A 310    -6.915 -17.667  30.655  1.00 117.59                C
ANISOU 2265  CB  ILE A 310    14379  18412  11888  -4973  -1597   1649           C
ATOM   2266  CG1 ILE A 310    -6.411 -19.095  30.901  1.00 117.07                C
ANISOU 2266  CG1 ILE A 310    14350  18239  11895  -5262  -1705   1689           C
ATOM   2267  CG2 ILE A 310    -8.017 -17.642  29.592  1.00 118.67                C
ANISOU 2267  CG2 ILE A 310    14273  18702  12113  -5118  -1649   1879           C
```

FIG. 13 Continued

```
ATOM   2268  CD1 ILE A 310      -7.501 -20.141  31.034  1.00119.25           C
ANISOU 2268  CD1 ILE A 310    14344  18761  12204  -5466  -1709   2070       C
ATOM   2269  N   THR A 311      -7.228 -15.107  29.241  1.00112.71           N
ANISOU 2269  N   THR A 311    13860  17707  11259  -4615  -1530   1428       N
ATOM   2270  CA  THR A 311      -7.856 -13.796  29.098  1.00113.96           C
ANISOU 2270  CA  THR A 311    13979  17971  11350  -4303  -1415   1451       C
ATOM   2271  C   THR A 311      -9.344 -13.980  28.941  1.00116.55           C
ANISOU 2271  C   THR A 311    13945  18656  11683  -4292  -1379   1830       C
ATOM   2272  O   THR A 311      -9.818 -15.050  28.551  1.00116.98           O
ANISOU 2272  O   THR A 311    13804  18818  11827  -4599  -1488   2042       O
ATOM   2273  CB  THR A 311      -7.385 -12.923  27.900  1.00112.48           C
ANISOU 2273  CB  THR A 311    13975  17527  11237  -4339  -1496   1248       C
ATOM   2274  OG1 THR A 311      -7.918 -11.645  28.017  1.00113.96           O
ANISOU 2274  OG1 THR A 311    14163  17797  11340  -3974  -1359   1258       O
ATOM   2275  CG2 THR A 311      -7.893 -13.603  26.609  1.00112.40           C
ANISOU 2275  CG2 THR A 311    13812  17540  11353  -4670  -1662   1415       C
ATOM   2276  N   LYS A 312     -10.073 -12.923  29.271  1.00119.37           N
ANISOU 2276  N   LYS A 312    14212  19196  11947  -3930  -1224   1911       N
ATOM   2277  CA  LYS A 312     -11.515 -12.940  29.172  1.00122.19           C
ANISOU 2277  CA  LYS A 312    14201  19921  12307  -3860  -1169   2269       C
ATOM   2278  C   LYS A 312     -11.875 -12.113  27.968  1.00122.35           C
ANISOU 2278  C   LYS A 312    14206  19889  12394  -3819  -1244   2277       C
ATOM   2279  O   LYS A 312     -12.502 -12.600  27.031  1.00122.92           O
ANISOU 2279  O   LYS A 312    14072  20066  12566  -4066  -1386   2472       O
ATOM   2280  CB  LYS A 312     -12.157 -12.369  30.435  1.00124.73           C
ANISOU 2280  CB  LYS A 312    14406  20515  12471  -3453   -924   2378       C
ATOM   2281  CG  LYS A 312     -13.677 -12.405  30.428  1.00128.02           C
ANISOU 2281  CG  LYS A 312    14400  21350  12893  -3361   -843   2763       C
ATOM   2282  CD  LYS A 312     -14.206 -13.800  30.128  1.00128.57           C
ANISOU 2282  CD  LYS A 312    14193  21588  13069  -3774   -972   3035       C
ATOM   2283  CE  LYS A 312     -14.655 -14.489  31.387  1.00130.52           C
ANISOU 2283  CE  LYS A 312    14262  22109  13221  -3733   -814   3237       C
ATOM   2284  NZ  LYS A 312     -15.628 -13.633  32.103  1.00133.65           N
ANISOU 2284  NZ  LYS A 312    14448  22835  13498  -3306   -573   3398       N
ATOM   2285  N   ARG A 313     -11.465 -10.817  27.989  1.00136.46           N
ANISOU 2285  N   ARG A 313    16223  21504  14120  -3511  -1156   2062       N
ATOM   2286  CA  ARG A 313     -11.711  -9.973  26.860  1.00136.65           C
ANISOU 2286  CA  ARG A 313    16285  21440  14197  -3446  -1221   2056       C
ATOM   2287  C   ARG A 313     -10.397  -9.250  26.645  1.00134.22           C
ANISOU 2287  C   ARG A 313    16398  20718  13882  -3410  -1232   1671       C
ATOM   2288  O   ARG A 313     -10.230  -8.067  26.969  1.00134.80           O
ANISOU 2288  O   ARG A 313    16649  20687  13882  -3070  -1101   1526       O
ATOM   2289  CB  ARG A 313     -12.911  -9.049  27.120  1.00139.87           C
ANISOU 2289  CB  ARG A 313    16468  22134  14543  -3045  -1068   2275       C
ATOM   2290  CG  ARG A 313     -14.259  -9.828  27.272  1.00142.56           C
ANISOU 2290  CG  ARG A 313    16338  22919  14909  -3117  -1063   2679       C
ATOM   2291  CD  ARG A 313     -15.459  -8.915  27.566  1.00146.05           C
ANISOU 2291  CD  ARG A 313    16527  23669  15297  -2691   -896   2901       C
ATOM   2292  NE  ARG A 313     -16.647  -9.611  28.083  1.00148.89           N
ANISOU 2292  NE  ARG A 313    16440  24476  15657  -2704   -825   3258       N
ATOM   2293  CZ  ARG A 313     -17.016  -9.635  29.365  1.00150.73           C
ANISOU 2293  CZ  ARG A 313    16554  24939  15778  -2460   -599   3339       C
ATOM   2294  NH1 ARG A 313     -16.289  -9.023  30.294  1.00150.02           N
ANISOU 2294  NH1 ARG A 313    16767  24676  15556  -2182   -433   3081       N
ATOM   2295  NH2 ARG A 313     -18.117 -10.280  29.723  1.00153.47           N
ANISOU 2295  NH2 ARG A 313    16478  25697  16138  -2504   -537   3680       N
ATOM   2296  N   MET A 314       9.470  10.037  26.096  1.00159.45           N
ANISOU 2296  N   MET A 314    19744  23679  17160  -3781  -1390   1512       N
ATOM   2297  CA  MET A 314      -8.075  -9.671  25.865  1.00156.90           C
ANISOU 2297  CA  MET A 314    19794  22965  16857  -3851  -1425   1143       C
ATOM   2298  C   MET A 314      -7.851  -8.273  25.312  1.00157.00           C
ANISOU 2298  C   MET A 314    20026  22774  16853  -3632  -1376    988       C
ATOM   2299  O   MET A 314      -6.736  -7.758  25.337  1.00155.39           O
ANISOU 2299  O   MET A 314    20131  22263  16649  -3621  -1359    676       O
ATOM   2300  CB  MET A 314      -7.373 -10.718  24.973  1.00154.67           C
ANISOU 2300  CB  MET A 314    19577  22500  16692  -4301  -1618   1059       C
ATOM   2301  CG  MET A 314      -7.572 -10.576  23.453  1.00154.41           C
ANISOU 2301  CG  MET A 314    19552  22381  16735  -4503  -1760   1107       C
ATOM   2302  SD  MET A 314      -8.695 -11.786  22.707  1.00155.68           S
```

FIG. 13 Continued

```
ANISOU 2302  SD  MET A 314    19362  22823  16967  -4832  -1927   1461       S
ATOM   2303  CE  MET A 314    -8.047 -11.874  21.039  1.00153.97             C
ANISOU 2303  CE  MET A 314    19353  22323  16826  -5172  -2116   1306       C
ATOM   2304  N   THR A 315    -8.896  -7.648  24.802  1.00161.58             N
ANISOU 2304  N   THR A 315    20448  23519  17426  -3460  -1357   1210       N
ATOM   2305  CA  THR A 315    -8.710  -6.312  24.288  1.00161.94             C
ANISOU 2305  CA  THR A 315    20718  23355  17457  -3240  -1307   1083       C
ATOM   2306  C   THR A 315    -8.103  -5.437  25.389  1.00162.07             C
ANISOU 2306  C   THR A 315    20974  23224  17382  -2921  -1128    833       C
ATOM   2307  O   THR A 315    -7.369  -4.483  25.096  1.00161.43             O
ANISOU 2307  O   THR A 315    21199  22835  17302  -2837  -1098    592       O
ATOM   2308  CB  THR A 315   -10.020  -5.726  23.759  1.00164.67             C
ANISOU 2308  CB  THR A 315    20837  23934  17796  -3029  -1297   1385       C
ATOM   2309  OG1 THR A 315   -10.751  -6.744  23.054  1.00165.06             O
ANISOU 2309  OG1 THR A 315    20586  24218  17911  -3323  -1459   1654       O
ATOM   2310  CG2 THR A 315    -9.726  -4.561  22.824  1.00164.70             C
ANISOU 2310  CG2 THR A 315    21099  23666  17812  -2924  -1313   1272       C
ATOM   2311  N   ALA A 316    -8.387  -5.790  26.649  1.00116.89             N
ANISOU 2311  N   ALA A 316    15122  17716  11575  -2765  -1014    888       N
ATOM   2312  CA  ALA A 316    -7.866  -5.054  27.805  1.00117.32             C
ANISOU 2312  CA  ALA A 316    15392  17668  11516  -2465   -849    655       C
ATOM   2313  C   ALA A 316    -6.353  -5.246  27.966  1.00114.65             C
ANISOU 2313  C   ALA A 316    15358  17005  11199  -2673   -914    294       C
ATOM   2314  O   ALA A 316    -5.747  -4.712  28.894  1.00114.80             O
ANISOU 2314  O   ALA A 316    15581  16913  11127  -2482   -812     61       O
ATOM   2315  CB  ALA A 316    -8.615  -5.435  29.075  1.00119.29             C
ANISOU 2315  CB  ALA A 316    15416  18260  11649  -2254   -709    829       C
ATOM   2316  N   ILE A 317     5.754   6.002  27.044  1.00117.35             N
ANISOU 2316  N   ILE A 317    15725  17203  11660  -3062  -1086    247       N
ATOM   2317  CA  ILE A 317    -4.314  -6.256  27.053  1.00114.90             C
ANISOU 2317  CA  ILE A 317    15666  16594  11395  -3283  -1159    -81       C
ATOM   2318  C   ILE A 317    -3.553  -4.997  26.665  1.00114.55             C
ANISOU 2318  C   ILE A 317    15943  16219  11362  -3182  -1116   -359       C
ATOM   2319  O   ILE A 317    -2.353  -4.877  26.903  1.00113.12             O
ANISOU 2319  O   ILE A 317    15991  15791  11197  -3272  -1132   -667       O
ATOM   2320  CB  ILE A 317    -3.916  -7.406  26.107  1.00112.87             C
ANISOU 2320  CB  ILE A 317    15347  16273  11267  -3715  -1340    -54       C
ATOM   2321  CG1 ILE A 317    -4.624  -8.700  26.501  1.00113.35             C
ANISOU 2321  CG1 ILE A 317    15110  16629  11328  -3847  -1389    215       C
ATOM   2322  CG2 ILE A 317    -2.422  -7.621  26.115  1.00110.60             C
ANISOU 2322  CG2 ILE A 317    15302  15685  11035  -3914  -1401   -395       C
ATOM   2323  CD1 ILE A 317    -5.250  -8.679  27.866  1.00115.23             C
ANISOU 2323  CD1 ILE A 317    15213  17131  11436  -3560  -1247    341       C
ATOM   2324  N   GLU A 318    -4.250  -4.058  26.043  1.00202.79             N
ANISOU 2324  N   GLU A 318    27131  27385  22534  -3001  -1065   -243       N
ATOM   2325  CA  GLU A 318    -3.631  -2.786  25.731  1.00202.93             C
ANISOU 2325  CA  GLU A 318    27464  27083  22556  -2878  -1005   -480       C
ATOM   2326  C   GLU A 318    -3.374  -2.135  27.078  1.00204.07             C
ANISOU 2326  C   GLU A 318    27749  27204  22585  -2570   -858   -667       C
ATOM   2327  O   GLU A 318    -2.583  -1.201  27.206  1.00204.08             O
ANISOU 2327  O   GLU A 318    28046  26918  22577  -2489   -803   -947       O
ATOM   2328  CB  GLU A 318    -4.574  -1.917  24.867  1.00204.79             C
ANISOU 2328  CB  GLU A 318    27672  27340  22799  -2696   -974   -273       C
ATOM   2329  CG  GLU A 318    -3.925  -0.654  24.278  1.00204.92             C
ANISOU 2329  CG  GLU A 318    28035  26983  22843  -2633   -933   -487       C
ATOM   2330  CD  GLU A 318    -4.124   0.614  25.114  1.00207.20             C
ANISOU 2330  CD  GLU A 318    28497  27187  23042  -2208   -755   -587       C
ATOM   2331  OE1 GLU A 318    -5.185   0.745  25.758  1.00209.37             O
ANISOU 2331  OE1 GLU A 318    28581  27732  23238  -1896   -658   -383       O
ATOM   2332  OE2 GLU A 318    -3.226   1.489  25.111  1.00207.02             O
ANISOU 2332  OE2 GLU A 318    28802  26825  23030  -2189   -707   -872       O
ATOM   2333  N   GLU A 319    -4.040  -2.663  28.096  1.00114.35             N
ANISOU 2333  N   GLU A 319    16173  16148  11126  -2415   -794   -512       N
ATOM   2334  CA  GLU A 319    -3.985  -2.071  29.421  1.00115.92             C
ANISOU 2334  CA  GLU A 319    16484  16381  11180  -2091   -643   -652       C
ATOM   2335  C   GLU A 319    -2.929  -2.682  30.336  1.00114.52             C
ANISOU 2335  C   GLU A 319    16407  16150  10955  -2223   -685   -894       C
ATOM   2336  O   GLU A 319    -2.406  -2.003  31.218  1.00115.32             O
ANISOU 2336  O   GLU A 319    16724  16140  10954  -2031   -600  -1140       O
```

FIG. 13 Continued

```
ATOM   2337  CB   GLU A 319      -5.375  -2.126  30.072  1.00118.54           C
ANISOU 2337  CB   GLU A 319    16542  17092  11407  -1787   -513   -344       C
ATOM   2338  CG   GLU A 319      -6.541  -1.600  29.190  1.00120.30           C
ANISOU 2338  CG   GLU A 319    16603  17424  11681  -1635   -484    -61       C
ATOM   2339  CD   GLU A 319      -6.841  -0.093  29.361  1.00122.71           C
ANISOU 2339  CD   GLU A 319    17108  17593  11924  -1221   -323   -146       C
ATOM   2340  OE1  GLU A 319      -5.889   0.727  29.421  1.00122.20           O
ANISOU 2340  OE1  GLU A 319    17396  17182  11854  -1192   -301   -466       O
ATOM   2341  OE2  GLU A 319      -8.043   0.268  29.416  1.00125.31           O
ANISOU 2341  OE2  GLU A 319    17237  18159  12217   -925   -218    113       O
ATOM   2342  N    MET A 320      -2.624  -3.961  30.134  1.00113.57           N
ANISOU 2342  N    MET A 320    16137  16107  10907  -2545   -821   -824       N
ATOM   2343  CA   MET A 320      -1.602  -4.637  30.939  1.00112.29           C
ANISOU 2343  CA   MET A 320    16054  15897  10713  -2680   -884  -1031       C
ATOM   2344  C    MET A 320      -0.233  -4.021  30.672  1.00110.91           C
ANISOU 2344  C    MET A 320    16186  15353  10603  -2797   -937  -1413       C
ATOM   2345  O    MET A 320       0.727  -4.253  31.405  1.00110.26           O
ANISOU 2345  O    MET A 320    16218  15193  10485  -2850   -980  -1647       O
ATOM   2346  CB   MET A 320      -1.567  -6.142  30.653  1.00110.71           C
ANISOU 2346  CB   MET A 320    15641  15822  10600  -3005  -1023   -866       C
ATOM   2347  CG   MET A 320      -2.918  -6.842  30.783  1.00112.10           C
ANISOU 2347  CG   MET A 320    15494  16358  10742  -2958   -987   -471       C
ATOM   2348  SD   MET A 320      -3.637  -6.876  32.442  1.00114.67           S
ANISOU 2348  SD   MET A 320    15708  17014  10848  -2615   -817   -340       S
ATOM   2349  CE   MET A 320      -2.189  -7.286  33.425  1.00113.36           C
ANISOU 2349  CE   MET A 320    15764  16691  10616  -2699   -888   -665       C
ATOM   2350  N    ALA A 321      -0.157  -3.243  29.599  1.00112.54           N
ANISOU 2350  N    ALA A 321    16514  15340  10905  -2844   -938  -1464       N
ATOM   2351  CA   ALA A 321       1.059  -2.540  29.236  1.00111.57           C
ANISOU 2351  CA   ALA A 321    16679  14861  10854  -2960   -967  -1806       C
ATOM   2352  C    ALA A 321       0.987  -1.126  29.795  1.00113.68           C
ANISOU 2352  C    ALA A 321    17175  14998  11019  -2632   -824  -1964       C
ATOM   2353  O    ALA A 321       2.016  -0.469  30.016  1.00113.56           O
ANISOU 2353  O    ALA A 321    17415  14720  11013  -2661   -822  -2290       O
ATOM   2354  CB   ALA A 321       1.208  -2.507  27.735  1.00110.30           C
ANISOU 2354  CB   ALA A 321    16542  14524  10844  -3213  -1039  -1765       C
ATOM   2355  N    GLY A 322      -0.247  -0.663  30.002  1.00161.24           N
ANISOU 2355  N    GLY A 322    23102  21207  16954  -2323   -703  -1731       N
ATOM   2356  CA   GLY A 322      -0.514   0.651  30.566  1.00163.68           C
ANISOU 2356  CA   GLY A 322    23616  21419  17157  -1962   -548  -1844       C
ATOM   2357  C    GLY A 322      -0.571   0.606  32.082  1.00165.14           C
ANISOU 2357  C    GLY A 322    23811  21777  17157  -1721   -462  -1931       C
ATOM   2358  O    GLY A 322      -0.398   1.622  32.754  1.00166.97           O
ANISOU 2358  O    GLY A 322    24279  21876  17286  -1470   -354  -2141       O
ATOM   2359  N    MET A 323      -0.810  -0.594  32.602  1.00116.12           N
ANISOU 2359  N    MET A 323    17358  15860  10902   1808    513   1767       N
ATOM   2360  CA   MET A 323      -0.869  -0.866  34.036  1.00117.41           C
ANISOU 2360  CA   MET A 323    17503  16233  10875  -1619   -446  -1809       C
ATOM   2361  C    MET A 323      -0.023   0.051  34.916  1.00118.53           C
ANISOU 2361  C    MET A 323    17968  16169  10898  -1464   -398  -2187       C
ATOM   2362  O    MET A 323       1.044  -0.331  35.391  1.00117.42           O
ANISOU 2362  O    MET A 323    17928  15945  10743  -1634   -506  -2421       O
ATOM   2363  CB   MET A 323      -0.459  -2.319  34.306  1.00115.57           C
ANISOU 2363  CB   MET A 323    17089  16159  10662  -1894   -584  -1737       C
ATOM   2364  CG   MET A 323      -1.594  -3.238  34.737  1.00116.51           C
ANISOU 2364  CG   MET A 323    16892  16672  10704  -1819   -531  -1368       C
ATOM   2365  SD   MET A 323       1.733   3.395  36.536  1.00118.72           S
ANISOU 2365  SD   MET A 323    17190  17210  10707  -1540   -416  -1399       S
ATOM   2366  CE   MET A 323      -1.086  -1.815  37.055  1.00120.26           C
ANISOU 2366  CE   MET A 323    17777  17126  10790  -1272   -323  -1806       C
ATOM   2367  N    ASP A 324      -0.533   1.243  35.171  1.00125.22           N
ANISOU 2367  N    ASP A 324    18975  16947  11657  -1130   -239  -2240       N
ATOM   2368  CA   ASP A 324       0.155   2.199  36.014  1.00126.77           C
ANISOU 2368  CA   ASP A 324    19496  16942  11728   -563   -182  -2599       C
ATOM   2369  C    ASP A 324       0.645   1.530  37.297  1.00126.95           C
ANISOU 2369  C    ASP A 324    19515  17145  11576   -964   -224  -2720       C
ATOM   2370  O    ASP A 324       1.851   1.379  37.511  1.00125.75           O
ANISOU 2370  O    ASP A 324    19506  16828  11446  -1177   -360  -3001       O
ATOM   2371  CB   ASP A 324      -0.794   3.349  36.342  1.00129.99           C
```

FIG. 13 Continued

```
ANISOU 2371  CB  ASP A 324    20012  17357  12020   -530     29  -2558      C
ATOM   2372  CG  ASP A 324    -0.073   4.573  36.805  1.00131.62            C
ANISOU 2372  CG  ASP A 324    20612  17241  12157   -396     82  -2945      C
ATOM   2373  OD1 ASP A 324     0.331   4.608  37.980  1.00132.81            O
ANISOU 2373  OD1 ASP A 324    20890  17449  12122   -291    100  -3156      O
ATOM   2374  OD2 ASP A 324     0.083   5.502  35.993  1.00131.90            O
ANISOU 2374  OD2 ASP A 324    20838  16960  12317   -400    101  -3037      O
ATOM   2375  N   VAL A 325    -0.301   1.100  38.127  1.00124.00            N
ANISOU 2375  N   VAL A 325    18961  17123  11029   -731   -111  -2491      N
ATOM   2376  CA  VAL A 325     0.012   0.480  39.412  1.00124.65            C
ANISOU 2376  CA  VAL A 325    19042  17412  10907   -689   -130  -2562      C
ATOM   2377  C   VAL A 325    -1.019  -0.561  39.838  1.00125.20            C
ANISOU 2377  C   VAL A 325    18785  17900  10885   -620    -63  -2179      C
ATOM   2378  O   VAL A 325    -2.167  -0.233  40.136  1.00127.53            O
ANISOU 2378  O   VAL A 325    18973  18408  11073   -316    128  -1973      O
ATOM   2379  CB  VAL A 325     0.104   1.529  40.522  1.00127.63            C
ANISOU 2379  CB  VAL A 325    19708  17737  11049   -356      3  -2832      C
ATOM   2380  CG1 VAL A 325    -0.813   2.691  40.213  1.00129.89            C
ANISOU 2380  CG1 VAL A 325    20074  17948  11331    -31    201  -2777      C
ATOM   2381  CG2 VAL A 325    -0.241   0.907  41.866  1.00129.32            C
ANISOU 2381  CG2 VAL A 325    19840  18302  10994   -183     70  -2744      C
ATOM   2382  N   LEU A 326    -0.599  -1.821  39.873  1.00123.48            N
ANISOU 2382  N   LEU A 326    18407  17794  10715   -902   -215  -2080      N
ATOM   2383  CA  LEU A 326    -1.501  -2.897  40.243  1.00123.97            C
ANISOU 2383  CA  LEU A 326    18165  18229  10709   -891   -166  -1711      C
ATOM   2384  C   LEU A 326    -1.550  -3.021  41.738  1.00126.24            C
ANISOU 2384  C   LEU A 326    18520  18742  10702   -666    -75  -1753      C
ATOM   2385  O   LEU A 326    -0.513  -2.973  42.400  1.00126.09            O
ANISOU 2385  O   LEU A 326    18718  18607  10583   -709   -175  -2042      O
ATOM   2386  CB  LEU A 326    -1.037  -4.221  39.647  1.00121.16            C
ANISOU 2386  CB  LEU A 326    17631  17874  10529  -1289   -366  -1583      C
ATOM   2387  CG  LEU A 326    -1.871  -5.448  40.018  1.00121.64            C
ANISOU 2387  CG  LEU A 326    17390  18290  10537  -1336   -337  -1202      C
ATOM   2388  CD1 LEU A 326    -1.944  -6.415  38.854  1.00119.23            C
ANISOU 2388  CD1 LEU A 326    16869  17952  10483  -1691   -481   -995      C
ATOM   2389  CD2 LEU A 326    -1.327  -6.139  41.253  1.00122.24            C
ANISOU 2389  CD2 LEU A 326    17528  18499  10421  -1331   -382  -1261      C
ATOM   2390  N   CYS A 327    -2.757  -3.156  42.273  1.00137.02            N
ANISOU 2390  N   CYS A 327    19698  20440  11923   -423    116  -1465      N
ATOM   2391  CA  CYS A 327    -2.913  -3.399  43.699  1.00139.38            C
ANISOU 2391  CA  CYS A 327    20036  21001  11922   -216    221  -1453      C
ATOM   2392  C   CYS A 327    -3.377  -4.842  43.893  1.00138.95            C
ANISOU 2392  C   CYS A 327    19680  21249  11866   -394    189  -1088      C
ATOM   2393  O   CYS A 327    -4.258  -5.328  43.173  1.00138.55            O
ANISOU 2393  O   CYS A 327    19337  21338  11967   -487    223   -760      O
ATOM   2394  CB  CYS A 327    -3.859  -2.388  44.350  1.00142.94            C
ANISOU 2394  CB  CYS A 327    20544  21603  12165    230    495  -1440      C
ATOM   2395  SG  CYS A 327    -5.530  -2.418  43.714  1.00144.33            S
ANISOU 2395  SG  CYS A 327    20342  22054  12443    384    693   -993      S
ATOM   2396  N   SER A 328    -2.760  -5.524  44.855  1.00132.61            N
ANISOU 2396  N   SER A 328    18957  20536  10893   -451    111  -1147      N
ATOM   2397  CA  SER A 328    -3.034  -6.932  45.087  1.00132.23            C
ANISOU 2397  CA  SER A 328    18671  20727  10844   -645     60   -824      C
ATOM   2398  C   SER A 328    -3.626  -7.291  46.432  1.00135.28            C
ANISOU 2398  C   SER A 328    19016  21470  10914   -423    228   -648      C
ATOM   2399  O   SER A 328    -3.518  -6.547  47.404  1.00137.59            O
ANISOU 2399  O   SER A 328    19526  21814  10938   -133    343   -848      O
ATOM   2400  CB  SER A 328    -1.753  -7.734  44.934  1.00129.64            C
ANISOU 2400  CB  SER A 328    18435  20196  10627   -969   -212   -977      C
ATOM   2401  OG  SER A 328    -1.818  -8.911  45.722  1.00130.36            O
ANISOU 2401  OG  SER A 328    18422  20518  10589  -1045   -240   -754      O
ATOM   2402  N   ASP A 329    -4.231  -8.474  46.459  1.00133.78            N
ANISOU 2402  N   ASP A 329    18554  21518  10757   -582    237   -271      N
ATOM   2403  CA  ASP A 329    -4.783  -9.061  47.662  1.00136.54            C
ANISOU 2403  CA  ASP A 329    18832  22218  10829   -443    384    -42      C
ATOM   2404  C   ASP A 329    -3.664  -9.709  48.435  1.00136.03            C
ANISOU 2404  C   ASP A 329    18967  22089  10630   -560    202   -190      C
ATOM   2405  O   ASP A 329    -2.700 -10.190  47.856  1.00133.26            O
ANISOU 2405  O   ASP A 329    18671  21486  10476   -841    -46   -317      O
```

FIG. 13 Continued

```
ATOM   2406  CB  ASP A 329      -5.799 -10.133  47.300  1.00136.77           C
ANISOU 2406  CB  ASP A 329    18492  22494  10982    -623    442    425      C
ATOM   2407  CG  ASP A 329       7.009   9.568  46.623  1.00137.79           C
ANISOU 2407  CG  ASP A 329    18378  22752  11225    -493    623    616      C
ATOM   2408  OD1 ASP A 329      -7.630 -10.300  45.828  1.00136.96           O
ANISOU 2408  OD1 ASP A 329    17978  22723  11337    -729    585    918      O
ATOM   2409  OD2 ASP A 329      -7.333  -8.391  46.887  1.00139.60           O
ANISOU 2409  OD2 ASP A 329    18714  23000  11328     153    796    461      O
ATOM   2410  N   LYS A 330      -3.810  -9.733  49.748  1.00139.78           N
ANISOU 2410  N   LYS A 330    19544  22806  10759    -334    329   -165      N
ATOM   2411  CA  LYS A 330      -2.822 -10.333  50.627  1.00139.92           C
ANISOU 2411  CA  LYS A 330    19755  22810  10598    -402    164   -282      C
ATOM   2412  C   LYS A 330      -2.645 -11.830  50.343  1.00138.32           C
ANISOU 2412  C   LYS A 330    19376  22620  10561    -743     -2      4      C
ATOM   2413  O   LYS A 330      -1.761 -12.218  49.581  1.00135.39           O
ANISOU 2413  O   LYS A 330    19030  21970  10441   -1012   -247   -124      O
ATOM   2414  CB  LYS A 330      -3.239 -10.115  52.082  1.00143.82           C
ANISOU 2414  CB  LYS A 330    20367  23616  10663     -81    368   -243      C
ATOM   2415  CG  LYS A 330      -2.133 -10.160  53.103  1.00144.64           C
ANISOU 2415  CG  LYS A 330    20774  23678  10505     -32    212   -508      C
ATOM   2416  CD  LYS A 330      -2.726 -10.495  54.445  1.00148.40           C
ANISOU 2416  CD  LYS A 330    21275  24529  10582     186    405   -298      C
ATOM   2417  CE  LYS A 330      -3.605 -11.723  54.322  1.00148.70           C
ANISOU 2417  CE  LYS A 330    20994  24801  10703      17    493    209      C
ATOM   2418  NZ  LYS A 330      -2.883 -12.845  53.667  1.00145.67           N
ANISOU 2418  NZ  LYS A 330    20531  24217  10601    -363    208    301      N
ATOM   2419  N   THR A 331       3.492 -12.667  50.936  1.00148.72           N
ANISOU 2419  N   THR A 331    20516  24251  11741    -733    139    392      N
ATOM   2420  CA  THR A 331      -3.366 -14.121  50.789  1.00147.74           C
ANISOU 2420  CA  THR A 331    20250  24137  11747   -1045     -4    681      C
ATOM   2421  C   THR A 331      -3.422 -14.635  49.341  1.00144.63           C
ANISOU 2421  C   THR A 331    19650  23534  11771   -1380   -141    784      C
ATOM   2422  O   THR A 331      -3.840 -13.915  48.434  1.00143.58           O
ANISOU 2422  O   THR A 331    19421  23316  11816   -1364    -84    721      O
ATOM   2423  CB  THR A 331      -4.446 -14.843  51.595  1.00150.87           C
ANISOU 2423  CB  THR A 331    20467  24916  11940    -983    214   1112      C
ATOM   2424  OG1 THR A 331      -4.878 -13.995  52.663  1.00154.13           O
ANISOU 2424  OG1 THR A 331    21000  25575  11988    -607    453   1039      O
ATOM   2425  CG2 THR A 331      -3.902 -16.159  52.146  1.00151.06           C
ANISOU 2425  CG2 THR A 331    20537  24951  11907   -1181     57   1290      C
ATOM   2426  N   GLY A 332      -2.981 -15.879  49.139  1.00134.98           N
ANISOU 2426  N   GLY A 332    18376  22218  10690   -1674   -325    938      N
ATOM   2427  CA  GLY A 332      -3.043 -16.546  47.845  1.00132.39           C
ANISOU 2427  CA  GLY A 332    17865  21706  10733   -2012   -458   1059      C
ATOM   2428  C   GLY A 332      -2.479 -15.803  46.652  1.00129.42           C
ANISOU 2428  C   GLY A 332    17542  21017  10615   -2098   -583    747      C
ATOM   2429  O   GLY A 332      -2.763 -16.134  45.500  1.00127.63           O
ANISOU 2429  O   GLY A 332    17148  20676  10671   -2336   -644    852      O
ATOM   2430  N   THR A 333      -1.671 -14.792  46.926  1.00130.07           N
ANISOU 2430  N   THR A 333    17868  20959  10594   -1913   -622    360      N
ATOM   2431  CA  THR A 333      -1.080 -13.996  45.867  1.00127.54           C
ANISOU 2431  CA  THR A 333    17626  20336  10497   -1983   -726     49      C
ATOM   2432  C   THR A 333       0.125 -13.255  46.446  1.00127.41           C
ANISOU 2432  C   THR A 333    17910  20155  10346   -1845   -831   -373      C
ATOM   2433  O   THR A 333       1.228 -13.807  46.535  1.00126.20           O
ANISOU 2433  O   THR A 333    17863  19838  10248   -1994  -1044   -523      O
ATOM   2434  CB  THR A 333      -2.118 -13.015  45.250  1.00128.04           C
ANISOU 2434  CB  THR A 333    17568  20469  10611   -1839   -533    102      C
ATOM   2435  OG1 THR A 333      -3.189 -13.759  44.664  1.00128.21           O
ANISOU 2435  OG1 THR A 333    17289  20650  10776   -2001   -467    492      O
ATOM   2436  CG2 THR A 333      -1.492 -12.166  44.172  1.00125.64           C
ANISOU 2436  CG2 THR A 333    17372  19842  10522   -1910   -634   -210      C
ATOM   2437  N   LEU A 334      -0.084 -12.018  46.867  1.00128.23           N
ANISOU 2437  N   LEU A 334    18148  20303  10270   -1557   -685   -567      N
ATOM   2438  CA  LEU A 334       0.989 -11.264  47.476  1.00128.56           C
ANISOU 2438  CA  LEU A 334    18479  20203  10164   -1427   -778   -972      C
ATOM   2439  C   LEU A 334       1.659 -12.158  48.519  1.00129.53           C
ANISOU 2439  C   LEU A 334    18688  20426  10103   -1452   -912   -946      C
ATOM   2440  O   LEU A 334       2.762 -11.875  48.973  1.00129.51           O
```

FIG. 13 Continued

```
ANISOU 2440  O   LEU A 334    18895  20295  10017  -1428  -1069  -1262       O
ATOM   2441  CB  LEU A 334       0.435  -9.994  48.126  1.00131.11           C
ANISOU 2441  CB  LEU A 334    18938  20644  10235  -1069   -558  -1106       C
ATOM   2442  CG  LEU A 334       1.394  -8.848  48.443  1.00131.43           C
ANISOU 2442  CG  LEU A 334    19286  20475  10176   -937   -626  -1573       C
ATOM   2443  CD1 LEU A 334       1.837  -8.185  47.159  1.00128.87           C
ANISOU 2443  CD1 LEU A 334    18987  19815  10163  -1092   -708  -1789       C
ATOM   2444  CD2 LEU A 334       0.728  -7.837  49.360  1.00134.72           C
ANISOU 2444  CD2 LEU A 334    19843  21069  10277   -557   -388  -1647       C
ATOM   2445  N   THR A 335       0.993 -13.242  48.898  1.00129.55           N
ANISOU 2445  N   THR A 335    18524  20658  10041  -1505   -855   -561       N
ATOM   2446  CA  THR A 335       1.566 -14.160  49.865  1.00130.67           C
ANISOU 2446  CA  THR A 335    18747  20895  10008  -1528   -980   -489       C
ATOM   2447  C   THR A 335       1.210 -15.593  49.531  1.00130.02           C
ANISOU 2447  C   THR A 335    18455  20860  10089  -1780  -1031   -103       C
ATOM   2448  O   THR A 335       0.321 -15.848  48.715  1.00129.28           O
ANISOU 2448  O   THR A 335    18139  20794  10186  -1907   -931    141       O
ATOM   2449  CB  THR A 335       1.089 -13.854  51.264  1.00134.26           C
ANISOU 2449  CB  THR A 335    19314  21657  10044  -1221   -807   -428       C
ATOM   2450  OG1 THR A 335      -0.320 -14.065  51.328  1.00135.91           O
ANISOU 2450  OG1 THR A 335    19310  22136  10192  -1149   -547    -49       O
ATOM   2451  CG2 THR A 335       1.377 -12.420  51.601  1.00135.22           C
ANISOU 2451  CG2 THR A 335    19659  21720   9997   -968   -745   -815       C
ATOM   2452  N   LEU A 336       1.890 -16.518  50.203  1.00129.68           N
ANISOU 2452  N   LEU A 336    18489  20827   9955  -1844  -1190    -45       N
ATOM   2453  CA  LEU A 336       1.805 -17.953  49.918  1.00129.08           C
ANISOU 2453  CA  LEU A 336    18269  20728  10048  -2100  -1285    278       C
ATOM   2454  C   LEU A 336       0.495 -18.706  50.235  1.00131.15           C
ANISOU 2454  C   LEU A 336    18336  21270  10224  -2123  -1083    758       C
ATOM   2455  O   LEU A 336       0.193 -19.717  49.608  1.00130.27           O
ANISOU 2455  O   LEU A 336    18061  21096  10338  -2382  -1129   1021       O
ATOM   2456  CB  LEU A 336       2.991 -18.660  50.584  1.00129.37           C
ANISOU 2456  CB  LEU A 336    18468  20677  10010  -2131  -1525    183       C
ATOM   2457  CG  LEU A 336       3.507 -19.942  49.928  1.00127.64           C
ANISOU 2457  CG  LEU A 336    18167  20249  10083  -2426  -1725    318       C
ATOM   2458  CD1 LEU A 336       4.949 -20.188  50.334  1.00127.36           C
ANISOU 2458  CD1 LEU A 336    18306  20054  10031  -2417  -1992     61       C
ATOM   2459  CD2 LEU A 336       2.632 -21.142  50.262  1.00129.36           C
ANISOU 2459  CD2 LEU A 336    18255  20637  10258  -2526  -1634    797       C
ATOM   2460  N   ASN A 337      -0.282 -18.221  51.189  1.00134.71           N
ANISOU 2460  N   ASN A 337    18805  22026  10353  -1863   -854    868       N
ATOM   2461  CA  ASN A 337      -1.473 -18.945  51.610  1.00137.10           C
ANISOU 2461  CA  ASN A 337    18922  22621  10549  -1880   -652   1326       C
ATOM   2462  C   ASN A 337      -1.169 -20.355  52.110  1.00137.99           C
ANISOU 2462  C   ASN A 337    19053  22742  10635  -2048   -776   1596       C
ATOM   2463  O   ASN A 337      -1.620 -21.354  51.558  1.00137.54           O
ANISOU 2463  O   ASN A 337    18817  22649  10793  -2309   -792   1900       O
ATOM   2464  CB  ASN A 337      -2.523 -19.037  50.519  1.00136.11           C
ANISOU 2464  CB  ASN A 337    18506  22514  10697  -2060   -533   1551       C
ATOM   2465  CG  ASN A 337      -3.519 -20.146  50.794  1.00136.20           C
ANISOU 2465  CG  ASN A 337    18560  23009  10941  -2191   -406   2042       C
ATOM   2466  OD1 ASN A 337      -4.009 -20.285  51.916  1.00141.36           O
ANISOU 2466  OD1 ASN A 337    18981  23699  11031  -2021   -235   2243       O
ATOM   2467  ND2 ASN A 337      -3.784 -20.972  49.786  1.00136.61           N
ANISOU 2467  ND2 ASN A 337    18170  22674  11063  -2516   -494   2235       N
ATOM   2468  N   LYS A 338      -0.370 -20.433  53.152  1.00133.84           N
ANISOU 2468  N   LYS A 338    16848  17927  16076   1308    727  -2117       N
ATOM   2469  CA  LYS A 338      -0.145 -21.700  53.807  1.00134.48           C
ANISOU 2469  CA  LYS A 338    16919  17931  16245    976    467  -2000       C
ATOM   2470  C   LYS A 338       0.100 -21.361  55.259  1.00135.71           C
ANISOU 2470  C   LYS A 338    17358  18005  16200    666    493  -1906       C
ATOM   2471  O   LYS A 338       1.057 -20.659  55.606  1.00135.33           O
ANISOU 2471  O   LYS A 338    17517  17788  16116    637    478  -1864       O
ATOM   2472  CB  LYS A 338       1.022 -22.466  53.201  1.00133.18           C
ANISOU 2472  CB  LYS A 338    16683  17583  16337    980    159  -1932       C
ATOM   2473  CG  LYS A 338       1.104 -23.925  53.649  1.00133.74           C
ANISOU 2473  CG  LYS A 338    16695  17602  16518    684   -129  -1836       C
ATOM   2474  CD  LYS A 338       0.033 -24.763  52.986  1.00133.99           C
ANISOU 2474  CD  LYS A 338    16442  17810  16659    785   -154  -1902       C
```

FIG. 13 Continued

```
ATOM   2475  CE  LYS A 338       0.357 -26.268  53.133  1.00134.17           C
ANISOU 2475  CE  LYS A 338    16385  17742  16853    550   -503  -1807       C
ATOM   2476  NZ  LYS A 338      -0.727 -27.150  52.624  1.00134.70           N
ANISOU 2476  NZ  LYS A 338    16183  17968  17030    608   -545  -1860       N
ATOM   2477  N   LEU A 339      -0.816 -21.840  56.091  1.00137.27           N
ANISOU 2477  N   LEU A 339    17554  18335  16268    452    540  -1876       N
ATOM   2478  CA  LEU A 339      -0.615 -21.566  57.515  1.00138.67           C
ANISOU 2478  CA  LEU A 339    17975  18483  16230    181    586  -1792       C
ATOM   2479  C   LEU A 339      -0.261 -22.722  58.347  1.00139.27           C
ANISOU 2479  C   LEU A 339    18117  18416  16385   -177    320  -1650       C
ATOM   2480  O   LEU A 339      -0.330 -23.888  57.942  1.00139.12           O
ANISOU 2480  O   LEU A 339    17919  18393  16547   -253    127  -1619       O
ATOM   2481  CB  LEU A 339      -2.239 -21.252  57.962  1.00140.13           C
ANISOU 2481  CB  LEU A 339    18126  18937  16181    191    835  -1844       C
ATOM   2482  CG  LEU A 339      -3.109 -20.579  56.906  1.00139.56           C
ANISOU 2482  CG  LEU A 339    17889  19066  16072    548   1068  -2009       C
ATOM   2483  CD1 LEU A 339      -4.355 -21.395  56.728  1.00140.47           C
ANISOU 2483  CD1 LEU A 339    17769  19407  16195    521   1110  -2043       C
ATOM   2484  CD2 LEU A 339      -3.428 -19.126  57.249  1.00139.90           C
ANISOU 2484  CD2 LEU A 339    18117  19199  15840    700   1334  -2086       C
ATOM   2485  N   SER A 340       0.298 -22.376  59.504  1.00140.88           N
ANISOU 2485  N   SER A 340    18583  18495  16450   -381    304  -1570       N
ATOM   2486  CA  SER A 340       0.780 -23.347  60.476  1.00141.63           C
ANISOU 2486  CA  SER A 340    18783  18458  16570   -723     86  -1442       C
ATOM   2487  C   SER A 340       1.038 -22.597  61.763  1.00142.60           C
ANISOU 2487  C   SER A 340    19193  18518  16472   -858    177  -1393       C
ATOM   2488  O   SER A 340       1.706  21.560  61.764  1.00141.96           O
ANISOU 2488  O   SER A 340    19270  18324  16343   -732    240  -1431       O
ATOM   2489  CB  SER A 340       2.023 -24.071  59.984  1.00140.25           C
ANISOU 2489  CB  SER A 340    18596  18058  16634   -774   -212  -1403       C
ATOM   2490  OG  SER A 340       1.668 -25.053  59.025  1.00139.73           O
ANISOU 2490  OG  SER A 340    18264  18064  16763   -706   -345  -1424       O
ATOM   2491  N   VAL A 341       0.474 -23.123  62.844  1.00147.21           N
ANISOU 2491  N   VAL A 341    19832  19179  16922  -1102    182  -1308       N
ATOM   2492  CA  VAL A 341       0.492 -22.466  64.141  1.00148.41           C
ANISOU 2492  CA  VAL A 341    20234  19319  16837  -1211    283  -1260       C
ATOM   2493  C   VAL A 341       1.483 -23.108  65.105  1.00148.65           C
ANISOU 2493  C   VAL A 341    20455  19122  16905  -1488     63  -1154       C
ATOM   2494  O   VAL A 341       1.826 -24.277  64.969  1.00148.40           O
ANISOU 2494  O   VAL A 341    20345  19001  17040  -1658   -154  -1096       O
ATOM   2495  CB  VAL A 341      -0.938 -22.451  64.751  1.00150.25           C
ANISOU 2495  CB  VAL A 341    20402  19840  16846  -1252    483  -1239       C
ATOM   2496  CG1 VAL A 341      -0.986 -21.634  66.017  1.00151.46           C
ANISOU 2496  CG1 VAL A 341    20804  20013  16732  -1300    600  -1202       C
ATOM   2497  CG2 VAL A 341      -1.925 -21.913  63.754  1.00149.94           C
ANISOU 2497  CG2 VAL A 341    20167  20031  16773   -978    690  -1361       C
ATOM   2498  N   ASP A 342       1.950 -22.313  66.064  1.00145.54           N
ANISOU 2498  N   ASP A 342    20317  18630  16352  -1516    113  -1138       N
ATOM   2499  CA  ASP A 342       2.884 -22.751  67.101  1.00145.84           C
ANISOU 2499  CA  ASP A 342    20570  18451  16391  -1752    -66  -1056       C
ATOM   2500  C   ASP A 342       2.223 -22.790  68.497  1.00147.82           C
ANISOU 2500  C   ASP A 342    20947  18816  16404  -1908     28   -972       C
ATOM   2501  O   ASP A 342       1.022 -22.590  68.608  1.00148.98           O
ANISOU 2501  O   ASP A 342    20989  19222  16394  -1850    216   -968       O
ATOM   2502  CB  ASP A 342       4.161 -21.886  67.093  1.00144.68           C
ANISOU 2502  CB  ASP A 342    20626  18056  16289  -1660   -128  -1104       C
ATOM   2503  CG  ASP A 342       3.909 -20.430  66.685  1.00144.40           C
ANISOU 2503  CG  ASP A 342    20621  18092  16151  -1377     86  -1197       C
ATOM   2504  OD1 ASP A 342       4.787 -19.580  66.941  1.00143.94           O
ANISOU 2504  OD1 ASP A 342    20756  17851  16083  -1314     67  -1224       O
ATOM   2505  OD2 ASP A 342       2.851 -20.124  66.108  1.00144.64           O
ANISOU 2505  OD2 ASP A 342    20489  18356  16113  -1216    268  -1248       O
ATOM   2506  N   LYS A 343       2.986 -23.060  69.556  1.00147.59           N
ANISOU 2506  N   LYS A 343    21134  18606  16340  -2093   -100   -907       N
ATOM   2507  CA  LYS A 343       2.407 -23.127  70.908  1.00149.50           C
ANISOU 2507  CA  LYS A 343    21494  18954  16357  -2224    -19   -818       C
ATOM   2508  C   LYS A 343       2.503 -21.865  71.739  1.00150.09           C
ANISOU 2508  C   LYS A 343    21792  19020  16215  -2089    112   -849       C
ATOM   2509  O   LYS A 343       3.014 -21.877  72.859  1.00150.76           O
```

FIG. 13 Continued

```
ANISOU 2509  O   LYS A 343     22090 18980 16213 -2196    46  -800        O
ATOM   2510  CB  LYS A 343      2.937 -24.322 71.682  1.00149.98          C
ANISOU 2510  CB  LYS A 343     21638 18867 16479 -2511  -222  -716        C
ATOM   2511  CG  LYS A 343      1.873 -25.365 71.900  1.00151.43          C
ANISOU 2511  CG  LYS A 343     21648 19255 16635 -2684  -201  -610        C
ATOM   2512  CD  LYS A 343      0.628 -25.080 71.058  1.00151.73          C
ANISOU 2512  CD  LYS A 343     21432 19578 16641 -2524   -11  -649        C
ATOM   2513  CE  LYS A 343      0.847 -25.301 69.561  1.00150.00          C
ANISOU 2513  CE  LYS A 343     21015 19314 16663 -2406   -94  -739        C
ATOM   2514  NZ  LYS A 343      1.704 -26.472 69.261  1.00149.10          N
ANISOU 2514  NZ  LYS A 343     20880 18992 16781 -2586  -377  -704        N
ATOM   2515  N   ASN A 344      1.949 -20.795 71.182  1.00151.43          N
ANISOU 2515  N   ASN A 344     21909 19336 16291 -1841   296  -935        N
ATOM   2516  CA  ASN A 344      1.983 -19.468 71.764  1.00151.86          C
ANISOU 2516  CA  ASN A 344     22159 19395 16144 -1664   417  -984        C
ATOM   2517  C   ASN A 344      0.576 -18.899 71.731  1.00152.97          C
ANISOU 2517  C   ASN A 344     22193 19878 16052 -1509   654 -1006        C
ATOM   2518  O   ASN A 344      0.373 -17.700 71.553  1.00152.84          O
ANISOU 2518  O   ASN A 344     22244 19925 15903 -1278   785 -1094        O
ATOM   2519  CB  ASN A 344      2.912 -18.590 70.934  1.00150.18          C
ANISOU 2519  CB  ASN A 344     22008 18982 16071 -1485   383 -1090        C
ATOM   2520  CG  ASN A 344      3.639 -19.376 69.847  1.00148.55          C
ANISOU 2520  CG  ASN A 344     21659 18621 16161 -1547   222 -1104        C
ATOM   2521  OD1 ASN A 344      3.062 -20.261 69.217  1.00148.45          O
ANISOU 2521  OD1 ASN A 344     21424 18738 16241 -1606   210 -1082        O
ATOM   2522  ND2 ASN A 344      4.905 -19.045 69.614  1.00147.30          N
ANISOU 2522  ND2 ASN A 344     21623 18192 16152 -1522    89 -1140        N
ATOM   2523  N   LEU A 345     -0.395 -19.793 71.865  1.00152.42          N
ANISOU 2523  N   LEU A 345     21951 20027 15936 -1641   700  -928        N
ATOM   2524  CA  LEU A 345     -1.802 -19.442 71.866  1.00153.63          C
ANISOU 2524  CA  LEU A 345     21977 20532 15863 -1526   917  -938        C
ATOM   2525  C   LEU A 345     -2.363 -19.606 73.270  1.00155.69          C
ANISOU 2525  C   LEU A 345     22334 20944 15876 -1639   963  -817        C
ATOM   2526  O   LEU A 345     -2.158 -20.638 73.908  1.00156.40          O
ANISOU 2526  O   LEU A 345     22430 20963 16031 -1882   845  -697        O
ATOM   2527  CB  LEU A 345     -2.544 -20.372 70.926  1.00153.47          C
ANISOU 2527  CB  LEU A 345     21660 20664 15988 -1586   936  -934        C
ATOM   2528  CG  LEU A 345      2.589  21.780 71.500  1.00154.45          C
ANISOU 2528  CG  LEU A 345     21718 20764 16202 -1892   799  -786        C
ATOM   2529  CD1 LEU A 345     -3.966 -22.035 72.073  1.00156.49          C
ANISOU 2529  CD1 LEU A 345     21855 21360 16244 -1947   957  -703        C
ATOM   2530  CD2 LEU A 345     -2.232 -22.811 70.454  1.00153.22          C
ANISOU 2530  CD2 LEU A 345     21375 20484 16359 -1989   638  -796        C
ATOM   2531  N   VAL A 346     -3.066 -18.585 73.750  1.00158.94          N
ANISOU 2531  N   VAL A 346     22825 21570 15996 -1452  1130  -850        N
ATOM   2532  CA  VAL A 346     -3.673 -18.621 75.079  1.00160.98          C
ANISOU 2532  CA  VAL A 346     23168 22013 15985 -1511  1188  -735        C
ATOM   2533  C   VAL A 346     -5.053 -19.312 75.052  1.00162.45          C
ANISOU 2533  C   VAL A 346     23110 22551 16061 -1595  1319  -655        C
ATOM   2534  O   VAL A 346     -5.573 -19.643 73.983  1.00161.83          O
ANISOU 2534  O   VAL A 346     22807 22575 16107  1578  1374   711        O
ATOM   2535  CB  VAL A 346     -3.733 -17.211 75.715  1.00161.46          C
ANISOU 2535  CB  VAL A 346     23443 22140 15764 -1262  1274  -799        C
ATOM   2536  CG1 VAL A 346     -2.375 -16.826 76.301  1.00160.79          C
ANISOU 2536  CG1 VAL A 346     23625 21702 15764 -1265  1110  -812        C
ATOM   2537  CG2 VAL A 346     -4.182 -16.188 74.689  1.00160.54          C
ANISOU 2537  CG2 VAL A 346     23266 22148 15585  -997  1415  -955        C
ATOM   2538  N   GLU A 347     -5.644 -19.522 76.224  1.00163.51          N
ANISOU 2538  N   GLU A 347     23284 22873 15968 -1673  1367  -523        N
ATOM   2539  CA  GLU A 347     -6.887 -20.278 76.330  1.00165.13          C
ANISOU 2539  CA  GLU A 347     23261 23400 16081 -1791  1475  -416        C
ATOM   2540  C   GLU A 347     -7.815 -19.678 77.389  1.00167.14          C
ANISOU 2540  C   GLU A 347     23575 23983 15948 -1678  1625  -347        C
ATOM   2541  O   GLU A 347     -7.712 -19.984 78.573  1.00168.53          O
ANISOU 2541  O   GLU A 347     23861 24164 16009 -1784  1580  -205        O
ATOM   2542  CB  GLU A 347     -6.554 -21.747 76.643  1.00165.64          C
ANISOU 2542  CB  GLU A 347     23253 23319 16362 -2119  1322  -263        C
ATOM   2543  CG  GLU A 347     -6.116 -22.077 78.104  1.00166.97          C
ANISOU 2543  CG  GLU A 347     23616 23401 16425 -2259  1238  -111        C
```

FIG. 13 Continued

```
ATOM   2544  CD  GLU A 347      -4.799 -21.419  78.589  1.00165.89           C
ANISOU 2544  CD  GLU A 347    23779  22940  16311  -2174   1112   -178       C
ATOM   2545  OE1 GLU A 347      -4.275 -21.860  79.643  1.00166.66           O
ANISOU 2545  OE1 GLU A 347    24028  22906  16388  -2305   1013    -72       O
ATOM   2546  OE2 GLU A 347      -4.291 -20.471  77.948  1.00164.34           O
ANISOU 2546  OE2 GLU A 347    23669  22620  16154  -1975   1113   -333       O
ATOM   2547  N   VAL A 348      -8.737 -18.828  76.959  1.00228.57           N
ANISOU 2547  N   VAL A 348    31282  32051  23513   1450   1801    449       N
ATOM   2548  CA  VAL A 348      -9.590 -18.101  77.904  1.00230.33           C
ANISOU 2548  CA  VAL A 348    31578  32603  23334  -1294   1934   -405       C
ATOM   2549  C   VAL A 348     -10.621 -18.932  78.696  1.00232.69           C
ANISOU 2549  C   VAL A 348    31721  33217  23474  -1460   2010   -212       C
ATOM   2550  O   VAL A 348     -11.229 -18.425  79.644  1.00234.32           O
ANISOU 2550  O   VAL A 348    31999  33689  23342  -1344   2055   -143       O
ATOM   2551  CB  VAL A 348     -10.253 -16.870  77.235  1.00229.78           C
ANISOU 2551  CB  VAL A 348    31503  32757  23048   -981   2093   -586       C
ATOM   2552  CG1 VAL A 348      -9.414 -15.622  77.472  1.00228.84           C
ANISOU 2552  CG1 VAL A 348    31668  32441  22838   -753   2033   -698       C
ATOM   2553  CG2 VAL A 348     -10.426 -17.113  75.752  1.00228.26           C
ANISOU 2553  CG2 VAL A 348    31103  32534  23091   -970   2139   -717       C
ATOM   2554  N   PHE A 349     -10.808 -20.194  78.316  1.00170.29           N
ANISOU 2554  N   PHE A 349    23605  25287  15812  -1724   1970   -118       N
ATOM   2555  CA  PHE A 349     -11.741 -21.081  79.020  1.00172.61           C
ANISOU 2555  CA  PHE A 349    23733  25852  15998  -1915   2032     84       C
ATOM   2556  C   PHE A 349     -11.024 -21.727  80.202  1.00173.54           C
ANISOU 2556  C   PHE A 349    24004  25779  16155  -2109   1894    263       C
ATOM   2557  O   PHE A 349     -10.348 -21.034  80.967  1.00173.39           O
ANISOU 2557  O   PHE A 349    24238  25634  16007  -1980   1841    248       O
ATOM   2558  CB  PHE A 349     -12.289 -22.150  78.066  1.00172.56           C
ANISOU 2558  CB  PHE A 349    23426  25895  16245  -2108   2038    103       C
ATOM   2559  CG  PHE A 349     -13.497 -22.893  78.591  1.00175.04           C
ANISOU 2559  CG  PHE A 349    23525  26558  16424  -2266   2143    287       C
ATOM   2560  CD1 PHE A 349     -14.654 -22.213  78.947  1.00176.52           C
ANISOU 2560  CD1 PHE A 349    23652  27173  16246  -2093   2340    293       C
ATOM   2561  CD2 PHE A 349     -13.484 -24.275  78.694  1.00175.91           C
ANISOU 2561  CD2 PHE A 349    23489  26574  16775  -2588   2039    453       C
ATOM   2562  CE1 PHE A 349     -15.764 -22.900  79.415  1.00178.88           C
ANISOU 2562  CE1 PHE A 349    23740  27804  16423  -2242   2438    472       C
ATOM   2563  CE2 PHE A 349     -14.588 -24.964  79.158  1.00178.30           C
ANISOU 2563  CE2 PHE A 349    23584  27191  16971  -2743   2134    634       C
ATOM   2564  CZ  PHE A 349     -15.729 -24.276  79.519  1.00179.81           C
ANISOU 2564  CZ  PHE A 349    23706  27812  16800  -2572   2339    647       C
ATOM   2565  N   CYS A 350     -11.178 -23.045  80.351  1.00175.20           N
ANISOU 2565  N   CYS A 350    24061  25965  16542  -2408   1832    427       N
ATOM   2566  CA  CYS A 350     -10.479 -23.798  81.394  1.00176.02           C
ANISOU 2566  CA  CYS A 350    24300  25868  16710  -2613   1695    594       C
ATOM   2567  C   CYS A 350     -10.826 -25.287  81.375  1.00177.19           C
ANISOU 2567  C   CYS A 350    24240  26023  17060  -2948   1637    769       C
ATOM   2568  O   CYS A 350     -11.745 -25.717  82.067  1.00179.48           O
ANISOU 2568  O   CYS A 350    24407  26600  17186  -3044   1735    950       O
ATOM   2569  CB  CYS A 350     -10.787 -23.216  82.771  1.00177.83           C
ANISOU 2569  CB  CYS A 350    24680  26306  16580  -2482   1776    705       C
ATOM   2570  SG  CYS A 350      -9.359 -23.152  83.858  1.00177.37           S
ANISOU 2570  SG  CYS A 350    24963  25872  16558  -2491   1598    736       S
ATOM   2571  N   LYS A 351     -10.079 -26.057  80.583  1.00174.78           N
ANISOU 2571  N   LYS A 351    23897  25405  17108  -3118   1469    717       N
ATOM   2572  CA  LYS A 351     -10.259 -27.510  80.455  1.00175.64           C
ANISOU 2572  CA  LYS A 351    23824  25460  17452  -3440   1367    864       C
ATOM   2573  C   LYS A 351      -9.710 -28.010  79.117  1.00173.54           C
ANISOU 2573  C   LYS A 351    23456  24939  17544  -3507   1216    729       C
ATOM   2574  O   LYS A 351      -9.979 -27.422  78.068  1.00172.27           O
ANISOU 2574  O   LYS A 351    23190  24844  17420  -3324   1286    562       O
ATOM   2575  CB  LYS A 351     -11.732 -27.917  80.609  1.00178.01           C
ANISOU 2575  CB  LYS A 351    23856  26164  17616  -3522   1529   1011       C
ATOM   2576  CG  LYS A 351     -11.987 -29.428  80.685  1.00179.38           C
ANISOU 2576  CG  LYS A 351    23851  26298  18008  -3870   1423   1201       C
ATOM   2577  CD  LYS A 351     -11.979 -30.089  79.306  1.00178.03           C
ANISOU 2577  CD  LYS A 351    23472  25995  18176  -3963   1311   1097       C
ATOM   2578  CE  LYS A 351     -12.906 -29.373  78.331  1.00177.58           C
```

FIG. 13 Continued

```
ANISOU 2578  CE  LYS A 351      23219  26205  18047  -3742   1484    943       C
ATOM   2579  NZ  LYS A 351     -12.795 -29.900  76.944  1.00175.99           N
ANISOU 2579  NZ  LYS A 351      22835  25854  18179  -3772   1369    813       N
ATOM   2580  N   GLY A 352      -6.957 -29.107  79.157  1.00173.74           N
ANISOU 2580  N   GLY A 352      23512  24681  17820  -3758   1004    802       N
ATOM   2581  CA  GLY A 352      -8.350 -29.662  77.959  1.00171.78           C
ANISOU 2581  CA  GLY A 352      23180  24183  17907  -3820    825    687       C
ATOM   2582  C   GLY A 352      -7.509 -28.600  77.284  1.00169.34           C
ANISOU 2582  C   GLY A 352      23017  23698  17626  -3562    811    469       C
ATOM   2583  O   GLY A 352      -7.760 -28.244  76.141  1.00168.10           O
ANISOU 2583  O   GLY A 352      22716  23590  17564  -3410    854    325       O
ATOM   2584  N   VAL A 353      -6.507 -28.095  77.999  1.00170.19           N
ANISOU 2584  N   VAL A 353      23410  23599  17657  -3507    750    444       N
ATOM   2585  CA  VAL A 353      -5.695 -26.972  77.526  1.00168.14           C
ANISOU 2585  CA  VAL A 353      23313  23175  17396  -3259    747    255       C
ATOM   2586  C   VAL A 353      -5.134 -27.155  76.105  1.00165.89           C
ANISOU 2586  C   VAL A 353      22926  22699  17407  -3221    621    109       C
ATOM   2587  O   VAL A 353      -5.018 -28.275  75.616  1.00165.66           O
ANISOU 2587  O   VAL A 353      22762  22569  17613  -3413    465    153       O
ATOM   2588  CB  VAL A 353      -4.560 -26.612  78.541  1.00167.81           C
ANISOU 2588  CB  VAL A 353      23594  22885  17281  -3251    652    260       C
ATOM   2589  CG1 VAL A 353      -4.452 -25.108  78.700  1.00167.29           C
ANISOU 2589  CG1 VAL A 353      23687  22868  17006  -2948    780    138       C
ATOM   2590  CG2 VAL A 353      -4.815 -27.248  79.910  1.00169.97           C
ANISOU 2590  CG2 VAL A 353      23941  23232  17409  -3431    655    456       C
ATOM   2591  N   GLU A 354      -4.842 -26.034  75.447  1.00164.08           N
ANISOU 2591  N   GLU A 354      22753  22437  17153  -2957    690    -60       N
ATOM   2592  CA  GLU A 354      -4.242 -25.985  74.103  1.00161.85           C
ANISOU 2592  CA  GLU A 354      22394  21980  17123  -2860    591   -207       C
ATOM   2593  C   GLU A 354      -4.450 -27.203  73.192  1.00161.51           C
ANISOU 2593  C   GLU A 354      22103  21913  17351  -3013    457   -184       C
ATOM   2594  O   GLU A 354      -5.441 -27.286  72.464  1.00161.83           O
ANISOU 2594  O   GLU A 354      21902  22174  17412  -2943    565   -215       O
ATOM   2595  CB  GLU A 354      -2.744 -25.669  74.214  1.00160.22           C
ANISOU 2595  CB  GLU A 354      22436  21423  17016  -2837    427   -274       C
ATOM   2596  CG  GLU A 354      -2.448 -24.272  74.762  1.00160.07           C
ANISOU 2596  CG  GLU A 354      22644  21395  16783  -2618    544   -347       C
ATOM   2597  CD  GLU A 354      -1.107 -24.164  75.492  1.00159.43           C
ANISOU 2597  CD  GLU A 354      22843  20996  16736  -2675    384   -348       C
ATOM   2598  OE1 GLU A 354      -0.668 -25.153  76.132  1.00159.92           O
ANISOU 2598  OE1 GLU A 354      22970  20924  16869  -2910    235   -247       O
ATOM   2599  OE2 GLU A 354      -0.505 -23.068  75.439  1.00158.48           O
ANISOU 2599  OE2 GLU A 354      22883  20762  16569  -2481    410   -454       O
ATOM   2600  N   LYS A 355      -3.489 -28.127  73.234  1.00161.68           N
ANISOU 2600  N   LYS A 355      22194  21662  17577  -3207    210   -140       N
ATOM   2601  CA  LYS A 355      -3.489 -29.345  72.407  1.00161.24           C
ANISOU 2601  CA  LYS A 355      21935  21534  17793  -3356     22   -119       C
ATOM   2602  C   LYS A 355      -4.902 -29.920  72.177  1.00162.87           C
ANISOU 2602  C   LYS A 355      21858  22030  17996  -3424    128    -45       C
ATOM   2603  O   LYS A 355      -5.225 -30.408  71.088  1.00162.22           O
ANISOU 2603  O   LYS A 355      21547  21976  18114  -3390     63   -101       O
ATOM   2604  CB  LYS A 355      -2.542 -30.420  73.006  1.00161.24           C
ANISOU 2604  CB  LYS A 355      22078  21272  17916  -3627   -238    -22       C
ATOM   2605  CG  LYS A 355      -1.056 -30.401  72.535  1.00158.98           C
ANISOU 2605  CG  LYS A 355      21948  20658  17799  -3588   -459   -126       C
ATOM   2606  CD  LYS A 355      -0.783 -31.352  71.335  1.00157.71           C
ANISOU 2606  CD  LYS A 355      21599  20393  17929  -3629   -689   -167       C
ATOM   2607  CE  LYS A 355      -0.885 -32.851  71.692  1.00158.82           C
ANISOU 2607  CE  LYS A 355      21683  20478  18182  -3937   -898    -31       C
ATOM   2608  NZ  LYS A 355      -0.914 -33.752  70.490  1.00157.91           N
ANISOU 2608  NZ  LYS A 355      21340  20324  18334  -3947  -1107    -67       N
ATOM   2609  N   ASP A 356      -5.741 -29.866  73.204  1.00224.29           N
ANISOU 2609  N   ASP A 356      29646  30025  25546  -3511    287     82       N
ATOM   2610  CA  ASP A 356      -7.107 -30.335  73.053  1.00226.00           C
ANISOU 2610  CA  ASP A 356      29596  30536  25738  -3575    405    158       C
ATOM   2611  C   ASP A 356      -7.829 -29.398  72.095  1.00225.26           C
ANISOU 2611  C   ASP A 356      29351  30652  25584  -3281    603     -4       C
ATOM   2612  O   ASP A 356      -8.064 -29.734  70.938  1.00224.34           O
ANISOU 2612  O   ASP A 356      29024  30541  25673  -3212    551    -94       O
```

FIG. 13 Continued

```
ATOM   2613  CB  ASP A 356      -7.844 -30.361  74.400  1.00228.54           C
ANISOU 2613  CB  ASP A 356    29966  31072  25796  -3704    551    335       C
ATOM   2614  CG  ASP A 356      -7.537 -31.603  75.228  1.00229.82           C
ANISOU 2614  CG  ASP A 356    30179  31098  26045  -4033    373    525       C
ATOM   2615  OD1 ASP A 356      -6.375 -32.063  75.220  1.00228.56           O
ANISOU 2615  OD1 ASP A 356    30173  30624  26047  -4130    149    507       O
ATOM   2616  OD2 ASP A 356      -8.464 -32.109  75.901  1.00232.14           O
ANISOU 2616  OD2 ASP A 356    30361  31606  26236  -4192    459    695       O
ATOM   2617  N   GLN A 357      -8.136 -28.203  72.586  1.00186.34           N
ANISOU 2617  N   GLN A 357    24544  25888  20368  -3092    819    -48       N
ATOM   2618  CA  GLN A 357      -8.904 -27.205  71.844  1.00185.86           C
ANISOU 2618  CA  GLN A 357    24373  26059  20184  -2804   1034   -201       C
ATOM   2619  C   GLN A 357      -8.775 -27.264  70.324  1.00183.92           C
ANISOU 2619  C   GLN A 357    23955  25734  20192  -2647    977   -366       C
ATOM   2620  O   GLN A 357      -9.781 -27.210  69.614  1.00184.19           O
ANISOU 2620  O   GLN A 357    23762  25999  20222  -2531   1107   -439       O
ATOM   2621  CB  GLN A 357      -8.593 -25.801  72.377  1.00185.47           C
ANISOU 2621  CB  GLN A 357    24572  26032  19866  -2584   1172   -277       C
ATOM   2622  CG  GLN A 357      -8.756 -24.666  71.381  1.00183.96           C
ANISOU 2622  CG  GLN A 357    24354  25916  19626  -2255   1313   -484       C
ATOM   2623  CD  GLN A 357      -7.418 -24.083  70.944  1.00181.77           C
ANISOU 2623  CD  GLN A 357    24266  25317  19481  -2130   1195   -596       C
ATOM   2624  OE1 GLN A 357      -6.509 -24.813  70.540  1.00180.62           O
ANISOU 2624  OE1 GLN A 357    24119  24901  19608  -2250    983   -585       O
ATOM   2625  NE2 GLN A 357      -7.292 -22.761  71.030  1.00181.24           N
ANISOU 2625  NE2 GLN A 357    24363  25283  19215  -1887   1325   -702       N
ATOM   2626  N   VAL A 358      -7.550 -27.377  69.821  1.00161.25           N
ANISOU 2626  N   VAL A 358    21185  22948  17536  -2631    782   -428       N
ATOM   2627  CA  VAL A 358      -7.358 -27.445  68.381  1.00159.39           C
ANISOU 2627  CA  VAL A 358    20785  22234  17541  -2461    714   -576       C
ATOM   2628  C   VAL A 358      -8.078 -28.658  67.821  1.00160.10           C
ANISOU 2628  C   VAL A 358    20586  22408  17836  -2595    620   -528       C
ATOM   2629  O   VAL A 358      -9.057 -28.513  67.091  1.00160.27           O
ANISOU 2629  O   VAL A 358    20388  22649  17857  -2444    759   -616       O
ATOM   2630  CB  VAL A 358      -5.877 -27.495  68.004  1.00157.36           C
ANISOU 2630  CB  VAL A 358    20679  21629  17483  -2447    493   -623       C
ATOM   2631  CG1 VAL A 358      -5.288 -26.104  68.035  1.00156.23           C
ANISOU 2631  CG1 VAL A 358    20746  21422  17192  -2213    611   -732       C
ATOM   2632  CG2 VAL A 358      -5.129 -28.414  68.940  1.00158.00           C
ANISOU 2632  CG2 VAL A 358    20905  21504  17623  -2754    277   -470       C
ATOM   2633  N   LEU A 359      -7.601 -29.846  68.188  1.00209.80           N
ANISOU 2633  N   LEU A 359    36888  28526  24300  -2876    380   -394       N
ATOM   2634  CA  LEU A 359      -8.188 -31.110  67.741  1.00210.61           C
ANISOU 2634  CA  LEU A 359    26733  28670  24620  -3039    242   -329       C
ATOM   2635  C   LEU A 359      -9.711 -31.120  67.883  1.00212.60           C
ANISOU 2635  C   LEU A 359    26772  29268  24738  -3046    460   -290       C
ATOM   2636  O   LEU A 359     -10.431 -31.568  66.988  1.00212.64           O
ANISOU 2636  O   LEU A 359    26511  29382  24902  -2985    452   -350       O
ATOM   2637  CB  LEU A 359      -7.585 -32.286  68.519  1.00211.45           C
ANISOU 2637  CB  LEU A 359    26932  28576  24833  -3379     -9   -154       C
ATOM   2638  CG  LEU A 359      -6.346 -33.000  67.969  1.00209.69           C
ANISOU 2638  CG  LEU A 359    26768  28029  24875  -3436   -333   -183       C
ATOM   2639  CD1 LEU A 359      -5.509 -33.562  69.109  1.00210.29           C
ANISOU 2639  CD1 LEU A 359    27087  27904  24911  -3712   -495    -41       C
ATOM   2640  CD2 LEU A 359      -6.726 -34.101  66.976  1.00209.59           C
ANISOU 2640  CD2 LEU A 359    26475  28008  25150  -3475   -528   -194       C
ATOM   2641  N   LEU A 360     -10.199 -30.643  69.021  1.00172.75           N
ANISOU 2641  N   LEU A 360    21840  24399  19398  -3115    647   -190       N
ATOM   2642  CA  LEU A 360     -11.630 -30.548  69.221  1.00174.68           C
ANISOU 2642  CA  LEU A 360    21898  25000  19474  -3109    868   -152       C
ATOM   2643  C   LEU A 360     -12.114 -29.718  68.051  1.00173.32           C
ANISOU 2643  C   LEU A 360    21591  24969  19294  -2771   1027   -374       C
ATOM   2644  O   LEU A 360     -12.892 -30.180  67.214  1.00173.50           O
ANISOU 2644  O   LEU A 360    21344  25114  19463  -2724   1037   -434       O
ATOM   2645  CB  LEU A 360     -11.950 -29.825  70.540  1.00176.28           C
ANISOU 2645  CB  LEU A 360    22382  25384  19311  -3135   1064    -49       C
ATOM   2646  CG  LEU A 360     -11.474 -30.389  71.890  1.00177.71           C
ANISOU 2646  CG  LEU A 360    22644  25454  19423  -3419    961    167       C
ATOM   2647  CD1 LEU A 360     -11.443 -29.306  72.961  1.00178.35           C
```

FIG. 13 Continued

```
ANISOU 2647  CD1 LEU A 360     22962  25652  19150  -3311   1138    193        C
ATOM   2648  CD2 LEU A 360    -12.323 -31.565  72.354  1.00180.12              C
ANISOU 2648  CD2 LEU A 360     22754  25899  19786  -3709    926    367        C
ATOM   2649  N   PHE A 361    -11.583 -28.500  67.990  1.00258.84              N
ANISOU 2649  N   PHE A 361     32621  35759  29968  -2031   1136   -501        N
ATOM   2650  CA  PHE A 361    -11.931 -27.502  66.989  1.00257.46              C
ANISOU 2650  CA  PHE A 361     32379  35706  29736  -2183   1309   -718        C
ATOM   2651  C   PHE A 361    -11.932 -27.995  65.546  1.00255.96              C
ANISOU 2651  C   PHE A 361     31957  35438  29859  -2050   1202   -853        C
ATOM   2652  O   PHE A 361    -12.987 -28.115  64.931  1.00256.46              O
ANISOU 2652  O   PHE A 361     31780  35725  29938  -1948   1317   -931        O
ATOM   2653  CB  PHE A 361    -10.990 -26.305  67.112  1.00255.93              C
ANISOU 2653  CB  PHE A 361     32465  35366  29410  -1991   1354   -810        C
ATOM   2654  CG  PHE A 361    -10.958 -25.441  65.895  1.00254.00              C
ANISOU 2654  CG  PHE A 361     32171  35134  29204  -1644   1454  -1033        C
ATOM   2655  CD1 PHE A 361    -11.897 -24.441  65.716  1.00254.28              C
ANISOU 2655  CD1 PHE A 361     32176  35456  28984  -1402   1721  -1159        C
ATOM   2656  CD2 PHE A 361     -9.991 -25.626  64.923  1.00251.92              C
ANISOU 2656  CD2 PHE A 361     31892  34603  29222  -1550   1281  -1116        C
ATOM   2657  CE1 PHE A 361    -11.870 -23.642  64.590  1.00252.52              C
ANISOU 2657  CE1 PHE A 361     31914  35240  28791  -1075   1820  -1367        C
ATOM   2658  CE2 PHE A 361     -9.965 -24.832  63.795  1.00250.20              C
ANISOU 2658  CE2 PHE A 361     31622  34401  29041  -1019   1382  -1311        C
ATOM   2659  CZ  PHE A 361    -10.901 -23.835  63.629  1.00250.49              C
ANISOU 2659  CZ  PHE A 361     31636  34711  28828   -982   1655  -1439        C
ATOM   2660  N   ALA A 362    -10.751 -28.271  65.005  1.00157.77              N
ANISOU 2660  N   ALA A 362     19589  22692  17665  -2034    980   -884        N
ATOM   2661  CA  ALA A 362    -10.645 -28.677  63.605  1.00156.19              C
ANISOU 2661  CA  ALA A 362     19179  22408  17757  -1864    862  -1016        C
ATOM   2662  C   ALA A 362    -11.579 -29.833  63.259  1.00157.45              C
ANISOU 2662  C   ALA A 362     19040  22687  18095  -1993    785   -970        C
ATOM   2663  O   ALA A 362    -12.069 -29.932  62.133  1.00156.68              O
ANISOU 2663  O   ALA A 362     18716  22666  18151  -1784    801  -1111        O
ATOM   2664  CB  ALA A 362     -9.208 -29.014  63.248  1.00154.37              C
ANISOU 2664  CB  ALA A 362     19065  21833  17756  -1885    591  -1011        C
ATOM   2665  N   ALA A 363    -11.827 -30.701  64.232  1.00161.08              N
ANISOU 2665  N   ALA A 363     19501  23163  18541  -2331    698   -771        N
ATOM   2666  CA  ALA A 363    -12.716 -31.828  64.022  1.00162.57              C
ANISOU 2666  CA  ALA A 363     19414  23457  18901  -2492    614   -701        C
ATOM   2667  C   ALA A 363    -13.978 -31.280  63.392  1.00162.94              C
ANISOU 2667  C   ALA A 363     19246  23814  18848  -2253    871   -848        C
ATOM   2668  O   ALA A 363    -14.469 -31.793  62.382  1.00162.59              O
ANISOU 2668  O   ALA A 363     18944  23806  19027  -2143    808   -946        O
ATOM   2669  CB  ALA A 363    -13.035 -32.493  65.351  1.00165.05              C
ANISOU 2669  CB  ALA A 363     19781  23827  19105  -2860    593   -461        C
ATOM   2670  N   MET A 364    -14.469 -30.204  64.002  1.00248.46              N
ANISOU 2670  N   MET A 364     30200  34869  29334  -2031   1154   -873        N
ATOM   2671  CA  MET A 364    -15.690 -29.518  63.600  1.00248.93              C
ANISOU 2671  CA  MET A 364     30108  35261  29213  -1930   1433  -1015        C
ATOM   2672  C   MET A 364    -15.412 -28.288  62.741  1.00246.72              C
ANISOU 2672  C   MET A 364     29910  34984  28850  -1534   1581  -1254        C
ATOM   2673  O   MET A 364    -16.341 -27.651  62.244  1.00246.73              O
ANISOU 2673  O   MET A 364     29798  35241  28708  -1296   1808  -1412        O
ATOM   2674  CB  MET A 364    -16.477 -29.086  64.849  1.00251.17              C
ANISOU 2674  CB  MET A 364     30476  35826  29130  -2059   1650   -891        C
ATOM   2675  CG  MET A 364    -17.068 -30.236  65.673  1.00253.75              C
ANISOU 2675  CG  MET A 364     30672  36237  29504   2426   1568    655        C
ATOM   2676  SD  MET A 364    -17.720 -29.772  67.300  1.00256.35              S
ANISOU 2676  SD  MET A 364     31143  36857  29402  -2590   1782   -462        S
ATOM   2677  CE  MET A 364    -16.215 -29.707  68.264  1.00255.69              C
ANISOU 2677  CE  MET A 364     31415  36438  29297  -2745   1608   -326        C
ATOM   2678  N   ALA A 365    -14.138 -27.950  62.572  1.00158.84              N
ANISOU 2678  N   ALA A 365     18979  23571  17802  -1465   1454  -1279        N
ATOM   2679  CA  ALA A 365    -13.764 -26.747  61.832  1.00156.82              C
ANISOU 2679  CA  ALA A 365     18826  23292  17467  -1107   1587  -1480        C
ATOM   2680  C   ALA A 365    -13.704 -26.919  60.330  1.00155.01              C
ANISOU 2680  C   ALA A 365     18393  22994  17510   -836   1524  -1660        C
ATOM   2681  O   ALA A 365    -13.320 -25.983  59.636  1.00153.26              O
ANISOU 2681  O   ALA A 365     18247  22732  17255   -533   1619  -1820        O
```

FIG. 13 Continued

```
ATOM   2682  CB  ALA A 365     -12.447 -26.221  62.320  1.00155.75           C
ANISOU 2682  CB  ALA A 365    18990  22899  17290  -1138   1495  -1427       C
ATOM   2683  N   SER A 366     -14.078 -28.102  59.841  1.00158.44           N
ANISOU 2683  N   SER A 366    18571  23414  18215   -936   1358  -1631       N
ATOM   2684  CA  SER A 366     -14.043 -28.423  58.408  1.00156.83           C
ANISOU 2684  CA  SER A 366    18146  23142  18300   -675   1261  -1793       C
ATOM   2685  C   SER A 366     -14.076 -29.931  58.182  1.00157.49           C
ANISOU 2685  C   SER A 366    18017  23113  18711   -886    968  -1690       C
ATOM   2686  O   SER A 366     -13.686 -30.694  59.067  1.00158.63           O
ANISOU 2686  O   SER A 366    18246  23134  18894  -1234    788  -1487       O
ATOM   2687  CB  SER A 366     -12.763 -27.853  57.780  1.00154.42           C
ANISOU 2687  CB  SER A 366    17993  22588  18091   -461   1170  -1872       C
ATOM   2688  OG  SER A 366     -12.311 -28.609  56.670  1.00153.04           O
ANISOU 2688  OG  SER A 366    17637  22248  18263   -335    932  -1930       O
ATOM   2689  N   ARG A 367     -14.551 -30.371  57.015  1.00157.91           N
ANISOU 2689  N   ARG A 367    17798  23204  18997   -672    911  -1830       N
ATOM   2690  CA  ARG A 367     -14.447 -31.791  56.691  1.00158.31           C
ANISOU 2690  CA  ARG A 367    17654  23111  19387   -837    587  -1745       C
ATOM   2691  C   ARG A 367     -12.979 -32.018  56.386  1.00156.47           C
ANISOU 2691  C   ARG A 367    17558  22559  19334   -820    311  -1709       C
ATOM   2692  O   ARG A 367     -12.141 -31.158  56.672  1.00155.38           O
ANISOU 2692  O   ARG A 367    17669  22327  19043   -763    384  -1711       O
ATOM   2693  CB  ARG A 367     -15.305 -32.210  55.493  1.00158.06           C
ANISOU 2693  CB  ARG A 367    17290  23191  19574   -584    575  -1914       C
ATOM   2694  CG  ARG A 367     -14.942 -31.555  54.177  1.00155.59           C
ANISOU 2694  CG  ARG A 367    16924  22835  19358   -123    616  -2144       C
ATOM   2695  CD  ARG A 367     -16.020 -30.574  53.781  1.00155.60           C
ANISOU 2695  CD  ARG A 367    16844  23126  19150    172    979  -2347       C
ATOM   2696  NE  ARG A 367     -15.662 -29.696  52.669  1.00153.28           N
ANISOU 2696  NE  ARG A 367    16555  22809  18874    623   1085  -2564       N
ATOM   2697  CZ  ARG A 367     -15.519 -30.090  51.407  1.00151.83           C
ANISOU 2697  CZ  ARG A 367    16165  22543  18979    922    938  -2701       C
ATOM   2698  NH1 ARG A 367     -15.665 -31.367  51.081  1.00152.40           N
ANISOU 2698  NH1 ARG A 367    16013  22534  19357    818    653  -2648       N
ATOM   2699  NH2 ARG A 367     -15.213 -29.200  50.472  1.00149.83           N
ANISOU 2699  NH2 ARG A 367    15933  22288  18709   1336   1069  -2887       N
ATOM   2700  N   VAL A 368     -12.657 -33.159  55.796  1.00151.98           N
ANISOU 2700  N   VAL A 368    16829  21829  19089   -861    -16  -1680       N
ATOM   2701  CA  VAL A 368     -11.264 -33.466  55.483  1.00150.26           C
ANISOU 2701  CA  VAL A 368    16729  21324  19041   -845   -306  -1645       C
ATOM   2702  C   VAL A 368     -10.734 -32.784  54.195  1.00147.75           C
ANISOU 2702  C   VAL A 368    16365  20956  18819   -393   -286  -1839       C
ATOM   2703  O   VAL A 368      -9.921 -31.838  54.248  1.00146.44           O
ANISOU 2703  O   VAL A 368    16411  20712  18517   -274   -186  -1868       O
ATOM   2704  CB  VAL A 368     -11.064 -34.998  55.427  1.00150.93           C
ANISOU 2704  CB  VAL A 368    16682  21250  19415  -1078   -659  -1524       C
ATOM   2705  CG1 VAL A 368     -11.031 -35.567  56.829  1.00152.94           C
ANISOU 2705  CG1 VAL A 368    17091  21461  19558  -1544   -762  -1297       C
ATOM   2706  CG2 VAL A 368     -12.185 -35.658  54.636  1.00151.68           C
ANISOU 2706  CG2 VAL A 368    16435  21485  19713   -956   -735  -1614       C
ATOM   2707  N   GLU A 369     -11.241 -33.267  53.058  1.00163.04           N
ANISOU 2707  N   GLU A 369    18017  22943  20990   -140   -376  -1970       N
ATOM   2708  CA  GLU A 369     -10.849 -32.864  51.702  1.00160.80           C
ANISOU 2708  CA  GLU A 369    17624  22621  20852    313   -399  -2152       C
ATOM   2709  C   GLU A 369     -11.554 -31.628  51.137  1.00160.14           C
ANISOU 2709  C   GLU A 369    17499  22748  20598    680    -19  -2356       C
ATOM   2710  O   GLU A 369     -12.543 -31.158  51.690  1.00161.51           O
ANISOU 2710  O   GLU A 369    17682  23133  20551    606    261  -2381       O
ATOM   2711  CB  GLU A 369     -11.151 -34.036  50.765  1.00160.71           C
ANISOU 2711  CB  GLU A 369    17309  22573  21179    428   -690  -2202       C
ATOM   2712  CG  GLU A 369     -12.645 -34.304  50.608  1.00162.25           C
ANISOU 2712  CG  GLU A 369    17254  22996  21399    457   -541  -2287       C
ATOM   2713  CD  GLU A 369     -13.018 -35.738  50.911  1.00163.97           C
ANISOU 2713  CD  GLU A 369    17315  23157  21832    148   -840  -2154       C
ATOM   2714  OE1 GLU A 369     -12.273 -36.401  51.660  1.00164.50           O
ANISOU 2714  OE1 GLU A 369    17531  23045  21927   -193  -1084  -1963       O
ATOM   2715  OE2 GLU A 369     -14.061 -36.202  50.410  1.00164.85           O
ANISOU 2715  OE2 GLU A 369    17155  23397  22082    245   -833  -2244       O
ATOM   2716  N   ASN A 370     -11.047 -31.123  50.014  1.00187.41           N
```

FIG. 13 Continued

```
ANISOU 2716  N    ASN A 370     20905  26153  24152   1086    -15  -2502       N
ATOM   2717  CA   ASN A 370     -11.692 -30.026  49.296  1.00 186.60           C
ANISOU 2717  CA   ASN A 370     20741  26236  23921   1483    320  -2718       C
ATOM   2718  C    ASN A 370     -11.752 -28.696  50.033  1.00 186.81           C
ANISOU 2718  C    ASN A 370     21029  26362  23590   1453    661  -2727       C
ATOM   2719  O    ASN A 370     -12.440 -27.787  49.574  1.00 186.43           O
ANISOU 2719  O    ASN A 370     20946  26496  23394   1746    957  -2906       O
ATOM   2720  CB   ASN A 370     -13.148 -30.405  48.950  1.00 187.77           C
ANISOU 2720  CB   ASN A 370     20619  26611  24114   1572    434  -2843       C
ATOM   2721  CG   ASN A 370     -13.312 -30.964  47.543  1.00 186.58           C
ANISOU 2721  CG   ASN A 370     20172  26445  24275   1951    273  -3002       C
ATOM   2722  OD1  ASN A 370     -14.191 -30.529  46.783  1.00 186.24           O
ANISOU 2722  OD1  ASN A 370     19965  26583  24216   2289    488  -3212       O
ATOM   2723  ND2  ASN A 370     -12.487 -31.945  47.197  1.00 185.96           N
ANISOU 2723  ND2  ASN A 370     20025  26157  24474   1908   -113  -2909       N
ATOM   2724  N    GLN A 371     -11.064 -28.538  51.156  1.00 143.96           N
ANISOU 2724  N    GLN A 371     15865  20822  18013   1124    625  -2551       N
ATOM   2725  CA   GLN A 371     -11.344 -27.319  51.927  1.00 144.52           C
ANISOU 2725  CA   GLN A 371     16160  21020  17729   1093    949  -2567       C
ATOM   2726  C    GLN A 371     -10.394 -26.130  51.834  1.00 143.02           C
ANISOU 2726  C    GLN A 371     16208  20721  17412   1268   1059  -2599       C
ATOM   2727  O    GLN A 371      -9.252 -26.257  51.395  1.00 141.60           O
ANISOU 2727  O    GLN A 371     16072  20324  17404   1335    860  -2559       O
ATOM   2728  CB   GLN A 371     -11.677 -27.640  53.397  1.00 146.70           C
ANISOU 2728  CB   GLN A 371     16570  21348  17821    648    961  -2384       C
ATOM   2729  CG   GLN A 371     -12.789 -26.745  54.019  1.00 148.02           C
ANISOU 2729  CG   GLN A 371     16802  21799  17640    656   1316  -2447       C
ATOM   2730  CD   GLN A 371     -14.228 -27.189  53.675  1.00 149.21           C
ANISOU 2730  CD   GLN A 371     16676  22208  17807    718   1429  -2548       C
ATOM   2731  OE1  GLN A 371     -14.886 -27.858  54.476  1.00 151.20           O
ANISOU 2731  OE1  GLN A 371     16871  22565  18015    413   1405  -2422       O
ATOM   2732  NE2  GLN A 371     -14.713 -26.810  52.488  1.00 148.02           N
ANISOU 2732  NE2  GLN A 371     16355  22164  17721   1118   1556  -2773       N
ATOM   2733  N    ASP A 372     -10.923 -24.978  52.258  1.00 141.22           N
ANISOU 2733  N    ASP A 372     16126  20659  16872   1342   1375  -2673       N
ATOM   2734  CA   ASP A 372     -10.211 -23.708  52.318  1.00 140.18           C
ANISOU 2734  CA   ASP A 372     16238  20453  16570   1490   1522  -2706       C
ATOM   2735  C    ASP A 372      -8.844 -23.990  52.902  1.00 139.83           C
ANISOU 2735  C    ASP A 372     16384  20130  16616   1241   1275  -2522       C
ATOM   2736  O    ASP A 372       8.692  24.909  53.704  1.00 140.95           O
ANISOU 2736  O    ASP A 372     16547  20197  16810    890   1083  -2361       O
ATOM   2737  CB   ASP A 372     -10.939 -22.717  53.250  1.00 141.45           C
ANISOU 2737  CB   ASP A 372     16583  20812  16348   1425   1814  -2728       C
ATOM   2738  CG   ASP A 372     -12.293 -22.206  52.690  1.00 141.69           C
ANISOU 2738  CG   ASP A 372     16466  21146  16225   1706   2100  -2939       C
ATOM   2739  OD1  ASP A 372      12.307  21.408  51.722  1.00 140.26           O
ANISOU 2739  OD1  ASP A 372     16260  20999  16034   2086   2251  -3119       O
ATOM   2740  OD2  ASP A 372     -13.353 -22.559  53.264  1.00 143.39           O
ANISOU 2740  OD2  ASP A 372     16600  21573  16307   1545   2186  -2925       O
ATOM   2741  N    ALA A 373      -7.849 -23.196  52.521  1.00 165.26           N
ANISOU 2741  N    ALA A 373     19746  23198  19849   1418   1282  -2544       N
ATOM   2742  CA   ALA A 373       6.486  23.410  53.007  1.00 164.80           C
ANISOU 2742  CA   ALA A 373     19868  22871  19879   1207   1049  -2385       C
ATOM   2743  C    ALA A 373      -6.446 -23.446  54.524  1.00 166.43           C
ANISOU 2743  C    ALA A 373     20298  23053  19885    818   1045  -2235       C
ATOM   2744  O    ALA A 373      -5.692 -24.218  55.115  1.00 166.70           O
ANISOU 2744  O    ALA A 373     20409  22910  20020    533    800  -2085       O
ATOM   2745  CB   ALA A 373      -5.550 -22.344  52.479  1.00 163.23           C
ANISOU 2745  CB   ALA A 373     19804  22543  19673   1455   1115  -2434       C
ATOM   2746  N    ILE A 374      -7.267 -22.610  55.151  1.00 173.01           N
ANISOU 2746  N    ILE A 374     21237  24075  20425    821   1314  -2280       N
ATOM   2747  CA   ILE A 374      -7.318 -22.560  56.601  1.00 174.64           C
ANISOU 2747  CA   ILE A 374     21650  24290  20415    495   1332  -2144       C
ATOM   2748  C    ILE A 374      -7.759 -23.904  57.153  1.00 176.07           C
ANISOU 2748  C    ILE A 374     21705  24505  20688    178   1166  -2017       C
ATOM   2749  O    ILE A 374      -7.134 -24.447  58.059  1.00 176.73           O
ANISOU 2749  O    ILE A 374     21924  24437  20788   -129    991  -1857       O
ATOM   2750  CB   ILE A 374      -8.287 -21.482  57.103  1.00 175.65           C
ANISOU 2750  CB   ILE A 374     21877  24663  20196    590   1645  -2226       C
```

FIG. 13 Continued

```
ATOM   2751  CG1 ILE A 374      -7.807 -20.082  56.700  1.00174.40           C
ANISOU 2751  CG1 ILE A 374    21887  24455  19923    876   1801  -2337       C
ATOM   2752  CG2 ILE A 374      -8.444 -21.591  58.608  1.00177.50           C
ANISOU 2752  CG2 ILE A 374    22288  24936  20217    259   1644  -2073       C
ATOM   2753  CD1 ILE A 374      -6.807 -19.450  57.658  1.00174.53           C
ANISOU 2753  CD1 ILE A 374    22210  24279  19824    725   1748  -2229       C
ATOM   2754  N   ASP A 375      -8.822 -24.450  56.574  1.00147.08           N
ANISOU 2754  N   ASP A 375    17772  21023  17088    262   1215  -2094       N
ATOM   2755  CA  ASP A 375      -9.415 -25.703  57.042  1.00148.65           C
ANISOU 2755  CA  ASP A 375    17824  21282  17376    -27   1079  -1979       C
ATOM   2756  C   ASP A 375      -8.623 -26.962  56.716  1.00148.09           C
ANISOU 2756  C   ASP A 375    17657  20981  17627   -173    724  -1884       C
ATOM   2757  O   ASP A 375      -9.060 -28.072  57.021  1.00149.35           O
ANISOU 2757  O   ASP A 375    17686  21165  17893   -410    578  -1787       O
ATOM   2758  CB  ASP A 375     -10.826 -25.814  56.502  1.00149.38           C
ANISOU 2758  CB  ASP A 375    17663  21654  17441    125   1252  -2104       C
ATOM   2759  CG  ASP A 375     -11.579 -24.517  56.637  1.00149.64           C
ANISOU 2759  CG  ASP A 375    17785  21922  17150    331   1595  -2233       C
ATOM   2760  OD1 ASP A 375     -11.307 -23.780  57.616  1.00150.22           O
ANISOU 2760  OD1 ASP A 375    18114  21991  16972    220   1690  -2161       O
ATOM   2761  OD2 ASP A 375     -12.424 -24.226  55.763  1.00149.24           O
ANISOU 2761  OD2 ASP A 375    17558  22057  17091    615   1761  -2412       O
ATOM   2762  N   ALA A 376      -7.480 -26.781  56.063  1.00143.33           N
ANISOU 2762  N   ALA A 376    17114  20168  17178    -21    582  -1914       N
ATOM   2763  CA  ALA A 376      -6.562 -27.876  55.802  1.00142.64           C
ANISOU 2763  CA  ALA A 376    16979  19855  17362   -148    227  -1824       C
ATOM   2764  C   ALA A 376      -5.462 -27.718  56.830  1.00142.70           C
ANISOU 2764  C   ALA A 376    17284  19661  17276   -401    126  -1686       C
ATOM   2765  O   ALA A 376      -4.851 -28.688  57.278  1.00142.99           O
ANISOU 2765  O   ALA A 376    17365  19535  17429   -666   -143  -1559       O
ATOM   2766  CB  ALA A 376      -6.002 -27.779  54.418  1.00140.57           C
ANISOU 2766  CB  ALA A 376    16584  19510  17315    201    132  -1942       C
ATOM   2767  N   ALA A 377      -5.220 -26.468  57.203  1.00144.26           N
ANISOU 2767  N   ALA A 377    17689  19866  17258   -307    340  -1722       N
ATOM   2768  CA  ALA A 377      -4.234 -26.155  58.216  1.00144.38           C
ANISOU 2768  CA  ALA A 377    17996  19700  17163   -516    278  -1612       C
ATOM   2769  C   ALA A 377      -4.648 -26.773  59.552  1.00146.41           C
ANISOU 2769  C   ALA A 377    18341  19998  17291   -885    250  -1464       C
ATOM   2770  O   ALA A 377      -3.899 -27.547  60.138  1.00146.62           O
ANISOU 2770  O   ALA A 377    18468  19842  17397  -1146     16  -1342       O
ATOM   2771  CB  ALA A 377      -4.064 -24.649  58.336  1.00143.91           C
ANISOU 2771  CB  ALA A 377    18122  19663  16893   -321    525  -1689       C
ATOM   2772  N   MET A 378      -5.851 -26.462  60.019  1.00146.19           N
ANISOU 2772  N   MET A 378    18269  20218  17060   -901    485  -1476       N
ATOM   2773  CA  MET A 378      -6.312 -27.008  61.289  1.00148.26           C
ANISOU 2773  CA  MET A 378    18600  20547  17185  -1232    481  -1325       C
ATOM   2774  C   MET A 378      -6.174 -28.534  61.342  1.00148.80           C
ANISOU 2774  C   MET A 378    18546  20509  17484  -1496    192  -1207       C
ATOM   2775  O   MET A 378      -5.506 -29.056  62.235  1.00149.35           O
ANISOU 2775  O   MET A 378    18779  20418  17548  -1770     28  -1071       O
ATOM   2776  CB  MET A 378       7.747 -26.581  61.590  1.00149.84           C
ANISOU 2776  CB  MET A 378    18707  21069  17155  -1183    763  -1359       C
ATOM   2777  CG  MET A 378      -8.038 -25.096  61.361  1.00149.25           C
ANISOU 2777  CG  MET A 378    18724  21132  16853   -881   1045  -1505       C
ATOM   2778  SD  MET A 378      -7.151 -23.932  62.416  1.00149.18           S
ANISOU 2778  SD  MET A 378    19091  20993  16598   -907   1114  -1461       S
ATOM   2779  CE  MET A 378      -6.902 -24.964  63.852  1.00150.94           C
ANISOU 2779  CE  MET A 378    19427  21127  16798  -1339    937  -1234       C
ATOM   2780  N   VAL A 379      -6.781 -29.251  60.395  1.00148.73           N
ANISOU 2780  N   VAL A 379    18256  20580  17675  -1406    118  -1264       N
ATOM   2781  CA  VAL A 379      -6.653 -30.713  60.366  1.00149.23           C
ANISOU 2781  CA  VAL A 379    18196  20535  17972  -1640   -184  -1159       C
ATOM   2782  C   VAL A 379      -5.198 -31.101  60.196  1.00147.70           C
ANISOU 2782  C   VAL A 379    18135  20455  17939  -1688   -478  -1126       C
ATOM   2783  O   VAL A 379      -4.785 -32.211  60.533  1.00148.14           O
ANISOU 2783  O   VAL A 379    18202  19960  18124  -1942   -749  -1013       O
ATOM   2784  CB  VAL A 379      -7.439 -31.354  59.230  1.00149.08           C
ANISOU 2784  CB  VAL A 379    17848  20624  18170  -1481   -243  -1249       C
ATOM   2785  CG1 VAL A 379      -7.234 -30.572  57.951  1.00147.02           C
```

FIG. 13 Continued

```
ANISOU 2785  CG1 VAL A 379    17502  20375  17985   -1065   -161  -1439       C
ATOM   2786  CG2 VAL A 379     -7.012 -32.819  59.055  1.00149.16             C
ANISOU 2786  CG2 VAL A 379    17758  20462  18453   -1682   -620  -1154       C
ATOM   2787  N   GLY A 380     -4.430 -30.184  59.630  1.00145.98             N
ANISOU 2787  N   GLY A 380    18012  19740  17714   -1434   -426  -1229       N
ATOM   2788  CA  GLY A 380     -3.004 -30.371  59.548  1.00144.54             C
ANISOU 2788  CA  GLY A 380    17982  19294  17644   -1470   -672  -1199       C
ATOM   2789  C   GLY A 380     -2.534 -30.162  60.972  1.00145.53             C
ANISOU 2789  C   GLY A 380    18399  19326  17572   -1748   -646  -1081       C
ATOM   2790  O   GLY A 380     -2.766 -31.009  61.831  1.00147.02             O
ANISOU 2790  O   GLY A 380    18619  19505  17738   -2049   -744   -955       O
ATOM   2791  N   MET A 381     -1.907 -29.020  61.232  1.00146.29             N
ANISOU 2791  N   MET A 381    18704  19355  17525   -1637   -509  -1121       N
ATOM   2792  CA  MET A 381     -1.439 -28.691  62.573  1.00147.16             C
ANISOU 2792  CA  MET A 381    19098  19372  17442   -1854   -473  -1028       C
ATOM   2793  C   MET A 381     -0.755 -29.901  63.219  1.00147.55             C
ANISOU 2793  C   MET A 381    19238  19237  17588   -2173   -768   -903       C
ATOM   2794  O   MET A 381     -0.153 -30.741  62.531  1.00146.49             O
ANISOU 2794  O   MET A 381    19016  18973  17671   -2182  -1038   -908       O
ATOM   2795  CB  MET A 381     -2.620 -28.216  63.433  1.00149.09             C
ANISOU 2795  CB  MET A 381    19360  19852  17434   -1912   -196   -994       C
ATOM   2796  CG  MET A 381     -2.265 -27.201  64.519  1.00149.58             C
ANISOU 2796  CG  MET A 381    19709  19878  17247   -1942    -48   -968       C
ATOM   2797  SD  MET A 381     -1.935 -25.529  63.906  1.00148.12             S
ANISOU 2797  SD  MET A 381    19620  19693  16965   -1580    161  -1122       S
ATOM   2798  CE  MET A 381     -3.580 -24.863  63.744  1.00149.28             C
ANISOU 2798  CE  MET A 381    19612  20204  16905   -1399    490  -1198       C
ATOM   2799  N   LEU A 382     -0.824 -29.968  64.547  1.00172.03             N
ANISOU 2799  N   LEU A 382    22523  22328  20513   -2418   -722   -794       N
ATOM   2800  CA  LEU A 382     -0.317 -31.119  65.283  1.00172.68             C
ANISOU 2800  CA  LEU A 382    22700  22256  20653   -2734   -972   -672       C
ATOM   2801  C   LEU A 382     -1.363 -32.205  65.120  1.00174.03             C
ANISOU 2801  C   LEU A 382    22631  22572  20920   -2869  -1031   -603       C
ATOM   2802  O   LEU A 382     -1.186 -33.332  65.585  1.00174.79             O
ANISOU 2802  O   LEU A 382    22747  22573  21092   -3134  -1248   -496       O
ATOM   2803  CB  LEU A 382     -0.142 -30.805  66.778  1.00173.98             C
ANISOU 2803  CB  LEU A 382    23131  22382  20590   -2926   -879   -579       C
ATOM   2804  CG  LEU A 382      0.847 -29.743  67.282  1.00173.12             C
ANISOU 2804  CG  LEU A 382    23300  22122  20357   -2842   -819   -625       C
ATOM   2805  CD1 LEU A 382      0.623 -29.477  68.767  1.00174.85             C
ANISOU 2805  CD1 LEU A 382    23723  22376  20335   -3002   -691   -530       C
ATOM   2806  CD2 LEU A 382      2.302 -30.133  67.018  1.00171.45             C
ANISOU 2806  CD2 LEU A 382    23215  21627  20300   -2885  -1099   -651       C
ATOM   2807  N   ALA A 383     -2.462 -31.841  64.458  1.00168.81             N
ANISOU 2807  N   ALA A 383    21746  22141  20254   -2683   -836   -670       N
ATOM   2808  CA  ALA A 383     -3.593 -32.741  64.268  1.00170.24             C
ANISOU 2808  CA  ALA A 383    21675  22486  20522   -2785   -854   -617       C
ATOM   2809  C   ALA A 383     -3.168 -34.023  63.583  1.00169.58             C
ANISOU 2809  C   ALA A 383    21460  22255  20719   -2869  -1204   -599       C
ATOM   2810  O   ALA A 383     -3.188 -34.126  62.358  1.00168.30             O
ANISOU 2810  O   ALA A 383    21103  22101  20741   -2642  -1288   -707       O
ATOM   2811  CB  ALA A 383     -4.720 -32.056  63.493  1.00170.31             C
ANISOU 2811  CB  ALA A 383    21465  22752  20494   -2517   -596   -732       C
ATOM   2812  N   ASP A 384     -2.782 -34.994  64.401  1.00171.21             N
ANISOU 2812  N   ASP A 384    21779  22327  20947   -3184  -1413   -464       N
ATOM   2813  CA  ASP A 384     -2.383 -36.298  63.927  1.00170.85             C
ANISOU 2813  CA  ASP A 384    21638  22136  21140   -3305  -1773   -430       C
ATOM   2814  C   ASP A 384     -3.406 -36.689  62.873  1.00171.09             C
ANISOU 2814  C   ASP A 384    21331  22328  21346   -3157  -1777   -488       C
ATOM   2815  O   ASP A 384     -4.567 -36.280  62.949  1.00172.34             O
ANISOU 2815  O   ASP A 384    21353  22715  21413   -3107  -1512   -493       O
ATOM   2816  CB  ASP A 384     -2.416 -37.301  65.079  1.00172.67             C
ANISOU 2816  CB  ASP A 384    21979  22297  21332   -3690  -1908   -257       C
ATOM   2817  CG  ASP A 384     -2.574 -36.634  66.442  1.00174.05             C
ANISOU 2817  CG  ASP A 384    22371  22531  21227   -3826  -1654   -169       C
ATOM   2818  OD1 ASP A 384     -2.093 -35.494  66.635  1.00173.12             O
ANISOU 2818  OD1 ASP A 384    22423  22396  20957   -3667  -1481   -242       O
ATOM   2819  OD2 ASP A 384     -3.182 -37.260  67.334  1.00176.14             O
ANISOU 2819  OD2 ASP A 384    22635  22862  21428   -4089  -1635    -20       O
```

FIG. 13 Continued

```
ATOM   2820  N   PRO A 385      -2.983 -37.496  61.897  1.00151.01           N
ANISOU 2820  N   PRO A 385    18652  19672  19052  -3078  -2086   -536       N
ATOM   2821  CA  PRO A 385      -3.778 -37.963  60.752  1.00150.93           C
ANISOU 2821  CA  PRO A 385    18316  19774  19255  -2898  -2157   -611       C
ATOM   2822  C   PRO A 385      -5.299 -37.739  60.836  1.00152.72           C
ANISOU 2822  C   PRO A 385    18340  20266  19420  -2886  -1873   -607       C
ATOM   2823  O   PRO A 385      -5.781 -36.623  61.048  1.00152.90           O
ANISOU 2823  O   PRO A 385    18400  20451  19244  -2755  -1530   -659       O
ATOM   2824  CB  PRO A 385      -3.465 -39.458  60.738  1.00151.36           C
ANISOU 2824  CB  PRO A 385    18326  19675  19510  -3126  -2564   -519       C
ATOM   2825  CG  PRO A 385      -2.006 -39.527  61.260  1.00150.20           C
ANISOU 2825  CG  PRO A 385    18483  19290  19297  -3247  -2759   -485       C
ATOM   2826  CD  PRO A 385      -1.717 -38.241  62.013  1.00150.01           C
ANISOU 2826  CD  PRO A 385    18692  19293  19014  -3215  -2437   -498       C
ATOM   2827  N   LYS A 386      -6.046 -38.808  60.601  1.00154.80           N
ANISOU 2827  N   LYS A 386    18379  20575  19861  -3006  -2032   -553       N
ATOM   2828  CA  LYS A 386      -7.495 -38.758  60.689  1.00156.67           C
ANISOU 2828  CA  LYS A 386    18405  21061  20060  -3026  -1798   -538       C
ATOM   2829  C   LYS A 386      -7.870 -39.237  62.069  1.00159.09           C
ANISOU 2829  C   LYS A 386    18821  21397  20229  -3424  -1755   -334       C
ATOM   2830  O   LYS A 386      -8.754 -40.076  62.243  1.00161.02           O
ANISOU 2830  O   LYS A 386    18886  21727  20568  -3614  -1809   -236       O
ATOM   2831  CB  LYS A 386      -8.148 -39.616  59.607  1.00156.78           C
ANISOU 2831  CB  LYS A 386    18091  21114  20362  -2911  -1989   -601       C
ATOM   2832  CG  LYS A 386      -7.813 -39.141  58.199  1.00154.38           C
ANISOU 2832  CG  LYS A 386    17663  20798  20198  -2479  -2026   -805       C
ATOM   2833  CD  LYS A 386      -7.881 -37.614  58.113  1.00153.39           C
ANISOU 2833  CD  LYS A 386    17630  20807  19844  -2213  -1643   -927       C
ATOM   2834  CE  LYS A 386      -6.904 -37.040  57.081  1.00150.70           C
ANISOU 2834  CE  LYS A 386    17323  20355  19582  -1859  -1717  -1075       C
ATOM   2835  NZ  LYS A 386      -7.105 -37.589  55.706  1.00149.68           N
ANISOU 2835  NZ  LYS A 386    16909  20227  19734  -1575  -1915  -1198       N
ATOM   2836  N   GLU A 387      -7.151 -38.698  63.046  1.00209.80           N
ANISOU 2836  N   GLU A 387    25541  27739  26434  -3540  -1665   -270       N
ATOM   2837  CA  GLU A 387      -7.324 -39.051  64.447  1.00211.91           C
ANISOU 2837  CA  GLU A 387    25959  28016  26541  -3892  -1617    -76       C
ATOM   2838  C   GLU A 387      -8.003 -37.913  65.223  1.00212.97           C
ANISOU 2838  C   GLU A 387    26172  28380  26369  -3848  -1213    -60       C
ATOM   2839  O   GLU A 387      -7.612 -37.554  66.340  1.00213.57           O
ANISOU 2839  O   GLU A 387    26494  28421  26231  -3990  -1119     33       O
ATOM   2840  CB  GLU A 387      -5.972 -39.474  65.035  1.00211.11           C
ANISOU 2840  CB  GLU A 387    26140  27635  26436  -4072  -1867    -10       C
ATOM   2841  CG  GLU A 387      -5.489 -40.830  64.477  1.00210.69           C
ANISOU 2841  CG  GLU A 387    26005  27386  26662  -4187  -2294     14       C
ATOM   2842  CD  GLU A 387      -4.060 -40.810  63.942  1.00208.18           C
ANISOU 2842  CD  GLU A 387    25845  26830  26423  -4056  -2546    -87       C
ATOM   2843  OE1 GLU A 387      -3.186 -40.147  64.543  1.00207.33           O
ANISOU 2843  OE1 GLU A 387    26008  26623  26144  -4059  -2471    -97       O
ATOM   2844  OE2 GLU A 387      -3.812 -41.476  62.913  1.00207.09           O
ANISOU 2844  OE2 GLU A 387    25555  26609  26520  -3941  -2831   -157       O
ATOM   2845  N   ALA A 388      -9.035 -37.365  64.586  1.00166.86           N
ANISOU 2845  N   ALA A 388    20114  22779  20508  -3631   -987   -162       N
ATOM   2846  CA  ALA A 388      -9.862 -36.289  65.120  1.00167.86           C
ANISOU 2846  CA  ALA A 388    20265  23170  20344  -3541   -608   -174       C
ATOM   2847  C   ALA A 388     -11.269 -36.446  64.529  1.00169.05           C
ANISOU 2847  C   ALA A 388    20093  23585  20554  -3458   -471   -218       C
ATOM   2848  O   ALA A 388     -11.969 -35.464  64.270  1.00168.95           O
ANISOU 2848  O   ALA A 388    20018  23799  20375  -3224   -183   -334       O
ATOM   2849  CB  ALA A 388      -9.275 -34.935  64.757  1.00165.80           C
ANISOU 2849  CB  ALA A 388    20161  22894  19943  -3226   -441   -341       C
ATOM   2850  N   ARG A 389     -11.656 -37.699  64.300  1.00222.11           N
ANISOU 2850  N   ARG A 389    26611  30266  27515  -3646   -694   -131       N
ATOM   2851  CA  ARG A 389     -12.939 -38.043  63.691  1.00223.31           C
ANISOU 2851  CA  ARG A 389    26436  30633  27780  -3591   -620   -169       C
ATOM   2852  C   ARG A 389     -14.063 -38.100  64.706  1.00226.17           C
ANISOU 2852  C   ARG A 389    26734  31253  27945  -3815   -400     -6       C
ATOM   2853  O   ARG A 389     -15.237 -38.097  64.343  1.00227.30           O
ANISOU 2853  O   ARG A 389    26628  31638  28099  -3748   -251    -47       O
ATOM   2854  CB  ARG A 389     -12.820 -39.389  62.987  1.00223.31           C
```

FIG. 13 Continued

```
ANISOU 2854  CB  ARG A 389     26245  30459  28143  -3690   -988   -146       C
ATOM   2855  CG  ARG A 389     -11.429 -39.650  62.461  1.00220.98            C
ANISOU 2855  CG  ARG A 389     26093  29857  28012  -3610  -1293   -210       C
ATOM   2856  CD  ARG A 389     -11.059 -38.695  61.330  1.00218.38            C
ANISOU 2856  CD  ARG A 389     25744  29530  27701  -3181  -1207   -447       C
ATOM   2857  NE  ARG A 389     -11.345 -37.289  61.623  1.00218.10            N
ANISOU 2857  NE  ARG A 389     25821  29681  27365  -3000   -823   -528       N
ATOM   2858  CZ  ARG A 389     -10.427 -36.363  61.898  1.00216.64            C
ANISOU 2858  CZ  ARG A 389     25901  29403  27009  -2897   -736   -571       C
ATOM   2859  NH1 ARG A 389      -9.137 -36.677  61.930  1.00215.28            N
ANISOU 2859  NH1 ARG A 389     25910  28958  26930  -2959   -992   -544       N
ATOM   2860  NH2 ARG A 389     -10.801 -35.114  62.148  1.00216.58            N
ANISOU 2860  NH2 ARG A 389     25979  29578  26732  -2729   -398   -645       N
ATOM   2861  N   ALA A 390     -13.692 -38.174  65.979  1.00170.08            N
ANISOU 2861  N   ALA A 390     19854  24103  20664  -4076   -385    180       N
ATOM   2862  CA  ALA A 390     -14.653 -38.194  67.076  1.00172.85            C
ANISOU 2862  CA  ALA A 390     20175  24702  20798  -4290   -176    363       C
ATOM   2863  C   ALA A 390     -15.782 -39.193  66.858  1.00175.01            C
ANISOU 2863  C   ALA A 390     20128  25114  21255  -4462   -232    458       C
ATOM   2864  O   ALA A 390     -16.873 -38.829  66.431  1.00175.70            O
ANISOU 2864  O   ALA A 390     19997  25469  21292  -4317    -26    376       O
ATOM   2865  CB  ALA A 390     -15.211 -36.795  67.321  1.00172.81            C
ANISOU 2865  CB  ALA A 390     20230  24978  20451  -4054    199    268       C
ATOM   2866  N   GLY A 391     -15.498 -40.454  67.151  1.00176.02            N
ANISOU 2866  N   GLY A 391     20235  25051  21595  -4769   -520    627       N
ATOM   2867  CA  GLY A 391     -16.483 -41.510  67.064  1.00178.33            C
ANISOU 2867  CA  GLY A 391     20240  25435  22081  -4983   -611    752       C
ATOM   2868  C   GLY A 391     -17.654 -41.239  66.147  1.00178.60            C
ANISOU 2868  C   GLY A 391     19961  25721  22179  -4766   -451    605       C
ATOM   2869  O   GLY A 391     -17.484 -40.752  65.031  1.00176.39            O
ANISOU 2869  O   GLY A 391     19617  25412  21993  -4438   -453    366       O
ATOM   2870  N   ILE A 392     -18.848 -41.554  66.652  1.00287.38            N
ANISOU 2870  N   ILE A 392     33543  39753  35896  -4950   -304    753       N
ATOM   2871  CA  ILE A 392     -20.117 -41.460  65.919  1.00288.22            C
ANISOU 2871  CA  ILE A 392     33323  40122  36063  -4803   -153    643       C
ATOM   2872  C   ILE A 392     -20.637 -40.045  65.624  1.00287.18            C
ANISOU 2872  C   ILE A 392     33199  40275  35642  -4450    212    437       C
ATOM   2873  O   ILE A 392     -20.448 -39.118  66.415  1.00287.08            O
ANISOU 2873  O   ILE A 392     33412  40378  35289  -4407    436    466       O
ATOM   2874  CB  ILE A 392     -21.238 -42.228  66.668  1.00291.78            C
ANISOU 2874  CB  ILE A 392     33570  40778  36517  -5137    -98    891       C
ATOM   2875  CG1 ILE A 392     -20.721 -43.575  67.181  1.00293.11            C
ANISOU 2875  CG1 ILE A 392     33775  40675  36919  -5521   -436   1130       C
ATOM   2876  CG2 ILE A 392     -22.462 -42.412  65.778  1.00292.64            C
ANISOU 2876  CG2 ILE A 392     33312  41096  36783  -5016    -30    775       C
ATOM   2877  CD1 ILE A 392     -20.392 -44.566  66.086  1.00292.11            C
ANISOU 2877  CD1 ILE A 392     33491  40278  37219  -5502   -815   1038       C
ATOM   2878  N   ARG A 393     -21.313 -39.917  64.482  1.00183.24            N
ANISOU 2878  N   ARG A 393     19784  27221  22618  -4194    258    226       N
ATOM   2879  CA  ARG A 393     -21.912 -38.669  64.015  1.00182.23            C
ANISOU 2879  CA  ARG A 393     19625  27364  22249  -3836    586     -2       C
ATOM   2880  C   ARG A 393     -22.107 -38.723  62.504  1.00180.46            C
ANISOU 2880  C   ARG A 393     19179  27092  22294  -3516    505   -270       C
ATOM   2881  O   ARG A 393     -21.296 -39.302  61.780  1.00178.86            O
ANISOU 2881  O   ARG A 393     18972  26593  22395  -3463    206   -329       O
ATOM   2882  CB  ARG A 393     -21.059 -37.460  64.391  1.00180.35            C
ANISOU 2882  CB  ARG A 393     19722  27092  21711  -3656    740    -77       C
ATOM   2883  CG  ARG A 393     -19.825 -37.244  63.528  1.00177.23            C
ANISOU 2883  CG  ARG A 393     19468  26385  21488  -3426    552   -250       C
ATOM   2884  CD  ARG A 393     -20.035 -36.138  62.498  1.00175.13            C
ANISOU 2884  CD  ARG A 393     19164  26242  21136  -2979    756   -549       C
ATOM   2885  NE  ARG A 393     -20.659 -36.619  61.269  1.00174.74            N
ANISOU 2885  NE  ARG A 393     18802  26221  21371  -2800    677   -714       N
ATOM   2886  CZ  ARG A 393     -20.018 -36.770  60.114  1.00172.45            C
ANISOU 2886  CZ  ARG A 393     18461  25714  21349  -2557    483   -885       C
ATOM   2887  NH1 ARG A 393     -18.726 -36.472  60.025  1.00170.36            N
ANISOU 2887  NH1 ARG A 393     18435  25194  21101  -2479    353   -908       N
ATOM   2888  NH2 ARG A 393     -20.672 -37.212  59.046  1.00172.28            N
ANISOU 2888  NH2 ARG A 393     18144  25738  21578  -2379    418  -1034       N
```

FIG. 13 Continued

```
ATOM   2889  N   GLU A 394     -23.189 -38.115  62.034  1.00257.66           N
ANISOU 2889  N   GLU A 394    28775  37174  31949  -3287    769   -436       N
ATOM   2890  CA  GLU A 394     -23.502 -38.070  60.609  1.00256.06           C
ANISOU 2890  CA  GLU A 394    28352  36967  31971  -2942    738   -711       C
ATOM   2891  C   GLU A 394     -24.285 -36.793  60.328  1.00255.48           C
ANISOU 2891  C   GLU A 394    28265  37223  31583  -2611   1121   -931       C
ATOM   2892  O   GLU A 394     -25.021 -36.700  59.340  1.00255.01           O
ANISOU 2892  O   GLU A 394    27973  37290  31629  -2348   1196  -1150       O
ATOM   2893  CB  GLU A 394     -24.321 -39.295  60.183  1.00257.87           C
ANISOU 2893  CB  GLU A 394    28236  37203  32541  -3094    551   -660       C
ATOM   2894  CG  GLU A 394     -23.590 -40.627  60.295  1.00258.37           C
ANISOU 2894  CG  GLU A 394    28290  36929  32949  -3391    133   -470       C
ATOM   2895  CD  GLU A 394     -22.474 -40.768  59.284  1.00255.47           C
ANISOU 2895  CD  GLU A 394    27988  36242  32838  -3150   -144   -630       C
ATOM   2896  OE1 GLU A 394     -22.424 -39.968  58.327  1.00253.26           O
ANISOU 2896  OE1 GLU A 394    27687  36006  32534  -2738    -23   -897       O
ATOM   2897  OE2 GLU A 394     -21.645 -41.685  59.447  1.00255.44           O
ANISOU 2897  OE2 GLU A 394    28056  35949  33049  -3366   -485   -486       O
ATOM   2898  N   VAL A 395     -24.124 -35.816  61.216  1.00175.40           N
ANISOU 2898  N   VAL A 395    18379  27218  21047  -2618   1355   -878       N
ATOM   2899  CA  VAL A 395     -24.828 -34.547  61.101  1.00174.97           C
ANISOU 2899  CA  VAL A 395    18355  27486  20638  -2323   1715  -1070       C
ATOM   2900  C   VAL A 395     -23.938 -33.372  60.678  1.00172.08           C
ANISOU 2900  C   VAL A 395    18249  27012  20122  -1986   1804  -1266       C
ATOM   2901  O   VAL A 395     -23.296 -32.733  61.512  1.00171.83           O
ANISOU 2901  O   VAL A 395    18503  26944  19839  -2047   1869  -1172       O
ATOM   2902  CB  VAL A 395      25.554  34.240  62.400  1.00177.50           C
ANISOU 2902  CB  VAL A 395    18737  28118  20586  -2543   1940   -878       C
ATOM   2903  CG1 VAL A 395     -27.031 -34.576  62.252  1.00179.66           C
ANISOU 2903  CG1 VAL A 395    18691  28723  20848  -2577   2083   -898       C
ATOM   2904  CG2 VAL A 395     -24.932 -35.042  63.529  1.00179.03           C
ANISOU 2904  CG2 VAL A 395    19058  28131  20835  -2961   1745   -551       C
ATOM   2905  N   HIS A 396     -23.936 -33.098  59.370  1.00203.72           N
ANISOU 2905  N   HIS A 396    22142  30971  24291  -1623   1806  -1539       N
ATOM   2906  CA  HIS A 396     -23.128 -32.044  58.738  1.00200.89           C
ANISOU 2906  CA  HIS A 396    21983  30498  23849  -1267   1878  -1744       C
ATOM   2907  C   HIS A 396     -23.764 -30.646  58.787  1.00200.53           C
ANISOU 2907  C   HIS A 396    22040  30765  23389   -988   2247  -1925       C
ATOM   2908  O   HIS A 396     -24.875 -30.444  58.292  1.00201.02           O
ANISOU 2908  O   HIS A 396    21904  31098  23378   -809   2433  -2091       O
ATOM   2909  CB  HIS A 396     -22.864 -32.390  57.260  1.00198.85           C
ANISOU 2909  CB  HIS A 396    21542  30058  23953   -971   1714  -1957       C
ATOM   2910  CG  HIS A 396     -21.798 -33.422  57.043  1.00198.13           C
ANISOU 2910  CG  HIS A 396    21453  29597  24232  -1128   1329  -1833       C
ATOM   2911  ND1 HIS A 396     -20.460 -33.167  57.252  1.00196.56           N
ANISOU 2911  ND1 HIS A 396    21520  29131  24032  -1148   1196  -1768       N
ATOM   2912  CD2 HIS A 396     -21.875 -34.699  56.597  1.00198.74           C
ANISOU 2912  CD2 HIS A 396    21297  29529  24667  -1254   1037  -1775       C
ATOM   2913  CE1 HIS A 396     -19.760 -34.251  56.964  1.00196.22           C
ANISOU 2913  CE1 HIS A 396    21413  28808  24333  -1284    842  -1675       C
ATOM   2914  NE2 HIS A 396     -20.594 -35.193  56.565  1.00197.52           N
ANISOU 2914  NE2 HIS A 396    21280  29037  24732   1348    733   1676       N
ATOM   2915  N   PHE A 397     -23.038 -29.682  59.349  1.00165.59           N
ANISOU 2915  N   PHE A 397    17928  26293  18697   -939   2340  -1904       N
ATOM   2916  CA  PHE A 397     -23.496 -28.296  59.413  1.00165.09           C
ANISOU 2916  CA  PHE A 397    18004  26493  18229   -664   2660  -2075       C
ATOM   2917  C   PHE A 397     -22.308 -27.334  59.339  1.00162.87           C
ANISOU 2917  C   PHE A 397    18029  25998  17856   -482   2658  -2139       C
ATOM   2918  O   PHE A 397     -22.312 -26.264  59.939  1.00162.88           O
ANISOU 2918  O   PHE A 397    18256  26136  17494   -400   2846  -2159       O
ATOM   2919  CB  PHE A 397     -24.335 -28.055  60.663  1.00167.60           C
ANISOU 2919  CB  PHE A 397    18372  27133  18174   -872   2644  -1920       C
ATOM   2920  CG  PHE A 397     -25.459 -29.024  60.818  1.00169.99           C
ANISOU 2920  CG  PHE A 397    18375  27643  18572  -1085   2840  -1823       C
ATOM   2921  CD1 PHE A 397     -26.722 -28.717  60.352  1.00170.61           C
ANISOU 2921  CD1 PHE A 397    18254  28064  18507   -892   3065  -2007       C
ATOM   2922  CD2 PHE A 397     -25.252 -30.256  61.413  1.00171.66           C
ANISOU 2922  CD2 PHE A 397    18500  27703  19019  -1479   2607  -1552       C
ATOM   2923  CE1 PHE A 397     -27.768 -29.620  60.490  1.00172.93           C
```

FIG. 13 Continued

```
ANISOU 2923  CE1 PHE A 397    18258  28549  18901  -1096   3058  -1913       C
ATOM   2924  CE2 PHE A 397   -26.288 -31.162  61.553  1.00174.01             C
ANISOU 2924  CE2 PHE A 397    18513  28181  19420  -1687   2597  -1450       C
ATOM   2925  CZ  PHE A 397   -27.549 -30.845  61.092  1.00174.68             C
ANISOU 2925  CZ  PHE A 397    18389  28609  19371  -1499   2822  -1627       C
ATOM   2926  N   LEU A 398   -21.313 -27.722  58.546  1.00161.47             N
ANISOU 2926  N   LEU A 398    17846  25491  18016   -403   2434  -2178       N
ATOM   2927  CA  LEU A 398   -20.100 -26.943  58.308  1.00159.26             C
ANISOU 2927  CA  LEU A 398    17818  24971  17724   -229   2396  -2238       C
ATOM   2928  C   LEU A 398   -20.271 -25.589  57.571  1.00157.55             C
ANISOU 2928  C   LEU A 398    17686  24880  17296    204   2650  -2508       C
ATOM   2929  O   LEU A 398   -19.280 -24.900  57.333  1.00155.77             O
ANISOU 2929  O   LEU A 398    17662  24458  17066    358   2626  -2557       O
ATOM   2930  CB  LEU A 398   -19.112 -27.812  57.517  1.00157.77             C
ANISOU 2930  CB  LEU A 398    17547  24433  17965   -233   2084  -2220       C
ATOM   2931  CG  LEU A 398   -19.304 -29.323  57.674  1.00159.25             C
ANISOU 2931  CG  LEU A 398    17522  24537  18450   -549   1828  -2049       C
ATOM   2932  CD1 LEU A 398   -19.003 -30.069  56.385  1.00157.78             C
ANISOU 2932  CD1 LEU A 398    17117  24163  18670   -373   1601  -2163       C
ATOM   2933  CD2 LEU A 398   -18.464 -29.838  58.813  1.00160.16             C
ANISOU 2933  CD2 LEU A 398    17830  24456  18567   -933   1638  -1780       C
ATOM   2934  N   PRO A 399   -21.509 -25.207  57.184  1.00207.87             N
ANISOU 2934  N   PRO A 399    23906  31576  23498    407   2889  -2689       N
ATOM   2935  CA  PRO A 399   -21.668 -23.937  56.470  1.00206.22             C
ANISOU 2935  CA  PRO A 399    23790  31482  23084    825   3125  -2954       C
ATOM   2936  C   PRO A 399   -20.673 -22.800  56.752  1.00204.87             C
ANISOU 2936  C   PRO A 399    23954  31165  22722    936   3171  -2960       C
ATOM   2937  O   PRO A 399   -20.491 -22.393  57.900  1.00205.93             O
ANISOU 2937  O   PRO A 399    24307  31341  22596    745   3205  -2810       O
ATOM   2938  CB  PRO A 399   -23.085 -23.518  56.882  1.00207.91             C
ANISOU 2938  CB  PRO A 399    23937  32118  22943    858   3394  -3034       C
ATOM   2939  CG  PRO A 399    23.835  24.838  56.971  1.00209.76             C
ANISOU 2939  CG  PRO A 399    23870  32432  23396    605   3281  -2921       C
ATOM   2940  CD  PRO A 399   -22.796 -25.933  57.186  1.00209.75             C
ANISOU 2940  CD  PRO A 399    23862  32074  23760    306   2946  -2691       C
ATOM   2941  N   PHE A 400   -20.053 -22.295  55.686  1.00156.81             N
ANISOU 2941  N   PHE A 400    17895  24914  16773   1259   3171  -3133       N
ATOM   2942  CA  PHE A 400   -19.190 -21.127  55.780  1.00155.46             C
ANISOU 2942  CA  PHE A 400    18019  24617  16432   1414   3237  -3170       C
ATOM   2943  C   PHE A 400   -19.616 -20.058  54.788  1.00153.99             C
ANISOU 2943  C   PHE A 400    17837  24572  16102   1864   3477  -3461       C
ATOM   2944  O   PHE A 400   -20.208 -20.363  53.762  1.00153.37             O
ANISOU 2944  O   PHE A 400    17521  24577  16177   2090   3526  -3638       O
ATOM   2945  CB  PHE A 400   -17.724 -21.463  55.527  1.00154.01             C
ANISOU 2945  CB  PHE A 400    17920  24041  16558   1350   2980  -3059       C
ATOM   2946  CG  PHE A 400   -16.857 -20.238  55.323  1.00152.39             C
ANISOU 2946  CG  PHE A 400    17970  23697  16233   1576   3055  -3137       C
ATOM   2947  CD1 PHE A 400   -16.944 -19.159  56.183  1.00153.00             C
ANISOU 2947  CD1 PHE A 400    18311  23890  15933   1571   3217  -3127       C
ATOM   2948  CD2 PHE A 400   -15.968 -20.163  54.277  1.00150.33             C
ANISOU 2948  CD2 PHE A 400    17684  23198  16236   1800   2956  -3213       C
ATOM   2949  CE1 PHE A 400   -16.174 -18.031  55.998  1.00151.64             C
ANISOU 2949  CE1 PHE A 400    18372  23584  15661   1773   3277  -3196       C
ATOM   2950  CE2 PHE A 400   -15.192 -19.035  54.101  1.00149.00             C
ANISOU 2950  CE2 PHE A 400    17744  22905  15963   1995   3029  -3270       C
ATOM   2951  CZ  PHE A 400    15.298  17.971  54.970  1.00149.68             C
ANISOU 2951  CZ  PHE A 400    18094  23095  15685   1973   3187  -3262       C
ATOM   2952  N   ASN A 401   -19.287 -18.808  55.106  1.00190.13             N
ANISOU 2952  N   ASN A 401    22691  29162  20388   1997   3615  -3511       N
ATOM   2953  CA  ASN A 401   -19.619 -17.648  54.289  1.00188.79             C
ANISOU 2953  CA  ASN A 401    22583  29117  20031   2417   3850  -3778       C
ATOM   2954  C   ASN A 401   -19.280 -16.356  55.023  1.00188.82             C
ANISOU 2954  C   ASN A 401    22927  29143  19674   2458   3963  -3768       C
ATOM   2955  O   ASN A 401   -19.366 -16.301  56.249  1.00190.40             O
ANISOU 2955  O   ASN A 401    23270  29422  19653   2197   3943  -3605       O
ATOM   2956  CB  ASN A 401   -21.112 -17.633  54.008  1.00189.64             C
ANISOU 2956  CB  ASN A 401    22507  29599  19948   2567   4067  -3966       C
ATOM   2957  CG  ASN A 401   -21.930 -17.494  55.273  1.00191.87             C
ANISOU 2957  CG  ASN A 401    22872  30169  19860   2335   4165  -3863       C
```

FIG. 13 Continued

```
ATOM   2958  OD1 ASN A 401      -22.644 -16.509  55.460  1.00192.17           O
ANISOU 2958  OD1 ASN A 401    23030  30479  19506   2517   4391  -4009        O
ATOM   2959  ND2 ASN A 401      -21.813 -18.474  56.162  1.00193.47           N
ANISOU 2959  ND2 ASN A 401    23017  30317  20175   1940   3990  -3607        N
ATOM   2960  N   PRO A 402      -18.908 -15.300  54.281  1.00147.21           N
ANISOU 2960  N   PRO A 402    17787  23805  14341   2797   4078  -3943        N
ATOM   2961  CA  PRO A 402      -18.658 -14.021  54.949  1.00147.32           C
ANISOU 2961  CA  PRO A 402    18125  23848  14002   2857   4182  -3950        C
ATOM   2962  C   PRO A 402      -19.888 -13.609  55.745  1.00149.03           C
ANISOU 2962  C   PRO A 402    18392  24453  13781   2832   4364  -4002        C
ATOM   2963  O   PRO A 402      -20.929 -14.246  55.618  1.00149.94           O
ANISOU 2963  O   PRO A 402    18279  24811  13879   2807   4435  -4059        O
ATOM   2964  CB  PRO A 402      -18.433 -13.062  53.784  1.00145.36           C
ANISOU 2964  CB  PRO A 402    17929  23542  13757   3277   4319  -4180        C
ATOM   2965  CG  PRO A 402      -17.895 -13.923  52.710  1.00144.00           C
ANISOU 2965  CG  PRO A 402    17525  23152  14038   3348   4183  -4185        C
ATOM   2966  CD  PRO A 402      -18.611 -15.234  52.843  1.00145.19           C
ANISOU 2966  CD  PRO A 402    17400  23422  14344   3136   4098  -4120        C
ATOM   2967  N   VAL A 403      -19.759 -12.569  56.560  1.00193.49           N
ANISOU 2967  N   VAL A 403    24312  30141  19064   2843   4425  -3980        N
ATOM   2968  CA  VAL A 403      -20.854 -12.081  57.403  1.00195.15           C
ANISOU 2968  CA  VAL A 403    24602  30730  18815   2836   4581  -4018        C
ATOM   2969  C   VAL A 403      -21.395 -13.119  58.399  1.00197.29           C
ANISOU 2969  C   VAL A 403    24736  31155  19069   2475   4501  -3810        C
ATOM   2970  O   VAL A 403      -22.284 -12.816  59.198  1.00198.87           O
ANISOU 2970  O   VAL A 403    24987  31683  18893   2439   4611  -3803        O
ATOM   2971  CB  VAL A 403      -22.005 -11.456  56.577  1.00194.66           C
ANISOU 2971  CB  VAL A 403    24464  30991  18508   3198   4841  -4325        C
ATOM   2972  CG1 VAL A 403      -21.442 -10.668  55.401  1.00192.44           C
ANISOU 2972  CG1 VAL A 403    24258  30525  18336   3554   4911  -4524        C
ATOM   2973  CG2 VAL A 403      -22.990 -12.521  56.106  1.00195.27           C
ANISOU 2973  CG2 VAL A 403    24196  31265  18732   3157   4888   4384        C
ATOM   2974  N   ASP A 404      -20.854 -14.335  58.346  1.00184.24           N
ANISOU 2974  N   ASP A 404    22914  29272  17818   2217   4303  -3636        N
ATOM   2975  CA  ASP A 404      -21.198 -15.393  59.298  1.00186.27           C
ANISOU 2975  CA  ASP A 404    23049  29614  18109   1846   4199  -3407        C
ATOM   2976  C   ASP A 404      -19.884 -15.836  59.904  1.00186.15           C
ANISOU 2976  C   ASP A 404    23164  29232  18334   1573   3949  -3165        C
ATOM   2977  O   ASP A 404      -19.779 -16.092  61.100  1.00187.72           O
ANISOU 2977  O   ASP A 404    23459  29449  18416   1300   3867  -2955        O
ATOM   2978  CB  ASP A 404      -21.918 -16.552  58.616  1.00186.60           C
ANISOU 2978  CB  ASP A 404    22738  29746  18416   1791   4185  -3442        C
ATOM   2979  CG  ASP A 404      -23.433 -16.433  58.711  1.00187.99           C
ANISOU 2979  CG  ASP A 404    22777  30370  18280   1876   4402  -3566        C
ATOM   2980  OD1 ASP A 404      -23.947 -16.255  59.837  1.00189.84           O
ANISOU 2980  OD1 ASP A 404    23101  30842  18188   1720   4454  -3446        O
ATOM   2981  OD2 ASP A 404      -24.112 -16.522  57.666  1.00187.25           O
ANISOU 2981  OD2 ASP A 404    22482  30399  18265   2110   4518  -3786        O
ATOM   2982  N   LYS A 405      -18.885 -15.933  59.043  1.00151.96           N
ANISOU 2982  N   LYS A 405    18829  24574  14337   1663   3832  -3202        N
ATOM   2983  CA  LYS A 405      -17.514 -16.090  59.476  1.00151.45           C
ANISOU 2983  CA  LYS A 405    18929  24145  14469   1477   3614  -3022        C
ATOM   2984  C   LYS A 405      -17.133 -17.336  60.282  1.00152.68           C
ANISOU 2984  C   LYS A 405    19018  24163  14830   1071   3394  -2760        C
ATOM   2985  O   LYS A 405      -16.190 -17.282  61.062  1.00152.81           O
ANISOU 2985  O   LYS A 405    19235  23962  14865    893   3252  -2600        O
ATOM   2986  CB  LYS A 405      -17.139 -14.838  60.265  1.00151.60           C
ANISOU 2986  CB  LYS A 405    19280  24162  14158   1546   3674  -3013        C
ATOM   2987  CG  LYS A 405      -15.718 -14.400  60.091  1.00150.10           C
ANISOU 2987  CG  LYS A 405    19283  23597  14152   1578   3536  -2974        C
ATOM   2988  CD  LYS A 405      -15.623 -12.888  60.130  1.00149.56           C
ANISOU 2988  CD  LYS A 405    19474  23569  13781   1845   3674  -3108        C
ATOM   2989  CE  LYS A 405      -16.316 -12.258  58.931  1.00148.40           C
ANISOU 2989  CE  LYS A 405    19234  23593  13559   2218   3883  -3375        C
ATOM   2990  NZ  LYS A 405      -15.841 -10.861  58.689  1.00147.35           N
ANISOU 2990  NZ  LYS A 405    19353  23374  13259   2485   3964  -3498        N
ATOM   2991  N   ARG A 406      -17.819 -18.460  60.099  1.00153.72           N
ANISOU 2991  N   ARG A 406    18877  24404  15126    926   3355  -2717        N
ATOM   2992  CA  ARG A 406      -17.429 -19.649  60.855  1.00154.91           C
```

FIG. 13 Continued

```
ANISOU 2992  CA  ARG A 406    18975 24409 15473    539   3136  -2466       C
ATOM   2993  C   ARG A 406    -17.980 -20.975  60.350  1.00 155.48         C
ANISOU 2993  C   ARG A 406    18724 24517 15834    405   3043  -2434       C
ATOM   2994  O   ARG A 406    -18.964 -21.011  59.602  1.00 155.48         O
ANISOU 2994  O   ARG A 406    18514 24738 15824    588   3182  -2598       O
ATOM   2995  CB  ARG A 406    -17.825 -19.492  62.321  1.00 157.05         C
ANISOU 2995  CB  ARG A 406    19389 24865 15416    323   3186  -2298       C
ATOM   2996  CG  ARG A 406    -19.333 -19.470  62.542  1.00 158.75         C
ANISOU 2996  CG  ARG A 406    19451 25511 15357    354   3390  -2349       C
ATOM   2997  CD  ARG A 406    -19.707 -19.624  64.008  1.00 161.10         C
ANISOU 2997  CD  ARG A 406    19836 25986 15390     95   3397  -2133       C
ATOM   2998  NE  ARG A 406    -21.151 -19.535  64.180  1.00 162.72         N
ANISOU 2998  NE  ARG A 406    19890 26624 15311    146   3599  -2186       N
ATOM   2999  CZ  ARG A 406    -21.970 -20.577  64.128  1.00 164.13         C
ANISOU 2999  CZ  ARG A 406    19791 26957 15615    -32   3593  -2112       C
ATOM   3000  NH1 ARG A 406    -21.473 -21.788  63.923  1.00 164.12         N
ANISOU 3000  NH1 ARG A 406    19643 26700 16014   -272   3382  -1980       N
ATOM   3001  NH2 ARG A 406    -23.278 -20.409  64.286  1.00 165.60         N
ANISOU 3001  NH2 ARG A 406    19847 27554 15521     30   3788  -2169       N
ATOM   3002  N   THR A 407    -17.334 -22.059  60.788  1.00 156.28         N
ANISOU 3002  N   THR A 407    18795 24395 16190     88   2799  -2225       N
ATOM   3003  CA  THR A 407    -17.766 -23.426  60.489  1.00 157.11         C
ANISOU 3003  CA  THR A 407    18614 24499 16581    -99   2660  -2151       C
ATOM   3004  C   THR A 407    -18.741 -23.889  61.589  1.00 159.80         C
ANISOU 3004  C   THR A 407    18889 25106 16720   -372   2728  -1987       C
ATOM   3005  O   THR A 407    -18.771 -23.297  62.669  1.00 160.86         O
ANISOU 3005  O   THR A 407    19228 25349 16542   -455   2818  -1889       O
ATOM   3006  CB  THR A 407    -16.562 -24.372  60.396  1.00 156.32         C
ANISOU 3006  CB  THR A 407    18525 24025 16846   -299   2346  -2011       C
ATOM   3007  OG1 THR A 407    -15.445 -23.654  59.872  1.00 154.16         O
ANISOU 3007  OG1 THR A 407    18426 23508 16639    -96   2300  -2100       O
ATOM   3008  CG2 THR A 407    -16.864 -25.547  59.478  1.00 156.16         C
ANISOU 3008  CG2 THR A 407    18194 23956 17185   -318   2192  -2040       C
ATOM   3009  N   ALA A 408    -19.532 -24.933  61.337  1.00 221.25         N
ANISOU 3009  N   ALA A 408    26387 32998 24678   -504   2680  -1949       N
ATOM   3010  CA  ALA A 408    -20.531 -25.349  62.329  1.00 223.92         C
ANISOU 3010  CA  ALA A 408    26640 33617 24823   -751   2763  -1789       C
ATOM   3011  C   ALA A 408    -20.929 -26.835  62.372  1.00 225.48         C
ANISOU 3011  C   ALA A 408    26574 33788 25311  -1051   2590  -1631       C
ATOM   3012  O   ALA A 408    -22.109 -27.162  62.286  1.00 226.98         O
ANISOU 3012  O   ALA A 408    26534 34254 25453  -1073   2703  -1651       O
ATOM   3013  CB  ALA A 408    -21.772 -24.470  62.219  1.00 224.53         C
ANISOU 3013  CB  ALA A 408    26662 34099 24551   -513   3066  -1960       C
ATOM   3014  N   LEU A 409    -19.954 -27.722  62.549  1.00 166.02         N
ANISOU 3014  N   LEU A 409    19082 25932 18066  -1289   2312  -1470       N
ATOM   3015  CA  LEU A 409     20.210  29.166  62.590  1.00 167.45         C
ANISOU 3015  CA  LEU A 409    19035 26044 18543  -1584   2108  -1310       C
ATOM   3016  C   LEU A 409    -21.271 -29.564  63.621  1.00 170.43         C
ANISOU 3016  C   LEU A 409    19314 26714 18727  -1849   2217  -1123       C
ATOM   3017  O   LEU A 409     21.775  28.719  64.359  1.00 171.38         O
ANISOU 3017  O   LEU A 409    19552 27098 18467  -1801   2444  -1109       O
ATOM   3018  CB  LEU A 409    -18.904 -29.922  62.852  1.00 166.80         C
ANISOU 3018  CB  LEU A 409    19083 25575 18717  -1812   1799  -1152       C
ATOM   3019  CG  LEU A 409    -18.804 -31.442  62.668  1.00 167.58         C
ANISOU 3019  CG  LEU A 409    18987 25495 19192  -2080   1507  -1015       C
ATOM   3020  CD1 LEU A 409    -19.137 -32.186  63.948  1.00 170.28         C
ANISOU 3020  CD1 LEU A 409    19337 25908 19455  -2481   1465   -734       C
ATOM   3021  CD2 LEU A 409    -19.653 -31.943  61.504  1.00 167.48         C
ANISOU 3021  CD2 LEU A 409    18639 25582 19415  -1925   1493  -1168       C
ATOM   3022  N   THR A 410    -21.613 -30.853  63.643  1.00 170.56         N
ANISOU 3022  N   THR A 410    19107 26688 19009  -2117   2046   -978       N
ATOM   3023  CA  THR A 410    -22.575 -31.415  64.596  1.00 173.58         C
ANISOU 3023  CA  THR A 410    19365 27321 19265  -2408   2116   -764       C
ATOM   3024  C   THR A 410    -22.418 -32.935  64.738  1.00 174.90         C
ANISOU 3024  C   THR A 410    19376 27288 19789  -2762   1831   -555       C
ATOM   3025  O   THR A 410    -22.654 -33.682  63.785  1.00 174.56         O
ANISOU 3025  O   THR A 410    19092 27161 20074  -2732   1688   -638       O
ATOM   3026  CB  THR A 410    -24.010 -31.098  64.204  1.00 174.62         C
ANISOU 3026  CB  THR A 410    19260 27845 19244  -2247   2363   -900       C
```

FIG. 13 Continued

```
ATOM   3027  OG1 THR A 410      -24.203 -29.678  64.219  1.00173.65           O
ANISOU 3027  OG1 THR A 410    19305  27933  18741  -1939   2629  -1077        O
ATOM   3028  CG2 THR A 410      -24.951 -31.731  65.189  1.00177.83           C
ANISOU 3028  CG2 THR A 410    19527  28505  19537  -2562   2421   -657        C
ATOM   3029  N   TYR A 411      -22.042 -33.373  65.943  1.00179.26           N
ANISOU 3029  N   TYR A 411    20072  27771  20269  -3084   1748   -287        N
ATOM   3030  CA  TYR A 411      -21.744 -34.783  66.241  1.00180.54           C
ANISOU 3030  CA  TYR A 411    20147  27713  20737  -3445   1464    -66        C
ATOM   3031  C   TYR A 411      -22.285 -35.205  67.600  1.00183.59           C
ANISOU 3031  C   TYR A 411    20537  28279  20939  -3779   1531    229        C
ATOM   3032  O   TYR A 411      -22.573 -34.362  68.456  1.00184.41           O
ANISOU 3032  O   TYR A 411    20783  28619  20666  -3735   1761    280        O
ATOM   3033  CB  TYR A 411      -20.227 -35.038  66.216  1.00178.63           C
ANISOU 3033  CB  TYR A 411    20139  27055  20676  -3498   1197    -43        C
ATOM   3034  CG  TYR A 411      -19.457 -34.244  67.250  1.00178.28           C
ANISOU 3034  CG  TYR A 411    20439  26965  20336  -3513   1281     35        C
ATOM   3035  CD1 TYR A 411      -18.386 -34.795  67.939  1.00178.21           C
ANISOU 3035  CD1 TYR A 411    20634  26664  20412  -3749   1063    199        C
ATOM   3036  CD2 TYR A 411      -19.816 -32.936  67.543  1.00178.06           C
ANISOU 3036  CD2 TYR A 411    20533  27186  19935  -3281   1573    -66        C
ATOM   3037  CE1 TYR A 411      -17.690 -34.048  68.888  1.00177.90           C
ANISOU 3037  CE1 TYR A 411    20907  26580  20107  -3743   1140    257        C
ATOM   3038  CE2 TYR A 411      -19.136 -32.193  68.484  1.00177.81           C
ANISOU 3038  CE2 TYR A 411    20810  27110  19639  -3275   1637     -2        C
ATOM   3039  CZ  TYR A 411      -18.078 -32.744  69.150  1.00177.72           C
ANISOU 3039  CZ  TYR A 411    20991  26805  19731  -3502   1424    157        C
ATOM   3040  OH  TYR A 411      -17.426 -31.971  70.079  1.00177.48           O
ANISOU 3040  OH  TYR A 411    21262  26733  19439  -3474   1492    205        O
ATOM   3041  N   ILE A 412      -22.400 -36.518  67.795  1.00257.18           N
ANISOU 3041  N   ILE A 412    29704  37484  30529  -4105   1317    426        N
ATOM   3042  CA  ILE A 412      -22.928 -37.072  69.039  1.00260.27           C
ANISOU 3042  CA  ILE A 412    30068  38032  30791  -4444   1361    729        C
ATOM   3043  C   ILE A 412      -22.061 -38.216  69.559  1.00260.84           C
ANISOU 3043  C   ILE A 412    30234  37768  31103  -4783   1055    949        C
ATOM   3044  O   ILE A 412      -21.030 -38.549  68.977  1.00258.78           O
ANISOU 3044  O   ILE A 412    30072  37163  31090  -4751    805    860        O
ATOM   3045  CB  ILE A 412      -24.398 -37.577  68.883  1.00262.78           C
ANISOU 3045  CB  ILE A 412    30029  38665  31151  -4543   1471    790        C
ATOM   3046  CG1 ILE A 412      -24.449 -39.094  68.674  1.00264.16           C
ANISOU 3046  CG1 ILE A 412    29995  38635  31739  -4857   1176    948        C
ATOM   3047  CG2 ILE A 412      -25.110 -36.849  67.749  1.00261.47           C
ANISOU 3047  CG2 ILE A 412    29693  38698  30955  -4183   1644    487        C
ATOM   3048  CD1 ILE A 412      -25.825 -39.690  68.877  1.00267.27           C
ANISOU 3048  CD1 ILE A 412    30068  39327  32156  -5047   1273   1094        C
ATOM   3049  N   ASP A 413      -22.498 -38.806  70.664  1.00234.94           N
ANISOU 3049  N   ASP A 413    26926  34605  27735  -5099   1079   1236        N
ATOM   3050  CA  ASP A 413      -21.796 -39.904  71.300  1.00235.87           C
ANISOU 3050  CA  ASP A 413    27138  34442  28041  -5441    814   1467        C
ATOM   3051  C   ASP A 413      -22.660 -40.407  72.451  1.00239.43           C
ANISOU 3051  C   ASP A 413    27486  35136  28349  -5743    927   1777        C
ATOM   3052  O   ASP A 413      -22.501 -41.533  72.924  1.00241.07           O
ANISOU 3052  O   ASP A 413    27664  35185  28745  -6075    726   2003        O
ATOM   3053  CB  ASP A 413      -20.441 -39.423  71.821  1.00233.98           C
ANISOU 3053  CB  ASP A 413    27275  33949  27680  -5390    745   1449        C
ATOM   3054  CG  ASP A 413      -19.736 -40.464  72.665  1.00235.09           C
ANISOU 3054  CG  ASP A 413    27550  33832  27941  -5739    509   1692        C
ATOM   3055  OD1 ASP A 413      -19.910 -41.671  72.394  1.00236.22           O
ANISOU 3055  OD1 ASP A 413    27516  33846  28389  -5979    282   1800        O
ATOM   3056  OD2 ASP A 413      -19.005 -40.072  73.600  1.00234.84           O
ANISOU 3056  OD2 ASP A 413    27807  33722  27700  -5764    545   1769        O
ATOM   3057  N   GLY A 414      -23.590 -39.561  72.883  1.00196.50           N
ANISOU 3057  N   GLY A 414    21992  30100  22569  -5618   1246   1786        N
ATOM   3058  CA  GLY A 414      -24.463 -39.884  73.992  1.00199.90           C
ANISOU 3058  CA  GLY A 414    22320  30819  22813  -5859   1391   2079        C
ATOM   3059  C   GLY A 414      -25.707 -39.025  73.993  1.00201.00           C
ANISOU 3059  C   GLY A 414    22295  31432  22644   5666   1718   2015        C
ATOM   3060  O   GLY A 414      -26.018 -38.378  72.993  1.00199.30           O
ANISOU 3060  O   GLY A 414    21992  31308  22426  -5377   1809   1739        O
ATOM   3061  N   SER A 415      -26.405 -39.017  75.127  1.00272.04           N
```

FIG. 13 Continued

```
ANISOU 3061  N    SER A 415     31255  40738  31368  -5815   1892   2271        N
ATOM   3062  CA   SER A 415     -27.664 -38.289  75.292  1.00273.56             C
ANISOU 3062  CA   SER A 415     31282  41427  31230   5667   2200   2255        C
ATOM   3063  C    SER A 415     -27.687 -36.914  74.622  1.00271.02             C
ANISOU 3063  C    SER A 415     31063  41243  30669  -5236   2381   1918        C
ATOM   3064  O    SER A 415     -28.122 -36.783  73.477  1.00269.85             O
ANISOU 3064  O    SER A 415     30736  41132  30663  -5064   2401   1679        O
ATOM   3065  CB   SER A 415     -28.011 -38.159  76.781  1.00276.25             C
ANISOU 3065  CB   SER A 415     31700  42044  31218  -5802   2359   2559        C
ATOM   3066  OG   SER A 415     -28.190 -39.433  77.379  1.00278.97             O
ANISOU 3066  OG   SER A 415     31908  42317  31771  -6201   2225   2882        O
ATOM   3067  N    GLY A 416     -27.227 -35.891  75.336  1.00200.11             N
ANISOU 3067  N    GLY A 416     22369  32337  21327  -5054   2508   1898        N
ATOM   3068  CA   GLY A 416     -27.206 -34.547  74.790  1.00197.81             C
ANISOU 3068  CA   GLY A 416     22204  32169  20787  -4651   2673   1594        C
ATOM   3069  C    GLY A 416     -26.397 -34.491  73.508  1.00194.59             C
ANISOU 3069  C    GLY A 416     21844  31398  20693  -4486   2511   1310        C
ATOM   3070  O    GLY A 416     -25.485 -35.300  73.305  1.00193.72             O
ANISOU 3070  O    GLY A 416     21792  30891  20922  -4658   2251   1358        O
ATOM   3071  N    ASN A 417     -26.745 -33.555  72.628  1.00193.32             N
ANISOU 3071  N    ASN A 417     21656  31382  20415  -4145   2660   1014        N
ATOM   3072  CA   ASN A 417     -26.006 -33.386  71.381  1.00190.21             C
ANISOU 3072  CA   ASN A 417     21306  30675  20289  -3940   2531    735        C
ATOM   3073  C    ASN A 417     -25.083 -32.167  71.368  1.00187.64             C
ANISOU 3073  C    ASN A 417     21311  30228  19756  -3648   2582    555        C
ATOM   3074  O    ASN A 417     -25.494 -31.059  71.740  1.00187.72             O
ANISOU 3074  O    ASN A 417     21430  30527  19367  -3428   2808    480        O
ATOM   3075  CB   ASN A 417     -26.935 -33.389  70.162  1.00189.80             C
ANISOU 3075  CB   ASN A 417     20962  30789  20365  -3764   2613    508        C
ATOM   3076  CG   ASN A 417     -26.886 -34.705  69.401  1.00189.97             C
ANISOU 3076  CG   ASN A 417     20743  30556  20881  -3963   2361    539        C
ATOM   3077  OD1  ASN A 417     -27.287 -34.789  68.237  1.00188.94             O
ANISOU 3077  OD1  ASN A 417     20411  30428  20951  -3792   2351    321        O
ATOM   3078  ND2  ASN A 417     -26.377 -35.740  70.058  1.00191.25             N
ANISOU 3078  ND2  ASN A 417     20933  30492  21241  -4312   2146    804        N
ATOM   3079  N    TRP A 418     -23.832 -32.402  70.952  1.00187.00             N
ANISOU 3079  N    TRP A 418     21385  29718  19946  -3655   2357    494        N
ATOM   3080  CA   TRP A 418     -22.805 -31.367  70.855  1.00184.47             C
ANISOU 3080  CA   TRP A 418     21371  29214  19504  -3406   2362    331        C
ATOM   3081  C    TRP A 418     -22.560 -30.976  69.419  1.00181.77             C
ANISOU 3081  C    TRP A 418     20977  28738  19351  -3118   2340     28        C
ATOM   3082  O    TRP A 418     -22.447 -31.826  68.539  1.00181.13             O
ANISOU 3082  O    TRP A 418     20715  28467  19641  -3178   2165    -21        O
ATOM   3083  CB   TRP A 418     -21.474 -31.852  71.426  1.00183.83             C
ANISOU 3083  CB   TRP A 418     21524  28743  19581  -3603   2126    474        C
ATOM   3084  CG   TRP A 418      21.619  32.610  72.677  1.00186.45             C
ANISOU 3084  CG   TRP A 418     21867  29124  19853  -3935   2082    787        C
ATOM   3085  CD1  TRP A 418     -21.668 -32.101  73.936  1.00187.84             C
ANISOU 3085  CD1  TRP A 418     22220  29468  19681  -3959   2208    941        C
ATOM   3086  CD2  TRP A 418     -21.744 -34.032  72.809  1.00188.11             C
ANISOU 3086  CD2  TRP A 418     21899  29216  20358  -4284   1895    993        C
ATOM   3087  NE1  TRP A 418     -21.821 -33.115  74.851  1.00190.26             N
ANISOU 3087  NE1  TRP A 418     22470  29776  20044  -4298   2126   1235        N
ATOM   3088  CE2  TRP A 418     -21.869 -34.312  74.185  1.00190.50             C
ANISOU 3088  CE2  TRP A 418     22285  29627  20467  -4513   1933   1274        C
ATOM   3089  CE3  TRP A 418     -21.765 -35.094  71.900  1.00187.85             C
ANISOU 3089  CE3  TRP A 418     21646  28996  20732   4414   1689    969        C
ATOM   3090  CZ2  TRP A 418     -22.011 -35.612  74.672  1.00192.64             C
ANISOU 3090  CZ2  TRP A 418     22433  29822  20941  -4879   1784   1534        C
ATOM   3091  CZ3  TRP A 418     -21.904 -36.382  72.387  1.00189.98             C
ANISOU 3091  CZ3  TRP A 418     21795  29184  21204  -4780   1524   1222        C
ATOM   3092  CH2  TRP A 418     -22.027 -36.630  73.763  1.00192.36             C
ANISOU 3092  CH2  TRP A 418     22189  29594  21306  -5016   1578   1504        C
ATOM   3093  N    HIS A 419     -22.497 -29.677  69.186  1.00180.69             N
ANISOU 3093  N    HIS A 419     20997  28706  18950  -2790   2514   -176        N
ATOM   3094  CA   HIS A 419     -22.081 -29.179  67.891  1.00177.94             C
ANISOU 3094  CA   HIS A 419     20649  28200  18758  -2491   2496   -458        C
ATOM   3095  C    HIS A 419     -21.319 -27.862  68.070  1.00176.16             C
ANISOU 3095  C    HIS A 419     20743  27905  18283  -2239   2582   -582        C
```

FIG. 13 Continued

```
ATOM   3096  O    HIS A 419     -21.867 -26.772  67.938  1.00175.82           O
ANISOU 3096  O    HIS A 419     20750  28116  17937  -1968   2804    -742     O
ATOM   3097  CB   HIS A 419     -23.199 -29.234  66.806  1.00177.92           C
ANISOU 3097  CB   HIS A 419     20344  28428  18829  -2313   2619    -652     C
ATOM   3098  CG   HIS A 419     -24.139 -28.061  66.756  1.00178.07           C
ANISOU 3098  CG   HIS A 419     20370  28836  18452  -2027   2923    -822     C
ATOM   3099  ND1  HIS A 419     -23.772 -26.819  66.284  1.00175.93           N
ANISOU 3099  ND1  HIS A 419     20290  28553  18001  -1681   3040   -1055     N
ATOM   3100  CD2  HIS A 419     -25.467 -27.978  67.011  1.00180.06           C
ANISOU 3100  CD2  HIS A 419     20445  29503  18468  -2025   3124    -811     C
ATOM   3101  CE1  HIS A 419     -24.813 -26.006  66.313  1.00176.59           C
ANISOU 3101  CE1  HIS A 419     20335  29026  17734  -1480   3296   -1178     C
ATOM   3102  NE2  HIS A 419     -25.855 -26.685  66.753  1.00179.07           N
ANISOU 3102  NE2  HIS A 419     20426  29612  18001  -1680   3353   -1036     N
ATOM   3103  N    ARG A 420     -20.044 -28.007  68.439  1.00252.19           N
ANISOU 3103  N    ARG A 420     30595  37188  28037  -2348   2392    -495     N
ATOM   3104  CA   ARG A 420     -19.138 -26.883  68.645  1.00250.52           C
ANISOU 3104  CA   ARG A 420     30694  36842  27651  -2150   2423    -587     C
ATOM   3105  C    ARG A 420     -18.483 -26.524  67.340  1.00247.76           C
ANISOU 3105  C    ARG A 420     30350  36265  27522  -1899   2362    -822     C
ATOM   3106  O    ARG A 420     -18.317 -27.372  66.476  1.00247.01           O
ANISOU 3106  O    ARG A 420     30074  36003  27775  -1948   2206    -857     O
ATOM   3107  CB   ARG A 420     -18.052 -27.236  69.659  1.00250.79           C
ANISOU 3107  CB   ARG A 420     30960  36603  27725  -2385   2243    -388     C
ATOM   3108  CG   ARG A 420     -16.729 -26.511  69.436  1.00248.40           C
ANISOU 3108  CG   ARG A 420     30928  35985  27469  -2226   2151    -501     C
ATOM   3109  CD   ARG A 420     -16.081 -26.083  70.753  1.00249.06           C
ANISOU 3109  CD   ARG A 420     31306  35997  27330  -2311   2134    -361     C
ATOM   3110  NE   ARG A 420     -15.743 -27.195  71.640  1.00250.51           N
ANISOU 3110  NE   ARG A 420     31505  36045  27633  -2658   1965    -117     N
ATOM   3111  CZ   ARG A 420     -14.513 -27.466  72.070  1.00249.72           C
ANISOU 3111  CZ   ARG A 420     31613  35609  27662  -2785   1772     -45     C
ATOM   3112  NH1  ARG A 420     -13.491 -26.705  71.698  1.00247.55           N
ANISOU 3112  NH1  ARG A 420     31539  35097  27423  -2601   1719    -189     N
ATOM   3113  NH2  ARG A 420     -14.307 -28.498  72.879  1.00251.16           N
ANISOU 3113  NH2  ARG A 420     31802  35693  27934  -3095   1633     171     N
ATOM   3114  N    VAL A 421     -18.103 -25.264  67.201  1.00222.47           N
ANISOU 3114  N    VAL A 421     27355  33057  24118  -1622   2477    -978     N
ATOM   3115  CA   VAL A 421     -17.461 -24.804  65.983  1.00219.87           C
ANISOU 3115  CA   VAL A 421     27044  32525  23973  -1359   2440   -1196     C
ATOM   3116  C    VAL A 421     -17.088 -23.359  66.139  1.00218.79           C
ANISOU 3116  C    VAL A 421     27172  32405  23554  -1098   2577   -1319     C
ATOM   3117  O    VAL A 421     -17.644 -22.666  66.992  1.00220.08           O
ANISOU 3117  O    VAL A 421     27448  32819  23354  -1061   2736   -1286     O
ATOM   3118  CB   VAL A 421     -18.393 -24.903  64.796  1.00219.43           C
ANISOU 3118  CB   VAL A 421     26711  32649  24014  -1162   2548   -1384     C
ATOM   3119  CG1  VAL A 421     -18.198 -26.229  64.095  1.00219.17           C
ANISOU 3119  CG1  VAL A 421     26446  32418  24409  -1316   2323   -1340     C
ATOM   3120  CG2  VAL A 421     -19.834 -24.687  65.244  1.00221.49           C
ANISOU 3120  CG2  VAL A 421     26847  33345  23964  -1151   2779   -1380     C
ATOM   3121  N    SER A 422     -16.177 -22.885  65.298  1.00173.49           N
ANISOU 3121  N    SER A 422     21526  26414  17977   -902   2513   -1463     N
ATOM   3122  CA   SER A 422     -15.710 -21.528  65.479  1.00172.51           C
ANISOU 3122  CA   SER A 422     21670  26265  17611   -675   2615   -1564     C
ATOM   3123  C    SER A 422     -14.542 -21.069  64.513  1.00170.02           C
ANISOU 3123  C    SER A 422     21441  25652  17507   -477   2533   -1702     C
ATOM   3124  O    SER A 422     -13.684 -21.778  64.248  1.00169.10           O
ANISOU 3124  O    SER A 422     21316  25232  17701   -606   2316   -1635     O
ATOM   3125  CB   SER A 422     -15.159 -21.408  66.890  1.00173.66           C
ANISOU 3125  CB   SER A 422     22061  26333  17587   -874   2544   -1373     C
ATOM   3126  OG   SER A 422     -14.519 -22.617  67.270  1.00174.09           O
ANISOU 3126  OG   SER A 422     22082  26153  17910  -1191   2316   -1187     O
ATOM   3127  N    LYS A 423     -14.806 -19.842  64.039  1.00182.56           N
ANISOU 3127  N    LYS A 423     23124  27337  18902   -158   2707   -1890     N
ATOM   3128  CA   LYS A 423     -13.881 -19.223  63.114  1.00180.30           C
ANISOU 3128  CA   LYS A 423     22926  26805  18775     69   2669   -2027     C
ATOM   3129  C    LYS A 423     -14.112 -17.708  63.153  1.00179.93           C
ANISOU 3129  C    LYS A 423     23074  26900  18392    359   2872   -2177     C
ATOM   3130  O    LYS A 423     -15.247 -17.262  63.115  1.00180.70           O
```

FIG. 13 Continued

```
ANISOU 3130  O   LYS A 423    23107  27325  18225    505   3074  -2282           O
ATOM   3131  CB  LYS A 423    -14.136 -19.746  61.693  1.00179.03                C
ANISOU 3131  CB  LYS A 423    22494  26633  18897    225   2661  -2167           C
ATOM   3132  CG  LYS A 423    -14.667 -21.192  61.581  1.00180.04                C
ANISOU 3132  CG  LYS A 423    22344  26809  19254     -1   2545  -2070           C
ATOM   3133  CD  LYS A 423    -13.564 -22.267  61.648  1.00179.59                C
ANISOU 3133  CD  LYS A 423    22281  26414  19540   -254   2244  -1911           C
ATOM   3134  CE  LYS A 423    -12.784 -22.441  60.334  1.00177.35                C
ANISOU 3134  CE  LYS A 423    21904  25894  19587    -64   2114  -2024           C
ATOM   3135  NZ  LYS A 423    -11.849 -23.612  60.377  1.00177.05                N
ANISOU 3135  NZ  LYS A 423    21832  25572  19869   -313   1806  -1874           N
ATOM   3136  N   GLY A 424    -13.048 -16.917  63.242  1.00153.54                N
ANISOU 3136  N   GLY A 424    19972  23315  15051    442   2812  -2188           N
ATOM   3137  CA  GLY A 424    -13.173 -15.464  63.216  1.00153.11                C
ANISOU 3137  CA  GLY A 424    20114  23357  14705    724   2978  -2332           C
ATOM   3138  C   GLY A 424    -13.214 -14.794  64.573  1.00154.54                C
ANISOU 3138  C   GLY A 424    20546  23627  14546    655   3000  -2240           C
ATOM   3139  O   GLY A 424    -13.990 -15.185  65.437  1.00156.36                O
ANISOU 3139  O   GLY A 424    20733  24092  14584    504   3038  -2137           O
ATOM   3140  N   ALA A 425    -12.396 -13.764  64.756  1.00154.01                N
ANISOU 3140  N   ALA A 425    20736  23378  14402    781   2973  -2274           N
ATOM   3141  CA  ALA A 425    -12.327 -13.097  66.051  1.00155.29                C
ANISOU 3141  CA  ALA A 425    21151  23593  14260    740   2963  -2190           C
ATOM   3142  C   ALA A 425    -13.681 -12.564  66.571  1.00156.83                C
ANISOU 3142  C   ALA A 425    21348  24220  14021    860   3154  -2246           C
ATOM   3143  O   ALA A 425    -14.387 -13.288  67.283  1.00158.49                O
ANISOU 3143  O   ALA A 425    21450  24643  14128    676   3165  -2123           O
ATOM   3144  CB  ALA A 425    -11.236 -12.015  66.061  1.00154.19                C
ANISOU 3144  CB  ALA A 425    21280  23179  14126    881   2897  -2236           C
ATOM   3145  N   PRO A 426    -14.071 -11.322  66.192  1.00165.17                N
ANISOU 3145  N   PRO A 426    22520  25420  14817   1172   3303  -2432           N
ATOM   3146  CA  PRO A 426    -15.304 -10.766  66.774  1.00166.67                C
ANISOU 3146  CA  PRO A 426    22739  26029  14557   1295   3464  -2485           C
ATOM   3147  C   PRO A 426    -16.503 -11.668  66.572  1.00167.66                C
ANISOU 3147  C   PRO A 426    22576  26474  14654   1208   3577  -2481           C
ATOM   3148  O   PRO A 426    -17.183 -12.011  67.534  1.00169.54                O
ANISOU 3148  O   PRO A 426    22783  26961  14674   1071   3596  -2356           O
ATOM   3149  CB  PRO A 426    -15.518  -9.456  65.996  1.00165.50                C
ANISOU 3149  CB  PRO A 426    22709  25956  14218   1658   3606  -2725           C
ATOM   3150  CG  PRO A 426    -14.201  -9.119  65.421  1.00163.77                C
ANISOU 3150  CG  PRO A 426    22607  25320  14298   1702   3490  -2745           C
ATOM   3151  CD  PRO A 426    -13.528 -10.439  65.141  1.00163.28                C
ANISOU 3151  CD  PRO A 426    22360  25004  14674   1435   3343  -2607           C
ATOM   3152  N   GLU A 427    -16.746 -12.050  65.324  1.00157.37                N
ANISOU 3152  N   GLU A 427    21056  25161  13577   1296   3646  -2613           N
ATOM   3153  CA  GLU A 427    -17.897 -12.875  64.972  1.00158.18                C
ANISOU 3153  CA  GLU A 427    20866  25551  13684   1243   3754  -2639           C
ATOM   3154  C   GLU A 427    -17.920 -14.234  65.671  1.00159.64                C
ANISOU 3154  C   GLU A 427    20895  25712  14049    874   3625  -2399           C
ATOM   3155  O   GLU A 427    -18.598 -15.156  65.218  1.00160.07                O
ANISOU 3155  O   GLU A 427    20677  25892  14251    781   3657  -2397           O
ATOM   3156  CB  GLU A 427    -17.996 -13.046  63.451  1.00156.42                C
ANISOU 3156  CB  GLU A 427    20447  25266  13721   1426   3824  -2832           C
ATOM   3157  CG  GLU A 427    -18.565 -11.837  62.708  1.00155.47                C
ANISOU 3157  CG  GLU A 427    20399  25335  13339   1812   4030  -3100           C
ATOM   3158  CD  GLU A 427    -17.591 -10.671  62.610  1.00154.19                C
ANISOU 3158  CD  GLU A 427    20523  24929  13132   1995   3994  -3164           C
ATOM   3159  OE1 GLU A 427    -17.228 -10.084  63.655  1.00155.01                O
ANISOU 3159  OE1 GLU A 427    20872  25004  13022   1938   3928  -3064           O
ATOM   3160  OE2 GLU A 427    -17.198 -10.329  61.477  1.00152.39                O
ANISOU 3160  OE2 GLU A 427    20272  24542  13088   2207   4032  -3316           O
ATOM   3161  N   GLN A 428    -17.191 -14.360  66.774  1.00164.27                N
ANISOU 3161  N   GLN A 428    21655  26134  14625    671   3476  -2202           N
ATOM   3162  CA  GLN A 428    -17.199 -15.605  67.518  1.00165.75                C
ANISOU 3162  CA  GLN A 428    21721  26299  14956    324   3356  -1968           C
ATOM   3163  C   GLN A 428    -17.396 -15.363  68.998  1.00167.70                C
ANISOU 3163  C   GLN A 428    22133  26707  14878    222   3348  -1803           C
ATOM   3164  O   GLN A 428    -17.579 -16.295  69.770  1.00169.28                O
ANISOU 3164  O   GLN A 428    22244  26958  15118    -48   3281  -1600           O
```

FIG. 13 Continued

```
ATOM   3165  CB  GLN A 428     -15.929 -16.396  67.277  1.00164.62           C
ANISOU 3165  CB  GLN A 428    21580  25723  15245    127   3133  -1866       C
ATOM   3166  CG  GLN A 428     -16.066 -17.814  67.753  1.00165.97           C
ANISOU 3166  CG  GLN A 428    21575  25879  15609   -216   3015  -1659       C
ATOM   3167  CD  GLN A 428     -17.501 -18.301  67.688  1.00167.53           C
ANISOU 3167  CD  GLN A 428    21515  26462  15675   -246   3164  -1661       C
ATOM   3168  OE1 GLN A 428     -18.222 -18.249  68.679  1.00169.49           O
ANISOU 3168  OE1 GLN A 428    21783  26989  15628   -322   3242  -1550       O
ATOM   3169  NE2 GLN A 428     -17.923 -18.767  66.517  1.00166.68           N
ANISOU 3169  NE2 GLN A 428    21163  26382  15787   -174   3200  -1788       N
ATOM   3170  N   ILE A 429     -17.328 -14.101  69.391  1.00165.10           N
ANISOU 3170  N   ILE A 429    22049  26450  14230    448   3407  -1888       N
ATOM   3171  CA  ILE A 429     -17.647 -13.714  70.751  1.00166.95           C
ANISOU 3171  CA  ILE A 429    22441  26894  14100    426   3414  -1760       C
ATOM   3172  C   ILE A 429     -19.102 -13.241  70.702  1.00168.03           C
ANISOU 3172  C   ILE A 429    22479  27523  13844    612   3627  -1870       C
ATOM   3173  O   ILE A 429     -19.942 -13.605  71.536  1.00170.09           O
ANISOU 3173  O   ILE A 429    22654  28099  13872    508   3680  -1736       O
ATOM   3174  CB  ILE A 429     -16.758 -12.553  71.217  1.00166.26           C
ANISOU 3174  CB  ILE A 429    22686  26611  13874    593   3336  -1802       C
ATOM   3175  CG1 ILE A 429     -15.357 -12.662  70.616  1.00164.31           C
ANISOU 3175  CG1 ILE A 429    22520  25877  14032    540   3180  -1822       C
ATOM   3176  CG2 ILE A 429     -16.671 -12.529  72.733  1.00168.08           C
ANISOU 3176  CG2 ILE A 429    23075  26913  13876    489   3255  -1607       C
ATOM   3177  CD1 ILE A 429     -14.314 -13.075  71.612  1.00164.76           C
ANISOU 3177  CD1 ILE A 429    22730  25646  14224    318   2982  -1628       C
ATOM   3178  N   LEU A 430     -19.382 -12.431  69.686  1.00166.68           N
ANISOU 3178  N   LEU A 430    22315  27417  13598    896   3751  -2118       N
ATOM   3179  CA  LEU A 430     -20.706 -11.882  69.448  1.00167.32           C
ANISOU 3179  CA  LEU A 430    22317  27946  13309   1115   3959  -2275       C
ATOM   3180  C   LEU A 430     -21.717 -13.010  69.204  1.00168.46           C
ANISOU 3180  C   LEU A 430    22126  28339  13543    944   4045  -2220       C
ATOM   3181  O   LEU A 430     -22.832 -12.958  69.710  1.00170.16           O
ANISOU 3181  O   LEU A 430    22262  28971  13421    969   4167  -2198       O
ATOM   3182  CB  LEU A 430     -20.649 -10.905  68.259  1.00165.28           C
ANISOU 3182  CB  LEU A 430    22130  27637  13032   1442   4061  -2561       C
ATOM   3183  CG  LEU A 430     -21.779  -9.938  67.895  1.00165.35           C
ANISOU 3183  CG  LEU A 430    22158  28047  12618   1763   4270  -2794       C
ATOM   3184  CD1 LEU A 430     -21.215  -8.678  67.257  1.00163.52           C
ANISOU 3184  CD1 LEU A 430    22162  27646  12322   2068   4289  -3003       C
ATOM   3185  CD2 LEU A 430     -22.787 -10.600  66.972  1.00165.29           C
ANISOU 3185  CD2 LEU A 430    21838  28268  12697   1779   4423  -2913       C
ATOM   3186  N   GLU A 431     -21.317 -14.042  68.461  1.00166.21           N
ANISOU 3186  N   GLU A 431    21641  27800  13710    768   3967  -2188       N
ATOM   3187  CA  GLU A 431     -22.229 -15.142  68.118  1.00167.21           C
ANISOU 3187  CA  GLU A 431    21437  28122  13973    609   4027  -2147       C
ATOM   3188  C   GLU A 431     -22.482 -16.138  69.252  1.00169.55           C
ANISOU 3188  C   GLU A 431    21636  28517  14267    272   3950  -1856       C
ATOM   3189  O   GLU A 431     -21.691 -17.039  69.493  1.00169.59           O
ANISOU 3189  O   GLU A 431    21616  28219  14600      6   3774  -1679       O
ATOM   3190  CB  GLU A 431     -21.767 -15.887  66.847  1.00165.48           C
ANISOU 3190  CB  GLU A 431    21029  27609  14238    574   3957  -2232       C
ATOM   3191  CG  GLU A 431     -21.960 -15.123  65.515  1.00163.49           C
ANISOU 3191  CG  GLU A 431    20756  27373  13988    924   4092  -2539       C
ATOM   3192  CD  GLU A 431     -21.712 -15.989  64.269  1.00162.08           C
ANISOU 3192  CD  GLU A 431    20336  26973  14273    905   4030  -2615       C
ATOM   3193  OE1 GLU A 431     -22.600 -16.801  63.917  1.00162.91           O
ANISOU 3193  OE1 GLU A 431    20161  27266  14470    831   4084  -2627       O
ATOM   3194  OE2 GLU A 431     -20.641 -15.841  63.633  1.00160.18           O
ANISOU 3194  OE2 GLU A 431    20182  26378  14302    977   3923  -2665       O
ATOM   3195  N   LEU A 432     -23.613 -15.970  69.923  1.00222.66           N
ANISOU 3195  N   LEU A 432    28305  35684  20613    294   4086  -1811       N
ATOM   3196  CA  LEU A 432     -24.041 -16.845  71.020  1.00225.16           C
ANISOU 3196  CA  LEU A 432    28510  36169  20872      3   4049  -1532       C
ATOM   3197  C   LEU A 432     -22.969 -17.149  72.074  1.00225.64           C
ANISOU 3197  C   LEU A 432    28758  35938  21037   -210   3858  -1292       C
ATOM   3198  O   LEU A 432     -23.257 -17.731  73.117  1.00227.76           O
ANISOU 3198  O   LEU A 432    28981  36347  21209   -422   3830  -1053       O
ATOM   3199  CB  LEU A 432     -24.713 -19.128  70.489  1.00226.00           C
```

FIG. 13 Continued

```
ANISOU 3199  CB  LEU A 432    28260  36345  21264    -219   4064  -1472       C
ATOM   3200  CG  LEU A 432    -26.215 -18.052  70.140  1.00 227.12            C
ANISOU 3200  CG  LEU A 432    28175  36965  21157    -101   4276  -1589       C
ATOM   3201  CD1 LEU A 432    -26.728 -19.340  69.488  1.00 227.71            C
ANISOU 3201  CD1 LEU A 432    27898  37032  21591    -315   4259  -1546       C
ATOM   3202  CD2 LEU A 432    -27.061 -17.699  71.365  1.00 229.56            C
ANISOU 3202  CD2 LEU A 432    28526  37711  20984    -104   4378  -1446       C
ATOM   3203  N   ALA A 433    -21.738 -16.738  71.812  1.00 172.39            N
ANISOU 3203  N   ALA A 433    22226  28795  14481    -146   3731  -1357       N
ATOM   3204  CA  ALA A 433    -20.676 -16.948  72.775  1.00 172.68            C
ANISOU 3204  CA  ALA A 433    22458  28543  14609    -320   3551  -1162       C
ATOM   3205  C   ALA A 433    -20.915 -15.993  73.923  1.00 173.93            C
ANISOU 3205  C   ALA A 433    22838  28942  14306    -167   3598  -1112       C
ATOM   3206  O   ALA A 433    -20.214 -16.012  74.936  1.00 174.55            O
ANISOU 3206  O   ALA A 433    23097  28866  14358    -263   3473   -949       O
ATOM   3207  CB  ALA A 433    -19.337 -16.684  72.143  1.00 170.29            C
ANISOU 3207  CB  ALA A 433    22317  27775  14611    -268   3412  -1263       C
ATOM   3208  N   LYS A 434    -21.927 -15.156  73.745  1.00 175.70            N
ANISOU 3208  N   LYS A 434    23048  29553  14155      89   3773  -1263       N
ATOM   3209  CA  LYS A 434    -22.278 -14.161  74.738  1.00 176.85            C
ANISOU 3209  CA  LYS A 434    23397  29978  13820     286   3818  -1245       C
ATOM   3210  C   LYS A 434    -21.104 -13.214  74.874  1.00 175.32            C
ANISOU 3210  C   LYS A 434    23527  29450  13636     447   3694  -1325       C
ATOM   3211  O   LYS A 434    -20.218 -13.413  75.709  1.00 175.63            O
ANISOU 3211  O   LYS A 434    23718  29240  13775     317   3538  -1163       O
ATOM   3212  CB  LYS A 434    -22.607 -14.825  76.079  1.00 179.40            C
ANISOU 3212  CB  LYS A 434    23674  30492  13999      75   3782   -954       C
ATOM   3213  CG  LYS A 434    -23.753 -15.846  76.014  1.00 181.19            C
ANISOU 3213  CG  LYS A 434    23565  31041  14240    -122   3895   -839       C
ATOM   3214  CD  LYS A 434    -25.135 -15.222  76.257  1.00 182.69            C
ANISOU 3214  CD  LYS A 434    23683  31801  13930      85   4083   -900       C
ATOM   3215  CE  LYS A 434    -25.508 -15.222  77.743  1.00 185.21            C
ANISOU 3215  CE  LYS A 434    24059  32411  13900      45   4072   -652       C
ATOM   3216  NZ  LYS A 434    -26.921 -14.813  77.988  1.00 186.91            N
ANISOU 3216  NZ  LYS A 434    24158  33216  13645     207   4250   -679       N
ATOM   3217  N   ALA A 435    -21.103 -12.192  74.026  1.00 172.44            N
ANISOU 3217  N   ALA A 435    23265  29078  13177     733   3764  -1580       N
ATOM   3218  CA  ALA A 435    -20.053 -11.192  74.028  1.00 170.97            C
ANISOU 3218  CA  ALA A 435    23377  28585  12999     909   3657  -1678       C
ATOM   3219  C   ALA A 435    -19.941 -10.575  75.411  1.00 172.41            C
ANISOU 3219  C   ALA A 435    23794  28876  12837     988   3578  -1557       C
ATOM   3220  O   ALA A 435    -20.568  -9.561  75.691  1.00 172.93            O
ANISOU 3220  O   ALA A 435    23984  29246  12476    1257   3649  -1660       O
ATOM   3221  CB  ALA A 435    -20.348 -10.120  72.987  1.00 169.41            C
ANISOU 3221  CB  ALA A 435    23243  28465  12661    1231   3777  -1967       C
ATOM   3222  N   SER A 436    -19.143 -11.189  76.276  1.00 173.45            N
ANISOU 3222  N   SER A 436    23991  28765  13148     769   3422  -1345       N
ATOM   3223  CA  SER A 436    -18.983 -10.696  77.635  1.00 174.86            C
ANISOU 3223  CA  SER A 436    24384  29026  13030     846   3332  -1218       C
ATOM   3224  C   SER A 436    -17.930  -9.600  77.730  1.00 173.54            C
ANISOU 3224  C   SER A 436    24533  28545  12860    1047   3199  -1328       C
ATOM   3225  O   SER A 436    -17.715  -8.854  76.780  1.00 171.85            O
ANISOU 3225  O   SER A 436    24390  28213  12693    1224   3231  -1539       O
ATOM   3226  CB  SER A 436    -18.646 -11.836  78.587  1.00 176.27            C
ANISOU 3226  CB  SER A 436    24495  29101  13377     540   3232   -943       C
ATOM   3227  OG  SER A 436    -18.832 -11.419  79.924  1.00 178.03            O
ANISOU 3227  OG  SER A 436    24869  29529  13244     645   3187   -814       O
ATOM   3228  N   ASN A 437    -17.258  -9.517  78.871  1.00 175.46            N
ANISOU 3228  N   ASN A 437    24963  28643  13060    1019   3048  -1185       N
ATOM   3229  CA  ASN A 437    -16.277  -8.463  79.085  1.00 174.46            C
ANISOU 3229  CA  ASN A 437    25141  28226  12920    1213   2906  -1278       C
ATOM   3230  C   ASN A 437    -15.008  -8.926  79.779  1.00 174.32            C
ANISOU 3230  C   ASN A 437    25254  27789  13191    1031   2713  -1135       C
ATOM   3231  O   ASN A 437    -13.917  -8.789  79.233  1.00 172.61            O
ANISOU 3231  O   ASN A 437    25138  27153  13295     994   2613  -1211       O
ATOM   3232  CB  ASN A 437    -16.897  -7.330  79.909  1.00 175.71            C
ANISOU 3232  CB  ASN A 437    25481  28722  12558    1530   2907  -1318       C
ATOM   3233  CG  ASN A 437    -17.795  -6.427  79.087  1.00 175.17            C
ANISOU 3233  CG  ASN A 437    25401  28954  12203    1797   3054  -1542       C
```

FIG. 13 Continued

```
ATOM   3234  OD1 ASN A 437     -17.558  -6.209  77.898  1.00173.38           O
ANISOU 3234  OD1 ASN A 437    25143  28549  12184    1829    3109   -1714    O
ATOM   3235  ND2 ASN A 437     -18.829  -5.883  79.723  1.00176.73           N
ANISOU 3235  ND2 ASN A 437    25626  29617  11907    2006    3115   -1543    N
ATOM   3236  N   ASP A 438     -15.161  -9.473  80.984  1.00239.08           N
ANISOU 3236  N   ASP A 438    33453  36115  21272     927    2665    -929    N
ATOM   3237  CA  ASP A 438     -14.020  -9.876  81.810  1.00239.16           C
ANISOU 3237  CA  ASP A 438    33608  35762  21499     784    2484    -795    C
ATOM   3238  C   ASP A 438     -12.845 -10.390  80.984  1.00237.17           C
ANISOU 3238  C   ASP A 438    33351  35018  21745     580    2393    -841    C
ATOM   3239  O   ASP A 438     -11.782  -9.767  80.949  1.00235.97           O
ANISOU 3239  O   ASP A 438    33411  34515  21731     665    2260    -925    O
ATOM   3240  CB  ASP A 438     -14.435 -10.900  82.879  1.00241.24           C
ANISOU 3240  CB  ASP A 438    33757  36214  21689     590    2489    -546    C
ATOM   3241  CG  ASP A 438     -14.792 -12.256  82.295  1.00241.34           C
ANISOU 3241  CG  ASP A 438    33476  36248  21974     263    2574    -447    C
ATOM   3242  OD1 ASP A 438     -15.344 -12.301  81.175  1.00240.50           O
ANISOU 3242  OD1 ASP A 438    33197  36249  21933     260    2695    -568    O
ATOM   3243  OD2 ASP A 438     -14.521 -13.280  82.960  1.00242.29           O
ANISOU 3243  OD2 ASP A 438    33541  36275  22244      18    2514    -252    O
ATOM   3244  N   LEU A 439     -13.039 -11.526  80.326  1.00262.42           N
ANISOU 3244  N   LEU A 439    36302  38196  25210     316    2454    -785    N
ATOM   3245  CA  LEU A 439     -12.014 -12.099  79.467  1.00260.56           C
ANISOU 3245  CA  LEU A 439    36031  37534  25435     127    2366    -826    C
ATOM   3246  C   LEU A 439     -12.390 -11.829  78.004  1.00259.05           C
ANISOU 3246  C   LEU A 439    35697  37389  25341     217    2485   -1011    C
ATOM   3247  O   LEU A 439     -11.549 -11.885  77.101  1.00257.20           O
ANISOU 3247  O   LEU A 439    35466  36824  25433     174    2423   -1102    O
ATOM   3248  CB  LEU A 439     -11.865 -13.611  79.725  1.00261.19           C
ANISOU 3248  CB  LEU A 439    35945  37522  25774    -225    2317    -636    C
ATOM   3249  CG  LEU A 439     -11.455 -14.149  81.108  1.00262.65           C
ANISOU 3249  CG  LEU A 439    36239  37633  25922    -362    2204    -437    C
ATOM   3250  CD1 LEU A 439     -11.745 -15.646  81.219  1.00263.60           C
ANISOU 3250  CD1 LEU A 439    36137  37792  26228    -695    2211    -254    C
ATOM   3251  CD2 LEU A 439      -9.987 -13.863  81.422  1.00261.46           C
ANISOU 3251  CD2 LEU A 439    36343  37027  25973    -359    2014    -470    C
ATOM   3252  N   SER A 440     -13.663 -11.515  77.785  1.00170.59           N
ANISOU 3252  N   SER A 440    24369  26610  13838     359    2658   -1069    N
ATOM   3253  CA  SER A 440     -14.188 -11.300  76.441  1.00169.35           C
ANISOU 3253  CA  SER A 440    24058  26550  13736     463    2794   -1250    C
ATOM   3254  C   SER A 440     -13.756  -9.967  75.812  1.00167.79           C
ANISOU 3254  C   SER A 440    24055  26219  13477     753    2794   -1464    C
ATOM   3255  O   SER A 440     -13.573  -9.867  74.597  1.00166.12           O
ANISOU 3255  O   SER A 440    23765  25876  13476     803    2842   -1608    O
ATOM   3256  CB  SER A 440     -15.711 -11.430  76.471  1.00170.84           C
ANISOU 3256  CB  SER A 440    24052  27249  13610     517    2980   -1246    C
ATOM   3257  OG  SER A 440     -16.109 -12.558  77.241  1.00172.62           O
ANISOU 3257  OG  SER A 440    24123  27611  13852     259    2972   -1023    O
ATOM   3258  N   LYS A 441     -13.604  -8.948  76.647  1.00178.65           N
ANISOU 3258  N   LYS A 441    25682  27631  14565     953    2734   -1479    N
ATOM   3259  CA  LYS A 441     -13.170  -7.637  76.191  1.00177.41           C
ANISOU 3259  CA  LYS A 441    25735  27338  14334    1225    2712   -1664    C
ATOM   3260  C   LYS A 441     -11.643  -7.598  76.141  1.00176.11           C
ANISOU 3260  C   LYS A 441    25728  26656  14530    1135    2528   -1647    C
ATOM   3261  O   LYS A 441     -11.054  -6.691  75.557  1.00174.81           O
ANISOU 3261  O   LYS A 441    25706  26282  14430    1303    2495   -1786    O
ATOM   3262  CB  LYS A 441     -13.705  -6.558  77.138  1.00178.76           C
ANISOU 3262  CB  LYS A 441    26108  27784  14027    1491    2704   -1689    C
ATOM   3263  CG  LYS A 441     -14.090  -5.235  76.476  1.00177.98           C
ANISOU 3263  CG  LYS A 441    26131  27811  13682    1821    2782   -1915    C
ATOM   3264  CD  LYS A 441     -12.921  -4.250  76.408  1.00176.84           C
ANISOU 3264  CD  LYS A 441    26257  27274  13660    1957    2629   -1999    C
ATOM   3265  CE  LYS A 441     -13.395  -2.827  76.102  1.00176.61           C
ANISOU 3265  CE  LYS A 441    26398  27419  13287    2310    2678   -2198    C
ATOM   3266  NZ  LYS A 441     -12.265  -1.893  75.808  1.00175.38           N
ANISOU 3266  NZ  LYS A 441    26475  26858  13303    2429    2543   -2289    N
ATOM   3267  N   LYS A 442     -11.010  -8.591  76.767  1.00171.43           N
ANISOU 3267  N   LYS A 442    25110  25864  14164     870    2410   -1473    N
ATOM   3268  CA  LYS A 442      -9.545  -8.693  76.812  1.00170.31           C
```

FIG. 13 Continued

```
ANISOU 3268  CA  LYS A 442    25108 25240 14362    756  2227 -1445       C
ATOM   3269  C   LYS A 442    -8.988  -9.685  75.781  1.00168.83         C
ANISOU 3269  C   LYS A 442    24733 24803 14610    530  2209  1439       C
ATOM   3270  O   LYS A 442    -7.790  -9.685  75.496  1.00167.54         O
ANISOU 3270  O   LYS A 442    24663 24251 14743    465  2077 -1453       O
ATOM   3271  CB  LYS A 442    -9.050  -9.030  78.237  1.00171.62         C
ANISOU 3271  CB  LYS A 442    25416 25307 14483    644  2081 -1279       C
ATOM   3272  CG  LYS A 442    -7.562  -8.700  78.535  1.00170.69         C
ANISOU 3272  CG  LYS A 442    25529 24724 14602    626  1881 -1286       C
ATOM   3273  CD  LYS A 442    -6.670  -9.951  78.721  1.00170.32         C
ANISOU 3273  CD  LYS A 442    25426 24379 14910    307  1760 -1157       C
ATOM   3274  CE  LYS A 442    -6.711 -10.499  80.159  1.00172.07         C
ANISOU 3274  CE  LYS A 442    25717 24666 14996    205  1688  -987       C
ATOM   3275  NZ  LYS A 442    -5.799 -11.662  80.385  1.00171.69         N
ANISOU 3275  NZ  LYS A 442    25648 24315 15273    -92  1561  -876       N
ATOM   3276  N   VAL A 443    -9.843 -10.539  75.229  1.00163.89         N
ANISOU 3276  N   VAL A 443    23843 24404 14025    416  2330 -1417       N
ATOM   3277  CA  VAL A 443    -9.371 -11.422  74.174  1.00162.45         C
ANISOU 3277  CA  VAL A 443    23478 24004 14242    244  2302 -1427       C
ATOM   3278  C   VAL A 443    -9.022 -10.582  72.946  1.00160.59         C
ANISOU 3278  C   VAL A 443    23267 23631 14119    453  2346 -1616       C
ATOM   3279  O   VAL A 443    -8.284 -11.035  72.070  1.00159.08         O
ANISOU 3279  O   VAL A 443    22992 23176 14277    367  2282 -1640       O
ATOM   3280  CB  VAL A 443   -10.389 -12.522  73.792  1.00163.11         C
ANISOU 3280  CB  VAL A 443    23260 24353 14363     89  2411 -1371       C
ATOM   3281  CG1 VAL A 443   -10.045 -13.845  74.476  1.00163.96         C
ANISOU 3281  CG1 VAL A 443    23295 24342 14658   -238  2286 -1171       C
ATOM   3282  CG2 VAL A 443   -11.800 -12.076  74.102  1.00164.59         C
ANISOU 3282  CG2 VAL A 443    23387 25009 14142    245  2590 -1402       C
ATOM   3283  N   LEU A 444    -9.551  -9.358  72.887  1.00166.02         N
ANISOU 3283  N   LEU A 444    24072 24505 14504    737  2450 -1747       N
ATOM   3284  CA  LEU A 444    -9.268  -8.451  71.770  1.00164.39         C
ANISOU 3284  CA  LEU A 444    23909 24183 14370    960  2503 -1927       C
ATOM   3285  C   LEU A 444    -7.847  -7.885  71.870  1.00163.43         C
ANISOU 3285  C   LEU A 444    24009 23638 14448    972  2333 -1926       C
ATOM   3286  O   LEU A 444    -7.247  -7.516  70.855  1.00161.85         O
ANISOU 3286  O   LEU A 444    23806 23228 14463   1060  2332 -2023       O
ATOM   3287  CB  LEU A 444   -10.301  -7.317  71.687  1.00164.89         C
ANISOU 3287  CB  LEU A 444    24041 24583 14026   1262  2662 -2075       C
ATOM   3288  CG  LEU A 444   -10.611  -6.712  70.305  1.00163.43         C
ANISOU 3288  CG  LEU A 444    23781 24447 13869   1486  2807 -2275       C
ATOM   3289  CD1 LEU A 444   -11.942  -5.946  70.311  1.00164.24         C
ANISOU 3289  CD1 LEU A 444    23893 24983 13529   1736  2986 -2408       C
ATOM   3290  CD2 LEU A 444    -9.479  -5.827  69.780  1.00161.99         C
ANISOU 3290  CD2 LEU A 444    23779 23904 13867   1613  2722 -2354       C
ATOM   3291  N   SER A 445    -7.320  -7.820  73.096  1.00157.95         N
ANISOU 3291  N   SER A 445    23503 22826 13684    893  2192 -1815       N
ATOM   3292  CA  SER A 445    -5.950  -7.359  73.341  1.00157.23         C
ANISOU 3292  CA  SER A 445    23625 22329 13786    882  2014 -1804       C
ATOM   3293  C   SER A 445    -4.938  -8.431  72.951  1.00156.15         C
ANISOU 3293  C   SER A 445    23386 21871 14071    623  1893 -1722       C
ATOM   3294  O   SER A 445    -3.882  -8.127  72.393  1.00154.82         O
ANISOU 3294  O   SER A 445    23287 21381 14155    636  1802 -1763       O
ATOM   3295  CB  SER A 445    -5.747  -6.987  74.811  1.00158.69         C
ANISOU 3295  CB  SER A 445    24037 22499 13757    898  1896 -1722       C
ATOM   3296  OG  SER A 445    -4.367  -6.937  75.134  1.00158.08         O
ANISOU 3296  OG  SER A 445    24123 22008 13932    808  1706  1682       O
ATOM   3297  N   ILE A 446    -5.261  -9.686  73.261  1.00158.07         N
ANISOU 3297  N   ILE A 446    23468 22211 14382    388  1884 -1602       N
ATOM   3298  CA  ILE A 446    -4.396 -10.810  72.915  1.00157.14         C
ANISOU 3298  CA  ILE A 446    23246 21822 14638    136  1758 -1524       C
ATOM   3299  C   ILE A 446    -4.369 -10.944  71.391  1.00155.48         C
ANISOU 3299  C   ILE A 446    22845 21570 14660    194  1823 -1623       C
ATOM   3300  O   ILE A 446    -3.395 -11.413  70.805  1.00154.18         O
ANISOU 3300  O   ILE A 446    22641 21122 14818     88  1706 -1610       O
ATOM   3301  CB  ILE A 446    -4.835 -12.121  73.635  1.00158.38         C
ANISOU 3301  CB  ILE A 446    23278 22107 14792   -125  1731 -1368       C
ATOM   3302  CG1 ILE A 446    -3.653 -13.088  73.788  1.00157.71         C
ANISOU 3302  CG1 ILE A 446    23213 21677 15032   -382  1534 -1273       C
```

FIG. 13 Continued

```
ATOM   3303  CG2 ILE A 446      -6.030 -12.762  72.949  1.00158.66           C
ANISOU 3303  CG2 ILE A 446    23035  22457  14792   -150   1884  -1379       C
ATOM   3304  CD1 ILE A 446      -2.601 -12.646  74.806  1.00157.93           C
ANISOU 3304  CD1 ILE A 446    23517  21434  15053   -395   1380  -1237       C
ATOM   3305  N   ILE A 447      -5.446 -10.496  70.756  1.00154.62           N
ANISOU 3305  N   ILE A 447    22622  21755  14369    384   2010  -1730       N
ATOM   3306  CA  ILE A 447      -5.525 -10.451  69.307  1.00153.09           C
ANISOU 3306  CA  ILE A 447    22260  21553  14355    504   2096  -1847       C
ATOM   3307  C   ILE A 447      -4.414  -9.540  68.797  1.00151.74           C
ANISOU 3307  C   ILE A 447    22246  21072  14336    640   2026  -1919       C
ATOM   3308  O   ILE A 447      -4.053  -9.594  67.624  1.00150.26           O
ANISOU 3308  O   ILE A 447    21940  20769  14383    709   2040  -1984       O
ATOM   3309  CB  ILE A 447      -6.888  -9.882  68.847  1.00153.49           C
ANISOU 3309  CB  ILE A 447    22214  21983  14121    733   2321  -1976       C
ATOM   3310  CG1 ILE A 447      -7.981 -10.940  68.948  1.00154.51           C
ANISOU 3310  CG1 ILE A 447    22108  22410  14188    594   2403  -1918       C
ATOM   3311  CG2 ILE A 447      -6.825  -9.393  67.417  1.00151.83           C
ANISOU 3311  CG2 ILE A 447    21914  21727  14047    946   2416  -2131       C
ATOM   3312  CD1 ILE A 447      -8.252 -11.645  67.656  1.00153.36           C
ANISOU 3312  CD1 ILE A 447    21691  22292  14288    598   2460  -1984       C
ATOM   3313  N   ASP A 448      -3.851  -8.725  69.688  1.00173.26           N
ANISOU 3313  N   ASP A 448    25233  23658  16941    682   1939  -1899       N
ATOM   3314  CA  ASP A 448      -2.862  -7.719  69.279  1.00172.23           C
ANISOU 3314  CA  ASP A 448    25266  23244  16928    824   1877  -1966       C
ATOM   3315  C   ASP A 448      -1.370  -7.910  69.601  1.00171.65           C
ANISOU 3315  C   ASP A 448    25321  22766  17133    666   1663  -1884       C
ATOM   3316  O   ASP A 448       0.552   7.088  69.190  1.00170.83           O
ANISOU 3316  O   ASP A 448    25332  22430  17145    779   1615  -1934       O
ATOM   3317  CB  ASP A 448      -3.333  -6.324  69.675  1.00172.98           C
ANISOU 3317  CB  ASP A 448    25562  23469  16692   1079   1954  -2060       C
ATOM   3318  CG  ASP A 448      -4.422  -5.819  68.765  1.00172.68           C
ANISOU 3318  CG  ASP A 448    25410  23724  16475   1311   2166  -2202       C
ATOM   3319  OD1 ASP A 448      -5.611  -5.984  69.116  1.00173.74           O
ANISOU 3319  OD1 ASP A 448    25473  24210  16331   1344   2285  -2218       O
ATOM   3320  OD2 ASP A 448      -4.084  -5.299  67.678  1.00171.38           O
ANISOU 3320  OD2 ASP A 448    25217  23443  16455   1460   2216  -2297       O
ATOM   3321  N   LYS A 449      -1.009  -8.949  70.350  1.00152.15           N
ANISOU 3321  N   LYS A 449    22839  20211  14760    411   1535  -1761       N
ATOM   3322  CA  LYS A 449       0.409  -9.277  70.509  1.00151.40           C
ANISOU 3322  CA  LYS A 449    22837  19741  14949    252   1335  -1697       C
ATOM   3323  C   LYS A 449       0.691 -10.093  69.256  1.00149.92           C
ANISOU 3323  C   LYS A 449    22416  19487  15059    182   1326  -1702       C
ATOM   3324  O   LYS A 449       1.806 -10.152  68.745  1.00148.72           O
ANISOU 3324  O   LYS A 449    22278  19056  15174    142   1206  -1694       O
ATOM   3325  CB  LYS A 449       0.659 -10.104  71.775  1.00152.46           C
ANISOU 3325  CB  LYS A 449    23052  19818  15057     19   1205  -1576       C
ATOM   3326  CG  LYS A 449       2.081 -10.682  71.915  1.00151.62           C
ANISOU 3326  CG  LYS A 449    23017  19344  15247   -175    995  -1517       C
ATOM   3327  CD  LYS A 449       2.984  -9.839  72.813  1.00152.00           C
ANISOU 3327  CD  LYS A 449    23345  19143  15264   -128    871  -1523       C
ATOM   3328  CE  LYS A 449       3.927  -8.962  72.018  1.00150.77           C
ANISOU 3328  CE  LYS A 449    23256  18732  15297      3    825   1594       C
ATOM   3329  NZ  LYS A 449       4.607  -7.985  72.902  1.00151.38           N
ANISOU 3329  NZ  LYS A 449    23604  18604  15309     79    721  -1613       N
ATOM   3330  N   TYR A 450      -0.383 -10.706  68.775  1.00153.06           N
ANISOU 3330  N   TYR A 450    22594  20165  15396    184   1454  -1715       N
ATOM   3331  CA  TYR A 450      -0.415 -11.487  67.557  1.00151.82           C
ANISOU 3331  CA  TYR A 450    22186  20020  15479    164   1466  -1734       C
ATOM   3332  C   TYR A 450      -0.029 -10.613  66.383  1.00150.44           C
ANISOU 3332  C   TYR A 450    21992  19748  15419    399   1528  -1839       C
ATOM   3333  O   TYR A 450       0.762 -10.999  65.535  1.00149.10           O
ANISOU 3333  O   TYR A 450    21725  19395  15533    378   1438  -1831       O
ATOM   3334  CB  TYR A 450      -1.840 -12.000  67.370  1.00152.56           C
ANISOU 3334  CB  TYR A 450    22077  20473  15417    181   1624  -1755       C
ATOM   3335  CG  TYR A 450      -2.154 -13.128  68.301  1.00153.78           C
ANISOU 3335  CG  TYR A 450    22187  20706  15537    -83   1549  -1628       C
ATOM   3336  CD1 TYR A 450      -1.610 -13.165  69.571  1.00154.72           C
ANISOU 3336  CD1 TYR A 450    22511  20692  15582   -232   1429  -1532       C
ATOM   3337  CD2 TYR A 450      -2.970 -14.168  67.909  1.00154.03           C
```

FIG. 13 Continued

```
ANISOU 3337  CD2 TYR A 450     21972  20934  15619    -180   1593  -1601         C
ATOM   3338  CE1 TYR A 450      -1.868 -14.203  70.425  1.00155.86              C
ANISOU 3338  CE1 TYR A 450     22621  20902  15697    -470   1364  -1409         C
ATOM   3339  CE2 TYR A 450      -3.237 -15.212  68.758  1.00155.24              C
ANISOU 3339  CE2 TYR A 450     22085  21148  15752    -433   1520  -1472         C
ATOM   3340  CZ  TYR A 450      -2.681 -15.223  70.015  1.00156.15              C
ANISOU 3340  CZ  TYR A 450     22411  21133  15785    -577   1410  -1373         C
ATOM   3341  OH  TYR A 450      -2.944 -16.262  70.865  1.00157.40              O
ANISOU 3341  OH  TYR A 450     22533  21351  15920    -821   1345  -1239         O
ATOM   3342  N   ALA A 451      -0.606  -9.420  66.362  1.00146.25              N
ANISOU 3342  N   ALA A 451     21562  19352  14652     632   1678  -1936         N
ATOM   3343  CA  ALA A 451      -0.384  -8.440  65.316  1.00145.15              C
ANISOU 3343  CA  ALA A 451     21428  19152  14572     884   1765  -2043         C
ATOM   3344  C   ALA A 451       1.061  -7.948  65.271  1.00144.41              C
ANISOU 3344  C   ALA A 451     21485  18691  14692     864   1611  -2005         C
ATOM   3345  O   ALA A 451       1.549  -7.523  64.229  1.00143.22              O
ANISOU 3345  O   ALA A 451     21280  18425  14713    1008   1636  -2050         O
ATOM   3346  CB  ALA A 451      -1.336  -7.268  65.513  1.00145.96              C
ANISOU 3346  CB  ALA A 451     21645  19483  14331    1120   1939  -2152         C
ATOM   3347  N   GLU A 452       1.742  -7.980  66.404  1.00145.66              N
ANISOU 3347  N   GLU A 452     21835  18670  14840     698   1456  -1923         N
ATOM   3348  CA  GLU A 452       3.129  -7.554  66.421  1.00145.04              C
ANISOU 3348  CA  GLU A 452     21899  18241  14970     665   1302  -1888         C
ATOM   3349  C   GLU A 452       3.971  -8.559  65.644  1.00143.71              C
ANISOU 3349  C   GLU A 452     21560  17907  15136     529   1183  -1829         C
ATOM   3350  O   GLU A 452       4.550  -8.229  64.612  1.00142.54              O
ANISOU 3350  O   GLU A 452     21342  17637  15179     645   1186  -1853         O
ATOM   3351  CB  GLU A 452       3.636  -7.413  67.853  1.00146.16              C
ANISOU 3351  CB  GLU A 452     22281  18234  15021     528   1159  -1826         C
ATOM   3352  CG  GLU A 452       3.052  -6.233  68.607  1.00147.40              C
ANISOU 3352  CG  GLU A 452     22640  18499  14867     701   1231  -1884         C
ATOM   3353  CD  GLU A 452       3.442  -4.904  67.998  1.00146.94              C
ANISOU 3353  CD  GLU A 452     22688  18310  14832     925   1267  -1962         C
ATOM   3354  OE1 GLU A 452       3.447  -3.899  68.740  1.00147.88              O
ANISOU 3354  OE1 GLU A 452     23029  18388  14770    1034   1238  -1992         O
ATOM   3355  OE2 GLU A 452       3.742  -4.861  66.785  1.00145.69              O
ANISOU 3355  OE2 GLU A 452     22393  18090  14872    1001   1317  -1988         O
ATOM   3356  N   ARG A 453       4.038   9.791  66.141  1.00176.99              N
ANISOU 3356  N   ARG A 453     25710  22124  19416     289   1071  -1749         N
ATOM   3357  CA  ARG A 453       4.726 -10.854  65.423  1.00175.78              C
ANISOU 3357  CA  ARG A 453     25387  21850  19552     162    942  -1698         C
ATOM   3358  C   ARG A 453       3.855 -11.073  64.191  1.00175.07              C
ANISOU 3358  C   ARG A 453     25040  21988  19490     327   1092  -1763         C
ATOM   3359  O   ARG A 453       4.188 -11.839  63.289  1.00173.94              O
ANISOU 3359  O   ARG A 453     24708  21808  19574     309   1022  -1747         O
ATOM   3360  CB  ARG A 453       4.814 -12.127  66.271  1.00176.33              C
ANISOU 3360  CB  ARG A 453     25450  21904  19644    -123    798  -1607         C
ATOM   3361  CG  ARG A 453       4.557 -11.932  67.783  1.00177.93              C
ANISOU 3361  CG  ARG A 453     25865  22130  19610    -226    786  -1571         C
ATOM   3362  CD  ARG A 453       5.826 -11.839  68.633  1.00177.98              C
ANISOU 3362  CD  ARG A 453     26094  21823  19705    -361    595  -1525         C
ATOM   3363  NE  ARG A 453       6.393 -10.497  68.656  1.00177.91              N
ANISOU 3363  NE  ARG A 453     26263  21653  19681    -193    606  -1577         N
ATOM   3364  CZ  ARG A 453       7.407 -10.111  67.892  1.00176.75              C
ANISOU 3364  CZ  ARG A 453     26116  21283  19756    -138    535  -1590         C
ATOM   3365  NH1 ARG A 453       7.964 -10.967  67.049  1.00175.50              N
ANISOU 3365  NH1 ARG A 453     25793  21052  19839    -222    445  -1559         N
ATOM   3366  NH2 ARG A 453       7.866  -8.873  67.970  1.00176.89              N
ANISOU 3366  NH2 ARG A 453     26298  21155  19756       7    545  -1630         N
ATOM   3367  N   GLY A 454       2.719 -10.377  64.194  1.00142.29              N
ANISOU 3367  N   GLY A 454     20889  18082  15091     502   1294  -1845         N
ATOM   3368  CA  GLY A 454       1.782 -10.349  63.090  1.00141.73              C
ANISOU 3368  CA  GLY A 454     20606  18246  14999     706   1470  -1938         C
ATOM   3369  C   GLY A 454       1.240 -11.690  62.676  1.00141.50              C
ANISOU 3369  C   GLY A 454     20325  18364  15076     597   1446  -1913         C
ATOM   3370  O   GLY A 454       1.528 -12.152  61.579  1.00140.25              O
ANISOU 3370  O   GLY A 454     19979  18165  15144     668   1411  -1928         O
ATOM   3371  N   LEU A 455       0.454 -12.323  63.538  1.00142.87              N
ANISOU 3371  N   LEU A 455     20487  18709  15090     435   1458  -1871         N
```

FIG. 13 Continued

```
ATOM   3372  CA  LEU A 455      -0.083 -13.638  63.202  1.00142.84           C
ANISOU 3372  CA  LEU A 455    20242  18835  15195    311   1420  -1838       C
ATOM   3373  C   LEU A 455      -1.572 -13.659  62.836  1.00143.41           C
ANISOU 3373  C   LEU A 455    20143  19252  15094    445   1627  -1925       C
ATOM   3374  O   LEU A 455      -2.256 -12.641  62.912  1.00143.89           O
ANISOU 3374  O   LEU A 455    20284  19476  14911    635   1810  -2016       O
ATOM   3375  CB  LEU A 455       0.285 -14.664  64.276  1.00143.68           C
ANISOU 3375  CB  LEU A 455    20411  18845  15335    -14   1237  -1704       C
ATOM   3376  CG  LEU A 455       1.812 -14.792  64.453  1.00142.85           C
ANISOU 3376  CG  LEU A 455    20444  18396  15437   -139   1018  -1637       C
ATOM   3377  CD1 LEU A 455       2.245 -16.166  64.964  1.00143.05           C
ANISOU 3377  CD1 LEU A 455    20436  18319  15596   -437    808  -1526       C
ATOM   3378  CD2 LEU A 455       2.522 -14.500  63.149  1.00141.15           C
ANISOU 3378  CD2 LEU A 455    20131  18049  15450     41    991  -1690       C
ATOM   3379  N   ARG A 456      -2.063 -14.817  62.416  1.00145.45           N
ANISOU 3379  N   ARG A 456    20166  19619  15478    354   1589  -1904       N
ATOM   3380  CA  ARG A 456      -3.437 -14.906  61.948  1.00145.89           C
ANISOU 3380  CA  ARG A 456    20032  19992  15407    487   1777  -1995       C
ATOM   3381  C   ARG A 456      -4.409 -15.316  63.058  1.00147.78           C
ANISOU 3381  C   ARG A 456    20283  20454  15411    306   1831  -1929       C
ATOM   3382  O   ARG A 456      -4.526 -16.491  63.400  1.00148.39           O
ANISOU 3382  O   ARG A 456    20252  20540  15590     68   1713  -1826       O
ATOM   3383  CB  ARG A 456      -3.528 -15.821  60.715  1.00144.75           C
ANISOU 3383  CB  ARG A 456    19602  19862  15537    549   1722  -2032       C
ATOM   3384  CG  ARG A 456      -4.612 -15.398  59.689  1.00144.36           C
ANISOU 3384  CG  ARG A 456    19371  20065  15412    851   1946  -2198       C
ATOM   3385  CD  ARG A 456      -4.194 -15.538  58.201  1.00142.54           C
ANISOU 3385  CD  ARG A 456    18953  19746  15458   1080   1915  -2279       C
ATOM   3386  NE  ARG A 456      -4.986 -14.708  57.280  1.00141.98           N
ANISOU 3386  NE  ARG A 456    18799  19867  15280   1429   2154  -2458       N
ATOM   3387  CZ  ARG A 456      -5.779 -13.688  57.626  1.00142.72           C
ANISOU 3387  CZ  ARG A 456    19015  20152  15061   1563   2373  -2554       C
ATOM   3388  NH1 ARG A 456      -5.927 -13.314  58.888  1.00144.11           N
ANISOU 3388  NH1 ARG A 456    19399  20368  14988   1396   2388  -2487       N
ATOM   3389  NH2 ARG A 456      -6.435 -13.024  56.691  1.00142.05           N
ANISOU 3389  NH2 ARG A 456    18846  20227  14900   1887   2576  -2727       N
ATOM   3390  N   SER A 457      -5.126 -14.329  63.589  1.00148.47           N
ANISOU 3390  N   SER A 457    20500  20734  15179    432   2007  -1989       N
ATOM   3391  CA  SER A 457      -6.030 -14.511  64.721  1.00150.37           C
ANISOU 3391  CA  SER A 457    20779  21207  15148    297   2072  -1922       C
ATOM   3392  C   SER A 457      -7.289 -15.320  64.423  1.00151.13           C
ANISOU 3392  C   SER A 457    20613  21599  15209    264   2172  -1938       C
ATOM   3393  O   SER A 457      -8.222 -14.796  63.831  1.00151.06           O
ANISOU 3393  O   SER A 457    20513  21832  15053    488   2364  -2075       O
ATOM   3394  CB  SER A 457      -6.462 -13.133  65.214  1.00151.02           C
ANISOU 3394  CB  SER A 457    21063  21433  14884    497   2228  -2004       C
ATOM   3395  OG  SER A 457      -5.675 -12.114  64.623  1.00149.71           O
ANISOU 3395  OG  SER A 457    21030  21071  14783    701   2231  -2093       O
ATOM   3396  N   LEU A 458      -7.351 -16.569  64.875  1.00172.70           N
ANISOU 3396  N   LEU A 458    23235  24320  18061    -14   2045  -1801       N
ATOM   3397  CA  LEU A 458      -8.544 -17.386  64.640  1.00173.60           C
ANISOU 3397  CA  LEU A 458    23093  24706  18161    -69   2126  -1801       C
ATOM   3398  C   LEU A 458      -9.193 -17.868  65.934  1.00175.76           C
ANISOU 3398  C   LEU A 458    23394  25158  18230   -304   2136  -1654       C
ATOM   3399  O   LEU A 458      -8.618 -18.686  66.648  1.00176.33           O
ANISOU 3399  O   LEU A 458    23513  25067  18416   -572   1962  -1496       O
ATOM   3400  CB  LEU A 458      -8.198 -18.596  63.777  1.00172.67           C
ANISOU 3400  CB  LEU A 458    22750  24444  18412   -172   1963  -1775       C
ATOM   3401  CG  LEU A 458      -9.161 -19.785  63.880  1.00173.97           C
ANISOU 3401  CG  LEU A 458    22675  24801  18624   -357   1951  -1702       C
ATOM   3402  CD1 LEU A 458     -10.592 -19.383  63.532  1.00174.69           C
ANISOU 3402  CD1 LEU A 458    22615  25256  18502   -169   2198  -1826       C
ATOM   3403  CD2 LEU A 458      -8.693 -20.959  63.015  1.00172.96           C
ANISOU 3403  CD2 LEU A 458    22345  24495  18875   -444   1747  -1680       C
ATOM   3404  N   ALA A 459     -10.405 -17.393  66.214  1.00155.30           N
ANISOU 3404  N   ALA A 459    20765  22909  15331   -197   2339  -1704       N
ATOM   3405  CA  ALA A 459     -11.097 -17.743  67.460  1.00157.49           C
ANISOU 3405  CA  ALA A 459    21064  23398  15376   -387   2370  -1558       C
ATOM   3406  C   ALA A 459     -11.842 -19.077  67.431  1.00158.63           C
```

FIG. 13 Continued

```
ANISOU 3406  C   ALA A 459     20942  23681  15647    -610   2340  -1456       C
ATOM   3407  O   ALA A 459     -12.174 -19.595  66.366  1.00157.86              O
ANISOU 3407  O   ALA A 459     20614  23610  15757    -559   2347  -1539       O
ATOM   3408  CB  ALA A 459     -12.046 -16.630  67.860  1.00158.43              C
ANISOU 3408  CB  ALA A 459     21272  23842  15083    -173   2584  -1644       C
ATOM   3409  N   VAL A 460     -12.113 -19.612  68.619  1.00161.62              N
ANISOU 3409  N   VAL A 460     21354  24152  15902    -846   2306  -1273       N
ATOM   3410  CA  VAL A 460     -12.845 -20.871  68.758  1.00163.05              C
ANISOU 3410  CA  VAL A 460     21297  24472  16184   -1087   2276  -1146       C
ATOM   3411  C   VAL A 460     -13.707 -20.946  70.033  1.00165.54              C
ANISOU 3411  C   VAL A 460     21633  25078  16168   -1215   2373   -992       C
ATOM   3412  O   VAL A 460     -13.194 -20.875  71.151  1.00166.36              C
ANISOU 3412  O   VAL A 460     21936  25094  16179   -1333   2301   -858       C
ATOM   3413  CB  VAL A 460     -11.913 -22.095  68.644  1.00162.51              C
ANISOU 3413  CB  VAL A 460     21183  24078  16488   -1349   2020  -1029       C
ATOM   3414  CG1 VAL A 460     -10.517 -21.749  69.127  1.00161.52              C
ANISOU 3414  CG1 VAL A 460     21335  23618  16417   -1384   1868   -994       C
ATOM   3415  CG2 VAL A 460     -12.493 -23.280  69.402  1.00164.60              C
ANISOU 3415  CG2 VAL A 460     21314  24456  16772   -1659   1965   -828       C
ATOM   3416  N   ALA A 461     -15.019 -21.091  69.841  1.00278.45              N
ANISOU 3416  N   ALA A 461     35719  39731  30348   -1179   2535  -1016       N
ATOM   3417  CA  ALA A 461     -16.000 -21.091  70.936  1.00280.89              C
ANISOU 3417  CA  ALA A 461     36011  40382  30331   -1261   2656   -881       C
ATOM   3418  C   ALA A 461     -16.336 -22.470  71.487  1.00282.72              C
ANISOU 3418  C   ALA A 461     36070  40649  30704   -1604   2566   -656       C
ATOM   3419  O   ALA A 461     -15.595 -23.425  71.270  1.00282.15              C
ANISOU 3419  O   ALA A 461     35956  40281  30967   -1809   2371   -580       C
ATOM   3420  CB  ALA A 461     -17.276 -20.381  70.506  1.00281.33              C
ANISOU 3420  CB  ALA A 461     35946  40838  30108   -1019   2896  -1033       C
ATOM   3421  N   ARG A 462     -17.458 -22.563  72.202  1.00172.65              N
ANISOU 3421  N   ARG A 462     22029  27076  16496   -1661   2705   -547       N
ATOM   3422  CA  ARG A 462     -17.865 -23.828  72.804  1.00174.70              C
ANISOU 3422  CA  ARG A 462     22120  27397  16861   -1989   2637   -312       C
ATOM   3423  C   ARG A 462     -18.868 -24.603  71.971  1.00175.31              C
ANISOU 3423  C   ARG A 462     21857  27653  17099   -2056   2690   -342       C
ATOM   3424  O   ARG A 462     -19.234 -24.188  70.876  1.00174.01              C
ANISOU 3424  O   ARG A 462     21582  27558  16976   -1836   2779   -558       C
ATOM   3425  CB  ARG A 462     -18.428 -23.610  74.199  1.00177.09              C
ANISOU 3425  CB  ARG A 462     22504  27982  16799   -2047   2735   -128       C
ATOM   3426  CG  ARG A 462     -18.547 -24.891  75.028  1.00179.19              C
ANISOU 3426  CG  ARG A 462     22665  28236  17183   -2406   2635    151       C
ATOM   3427  CD  ARG A 462     -17.199 -25.365  75.602  1.00178.57              C
ANISOU 3427  CD  ARG A 462     22799  27749  17302   -2587   2415    266       C
ATOM   3428  NE  ARG A 462     -17.374 -26.303  76.715  1.00180.91              N
ANISOU 3428  NE  ARG A 462     23062  28095  17580   -2879   2361    545       N
ATOM   3429  CZ  ARG A 462     -17.214 -27.621  76.626  1.00181.50              C
ANISOU 3429  CZ  ARG A 462     22998  27999  17964   -3183   2208    684       C
ATOM   3430  NH1 ARG A 462     -16.856 -28.176  75.476  1.00179.88              N
ANISOU 3430  NH1 ARG A 462     22672  27562  18113   -3230   2077    569       N
ATOM   3431  NH2 ARG A 462     -17.406 -28.385  77.694  1.00183.73              N
ANISOU 3431  NH2 ARG A 462     23266  28345  18198   -3431   2178    941       N
ATOM   3432  N   GLN A 463     -19.287 -25.748  72.499  1.00193.71              N
ANISOU 3432  N   GLN A 463     24024  30044  19532   -2360   2627   -123       N
ATOM   3433  CA  GLN A 463     -20.273 -26.588  71.837  1.00194.66              C
ANISOU 3433  CA  GLN A 463     23810  30333  19819   -2461   2659   -120       C
ATOM   3434  C   GLN A 463     -21.697 -26.273  72.262  1.00196.82              C
ANISOU 3434  C   GLN A 463     23939  31095  19750   -2407   2894    -83       C
ATOM   3435  O   GLN A 463     -22.032 -26.335  73.446  1.00198.94              O
ANISOU 3435  O   GLN A 463     24257  31554  19778   -2536   2945    125       O
ATOM   3436  CB  GLN A 463     -19.975 -28.080  72.029  1.00195.66              C
ANISOU 3436  CB  GLN A 463     23811  30243  20287   -2828   2443     90       C
ATOM   3437  CG  GLN A 463      19.081 -28.436  73.196  1.00196.34              C
ANISOU 3437  CG  GLN A 463     24120  30117  20364   -3049   2301    306       C
ATOM   3438  CD  GLN A 463     -18.439 -29.793  72.995  1.00196.25              C
ANISOU 3438  CD  GLN A 463     24033  29777  20756   -3344   2038    424       C
ATOM   3439  OE1 GLN A 463     -18.660 -30.442  71.971  1.00195.67              O
ANISOU 3439  OE1 GLN A 463     23737  29635  20972   -3372   1952    345       O
ATOM   3440  NE2 GLN A 463     -17.637 -30.228  73.963  1.00196.80              N
ANISOU 3440  NE2 GLN A 463     24291  29641  20843   -3552   1899    605       N
```

FIG. 13 Continued

```
ATOM   3441  N   VAL A 464     -22.529 -25.960  71.271  1.00178.96           N
ANISOU 3441  N   VAL A 464     21489  29038  17469   -2207   3032   -288     N
ATOM   3442  CA  VAL A 464     -23.923 -25.605  71.487  1.00180.76           C
ANISOU 3442  CA  VAL A 464     21563  29748  17370   -2118   3263   -300     C
ATOM   3443  C   VAL A 464     -24.548 -26.388  72.642  1.00183.85           C
ANISOU 3443  C   VAL A 464     21844  30354  17657   -2419   3272      8     C
ATOM   3444  O   VAL A 464     -25.053 -25.795  73.601  1.00185.39           O
ANISOU 3444  O   VAL A 464     22127  30860  17453   -2362   3411    101     O
ATOM   3445  CB  VAL A 464     -24.748 -25.826  70.200  1.00180.18           C
ANISOU 3445  CB  VAL A 464     21203  29798  17460   -1997   3341   -504     C
ATOM   3446  CG1 VAL A 464     -24.231 -24.961  69.072  1.00177.25           C
ANISOU 3446  CG1 VAL A 464     20936  29262  17147   -1662   3365   -811     C
ATOM   3447  CG2 VAL A 464     -24.690 -27.273  69.795  1.00180.75           C
ANISOU 3447  CG2 VAL A 464     21033  29664  17978   -2286   3153   -386     C
ATOM   3448  N   VAL A 465     -24.480 -27.715  72.558  1.00185.09           N
ANISOU 3448  N   VAL A 465     21816  30339  18172   -2731   3112    170     N
ATOM   3449  CA  VAL A 465     -25.090 -28.583  73.550  1.00188.12           C
ANISOU 3449  CA  VAL A 465     22062  30905  18509   -3040   3112    474     C
ATOM   3450  C   VAL A 465     -26.412 -27.961  74.021  1.00190.08           C
ANISOU 3450  C   VAL A 465     22207  31690  18325   -2916   3371    490     C
ATOM   3451  O   VAL A 465     -26.466 -27.315  75.071  1.00191.10           O
ANISOU 3451  O   VAL A 465     22511  32015  18083   -2851   3462    597     O
ATOM   3452  CB  VAL A 465     -24.122 -28.889  74.721  1.00188.71           C
ANISOU 3452  CB  VAL A 465     22374  30748  18580   -3243   2968    713     C
ATOM   3453  CG1 VAL A 465     -22.870 -29.537  74.192  1.00186.77           C
ANISOU 3453  CG1 VAL A 465     22215  29997  18752   -3363   2710    681     C
ATOM   3454  CG2 VAL A 465     -23.761 -27.628  75.484  1.00188.20           C
ANISOU 3454  CG2 VAL A 465     22614  30777  18118   -3005   3071    671     C
ATOM   3455  N   PRO A 466     -27.478 -28.123  73.212  1.00200.15           N
ANISOU 3455  N   PRO A 466     23200  33211  19639   -2857   3485    367     N
ATOM   3456  CA  PRO A 466     -28.811 -27.596  73.523  1.00201.99           C
ANISOU 3456  CA  PRO A 466     23300  33974  19472   -2737   3730    359     C
ATOM   3457  C   PRO A 466     -29.621 -28.619  74.293  1.00205.31           C
ANISOU 3457  C   PRO A 466     23481  34619  19908   -3067   3740    671     C
ATOM   3458  O   PRO A 466     -29.758 -28.531  75.511  1.00207.26           O
ANISOU 3458  O   PRO A 466     23815  35058  19877   -3159   3789    908     O
ATOM   3459  CB  PRO A 466     -29.455 -27.416  72.139  1.00200.65           C
ANISOU 3459  CB  PRO A 466     22929  33894  19416   -2528   3820     56     C
ATOM   3460  CG  PRO A 466     -28.448 -27.939  71.131  1.00198.26           C
ANISOU 3460  CG  PRO A 466     22635  33098  19597   -2553   3607    -65     C
ATOM   3461  CD  PRO A 466     -27.453 -28.757  71.886  1.00198.77           C
ANISOU 3461  CD  PRO A 466     22819  32822  19883   -2863   3383    201     C
ATOM   3462  N   GLU A 467     -30.141 -29.596  73.561  1.00215.93           N
ANISOU 3462  N   GLU A 467     24521  35930  21592   -3236   3685    673     N
ATOM   3463  CA  GLU A 467     -30.948 -30.660  74.130  1.00219.12           C
ANISOU 3463  CA  GLU A 467     24659  36523  22075   -3568   3681    962     C
ATOM   3464  C   GLU A 467     -30.769 -31.895  73.269  1.00218.87           C
ANISOU 3464  C   GLU A 467     24405  36167  22588   -3792   3476    966     C
ATOM   3465  O   GLU A 467     -30.284 -32.932  73.724  1.00219.95           O
ANISOU 3465  O   GLU A 467     24525  36053  22994   -4116   3285   1212     O
ATOM   3466  CB  GLU A 467     -32.428 -30.263  74.131  1.00220.94           C
ANISOU 3466  CB  GLU A 467     24665  37303  21978   -3452   3933    917     C
ATOM   3467  CG  GLU A 467     -32.800 -29.166  75.123  1.00221.84           C
ANISOU 3467  CG  GLU A 467     24958  37817  21516   -3257   4128    963     C
ATOM   3468  CD  GLU A 467     -34.282 -28.816  75.088  1.00223.65           C
ANISOU 3468  CD  GLU A 467     24956  38608  21413   -3142   4367    913     C
ATOM   3469  OE1 GLU A 467     -34.860 -28.763  73.979  1.00222.72           O
ANISOU 3469  OE1 GLU A 467     24655  38560  21407   -3007   4434    657     O
ATOM   3470  OE2 GLU A 467     -34.864 -28.588  76.172  1.00226.00           O
ANISOU 3470  OE2 GLU A 467     25256  39286  21328   -3173   4486   1125     O
ATOM   3471  N   LYS A 468     -31.155 -31.758  72.006  1.00200.58           N
ANISOU 3471  N   LYS A 468     21929  33855  20426   -3597   3509    680     N
ATOM   3472  CA  LYS A 468     -31.067 -32.848  71.050  1.00200.18           C
ANISOU 3472  CA  LYS A 468     21651  33522  20687   -3745   3310    640     C
ATOM   3473  C   LYS A 468     -30.716 -32.354  69.651  1.00196.98           C
ANISOU 3473  C   LYS A 468     21262  32928  20652   -3417   3286    267     C
ATOM   3474  O   LYS A 468     -30.490 -31.160  69.434  1.00195.04           O
ANISOU 3474  O   LYS A 468     21219  32752  20134   -3090   3424     46     O
ATOM   3475  CB  LYS A 468     -32.369 -33.648  71.025  1.00203.05           C
```

FIG. 13 Continued

```
ANISOU 3475  CB  LYS A 468    21639  34179  21331  -3942   3374    763       C
ATOM   3476  CG  LYS A 468    32.372  34.809  71.987  1.00205.90             C
ANISOU 3476  CG  LYS A 468    21911  34477  21846  -4379   3238   1155       C
ATOM   3477  CD  LYS A 468   -31.190 -35.711  71.706  1.00204.64             C
ANISOU 3477  CD  LYS A 468    21836  33782  22136  -4568   2917   1215       C
ATOM   3478  CE  LYS A 468   -31.158 -36.108  70.243  1.00202.80             C
ANISOU 3478  CE  LYS A 468    21423  33326  22306  -4448   2776    954       C
ATOM   3479  NZ  LYS A 468   -29.979 -36.950  69.924  1.00201.42             N
ANISOU 3479  NZ  LYS A 468    21340  32642  22548  -4602   2446    996       N
ATOM   3480  N   THR A 469   -30.688 -33.289  68.706  1.00250.69             N
ANISOU 3480  N   THR A 469    27846  39497  27909  -3500   3103    204       N
ATOM   3481  CA  THR A 469   -30.289 -33.019  67.327  1.00247.72             C
ANISOU 3481  CA  THR A 469    27457  38902  27764  -3203   3040   -126       C
ATOM   3482  C   THR A 469   -31.268 -32.146  66.520  1.00246.98             C
ANISOU 3482  C   THR A 469    27240  39141  27460  -2843   3294   -437       C
ATOM   3483  O   THR A 469   -32.393 -31.880  66.949  1.00248.97             O
ANISOU 3483  O   THR A 469    27366  39816  27416  -2844   3510   -402       O
ATOM   3484  CB  THR A 469   -30.052 -34.345  66.568  1.00247.68             C
ANISOU 3484  CB  THR A 469    27229  38571  28307  -3387   2751    -94       C
ATOM   3485  OG1 THR A 469   -29.774 -35.394  67.505  1.00249.83             O
ANISOU 3485  OG1 THR A 469    27496  38704  28726  -3809   2568    255       O
ATOM   3486  CG2 THR A 469   -28.889 -34.215  65.604  1.00244.39             C
ANISOU 3486  CG2 THR A 469    26953  37751  28154  -3178   2566   -301       C
ATOM   3487  N   LYS A 470   -30.800 -31.700  65.354  1.00188.88             N
ANISOU 3487  N   LYS A 470    19926  31590  20250  -2526   3264   -741       N
ATOM   3488  CA  LYS A 470   -31.583 -30.915  64.394  1.00187.70             C
ANISOU 3488  CA  LYS A 470    19671  31685  19960  -2146   3478  -1079       C
ATOM   3489  C   LYS A 470   -32.052 -29.548  64.894  1.00187.66             C
ANISOU 3489  C   LYS A 470    19852  32054  19395  -1910   3775  -1184       C
ATOM   3490  O   LYS A 470   -31.519 -28.514  64.483  1.00185.25             O
ANISOU 3490  O   LYS A 470    19772  31681  18935  -1595   3851  -1404       O
ATOM   3491  CB  LYS A 470   -32.773 -31.732  63.862  1.00189.44             C
ANISOU 3491  CB  LYS A 470    19499  32096  20383  -2220   3495  -1112       C
ATOM   3492  CG  LYS A 470   -32.394 -33.028  63.116  1.00189.20             C
ANISOU 3492  CG  LYS A 470    19260  31699  20930  -2376   3188  -1076       C
ATOM   3493  CD  LYS A 470   -32.294 -34.241  64.053  1.00191.86             C
ANISOU 3493  CD  LYS A 470    19515  31924  21458  -2861   2987   -690       C
ATOM   3494  CE  LYS A 470   -31.813 -35.495  63.324  1.00191.47             C
ANISOU 3494  CE  LYS A 470    19295  31486  21970  -3004   2648   -659       C
ATOM   3495  NZ  LYS A 470   -31.564 -36.627  64.260  1.00193.84             N
ANISOU 3495  NZ  LYS A 470    19566  31638  22445  -3471   2436   -285       N
ATOM   3496  N   GLU A 471   -33.051 -29.553  65.775  1.00188.34             N
ANISOU 3496  N   GLU A 471    19841  32539  19179  -2057   3933  -1023       N
ATOM   3497  CA  GLU A 471   -33.631 -28.310  66.282  1.00188.59             C
ANISOU 3497  CA  GLU A 471    20026  32977  18652  -1831   4205  -1116       C
ATOM   3498  C   GLU A 471   -32.608 -27.415  66.979  1.00187.32             C
ANISOU 3498  C   GLU A 471    20255  32682  18236  -1747   4194  -1068       C
ATOM   3499  O   GLU A 471   -31.815 -27.871  67.802  1.00187.95             O
ANISOU 3499  O   GLU A 471    20466  32536  18412  -2007   4033   -804       O
ATOM   3500  CB  GLU A 471   -34.859 -28.565  67.178  1.00191.96             C
ANISOU 3500  CB  GLU A 471    20267  33867  18802  -2025   4354   -913       C
ATOM   3501  CG  GLU A 471   -36.177 -28.770  66.402  1.00192.84             C
ANISOU 3501  CG  GLU A 471    20043  34290  18936  -1922   4498  -1099       C
ATOM   3502  CD  GLU A 471   -37.405 -28.141  67.082  1.00194.94             C
ANISOU 3502  CD  GLU A 471    20255  35140  18674  -1865   4765  -1081       C
ATOM   3503  OE1 GLU A 471   -37.363 -26.943  67.444  1.00194.09             O
ANISOU 3503  OE1 GLU A 471    20403  35236  18107  -1605   4919  -1190       O
ATOM   3504  OE2 GLU A 471   -38.432 -28.839  67.233  1.00197.48             O
ANISOU 3504  OE2 GLU A 471    20273  35725  19035  -2045   4816   -963       O
ATOM   3505  N   SER A 472   -32.661 -26.131  66.637  1.00185.18             N
ANISOU 3505  N   SER A 472    20167  32556  17638  -1374   4368  -1336       N
ATOM   3506  CA  SER A 472   -31.729 -25.125  67.133  1.00183.73             C
ANISOU 3506  CA  SER A 472    20354  32247  17207  -1229   4367  -1349       C
ATOM   3507  C   SER A 472   -31.478 -25.178  68.637  1.00185.71             C
ANISOU 3507  C   SER A 472    20764  32569  17228  -1473   4328  -1020       C
ATOM   3508  O   SER A 472   -32.261 -25.753  69.393  1.00188.45             O
ANISOU 3508  O   SER A 472    20943  33188  17473  -1704   4371   -795       O
ATOM   3509  CB  SER A 472   -32.221 -23.728  66.761  1.00182.47             C
ANISOU 3509  CB  SER A 472    20330  32378  16622   -816   4600  -1651       C
```

FIG. 13 Continued

```
ATOM   3510  OG  SER A 472     -32.924 -23.155  67.846  1.00184.45           O
ANISOU 3510  OG  SER A 472    20660  33051  16371   -815   4753  -1536       O
ATOM   3511  N   PRO A 473     -30.363 -24.573  69.069  1.00194.39           N
ANISOU 3511  N   PRO A 473    22187  33419  18254  -1412   4245   -992       N
ATOM   3512  CA  PRO A 473     -29.959 -24.536  70.466  1.00195.91           C
ANISOU 3512  CA  PRO A 473    22568  33628  18239  -1594   4193   -708       C
ATOM   3513  C   PRO A 473     -30.183 -23.163  71.048  1.00195.81           C
ANISOU 3513  C   PRO A 473    22799  33911  17689  -1314   4359   -798       C
ATOM   3514  O   PRO A 473     -31.251 -22.867  71.579  1.00197.72           O
ANISOU 3514  O   PRO A 473    22959  34612  17553  -1268   4525   -756       O
ATOM   3515  CB  PRO A 473     -28.445 -24.751  70.381  1.00194.00           C
ANISOU 3515  CB  PRO A 473    22535  32855  18323  -1675   3965   -667       C
ATOM   3516  CG  PRO A 473     -28.067 -24.506  68.903  1.00191.15           C
ANISOU 3516  CG  PRO A 473    22145  32255  18228  -1433   3940   -979       C
ATOM   3517  CD  PRO A 473     -29.306 -24.010  68.219  1.00191.28           C
ANISOU 3517  CD  PRO A 473    21986  32658  18032  -1185   4165  -1214       C
ATOM   3518  N   GLY A 474     -29.165 -22.319  70.904  1.00206.05           N
ANISOU 3518  N   GLY A 474    24392  34942  18954  -1117   4302   -929       N
ATOM   3519  CA  GLY A 474     -29.158 -21.011  71.524  1.00205.84           C
ANISOU 3519  CA  GLY A 474    24642  35119  18449   -858   4406   -999       C
ATOM   3520  C   GLY A 474     -28.696 -21.212  72.955  1.00207.53           C
ANISOU 3520  C   GLY A 474    25008  35303  18540  -1064   4308   -686       C
ATOM   3521  O   GLY A 474     -28.528 -20.256  73.714  1.00207.64           O
ANISOU 3521  O   GLY A 474    25272  35440  18182   -894   4342   -679       O
ATOM   3522  N   ALA A 475     -28.490 -22.481  73.307  1.00230.06           N
ANISOU 3522  N   ALA A 475    27710  37988  21716  -1424   4175   -431       N
ATOM   3523  CA  ALA A 475     -28.044 -22.898  74.634  1.00231.79           C
ANISOU 3523  CA  ALA A 475    28039  38149  21882  -1658   4072   -114       C
ATOM   3524  C   ALA A 475     -26.721 -22.238  75.012  1.00230.07           C
ANISOU 3524  C   ALA A 475    28176  37584  21656  -1556   3945   -137       C
ATOM   3525  O   ALA A 475     -26.195 -21.429  74.252  1.00227.66           O
ANISOU 3525  O   ALA A 475    28023  37104  21374  -1309   3943   -388       O
ATOM   3526  CB  ALA A 475     -27.922 -24.418  74.682  1.00233.02           C
ANISOU 3526  CB  ALA A 475    27976  38101  22462  -2054   3929    117       C
ATOM   3527  N   PRO A 476     -26.172 -22.575  76.190  1.00189.04           N
ANISOU 3527  N   PRO A 476    23110  32285  16431  -1740   3838    125       N
ATOM   3528  CA  PRO A 476     -24.918 -21.912  76.547  1.00187.40           C
ANISOU 3528  CA  PRO A 476    23240  31749  16216  -1629   3716     86       C
ATOM   3529  C   PRO A 476     -23.873 -22.074  75.457  1.00184.66           C
ANISOU 3529  C   PRO A 476    22945  30926  16291  -1629   3577    -86       C
ATOM   3530  O   PRO A 476     -23.868 -23.096  74.776  1.00184.47           O
ANISOU 3530  O   PRO A 476    22709  30739  16641  -1830   3501    -64       O
ATOM   3531  CB  PRO A 476     -24.469 -22.669  77.798  1.00189.19           C
ANISOU 3531  CB  PRO A 476    23528  31871  16487  -1903   3597    405       C
ATOM   3532  CG  PRO A 476     -25.717 -23.206  78.385  1.00192.13           C
ANISOU 3532  CG  PRO A 476    23655  32680  16664  -2039   3722    606       C
ATOM   3533  CD  PRO A 476     -26.610 -23.527  77.226  1.00191.91           C
ANISOU 3533  CD  PRO A 476    23335  32808  16774  -2039   3822    455       C
ATOM   3534  N   TRP A 477     -23.021 -21.065  75.297  1.00180.90           N
ANISOU 3534  N   TRP A 477    22742  30243  15748  -1395   3539   -251       N
ATOM   3535  CA  TRP A 477     -21.895 -21.101  74.365  1.00178.27           C
ANISOU 3535  CA  TRP A 477    22495  29453  15787  -1373   3400   -399       C
ATOM   3536  C   TRP A 477     -20.726 -20.513  75.149  1.00177.56           C
ANISOU 3536  C   TRP A 477    22738  29096  15631  -1325   3278   -352       C
ATOM   3537  O   TRP A 477     -20.805 -19.372  75.611  1.00177.56           O
ANISOU 3537  O   TRP A 477    22937  29251  15275  -1078   3355   -425       O
ATOM   3538  CB  TRP A 477     -22.201 -20.325  73.080  1.00176.35           C
ANISOU 3538  CB  TRP A 477    22208  29267  15528  -1075   3516   -708       C
ATOM   3539  CG  TRP A 477     -22.736 -21.206  71.966  1.00176.04           C
ANISOU 3539  CG  TRP A 477    21854  29233  15801  -1164   3531   -782       C
ATOM   3540  CD1 TRP A 477     -23.451 -22.357  72.109  1.00177.91           C
ANISOU 3540  CD1 TRP A 477    21819  29607  16172  -1427   3524   -616       C
ATOM   3541  CD2 TRP A 477     -22.599 -20.995  70.550  1.00173.79           C
ANISOU 3541  CD2 TRP A 477    21491  28807  15735   -974   3548  -1039       C
ATOM   3542  NE1 TRP A 477     -23.760 -22.877  70.879  1.00176.96           N
ANISOU 3542  NE1 TRP A 477    21459  29432  16345  -1411   3524   -761       N
ATOM   3543  CE2 TRP A 477     -23.249 -22.064  69.905  1.00174.41           C
ANISOU 3543  CE2 TRP A 477    21247  28943  16076  -1126   3542  -1023       C
ATOM   3544  CE3 TRP A 477     -21.991 -20.010  69.769  1.00171.39           C
```

FIG. 13 Continued

```
ANISOU 3544  CE3 TRP A 477     21354  28334  15434    -684   3567  -1276        C
ATOM   3545  CZ2 TRP A 477     -23.310 -22.176  68.519  1.00172.65              C
ANISOU 3545  CZ2 TRP A 477     20867  28619  16113    -978   3550  -1243        C
ATOM   3546  CZ3 TRP A 477     -22.052 -20.125  68.393  1.00169.67              C
ANISOU 3546  CZ3 TRP A 477     20978  28021  15469    -545   3587  -1485        C
ATOM   3547  CH2 TRP A 477     -22.707 -21.201  67.783  1.00170.28              C
ANISOU 3547  CH2 TRP A 477     20735  28163  15800    -682   3577  -1471        C
ATOM   3548  N   GLU A 478     -19.655 -21.298  75.300  1.00185.95              N
ANISOU 3548  N   GLU A 478     23862  29760  17032   -1555   3081   -235        N
ATOM   3549  CA  GLU A 478     -18.579 -20.976  76.253  1.00185.75              C
ANISOU 3549  CA  GLU A 478     24132  29487  16958   -1570   2953   -142        C
ATOM   3550  C   GLU A 478     -17.287 -20.290  75.796  1.00183.24              C
ANISOU 3550  C   GLU A 478     24056  28774  16793   -1426   2835   -303        C
ATOM   3551  O   GLU A 478     -16.528 -19.832  76.651  1.00183.23              O
ANISOU 3551  O   GLU A 478     24309  28623  16688   -1390   2754   -248        O
ATOM   3552  CB  GLU A 478     -18.210 -22.223  77.080  1.00187.18              C
ANISOU 3552  CB  GLU A 478     24276  29515  17329   -1921   2812    125        C
ATOM   3553  CG  GLU A 478     -19.391 -23.140  77.443  1.00189.73              C
ANISOU 3553  CG  GLU A 478     24324  30170  17594   -2128   2899    317        C
ATOM   3554  CD  GLU A 478     -20.015 -22.843  78.797  1.00192.16              C
ANISOU 3554  CD  GLU A 478     24693  30819  17500    2103   2998    502        C
ATOM   3555  OE1 GLU A 478     -19.755 -23.615  79.747  1.00193.66              O
ANISOU 3555  OE1 GLU A 478     24906  30936  17739   -2334   2912    741        O
ATOM   3556  OE2 GLU A 478     -20.768 -21.850  78.911  1.00192.59              O
ANISOU 3556  OE2 GLU A 478     24774  31221  17182   -1842   3157    408        O
ATOM   3557  N   PHE A 479     -17.027 -20.217  74.492  1.00173.95              N
ANISOU 3557  N   PHE A 479     22801  27430  15861   -1335   2824   -495        N
ATOM   3558  CA  PHE A 479     -15.780 -19.605  74.004  1.00171.61              C
ANISOU 3558  CA  PHE A 479     22716  26758  15731   -1207   2712   -634        C
ATOM   3559  C   PHE A 479     -14.591 -20.265  74.705  1.00171.53              C
ANISOU 3559  C   PHE A 479     22854  26385  15936   -1443   2499   -475        C
ATOM   3560  O   PHE A 479     -14.532 -20.302  75.935  1.00173.05              O
ANISOU 3560  O   PHE A 479     23173  26630  15947   -1526   2474   -314        O
ATOM   3561  CB  PHE A 479     -15.774 -18.079  74.248  1.00171.16              C
ANISOU 3561  CB  PHE A 479     22895  26809  15330    -884   2808   -773        C
ATOM   3562  CG  PHE A 479     -14.644 -17.317  73.539  1.00168.74              C
ANISOU 3562  CG  PHE A 479     22773  26154  15188    -715   2726   -944        C
ATOM   3563  CD1 PHE A 479     -14.772 -16.918  72.212  1.00167.04              C
ANISOU 3563  CD1 PHE A 479     22462  25923  15082    -526   2802  -1154        C
ATOM   3564  CD2 PHE A 479     -13.485 -16.955  74.218  1.00168.26              C
ANISOU 3564  CD2 PHE A 479     22979  25795  15159    -728   2580   -896        C
ATOM   3565  CE1 PHE A 479     -13.758 -16.210  71.575  1.00164.97              C
ANISOU 3565  CE1 PHE A 479     22360  25356  14966    -370   2735  -1292        C
ATOM   3566  CE2 PHE A 479     -12.472 -16.242  73.579  1.00166.20              C
ANISOU 3566  CE2 PHE A 479     22876  25225  15048    -579   2508  -1041        C
ATOM   3567  CZ  PHE A 479     -12.610 -15.873  72.261  1.00164.60              C
ANISOU 3567  CZ  PHE A 479     22569  25014  14956    -405   2587  -1230        C
ATOM   3568  N   VAL A 480     -13.647 -20.799  73.936  1.00168.09              N
ANISOU 3568  N   VAL A 480     22401  25590  15876   -1538   2342   -521        N
ATOM   3569  CA  VAL A 480     -12.499 -21.452  74.555  1.00167.91              C
ANISOU 3569  CA  VAL A 480     22523  25223  16053   -1759   2134   -388        C
ATOM   3570  C   VAL A 480     -11.189 -20.666  74.438  1.00165.99              C
ANISOU 3570  C   VAL A 480     22542  24639  15888   -1625   2025   -498        C
ATOM   3571  O   VAL A 480     -10.524 -20.400  75.442  1.00166.39              O
ANISOU 3571  O   VAL A 480     22822  24557  15841   -1652   1949   -422        O
ATOM   3572  CB  VAL A 480     -12.353 -22.933  74.105  1.00167.90              C
ANISOU 3572  CB  VAL A 480     22318  25067  16411   -2049   1988   -291        C
ATOM   3573  CG1 VAL A 480     -13.181 -23.208  72.870  1.00167.44              C
ANISOU 3573  CG1 VAL A 480     21974  25165  16480   -1984   2071   -405        C
ATOM   3574  CG2 VAL A 480     -10.897 -23.284  73.864  1.00166.14              C
ANISOU 3574  CG2 VAL A 480     22235  24401  16489   -2144   1761   -307        C
ATOM   3575  N   GLY A 481     -10.826 -20.274  73.226  1.00163.89              N
ANISOU 3575  N   GLY A 481     22239  24236  15797   -1468   2021   -676        N
ATOM   3576  CA  GLY A 481      -9.581 -19.560  73.039  1.00162.12              C
ANISOU 3576  CA  GLY A 481     22241  23687  15671   -1351   1917   -772        C
ATOM   3577  C   GLY A 481      -9.343 -19.144  71.607  1.00160.05              C
ANISOU 3577  C   GLY A 481     21896  23324  15591   -1161   1939   -960        C
ATOM   3578  O   GLY A 481     -10.225 -19.252  70.761  1.00159.94              O
ANISOU 3578  O   GLY A 481     21664  23519  15588   -1072   2058  -1044        O
```

FIG. 13 Continued

```
ATOM   3579  N   LEU A 482      -8.136 -18.678  71.325  1.00174.07           N
ANISOU 3579  N   LEU A 482    23842  24780  17518  -1092   1823  -1027       N
ATOM   3580  CA  LEU A 482      -7.835 -18.196  69.989  1.00172.11           C
ANISOU 3580  CA  LEU A 482    23530  24431  17435   -888   1847  -1197       C
ATOM   3581  C   LEU A 482      -6.457 -18.609  69.487  1.00170.41           C
ANISOU 3581  C   LEU A 482    23363  23826  17558   -974   1637  -1195       C
ATOM   3582  O   LEU A 482      -5.492 -18.678  70.250  1.00170.41           O
ANISOU 3582  O   LEU A 482    23559  23590  17600  -1101   1492  -1115       O
ATOM   3583  CB  LEU A 482      -7.991 -16.678  69.925  1.00171.77           C
ANISOU 3583  CB  LEU A 482    23646  24479  17138   -585   1994  -1336       C
ATOM   3584  CG  LEU A 482      -7.225 -15.833  70.948  1.00172.06           C
ANISOU 3584  CG  LEU A 482    23991  24361  17022   -548   1930  -1303       C
ATOM   3585  CD1 LEU A 482      -6.742 -14.549  70.288  1.00170.64           C
ANISOU 3585  CD1 LEU A 482    23946  24065  16823   -272   1975  -1463       C
ATOM   3586  CD2 LEU A 482      -8.058 -15.530  72.204  1.00174.15           C
ANISOU 3586  CD2 LEU A 482    24345  24906  16917   -544   2022  -1222       C
ATOM   3587  N   LEU A 483      -6.389 -18.870  68.184  1.00153.79           N
ANISOU 3587  N   LEU A 483    21076  21670  15688   -885   1623  -1291       N
ATOM   3588  CA  LEU A 483      -5.185 -19.353  67.531  1.00152.12           C
ANISOU 3588  CA  LEU A 483    20862  21133  15804   -945   1422  -1294       C
ATOM   3589  C   LEU A 483      -4.404 -18.295  66.786  1.00150.41           C
ANISOU 3589  C   LEU A 483    20752  20747  15649   -701   1438  -1421       C
ATOM   3590  O   LEU A 483      -4.998 -17.403  66.176  1.00150.06           O
ANISOU 3590  O   LEU A 483    20670  20864  15482   -444   1619  -1550       O
ATOM   3591  CB  LEU A 483      -5.562 -20.423  66.516  1.00151.60           C
ANISOU 3591  CB  LEU A 483    20505  21112  15984   -992   1364  -1307       C
ATOM   3592  CG  LEU A 483      -6.281 -21.630  67.081  1.00153.23           C
ANISOU 3592  CG  LEU A 483    20569  21456  16196  -1255   1317  -1172       C
ATOM   3593  CD1 LEU A 483      -6.008 -22.793  66.182  1.00152.33           C
ANISOU 3593  CD1 LEU A 483    20247  21218  16413  -1349   1135  -1162       C
ATOM   3594  CD2 LEU A 483      -5.767 -21.915  68.467  1.00154.39           C
ANISOU 3594  CD2 LEU A 483    20924  21488  16250  -1497   1212  -1018       C
ATOM   3595  N   PRO A 484      -3.060 -18.397  66.846  1.00148.89           N
ANISOU 3595  N   PRO A 484    20696  20230  15644   -785   1247  -1384       N
ATOM   3596  CA  PRO A 484      -2.084 -17.625  66.074  1.00147.17           C
ANISOU 3596  CA  PRO A 484    20559  19796  15564   -603   1210  -1474       C
ATOM   3597  C   PRO A 484      -1.762 -18.409  64.804  1.00145.70           C
ANISOU 3597  C   PRO A 484    20149  19526  15684   -578   1102  -1504       C
ATOM   3598  O   PRO A 484      -0.971 -19.338  64.860  1.00145.26           O
ANISOU 3598  O   PRO A 484    20083  19278  15831   -769    886  -1424       O
ATOM   3599  CB  PRO A 484      -0.851 -17.601  66.992  1.00147.17           C
ANISOU 3599  CB  PRO A 484    20806  19507  15604   -766   1033  -1390       C
ATOM   3600  CG  PRO A 484      -1.301 -18.168  68.315  1.00148.97           C
ANISOU 3600  CG  PRO A 484    21107  19830  15665   -990   1014  -1271       C
ATOM   3601  CD  PRO A 484      -2.405 -19.102  67.955  1.00149.64           C
ANISOU 3601  CD  PRO A 484    20933  20159  15767  -1064   1072  -1244       C
ATOM   3602  N   LEU A 485      -2.381 -18.060  63.682  1.00144.92           N
ANISOU 3602  N   LEU A 485    19875  19578  15612   -332   1243  -1623       N
ATOM   3603  CA  LEU A 485      -2.168 -18.796  62.443  1.00143.57           C
ANISOU 3603  CA  LEU A 485    19473  19353  15724   -267   1142  -1659       C
ATOM   3604  C   LEU A 485      -1.115 -18.102  61.603  1.00141.84           C
ANISOU 3604  C   LEU A 485    19309  18928  15658    -71   1099  -1720       C
ATOM   3605  O   LEU A 485      -1.095 -16.875  61.541  1.00141.66           O
ANISOU 3605  O   LEU A 485    19412  18915  15497    124   1250  -1795       O
ATOM   3606  CB  LEU A 485      -3.470 -18.914  61.656  1.00143.75           C
ANISOU 3606  CB  LEU A 485    19248  19663  15708    -97   1314  -1759       C
ATOM   3607  CG  LEU A 485      -4.701 -19.549  62.311  1.00145.53           C
ANISOU 3607  CG  LEU A 485    19370  20144  15782   -254   1392  -1710       C
ATOM   3608  CD1 LEU A 485      -5.938 -19.164  61.531  1.00145.59           C
ANISOU 3608  CD1 LEU A 485    19192  20439  15686     -5   1620  -1853       C
ATOM   3609  CD2 LEU A 485      -4.595 -21.064  62.414  1.00145.90           C
ANISOU 3609  CD2 LEU A 485    19273  20124  16039   -522   1175  -1593       C
ATOM   3610  N   PHE A 486      -0.234 -18.876  60.964  1.00145.30           N
ANISOU 3610  N   PHE A 486    19653  19182  16372   -120    887  -1684       N
ATOM   3611  CA  PHE A 486       0.827 -18.266  60.171  1.00143.72           C
ANISOU 3611  CA  PHE A 486    19494  18789  16325     58    835  -1722       C
ATOM   3612  C   PHE A 486       0.847 -18.483  58.659  1.00142.23           C
ANISOU 3612  C   PHE A 486    19059  18631  16351    305    822  -1798       C
ATOM   3613  O   PHE A 486       0.713 -19.605  58.184  1.00141.93           O
```

FIG. 13 Continued

```
ANISOU 3613  O   PHE A 486     18824  18621  16481    249    680  -1777          O
ATOM   3614  CB  PHE A 486        2.204 -18.548  60.729  1.00143.35           C
ANISOU 3614  CB  PHE A 486     19619  18455  16392   -145    602  -1622          C
ATOM   3615  CG  PHE A 486        3.192 -17.575  60.242  1.00142.22           C
ANISOU 3615  CG  PHE A 486     19581  18135  16322     27    604  -1653          C
ATOM   3616  CD1 PHE A 486        2.795 -16.257  60.056  1.00142.32           C
ANISOU 3616  CD1 PHE A 486     19665  18227  16183    260    832  -1739          C
ATOM   3617  CD2 PHE A 486        4.484 -17.946  59.919  1.00141.09           C
ANISOU 3617  CD2 PHE A 486     19456  17759  16393    -30    383  -1600          C
ATOM   3618  CE1 PHE A 486        3.666 -15.313  59.578  1.00141.40           C
ANISOU 3618  CE1 PHE A 486     19639  17949  16139    423    844  -1761          C
ATOM   3619  CE2 PHE A 486        5.379 -17.003  59.441  1.00140.16           C
ANISOU 3619  CE2 PHE A 486     19421  17487  16346    133    397  -1619          C
ATOM   3620  CZ  PHE A 486        4.963 -15.680  59.269  1.00140.35           C
ANISOU 3620  CZ  PHE A 486     19515  17581  16231    357    630  -1695          C
ATOM   3621  N   ASP A 487        1.085 -17.380  57.933  1.00147.29           N
ANISOU 3621  N   ASP A 487     19727  19250  16988    585    957  -1881          N
ATOM   3622  CA  ASP A 487        1.113 -17.308  56.456  1.00145.84           C
ANISOU 3622  CA  ASP A 487     19329  19103  16981    890    989  -1966          C
ATOM   3623  C   ASP A 487        2.348 -16.530  55.961  1.00144.65           C
ANISOU 3623  C   ASP A 487     19276  18738  16946   1027    943  -1950          C
ATOM   3624  O   ASP A 487        2.339 -15.291  55.934  1.00144.68           O
ANISOU 3624  O   ASP A 487     19409  18739  16825   1191   1121  -2005          O
ATOM   3625  CB  ASP A 487       -0.149 -16.598  55.952  1.00146.08           C
ANISOU 3625  CB  ASP A 487     19267  19390  16848   1157   1276  -2109          C
ATOM   3626  CG  ASP A 487       -0.472 -16.931  54.519  1.00144.88           C
ANISOU 3626  CG  ASP A 487     18836  19335  16876   1442   1301  -2204          C
ATOM   3627  OD1 ASP A 487        0.371 -17.564  53.860  1.00143.77           O
ANISOU 3627  OD1 ASP A 487     18584  19056  16984   1465   1098  -2153          O
ATOM   3628  OD2 ASP A 487       -1.573 -16.568  54.054  1.00145.04           O
ANISOU 3628  OD2 ASP A 487     18747  19578  16782   1656   1518  -2334          O
ATOM   3629  N   PRO A 488        3.397 -17.268  55.537  1.00134.18           N
ANISOU 3629  N   PRO A 488     17882  17243  15858    968    697  -1874          N
ATOM   3630  CA  PRO A 488        4.738 -16.822  55.116  1.00133.09           C
ANISOU 3630  CA  PRO A 488     17814  16886  15867   1040    587  -1824          C
ATOM   3631  C   PRO A 488        4.763 -16.106  53.765  1.00131.91           C
ANISOU 3631  C   PRO A 488     17522  16787  15813   1420    720  -1900          C
ATOM   3632  O   PRO A 488        3.772 -16.161  53.042  1.00131.74           O
ANISOU 3632  O   PRO A 488     17316  16966  15774   1636    864  -2000          O
ATOM   3633  CB  PRO A 488        5.513 -18.138  54.985  1.00132.45           C
ANISOU 3633  CB  PRO A 488     17638  16695  15992    872    276  -1737          C
ATOM   3634  CG  PRO A 488        4.594 -19.231  55.489  1.00133.38           C
ANISOU 3634  CG  PRO A 488     17669  16947  16061    678    222  -1732          C
ATOM   3635  CD  PRO A 488        3.221 -18.715  55.329  1.00134.05           C
ANISOU 3635  CD  PRO A 488     17675  17270  15989    843    498  -1837          C
ATOM   3636  N   PRO A 489        5.883  15.451  53.410  1.00135.19           N
ANISOU 3636  N   PRO A 489     20048  21437   9882  -1390  -1807  -1133          N
ATOM   3637  CA  PRO A 489        5.884 -14.807  52.091  1.00132.31           C
ANISOU 3637  CA  PRO A 489     19592  20820   9858  -1528  -1783  -1308          C
ATOM   3638  C   PRO A 489        6.276 -15.832  51.030  1.00129.49           C
ANISOU 3638  C   PRO A 489     19064  20249   9887  -1837  -1942  -1185          C
ATOM   3639  O   PRO A 489        7.272 -16.501  51.282  1.00129.34           O
ANISOU 3639  O   PRO A 489     19094  20147   9902  -1919  -2174  -1254          O
ATOM   3640  CB  PRO A 489        7.020 -13.781  52.205  1.00132.12           C
ANISOU 3640  CB  PRO A 489     19772  20622   9806  -1471  -1938  -1802          C
ATOM   3641  CG  PRO A 489        7.767 -14.113  53.465  1.00134.51           C
ANISOU 3641  CG  PRO A 489     20238  21061   9807  -1355  -2106  -1879          C
ATOM   3642  CD  PRO A 489        7.201 -15.369  54.054  1.00135.90           C
ANISOU 3642  CD  PRO A 489     20326  21458   9851  -1353  -2069  -1440          C
ATOM   3643  N   ARG A 490        5.567 -15.988  49.906  1.00150.40           N
ANISOU 3643  N   ARG A 490     21525  22811  12810  -1999  -1837  -1014          N
ATOM   3644  CA  ARG A 490        6.064 -16.927  48.887  1.00147.84           C
ANISOU 3644  CA  ARG A 490     21074  22257  12843  -2296  -2003   -952          C
ATOM   3645  C   ARG A 490        7.390 -16.377  48.336  1.00145.95           C
ANISOU 3645  C   ARG A 490     20931  21734  12790  -2383  -2202  -1383          C
ATOM   3646  O   ARG A 490        7.519 -15.173  48.137  1.00145.67           O
ANISOU 3646  O   ARG A 490     20986  21624  12737  -2297  -2146  -1668          O
ATOM   3647  CB  ARG A 490        5.059 -17.169  47.766  1.00146.30           C
ANISOU 3647  CB  ARG A 490     20670  22027  12891  -2464  -1866   -705          C
```

FIG. 13 Continued

```
ATOM   3648  CG  ARG A 490       5.471 -18.349  46.895  1.00144.30           C
ANISOU 3648  CG  ARG A 490    20302  21573  12953  -2763  -2028   -587       C
ATOM   3649  CD  ARG A 490       4.704 -18.444  45.588  1.00142.45           C
ANISOU 3649  CD  ARG A 490    19887  21247  12991  -2964  -1941   -442       C
ATOM   3650  NE  ARG A 490       3.396 -19.058  45.763  1.00143.90           N
ANISOU 3650  NE  ARG A 490    19909  21660  13108  -2983  -1777    -17       N
ATOM   3651  CZ  ARG A 490       2.298 -18.376  46.059  1.00145.42           C
ANISOU 3651  CZ  ARG A 490    20035  22086  13132  -2810  -1551    115       C
ATOM   3652  NH1 ARG A 490       2.367 -17.058  46.209  1.00145.65           N
ANISOU 3652  NH1 ARG A 490    20173  22125  13041  -2595  -1466   -154       N
ATOM   3653  NH2 ARG A 490       1.136 -19.007  46.203  1.00146.91           N
ANISOU 3653  NH2 ARG A 490    20047  22494  13279  -2851  -1407    513       N
ATOM   3654  N   HIS A 491       8.366 -17.239  48.075  1.00124.42           N
ANISOU 3654  N   HIS A 491    18182  18843  10248  -2553  -2426  -1429       N
ATOM   3655  CA  HIS A 491       9.720 -16.771  47.725  1.00123.15           C
ANISOU 3655  CA  HIS A 491    18102  18452  10238  -2621  -2621  -1839       C
ATOM   3656  C   HIS A 491       9.856 -15.710  46.641  1.00121.13           C
ANISOU 3656  C   HIS A 491    17845  17937  10190  -2709  -2563  -2112       C
ATOM   3657  O   HIS A 491      10.331 -14.598  46.901  1.00121.67           O
ANISOU 3657  O   HIS A 491    18053  18014  10162  -2603  -2571  -2437       O
ATOM   3658  CB  HIS A 491      10.630 -17.939  47.370  1.00122.08           C
ANISOU 3658  CB  HIS A 491    17895  18157  10334  -2808  -2842  -1811       C
ATOM   3659  CG  HIS A 491      10.492 -18.418  45.957  1.00119.46           C
ANISOU 3659  CG  HIS A 491    17415  17610  10363  -3065  -2827  -1734       C
ATOM   3660  ND1 HIS A 491       9.431 -19.187  45.525  1.00119.12           N
ANISOU 3660  ND1 HIS A 491    17244  17619  10396  -3171  -2707  -1364       N
ATOM   3661  CD2 HIS A 491      11.304 -18.259  44.883  1.00117.25           C
ANISOU 3661  CD2 HIS A 491    17099  17068  10382  -3246  -2920  -1982       C
ATOM   3662  CE1 HIS A 491       9.587 -19.472  44.247  1.00116.81           C
ANISOU 3662  CE1 HIS A 491    16856  17103  10423  -3403  -2737  -1398       C
ATOM   3663  NE2 HIS A 491      10.722 -18.931  43.835  1.00115.63           N
ANISOU 3663  NE2 HIS A 491    16762  16762  10409  -3447  -2858  -1766       N
ATOM   3664  N   ASP A 492       9.480 -16.072  45.419  1.00116.71           N
ANISOU 3664  N   ASP A 492    17143  17286   9915  -2916  -2515  -1984       N
ATOM   3665  CA  ASP A 492       9.586 -15.150  44.297  1.00114.80           C
ANISOU 3665  CA  ASP A 492    16901  16839   9878  -3017  -2460  -2207       C
ATOM   3666  C   ASP A 492       8.914 -13.830  44.642  1.00116.01           C
ANISOU 3666  C   ASP A 492    17160  17090   9830   2804   2276   2300       C
ATOM   3667  O   ASP A 492       9.541 -12.778  44.551  1.00115.92           O
ANISOU 3667  O   ASP A 492    17278  16942   9823  -2767  -2298  -2640       O
ATOM   3668  CB  ASP A 492       9.022 -15.747  42.994  1.00112.71           C
ANISOU 3668  CB  ASP A 492    16472  16461   9893  -3248  -2409  -1996       C
ATOM   3669  CG  ASP A 492       7.897 -16.737  43.228  1.00113.56           C
ANISOU 3669  CG  ASP A 492    16448  16764   9936  -3257  -2320  -1559       C
ATOM   3670  OD1 ASP A 492       7.428 -17.334  42.237  1.00112.16           O
ANISOU 3670  OD1 ASP A 492    16137  16508   9973  -3459  -2299  -1376       O
ATOM   3671  OD2 ASP A 492       7.487 -16.932  44.387  1.00115.76           O
ANISOU 3671  OD2 ASP A 492    16761  17276   9949  -3076  -2271  -1399       O
ATOM   3672  N   SER A 493       7.658 -13.912  45.085  1.00117.25           N
ANISOU 3672  N   SER A 493    17261  17483   9807  -2660  -2093  -1997       N
ATOM   3673  CA  SER A 493       6.850 -12.744  45.461  1.00118.79           C
ANISOU 3673  CA  SER A 493    17538  17799   9797  -2421  -1888  -2035       C
ATOM   3674  C   SER A 493       7.640 -11.684  46.236  1.00120.20           C
ANISOU 3674  C   SER A 493    17950  17935   9784  -2248  -1936  -2421       C
ATOM   3675  O   SER A 493       7.260 -10.514  46.286  1.00121.08           O
ANISOU 3675  O   SER A 493    18172  18034   9798  -2085  -1793  -2566       O
ATOM   3676  CB  SER A 493       5.587 -13.165  46.232  1.00120.91           C
ANISOU 3676  CB  SER A 493    17720  18389   9833  -2254  -1709  -1660       C
ATOM   3677  OG  SER A 493       5.823 -13.266  47.624  1.00123.39           O
ANISOU 3677  OG  SER A 493    18163  18894   9827  -2061  -1733  -1683       O
ATOM   3678  N   ALA A 494       8.739 -12.096  46.846  1.00121.27           N
ANISOU 3678  N   ALA A 494    18163  18045   9868  -2282  -2143  -2587       N
ATOM   3679  CA  ALA A 494       9.611 -11.140  47.486  1.00122.57           C
ANISOU 3679  CA  ALA A 494    18538  18149   9884  -2169  -2229  -2979       C
ATOM   3680  C   ALA A 494      10.207 -10.284  46.371  1.00120.62           C
ANISOU 3680  C   ALA A 494    18325  17597   9910  -2326  -2255  -3278       C
ATOM   3681  O   ALA A 494      10.045  -9.059  46.316  1.00121.30           O
ANISOU 3681  O   ALA A 494    18551  17602   9937  -2218  -2144  -3486       O
ATOM   3682  CB  ALA A 494      10.702 -11.876  48.222  1.00123.31           C
```

FIG. 13 Continued

```
ANISOU 3682  CB  ALA A 494    18664 18276  9911 -2208 -2476 -3072        C
ATOM   3683  N   GLU A 495    10.897 -10.973  45.475 1.00 163.78         N
ANISOU 3683  N   GLU A 495    23666 22888 15676  2584  2397  3290        N
ATOM   3684  CA  GLU A 495    11.528 -10.365  44.323 1.00 161.83         C
ANISOU 3684  CA  GLU A 495    23425 22353 15711 -2775 -2428 -3539        C
ATOM   3685  C   GLU A 495    10.479  -9.678  43.466 1.00 161.03         C
ANISOU 3685  C   GLU A 495    23306 22193 15685 -2756 -2212 -3424        C
ATOM   3686  O   GLU A 495    10.583  -8.501  43.164 1.00 161.21         O
ANISOU 3686  O   GLU A 495    23461 22067 15726 -2719 -2140 -3657        O
ATOM   3687  CB  GLU A 495    12.223 -11.457  43.501 1.00 159.69         C
ANISOU 3687  CB  GLU A 495    22992 21951 15734 -3039 -2582 -3485        C
ATOM   3688  CG  GLU A 495    13.244 -12.284  44.282 1.00 160.54         C
ANISOU 3688  CG  GLU A 495    23086 22115 15796 -3052 -2809 -3557        C
ATOM   3689  CD  GLU A 495    14.666 -11.749  44.146 1.00 160.43         C
ANISOU 3689  CD  GLU A 495    23131 21917 15907 -3158 -2978 -3969        C
ATOM   3690  OE1 GLU A 495    15.203 -11.197  45.136 1.00 162.46         O
ANISOU 3690  OE1 GLU A 495    23522 22248 15959 -3027 -3068 -4195        O
ATOM   3691  OE2 GLU A 495    15.245 -11.879  43.043 1.00 158.47         O
ANISOU 3691  OE2 GLU A 495    22794 21457 15959 -3380 -3019 -4070        O
ATOM   3692  N   THR A 496     9.460 -10.434  43.084 1.00 155.28         N
ANISOU 3692  N   THR A 496    22412 21585 15001 -2783 -2114 -3053        N
ATOM   3693  CA  THR A 496     8.409  -9.935  42.206 1.00 154.57         C
ANISOU 3693  CA  THR A 496    22263 21469 14999 -2775 -1929 -2897        C
ATOM   3694  C   THR A 496     8.021  -8.496  42.507 1.00 156.15         C
ANISOU 3694  C   THR A 496    22636 21652 15041 -2546 -1776 -3067        C
ATOM   3695  O   THR A 496     8.079  -7.634  41.624 1.00 155.28         O
ANISOU 3695  O   THR A 496    22588 21332 15079 -2604 -1722 -3212        O
ATOM   3696  CB  THR A 496     7.157 -10.843  42.248 1.00 154.85         C
ANISOU 3696  CB  THR A 496    22108 21741 14988 -2748 -1823 -2453        C
ATOM   3697  OG1 THR A 496     7.202 -11.764  41.151 1.00 152.65         O
ANISOU 3697  OG1 THR A 496    21667 21353 14981 -3024 -1900 -2301        O
ATOM   3698  CG2 THR A 496     5.889 -10.023  42.146 1.00 155.94         C
ANISOU 3698  CG2 THR A 496    22230 21992 15027 -2555 -1596 -2307        C
ATOM   3699  N   ILE A 497     7.632  -8.231  43.748 1.00 118.15         N
ANISOU 3699  N   ILE A 497    17917 17050  9923 -2283 -1700 -3051        N
ATOM   3700  CA  ILE A 497     7.242  -6.877  44.104 1.00 119.99         C
ANISOU 3700  CA  ILE A 497    18335 17263  9992 -2040 -1544 -3221        C
ATOM   3701  C   ILE A 497     8.438  -5.964  43.867 1.00 119.67         C
ANISOU 3701  C   ILE A 497    18493 16932 10046 -2133 -1656 -3656        C
ATOM   3702  O   ILE A 497     8.302  -4.830  43.411 1.00 119.96         O
ANISOU 3702  O   ILE A 497    18660 16791 10128 -2075 -1553 -3816        O
ATOM   3703  CB  ILE A 497     6.742  -6.789  45.550 1.00 122.98         C
ANISOU 3703  CB  ILE A 497    18803 17921 10004 -1743 -1450 -3164        C
ATOM   3704  CG1 ILE A 497     6.689  -5.329  46.003 1.00 125.11         C
ANISOU 3704  CG1 ILE A 497    19325 18109 10101 -1504 -1331 -3452        C
ATOM   3705  CG2 ILE A 497     7.612  -7.634  46.467 1.00 123.55         C
ANISOU 3705  CG2 ILE A 497    18898 18096  9950 -1793 -1647 -3221        C
ATOM   3706  CD1 ILE A 497     5.682  -4.487  45.256 1.00 125.17         C
ANISOU 3706  CD1 ILE A 497    19318 18050 10191 -1385 -1116 -3353        C
ATOM   3707  N   ARG A 498     9.618  -6.490  44.160 1.00 161.54         N
ANISOU 3707  N   ARG A 498    23807 22183 15387 -2285 -1872 -3835        N
ATOM   3708  CA  ARG A 498    10.854  -5.771  43.919 1.00 161.28         C
ANISOU 3708  CA  ARG A 498    23918 21890 15470 -2421 -2002 -4240        C
ATOM   3709  C   ARG A 498    10.891  -5.343  42.447 1.00 159.12         C
ANISOU 3709  C   ARG A 498    23606 21349 15502 -2619 -1949 -4273        C
ATOM   3710  O   ARG A 498    11.005  -4.159  42.139 1.00 159.68         O
ANISOU 3710  O   ARG A 498    23845 21222 15602 -2591 -1875 -4496        O
ATOM   3711  CB  ARG A 498    12.045  -6.678  44.276 1.00 160.84         C
ANISOU 3711  CB  ARG A 498    23795 21851 15466 -2582 -2252 -4349        C
ATOM   3712  CG  ARG A 498    13.420  -6.174  43.860 1.00 160.29         C
ANISOU 3712  CG  ARG A 498    23796 21525 15583 -2786 -2410 -4736        C
ATOM   3713  CD  ARG A 498    14.512  -7.223  44.111 1.00 159.83         C
ANISOU 3713  CD  ARG A 498    23614 21506 15607 -2936 -2654 -4788        C
ATOM   3714  NE  ARG A 498    14.937  -7.284  45.511 1.00 162.33         N
ANISOU 3714  NE  ARG A 498    24030 22005 15642 -2776 -2786 -4906        N
ATOM   3715  CZ  ARG A 498    15.726  -6.384  46.099 1.00 164.19         C
ANISOU 3715  CZ  ARG A 498    24440 22175 15770 -2747 -2880 -5274        C
ATOM   3716  NH1 ARG A 498    16.172  -5.334  45.416 1.00 163.85         N
ANISOU 3716  NH1 ARG A 498    24494 21873 15889 -2872 -2845 -5557        N
```

FIG. 13 Continued

```
ATOM   3717  NH2 ARG A 498      16.064  -6.524  47.375  1.00166.59           N
ANISOU 3717  NH2 ARG A 498    24831  22670  15796  -2602  -3013  -5359       N
ATOM   3718  N   ARG A 499      10.740  -6.317  41.551  1.00133.18           N
ANISOU 3718  N   ARG A 499    20113  18060  12431  -2813  -1981  -4038       N
ATOM   3719  CA  ARG A 499      10.814  -6.110  40.102  1.00131.07           C
ANISOU 3719  CA  ARG A 499    19793  17559  12447  -3029  -1950  -4043       C
ATOM   3720  C   ARG A 499       9.789  -5.121  39.558  1.00131.47           C
ANISOU 3720  C   ARG A 499    19915  17552  12486  -2899  -1746  -3954       C
ATOM   3721  O   ARG A 499      10.122  -4.273  38.730  1.00130.93           O
ANISOU 3721  O   ARG A 499    19951  17232  12564  -2998  -1713  -4131       O
ATOM   3722  CB  ARG A 499      10.657  -7.454  39.394  1.00129.01           C
ANISOU 3722  CB  ARG A 499    19301  17354  12364  -3227  -2013  -3769       C
ATOM   3723  CG  ARG A 499      10.747  -7.395  37.893  1.00126.90           C
ANISOU 3723  CG  ARG A 499    18975  16870  12370  -3463  -1992  -3761       C
ATOM   3724  CD  ARG A 499      10.781  -8.806  37.318  1.00125.15           C
ANISOU 3724  CD  ARG A 499    18550  16692  12311  -3669  -2083  -3543       C
ATOM   3725  NE  ARG A 499      11.878  -9.598  37.878  1.00125.12           N
ANISOU 3725  NE  ARG A 499    18512  16695  12334  -3750  -2265  -3677       N
ATOM   3726  CZ  ARG A 499      12.366 -10.713  37.333  1.00123.69           C
ANISOU 3726  CZ  ARG A 499    18196  16463  12338  -3955  -2377  -3611       C
ATOM   3727  NH1 ARG A 499      11.860 -11.190  36.194  1.00122.11           N
ANISOU 3727  NH1 ARG A 499    17892  16200  12306  -4121  -2328  -3423       N
ATOM   3728  NH2 ARG A 499      13.370 -11.348  37.930  1.00124.04           N
ANISOU 3728  NH2 ARG A 499    18214  16518  12396  -3987  -2543  -3740       N
ATOM   3729  N   ALA A 500       8.546  -5.243  40.018  1.00131.62           N
ANISOU 3729  N   ALA A 500    19870  17806  12334  -2674  -1607  -3670       N
ATOM   3730  CA  ALA A 500       7.468  -4.359  39.589  1.00132.37           C
ANISOU 3730  CA  ALA A 500    20005  17887  12404  -2505  -1410  -3550       C
ATOM   3731  C   ALA A 500       7.874  -2.897  39.662  1.00133.73           C
ANISOU 3731  C   ALA A 500    20447  17825  12538  -2400  -1351  -3882       C
ATOM   3732  O   ALA A 500       7.637  -2.135  38.732  1.00133.33           O
ANISOU 3732  O   ALA A 500    20459  17580  12619  -2427  -1267  -3899       O
ATOM   3733  CB  ALA A 500       6.238  -4.589  40.436  1.00134.20           C
ANISOU 3733  CB  ALA A 500    20151  18436  12404  -2228  -1268  -3265       C
ATOM   3734  N   LEU A 501       8.482  -2.513  40.779  1.00129.31           N
ANISOU 3734  N   LEU A 501    20059  17283  11791  -2282  -1400  -4141       N
ATOM   3735  CA  LEU A 501       8.926  -1.137  40.986  1.00131.00           C
ANISOU 3735  CA  LEU A 501    20554  17268  11951  -2189  -1356  -4486       C
ATOM   3736  C   LEU A 501      10.054  -0.732  40.044  1.00129.55           C
ANISOU 3736  C   LEU A 501    20446  16752  12023   2486   1462   4752       C
ATOM   3737  O   LEU A 501      10.217   0.444  39.745  1.00130.52           O
ANISOU 3737  O   LEU A 501    20779  16627  12184  -2461  -1391  -4962       O
ATOM   3738  CB  LEU A 501       9.342  -0.891  42.442  1.00133.49           C
ANISOU 3738  CB  LEU A 501    21036  17695  11987  -2013  -1406  -4713       C
ATOM   3739  CG  LEU A 501       8.248  -0.411  43.408  1.00136.24           C
ANISOU 3739  CG  LEU A 501    21482  18249  12036  -1632  -1216  -4610       C
ATOM   3740  CD1 LEU A 501       7.117  -1.445  43.520  1.00135.81           C
ANISOU 3740  CD1 LEU A 501    21165  18523  11914  -1530  -1126  -4168       C
ATOM   3741  CD2 LEU A 501       8.812  -0.035  44.796  1.00138.93           C
ANISOU 3741  CD2 LEU A 501    22039  18658  12090  -1482  -1279  -4900       C
ATOM   3742  N   ASN A 502      10.856  -1.685  39.594  1.00145.88           N
ANISOU 3742  N   ASN A 502    22353  18807  14268  -2765  -1626  -4752       N
ATOM   3743  CA  ASN A 502      11.862  -1.338  38.600  1.00144.55           C
ANISOU 3743  CA  ASN A 502    22227  18340  14353  -3053  -1698  -4976       C
ATOM   3744  C   ASN A 502      11.206  -1.293  37.220  1.00142.85           C
ANISOU 3744  C   ASN A 502    21934  18016  14328  -3152  -1589  -4753       C
ATOM   3745  O   ASN A 502      11.836  -0.945  36.224  1.00141.78           O
ANISOU 3745  O   ASN A 502    21840  17632  14399  -3380  -1606  -4885       O
ATOM   3746  CB  ASN A 502      13.080  -2.274  38.645  1.00143.31           C
ANISOU 3746  CB  ASN A 502    21940  18194  14319  -3301  -1909  -5104       C
ATOM   3747  CG  ASN A 502      14.308  -1.615  39.292  1.00144.89           C
ANISOU 3747  CG  ASN A 502    22302  18263  14486  -3362  -2032  -5519       C
ATOM   3748  OD1 ASN A 502      14.189  -0.612  40.003  1.00147.16           O
ANISOU 3748  OD1 ASN A 502    22809  18507  14598  -3184  -1974  -5699       O
ATOM   3749  ND2 ASN A 502      15.491  -2.178  39.038  1.00143.87           N
ANISOU 3749  ND2 ASN A 502    22062  18073  14530  -3613  -2202  -5675       N
ATOM   3750  N   LEU A 503       9.925  -1.652  37.184  1.00111.44           N
ANISOU 3750  N   LEU A 503    17835  14240  10267  -2980  -1478  -4407       N
ATOM   3751  CA  LEU A 503       9.129  -1.593  35.959  1.00110.25           C
```

FIG. 13 Continued

```
ANISOU 3751  CA  LEU A 503    17603  14030  10258  -3035  -1379  -4164       C
ATOM   3752  C   LEU A 503     8.068  -0.477  35.985  1.00112.13            C
ANISOU 3752  C   LEU A 503    17973  14246  10385   2748   1190   4081       C
ATOM   3753  O   LEU A 503     7.089  -0.509  35.225  1.00111.71            O
ANISOU 3753  O   LEU A 503    17815  14244  10386  -2703  -1100  -3802       O
ATOM   3754  CB  LEU A 503     8.511  -2.954  35.652  1.00108.67            C
ANISOU 3754  CB  LEU A 503    17124  14063  10104  -3118  -1419  -3816       C
ATOM   3755  CG  LEU A 503     9.576  -3.853  35.027  1.00106.51            C
ANISOU 3755  CG  LEU A 503    16748  13690  10033  -3453  -1581  -3906       C
ATOM   3756  CD1 LEU A 503     8.968  -4.985  34.206  1.00104.77            C
ANISOU 3756  CD1 LEU A 503    16296  13584   9927  -3602  -1603  -3582       C
ATOM   3757  CD2 LEU A 503    10.485  -2.992  34.163  1.00106.02            C
ANISOU 3757  CD2 LEU A 503    16842  13301  10139  -3641  -1587  -4185       C
ATOM   3758  N   GLY A 504     8.288   0.505  36.866  1.00129.59            N
ANISOU 3758  N   GLY A 504    20418  16378  12442  -2551  -1139  -4330       N
ATOM   3759  CA  GLY A 504     7.415   1.659  37.018  1.00131.82            C
ANISOU 3759  CA  GLY A 504    20871  16604  12611  -2249   -956  -4309       C
ATOM   3760  C   GLY A 504     6.081   1.378  37.689  1.00133.19            C
ANISOU 3760  C   GLY A 504    20914  17103  12590  -1931   -826  -4009       C
ATOM   3761  O   GLY A 504     5.426   2.288  38.190  1.00135.63            O
ANISOU 3761  O   GLY A 504    21371  17412  12750  -1620   -672  -4032       O
ATOM   3762  N   VAL A 505     5.680   0.112  37.698  1.00132.60            N
ANISOU 3762  N   VAL A 505    20560  17301  12521  -2009   -880  -3727       N
ATOM   3763  CA  VAL A 505     4.402  -0.301  38.270  1.00133.85            C
ANISOU 3763  CA  VAL A 505    20546  17796  12516  -1752   -757  -3404       C
ATOM   3764  C   VAL A 505     4.461  -0.597  39.787  1.00135.65            C
ANISOU 3764  C   VAL A 505    20809  18256  12475  -1564   -752  -3469       C
ATOM   3765  O   VAL A 505     5.174  -1.513  40.231  1.00134.67            O
ANISOU 3765  O   VAL A 505    20616  18218  12334  -1731   -903  -3514       O
ATOM   3766  CB  VAL A 505     3.838  -1.514  37.492  1.00131.80            C
ANISOU 3766  CB  VAL A 505    19969  17714  12395  -1942   -809  -3042       C
ATOM   3767  CG1 VAL A 505     4.790  -2.700  37.592  1.00129.84            C
ANISOU 3767  CG1 VAL A 505    19621  17492  12219  -2232  -1002  -3094       C
ATOM   3768  CG2 VAL A 505     2.444  -1.875  37.979  1.00133.33            C
ANISOU 3768  CG2 VAL A 505    19962  18255  12444  -1694   -668  -2689       C
ATOM   3769  N   ASN A 506     3.708   0.199  40.563  1.00129.88            N
ANISOU 3769  N   ASN A 506    20195  17622  11531  -1207   -573  -3473       N
ATOM   3770  CA  ASN A 506     3.596   0.067  42.028  1.00132.15            C
ANISOU 3770  CA  ASN A 506    20544  18148  11520   -976   -527  -3523       C
ATOM   3771  C   ASN A 506     2.653  -1.067  42.422  1.00132.26            C
ANISOU 3771  C   ASN A 506    20265  18551  11436   -912   -471  -3128       C
ATOM   3772  O   ASN A 506     1.628  -1.293  41.779  1.00131.94            O
ANISOU 3772  O   ASN A 506    20010  18633  11488   -876   -370  -2808       O
ATOM   3773  CB  ASN A 506     3.042   1.350  42.686  1.00135.45            C
ANISOU 3773  CB  ASN A 506    21198  18532  11735   -594   -326  -3663       C
ATOM   3774  CG  ASN A 506     3.767   2.623  42.264  1.00135.91            C
ANISOU 3774  CG  ASN A 506    21567  18184  11889   -623   -340  -4025       C
ATOM   3775  OD1 ASN A 506     3.724   3.627  42.978  1.00138.67            O
ANISOU 3775  OD1 ASN A 506    22180  18447  12060   -368   -233  -4251       O
ATOM   3776  ND2 ASN A 506     4.410   2.601  41.105  1.00133.44            N
ANISOU 3776  ND2 ASN A 506    21235  17615  11852   -933   -461  -4078       N
ATOM   3777  N   VAL A 507     2.984  -1.790  43.477  1.00126.10            N
ANISOU 3777  N   VAL A 507    19473  17971  10468   -904   -539  -3139       N
ATOM   3778  CA  VAL A 507     2.041  -2.779  43.958  1.00126.74            C
ANISOU 3778  CA  VAL A 507    19303  18421  10431   -822   -458  -2763       C
ATOM   3779  C   VAL A 507     1.517  -2.269  45.295  1.00130.24            C
ANISOU 3779  C   VAL A 507    19879  19079  10527   -451   -281  -2804       C
ATOM   3780  O   VAL A 507     2.243  -1.588  46.026  1.00131.66            O
ANISOU 3780  O   VAL A 507    20339  19143  10544   -351   -316  -3148       O
ATOM   3781  CB  VAL A 507     2.661  -4.182  44.041  1.00124.84            C
ANISOU 3781  CB  VAL A 507    18911  18270  10252  -1107   -657  -2655       C
ATOM   3782  CG1 VAL A 507     1.598  -5.229  44.340  1.00125.43            C
ANISOU 3782  CG1 VAL A 507    18710  18695  10251  -1067   -565  -2223       C
ATOM   3783  CG2 VAL A 507     3.332  -4.509  42.729  1.00121.65            C
ANISOU 3783  CG2 VAL A 507    18435  17606  10180  -1455   -823  -2698       C
ATOM   3784  N   LYS A 508     0.254  -2.565  45.596  1.00132.74            N
ANISOU 3784  N   LYS A 508    19997  19708  10729   -250    -87  -2463       N
ATOM   3785  CA  LYS A 508    -0.372  -2.097  46.832  1.00136.33            C
ANISOU 3785  CA  LYS A 508    20557  20398  10846    124    120  -2471       C
```

FIG. 13 Continued

```
ATOM   3786  C   LYS A 508      -1.086  -3.236  47.541  1.00137.33           C
ANISOU 3786  C   LYS A 508    20444  20925  10811    156    193  -2107       C
ATOM   3787  O   LYS A 508      -1.731  -4.065  46.904  1.00136.04           O
ANISOU 3787  O   LYS A 508    19977  20897  10816      4    199  -1757       O
ATOM   3788  CB  LYS A 508      -1.375  -0.985  46.535  1.00138.29           C
ANISOU 3788  CB  LYS A 508    20826  20625  11092    435    362  -2432       C
ATOM   3789  CG  LYS A 508      -0.766   0.250  45.916  1.00137.92           C
ANISOU 3789  CG  LYS A 508    21052  20172  11178    443    323  -2780       C
ATOM   3790  CD  LYS A 508      -1.831   1.230  45.470  1.00139.72           C
ANISOU 3790  CD  LYS A 508    21267  20374  11447    741    552  -2680       C
ATOM   3791  CE  LYS A 508      -1.197   2.461  44.860  1.00139.54           C
ANISOU 3791  CE  LYS A 508    21544  19919  11556    740    513  -3019       C
ATOM   3792  NZ  LYS A 508      -0.051   2.915  45.693  1.00140.39           N
ANISOU 3792  NZ  LYS A 508    21997  19845  11499    720    411  -3450       N
ATOM   3793  N   MET A 509      -0.976  -3.274  48.861  1.00142.72           N
ANISOU 3793  N   MET A 509    21270  21798  11160    345    249  -2189       N
ATOM   3794  CA  MET A 509      -1.585  -4.345  49.629  1.00143.99           C
ANISOU 3794  CA  MET A 509    21235  22335  11139    373    325  -1851       C
ATOM   3795  C   MET A 509      -3.085  -4.158  49.743  1.00146.40           C
ANISOU 3795  C   MET A 509    21332  22932  11360    644    629  -1534       C
ATOM   3796  O   MET A 509      -3.575  -3.039  49.789  1.00148.34           O
ANISOU 3796  O   MET A 509    21687  23139  11537    939    815  -1656       O
ATOM   3797  CB  MET A 509      -0.957  -4.411  51.017  1.00146.14           C
ANISOU 3797  CB  MET A 509    21749  22722  11056    494    284  -2045       C
ATOM   3798  CG  MET A 509      -1.067  -5.759  51.689  1.00146.51           C
ANISOU 3798  CG  MET A 509    21638  23061  10967    387    241  -1743       C
ATOM   3799  SD  MET A 509       0.113  -5.915  53.037  1.00148.07           S
ANISOU 3799  SD  MET A 509    22148  23287  10824    420     63  -2034       S
ATOM   3800  CE  MET A 509      -0.033  -7.661  53.353  1.00147.54           C
ANISOU 3800  CE  MET A 509    21835  23482  10741    206    -22  -1598       C
ATOM   3801  N   ILE A 510      -3.815  -5.263  49.795  1.00160.16           N
ANISOU 3801  N   ILE A 510    22770  24967  13115    545    683  -1122       N
ATOM   3802  CA  ILE A 510      -5.264  -5.202  49.957  1.00162.72           C
ANISOU 3802  CA  ILE A 510    22847  25618  13360    783    974   -788       C
ATOM   3803  C   ILE A 510      -5.803  -6.426  50.690  1.00164.06           C
ANISOU 3803  C   ILE A 510    22801  26160  13375    721   1045   -416       C
ATOM   3804  O   ILE A 510      -6.043  -7.481  50.096  1.00162.33           O
ANISOU 3804  O   ILE A 510    22312  26004  13362    429    952   -112       O
ATOM   3805  CB  ILE A 510      -5.988  -5.019  48.613  1.00161.23           C
ANISOU 3805  CB  ILE A 510    22402  25355  13505    702   1002   -599       C
ATOM   3806  CG1 ILE A 510      -6.066  -3.533  48.266  1.00162.12           C
ANISOU 3806  CG1 ILE A 510    22708  25246  13645    973   1105   -871       C
ATOM   3807  CG2 ILE A 510      -7.390  -5.600  48.670  1.00163.15           C
ANISOU 3807  CG2 ILE A 510    22263  25991  13736    776   1213   -136       C
ATOM   3808  CD1 ILE A 510      -7.088  -3.203  47.194  1.00162.03           C
ANISOU 3808  CD1 ILE A 510    22431  25258  13873   1024   1208   -635       C
ATOM   3809  N   THR A 511      -6.000  -6.267  51.994  1.00150.83           N
ANISOU 3809  N   THR A 511    21260  24725  11324    995   1217   -443       N
ATOM   3810  CA  THR A 511      -6.477  -7.365  52.810  1.00152.57           C
ANISOU 3810  CA  THR A 511    21316  25302  11353    956   1304    -98       C
ATOM   3811  C   THR A 511      -7.362  -6.880  53.952  1.00157.11           C
ANISOU 3811  C   THR A 511    21919  26222  11553   1362   1642    -24       C
ATOM   3812  O   THR A 511      -7.100  -5.851  54.589  1.00159.07           O
ANISOU 3812  O   THR A 511    22465  26410  11563   1660   1733   -352       O
ATOM   3813  CB  THR A 511      -5.309  -8.208  53.353  1.00151.34           C
ANISOU 3813  CB  THR A 511    21341  25061  11099    729   1044   -200       C
ATOM   3814  OG1 THR A 511      -5.810  -9.416  53.935  1.00152.68           O
ANISOU 3814  OG1 THR A 511    21319  25543  11149    630   1108    196       O
ATOM   3815  CG2 THR A 511      -4.508  -7.436  54.375  1.00153.12           C
ANISOU 3815  CG2 THR A 511    21962  25221  10997    958   1021   -601       C
ATOM   3816  N   GLY A 512      -8.436  -7.631  54.169  1.00159.23           N
ANISOU 3816  N   GLY A 512    21739  26725  11655   1361   1836    414       N
ATOM   3817  CA  GLY A 512      -9.389  -7.362  55.223  1.00162.72           C
ANISOU 3817  CA  GLY A 512    22267  27678  11882   1717   2184    561       C
ATOM   3818  C   GLY A 512      -8.887  -7.929  56.524  1.00164.61           C
ANISOU 3818  C   GLY A 512    22719  28083  11742   1740   2173    546       C
ATOM   3819  O   GLY A 512      -9.507  -8.812  57.103  1.00166.60           O
ANISOU 3819  O   GLY A 512    22783  28668  11849   1701   2312    912       O
ATOM   3820  N   ASP A 513      -7.737  -7.428  56.958  1.00163.22           N
```

FIG. 13 Continued

```
ANISOU 3820  N   ASP A 513    22937  27668  11409   1787   1992    125       N
ATOM   3821  CA  ASP A 513     -7.095  -7.835  58.201  1.00 165.05           C
ANISOU 3821  CA  ASP A 513    23430  28022  11259   1825   1934     42       C
ATOM   3822  C   ASP A 513     -6.549  -6.561  58.843  1.00 166.88           C
ANISOU 3822  C   ASP A 513    24068  28122  11217   2138   1965   -442       C
ATOM   3823  O   ASP A 513     -5.807  -5.815  58.212  1.00 164.66           O
ANISOU 3823  O   ASP A 513    23960  27477  11125   2090   1783   -800       O
ATOM   3824  CB  ASP A 513     -5.933  -8.797  57.913  1.00 161.70           C
ANISOU 3824  CB  ASP A 513    23064  27375  10998   1434   1550     13       C
ATOM   3825  CG  ASP A 513     -6.228 -10.240  58.300  1.00 162.27           C
ANISOU 3825  CG  ASP A 513    22938  27700  11016   1227   1545    455       C
ATOM   3826  OD1 ASP A 513     -5.263 -11.006  58.483  1.00 160.81           O
ANISOU 3826  OD1 ASP A 513    22875  27395  10830   1002   1270    419       O
ATOM   3827  OD2 ASP A 513     -7.405 -10.617  58.421  1.00 164.32           O
ANISOU 3827  OD2 ASP A 513    22920  28273  11242   1284   1812    841       O
ATOM   3828  N   GLN A 514     -6.927  -6.307  60.088  1.00 172.59           N
ANISOU 3828  N   GLN A 514    24948  29137  11493   2450   2202   -454       N
ATOM   3829  CA  GLN A 514     -6.472  -5.130  60.823  1.00 174.98           C
ANISOU 3829  CA  GLN A 514    25658  29343  11484   2761   2251   -913       C
ATOM   3830  C   GLN A 514     -5.114  -4.591  60.334  1.00 172.00           C
ANISOU 3830  C   GLN A 514    25563  28511  11278   2592   1896  -1375       C
ATOM   3831  O   GLN A 514     -4.166  -5.346  60.165  1.00 169.39           O
ANISOU 3831  O   GLN A 514    25255  28044  11061   2276   1578  -1395       O
ATOM   3832  CB  GLN A 514     -6.381  -5.509  62.298  1.00 178.71           C
ANISOU 3832  CB  GLN A 514    26333  30128  11439   2912   2337   -883       C
ATOM   3833  CG  GLN A 514     -7.353  -6.632  62.676  1.00 180.41           C
ANISOU 3833  CG  GLN A 514    26227  30762  11559   2868   2548   -336       C
ATOM   3834  CD  GLN A 514     -6.779  -7.601  63.699  1.00 181.69           C
ANISOU 3834  CD  GLN A 514    26538  31103  11393   2754   2415   -225       C
ATOM   3835  OE1 GLN A 514     -6.023  -7.208  64.588  1.00 183.48           O
ANISOU 3835  OE1 GLN A 514    27140  31306  11268   2887   2317   -548       O
ATOM   3836  NE2 GLN A 514     -7.140  -8.876  63.574  1.00 180.96           N
ANISOU 3836  NE2 GLN A 514    26158  31186  11414   2501   2402    237       N
ATOM   3837  N   LEU A 515     -5.020  -3.282  60.123  1.00 172.38           N
ANISOU 3837  N   LEU A 515    25826  28326  11344   2807   1960  -1746       N
ATOM   3838  CA  LEU A 515     -3.786  -2.653  59.635  1.00 169.92           C
ANISOU 3838  CA  LEU A 515    25781  27577  11204   2650   1654  -2193       C
ATOM   3839  C   LEU A 515     -2.512  -3.070  60.360  1.00 169.73           C
ANISOU 3839  C   LEU A 515    26017  27497  10974   2482   1347  -2426       C
ATOM   3840  O   LEU A 515     -1.431  -3.052  59.785  1.00 166.76           O
ANISOU 3840  O   LEU A 515    25727  26803  10833   2217   1032  -2664       O
ATOM   3841  CB  LEU A 515     -3.923  -1.125  59.649  1.00 171.98           C
ANISOU 3841  CB  LEU A 515    26310  27638  11395   2969   1815  -2572       C
ATOM   3842  CG  LEU A 515     -2.841  -0.220  60.261  1.00 173.34           C
ANISOU 3842  CG  LEU A 515    26954  27563  11346   3042   1655  -3120       C
ATOM   3843  CD1 LEU A 515     -1.463  -0.394  59.638  1.00 169.60           C
ANISOU 3843  CD1 LEU A 515    26569  26734  11138   2657   1244  -3367       C
ATOM   3844  CD2 LEU A 515     -3.278   1.242  60.160  1.00 175.65           C
ANISOU 3844  CD2 LEU A 515    27460  27670  11611   3380   1882  -3405       C
ATOM   3845  N   ALA A 516     -2.633  -3.444  61.621  1.00 173.77           N
ANISOU 3845  N   ALA A 516    26651  28330  11045   2639   1437  -2354       N
ATOM   3846  CA  ALA A 516     -1.460  -3.820  62.393  1.00 174.12           C
ANISOU 3846  CA  ALA A 516    26949  28354  10854   2513   1142  -2566       C
ATOM   3847  C   ALA A 516     -0.701  -5.009  61.803  1.00 170.27           C
ANISOU 3847  C   ALA A 516    26269  27763  10664   2101    809  -2386       C
ATOM   3848  O   ALA A 516      0.520  -5.075  61.919  1.00 169.17           O
ANISOU 3848  O   ALA A 516    26311  27436  10528   1930    483  -2664       O
ATOM   3849  CB  ALA A 516     -1.848  -4.096  63.841  1.00 178.63           C
ANISOU 3849  CB  ALA A 516    27665  29327  10879   2762   1321  -2457       C
ATOM   3850  N   ILE A 517     -1.413  -5.939  61.170  1.00 168.06           N
ANISOU 3850  N   ILE A 517    25619  27600  10636   1943    888  -1932       N
ATOM   3851  CA  ILE A 517     -0.772  -7.143  60.631  1.00 164.72           C
ANISOU 3851  CA  ILE A 517    25016  27085  10487   1566    597  -1735       C
ATOM   3852  C   ILE A 517     -0.162  -6.989  59.245  1.00 160.30           C
ANISOU 3852  C   ILE A 517    24351  26130  10426   1287    375  -1886       C
ATOM   3853  O   ILE A 517      0.956  -7.435  58.993  1.00 158.03           O
ANISOU 3853  O   ILE A 517    24112  25642  10290   1034     51  -2026       O
ATOM   3854  CB  ILE A 517     -1.725  -8.358  60.610  1.00 164.89           C
ANISOU 3854  CB  ILE A 517    24703  27397  10548   1474    749   1172       C
```

FIG. 13 Continued

```
ATOM   3855  CG1 ILE A 517      -3.150  -7.916  60.314  1.00166.26           C
ANISOU 3855  CG1 ILE A 517    24658  27748  10764   1677   1128   -944       C
ATOM   3856  CG2 ILE A 517      -1.659  -9.124  61.917  1.00167.99           C
ANISOU 3856  CG2 ILE A 517    25210  28104  10513   1548    758   -997       C
ATOM   3857  CD1 ILE A 517      -3.349  -7.565  58.894  1.00162.91           C
ANISOU 3857  CD1 ILE A 517    24030  27058  10810   1533   1099   -959       C
ATOM   3858  N   GLY A 518      -0.901  -6.378  58.337  1.00159.53           N
ANISOU 3858  N   GLY A 518    24101  25929  10583   1338    553  -1846       N
ATOM   3859  CA  GLY A 518      -0.383  -6.196  57.005  1.00155.58           C
ANISOU 3859  CA  GLY A 518    23512  25066  10535   1083    366  -1975       C
ATOM   3860  C   GLY A 518       0.985  -5.582  57.126  1.00154.93           C
ANISOU 3860  C   GLY A 518    23737  24693  10437   1012     97  -2462       C
ATOM   3861  O   GLY A 518       1.925  -6.015  56.479  1.00151.92           O
ANISOU 3861  O   GLY A 518    23315  24082  10326    714   -184  -2552       O
ATOM   3862  N   LYS A 519       1.099  -4.587  57.995  1.00156.30           N
ANISOU 3862  N   LYS A 519    24218  24888  10281   1288    185  -2780       N
ATOM   3863  CA  LYS A 519       2.359  -3.888  58.187  1.00156.28           C
ANISOU 3863  CA  LYS A 519    24523  24619  10236   1231    -60  -3270       C
ATOM   3864  C   LYS A 519       3.447  -4.785  58.778  1.00155.98           C
ANISOU 3864  C   LYS A 519    24544  24633  10086   1038   -376  -3313       C
ATOM   3865  O   LYS A 519       4.524  -4.306  59.126  1.00156.53           O
ANISOU 3865  O   LYS A 519    24861  24543  10069    995   -599  -3708       O
ATOM   3866  CB  LYS A 519       2.164  -2.626  59.031  1.00160.12           C
ANISOU 3866  CB  LYS A 519    25343  25122  10372   1576    117  -3600       C
ATOM   3867  CG  LYS A 519       3.285  -1.609  58.884  1.00159.89           C
ANISOU 3867  CG  LYS A 519    25613  24733  10405   1505    -90  -4129       C
ATOM   3868  CD  LYS A 519       3.036  -0.390  59.753  1.00164.04           C
ANISOU 3868  CD  LYS A 519    26488  25269  10570   1851     95  -4452       C
ATOM   3869  CE  LYS A 519       4.276   0.490  59.868  1.00164.49           C
ANISOU 3869  CE  LYS A 519    26876  25007  10617   1753   -152  -4993       C
ATOM   3870  NZ  LYS A 519       4.141   1.536  60.934  1.00169.09           N
ANISOU 3870  NZ  LYS A 519    27843  25630  10774   2079     -8  -5327       N
ATOM   3871  N   GLU A 520       3.156  -6.076  58.930  1.00156.18           N
ANISOU 3871  N   GLU A 520    24348  24887  10106    931   -395  -2906       N
ATOM   3872  CA  GLU A 520       4.184  -7.035  59.335  1.00155.60           C
ANISOU 3872  CA  GLU A 520    24295  24835   9989    734   -711  -2900       C
ATOM   3873  C   GLU A 520       4.479  -7.949  58.160  1.00151.47           C
ANISOU 3873  C   GLU A 520    23489  24134   9930    395   -879  -2696       C
ATOM   3874  O   GLU A 520       5.637  -8.145  57.792  1.00145.50           O
ANISOU 3874  O   GLU A 520    23265  23663   9876    173   1179   2905       O
ATOM   3875  CB  GLU A 520       3.789  -7.865  60.546  1.00158.62           C
ANISOU 3875  CB  GLU A 520    24701  25599   9969    871   -639  -2611       C
ATOM   3876  CG  GLU A 520       4.781  -8.986  60.840  1.00157.86           C
ANISOU 3876  CG  GLU A 520    24588  25514   9877    661   -969  -2536       C
ATOM   3877  CD  GLU A 520       6.215  -8.496  61.004  1.00157.67           C
ANISOU 3877  CD  GLU A 520    24786  25275   9846    577  -1303  -3007       C
ATOM   3878  OE1 GLU A 520       7.122  -9.348  61.071  1.00156.72           O
ANISOU 3878  OE1 GLU A 520    24626  25120   9801    393  -1599  -2977       O
ATOM   3879  OE2 GLU A 520       6.445  -7.271  61.067  1.00158.64           O
ANISOU 3879  OE2 GLU A 520    25121  25260   9896    692  -1275  -3405       O
ATOM   3880  N   THR A 521       3.427  -8.513  57.568  1.00149.78           N
ANISOU 3880  N   THR A 521    22997  24021   9890    351   -684  -2291       N
ATOM   3881  CA  THR A 521       3.586  -9.309  56.354  1.00145.97           C
ANISOU 3881  CA  THR A 521    22252  23356   9854     33   -815  -2103       C
ATOM   3882  C   THR A 521       3.741  -8.248  55.255  1.00143.81           C
ANISOU 3882  C   THR A 521    21995  22764   9882    -21   -805  -2386       C
ATOM   3883  O   THR A 521       3.472  -8.467  54.085  1.00141.04           O
ANISOU 3883  O   THR A 521    21433  22265   9889   -206   -796  -2247       O
ATOM   3884  CB  THR A 521       2.407 -10.315  56.160  1.00145.92           C
ANISOU 3884  CB  THR A 521    21953  23581   9910    -13   -625  -1572       C
ATOM   3885  OG1 THR A 521       2.902 -11.599  55.757  1.00143.78           O
ANISOU 3885  OG1 THR A 521    21527  23240   9861   -305   -843  -1363       O
ATOM   3886  CG2 THR A 521       1.391  -9.812  55.175  1.00144.77           C
ANISOU 3886  CG2 THR A 521    21615  23388  10002      5   -401  -1449       C
ATOM   3887  N   GLY A 522       4.171  -7.069  55.694  1.00145.83           N
ANISOU 3887  N   GLY A 522    22527  22919   9963    150   -803  -2790       N
ATOM   3888  CA  GLY A 522       4.450  -5.934  54.842  1.00144.46           C
ANISOU 3888  CA  GLY A 522    22443  22427  10017    121   -803  -3110       C
ATOM   3889  C   GLY A 522       5.946  -5.711  54.825  1.00143.53           C
```

FIG. 13 Continued

```
ANISOU 3889  C   GLY A 522   22496  22060   9977    -58  -1117  -3511       C
ATOM   3890  O   GLY A 522    6.566  -5.884  53.796  1.00140.47              O
ANISOU 3890  O   GLY A 522   22001  21423   9950   -324  -1277  -3577       O
ATOM   3891  N   ARG A 523    6.531  -5.341  55.961  1.00145.48              N
ANISOU 3891  N   ARG A 523   23004  22389   9883     81  -1208  -3779       N
ATOM   3892  CA  ARG A 523    7.981  -5.139  56.054  1.00145.08              C
ANISOU 3892  CA  ARG A 523   23103  22138   9883    -89  -1526  -4167       C
ATOM   3893  C   ARG A 523    8.730  -6.452  55.810  1.00142.92              C
ANISOU 3893  C   ARG A 523   22632  21875   9797   -353  -1790  -3998       C
ATOM   3894  O   ARG A 523    9.959  -6.504  55.840  1.00142.45              O
ANISOU 3894  O   ARG A 523   22632  21679   9815   -514  -2074  -4265       O
ATOM   3895  CB  ARG A 523    8.393  -4.505  57.404  1.00148.99              C
ANISOU 3895  CB  ARG A 523   23921  22754   9935    122  -1578  -4478       C
ATOM   3896  CG  ARG A 523    7.436  -4.795  58.601  1.00152.38              C
ANISOU 3896  CG  ARG A 523   24416  23571   9912    423  -1366  -4230       C
ATOM   3897  CD  ARG A 523    8.073  -4.663  60.013  1.00156.07              C
ANISOU 3897  CD  ARG A 523   25165  24212   9921    564  -1514  -4469       C
ATOM   3898  NE  ARG A 523    6.328  -3.280  60.429  1.00158.56              N
ANISOU 3898  NE  ARG A 523   25807  24395  10045    719  -1480  -4929       N
ATOM   3899  CZ  ARG A 523    8.491  -2.886  61.696  1.00162.56              C
ANISOU 3899  CZ  ARG A 523   26604  25078  10084    927  -1497  -5140       C
ATOM   3900  NH1 ARG A 523    8.407  -3.763  62.690  1.00164.56              N
ANISOU 3900  NH1 ARG A 523   26861  25665   9999   1016  -1542  -4916       N
ATOM   3901  NH2 ARG A 523    8.729  -1.607  61.979  1.00164.79              N
ANISOU 3901  NH2 ARG A 523   27190  25197  10225   1045  -1469  -5575       N
ATOM   3902  N   ARG A 524    7.976  -7.520  55.589  1.00142.20              N
ANISOU 3902  N   ARG A 524   22303  21948   9777   -392  -1695  -3552       N
ATOM   3903  CA  ARG A 524    8.562  -8.813  55.285  1.00140.21              C
ANISOU 3903  CA  ARG A 524   21863  21685   9725   -631  -1917  -3356       C
ATOM   3904  C   ARG A 524    8.597  -8.978  53.756  1.00136.36              C
ANISOU 3904  C   ARG A 524   21162  20931   9719   -891  -1930  -3297       C
ATOM   3905  O   ARG A 524    9.145  -9.951  53.222  1.00134.25              O
ANISOU 3905  O   ARG A 524   20733  20576   9698  -1120  -2110  -3182       O
ATOM   3906  CB  ARG A 524    7.745  -9.923  55.945  1.00141.55              C
ANISOU 3906  CB  ARG A 524   21920  22172   9692   -545  -1811  -2901       C
ATOM   3907  CG  ARG A 524    8.506 -11.213  56.219  1.00141.15              C
ANISOU 3907  CG  ARG A 524   21791  22166   9673   -699  -2072  -2749       C
ATOM   3908  CD  ARG A 524    7.604 -12.252  56.882  1.00142.80              C
ANISOU 3908  CD  ARG A 524   21909  22678   9671   -613  -1936  -2279       C
ATOM   3909  NE  ARG A 524    7.510 -12.059  58.330  1.00146.73              N
ANISOU 3909  NE  ARG A 524   22625  23454   9671   -355  -1896  -2306       N
ATOM   3910  CZ  ARG A 524    6.480 -12.440  59.087  1.00149.20              C
ANISOU 3910  CZ  ARG A 524   22927  24074   9687   -185  -1667  -1968       C
ATOM   3911  NH1 ARG A 524    5.427 -13.032  58.538  1.00148.18              N
ANISOU 3911  NH1 ARG A 524   22563  24016   9722   -253  -1459  -1571       N
ATOM   3912  NH2 ARG A 524    6.499 -12.214  60.397  1.00152.89              N
ANISOU 3912  NH2 ARG A 524   23620  24785   9686     47  -1642  -2031       N
ATOM   3913  N   LEU A 525    8.016  -8.007  53.052  1.00139.93              N
ANISOU 3913  N   LEU A 525   21627  21245  10294   -843  -1739  -3383       N
ATOM   3914  CA  LEU A 525    7.953  -8.021  51.589  1.00136.60              C
ANISOU 3914  CA  LEU A 525   21030  20579  10294  -1067  -1728  -3333       C
ATOM   3915  C   LEU A 525    8.421  -6.708  50.958  1.00135.98              C
ANISOU 3915  C   LEU A 525   21101  20203  10362  -1096  -1726  -3721       C
ATOM   3916  O   LEU A 525    7.851  -6.256  49.973  1.00134.50              O
ANISOU 3916  O   LEU A 525   20839  19876  10388  -1133  -1583  -3662       O
ATOM   3917  CB  LEU A 525    6.536  -8.339  51.124  1.00136.15              C
ANISOU 3917  CB  LEU A 525   20774  20663  10295   1011   1474   2928       C
ATOM   3918  CG  LEU A 525    6.261  -9.799  50.780  1.00134.63              C
ANISOU 3918  CG  LEU A 525   20327  20570  10255  -1198  -1528  -2532       C
ATOM   3919  CD1 LEU A 525    6.995 -10.735  51.703  1.00135.68              C
ANISOU 3919  CD1 LEU A 525   20503  20826  10224  -1226  -1728  -2498       C
ATOM   3920  CD2 LEU A 525    4.782 -10.070  50.813  1.00135.59              C
ANISOU 3920  CD2 LEU A 525   20285  20935  10299  -1077  -1263  -2132       C
ATOM   3921  N   GLY A 526    9.446  -6.098  51.549  1.00132.53              N
ANISOU 3921  N   GLY A 526   20881  19674   9802  -1081  -1888  -4111       N
ATOM   3922  CA  GLY A 526   10.061  -4.883  51.031  1.00132.25              C
ANISOU 3922  CA  GLY A 526   21008  19336   9904  -1144  -1917  -4507       C
ATOM   3923  C   GLY A 526    9.237  -3.608  50.951  1.00133.66              C
ANISOU 3923  C   GLY A 526   21351  19440   9995   -928  -1662  -4604       C
```

FIG. 13 Continued

```
ATOM   3924  O   GLY A 526       9.789  -2.515  51.037  1.00134.82           O
ANISOU 3924  O   GLY A 526    21727  19384  10115   -907  -1692  -4980       O
ATOM   3925  N   MET A 527       7.925  -3.746  50.786  1.00138.59           N
ANISOU 3925  N   MET A 527    21855  20221  10583   -768  -1414  -4265       N
ATOM   3926  CA  MET A 527       7.017  -2.607  50.616  1.00139.95           C
ANISOU 3926  CA  MET A 527    22142  20332  10701   -536  -1153  -4302       C
ATOM   3927  C   MET A 527       7.272  -1.443  51.567  1.00143.27           C
ANISOU 3927  C   MET A 527    22904  20706  10827   -308  -1111  -4676       C
ATOM   3928  O   MET A 527       6.480  -1.199  52.478  1.00146.13           O
ANISOU 3928  O   MET A 527    23361  21295  10867     -4   -923  -4603       O
ATOM   3929  CB  MET A 527       5.564  -3.075  50.737  1.00140.65           C
ANISOU 3929  CB  MET A 527    22042  20712  10686   -340   -903  -3868       C
ATOM   3930  CG  MET A 527       5.058  -3.796  49.500  1.00137.58           C
ANISOU 3930  CG  MET A 527    21348  20292  10636   -544   -882  -3534       C
ATOM   3931  SD  MET A 527       3.736  -4.978  49.812  1.00138.14           S
ANISOU 3931  SD  MET A 527    21123  20765  10599   -455   -716  -2983       S
ATOM   3932  CE  MET A 527       3.150  -5.283  48.155  1.00134.93           C
ANISOU 3932  CE  MET A 527    20432  20222  10612   -678   -682  -2719       C
ATOM   3933  N   GLY A 528       8.347  -0.699  51.304  1.00174.84           N
ANISOU 3933  N   GLY A 528    27085  24402  14944   -460  -1272  -5076       N
ATOM   3934  CA  GLY A 528       8.795   0.397  52.154  1.00177.99           C
ANISOU 3934  CA  GLY A 528    27827  24708  15092   -308  -1284  -5486       C
ATOM   3935  C   GLY A 528       8.285   1.814  51.910  1.00179.63           C
ANISOU 3935  C   GLY A 528    28267  24690  15295   -115  -1070  -5678       C
ATOM   3936  O   GLY A 528       9.073   2.725  51.612  1.00179.93           O
ANISOU 3936  O   GLY A 528    28509  24408  15448   -235  -1160  -6044       O
ATOM   3937  N   THR A 529       6.972   2.001  52.056  1.00255.35           N
ANISOU 3937  N   THR A 529    37823  34445  24752    185   -783  -5428       N
ATOM   3938  CA  THR A 529       6.329   3.314  51.930  1.00257.43           C
ANISOU 3938  CA  THR A 529    38306  34527  24978    439   -548  -5570       C
ATOM   3939  C   THR A 529       5.365   3.551  53.112  1.00261.21           C
ANISOU 3939  C   THR A 529    38905  35299  25045    852   -309  -5501       C
ATOM   3940  O   THR A 529       5.136   4.686  53.526  1.00264.20           O
ANISOU 3940  O   THR A 529    39575  35550  25257   1102   -161  -5753       O
ATOM   3941  CB  THR A 529       5.604   3.480  50.565  1.00255.10           C
ANISOU 3941  CB  THR A 529    37822  34078  25025    399   -406  -5321       C
ATOM   3942  OG1 THR A 529       6.574   3.555  49.515  1.00252.28           O
ANISOU 3942  OG1 THR A 529    37443  33397  25014     42   -602  -5473       O
ATOM   3943  CG2 THR A 529       4.774   4.749  50.542  1.00257.68           C
ANISOU 3943  CG2 THR A 529    38357  34269  25283    727   -139  -5405       C
ATOM   3944  N   ASN A 530       4.832   2.459  53.653  1.00152.50           N
ANISOU 3944  N   ASN A 530    24916  21914  11112    915   -270  -5162       N
ATOM   3945  CA  ASN A 530       3.934   2.458  54.799  1.00156.00           C
ANISOU 3945  CA  ASN A 530    25425  22695  11155   1276    -44  -5042       C
ATOM   3946  C   ASN A 530       4.712   2.634  56.070  1.00158.85           C
ANISOU 3946  C   ASN A 530    26082  23130  11146   1338   -178  -5372       C
ATOM   3947  O   ASN A 530       4.568   1.838  56.994  1.00160.17           O
ANISOU 3947  O   ASN A 530    26197  23636  11026   1413   -187  -5208       O
ATOM   3948  CB  ASN A 530       3.282   1.094  54.874  1.00154.77           C
ANISOU 3948  CB  ASN A 530    24918  22905  10983   1236     -3  -4560       C
ATOM   3949  CG  ASN A 530       4.295  -0.030  54.714  1.00152.01           C
ANISOU 3949  CG  ASN A 530    24424  22561  10771    873   -323  -4513       C
ATOM   3950  OD1 ASN A 530       5.341  -0.031  55.373  1.00152.85           O
ANISOU 3950  OD1 ASN A 530    24721  22628  10727    784   -546  -4801       O
ATOM   3951  ND2 ASN A 530       4.004  -0.976  53.819  1.00148.86           N
ANISOU 3951  ND2 ASN A 530    23690  22203  10665    663   -355  -4158       N
ATOM   3952  N   MET A 531       5.555   3.655  56.117  1.00159.75           N
ANISOU 3952  N   MET A 531    26508  22927  11262   1291   -294  -5832       N
ATOM   3953  CA  MET A 531       6.419   3.855  57.276  1.00162.51           C
ANISOU 3953  CA  MET A 531    27148  23325  11274   1307   -470  -6187       C
ATOM   3954  C   MET A 531       5.874   4.829  58.336  1.00167.31           C
ANISOU 3954  C   MET A 531    28101  24003  11465   1700   -246  -6412       C
ATOM   3955  O   MET A 531       5.662   4.456  59.496  1.00170.02           O
ANISOU 3955  O   MET A 531    28525  24674  11402   1885   -204  -6369       O
ATOM   3956  CB  MET A 531       7.821   4.253  56.802  1.00161.11           C
ANISOU 3956  CB  MET A 531    27093  22791  11330    969   -780  -6574       C
ATOM   3957  CG  MET A 531       8.319   3.400  55.630  1.00156.47           C
ANISOU 3957  CG  MET A 531    26172  22100  11181    600   -963  -6370       C
ATOM   3958  SD  MET A 531      10.070   2.975  55.728  1.00155.34           S
```

FIG. 13 Continued

```
ANISOU 3958  SD  MET A 531    26039 21844 11137   210 -1403 -6674          S
ATOM   3959  CE  MET A 531    10.754   4.499  56.409  1.00 159.30          C
ANISOU 3959  CE  MET A 531    27013 22085 11427   284 -1458 -7278          C
ATOM   3960  N   TYR A 532     5.660   6.074  57.931  1.00 261.51          N
ANISOU 3960  N   TYR A 532    40252 35617 23493  1828   -98 -6651          N
ATOM   3961  CA  TYR A 532     5.135   7.095  58.828  1.00 266.16          C
ANISOU 3961  CA  TYR A 532    41192 36216 23722  2212   133 -6890          C
ATOM   3962  C   TYR A 532     3.610   7.151  58.691  1.00 267.08          C
ANISOU 3962  C   TYR A 532    41149 36525 23805  2570   523 -6529          C
ATOM   3963  O   TYR A 532     3.073   6.790  57.644  1.00 264.05          O
ANISOU 3963  O   TYR A 532    40449 36117 23761  2488   596 -6195          O
ATOM   3964  CB  TYR A 532     5.788   8.443  58.511  1.00 267.38          C
ANISOU 3964  CB  TYR A 532    41702 35895 23997  2157    72 -7370          C
ATOM   3965  CG  TYR A 532     7.286   8.336  58.287  1.00 265.65          C
ANISOU 3965  CG  TYR A 532    41534 35453 23946  1731  -318 -7668          C
ATOM   3966  CD1 TYR A 532     8.184   8.573  59.322  1.00 268.49          C
ANISOU 3966  CD1 TYR A 532    42184 35833 23998  1683  -528 -8060          C
ATOM   3967  CD2 TYR A 532     7.799   7.979  57.044  1.00 261.35          C
ANISOU 3967  CD2 TYR A 532    40737 34699 23863  1376  -478 -7555          C
ATOM   3968  CE1 TYR A 532     9.549   8.467  59.121  1.00 267.14          C
ANISOU 3968  CE1 TYR A 532    42027 35483 23991  1295  -888 -8325          C
ATOM   3969  CE2 TYR A 532     9.161   7.870  56.835  1.00 259.95          C
ANISOU 3969  CE2 TYR A 532    40581 34340 23849   995  -817 -7820          C
ATOM   3970  CZ  TYR A 532    10.031   8.115  57.876  1.00 262.87          C
ANISOU 3970  CZ  TYR A 532    41216 34738 23923   955 -1023 -8202          C
ATOM   3971  OH  TYR A 532    11.387   8.007  57.668  1.00 261.70          O
ANISOU 3971  OH  TYR A 532    41059 34428 23949   576  1365  8462          O
ATOM   3972  N   PRO A 533     2.904   7.594  59.748  1.00 194.49          N
ANISOU 3972  N   PRO A 533    32165 27536 14196  2968   774 -6593          N
ATOM   3973  CA  PRO A 533     1.437   7.614  59.690  1.00 195.76          C
ANISOU 3973  CA  PRO A 533    32144 27923 14312  3325  1157 -6240          C
ATOM   3974  C   PRO A 533     0.892   8.104  58.350  1.00 193.55          C
ANISOU 3974  C   PRO A 533    31701 27371 14469  3326  1279 -6092          C
ATOM   3975  O   PRO A 533     0.065   7.412  57.762  1.00 191.56          O
ANISOU 3975  O   PRO A 533    31062 27323 14399  3330  1398 -5646          O
ATOM   3976  CB  PRO A 533     1.061   8.591  60.808  1.00 201.20          C
ANISOU 3976  CB  PRO A 533    33231 28650 14564  3743  1389 -6542          C
ATOM   3977  CG  PRO A 533     2.156   8.440  61.812  1.00 202.74          C
ANISOU 3977  CG  PRO A 533    33701 28891 14438  3597  1120 -6879          C
ATOM   3978  CD  PRO A 533     3.413   8.128  61.027  1.00 198.71          C
ANISOU 3978  CD  PRO A 533    33114 28104 14282  3111   723 -7004          C
ATOM   3979  N   SER A 534     1.366   9.256  57.874  1.00 262.60          N
ANISOU 3979  N   SER A 534    40736 35662 23376  3305  1236 -6454          N
ATOM   3980  CA  SER A 534     0.882   9.869  56.628  1.00 261.03          C
ANISOU 3980  CA  SER A 534    40445 35167 23567  3331  1352 -6345          C
ATOM   3981  C   SER A 534     1.117   9.033  55.362  1.00 255.85          C
ANISOU 3981  C   SER A 534    39406 34461 23346  2943  1166 -6041          C
ATOM   3982  O   SER A 534     0.247   8.954  54.486  1.00 254.44          O
ANISOU 3982  O   SER A 534    38961 34305 23411  3017  1318 -5709          O
ATOM   3983  CB  SER A 534     1.496  11.266  56.446  1.00 262.83          C
ANISOU 3983  CB  SER A 534    41113 34888 23864  3348  1316 -6825          C
ATOM   3984  OG  SER A 534     1.141  12.140  57.506  1.00 267.89          O
ANISOU 3984  OG  SER A 534    42123 35539 24125  3744  1526 -7103          O
ATOM   3985  N   SER A 535     2.300   8.428  55.273  1.00 167.70          N
ANISOU 3985  N   SER A 535    28217 23228 12271  2538   836 -6167          N
ATOM   3986  CA  SER A 535     2.677   7.601  54.130  1.00 162.93          C
ANISOU 3986  CA  SER A 535    27284 22564 12059  2149   639  5928          C
ATOM   3987  C   SER A 535     1.637   6.539  53.802  1.00 161.20          C
ANISOU 3987  C   SER A 535    26626 22708 11913  2195   769 -5390          C
ATOM   3988  O   SER A 535     0.479   6.843  53.499  1.00 162.23          O
ANISOU 3988  O   SER A 535    26637 22921 12082  2469  1037 -5151          O
ATOM   3989  CB  SER A 535     4.036   6.920  54.367  1.00 161.08          C
ANISOU 3989  CB  SER A 535    27061 22312 11831  1765   284 -6113          C
ATOM   3990  OG  SER A 535     5.123   7.628  53.788  1.00 160.12          O
ANISOU 3990  OG  SER A 535    27144 21761 11935  1501    86 -6479          O
ATOM   3991  N   ALA A 536     2.071   5.284  53.891  1.00 158.80          N
ANISOU 3991  N   ALA A 536    26085 22622 11628  1924   573 -5203          N
ATOM   3992  CA  ALA A 536     1.270   4.161  53.428  1.00 156.63          C
ANISOU 3992  CA  ALA A 536    25385 22641 11486  1861   637 -4701          C
```

FIG. 13 Continued

```
ATOM   3993  C   ALA A 536       0.733   3.169  54.449  1.00158.10           C
ANISOU 3993  C   ALA A 536    25413  23294  11362   1983    720  -4424       C
ATOM   3994  O   ALA A 536       1.110   3.163  55.620  1.00160.60           O
ANISOU 3994  O   ALA A 536    25944  23752  11326   2089    689  -4611       O
ATOM   3995  CB  ALA A 536       2.034   3.416  52.364  1.00152.17           C
ANISOU 3995  CB  ALA A 536    24611  21916  11291   1420    368  -4617       C
ATOM   3996  N   LEU A 537      -0.121   2.293  53.927  1.00158.06           N
ANISOU 3996  N   LEU A 537    25026  23520  11509   1936    812  -3965       N
ATOM   3997  CA  LEU A 537      -0.813   1.248  54.674  1.00159.18           C
ANISOU 3997  CA  LEU A 537    24944  24109  11427   2018    922  -3604       C
ATOM   3998  C   LEU A 537      -1.783   1.826  55.713  1.00163.79           C
ANISOU 3998  C   LEU A 537    25645  24954  11633   2475   1254  -3589       C
ATOM   3999  O   LEU A 537      -1.842   1.369  56.852  1.00166.12           O
ANISOU 3999  O   LEU A 537    26000  25547  11572   2588   1304  -3546       O
ATOM   4000  CB  LEU A 537       0.162   0.203  55.259  1.00158.07           C
ANISOU 4000  CB  LEU A 537    24812  24074  11173   1755    649  -3625       C
ATOM   4001  CG  LEU A 537       0.807  -0.784  54.258  1.00153.62           C
ANISOU 4001  CG  LEU A 537    24007  23383  10981   1322    376  -3474       C
ATOM   4002  CD1 LEU A 537       1.436  -1.982  54.946  1.00153.20           C
ANISOU 4002  CD1 LEU A 537    23900  23524  10783   1140    173  -3374       C
ATOM   4003  CD2 LEU A 537      -0.175  -1.274  53.231  1.00151.65           C
ANISOU 4003  CD2 LEU A 537    23390  23209  11021   1251    498  -3060       C
ATOM   4004  N   LEU A 538      -2.542   2.842  55.308  1.00167.33           N
ANISOU 4004  N   LEU A 538    26133  25288  12158   2746   1486  -3623       N
ATOM   4005  CA  LEU A 538      -3.538   3.431  56.183  1.00171.82           C
ANISOU 4005  CA  LEU A 538    26787  26094  12402   3205   1831  -3598       C
ATOM   4006  C   LEU A 538      -4.677   2.437  56.315  1.00172.28           C
ANISOU 4006  C   LEU A 538    26435  26605  12420   3270   2026  -3080       C
ATOM   4007  O   LEU A 538      -5.067   1.824  55.331  1.00169.48           O
ANISOU 4007  O   LEU A 538    25731  26274  12390   3066   1981  -2755       O
ATOM   4008  CB  LEU A 538      -4.098   4.723  55.579  1.00173.16           C
ANISOU 4008  CB  LEU A 538    27066  26010  12719   3479   2025  -3727       C
ATOM   4009  CG  LEU A 538      -3.481   5.438  54.372  1.00170.49           C
ANISOU 4009  CG  LEU A 538    26836  25185  12759   3285   1852  -3939       C
ATOM   4010  CD1 LEU A 538      -4.414   6.553  53.939  1.00172.73           C
ANISOU 4010  CD1 LEU A 538    27159  25341  13128   3648   2123  -3932       C
ATOM   4011  CD2 LEU A 538      -2.093   5.980  54.648  1.00170.24           C
ANISOU 4011  CD2 LEU A 538    27210  24805  12668   3110   1605  -4437       C
ATOM   4012  N   GLY A 539      -5.215   2.263  57.516  1.00173.13           N
ANISOU 4012  N   GLY A 539    26582  27073  12126   3539   2243  -2999       N
ATOM   4013  CA  GLY A 539      -6.379   1.410  57.660  1.00174.10           C
ANISOU 4013  CA  GLY A 539    26311  27632  12207   3618   2467  -2502       C
ATOM   4014  C   GLY A 539      -7.388   1.949  56.665  1.00173.96           C
ANISOU 4014  C   GLY A 539    26045  27564  12487   3773   2659  -2313       C
ATOM   4015  O   GLY A 539      -7.271   3.096  56.250  1.00174.42           O
ANISOU 4015  O   GLY A 539    26319  27305  12647   3935   2688   2596       O
ATOM   4016  N   THR A 540      -8.368   1.149  56.266  1.00174.07           N
ANISOU 4016  N   THR A 540    25613  27879  12645   3720   2780  -1837       N
ATOM   4017  CA  THR A 540      -9.347   1.599  55.268  1.00173.97           C
ANISOU 4017  CA  THR A 540    25326  27845  12929   3852   2934  -1629       C
ATOM   4018  C   THR A 540     -10.152   2.829  55.651  1.00178.26           C
ANISOU 4018  C   THR A 540    26000  28421  13311   4375   3272  -1756       C
ATOM   4019  O   THR A 540     -10.513   3.644  54.800  1.00178.11           O
ANISOU 4019  O   THR A 540    25953  28186  13535   4511   3324  -1791       O
ATOM   4020  CB  THR A 540     -10.405   0.525  54.975  1.00173.76           C
ANISOU 4020  CB  THR A 540    24780  28216  13025   3747   3046  -1081       C
ATOM   4021  OG1 THR A 540     -10.041  -0.204  53.797  1.00169.25           O
ANISOU 4021  OG1 THR A 540    23989  27478  12840   3306   2761   -921       O
ATOM   4022  CG2 THR A 540     -11.773   1.184  54.755  1.00176.86           C
ANISOU 4022  CG2 THR A 540    24933  28801  13463   4137   3385   -877       C
ATOM   4023  N   HIS A 541     -10.443   2.942  56.936  1.00182.39           N
ANISOU 4023  N   HIS A 541    26669  29218  13415   4675   3506  -1816       N
ATOM   4024  CA  HIS A 541     -11.342   3.970  57.438  1.00187.09           C
ANISOU 4024  CA  HIS A 541    27350  29922  13814   5206   3878  -1890       C
ATOM   4025  C   HIS A 541     -10.893   5.425  57.347  1.00188.37           C
ANISOU 4025  C   HIS A 541    27955  29649  13969   5457   3887  -2367       C
ATOM   4026  O   HIS A 541     -11.719   6.331  57.447  1.00191.87           O
ANISOU 4026  O   HIS A 541    28426  30118  14358   5896   4185  -2396       O
ATOM   4027  CB  HIS A 541     -11.743   3.620  58.861  1.00191.14           C
```

FIG. 13 Continued

```
ANISOU 4027  CB  HIS A 541    27906  30862  13857   5439   4130  -1821         C
ATOM   4028  CG  HIS A 541   -12.645   2.432  58.938  1.00191.38              C
ANISOU 4028  CG  HIS A 541    27445  31371  13901   5333   4262  -1285         C
ATOM   4029  ND1 HIS A 541   -12.795   1.551  57.888  1.00187.59              N
ANISOU 4029  ND1 HIS A 541    26565  30905  13806   4955   4077   -937         N
ATOM   4030  CD2 HIS A 541   -13.439   1.974  59.936  1.00195.14              C
ANISOU 4030  CD2 HIS A 541    27770  32325  14050   5540   4564  -1038         C
ATOM   4031  CE1 HIS A 541   -13.650   0.605  58.235  1.00189.03              C
ANISOU 4031  CE1 HIS A 541    26369  31544  13910   4925   4253   -499         C
ATOM   4032  NE2 HIS A 541   -14.054   0.838  59.473  1.00193.58              N
ANISOU 4032  NE2 HIS A 541    27081  32413  14059   5275   4554   -543         N
ATOM   4033  N   LYS A 542    -9.599   5.661  57.177  1.00204.93              N
ANISOU 4033  N   LYS A 542    30397  31346  16120   5190   3573  -2739         N
ATOM   4034  CA  LYS A 542    -9.128   7.030  57.010  1.00206.05              C
ANISOU 4034  CA  LYS A 542    30963  31037  16290   5376   3562  -3188         C
ATOM   4035  C   LYS A 542    -9.477   7.497  55.587  1.00203.91              C
ANISOU 4035  C   LYS A 542    30512  30495  16469   5340   3525  -3064         C
ATOM   4036  O   LYS A 542    -8.805   8.356  55.016  1.00202.86              O
ANISOU 4036  O   LYS A 542    30673  29899  16507   5283   3383  -3381         O
ATOM   4037  CB  LYS A 542    -7.622   7.130  57.268  1.00204.24              C
ANISOU 4037  CB  LYS A 542    31138  30477  15986   5076   3231  -3621         C
ATOM   4038  CG  LYS A 542    -7.149   6.504  58.577  1.00205.79              C
ANISOU 4038  CG  LYS A 542    31488  30945  15760   5035   3190  -3714         C
ATOM   4039  CD  LYS A 542    -7.169   7.485  59.745  1.00210.84              C
ANISOU 4039  CD  LYS A 542    32566  31574  15970   5444   3399  -4093         C
ATOM   4040  CE  LYS A 542    -6.518   6.871  60.989  1.00212.16              C
ANISOU 4040  CE  LYS A 542    32926  31971  15713   5354   3294  -4221         C
ATOM   4041  NZ  LYS A 542    -6.599   7.738  62.201  1.00217.43              N
ANISOU 4041  NZ  LYS A 542    34017  32682  15913   5754   3509  -4573         N
ATOM   4042  N   ASP A 543   -10.540   6.920  55.026  1.00182.42              N
ANISOU 4042  N   ASP A 543    27306  28073  13932   5366   3653  -2594         N
ATOM   4043  CA  ASP A 543   -10.987   7.224  53.671  1.00180.55              C
ANISOU 4043  CA  ASP A 543    26840  27653  14107   5327   3614  -2409         C
ATOM   4044  C   ASP A 543   -12.508   7.060  53.601  1.00183.19              C
ANISOU 4044  C   ASP A 543    26731  28405  14469   5640   3926  -1974         C
ATOM   4045  O   ASP A 543   -13.056   6.432  52.688  1.00181.08              O
ANISOU 4045  O   ASP A 543    26035  28277  14489   5452   3862  -1594         O
ATOM   4046  CB  ASP A 543   10.258    6.320  52.682  1.00176.16              C
ANISOU 4046  CB  ASP A 543    25980  26833  13741   4767   3251  -2283         C
ATOM   4047  CG  ASP A 543    -8.745   6.345  52.886  1.00172.85              C
ANISOU 4047  CG  ASP A 543    26079  26199  13396   4452   2952  -2693         C
ATOM   4048  OD1 ASP A 543    -8.135   7.424  52.730  1.00173.34              O
ANISOU 4048  OD1 ASP A 543    26527  25846  13490   4531   2901  -3079         O
ATOM   4049  OD2 ASP A 543    -8.161   5.293  53.217  1.00170.77              O
ANISOU 4049  OD2 ASP A 543    25739  26082  13062   4128   2768  -2630         O
ATOM   4050  N   ALA A 544   -13.159   7.635  54.616  1.00187.70              N
ANISOU 4050  N   ALA A 544    27415  29181  14720   6119   4264  -2050         N
ATOM   4051  CA  ALA A 544   -14.614   7.639  54.788  1.00191.34              C
ANISOU 4051  CA  ALA A 544    27496  30063  15141   6506   4622  -1693         C
ATOM   4052  C   ALA A 544   -15.070   8.587  55.922  1.00197.01              C
ANISOU 4052  C   ALA A 544    28498  30870  15489   7076   4988   1929         C
ATOM   4053  O   ALA A 544   -16.218   9.033  55.938  1.00200.61              O
ANISOU 4053  O   ALA A 544    28733  31541  15950   7501   5305  -1740         O
ATOM   4054  CB  ALA A 544   -15.133   6.224  55.029  1.00190.55              C
ANISOU 4054  CB  ALA A 544    26926  30472  15002   6270   4644  -1244         C
ATOM   4055  N   ASN A 545   -14.169   8.908  56.854  1.00199.37              N
ANISOU 4055  N   ASN A 545    29283  31000  15468   7090   4941  -2350         N
ATOM   4056  CA  ASN A 545   -14.520   9.784  57.985  1.00204.88              C
ANISOU 4056  CA  ASN A 545    30299  31768  15778   7612   5278  -2614         C
ATOM   4057  C   ASN A 545   -13.403  10.552  58.754  1.00206.07              C
ANISOU 4057  C   ASN A 545    31102  31553  15643   7650   5178  -3198         C
ATOM   4058  O   ASN A 545   -13.619  11.705  59.136  1.00210.04              O
ANISOU 4058  O   ASN A 545    31937  31870  16000   8085   5398  -3494         O
ATOM   4059  CB  ASN A 545   -15.450   9.047  58.979  1.00208.22              C
ANISOU 4059  CB  ASN A 545    30418  32809  15885   7595   5595  -2298         C
ATOM   4060  CG  ASN A 545   -14.810   7.799  59.598  1.00206.04              C
ANISOU 4060  CG  ASN A 545    30103  32773  15408   7399   5405  -2206         C
ATOM   4061  OD1 ASN A 545   -13.613   7.775  59.886  1.00204.13              O
ANISOU 4061  OD1 ASN A 545    30242  32265  15052   7141   5132  -2542         O
```

FIG. 13 Continued

```
ATOM   4062  ND2 ASN A 545     -15.621   6.767  59.826  1.00206.62           N
ANISOU 4062  ND2 ASN A 545    29715  33356  15437   7342   5555  -1744       N
ATOM   4063  N   LEU A 546     -12.226   9.949  58.958  1.00211.16           N
ANISOU 4063  N   LEU A 546    31929  32082  16219   7207   4846  -3370       N
ATOM   4064  CA  LEU A 546     -11.175  10.556  59.809  1.00212.64           C
ANISOU 4064  CA  LEU A 546    32701  31996  16096   7218   4740  -3907       C
ATOM   4065  C   LEU A 546     -10.192  11.619  59.248  1.00211.42           C
ANISOU 4065  C   LEU A 546    32994  31211  16126   7118   4513  -4370       C
ATOM   4066  O   LEU A 546     -10.337  12.807  59.553  1.00215.17           O
ANISOU 4066  O   LEU A 546    33833  31443  16480   7499   4699  -4690       O
ATOM   4067  CB  LEU A 546     -10.388   9.464  60.549  1.00210.94           C
ANISOU 4067  CB  LEU A 546    32508  32005  15634   6857   4520  -3904       C
ATOM   4068  CG  LEU A 546      -9.531   9.941  61.730  1.00213.70           C
ANISOU 4068  CG  LEU A 546    33405  32244  15547   6936   4471  -4396       C
ATOM   4069  CD1 LEU A 546      -9.435   8.881  62.823  1.00214.62           C
ANISOU 4069  CD1 LEU A 546    33455  32816  15273   6838   4473  -4251       C
ATOM   4070  CD2 LEU A 546      -8.139  10.385  61.279  1.00210.79           C
ANISOU 4070  CD2 LEU A 546    33397  31348  15347   6590   4079  -4818       C
ATOM   4071  N   ALA A 547      -9.188  11.191  58.474  1.00196.70           N
ANISOU 4071  N   ALA A 547    31115  29081  14540   6610   4123  -4414       N
ATOM   4072  CA  ALA A 547      -8.112  12.085  57.985  1.00195.38           C
ANISOU 4072  CA  ALA A 547    31368  28329  14539   6436   3880  -4856       C
ATOM   4073  C   ALA A 547      -8.428  13.011  56.780  1.00194.81           C
ANISOU 4073  C   ALA A 547    31300  27858  14859   6545   3916  -4847       C
ATOM   4074  O   ALA A 547      -9.087  12.602  55.827  1.00192.61           O
ANISOU 4074  O   ALA A 547    30603  27690  14892   6486   3932  -4446       O
ATOM   4075  CB  ALA A 547      -6.835  11.278  57.728  1.00190.77           C
ANISOU 4075  CB  ALA A 547    30786  27630  14067   5858   3458  -4936       C
ATOM   4076  N   SER A 548      -7.933  14.252  56.831  1.00223.90           N
ANISOU 4076  N   SER A 548    35474  31073  18523   6690   3916  -5293       N
ATOM   4077  CA  SER A 548      -8.188  15.264  55.787  1.00224.05           C
ANISOU 4077  CA  SER A 548    35583  30669  18878   6830   3964  -5326       C
ATOM   4078  C   SER A 548      -7.318  15.094  54.545  1.00219.01           C
ANISOU 4078  C   SER A 548    34893  29674  18647   6327   3615  -5318       C
ATOM   4079  O   SER A 548      -7.038  13.972  54.149  1.00214.90           O
ANISOU 4079  O   SER A 548    34034  29361  18259   5932   3405  -5062       O
ATOM   4080  CB  SER A 548      -7.997  16.676  56.343  1.00228.65           C
ANISOU 4080  CB  SER A 548    36740  30858  19277   7181   4111  -5811       C
ATOM   4081  OG  SER A 548      -6.623  17.009  56.434  1.00227.40           O
ANISOU 4081  OG  SER A 548    36999  30295  19107   6826   3816  -6258       O
ATOM   4082  N   ILE A 549      -6.910  16.207  53.926  1.00251.47           N
ANISOU 4082  N   ILE A 549    39346  33246  22955   6347   3565  -5591       N
ATOM   4083  CA  ILE A 549      -6.038  16.168  52.739  1.00247.09           C
ANISOU 4083  CA  ILE A 549    38790  32317  22777   5877   3253  -5616       C
ATOM   4084  C   ILE A 549      -6.721  15.429  51.579  1.00243.69           C
ANISOU 4084  C   ILE A 549    37829  32085  22677   5747   3221  -5097       C
ATOM   4085  O   ILE A 549      -7.771  14.814  51.781  1.00244.46           O
ANISOU 4085  O   ILE A 549    37540  32641  22702   5962   3407  -4724       O
ATOM   4086  CB  ILE A 549      -4.640  15.551  53.096  1.00244.27           C
ANISOU 4086  CB  ILE A 549    38563  31906  22341   5370   2917  -5881       C
ATOM   4087  CG1 ILE A 549      -3.613  16.655  53.373  1.00246.17           C
ANISOU 4087  CG1 ILE A 549    39379  31632  22524   5308   2812  -6438       C
ATOM   4088  CG2 ILE A 549      -4.123  14.596  52.016  1.00238.67           C
ANISOU 4088  CG2 ILE A 549    37509  31205  21970   4853   2628  -5628       C
ATOM   4089  CD1 ILE A 549      -3.091  17.344  52.132  1.00244.25           C
ANISOU 4089  CD1 ILE A 549    39273  30860  22669   5078   2669  -6527       C
ATOM   4090  N   PRO A 550      -6.170  15.524  50.349  1.00181.94           N
ANISOU 4090  N   PRO A 550    29990  23921  15217   5403   2999  -5069       N
ATOM   4091  CA  PRO A 550      -6.830  14.728  49.311  1.00178.85           C
ANISOU 4091  CA  PRO A 550    29091  23764  15102   5267   2958  -4576       C
ATOM   4092  C   PRO A 550      -6.811  13.264  49.721  1.00176.32           C
ANISOU 4092  C   PRO A 550    28390  23928  14675   5005   2857  -4330       C
ATOM   4093  O   PRO A 550      -5.736  12.739  50.017  1.00174.05           O
ANISOU 4093  O   PRO A 550    28208  23594  14328   4632   2621  -4529       O
ATOM   4094  CB  PRO A 550      -5.944  14.947  48.084  1.00175.34           C
ANISOU 4094  CB  PRO A 550    28749  22872  15000   4854   2692  -4662       C
ATOM   4095  CG  PRO A 550      -5.304  16.261  48.307  1.00177.98           C
ANISOU 4095  CG  PRO A 550    29639  22695  15289   4969   2714  -5126       C
ATOM   4096  CD  PRO A 550      -5.118  16.394  49.792  1.00181.19           C
```

FIG. 13 Continued

```
ANISOU 4096  CD  PRO A 550    30305  23240  15299   5171   2818  -5434         C
ATOM   4097  N   VAL A 551     -7.979  12.629  49.781  1.00178.48              N
ANISOU 4097  N   VAL A 551    28234  24660  14919   5207   3035  -3908         N
ATOM   4098  CA  VAL A 551     -8.059  11.219  50.148  1.00176.37              C
ANISOU 4098  CA  VAL A 551    27598  24853  14561   4965   2959  -3635         C
ATOM   4099  C   VAL A 551     -7.637  10.371  48.957  1.00171.32              C
ANISOU 4099  C   VAL A 551    26676  24158  14258   4468   2674  -3411         C
ATOM   4100  O   VAL A 551     -7.018   9.315  49.101  1.00168.44              O
ANISOU 4100  O   VAL A 551    26181  23941  13877   4094   2473  -3364         O
ATOM   4101  CB  VAL A 551     -9.470  10.827  50.624  1.00179.16              C
ANISOU 4101  CB  VAL A 551    27577  25722  14772   5331   3259  -3253         C
ATOM   4102  CG1 VAL A 551     -9.484  10.622  52.134  1.00182.17              C
ANISOU 4102  CG1 VAL A 551    28096  26397  14723   5530   3417  -3394         C
ATOM   4103  CG2 VAL A 551    -10.467  11.878  50.196  1.00182.39              C
ANISOU 4103  CG2 VAL A 551    27979  26035  15285   5798   3513  -3165         C
ATOM   4104  N   GLU A 552     -7.965  10.852  47.770  1.00211.38              N
ANISOU 4104  N   GLU A 552    31672  29008  19634   4474   2656  -3278         N
ATOM   4105  CA  GLU A 552     -7.560  10.156  46.570  1.00206.85              C
ANISOU 4105  CA  GLU A 552    30872  28347  19376   4016   2395  -3093         C
ATOM   4106  C   GLU A 552     -6.037  10.259  46.436  1.00204.26              C
ANISOU 4106  C   GLU A 552    30878  27625  19105   3619   2124  -3479         C
ATOM   4107  O   GLU A 552     -5.420   9.509  45.683  1.00200.33              O
ANISOU 4107  O   GLU A 552    30231  27074  18812   3181   1882  -3397         O
ATOM   4108  CB  GLU A 552     -8.290  10.723  45.350  1.00206.96              C
ANISOU 4108  CB  GLU A 552    30750  28215  19670   4143   2445  -2865         C
ATOM   4109  CG  GLU A 552     -9.818  10.556  45.405  1.00209.54              C
ANISOU 4109  CG  GLU A 552    30680  28966  19971   4516   2693  -2453         C
ATOM   4110  CD  GLU A 552    -10.537  11.721  46.083  1.00214.66              C
ANISOU 4110  CD  GLU A 552    31539  29579  20442   5108   3006  -2577         C
ATOM   4111  OE1 GLU A 552    -11.018  11.552  47.225  1.00217.49              O
ANISOU 4111  OE1 GLU A 552    31852  30266  20517   5381   3217  -2570         O
ATOM   4112  OE2 GLU A 552    -10.627  12.807  45.471  1.00216.03              O
ANISOU 4112  OE2 GLU A 552    31932  29392  20757   5307   3050  -2677         O
ATOM   4113  N   GLU A 553     -5.433  11.181  47.185  1.00166.14              N
ANISOU 4113  N   GLU A 553    26501  22530  14095   3772   2168  -3906         N
ATOM   4114  CA  GLU A 553     -3.978  11.351  47.174  1.00164.29              C
ANISOU 4114  CA  GLU A 553    26590  21935  13896   3411   1920  -4300         C
ATOM   4115  C   GLU A 553     -3.289  10.200  47.875  1.00162.34              C
ANISOU 4115  C   GLU A 553    26231  21951  13499   3115   1744  -4328         C
ATOM   4116  O   GLU A 553     -2.611   9.397  47.233  1.00158.51              O
ANISOU 4116  O   GLU A 553    25581  21436  13208   2687   1503  -4255         O
ATOM   4117  CB  GLU A 553     -3.554  12.663  47.845  1.00167.87              C
ANISOU 4117  CB  GLU A 553    27562  22040  14181   3655   2013  -4759         C
ATOM   4118  CG  GLU A 553     -2.156  12.631  48.501  1.00167.26              C
ANISOU 4118  CG  GLU A 553    27791  21786  13973   3357   1794  -5188         C
ATOM   4119  CD  GLU A 553     -1.066  13.266  47.650  1.00165.54              C
ANISOU 4119  CD  GLU A 553    27834  21050  14013   3027   1593  -5469         C
ATOM   4120  OE1 GLU A 553     -1.184  13.244  46.407  1.00163.14              O
ANISOU 4120  OE1 GLU A 553    27371  20594  14021   2863   1538  -5260         O
ATOM   4121  OE2 GLU A 553     -0.087  13.788  48.230  1.00166.76              O
ANISOU 4121  OE2 GLU A 553    28353  20957  14052   2921   1489  -5897         O
ATOM   4122  N   LEU A 554     -3.466  10.120  49.191  1.00164.39              N
ANISOU 4122  N   LEU A 554    26588  22465  13407   3354   1869  -4429         N
ATOM   4123  CA  LEU A 554     -2.812   9.084  49.967  1.00163.09              C
ANISOU 4123  CA  LEU A 554    26355  22549  13063   3111   1705  -4463         C
ATOM   4124  C   LEU A 554     -2.880   7.763  49.219  1.00159.05              C
ANISOU 4124  C   LEU A 554    25405  22255  12773   2762   1549  -4079         C
ATOM   4125  O   LEU A 554     -1.889   7.038  49.131  1.00156.23              O
ANISOU 4125  O   LEU A 554    25023  21854  12481   2377   1291  -4160         O
ATOM   4126  CB  LEU A 554     -3.417   8.960  51.368  1.00166.79              C
ANISOU 4126  CB  LEU A 554    26859  23392  13122   3463   1919  -4450         C
ATOM   4127  CG  LEU A 554     -2.890   9.950  52.415  1.00170.44              C
ANISOU 4127  CG  LEU A 554    27813  23666  13281   3679   1972  -4929         C
ATOM   4128  CD1 LEU A 554     -3.728  11.233  52.431  1.00174.30              C
ANISOU 4128  CD1 LEU A 554    28508  23992  13728   4150   2268  -5018         C
ATOM   4129  CD2 LEU A 554     -2.818   9.313  53.807  1.00172.38              C
ANISOU 4129  CD2 LEU A 554    28090  24289  13118   3762   2000  -4966         C
ATOM   4130  N   ILE A 555     -4.038   7.463  48.643  1.00157.40              N
ANISOU 4130  N   ILE A 555    24849  22266  12689   2894   1700  -3669         N
```

FIG. 13 Continued

```
ATOM   4131  CA   ILE A 555      -4.169    6.230   47.881  1.00153.81           C
ANISOU 4131  CA   ILE A 555    23986  22004  12452   2559   1555  -3303         C
ATOM   4132  C    ILE A 555      -2.892    5.978   47.076  1.00149.95           C
ANISOU 4132  C    ILE A 555    23581  21186  12208   2090   1243  -3486         C
ATOM   4133  O    ILE A 555      -2.183    5.017   47.364  1.00147.95           O
ANISOU 4133  O    ILE A 555    23254  21039  11923   1800   1055  -3495         O
ATOM   4134  CB   ILE A 555      -5.413    6.236   46.977  1.00153.90           C
ANISOU 4134  CB   ILE A 555    23664  22148  12663   2702   1703  -2905         C
ATOM   4135  CG1  ILE A 555      -6.651    6.614   47.792  1.00158.18           C
ANISOU 4135  CG1  ILE A 555    24131  23002  12969   3200   2033  -2756         C
ATOM   4136  CG2  ILE A 555      -5.610    4.874   46.340  1.00150.67           C
ANISOU 4136  CG2  ILE A 555    22833  21980  12433   2359   1561  -2527         C
ATOM   4137  CD1  ILE A 555      -6.962    5.634   48.884  1.00159.24           C
ANISOU 4137  CD1  ILE A 555    24086  23587  12833   3232   2110  -2587         C
ATOM   4138  N    GLU A 556      -2.564    6.850   46.117  1.00176.38           N
ANISOU 4138  N    GLU A 556    27097  24133  15786   2026   1194  -3639         N
ATOM   4139  CA   GLU A 556      -1.338    6.638   45.344  1.00172.95           C
ANISOU 4139  CA   GLU A 556    26738  23393  15582   1580    919  -3818         C
ATOM   4140  C    GLU A 556      -0.048    6.847   46.140  1.00173.28           C
ANISOU 4140  C    GLU A 556    27103  23259  15478   1440    765  -4254         C
ATOM   4141  O    GLU A 556       0.670    5.878   46.389  1.00171.27           O
ANISOU 4141  O    GLU A 556    26743  23123  15208   1156    572  -4263         O
ATOM   4142  CB   GLU A 556      -1.264    7.427   44.020  1.00171.84           C
ANISOU 4142  CB   GLU A 556    26680  22873  15739   1493    894  -3843         C
ATOM   4143  CG   GLU A 556      -0.540    6.596   42.891  1.00167.50           C
ANISOU 4143  CG   GLU A 556    25945  22217  15479   1003    645  -3750         C
ATOM   4144  CD   GLU A 556       0.547    7.340   42.083  1.00166.21           C
ANISOU 4144  CD   GLU A 556    26054  21574  15522    747    507  -4057         C
ATOM   4145  OE1  GLU A 556       1.558    6.703   41.704  1.00163.36           O
ANISOU 4145  OE1  GLU A 556    25649  21125  15295    352    291  -4151         O
ATOM   4146  OE2  GLU A 556       0.392    8.545   41.805  1.00168.15           O
ANISOU 4146  OE2  GLU A 556    26554  21529  15805    937    619  -4196         O
ATOM   4147  N    LYS A 557       0.258    8.087   46.527  1.00187.43           N
ANISOU 4147  N    LYS A 557    29284  24764  17168   1630    838  -4613         N
ATOM   4148  CA   LYS A 557       1.525    8.386   47.226  1.00188.02           C
ANISOU 4148  CA   LYS A 557    29678  24644  17118   1475    672  -5057         C
ATOM   4149  C    LYS A 557       1.728    7.590   48.514  1.00188.96           C
ANISOU 4149  C    LYS A 557    29761  25111  16924   1505    621  -5085         C
ATOM   4150  O    LYS A 557       2.259    8.110   49.498  1.00191.49           O
ANISOU 4150  O    LYS A 557    30390  25371  16997   1605    602  -5432         O
ATOM   4151  CB   LYS A 557       1.670    9.885   47.514  1.00191.38           C
ANISOU 4151  CB   LYS A 557    30542  24716  17458   1710    787  -5429         C
ATOM   4152  CG   LYS A 557       1.875   10.751   46.278  1.00190.48           C
ANISOU 4152  CG   LYS A 557    30557  24161  17657   1595    775  -5498         C
ATOM   4153  CD   LYS A 557       2.086   12.213   46.660  1.00194.13           C
ANISOU 4153  CD   LYS A 557    31487  24249  18023   1814    880  -5887         C
ATOM   4154  CE   LYS A 557       1.948   13.143   45.459  1.00193.98           C
ANISOU 4154  CE   LYS A 557    31592  23821  18290   1806    939  -5870         C
ATOM   4155  NZ   LYS A 557       2.986   12.896   44.420  1.00190.49           N
ANISOU 4155  NZ   LYS A 557    31105  23127  18146   1317    707  -5928         N
ATOM   4156  N    ALA A 558       1.329    6.321   48.473  1.00148.98           N
ANISOU 4156  N    ALA A 558    24331  20400  11876   1400    587  -4721         N
ATOM   4157  CA   ALA A 558       1.366    5.428   49.616  1.00149.82           C
ANISOU 4157  CA   ALA A 558    24358  20873  11695   1434    555  -4654         C
ATOM   4158  C    ALA A 558       1.658    3.994   49.223  1.00146.33           C
ANISOU 4158  C    ALA A 558    23581  20616  11404   1092    363  -4381         C
ATOM   4159  O    ALA A 558       2.596    3.708   48.481  1.00143.42           O
ANISOU 4159  O    ALA A 558    23182  20029  11281    735    136  -4479         O
ATOM   4160  CB   ALA A 558       0.036    5.471   50.328  1.00152.88           C
ANISOU 4160  CB   ALA A 558    24656  21601  11831   1852    853  -4412         C
ATOM   4161  N    ASP A 559       0.825    3.109   49.764  1.00146.91           N
ANISOU 4161  N    ASP A 559    23408  21095  11315   1215    474  -4039         N
ATOM   4162  CA   ASP A 559       0.871    1.667   49.546  1.00144.27           C
ANISOU 4162  CA   ASP A 559    22747  20987  11081    945    337  -3722         C
ATOM   4163  C    ASP A 559      -0.543    1.136   49.785  1.00145.63           C
ANISOU 4163  C    ASP A 559    22635  21549  11148   1168    577  -3287         C
ATOM   4164  O    ASP A 559      -1.497    1.922   49.895  1.00148.13           O
ANISOU 4164  O    ASP A 559    22981  21924  11379   1505    831  -3234         O
ATOM   4165  CB   ASP A 559       1.860    0.975   50.500  1.00144.34           C
```

FIG. 13 Continued

```
ATOM   4165  CB  ASP A 559      22851 21099 10892    801    132  -3879       C
ANISOU 4165  CB  ASP A 559      22851 21099 10892    801    132  -3879       C
ATOM   4166  CG  ASP A 559       3.143   0.528  49.809  1.00141.02           C
ANISOU 4166  CG  ASP A 559      22416 20430 10736    388   -178  -4036       C
ATOM   4167  OD1 ASP A 559       4.229   0.805  50.353  1.00141.65           O
ANISOU 4167  OD1 ASP A 559      22730 20377 10714    308   -351  -4391       O
ATOM   4168  OD2 ASP A 559       3.067  -0.112  48.737  1.00137.99           O
ANISOU 4168  OD2 ASP A 559      21781 19993 10654    145   -249  -3809       O
ATOM   4169  N   GLY A 560      -0.666  -0.189  49.871  1.00144.57           N
ANISOU 4169  N   GLY A 560      22228 21676 11027    981    497  -2977       N
ATOM   4170  CA  GLY A 560      -1.943  -0.855  50.076  1.00145.76           C
ANISOU 4170  CA  GLY A 560      22071 22209 11100   1123    701  -2538       C
ATOM   4171  C   GLY A 560      -2.615  -0.563  51.405  1.00149.92           C
ANISOU 4171  C   GLY A 560      22697 23038 11228   1508    948  -2523       C
ATOM   4172  O   GLY A 560      -2.259   0.400  52.076  1.00152.22           O
ANISOU 4172  O   GLY A 560      23320 23211 11305   1728   1000  -2870       O
ATOM   4173  N   PHE A 561      -3.583  -1.387  51.799  1.00154.65           N
ANISOU 4173  N   PHE A 561      23017 24026 11585   1105  -2126              N
ATOM   4174  CA  PHE A 561      -4.272  -1.130  53.057  1.00158.84           C
ANISOU 4174  CA  PHE A 561      23629 24870 11855   1957   1369  -2091       C
ATOM   4175  C   PHE A 561      -5.079  -2.259  53.693  1.00160.21           C
ANISOU 4175  C   PHE A 561      23519 25492 11862   1970   1502  -1665       C
ATOM   4176  O   PHE A 561      -5.212  -3.355  53.150  1.00157.92           O
ANISOU 4176  O   PHE A 561      22937 25292 11775   1679   1393  -1349       O
ATOM   4177  CB  PHE A 561      -5.138   0.114  52.924  1.00161.41           C
ANISOU 4177  CB  PHE A 561      24016 25157 12157   2340   1644  -2158       C
ATOM   4178  CG  PHE A 561      -5.413   0.506  51.508  1.00159.12           C
ANISOU 4178  CG  PHE A 561      23573 24626 12259   2241   1610  -2084       C
ATOM   4179  CD1 PHE A 561      -6.272  -0.235  50.728  1.00157.78           C
ANISOU 4179  CD1 PHE A 561      22990 24644 12317   2115   1648  -1656       C
ATOM   4180  CD2 PHE A 561      -4.812   1.628  50.963  1.00158.53           C
ANISOU 4180  CD2 PHE A 561      23780 24138 12317   2269   1537  -2441       C
ATOM   4181  CE1 PHE A 561      -6.524   0.136  49.440  1.00155.91           C
ANISOU 4181  CE1 PHE A 561      22627 24199 12414   2031   1606  -1588       C
ATOM   4182  CE2 PHE A 561      -5.061   2.004  49.676  1.00156.65           C
ANISOU 4182  CE2 PHE A 561      23423 23682 12417   2186   1507  -2363       C
ATOM   4183  CZ  PHE A 561      -5.914   1.257  48.913  1.00155.33           C
ANISOU 4183  CZ  PHE A 561      22846 23716 12456   2072   1537  -1938       C
ATOM   4184  N   ALA A 562      -5.609  -1.943  54.871  1.00160.89           N
ANISOU 4184  N   ALA A 562      23717 25848 11565   2316   1748  -1674       N
ATOM   4185  CA  ALA A 562      -6.335  -2.887  55.711  1.00163.05           C
ANISOU 4185  CA  ALA A 562      23787 26565 11600   2374   1912  -1309       C
ATOM   4186  C   ALA A 562      -7.797  -2.553  55.909  1.00166.38           C
ANISOU 4186  C   ALA A 562      23986 27304 11926   2717   2295  -1039       C
ATOM   4187  O   ALA A 562      -8.239  -1.435  55.672  1.00167.87           O
ANISOU 4187  O   ALA A 562      24253 27387 12142   3006   2465  -1192       O
ATOM   4188  CB  ALA A 562      -5.665  -3.000  57.058  1.00165.29           C
ANISOU 4188  CB  ALA A 562      24379 26957 11465   2464   1872  -1513       C
ATOM   4189  N   GLY A 563      -8.518  -3.533  56.433  1.00166.62           N
ANISOU 4189  N   GLY A 563      23754 27731 11822   2695   2437   -642       N
ATOM   4190  CA  GLY A 563      -9.953  -3.450  56.555  1.00169.67           C
ANISOU 4190  CA  GLY A 563      23839 28473 12157   2960   2793   -310       C
ATOM   4191  C   GLY A 563     -10.371  -3.964  55.203  1.00166.55           C
ANISOU 4191  C   GLY A 563      23059 28010 12211   2673   2683    -17       C
ATOM   4192  O   GLY A 563     -10.716  -5.130  55.041  1.00165.67           O
ANISOU 4192  O   GLY A 563      22644 28102 12202   2407   2642    358       O
ATOM   4193  N   VAL A 564     -10.290  -3.082  54.216  1.00174.45           N
ANISOU 4193  N   VAL A 564      24100 28702 13479   2712   2619   -203       N
ATOM   4194  CA  VAL A 564     -10.574  -3.422  52.827  1.00171.37           C
ANISOU 4194  CA  VAL A 564      23400 28196 13516   2441   2482     13       C
ATOM   4195  C   VAL A 564     -11.801  -4.314  52.622  1.00172.44           C
ANISOU 4195  C   VAL A 564      23045 28725 13749   2365   2636    535       C
ATOM   4196  O   VAL A 564     -11.766  -5.255  51.835  1.00169.69           O
ANISOU 4196  O   VAL A 564      22454 28353 13667   1984   2446    769       O
ATOM   4197  CB  VAL A 564      -9.358  -4.090  52.167  1.00166.85           C
ANISOU 4197  CB  VAL A 564      22924 27303 13167   1984   2096   -110       C
ATOM   4198  CG1 VAL A 564      -9.195  -3.578  50.744  1.00163.91           C
ANISOU 4198  CG1 VAL A 564      22509 26594 13175   1845   1943   -201       C
ATOM   4199  CG2 VAL A 564      -8.099  -3.806  52.968  1.00166.69           C
ANISOU 4199  CG2 VAL A 564      23342 27079 12913   1994   1947   -523       C
```

FIG. 13 Continued

```
ATOM   4200  N   PHE A 565     -12.882  -4.034  53.335  1.00168.63           N
ANISOU 4200  N   PHE A 565    22414  28607  13050   2719   2983    715       N
ATOM   4201  CA  PHE A 565     -14.098  -4.798  53.135  1.00170.06           C
ANISOU 4201  CA  PHE A 565    22105  29177  13333   2656   3146   1209       C
ATOM   4202  C   PHE A 565     -14.501  -4.565  51.687  1.00167.90           C
ANISOU 4202  C   PHE A 565    21576  28749  13471   2534   3035   1316       C
ATOM   4203  O   PHE A 565     -14.296  -3.484  51.156  1.00167.36           O
ANISOU 4203  O   PHE A 565    21686  28401  13503   2716   3009   1049       O
ATOM   4204  CB  PHE A 565     -15.185  -4.341  54.107  1.00175.26           C
ANISOU 4204  CB  PHE A 565    22654  30241  13696   3108   3563   1342       C
ATOM   4205  CG  PHE A 565     -14.790  -4.468  55.552  1.00177.73           C
ANISOU 4205  CG  PHE A 565    23258  30707  13565   3259   3684   1212       C
ATOM   4206  CD1 PHE A 565     -13.950  -3.538  56.138  1.00178.26           C
ANISOU 4206  CD1 PHE A 565    23808  30526  13397   3490   3659    744       C
ATOM   4207  CD2 PHE A 565     -15.251  -5.523  56.321  1.00179.70           C
ANISOU 4207  CD2 PHE A 565    23307  31345  13626   3156   3816   1559       C
ATOM   4208  CE1 PHE A 565     -13.579  -3.656  57.459  1.00180.69           C
ANISOU 4208  CE1 PHE A 565    24393  30983  13279   3624   3752    618       C
ATOM   4209  CE2 PHE A 565     -14.863  -5.646  57.647  1.00182.14           C
ANISOU 4209  CE2 PHE A 565    23897  31802  13505   3296   3922   1450       C
ATOM   4210  CZ  PHE A 565     -14.048  -4.710  58.216  1.00182.64           C
ANISOU 4210  CZ  PHE A 565    24440  31628  13325   3535   3884    976       C
ATOM   4211  N   PRO A 566     -15.057  -5.565  51.032  1.00176.79           N
ANISOU 4211  N   PRO A 566    22298  30045  14830   2211   2959   1707       N
ATOM   4212  CA  PRO A 566     -15.436  -5.482  49.620  1.00174.76           C
ANISOU 4212  CA  PRO A 566    21785  29660  14954   2052   2822   1831       C
ATOM   4213  C   PRO A 566     -15.807  -4.072  49.130  1.00175.95           C
ANISOU 4213  C   PRO A 566    22002  29672  15180   2432   2937   1652       C
ATOM   4214  O   PRO A 566     -15.049  -3.508  48.340  1.00173.15           O
ANISOU 4214  O   PRO A 566    21883  28910  14995   2348   2726   1376       O
ATOM   4215  CB  PRO A 566     -16.633  -6.426  49.535  1.00176.62           C
ANISOU 4215  CB  PRO A 566    21504  30329  15274   1918   2950   2338       C
ATOM   4216  CG  PRO A 566     -16.263  -7.526  50.497  1.00176.88           C
ANISOU 4216  CG  PRO A 566    21594  30516  15096   1709   2942   2450       C
ATOM   4217  CD  PRO A 566     -15.406  -6.901  51.592  1.00177.71           C
ANISOU 4217  CD  PRO A 566    22175  30491  14857   1974   3001   2067       C
ATOM   4218  N   GLU A 567     -16.925  -3.517  49.600  1.00169.65           N
ANISOU 4218  N   GLU A 567    21008  29197  14254   2843   3270   1804       N
ATOM   4219  CA  GLU A 567     -17.401  -2.205  49.149  1.00171.32           C
ANISOU 4219  CA  GLU A 567    21252  29299  14543   3240   3401   1677       C
ATOM   4220  C   GLU A 567     -16.252  -1.225  48.955  1.00169.25           C
ANISOU 4220  C   GLU A 567    21505  28527  14275   3311   3244   1189       C
ATOM   4221  O   GLU A 567     -16.291  -0.352  48.086  1.00168.66           O
ANISOU 4221  O   GLU A 567    21491  28197  14395   3430   3190   1075       O
ATOM   4222  CB  GLU A 567     -18.380  -1.615  50.167  1.00176.61           C
ANISOU 4222  CB  GLU A 567    21831  30329  14943   3757   3813   1753       C
ATOM   4223  CG  GLU A 567     -19.072  -2.637  51.051  1.00179.14           C
ANISOU 4223  CG  GLU A 567    21842  31145  15078   3699   4013   2106       C
ATOM   4224  CD  GLU A 567     -20.426  -3.056  50.525  1.00181.17           C
ANISOU 4224  CD  GLU A 567    21503  31797  15534   3687   4144   2577       C
ATOM   4225  OE1 GLU A 567     -20.810  -2.607  49.420  1.00180.38           O
ANISOU 4225  OE1 GLU A 567    21224  31588  15724   3705   4048   2639       O
ATOM   4226  OE2 GLU A 567     -21.105  -3.834  51.228  1.00183.74           O
ANISOU 4226  OE2 GLU A 567    21541  32550  15721   3653   4340   2891       O
ATOM   4227  N   HIS A 568     -15.231  -1.386  49.786  1.00169.01           N
ANISOU 4227  N   HIS A 568    21843  28357  14016   3231   3168    910       N
ATOM   4228  CA  HIS A 568     -14.054  -0.538  49.762  1.00167.32           C
ANISOU 4228  CA  HIS A 568    22127  27681  13766   3263   3016    431       C
ATOM   4229  C   HIS A 568     -13.411  -0.550  48.389  1.00163.04           C
ANISOU 4229  C   HIS A 568    21611  26758  13580   2917   2698    355       C
ATOM   4230  O   HIS A 568     -13.324   0.482  47.734  1.00162.87           O
ANISOU 4230  O   HIS A 568    21746  26447  13690   3074   2681    168       O
ATOM   4231  CB  HIS A 568     -13.055  -1.021  50.814  1.00166.79           C
ANISOU 4231  CB  HIS A 568    22366  27584  13422   3133   2929    214       C
ATOM   4232  CG  HIS A 568     -13.647  -1.174  52.184  1.00170.94           C
ANISOU 4232  CG  HIS A 568    22867  28510  13571   3423   3229    317       C
ATOM   4233  ND1 HIS A 568     -12.894  -1.090  53.334  1.00172.06           N
ANISOU 4233  ND1 HIS A 568    23379  28626  13369   3509   3240     37       N
ATOM   4234  CD2 HIS A 568     -14.923  -1.390  52.587  1.00174.46           C
```

FIG. 13 Continued

```
ANISOU 4234  CD2 HIS A 568    22960  29404  13922   3650   3534    670        C
ATOM   4235  CE1 HIS A 568   -13.676  -1.255  54.386  1.00 176.05             C
ANISOU 4235  CE1 HIS A 568    23779  29542  13570   3776   3543    214        C
ATOM   4236  NE2 HIS A 568   -14.912  -1.439  53.960  1.00 177.58             N
ANISOU 4236  NE2 HIS A 568    23529  30030  13913   3866   3736    599        N
ATOM   4237  N   LYS A 569   -12.981  -1.731  47.957  1.00 160.12             N
ANISOU 4237  N   LYS A 569    21092  26388  13357   2451   2456    509        N
ATOM   4238  CA  LYS A 569   -12.319  -1.903  46.666  1.00 155.99             C
ANISOU 4238  CA  LYS A 569    20587  25524  13157   2081   2150    447        C
ATOM   4239  C   LYS A 569   -12.960  -1.052  45.570  1.00 156.30             C
ANISOU 4239  C   LYS A 569    20506  25449  13430   2232   2181    510        C
ATOM   4240  O   LYS A 569   -12.366  -0.074  45.114  1.00 155.41             O
ANISOU 4240  O   LYS A 569    20698  24961  13390   2316   2109    205        O
ATOM   4241  CB  LYS A 569   -12.314  -3.383  46.267  1.00 153.60             C
ANISOU 4241  CB  LYS A 569    19989  25368  13005   1621   1967    751        C
ATOM   4242  CG  LYS A 569   -11.305  -4.240  47.039  1.00 152.12             C
ANISOU 4242  CG  LYS A 569    19995  25141  12664   1377   1826    628        C
ATOM   4243  CD  LYS A 569   -11.626  -5.743  46.967  1.00 151.25             C
ANISOU 4243  CD  LYS A 569    19555  25279  12633   1022   1744   1007        C
ATOM   4244  CE  LYS A 569   -10.491  -6.585  47.556  1.00 149.40             C
ANISOU 4244  CE  LYS A 569    19539  24934  12294    760   1554    870        C
ATOM   4245  NZ  LYS A 569   -10.907  -7.955  47.980  1.00 150.01             N
ANISOU 4245  NZ  LYS A 569    19357  25313  12328    537   1566   1238        N
ATOM   4246  N   TYR A 570   -14.170  -1.425  45.158  1.00 181.10             N
ANISOU 4246  N   TYR A 570    23205  28919  16688   2264   2284    913        N
ATOM   4247  CA  TYR A 570   -14.921  -0.679  44.150  1.00 181.92             C
ANISOU 4247  CA  TYR A 570    23141  28978  17001   2433   2318   1030        C
ATOM   4248  C   TYR A 570   -14.535   0.780  44.296  1.00 183.16             C
ANISOU 4248  C   TYR A 570    23705  28811  17077   2806   2411    659        C
ATOM   4249  O   TYR A 570   -14.154   1.432  43.326  1.00 181.50             O
ANISOU 4249  O   TYR A 570    23652  28251  17059   2757   2269    516        O
ATOM   4250  CB  TYR A 570   -16.433  -0.896  44.374  1.00 185.62             C
ANISOU 4250  CB  TYR A 570    23136  29945  17448   2666   2567   1446        C
ATOM   4251  CG  TYR A 570   -17.437  -0.104  43.514  1.00 187.59             C
ANISOU 4251  CG  TYR A 570    23148  30250  17878   2934   2649   1620        C
ATOM   4252  CD1 TYR A 570   -17.152   0.267  42.197  1.00 185.16             C
ANISOU 4252  CD1 TYR A 570    22897  29624  17832   2775   2422   1569        C
ATOM   4253  CD2 TYR A 570   -18.708   0.225  44.023  1.00 192.14             C
ANISOU 4253  CD2 TYR A 570    23419  31224  18360   3349   2960   1860        C
ATOM   4254  CE1 TYR A 570   -18.093   0.972  41.426  1.00 187.23             C
ANISOU 4254  CE1 TYR A 570    22938  29953  18248   3034   2487   1751        C
ATOM   4255  CE2 TYR A 570   -19.647   0.925  43.263  1.00 194.23             C
ANISOU 4255  CE2 TYR A 570    23444  31562  18794   3616   3030   2037        C
ATOM   4256  CZ  TYR A 570   -19.334   1.294  41.969  1.00 191.76             C
ANISOU 4256  CZ  TYR A 570    23207  30922  18733   3458   2784   1985        C
ATOM   4257  OH  TYR A 570   -20.263   1.981  41.224  1.00 194.04             O
ANISOU 4257  OH  TYR A 570    23261  31287  19177   3732   2840   2173        O
ATOM   4258  N   GLU A 571   -14.579   1.267  45.534  1.00 161.56             N
ANISOU 4258  N   GLU A 571    21166  26175  14045   3158   2647    493        N
ATOM   4259  CA  GLU A 571    14.268   2.663  45.818  1.00 163.38             C
ANISOU 4259  CA  GLU A 571    21802  26106  14167   3540   2764    129        C
ATOM   4260  C   GLU A 571   -12.772   2.985  45.698  1.00 160.34             C
ANISOU 4260  C   GLU A 571    21891  25237  13794   3307   2528   -306        C
ATOM   4261  O   GLU A 571   -12.383   3.812  44.877  1.00 159.27             O
ANISOU 4261  O   GLU A 571    21963  24724  13829   3313   2427   -489        O
ATOM   4262  CB  GLU A 571   -14.833   3.084  47.190  1.00 167.91             C
ANISOU 4262  CB  GLU A 571    22442  26953  14405   4002   3104     82        C
ATOM   4263  CG  GLU A 571   -15.038   4.604  47.377  1.00 171.14             C
ANISOU 4263  CG  GLU A 571    23147  27145  14732   4511   3308   -180        C
ATOM   4264  CD  GLU A 571   -16.385   5.119  46.863  1.00 174.16             C
ANISOU 4264  CD  GLU A 571    23191  27732  15249   4870   3514    117        C
ATOM   4265  OE1 GLU A 571   -17.264   5.411  47.700  1.00 178.44             O
ANISOU 4265  OE1 GLU A 571    23618  28589  15593   5293   3834    210        O
ATOM   4266  OE2 GLU A 571   -16.569   5.243  45.631  1.00 172.47             O
ANISOU 4266  OE2 GLU A 571    22825  27373  15332   4742   3358    258        O
ATOM   4267  N   ILE A 572   -11.931   2.323  46.485  1.00 160.81             N
ANISOU 4267  N   ILE A 572    22109  25310  13680   3094   2432   -457        N
ATOM   4268  CA  ILE A 572   -10.507   2.633  46.463  1.00 158.35             C
ANISOU 4268  CA  ILE A 572    22226  24572  13368   2886   2214   -877        C
```

FIG. 13 Continued

```
ATOM   4269  C    ILE A 572      -9.963   2.676  45.053  1.00154.72           C
ANISOU 4269  C    ILE A 572    21774  23767  13244    2557    1958    -909    C
ATOM   4270  O    ILE A 572      -8.945   3.312  44.782  1.00153.26           O
ANISOU 4270  O    ILE A 572    21944  23174  13114    2461    1819   -1261    O
ATOM   4271  CB   ILE A 572      -9.690   1.606  47.218  1.00156.76           C
ANISOU 4271  CB   ILE A 572    22084  24464  13013    2597    2072    -941    C
ATOM   4272  CG1  ILE A 572     -10.504   1.028  48.369  1.00159.83           C
ANISOU 4272  CG1  ILE A 572    22276  25328  13123    2798    2305    -704    C
ATOM   4273  CG2  ILE A 572      -8.419   2.248  47.707  1.00156.30           C
ANISOU 4273  CG2  ILE A 572    22507  24053  12825    2582    1959   -1426    C
ATOM   4274  CD1  ILE A 572      -9.924  -0.236  48.931  1.00158.19           C
ANISOU 4274  CD1  ILE A 572    22020  25273  12811    2473    2156    -628    C
ATOM   4275  N    VAL A 573     -10.644   1.975  44.159  1.00151.25           N
ANISOU 4275  N    VAL A 573    20941  23505  13023    2370    1895    -538    N
ATOM   4276  CA   VAL A 573     -10.238   1.925  42.769  1.00147.99           C
ANISOU 4276  CA   VAL A 573    20504  22810  12917    2051    1661    -525    C
ATOM   4277  C    VAL A 573     -10.836   3.087  41.984  1.00149.56           C
ANISOU 4277  C    VAL A 573    20735  22844  13249    2332    1754    -509    C
ATOM   4278  O    VAL A 573     -10.136   3.755  41.228  1.00147.99           O
ANISOU 4278  O    VAL A 573    20796  22240  13191    2234    1624    -733    O
ATOM   4279  CB   VAL A 573     -10.621   0.578  42.134  1.00145.85           C
ANISOU 4279  CB   VAL A 573    19819  22785  12813    1680    1520    -152    C
ATOM   4280  CG1  VAL A 573     -11.204   0.779  40.742  1.00145.08           C
ANISOU 4280  CG1  VAL A 573    19513  22623  12987    1607    1443      59    C
ATOM   4281  CG2  VAL A 573      -9.413  -0.369  42.117  1.00142.28           C
ANISOU 4281  CG2  VAL A 573    19480  22181  12400    1229    1265    -294    C
ATOM   4282  N    LYS A 574     -12.127   3.331  42.186  1.00164.08           N
ANISOU 4282  N    LYS A 574    22307  24998  15038    2689    1985    -239    N
ATOM   4283  CA   LYS A 574     -12.834   4.421  41.518  1.00166.19           C
ANISOU 4283  CA   LYS A 574    22571  25154  15420    3018    2094    -182    C
ATOM   4284  C    LYS A 574     -12.068   5.731  41.635  1.00166.90           C
ANISOU 4284  C    LYS A 574    23172  24783  15460    3222    2123    -605    C
ATOM   4285  O    LYS A 574     -12.114   6.581  40.742  1.00167.04           O
ANISOU 4285  O    LYS A 574    23309  24516  15643    3311    2089    -643    O
ATOM   4286  CB   LYS A 574     -14.223   4.578  42.131  1.00170.49           C
ANISOU 4286  CB   LYS A 574    22811  26126  15843    3458    2391      93    C
ATOM   4287  CG   LYS A 574     -15.000   5.787  41.654  1.00173.49           C
ANISOU 4287  CG   LYS A 574    23203  26410  16304    3893    2543     138    C
ATOM   4288  CD   LYS A 574      16.481   5.460  41.652  1.00176.45           C
ANISOU 4288  CD   LYS A 574    23057  27282  16705    4125    2720     577    C
ATOM   4289  CE   LYS A 574     -16.721   4.155  40.892  1.00173.73           C
ANISOU 4289  CE   LYS A 574    22287  27180  16541    3656    2507     922    C
ATOM   4290  NZ   LYS A 574     -18.152   3.741  40.864  1.00176.63           N
ANISOU 4290  NZ   LYS A 574    22108  28054  16949    3820    2656    1365    N
ATOM   4291  N    LYS A 575     -11.375   5.886  42.758  1.00170.83           N
ANISOU 4291  N    LYS A 575    23976  25210  15720    3291    2183    -919    N
ATOM   4292  CA   LYS A 575     -10.564   7.067  43.014  1.00171.70           C
ANISOU 4292  CA   LYS A 575    24594  24885  15759    3449    2202   -1356    C
ATOM   4293  C    LYS A 575      -9.198   6.855  42.378  1.00167.63           C
ANISOU 4293  C    LYS A 575    24306  23992  15392    2975    1905   -1599    C
ATOM   4294  O    LYS A 575      -8.625   7.764  41.779  1.00167.22           O
ANISOU 4294  O    LYS A 575    24561  23516  15459    2960    1838   -1834    O
ATOM   4295  CB   LYS A 575     -10.427   7.309  44.522  1.00174.51           C
ANISOU 4295  CB   LYS A 575    25177  25354  15777    3722    2386   -1594    C
ATOM   4296  CG   LYS A 575     -11.746   7.218  45.302  1.00178.43           C
ANISOU 4296  CG   LYS A 575    25389  26316  16089    4138    2692   -1324    C
ATOM   4297  CD   LYS A 575     -12.703   8.358  44.954  1.00181.89           C
ANISOU 4297  CD   LYS A 575    25824  26693  16594    4614    2909   -1252    C
ATOM   4298  CE   LYS A 575     -14.073   8.177  45.610  1.00185.76           C
ANISOU 4298  CE   LYS A 575    25954  27689  16940    5008    3213    -938    C
ATOM   4299  NZ   LYS A 575     -14.918   7.172  44.902  1.00184.53           N
ANISOU 4299  NZ   LYS A 575    25235  27905  16972    4810    3153    -455    N
ATOM   4300  N    LEU A 576      -8.685   5.638  42.505  1.00153.81           N
ANISOU 4300  N    LEU A 576    22400  22400  13642    2588    1734   -1533    N
ATOM   4301  CA   LEU A 576      -7.400   5.300  41.920  1.00150.00           C
ANISOU 4301  CA   LEU A 576    22083  21606  13305    2132    1457   -1741    C
ATOM   4302  C    LEU A 576      -7.358   5.686  40.447  1.00148.23           C
ANISOU 4302  C    LEU A 576    21847  21101  13371    1973    1336   -1673    C
ATOM   4303  O    LEU A 576      -6.517   6.495  40.035  1.00147.55           O
```

FIG. 13 Continued

```
ANISOU 4303  O   LEU A 576    22102  20594  13367   1899   1257  -1970           O
ATOM   4304  CB  LEU A 576     -7.104   3.815  42.096  1.00147.40           C
ANISOU 4304  CB  LEU A 576    21500  21533  12973   1763   1301  -1579           C
ATOM   4305  CG  LEU A 576     -6.136   3.517  43.237  1.00147.25           C
ANISOU 4305  CG  LEU A 576    21711  21502  12735   1682   1243  -1867           C
ATOM   4306  CD1 LEU A 576     -6.287   2.089  43.689  1.00146.16           C
ANISOU 4306  CD1 LEU A 576    21277  21729  12530   1476   1185  -1613           C
ATOM   4307  CD2 LEU A 576     -4.705   3.799  42.806  1.00144.70           C
ANISOU 4307  CD2 LEU A 576    21699  20750  12530   1377   1017  -2233           C
ATOM   4308  N   GLN A 577     -8.264   5.111  39.656  1.00158.87           N
ANISOU 4308  N   GLN A 577    22808  22687  14867   1912   1320  -1278           N
ATOM   4309  CA  GLN A 577     -8.340   5.442  38.238  1.00157.50           C
ANISOU 4309  CA  GLN A 577    22604  22291  14946   1777   1206  -1174           C
ATOM   4310  C   GLN A 577     -8.502   6.958  38.105  1.00160.20           C
ANISOU 4310  C   GLN A 577    23253  22328  15287   2149   1348  -1344           C
ATOM   4311  O   GLN A 577     -7.895   7.576  37.231  1.00159.02           O
ANISOU 4311  O   GLN A 577    23338  21791  15289   2013   1241  -1493           O
ATOM   4312  CB  GLN A 577     -9.518   4.740  37.544  1.00157.58           C
ANISOU 4312  CB  GLN A 577    22142  22655  15077   1749   1202   -710           C
ATOM   4313  CG  GLN A 577     -9.970   3.413  38.146  1.00157.21           C
ANISOU 4313  CG  GLN A 577    21732  23053  14947   1613   1205   -456           C
ATOM   4314  CD  GLN A 577    -11.385   3.022  37.709  1.00158.84           C
ANISOU 4314  CD  GLN A 577    21476  23646  15231   1725   1278     -5           C
ATOM   4315  OE1 GLN A 577    -12.203   2.584  38.520  1.00161.01           O
ANISOU 4315  OE1 GLN A 577    21491  24314  15373   1903   1439    201           O
ATOM   4316  NE2 GLN A 577    -11.675   3.191  36.424  1.00158.00           N
ANISOU 4316  NE2 GLN A 577    21263  23437  15333   1616   1159    152           N
ATOM   4317  N   GLU A 578     -9.304   7.556  38.987  1.00156.45           N
ANISOU 4317  N   GLU A 578    22788  22020  14637   2622   1598  -1325           N
ATOM   4318  CA  GLU A 578     -9.576   8.991  38.925  1.00159.55           C
ANISOU 4318  CA  GLU A 578    23466  22134  15021   3027   1757  -1467           C
ATOM   4319  C   GLU A 578     -8.302   9.841  38.977  1.00158.92           C
ANISOU 4319  C   GLU A 578    23905  21539  14939   2921   1682  -1924           C
ATOM   4320  O   GLU A 578     -8.296  10.977  38.508  1.00160.52           O
ANISOU 4320  O   GLU A 578    24377  21395  15221   3111   1736  -2039           O
ATOM   4321  CB  GLU A 578    -10.572   9.418  40.010  1.00163.92           C
ANISOU 4321  CB  GLU A 578    23957  22966  15359   3557   2053  -1407           C
ATOM   4322  CG  GLU A 578    -11.261  10.763  39.737  1.00167.57           C
ANISOU 4322  CG  GLU A 578    24576  23232  15860   4034   2237  -1407           C
ATOM   4323  CD  GLU A 578    -12.074  11.276  40.923  1.00172.14           C
ANISOU 4323  CD  GLU A 578    25168  24034  16201   4575   2549  -1431           C
ATOM   4324  OE1 GLU A 578    -12.486  10.463  41.784  1.00172.72           O
ANISOU 4324  OE1 GLU A 578    24983  24536  16106   4607   2645  -1301           O
ATOM   4325  OE2 GLU A 578    -12.304  12.502  40.989  1.00175.33           O
ANISOU 4325  OE2 GLU A 578    25854  24178  16587   4974   2707  -1580           O
ATOM   4326  N   ARG A 579     -7.232   9.302  39.553  1.00150.70           N
ANISOU 4326  N   ARG A 579    23002  20446  13811   2618   1556  -2179           N
ATOM   4327  CA  ARG A 579     -5.947   9.999  39.559  1.00149.94           C
ANISOU 4327  CA  ARG A 579    23357  19880  13732   2448   1454  -2611           C
ATOM   4328  C   ARG A 579     -5.261   9.792  38.213  1.00146.47           C
ANISOU 4328  C   ARG A 579    22915  19178  13559   2016   1229  -2586           C
ATOM   4329  O   ARG A 579     -4.047   9.972  38.083  1.00144.80           O
ANISOU 4329  O   ARG A 579    22975  18641  13401   1724   1089  -2898           O
ATOM   4330  CB  ARG A 579     -5.044   9.486  40.682  1.00149.23           C
ANISOU 4330  CB  ARG A 579    23395  19857  13448   2288   1387  -2889           C
ATOM   4331  CG  ARG A 579     -4.960  10.396  41.898  1.00152.87           C
ANISOU 4331  CG  ARG A 579    24204  20226  13655   2647   1561  -3209           C
ATOM   4332  CD  ARG A 579     -4.096  11.636  41.646  1.00153.73           C
ANISOU 4332  CD  ARG A 579    24789  19790  13830   2630   1528  -3601           C
ATOM   4333  NE  ARG A 579     -2.655  11.365  41.649  1.00151.13           N
ANISOU 4333  NE  ARG A 579    24644  19232  13545   2190   1296  -3912           N
ATOM   4334  CZ  ARG A 579     -1.949  11.008  42.721  1.00151.25           C
ANISOU 4334  CZ  ARG A 579    24770  19340  13357   2103   1233  -4163           C
ATOM   4335  NH1 ARG A 579     -2.537  10.840  43.898  1.00153.74           N
ANISOU 4335  NH1 ARG A 579    25045  19976  13393   2412   1387  -4138           N
ATOM   4336  NH2 ARG A 579     -0.647  10.802  42.615  1.00149.01           N
ANISOU 4336  NH2 ARG A 579    24629  18843  13146   1705   1012  -4432           N
ATOM   4337  N   LYS A 580     -6.057   9.418  37.215  1.00144.39           N
ANISOU 4337  N   LYS A 580    22336  19070  13455   1978   1199  -2214           N
```

FIG. 13 Continued

```
ATOM   4338  CA  LYS A 580      -5.556    9.097   35.878  1.00141.22           C
ANISOU 4338  CA  LYS A 580    21886  18482  13289    1574    994  -2136        C
ATOM   4339  C   LYS A 580      -4.546    7.958   35.993  1.00137.66           C
ANISOU 4339  C   LYS A 580    21359  18091  12856    1109    796  -2245        C
ATOM   4340  O   LYS A 580      -3.392    8.074   35.573  1.00135.65           O
ANISOU 4340  O   LYS A 580    21327  17514  12700     792    654  -2498        O
ATOM   4341  CB  LYS A 580      -4.972   10.325   35.150  1.00141.80           C
ANISOU 4341  CB  LYS A 580    22353  18041  13483    1571    982  -2358        C
ATOM   4342  CG  LYS A 580      -5.982   11.449   34.815  1.00145.29           C
ANISOU 4342  CG  LYS A 580    22872  18384  13948    2021   1156  -2210        C
ATOM   4343  CD  LYS A 580      -7.393   10.931   34.515  1.00146.24           C
ANISOU 4343  CD  LYS A 580    22541  18936  14086    2229   1217  -1751        C
ATOM   4344  CE  LYS A 580      -7.449   10.044   33.280  1.00143.15           C
ANISOU 4344  CE  LYS A 580    21858  18656  13876    1844   1015  -1473        C
ATOM   4345  NZ  LYS A 580      -8.697    9.231   33.234  1.00143.76           N
ANISOU 4345  NZ  LYS A 580    21445  19231  13945    1957   1044  -1056        N
ATOM   4346  N   HIS A 581      -5.010    6.853   36.569  1.00142.27           N
ANISOU 4346  N   HIS A 581    21618  19093  13347    1080    795  -2039        N
ATOM   4347  CA  HIS A 581      -4.169    5.695   36.810  1.00139.33           C
ANISOU 4347  CA  HIS A 581    21152  18815  12973     692    622  -2108        C
ATOM   4348  C   HIS A 581      -4.750    4.402   36.246  1.00137.38           C
ANISOU 4348  C   HIS A 581    20479  18895  12824     462    525  -1732        C
ATOM   4349  O   HIS A 581      -5.848    3.989   36.624  1.00138.95           O
ANISOU 4349  O   HIS A 581    20388  19464  12942     663    638  -1437        O
ATOM   4350  CB  HIS A 581      -3.925    5.549   38.314  1.00140.78           C
ANISOU 4350  CB  HIS A 581    21430  19155  12905     848    701  -2294        C
ATOM   4351  CG  HIS A 581      -2.817    6.415   38.825  1.00141.41           C
ANISOU 4351  CG  HIS A 581    21938  18878  12912     851    681  -2748        C
ATOM   4352  ND1 HIS A 581      -2.824    7.786   38.686  1.00143.66           N
ANISOU 4352  ND1 HIS A 581    22539  18839  13204    1091    792  -2941        N
ATOM   4353  CD2 HIS A 581      -1.657    6.107   39.454  1.00140.26           C
ANISOU 4353  CD2 HIS A 581    21956  18644  12694     631    552  -3047        C
ATOM   4354  CE1 HIS A 581      -1.719    8.286   39.211  1.00143.88           C
ANISOU 4354  CE1 HIS A 581    22909  18590  13166    1002    734  -3346        C
ATOM   4355  NE2 HIS A 581      -0.993    7.288   39.685  1.00141.84           N
ANISOU 4355  NE2 HIS A 581    22555  18480  12858     725    584  -3418        N
ATOM   4356  N   ILE A 582      -4.006    3.780   35.331  1.00129.32           N
ANISOU 4356  N   ILE A 582    19425  17731  11978      37    321  -1748        N
ATOM   4357  CA  ILE A 582      -4.384    2.490   34.756  1.00127.28           C
ANISOU 4357  CA  ILE A 582    18806  17733  11823    -241    200  -1438        C
ATOM   4358  C   ILE A 582      -4.148    1.495   35.874  1.00126.89           C
ANISOU 4358  C   ILE A 582    18648  17934  11631    -309    183  -1450        C
ATOM   4359  O   ILE A 582      -3.033    1.412   36.379  1.00125.81           O
ANISOU 4359  O   ILE A 582    18720  17633  11448    -450    101  -1748        O
ATOM   4360  CB  ILE A 582      -3.499    2.109   33.517  1.00124.04           C
ANISOU 4360  CB  ILE A 582    18441  17064  11623    -683     -9  -1509        C
ATOM   4361  CG1 ILE A 582      -3.536    3.211   32.429  1.00124.52           C
ANISOU 4361  CG1 ILE A 582    18687  16818  11808    -631      6  -1543        C
ATOM   4362  CG2 ILE A 582      -3.921    0.742   32.957  1.00122.21           C
ANISOU 4362  CG2 ILE A 582    17850  17096  11486    -968   -133  -1198        C
ATOM   4363  CD1 ILE A 582      -2.239    3.403   31.607  1.00122.18           C
ANISOU 4363  CD1 ILE A 582    18639  16128  11654    -979   -135  -1812        C
ATOM   4364  N   VAL A 583      -5.171    0.753   36.289  1.00128.70           N
ANISOU 4364  N   VAL A 583    18553  18560  11785    -210    258  -1128        N
ATOM   4365  CA  VAL A 583      -4.983   -0.156   37.426  1.00128.72           C
ANISOU 4365  CA  VAL A 583    18475  18803  11630    -250    260  -1123        C
ATOM   4366  C   VAL A 583      -5.818   -1.419   37.426  1.00128.52           C
ANISOU 4366  C   VAL A 583    18053  19156  11622    -378    245   -735        C
ATOM   4367  O   VAL A 583      -7.043   -1.378   37.255  1.00130.37           O
ANISOU 4367  O   VAL A 583    18030  19646  11860    -198    364   -430        O
ATOM   4368  CB  VAL A 583      -5.266    0.528   38.781  1.00131.90           C
ANISOU 4368  CB  VAL A 583    19024  19323  11770     161    467  -1246        C
ATOM   4369  CG1 VAL A 583      -5.338   -0.515   39.887  1.00132.31           C
ANISOU 4369  CG1 VAL A 583    18930  19696  11645     133    485  -1139        C
ATOM   4370  CG2 VAL A 583      -4.206    1.560   39.099  1.00132.13           C
ANISOU 4370  CG2 VAL A 583    19477  18984  11741     231    454  -1687        C
ATOM   4371  N   GLY A 584      -5.129   -2.538   37.641  1.00131.62           N
ANISOU 4371  N   GLY A 584    18402  19579  12029    -689     96   -754        N
ATOM   4372  CA  GLY A 584      -5.762   -3.830   37.775  1.00131.47           C
```

FIG. 13 Continued

```
ANISOU 4372  CA  GLY A 584    18050  19887  12017   -848     70   -417       C
ATOM   4373  C   GLY A 584     -5.638  -4.262  39.216  1.00132.86            C
ANISOU 4373  C   GLY A 584    18257  20267  11957    723    151    445       C
ATOM   4374  O   GLY A 584     -4.661  -3.922  39.890  1.00132.65            O
ANISOU 4374  O   GLY A 584    18516  20069  11816   -680    120   -766       O
ATOM   4375  N   MET A 585     -6.634  -4.994  39.699  1.00132.46            N
ANISOU 4375  N   MET A 585    17914  20591  11826   -667    256   -106       N
ATOM   4376  CA  MET A 585     -6.589  -5.507  41.062  1.00133.99            C
ANISOU 4376  CA  MET A 585    18121  21008  11780   -562    341    -85       C
ATOM   4377  C   MET A 585     -7.195  -6.891  41.150  1.00134.01            C
ANISOU 4377  C   MET A 585    17798  21307  11812   -780    316    289       C
ATOM   4378  O   MET A 585     -8.096  -7.244  40.391  1.00134.16            O
ANISOU 4378  O   MET A 585    17522  21473  11981   -880    323    588       O
ATOM   4379  CB  MET A 585     -7.307  -4.596  42.045  1.00137.58            C
ANISOU 4379  CB  MET A 585    18629  21656  11990   -101    608    -98       C
ATOM   4380  CG  MET A 585     -7.578  -5.300  43.362  1.00139.59            C
ANISOU 4380  CG  MET A 585    18810  22236  11992     -7    724     41       C
ATOM   4381  SD  MET A 585     -8.652  -4.364  44.453  1.00144.26            S
ANISOU 4381  SD  MET A 585    19394  23126  12294    537   1078     96       S
ATOM   4382  CE  MET A 585     -9.674  -3.535  43.237  1.00144.89            C
ANISOU 4382  CE  MET A 585    19271  23181  12599    684   1162    256       C
ATOM   4383  N   THR A 586     -6.688  -7.665  42.099  1.00149.86            N
ANISOU 4383  N   THR A 586    19869  23398  13672   -855    280    270       N
ATOM   4384  CA  THR A 586     -7.115  -9.034  42.290  1.00149.97            C
ANISOU 4384  CA  THR A 586    19625  23653  13704  -1082    248    605       C
ATOM   4385  C   THR A 586     -8.546  -9.127  42.779  1.00153.24            C
ANISOU 4385  C   THR A 586    19741  24479  14002   -876    489    965       C
ATOM   4386  O   THR A 586     -9.136  -8.139  43.212  1.00155.68            O
ANISOU 4386  O   THR A 586    20073  24911  14168   -506    700    931       O
ATOM   4387  CB  THR A 586     -6.228  -9.721  43.321  1.00149.78            C
ANISOU 4387  CB  THR A 586    19775  23622  13513  -1151    170    493       C
ATOM   4388  OG1 THR A 586     -4.925  -9.118  43.307  1.00148.05            O
ANISOU 4388  OG1 THR A 586    19892  23067  13294  -1157     30     70       O
ATOM   4389  CG2 THR A 586     -6.131 -11.217  43.029  1.00148.36            C
ANISOU 4389  CG2 THR A 586    19419  23477  13472  -1532     13    736       C
ATOM   4390  N   GLY A 587     -9.088 -10.337  42.711  1.00140.61            N
ANISOU 4390  N   GLY A 587    17864  23090  12472  -1122    460   1309       N
ATOM   4391  CA  GLY A 587    -10.427 -10.630  43.185  1.00143.80            C
ANISOU 4391  CA  GLY A 587    17943  23912  12783   -992    679   1688       C
ATOM   4392  C   GLY A 587    -10.508 -12.116  43.470  1.00143.76            C
ANISOU 4392  C   GLY A 587    17773  24053  12797  -1310    607   1969       C
ATOM   4393  O   GLY A 587     -9.625 -12.872  43.064  1.00141.10            O
ANISOU 4393  O   GLY A 587    17546  23473  12591  -1632    374   1882       O
ATOM   4394  N   ASP A 588    -11.556 -12.539  44.171  1.00140.65            N
ANISOU 4394  N   ASP A 588    17119  24047  12273  -1220    813   2308       N
ATOM   4395  CA  ASP A 588    -11.749 -13.949  44.502  1.00141.16            C
ANISOU 4395  CA  ASP A 588    17021  24267  12347  -1517    773   2614       C
ATOM   4396  C   ASP A 588    -13.143 -14.150  45.054  1.00145.03            C
ANISOU 4396  C   ASP A 588    17161  25213  12731  -1388   1041   3006       C
ATOM   4397  O   ASP A 588    -13.838 -15.104  44.719  1.00145.76            O
ANISOU 4397  O   ASP A 588    16948  25472  12961  -1667   1021   3350       O
ATOM   4398  CB  ASP A 588    -10.716 -14.415  45.536  1.00140.78            C
ANISOU 4398  CB  ASP A 588    17275  24120  12096  -1525    712   2457       C
ATOM   4399  CG  ASP A 588    -10.565 -13.445  46.703  1.00142.90            C
ANISOU 4399  CG  ASP A 588    17772  24491  12035  -1093    909   2249       C
ATOM   4400  OD1 ASP A 588    -10.540 -12.222  46.456  1.00142.83            O
ANISOU 4400  OD1 ASP A 588    17873  24382  12014   -830    971   2004       O
ATOM   4401  OD2 ASP A 588    -10.451 -13.900  47.867  1.00144.78            O
ANISOU 4401  OD2 ASP A 588    18098  24894  12016  -1017    997   2323       O
ATOM   4402  N   GLY A 589    -13.530 -13.220  45.913  1.00148.23            N
ANISOU 4402  N   GLY A 589    17618  25814  12888   -961   1297   2939       N
ATOM   4403  CA  GLY A 589    -14.818 -13.244  46.564  1.00152.32            C
ANISOU 4403  CA  GLY A 589    17822  26784  13268   -765   1596   3274       C
ATOM   4404  C   GLY A 589    -15.922 -12.879  45.605  1.00153.27            C
ANISOU 4404  C   GLY A 589    17570  27060  13605   -745   1653   3477       C
ATOM   4405  O   GLY A 589    -15.678 -12.241  44.574  1.00151.10            O
ANISOU 4405  O   GLY A 589    17352  26538  13522   -753   1505   3293       O
ATOM   4406  N   VAL A 590    -17.136 -13.290  45.970  1.00157.14            N
ANISOU 4406  N   VAL A 590    17675  27974  14056   -717   1869   3867       N
```

FIG. 13 Continued

```
ATOM   4407  CA  VAL A 590     -18.333 -13.073  45.172  1.00158.80           C
ANISOU 4407  CA  VAL A 590    17458  28418  14461   -704   1937   4127       C
ATOM   4408  C   VAL A 590     -18.809 -11.630  45.300  1.00160.82           C
ANISOU 4408  C   VAL A 590    17721  28766  14618   -189   2154   3985       C
ATOM   4409  O   VAL A 590     -19.276 -11.035  44.330  1.00160.62           O
ANISOU 4409  O   VAL A 590    17528  28713  14788   -127   2101   3999       O
ATOM   4410  CB  VAL A 590     -19.428 -14.059  45.580  1.00162.10           C
ANISOU 4410  CB  VAL A 590    17450  29267  14873    874   2096   4596       C
ATOM   4411  CG1 VAL A 590     -20.061 -13.623  46.884  1.00166.31           C
ANISOU 4411  CG1 VAL A 590    17924  30172  15095   -462   2473   4693       C
ATOM   4412  CG2 VAL A 590     -20.451 -14.191  44.475  1.00162.89           C
ANISOU 4412  CG2 VAL A 590    17100  29534  15256  -1046   2035   4869       C
ATOM   4413  N   ASN A 591     -18.682 -11.068  46.497  1.00161.19           N
ANISOU 4413  N   ASN A 591    17977  28914  14355    187   2393   3844       N
ATOM   4414  CA  ASN A 591     -18.985  -9.664  46.680  1.00163.08           C
ANISOU 4414  CA  ASN A 591    18302  29178  14484    694   2596   3653       C
ATOM   4415  C   ASN A 591     -17.982  -8.884  45.858  1.00159.44           C
ANISOU 4415  C   ASN A 591    18195  28233  14152    694   2355   3256       C
ATOM   4416  O   ASN A 591     -18.296  -7.848  45.298  1.00159.93           O
ANISOU 4416  O   ASN A 591    18246  28221  14300    956   2397   3155       O
ATOM   4417  CB  ASN A 591     -18.834  -9.240  48.139  1.00165.75           C
ANISOU 4417  CB  ASN A 591    18884  29653  14440   1066   2866   3512       C
ATOM   4418  CG  ASN A 591     -19.983  -9.687  49.003  1.00170.25           C
ANISOU 4418  CG  ASN A 591    19099  30742  14847   1190   3189   3890       C
ATOM   4419  OD1 ASN A 591     -20.364  -8.997  49.946  1.00173.65           O
ANISOU 4419  OD1 ASN A 591    19589  31383  15007   1620   3495   3835       O
ATOM   4420  ND2 ASN A 591     -20.537 -10.851  48.699  1.00170.51           N
ANISOU 4420  ND2 ASN A 591    18765  30983  15036    808   3131   4274       N
ATOM   4421  N   ASP A 592     -16.765  -9.407  45.775  1.00157.42           N
ANISOU 4421  N   ASP A 592    18250  27646  13916    394   2103   3042       N
ATOM   4422  CA  ASP A 592     -15.668  -8.719  45.107  1.00153.99           C
ANISOU 4422  CA  ASP A 592    18182  26744  13584    369   1881   2644       C
ATOM   4423  C   ASP A 592     -15.899  -8.315  43.662  1.00152.30           C
ANISOU 4423  C   ASP A 592    17835  26360  13672    266   1723   2656       C
ATOM   4424  O   ASP A 592     -15.110  -7.563  43.094  1.00150.01           O
ANISOU 4424  O   ASP A 592    17840  25701  13458    300   1584   2335       O
ATOM   4425  CB  ASP A 592     -14.398  -9.547  45.207  1.00150.71           C
ANISOU 4425  CB  ASP A 592    18042  26050  13172     16   1630   2472       C
ATOM   4426  CG  ASP A 592     -13.710  -9.369  46.529  1.00151.71           C
ANISOU 4426  CG  ASP A 592    18500  26166  12976    222   1728   2247       C
ATOM   4427  OD1 ASP A 592     -12.556  -8.895  46.523  1.00149.49           O
ANISOU 4427  OD1 ASP A 592    18597  25536  12666    229   1577   1864       O
ATOM   4428  OD2 ASP A 592     -14.333  -9.677  47.571  1.00154.91           O
ANISOU 4428  OD2 ASP A 592    18786  26921  13150    376   1959   2452       O
ATOM   4429  N   ALA A 593     -16.977  -8.797  43.065  1.00152.23           N
ANISOU 4429  N   ALA A 593    17387  26624  13830    135   1739   3027       N
ATOM   4430  CA  ALA A 593     -17.227  -8.482  41.671  1.00150.82           C
ANISOU 4430  CA  ALA A 593    17072  26308  13925     18   1569   3062       C
ATOM   4431  C   ALA A 593     -16.918  -7.016  41.325  1.00150.55           C
ANISOU 4431  C   ALA A 593    17311  26006  13887    372   1597   2750       C
ATOM   4432  O   ALA A 593     -15.983  -6.749  40.567  1.00147.33           O
ANISOU 4432  O   ALA A 593    17179  25201  13598    212   1377   2488       O
ATOM   4433  CB  ALA A 593     -18.650  -8.857  41.285  1.00153.61           C
ANISOU 4433  CB  ALA A 593    16892  27071  14401    -15   1657   3497       C
ATOM   4434  N   PRO A 594     -17.664  -6.066  41.923  1.00161.12           N
ANISOU 4434  N   PRO A 594    18590  27548  15079    857   1879   2770       N
ATOM   4435  CA  PRO A 594     -17.599  -4.621  41.651  1.00161.80           C
ANISOU 4435  CA  PRO A 594    18899  27418  15160   1250   1952   2524       C
ATOM   4436  C   PRO A 594     -16.205  -4.086  41.384  1.00158.45           C
ANISOU 4436  C   PRO A 594    18978  26483  14744   1172   1768   2088       C
ATOM   4437  O   PRO A 594     -16.010  -3.288  40.465  1.00157.38           O
ANISOU 4437  O   PRO A 594    18970  26072  14754   1225   1667   1951       O
ATOM   4438  CB  PRO A 594     -18.138  -4.008  42.942  1.00165.84           C
ANISOU 4438  CB  PRO A 594    19431  28186  15395   1737   2302   2508       C
ATOM   4439  CG  PRO A 594     -19.121  -4.998  43.419  1.00168.25           C
ANISOU 4439  CG  PRO A 594    19292  28975  15662   1642   2440   2915       C
ATOM   4440  CD  PRO A 594     -18.569  -6.353  43.045  1.00165.02           C
ANISOU 4440  CD  PRO A 594    18831  28495  15375   1074   2175   3018       C
ATOM   4441  N   ALA A 595     -15.250  -4.506  42.199  1.00184.13           N
```

FIG. 13 Continued

```
ANISOU 4441  N   ALA A 595    22507  29617  17836   1051   1730   1878       N
ATOM   4442  CA  ALA A 595    -13.884  -4.073  42.010  1.00181.12           C
ANISOU 4442  CA  ALA A 595    22577  28776  17464    950   1551   1464       C
ATOM   4443  C   ALA A 595    -13.450  -4.494  40.618  1.00177.58           C
ANISOU 4443  C   ALA A 595    22090  28080  17304    539   1258   1481       C
ATOM   4444  O   ALA A 595    -13.220  -3.653  39.746  1.00176.60           O
ANISOU 4444  O   ALA A 595    22110  27679  17311    591   1178   1328       O
ATOM   4445  CB  ALA A 595    -12.988  -4.697  43.054  1.00180.26           C
ANISOU 4445  CB  ALA A 595    22695  28638  17158    828   1520   1300       C
ATOM   4446  N   LEU A 596    -13.385  -5.807  40.415  1.00160.84           N
ANISOU 4446  N   LEU A 596    19774  26065  15274    134   1108   1681       N
ATOM   4447  CA  LEU A 596    -12.938  -6.403  39.158  1.00157.55           C
ANISOU 4447  CA  LEU A 596    19320  25430  15111   -297    827   1700       C
ATOM   4448  C   LEU A 596    -13.521  -5.744  37.909  1.00157.65           C
ANISOU 4448  C   LEU A 596    19202  25381  15317   -253    773   1790       C
ATOM   4449  O   LEU A 596    -12.790  -5.337  37.001  1.00155.22           O
ANISOU 4449  O   LEU A 596    19113  24721  15141   -387    603   1578       O
ATOM   4450  CB  LEU A 596    -13.261  -7.896  39.166  1.00157.15           C
ANISOU 4450  CB  LEU A 596    18975  25609  15125   -667    740   2008       C
ATOM   4451  CG  LEU A 596    -12.603  -8.651  40.325  1.00156.90           C
ANISOU 4451  CG  LEU A 596    19091  25610  14913   -747    758   1936       C
ATOM   4452  CD1 LEU A 596    -13.067 -10.102  40.397  1.00157.15           C
ANISOU 4452  CD1 LEU A 596    18823  25884  15003  -1083    706   2282       C
ATOM   4453  CD2 LEU A 596    -11.083  -8.570  40.214  1.00153.63           C
ANISOU 4453  CD2 LEU A 596    19081  24775  14516   -904    563   1544       C
ATOM   4454  N   LYS A 597    -14.842  -5.646  37.860  1.00142.40           N
ANISOU 4454  N   LYS A 597    16904  23802  13400    -65    918   2113       N
ATOM   4455  CA  LYS A 597    -15.482  -5.017  36.723  1.00142.98           C
ANISOU 4455  CA  LYS A 597    16828  23856  13642      9    866   2229       C
ATOM   4456  C   LYS A 597    -14.980  -3.572  36.591  1.00143.00           C
ANISOU 4456  C   LYS A 597    17199  23526  13607    339    921   1908       C
ATOM   4457  O   LYS A 597    -14.398  -3.206  35.572  1.00140.78           O
ANISOU 4457  O   LYS A 597    17105  22919  13467    190    743   1758       O
ATOM   4458  CB  LYS A 597    -17.011  -5.094  36.852  1.00146.78           C
ANISOU 4458  CB  LYS A 597    16834  24809  14127    209   1036   2627       C
ATOM   4459  CG  LYS A 597    -17.762  -5.299  35.521  1.00146.87           C
ANISOU 4459  CG  LYS A 597    16520  24919  14365     17    868   2897       C
ATOM   4460  CD  LYS A 597    -19.120  -5.980  35.737  1.00150.08           C
ANISOU 4460  CD  LYS A 597    16388  25839  14794      9    973   3331       C
ATOM   4461  CE  LYS A 597    -20.041  -5.849  34.533  1.00151.28           C
ANISOU 4461  CE  LYS A 597    16202  26137  15139    -40    848   3593       C
ATOM   4462  NZ  LYS A 597    -19.484  -6.492  33.316  1.00147.96           N
ANISOU 4462  NZ  LYS A 597    15846  25477  14894   -529    521   3562       N
ATOM   4463  N   LYS A 598    -15.153  -2.763  37.630  1.00145.17           N
ANISOU 4463  N   LYS A 598    17606  23866  13686    774   1170   1790       N
ATOM   4464  CA  LYS A 598    -14.743  -1.364  37.529  1.00145.63           C
ANISOU 4464  CA  LYS A 598    18021  23599  13713   1098   1234   1491       C
ATOM   4465  C   LYS A 598    -13.256  -1.171  37.311  1.00142.23           C
ANISOU 4465  C   LYS A 598    18037  22700  13303    874   1057   1097       C
ATOM   4466  O   LYS A 598    -12.860  -0.548  36.336  1.00140.86           O
ANISOU 4466  O   LYS A 598    18039  22213  13269    817    935    969       O
ATOM   4467  CB  LYS A 598    -15.212  -0.519  38.720  1.00149.35           C
ANISOU 4467  CB  LYS A 598    18572  24217  13958   1620   1544   1417       C
ATOM   4468  CG  LYS A 598    -14.996   1.003  38.522  1.00150.52           C
ANISOU 4468  CG  LYS A 598    19061  24033  14096   1990   1625   1150       C
ATOM   4469  CD  LYS A 598    -15.142   1.408  37.048  1.00149.42           C
ANISOU 4469  CD  LYS A 598    18878  23695  14199   1889   1454   1236       C
ATOM   4470  CE  LYS A 598    -14.922   2.895  36.814  1.00150.70           C
ANISOU 4470  CE  LYS A 598    19394  23503  14363   2240   1531    991       C
ATOM   4471  NZ  LYS A 598    -16.182   3.678  36.935  1.00155.01           N
ANISOU 4471  NZ  LYS A 598    19732  24278  14887   2742   1758   1199       N
ATOM   4472  N   ALA A 599    -12.434  -1.684  38.216  1.00181.91           N
ANISOU 4472  N   ALA A 599    23242  27685  18189    751   1046    909       N
ATOM   4473  CA  ALA A 599    -10.991  -1.523  38.077  1.00178.91           C
ANISOU 4473  CA  ALA A 599    23263  26886  17831    539    879    529       C
ATOM   4474  C   ALA A 599    -10.620  -1.679  36.614  1.00176.07           C
ANISOU 4474  C   ALA A 599    22897  26280  17721    198    643    541       C
ATOM   4475  O   ALA A 599    -11.225  -2.491  35.911  1.00175.51           O
ANISOU 4475  O   ALA A 599    22503  26400  17784    -32    546    842       O
```

FIG. 13 Continued

```
ATOM   4476  CB  ALA A 599     -10.256  -2.544  38.921  1.00177.49           C
ANISOU 4476  CB  ALA A 599    23136  26763  17538    304    810    450       C
ATOM   4477  N   ASP A 600      -9.647  -0.898  36.150  1.00136.81           N
ANISOU 4477  N   ASP A 600    18283  20892  12805    160    556    217       N
ATOM   4478  CA  ASP A 600      -9.246  -0.959  34.748  1.00134.29           C
ANISOU 4478  CA  ASP A 600    17994  20325  12705   -150    351    210       C
ATOM   4479  C   ASP A 600      -9.188  -2.408  34.290  1.00132.03           C
ANISOU 4479  C   ASP A 600    17455  20181  12529    587    169    405       C
ATOM   4480  O   ASP A 600      -9.990  -2.851  33.449  1.00132.17           O
ANISOU 4480  O   ASP A 600    17181  20369  12670   -715    101    703       O
ATOM   4481  CB  ASP A 600      -7.889  -0.296  34.544  1.00132.37           C
ANISOU 4481  CB  ASP A 600    18178  19626  12491   -251    263   -200       C
ATOM   4482  CG  ASP A 600      -7.987   1.203  34.489  1.00134.41           C
ANISOU 4482  CG  ASP A 600    18693  19658  12717    107    395   -362       C
ATOM   4483  OD1 ASP A 600      -7.006   1.855  34.873  1.00134.02           O
ANISOU 4483  OD1 ASP A 600    19004  19306  12614    137    401   -718       O
ATOM   4484  OD2 ASP A 600      -9.043   1.732  34.071  1.00136.58           O
ANISOU 4484  OD2 ASP A 600    18812  20056  13026    358    490   -134       O
ATOM   4485  N   ILE A 601      -8.237  -3.144  34.855  1.00128.49           N
ANISOU 4485  N   ILE A 601    17126  19659  12034   -813     85    234       N
ATOM   4486  CA  ILE A 601      -8.112  -4.559  34.563  1.00126.55           C
ANISOU 4486  CA  ILE A 601    16677  19525  11882  -1211    -76    398       C
ATOM   4487  C   ILE A 601      -9.043  -5.310  35.511  1.00128.69           C
ANISOU 4487  C   ILE A 601    16651  20215  12028  -1111     50    690       C
ATOM   4488  O   ILE A 601     -10.086  -4.782  35.904  1.00131.62           O
ANISOU 4488  O   ILE A 601    16865  20834  12311   -780    239    864       O
ATOM   4489  CB  ILE A 601      -6.666  -5.056  34.704  1.00123.75           C
ANISOU 4489  CB  ILE A 601    16571  18900  11548  -1493   -230    100       C
ATOM   4490  CG1 ILE A 601      -5.671  -3.900  34.527  1.00122.98           C
ANISOU 4490  CG1 ILE A 601    16852  18419  11456  -1403   -239   -285       C
ATOM   4491  CG2 ILE A 601      -6.407  -6.210  33.732  1.00121.26           C
ANISOU 4491  CG2 ILE A 601    16116  18540  11419  -1940   -440    215       C
ATOM   4492  CD1 ILE A 601      -5.873  -3.064  33.294  1.00122.79           C
ANISOU 4492  CD1 ILE A 601    16883  18199  11571  -1394   -266   -283       C
ATOM   4493  N   GLY A 602      -8.676  -6.532  35.885  1.00128.45           N
ANISOU 4493  N   GLY A 602    16545  20265  11993  -1389    -44    750       N
ATOM   4494  CA  GLY A 602      -9.532  -7.334  36.745  1.00130.51           C
ANISOU 4494  CA  GLY A 602    16528  20916  12144  -1341     71   1048       C
ATOM   4495  C   GLY A 602      -8.987  -8.724  36.971  1.00128.83           C
ANISOU 4495  C   GLY A 602    16274  20714  11961  -1700    -72   1103       C
ATOM   4496  O   GLY A 602      -9.635  -9.734  36.700  1.00129.11           O
ANISOU 4496  O   GLY A 602    16023  20953  12081  -1928   -120   1408       O
ATOM   4497  N   ILE A 603      -7.767  -8.755  37.472  1.00125.81           N
ANISOU 4497  N   ILE A 603    16190  20099  11513  -1749   -145    798       N
ATOM   4498  CA  ILE A 603      -7.064  -9.968  37.744  1.00124.23           C
ANISOU 4498  CA  ILE A 603    16007  19857  11336  -2053   -289    801       C
ATOM   4499  C   ILE A 603      -7.796 -10.842  38.784  1.00126.47           C
ANISOU 4499  C   ILE A 603    16081  20499  11473  -2011   -171   1099       C
ATOM   4500  O   ILE A 603      -8.194 -10.342  39.839  1.00128.93           O
ANISOU 4500  O   ILE A 603    16413  21009  11564  -1684     27   1113       O
ATOM   4501  CB  ILE A 603      -5.678  -9.654  38.293  1.00122.85           C
ANISOU 4501  CB  ILE A 603    16188  19411  11079  -2019   -359    408       C
ATOM   4502  CG1 ILE A 603      -5.386  -8.154  38.125  1.00123.09           C
ANISOU 4502  CG1 ILE A 603    16455  19237  11075  -1758   -288    117       C
ATOM   4503  CG2 ILE A 603      -4.628 -10.531  37.651  1.00119.88           C
ANISOU 4503  CG2 ILE A 603    15890  18782  10879  -2405   -596    289       C
ATOM   4504  CD1 ILE A 603      -5.232  -7.688  36.708  1.00121.31           C
ANISOU 4504  CD1 ILE A 603    16260  18763  11068  -1908   -393     43       C
ATOM   4505  N   ALA A 604      -7.949 -12.134  38.506  1.00134.30           N
ANISOU 4505  N   ALA A 604    16888  21563  12577  -2343   -284   1331       N
ATOM   4506  CA  ALA A 604      -8.624 -13.019  39.449  1.00136.51           C
ANISOU 4506  CA  ALA A 604    16972  22166  12731  -2345   -176   1636       C
ATOM   4507  C   ALA A 604      -7.955 -14.385  39.496  1.00135.00           C
ANISOU 4507  C   ALA A 604    16811  21866  12615  -2700   -353   1684       C
ATOM   4508  O   ALA A 604      -8.225 -15.238  38.655  1.00134.15           O
ANISOU 4508  O   ALA A 604    16532  21736  12702  -3025   -478   1866       O
ATOM   4509  CB  ALA A 604     -10.087 -13.161  39.076  1.00138.71           C
ANISOU 4509  CB  ALA A 604    16868  22763  13070  -2343    -63   2015       C
ATOM   4510  N   VAL A 605      -7.096 -14.598  40.489  1.00125.89           N
```

FIG. 13 Continued

```
ANISOU 4510  N   VAL A 605       15880  20648  11303  -2631   -368   1523       N
ATOM   4511  CA  VAL A 605       -6.352 -15.854  40.601  1.00124.59              C
ANISOU 4511  CA  VAL A 605       15778  20354  11206  -2928   -541   1548       C
ATOM   4512  C   VAL A 605       -7.241 -17.080  40.825  1.00126.33              C
ANISOU 4512  C   VAL A 605       15732  20822  11445  -3126   -503   1968       C
ATOM   4513  O   VAL A 605       -8.224 -17.016  41.553  1.00129.17              O
ANISOU 4513  O   VAL A 605       15917  21513  11648  -2953   -300   2218       O
ATOM   4514  CB  VAL A 605       -5.303 -15.769  41.708  1.00124.60              C
ANISOU 4514  CB  VAL A 605       16062  20271  11009  -2774   -564   1306       C
ATOM   4515  CG1 VAL A 605       -5.856 -14.974  42.878  1.00127.48              C
ANISOU 4515  CG1 VAL A 605       16453  20906  11077  -2383   -326   1326       C
ATOM   4516  CG2 VAL A 605       -4.858 -17.170  42.134  1.00124.46              C
ANISOU 4516  CG2 VAL A 605       16055  20231  11004  -3013   -687   1447       C
ATOM   4517  N   ALA A 606       -6.868 -18.201  40.212  1.00124.44              N
ANISOU 4517  N   ALA A 606       15470  20412  11399  -3492   -692   2038       N
ATOM   4518  CA  ALA A 606       -7.663 -19.431  40.268  1.00126.01              C
ANISOU 4518  CA  ALA A 606       15430  20789  11658  -3743   -683   2429       C
ATOM   4519  C   ALA A 606       -8.187 -19.759  41.647  1.00129.05              C
ANISOU 4519  C   ALA A 606       15753  21482  11798  -3577   -498   2670       C
ATOM   4520  O   ALA A 606       -7.700 -19.254  42.655  1.00129.70              O
ANISOU 4520  O   ALA A 606       16031  21599  11651  -3298   -416   2510       O
ATOM   4521  CB  ALA A 606       -6.897 -20.621  39.701  1.00124.09              C
ANISOU 4521  CB  ALA A 606       15272  20264  11612  -4117   -915   2406       C
ATOM   4522  N   ASP A 607       -9.181 -20.635  41.664  1.00188.16              N
ANISOU 4522  N   ASP A 607       22968  29190  19333  -3771   -435   3059       N
ATOM   4523  CA  ASP A 607       -9.876 -20.977  42.883  1.00191.48              C
ANISOU 4523  CA  ASP A 607       23278  29943  19530  -3641   -228   3349       C
ATOM   4524  C   ASP A 607      -10.622 -19.717  43.298  1.00193.36              C
ANISOU 4524  C   ASP A 607       23418  30460  19590  -3248     16   3332       C
ATOM   4525  O   ASP A 607      -11.212 -19.658  44.375  1.00196.34              O
ANISOU 4525  O   ASP A 607       23722  31145  19734  -3038    239   3515       O
ATOM   4526  CB  ASP A 607       -8.898 -21.434  43.967  1.00191.54              C
ANISOU 4526  CB  ASP A 607       23571  29853  19352  -3571   -269   3249       C
ATOM   4527  CG  ASP A 607       -9.555 -22.330  45.007  1.00194.82              C
ANISOU 4527  CG  ASP A 607       23869  30549  19604  -3608   -121   3631       C
ATOM   4528  OD1 ASP A 607      -10.778 -22.572  44.897  1.00197.09              O
ANISOU 4528  OD1 ASP A 607       23840  31115  19930  -3694     27   3968       O
ATOM   4529  OD2 ASP A 607       -8.848 -22.793  45.932  1.00195.30              O
ANISOU 4529  OD2 ASP A 607       24151  30558  19498  -3557   -153   3602       O
ATOM   4530  N   ALA A 608      -10.587 -18.711  42.423  1.00135.04              N
ANISOU 4530  N   ALA A 608       16040  22955  12313  -3144    -22   3112       N
ATOM   4531  CA  ALA A 608      -11.270 -17.436  42.660  1.00136.75              C
ANISOU 4531  CA  ALA A 608       16177  23385  12395  -2759    195   3071       C
ATOM   4532  C   ALA A 608      -12.783 -17.583  42.545  1.00139.72              C
ANISOU 4532  C   ALA A 608       16137  24144  12808  -2766    370   3468       C
ATOM   4533  O   ALA A 608      -13.510 -16.589  42.518  1.00141.30              O
ANISOU 4533  O   ALA A 608       16203  24532  12952  -2472    541   3479       O
ATOM   4534  CB  ALA A 608      -10.777 -16.373  41.691  1.00134.28              C
ANISOU 4534  CB  ALA A 608       16006  22805  12209  -2671     90   2741       C
ATOM   4535  N   THR A 609      -13.239 -18.832  42.488  1.00142.65              N
ANISOU 4535  N   THR A 609       16302  24623  13276  -3103    326   3792       N
ATOM   4536  CA  THR A 609      -14.648 -19.171  42.337  1.00145.60              C
ANISOU 4536  CA  THR A 609       16248  25360  13715  -3193    463   4196       C
ATOM   4537  C   THR A 609      -15.116 -18.812  40.938  1.00144.51              C
ANISOU 4537  C   THR A 609       15910  25167  13828  -3323    337   4197       C
ATOM   4538  O   THR A 609      -14.630 -17.859  40.325  1.00142.43              O
ANISOU 4538  O   THR A 609       15813  24692  13610  -3167    260   3900       O
ATOM   4539  CB  THR A 609      -15.532 -18.469  43.369  1.00149.26              C
ANISOU 4539  CB  THR A 609       16557  26224  13931  -2791    795   4339       C
ATOM   4540  OG1 THR A 609      -15.863 -17.160  42.897  1.00149.26              O
ANISOU 4540  OG1 THR A 609       16511  26255  13945  -2478    869   4179       O
ATOM   4541  CG2 THR A 609      -14.813 -18.369  44.709  1.00149.84              C
ANISOU 4541  CG2 THR A 609       16944  26286  13702  -2549    907   4190       C
ATOM   4542  N   ASP A 610      -16.066 -19.584  40.435  1.00214.39              N
ANISOU 4542  N   ASP A 610       24408  34212  22839  -3619    311   4538       N
ATOM   4543  CA  ASP A 610      -16.565 -19.383  39.085  1.00213.68              C
ANISOU 4543  CA  ASP A 610       24109  34096  22983  -3786    165   4574       C
ATOM   4544  C   ASP A 610      -17.502 -18.177  38.969  1.00215.73              C
ANISOU 4544  C   ASP A 610       24135  34634  23199  -3417    344   4627       C
```

FIG. 13 Continued

```
ATOM   4545  O   ASP A 610     -17.999 -17.870  37.889  1.00215.55           O
ANISOU 4545  O   ASP A 610      23924  34628  23347   -3497    235   4670    O
ATOM   4546  CB  ASP A 610     -17.229 -20.667  38.587  1.00214.89           C
ANISOU 4546  CB  ASP A 610      23974  34352  23322   -4257     53   4910    C
ATOM   4547  CG  ASP A 610     -16.373 -21.896  38.853  1.00213.47           C
ANISOU 4547  CG  ASP A 610      24028  33910  23172   -4584    -88   4890    C
ATOM   4548  OD1 ASP A 610     -16.202 -22.259  40.039  1.00214.81           O
ANISOU 4548  OD1 ASP A 610      24292  34169  23159   -4485     57   4971    O
ATOM   4549  OD2 ASP A 610     -15.865 -22.495  37.879  1.00211.18           O
ANISOU 4549  OD2 ASP A 610      23837  33323  23079   -4930   -342   4792    O
ATOM   4550  N   ALA A 611     -17.737 -17.494  40.085  1.00147.46           N
ANISOU 4550  N   ALA A 611      15510  26203  14315   -3004    615   4621    N
ATOM   4551  CA  ALA A 611     -18.594 -16.316  40.096  1.00149.73           C
ANISOU 4551  CA  ALA A 611      15601  26745  14544   -2599    812   4658    C
ATOM   4552  C   ALA A 611     -17.749 -15.105  39.809  1.00147.30           C
ANISOU 4552  C   ALA A 611      15647  26125  14196   -2308    763   4248    C
ATOM   4553  O   ALA A 611     -18.036 -14.318  38.917  1.00146.95           O
ANISOU 4553  O   ALA A 611      15531  26034  14268   -2201    707   4187    O
ATOM   4554  CB  ALA A 611     -19.256 -16.160  41.446  1.00153.48           C
ANISOU 4554  CB  ALA A 611      15943  27599  14773   -2285   1147   4837    C
ATOM   4555  N   ALA A 612     -16.695 -14.966  40.592  1.00144.72           N
ANISOU 4555  N   ALA A 612      15707  25582  13697   -2184    780   3972    N
ATOM   4556  CA  ALA A 612     -15.801 -13.846  40.440  1.00142.58           C
ANISOU 4556  CA  ALA A 612      15800  24999  13375   -1928    739   3565    C
ATOM   4557  C   ALA A 612     -15.345 -13.734  38.992  1.00139.47           C
ANISOU 4557  C   ALA A 612      15477  24286  13230   -2172    468   3416    C
ATOM   4558  O   ALA A 612     -15.459 -12.674  38.378  1.00139.23           O
ANISOU 4558  O   ALA A 612      15483  24170  13247   -1960    472   3282    O
ATOM   4559  CB  ALA A 612     -14.609 -13.992  41.378  1.00141.16           C
ANISOU 4559  CB  ALA A 612      16015  24609  13012   -1883    723   3299    C
ATOM   4560  N   ARG A 613     -14.857 -14.837  38.439  1.00152.00           N
ANISOU 4560  N   ARG A 613      17087  25697  14970   -2615    241   3448    N
ATOM   4561  CA  ARG A 613     -14.345 -14.816  37.081  1.00149.07           C
ANISOU 4561  CA  ARG A 613      16810  25014  14816   -2869    -14   3293    C
ATOM   4562  C   ARG A 613     -15.246 -14.005  36.162  1.00150.21           C
ANISOU 4562  C   ARG A 613      16724  25283  15064   -2743     -2   3395    C
ATOM   4563  O   ARG A 613     -14.764 -13.250  35.320  1.00148.30           O
ANISOU 4563  O   ARG A 613      16665  24781  14901   -2697   -112   3165    O
ATOM   4564  CB  ARG A 613     -14.204 -16.231  36.537  1.00147.89           C
ANISOU 4564  CB  ARG A 613      16574  24784  14834   -3371   -221   3441    C
ATOM   4565  CG  ARG A 613     -13.409 -17.166  37.418  1.00147.16           C
ANISOU 4565  CG  ARG A 613      16675  24584  14656   -3511   -244   3397    C
ATOM   4566  CD  ARG A 613     -12.743 -18.238  36.569  1.00144.68           C
ANISOU 4566  CD  ARG A 613      16450  23982  14541   -3970   -510   3352    C
ATOM   4567  NE  ARG A 613     -12.578 -19.495  37.291  1.00145.35           N
ANISOU 4567  NE  ARG A 613      16538  24093  14596   -4190   -523   3515    N
ATOM   4568  CZ  ARG A 613     -11.514 -19.804  38.024  1.00144.10           C
ANISOU 4568  CZ  ARG A 613      16675  23738  14340   -4160   -554   3328    C
ATOM   4569  NH1 ARG A 613     -10.510 -18.942  38.137  1.00142.10           N
ANISOU 4569  NH1 ARG A 613      16726  23255  14012   -3936   -577   2960    N
ATOM   4570  NH2 ARG A 613     -11.453 -20.976  38.648  1.00145.05           N
ANISOU 4570  NH2 ARG A 613      16786  23891  14437   -4360   -567   3517    N
ATOM   4571  N   GLY A 614     -16.555 -14.147  36.351  1.00141.16           N
ANISOU 4571  N   GLY A 614      15175  24544  13915   -2677    139   3748    N
ATOM   4572  CA  GLY A 614     -17.552 -13.489  35.518  1.00142.83           C
ANISOU 4572  CA  GLY A 614      15102  24935  14231   -2559    145   3906    C
ATOM   4573  C   GLY A 614     -17.454 -11.990  35.267  1.00142.78           C
ANISOU 4573  C   GLY A 614      15262  24809  14180   -2143    219   3686    C
ATOM   4574  O   GLY A 614     -18.175 -11.461  34.422  1.00143.90           O
ANISOU 4574  O   GLY A 614      15199  25049  14427   -2067    181   3804    O
ATOM   4575  N   ALA A 615     -16.575 -11.298  35.985  1.00140.83           N
ANISOU 4575  N   ALA A 615      15387  24346  13777   -1875    317   3371    N
ATOM   4576  CA  ALA A 615     -16.413  -9.856  35.797  1.00140.91           C
ANISOU 4576  CA  ALA A 615      15601  24198  13742   -1485    393   3140    C
ATOM   4577  C   ALA A 615     -14.938  -9.486  35.744  1.00137.54           C
ANISOU 4577  C   ALA A 615      15660  23311  13287   -1523    280   2716    C
ATOM   4578  O   ALA A 615     -14.570  -8.308  35.734  1.00137.39           O
ANISOU 4578  O   ALA A 615      15893  23096  13214   -1221    343   2467    O
ATOM   4579  CB  ALA A 615     -17.113  -9.090  36.904  1.00144.42           C
```

FIG. 13 Continued

```
ANISOU 4579  CB  ALA A 615    15961  24922  13991   -996    708   3202        C
ATOM   4580  N   SER A 616   -14.103 -10.516  35.710  1.00 134.63             N
ANISOU 4580  N   SER A 616    15415  22772  12967  -1899    111   2641        N
ATOM   4581  CA  SER A 616   -12.660 -10.357  35.677  1.00 131.49             C
ANISOU 4581  CA  SER A 616    15437  21964  12560  -1987    -12   2257        C
ATOM   4582  C   SER A 616   -12.204  -9.999  34.270  1.00 129.11             C
ANISOU 4582  C   SER A 616    15255  21357  12442  -2168   -213   2109        C
ATOM   4583  O   SER A 616   -12.732 -10.524  33.290  1.00 128.93             O
ANISOU 4583  O   SER A 616    15008  21404  12577  -2428   -348   2313        O
ATOM   4584  CB  SER A 616   -11.998 -11.658  36.127  1.00 130.03             C
ANISOU 4584  CB  SER A 616    15305  21729  12370  -2315   -119   2263        C
ATOM   4585  OG  SER A 616   -12.831 -12.365  37.035  1.00 132.64             O
ANISOU 4585  OG  SER A 616    15375  22426  12598  -2289     27   2570        O
ATOM   4586  N   ASP A 617   -11.226  -9.104  34.175  1.00 127.08             N
ANISOU 4586  N   ASP A 617    15358  20768  12159  -2039   -233   1754        N
ATOM   4587  CA  ASP A 617   -10.701  -8.674  32.879  1.00 124.92             C
ANISOU 4587  CA  ASP A 617    15240  20184  12041  -2196   -402   1592        C
ATOM   4588  C   ASP A 617    -9.521  -9.552  32.418  1.00 121.64             C
ANISOU 4588  C   ASP A 617    15005  19483  11732  -2607   -614   1408        C
ATOM   4589  O   ASP A 617    -8.866  -9.260  31.420  1.00 119.63             O
ANISOU 4589  O   ASP A 617    14925  18939  11590  -2762   -748   1227        O
ATOM   4590  CB  ASP A 617   -10.356  -7.168  32.883  1.00 125.25             C
ANISOU 4590  CB  ASP A 617    15560  20009  12021  -1848   -302   1329        C
ATOM   4591  CG  ASP A 617   -11.602  -6.263  33.009  1.00 128.59             C
ANISOU 4591  CG  ASP A 617    15789  20683  12386  -1449   -117   1531        C
ATOM   4592  OD1 ASP A 617   -11.437  -5.040  33.211  1.00 129.48             O
ANISOU 4592  OD1 ASP A 617    16125  20643  12426   1114      0   1338        O
ATOM   4593  OD2 ASP A 617   -12.743  -6.769  32.905  1.00 130.50             O
ANISOU 4593  OD2 ASP A 617    15654  21270  12661  -1468    -86   1880        O
ATOM   4594  N   ILE A 618    -9.275 -10.628  33.164  1.00 125.72             N
ANISOU 4594  N   ILE A 618    15474  20088  12205  -2769   -632   1466        N
ATOM   4595  CA  ILE A 618    -8.272 -11.649  32.855  1.00 123.10             C
ANISOU 4595  CA  ILE A 618    15265  19532  11975  -3146   -822   1342        C
ATOM   4596  C   ILE A 618    -8.778 -12.865  33.609  1.00 124.36             C
ANISOU 4596  C   ILE A 618    15204  19954  12092  -3275   -797   1614        C
ATOM   4597  O   ILE A 618    -9.979 -13.017  33.749  1.00 126.74             O
ANISOU 4597  O   ILE A 618    15206  20577  12372  -3209   -701   1929        O
ATOM   4598  CB  ILE A 618    -6.861 -11.281  33.354  1.00 121.28             C
ANISOU 4598  CB  ILE A 618    15396  19001  11684  -3087   -846    952        C
ATOM   4599  CG1 ILE A 618    -6.489  -9.855  32.934  1.00 120.91             C
ANISOU 4599  CG1 ILE A 618    15574  18733  11631  -2870   -802    693        C
ATOM   4600  CG2 ILE A 618    -5.842 -12.275  32.839  1.00 118.67             C
ANISOU 4600  CG2 ILE A 618    15171  18427  11490  -3468  -1047    824        C
ATOM   4601  CD1 ILE A 618    -5.039  -9.550  33.058  1.00 118.85             C
ANISOU 4601  CD1 ILE A 618    15649  18137  11373  -2916   -875    303        C
ATOM   4602  N   VAL A 619    -7.879 -13.718  34.090  1.00 120.01             N
ANISOU 4602  N   VAL A 619    14794  19269  11534  -3453   -881   1503        N
ATOM   4603  CA  VAL A 619    -8.212 -14.888  34.931  1.00 121.27             C
ANISOU 4603  CA  VAL A 619    14802  19639  11638  -3568   -854   1745        C
ATOM   4604  C   VAL A 619    -7.055 -15.861  34.896  1.00 119.06             C
ANISOU 4604  C   VAL A 619    14705  19096  11436  -3852  -1029   1589        C
ATOM   4605  O   VAL A 619    -6.763 -16.451  33.854  1.00 117.38             O
ANISOU 4605  O   VAL A 619    14492  18700  11407  -4170  -1200   1567        O
ATOM   4606  CB  VAL A 619    -9.498 -15.670  34.527  1.00 123.10             C
ANISOU 4606  CB  VAL A 619    14661  20154  11957  -3763   -854   2152        C
ATOM   4607  CG1 VAL A 619    -9.307 -17.167  34.769  1.00 122.91             C
ANISOU 4607  CG1 VAL A 619    14587  20122  11991  -4096   -956   2302        C
ATOM   4608  CG2 VAL A 619   -10.703 -15.188  35.313  1.00 126.40             C
ANISOU 4608  CG2 VAL A 619    14837  20961  12227  -3454   -621   2403        C
ATOM   4609  N   LEU A 620    -6.401 -16.037  36.036  1.00 119.15             N
ANISOU 4609  N   LEU A 620    14875  19094  11303  -3729   -987   1481        N
ATOM   4610  CA  LEU A 620    -5.233 -16.898  36.094  1.00 117.28             C
ANISOU 4610  CA  LEU A 620    14820  18607  11133  -3949  -1151   1319        C
ATOM   4611  C   LEU A 620    -5.576 -18.362  36.397  1.00 118.21             C
ANISOU 4611  C   LEU A 620    14790  18835  11290  -4199  -1200   1612        C
ATOM   4612  O   LEU A 620    -6.722 -18.705  36.744  1.00 120.55             O
ANISOU 4612  O   LEU A 620    14839  19432  11532  -4191  -1086   1949        O
ATOM   4613  CB  LEU A 620    -4.215 -16.357  37.110  1.00 116.99             C
ANISOU 4613  CB  LEU A 620    15051  18471  10931  -3707  -1121   1026        C
```

FIG. 13 Continued

```
ATOM   4614  CG  LEU A 620      -3.755 -14.905  36.936  1.00116.28           C
ANISOU 4614  CG  LEU A 620    15150  18237  10795  -3466  -1073    706       C
ATOM   4615  CD1 LEU A 620      -4.899 -13.935  37.166  1.00118.50           C
ANISOU 4615  CD1 LEU A 620    15303  18767  10955  -3167   -869    845       C
ATOM   4616  CD2 LEU A 620      -2.598 -14.570  37.864  1.00115.91           C
ANISOU 4616  CD2 LEU A 620    15372  18058  10612  -3310  -1095    397       C
ATOM   4617  N   THR A 621      -4.567 -19.214  36.199  1.00153.72           N
ANISOU 4617  N   THR A 621    19436  23074  15896  -4430  -1371   1481       N
ATOM   4618  CA  THR A 621      -4.593 -20.618  36.612  1.00154.52           C
ANISOU 4618  CA  THR A 621    19482  23199  16028  -4649  -1433   1701       C
ATOM   4619  C   THR A 621      -3.300 -20.834  37.412  1.00153.66           C
ANISOU 4619  C   THR A 621    19631  22911  15843  -4564  -1507   1465       C
ATOM   4620  O   THR A 621      -2.991 -21.947  37.864  1.00154.13           O
ANISOU 4620  O   THR A 621    19721  22923  15917  -4704  -1580   1579       O
ATOM   4621  CB  THR A 621      -4.678 -21.632  35.445  1.00153.55           C
ANISOU 4621  CB  THR A 621    19276  22915  16149  -5053  -1596   1799       C
ATOM   4622  OG1 THR A 621      -4.140 -21.053  34.248  1.00151.24           O
ANISOU 4622  OG1 THR A 621    19083  22383  15997  -5134  -1698   1532       O
ATOM   4623  CG2 THR A 621      -6.125 -22.091  35.232  1.00155.75           C
ANISOU 4623  CG2 THR A 621    19247  23473  16460  -5195  -1528   2193       C
ATOM   4624  N   GLU A 622      -2.557 -19.748  37.603  1.00138.10           N
ANISOU 4624  N   GLU A 622    17844  20839  13789  -4331  -1469   1140       N
ATOM   4625  CA  GLU A 622      -1.312 -19.823  38.340  1.00137.45           C
ANISOU 4625  CA  GLU A 622    17991  20602  13630  -4238  -1572    891       C
ATOM   4626  C   GLU A 622      -1.229 -18.820  39.486  1.00138.79           C
ANISOU 4626  C   GLU A 622    18272  20926  13536  -3872  -1440    766       C
ATOM   4627  O   GLU A 622      -1.515 -17.639  39.332  1.00138.87           O
ANISOU 4627  O   GLU A 622    18299  20979  13487  -3680  -1334    642       O
ATOM   4628  CB  GLU A 622      -0.113 -19.716  37.392  1.00134.72           C
ANISOU 4628  CB  GLU A 622    17803  19905  13481  -4391  -1740    553       C
ATOM   4629  CG  GLU A 622       0.327 -21.069  36.798  1.00133.76           C
ANISOU 4629  CG  GLU A 622    17671  19587  13564  -4717  -1906    618       C
ATOM   4630  CD  GLU A 622      -0.847 -21.924  36.314  1.00134.81           C
ANISOU 4630  CD  GLU A 622    17587  19849  13787  -4945  -1884    985       C
ATOM   4631  OE1 GLU A 622      -1.560 -21.486  35.378  1.00134.48           O
ANISOU 4631  OE1 GLU A 622    17422  19847  13826  -5025  -1850   1040       O
ATOM   4632  OE2 GLU A 622      -1.059 -23.033  36.870  1.00136.16           O
ANISOU 4632  OE2 GLU A 622    17710  20081  13944  -5050  -1906   1224       O
ATOM   4633  N   PRO A 623      -0.850 -19.330  40.653  1.00123.45           N
ANISOU 4633  N   PRO A 623    16416  19062  11426  -3776  -1448    806       N
ATOM   4634  CA  PRO A 623      -0.676 -18.737  41.976  1.00125.20           C
ANISOU 4634  CA  PRO A 623    16768  19446  11358  -3459  -1351    719       C
ATOM   4635  C   PRO A 623      -0.080 -17.337  42.087  1.00124.63           C
ANISOU 4635  C   PRO A 623    16878  19282  11193  -3221  -1324    343       C
ATOM   4636  O   PRO A 623      -0.759 -16.328  41.892  1.00125.19           O
ANISOU 4636  O   PRO A 623    16906  19446  11214  -3056  -1176    324       O
ATOM   4637  CB  PRO A 623       0.286 -19.727  42.647  1.00125.26           C
ANISOU 4637  CB  PRO A 623    16904  19356  11334  -3534  -1507    694       C
ATOM   4638  CG  PRO A 623      -0.106 -21.047  42.089  1.00125.08           C
ANISOU 4638  CG  PRO A 623    16732  19291  11502  -3840  -1576    988       C
ATOM   4639  CD  PRO A 623      -0.694 -20.795  40.708  1.00123.60           C
ANISOU 4639  CD  PRO A 623    16394  19026  11543  -4022  -1564   1013       C
ATOM   4640  N   GLY A 624       1.205 -17.325  42.431  1.00138.11           N
ANISOU 4640  N   GLY A 624    18788  20804  12883  -3208  -1475     52       N
ATOM   4641  CA  GLY A 624       1.950 -16.145  42.834  1.00138.07           C
ANISOU 4641  CA  GLY A 624    18990  20718  12754  -2992  -1475   -318       C
ATOM   4642  C   GLY A 624       1.912 -14.848  42.062  1.00137.06           C
ANISOU 4642  C   GLY A 624    18914  20459  12704  -2920  -1411   -551       C
ATOM   4643  O   GLY A 624       1.755 -14.830  40.846  1.00135.33           O
ANISOU 4643  O   GLY A 624    18606  20095  12716  -3106  -1440   -538       O
ATOM   4644  N   LEU A 625       2.083 -13.752  42.796  1.00116.14           N
ANISOU 4644  N   LEU A 625    16429  17852   9847  -2647  -1327   -773       N
ATOM   4645  CA  LEU A 625       2.147 -12.424  42.209  1.00115.56           C
ANISOU 4645  CA  LEU A 625    16455  17627   9824  -2549  -1264  -1024       C
ATOM   4646  C   LEU A 625       3.265 -12.442  41.178  1.00112.86           C
ANISOU 4646  C   LEU A 625    16184  16952   9745  -2801  -1447  -1284       C
ATOM   4647  O   LEU A 625       3.341 -11.579  40.308  1.00111.81           O
ANISOU 4647  O   LEU A 625    16102  16642   9739  -2825  -1422  -1445       O
ATOM   4648  CB  LEU A 625       2.416 -11.371  43.290  1.00117.52           C
```

FIG. 13 Continued

```
ANISOU 4648  CB  LEU A 625      16920  17930   9803  -2241  -1184  -1273           C
ATOM   4649  CG  LEU A 625        2.471  -9.923  42.808  1.00117.40              C
ANISOU 4649  CG  LEU A 625      17045  17741   9819  -2112  -1104  -1541           C
ATOM   4650  CD1 LEU A 625        1.296  -9.642  41.894  1.00117.25              C
ANISOU 4650  CD1 LEU A 625      16851  17777   9921  -2103   -961  -1304           C
ATOM   4651  CD2 LEU A 625        2.505  -8.941  43.964  1.00119.92              C
ANISOU 4651  CD2 LEU A 625      17573  18148   9843  -1788   -994  -1741           C
ATOM   4652  N   SER A 626        4.123 -13.454  41.279  1.00168.60              N
ANISOU 4652  N   SER A 626      23245  23929  16884  -2982  -1624  -1311           N
ATOM   4653  CA  SER A 626        5.230 -13.630  40.352  1.00166.25              C
ANISOU 4653  CA  SER A 626      22993  23336  16838  -3225  -1795  -1544           C
ATOM   4654  C   SER A 626        4.706 -13.929  38.964  1.00164.55              C
ANISOU 4654  C   SER A 626      22633  23023  16866  -3452  -1783  -1391           C
ATOM   4655  O   SER A 626        5.471 -14.024  38.011  1.00162.63              O
ANISOU 4655  O   SER A 626      22416  22538  16838  -3662  -1891  -1563           O
ATOM   4656  CB  SER A 626        6.149 -14.764  40.807  1.00166.00              C
ANISOU 4656  CB  SER A 626      22968  23265  16838  -3344  -1977  -1560           C
ATOM   4657  OG  SER A 626        7.274 -14.886  39.952  1.00163.97              O
ANISOU 4657  OG  SER A 626      22750  22731  16822  -3555  -2128  -1809           O
ATOM   4658  N   VAL A 627        3.398 -14.099  38.853  1.00109.74              N
ANISOU 4658  N   VAL A 627      15531  16283   9882  -3414  -1653  -1065           N
ATOM   4659  CA  VAL A 627        2.794 -14.357  37.560  1.00108.48              C
ANISOU 4659  CA  VAL A 627      15227  16063   9929  -3624  -1650   -903           C
ATOM   4660  C   VAL A 627        2.180 -13.096  36.959  1.00108.64              C
ANISOU 4660  C   VAL A 627      15261  16068   9948  -3497  -1521   -952           C
ATOM   4661  O   VAL A 627        2.380 -12.805  35.777  1.00107.07              O
ANISOU 4661  O   VAL A 627      15077  15676   9929  -3657  -1564  -1046           O
ATOM   4662  CB  VAL A 627        1.745 -15.449  37.649  1.00109.44              C
ANISOU 4662  CB  VAL A 627      15131  16402  10047  -3718  -1616   -497           C
ATOM   4663  CG1 VAL A 627        1.404 -15.945  36.255  1.00107.96              C
ANISOU 4663  CG1 VAL A 627      14816  16106  10098  -4005  -1678   -377           C
ATOM   4664  CG2 VAL A 627        2.268  16.582  38.509  1.00109.94              C
ANISOU 4664  CG2 VAL A 627      15213  16503  10058  -3772  -1715   -428           C
ATOM   4665  N   ILE A 628        1.431 -12.353  37.768  1.00112.27              N
ANISOU 4665  N   ILE A 628      15726  16732  10200  -3201  -1358   -882           N
ATOM   4666  CA  ILE A 628        0.847 -11.101  37.311  1.00112.82              C
ANISOU 4666  CA  ILE A 628      15827  16782  10255  -3031  -1227   -929           C
ATOM   4667  C   ILE A 628        1.933 -10.177  36.772  1.00111.43              C
ANISOU 4667  C   ILE A 628      15878  16287  10172  -3066  -1292  -1313           C
ATOM   4668  O   ILE A 628        1.729  -9.472  35.785  1.00110.79              O
ANISOU 4668  O   ILE A 628      15819  16072  10205  -3098  -1261  -1353           O
ATOM   4669  CB  ILE A 628        0.160 -10.372  38.447  1.00115.46              C
ANISOU 4669  CB  ILE A 628      16193  17345  10333  -2669  -1044   -883           C
ATOM   4670  CG1 ILE A 628       -1.231 -10.943  38.681  1.00117.18              C
ANISOU 4670  CG1 ILE A 628      16145  17894  10464  -2608   -919   -469           C
ATOM   4671  CG2 ILE A 628        0.063  -8.897  38.135  1.00115.99              C
ANISOU 4671  CG2 ILE A 628      16406  17283  10380  -2465   -939  -1079           C
ATOM   4672  CD1 ILE A 628       -1.996 -10.170  39.741  1.00120.06              C
ANISOU 4672  CD1 ILE A 628      16525  18499  10593  -2229   -705   -414           C
ATOM   4673  N   ILE A 629        3.081 -10.178  37.442  1.00110.11              N
ANISOU 4673  N   ILE A 629      15877  16007   9952  -3063  -1384  -1587           N
ATOM   4674  CA  ILE A 629        4.229  -9.377  37.034  1.00109.01              C
ANISOU 4674  CA  ILE A 629      15944  15571   9904  -3125  -1455  -1965           C
ATOM   4675  C   ILE A 629        4.813  -9.926  35.738  1.00106.60              C
ANISOU 4675  C   ILE A 629      15590  15050   9863  -3457  -1581  -2006           C
ATOM   4676  O   ILE A 629        5.603  -9.271  35.061  1.00105.56              O
ANISOU 4676  O   ILE A 629      15591  14666   9850  -3555  -1618  -2268           O
ATOM   4677  CB  ILE A 629        5.315  -9.412  38.111  1.00109.57              C
ANISOU 4677  CB  ILE A 629      16163  15611   9856  -3064  -1548  -2225           C
ATOM   4678  CG1 ILE A 629        6.421  -8.384  37.824  1.00109.03              C
ANISOU 4678  CG1 ILE A 629      16309  15259   9859  -3098  -1597  -2629           C
ATOM   4679  CG2 ILE A 629        5.884 -10.827  38.232  1.00108.56              C
ANISOU 4679  CG2 ILE A 629      15931  15509   9810  -3269  -1708  -2142           C
ATOM   4680  CD1 ILE A 629        6.102  -6.985  38.277  1.00110.86              C
ANISOU 4680  CD1 ILE A 629      16718  15471   9932  -2829  -1455  -2779           C
ATOM   4681  N   SER A 630        4.451 -11.154  35.409  1.00121.63              N
ANISOU 4681  N   SER A 630      17311  17048  11854  -3638  -1644  -1751           N
ATOM   4682  CA  SER A 630        4.879 -11.715  34.147  1.00119.60              C
ANISOU 4682  CA  SER A 630      17009  16601  11832  -3945  -1749  -1772           C
```

FIG. 13 Continued

```
ATOM   4683  C   SER A 630       3.923 -11.190  33.093  1.00119.48           C
ANISOU 4683  C   SER A 630    16927  16589  11881  -3968  -1663  -1616       C
ATOM   4684  O   SER A 630       4.339 -10.555  32.106  1.00118.41           O
ANISOU 4684  O   SER A 630    16884  16239  11866  -4078  -1675  -1778       O
ATOM   4685  CB  SER A 630       4.884 -13.241  34.199  1.00119.12           C
ANISOU 4685  CB  SER A 630    16804  16613  11842  -4134  -1856  -1575       C
ATOM   4686  OG  SER A 630       6.008 -13.710  34.934  1.00118.98           O
ANISOU 4686  OG  SER A 630    16867  16528  11812  -4145  -1968  -1764       O
ATOM   4687  N   ALA A 631       2.632 -11.374  33.336  1.00104.78           N
ANISOU 4687  N   ALA A 631    14901  14983   9928  -3854  -1572  -1295       N
ATOM   4688  CA  ALA A 631       1.596 -10.902  32.423  1.00105.10           C
ANISOU 4688  CA  ALA A 631    14843  15076  10013  -3845  -1498  -1107       C
ATOM   4689  C   ALA A 631       1.652  -9.387  32.140  1.00105.54           C
ANISOU 4689  C   ALA A 631    15070  14992  10038  -3659  -1402  -1296       C
ATOM   4690  O   ALA A 631       0.875  -8.855  31.341  1.00105.92           O
ANISOU 4690  O   ALA A 631    15065  15057  10124  -3628  -1346  -1163       O
ATOM   4691  CB  ALA A 631       0.211 -11.333  32.918  1.00106.93           C
ANISOU 4691  CB  ALA A 631    14845  15643  10141  -3725  -1408   -733       C
ATOM   4692  N   VAL A 632       2.554  -8.689  32.811  1.00149.24           N
ANISOU 4692  N   VAL A 632    20813  20390  15501  -3533  -1388  -1601       N
ATOM   4693  CA  VAL A 632       2.762  -7.294  32.485  1.00149.64           C
ANISOU 4693  CA  VAL A 632    21059  20250  15547  -3401  -1310  -1810       C
ATOM   4694  C   VAL A 632       3.974  -7.231  31.570  1.00147.69           C
ANISOU 4694  C   VAL A 632    20946  19692  15476  -3671  -1418  -2075       C
ATOM   4695  O   VAL A 632       4.071  -6.361  30.704  1.00147.45           O
ANISOU 4695  O   VAL A 632    21034  19471  15520  -3699  -1382  -2171       O
ATOM   4696  CB  VAL A 632       3.034  -6.433  33.709  1.00151.32           C
ANISOU 4696  CB  VAL A 632    21444  20472  15577  -3114  -1225  -2013       C
ATOM   4697  CG1 VAL A 632       4.376  -6.788  34.288  1.00150.50           C
ANISOU 4697  CG1 VAL A 632    21457  20248  15479  -3229  -1346  -2297       C
ATOM   4698  CG2 VAL A 632       3.005  -4.956  33.323  1.00152.16           C
ANISOU 4698  CG2 VAL A 632    21750  20383  15681   2957   1123   2178       C
ATOM   4699  N   LEU A 633       4.905  -8.159  31.754  1.00112.41           N
ANISOU 4699  N   LEU A 633    16461  15175  11077  -3865  -1544  -2188       N
ATOM   4700  CA  LEU A 633       6.089  -8.165  30.907  1.00110.73           C
ANISOU 4700  CA  LEU A 633    16351  14687  11036  -4121  -1635  -2442       C
ATOM   4701  C   LEU A 633       5.870  -8.959  29.628  1.00109.29           C
ANISOU 4701  C   LEU A 633    16047  14464  11013  -4396  -1697  -2282       C
ATOM   4702  O   LEU A 633       6.645  -8.843  28.695  1.00108.08           O
ANISOU 4702  O   LEU A 633    15978  14089  10998  -4602  -1738  -2455       O
ATOM   4703  CB  LEU A 633       7.324  -8.649  31.668  1.00110.33           C
ANISOU 4703  CB  LEU A 633    16350  14576  10996  -4183  -1742  -2683       C
ATOM   4704  CG  LEU A 633       8.570  -7.806  31.351  1.00109.89           C
ANISOU 4704  CG  LEU A 633    16482  14241  11029  -4272  -1763  -3057       C
ATOM   4705  CD1 LEU A 633       9.553  -7.756  32.545  1.00110.63           C
ANISOU 4705  CD1 LEU A 633    16656  14335  11045  -4187  -1835  -3312       C
ATOM   4706  CD2 LEU A 633       9.258  -8.240  30.032  1.00108.08           C
ANISOU 4706  CD2 LEU A 633    16233  13814  11018  -4589  -1827  -3135       C
ATOM   4707  N   THR A 634       4.822  -9.776  29.597  1.00112.19           N
ANISOU 4707  N   THR A 634    16222  15051  11355  -4407  -1702  -1956       N
ATOM   4708  CA  THR A 634       4.463 -10.497  28.382  1.00111.18           C
ANISOU 4708  CA  THR A 634    15982  14902  11357  -4664  -1765  -1789       C
ATOM   4709  C   THR A 634       3.929  -9.451  27.451  1.00111.51           C
ANISOU 4709  C   THR A 634    16088  14873  11407  -4622  -1691  -1755       C
ATOM   4710  O   THR A 634       4.321  -9.379  26.294  1.00110.47           O
ANISOU 4710  O   THR A 634    16022  14561  11389  -4830  -1729  -1835       O
ATOM   4711  CB  THR A 634       3.306 -11.537  28.584  1.00111.89           C
ANISOU 4711  CB  THR A 634    15837  15263  11411  -4686  -1784  -1422       C
ATOM   4712  OG1 THR A 634       3.481 -12.656  27.704  1.00110.70           O
ANISOU 4712  OG1 THR A 634    15611  15046  11403  -4998  -1899  -1357       O
ATOM   4713  CG2 THR A 634       1.936 -10.922  28.305  1.00113.28           C
ANISOU 4713  CG2 THR A 634    15907  15618  11514  -4534  -1690  -1163       C
ATOM   4714  N   SER A 635       3.033  -8.624  27.975  1.00100.41           N
ANISOU 4714  N   SER A 635    14670  13611   9872  -4337  -1578  -1632       N
ATOM   4715  CA  SER A 635       2.383  -7.630  27.156  1.00101.12           C
ANISOU 4715  CA  SER A 635    14807  13654   9960  -4253  -1507  -1555       C
ATOM   4716  C   SER A 635       3.151  -6.324  27.085  1.00101.28           C
ANISOU 4716  C   SER A 635    15090  13413   9978  -4155  -1439  -1848       C
ATOM   4717  O   SER A 635       2.836  -5.500  26.247  1.00101.70           O
```

FIG. 13 Continued

```
ANISOU 4717  O   SER A 635    15227 13360 10054 -4128 -1393 -1818          O
ATOM   4718  CB  SER A 635       0.926  -7.411  27.572  1.00103.08         C
ANISOU 4718  CB  SER A 635    14885 14188 10093  3998  1417  1243          C
ATOM   4719  OG  SER A 635       0.168  -6.970  26.459  1.00103.53         O
ANISOU 4719  OG  SER A 635    14900 14245 10192 -4019 -1411 -1074          O
ATOM   4720  N   ARG A 636       4.152  -6.102  27.929  1.00124.00         N
ANISOU 4720  N   ARG A 636    28996  6864 11254 -10095 -3336 -1105         N
ATOM   4721  CA  ARG A 636       4.908  -4.876  27.719  1.00123.54         C
ANISOU 4721  CA  ARG A 636    28932  7051 10954 -10048 -3772 -1231         C
ATOM   4722  C   ARG A 636       5.778  -5.052  26.464  1.00120.23         C
ANISOU 4722  C   ARG A 636    27495  6941 11256 -9648 -4090 -1090          C
ATOM   4723  O   ARG A 636       6.556  -4.166  26.074  1.00119.68         O
ANISOU 4723  O   ARG A 636    27217  7067 11189 -9577 -4459 -1117          O
ATOM   4724  CB  ARG A 636       5.693  -4.420  28.953  1.00128.40         C
ANISOU 4724  CB  ARG A 636    30498  7381 10908 -10567 -4481 -1143         C
ATOM   4725  CG  ARG A 636       6.013  -2.900  28.909  1.00129.09         C
ANISOU 4725  CG  ARG A 636    30822  7673 10555 -10616 -4629 -1427         C
ATOM   4726  CD  ARG A 636       6.228  -2.254  30.284  1.00134.96         C
ANISOU 4726  CD  ARG A 636    32777  8151 10349 -11200 -5020 -1589         C
ATOM   4727  NE  ARG A 636       4.985  -2.100  31.038  1.00136.73         N
ANISOU 4727  NE  ARG A 636    33831  8156  9964 -11323 -4283 -1919         N
ATOM   4728  CZ  ARG A 636       4.884  -1.507  32.226  1.00143.46         C
ANISOU 4728  CZ  ARG A 636    35761  8965  9782 -11626 -4310 -2022         C
ATOM   4729  NH1 ARG A 636       5.952  -0.986  32.821  1.00148.34         N
ANISOU 4729  NH1 ARG A 636    36849  9637  9878 -11999 -5163 -1956         N
ATOM   4730  NH2 ARG A 636       3.703  -1.428  32.823  1.00146.11         N
ANISOU 4730  NH2 ARG A 636    36693  9241  9583 -11557 -3456 -2186         N
ATOM   4731  N   ALA A 637       5.581  -6.205  25.824  1.00141.62         N
ANISOU 4731  N   ALA A 637    29574  9652 14583 -9406 -3866  -972          N
ATOM   4732  CA  ALA A 637       6.256  -6.576  24.584  1.00138.77         C
ANISOU 4732  CA  ALA A 637    28265  9523 14938 -9008 -4019  -902          C
ATOM   4733  C   ALA A 637       5.269  -6.946  23.457  1.00135.30         C
ANISOU 4733  C   ALA A 637    27145  9374 14890 -8618 -3295 -1170          C
ATOM   4734  O   ALA A 637       5.417  -6.454  22.344  1.00132.23         O
ANISOU 4734  O   ALA A 637    26140  9337 14764 -8274 -3198 -1324          O
ATOM   4735  CB  ALA A 637       7.260  -7.707  24.823  1.00141.06         C
ANISOU 4735  CB  ALA A 637    28441  9454 15702 -9117 -4588  -496          C
ATOM   4736  N   ILE A 638       4.268  -7.790  23.725  1.00102.88         N
ANISOU 4736  N   ILE A 638    23157  5103 10830 -8718 -2799 -1228          N
ATOM   4737  CA  ILE A 638       3.292  -8.159  22.679  1.00100.35         C
ANISOU 4737  CA  ILE A 638    22184  5057 10887 -8448 -2169 -1518          C
ATOM   4738  C   ILE A 638       2.552  -6.929  22.103  1.00 97.55         C
ANISOU 4738  C   ILE A 638    21645  5119 10302 -8249 -1790 -1852          C
ATOM   4739  O   ILE A 638       2.308  -6.857  20.894  1.00 94.74         O
ANISOU 4739  O   ILE A 638    20598  5097 10300 -7934 -1572 -2042          O
ATOM   4740  CB  ILE A 638       2.275  -9.253  23.132  1.00102.65         C
ANISOU 4740  CB  ILE A 638    22648  5062 11294 -8684 -1669 -1537          C
ATOM   4741  CG1 ILE A 638       2.157 -10.342  22.079  1.00101.94         C
ANISOU 4741  CG1 ILE A 638    21837  5012 11886 -8486 -1455 -1627          C
ATOM   4742  CG2 ILE A 638       0.907  -8.663  23.362  1.00102.39         C
ANISOU 4742  CG2 ILE A 638    22801  5167 10935 -8795 -1040 -1847          C
ATOM   4743  CD1 ILE A 638       3.479 -10.765  21.539  1.00101.62         C
ANISOU 4743  CD1 ILE A 638    21446  4886 12278 -8267 -1974 -1421          C
ATOM   4744  N   PHE A 639       2.200  -5.969  22.959  1.00 96.18         N
ANISOU 4744  N   PHE A 639    22126  4870  9548 -8444 -1706 -1925          N
ATOM   4745  CA  PHE A 639       1.566  -4.736  22.500  1.00 94.20         C
ANISOU 4745  CA  PHE A 639    21779  4899  9115 -8250 -1361 -2206          C
ATOM   4746  C   PHE A 639       2.589  -3.926  21.733  1.00 92.24         C
ANISOU 4746  C   PHE A 639    21207  4871  8969 -7995 -1770 -2135          C
ATOM   4747  O   PHE A 639       2.229  -3.176  20.825  1.00 89.77         O
ANISOU 4747  O   PHE A 639    20495  4838  8777 -7712 -1520 -2316          O
ATOM   4748  CB  PHE A 639       0.992  -3.938  23.686  1.00 96.87         C
ANISOU 4748  CB  PHE A 639    23006  4986  8815 -8537 -1131 -2333          C
ATOM   4749  CG  PHE A 639       1.129  -2.409  23.570  1.00 96.43         C
ANISOU 4749  CG  PHE A 639    23177  5022  8441 -8411 -1140 -2486          C
ATOM   4750  CD1 PHE A 639       0.091  -1.635  23.074  1.00 95.02         C
ANISOU 4750  CD1 PHE A 639    22809  4988  8305 -8167  -574 -2788          C
ATOM   4751  CD2 PHE A 639       2.277  -1.750  24.015  1.00 98.14         C
ANISOU 4751  CD2 PHE A 639    23835  5115  8340 -8563 -1719 -2334          C
```

FIG. 13 Continued

```
ATOM   4752  CE1 PHE A 639       0.212  -0.249  22.997  1.00 95.24           C
ANISOU 4752  CE1 PHE A 639    23114   4996   8078  -8072   -548  -2918       C
ATOM   4753  CE2 PHE A 639       2.391  -0.361  23.927  1.00 98.51           C
ANISOU 4753  CE2 PHE A 639    24142   5168   8120  -8496  -1685  -2489       C
ATOM   4754  CZ  PHE A 639       1.362   0.380  23.422  1.00 97.06           C
ANISOU 4754  CZ  PHE A 639    23807   5083   7989  -8235  -1080  -2772       C
ATOM   4755  N   GLN A 640       3.864  -4.099  22.082  1.00 92.42           N
ANISOU 4755  N   GLN A 640    21387   4737   8993  -8122  -2407  -1860       N
ATOM   4756  CA  GLN A 640       4.945  -3.357  21.435  1.00 91.28           C
ANISOU 4756  CA  GLN A 640    20948   4743   8991  -7958  -2815  -1776       C
ATOM   4757  C   GLN A 640       5.107  -3.614  19.911  1.00 87.82           C
ANISOU 4757  C   GLN A 640    19606   4619   9140  -7540  -2679  -1839       C
ATOM   4758  O   GLN A 640       5.272  -2.671  19.136  1.00 86.02           O
ANISOU 4758  O   GLN A 640    19132   4600   8953  -7334  -2620  -1927       O
ATOM   4759  CB  GLN A 640       6.261  -3.538  22.201  1.00 94.25           C
ANISOU 4759  CB  GLN A 640    21650   4856   9303  -8256  -3567  -1477       C
ATOM   4760  CG  GLN A 640       7.503  -2.970  21.511  1.00 93.63           C
ANISOU 4760  CG  GLN A 640    21158   4899   9520  -8142  -4023  -1367       C
ATOM   4761  CD  GLN A 640       7.595  -1.456  21.570  1.00 94.22           C
ANISOU 4761  CD  GLN A 640    21564   5028   9209  -8221  -4020  -1500       C
ATOM   4762  OE1 GLN A 640       8.544  -0.908  22.145  1.00 97.23           O
ANISOU 4762  OE1 GLN A 640    22283   5254   9406  -8541  -4576  -1383       O
ATOM   4763  NE2 GLN A 640       6.610  -0.765  20.979  1.00 91.89           N
ANISOU 4763  NE2 GLN A 640    21178   4916   8819  -7965  -3415  -1754       N
ATOM   4764  N   ARG A 641       5.050  -4.860  19.454  1.00176.46           N
ANISOU 4764  N   ARG A 641    30393  15840  20813  -7438  -2599  -1816       N
ATOM   4765  CA  ARG A 641       5.175  -5.057  18.014  1.00173.74           C
ANISOU 4765  CA  ARG A 641    29297  15765  20951  -7086  -2441  -1939       C
ATOM   4766  C   ARG A 641       4.056  -4.301  17.339  1.00171.52           C
ANISOU 4766  C   ARG A 641    28838  15786  20544  -6912  -1939  -2217       C
ATOM   4767  O   ARG A 641       4.297  -3.513  16.430  1.00169.58           O
ANISOU 4767  O   ARG A 641    28297  15756  20380  -6687  -1920  -2282       O
ATOM   4768  CB  ARG A 641       5.156  -6.526  17.615  1.00174.17           C
ANISOU 4768  CB  ARG A 641    28974  15710  21493  -7036  -2349  -1951       C
ATOM   4769  CG  ARG A 641       4.200  -7.390  18.383  1.00176.10           C
ANISOU 4769  CG  ARG A 641    29515  15746  21647  -7276  -2066  -1989       C
ATOM   4770  CD  ARG A 641       4.911  -8.676  18.720  1.00178.55           C
ANISOU 4770  CD  ARG A 641    29840  15664  22337  -7382  -2336  -1767       C
ATOM   4771  NE  ARG A 641       6.313  -8.406  19.045  1.00179.47           N
ANISOU 4771  NE  ARG A 641    30055  15619  22517  -7402  -2969  -1471       N
ATOM   4772  CZ  ARG A 641       7.092  -9.207  19.770  1.00182.43           C
ANISOU 4772  CZ  ARG A 641    30646  15563  23105  -7583  -3390  -1158       C
ATOM   4773  NH1 ARG A 641       6.607 -10.345  20.260  1.00184.79           N
ANISOU 4773  NH1 ARG A 641    31149  15508  23553  -7742  -3197  -1078       N
ATOM   4774  NH2 ARG A 641       8.355  -8.872  20.010  1.00183.48           N
ANISOU 4774  NH2 ARG A 641    30787  15579  23350  -7637  -4010   -900       N
ATOM   4775  N   MET A 642       2.836  -4.525  17.814  1.00 98.62           N
ANISOU 4775  N   MET A 642    19801   6529  11139  -7044  -1541  -2373       N
ATOM   4776  CA  MET A 642       1.670  -3.819  17.298  1.00 97.09           C
ANISOU 4776  CA  MET A 642    19442   6573  10876  -6917  -1085  -2642       C
ATOM   4777  C   MET A 642       1.923  -2.323  17.166  1.00 96.24           C
ANISOU 4777  C   MET A 642    19533   6526  10508  -6793  -1150  -2643       C
ATOM   4778  O   MET A 642       1.513  -1.703  16.193  1.00 94.29           O
ANISOU 4778  O   MET A 642    18931   6507  10388  -6556   -956  -2793       O
ATOM   4779  CB  MET A 642       0.484  -4.019  18.222  1.00 98.90           C
ANISOU 4779  CB  MET A 642    20040   6655  10883   7167    701   2779       C
ATOM   4780  CG  MET A 642      -0.168  -5.375  18.144  1.00 99.89           C
ANISOU 4780  CG  MET A 642    19886   6742  11327  -7309   -459  -2875       C
ATOM   4781  SD  MET A 642      -1.693  -5.323  19.110  1.00102.07           S
ANISOU 4781  SD  MET A 642    20543   6860  11380  -7614    102  -3090       S
ATOM   4782  CE  MET A 642      -1.164  -4.178  20.414  1.00103.64           C
ANISOU 4782  CE  MET A 642    21691   6772  10917  -7743    -84  -2934       C
ATOM   4783  N   LYS A 643       2.561  -1.736  18.170  1.00 95.27           N
ANISOU 4783  N   LYS A 643    20031   6157  10011  -6994  -1428  -2490       N
ATOM   4784  CA  LYS A 643       2.940  -0.338  18.082  1.00 95.30           C
ANISOU 4784  CA  LYS A 643    20286   6135   9789  -6936  -1514  -2497       C
ATOM   4785  C   LYS A 643       3.878  -0.172  16.885  1.00 93.27           C
ANISOU 4785  C   LYS A 643    19478   6071   9891  -6699  -1753  -2407       C
ATOM   4786  O   LYS A 643       3.428   0.051  15.762  1.00 90.96           O
```

FIG. 13 Continued

```
ANISOU 4786  O   LYS A 643     18720   6014   9827  -6431  -1502  -2542       O
ATOM   4787  CB  LYS A 643        3.626   0.147  19.369  1.00 98.66           C
ANISOU 4787  CB  LYS A 643     21494   6233   9758  -7283  -1862  -2369       C
ATOM   4788  CG  LYS A 643        2.828   1.175  20.179  1.00100.76           C
ANISOU 4788  CG  LYS A 643     22471   6279   9535  -7420  -1528  -2573       C
ATOM   4789  CD  LYS A 643        3.267   2.657  19.925  1.00101.48           C
ANISOU 4789  CD  LYS A 643     22813   6275   9470  -7372  -1586  -2634       C
ATOM   4790  CE  LYS A 643        2.421   3.699  20.751  1.00104.32           C
ANISOU 4790  CE  LYS A 643     23969   6315   9354  -7484  -1173  -2898       C
ATOM   4791  NZ  LYS A 643        3.061   5.031  21.059  1.00107.30           N
ANISOU 4791  NZ  LYS A 643     24951   6401   9417  -7647  -1333  -2960       N
ATOM   4792  N   ASN A 644        5.178  -0.325  17.112  1.00149.96           N
ANISOU 4792  N   ASN A 644     26704  13133  17142  -6824  -2248  -2189       N
ATOM   4793  CA  ASN A 644        6.162  -0.084  16.057  1.00148.63           C
ANISOU 4793  CA  ASN A 644     26063  13090  17320  -6647  -2451  -2118       C
ATOM   4794  C   ASN A 644        5.795  -0.654  14.690  1.00145.78           C
ANISOU 4794  C   ASN A 644     25021  13008  17362  -6326  -2162  -2250       C
ATOM   4795  O   ASN A 644        6.127  -0.053  13.669  1.00144.36           O
ANISOU 4795  O   ASN A 644     24551  12962  17338  -6148  -2115  -2290       O
ATOM   4796  CB  ASN A 644        7.565  -0.509  16.497  1.00150.67           C
ANISOU 4796  CB  ASN A 644     26330  13170  17747  -6846  -3029  -1876       C
ATOM   4797  CG  ASN A 644        8.148   0.412  17.572  1.00153.94           C
ANISOU 4797  CG  ASN A 644     27390  13338  17763  -7211  -3407  -1777       C
ATOM   4798  OD1 ASN A 644        8.276   1.620  17.372  1.00154.37           O
ANISOU 4798  OD1 ASN A 644     27629  13371  17654  -7241  -3358  -1850       O
ATOM   4799  ND2 ASN A 644        8.507  -0.163  18.714  1.00156.75           N
ANISOU 4799  ND2 ASN A 644     28131  13469  17958  -7530  -3800  -1622       N
ATOM   4800  N   TYR A 645        5.106  -1.793  14.658  1.00114.13           N
ANISOU 4800  N   TYR A 645     20801   9057  13505  -6299  -1963  -2339       N
ATOM   4801  CA  TYR A 645        4.650  -2.322  13.374  1.00112.15           C
ANISOU 4801  CA  TYR A 645     19971   9055  13585  -6067  -1686  -2529       C
ATOM   4802  C   TYR A 645        3.588  -1.417  12.746  1.00110.62           C
ANISOU 4802  C   TYR A 645     19706   9072  13253  -5924  -1346  -2728       C
ATOM   4803  O   TYR A 645        3.594  -1.179  11.539  1.00109.07           O
ANISOU 4803  O   TYR A 645     19137   9073  13230  -5731  -1255  -2834       O
ATOM   4804  CB  TYR A 645        4.050  -3.718  13.469  1.00112.82           C
ANISOU 4804  CB  TYR A 645     19875   9118  13875  -6136  -1522  -2634       C
ATOM   4805  CG  TYR A 645        3.031  -3.859  12.373  1.00111.44           C
ANISOU 4805  CG  TYR A 645     19276   9222  13843  -6000  -1159  -2925       C
ATOM   4806  CD1 TYR A 645        3.421  -4.146  11.077  1.00110.43           C
ANISOU 4806  CD1 TYR A 645     18697   9250  14011  -5829  -1138  -3045       C
ATOM   4807  CD2 TYR A 645        1.691  -3.607  12.610  1.00111.49           C
ANISOU 4807  CD2 TYR A 645     19349   9328  13684  -6068   -856  -3103       C
ATOM   4808  CE1 TYR A 645        2.504  -4.234  10.060  1.00109.71           C
ANISOU 4808  CE1 TYR A 645     18263   9420  14003  -5760   -879  -3329       C
ATOM   4809  CE2 TYR A 645        0.765  -3.689  11.601  1.00110.71           C
ANISOU 4809  CE2 TYR A 645     18834   9495  13737  -5967   -614  -3381       C
ATOM   4810  CZ  TYR A 645        1.174  -4.008  10.327  1.00109.90           C
ANISOU 4810  CZ  TYR A 645     18317   9560  13880  -5845   -654  -3491       C
ATOM   4811  OH  TYR A 645        0.248  -4.091   9.314  1.00109.70           O
ANISOU 4811  OH  TYR A 645     17915   9810  13957  -5819   -481  -3794       O
ATOM   4812  N   THR A 646        2.637  -0.961  13.553  1.00116.24           N
ANISOU 4812  N   THR A 646     20783   9711  13671  -6030  -1149  -2799       N
ATOM   4813  CA  THR A 646        1.617  -0.070  13.030  1.00115.24           C
ANISOU 4813  CA  THR A 646     20596   9717  13473  -5886   -851  -2994       C
ATOM   4814  C   THR A 646        2.345   1.074  12.373  1.00114.41           C
ANISOU 4814  C   THR A 646     20530   9605  13337  -5736   -983  -2913       C
ATOM   4815  O   THR A 646        2.308   1.215  11.154  1.00112.86           O
ANISOU 4815  O   THR A 646     19943   9606  13332  -5546   -932  -2996       O
ATOM   4816  CB  THR A 646        0.663   0.470  14.132  1.00116.79           C
ANISOU 4816  CB  THR A 646     21291   9727  13358  -6023   -607  -3089       C
ATOM   4817  OG1 THR A 646       -0.533  -0.312  14.149  1.00117.00           O
ANISOU 4817  OG1 THR A 646     21064   9865  13526  -6086   -310  -3302       O
ATOM   4818  CG2 THR A 646        0.255   1.918  13.871  1.00116.61           C
ANISOU 4818  CG2 THR A 646     21481   9634  13191  -5862   -446  -3189       C
ATOM   4819  N   ILE A 647        3.056   1.848  13.186  1.00 78.47           N
ANISOU 4819  N   ILE A 647     16483   4799   8531  -5873  -1169  -2763       N
ATOM   4820  CA  ILE A 647        3.766   3.030  12.722  1.00 78.52           C
ANISOU 4820  CA  ILE A 647     16625   4715   8492  -5814  -1278  -2696       C
```

FIG. 13 Continued

```
ATOM   4821  C   ILE A 647       4.416   2.866  11.326  1.00 76.67           C
ANISOU 4821  C   ILE A 647    15858   4687   8587  -5634  -1351  -2673       C
ATOM   4822  O   ILE A 647       4.279   3.735  10.449  1.00 75.84           O
ANISOU 4822  O   ILE A 647    15700   4613   8502  -5483  -1231  -2734       O
ATOM   4823  CB  ILE A 647       4.768   3.479  13.786  1.00 81.16           C
ANISOU 4823  CB  ILE A 647    17485   4759   8592  -6098  -1601  -2534       C
ATOM   4824  CG1 ILE A 647       4.016   4.208  14.909  1.00 83.40           C
ANISOU 4824  CG1 ILE A 647    18454   4775   8460  -6250  -1413  -2642       C
ATOM   4825  CG2 ILE A 647       5.878   4.330  13.163  1.00 81.53           C
ANISOU 4825  CG2 ILE A 647    17499   4734   8745  -6113  -1807  -2440       C
ATOM   4826  CD1 ILE A 647       2.675   3.609  15.247  1.00 82.90           C
ANISOU 4826  CD1 ILE A 647    18361   4786   8354  -6192  -1057  -2806       C
ATOM   4827  N   TYR A 648       5.100   1.746  11.110  1.00133.07           N
ANISOU 4827  N   TYR A 648    22649  11923  15988  -5654  -1523  -2606       N
ATOM   4828  CA  TYR A 648       5.685   1.448   9.801  1.00131.75           C
ANISOU 4828  CA  TYR A 648    22006  11920  16134  -5504  -1526  -2640       C
ATOM   4829  C   TYR A 648       4.571   1.284   8.769  1.00130.16           C
ANISOU 4829  C   TYR A 648    21494  11973  15986  -5322  -1233  -2870       C
ATOM   4830  O   TYR A 648       4.569   1.953   7.737  1.00129.27           O
ANISOU 4830  O   TYR A 648    21274  11949  15893  -5196  -1154  -2933       O
ATOM   4831  CB  TYR A 648       6.561   0.187   9.892  1.00132.37           C
ANISOU 4831  CB  TYR A 648    21815  11963  16515  -5562  -1726  -2569       C
ATOM   4832  CG  TYR A 648       6.603  -0.706   8.657  1.00131.35           C
ANISOU 4832  CG  TYR A 648    21184  12010  16713  -5414  -1570  -2739       C
ATOM   4833  CD1 TYR A 648       7.687  -0.671   7.781  1.00131.33           C
ANISOU 4833  CD1 TYR A 648    20928  11992  16978  -5365  -1633  -2729       C
ATOM   4834  CD2 TYR A 648       5.575   1.614   8.395  1.00131.02           C
ANISOU 4834  CD2 TYR A 648    20946  12116  16719  -5379  -1348  -2947       C
ATOM   4835  CE1 TYR A 648       7.733  -1.493   6.672  1.00130.94           C
ANISOU 4835  CE1 TYR A 648    20501  12060  17192  -5267  -1454  -2936       C
ATOM   4836  CE2 TYR A 648       5.610  -2.434   7.289  1.00130.86           C
ANISOU 4836  CE2 TYR A 648    20542  12219  16958  -5307  -1209  -3159       C
ATOM   4837  CZ  TYR A 648       6.690  -2.373   6.430  1.00130.80           C
ANISOU 4837  CZ  TYR A 648    20346  12183  17171  -5243  -1252  -3160       C
ATOM   4838  OH  TYR A 648       6.709  -3.200   5.324  1.00131.13           O
ANISOU 4838  OH  TYR A 648    20075  12314  17435  -5205  -1074  -3426       O
ATOM   4839  N   ALA A 649       3.617   0.406   9.079  1.00118.30           N
ANISOU 4839  N   ALA A 649    19876  10570  14503  -5353  -1097  -3004       N
ATOM   4840  CA  ALA A 649       2.475   0.132   8.213  1.00117.57           C
ANISOU 4840  CA  ALA A 649    19461  10731  14481  -5262   -882  -3266       C
ATOM   4841  C   ALA A 649       1.771   1.433   7.820  1.00116.99           C
ANISOU 4841  C   ALA A 649    19525  10685  14240  -5131   -782  -3336       C
ATOM   4842  O   ALA A 649       0.963   1.468   6.882  1.00116.53           O
ANISOU 4842  O   ALA A 649    19196  10848  14234  -5035   -699  -3551       O
ATOM   4843  CB  ALA A 649       1.509  -0.827   8.894  1.00118.52           C
ANISOU 4843  CB  ALA A 649    19519  10882  14631  -5402   -748  -3400       C
ATOM   4844  N   VAL A 650       2.067   2.499   8.556  1.00101.43           N
ANISOU 4844  N   VAL A 650    18015   8459  12067  -5146   -814  -3181       N
ATOM   4845  CA  VAL A 650       1.540   3.808   8.219  1.00101.38           C
ANISOU 4845  CA  VAL A 650    18235   8353  11931  -5003   -707  -3240       C
ATOM   4846  C   VAL A 650       2.558   4.450   7.323  1.00100.92           C
ANISOU 4846  C   VAL A 650    18185   8246  11915  -4941   -819  -3125       C
ATOM   4847  O   VAL A 650       2.212   4.924   6.251  1.00100.26           O
ANISOU 4847  O   VAL A 650    17985   8250  11858  -4787   -767  -3228       O
ATOM   4848  CB  VAL A 650       1.328   4.718   9.441  1.00102.99           C
ANISOU 4848  CB  VAL A 650    19032   8215  11886  -5072   -617  -3189       C
ATOM   4849  CG1 VAL A 650       1.341   6.168   9.011  1.00103.50           C
ANISOU 4849  CG1 VAL A 650    19432   8035  11858  -4925   -542  -3191       C
ATOM   4850  CG2 VAL A 650       0.013   4.398  10.129  1.00103.64           C
ANISOU 4850  CG2 VAL A 650    19143   8308  11925  -5088   -390  -3383       C
ATOM   4851  N   SER A 651       3.819   4.443   7.755  1.00 87.71           N
ANISOU 4851  N   SER A 651    16647   6423  10255  -5088   -993  -2928       N
ATOM   4852  CA  SER A 651       4.903   5.045   6.965  1.00 87.77           C
ANISOU 4852  CA  SER A 651    16648   6351  10349  -5096  -1080  -2827       C
ATOM   4853  C   SER A 651       4.946   4.487   5.527  1.00 86.39           C
ANISOU 4853  C   SER A 651    16022   6443  10360  -4975  -1023  -2948       C
ATOM   4854  O   SER A 651       5.484   5.115   4.599  1.00 86.34           O
ANISOU 4854  O   SER A 651    16031   6386  10389  -4948   -998  -2928       O
ATOM   4855  CB  SER A 651       6.255   4.936   7.687  1.00 89.24           C
```

FIG. 13 Continued

```
ANISOU 4855  CB  SER A 651    16942   6366  10600  -5319  -1329  -2640       C
ATOM   4856  OG  SER A 651       6.405   5.993   8.621  1.00 91.28           O
ANISOU 4856  OG  SER A 651    17744   6312  10627  -5478  -1390  -2563       O
ATOM   4857  N   ILE A 652       4.370   3.299   5.371  1.00 90.18           N
ANISOU 4857  N   ILE A 652    16153   7173  10939  -4945   -984  -3099       N
ATOM   4858  CA  ILE A 652       4.158   2.724   4.061  1.00 89.58           C
ANISOU 4858  CA  ILE A 652    15714   7357  10966  -4873   -917  -3303       C
ATOM   4859  C   ILE A 652       3.265   3.707   3.335  1.00 89.28           C
ANISOU 4859  C   ILE A 652    15795   7374  10753  -4737   -860  -3417       C
ATOM   4860  O   ILE A 652       3.634   4.265   2.301  1.00 89.19           O
ANISOU 4860  O   ILE A 652    15826   7360  10702  -4688   -855  -3437       O
ATOM   4861  CB  ILE A 652       3.465   1.332   4.160  1.00 89.83           C
ANISOU 4861  CB  ILE A 652    15419   7603  11111  -4920   -872  -3502       C
ATOM   4862  CG1 ILE A 652       4.456   0.248   3.760  1.00 90.32           C
ANISOU 4862  CG1 ILE A 652    15232   7666  11418  -4984   -883  -3541       C
ATOM   4863  CG2 ILE A 652       2.215   1.234   3.281  1.00 89.94           C
ANISOU 4863  CG2 ILE A 652    15216   7909  11047  -4868   -814  -3801       C
ATOM   4864  CD1 ILE A 652       5.890   0.603   4.142  1.00 90.54           C
ANISOU 4864  CD1 ILE A 652    15393   7444  11563  -5023  -1005  -3289       C
ATOM   4865  N   THR A 653       2.101   3.953   3.923  1.00 92.90           N
ANISOU 4865  N   THR A 653    16346   7839  11111  -4680   -817  -3501       N
ATOM   4866  CA  THR A 653       1.103   4.824   3.327  1.00 92.99           C
ANISOU 4866  CA  THR A 653    16457   7883  10994  -4508   -798  -3658       C
ATOM   4867  C   THR A 653       1.448   6.297   3.527  1.00 93.42           C
ANISOU 4867  C   THR A 653    17036   7524  10936  -4410   -743  -3484       C
ATOM   4868  O   THR A 653       0.626   7.169   3.286  1.00 93.91           O
ANISOU 4868  O   THR A 653    17319   7458  10903  -4212   -693  -3594       O
ATOM   4869  CB  THR A 653      -0.313   4.477   3.834  1.00 93.47           C
ANISOU 4869  CB  THR A 653    16360   8098  11056  -4484   -753  -3882       C
ATOM   4870  OG1 THR A 653      -0.579   3.081   3.590  1.00 93.73           O
ANISOU 4870  OG1 THR A 653    15924   8474  11213  -4635   -787  -4062       O
ATOM   4871  CG2 THR A 653      -1.361   5.331   3.135  1.00 93.96           C
ANISOU 4871  CG2 THR A 653    16471   8229  11000  -4260   -797  -4112       C
ATOM   4872  N   ILE A 654       2.663   6.567   3.992  1.00 66.31           N
ANISOU 4872  N   ILE A 654    13818   3848   7526  -4552   -757  -3243       N
ATOM   4873  CA  ILE A 654       3.167   7.943   4.076  1.00 67.48           C
ANISOU 4873  CA  ILE A 654    14476   3572   7592  -4540   -696  -3094       C
ATOM   4874  C   ILE A 654       4.351   8.067   3.131  1.00 67.46           C
ANISOU 4874  C   ILE A 654    14400   3549   7683  -4638   -737  -2991       C
ATOM   4875  O   ILE A 654       5.078   9.068   3.136  1.00 68.86           O
ANISOU 4875  O   ILE A 654    14939   3368   7856  -4725   -691  -2844       O
ATOM   4876  CB  ILE A 654       3.490   8.434   5.517  1.00 69.15           C
ANISOU 4876  CB  ILE A 654    15114   3452   7706  -4692   -679  -2964       C
ATOM   4877  CG1 ILE A 654       2.188   8.696   6.252  1.00 69.73           C
ANISOU 4877  CG1 ILE A 654    15413   3416   7666  -4548   -520  -3110       C
ATOM   4878  CG2 ILE A 654       4.259   9.756   5.496  1.00 71.17           C
ANISOU 4878  CG2 ILE A 654    15872   3257   7913  -4775   -628  -2831       C
ATOM   4879  CD1 ILE A 654       1.189   9.437   5.384  1.00 69.72           C
ANISOU 4879  CD1 ILE A 654    15506   3316   7670  -4226   -384  -3267       C
ATOM   4880  N   ARG A 655       4.543   7.020   2.328  1.00135.69           N
ANISOU 4880  N   ARG A 655    22586  12546  16425  -4656   -789  -3097       N
ATOM   4881  CA  ARG A 655       5.513   7.074   1.242  1.00135.84           C
ANISOU 4881  CA  ARG A 655    22524  12560  16528  -4733   -760  -3075       C
ATOM   4882  C   ARG A 655       4.790   7.734   0.067  1.00135.84           C
ANISOU 4882  C   ARG A 655    22697  12567  16349  -4560   -709  -3219       C
ATOM   4883  O   ARG A 655       5.397   8.535  -0.641  1.00135.63           O
ANISOU 4883  O   ARG A 655    23067  12408  16439  -4594   -620  -3133       O
ATOM   4884  CB  ARG A 655       6.105   5.696   0.894  1.00135.38           C
ANISOU 4884  CB  ARG A 655    21994  12793  16652  -4825   -786  -3174       C
ATOM   4885  CG  ARG A 655       7.467   5.754   0.178  1.00136.13           C
ANISOU 4885  CG  ARG A 655    22025  12768  16928  -4973   -716  -3115       C
ATOM   4886  CD  ARG A 655       8.183   4.421   0.208  1.00136.23           C
ANISOU 4886  CD  ARG A 655    21626  12927  17208  -5050   -725  -3196       C
ATOM   4887  NE  ARG A 655       7.237   3.303   0.301  1.00135.60           N
ANISOU 4887  NE  ARG A 655    21305  13133  17082  -4959   -744  -3402       N
ATOM   4888  CZ  ARG A 655       7.565   2.007   0.304  1.00135.99           C
ANISOU 4888  CZ  ARG A 655    21041  13276  17353  -4997   -719  -3535       C
ATOM   4889  NH1 ARG A 655       8.834   1.629   0.207  1.00136.84           N
ANISOU 4889  NH1 ARG A 655    20999  13225  17770  -5088   -685  -3494       N
```

FIG. 13 Continued

```
ATOM   4890  NH2 ARG A 655       6.616   1.077   0.400  1.00135.96           N
ANISOU 4890  NH2 ARG A 655    20869  13484  17308  -4962   -714  -3733       N
ATOM   4891  N   ILE A 656       3.490   7.439  -0.096  1.00100.18           N
ANISOU 4891  N   ILE A 656    18055   8320  11690  -4383   -783  -3448       N
ATOM   4892  CA  ILE A 656       2.656   8.058  -1.148  1.00100.68           C
ANISOU 4892  CA  ILE A 656    18299   8453  11502  -4162   -839  -3656       C
ATOM   4893  C   ILE A 656       2.666   9.581  -1.181  1.00102.44           C
ANISOU 4893  C   ILE A 656    19073   8210  11642  -3926   -677  -3392       C
ATOM   4894  O   ILE A 656       1.651  10.226  -1.403  1.00105.29           O
ANISOU 4894  O   ILE A 656    19457   8788  11759  -3451   -604  -3207       O
ATOM   4895  CB  ILE A 656       1.177   7.583  -1.180  1.00100.79           C
ANISOU 4895  CB  ILE A 656    18042   8898  11356  -3995  -1002  -3975       C
ATOM   4896  CG1 ILE A 656       0.322   8.376  -0.154  1.00101.69           C
ANISOU 4896  CG1 ILE A 656    18386   8753  11500  -3748   -867  -3842       C
ATOM   4897  CG2 ILE A 656       1.111   6.085  -1.005  1.00100.47           C
ANISOU 4897  CG2 ILE A 656    17443   9283  11447  -4198  -1057  -4097       C
ATOM   4898  CD1 ILE A 656      -1.033   8.905  -0.675  1.00105.81           C
ANISOU 4898  CD1 ILE A 656    18678   9789  11735  -3165   -854  -3661       C
ATOM   4899  N   VAL A 657       3.803  10.158  -0.866  1.00116.91           N
ANISOU 4899  N   VAL A 657    21238   9507  13677  -4174   -561  -3205       N
ATOM   4900  CA  VAL A 657       4.024  11.512  -1.270  1.00120.10           C
ANISOU 4900  CA  VAL A 657    22087   9564  13982  -3941   -327  -2837       C
ATOM   4901  C   VAL A 657       4.960  11.228  -2.458  1.00120.80           C
ANISOU 4901  C   VAL A 657    21994   9881  14024  -4062   -269  -2749       C
ATOM   4902  O   VAL A 657       5.559  12.130  -3.023  1.00123.67           O
ANISOU 4902  O   VAL A 657    22641  10004  14343  -3997    -39  -2408       O
ATOM   4903  CB  VAL A 657       4.634  12.404  -0.166  1.00120.50           C
ANISOU 4903  CB  VAL A 657    22675   8823  14287  -4210   -219  -2740       C
ATOM   4904  CG1 VAL A 657       3.549  13.225   0.533  1.00122.54           C
ANISOU 4904  CG1 VAL A 657    23293   8840  14427  -3832    -73  -2672       C
ATOM   4905  CG2 VAL A 657       5.382  11.562   0.829  1.00119.90           C
ANISOU 4905  CG2 VAL A 657    22218   9046  14293  -4527   -356  -2710       C
ATOM   4906  N   PHE A 658       5.065   9.947  -2.835  1.00170.76           N
ANISOU 4906  N   PHE A 658    27869  16651  20362  -4239   -432  -3067       N
ATOM   4907  CA  PHE A 658       5.907   9.532  -3.972  1.00171.87           C
ANISOU 4907  CA  PHE A 658    27828  17042  20435  -4335   -322  -3054       C
ATOM   4908  C   PHE A 658       5.296   9.828  -5.342  1.00175.79           C
ANISOU 4908  C   PHE A 658    28299  18115  20377  -3881   -229  -2866       C
ATOM   4909  O   PHE A 658       5.829  10.631  -6.105  1.00179.01           O
ANISOU 4909  O   PHE A 658    28953  18438  20626   3751     24   2504       O
ATOM   4910  CB  PHE A 658       6.391   8.057  -3.887  1.00169.09           C
ANISOU 4910  CB  PHE A 658    27070  16844  20332  -4696   -460  -3474       C
ATOM   4911  CG  PHE A 658       5.380   7.055  -3.298  1.00167.92           C
ANISOU 4911  CG  PHE A 658    26550  17116  20137  -4608   -654  -3683       C
ATOM   4912  CD1 PHE A 658       5.763   6.190  -2.274  1.00167.29           C
ANISOU 4912  CD1 PHE A 658    26135  17083  20344  -4718   -658  -3579       C
ATOM   4913  CD2 PHE A 658       4.090   6.936  -3.787  1.00168.36           C
ANISOU 4913  CD2 PHE A 658    26552  17576  19842  -4394   -822  -3945       C
ATOM   4914  CE1 PHE A 658       4.873   5.255  -1.731  1.00166.78           C
ANISOU 4914  CE1 PHE A 658    25764  17325  20282  -4663   -760  -3723       C
ATOM   4915  CE2 PHE A 658       3.206   5.991  -3.244  1.00167.85           C
ANISOU 4915  CE2 PHE A 658    26105  17851  19821  -4395   -960  -4128       C
ATOM   4916  CZ  PHE A 658       3.607   5.161  -2.212  1.00167.09           C
ANISOU 4916  CZ  PHE A 658    25734  17684  20067  -4533   -864  -3986       C
ATOM   4917  N   GLY A 659       4.187   9.167  -5.648  1.00109.77           N
ANISOU 4917  N   GLY A 659    19637  10356  11713  -3670   -447  -3101       N
ATOM   4918  CA  GLY A 659       3.473   9.389  -6.894  1.00114.20           C
ANISOU 4918  CA  GLY A 659    20136  11570  11683  -3243   -471  -2937       C
ATOM   4919  C   GLY A 659       2.846  10.770  -6.899  1.00117.58           C
ANISOU 4919  C   GLY A 659    20877  11878  11920  -2740   -373  -2425       C
ATOM   4920  O   GLY A 659       2.650  11.392  -7.940  1.00122.26           O
ANISOU 4920  O   GLY A 659    21604  12789  12061  -2354   -290  -2060       O
ATOM   4921  N   PHE A 660       2.511  11.244  -5.712  1.00134.09           N
ANISOU 4921  N   PHE A 660    23120  13488  14341  -2722   -363  -2390       N
ATOM   4922  CA  PHE A 660       2.000  12.588  -5.569  1.00137.59           C
ANISOU 4922  CA  PHE A 660    23930  13645  14700  -2244   -188  -1923       C
ATOM   4923  C   PHE A 660       3.162  13.547  -5.861  1.00139.39           C
ANISOU 4923  C   PHE A 660    24659  13281  15020  -2350    148  -1548       C
ATOM   4924  O   PHE A 660       2.950  14.730  -6.123  1.00143.66           O
```

FIG. 13 Continued

```
ANISOU 4924  O   PHE A 660    25588 13570 15428 -1941   373 -1073       O
ATOM   4925  CB  PHE A 660       1.445  12.789  -4.157  1.00135.52      C
ANISOU 4925  CB  PHE A 660    23766 12950 14774 -2259  -190 -2057       C
ATOM   4926  CG  PHE A 660       1.221  14.222  -3.791  1.00139.02      C
ANISOU 4926  CG  PHE A 660    24735 12823 15262 -1871   101 -1634       C
ATOM   4927  CD1 PHE A 660      -0.063  14.716  -3.652  1.00142.37      C
ANISOU 4927  CD1 PHE A 660    25093 13444 15557 -1270   129 -1448       C
ATOM   4928  CD2 PHE A 660       2.296  15.082  -3.582  1.00139.68      C
ANISOU 4928  CD2 PHE A 660    25370 12148 15553 -2112   371 -1422       C
ATOM   4929  CE1 PHE A 660      -0.278  16.054  -3.314  1.00146.35      C
ANISOU 4929  CE1 PHE A 660    26132 13342 16132  -857   465 -1057       C
ATOM   4930  CE2 PHE A 660       2.095  16.417  -3.255  1.00143.64      C
ANISOU 4930  CE2 PHE A 660    26433 12036 16109 -1779   683 -1060       C
ATOM   4931  CZ  PHE A 660       0.805  16.906  -3.117  1.00146.98      C
ANISOU 4931  CZ  PHE A 660    26845 12603 16396 -1124   751  -878       C
ATOM   4932  N   MET A 661       4.391  13.035  -5.820  1.00146.92      N
ANISOU 4932  N   MET A 661    25584 14000 16241 -2896   205 -1739       N
ATOM   4933  CA  MET A 661       5.570  13.864  -6.082  1.00149.01      C
ANISOU 4933  CA  MET A 661    26230 13723 16664 -3095   533 -1405       C
ATOM   4934  C   MET A 661       5.966  13.876  -7.548  1.00152.74      C
ANISOU 4934  C   MET A 661    26677 14622 16736 -2942   721 -1155       C
ATOM   4935  O   MET A 661       5.977  14.921  -8.196  1.00157.56      O
ANISOU 4935  O   MET A 661    27658 15102 17105 -2623   987  -650       O
ATOM   4936  CB  MET A 661       6.762  13.414  -5.235  1.00145.34      C
ANISOU 4936  CB  MET A 661    25705 12770 16749 -3764   511 -1673       C
ATOM   4937  CG  MET A 661       6.845  14.102  -3.889  1.00144.40      C
ANISOU 4937  CG  MET A 661    25950 11925 16991 -3979   499 -1679       C
ATOM   4938  SD  MET A 661       7.665  15.693  -3.932  1.00149.26      S
ANISOU 4938  SD  MET A 661    27199 11742 17771 -4088   891 -1196       S
ATOM   4939  CE  MET A 661       9.384  15.175  -3.959  1.00148.18      C
ANISOU 4939  CE  MET A 661    26786 11420 18095 -4825   910 -1295       C
ATOM   4940  N   LEU A 662       6.304  12.709  -8.072  1.00136.98      N
ANISOU 4940  N   LEU A 662    24288 13103 14655 -3166   621 -1503       N
ATOM   4941  CA  LEU A 662       6.724  12.632  -9.459  1.00140.94      C
ANISOU 4941  CA  LEU A 662    24801 14025 14723 -3055   841 -1328       C
ATOM   4942  C   LEU A 662       5.576  12.919 -10.420  1.00145.48      C
ANISOU 4942  C   LEU A 662    25427 15268 14582 -2461   718 -1087       C
ATOM   4943  O   LEU A 662       5.366  12.190 -11.388  1.00147.44      O
ANISOU 4943  O   LEU A 662    25475 16203 14342 -2388   621 -1268       O
ATOM   4944  CB  LEU A 662       7.407  11.299  -9.758  1.00138.74      C
ANISOU 4944  CB  LEU A 662    24138 14027 14549 -3437   828 -1803       C
ATOM   4945  CG  LEU A 662       8.900  11.376  -9.437  1.00137.86      C
ANISOU 4945  CG  LEU A 662    24035 13334 15013 -3909  1132 -1748       C
ATOM   4946  CD1 LEU A 662       9.570  12.397 -10.345  1.00143.26      C
ANISOU 4946  CD1 LEU A 662    25065 13870 15498 -3808  1594 -1209       C
ATOM   4947  CD2 LEU A 662       9.117  11.739  -7.976  1.00134.29      C
ANISOU 4947  CD2 LEU A 662    23647 12207 15172 -4205   979 -1774       C
ATOM   4948  N   ILE A 663       4.832  13.982 -10.121  1.00139.39      N
ANISOU 4948  N   ILE A 663    24929 14282 13751 -2035   713  -682       N
ATOM   4949  CA  ILE A 663       3.756  14.481 -10.977  1.00144.91      C
ANISOU 4949  CA  ILE A 663    25666 15554 13820 -1383   595  -298       C
ATOM   4950  C   ILE A 663       3.742  15.987 -10.841  1.00148.90      C
ANISOU 4950  C   ILE A 663    26729 15440 14407 -1014   908   350       C
ATOM   4951  O   ILE A 663       4.198  16.696 -11.737  1.00153.96      O
ANISOU 4951  O   ILE A 663    27732 16018 14747  -838  1217   849       O
ATOM   4952  CB  ILE A 663       2.362  13.917 -10.618  1.00143.92      C
ANISOU 4952  CB  ILE A 663    25119 15993 13569 -1120   131  -582       C
ATOM   4953  CG1 ILE A 663       2.025  12.728 -11.520  1.00144.82      C
ANISOU 4953  CG1 ILE A 663    24812 17026 13186 -1212  -184  -977       C
ATOM   4954  CG2 ILE A 663       1.277  14.984 -10.807  1.00149.41      C
ANISOU 4954  CG2 ILE A 663    25961 16819 13988  -384    89   -17       C
ATOM   4955  CD1 ILE A 663       1.591  13.128 -12.913  1.00152.21      C
ANISOU 4955  CD1 ILE A 663    25859 18654 13318  -735  -249  -554       C
ATOM   4956  N   ALA A 664       3.246  16.473  -9.707  1.00166.88      N
ANISOU 4956  N   ALA A 664    29105 17208 17093  -914   879   337       N
ATOM   4957  CA  ALA A 664       3.244  17.899  -9.449  1.00170.92      C
ANISOU 4957  CA  ALA A 664    30195 16988 17757  -594  1226   885       C
ATOM   4958  C   ALA A 664       4.682  18.383  -9.634  1.00171.69      C
ANISOU 4958  C   ALA A 664    30695 16443 18097 -1071  1642  1071       C
```

FIG. 13 Continued

```
ATOM   4959  O    ALA A 664       4.933  19.574  -9.844  1.00176.68           O
ANISOU 4959  O    ALA A 664    31873  16506  18753   -870   2020   1614       O
ATOM   4960  CB   ALA A 664       2.749  18.185  -8.034  1.00168.20           C
ANISOU 4960  CB   ALA A 664    29941  16078  17890   -600   1197    675       C
ATOM   4961  N    LEU A 665       5.620  17.434  -9.584  1.00182.81           N
ANISOU 4961  N    LEU A 665    31803  17949  19709  -1695   1591    637       N
ATOM   4962  CA   LEU A 665       7.048  17.731  -9.672  1.00183.40           C
ANISOU 4962  CA   LEU A 665    32092  17477  20116  -2230   1961    749       C
ATOM   4963  C    LEU A 665       7.614  17.610 -11.075  1.00187.49           C
ANISOU 4963  C    LEU A 665    32609  18435  20193  -2182   2223   1021       C
ATOM   4964  O    LEU A 665       7.411  18.477 -11.929  1.00193.67           O
ANISOU 4964  O    LEU A 665    33778  19244  20563  -1752   2484   1605       O
ATOM   4965  CB   LEU A 665       7.831  16.803  -8.738  1.00177.20           C
ANISOU 4965  CB   LEU A 665    30946  16497  19885  -2919   1785    170       C
ATOM   4966  CG   LEU A 665       9.299  17.105  -8.432  1.00177.47           C
ANISOU 4966  CG   LEU A 665    31088  15886  20458  -3562   2070    222       C
ATOM   4967  CD1  LEU A 665       9.457  18.373  -7.588  1.00179.72           C
ANISOU 4967  CD1  LEU A 665    31925  15258  21102  -3695   2247    473       C
ATOM   4968  CD2  LEU A 665       9.905  15.909  -7.729  1.00171.88           C
ANISOU 4968  CD2  LEU A 665    29869  15266  20172  -4097   1795   -334       C
ATOM   4969  N    ILE A 666       8.339  16.520 -11.291  1.00147.69           N
ANISOU 4969  N    ILE A 666    27159  13716  15240  -2611   2187    606       N
ATOM   4970  CA   ILE A 666       8.996  16.280 -12.564  1.00151.60           C
ANISOU 4970  CA   ILE A 666    27646  14611  15342  -2634   2507    771       C
ATOM   4971  C    ILE A 666       8.043  15.611 -13.569  1.00153.60           C
ANISOU 4971  C    ILE A 666    27737  15838  14787  -2181   2244    665       C
ATOM   4972  O    ILE A 666       6.971  16.150  13.870  1.00156.85           O
ANISOU 4972  O    ILE A 666    28325  16539  14734  -1619   2056    985       O
ATOM   4973  CB   ILE A 666      10.308  15.470 -12.392  1.00148.80           C
ANISOU 4973  CB   ILE A 666    26939  14106  15492  -3274   2687    407       C
ATOM   4974  CG1  ILE A 666      11.097  15.957 -11.177  1.00146.34           C
ANISOU 4974  CG1  ILE A 666    26663  12935  16003  -3782   2739    396       C
ATOM   4975  CG2  ILE A 666      11.182  15.637 -13.604  1.00154.38           C
ANISOU 4975  CG2  ILE A 666    27777  14963  15916  -3319   3226    732       C
ATOM   4976  CD1  ILE A 666      11.876  17.224 -11.435  1.00151.82           C
ANISOU 4976  CD1  ILE A 666    27799  13008  16876  -3925   3243    976       C
ATOM   4977  N    TRP A 667       8.428  14.439 -14.069  1.00177.89           N
ANISOU 4977  N    TRP A 667    30471  19412  17709  -2428   2221    209       N
ATOM   4978  CA   TRP A 667       7.650  13.747 -15.097  1.00180.76           C
ANISOU 4978  CA   TRP A 667    30719  20703  17258   2114   1983     34       C
ATOM   4979  C    TRP A 667       6.199  13.495 -14.720  1.00179.21           C
ANISOU 4979  C    TRP A 667    30296  20952  16844  -1778   1388   -159       C
ATOM   4980  O    TRP A 667       5.809  13.651 -13.569  1.00174.89           O
ANISOU 4980  O    TRP A 667    29631  19998  16821  -1817   1179   -266       O
ATOM   4981  CB   TRP A 667       8.358  12.463 -15.583  1.00179.74           C
ANISOU 4981  CB   TRP A 667    30299  20914  17082  -2493   2109   -525       C
ATOM   4982  CG   TRP A 667       7.977  11.096 -14.950  1.00174.11           C
ANISOU 4982  CG   TRP A 667    29092  20429  16634  -2753   1689  -1293       C
ATOM   4983  CD1  TRP A 667       6.760  10.457 -15.005  1.00173.65           C
ANISOU 4983  CD1  TRP A 667    28814  20985  16182  -2572   1172  -1642       C
ATOM   4984  CD2  TRP A 667       8.863  10.188 -14.267  1.00169.33           C
ANISOU 4984  CD2  TRP A 667    28156  19451  16731  -3244   1788  -1765       C
ATOM   4985  NE1  TRP A 667       6.832   9.237 -14.367  1.00168.70           N
ANISOU 4985  NE1  TRP A 667    27793  20320  15984  -2947    983  -2302       N
ATOM   4986  CE2  TRP A 667       8.108   9.050 -13.910  1.00166.00           C
ANISOU 4986  CE2  TRP A 667    27392  19375  16305  -3326   1349  -2369       C
ATOM   4987  CE3  TRP A 667      10.214  10.242 -13.906  1.00168.14           C
ANISOU 4987  CE3  TRP A 667    27933  18710  17243  -3620   2193  -1699       C
ATOM   4988  CZ2  TRP A 667       8.658   7.988 -13.212  1.00161.54           C
ANISOU 4988  CZ2  TRP A 667    26485  18539  16353  -3724   1329  -2872       C
ATOM   4989  CZ3  TRP A 667      10.755   9.184 -13.215  1.00163.81           C
ANISOU 4989  CZ3  TRP A 667    26983  17956  17303  -3991   2124  -2192       C
ATOM   4990  CH2  TRP A 667       9.981   8.073 -12.873  1.00160.52           C
ANISOU 4990  CH2  TRP A 667    26296  17846  16849  -4020   1707  -2758       C
ATOM   4991  N    GLU A 668       5.404  13.132 -15.719  1.00160.39           N
ANISOU 4991  N    GLU A 668    27856  19430  13655  -1457   1128   -189       N
ATOM   4992  CA   GLU A 668       3.982  12.856 -15.532  1.00160.43           C
ANISOU 4992  CA   GLU A 668    27553  20004  13398  -1139    543   -349       C
ATOM   4993  C    GLU A 668       3.719  11.385 -15.189  1.00155.94           C
```

FIG. 13 Continued

```
ANISOU 4993  C   GLU A 668    26481  19792  12976  -1541    198  -1174       C
ATOM   4994  O   GLU A 668       4.179  10.889 -14.159  1.00149.65           O
ANISOU 4994  O   GLU A 668    25492  18467  12902  -1949    242  -1552       O
ATOM   4995  CB  GLU A 668       3.188  13.271 -16.779  1.00168.65           C
ANISOU 4995  CB  GLU A 668    28757  21851  13473   -589    352    88        C
ATOM   4996  CG  GLU A 668       3.067  14.777 -16.984  1.00173.76           C
ANISOU 4996  CG  GLU A 668    29871  22160  13990    -42    591   980        C
ATOM   4997  CD  GLU A 668       2.056  15.403  16.048  1.00172.57           C
ANISOU 4997  CD  GLU A 668    29578  21766  14224    357    328  1196        C
ATOM   4998  OE1 GLU A 668       2.058  15.049 -14.851  1.00165.85           O
ANISOU 4998  OE1 GLU A 668    28476  20456  14083     44    263   765        O
ATOM   4999  OE2 GLU A 668       1.259  16.248 -16.508  1.00178.91           O
ANISOU 4999  OE2 GLU A 668    30531  22838  14608   1011    207  1816        O
ATOM   5000  N   PHE A 669       2.981  10.697 -16.062  1.00209.54           N
ANISOU 5000  N   PHE A 669    33085  27471  19060  -1443   -155  -1439       N
ATOM   5001  CA  PHE A 669       2.636   9.296 -15.831  1.00206.54           C
ANISOU 5001  CA  PHE A 669    32267  27436  18773  -1838   -478  -2230       C
ATOM   5002  C   PHE A 669       3.742   8.564 -15.072  1.00200.17           C
ANISOU 5002  C   PHE A 669    31383  25945  18729  -2380   -161  -2674       C
ATOM   5003  O   PHE A 669       4.832   8.338 -15.593  1.00201.10           O
ANISOU 5003  O   PHE A 669    31695  25888  18827  -2591    264  -2737       O
ATOM   5004  CB  PHE A 669       2.236   8.566 -17.130  1.00212.79           C
ANISOU 5004  CB  PHE A 669    33037  29163  18649  -1848   -711  -2540       C
ATOM   5005  CG  PHE A 669       3.032   8.972 -18.356  1.00218.66           C
ANISOU 5005  CG  PHE A 669    34276  30067  18737  -1730   -294  -2211       C
ATOM   5006  CD1 PHE A 669       4.056   8.167 -18.836  1.00218.75           C
ANISOU 5006  CD1 PHE A 669    34424  29982  18708  -2123    117  -2649       C
ATOM   5007  CD2 PHE A 669       2.731  10.139 -19.049  1.00224.84           C
ANISOU 5007  CD2 PHE A 669    35396  31103  18932  -1197   -277  -1445       C
ATOM   5008  CE1 PHE A 669       4.775   8.525 -19.967  1.00224.75           C
ANISOU 5008  CE1 PHE A 669    35645  30907  18843  -2015    570  -2350       C
ATOM   5009  CE2 PHE A 669       3.453  10.504 -20.182  1.00230.83           C
ANISOU 5009  CE2 PHE A 669    36646  32014  19045  -1099    147  -1111       C
ATOM   5010  CZ  PHE A 669       4.475   9.695 -20.639  1.00230.75           C
ANISOU 5010  CZ  PHE A 669    36763  31925  18985  -1523    584  -1576       C
ATOM   5011  N   ASP A 670       3.455   8.222 -13.820  1.00175.39           N
ANISOU 5011  N   ASP A 670    27949  22425  16266  -2576   -354  -2938       N
ATOM   5012  CA  ASP A 670       4.419   7.525 -12.978  1.00169.68           C
ANISOU 5012  CA  ASP A 670    27116  21067  16287  -3054   -141  -3305       C
ATOM   5013  C   ASP A 670       3.817   6.297 -12.286  1.00166.07           C
ANISOU 5013  C   ASP A 670    26248  20723  16127  -3357   -480  -3939       C
ATOM   5014  O   ASP A 670       2.629   6.012 -12.437  1.00167.97           O
ANISOU 5014  O   ASP A 670    26257  21536  16027  -3236   -877  -4110       O
ATOM   5015  CB  ASP A 670       5.122   8.474 -11.991  1.00166.22           C
ANISOU 5015  CB  ASP A 670    26868  19792  16495  -3089    104  -2892       C
ATOM   5016  CG  ASP A 670       4.188   9.040 -10.929  1.00163.81           C
ANISOU 5016  CG  ASP A 670    26508  19284  16449  -2897   -171  -2737       C
ATOM   5017  OD1 ASP A 670       3.036   8.565 -10.807  1.00163.95           O
ANISOU 5017  OD1 ASP A 670    26231  19778  16283  -2782   -545  -2981       O
ATOM   5018  OD2 ASP A 670       4.624   9.965 -10.203  1.00162.31           O
ANISOU 5018  OD2 ASP A 670    26572  18441  16660  -2886     16  -2386       O
ATOM   5019  N   PHE A 671       4.654   5.566 -11.552  1.00129.73           N
ANISOU 5019  N   PHE A 671    21538  15582  12171  -3756   -320  -4254       N
ATOM   5020  CA  PHE A 671       4.253   4.308 -10.933  1.00126.80           C
ANISOU 5020  CA  PHE A 671    20839  15223  12118  -4081   -554  -4840       C
ATOM   5021  C   PHE A 671       3.332   3.634 -11.917  1.00131.43           C
ANISOU 5021  C   PHE A 671    21293  16604  12042   4056    813  5217        C
ATOM   5022  O   PHE A 671       3.441   3.830 -13.119  1.00136.53           O
ANISOU 5022  O   PHE A 671    22133  17700  12043  -3899   -715  -5143       O
ATOM   5023  CB  PHE A 671       3.493   4.504  -9.615  1.00122.77           C
ANISOU 5023  CB  PHE A 671    20162  14457  12029  -4081   -826  -4783       C
ATOM   5024  CG  PHE A 671       4.319   5.097  -8.485  1.00118.50           C
ANISOU 5024  CG  PHE A 671    19776  13129  12118  -4184   -651  -4491       C
ATOM   5025  CD1 PHE A 671       5.621   4.664  -8.243  1.00116.50           C
ANISOU 5025  CD1 PHE A 671    19543  12388  12334  -4492   -403  -4576       C
ATOM   5026  CD2 PHE A 671       3.765   6.069  -7.640  1.00117.18           C
ANISOU 5026  CD2 PHE A 671    19724  12722  12078  -3978   -747  -4149       C
ATOM   5027  CE1 PHE A 671       6.356   5.218  -7.192  1.00113.41           C
ANISOU 5027  CE1 PHE A 671    19266  11338  12487  -4636   -329  -4312       C
```

FIG. 13 Continued

```
ATOM   5028  CE2 PHE A 671       4.490   6.607  -6.609  1.00114.09           C
ANISOU 5028  CE2 PHE A 671    19530 11630 12190  -4129   -623  -3939         C
ATOM   5029  CZ  PHE A 671       5.777   6.192  -6.376  1.00112.23           C
ANISOU 5029  CZ  PHE A 671    19295 10965 12384  -4482   -455  -4018         C
ATOM   5030  N   SER A 672       2.389   2.865 -11.407  1.00 95.13           N
ANISOU 5030  N   SER A 672    16372 12204  7569  -4235  -1156  -5612         N
ATOM   5031  CA  SER A 672       1.474   2.188 -12.297  1.00100.19           C
ANISOU 5031  CA  SER A 672    16844 13618  7606  -4302  -1463  -6019         C
ATOM   5032  C   SER A 672       0.290   1.591 -11.588  1.00 99.28           C
ANISOU 5032  C   SER A 672    16310 13711  7703  -4481  -1857  -6327         C
ATOM   5033  O   SER A 672       0.088   1.757 -10.384  1.00 94.73           O
ANISOU 5033  O   SER A 672    15596 12702  7697  -4498  -1876  -6190         O
ATOM   5034  CB  SER A 672       2.189   1.077 -13.073  1.00102.54           C
ANISOU 5034  CB  SER A 672    17270 13937  7752  -4633  -1228  -6577         C
ATOM   5035  OG  SER A 672       2.875   1.593 -14.194  1.00106.65           O
ANISOU 5035  OG  SER A 672    18143 14656  7721  -4424  -1093  -6347         O
ATOM   5036  N   ALA A 673      -0.518   0.930 -12.402  1.00123.95           N
ANISOU 5036  N   ALA A 673    19245 17549 10303  -4628  -2169  -6741         N
ATOM   5037  CA  ALA A 673      -1.621   0.146 -11.924  1.00124.57           C
ANISOU 5037  CA  ALA A 673    18879 17898 10553  -4918  -2525  -7145         C
ATOM   5038  C   ALA A 673      -0.914  -1.128 -11.534  1.00121.80           C
ANISOU 5038  C   ALA A 673    18604 16971 10703  -5424  -2268  -7714         C
ATOM   5039  O   ALA A 673      -0.489  -1.285 -10.387  1.00116.79           O
ANISOU 5039  O   ALA A 673    17907 15647 10821  -5482  -2019  -7536         O
ATOM   5040  CB  ALA A 673      -2.599  -0.110 -13.040  1.00132.28           C
ANISOU 5040  CB  ALA A 673    19649 19851 10761  -4959  -2964  -7403         C
ATOM   5041  N   PHE A 674      -0.723  -2.002 -12.518  1.00131.42           N
ANISOU 5041  N   PHE A 674    19954 18458 11523  -5706  -2237  -8256         N
ATOM   5042  CA  PHE A 674      -0.064  -3.280 -12.297  1.00131.54           C
ANISOU 5042  CA  PHE A 674    19962 17932 12086  -6054  -1833  -8612         C
ATOM   5043  C   PHE A 674       1.354  -3.187 -11.717  1.00126.71           C
ANISOU 5043  C   PHE A 674    19556 16489 12099  -5927  -1304  -8284         C
ATOM   5044  O   PHE A 674       2.029  -4.212 -11.600  1.00127.41           O
ANISOU 5044  O   PHE A 674    19648 16143 12620  -6125   -936  -8511         O
ATOM   5045  CB  PHE A 674      -0.041  -4.106 -13.578  1.00138.31           C
ANISOU 5045  CB  PHE A 674    21033 19204 12316  -6337  -1833  -9265         C
ATOM   5046  CG  PHE A 674       0.249  -5.562 -13.349  1.00140.29           C
ANISOU 5046  CG  PHE A 674    21201 18990 13114  -6722  -1482  -9699         C
ATOM   5047  CD1 PHE A 674      -0.789  -6.470 -13.188  1.00144.17           C
ANISOU 5047  CD1 PHE A 674    21354 19718 13706  -7104  -1713 -10086         C
ATOM   5048  CD2 PHE A 674       1.555  -6.030 -13.296  1.00138.80           C
ANISOU 5048  CD2 PHE A 674    21273 18122 13343  -6704   -917  -9734         C
ATOM   5049  CE1 PHE A 674      -0.533  -7.824 -12.981  1.00146.55           C
ANISOU 5049  CE1 PHE A 674    21654 19543 14485  -7461  -1363 -10501         C
ATOM   5050  CE2 PHE A 674       1.820  -7.379 -13.084  1.00141.13           C
ANISOU 5050  CE2 PHE A 674    21528 17966 14127  -7009   -588 -10130         C
ATOM   5051  CZ  PHE A 674       0.773  -8.277 -12.929  1.00145.01           C
ANISOU 5051  CZ  PHE A 674    21757 18656 14685  -7386   -801 -10514         C
ATOM   5052  N   MET A 675       1.825  -1.986 -11.372  1.00112.08           N
ANISOU 5052  N   MET A 675    17878 14416 10289  -5614  -1275  -7778         N
ATOM   5053  CA  MET A 675       3.145  -1.885 -10.751  1.00108.09           C
ANISOU 5053  CA  MET A 675    17487 13167 10415  -5554   -844  -7458         C
ATOM   5054  C   MET A 675       3.125  -1.592  -9.262  1.00103.37           C
ANISOU 5054  C   MET A 675    16651 12109 10517  -5461   -835  -6944         C
ATOM   5055  O   MET A 675       3.964  -2.089  -8.528  1.00101.47           O
ANISOU 5055  O   MET A 675    16320 11354 10881  -5508   -552  -6772         O
ATOM   5056  CB  MET A 675       4.079  -0.949 -11.501  1.00108.21           C
ANISOU 5056  CB  MET A 675    17904 13143 10069  -5343   -628  -7258         C
ATOM   5057  CG  MET A 675       5.272  -1.688 -12.130  1.00110.37           C
ANISOU 5057  CG  MET A 675    18348 13138 10449  -5466   -145  -7551         C
ATOM   5058  SD  MET A 675       5.147  -3.512 -12.387  1.00114.10           S
ANISOU 5058  SD  MET A 675    18709 13560 11084  -5839     -9  -8317         S
ATOM   5059  CE  MET A 675       5.958  -4.081 -10.884  1.00109.75           C
ANISOU 5059  CE  MET A 675    17804 12197 11700  -5855    257  -7924         C
ATOM   5060  N   VAL A 676       2.178  -0.786  -8.809  1.00116.34           N
ANISOU 5060  N   VAL A 676    18215 13966 12022  -5305  -1149  -6712         N
ATOM   5061  CA  VAL A 676       2.062  -0.550  -7.377  1.00112.66           C
ANISOU 5061  CA  VAL A 676    17587 13098 12119  -5225  -1114  -6288         C
ATOM   5062  C   VAL A 676       1.371  -1.771  -6.808  1.00114.05           C
```

FIG. 13 Continued

```
ANISOU 5062  C   VAL A 676    17401  13339  12594  -5429  -1114  -6501        C
ATOM   5063  O   VAL A 676       1.679  -2.226  -5.721  1.00112.14            O
ANISOU 5063  O   VAL A 676    17051  12704  12854  -5448   -934  -6274        O
ATOM   5064  CB  VAL A 676       1.292   0.743  -7.041  1.00111.03            C
ANISOU 5064  CB  VAL A 676    17484  13013  11691  -4980  -1381  -6024        C
ATOM   5065  CG1 VAL A 676       0.216   0.470  -5.991  1.00110.45            C
ANISOU 5065  CG1 VAL A 676    17088  12987  11889  -5000  -1503  -5979        C
ATOM   5066  CG2 VAL A 676       2.270   1.855  -6.601  1.00107.86            C
ANISOU 5066  CG2 VAL A 676    17433  12073  11475  -4822  -1206  -5581        C
ATOM   5067  N   LEU A 677       0.439  -2.314  -7.569  1.00 94.57            N
ANISOU 5067  N   LEU A 677    14771  11404   9759  -5601  -1336  -6958        N
ATOM   5068  CA  LEU A 677      -0.212  -3.549  -7.181  1.00 96.89            C
ANISOU 5068  CA  LEU A 677    14754  11743  10318  -5882  -1311  -7252        C
ATOM   5069  C   LEU A 677       0.873  -4.619  -6.977  1.00 96.98            C
ANISOU 5069  C   LEU A 677    14840  11243  10764  -6013   -911  -7323        C
ATOM   5070  O   LEU A 677       0.940  -5.267  -5.936  1.00 95.82            O
ANISOU 5070  O   LEU A 677    14569  10743  11097  -6062   -747  -7176        O
ATOM   5071  CB  LEU A 677      -1.161  -3.986  -8.293  1.00102.40            C
ANISOU 5071  CB  LEU A 677    15312  13118  10476  -6124  -1624  -7814        C
ATOM   5072  CG  LEU A 677      -2.480  -4.695  -7.988  1.00105.60            C
ANISOU 5072  CG  LEU A 677    15304  13865  10953  -6417  -1848  -8119        C
ATOM   5073  CD1 LEU A 677      -2.225  -6.051  -7.360  1.00106.46            C
ANISOU 5073  CD1 LEU A 677    15342  13501  11609  -6706  -1497  -8288        C
ATOM   5074  CD2 LEU A 677      -3.371  -3.817  -7.111  1.00102.98            C
ANISOU 5074  CD2 LEU A 677    14744  13662  10723  -6215  -2070  -7780        C
ATOM   5075  N   ILE A 678       1.736  -4.794  -7.972  1.00114.72            N
ANISOU 5075  N   ILE A 678    17321  13457  12812  -6051   -750  -7563        N
ATOM   5076  CA  ILE A 678       2.816  -5.771  -7.870  1.00115.27            C
ANISOU 5076  CA  ILE A 678    17463  13032  13304  -6142   -363  -7678        C
ATOM   5077  C   ILE A 678       3.936  -5.239  -6.980  1.00110.79            C
ANISOU 5077  C   ILE A 678    16944  11965  13187  -5897   -184  -7118        C
ATOM   5078  O   ILE A 678       5.126  -5.380  -7.282  1.00110.78            O
ANISOU 5078  O   ILE A 678    17074  11647  13370  -5862     82  -7134        O
ATOM   5079  CB  ILE A 678       3.362  -6.179  -9.250  1.00119.30            C
ANISOU 5079  CB  ILE A 678    18234  13651  13445  -6278   -195  -8204        C
ATOM   5080  CG1 ILE A 678       2.211  -6.490 -10.194  1.00124.44            C
ANISOU 5080  CG1 ILE A 678    18872  14932  13479  -6528   -487  -8751        C
ATOM   5081  CG2 ILE A 678       4.252  -7.404  -9.133  1.00121.01            C
ANISOU 5081  CG2 ILE A 678    18490  13336  14153  -6404    216  -8452        C
ATOM   5082  CD1 ILE A 678       1.225   7.457   9.614  1.00126.64            C
ANISOU 5082  CD1 ILE A 678    18850  15247  14023  -6813   -587  -8973        C
ATOM   5083  N   ILE A 679       3.535  -4.591  -5.894  1.00 82.34            N
ANISOU 5083  N   ILE A 679    13241   8311   9733  -5744   -340  -6658        N
ATOM   5084  CA  ILE A 679       4.481  -4.129  -4.896  1.00 78.89            C
ANISOU 5084  CA  ILE A 679    12846   7455   9675  -5560   -246  -6145        C
ATOM   5085  C   ILE A 679       3.828  -4.258  -3.537  1.00 77.36            C
ANISOU 5085  C   ILE A 679    12522   7178   9693  -5522   -348  -5871        C
ATOM   5086  O   ILE A 679       4.465  -4.704  -2.576  1.00 76.43            O
ANISOU 5086  O   ILE A 679    12380   6717   9945  -5482   -262  -5637        O
ATOM   5087  CB  ILE A 679       4.985  -2.690  -5.130  1.00 76.58            C
ANISOU 5087  CB  ILE A 679    12766   7143   9188  -5390   -308  -5824        C
ATOM   5088  CG1 ILE A 679       6.275   2.467   4.344  1.00 74.57            C
ANISOU 5088  CG1 ILE A 679    12536   6443   9356  -5306   -180  -5432        C
ATOM   5089  CG2 ILE A 679       3.965  -1.662  -4.708  1.00 74.96            C
ANISOU 5089  CG2 ILE A 679    12605   7137   8738  -5266   -563  -5598        C
ATOM   5090  CD1 ILE A 679       6.752  -1.055  -4.383  1.00 72.72            C
ANISOU 5090  CD1 ILE A 679    12519   6109   9002  -5207   -230  -5100        C
ATOM   5091  N   ALA A 680       2.552  -3.886  -3.470  1.00114.46            N
ANISOU 5091  N   ALA A 680    17145  12204  14141  -5540   -546  -5931        N
ATOM   5092  CA  ALA A 680       1.787  -3.992  -2.236  1.00113.48            C
ANISOU 5092  CA  ALA A 680    16921  12022  14175  -5537   -601  -5743        C
ATOM   5093  C   ALA A 680       1.232  -5.405  -2.109  1.00116.44            C
ANISOU 5093  C   ALA A 680    17104  12407  14729  -5799   -514  -6097        C
ATOM   5094  O   ALA A 680       1.340  -6.021  -1.062  1.00116.11            O
ANISOU 5094  O   ALA A 680    17058  12080  14978  -5833   -415  -5943        O
ATOM   5095  CB  ALA A 680       0.682  -2.944  -2.172  1.00112.67            C
ANISOU 5095  CB  ALA A 680    16803  12211  13796  -5444   -817  -5681        C
ATOM   5096  N   ILE A 681       0.648  -5.942  -3.166  1.00118.36            N
ANISOU 5096  N   ILE A 681    17229  12969  14774  -6020   -564  -6593        N
```

FIG. 13 Continued

```
ATOM   5097  CA  ILE A 681       0.224  -7.326  -3.074  1.00121.85           C
ANISOU 5097  CA  ILE A 681    17540  13338  15422  -6332    449  -6971       C
ATOM   5098  C   ILE A 681       1.533  -8.099  -2.959  1.00121.94           C
ANISOU 5098  C   ILE A 681    17702  12856  15774  -6299   -180  -6932       C
ATOM   5099  O   ILE A 681       1.571  -9.252  -2.529  1.00124.08           O
ANISOU 5099  O   ILE A 681    17958  12826  16362  -6477    -16  -7092       O
ATOM   5100  CB  ILE A 681      -0.600  -7.803  -4.307  1.00126.65           C
ANISOU 5100  CB  ILE A 681    18017  14397  15707  -6650   -585  -7593       C
ATOM   5101  CG1 ILE A 681      -1.913  -8.494  -3.874  1.00129.67           C
ANISOU 5101  CG1 ILE A 681    18128  14961  16179  -6985   -672  -7869       C
ATOM   5102  CG2 ILE A 681       0.273  -8.664  -5.272  1.00129.76           C
ANISOU 5102  CG2 ILE A 681    18587  14611  16105  -6801   -372  -7999       C
ATOM   5103  CD1 ILE A 681      -1.791  -9.985  -3.580  1.00132.99           C
ANISOU 5103  CD1 ILE A 681    18576  14988  16968  -7311   -408  -8168       C
ATOM   5104  N   LEU A 682       2.623  -7.462  -3.356  1.00111.27           N
ANISOU 5104  N   LEU A 682    16495  11395  14388  -6083   -131  -6737       N
ATOM   5105  CA  LEU A 682       3.898  -8.110  -3.185  1.00111.43           C
ANISOU 5105  CA  LEU A 682    16597  10949  14794  -6029     98  -6686       C
ATOM   5106  C   LEU A 682       4.062  -8.331  -1.693  1.00109.59           C
ANISOU 5106  C   LEU A 682    16343  10397  14899  -5931     72  -6269       C
ATOM   5107  O   LEU A 682       3.996  -9.479  -1.237  1.00111.80           O
ANISOU 5107  O   LEU A 682    16605  10397  15478  -6077    191  -6417       O
ATOM   5108  CB  LEU A 682       5.033  -7.246  -3.727  1.00109.57           C
ANISOU 5108  CB  LEU A 682    16477  10651  14503  -5834    144  -6502       C
ATOM   5109  CG  LEU A 682       6.493  -7.641  -3.455  1.00109.35           C
ANISOU 5109  CG  LEU A 682    16465  10143  14940  -5732    338  -6363       C
ATOM   5110  CD1 LEU A 682       7.016  -7.021  -2.142  1.00106.12           C
ANISOU 5110  CD1 LEU A 682    16031   9542  14749  -5535    168  -5767       C
ATOM   5111  CD2 LEU A 682       6.673  -9.175  -3.509  1.00113.01           C
ANISOU 5111  CD2 LEU A 682    16905  10259  15774  -5894    575  -6753       C
ATOM   5112  N   ASN A 683       4.224  -7.224  -0.948  1.00125.10           N
ANISOU 5112  N   ASN A 683    18363  12395  16774  -5715    -91  -5782       N
ATOM   5113  CA  ASN A 683       4.493  -7.217   0.509  1.00123.46           C
ANISOU 5113  CA  ASN A 683    18219  11920  16771  -5618   -176  -5358       C
ATOM   5114  C   ASN A 683       3.341  -7.522   1.493  1.00123.78           C
ANISOU 5114  C   ASN A 683    18257  12006  16768  -5736   -222  -5316       C
ATOM   5115  O   ASN A 683       3.469  -7.272   2.689  1.00122.38           O
ANISOU 5115  O   ASN A 683    18209  11665  16626  -5663   -318  -4959       O
ATOM   5116  CB  ASN A 683       5.235  -5.923   0.932  1.00120.47           C
ANISOU 5116  CB  ASN A 683    17965  11511  16299  -5405   -328  -4909       C
ATOM   5117  CG  ASN A 683       4.285  -4.728   1.218  1.00118.56           C
ANISOU 5117  CG  ASN A 683    17818  11532  15697  -5339   -460  -4737       C
ATOM   5118  OD1 ASN A 683       4.662  -3.564   1.014  1.00116.91           O
ANISOU 5118  OD1 ASN A 683    17732  11361  15329  -5217   -534  -4534       O
ATOM   5119  ND2 ASN A 683       3.072  -5.012   1.705  1.00119.15           N
ANISOU 5119  ND2 ASN A 683    17847  11738  15688   5441    466   4835       N
ATOM   5120  N   ASP A 684       2.221  -8.041   1.001  1.00141.57           N
ANISOU 5120  N   ASP A 684    20377  14484  18931  -5957   -163  -5706       N
ATOM   5121  CA  ASP A 684       1.110  -8.390   1.882  1.00142.43           C
ANISOU 5121  CA  ASP A 684    20446  14619  19051  -6128   -160  -5720       C
ATOM   5122  C   ASP A 684       1.435  -9.703   2.585  1.00144.62           C
ANISOU 5122  C   ASP A 684    20798  14467  19686  -6283    -21  -5750       C
ATOM   5123  O   ASP A 684       1.699  -9.727   3.785  1.00143.59           O
ANISOU 5123  O   ASP A 684    20830  14081  19647  -6221    -63  -5401       O
ATOM   5124  CB  ASP A 684      -0.201  -8.515   1.100  1.00144.84           C
ANISOU 5124  CB  ASP A 684    20524  15328  19182  -6373   -186  -6166       C
ATOM   5125  CG  ASP A 684      -1.354  -7.771   1.764  1.00143.75           C
ANISOU 5125  CG  ASP A 684    20303  15427  18888  -6380   -286  -6050       C
ATOM   5126  OD1 ASP A 684      -1.113  -6.666   2.313  1.00140.55           O
ANISOU 5126  OD1 ASP A 684    20051  14997  18352  -6117   -364  -5664       O
ATOM   5127  OD2 ASP A 684      -2.497  -8.287   1.723  1.00146.54           O
ANISOU 5127  OD2 ASP A 684    20437  15973  19268  -6679   -277  -6381       O
ATOM   5128  N   GLY A 685       1.428 -10.797   1.836  1.00112.77           N
ANISOU 5128  N   GLY A 685    16692  10318  15838  -6506    136  -6187       N
ATOM   5129  CA  GLY A 685       1.772 -12.087   2.401  1.00115.48           C
ANISOU 5129  CA  GLY A 685    17141  10160  16576  -6660    296  -6248       C
ATOM   5130  C   GLY A 685       3.193 -12.137   2.950  1.00114.04           C
ANISOU 5130  C   GLY A 685    17102   9567  16660  -6396    251  -5874       C
ATOM   5131  O   GLY A 685       3.831 -13.191   2.958  1.00116.69           O
```

FIG. 13 Continued

```
ANISOU 5131  O   GLY A 685     17503  9440 17395 -6456   394 -5995           O
ATOM   5132  N   THR A 686      3.688 -10.997   3.414  1.00101.08           N
ANISOU 5132  N   THR A 686     15509  8064 14833 -6128    41 -5439           N
ATOM   5133  CA  THR A 686      5.037 -10.906   3.553  1.00100.02           C
ANISOU 5133  CA  THR A 686     15461  7602 14941 -5919   -90 -5083           C
ATOM   5134  C   THR A 686      5.133  -9.877   5.094  1.00 97.17           C
ANISOU 5134  C   THR A 686     15257  7325 14338 -5787  -361 -4592           C
ATOM   5135  O   THR A 686      6.231  -9.524   5.569  1.00 96.26           O
ANISOU 5135  O   THR A 686     15203  7024 14346 -5645  -568 -4272           O
ATOM   5136  CB  THR A 686      6.063 -10.570   2.855  1.00 99.58           C
ANISOU 5136  CB  THR A 686     15287  7564 14983 -5767   -40 -5193           C
ATOM   5137  OG1 THR A 686      5.701  -9.340   2.216  1.00 97.17           O
ANISOU 5137  OG1 THR A 686     14945  7715 14261 -5686  -102 -5180           O
ATOM   5138  CG2 THR A 686      6.109 -11.674   1.826  1.00103.12           C
ANISOU 5138  CG2 THR A 686     15672  7827 15682 -5923   255 -5712           C
ATOM   5139  N   ILE A 687      3.980  -9.366   5.510  1.00177.33           N
ANISOU 5139  N   ILE A 687     25473 17745 24158 -5868  -363 -4567           N
ATOM   5140  CA  ILE A 687      3.932  -8.469   6.651  1.00175.40           C
ANISOU 5140  CA  ILE A 687     25460 17525 23659 -5803  -558 -4178           C
ATOM   5141  C   ILE A 687      3.496  -9.353   7.793  1.00177.33           C
ANISOU 5141  C   ILE A 687     25890 17494 23995 -6003  -531 -4107           C
ATOM   5142  O   ILE A 687      3.783  -9.086   8.962  1.00177.01           O
ANISOU 5142  O   ILE A 687     26131 17285 23841 -6013  -718 -3777           O
ATOM   5143  CB  ILE A 687      2.907  -7.344   6.461  1.00173.60           C
ANISOU 5143  CB  ILE A 687     25225 17681 23054 -5773  -525 -4214           C
ATOM   5144  CG1 ILE A 687      3.210  -6.185   7.414  1.00171.72           C
ANISOU 5144  CG1 ILE A 687     25278 17412 22557 -5669  -713 -3837           C
ATOM   5145  CG2 ILE A 687      1.488  -7.871   6.655  1.00175.18           C
ANISOU 5145  CG2 ILE A 687     25350 17994 23218 -6004  -346 -4467           C
ATOM   5146  CD1 ILE A 687      4.424  -5.379   7.021  1.00170.38           C
ANISOU 5146  CD1 ILE A 687     25127 17215 22392 -5493  -886 -3647           C
ATOM   5147  N   MET A 688      2.807 -10.426   7.423  1.00143.82           N
ANISOU 5147  N   MET A 688     21521 13178 19947 -6210  -298 -4443           N
ATOM   5148  CA  MET A 688      2.311 -11.391   8.379  1.00146.36           C
ANISOU 5148  CA  MET A 688     22018 13186 20405 -6461  -202 -4426           C
ATOM   5149  C   MET A 688      3.444 -12.203   8.975  1.00147.99           C
ANISOU 5149  C   MET A 688     22399 12876 20956 -6429  -333 -4194           C
ATOM   5150  O   MET A 688      3.271 -13.357   9.356  1.00151.16           O
ANISOU 5150  O   MET A 688     22906 12883 21646 -6635  -195 -4264           O
ATOM   5151  CB  MET A 688      1.270 -12.292   7.729  1.00149.31           C
ANISOU 5151  CB  MET A 688     22197 13600 20933 -6753    88 -4894           C
ATOM   5152  CG  MET A 688     -0.070 -11.598   7.550  1.00148.56           C
ANISOU 5152  CG  MET A 688     21943 13958 20546 -6873   165 -5076           C
ATOM   5153  SD  MET A 688     -0.596 -10.788   9.078  1.00146.90           S
ANISOU 5153  SD  MET A 688     22034 13751 20031 -6887   115 -4701           S
ATOM   5154  CE  MET A 688     -0.368 -12.132  10.245  1.00150.25           C
ANISOU 5154  CE  MET A 688     22787 13581 20722 -7153   204 -4551           C
ATOM   5155  N   THR A 689      4.617 -11.592   9.026  1.00176.42           N
ANISOU 5155  N   THR A 689     26014 16444 24572 -6191  -607 -3919           N
ATOM   5156  CA  THR A 689      5.771 -12.204   9.652  1.00178.04           C
ANISOU 5156  CA  THR A 689     26341 16167 25139 -6150  -830 -3647           C
ATOM   5157  C   THR A 689      6.016 11.507  10.974  1.00177.10           C
ANISOU 5157  C   THR A 689     26554 16018 24719 -6175 -1186 -3213           C
ATOM   5158  O   THR A 689      7.162 -11.368  11.408  1.00177.39           O
ANISOU 5158  O   THR A 689     26644 15832 24923 -6098 -1540 -2916           O
ATOM   5159  CB  THR A 689      7.020 -12.056   8.798  1.00177.55           C
ANISOU 5159  CB  THR A 689     26024 16043 25395 -5928  -922 -3665           C
ATOM   5160  OG1 THR A 689      6.648 -12.083   7.418  1.00177.30           O
ANISOU 5160  OG1 THR A 689     25737 16263 25365 -5899  -608 -4095           O
ATOM   5161  CG2 THR A 689      7.996 -13.186   9.090  1.00180.71           C
ANISOU 5161  CG2 THR A 689     26428 15824 26408 -5925  -992 -3553           C
ATOM   5162  N   ILE A 690      4.944 -11.014  11.590  1.00137.56           N
ANISOU 5162  N   ILE A 690     21765 11227 19273 -6314 -1097 -3200           N
ATOM   5163  CA  ILE A 690      5.077 -10.423  12.915  1.00137.43           C
ANISOU 5163  CA  ILE A 690     22173 11129 18914 -6411 -1386 -2847           C
ATOM   5164  C   ILE A 690      4.604 -11.371  14.010  1.00140.37           C
ANISOU 5164  C   ILE A 690     22899 11119 19315 -6690 -1327 -2735           C
ATOM   5165  O   ILE A 690      3.407 -11.621  14.222  1.00141.14           O
ANISOU 5165  O   ILE A 690     23080 11276 19272 -6886  -992 -2911           O
```

FIG. 13 Continued

```
ATOM   5166  CB   ILE A 690       4.477  -9.036  13.041  1.00 134.94           C
ANISOU 5166  CB   ILE A 690    21980  11207  18084  -6374  -1361  -2844        C
ATOM   5167  CG1  ILE A 690       5.057  -8.149  11.939  1.00 132.56           C
ANISOU 5167  CG1  ILE A 690    21369  11192  17806  -6116  -1419  -2909        C
ATOM   5168  CG2  ILE A 690       4.786  -8.483  14.426  1.00 135.62           C
ANISOU 5168  CG2  ILE A 690    22588  11126  17816  -6523  -1675  -2517        C
ATOM   5169  CD1  ILE A 690       6.530  -8.388  11.684  1.00 133.12           C
ANISOU 5169  CD1  ILE A 690    21288  11045  18245  -6004  -1719  -2753        C
ATOM   5170  N    SER A 691       5.627 -11.901  14.664  1.00 122.13           N
ANISOU 5170  N    SER A 691    20772   8379  17252  -6722  -1672  -2425        N
ATOM   5171  CA   SER A 691       5.576 -12.854  15.747  1.00 125.55           C
ANISOU 5171  CA   SER A 691    21599   8306  17799  -6969  -1730  -2193        C
ATOM   5172  C    SER A 691       6.975 -12.577  16.251  1.00 126.05           C
ANISOU 5172  C    SER A 691    21765   8150  17980  -6903  -2319  -1805        C
ATOM   5173  O    SER A 691       7.697 -13.466  16.688  1.00 129.06           O
ANISOU 5173  O    SER A 691    22241   8006  18790  -6956  -2542  -1537        O
ATOM   5174  CB   SER A 691       5.464 -14.290  15.213  1.00 128.46           C
ANISOU 5174  CB   SER A 691    21777   8273  18760  -7005  -1411  -2368        C
ATOM   5175  OG   SER A 691       4.303 -14.460  14.411  1.00 128.04           O
ANISOU 5175  OG   SER A 691    21481   8498  18669  -7077   -919  -2813        O
ATOM   5176  N    LYS A 692       7.352 -11.308  16.124  1.00 138.43           N
ANISOU 5176  N    LYS A 692    23284  10097  19215  -6799  -2563  -1775        N
ATOM   5177  CA   LYS A 692       8.684 -10.821  16.462  1.00 138.90           C
ANISOU 5177  CA   LYS A 692    23354  10038  19382  -6785  -3149  -1462        C
ATOM   5178  C    LYS A 692       9.154 -11.054  17.897  1.00 142.04           C
ANISOU 5178  C    LYS A 692    24278  10023  19666  -7086  -3650  -1039        C
ATOM   5179  O    LYS A 692       8.446 -11.639  18.717  1.00 143.98           O
ANISOU 5179  O    LYS A 692    24956  10024  19723  -7303  -3510   -956        O
ATOM   5180  CB   LYS A 692       8.785  -9.331  16.136  1.00 136.07           C
ANISOU 5180  CB   LYS A 692    22946  10144  18612  -6698  -3237  -1539        C
ATOM   5181  CG   LYS A 692       9.127  -9.081  14.705  1.00 133.90           C
ANISOU 5181  CG   LYS A 692    22102  10121  18653  -6404  -3027  -1774        C
ATOM   5182  CD   LYS A 692      10.384  -9.870  14.314  1.00 135.72           C
ANISOU 5182  CD   LYS A 692    21963   9998  19605  -6313  -3255  -1654        C
ATOM   5183  CE   LYS A 692      11.521  -9.752  15.343  1.00 138.22           C
ANISOU 5183  CE   LYS A 692    22456   9997  20065  -6514  -3928  -1223        C
ATOM   5184  NZ   LYS A 692      12.836 -10.188  14.786  1.00 139.73           N
ANISOU 5184  NZ   LYS A 692    22152   9905  21036  -6403  -4143  -1104        N
ATOM   5185  N    ASP A 693      10.363 -10.581  18.184  1.00 200.12           N
ANISOU 5185  N    ASP A 693    31596  17287  27153  -7141  -4245   -763        N
ATOM   5186  CA   ASP A 693      10.957 -10.690  19.505  1.00 203.51           C
ANISOU 5186  CA   ASP A 693    32512  17336  27476  -7484  -4855   -329        C
ATOM   5187  C    ASP A 693      11.373  -9.278  19.836  1.00 202.79           C
ANISOU 5187  C    ASP A 693    32604  17557  26889  -7648  -5261   -308        C
ATOM   5188  O    ASP A 693      12.202  -8.708  19.142  1.00 201.82           O
ANISOU 5188  O    ASP A 693    32028  17609  27045  -7520  -5448   -336        O
ATOM   5189  CB   ASP A 693      12.193 -11.595  19.466  1.00 206.47           C
ANISOU 5189  CB   ASP A 693    32559  17202  28687  -7450  -5261     28        C
ATOM   5190  CG   ASP A 693      11.885 -13.009  18.948  1.00 207.73           C
ANISOU 5190  CG   ASP A 693    32505  16966  29458  -7236  -4772    -28        C
ATOM   5191  OD1  ASP A 693      12.837 -13.795  18.720  1.00 210.24           O
ANISOU 5191  OD1  ASP A 693    32501  16805  30575  -7116  -4944    232        O
ATOM   5192  OD2  ASP A 693      10.692 -13.343  18.770  1.00 206.75           O
ANISOU 5192  OD2  ASP A 693    32532  16960  29065  -7209  -4194   -326        O
ATOM   5193  N    ARG A 694      10.808  -8.704  20.890  1.00 156.75           N
ANISOU 5193  N    ARG A 694    27466  11753  20337  -7961  -5358   -277        N
ATOM   5194  CA   ARG A 694      11.085  -7.301  21.181  1.00 156.58           C
ANISOU 5194  CA   ARG A 694    27702  11992  19799  -8138  -5648   -329        C
ATOM   5195  C    ARG A 694      11.320  -6.925  22.662  1.00 160.42           C
ANISOU 5195  C    ARG A 694    28993  12243  19715  -8672  -6224   -107        C
ATOM   5196  O    ARG A 694      11.137  -7.736  23.574  1.00 163.08           O
ANISOU 5196  O    ARG A 694    29787  12208  19967  -8925  -6373    116        O
ATOM   5197  CB   ARG A 694       9.999  -6.415  20.547  1.00 153.07           C
ANISOU 5197  CB   ARG A 694    27249  11974  18938  -7907  -4986   -716        C
ATOM   5198  CG   ARG A 694       9.776  -6.645  19.033  1.00 149.60           C
ANISOU 5198  CG   ARG A 694    26061  11805  18974  -7448  -4483   -959        C
ATOM   5199  CD   ARG A 694       8.956  -5.511  18.347  1.00 146.53           C
ANISOU 5199  CD   ARG A 694    25619  11827  18228  -7255  -3997  -1260        C
ATOM   5200  NE   ARG A 694       9.666  -4.216  18.280  1.00 146.66           N
```

FIG. 13 Continued

```
ANISOU 5200  NE  ARG A 694    25703 11953 18067 -7322 -4281 -1223      N
ATOM   5201  CZ  ARG A 694      9.319  -3.180  17.511  1.00144.41      C
ANISOU 5201  CZ  ARG A 694    25288 11941 17640 -7135 -3954 -1417      C
ATOM   5202  NH1 ARG A 694      8.260  -3.252  16.709  1.00141.66      N
ANISOU 5202  NH1 ARG A 694    24694 11830 17300 -6863 -3376 -1657      N
ATOM   5203  NH2 ARG A 694     10.045  -2.068  17.543  1.00145.38      N
ANISOU 5203  NH2 ARG A 694    25529 12067 17642 -7263 -4230 -1364      N
ATOM   5204  N   VAL A 695     11.717  -5.669  22.867  1.00114.81      N
ANISOU 5204  N   VAL A 695    23429  6654 13538 -8869 -6521  -182      N
ATOM   5205  CA  VAL A 695     12.098  -5.112  24.177  1.00119.14      C
ANISOU 5205  CA  VAL A 695    24742  7028 13497 -9444 -7153   -55      C
ATOM   5206  C   VAL A 695     11.109  -5.153  25.368  1.00121.10      C
ANISOU 5206  C   VAL A 695    25960  7083 12968 -9766 -6967  -129      C
ATOM   5207  O   VAL A 695     10.230  -6.024  25.464  1.00120.13      O
ANISOU 5207  O   VAL A 695    25950  6813 12881 -9640 -6477  -129      O
ATOM   5208  CB  VAL A 695     12.606  -3.654  24.021  1.00119.85      C
ANISOU 5208  CB  VAL A 695    24876  7356 13304 -9585 -7367  -213      C
ATOM   5209  CG1 VAL A 695     14.113  -3.631  23.767  1.00122.13      C
ANISOU 5209  CG1 VAL A 695    24589  7631 14185 -9749 -8125    37      C
ATOM   5210  CG2 VAL A 695     11.835  -2.940  22.912  1.00115.34      C
ANISOU 5210  CG2 VAL A 695    23989  7107 12728 -9113 -6564  -536      C
ATOM   5211  N   LYS A 696     11.301  -4.183  26.269  1.00215.90      N
ANISOU 5211  N   LYS A 696    38682 19069 24280 -10223 -7357  -218     N
ATOM   5212  CA  LYS A 696     10.582  -4.075  27.543  1.00219.05      C
ANISOU 5212  CA  LYS A 696    40142 19243 23844 -10644 -7306  -323     C
ATOM   5213  C   LYS A 696     10.546  -2.627  28.100  1.00221.83      C
ANISOU 5213  C   LYS A 696    41196 19688 23400 -10969 -7398  -634     C
ATOM   5214  O   LYS A 696     11.463  -2.200  28.815  1.00226.64      O
ANISOU 5214  O   LYS A 696    42180 20254 23679 -11475 -8227  -574     O
ATOM   5215  CB  LYS A 696     11.239  -5.012  28.579  1.00223.52      C
ANISOU 5215  CB  LYS A 696    41099 19429 24401 -11127 -8096    49     C
ATOM   5216  CG  LYS A 696     12.705  -4.663  28.928  1.00228.96      C
ANISOU 5216  CG  LYS A 696    41609 20329 25058 -11396 -9164   370     C
ATOM   5217  CD  LYS A 696     13.471  -5.809  29.605  1.00235.72      C
ANISOU 5217  CD  LYS A 696    42339 21229 25996 -11308 -9806  1157     C
ATOM   5218  CE  LYS A 696     13.423  -5.739  31.129  1.00244.28      C
ANISOU 5218  CE  LYS A 696    44443 22437 25935 -11650 -10250 1449     C
ATOM   5219  NZ  LYS A 696     12.341  -6.571  31.722  1.00245.35      N
ANISOU 5219  NZ  LYS A 696    45186 22368 25668 -11493 -9599  1628     N
ATOM   5220  N   PRO A 697      9.476  -1.871  27.788  1.00119.64      N
ANISOU 5220  N   PRO A 697    28438  6862 10159 -10708 -6559  -982     N
ATOM   5221  CA  PRO A 697      9.374  -0.474  28.264  1.00122.65      C
ANISOU 5221  CA  PRO A 697    29524  7225  9852 -10977 -6517 -1300     C
ATOM   5222  C   PRO A 697      8.907  -0.265  29.739  1.00128.01      C
ANISOU 5222  C   PRO A 697    31472  7628  9540 -11508 -6587 -1513     C
ATOM   5223  O   PRO A 697      9.561  -0.734  30.684  1.00132.52      O
ANISOU 5223  O   PRO A 697    32520  8070  9762 -12003 -7373 -1358     O
ATOM   5224  CB  PRO A 697      9.373   0.165  27.271  1.00118.01      C
ANISOU 5224  CB  PRO A 697    28562  6824  9454 -10439 -5563 -1565     C
ATOM   5225  CG  PRO A 697      8.143  -0.870  26.160  1.00112.68      C
ANISOU 5225  CG  PRO A 697    26878  6369  9567 -9913 -5249 -1390      C
ATOM   5226  CD  PRO A 697      8.453  -2.200  26.773  1.00114.25      C
ANISOU 5226  CD  PRO A 697    27149  6366  9895 -10126 -5670 -1098     C
ATOM   5227  N   SER A 698      7.802   0.480  29.896  1.00140.82      N
ANISOU 5227  N   SER A 698    33629  9177 10700 -11398 -5784 -1894     N
ATOM   5228  CA  SER A 698      7.146   0.792  31.185  1.00145.84      C
ANISOU 5228  CA  SER A 698    35518  9544 10350 -11801 -5590 -2216     C
ATOM   5229  C   SER A 698      5.758   1.513  31.043  1.00144.45      C
ANISOU 5229  C   SER A 698    35647  9283  9954 -11487 -4474 -2632     C
ATOM   5230  O   SER A 698      4.718   0.933  31.373  1.00143.75      O
ANISOU 5230  O   SER A 698    35814  9076  9730 -11401 -3860 -2740     O
ATOM   5231  CB  SER A 698      8.105   1.519  32.141  1.00152.99      C
ANISOU 5231  CB  SER A 698    37251 10378 10500 -12434 -6443 -2330     C
ATOM   5232  OG  SER A 698      8.920   2.466  31.458  1.00153.02      O
ANISOU 5232  OG  SER A 698    36793 10499 10851 -12417 -6733 -2327     O
ATOM   5233  N   PRO A 699      5.738   2.779  30.566  1.00193.43      N
ANISOU 5233  N   PRO A 699    41831 15500 16162 -11337 -4204 -2871     N
ATOM   5234  CA  PRO A 699      4.446   3.427  30.291  1.00191.89      C
ANISOU 5234  CA  PRO A 699    41767 15220 15924 -10965 -3174 -3228     C
```

FIG. 13 Continued

```
ATOM    5235  C   PRO A 699       4.029   3.143  28.842  1.00 184.82           C
ANISOU  5235  C   PRO A 699    39624  14651  15949 -10342  -2750  -3065        C
ATOM    5236  O   PRO A 699       4.843   3.401  27.955  1.00 182.51           O
ANISOU  5236  O   PRO A 699    38636  14570  16140 -10186  -3124  -2874        O
ATOM    5237  CB  PRO A 699       4.765   4.923  30.442  1.00 195.99           C
ANISOU  5237  CB  PRO A 699    42882  15537  16050 -11133  -3187  -3539        C
ATOM    5238  CG  PRO A 699       6.209   5.009  30.891  1.00 200.15           C
ANISOU  5238  CG  PRO A 699    43627  16070  16349 -11679  -4256  -3365        C
ATOM    5239  CD  PRO A 699       6.842   3.744  30.445  1.00 196.29           C
ANISOU  5239  CD  PRO A 699    42237  15867  16475 -11590  -4816  -2880        C
ATOM    5240  N   THR A 700       2.802   2.668  28.580  1.00 190.58           N
ANISOU  5240  N   THR A 700    40087  15432  16893 -10019  -1993  -3177        N
ATOM    5241  CA  THR A 700       2.452   2.274  27.212  1.00 184.51           C
ANISOU  5241  CA  THR A 700    38126  15034  16945  -9497  -1715  -3035        C
ATOM    5242  C   THR A 700       1.132   2.758  26.598  1.00 182.23           C
ANISOU  5242  C   THR A 700    37545  14807  16886  -9077   -844  -3330        C
ATOM    5243  O   THR A 700       0.051   2.301  26.974  1.00 182.59           O
ANISOU  5243  O   THR A 700    37748  14757  16872  -9063   -273  -3503        O
ATOM    5244  CB  THR A 700       2.396   0.755  27.135  1.00 182.38           C
ANISOU  5244  CB  THR A 700    37367  14892  17038  -9500  -1837  -2766        C
ATOM    5245  OG1 THR A 700       1.209   0.308  27.799  1.00 183.72           O
ANISOU  5245  OG1 THR A 700    37968  14861  16976  -9595  -1205  -2966        O
ATOM    5246  CG2 THR A 700       3.629   0.134  27.792  1.00 184.95           C
ANISOU  5246  CG2 THR A 700    37972  15099  17201  -9901  -2710  -2452        C
ATOM    5247  N   PRO A 701       1.223   3.678  25.632  1.00 156.83           N
ANISOU  5247  N   PRO A 701    33889  11728  13970  -8749   -754  -3367        N
ATOM    5248  CA  PRO A 701       0.024   4.151  24.938  1.00 154.71           C
ANISOU  5248  CA  PRO A 701    33263  11524  13997  -8323    -27  -3641        C
ATOM    5249  C   PRO A 701       0.173   4.299  23.403  1.00 149.91           C
ANISOU  5249  C   PRO A 701    31619  11300  14040  -7894    -96  -3515        C
ATOM    5250  O   PRO A 701       1.256   4.650  22.925  1.00 149.26           O
ANISOU  5250  O   PRO A 701    31342  11307  14061  -7905   -590  -3328        O
ATOM    5251  CB  PRO A 701      -0.155   5.552  25.544  1.00 159.13           C
ANISOU  5251  CB  PRO A 701    34756  11656  14051  -8383    273  -3967        C
ATOM    5252  CG  PRO A 701       1.233   5.882  26.255  1.00 162.91           C
ANISOU  5252  CG  PRO A 701    35887  11952  14060  -8868   -469  -3837        C
ATOM    5253  CD  PRO A 701       2.167   4.782  25.832  1.00 159.82           C
ANISOU  5253  CD  PRO A 701    34764  11915  14044  -8946  -1149  -3417        C
ATOM    5254  N   ASP A 702      -0.895   4.026  22.646  1.00 136.51           N
ANISOU  5254  N   ASP A 702    29287   9815  12767  -7556    378  -3640        N
ATOM    5255  CA  ASP A 702      -0.899   4.307  21.200  1.00 132.65           C
ANISOU  5255  CA  ASP A 702    27951   9649  12800  -7157    358  -3594        C
ATOM    5256  C   ASP A 702      -1.864   5.463  20.829  1.00 133.16           C
ANISOU  5256  C   ASP A 702    28128   9541  12927  -6825    902  -3895        C
ATOM    5257  O   ASP A 702      -3.078   5.323  21.002  1.00 133.66           O
ANISOU  5257  O   ASP A 702    28168   9541  13076  -6704   1430  -4147        O
ATOM    5258  CB  ASP A 702      -1.140   3.044  20.329  1.00 128.93           C
ANISOU  5258  CB  ASP A 702    26532   9609  12848  -7026    293  -3477        C
ATOM    5259  CG  ASP A 702      -2.383   2.238  20.736  1.00 129.46           C
ANISOU  5259  CG  ASP A 702    26522   9665  13004  -7105    764  -3671        C
ATOM    5260  OD1 ASP A 702      -2.787   1.317  19.963  1.00 127.09           O
ANISOU  5260  OD1 ASP A 702    25457   9678  13151  -7018    797  -3667        O
ATOM    5261  OD2 ASP A 702      -2.941   2.515  21.826  1.00 132.71           O
ANISOU  5261  OD2 ASP A 702    27662   9726  13035  -7285   1116  -3855        O
ATOM    5262  N   SER A 703      -1.316   6.598  20.351  1.00  93.29           N
ANISOU  5262  N   SER A 703    23227   4362   7858  -6684    785  -3882        N
ATOM    5263  CA  SER A 703      -2.098   7.791  19.923  1.00  94.21           C
ANISOU  5263  CA  SER A 703    23506   4227   8064  -6312   1263  -4137        C
ATOM    5264  C   SER A 703      -1.330   8.772  18.995  1.00  93.44           C
ANISOU  5264  C   SER A 703    23303   4090   8111  -6148   1024  -4022        C
ATOM    5265  O   SER A 703      -1.531   8.774  17.790  1.00  90.21           O
ANISOU  5265  O   SER A 703    22210   3948   8118  -5830   1004  -3967        O
ATOM    5266  CB  SER A 703      -2.769   8.535  21.115  1.00  99.33           C
ANISOU  5266  CB  SER A 703    25165   4321   8256  -6361   1803  -4469        C
ATOM    5267  OG  SER A 703      -1.975   8.573  22.292  1.00 103.05           O
ANISOU  5267  OG  SER A 703    26468   4529   8158  -6837   1549  -4441        O
ATOM    5268  N   TRP A 704      -0.448   9.581  19.571  1.00 143.40           N
ANISOU  5268  N   TRP A 704    30346  10062  14079  -6415    835  -4009        N
ATOM    5269  CA  TRP A 704       0.340  10.601  18.862  1.00 143.83           C
```

FIG. 13 Continued

```
ATOM   5269  CA  TRP A 704      30457   9963  14228  -6361    650  -3933           C
ANISOU 5270  C   TRP A 704         1.459  10.083  17.959  1.00140.43              C
ATOM   5270  C   TRP A 704      29306   9955  14096  -6435     84  -3615           C
ANISOU 5271  O   TRP A 704         2.258  10.858  17.430  1.00141.12              O
ATOM   5271  O   TRP A 704      29451   9912  14257  -6476    -99  -3543           O
ANISOU 5272  CB  TRP A 704         0.945  11.560  19.893  1.00149.57              C
ATOM   5272  CB  TRP A 704      32235  10137  14457  -6740    613  -4078           C
ANISOU 5273  CG  TRP A 704         0.968  11.012  21.337  1.00152.82              C
ATOM   5273  CG  TRP A 704      33286  10420  14357  -7165    536  -4169           C
ANISOU 5274  CD1 TRP A 704         0.782  11.731  22.496  1.00158.74              C
ATOM   5274  CD1 TRP A 704      35137  10621  14557  -7411    806  -4474           C
ANISOU 5275  CD2 TRP A 704         1.168   9.639  21.750  1.00150.82              C
ATOM   5275  CD2 TRP A 704      32683  10546  14077  -7384    195  -3972           C
ANISOU 5276  NE1 TRP A 704         0.865  10.895  23.587  1.00160.39              N
ATOM   5276  NE1 TRP A 704      35700  10879  14363  -7790    618  -4472           N
ANISOU 5277  CE2 TRP A 704         1.096   9.611  23.158  1.00155.56              C
ATOM   5277  CE2 TRP A 704      34211  10813  14083  -7772    242  -4148           C
ANISOU 5278  CE3 TRP A 704         1.408   8.438  21.064  1.00146.01              C
ATOM   5278  CE3 TRP A 704      31132  10473  13874  -7287   -124  -3685           C
ANISOU 5279  CZ2 TRP A 704         1.254   8.431  23.889  1.00155.42              C
ATOM   5279  CZ2 TRP A 704      34197  10977  13879  -8065    -44  -4009           C
ANISOU 5280  CZ3 TRP A 704         1.560   7.274  21.791  1.00146.04              C
ATOM   5280  CZ3 TRP A 704      31135  10621  13733  -7555   -373  -3558           C
ANISOU 5281  CH2 TRP A 704         1.486   7.280  23.187  1.00150.60              C
ATOM   5281  CH2 TRP A 704      32638  10855  13728  -7941   -347  -3700           C
ANISOU 5282  N   LYS A 705         1.529   8.768  17.817  1.00114.82              N
ATOM   5282  N   LYS A 705      25433   7160  11032  -6462   -150  -3449           N
ANISOU 5283  CA  LYS A 705         2.506   8.130  16.946  1.00111.82              C
ATOM   5283  CA  LYS A 705      24352   7162  10974  -6460   -598  -3186           C
ANISOU 5284  C   LYS A 705         2.157   8.343  15.470  1.00108.49              C
ATOM   5284  C   LYS A 705      23294   6971  10955  -6056   -442  -3187           C
ANISOU 5285  O   LYS A 705         3.043   8.440  14.618  1.00107.18              O
ATOM   5285  O   LYS A 705      22782   6940  11000  -6033   -701  -3035           O
ANISOU 5286  CB  LYS A 705         2.527   6.629  17.210  1.00110.04              C
ATOM   5286  CB  LYS A 705      23703   7261  10846  -6550   -792  -3055           C
ANISOU 5287  CG  LYS A 705         1.301   5.889  16.649  1.00107.20              C
ATOM   5287  CG  LYS A 705      22785   7186  10759  -6263   -437  -3171           C
ANISOU 5288  CD  LYS A 705        -0.003   6.362  17.301  1.00109.08              C
ATOM   5288  CD  LYS A 705      23475   7167  10803  -6200     84  -3451           C
ANISOU 5289  CE  LYS A 705        -1.227   5.594  16.800  1.00106.89              C
ATOM   5289  CE  LYS A 705      22603   7167  10845  -5993    394  -3602           C
ANISOU 5290  NZ  LYS A 705        -2.482   6.037  17.474  1.00109.18              N
ATOM   5290  NZ  LYS A 705      23310   7170  11002  -5921    933  -3906           N
ANISOU 5291  N   LEU A 706         0.858   8.394  15.178  1.00136.44              N
ATOM   5291  N   LEU A 706      26696  10541  14605  -5757    -26  -3376           N
ANISOU 5292  CA  LEU A 706         0.353   8.571  13.816  1.00133.75              C
ATOM   5292  CA  LEU A 706      25805  10403  14610  -5386     92  -3415           C
ANISOU 5293  C   LEU A 706         0.966   9.821  13.169  1.00134.73              C
ATOM   5293  C   LEU A 706      26193  10250  14749  -5293     67  -3364           C
ANISOU 5294  O   LEU A 706         1.130   9.868  11.949  1.00132.49              O
ATOM   5294  O   LEU A 706      25459  10164  14719  -5098    -17  -3295           O
ANISOU 5295  CB  LEU A 706        -1.186   8.648  13.822  1.00133.84              C
ATOM   5295  CB  LEU A 706      25775  10366  14713  -5105    532  -3684           C
ANISOU 5296  CG  LEU A 706        -2.076   8.091  12.698  1.00131.02              C
ATOM   5296  CG  LEU A 706      24667  10392  14721  -4826    580  -3798           C
ANISOU 5297  CD1 LEU A 706        -3.467   7.858  13.266  1.00132.18              C
ATOM   5297  CD1 LEU A 706      24833  10477  14911  -4727    968  -4089           C
ANISOU 5298  CD2 LEU A 706        -2.139   8.972  11.429  1.00130.17              C
ATOM   5298  CD2 LEU A 706      24433  10233  14791  -4483    573  -3814           C
ANISOU 5299  N   LYS A 707         1.305  10.827  13.981  1.00182.97              N
ATOM   5299  N   LYS A 707      33084  15865  20571  -5467    154  -3420           N
ANISOU 5300  CA  LYS A 707         1.931  12.054  13.467  1.00184.83              C
ATOM   5300  CA  LYS A 707      33664  15739  20823  -5452    163  -3386           C
ANISOU 5301  C   LYS A 707         3.445  11.913  13.301  1.00184.91              C
ATOM   5301  C   LYS A 707      33524  15869  20866  -5809   -304  -3176           C
ANISOU 5302  O   LYS A 707         4.036  12.515  12.404  1.00184.81              O
ATOM   5302  O   LYS A 707      33416  15774  21029  -5772   -354  -3091           O
ANISOU 5303  CB  LYS A 707         1.596  13.270  14.338  1.00189.80              C
ATOM   5303  CB  LYS A 707      35253  15699  21165  -5486    521  -3594           C
```

FIG. 13 Continued

```
ATOM   5304  CG  LYS A 707       2.666  14.371  14.341  1.00193.41           C
ANISOU 5304  CG  LYS A 707    36252  15710  21526   5768    404   3559       C
ATOM   5305  CD  LYS A 707       2.791  15.126  13.018  1.00192.55           C
ANISOU 5305  CD  LYS A 707    35967  15467  21727  -5482    514  -3464       C
ATOM   5306  CE  LYS A 707       3.966  16.099  13.077  1.00196.53           C
ANISOU 5306  CE  LYS A 707    36970  15534  22170  -5878    377  -3428       C
ATOM   5307  NZ  LYS A 707       4.262  16.760  11.782  1.00195.93           N
ANISOU 5307  NZ  LYS A 707    36730  15315  22401   5679    465   3289       N
ATOM   5308  N   GLU A 708       4.071  11.119  14.163  1.00130.81           N
ANISOU 5308  N   GLU A 708    26663   9171  13868  -6151   -637  -3094       N
ATOM   5309  CA  GLU A 708       5.508  10.873  14.062  1.00131.25           C
ANISOU 5309  CA  GLU A 708    26510   9336  14025  -6469  -1114  -2903       C
ATOM   5310  C   GLU A 708       5.893  10.209  12.725  1.00127.28           C
ANISOU 5310  C   GLU A 708    25167   9260  13934  -6242  -1226  -2748       C
ATOM   5311  O   GLU A 708       7.073  10.040  12.420  1.00127.57           O
ANISOU 5311  O   GLU A 708    24944   9373  14153  -6435  -1548  -2605       O
ATOM   5312  CB  GLU A 708       5.970  10.045  15.265  1.00132.80           C
ANISOU 5312  CB  GLU A 708    26860   9590  14008  -6822  -1468  -2839       C
ATOM   5313  CG  GLU A 708       6.829   8.850  14.928  1.00130.54           C
ANISOU 5313  CG  GLU A 708    25891   9691  14015  -6863  -1876  -2616       C
ATOM   5314  CD  GLU A 708       6.028   7.697  14.365  1.00126.39           C
ANISOU 5314  CD  GLU A 708    24746   9569  13708  -6510  -1691  -2598       C
ATOM   5315  OE1 GLU A 708       5.191   7.928  13.474  1.00124.11           O
ANISOU 5315  OE1 GLU A 708    24211   9394  13552  -6176  -1346  -2697       O
ATOM   5316  OE2 GLU A 708       6.236   6.555  14.815  1.00125.86           O
ANISOU 5316  OE2 GLU A 708    24461   9670  13668  -6595  -1913  -2497       O
ATOM   5317  N   ILE A 709       4.881   9.856  11.932  1.00165.58           N
ANISOU 5317  N   ILE A 709    29623  14355  18935  -5855   -952  -2810       N
ATOM   5318  CA  ILE A 709       5.074   9.187  10.647  1.00162.22           C
ANISOU 5318  CA  ILE A 709    28483  14316  18836  -5648  -1010  -2730       C
ATOM   5319  C   ILE A 709       5.541  10.108   9.533  1.00162.33           C
ANISOU 5319  C   ILE A 709    28494  14188  18996  -5571   -943  -2694       C
ATOM   5320  O   ILE A 709       6.408   9.741   8.748  1.00161.25           O
ANISOU 5320  O   ILE A 709    27946  14236  19085  -5614  -1100  -2590       O
ATOM   5321  CB  ILE A 709       3.776   8.546  10.149  1.00159.54           C
ANISOU 5321  CB  ILE A 709    27765  14264  18589  -5331   -780  -2858       C
ATOM   5322  CG1 ILE A 709       3.095   7.756  11.271  1.00159.89           C
ANISOU 5322  CG1 ILE A 709    27888  14373  18492  -5416   -733  -2927       C
ATOM   5323  CG2 ILE A 709       4.066   7.683   8.928  1.00156.78           C
ANISOU 5323  CG2 ILE A 709    26736  14310  18523  -5205   -880  -2817       C
ATOM   5324  CD1 ILE A 709       3.683   6.392  11.507  1.00158.90           C
ANISOU 5324  CD1 ILE A 709    27372  14523  18481  -5561   -993  -2810       C
ATOM   5325  N   PHE A 710       4.923  11.277   9.434  1.00193.33           N
ANISOU 5325  N   PHE A 710    32900  17740  22815  -5434   -664  -2789       N
ATOM   5326  CA  PHE A 710       5.322  12.252   8.439  1.00194.10           C
ANISOU 5326  CA  PHE A 710    33125  17586  23037  -5373   -558  -2738       C
ATOM   5327  C   PHE A 710       6.849  12.222   8.410  1.00195.45           C
ANISOU 5327  C   PHE A 710    33181  17751  23328  -5752   -846  -2596       C
ATOM   5328  O   PHE A 710       7.445  12.148   7.339  1.00194.32           O
ANISOU 5328  O   PHE A 710    32688  17730  23413  -5731   -870  -2509       O
ATOM   5329  CB  PHE A 710       4.791  13.643   8.831  1.00197.58           C
ANISOU 5329  CB  PHE A 710    34343  17407  23323  -5295   -243  -2837       C
ATOM   5330  CG  PHE A 710       4.981  14.733   7.770  1.00198.86           C
ANISOU 5330  CG  PHE A 710    34741  17183  23632  -5155    -41  -2764       C
ATOM   5331  CD1 PHE A 710       4.087  14.869   6.710  1.00196.98           C
ANISOU 5331  CD1 PHE A 710    34365  16959  23521  -4696    161  -2768       C
ATOM   5332  CD2 PHE A 710       6.022  15.659   7.873  1.00202.59           C
ANISOU 5332  CD2 PHE A 710    35638  17214  24124  -5500    -53  -2692       C
ATOM   5333  CE1 PHE A 710       4.254  15.883   5.756  1.00198.63           C
ANISOU 5333  CE1 PHE A 710    34886  16725  23860  -4540    366  -2645       C
ATOM   5334  CE2 PHE A 710       6.192  16.670   6.921  1.00204.33           C
ANISOU 5334  CE2 PHE A 710    36135  16998  24503  -5386    190  -2586       C
ATOM   5335  CZ  PHE A 710       5.309  16.780   5.867  1.00202.30           C
ANISOU 5335  CZ  PHE A 710    35777  16731  24357  -4885    413  -2534       C
ATOM   5336  N   ALA A 711       7.474  12.222   9.590  1.00126.52           N
ANISOU 5336  N   ALA A 711    24736   8879  14456  -6116  -1079  -2588       N
ATOM   5337  CA  ALA A 711       8.945  12.238   9.710  1.00128.72           C
ANISOU 5337  CA  ALA A 711    24911   9105  14892  -6530  -1419  -2472       C
ATOM   5338  C   ALA A 711       9.617  10.871   9.474  1.00126.29           C
```

FIG. 13 Continued

```
ANISOU 5338  C   ALA A 711    23885   9256  14842  -6532  -1713  -2352       C
ATOM   5339  O   ALA A 711     10.839  10.767   9.329  1.00127.78            O
ANISOU 5339  O   ALA A 711    23827   9437  15288   6803   1973   2248       O
ATOM   5340  CB  ALA A 711      9.373  12.644  11.053  1.00133.46            C
ANISOU 5340  CB  ALA A 711    26157   9318  15235  -6976  -1619  -2536       C
ATOM   5341  N   THR A 712      8.815   9.820   9.457  1.00128.18            N
ANISOU 5341  N   THR A 712    23798   9845  15059  -6245  -1652  -2380       N
ATOM   5342  CA  THR A 712      9.329   8.515   9.119  1.00126.13            C
ANISOU 5342  CA  THR A 712    22910   9941  15073  -6188  -1837  -2301       C
ATOM   5343  C   THR A 712      9.296   8.473   7.611  1.00123.83            C
ANISOU 5343  C   THR A 712    22219   9823  15008  -5949  -1609  -2330       C
ATOM   5344  O   THR A 712     10.334   8.581   6.948  1.00124.58            O
ANISOU 5344  O   THR A 712    22081   9884  15372  -6077  -1670  -2263       O
ATOM   5345  CB  THR A 712      8.411   7.425   9.625  1.00124.15            C
ANISOU 5345  CB  THR A 712    22517   9935  14719  -6010  -1803  -2350       C
ATOM   5346  OG1 THR A 712      7.895   7.798  10.906  1.00126.16            O
ANISOU 5346  OG1 THR A 712    23336   9970  14628  -6162  -1823  -2390       O
ATOM   5347  CG2 THR A 712      9.159   6.104   9.732  1.00123.62            C
ANISOU 5347  CG2 THR A 712    21987  10062  14922  -6059  -2070  -2256       C
ATOM   5348  N   GLY A 713      8.079   8.354   7.079  1.00 79.42            N
ANISOU 5348  N   GLY A 713    16543   4359   9275  -5638  -1349  -2444       N
ATOM   5349  CA  GLY A 713      7.845   8.316   5.642  1.00 77.51            C
ANISOU 5349  CA  GLY A 713    16011   4279   9160  -5425  -1157  -2507       C
ATOM   5350  C   GLY A 713      8.405   9.449   4.783  1.00 78.83            C
ANISOU 5350  C   GLY A 713    16389   4171   9390  -5494  -1032  -2453       C
ATOM   5351  O   GLY A 713      8.006   9.591   3.632  1.00 77.57            O
ANISOU 5351  O   GLY A 713    16149   4079   9246  -5312   -856  -2511       O
ATOM   5352  N   VAL A 714      9.292  10.278   5.329  1.00137.72            N
ANISOU 5352  N   VAL A 714    24164  11287  16878  -5791  -1125  -2351       N
ATOM   5353  CA  VAL A 714      9.914  11.322   4.519  1.00139.61            C
ANISOU 5353  CA  VAL A 714    24601  11206  17237  -5919   -971  -2280       C
ATOM   5354  C   VAL A 714     11.142  10.748   3.865  1.00139.76            C
ANISOU 5354  C   VAL A 714    24129  11368  17606  -6099  -1051  -2213       C
ATOM   5355  O   VAL A 714     11.251  10.742   2.649  1.00138.84            O
ANISOU 5355  O   VAL A 714    23846  11298  17609  -6010   -842  -2217       O
ATOM   5356  CB  VAL A 714     10.349  12.549   5.319  1.00143.75            C
ANISOU 5356  CB  VAL A 714    25706  11226  17686  -6232   -996  -2232       C
ATOM   5357  CG1 VAL A 714      9.204  13.541   5.431  1.00144.48            C
ANISOU 5357  CG1 VAL A 714    26404  10970  17522  -6004   -719  -2301       C
ATOM   5358  CG2 VAL A 714     10.902  12.145   6.677  1.00145.57            C
ANISOU 5358  CG2 VAL A 714    25958  11482  17870  -6536  -1356  -2228       C
ATOM   5359  N   VAL A 715     12.084  10.274   4.670  1.00125.18            N
ANISOU 5359  N   VAL A 715    22073   9550  15940  -6366  -1352  -2153       N
ATOM   5360  CA  VAL A 715     13.245   9.626   4.088  1.00125.61            C
ANISOU 5360  CA  VAL A 715    21594   9714  16418  -6506  -1414  -2100       C
ATOM   5361  C   VAL A 715     12.677   8.455   3.258  1.00122.01            C
ANISOU 5361  C   VAL A 715    20735   9640  15984  -6158  -1257  -2228       C
ATOM   5362  O   VAL A 715     13.202   8.082   2.205  1.00121.68            O
ANISOU 5362  O   VAL A 715    20365   9670  16196  -6152  -1081  -2267       O
ATOM   5363  CB  VAL A 715     14.307   9.245   5.171  1.00128.31            C
ANISOU 5363  CB  VAL A 715    21753   9997  17002  -6839  -1841  -2002       C
ATOM   5364  CG1 VAL A 715     15.119   8.051   4.757  1.00127.72            C
ANISOU 5364  CG1 VAL A 715    21027  10124  17379  -6810  -1920  -1985       C
ATOM   5365  CG2 VAL A 715     15.232  10.426   5.435  1.00132.88            C
ANISOU 5365  CG2 VAL A 715    22582  10183  17722  -7309  -1944  -1902       C
ATOM   5366  N   LEU A 716     11.533   7.947   3.687  1.00152.73            N
ANISOU 5366  N   LEU A 716    24699  13737  19595  -5905  -1275  -2318       N
ATOM   5367  CA  LEU A 716     10.897   6.841   2.987  1.00150.06            C
ANISOU 5367  CA  LEU A 716    24018  13738  19261  -5641  -1149  -2475       C
ATOM   5368  C   LEU A 716     10.414   7.168   1.565  1.00148.95            C
ANISOU 5368  C   LEU A 716    23910  13660  19024  -5501   -867  -2593       C
ATOM   5369  O   LEU A 716     10.871   6.564   0.599  1.00148.67            O
ANISOU 5369  O   LEU A 716    23576  13743  19168  -5504   -739  -2698       O
ATOM   5370  CB  LEU A 716      9.756   6.283   3.835  1.00148.66            C
ANISOU 5370  CB  LEU A 716    23909  13728  18846  -5474  -1225  -2535       C
ATOM   5371  CG  LEU A 716     10.216   5.327   4.944  1.00149.31            C
ANISOU 5371  CG  LEU A 716    23827  13837  19067  -5571  -1486  -2466       C
ATOM   5372  CD1 LEU A 716     11.566   5.750   5.519  1.00152.06            C
ANISOU 5372  CD1 LEU A 716    24215  13933  19628  -5874  -1747  -2299       C
```

FIG. 13 Continued

```
ATOM   5373  CD2 LEU A 716       9.166   5.183   6.047  1.00148.91           C
ANISOU 5373  CD2 LEU A 716    24037  13813  18728   -5515  -1541  -2472       C
ATOM   5374  N   GLY A 717       9.484   8.109   1.442  1.00130.37           N
ANISOU 5374  N   GLY A 717    21957  11187  16391   -5382   -773  -2593       N
ATOM   5375  CA  GLY A 717       8.957   8.503   0.141  1.00129.73           C
ANISOU 5375  CA  GLY A 717    21997  11112  16183   -5247   -577  -2690       C
ATOM   5376  C   GLY A 717       9.223   9.953  -0.218  1.00131.65           C
ANISOU 5376  C   GLY A 717    22728  10892  16400   -5328   -419  -2530       C
ATOM   5377  O   GLY A 717       8.583  10.488  -1.119  1.00131.45           O
ANISOU 5377  O   GLY A 717    22969  10755  16220   -5166   -280  -2570       O
ATOM   5378  N   GLY A 718      10.173  10.573   0.483  1.00 76.51           N
ANISOU 5378  N   GLY A 718    15886   3604   9582   -5596   -456  -2355       N
ATOM   5379  CA  GLY A 718      10.534  11.979   0.315  1.00 79.40           C
ANISOU 5379  CA  GLY A 718    16747   3439   9980   -5748   -279  -2179       C
ATOM   5380  C   GLY A 718      12.045  12.077   0.232  1.00 82.00           C
ANISOU 5380  C   GLY A 718    16864   3621  10669   -6145   -271  -2049       C
ATOM   5381  O   GLY A 718      12.676  13.102   0.555  1.00 85.53           O
ANISOU 5381  O   GLY A 718    17623   3638  11235   -6434   -220  -1898       O
ATOM   5382  N   TYR A 719      12.608  10.952  -0.202  1.00134.09           N
ANISOU 5382  N   TYR A 719    22910  10560  17479   -6170   -309  -2131       N
ATOM   5383  CA  TYR A 719      14.026  10.771  -0.439  1.00136.38           C
ANISOU 5383  CA  TYR A 719    22837  10769  18213   -6501   -273  -2037       C
ATOM   5384  C   TYR A 719      14.061   9.931  -1.693  1.00134.65           C
ANISOU 5384  C   TYR A 719    22309  10777  18075   -6377    -32  -2168       C
ATOM   5385  O   TYR A 719      14.934  10.107  -2.547  1.00136.56           O
ANISOU 5385  O   TYR A 719    22433  10842  18612   -6597    247  -2073       O
ATOM   5386  CB  TYR A 719      14.654   9.999   0.705  1.00136.94           C
ANISOU 5386  CB  TYR A 719    22530  11003  18497   -6629   -645  -2050       C
ATOM   5387  CG  TYR A 719      16.159  10.010   0.710  1.00140.37           C
ANISOU 5387  CG  TYR A 719    22591  11274  19470   -7025   -695  -1917       C
ATOM   5388  CD1 TYR A 719      16.875   8.949   1.249  1.00140.70           C
ANISOU 5388  CD1 TYR A 719    22109  11487  19862   -7083   -969  -1930       C
ATOM   5389  CD2 TYR A 719      16.863  11.083   0.181  1.00143.81           C
ANISOU 5389  CD2 TYR A 719    23182  11339  20121   -7357   -456  -1746       C
ATOM   5390  CE1 TYR A 719      18.243   8.956   1.269  1.00144.31           C
ANISOU 5390  CE1 TYR A 719    22152  11784  20897   -7457  -1042  -1789       C
ATOM   5391  CE2 TYR A 719      18.240  11.099   0.191  1.00147.57           C
ANISOU 5391  CE2 TYR A 719    23234  11672  21163   -7772   -492  -1603       C
ATOM   5392  CZ  TYR A 719      18.925  10.029   0.735  1.00147.78           C
ANISOU 5392  CZ  TYR A 719    22683  11908  21559    7817    803   1630       C
ATOM   5393  OH  TYR A 719      20.301  10.033   0.746  1.00152.00           O
ANISOU 5393  OH  TYR A 719    22713  12297  22743   -8242   -862  -1462       O
ATOM   5394  N   GLN A 720      13.089   9.015  -1.789  1.00 94.05           N
ANISOU 5394  N   GLN A 720    17058   6006  12670   -6064   -114  -2396       N
ATOM   5395  CA  GLN A 720      12.880   8.217  -2.996  1.00 92.72           C
ANISOU 5395  CA  GLN A 720    16716   6060  12452    5952     90   2624       C
ATOM   5396  C   GLN A 720      12.745   9.161  -4.190  1.00 93.69           C
ANISOU 5396  C   GLN A 720    17269   5900  12428   -5999    396  -2548       C
ATOM   5397  O   GLN A 720      13.160   8.852  -5.306  1.00 95.03           O
ANISOU 5397  O   GLN A 720    17327   6183  12597   -6005    690  -2592       O
ATOM   5398  CB  GLN A 720      11.634   7.360  -2.863  1.00 90.08           C
ANISOU 5398  CB  GLN A 720    16312   6126  11789   -5650    -74  -2877       C
ATOM   5399  CG  GLN A 720      11.564   6.266  -3.896  1.00 89.55           C
ANISOU 5399  CG  GLN A 720    15998   6333  11694   -5600     66  -3204       C
ATOM   5400  CD  GLN A 720      11.146   4.922  -3.304  1.00 88.39           C
ANISOU 5400  CD  GLN A 720    15485   6514  11586   -5461    -95  -3389       C
ATOM   5401  OE1 GLN A 720      10.654   4.858  -2.171  1.00 87.53           O
ANISOU 5401  OE1 GLN A 720    15359   6459  11438   -5368   -317  -3266       O
ATOM   5402  NE2 GLN A 720      11.334   3.845  -4.068  1.00 88.83           N
ANISOU 5402  NE2 GLN A 720    15301   6730  11721   -5470     55  -3697       N
ATOM   5403  N   ALA A 721      12.168  10.332  -3.930  1.00138.15           N
ANISOU 5403  N   ALA A 721    23396  11235  17861   -5932    384  -2357       N
ATOM   5404  CA  ALA A 721      12.051  11.375  -4.933  1.00141.49           C
ANISOU 5404  CA  ALA A 721    24191  11571  17997   -5741    733  -2040       C
ATOM   5405  C   ALA A 721      13.445  11.653  -5.440  1.00144.99           C
ANISOU 5405  C   ALA A 721    24482  11817  18790   -6057   1068  -1788       C
ATOM   5406  O   ALA A 721      13.636  11.935  -6.614  1.00148.51           O
ANISOU 5406  O   ALA A 721    24983  12483  18962   -5859   1462  -1558       O
ATOM   5407  CB  ALA A 721      11.451  12.635  -4.339  1.00142.59           C
```

FIG. 13 Continued

```
ANISOU 5407  CB  ALA A 721    24878  11285  18015  -5640    709  -1817       C
ATOM   5408  N   ILE A 722    14.434  11.559   4.563  1.00119.89             N
ANISOU 5408  N   ILE A 722    21086   8256  16210  -6559    913  -1812       N
ATOM   5409  CA  ILE A 722    15.801  11.795  -5.014  1.00123.90             C
ANISOU 5409  CA  ILE A 722    21332   8606  17139  -6894   1235  -1559       C
ATOM   5410  C   ILE A 722    16.426  10.598  -5.750  1.00124.21             C
ANISOU 5410  C   ILE A 722    20798   9058  17339  -6837   1436  -1716       C
ATOM   5411  O   ILE A 722    17.601  10.283  -5.596  1.00126.10             O
ANISOU 5411  O   ILE A 722    20579   9175  18158  -7176   1509  -1654       O
ATOM   5412  CB  ILE A 722    16.698  12.410  -3.925  1.00126.57             C
ANISOU 5412  CB  ILE A 722    21588   8597  17908  -7328   1033  -1410       C
ATOM   5413  CG1 ILE A 722    16.024  13.671  -3.414  1.00127.81             C
ANISOU 5413  CG1 ILE A 722    22407   8387  17769  -7281    982  -1270       C
ATOM   5414  CG2 ILE A 722    18.071  12.788  -4.484  1.00131.14             C
ANISOU 5414  CG2 ILE A 722    21901   8897  19030  -7789   1405  -1117       C
ATOM   5415  CD1 ILE A 722    15.500  14.547  -4.534  1.00129.41             C
ANISOU 5415  CD1 ILE A 722    23147   8337  17686  -7067   1438   -983       C
ATOM   5416  N   MET A 723    15.606   9.913  -6.531  1.00 87.90             N
ANISOU 5416  N   MET A 723    16219   4949  12229  -6402   1520  -1937       N
ATOM   5417  CA  MET A 723    16.127   8.953  -7.478  1.00 89.65             C
ANISOU 5417  CA  MET A 723    16061   5537  12463  -6291   1855  -2083       C
ATOM   5418  C   MET A 723    15.903   9.637  -8.831  1.00 93.90             C
ANISOU 5418  C   MET A 723    16942   6345  12392  -5989   2334  -1819       C
ATOM   5419  O   MET A 723    16.831   9.784  -9.629  1.00 98.40             O
ANISOU 5419  O   MET A 723    17377   6938  13072  -6063   2840  -1602       O
ATOM   5420  CB  MET A 723    15.399   7.606  -7.375  1.00 86.01             C
ANISOU 5420  CB  MET A 723    15417   5416  11848  -6092   1595  -2580       C
ATOM   5421  CG  MET A 723    15.646   6.601  -8.524  1.00 88.44             C
ANISOU 5421  CG  MET A 723    15498   6134  11974  -5894   1987  -2828       C
ATOM   5422  SD  MET A 723    17.122   5.554  -8.375  1.00 90.28             S
ANISOU 5422  SD  MET A 723    15075   6183  13043  -6122   2231  -2926       S
ATOM   5423  CE  MET A 723    18.458   6.599  -8.958  1.00 96.16             C
ANISOU 5423  CE  MET A 723    15695   6745  14099  -6321   2791  -2393       C
ATOM   5424  N   THR A 724    14.677  10.100  -9.075  1.00116.27             N
ANISOU 5424  N   THR A 724    20212   9383  14581  -5636   2186  -1790       N
ATOM   5425  CA  THR A 724    14.398  10.761 -10.346  1.00120.92             C
ANISOU 5425  CA  THR A 724    21159  10264  14522  -5305   2578  -1482       C
ATOM   5426  C   THR A 724    15.475  11.787 -10.651  1.00125.76             C
ANISOU 5426  C   THR A 724    21887  10481  15413  -5544   3057   -978       C
ATOM   5427  O   THR A 724    16.182  11.612 -11.646  1.00130.01             O
ANISOU 5427  O   THR A 724    22316  11227  15855  -5534   3563   -863       O
ATOM   5428  CB  THR A 724    12.959  11.347 -10.455  1.00120.47             C
ANISOU 5428  CB  THR A 724    21536  10424  13813  -4871   2315  -1385       C
ATOM   5429  OG1 THR A 724    12.218  10.597 -11.426  1.00121.53             O
ANISOU 5429  OG1 THR A 724    21642  11253  13279  -4525   2287  -1636       O
ATOM   5430  CG2 THR A 724    12.977  12.808 -10.897  1.00125.16             C
ANISOU 5430  CG2 THR A 724    22629  10754  14172  -4719   2624   -783       C
ATOM   5431  N   VAL A 725    15.643  12.806  -9.789  1.00100.80             N
ANISOU 5431  N   VAL A 725    18944   6738  12618  -5798   2935   -710       N
ATOM   5432  CA  VAL A 725    16.645  13.867 -10.039  1.00106.14             C
ANISOU 5432  CA  VAL A 725    19757   6970  13600  -6105   3392   -223       C
ATOM   5433  C   VAL A 725    18.086  13.338 -10.161  1.00108.45             C
ANISOU 5433  C   VAL A 725    19460   7219  14527  -6528   3701   -234       C
ATOM   5434  O   VAL A 725    19.056  14.118 -10.147  1.00112.87             O
ANISOU 5434  O   VAL A 725    19979   7375  15530  -6925   4022    125       O
ATOM   5435  CB  VAL A 725    16.532  15.067  -9.068  1.00106.38             C
ANISOU 5435  CB  VAL A 725    20197   6324  13900  -6351   3205      6       C
ATOM   5436  CG1 VAL A 725    17.556  16.172  -9.425  1.00112.90             C
ANISOU 5436  CG1 VAL A 725    21191   6668  15039  -6718   3724    510       C
ATOM   5437  CG2 VAL A 725    15.126  15.613  -9.123  1.00105.44             C
ANISOU 5437  CG2 VAL A 725    20633   6274  13158  -5822   3034     83       C
ATOM   5438  N   ILE A 726    18.188  12.009 -10.284  1.00172.57             N
ANISOU 5438  N   ILE A 726    27114  15743  22711  -6432   3621   -645       N
ATOM   5439  CA  ILE A 726    19.433  11.292 -10.555  1.00175.20             C
ANISOU 5439  CA  ILE A 726    26834  16142  23593  -6667   3971   -692       C
ATOM   5440  C   ILE A 726    19.427  10.851 -12.004  1.00179.01             C
ANISOU 5440  C   ILE A 726    27381  17124  23510  -6302   4554   -713       C
ATOM   5441  O   ILE A 726    20.481  10.701 -12.613  1.00183.85             O
ANISOU 5441  O   ILE A 726    27667  17770  24417  -6429   5127   -567       O
```

FIG. 13 Continued

```
ATOM   5442  CB  ILE A 726      19.556   9.995  -9.729  1.00170.73           C
ANISOU 5442  CB  ILE A 726    25736  15644  23489  -6745   3542  -1153       C
ATOM   5443  CG1 ILE A 726      19.353  10.276  -8.235  1.00166.59           C
ANISOU 5443  CG1 ILE A 726    25229  14714  23354  -7056   2874  -1207       C
ATOM   5444  CG2 ILE A 726      20.889   9.271 -10.031  1.00174.48           C
ANISOU 5444  CG2 ILE A 726    25528  16163  24604  -6915   3957  -1148       C
ATOM   5445  CD1 ILE A 726      19.495   9.052  -7.351  1.00162.80           C
ANISOU 5445  CD1 ILE A 726    24267  14265  23323  -7139   2435  -1575       C
ATOM   5446  N   PHE A 727      18.228  10.626 -12.538  1.00163.91           N
ANISOU 5446  N   PHE A 727    25879  15627  20774  -5859   4401   -908       N
ATOM   5447  CA  PHE A 727      18.054  10.140 -13.911  1.00167.79           C
ANISOU 5447  CA  PHE A 727    26525  16667  20559  -5511   4854  -1010       C
ATOM   5448  C   PHE A 727      17.681  11.154 -15.003  1.00173.11           C
ANISOU 5448  C   PHE A 727    27798  17537  20438  -5237   5231   -546       C
ATOM   5449  O   PHE A 727      17.000  10.823 -15.980  1.00175.26           O
ANISOU 5449  O   PHE A 727    28366  18361  19863  -4867   5315   -677       O
ATOM   5450  CB  PHE A 727      17.110   8.952 -13.924  1.00163.93           C
ANISOU 5450  CB  PHE A 727    25996  16612  19679  -5253   4457  -1608       C
ATOM   5451  CG  PHE A 727      17.796   7.661 -13.624  1.00162.64           C
ANISOU 5451  CG  PHE A 727    25278  16416  20103  -5402   4517  -2044       C
ATOM   5452  CD1 PHE A 727      17.657   6.569 -14.474  1.00164.66           C
ANISOU 5452  CD1 PHE A 727    25514  17093  19955  -5188   4770  -2491       C
ATOM   5453  CD2 PHE A 727      18.620   7.549 -12.509  1.00160.33           C
ANISOU 5453  CD2 PHE A 727    24499  15656  20764  -5753   4334  -1994       C
ATOM   5454  CE1 PHE A 727      18.301   5.380 -14.203  1.00164.19           C
ANISOU 5454  CE1 PHE A 727    24975  16925  20484  -5277   4887  -2874       C
ATOM   5455  CE2 PHE A 727      19.269   6.366 -12.230  1.00159.89           C
ANISOU 5455  CE2 PHE A 727    23912  15554  21286  -5826   4393  -2323       C
ATOM   5456  CZ  PHE A 727      19.103   5.277 -13.077  1.00161.76           C
ANISOU 5456  CZ  PHE A 727    24149  16149  21163  -5564   4698  -2759       C
ATOM   5457  N   PHE A 728      18.158  12.380 -14.820  1.00146.16           N
ANISOU 5457  N   PHE A 728    24573  13655  17306  -5448   5447      2       N
ATOM   5458  CA  PHE A 728      17.996  13.478 -15.762  1.00152.15           C
ANISOU 5458  CA  PHE A 728    25910  14445  17458  -5237   5879    572       C
ATOM   5459  C   PHE A 728      19.380  14.128 -15.791  1.00157.14           C
ANISOU 5459  C   PHE A 728    26341  14598  18767  -5697   6483    997       C
ATOM   5460  O   PHE A 728      19.934  14.396 -16.854  1.00163.81           O
ANISOU 5460  O   PHE A 728    27328  15591  19322  -5651   7184   1331       O
ATOM   5461  CB  PHE A 728      16.886  14.436 -15.296  1.00150.25           C
ANISOU 5461  CB  PHE A 728    26183  13996  16908  -5004   5423    818       C
ATOM   5462  CG  PHE A 728      15.488  13.950 -15.626  1.00147.95           C
ANISOU 5462  CG  PHE A 728    26105  14311  15798  -4481   4964    544       C
ATOM   5463  CD1 PHE A 728      15.095  12.647 -15.325  1.00143.01           C
ANISOU 5463  CD1 PHE A 728    25090  14063  15183  -4461   4556   -114       C
ATOM   5464  CD2 PHE A 728      14.572  14.788 -16.243  1.00151.47           C
ANISOU 5464  CD2 PHE A 728    27114  14948  15489  -4020   4937    966       C
ATOM   5465  CE1 PHE A 728      13.825  12.189 -15.636  1.00141.66           C
ANISOU 5465  CE1 PHE A 728    25059  14467  14299  -4060   4127   -382       C
ATOM   5466  CE2 PHE A 728      13.296  14.333 -16.554  1.00150.21           C
ANISOU 5466  CE2 PHE A 728    27052  15414  14607  -3565   4468    730       C
ATOM   5467  CZ  PHE A 728      12.925  13.031 -16.249  1.00145.31           C
ANISOU 5467  CZ  PHE A 728    26009  15183  14018  -3621   4059     35       C
ATOM   5468  N   TRP A 729      19.934  14.338 -14.598  1.00178.94           N
ANISOU 5468  N   TRP A 729    28750  16817  22424  -6170   6194    966       N
ATOM   5469  CA  TRP A 729      21.308  14.775 -14.393  1.00183.29           C
ANISOU 5469  CA  TRP A 729    28908  16931  23802  -6728   6618   1264       C
ATOM   5470  C   TRP A 729      21.977  13.535 -13.804  1.00180.14           C
ANISOU 5470  C   TRP A 729    27702  16657  24085  -6936   6412    798       C
ATOM   5471  O   TRP A 729      21.643  13.125 -12.695  1.00174.18           O
ANISOU 5471  O   TRP A 729    26754  15769  23657  -7042   5729    463       O
ATOM   5472  CB  TRP A 729      21.341  15.902 -13.362  1.00182.75           C
ANISOU 5472  CB  TRP A 729    29061  16167  24209  -7135   6297   1518       C
ATOM   5473  CG  TRP A 729      22.447  16.931 -13.511  1.00189.96           C
ANISOU 5473  CG  TRP A 729    29943  16578  25657  -7663   6857   2045       C
ATOM   5474  CD1 TRP A 729      22.520  17.928 -14.445  1.00196.75           C
ANISOU 5474  CD1 TRP A 729    31333  17287  26136  -7585   7501   2611       C
ATOM   5475  CD2 TRP A 729      23.600  17.098 -12.660  1.00191.71           C
ANISOU 5475  CD2 TRP A 729    29580  16369  26893  -8385   6786   2075       C
ATOM   5476  NE1 TRP A 729      23.654  18.687 -14.245  1.00202.57           N
```

FIG. 13 Continued

```
ANISOU 5476  NE1 TRP A 729    31850  17496  27620  -8241   7888   2971        N
ATOM   5477  CE2 TRP A 729    24.333  18.200 -13.159  1.00199.72              C
ANISOU 5477  CE2 TRP A 729    30779  16981  28124  -8755   7435   2639        C
ATOM   5478  CE3 TRP A 729    24.088  16.415 -11.536  1.00187.96              C
ANISOU 5478  CE3 TRP A 729    28435  15831  27150  -8762   6222   1706        C
ATOM   5479  CZ2 TRP A 729    25.528  18.635 -12.575  1.00204.14              C
ANISOU 5479  CZ2 TRP A 729    30829  17100  29635  -9535   7519   2806        C
ATOM   5480  CZ3 TRP A 729    25.278  16.849 -10.956  1.00192.42              C
ANISOU 5480  CZ3 TRP A 729    28494  15999  28618  -9496   6260   1895        C
ATOM   5481  CH2 TRP A 729    25.983  17.951 -11.479  1.00200.47              C
ANISOU 5481  CH2 TRP A 729    29667  16641  29861  -9896   6897   2422        C
ATOM   5482  N   ALA A 730    22.902  12.917 -14.530  1.00171.49              N
ANISOU 5482  N   ALA A 730    26151  15809  23201  -6958   7023    790        N
ATOM   5483  CA  ALA A 730    23.530  11.696 -14.026  1.00169.34              C
ANISOU 5483  CA  ALA A 730    25106  15640  23595  -7061   6875    384        C
ATOM   5484  C   ALA A 730    24.855  11.351 -14.693  1.00176.25              C
ANISOU 5484  C   ALA A 730    25381  16607  24980  -7199   7675    542        C
ATOM   5485  O   ALA A 730    25.174  10.166 -14.837  1.00176.07              O
ANISOU 5485  O   ALA A 730    24892  16839  25167  -7010   7812    178        O
ATOM   5486  CB  ALA A 730    22.579  10.523 -14.159  1.00164.31              C
ANISOU 5486  CB  ALA A 730    24585  15436  22412  -6597   6544   -188        C
ATOM   5487  N   ALA A 731    25.616  12.370 -15.094  1.00242.40              N
ANISOU 5487  N   ALA A 731    33768  24749  33583  -7518   8243   1084        N
ATOM   5488  CA  ALA A 731    26.914  12.167 -15.743  1.00250.09              C
ANISOU 5488  CA  ALA A 731    34133  25802  35089  -7680   9095   1306        C
ATOM   5489  C   ALA A 731    27.906  11.458 -14.814  1.00249.78              C
ANISOU 5489  C   ALA A 731    33065  25636  36203   8002   8841   1161        C
ATOM   5490  O   ALA A 731    28.672  12.103 -14.097  1.00252.15              O
ANISOU 5490  O   ALA A 731    32921  25578  37307  -8572   8676   1468        O
ATOM   5491  CB  ALA A 731    27.481  13.495 -16.230  1.00257.39              C
ANISOU 5491  CB  ALA A 731    35279  26435  36081  -8041   9704   1955        C
ATOM   5492  N   HIS A 732    27.892  10.126 -14.876  1.00231.22              N
ANISOU 5492  N   HIS A 732    30356  23584  33912  -7632   8824    704        N
ATOM   5493  CA  HIS A 732    28.692   9.219 -14.033  1.00230.75              C
ANISOU 5493  CA  HIS A 732    29344  23462  34867  -7764   8542    534        C
ATOM   5494  C   HIS A 732    27.960   8.836 -12.728  1.00222.20              C
ANISOU 5494  C   HIS A 732    28311  22228  33885  -7805   7442    204        C
ATOM   5495  O   HIS A 732    28.489   8.112 -11.887  1.00221.26              O
ANISOU 5495  O   HIS A 732    27491  22040  34537  -7904   7052     91        O
ATOM   5496  CB  HIS A 732    30.180   9.652 -13.881  1.00238.53              C
ANISOU 5496  CB  HIS A 732    29433  24274  36925  -8265   8957   1006        C
ATOM   5497  CG  HIS A 732    30.528  10.320 -12.581  1.00237.20              C
ANISOU 5497  CG  HIS A 732    28908  23736  37480  -8898   8171   1220        C
ATOM   5498  ND1 HIS A 732    30.791  11.670 -12.485  1.00240.73              N
ANISOU 5498  ND1 HIS A 732    29565  23863  38037  -9457   8228   1652        N
ATOM   5499  CD2 HIS A 732    30.724   9.812  11.341  1.00233.82              C
ANISOU 5499  CD2 HIS A 732    27931  23203  37706  -9091   7340   1066        C
ATOM   5500  CE1 HIS A 732    31.095  11.971 -11.235  1.00239.42              C
ANISOU 5500  CE1 HIS A 732    29030  23416  38522  -9994   7437   1697        C
ATOM   5501  NE2 HIS A 732    31.062  10.861 -10.520  1.00235.23              N
ANISOU 5501  NE2 HIS A 732    28033  23040  38305  -9775   6871   1362        N
ATOM   5502  N   LYS A 733    26.719   9.308 -12.600  1.00164.09              N
ANISOU 5502  N   LYS A 733    21792  14840  25715  -7688   6980     76        N
ATOM   5503  CA  LYS A 733    25.838   8.919 -11.503  1.00156.13              C
ANISOU 5503  CA  LYS A 733    20962  13739  24623  -7650   6047   -270        C
ATOM   5504  C   LYS A 733    25.305   7.574 -11.943  1.00153.58              C
ANISOU 5504  C   LYS A 733    20668  13755  23930   7127   6125    777        C
ATOM   5505  O   LYS A 733    24.214   7.125 -11.554  1.00147.38              O
ANISOU 5505  O   LYS A 733    20269  13046  22683  -6913   5576  -1147        O
ATOM   5506  CB  LYS A 733    24.694   9.917 -11.342  1.00152.27              C
ANISOU 5506  CB  LYS A 733    21337  13118  23400  -7649   5666   -206        C
ATOM   5507  CG  LYS A 733    25.092  11.229 -10.673  1.00154.24              C
ANISOU 5507  CG  LYS A 733    21667  12903  24036  -8208   5465    207        C
ATOM   5508  CD  LYS A 733    25.262  11.048  -9.171  1.00150.60              C
ANISOU 5508  CD  LYS A 733    20851  12169  24201  -8589   4636     69        C
ATOM   5509  CE  LYS A 733    25.455  12.381  -8.464  1.00152.46              C
ANISOU 5509  CE  LYS A 733    21349  11914  24666  -9163   4368    372        C
ATOM   5510  NZ  LYS A 733    25.279  12.231  -6.992  1.00148.21              N
ANISOU 5510  NZ  LYS A 733    20729  11150  24433  -9463   3479    154        N
```

FIG. 13 Continued

```
ATOM   5511  N   THR A 734      26.114   6.961 -12.795  1.00234.56           N
ANISOU 5511  N   THR A 734    30514  24197  34409  -6947   6884    -788      N
ATOM   5512  CA  THR A 734      25.855   5.682 -13.408  1.00234.59           C
ANISOU 5512  CA  THR A 734    30529  24475  34129  -6482   7185   -1270      C
ATOM   5513  C   THR A 734      27.232   5.116 -13.733  1.00241.66           C
ANISOU 5513  C   THR A 734    30607  25356  35855  -6462   7889   -1143      C
ATOM   5514  O   THR A 734      27.362   4.176 -14.515  1.00244.84           O
ANISOU 5514  O   THR A 734    30973  25947  36107  -6082   8480   -1462      O
ATOM   5515  CB  THR A 734      25.076   5.861 -14.718  1.00236.31           C
ANISOU 5515  CB  THR A 734    31530  25051  33205  -6152   7667   -1409      C
ATOM   5516  OG1 THR A 734      25.932   6.448 -15.705  1.00244.23           O
ANISOU 5516  OG1 THR A 734    32468  26133  34195  -6201   8570   -1020      O
ATOM   5517  CG2 THR A 734      23.861   6.761 -14.513  1.00231.39           C
ANISOU 5517  CG2 THR A 734    31645  24447  31823  -6179   7086   -1332      C
ATOM   5518  N   ASP A 735      28.258   5.711 -13.127  1.00200.79           N
ANISOU 5518  N   ASP A 735    24771  19952  31568  -6886   7834    -682      N
ATOM   5519  CA  ASP A 735      29.646   5.314 -13.362  1.00208.49           C
ANISOU 5519  CA  ASP A 735    24824  20927  33465  -6906   8486    -457      C
ATOM   5520  C   ASP A 735      29.986   3.931 -12.813  1.00207.97           C
ANISOU 5520  C   ASP A 735    24123  20820  34078  -6619   8301    -749      C
ATOM   5521  O   ASP A 735      31.136   3.658 -12.478  1.00213.24           O
ANISOU 5521  O   ASP A 735    23843  21414  35765  -6712   8467    -478      O
ATOM   5522  CB  ASP A 735      30.621   6.352 -12.794  1.00212.53           C
ANISOU 5522  CB  ASP A 735    24741  21233  34777  -7514   8374     121      C
ATOM   5523  CG  ASP A 735      30.536   6.472 -11.284  1.00207.52           C
ANISOU 5523  CG  ASP A 735    23842  20354  34651  -7891   7267     158      C
ATOM   5524  OD1 ASP A 735      31.329   7.256 -10.714  1.00211.13           O
ANISOU 5524  OD1 ASP A 735    23798  20642  35778  -8452   7060     570      O
ATOM   5525  OD2 ASP A 735      29.678   5.790 -10.674  1.00200.57           O
ANISOU 5525  OD2 ASP A 735    23275  19455  33478  -7661   6617    -229      O
ATOM   5526  N   PHE A 736      28.981   3.067 -12.715  1.00274.11           N
ANISOU 5526  N   PHE A 736    32999  29232  41917  -6274   7953   -1272      N
ATOM   5527  CA  PHE A 736      29.182   1.692 -12.269  1.00273.84           C
ANISOU 5527  CA  PHE A 736    32509  29096  42443  -5950   7836   -1575      C
ATOM   5528  C   PHE A 736      29.885   0.901 -13.376  1.00281.65           C
ANISOU 5528  C   PHE A 736    33221  30192  43600  -5523   8937   -1727      C
ATOM   5529  O   PHE A 736      30.058  -0.315 -13.271  1.00282.95           O
ANISOU 5529  O   PHE A 736    33101  30240  44167  -5153   9075   -2026      O
ATOM   5530  CB  PHE A 736      27.830   1.061 -11.905  1.00265.97           C
ANISOU 5530  CB  PHE A 736    32207  28081  40769  -5766   7204   -2100      C
ATOM   5531  CG  PHE A 736      27.913  -0.373 -11.437  1.00265.65           C
ANISOU 5531  CG  PHE A 736    31828  27863  41245  -5440   7082   -2424      C
ATOM   5532  CD1 PHE A 736      27.204  -1.370 -12.093  1.00265.14           C
ANISOU 5532  CD1 PHE A 736    32272  27846  40623  -5055   7398   -3018      C
ATOM   5533  CD2 PHE A 736      28.678  -0.721 -10.337  1.00266.47           C
ANISOU 5533  CD2 PHE A 736    31137  27739  42370  -5533   6628   -2128      C
ATOM   5534  CE1 PHE A 736      27.266  -2.685 -11.668  1.00265.41           C
ANISOU 5534  CE1 PHE A 736    32060  27631  41155  -4764   7334   -3312      C
ATOM   5535  CE2 PHE A 736      28.744  -2.037  -9.908  1.00266.76           C
ANISOU 5535  CE2 PHE A 736    30903  27567  42886  -5189   6536   -2366      C
ATOM   5536  CZ  PHE A 736      28.036  -3.019 -10.576  1.00266.18           C
ANISOU 5536  CZ  PHE A 736    31375  27468  42292  -4802   6921   -2961      C
ATOM   5537  N   PHE A 737      30.291   1.607 -14.434  1.00171.71           N
ANISOU 5537  N   PHE A 737    19421  16457  29363  -5569   9763   -1509      N
ATOM   5538  CA  PHE A 737      30.967   0.995 -15.582  1.00180.12           C
ANISOU 5538  CA  PHE A 737    20312  17647  30480  -5181  10937   -1640      C
ATOM   5539  C   PHE A 737      30.215  -0.258 -16.084  1.00178.86           C
ANISOU 5539  C   PHE A 737    20723  17514  29724  -4690  11138   -2364      C
ATOM   5540  O   PHE A 737      30.827  -1.201 -16.594  1.00185.20           O
ANISOU 5540  O   PHE A 737    21214  18257  30898  -4300  11917   -2586      O
ATOM   5541  CB  PHE A 737      32.440   0.672 -15.258  1.00187.54           C
ANISOU 5541  CB  PHE A 737    20027  18455  32772  -5160  11349   -1250      C
ATOM   5542  CG  PHE A 737      33.342   1.889 -15.157  1.00192.07           C
ANISOU 5542  CG  PHE A 737    20022  19068  33887  -5664  11490    -570      C
ATOM   5543  CD1 PHE A 737      34.357   2.094 -16.078  1.00201.94           C
ANISOU 5543  CD1 PHE A 737    20811  20448  35470  -5607  12628    -280      C
ATOM   5544  CD2 PHE A 737      33.189   2.810 -14.133  1.00187.19           C
ANISOU 5544  CD2 PHE A 737    19327  18333  33463  -6221  10525    -238      C
ATOM   5545  CE1 PHE A 737      35.193   3.201 -15.987  1.00206.81           C
```

FIG. 13 Continued

```
ANISOU 5545  CE1 PHE A 737     20865  21079  36633  -6131  12783    347           C
ATOM   5546  CE2 PHE A 737      34.020   3.917 -14.039  1.00192.10                 C
ANISOU 5546  CE2 PHE A 737     19443  18943  34602  -6753  10656    345           C
ATOM   5547  CZ  PHE A 737      35.021   4.112 -14.968  1.00201.90                 C
ANISOU 5547  CZ  PHE A 737     20189  20316  36207  -6725  11778    648           C
ATOM   5548  N   SER A 738      28.890  -0.255 -15.935  1.00184.31                 N
ANISOU 5548  N   SER A 738     22237  18277  29515  -4724  10454  -2737           N
ATOM   5549  CA  SER A 738      28.045  -1.371 -16.369  1.00182.98                 C
ANISOU 5549  CA  SER A 738     22666  18143  28716  -4375  10526  -3457           C
ATOM   5550  C   SER A 738      26.555  -0.980 -16.464  1.00176.09                 C
ANISOU 5550  C   SER A 738     22729  17504  26672  -4499   9861  -3749           C
ATOM   5551  O   SER A 738      25.698  -1.832 -16.733  1.00174.43                 O
ANISOU 5551  O   SER A 738     23035  17354  25885  -4312   9753  -4361           O
ATOM   5552  CB  SER A 738      28.227  -2.572 -15.434  1.00181.29                 C
ANISOU 5552  CB  SER A 738     21950  17560  29371  -4190  10166  -3677           C
ATOM   5553  OG  SER A 738      27.448  -3.681 -15.856  1.00180.85                 O
ANISOU 5553  OG  SER A 738     22478  17464  28772  -3903  10289  -4396           O
ATOM   5554  N   ASP A 739      26.266   0.309 -16.248  1.00157.17                 N
ANISOU 5554  N   ASP A 739     20524  15225  23969  -4815   9441  -3302           N
ATOM   5555  CA  ASP A 739      24.902   0.867 -16.289  1.00151.29                 C
ANISOU 5555  CA  ASP A 739     20573  14710  22200  -4905   8807  -3442           C
ATOM   5556  C   ASP A 739      24.330   0.939 -17.712  1.00155.49                 C
ANISOU 5556  C   ASP A 739     21874  15678  21527  -4697   9357  -3712           C
ATOM   5557  O   ASP A 739      24.780   0.220 -18.608  1.00162.00                 O
ANISOU 5557  O   ASP A 739     22741  16598  22213  -4455  10164  -4018           O
ATOM   5558  CB  ASP A 739      24.896   2.275 -15.677  1.00148.16                 C
ANISOU 5558  CB  ASP A 739     20147  14233  21912  -5265   8327  -2836           C
ATOM   5559  CG  ASP A 739      25.584   3.296 -16.563  1.00154.70                 C
ANISOU 5559  CG  ASP A 739     21030  15187  22562  -5357   9068  -2344           C
ATOM   5560  OD1 ASP A 739      26.805   3.175 -16.771  1.00160.89                 O
ANISOU 5560  OD1 ASP A 739     21195  15866  24069  -5381   9739  -2110           O
ATOM   5561  OD2 ASP A 739      24.904   4.221 -17.053  1.00154.21                 O
ANISOU 5561  OD2 ASP A 739     21611  15324  21657  -5391   9003  -2158           O
ATOM   5562  N   THR A 740      23.318   1.787 -17.908  1.00163.40                 N
ANISOU 5562  N   THR A 740     23501  16949  21635  -4772   6910  -3604           N
ATOM   5563  CA  THR A 740      22.788   2.072 -19.251  1.00168.13                 C
ANISOU 5563  CA  THR A 740     24839  18026  21017  -4597   9345  -3714           C
ATOM   5564  C   THR A 740      22.263   3.520 -19.362  1.00166.79                 C
ANISOU 5564  C   THR A 740     25093  18016  20262  -4712   9044  -3155           C
ATOM   5565  O   THR A 740      22.315   4.292 -18.393  1.00162.20                 O
ANISOU 5565  O   THR A 740     24261  17132  20236  -4947   6538  -2738           O
ATOM   5566  CB  THR A 740      21.742   1.025 -19.772  1.00167.87                 C
ANISOU 5566  CB  THR A 740     25336  18310  20139  -4401   9160  -4487           C
ATOM   5567  OG1 THR A 740      20.436   1.330 -19.276  1.00161.26                 O
ANISOU 5567  OG1 THR A 740     24828  17637  18805  -4472   8217  -4564           O
ATOM   5568  CG2 THR A 740      22.127  -0.391 -19.384  1.00168.00                 C
ANISOU 5568  CG2 THR A 740     24955  18010  20867  -4315   9304  -5032           C
ATOM   5569  N   PHE A 741      21.792   3.884 -20.552  1.00149.94                 N
ANISOU 5569  N   PHE A 741     23630  16339  17002  -4538   9384  -3136           N
ATOM   5570  CA  PHE A 741      21.315   5.237 -20.800  1.00150.19                 C
ANISOU 5570  CA  PHE A 741     24119  16515  16430  -4564   9203  -2556           C
ATOM   5571  C   PHE A 741      20.618   5.746 -19.541  1.00141.73                 C
ANISOU 5571  C   PHE A 741     22931  15174  15746  -4719   8234  -2402           C
ATOM   5572  O   PHE A 741      21.173   6.562 -18.800  1.00140.07                 O
ANISOU 5572  O   PHE A 741     22413  14546  16263  -4969   8148  -1912           O
ATOM   5573  CB  PHE A 741      20.361   5.268 -22.009  1.00154.34                 C
ANISOU 5573  CB  PHE A 741     25448  17671  15525  -4293   9254  -2734           C
ATOM   5574  CG  PHE A 741      21.055   5.188 -23.365  1.00164.21                 C
ANISOU 5574  CG  PHE A 741     27003  19209  16182  -4157  10296  -2691           C
ATOM   5575  CD1 PHE A 741      20.838   4.108 -24.214  1.00168.65                 C
ANISOU 5575  CD1 PHE A 741     27880  20151  16049  -3982  10610  -3369           C
ATOM   5576  CD2 PHE A 741      21.903   6.201 -23.796  1.00169.69                 C
ANISOU 5576  CD2 PHE A 741     27716  19779  16979  -4228  10989  -1987           C
ATOM   5577  CE1 PHE A 741      21.459   4.033 -25.457  1.00178.33                 C
ANISOU 5577  CE1 PHE A 741     29455  21645  16657  -3851  11610  -3358           C
ATOM   5578  CE2 PHE A 741      22.528   6.128 -25.042  1.00179.29                 C
ANISOU 5578  CE2 PHE A 741     29239  21271  17613  -4100  12008  -1930           C
ATOM   5579  CZ  PHE A 741      22.303   5.042 -25.867  1.00183.58                 C
ANISOU 5579  CZ  PHE A 741     30117  22210  17425  -3896  12321  -2622           C
```

FIG. 13 Continued

```
ATOM    5580  N   GLY A 742      19.418    5.222  -19.296  1.00138.00           N
ANISOU  5580  N   GLY A 742    22696  14938  14801  -4599   7534  -2857         N
ATOM    5581  CA  GLY A 742      18.618    5.576  -18.137  1.00130.36           C
ANISOU  5581  CA  GLY A 742    21662  13766  14103  -4698   6650  -2796         C
ATOM    5582  C   GLY A 742      17.809    6.850  -18.286  1.00130.17           C
ANISOU  5582  C   GLY A 742    22136  13881  13443  -4591   6343  -2306         C
ATOM    5583  O   GLY A 742      16.584    6.814  -18.259  1.00127.59           O
ANISOU  5583  O   GLY A 742    22101  13869  12509  -4417   5765  -2492         O
ATOM    5584  N   VAL A 743      18.508    7.970  -18.466  1.00172.65           N
ANISOU  5584  N   VAL A 743    27593  19012  18994  -4689   6766  -1663         N
ATOM    5585  CA  VAL A 743      17.896    9.302  -18.536  1.00173.27           C
ANISOU  5585  CA  VAL A 743    28152  19061  18622  -4584   6568  -1094         C
ATOM    5586  C   VAL A 743      16.618    9.381  -19.371  1.00175.16           C
ANISOU  5586  C   VAL A 743    28966  19921  17664  -4183   6288  -1155         C
ATOM    5587  O   VAL A 743      15.534    9.029  -18.897  1.00170.45           O
ANISOU  5587  O   VAL A 743    28380  19517  16866  -4063   5589  -1481         O
ATOM    5588  CB  VAL A 743      18.891   10.364  -19.087  1.00179.81           C
ANISOU  5588  CB  VAL A 743    29113  19635  19573  -4713   7313   -414         C
ATOM    5589  CG1 VAL A 743      18.493   11.765  -18.634  1.00179.07           C
ANISOU  5589  CG1 VAL A 743    29367  19173  19499  -4738   7049    182         C
ATOM    5590  CG2 VAL A 743      20.309   10.050   18.655  1.00180.76           C
ANISOU  5590  CG2 VAL A 743    28574  19345  20760  -5093   7764   -410         C
ATOM    5591  N   ARG A 744      16.774    9.833  -20.617  1.00144.22           N
ANISOU  5591  N   ARG A 744    25499  16339  12958  -3991   6846   -818         N
ATOM    5592  CA  ARG A 744      15.666   10.087  -21.547  1.00148.05           C
ANISOU  5592  CA  ARG A 744    26568  17467  12217  -3598   6614   -721         C
ATOM    5593  C   ARG A 744      14.401    9.277  -21.285  1.00143.78           C
ANISOU  5593  C   ARG A 744    25972  17370  11286  -3453   5808  -1313         C
ATOM    5594  O   ARG A 744      13.418    9.789  -20.741  1.00140.39           O
ANISOU  5594  O   ARG A 744    25608  16956  10778  -3292   5173  -1145         O
ATOM    5595  CB  ARG A 744      16.109    9.845  -22.995  1.00156.90           C
ANISOU  5595  CB  ARG A 744    28060  19070  12485  -3470   7338   -710         C
ATOM    5596  CG  ARG A 744      17.592   10.028  -23.257  1.00161.23           C
ANISOU  5596  CG  ARG A 744    28430  19229  13600  -3709   8290   -432         C
ATOM    5597  CD  ARG A 744      18.094   11.379  -22.792  1.00161.53           C
ANISOU  5597  CD  ARG A 744    28483  18670  14223  -3860   8481    356         C
ATOM    5598  NE  ARG A 744      17.132   12.446  -23.041  1.00163.20           N
ANISOU  5598  NE  ARG A 744    29275  19013  13718  -3551   8132    903         N
ATOM    5599  CZ  ARG A 744      16.793   12.882  -24.248  1.00170.89           C
ANISOU  5599  CZ  ARG A 744    30876  20476  13578  -3224   8421   1282         C
ATOM    5600  NH1 ARG A 744      17.325   12.331  -25.330  1.00177.58           N
ANISOU  5600  NH1 ARG A 744    31898  21740  13834  -3198   9086   1121         N
ATOM    5601  NH2 ARG A 744      15.916   13.866  -24.371  1.00172.48           N
ANISOU  5601  NH2 ARG A 744    31550  20748  13239  -2898   8059   1836         N
ATOM    5602  N   SER A 745      14.444    8.008  -21.676  1.00150.79           N
ANISOU  5602  N   SER A 745    26735  18592  11965  -3521   5885  -2011         N
ATOM    5603  CA  SER A 745      13.295    7.120  -21.574  1.00148.19           C
ANISOU  5603  CA  SER A 745    26362  18720  11224  -3459   5197  -2637         C
ATOM    5604  C   SER A 745      12.629    7.111  -20.221  1.00139.84           C
ANISOU  5604  C   SER A 745    24934  17342  10856  -3545   4473  -2740         C
ATOM    5605  O   SER A 745      13.292    6.944  -19.204  1.00134.67           O
ANISOU  5605  O   SER A 745    23875  16080  11214  -3796   4516  -2791         O
ATOM    5606  CB  SER A 745      13.718    5.683  -21.856  1.00149.26           C
ANISOU  5606  CB  SER A 745    26324  18950  11437  -3641   5479  -3425         C
ATOM    5607  OG  SER A 745      12.589    4.844  -22.026  1.00148.97           O
ANISOU  5607  OG  SER A 745    26357  19432  10813  -3620   4889  -4041         O
ATOM    5608  N   ILE A 746      11.315    7.294  -20.210  1.00160.27           N
ANISOU  5608  N   ILE A 746    27648  20368  12878  -3329   3809  -2751         N
ATOM    5609  CA  ILE A 746      10.555    7.053  -19.001  1.00153.07           C
ANISOU  5609  CA  ILE A 746    26382  19256  12521  -3409   3149  -2982         C
ATOM    5610  C   ILE A 746      10.358    5.555  -19.105  1.00152.44           C
ANISOU  5610  C   ILE A 746    26093  19436  12392  -3619   3018  -3824         C
ATOM    5611  O   ILE A 746      11.181    4.866  -19.698  1.00155.66           O
ANISOU  5611  O   ILE A 746    26540  19831  12772  -3748   3546  -4136         O
ATOM    5612  CB  ILE A 746       9.198    7.810  -18.964  1.00153.49           C
ANISOU  5612  CB  ILE A 746    26583  19699  12037   3067   2538   2657         C
ATOM    5613  CG1 ILE A 746       8.680    8.067  -20.383  1.00161.84           C
ANISOU  5613  CG1 ILE A 746    28066  21544  11881  -2753   2548  -2469         C
ATOM    5614  CG2 ILE A 746       9.328    9.131  -18.201  1.00151.06           C
```

FIG. 13 Continued

```
ANISOU 5614  CG2 ILE A 746    26355  18806  12237  -2943   2561  -1963       C
ATOM   5615  CD1 ILE A 746       7.759   9.269 -20.489  1.00164.32           C
ANISOU 5615  CD1 ILE A 746    28602  22088  11745  -2303   2194  -1787       C
ATOM   5616  N   ARG A 747       9.277   5.040 -18.551  1.00156.69           N
ANISOU 5616  N   ARG A 747    26419  20182  12934  -3656   2371  -4199       N
ATOM   5617  CA  ARG A 747       9.024   3.615 -18.660  1.00156.79           C
ANISOU 5617  CA  ARG A 747    26276  20399  12898  -3897   2246  -5012       C
ATOM   5618  C   ARG A 747      10.190   2.782 -18.137  1.00154.00           C
ANISOU 5618  C   ARG A 747    25670  19408  13434  -4169   2704  -5329       C
ATOM   5619  O   ARG A 747      11.055   3.282 -17.415  1.00150.58           O
ANISOU 5619  O   ARG A 747    25056  18383  13776  -4220   2941  -4937       O
ATOM   5620  CB  ARG A 747       8.693   3.259 -20.102  1.00164.95           C
ANISOU 5620  CB  ARG A 747    27687  22181  12805  -3816   2338  -5298       C
ATOM   5621  CG  ARG A 747       7.317   3.722 -20.499  1.00167.87           C
ANISOU 5621  CG  ARG A 747    28161  23287  12334  -3592   1678  -5146       C
ATOM   5622  CD  ARG A 747       7.345   4.475 -21.807  1.00176.04           C
ANISOU 5622  CD  ARG A 747    29695  24883  12310  -3293   1891  -4709       C
ATOM   5623  NE  ARG A 747       6.041   5.055 -22.116  1.00179.23           N
ANISOU 5623  NE  ARG A 747    30139  25987  11975  -3001   1211  -4417       N
ATOM   5624  CZ  ARG A 747       5.252   4.647 -23.108  1.00186.35           C
ANISOU 5624  CZ  ARG A 747    31220  27763  11823   2983    840   4725       C
ATOM   5625  NH1 ARG A 747       5.636   3.654 -23.905  1.00191.04           N
ANISOU 5625  NH1 ARG A 747    32059  28597  11931  -3263   1127  -5390       N
ATOM   5626  NH2 ARG A 747       4.079   5.237 -23.309  1.00189.51           N
ANISOU 5626  NH2 ARG A 747    31554  28804  11648  -2679    181  -4369       N
ATOM   5627  N   ASP A 748      10.209   1.513 -18.520  1.00170.45           N
ANISOU 5627  N   ASP A 748    27743  21616  15405  -4346   2821  -6038       N
ATOM   5628  CA  ASP A 748      11.185   0.566 -17.994  1.00168.37           C
ANISOU 5628  CA  ASP A 748    27205  20751  16016  -4550   3212  -6379       C
ATOM   5629  C   ASP A 748      12.639   1.018 -18.042  1.00169.47           C
ANISOU 5629  C   ASP A 748    27260  20439  16690  -4502   3905  -5948       C
ATOM   5630  O   ASP A 748      13.492   0.427 -17.389  1.00167.22           O
ANISOU 5630  O   ASP A 748    26630  19612  17296  -4628   4151  -6061       O
ATOM   5631  CB  ASP A 748      10.996  -0.801 -18.645  1.00172.67           C
ANISOU 5631  CB  ASP A 748    27885  21502  16220  -4700   3354  -7205       C
ATOM   5632  CG  ASP A 748       9.638  -1.401 -18.328  1.00171.01           C
ANISOU 5632  CG  ASP A 748    27611  21605  15760  -4870   2642  -7677       C
ATOM   5633  OD1 ASP A 748       8.728  -1.274 -19.173  1.00175.61           O
ANISOU 5633  OD1 ASP A 748    28461  22895  15370  -4834   2337  -7831       O
ATOM   5634  OD2 ASP A 748       9.466  -1.971 -17.224  1.00165.59           O
ANISOU 5634  OD2 ASP A 748    26590  20484  15843  -5048   2373  -7856       O
ATOM   5635  N   ASN A 749      12.925   2.061 -18.809  1.00222.44           N
ANISOU 5635  N   ASN A 749    34257  27378  22881  -4321   4218  -5424       N
ATOM   5636  CA  ASN A 749      14.281   2.591 -18.864  1.00224.14           C
ANISOU 5636  CA  ASN A 749    34354  27185  23625  -4321   4889  -4961       C
ATOM   5637  C   ASN A 749      14.495   3.607 -17.741  1.00218.62           C
ANISOU 5637  C   ASN A 749    33400  26012  23654  -4394   4611  -4354       C
ATOM   5638  O   ASN A 749      15.627   4.015 -17.461  1.00218.99           O
ANISOU 5638  O   ASN A 749    33207  25624  24375  -4499   5031  -3982       O
ATOM   5639  CB  ASN A 749      14.575   3.196 -20.244  1.00232.08           C
ANISOU 5639  CB  ASN A 749    35825  28610  23744  -4135   5462  -4676       C
ATOM   5640  CG  ASN A 749      16.031   3.625 -20.413  1.00235.17           C
ANISOU 5640  CG  ASN A 749    36054  28605  24693  -4173   6278  -4245       C
ATOM   5641  OD1 ASN A 749      16.475   4.615 -19.827  1.00232.88           O
ANISOU 5641  OD1 ASN A 749    35595  27948  24941  -4240   6277  -3634       O
ATOM   5642  ND2 ASN A 749      16.771   2.893 -21.241  1.00241.16           N
ANISOU 5642  ND2 ASN A 749    36873  29441  25315  -4146   7008  -4574       N
ATOM   5643  N   ASN A 750      13.402   3.997 -17.088  1.00150.93           N
ANISOU 5643  N   ASN A 750    24867  17524  14954  -4358   3911  -4281       N
ATOM   5644  CA  ASN A 750      13.476   4.967 -16.000  1.00146.16           C
ANISOU 5644  CA  ASN A 750    24125  16462  14949  -4429   3628  -3776       C
ATOM   5645  C   ASN A 750      12.270   4.907 -15.082  1.00140.70           C
ANISOU 5645  C   ASN A 750    23371  15805  14282  -4419   2887  -3933       C
ATOM   5646  O   ASN A 750      12.406   4.666 -13.891  1.00135.49           O
ANISOU 5646  O   ASN A 750    22415  14704  14362  -4615   2619  -4006       O
ATOM   5647  CB  ASN A 750      13.663   6.390 -16.541  1.00149.86           C
ANISOU 5647  CB  ASN A 750    24940  16950  15051  -4272   3896  -3077       C
ATOM   5648  CG  ASN A 750      13.828   7.429 -15.437  1.00145.94           C
ANISOU 5648  CG  ASN A 750    24370  15889  15191  -4394   3677  -2592       C
```

FIG. 13 Continued

```
ATOM   5649  OD1 ASN A 750      13.435   7.203 -14.293  1.00140.25           O
ANISOU 5649  OD1 ASN A 750    23432  14909  14949  -4519   3185  -2769       O
ATOM   5650  ND2 ASN A 750      14.406   8.581  15.784  1.00149.60           N
ANISOU 5650  ND2 ASN A 750    25065  16143  15634  -4379   4072  -1986       N
ATOM   5651  N   HIS A 751      11.085   5.123 -15.626  1.00179.75           N
ANISOU 5651  N   HIS A 751    28578  21306  18414  -4187   2554  -3966       N
ATOM   5652  CA  HIS A 751       9.897   5.123 -14.784  1.00175.37           C
ANISOU 5652  CA  HIS A 751    27915  20823  17896  -4151   1902  -4075       C
ATOM   5653  C   HIS A 751       9.660   3.766 -14.116  1.00171.69           C
ANISOU 5653  C   HIS A 751    27119  20264  17853  -4405   1648  -4724       C
ATOM   5654  O   HIS A 751       9.965   3.593 -12.938  1.00166.71           O
ANISOU 5654  O   HIS A 751    26241  19112  17989  -4597   1515  -4730       O
ATOM   5655  CB  HIS A 751       8.675   5.576 -15.577  1.00179.19           C
ANISOU 5655  CB  HIS A 751    28650  21997  17435  -3827   1588  -3960       C
ATOM   5656  CG  HIS A 751       7.374   5.203 -14.942  1.00176.20           C
ANISOU 5656  CG  HIS A 751    28056  21865  17027  -3811    960  -4244       C
ATOM   5657  ND1 HIS A 751       6.812   3.952 -15.078  1.00176.44           N
ANISOU 5657  ND1 HIS A 751    27893  22241  16906  -4001    715  -4913       N
ATOM   5658  CD2 HIS A 751       6.522   5.917 -14.171  1.00173.57           C
ANISOU 5658  CD2 HIS A 751    27665  21467  16815  -3636    575  -3953       C
ATOM   5659  CE1 HIS A 751       5.570   3.908 -14.418  1.00174.02           C
ANISOU 5659  CE1 HIS A 751    27372  22102  16646  -3970    194  -5001       C
ATOM   5660  NE2 HIS A 751       5.470   5.087 -13.860  1.00172.24           N
ANISOU 5660  NE2 HIS A 751    27218  21646  16580  -3722    115  -4423       N
ATOM   5661  N   GLU A 752       9.131   2.805 -14.869  1.00148.67           N
ANISOU 5661  N   GLU A 752    24234  17835  14417  -4430   1584  -5265       N
ATOM   5662  CA  GLU A 752       8.881   1.464 -14.342  1.00146.28           C
ANISOU 5662  CA  GLU A 752    23676  17413  14490  -4691   1399  -5901       C
ATOM   5663  C   GLU A 752      10.209   0.898 -13.855  1.00144.60           C
ANISOU 5663  C   GLU A 752    23264  16561  15117  -4868   1824  -5965       C
ATOM   5664  O   GLU A 752      10.295  -0.231 -13.389  1.00143.10           O
ANISOU 5664  O   GLU A 752    22876  16119  15376  -5061   1797  -6418       O
ATOM   5665  CB  GLU A 752       8.228   0.560 -15.404  1.00151.53           C
ANISOU 5665  CB  GLU A 752    24484  18681  14408  -4741   1345  -6503       C
ATOM   5666  CG  GLU A 752       6.717   0.800 -15.591  1.00152.80           C
ANISOU 5666  CG  GLU A 752    24650  19497  13910  -4651    733  -6555       C
ATOM   5667  CD  GLU A 752       6.176   0.281 -16.918  1.00160.09           C
ANISOU 5667  CD  GLU A 752    25805  21157  13865  -4673    674  -6997       C
ATOM   5668  OE1 GLU A 752       4.952   0.373 -17.146  1.00162.28           O
ANISOU 5668  OE1 GLU A 752    26015  22051  13592   4632    133   7075       O
ATOM   5669  OE2 GLU A 752       6.977  -0.206 -17.737  1.00164.27           O
ANISOU 5669  OE2 GLU A 752    26577  21669  14167  -4734   1172  -7265       O
ATOM   5670  N   LEU A 753      11.246   1.714 -13.977  1.00124.59           N
ANISOU 5670  N   LEU A 753    20764  13766  12809  -4796   2222  -5470       N
ATOM   5671  CA  LEU A 753      12.573   1.368 -13.522  1.00123.86           C
ANISOU 5671  CA  LEU A 753    20394  13117  13551  -4937   2610  -5404       C
ATOM   5672  C   LEU A 753      12.656   1.481 -12.001  1.00117.79           C
ANISOU 5672  C   LEU A 753    19341  11835  13579  -5109   2214  -5220       C
ATOM   5673  O   LEU A 753      12.692   0.484 -11.308  1.00115.47           O
ANISOU 5673  O   LEU A 753    18813  11281  13779  -5251   2068  -5548       O
ATOM   5674  CB  LEU A 753      13.577   2.314 -14.178  1.00127.70           C
ANISOU 5674  CB  LEU A 753    20981  13552  13988  -4847   3147  -4895       C
ATOM   5675  CG  LEU A 753      15.095   2.117 -14.185  1.00129.96           C
ANISOU 5675  CG  LEU A 753    20963  13433  14982  -4941   3733  -4747       C
ATOM   5676  CD1 LEU A 753      15.535   1.320 -15.423  1.00136.29           C
ANISOU 5676  CD1 LEU A 753    21881  14493  15412  -4827   4367  -5122       C
ATOM   5677  CD2 LEU A 753      15.811   3.472 -14.147  1.00131.12           C
ANISOU 5677  CD2 LEU A 753    21126  13380  15312  -4976   3957  -4057       C
ATOM   5678  N   MET A 754      12.666   2.696 -11.474  1.00126.66           N
ANISOU 5678  N   MET A 754    20538  12791  14794  -5101   2047  -4699       N
ATOM   5679  CA  MET A 754      12.821   2.865 -10.030  1.00121.76           C
ANISOU 5679  CA  MET A 754    19718  11682  14862  -5298   1690  -4532       C
ATOM   5680  C   MET A 754      11.540   2.922  -9.224  1.00117.71           C
ANISOU 5680  C   MET A 754    19301  11245  14180  -5285   1137  -4646       C
ATOM   5681  O   MET A 754      11.464   2.332  -8.156  1.00114.20           O
ANISOU 5681  O   MET A 754    18674  10509  14209  -5460    855  -4801       O
ATOM   5682  CB  MET A 754      13.723   4.054  -9.696  1.00122.25           C
ANISOU 5682  CB  MET A 754    19786  11383  15279  -5400   1837  -3963       C
ATOM   5683  CG  MET A 754      15.168   3.723  -9.968  1.00125.36           C
```

FIG. 13 Continued

```
ANISOU 5683  CG  MET A 754    19856 11554 16223  -5526   2308  -3873     C
ATOM   5684  SD  MET A 754    15.449   1.927  -9.932  1.00 125.49        S
ANISOU 5684  SD  MET A 754    19515 11536 16629  -5534   2403  -4443     S
ATOM   5685  CE  MET A 754    17.101   1.846 -10.630  1.00 131.28        C
ANISOU 5685  CE  MET A 754    19904 12122 17854  -5541   3135  -4230     C
ATOM   5686  N   GLY A 755    10.541   3.642  -9.715  1.00 135.80        N
ANISOU 5686  N   GLY A 755    21862 13927 15808  -5059    999  -4529     N
ATOM   5687  CA  GLY A 755     9.263   3.691  -9.034  1.00 132.89        C
ANISOU 5687  CA  GLY A 755    21524 13691 15278  -5002    532  -4632     C
ATOM   5688  C   GLY A 755     8.674   2.290  -8.925  1.00 131.97        C
ANISOU 5688  C   GLY A 755    21198 13758 15189  -5134    346  -5215     C
ATOM   5689  O   GLY A 755     7.448   2.153  -8.791  1.00 131.40        O
ANISOU 5689  O   GLY A 755    21109 14012 14805  -5071     17  -5393     O
ATOM   5690  N   ALA A 756     9.542   1.263  -9.008  1.00 121.55        N
ANISOU 5690  N   ALA A 756    19704 12215 14266  -5310    587  -5497     N
ATOM   5691  CA  ALA A 756     9.165  -0.161  -8.884  1.00 121.70        C
ANISOU 5691  CA  ALA A 756    19532 12289 14418  -5444    519  -6007     C
ATOM   5692  C   ALA A 756    10.239  -1.058  -8.229  1.00 121.69        C
ANISOU 5692  C   ALA A 756    19209 11861 15168  -5520    755  -5938     C
ATOM   5693  O   ALA A 756    10.068  -2.282  -8.184  1.00 123.28        O
ANISOU 5693  O   ALA A 756    19233 12089 15517  -5552    829  -6241     O
ATOM   5694  CB  ALA A 756     8.720  -0.745 -10.229  1.00 126.20        C
ANISOU 5694  CB  ALA A 756    20250 13360 14341  -5411    652  -6495     C
ATOM   5695  N   VAL A 757    11.337  -0.449  -7.760  1.00 109.65        N
ANISOU 5695  N   VAL A 757    17613  9935 14112  -5556    861  -5557     N
ATOM   5696  CA  VAL A 757    12.394  -1.132  -6.978  1.00 109.88        C
ANISOU 5696  CA  VAL A 757    17282  9591 14876  -5593    975  -5397     C
ATOM   5697  C   VAL A 757    13.117  -0.234  -5.983  1.00 108.45        C
ANISOU 5697  C   VAL A 757    16967  9164 15074  -5618    820  -4831     C
ATOM   5698  O   VAL A 757    13.664  -0.714  -4.999  1.00 108.46        O
ANISOU 5698  O   VAL A 757    16667  8990 15552  -5591    704  -4628     O
ATOM   5699  CB  VAL A 757    13.496  -1.822  -7.799  1.00 112.64        C
ANISOU 5699  CB  VAL A 757    17581  9620 15597  -5696   1423  -5742     C
ATOM   5700  CG1 VAL A 757    13.578  -3.314  -7.440  1.00 114.17        C
ANISOU 5700  CG1 VAL A 757    17522  9673 16183  -5642   1510  -6006     C
ATOM   5701  CG2 VAL A 757    13.309  -1.575  -9.266  1.00 116.31        C
ANISOU 5701  CG2 VAL A 757    18317 10487 15389  -5574   1778  -5957     C
ATOM   5702  N   TYR A 758    13.172   1.063  -6.236  1.00 118.21        N
ANISOU 5702  N   TYR A 758    18457 10356 16100  -5688    806  -4593     N
ATOM   5703  CA  TYR A 758    13.697   1.928  -5.204  1.00 117.55        C
ANISOU 5703  CA  TYR A 758    18296 10075 16293  -5738    614  -4096     C
ATOM   5704  C   TYR A 758    12.792   1.619  -4.024  1.00 115.79        C
ANISOU 5704  C   TYR A 758    18024 10058 15914  -5556    256  -3986     C
ATOM   5705  O   TYR A 758    13.113   1.891  -2.883  1.00 115.53        O
ANISOU 5705  O   TYR A 758    17907  9911 16080  -5560     22  -3675     O
ATOM   5706  CB  TYR A 758    13.558   3.386  -5.599  1.00 117.37        C
ANISOU 5706  CB  TYR A 758    18660  9951 15985  -5826    644  -3876     C
ATOM   5707  CG  TYR A 758    14.226   4.321  -4.628  1.00 117.86        C
ANISOU 5707  CG  TYR A 758    18687  9758 16335  -5949    494  -3421     C
ATOM   5708  CD1 TYR A 758    14.520   3.916  -3.335  1.00 117.76        C
ANISOU 5708  CD1 TYR A 758    18399  9749 16596  -5913    197  -3261     C
ATOM   5709  CD2 TYR A 758    14.559   5.616  -4.997  1.00 119.02        C
ANISOU 5709  CD2 TYR A 758    19132  9632 16459  -6128    637  -3166     C
ATOM   5710  CE1 TYR A 758    15.136   4.769  -2.431  1.00 118.99        C
ANISOU 5710  CE1 TYR A 758    18571  9697 16942  -6072     -6  -2921     C
ATOM   5711  CE2 TYR A 758    15.177   6.482  -4.104  1.00 120.40        C
ANISOU 5711  CE2 TYR A 758    19302  9569 16875  -6293    491  -2803     C
ATOM   5712  CZ  TYR A 758    15.460   6.054  -2.820  1.00 120.44        C
ANISOU 5712  CZ  TYR A 758    19029  9637 17095  -6274    141  -2718     C
ATOM   5713  OH  TYR A 758    16.071   6.907  -1.925  1.00 122.48        O
ANISOU 5713  OH  TYR A 758    19334  9671 17531  -6492    -68  -2433     O
ATOM   5714  N   LEU A 759    11.640   1.035  -4.339  1.00  97.45        N
ANISOU 5714  N   LEU A 759    15771  8038 13218  -5432    221  -4268     N
ATOM   5715  CA  LEU A 759    10.636   0.618  -3.364  1.00  96.19        C
ANISOU 5715  CA  LEU A 759    15556  8063 12929  -5297    -28  -4206     C
ATOM   5716  C   LEU A 759    10.844  -0.809  -2.855  1.00  97.01        C
ANISOU 5716  C   LEU A 759    15364  8112 13383  -5278    -18  -4344     C
ATOM   5717  O   LEU A 759    10.000  -1.684  -3.059  1.00  97.47        O
ANISOU 5717  O   LEU A 759    15372  8357 13304  -5252     10  -4627     O
```

FIG. 13 Continued

```
ATOM   5718  CB  LEU A 759       9.237   0.741  -3.967  1.00 95.78           C
ANISOU 5718  CB  LEU A 759    15673   8354  12364   -5223    -87  -4431      C
ATOM   5719  CG  LEU A 759       8.693   2.162   4.074  1.00 94.78           C
ANISOU 5719  CG  LEU A 759    15877   6242  11894   -5166   -199  -4236      C
ATOM   5720  CD1 LEU A 759       7.219   2.160  -4.472  1.00 94.76           C
ANISOU 5720  CD1 LEU A 759    15944   8605  11454   -5061   -350  -4461      C
ATOM   5721  CD2 LEU A 759       8.889   2.825  -2.740  1.00 93.70           C
ANISOU 5721  CD2 LEU A 759    15802   7877  11924   -5138   -346  -3832      C
ATOM   5722  N   GLN A 760      11.982  -1.008  -2.200  1.00 86.83           N
ANISOU 5722  N   GLN A 760    13685   6533  12572   -5317    -58  -4145      N
ATOM   5723  CA  GLN A 760      12.386  -2.259  -1.585  1.00 87.94           C
ANISOU 5723  CA  GLN A 760    13772   6496  13145   -5291    -89  -4200      C
ATOM   5724  C   GLN A 760      13.628  -1.852  -0.833  1.00 88.69           C
ANISOU 5724  C   GLN A 760    13710   6308  13679   -5361   -267  -3855      C
ATOM   5725  O   GLN A 760      14.743  -2.332  -1.072  1.00 90.60           O
ANISOU 5725  O   GLN A 760    13681   6273  14471   -5429   -143  -3891      O
ATOM   5726  CB  GLN A 760      12.703  -3.313  -2.623  1.00 89.96           C
ANISOU 5726  CB  GLN A 760    13903   6647  13630   -5329    255  -4635      C
ATOM   5727  CG  GLN A 760      11.504  -3.775  -3.414  1.00 90.26           C
ANISOU 5727  CG  GLN A 760    14094   6983  13217   -5334    379  -5036      C
ATOM   5728  CD  GLN A 760      10.454  -4.449  -2.556  1.00 89.83           C
ANISOU 5728  CD  GLN A 760    14017   7053  13062   -5287    195  -5026      C
ATOM   5729  OE1 GLN A 760      10.736  -5.440  -1.867  1.00 90.89           O
ANISOU 5729  OE1 GLN A 760    14012   6937  13583   -5275    181  -5021      O
ATOM   5730  NE2 GLN A 760       9.223  -3.932  -2.612  1.00 88.66           N
ANISOU 5730  NE2 GLN A 760    14005   7250  12430   -5277     66  -5029      N
ATOM   5731  N   VAL A 761      13.385  -0.895   0.049  1.00140.56           N
ANISOU 5731  N   VAL A 761    20466  12936  20002   -5373   -556  -3534      N
ATOM   5732  CA  VAL A 761      14.376  -0.236   0.867  1.00141.68           C
ANISOU 5732  CA  VAL A 761    20550  12869  20411   -5509   -825  -3197      C
ATOM   5733  C   VAL A 761      13.519   0.424   1.902  1.00140.39           C
ANISOU 5733  C   VAL A 761    20725  12823  19796   -5480  -1097  -3002      C
ATOM   5734  O   VAL A 761      13.669   0.227   3.100  1.00141.02           O
ANISOU 5734  O   VAL A 761    20837  12804  19941   -5524  -1419  -2811      O
ATOM   5735  CB  VAL A 761      15.051   0.902   0.086  1.00142.48           C
ANISOU 5735  CB  VAL A 761    20692  12889  20556   -5675   -659  -3123      C
ATOM   5736  CG1 VAL A 761      15.625   1.959   1.043  1.00143.71           C
ANISOU 5736  CG1 VAL A 761    20952  12898  20754   -5869   -989  -2775      C
ATOM   5737  CG2 VAL A 761      16.117   0.356  -0.856  1.00144.44           C
ANISOU 5737  CG2 VAL A 761    20589  12940  21352   -5771   -346  -3271      C
ATOM   5738  N   SER A 762      12.597   1.223   1.400  1.00130.97           N
ANISOU 5738  N   SER A 762    19811  11807  18144   -5421   -955  -3063      N
ATOM   5739  CA  SER A 762      11.628   1.869   2.237  1.00129.89           C
ANISOU 5739  CA  SER A 762    20009  11748  17595   -5375  -1109  -2935      C
ATOM   5740  C   SER A 762      10.605   0.791   2.566  1.00128.92           C
ANISOU 5740  C   SER A 762    19824  11798  17363   -5239  -1095  -3081      C
ATOM   5741  O   SER A 762       9.742   0.975   3.425  1.00128.28           O
ANISOU 5741  O   SER A 762    19957  11766  17018   -5207  -1199  -3001      O
ATOM   5742  CB  SER A 762      10.988   3.019   1.470  1.00129.02           C
ANISOU 5742  CB  SER A 762    20182  11704  17138   -5343   -941  -2966      C
ATOM   5743  OG  SER A 762      10.526   4.036   2.336  1.00129.00           O
ANISOU 5743  OG  SER A 762    20548  11601  16866   -5368  -1080  -2788      O
ATOM   5744  N   ILE A 763      10.704  -0.342   1.872  1.00126.73           N
ANISOU 5744  N   ILE A 763    19269  11571  17312   -5197   -929  -3324      N
ATOM   5745  CA  ILE A 763       9.811  -1.466   2.137  1.00126.60           C
ANISOU 5745  CA  ILE A 763    19177  11663  17263   -5135   -891  -3494      C
ATOM   5746  C   ILE A 763      10.329  -2.336   3.278  1.00127.71           C
ANISOU 5746  C   ILE A 763    19241  11576  17708   -5172  -1096  -3350      C
ATOM   5747  O   ILE A 763       9.548  -2.900   4.034  1.00127.65           O
ANISOU 5747  O   ILE A 763    19317  11591  17592   -5169  -1153  -3345      O
ATOM   5748  CB  ILE A 763       9.624  -2.352   0.917  1.00127.34           C
ANISOU 5748  CB  ILE A 763    19078  11860  17445   -5127   -620  -3878      C
ATOM   5749  CG1 ILE A 763       8.175  -2.877   0.846  1.00127.16           C
ANISOU 5749  CG1 ILE A 763    19075  12081  17159   -5117   -560  -4099      C
ATOM   5750  CG2 ILE A 763      10.667  -3.462   0.918  1.00129.16           C
ANISOU 5750  CG2 ILE A 763    19066  11813  18194   -5158   -561  -3968      C
ATOM   5751  CD1 ILE A 763       7.573  -3.362   2.166  1.00127.08           C
ANISOU 5751  CD1 ILE A 763    19120  12010  17155   -5128   -700  -3955      C
ATOM   5752  N   ILE A 764      11.645  -2.476   3.381  1.00142.67           N
```

FIG. 13 Continued

```
ANISOU 5752  N    ILE A 764      20963  13224  20020  -5232  -1213  -3235       N
ATOM   5753  CA   ILE A 764      12.225  -3.175   4.520  1.00144.13            C
ANISOU 5753  CA   ILE A 764      21095  13153  20516  -5289  -1508  -3042       C
ATOM   5754  C    ILE A 764      12.568  -2.132   5.592  1.00144.43            C
ANISOU 5754  C    ILE A 764      21378  13131  20369  -5421  -1878  -2707       C
ATOM   5755  O    ILE A 764      13.713  -2.007   6.034  1.00146.30            O
ANISOU 5755  O    ILE A 764      21492  13150  20948  -5561  -2168  -2507       O
ATOM   5756  CB   ILE A 764      13.435  -4.062   4.134  1.00146.23            C
ANISOU 5756  CB   ILE A 764      20993  13120  21449  -5304  -1474  -3103       C
ATOM   5757  CG1  ILE A 764      12.980  -5.221   3.236  1.00146.66            C
ANISOU 5757  CG1  ILE A 764      20918  13161  21646  -5216  -1090  -3492       C
ATOM   5758  CG2  ILE A 764      14.131  -4.610   5.382  1.00148.15            C
ANISOU 5758  CG2  ILE A 764      21184  13054  22053  -5391  -1888  -2818       C
ATOM   5759  CD1  ILE A 764      14.014  -6.310   3.045  1.00149.24            C
ANISOU 5759  CD1  ILE A 764      20943  13076  22687  -5215  -1008  -3576       C
ATOM   5760  N    SER A 765      11.550  -1.355   5.961  1.00132.42            N
ANISOU 5760  N    SER A 765      20201  11784  18328  -5410  -1858  -2673       N
ATOM   5761  CA   SER A 765      11.654  -0.334   6.994  1.00133.07            C
ANISOU 5761  CA   SER A 765      20637  11785  18139  -5565  -2143  -2434       C
ATOM   5762  C    SER A 765      11.157  -0.943   8.285  1.00133.68            C
ANISOU 5762  C    SER A 765      20947  11783  18061  -5630  -2348  -2332       C
ATOM   5763  O    SER A 765      11.419  -0.420   9.367  1.00135.12            O
ANISOU 5763  O    SER A 765      21450  11826  18065  -5825  -2664  -2138       O
ATOM   5764  CB   SER A 765      10.804   0.887   6.640  1.00131.66            C
ANISOU 5764  CB   SER A 765      20746  11755  17524  -5519  -1941  -2484       C
ATOM   5765  OG   SER A 765      11.012   1.949   7.556  1.00132.96            O
ANISOU 5765  OG   SER A 765      21301  11765  17452  -5705  -2169  -2305       O
ATOM   5766  N    GLN A 766      10.424  -2.048   8.158  1.00183.35            N
ANISOU 5766  N    GLN A 766      27117  18141  24407  -5517  -2157  -2486       N
ATOM   5767  CA   GLN A 766       9.932  -2.778   9.316  1.00184.21            C
ANISOU 5767  CA   GLN A 766      27443  18137  24412  -5606  -2296  -2403       C
ATOM   5768  C    GLN A 766      11.127  -3.344  10.068  1.00186.60            C
ANISOU 5768  C    GLN A 766      27694  18134  25073  -5752  -2720  -2179       C
ATOM   5769  O    GLN A 766      11.137  -3.370  11.296  1.00188.06            O
ANISOU 5769  O    GLN A 766      28214  18165  25076  -5938  -3032  -1985       O
ATOM   5770  CB   GLN A 766       9.019  -3.908   8.892  1.00183.71            C
ANISOU 5770  CB   GLN A 766      27210  18156  24434  -5509  -1985  -2640       C
ATOM   5771  CG   GLN A 766       9.768  -5.130   8.466  1.00185.08            C
ANISOU 5771  CG   GLN A 766      27057  18125  25140  -5474  -1981  -2720       C
ATOM   5772  CD   GLN A 766       8.844  -6.204   7.973  1.00185.26            C
ANISOU 5772  CD   GLN A 766      26956  18195  25238  -5441  -1644  -3013       C
ATOM   5773  OE1  GLN A 766       7.755  -5.922   7.465  1.00184.03            O
ANISOU 5773  OE1  GLN A 766      26807  18319  24796  -5415  -1388  -3212       O
ATOM   5774  NE2  GLN A 766       9.265  -7.453   8.117  1.00187.30            N
ANISOU 5774  NE2  GLN A 766      27098  18142  25924  -5474  -1656  -3050       N
ATOM   5775  N    ALA A 767      12.130  -3.808   9.322  1.00 83.21            N
ANISOU 5775  N    ALA A 767      14184   4923  12508  -5692  -2734  -2212       N
ATOM   5776  CA   ALA A 767      13.395  -4.248   9.911  1.00 85.88            C
ANISOU 5776  CA   ALA A 767      14363   4941  13327  -5840  -3171  -1974       C
ATOM   5777  C    ALA A 767      14.052  -3.072  10.665  1.00 87.33            C
ANISOU 5777  C    ALA A 767      14773   5090  13317   6100   3608   1723       C
ATOM   5778  O    ALA A 767      15.030  -3.247  11.395  1.00 90.12            O
ANISOU 5778  O    ALA A 767      15061   5200  13980  -6325  -4102  -1474       O
ATOM   5779  CB   ALA A 767      14.338  -4.817   8.813  1.00 86.62            C
ANISOU 5779  CB   ALA A 767      13920   4898  14093  -5729  -3003  -2092       C
ATOM   5780  N    LEU A 768      13.489  -1.878  10.473  1.00139.03            N
ANISOU 5780  N    LEU A 768      21595  11852  19379  -6103  -3433  -1798       N
ATOM   5781  CA   LEU A 768      13.996  -0.635  11.060  1.00140.77            C
ANISOU 5781  CA   LEU A 768      22102  12014  19370  -6382  -3751  -1640       C
ATOM   5782  C    LEU A 768      13.004  -0.023  12.065  1.00140.69            C
ANISOU 5782  C    LEU A 768      22729  12031  18696  -6497  -3768  -1630       C
ATOM   5783  O    LEU A 768      13.299   0.968  12.754  1.00142.78            O
ANISOU 5783  O    LEU A 768      23376  12188  18688  -6784  -4034  -1538       O
ATOM   5784  CB   LEU A 768      14.334   0.354   9.943  1.00140.04            C
ANISOU 5784  CB   LEU A 768      21829  12025  19353  -6339  -3496  -1741       C
ATOM   5785  CG   LEU A 768      15.508   0.001   9.006  1.00141.01            C
ANISOU 5785  CG   LEU A 768      21363  12069  20146  -6329  -3473  -1742       C
ATOM   5786  CD1  LEU A 768      15.822  -1.494   8.959  1.00141.43            C
ANISOU 5786  CD1  LEU A 768      21035  11991  20711  -6200  -3505  -1748       C
```

FIG. 13 Continued

```
ATOM   5787  CD2 LEU A 768      15.286   0.544   7.591  1.00139.02           C
ANISOU 5787  CD2 LEU A 768    20968  11984  19871  -6157  -2971  -1951       C
ATOM   5788  N   ILE A 769      11.818  -0.623  12.117  1.00136.75           N
ANISOU 5788  N   ILE A 769    22341  11650  17967  -6307  -3450  -1757       N
ATOM   5789  CA  ILE A 769      10.788  -0.261  13.082  1.00136.86           C
ANISOU 5789  CA  ILE A 769    22912  11659  17429  -6408  -3386  -1772       C
ATOM   5790  C   ILE A 769      10.914  -1.243  14.260  1.00138.91           C
ANISOU 5790  C   ILE A 769    23379  11714  17686  -6603  -3724  -1615       C
ATOM   5791  O   ILE A 769       9.975  -1.944  14.646  1.00138.32           O
ANISOU 5791  O   ILE A 769    23453  11651  17451  -6559  -3516  -1679       O
ATOM   5792  CB  ILE A 769       9.373  -0.220  12.430  1.00134.02           C
ANISOU 5792  CB  ILE A 769    22519  11539  16863  -6146  -2833  -2003       C
ATOM   5793  CG1 ILE A 769       8.632   1.039  12.872  1.00134.18           C
ANISOU 5793  CG1 ILE A 769    23037  11545  16399  -6222  -2683  -2056       C
ATOM   5794  CG2 ILE A 769       8.570  -1.501  12.674  1.00133.53           C
ANISOU 5794  CG2 ILE A 769    22372  11507  16856  -6081  -2667  -2077       C
ATOM   5795  CD1 ILE A 769       9.476   2.287  12.738  1.00135.55           C
ANISOU 5795  CD1 ILE A 769    23373  11600  16531  -6364  -2859  -1992       C
ATOM   5796  N   PHE A 770      12.117  -1.268  14.823  1.00 90.27           N
ANISOU 5796  N   PHE A 770    17221   5344  11735  -6866  -4276  -1397       N
ATOM   5797  CA  PHE A 770      12.478  -2.175  15.893  1.00 92.83           C
ANISOU 5797  CA  PHE A 770    17716   5420  12134  -7096  -4721  -1190       C
ATOM   5798  C   PHE A 770      13.375  -1.398  16.849  1.00 96.61           C
ANISOU 5798  C   PHE A 770    18551   5723  12434  -7546  -5342   -996       C
ATOM   5799  O   PHE A 770      13.878  -1.906  17.849  1.00 99.70           O
ANISOU 5799  O   PHE A 770    19148   5889  12844  -7857  -5880   -777       O
ATOM   5800  CB  PHE A 770      13.232   3.362  15.285  1.00 92.95           C
ANISOU 5800  CB  PHE A 770    17117   5321  12879  -6936  -4812  -1114       C
ATOM   5801  CG  PHE A 770      12.373  -4.577  15.033  1.00 91.43           C
ANISOU 5801  CG  PHE A 770    16816   5115  12808  -6701  -4416  -1243       C
ATOM   5802  CD1 PHE A 770      11.013  -4.453  14.791  1.00 89.03           C
ANISOU 5802  CD1 PHE A 770    16690   5040  12098  -6549  -3886  -1480       C
ATOM   5803  CD2 PHE A 770      12.933  -5.846  15.034  1.00 92.96           C
ANISOU 5803  CD2 PHE A 770    16711   5023  13584  -6670  -4571  -1128       C
ATOM   5804  CE1 PHE A 770      10.227  -5.572  14.571  1.00 88.38           C
ANISOU 5804  CE1 PHE A 770    16492   4933  12155  -6419  -3539  -1619       C
ATOM   5805  CE2 PHE A 770      12.151  -6.956  14.808  1.00 92.29           C
ANISOU 5805  CE2 PHE A 770    16573   4865  13627  -6511  -4183  -1273       C
ATOM   5806  CZ  PHE A 770      10.801  -6.814  14.579  1.00 90.08           C
ANISOU 5806  CZ  PHE A 770    16472   4849  12906  -6410  -3678  -1528       C
ATOM   5807  N   VAL A 771      13.557  -0.131  16.534  1.00219.44           N
ANISOU 5807  N   VAL A 771    34208  21362  27807  -7627  -5280  -1086       N
ATOM   5808  CA  VAL A 771      14.415   0.712  17.331  1.00223.66           C
ANISOU 5808  CA  VAL A 771    35072  21731  28179  -8117  -5845   -963       C
ATOM   5809  C   VAL A 771      13.643   1.569  18.327  1.00225.29           C
ANISOU 5809  C   VAL A 771    36140  21846  27615  -8382  -5792  -1082       C
ATOM   5810  O   VAL A 771      12.946   2.509  17.946  1.00223.83           O
ANISOU 5810  O   VAL A 771    36186  21728  27130  -8250  -5323  -1289       O
ATOM   5811  CB  VAL A 771      15.222   1.605  16.410  1.00224.01           C
ANISOU 5811  CB  VAL A 771    34730  21835  28551  -8140  -5823  -1002       C
ATOM   5812  CG1 VAL A 771      16.141   0.747  15.568  1.00223.50           C
ANISOU 5812  CG1 VAL A 771    33847  21792  29280  -7966  -5919   -883       C
ATOM   5813  CG2 VAL A 771      14.283   2.383  15.509  1.00220.54           C
ANISOU 5813  CG2 VAL A 771    34367  21566  27863  -7806  -5133  -1251       C
ATOM   5814  N   THR A 772      13.747   1.229  19.605  1.00135.02           N
ANISOU 5814  N   THR A 772    25210  10223  15866  -8767  -6262   -960       N
ATOM   5815  CA  THR A 772      13.156   2.068  20.649  1.00137.69           C
ANISOU 5815  CA  THR A 772    26456  10411  15448  -9108  -6251  -1106       C
ATOM   5816  C   THR A 772      14.250   2.986  21.267  1.00143.29           C
ANISOU 5816  C   THR A 772    27474  10951  16019  -9714  -6915  -1066       C
ATOM   5817  O   THR A 772      13.984   3.808  22.171  1.00146.89           O
ANISOU 5817  O   THR A 772    28753  11224  15836 -10111  -6997  -1229       O
ATOM   5818  CB  THR A 772      12.428   1.234  21.724  1.00138.47           C
ANISOU 5818  CB  THR A 772    27085  10388  15140  -9224  -6278  -1068       C
ATOM   5819  OG1 THR A 772      12.924  -0.107  21.690  1.00138.07           O
ANISOU 5819  OG1 THR A 772    26555  10318  15586  -9149  -6610   -812       O
ATOM   5820  CG2 THR A 772      10.922   1.229  21.470  1.00134.86           C
ANISOU 5820  CG2 THR A 772    26799  10032  14408  -8847  -5454  -1298       C
ATOM   5821  N   ARG A 773      15.477   2.813  20.748  1.00182.16           N
```

FIG. 13 Continued

```
ANISOU 5821  N   ARG A 773    31713  15924  21574  -9807  -7366   -875       N
ATOM   5822  CA  ARG A 773    16.719   3.544  21.117  1.00187.86             C
ANISOU 5822  CA  ARG A 773    32439  16546  22392 -10414  -8070   -801       C
ATOM   5823  C   ARG A 773    17.941   2.746  20.603  1.00188.53             C
ANISOU 5823  C   ARG A 773    31571  16714  23349 -10415  -8557   -504       C
ATOM   5824  O   ARG A 773    19.108   3.114  20.855  1.00193.65             O
ANISOU 5824  O   ARG A 773    31979  17334  24265 -10937  -9236   -374       O
ATOM   5825  CB  ARG A 773    16.833   3.780  22.624  1.00193.78             C
ANISOU 5825  CB  ARG A 773    34031  17113  22483 -11073  -8698   -813       C
ATOM   5826  CG  ARG A 773    17.909   4.745  23.005  1.00200.35             C
ANISOU 5826  CG  ARG A 773    34982  17664  23276 -11766  -9354   -842       C
ATOM   5827  CD  ARG A 773    17.454   5.556  24.181  1.00205.15             C
ANISOU 5827  CD  ARG A 773    36727  18261  22960 -12282  -9484  -1110       C
ATOM   5828  NE  ARG A 773    16.100   6.058  23.989  1.00201.30             N
ANISOU 5828  NE  ARG A 773    36804  17669  22012 -11864  -8549  -1405       N
ATOM   5829  CZ  ARG A 773    15.010   5.407  24.376  1.00198.28             C
ANISOU 5829  CZ  ARG A 773    36787  17281  21270 -11546  -8135  -1440       C
ATOM   5830  NH1 ARG A 773    15.118   4.227  24.966  1.00198.49             N
ANISOU 5830  NH1 ARG A 773    36743  17359  21317 -11599  -8556  -1202       N
ATOM   5831  NH2 ARG A 773    13.813   5.930  24.168  1.00195.41             N
ANISOU 5831  NH2 ARG A 773    36837  16844  20567 -11198  -7305  -1706       N
ATOM   5832  N   SER A 774    17.619   1.651  19.869  1.00160.61             N
ANISOU 5832  N   SER A 774    27494  13270  20262  -9852  -8180   -422       N
ATOM   5833  CA  SER A 774    18.557   0.690  19.295  1.00160.49             C
ANISOU 5833  CA  SER A 774    26573  13270  21134  -9713  -8438   -179       C
ATOM   5834  C   SER A 774    18.885   0.989  17.823  1.00157.66             C
ANISOU 5834  C   SER A 774    25516  13045  21342  -9353  -7932   -283       C
ATOM   5835  O   SER A 774    18.409   1.972  17.245  1.00155.79             O
ANISOU 5835  O   SER A 774    25489  12898  20807  -9225  -7430   -518       O
ATOM   5836  CB  SER A 774    17.993  -0.748  19.427  1.00157.81             C
ANISOU 5836  CB  SER A 774    26155  12858  20948  -9360  -8291    -74       C
ATOM   5837  OG  SER A 774    16.592  -0.813  19.170  1.00153.27             O
ANISOU 5837  OG  SER A 774    25963  12374  19897  -8935  -7528   -323       O
ATOM   5838  N   ARG A 775    19.737   0.153  17.238  1.00144.38             N
ANISOU 5838  N   ARG A 775    23018  11339  20499  -9229  -8076   -101       N
ATOM   5839  CA  ARG A 775    20.002   0.215  15.809  1.00141.67             C
ANISOU 5839  CA  ARG A 775    22027  11097  20704  -8863  -7530   -219       C
ATOM   5840  C   ARG A 775    19.284  -0.993  15.219  1.00137.25             C
ANISOU 5840  C   ARG A 775    21273  10541  20336  -8290  -7007   -310       C
ATOM   5841  O   ARG A 775    19.372  -2.085  15.767  1.00138.17             O
ANISOU 5841  O   ARG A 775    21310  10486  20700  -8285  -7291   -130       O
ATOM   5842  CB  ARG A 775    21.499   0.132  15.514  1.00145.77             C
ANISOU 5842  CB  ARG A 775    21723  11556  22106  -9168  -7984     19       C
ATOM   5843  CG  ARG A 775    22.361   0.838  16.532  1.00152.13             C
ANISOU 5843  CG  ARG A 775    22638  12335  22830  -9897  -8832    215       C
ATOM   5844  CD  ARG A 775    22.013   2.297  16.621  1.00152.93             C
ANISOU 5844  CD  ARG A 775    23366  12478  22261 -10154  -8670    -21       C
ATOM   5845  NE  ARG A 775    22.568   3.042  15.502  1.00153.02             N
ANISOU 5845  NE  ARG A 775    22899  12540  22703 -10153  -8303   -108       N
ATOM   5846  CZ  ARG A 775    23.869   3.182  15.274  1.00157.70             C
ANISOU 5846  CZ  ARG A 775    22744  13139  24038 -10557  -8700     92       C
ATOM   5847  NH1 ARG A 775    24.751   2.612  16.079  1.00162.69             N
ANISOU 5847  NH1 ARG A 775    22956  13775  25086 -10974  -9531    405       N
ATOM   5848  NH2 ARG A 775    24.292   3.888  14.235  1.00157.81             N
ANISOU 5848  NH2 ARG A 775    22384  13172  24405 -10572  -8275      2       N
ATOM   5849  N   SER A 776    18.542  -0.805  14.135  1.00192.25             N
ANISOU 5849  N   SER A 776    28199  17681  27167  -7855  -6267   -592       N
ATOM   5850  CA  SER A 776    17.893  -1.935  13.501  1.00188.86             C
ANISOU 5850  CA  SER A 776    27563  17269  26927  -7386  -5782   -730       C
ATOM   5851  C   SER A 776    19.062  -2.817  13.109  1.00191.02             C
ANISOU 5851  C   SER A 776    27106  17326  28148  -7394  -5983   -560       C
ATOM   5852  O   SER A 776    16.923  -4.024  12.893  1.00190.26             O
ANISOU 5852  O   SER A 776    26788  17066  28437  -7143  -5803   -575       O
ATOM   5853  CB  SER A 776    17.127  -1.476  12.269  1.00184.90             C
ANISOU 5853  CB  SER A 776    27030  17020  26204  -7022  -5054  -1050       C
ATOM   5854  OG  SER A 776    16.531  -0.209  12.491  1.00184.31             O
ANISOU 5854  OG  SER A 776    27471  17085  25473  -7135  -4956  -1136       O
ATOM   5855  N   TRP A 777    20.222  -2.164  13.050  1.00205.54             N
ANISOU 5855  N   TRP A 777    28569  19132  30393  -7731  -6345   -393       N
```

FIG. 13 Continued

```
ATOM   5856  CA   TRP A 777      21.512  -2.749  12.721  1.00208.68           C
ANISOU 5856  CA   TRP A 777    28161  19335  31794  -7851  -6584   -170       C
ATOM   5857  C    TRP A 777      22.031  -3.653  13.840  1.00212.28           C
ANISOU 5857  C    TRP A 777    28500  19530  32628  -8109  -7291    202       C
ATOM   5858  O    TRP A 777      22.379  -4.811  13.607  1.00212.87           O
ANISOU 5858  O    TRP A 777    28119  19331  33432  -7931  -7222    325       O
ATOM   5859  CB   TRP A 777      22.486  -1.598  12.468  1.00211.82           C
ANISOU 5859  CB   TRP A 777    28232  19834  32417  -8246  -6795    -84       C
ATOM   5860  CG   TRP A 777      23.936  -1.933  12.565  1.00216.98           C
ANISOU 5860  CG   TRP A 777    28031  20350  34061  -8600  -7296    265       C
ATOM   5861  CD1  TRP A 777      24.569  -2.569  13.593  1.00221.13           C
ANISOU 5861  CD1  TRP A 777    28303  20739  34977  -8926  -8070    640       C
ATOM   5862  CD2  TRP A 777      24.955  -1.601  11.610  1.00219.19           C
ANISOU 5862  CD2  TRP A 777    27524  20653  35105  -8721  -7078    314       C
ATOM   5863  NE1  TRP A 777      25.912  -2.678  13.327  1.00225.85           N
ANISOU 5863  NE1  TRP A 777    27907  21321  36586  -9224  -8366    936       N
ATOM   5864  CE2  TRP A 777      26.177  -2.089  12.119  1.00224.81           C
ANISOU 5864  CE2  TRP A 777    27430  21277  36709  -9108  -7731    739       C
ATOM   5865  CE3  TRP A 777      24.951  -0.950  10.370  1.00217.32           C
ANISOU 5865  CE3  TRP A 777    27155  20514  34901  -8569  -6387     67       C
ATOM   5866  CZ2  TRP A 777      27.388  -1.945  11.430  1.00228.75           C
ANISOU 5866  CZ2  TRP A 777    26925  21815  38174  -9336  -7665    928       C
ATOM   5867  CZ3  TRP A 777      26.155  -0.808   9.688  1.00221.06           C
ANISOU 5867  CZ3  TRP A 777    26745  20965  36283  -8810  -6300    235       C
ATOM   5868  CH2  TRP A 777      27.355  -1.304  10.221  1.00226.78           C
ANISOU 5868  CH2  TRP A 777    26609  21629  37927  -9185  -6910    664       C
ATOM   5869  N    SER A 778      22.074  -3.103  15.052  1.00158.43           N
ANISOU 5869  N    SER A 778    22135  12757  25306  -8559  -7960    378       N
ATOM   5870  CA   SER A 778      22.555  -3.795  16.257  1.00162.55           C
ANISOU 5870  CA   SER A 778    22643  13078  26040  -8927  -8775    760       C
ATOM   5871  C    SER A 778      21.748  -5.041  16.647  1.00160.50           C
ANISOU 5871  C    SER A 778    22731  12552  25698  -8629  -8604    793       C
ATOM   5872  O    SER A 778      22.260  -5.982  17.260  1.00163.55           O
ANISOU 5872  O    SER A 778    22884  12638  26620  -8798  -9095   1151       O
ATOM   5873  CB   SER A 778      22.521  -2.818  17.430  1.00165.76           C
ANISOU 5873  CB   SER A 778    23686  13631  25665  -9483  -9427    816       C
ATOM   5874  OG   SER A 778      21.185  -2.417  17.709  1.00162.14           O
ANISOU 5874  OG   SER A 778    24149  13243  24213  -9289  -8985    526       O
ATOM   5875  N    PHE A 779      20.469  -5.018  16.312  1.00190.77           N
ANISOU 5875  N    PHE A 779    27110  16498  28877  -8230  -7916    445       N
ATOM   5876  CA   PHE A 779      19.574  -6.117  16.602  1.00189.01           C
ANISOU 5876  CA   PHE A 779    27235  16061  28518  -7968  -7642    420       C
ATOM   5877  C    PHE A 779      20.048  -7.361  15.863  1.00189.30           C
ANISOU 5877  C    PHE A 779    26637  15743  29544  -7664  -7365    499       C
ATOM   5878  O    PHE A 779      19.278  -8.289  15.639  1.00187.46           O
ANISOU 5878  O    PHE A 779    26581  15334  29321   7338   6882    358       O
ATOM   5879  CB   PHE A 779      18.159  -5.738  16.166  1.00184.32           C
ANISOU 5879  CB   PHE A 779    27134  15762  27136  -7628  -6910      4       C
ATOM   5880  CG   PHE A 779      17.246  -5.323  17.293  1.00184.37           C
ANISOU 5880  CG   PHE A 779    27978  15848  26227  -7852  -7055     -3       C
ATOM   5881  CD1  PHE A 779      17.355  -4.062  17.873  1.00185.88           C
ANISOU 5881  CD1  PHE A 779    28577  16207  25842  -8210  -7378     -6       C
ATOM   5882  CD2  PHE A 779      16.258  -6.180  17.751  1.00183.37           C
ANISOU 5882  CD2  PHE A 779    28254  15590  25827  -7735  -6803    -35       C
ATOM   5883  CE1  PHE A 779      16.510  -3.674  18.900  1.00186.35           C
ANISOU 5883  CE1  PHE A 779    29452  16285  25067  -8431  -7436    -52       C
ATOM   5884  CE2  PHE A 779      15.410  -5.802  18.773  1.00183.70           C
ANISOU 5884  CE2  PHE A 779    29064  15680  25055  -7964  -6860    -56       C
ATOM   5885  CZ   PHE A 779      15.535  -4.546  19.349  1.00185.15           C
ANISOU 5885  CZ   PHE A 779    29670  16016  24661  -8303  -7167    -73       C
ATOM   5886  N    VAL A 780      21.320  -7.366  15.474  1.00202.79           N
ANISOU 5886  N    VAL A 780    27596  17330  32124  -7801  -7632    717       N
ATOM   5887  CA   VAL A 780      21.909  -8.501  14.777  1.00203.92           C
ANISOU 5887  CA   VAL A 780    27111  17036  33334  -7542  -7330    831       C
ATOM   5888  C    VAL A 780      21.432  -9.811  15.399  1.00205.55           C
ANISOU 5888  C    VAL A 780    27648  16839  33614  -7293  -7289   1064       C
ATOM   5889  O    VAL A 780      21.308  -9.917  16.618  1.00208.47           O
ANISOU 5889  O    VAL A 780    28433  17221  33553  -7473  -7856   1418       O
ATOM   5890  CB   VAL A 780      23.450  -8.444  14.801  1.00210.89           C
```

FIG. 13 Continued

```
ANISOU 5890  CB  VAL A 780    27084  18074  34971  -7525  -7810   1356       C
ATOM   5891  CG1 VAL A 780     23.955  -7.304  13.925  1.00 209.33           C
ANISOU 5891  CG1 VAL A 780    26473  18150  34914   7771   7648   1091       C
ATOM   5892  CG2 VAL A 780     23.959  -8.296  16.228  1.00 217.01           C
ANISOU 5892  CG2 VAL A 780    27948  19041  35465  -7821  -8803   1918       C
ATOM   5893  N   GLU A 781     21.172 -10.799  14.545  1.00 142.43           N
ANISOU 5893  N   GLU A 781    19497   8507  26111  -6853  -6586    869       N
ATOM   5894  CA  GLU A 781     20.626 -12.110  14.939  1.00 144.21           C
ANISOU 5894  CA  GLU A 781    20060   8285  26450  -6562  -6359   1021       C
ATOM   5895  C   GLU A 781     19.205 -12.017  15.524  1.00 140.29           C
ANISOU 5895  C   GLU A 781    20422   7860  25022  -6762  -6241    730       C
ATOM   5896  O   GLU A 781     18.432 -12.990  15.436  1.00 140.22           O
ANISOU 5896  O   GLU A 781    20694   7569  25013  -6528  -5763    599       O
ATOM   5897  CB  GLU A 781     21.557 -12.912  15.869  1.00 152.78           C
ANISOU 5897  CB  GLU A 781    20841   9233  27978  -6290  -6922   1843       C
ATOM   5898  CG  GLU A 781     21.511 -14.431  15.640  1.00 156.47           C
ANISOU 5898  CG  GLU A 781    21247   9115  29091  -5743  -6419   2023       C
ATOM   5899  CD  GLU A 781     20.113 -14.954  15.314  1.00 151.22           C
ANISOU 5899  CD  GLU A 781    21276   8089  28092  -5814  -5728   1448       C
ATOM   5900  OE1 GLU A 781     19.299 -15.151  16.244  1.00 150.76           O
ANISOU 5900  OE1 GLU A 781    21892   7922  27469  -6038  -5891   1552       O
ATOM   5901  OE2 GLU A 781     19.826 -15.180  14.121  1.00 148.15           O
ANISOU 5901  OE2 GLU A 781    20751   7543  27995  -5664  -5013    890       O
ATOM   5902  N   ARG A 782     18.865 -10.868  16.118  1.00 249.03           N
ANISOU 5902  N   ARG A 782    34548  22156  37916  -7056  -6612    667       N
ATOM   5903  CA  ARG A 782     17.515 -10.642  16.644  1.00 246.64           C
ANISOU 5903  CA  ARG A 782    34963  22142  36608   7080   6407    435       C
ATOM   5904  C   ARG A 782     16.558 -10.393  15.475  1.00 242.31           C
ANISOU 5904  C   ARG A 782    34347  22021  35700  -6723  -5607   -140       C
ATOM   5905  O   ARG A 782     15.792 -11.292  15.110  1.00 241.69           O
ANISOU 5905  O   ARG A 782    34349  21801  35683  -6505  -5080   -356       O
ATOM   5906  CB  ARG A 782     17.477  -9.519  17.686  1.00 247.17           C
ANISOU 5906  CB  ARG A 782    35505  22513  35896  -7508  -7001    566       C
ATOM   5907  CG  ARG A 782     17.908  -9.968  19.069  1.00 251.53           C
ANISOU 5907  CG  ARG A 782    36420  22643  36506  -7933  -7738   1088       C
ATOM   5908  CD  ARG A 782     17.042  -9.345  20.144  1.00 251.37           C
ANISOU 5908  CD  ARG A 782    37254  22833  35422  -8250  -7913   1027       C
ATOM   5909  NE  ARG A 782     17.125 -10.093  21.393  1.00 255.54           N
ANISOU 5909  NE  ARG A 782    38270  22906  35917  -8559  -8398   1504       N
ATOM   5910  CZ  ARG A 782     16.308  -9.913  22.424  1.00 256.23           C
ANISOU 5910  CZ  ARG A 782    39194  23004  35157  -8838  -8461   1504       C
ATOM   5911  NH1 ARG A 782     15.341  -9.008  22.353  1.00 252.93           N
ANISOU 5911  NH1 ARG A 782    39173  23004  33924  -8836  -8051   1043       N
ATOM   5912  NH2 ARG A 782     16.455 -10.639  23.524  1.00 262.66           N
ANISOU 5912  NH2 ARG A 782    40362  23716  35721  -8810  -8846   2100       N
ATOM   5913  N   PRO A 783     16.555   9.175  14.901  1.00 112.59           N
ANISOU 5913  N   PRO A 783    17804   6090  18886  -6702  -5518   -370       N
ATOM   5914  CA  PRO A 783     15.791  -9.256  13.668  1.00 109.35           C
ANISOU 5914  CA  PRO A 783    17234   5941  18373  -6357  -4770   -834       C
ATOM   5915  C   PRO A 783     16.407 -10.398  12.865  1.00 111.01           C
ANISOU 5915  C   PRO A 783    16954   5725  19497  -6144  -4488   -888       C
ATOM   5916  O   PRO A 783     17.606 -10.352  12.580  1.00 112.91           O
ANISOU 5916  O   PRO A 783    16726   5753  20421  -6173  -4704   -705       O
ATOM   5917  CB  PRO A 783     16.072  -7.893  13.016  1.00 107.39           C
ANISOU 5917  CB  PRO A 783    16818   6120  17866  -6353  -4735   -969       C
ATOM   5918  CG  PRO A 783     16.170  -6.947  14.177  1.00 108.51           C
ANISOU 5918  CG  PRO A 783    17388   6367  17475  -6698  -5297   -715       C
ATOM   5919  CD  PRO A 783     16.659  -7.782  15.365  1.00 112.19           C
ANISOU 5919  CD  PRO A 783    18002   6395  18229  -6962  -5879   -321       C
ATOM   5920  N   GLY A 784     15.625 -11.430  12.563  1.00  95.99           N
ANISOU 5920  N   GLY A 784    15167   3641  17662  -5976  -4007  -1120       N
ATOM   5921  CA  GLY A 784     16.137 -12.539  11.786  1.00  98.16           C
ANISOU 5921  CA  GLY A 784    15081   3427  18787  -5774  -3645  -1226       C
ATOM   5922  C   GLY A 784     15.185 -13.698  11.846  1.00  99.27           C
ANISOU 5922  C   GLY A 784    15518   3291  18908  -5711  -3230  -1411       C
ATOM   5923  O   GLY A 784     14.976 -14.406  10.859  1.00  99.84           O
ANISOU 5923  O   GLY A 784    15437   3202  19296  -5542  -2667  -1791       O
ATOM   5924  N   ALA A 785     14.598 -13.879  13.019  1.00 221.06           N
ANISOU 5924  N   ALA A 785    31409  18639  33944  -5899  -3492  -1157       N
```

FIG. 13 Continued

```
ATOM   5925  CA   ALA A 785      13.668 -14.967  13.235  1.00222.76           C
ANISOU 5925  CA   ALA A 785    31945  18552  34142  -5919  -3115  -1275       C
ATOM   5926  C    ALA A 785      12.653 -15.063  12.096  1.00220.68           C
ANISOU 5926  C    ALA A 785    31594  18652  33603  -5826  -2457  -1890       C
ATOM   5927  O    ALA A 785      11.726 -14.251  12.026  1.00217.50           O
ANISOU 5927  O    ALA A 785    31321  18847  32473  -5896  -2368  -2092       O
ATOM   5928  CB   ALA A 785      12.961 -14.785  14.572  1.00222.95           C
ANISOU 5928  CB   ALA A 785    32528  18642  33542  -6187  -3416   -998       C
ATOM   5929  N    LEU A 786      12.848 -16.043  11.205  1.00107.32           N
ANISOU 5929  N    LEU A 786    17034   3866  19858  -5684  -2000  -2169       N
ATOM   5930  CA   LEU A 786      11.925 -16.314  10.095  1.00106.55           C
ANISOU 5930  CA   LEU A 786    16883   4039  19562  -5677  -1401  -2773       C
ATOM   5931  C    LEU A 786      11.485 -15.027   9.381  1.00101.99           C
ANISOU 5931  C    LEU A 786    16151   4274  18328  -5649  -1370  -3031       C
ATOM   5932  O    LEU A 786      10.544 -15.040   8.582  1.00101.05           O
ANISOU 5932  O    LEU A 786    16022   4481  17891  -5699   -980  -3468       O
ATOM   5933  CB   LEU A 786      10.685 -17.101  10.584  1.00108.33           C
ANISOU 5933  CB   LEU A 786    17478   4129  19554  -5898  -1139  -2892       C
ATOM   5934  CG   LEU A 786      10.733 -18.490  11.271  1.00113.52           C
ANISOU 5934  CG   LEU A 786    18423   3939  20769  -5981  -1017  -2680       C
ATOM   5935  CD1  LEU A 786      10.258 -19.664  10.368  1.00117.15           C
ANISOU 5935  CD1  LEU A 786    18899   3987  21627  -6035   -370  -3194       C
ATOM   5936  CD2  LEU A 786      12.091 -18.794  11.930  1.00116.18           C
ANISOU 5936  CD2  LEU A 786    18729   3639  21774  -5814  -1415  -2101       C
ATOM   5937  N    LEU A 787      12.161 -13.921   9.684  1.00124.82           N
ANISOU 5937  N    LEU A 787    18939   7444  21041  -5599  -1794  -2737       N
ATOM   5938  CA   LEU A 787      11.820 -12.626   9.108  1.00120.99           C
ANISOU 5938  CA   LEU A 787    18372   7628  19972  -5558  -1773  -2889       C
ATOM   5939  C    LEU A 787      12.749 -12.246   7.965  1.00120.52           C
ANISOU 5939  C    LEU A 787    17929   7614  20248  -5407  -1640  -3050       C
ATOM   5940  O    LEU A 787      12.300 -11.802   6.905  1.00118.72           O
ANISOU 5940  O    LEU A 787    17612   7765  19732  -5356  -1315  -3397       O
ATOM   5941  CB   LEU A 787      11.883 -11.536  10.172  1.00119.30           C
ANISOU 5941  CB   LEU A 787    18380   7670  19280  -5655  -2267  -2501       C
ATOM   5942  CG   LEU A 787      11.375 -10.203   9.614  1.00115.82           C
ANISOU 5942  CG   LEU A 787    17933   7831  18240  -5604  -2168  -2645       C
ATOM   5943  CD1  LEU A 787       9.846 -10.258   9.524  1.00114.58           C
ANISOU 5943  CD1  LEU A 787    17975   7973  17587  -5657  -1827  -2894       C
ATOM   5944  CD2  LEU A 787      11.868  -8.964  10.406  1.00114.85           C
ANISOU 5944  CD2  LEU A 787    17975   7869  17796  -5691  -2636  -2300       C
ATOM   5945  N    MET A 788      14.050 -12.395   8.209  1.00161.51           N
ANISOU 5945  N    MET A 788    22897  12399  26070  -5368  -1906  -2766       N
ATOM   5946  CA   MET A 788      15.062 -12.114   7.204  1.00161.80           C
ANISOU 5946  CA   MET A 788    22540  12371  26564  -5261  -1747  -2881       C
ATOM   5947  C    MET A 788      14.596 -12.743   5.910  1.00162.31           C
ANISOU 5947  C    MET A 788    22567  12415  26690  -5177  -1109  -3438       C
ATOM   5948  O    MET A 788      14.542 -12.104   4.862  1.00160.64           O
ANISOU 5948  O    MET A 788    22250  12552  26235  -5145   -850  -3723       O
ATOM   5949  CB   MET A 788      16.394 -12.755   7.610  1.00165.41           C
ANISOU 5949  CB   MET A 788    22722  12163  27962  -5236  -1974  -2533       C
ATOM   5950  CG   MET A 788      17.292 -11.898   8.485  1.00165.55           C
ANISOU 5950  CG   MET A 788    22595  12232  28075   5385   2632   2018       C
ATOM   5951  SD   MET A 788      18.475 -10.911   7.542  1.00165.31           S
ANISOU 5951  SD   MET A 788    22038  12349  28422  -5405  -2583  -2025       S
ATOM   5952  CE   MET A 788      17.416  -9.694   6.758  1.00160.72           C
ANISOU 5952  CE   MET A 788    21719  12549  26799  -5381  -2291  -2418       C
ATOM   5953  N    ILE A 789      14.222  14.008   6.028  1.00170.37           N
ANISOU 5953  N    ILE A 789    23733  12991  28008  -5183   -866  -3589       N
ATOM   5954  CA   ILE A 789      13.805 -14.839   4.912  1.00172.31           C
ANISOU 5954  CA   ILE A 789    24015  13072  28383  -5173   -270  -4152       C
ATOM   5955  C    ILE A 789      12.710 -14.252   4.019  1.00169.77           C
ANISOU 5955  C    ILE A 789    23784  13414  27307  -5269    -32  -4577       C
ATOM   5956  O    ILE A 789      12.832 -14.280   2.797  1.00170.43           O
ANISOU 5956  O    ILE A 789    23792  13547  27418  -5256    347  -5001       O
ATOM   5957  CB   ILE A 789      13.364 -16.217   5.436  1.00176.08           C
ANISOU 5957  CB   ILE A 789    24737  12972  29192  -5237   -102  -4198       C
ATOM   5958  CG1  ILE A 789      14.384 -16.723   6.465  1.00178.75           C
ANISOU 5958  CG1  ILE A 789    25027  12637  30253  -5133   -424  -3647       C
ATOM   5959  CG2  ILE A 789      13.152 -17.200   4.291  1.00179.52           C
```

FIG. 13 Continued

```
ANISOU 5959  CG2 ILE A 789     25241  13064  29906  -5257    531  -4808       C
ATOM   5960  CD1 ILE A 789      15.842 -16.416   6.121  1.00179.58           C
ANISOU 5960  CD1 ILE A 789     24742  12454  31036  -4952   -500  -3438       C
ATOM   5961  N   ALA A 790      11.648 -13.718   4.611  1.00115.04           N
ANISOU 5961  N   ALA A 790     17030   6954  19726  -5373   -243  -4458       N
ATOM   5962  CA  ALA A 790      10.546 -13.191   3.800  1.00113.16           C
ANISOU 5962  CA  ALA A 790     16846   7293  18858  -5464    -46  -4803       C
ATOM   5963  C   ALA A 790      10.640 -11.711   3.372  1.00109.51           C
ANISOU 5963  C   ALA A 790     16297   7376  17935  -5377   -191  -4665       C
ATOM   5964  O   ALA A 790       9.649 -11.108   2.970  1.00107.74           O
ANISOU 5964  O   ALA A 790     16141   7627  17168  -5434   -137  -4826       O
ATOM   5965  CB  ALA A 790       9.181 -13.527   4.422  1.00113.32           C
ANISOU 5965  CB  ALA A 790     17075   7467  18514  -5648    -49  -4842       C
ATOM   5966  N   PHE A 791      11.823 -11.128   3.485  1.00130.69           N
ANISOU 5966  N   PHE A 791     18826   9943  20887  -5262   -380  -4409       N
ATOM   5967  CA  PHE A 791      12.079  -9.821   2.877  1.00128.19           C
ANISOU 5967  CA  PHE A 791     18437  10016  20251  -5214   -419  -4356       C
ATOM   5968  C   PHE A 791      13.515  -9.783   2.363  1.00129.57           C
ANISOU 5968  C   PHE A 791     18351   9871  21007  -5157   -340  -4333       C
ATOM   5969  O   PHE A 791      14.248  -8.795   2.496  1.00128.44           O
ANISOU 5969  O   PHE A 791     18095   9817  20889  -5153   -553  -4052       O
ATOM   5970  CB  PHE A 791      11.641  -8.610   3.720  1.00125.32           C
ANISOU 5970  CB  PHE A 791     18235  10014  19368  -5215   -775  -3984       C
ATOM   5971  CG  PHE A 791      10.437  -7.880   3.134  1.00123.23           C
ANISOU 5971  CG  PHE A 791     18106  10238  18478  -5231   -632  -4157       C
ATOM   5972  CD1 PHE A 791       9.212  -8.531   2.978  1.00123.83           C
ANISOU 5972  CD1 PHE A 791     18259  10448  18343  -5316   -454  -4432       C
ATOM   5973  CD2 PHE A 791      10.533  -6.563   2.709  1.00121.22           C
ANISOU 5973  CD2 PHE A 791     17888  10263  17907  -5191   -677  -4050       C
ATOM   5974  CE1 PHE A 791       8.110  -7.874   2.426  1.00122.44           C
ANISOU 5974  CE1 PHE A 791     18142  10699  17679  -5347   -373  -4581       C
ATOM   5975  CE2 PHE A 791       9.432  -5.912   2.166  1.00119.71           C
ANISOU 5975  CE2 PHE A 791     17813  10455  17218  -5195   -572  -4183       C
ATOM   5976  CZ  PHE A 791       8.222  -6.572   2.022  1.00120.32           C
ANISOU 5976  CZ  PHE A 791     17914  10685  17118  -5266   -442  -4445       C
ATOM   5977  N   LEU A 792      13.842 -10.928   1.759  1.00 88.85           N
ANISOU 5977  N   LEU A 792     13120   4294  16347  -5145     20  -4667       N
ATOM   5978  CA  LEU A 792      15.089 -11.278   1.101  1.00 91.34           C
ANISOU 5978  CA  LEU A 792     13198   4149  17358  -5088    289  -4777       C
ATOM   5979  C   LEU A 792      14.589 -12.436   0.259  1.00 94.22           C
ANISOU 5979  C   LEU A 792     13728   4270  17801  -5116    789  -5348       C
ATOM   5980  O   LEU A 792      15.294 -13.417   0.005  1.00 97.90           O
ANISOU 5980  O   LEU A 792     14136   4101  18959  -5045   1107  -5522       O
ATOM   5981  CB  LEU A 792      16.139 -11.751   2.098  1.00 93.40           C
ANISOU 5981  CB  LEU A 792     13236   3856  18395  -5029      7  -4348       C
ATOM   5982  CG  LEU A 792      17.160 -10.732   2.634  1.00 92.52           C
ANISOU 5982  CG  LEU A 792     12844   3802  18508  -5071   -417  -3854       C
ATOM   5983  CD1 LEU A 792      18.242 -10.491   1.593  1.00 94.05           C
ANISOU 5983  CD1 LEU A 792     12725   3774  19236  -5072    -53  -3976       C
ATOM   5984  CD2 LEU A 792      16.576  -9.387   3.150  1.00 88.93           C
ANISOU 5984  CD2 LEU A 792     12564   3971  17254  -5157   -817  -3614       C
ATOM   5985  N   ILE A 793      13.305 -12.317  -0.078  1.00 91.66           N
ANISOU 5985  N   ILE A 793     13628   4421  16779  -5234    835  -5617       N
ATOM   5986  CA  ILE A 793      12.568 -13.211  -0.974  1.00 94.53           C
ANISOU 5986  CA  ILE A 793     14190   4728  16999  -5370   1242  -6224       C
ATOM   5987  C   ILE A 793      11.728 -12.234  -1.782  1.00 92.16           C
ANISOU 5987  C   ILE A 793     13980   5119  15916  -5472   1213  -6402       C
ATOM   5988  O   ILE A 793      11.651 -12.319  -3.006  1.00 93.97           O
ANISOU 5988  O   ILE A 793     14326   5432  15946  -5564   1532  -6888       O
ATOM   5989  CB  ILE A 793      11.663 -14.248  -0.238  1.00 96.43           C
ANISOU 5989  CB  ILE A 793     14584   4781  17275  -5493   1208  -6283       C
ATOM   5990  CG1 ILE A 793      12.413 -15.569  -0.050  1.00100.97           C
ANISOU 5990  CG1 ILE A 793     15190   4509  18663  -5429   1485  -6387       C
ATOM   5991  CG2 ILE A 793      10.347 -14.483  -0.985  1.00 97.59           C
ANISOU 5991  CG2 ILE A 793     14909   5303  16866  -5746   1377  -6786       C
ATOM   5992  CD1 ILE A 793      13.468 -15.816  -1.079  1.00103.66           C
ANISOU 5992  CD1 ILE A 793     15486   4432  19470  -5311   1923  -6710       C
ATOM   5993  N   ALA A 794      11.124 -11.279  -1.083  1.00105.35           N
ANISOU 5993  N   ALA A 794     15637   7244  17149  -5447    830  -6001       N
```

FIG. 13 Continued

```
ATOM   5994  CA  ALA A 794      10.416 -10.193  -1.740  1.00103.04           C
ANISOU 5994  CA  ALA A 794    15416   7536  16200  -5489    761  -6051       C
ATOM   5995  C   ALA A 794      11.468  -9.147  -2.067  1.00101.35           C
ANISOU 5995  C   ALA A 794    15120   7336  16051  -5380    741  -5821       C
ATOM   5996  O   ALA A 794      11.210  -7.947  -2.086  1.00 98.66           O
ANISOU 5996  O   ALA A 794    14828   7358  15300  -5351    557  -5582       O
ATOM   5997  CB  ALA A 794       9.348  -9.622  -0.847  1.00100.46           C
ANISOU 5997  CB  ALA A 794    15136   7567  15465  -5491    439  -5737       C
ATOM   5998  N   GLN A 795      12.677  -9.631  -2.284  1.00 90.65           N
ANISOU 5998  N   GLN A 795    13640   5511  15294  -5333    956  -5887       N
ATOM   5999  CA  GLN A 795      13.759  -8.780  -2.695  1.00 90.00           C
ANISOU 5999  CA  GLN A 795    13440   5358  15399  -5296   1019  -5729       C
ATOM   6000  C   GLN A 795      14.389  -9.481  -3.864  1.00 93.44           C
ANISOU 6000  C   GLN A 795    13016   5437  16151  -5328   1542  -6237       C
ATOM   6001  O   GLN A 795      15.151  -8.907  -4.644  1.00 93.82           O
ANISOU 6001  O   GLN A 795    13950   5414  16285  -5349   1781  -6305       O
ATOM   6002  CB  GLN A 795      14.761  -8.596  -1.579  1.00 89.60           C
ANISOU 6002  CB  GLN A 795    13128   5006  15910  -5220    722  -5212       C
ATOM   6003  CG  GLN A 795      15.466  -7.254  -1.677  1.00 88.01           C
ANISOU 6003  CG  GLN A 795    12825   4949  15667  -5261    595  -4894       C
ATOM   6004  CD  GLN A 795      14.493   6.079   1.611  1.00 84.89           C
ANISOU 6004  CD  GLN A 795    12675   5090  14491  -5279    374  -4748       C
ATOM   6005  OE1 GLN A 795      14.912  -4.911  -1.690  1.00 83.81           O
ANISOU 6005  OE1 GLN A 795    12542   5057  14245  -5335    283  -4501       O
ATOM   6006  NE2 GLN A 795      13.189  -6.379  -1.451  1.00 83.91           N
ANISOU 6006  NE2 GLN A 795    12747   5249  13886  -5253    306  -4885       N
ATOM   6007  N   LEU A 796      14.089 -10.761  -3.953  1.00127.72           N
ANISOU 6007  N   LEU A 796    18351   9480  20698  -5344   1766  -6612       N
ATOM   6008  CA  LEU A 796      14.451 -11.499  -5.126  1.00131.76           C
ANISOU 6008  CA  LEU A 796    19041   9654  21369  -5374   2323  -7225       C
ATOM   6009  C   LEU A 796      13.310 -11.160  -6.041  1.00131.64           C
ANISOU 6009  C   LEU A 796    19317  10229  20470  -5546   2328  -7622       C
ATOM   6010  O   LEU A 796      13.436 -10.305  -6.913  1.00130.94           O
ANISOU 6010  O   LEU A 796    19359  10421  19972  -5576   2421  -7731       O
ATOM   6011  CB  LEU A 796      14.514 -12.996  -4.841  1.00135.82           C
ANISOU 6011  CB  LEU A 796    19606   9561  22438  -5339   2570  -7489       C
ATOM   6012  CG  LEU A 796      15.960 -13.496  -4.771  1.00138.56           C
ANISOU 6012  CG  LEU A 796    19774   9113  23761  -5129   2900  -7406       C
ATOM   6013  CD1 LEU A 796      16.287 -14.418  -5.952  1.00144.07           C
ANISOU 6013  CD1 LEU A 796    20783   9294  24661  -5070   3628  -8141       C
ATOM   6014  CD2 LEU A 796      16.966 -12.315  -4.664  1.00135.88           C
ANISOU 6014  CD2 LEU A 796    19119   8850  23657  -5072   2744  -6926       C
ATOM   6015  N   ILE A 797      12.168 -11.779  -5.779  1.00117.61           N
ANISOU 6015  N   ILE A 797    17632   8642  18412  -5678   2185  -7790       N
ATOM   6016  CA  ILE A 797      10.989 -11.556  -6.597  1.00118.31           C
ANISOU 6016  CA  ILE A 797    17936   9296  17721  -5881   2116  -8165       C
ATOM   6017  C   ILE A 797      10.802 -10.072  -6.974  1.00114.78           C
ANISOU 6017  C   ILE A 797    17506   9400  16704  -5840   1874  -7897       C
ATOM   6018  O   ILE A 797      10.311  -9.760  -8.055  1.00116.29           O
ANISOU 6018  O   ILE A 797    17930   9966  16289  -5956   1924  -8276       O
ATOM   6019  CB  ILE A 797       9.704 -12.168  -5.951  1.00118.84           C
ANISOU 6019  CB  ILE A 797    17977   9540  17638  -6051   1874  -8193       C
ATOM   6020  CG1 ILE A 797       8.690 -12.556  -7.035  1.00122.72           C
ANISOU 6020  CG1 ILE A 797    18697  10374  17558  -6351   1950  -8850       C
ATOM   6021  CG2 ILE A 797       9.103 -11.227  -4.892  1.00113.99           C
ANISOU 6021  CG2 ILE A 797    17177   9308  16828  -5951   1409  -7563       C
ATOM   6022  CD1 ILE A 797       7.438 -13.207  -6.510  1.00124.18           C
ANISOU 6022  CD1 ILE A 797    18829  10693  17662  -6595   1761  -8958       C
ATOM   6023  N   ALA A 798      11.212  -9.153  -6.113  1.00114.25           N
ANISOU 6023  N   ALA A 798    17242   9359  16807  -5683   1609  -7270       N
ATOM   6024  CA  ALA A 798      11.026  -7.747  -6.448  1.00111.42           C
ANISOU 6024  CA  ALA A 798    16959   9420  15954  -5655   1419  -7022       C
ATOM   6025  C   ALA A 798      12.204  -7.189  -7.232  1.00111.93           C
ANISOU 6025  C   ALA A 798    17105   9273  16151  -5629   1714  -7076       C
ATOM   6026  O   ALA A 798      12.368  -5.964  -7.331  1.00109.60           O
ANISOU 6026  O   ALA A 798    16862   9155  15628  -5608   1587  -6765       O
ATOM   6027  CB  ALA A 798      10.750  -6.927  -5.204  1.00107.49           C
ANISOU 6027  CB  ALA A 798    16310   9060  15470  -5540   1014  -6388       C
ATOM   6028  N   THR A 799      13.020  -8.094  -7.776  1.00 95.72           N
```

FIG. 13 Continued

```
ANISOU 6028  N   THR A 799    15093   6772  14504  -5635   2156  -7484       N
ATOM   6029  CA  THR A 799    14.166  -7.711  -8.604  1.00 97.09             C
ANISOU 6029  CA  THR A 799    15368   6652  14869  -5612   2566  -7627       C
ATOM   6030  C   THR A 799    14.255  -8.618  -9.844  1.00102.84             C
ANISOU 6030  C   THR A 799    16390   7317  15367  -5578   3137  -8330       C
ATOM   6031  O   THR A 799    14.586  -8.157 -10.935  1.00106.31             O
ANISOU 6031  O   THR A 799    16960   8094  15342  -5453   3533  -8380       O
ATOM   6032  CB  THR A 799    15.505  -7.608  -7.803  1.00 96.33             C
ANISOU 6032  CB  THR A 799    14882   6014  15704  -5534   2613  -7153       C
ATOM   6033  OG1 THR A 799    15.374  -6.633  -6.761  1.00 92.45             O
ANISOU 6033  OG1 THR A 799    14163   5774  15188  -5536   2103  -6485       O
ATOM   6034  CG2 THR A 799    16.629  -7.159  -8.706  1.00100.65             C
ANISOU 6034  CG2 THR A 799    15256   6661  16324  -5328   3188  -6965       C
ATOM   6035  N   LEU A 800    13.929  -9.898  -9.676  1.00126.52             N
ANISOU 6035  N   LEU A 800    19470   9990  18613  -5647   3230  -8770       N
ATOM   6036  CA  LEU A 800    13.797 -10.825 -10.805  1.00132.73             C
ANISOU 6036  CA  LEU A 800    20621  10737  19074  -5666   3737  -9523       C
ATOM   6037  C   LEU A 800    12.755 -10.222 -11.736  1.00133.23             C
ANISOU 6037  C   LEU A 800    21031  11544  18047  -5837   3525  -9832       C
ATOM   6038  O   LEU A 800    12.589 -10.650 -12.885  1.00139.04             O
ANISOU 6038  O   LEU A 800    22115  12504  18210  -5867   3892 -10398       O
ATOM   6039  CB  LEU A 800    13.242 -12.173 -10.334  1.00135.17             C
ANISOU 6039  CB  LEU A 800    20952  10712  19693  -5798   3725  -9844       C
ATOM   6040  CG  LEU A 800    14.064 -13.211  -9.575  1.00136.94             C
ANISOU 6040  CG  LEU A 800    20984  10109  20938  -5632   3999  -9755       C
ATOM   6041  CD1 LEU A 800    13.248 -13.788  -8.413  1.00135.61             C
ANISOU 6041  CD1 LEU A 800    20600   9954  20970  -5748   3574  -9450       C
ATOM   6042  CD2 LEU A 800    14.546 -14.323 -10.518  1.00144.21             C
ANISOU 6042  CD2 LEU A 800    22271  10499  22024  -5541   4749 -10505       C
ATOM   6043  N   ILE A 801    12.014  -9.261 -11.184  1.00137.78             N
ANISOU 6043  N   ILE A 801    21449  12574  18328  -5905   2936  -9353       N
ATOM   6044  CA  ILE A 801    10.952  -8.552 -11.881  1.00137.92             C
ANISOU 6044  CA  ILE A 801    21693  13324  17388  -6011   2615  -9475       C
ATOM   6045  C   ILE A 801    11.457  -7.164 -12.167  1.00135.77             C
ANISOU 6045  C   ILE A 801    21441  13292  16854  -5824   2622  -8992       C
ATOM   6046  O   ILE A 801    11.141  -6.578 -13.194  1.00138.71             O
ANISOU 6046  O   ILE A 801    22059  14230  16414  -5761   2680  -9048       O
ATOM   6047  CB  ILE A 801     9.667  -8.441 -11.014  1.00135.29             C
ANISOU 6047  CB  ILE A 801    21075  13369  16960  -6114   2032  -9127       C
ATOM   6048  CG1 ILE A 801     8.463  -8.028 -11.866  1.00137.33             C
ANISOU 6048  CG1 ILE A 801    21541  14356  16283  -6246   1713  -9407       C
ATOM   6049  CG2 ILE A 801     9.871  -7.474  -9.852  1.00129.44             C
ANISOU 6049  CG2 ILE A 801    20024  12563  16594  -5948   1731  -8330       C
ATOM   6050  CD1 ILE A 801     7.136  -8.294 -11.198  1.00136.82             C
ANISOU 6050  CD1 ILE A 801    21203  14594  16168  -6394   1272  -9301       C
ATOM   6051  N   ALA A 802    12.262  -6.647 -11.247  1.00180.89             N
ANISOU 6051  N   ALA A 802    26844  18631  23254  -5721   2583  -8401       N
ATOM   6052  CA  ALA A 802    12.796  -5.305 -11.378  1.00179.64             C
ANISOU 6052  CA  ALA A 802    26620  18668  22968  -5568   2621  -7797       C
ATOM   6053  C   ALA A 802    13.885  -5.250 -12.430  1.00185.20             C
ANISOU 6053  C   ALA A 802    27358  19398  23612  -5376   3324  -7773       C
ATOM   6054  O   ALA A 802    14.589  -4.246 -12.526  1.00185.13             O
ANISOU 6054  O   ALA A 802    27240  19432  23669  -5271   3485  -7244       O
ATOM   6055  CB  ALA A 802    13.323  -4.820 -10.060  1.00174.71             C
ANISOU 6055  CB  ALA A 802    25668  17630  23084  -5598   2337  -7237       C
ATOM   6056  N   VAL A 803    14.033  -6.341 -13.186  1.00126.06             N
ANISOU 6056  N   VAL A 803    20032  11841  16025  -5350   3781  -8354       N
ATOM   6057  CA  VAL A 803    14.979  -6.435 -14.303  1.00132.63             C
ANISOU 6057  CA  VAL A 803    20967  12720  16706  -5153   4557  -8446       C
ATOM   6058  C   VAL A 803    15.049  -7.857 -14.797  1.00138.03             C
ANISOU 6058  C   VAL A 803    21840  13145  17460  -5154   5004  -9169       C
ATOM   6059  O   VAL A 803    14.169  -8.655 -14.488  1.00137.09             O
ANISOU 6059  O   VAL A 803    21863  12941  17285  -5360   4661  -9641       O
ATOM   6060  CB  VAL A 803    16.388  -6.015 -13.923  1.00132.79             C
ANISOU 6060  CB  VAL A 803    20538  12373  17543  -4985   4936  -7861       C
ATOM   6061  CG1 VAL A 803    16.595  -4.539 -14.200  1.00131.87             C
ANISOU 6061  CG1 VAL A 803    20431  12606  17068  -4953   4908  -7263       C
ATOM   6062  CG2 VAL A 803    16.677  -6.375 -12.471  1.00128.06             C
ANISOU 6062  CG2 VAL A 803    19491  11230  17934  -5050   4545  -7598       C
```

FIG. 13 Continued

```
ATOM   6063  N   TYR A 804      16.102  -8.161 -15.555  1.00178.10           N
ANISOU 6063  N   TYR A 804    26923  18064  22685   -4932   5811  -9254      N
ATOM   6064  CA  TYR A 804      16.328  9.494  16.122  1.00184.68           C
ANISOU 6064  CA  TYR A 804    27993  18569  23609   -4875   6406  -9956      C
ATOM   6065  C   TYR A 804      15.077 -10.138 -16.745  1.00187.31           C
ANISOU 6065  C   TYR A 804    28892  19213  23063   -5154   6167 -10755      C
ATOM   6066  O   TYR A 804      15.173 -11.105 -17.507  1.00194.30           O
ANISOU 6066  O   TYR A 804    30148  19939  23738   -5156   6709 -11436      O
ATOM   6067  CB  TYR A 804      16.962 -10.435 -15.091  1.00183.69           C
ANISOU 6067  CB  TYR A 804    27453  17659  24684   -4770   6502  -9893      C
ATOM   6068  CG  TYR A 804      16.632 -11.901 -15.327  1.00188.57           C
ANISOU 6068  CG  TYR A 804    28412  17858  25377   -4835   6794 -10695      C
ATOM   6069  CD1 TYR A 804      17.537 -12.752 -15.956  1.00196.44           C
ANISOU 6069  CD1 TYR A 804    29493  18431  26715   -4557   7706 -11034      C
ATOM   6070  CD2 TYR A 804      15.406 -12.434 -14.926  1.00185.98           C
ANISOU 6070  CD2 TYR A 804    28331  17531  24801   -5186   6202 -11124      C
ATOM   6071  CE1 TYR A 804      17.228 -14.099 -16.174  1.00201.62           C
ANISOU 6071  CE1 TYR A 804    30537  18616  27454   -4629   8017 -11804      C
ATOM   6072  CE2 TYR A 804      15.091 -13.772 -15.139  1.00191.06           C
ANISOU 6072  CE2 TYR A 804    29323  17736  25536   -5312   6482 -11877      C
ATOM   6073  CZ  TYR A 804      16.002 -14.600 -15.762  1.00198.87           C
ANISOU 6073  CZ  TYR A 804    30457  18251  26854   -5035   7387 -12227      C
ATOM   6074  OH  TYR A 804      15.681 -15.926 -15.968  1.00204.53           O
ANISOU 6074  OH  TYR A 804    31586  18450  27675   -5173   7700 -13004      O
ATOM   6075  N   ALA A 805      13.909  -9.596 -16.425  1.00223.26           N
ANISOU 6075  N   ALA A 805    33505  24212  27113   -5400   5367 -10681      N
ATOM   6076  CA  ALA A 805      12.649 -10.119 -16.929  1.00225.79           C
ANISOU 6076  CA  ALA A 805    34242  24913  26635   -5721   5010 -11374      C
ATOM   6077  C   ALA A 805      11.526  -9.122 -16.670  1.00220.73           C
ANISOU 6077  C   ALA A 805    33539  24906  25422   -5866   4181 -11047      C
ATOM   6078  O   ALA A 805      11.764  -8.021 -16.164  1.00215.61           O
ANISOU 6078  O   ALA A 805    32614  24349  24958   -5701   3960 -10318      O
ATOM   6079  CB  ALA A 805      12.332 -11.470 -16.293  1.00226.15           C
ANISOU 6079  CB  ALA A 805    34285  24352  27292   -5944   4959 -11912      C
ATOM   6080  N   ASN A 806      10.308  -9.524 -17.031  1.00278.54           N
ANISOU 6080  N   ASN A 806    41112  32650  32071   -6181   3745 -11602      N
ATOM   6081  CA  ASN A 806       9.116  -8.691 -16.899  1.00275.34           C
ANISOU 6081  CA  ASN A 806    40625  32911  31079   -6296   2970 -11364      C
ATOM   6082  C   ASN A 806       7.925  -9.338 -17.605  1.00280.86           C
ANISOU 6082  C   ASN A 806    41612  34131  30970   -6672   2619 -12117      C
ATOM   6083  O   ASN A 806       7.966  -9.558 -18.817  1.00288.37           O
ANISOU 6083  O   ASN A 806    42998  35460  31108   -6714   2899 -12570      O
ATOM   6084  CB  ASN A 806       9.387  -7.302 -17.477  1.00275.27           C
ANISOU 6084  CB  ASN A 806    40679  33423  30487   -5987   2999 -10731      C
ATOM   6085  CG  ASN A 806      10.369  -7.334 -18.641  1.00282.08           C
ANISOU 6085  CG  ASN A 806    41895  34338  30943    5794   3774  10854      C
ATOM   6086  OD1 ASN A 806      11.424  -6.697 -18.597  1.00280.99           O
ANISOU 6086  OD1 ASN A 806    41629  33970  31165   -5516   4221 -10304      O
ATOM   6087  ND2 ASN A 806      10.030  -8.086 -19.681  1.00289.76           N
ANISOU 6087  ND2 ASN A 806    43319  35614  31162   -5971   3956 -11595      N
ATOM   6088  N   TRP A 807       6.868  -9.650 -16.857  1.00290.14           N
ANISOU 6088  N   TRP A 807    42501  35366  32373   -6959   2031 -12189      N
ATOM   6089  CA  TRP A 807       5.707 -10.314 -17.463  1.00296.71           C
ANISOU 6089  CA  TRP A 807    43434  36725  32576   -7368   1683 -12788      C
ATOM   6090  C   TRP A 807       4.542  -9.409 -17.891  1.00297.49           C
ANISOU 6090  C   TRP A 807    43456  37805  31774   -7403    963 -12624      C
ATOM   6091  O   TRP A 807       3.708  -9.830 -18.703  1.00304.50           O
ANISOU 6091  O   TRP A 807    44518  39277  31899   -7734    667 -13193      O
ATOM   6092  CB  TRP A 807       5.231 -11.537 -16.652  1.00297.75           C
ANISOU 6092  CB  TRP A 807    43258  36385  33487   -7710   1660 -13005      C
ATOM   6093  CG  TRP A 807       5.000 -11.320 -15.181  1.00290.52           C
ANISOU 6093  CG  TRP A 807    41755  35172  33458   -7596   1414 -12275      C
ATOM   6094  CD1 TRP A 807       5.468 -10.293 -14.411  1.00283.10           C
ANISOU 6094  CD1 TRP A 807    40560  34113  32891   -7220   1336 -11487      C
ATOM   6095  CD2 TRP A 807       4.278 -12.188 -14.298  1.00290.83           C
ANISOU 6095  CD2 TRP A 807    41458  34971  34073   -7872   1271 -12302      C
ATOM   6096  NE1 TRP A 807       5.060 -10.457 -13.108  1.00278.93           N
ANISOU 6096  NE1 TRP A 807    39577  33336  33068   -7224   1139 -11022      N
ATOM   6097  CE2 TRP A 807       4.330 -11.613 -13.013  1.00283.43           C
```

FIG. 13 Continued

```
ANISOU 6097  CE2 TRP A 807    40089  33834  33769  -7601   1115 -11494       C
ATOM   6098  CE3 TRP A 807       3.584 -13.390 -14.473  1.00297.18           C
ANISOU 6098  CE3 TRP A 807    42328  35704  34882  -8347   1279 -12955       C
ATOM   6099  CZ2 TRP A 807       3.715 -12.199 -11.909  1.00282.14           C
ANISOU 6099  CZ2 TRP A 807    39579  33440  34181  -7740    997 -11300       C
ATOM   6100  CZ3 TRP A 807       2.974 -13.971 -13.376  1.00295.74           C
ANISOU 6100  CZ3 TRP A 807    41773  35252  35342  -8517   1162 -12758       C
ATOM   6101  CH2 TRP A 807       3.043 -13.375 -12.110  1.00288.23           C
ANISOU 6101  CH2 TRP A 807    40413  34141  34960  -8191   1035 -11926       C
ATOM   6102  N   GLU A 808       4.479  -8.185 -17.359  1.00222.92           N
ANISOU 6102  N   GLU A 808    33763  28535  22401  -7074    668 -11877       N
ATOM   6103  CA  GLU A 808       3.443  -7.239 -17.799  1.00224.06           C
ANISOU 6103  CA  GLU A 808    33855  29592  21684  -7001     22 -11664       C
ATOM   6104  C   GLU A 808       3.939  -6.374 -18.962  1.00228.46           C
ANISOU 6104  C   GLU A 808    34785  30652  21370  -6649    255 -11352       C
ATOM   6105  O   GLU A 808       5.096  -5.948 -18.992  1.00226.54           O
ANISOU 6105  O   GLU A 808    34686  29992  21397  -6342    826 -10962       O
ATOM   6106  CB  GLU A 808       2.906  -6.369 -16.651  1.00216.89           C
ANISOU 6106  CB  GLU A 808    32444  28662  21300  -6796   -397 -10928       C
ATOM   6107  CG  GLU A 808       2.024  -5.174 -17.094  1.00218.30           C
ANISOU 6107  CG  GLU A 808    32540  29713  20692  -6532   -944 -10479       C
ATOM   6108  CD  GLU A 808       0.666  -5.573 -17.694  1.00224.90           C
ANISOU 6108  CD  GLU A 808    33235  31399  20818  -6851  -1571 -10955       C
ATOM   6109  OE1 GLU A 808       0.380  -6.783 -17.811  1.00228.89           O
ANISOU 6109  OE1 GLU A 808    33725  31816  21427  -7332  -1559 -11654       O
ATOM   6110  OE2 GLU A 808      -0.122  -4.667 -18.048  1.00227.18           O
ANISOU 6110  OE2 GLU A 808    33364  32442  20511  -6598  -2050 -10537       O
ATOM   6111  N   PHE A 809       3.048  -6.143 -19.922  1.00205.53           N
ANISOU 6111  N   PHE A 809    32017  28663  17411  -6716   -198 -11515       N
ATOM   6112  CA  PHE A 809       3.358  -5.373 -21.116  1.00211.21           C
ANISOU 6112  CA  PHE A 809    33149  29964  17136  -6411    -38 -11234       C
ATOM   6113  C   PHE A 809       3.009  -3.894 -20.899  1.00207.96           C
ANISOU 6113  C   PHE A 809    32520  29927  16567  -5944   -392 -10279       C
ATOM   6114  O   PHE A 809       3.245  -3.056 -21.770  1.00212.06           O
ANISOU 6114  O   PHE A 809    33362  30894  16326  -5618   -276  -9851       O
ATOM   6115  CB  PHE A 809       2.673  -6.011 -22.330  1.00221.54           C
ANISOU 6115  CB  PHE A 809    34808  32049  17320  -6753   -317 -11967       C
ATOM   6116  CG  PHE A 809       2.812  -7.525 -22.372  1.00224.80           C
ANISOU 6116  CG  PHE A 809    35411  32003  17998  -7283    -37 -12979       C
ATOM   6117  CD1 PHE A 809       4.031  -8.118 -22.676  1.00226.44           C
ANISOU 6117  CD1 PHE A 809    36041  31554  18443  -7247    838 -13303       C
ATOM   6118  CD2 PHE A 809       1.728  -8.349 -22.089  1.00226.75           C
ANISOU 6118  CD2 PHE A 809    35403  32437  18315  -7810   -606 -13587       C
ATOM   6119  CE1 PHE A 809       4.162  -9.498 -22.705  1.00230.03           C
ANISOU 6119  CE1 PHE A 809    36713  31503  19184  -7683   1149 -14215       C
ATOM   6120  CE2 PHE A 809       1.856  -9.731 -22.118  1.00230.30           C
ANISOU 6120  CE2 PHE A 809    36083  32377  19043  -8314   -310 -14511       C
ATOM   6121  CZ  PHE A 809       3.073 -10.303 -22.426  1.00231.94           C
ANISOU 6121  CZ  PHE A 809    36766  31887  19475  -8229    573 -14825       C
ATOM   6122  N   ALA A 810       2.428  -3.606 -19.728  1.00136.59           N
ANISOU 6122  N   ALA A 810    22975  20675   8248  -5915   -787  -9957       N
ATOM   6123  CA  ALA A 810       2.223  -2.243 -19.232  1.00132.29           C
ANISOU 6123  CA  ALA A 810    22221  20204   7838  -5458   -997  -9055       C
ATOM   6124  C   ALA A 810       3.504  -1.986 -18.466  1.00125.52           C
ANISOU 6124  C   ALA A 810    21401  18414   7877  -5314   -383  -8696       C
ATOM   6125  O   ALA A 810       3.538   1.220  17.505  1.00119.35           O
ANISOU 6125  O   ALA A 810    20385  17270   7692  -5106   -456  -8128       O
ATOM   6126  CB  ALA A 810       1.021  -2.148 -18.306  1.00128.94           C
ANISOU 6126  CB  ALA A 810    21258  19947   7786  -5519  -1630  -8960       C
ATOM   6127  N   LYS A 811       4.537  -2.703 -18.918  1.00223.10           N
ANISOU 6127  N   LYS A 811    34050  30403  20314  -5454    221  -9089       N
ATOM   6128  CA  LYS A 811       5.903  -2.664 -18.409  1.00218.81           C
ANISOU 6128  CA  LYS A 811    33522  29037  20578  -5360    868  -8849       C
ATOM   6129  C   LYS A 811       6.757  -3.681 -19.186  1.00224.02           C
ANISOU 6129  C   LYS A 811    34501  29495  21120  -5522   1495  -9460       C
ATOM   6130  O   LYS A 811       6.271  -4.326 -20.111  1.00230.82           O
ANISOU 6130  O   LYS A 811    35644  30845  21213  -5718   1419 -10063       O
ATOM   6131  CB  LYS A 811       5.956  -2.986 -16.910  1.00210.88           C
ANISOU 6131  CB  LYS A 811    32104  27333  20688  -5498    739  -8798       C
```

FIG. 13 Continued

```
ATOM   6132  CG  LYS A 811       6.260  -4.459 -16.606  1.00211.05           C
ANISOU 6132  CG  LYS A 811    32080  26853  21258  -5847    972  -9507       C
ATOM   6133  CD  LYS A 811       6.505  -4.730 -15.118  1.00203.71           C
ANISOU 6133  CD  LYS A 811    30793  25184  21423  -5936    911  -9341       C
ATOM   6134  CE  LYS A 811       7.086  -6.137 -14.876  1.00204.67           C
ANISOU 6134  CE  LYS A 811    30922  24685  22158  -6182   1285  -9916       C
ATOM   6135  NZ  LYS A 811       6.303  -7.269 -15.479  1.00210.53           N
ANISOU 6135  NZ  LYS A 811    31802  25694  22495  -6526   1186 -10694       N
ATOM   6136  N   ILE A 812       8.027  -3.784 -18.796  1.00202.15           N
ANISOU 6136  N   ILE A 812    31676  26015  19117  -5435   2111  -9288       N
ATOM   6137  CA  ILE A 812       9.037  -4.729 -19.308  1.00206.43           C
ANISOU 6137  CA  ILE A 812    32427  26172  19836  -5503   2643  -9771       C
ATOM   6138  C   ILE A 812      10.411  -4.154 -18.932  1.00203.59           C
ANISOU 6138  C   ILE A 812    31895  25250  20212  -5253   3426  -9166       C
ATOM   6139  O   ILE A 812      11.124  -3.573 -19.749  1.00207.72           O
ANISOU 6139  O   ILE A 812    32648  25928  20348  -5049   3938  -8876       O
ATOM   6140  CB  ILE A 812       8.923  -5.083 -20.827  1.00216.16           C
ANISOU 6140  CB  ILE A 812    34212  27990  19929  -5547   3124 -10291       C
ATOM   6141  CG1 ILE A 812       7.944  -6.244 -21.049  1.00219.94           C
ANISOU 6141  CG1 ILE A 812    34820  28698  20049  -5953   2748 -11184       C
ATOM   6142  CG2 ILE A 812      10.277  -5.517 -21.398  1.00220.60           C
ANISOU 6142  CG2 ILE A 812    35004  28130  20684  -5425   4094 -10454       C
ATOM   6143  CD1 ILE A 812       7.893  -6.758 -22.490  1.00230.35           C
ANISOU 6143  CD1 ILE A 812    36745  30518  20261  -6077   3042 -11833       C
ATOM   6144  N   ARG A 813      10.758  -4.324 -17.665  1.00233.72           N
ANISOU 6144  N   ARG A 813    35286  28428  25088  -5302   3323  -8966       N
ATOM   6145  CA  ARG A 813      11.961  -3.738 -17.089  1.00230.59           C
ANISOU 6145  CA  ARG A 813    34610  27517  25488  -5137   3695  -8357       C
ATOM   6146  C   ARG A 813      13.248  -3.956 -17.869  1.00236.22           C
ANISOU 6146  C   ARG A 813    35413  28037  26303  -4990   4572  -8380       C
ATOM   6147  O   ARG A 813      13.265  -4.609 -18.909  1.00242.92           O
ANISOU 6147  O   ARG A 813    36622  29115  26562  -4992   4979  -8914       O
ATOM   6148  CB  ARG A 813      12.134  -4.239 -15.660  1.00224.31           C
ANISOU 6148  CB  ARG A 813    33384  26078  25766  -5263   3443  -8311       C
ATOM   6149  CG  ARG A 813      13.252  -3.567 -14.895  1.00220.92           C
ANISOU 6149  CG  ARG A 813    32602  25173  26164  -5160   3631  -7655       C
ATOM   6150  CD  ARG A 813      12.945  -2.123 -14.555  1.00217.31           C
ANISOU 6150  CD  ARG A 813    32145  24912  25512  -5099   3259  -7002       C
ATOM   6151  NE  ARG A 813      13.793  -1.671 -13.456  1.00213.15           N
ANISOU 6151  NE  ARG A 813    31246  23850  25891  -5141   3224  -6497       N
ATOM   6152  CZ  ARG A 813      15.096  -1.432 -13.570  1.00215.43           C
ANISOU 6152  CZ  ARG A 813    31320  23857  26676  -5088   3736  -6173       C
ATOM   6153  NH1 ARG A 813      15.702  -1.591 -14.735  1.00221.67           N
ANISOU 6153  NH1 ARG A 813    32253  24824  27147  -4956   4400  -6291       N
ATOM   6154  NH2 ARG A 813      15.794  -1.029 -12.518  1.00212.11           N
ANISOU 6154  NH2 ARG A 813    30534  23000  27057  -5186   3590  -5735       N
ATOM   6155  N   GLY A 814      14.331  -3.400 -17.339  1.00136.47           N
ANISOU 6155  N   GLY A 814    22438  14983  14432  -4882   4870  -7804       N
ATOM   6156  CA  GLY A 814      15.626  -3.509 -17.974  1.00141.90           C
ANISOU 6156  CA  GLY A 814    23081  15475  15361  -4729   5738  -7719       C
ATOM   6157  C   GLY A 814      16.886  -3.395 -17.118  1.00139.72           C
ANISOU 6157  C   GLY A 814    22225  14596  16266  -4686   6018  -7250       C
ATOM   6158  O   GLY A 814      17.000  -2.550 -16.211  1.00134.45           O
ANISOU 6158  O   GLY A 814    21261  13761  16064  -4758   5613  -6681       O
ATOM   6159  N   ILE A 815      17.843  -4.265 -17.459  1.00198.02           N
ANISOU 6159  N   ILE A 815    29461  21668  24111  -4564   6737  -7513       N
ATOM   6160  CA  ILE A 815      19.190  -4.343 -16.865  1.00198.51           C
ANISOU 6160  CA  ILE A 815    28905  21212  25308  -4471   7141  -7117       C
ATOM   6161  C   ILE A 815      19.304  -5.037 -15.502  1.00193.56           C
ANISOU 6161  C   ILE A 815    27801  20044  25701  -4538   6687  -7106       C
ATOM   6162  O   ILE A 815      19.641  -4.415 -14.487  1.00188.99           O
ANISOU 6162  O   ILE A 815    26797  19261  25748  -4640   6272  -6555       O
ATOM   6163  CB  ILE A 815      19.915  -2.992 -16.875  1.00198.55           C
ANISOU 6163  CB  ILE A 815    28676  21306  25459  -4484   7296  -6347       C
ATOM   6164  CG1 ILE A 815      20.054  -2.503 -18.315  1.00205.44           C
ANISOU 6164  CG1 ILE A 815    30008  22633  25418  -4362   7970  -6342       C
ATOM   6165  CG2 ILE A 815      21.291  -3.132 -16.268  1.00199.99           C
ANISOU 6165  CG2 ILE A 815    28134  21015  26836  -4435   7659  -5966       C
ATOM   6166  CD1 ILE A 815      20.826  -3.445 -19.220  1.00213.65           C
```

FIG. 13 Continued

```
ANISOU 6166  CD1 ILE A 815    31095  23589  26493   -4152   8933  -6767        C
ATOM   6167  N   GLY A 816    19.037  -6.342 -15.515  1.00259.61              N
ANISOU 6167  N   GLY A 816    36288  28162  34192   -4494   6793  -7726        N
ATOM   6168  CA  GLY A 816    19.080  -7.182 -14.332  1.00256.20              C
ANISOU 6168  CA  GLY A 816    35505  27195  34646   -4525   6433  -7767        C
ATOM   6169  C   GLY A 816    20.437  -7.336 -13.685  1.00257.74              C
ANISOU 6169  C   GLY A 816    35014  26920  35997   -4348   6725  -7294        C
ATOM   6170  O   GLY A 816    21.370  -7.852 -14.297  1.00264.47              O
ANISOU 6170  O   GLY A 816    35696  27590  37200   -4087   7524  -7389        O
ATOM   6171  N   TRP A 817    20.537  -6.896 -12.435  1.00200.83              N
ANISOU 6171  N   TRP A 817    27402  19532  29372   -4487   6072  -6784        N
ATOM   6172  CA  TRP A 817    21.765  -7.026 -11.665  1.00202.33              C
ANISOU 6172  CA  TRP A 817    26874  19327  30674   -4366   6162  -6285        C
ATOM   6173  C   TRP A 817    22.765  -5.931 -12.005  1.00204.99              C
ANISOU 6173  C   TRP A 817    26832  19865  31190   -4373   6497  -5720        C
ATOM   6174  O   TRP A 817    23.701  -5.684 -11.247  1.00205.47              O
ANISOU 6174  O   TRP A 817    26241  19722  32106   -4395   6363  -5189        O
ATOM   6175  CB  TRP A 817    22.379  -8.417 -11.879  1.00208.45              C
ANISOU 6175  CB  TRP A 817    27472  19656  32073   -4035   6782  -6619        C
ATOM   6176  CG  TRP A 817    21.374  -9.529 -11.704  1.00207.07              C
ANISOU 6176  CG  TRP A 817    27760  19241  31675   -4073   6567  -7241        C
ATOM   6177  CD1 TRP A 817    20.539 -10.098 -12.671  1.00209.72              C
ANISOU 6177  CD1 TRP A 817    28738  19712  31235   -4097   6884  -7973        C
ATOM   6178  CD2 TRP A 817    21.039 -10.190 -10.478  1.00203.33              C
ANISOU 6178  CD2 TRP A 817    27157  18357  31743   -4142   5976  -7177        C
ATOM   6179  NE1 TRP A 817    19.793 -11.070 -12.120  1.00207.89              N
ANISOU 6179  NE1 TRP A 817    28748  19152  31089   -4209   6539  -8380        N
ATOM   6180  CE2 TRP A 817    20.050 -11.149 -10.776  1.00203.90              C
ANISOU 6180  CE2 TRP A 817    27790  18296  31387   -4219   6009  -7884        C
ATOM   6181  CE3 TRP A 817    21.484 -10.063  -9.154  1.00200.18              C
ANISOU 6181  CE3 TRP A 817    26243  17701  32117   -4172   5415  -6584        C
ATOM   6182  CZ2 TRP A 817    19.497 -11.979  -9.801  1.00201.33              C
ANISOU 6182  CZ2 TRP A 817    27519  17552  31424   -4317   5561  -7987        C
ATOM   6183  CZ3 TRP A 817    20.934 -10.888  -8.186  1.00197.62              C
ANISOU 6183  CZ3 TRP A 817    26009  16992  32086   -4234   4952  -6674        C
ATOM   6184  CH2 TRP A 817    19.950 -11.835  -8.515  1.00198.15              C
ANISOU 6184  CH2 TRP A 817    26635  16896  31755   -4301   5057  -7358        C
ATOM   6185  N   GLY A 818    22.566  -5.268 -13.139  1.00132.06              N
ANISOU 6185  N   GLY A 818    17999  11041  21138   -4380   6914  -5814        N
ATOM   6186  CA  GLY A 818    23.475  -4.208 -13.552  1.00135.31              C
ANISOU 6186  CA  GLY A 818    18114  11629  21670   -4418   7316  -5276        C
ATOM   6187  C   GLY A 818    22.980  -2.832 -13.148  1.00129.98              C
ANISOU 6187  C   GLY A 818    17611  11180  20596   -4733   6697  -4851        C
ATOM   6188  O   GLY A 818    23.734  -1.990 -12.631  1.00129.97              O
ANISOU 6188  O   GLY A 818    17158  11090  21135   -4917   6579  -4273        O
ATOM   6189  N   TRP A 819    21.693  -2.611 -13.401  1.00177.03              N
ANISOU 6189  N   TRP A 819    24226  17423  25613   -4801   6312  -5151        N
ATOM   6190  CA  TRP A 819    21.066  -1.354 -13.035  1.00172.25              C
ANISOU 6190  CA  TRP A 819    23865  17000  24582   -5028   5743  -4792        C
ATOM   6191  C   TRP A 819    20.645  -1.408 -11.565  1.00165.55              C
ANISOU 6191  C   TRP A 819    22838  15874  24189    5222   4888   4692        C
ATOM   6192  O   TRP A 819    21.039  -0.553 -10.752  1.00163.41              O
ANISOU 6192  O   TRP A 819    22313  15445  24330   -5445   4535  -4205        O
ATOM   6193  CB  TRP A 819    19.856  -1.074 -13.928  1.00171.85              C
ANISOU 6193  CB  TRP A 819    24531  17415  23350   -4965   5681  -5097        C
ATOM   6194  CG  TRP A 819    20.019   0.218 -14.624  1.00174.31              C
ANISOU 6194  CG  TRP A 819    25072  17989  23167   -4986   5947  -4644        C
ATOM   6195  CD1 TRP A 819    19.704   0.491 -15.917  1.00178.90              C
ANISOU 6195  CD1 TRP A 819    26154  19005  22816   -4836   6386  -4746        C
ATOM   6196  CD2 TRP A 819    20.601   1.402 -14.091  1.00173.32              C
ANISOU 6196  CD2 TRP A 819    24713  17681  23460   -5186   5835  -4000        C
ATOM   6197  NE1 TRP A 819    20.032   1.788 -16.216  1.00180.66              N
ANISOU 6197  NE1 TRP A 819    26476  19306  22858   -4897   6571  -4155        N
ATOM   6198  CE2 TRP A 819    20.586   2.367 -15.107  1.00177.29              C
ANISOU 6198  CE2 TRP A 819    25605  18478  23279   -5131   6251  -3711        C
ATOM   6199  CE3 TRP A 819    21.117   1.744 -12.842  1.00170.01              C
ANISOU 6199  CE3 TRP A 819    23829  16873  23893   -5435   5401  -3646        C
ATOM   6200  CZ2 TRP A 819    21.071   3.646 -14.918  1.00178.01              C
ANISOU 6200  CZ2 TRP A 819    25638  18425  23574   -5325   6294  -3090        C
```

FIG. 13 Continued

```
ATOM   6201  CZ3 TRP A 819      21.595   3.005 -12.655  1.00170.81           C
ANISOU 6201  CZ3 TRP A 819    23870  16865  24165   5661   5406   3084       C
ATOM   6202  CH2 TRP A 819      21.576   3.945 -13.687  1.00174.77           C
ANISOU 6202  CH2 TRP A 819    24764  17602  24037  -5610   5873  -2810       C
ATOM   6203  N   ALA A 820      19.839  -2.413 -11.236  1.00121.92           N
ANISOU 6203  N   ALA A 820    17483  10281  18558  -5170   4578  -5170       N
ATOM   6204  CA  ALA A 820      19.417  -2.599  -9.870  1.00116.29           C
ANISOU 6204  CA  ALA A 820    16645   9305  18235  -5334   3843  -5102       C
ATOM   6205  C   ALA A 820      20.704  -2.627  -9.048  1.00117.80           C
ANISOU 6205  C   ALA A 820    16179   9132  19449  -5395   3828  -4654       C
ATOM   6206  O   ALA A 820      20.757  -2.110  -7.932  1.00114.31           O
ANISOU 6206  O   ALA A 820    15575   8530  19328  -5623   3243  -4311       O
ATOM   6207  CB  ALA A 820      18.644  -3.898  -9.743  1.00115.25           C
ANISOU 6207  CB  ALA A 820    16697   9073  18019  -5259   3717  -5674       C
ATOM   6208  N   GLY A 821      21.748  -3.206  -9.642  1.00131.86           N
ANISOU 6208  N   GLY A 821    17578  10810  21712  -5188   4493  -4657       N
ATOM   6209  CA  GLY A 821      23.051  -3.334  -9.010  1.00134.98           C
ANISOU 6209  CA  GLY A 821    17231  10922  23133  -5189   4547  -4222       C
ATOM   6210  C   GLY A 821      23.484  -2.061  -8.323  1.00133.39           C
ANISOU 6210  C   GLY A 821    16786  10739  23156  -5534   4120  -3648       C
ATOM   6211  O   GLY A 821      24.102  -2.106  -7.260  1.00133.27           O
ANISOU 6211  O   GLY A 821    16274  10501  23862  -5680   3680  -3310       O
ATOM   6212  N   VAL A 822      23.171  -0.919  -8.928  1.00142.23           N
ANISOU 6212  N   VAL A 822    18280  12113  23647  -5676   4241  -3528       N
ATOM   6213  CA  VAL A 822      23.483   0.352  -8.289  1.00141.01           C
ANISOU 6213  CA  VAL A 822    18017  11909  23651  -6048   3852  -3033       C
ATOM   6214  C   VAL A 822      22.355   0.739  -7.363  1.00134.16           C
ANISOU 6214  C   VAL A 822    17625  10994  22357  -6232   3066  -3111       C
ATOM   6215  O   VAL A 822      22.574   1.438  -6.387  1.00132.59           O
ANISOU 6215  O   VAL A 822    17312  10625  22440  -6555   2555  -2792       O
ATOM   6216  CB  VAL A 822      23.770   1.475  -9.285  1.00144.50           C
ANISOU 6216  CB  VAL A 822    18635  12550  23719  -6128   4384  -2777       C
ATOM   6217  CG1 VAL A 822      23.847   2.809  -8.567  1.00142.81           C
ANISOU 6217  CG1 VAL A 822    18483  12206  23572  -6550   3924  -2345       C
ATOM   6218  CG2 VAL A 822      25.078   1.198  -9.997  1.00152.06           C
ANISOU 6218  CG2 VAL A 822    18991  13519  25265  -6015   5167  -2594       C
ATOM   6219  N   ILE A 823      21.147   0.271  -7.656  1.00168.18           N
ANISOU 6219  N   ILE A 823    22456  15456  25989  -6043   2979  -3553       N
ATOM   6220  CA  ILE A 823      20.023   0.533  -6.763  1.00162.16           C
ANISOU 6220  CA  ILE A 823    22093  14659  24860  -6176   2293  -3645       C
ATOM   6221  C   ILE A 823      20.315  -0.083  -5.395  1.00160.27           C
ANISOU 6221  C   ILE A 823    21518  14103  25275  -6318   1753  -3562       C
ATOM   6222  O   ILE A 823      20.084   0.547  -4.366  1.00157.58           O
ANISOU 6222  O   ILE A 823    21281  13677  24915  -6533   1202  -3347       O
ATOM   6223  CB  ILE A 823      18.667   0.023  -7.335  1.00159.69           C
ANISOU 6223  CB  ILE A 823    22292  14614  23768  -5964   2293  -4145       C
ATOM   6224  CG1 ILE A 823      17.564   1.053  -7.063  1.00155.70           C
ANISOU 6224  CG1 ILE A 823    22275  14253  22632  -6051   1882  -4067       C
ATOM   6225  CG2 ILE A 823      18.296  -1.366  -6.780  1.00158.04           C
ANISOU 6225  CG2 ILE A 823    21990  14240  23817  -5889   2083  -4525       C
ATOM   6226  CD1 ILE A 823      18.056   2.496  -7.142  1.00157.14           C
ANISOU 6226  CD1 ILE A 823    22532  14385  22788  -6207   1961  -3584       C
ATOM   6227  N   TRP A 824      20.841  -1.305  -5.394  1.00128.33           N
ANISOU 6227  N   TRP A 824    17090   9919  21750  -6130   1948  -3702       N
ATOM   6228  CA  TRP A 824      21.213  -1.975  -4.154  1.00127.74           C
ANISOU 6228  CA  TRP A 824    16669   9547  22321  -6206   1467  -3553       C
ATOM   6229  C   TRP A 824      22.445  -1.353  -3.491  1.00130.80           C
ANISOU 6229  C   TRP A 824    16498   9816  23385  -6459   1240  -3013       C
ATOM   6230  O   TRP A 824      23.106  -1.972  -2.661  1.00132.70           O
ANISOU 6230  O   TRP A 824    16274   9861  24285  -6465    943  -2801       O
ATOM   6231  CB  TRP A 824      21.374  -3.482  -4.343  1.00130.17           C
ANISOU 6231  CB  TRP A 824    16768   9681  23009  -5888   1760  -3834       C
ATOM   6232  CG  TRP A 824      20.160  -4.197  -3.934  1.00126.02           C
ANISOU 6232  CG  TRP A 824    16693   9086  22104  -5863   1460  -4221       C
ATOM   6233  CD1 TRP A 824      19.069  -3.653  -3.332  1.00122.51           C
ANISOU 6233  CD1 TRP A 824    16599   9028  20919  -5819   1016  -4163       C
ATOM   6234  CD2 TRP A 824      19.905  -5.600  -4.044  1.00127.41           C
ANISOU 6234  CD2 TRP A 824    16900   9045  22464  -5634   1669  -4590       C
ATOM   6235  NE1 TRP A 824      18.137  -4.626  -3.073  1.00121.56           N
```

FIG. 13 Continued

```
ANISOU 6235  NE1 TRP A 824     16669   8997  20521  -5617    939  -4439      N
ATOM   6236  CE2 TRP A 824     18.625  -5.832  -3.501  1.00124.25            C
ANISOU 6236  CE2 TRP A 824     16859   8913  21438  -5560   1309  -4742      C
ATOM   6237  CE3 TRP A 824     20.626  -6.680  -4.557  1.00132.74            C
ANISOU 6237  CE3 TRP A 824     17274   9493  23669  -5325   2213  -4725      C
ATOM   6238  CZ2 TRP A 824     18.048  -7.100  -3.456  1.00125.16            C
ANISOU 6238  CZ2 TRP A 824     17101   8888  21565  -5409   1416  -5092      C
ATOM   6239  CZ3 TRP A 824     20.050  -7.945  -4.514  1.00133.21            C
ANISOU 6239  CZ3 TRP A 824     17559   9283  23770  -5187   2313  -5141      C
ATOM   6240  CH2 TRP A 824     18.771  -8.141  -3.968  1.00128.68            C
ANISOU 6240  CH2 TRP A 824     17429   8760  22703  -5354   1877  -5382      C
ATOM   6241  N   LEU A 825     22.770  -0.139  -3.907  1.00125.16            N
ANISOU 6241  N   LEU A 825     15815   9228  22510  -6671   1394  -2776      N
ATOM   6242  CA  LEU A 825     23.771   0.670  -3.235  1.00127.98            C
ANISOU 6242  CA  LEU A 825     15738   9489  23400  -7048   1094  -2298      C
ATOM   6243  C   LEU A 825     22.990   1.830  -2.633  1.00124.46            C
ANISOU 6243  C   LEU A 825     15874   9101  22313  -7274    622  -2241      C
ATOM   6244  O   LEU A 825     23.057   2.125  -1.433  1.00124.88            O
ANISOU 6244  O   LEU A 825     15904   9207  22338  -7337      2  -2030      O
ATOM   6245  CB  LEU A 825     24.788   1.189  -4.237  1.00133.84            C
ANISOU 6245  CB  LEU A 825     16071  10346  24437  -7065   1754  -2056      C
ATOM   6246  CG  LEU A 825     26.179   0.595  -4.075  1.00140.19            C
ANISOU 6246  CG  LEU A 825     15943  11094  26231  -7023   1897  -1749      C
ATOM   6247  CD1 LEU A 825     27.047   1.504  -3.167  1.00143.04            C
ANISOU 6247  CD1 LEU A 825     15854  11387  27109  -7563   1365  -1272      C
ATOM   6248  CD2 LEU A 825     26.072  -0.862  -3.569  1.00139.58            C
ANISOU 6248  CD2 LEU A 825     15666  10878  26490  -6672   1712  -1929      C
ATOM   6249  N   TYR A 826     22.220   2.465  -3.511  1.00132.70            N
ANISOU 6249  N   TYR A 826     17463  10247  22709  -7226    963  -2410      N
ATOM   6250  CA  TYR A 826     21.313   3.530  -3.148  1.00130.45            C
ANISOU 6250  CA  TYR A 826     17773  10131  21662  -7185    678  -2363      C
ATOM   6251  C   TYR A 826     20.214   2.883  -2.339  1.00126.93            C
ANISOU 6251  C   TYR A 826     17597   9916  20715  -6821    257  -2569      C
ATOM   6252  O   TYR A 826     19.304   3.543  -1.842  1.00124.84            O
ANISOU 6252  O   TYR A 826     17792   9810  19833  -6721     -5  -2542      O
ATOM   6253  CB  TYR A 826     20.729   4.170  -4.392  1.00129.34            C
ANISOU 6253  CB  TYR A 826     18111  10000  21031  -7195   1171  -2479      C
ATOM   6254  CG  TYR A 826     20.150   5.525  -4.131  1.00128.67            C
ANISOU 6254  CG  TYR A 826     18548   9927  20415  -7263    993  -2292      C
ATOM   6255  CD1 TYR A 826     20.946   6.556  -3.662  1.00132.04            C
ANISOU 6255  CD1 TYR A 826     18879  10152  21139  -7619    883  -1932      C
ATOM   6256  CD2 TYR A 826     18.808   5.775  -4.357  1.00125.28            C
ANISOU 6256  CD2 TYR A 826     18696   9672  19232  -6995    942  -2479      C
ATOM   6257  CE1 TYR A 826     20.415   7.794  -3.426  1.00131.98            C
ANISOU 6257  CE1 TYR A 826     19415  10053  20678  -7691    773  -1793      C
ATOM   6258  CE2 TYR A 826     18.270   7.004  -4.128  1.00125.04            C
ANISOU 6258  CE2 TYR A 826     19150   9565  18793  -7035    830  -2296      C
ATOM   6259  CZ  TYR A 826     19.070   8.004  -3.662  1.00128.35            C
ANISOU 6259  CZ  TYR A 826     19540   9721  19504  -7371    768  -1967      C
ATOM   6260  OH  TYR A 826     18.507   9.226  -3.436  1.00128.56            O
ANISOU 6260  OH  TYR A 826     20123   9584  19142  -7409    704  -1818      O
ATOM   6261  N   SER A 827     20.299   1.564  -2.245  1.00130.56            N
ANISOU 6261  N   SER A 827     17764  10350  21491  -6638    266  -2758      N
ATOM   6262  CA  SER A 827     19.421   0.811  -1.386  1.00128.17            C
ANISOU 6262  CA  SER A 827     17621  10215  20864  -6351    -99  -2879      C
ATOM   6263  C   SER A 827     19.887   1.160   0.043  1.00129.58            C
ANISOU 6263  C   SER A 827     17676  10336  21224  -6493   -698  -2518      C
ATOM   6264  O   SER A 827     19.223   1.917   0.770  1.00128.29            O
ANISOU 6264  O   SER A 827     17916  10311  20517  -6491  -1010  -2410      O
ATOM   6265  CB  SER A 827     19.576  -0.692  -1.672  1.00128.69            C
ANISOU 6265  CB  SER A 827     17402  10139  21355  -6184    110  -3147      C
ATOM   6266  OG  SER A 827     18.328  -1.356  -1.798  1.00126.11            O
ANISOU 6266  OG  SER A 827     17410  10030  20476  -5918    150  -3474      O
ATOM   6267  N   ILE A 828     21.070   0.663   0.411  1.00 97.64            N
ANISOU 6267  N   ILE A 828     13074   6052  17972  -6665   -848  -2326      N
ATOM   6268  CA  ILE A 828     21.607   0.821   1.759  1.00 99.79            C
ANISOU 6268  CA  ILE A 828     13189   6253  18474  -6860  -1491  -1995      C
ATOM   6269  C   ILE A 828     22.015   2.228   2.104  1.00101.92            C
ANISOU 6269  C   ILE A 828     13583   6524  18617  -7230  -1723  -1750      C
```

FIG. 13 Continued

```
ATOM   6270  O   ILE A 828      21.912   2.638   3.248  1.00102.68           O
ANISOU 6270  O   ILE A 828    13908   6639  18466  -7372  -2261  -1587       O
ATOM   6271  CB  ILE A 828      22.825  -0.072   1.978  1.00103.43           C
ANISOU 6271  CB  ILE A 828    12929   6447  19922  -6992  -1610  -1806       C
ATOM   6272  CG1 ILE A 828      22.495  -1.522   1.598  1.00102.08           C
ANISOU 6272  CG1 ILE A 828    12663   6143  19978  -6650  -1309  -2074       C
ATOM   6273  CG2 ILE A 828      23.288   0.036   3.413  1.00105.89           C
ANISOU 6273  CG2 ILE A 828    13121   6712  20400  -7229  -2377  -1461       C
ATOM   6274  CD1 ILE A 828      21.243  -2.080   2.250  1.00 98.76           C
ANISOU 6274  CD1 ILE A 828    12752   5874  18898  -6346  -1529  -2245       C
ATOM   6275  N   VAL A 829      22.482   2.974   1.122  1.00109.71           N
ANISOU 6275  N   VAL A 829    14466   7449  19770  -7432  -1292  -1729       N
ATOM   6276  CA  VAL A 829      22.941   4.322   1.402  1.00112.60           C
ANISOU 6276  CA  VAL A 829    14948   7741  20094  -7847  -1463  -1498       C
ATOM   6277  C   VAL A 829      21.843   5.228   1.940  1.00110.24           C
ANISOU 6277  C   VAL A 829    15424   7536  18924  -7770  -1657  -1566       C
ATOM   6278  O   VAL A 829      22.126   6.244   2.581  1.00112.97           O
ANISOU 6278  O   VAL A 829    15976   7767  19180  -8127  -1955  -1403       O
ATOM   6279  CB  VAL A 829      23.505   4.966   0.151  1.00114.58           C
ANISOU 6279  CB  VAL A 829    15028   7878  20631  -8070   -854  -1446       C
ATOM   6280  CG1 VAL A 829      24.566   4.059  -0.476  1.00117.26           C
ANISOU 6280  CG1 VAL A 829    14570   8109  21875  -8147   -513  -1371       C
ATOM   6281  CG2 VAL A 829      22.386   5.227  -0.831  1.00110.59           C
ANISOU 6281  CG2 VAL A 829    15110   7470  19438  -7772   -371  -1705       C
ATOM   6282  N   THR A 830      20.596   4.868   1.644  1.00140.72           N
ANISOU 6282  N   THR A 830    19694  11586  22189  -7344  -1457  -1812       N
ATOM   6283  CA  THR A 830      19.441   5.643   2.086  1.00138.46           C
ANISOU 6283  CA  THR A 830    20080  11391  21135  -7224  -1555  -1865       C
ATOM   6284  C   THR A 830      18.940   5.137   3.422  1.00137.55           C
ANISOU 6284  C   THR A 830    20135  11367  20762  -7114  -2040  -1840       C
ATOM   6285  O   THR A 830      18.129   5.784   4.078  1.00136.67           O
ANISOU 6285  O   THR A 830    20549  11279  20101  -7093  -2179  -1838       O
ATOM   6286  CB  THR A 830      18.257   5.536   1.097  1.00134.53           C
ANISOU 6286  CB  THR A 830    19892  11080  20142  -6858  -1117  -2107       C
ATOM   6287  OG1 THR A 830      17.823   4.173   1.003  1.00132.25           O
ANISOU 6287  OG1 THR A 830    19391  10977  19880  -6547  -1079  -2305       O
ATOM   6288  CG2 THR A 830      18.652   6.025  -0.273  1.00135.44           C
ANISOU 6288  CG2 THR A 830    19957  11082  20423  -6978   -612  -2127       C
ATOM   6289  N   TYR A 831      19.437   3.975   3.816  1.00169.10           N
ANISOU 6289  N   TYR A 831    23701  15361  25189  -7062  -2262  -1805       N
ATOM   6290  CA  TYR A 831      18.980   3.285   5.011  1.00168.38           C
ANISOU 6290  CA  TYR A 831    23759  15321  24898  -6954  -2679  -1760       C
ATOM   6291  C   TYR A 831      19.462   3.842   6.371  1.00171.73           C
ANISOU 6291  C   TYR A 831    24366  15604  25277  -7341  -3288  -1525       C
ATOM   6292  O   TYR A 831      18.813   3.636   7.398  1.00171.02           O
ANISOU 6292  O   TYR A 831    24650  15551  24778  -7293  -3576  -1499       O
ATOM   6293  CB  TYR A 831      19.332   1.813   4.856  1.00168.22           C
ANISOU 6293  CB  TYR A 831    23251  15265  25399  -6767  -2658  -1806       C
ATOM   6294  CG  TYR A 831      19.337   1.067   6.139  1.00169.12           C
ANISOU 6294  CG  TYR A 831    23390  15308  25560  -6791  -3172  -1653       C
ATOM   6295  CD1 TYR A 831      18.439   0.046   6.361  1.00166.66           C
ANISOU 6295  CD1 TYR A 831    23221  15071  25029  -6480  -3092  -1783       C
ATOM   6296  CD2 TYR A 831      20.245   1.383   7.139  1.00172.98           C
ANISOU 6296  CD2 TYR A 831    23772  15639  26315  -7186  -3757  -1366       C
ATOM   6297  CE1 TYR A 831      18.442  -0.646   7.536  1.00167.77           C
ANISOU 6297  CE1 TYR A 831    23432  15098  25213  -6533  -3541  -1615       C
ATOM   6298  CE2 TYR A 831      20.256   0.712   8.323  1.00174.17           C
ANISOU 6298  CE2 TYR A 831    23998  15703  26475  -7255  -4267  -1200       C
ATOM   6299  CZ  TYR A 831      19.349  -0.310   8.521  1.00171.42           C
ANISOU 6299  CZ  TYR A 831    23829  15398  25904  -6913  -4140  -1316       C
ATOM   6300  OH  TYR A 831      19.350  -1.004   9.710  1.00172.84           O
ANISOU 6300  OH  TYR A 831    24132  15447  26093  -7010  -4631  -1125       O
ATOM   6301  N   PHE A 832      20.602   4.526   6.382  1.00115.56           N
ANISOU 6301  N   PHE A 832    16996   8324  18589  -7778  -3480  -1358       N
ATOM   6302  CA  PHE A 832      21.141   5.121   7.613  1.00119.76           C
ANISOU 6302  CA  PHE A 832    17706   8716  19081  -8260  -4100  -1165       C
ATOM   6303  C   PHE A 832      20.555   6.497   7.977  1.00120.41           C
ANISOU 6303  C   PHE A 832    18515   8715  18521  -8465  -4077  -1239       C
ATOM   6304  O   PHE A 832      20.656   6.940   9.125  1.00123.43           O
```

FIG. 13 Continued

```
ANISOU 6304  O   PHE A 832     19266  8981 18651  -8827 -4558 -1167       O
ATOM   6305  CB  PHE A 832     22.672    5.215    7.559  1.00125.08       C
ANISOU 6305  CB  PHE A 832     17704  9249 20570  -8742 -4390  -937       C
ATOM   6306  CG  PHE A 832     23.370    3.892    7.756  1.00126.17       C
ANISOU 6306  CG  PHE A 832     17164  9379 21396  -8676 -4661  -776       C
ATOM   6307  CD1 PHE A 832     22.743    2.692    7.372  1.00122.03       C
ANISOU 6307  CD1 PHE A 832     16563  8923 20880  -8142 -4352  -917       C
ATOM   6308  CD2 PHE A 832     24.656    3.848    8.302  1.00131.91       C
ANISOU 6308  CD2 PHE A 832     17299 10012 22810  -9184 -5221  -479       C
ATOM   6309  CE1 PHE A 832     23.365    1.469    7.534  1.00123.36       C
ANISOU 6309  CE1 PHE A 832     16147  8989 21735  -8078 -4548  -774       C
ATOM   6310  CE2 PHE A 832     25.292    2.628    8.467  1.00133.25       C
ANISOU 6310  CE2 PHE A 832     16795 10139 23694  -9113 -5461  -289       C
ATOM   6311  CZ  PHE A 832     24.636    1.429    8.076  1.00128.82       C
ANISOU 6311  CZ  PHE A 832     16233  9568 23145  -8539 -5093  -442       C
ATOM   6312  N   PRO A 833     19.995    7.212    6.994  1.00211.58       N
ANISOU 6312  N   PRO A 833     30292 20270 29828  -8285 -3522 -1382       N
ATOM   6313  CA  PRO A 833     19.302    8.419    7.443  1.00212.21       C
ANISOU 6313  CA  PRO A 833     31113 20206 29311  -8423 -3486 -1457       C
ATOM   6314  C   PRO A 833     18.089    8.027    8.291  1.00209.29       C
ANISOU 6314  C   PRO A 833     31224 19961 28337  -8123 -3566 -1547       C
ATOM   6315  O   PRO A 833     17.397    8.906    8.803  1.00209.84       O
ANISOU 6315  O   PRO A 833     31935 19892 27902  -8201 -3519 -1627       O
ATOM   6316  CB  PRO A 833     18.851    9.068    6.133  1.00210.10       C
ANISOU 6316  CB  PRO A 833     30953 19919 28955  -8210 -2865 -1559       C
ATOM   6317  CG  PRO A 833     19.851    8.616    5.135  1.00210.98       C
ANISOU 6317  CG  PRO A 833     30378 20057 29728  -8271 -2677 -1484       C
ATOM   6318  CD  PRO A 833     20.259    7.229    5.545  1.00210.43       C
ANISOU 6318  CD  PRO A 833     29780 20151 30023  -8143 -2981 -1434       C
ATOM   6319  N   LEU A 834     17.833    6.723    8.426  1.00114.04       N
ANISOU 6319  N   LEU A 834     18858  8109 16362  -7806 -3637 -1540       N
ATOM   6320  CA  LEU A 834     16.707    6.229    9.227  1.00111.64       C
ANISOU 6320  CA  LEU A 834     18944  7918 15557  -7559 -3677 -1598       C
ATOM   6321  C   LEU A 834     17.002    6.173   10.712  1.00114.97       C
ANISOU 6321  C   LEU A 834     19673  8195 15815  -7924 -4252 -1477       C
ATOM   6322  O   LEU A 834     16.277    6.758   11.529  1.00115.59       O
ANISOU 6322  O   LEU A 834     20395  8180 15344  -8023 -4280 -1543       O
ATOM   6323  CB  LEU A 834     16.253    4.844    8.772  1.00108.04       C
ANISOU 6323  CB  LEU A 834     18098  7695 15258  -7125 -3487 -1655       C
ATOM   6324  CG  LEU A 834     14.863    4.964    8.169  1.00104.15       C
ANISOU 6324  CG  LEU A 834     17845  7390 14336  -6740 -2996 -1840       C
ATOM   6325  CD1 LEU A 834     14.980    5.407    6.725  1.00102.98       C
ANISOU 6325  CD1 LEU A 834     17481  7294 14352  -6622 -2584 -1939       C
ATOM   6326  CD2 LEU A 834     14.073    3.687    8.290  1.00101.52       C
ANISOU 6326  CD2 LEU A 834     17376  7248 13949  -6430 -2908 -1912       C
ATOM   6327  N   ASP A 835     18.063    5.448   11.053  1.00125.49       N
ANISOU 6327  N   ASP A 835     20552  9487 17642  -8140 -4711 -1302       N
ATOM   6328  CA  ASP A 835     18.447    5.301   12.444  1.00129.21       C
ANISOU 6328  CA  ASP A 835     21281  9825 17989  -8545 -5355 -1156       C
ATOM   6329  C   ASP A 835     18.675    6.647   13.067  1.00133.48       C
ANISOU 6329  C   ASP A 835     22373 10152 18191  -9068 -5579 -1197       C
ATOM   6330  O   ASP A 835     18.085    6.944   14.090  1.00134.69       O
ANISOU 6330  O   ASP A 835     23196 10206 17773  -9232 -5737 -1258       O
ATOM   6331  CB  ASP A 835     19.657    4.398   12.604  1.00131.92       C
ANISOU 6331  CB  ASP A 835     20959 10133 19031  -8738 -5856  -923       C
ATOM   6332  CG  ASP A 835     19.292    2.937   12.509  1.00128.76       C
ANISOU 6332  CG  ASP A 835     20261  9824 18840  -8305 -5760  -889       C
ATOM   6333  OD1 ASP A 835     18.577    2.550   11.552  1.00124.41       O
ANISOU 6333  OD1 ASP A 835     19582  9418 18271  -7821 -5166 -1066       O
ATOM   6334  OD2 ASP A 835     19.716    2.181   13.403  1.00131.11       O
ANISOU 6334  OD2 ASP A 835     20476 10023 19315  -8495 -6302  -689       O
ATOM   6335  N   VAL A 836     19.498    7.484   12.455  1.00141.12       N
ANISOU 6335  N   VAL A 836     23109 11011 19501  -9366 -5549 -1191       N
ATOM   6336  CA  VAL A 836     19.687    8.801   13.035  1.00145.83       C
ANISOU 6336  CA  VAL A 836     24291 11339 19778  -9917 -5729 -1277       C
ATOM   6337  C   VAL A 836     18.346    9.544   13.048  1.00143.21       C
ANISOU 6337  C   VAL A 836     24726 10920 18768  -9642 -5208 -1507       C
ATOM   6338  O   VAL A 836     18.187   10.540   13.757  1.00146.89       O
ANISOU 6338  O   VAL A 836     25889 11104 18818 -10033 -5299 -1637       O
```

FIG. 13 Continued

```
ATOM   6339  CB   VAL A 836      20.768   9.636  12.304  1.00149.65           C
ANISOU 6339  CB   VAL A 836    24399  11676  20786 -10330  -5712  -1236       C
ATOM   6340  CG1  VAL A 836      20.128  10.603  11.308  1.00147.40           C
ANISOU 6340  CG1  VAL A 836    24417  11274  20313 -10093  -5008  -1406       C
ATOM   6341  CG2  VAL A 836      21.654  10.387  13.314  1.00157.30           C
ANISOU 6341  CG2  VAL A 836    25619  12401  21746 -11176  -6367  -1206       C
ATOM   6342  N    PHE A 837      17.378   9.057  12.272  1.00132.84           N
ANISOU 6342  N    PHE A 837    23281   9826  17367  -9003  -4669  -1570       N
ATOM   6343  CA   PHE A 837      16.068   9.709  12.233  1.00130.54           C
ANISOU 6343  CA   PHE A 837    23602   9470  16526  -8723  -4184  -1758       C
ATOM   6344  C    PHE A 837      15.087   9.257  13.312  1.00129.54           C
ANISOU 6344  C    PHE A 837    23956   9381  15883  -8605  -4238  -1813       C
ATOM   6345  O    PHE A 837      14.518  10.109  13.996  1.00131.69           O
ANISOU 6345  O    PHE A 837    24955   9398  15683  -8781  -4145  -1961       O
ATOM   6346  CB   PHE A 837      15.442   9.721  10.829  1.00125.93           C
ANISOU 6346  CB   PHE A 837    22726   9059  16061  -8206  -3581  -1820       C
ATOM   6347  CG   PHE A 837      15.692  11.015  10.074  1.00127.89           C
ANISOU 6347  CG   PHE A 837    23169   9035  16387  -8375  -3293  -1876       C
ATOM   6348  CD1  PHE A 837      15.420  11.121   8.716  1.00124.87           C
ANISOU 6348  CD1  PHE A 837    22515   8753  16177  -8033  -2827  -1892       C
ATOM   6349  CD2  PHE A 837      16.218  12.135  10.739  1.00133.40           C
ANISOU 6349  CD2  PHE A 837    24380   9327  16981  -8936  -3498  -1919       C
ATOM   6350  CE1  PHE A 837      15.657  12.326   8.035  1.00127.12           C
ANISOU 6350  CE1  PHE A 837    23043   8717  16541  -8214  -2547  -1908       C
ATOM   6351  CE2  PHE A 837      16.460  13.336  10.067  1.00135.86           C
ANISOU 6351  CE2  PHE A 837    24921   9301  17399  -9133  -3202  -1964       C
ATOM   6352  CZ   PHE A 837      16.180  13.430   8.716  1.00132.63           C
ANISOU 6352  CZ   PHE A 837    24240   8975  17178  -8755  -2717  -1935       C
ATOM   6353  N    LYS A 838      14.879   7.946  13.480  1.00114.37           N
ANISOU 6353  N    LYS A 838    21679   7718  14060  -8337  -4345  -1715       N
ATOM   6354  CA   LYS A 838      14.012   7.503  14.572  1.00114.11           C
ANISOU 6354  CA   LYS A 838    22122   7679  13556  -8307  -4398  -1749       C
ATOM   6355  C    LYS A 838      14.421   8.298  15.814  1.00119.80           C
ANISOU 6355  C    LYS A 838    23543   8069  13905  -8912  -4816  -1790       C
ATOM   6356  O    LYS A 838      13.601   8.962  16.455  1.00121.02           O
ANISOU 6356  O    LYS A 838    24421   8026  13534  -8986  -4600  -1967       O
ATOM   6357  CB   LYS A 838      14.136   6.007  14.836  1.00112.48           C
ANISOU 6357  CB   LYS A 838    21497   7666  13575  -8154  -4644  -1593       C
ATOM   6358  CG   LYS A 838      15.426   5.367  14.361  1.00113.41           C
ANISOU 6358  CG   LYS A 838    20906   7837  14347  -8239  -5006  -1413       C
ATOM   6359  CD   LYS A 838      15.202   4.586  13.050  1.00108.91           C
ANISOU 6359  CD   LYS A 838    19683   7513  14185  -7720  -4569  -1451       C
ATOM   6360  CE   LYS A 838      16.076   3.302  12.942  1.00109.27           C
ANISOU 6360  CE   LYS A 838    19098   7584  14836  -7682  -4879  -1287       C
ATOM   6361  NZ   LYS A 838      15.567   2.207  12.044  1.00105.33           N
ANISOU 6361  NZ   LYS A 838    18162   7268  14591  -7197  -4463  -1381       N
ATOM   6362  N    PHE A 839      15.719   8.274  16.099  1.00158.33           N
ANISOU 6362  N    PHE A 839    28197  12868  19092  -9379  -5410  -1650       N
ATOM   6363  CA   PHE A 839      16.296   8.958  17.249  1.00164.75           C
ANISOU 6363  CA   PHE A 839    29610  13390  19598 -10073  -5941  -1694       C
ATOM   6364  C    PHE A 839      16.006  10.446  17.186  1.00167.39           C
ANISOU 6364  C    PHE A 839    30586  13399  19614 -10293  -5613  -1950       C
ATOM   6365  O    PHE A 839      16.360  11.191  18.090  1.00173.27           O
ANISOU 6365  O    PHE A 839    31965  13837  20031 -10899  -5955  -2079       O
ATOM   6366  CB   PHE A 839      17.812   8.709  17.300  1.00168.83           C
ANISOU 6366  CB   PHE A 839    29563  13924  20660 -10545  -6637  -1483       C
ATOM   6367  CG   PHE A 839      18.201   7.240  17.415  1.00167.14           C
ANISOU 6367  CG   PHE A 839    28726  13937  20841 -10361  -7005  -1217       C
ATOM   6368  CD1  PHE A 839      17.559   6.261  16.650  1.00161.03           C
ANISOU 6368  CD1  PHE A 839    27506  13393  20284  -9682  -6536  -1175       C
ATOM   6369  CD2  PHE A 839      19.222   6.844  18.273  1.00172.26           C
ANISOU 6369  CD2  PHE A 839    29233  14547  21671 -10905  -7842  -1018       C
ATOM   6370  CE1  PHE A 839      17.915   4.921  16.743  1.00159.99           C
ANISOU 6370  CE1  PHE A 839    26858  13376  20555  -9527  -6830   -961       C
ATOM   6371  CE2  PHE A 839      19.583   5.506  18.376  1.00171.11           C
ANISOU 6371  CE2  PHE A 839    28525  14541  21947 -10733  -8179   -758       C
ATOM   6372  CZ   PHE A 839      18.928   4.544  17.604  1.00164.92           C
ANISOU 6372  CZ   PHE A 839    27353  13912  21395 -10032  -7637   -738       C
ATOM   6373  N    ALA A 840      15.368  10.876  16.106  1.00153.49           N
```

FIG. 13 Continued

```
ANISOU 6373  N   ALA A 840    28690 11675 17954  -9826 -4965 -2036        N
ATOM   6374  CA  ALA A 840      15.044  12.286  15.918  1.00155.89        C
ANISOU 6374  CA  ALA A 840    29594 11604 18033  -9966 -4586 -2262        C
ATOM   6375  C   ALA A 840      13.668  12.640  16.470  1.00155.02        C
ANISOU 6375  C   ALA A 840    30236 11322 17344  -9722 -4132 -2480        C
ATOM   6376  O   ALA A 840      13.521  13.569  17.279  1.00159.94        O
ANISOU 6376  O   ALA A 840    31707 11514 17550 -10115 -4121 -2707        O
ATOM   6377  CB  ALA A 840      15.131  12.652  14.445  1.00152.98        C
ANISOU 6377  CB  ALA A 840    28729 11300 18098  -9639 -4151 -2221        C
ATOM   6378  N   ILE A 841      12.656  11.914  16.008  1.00131.89        N
ANISOU 6378  N   ILE A 841    26995  8701 14417  -9099 -3733 -2437        N
ATOM   6379  CA  ILE A 841      11.305  12.133  16.503  1.00131.05        C
ANISOU 6379  CA  ILE A 841    27474  8465 13855  -8845 -3282 -2627        C
ATOM   6380  C   ILE A 841      11.210  11.705  17.977  1.00134.13        C
ANISOU 6380  C   ILE A 841    28420  8757 13786  -9194 -3605 -2679        C
ATOM   6381  O   ILE A 841      10.574  12.383  18.796  1.00137.38        O
ANISOU 6381  O   ILE A 841    29676  8806 13715  -9353 -3379 -2924        O
ATOM   6382  CB  ILE A 841      10.239  11.380  15.656  1.00124.68        C
ANISOU 6382  CB  ILE A 841    26121  8042 13210  -8167 -2832 -2572        C
ATOM   6383  CG1 ILE A 841      10.545   9.883  15.600  1.00121.54        C
ANISOU 6383  CG1 ILE A 841    25034  8082 13062  -8034 -3137 -2360        C
ATOM   6384  CG2 ILE A 841      10.142  11.959  14.260  1.00122.32        C
ANISOU 6384  CG2 ILE A 841    25474  7770 13233  -7845 -2474 -2568        C
ATOM   6385  CD1 ILE A 841       9.813   9.160  14.518  1.00116.04        C
ANISOU 6385  CD1 ILE A 841    23693  7762 12635  -7474 -2774 -2323        C
ATOM   6386  N   ARG A 842      11.860  10.584  18.302  1.00117.99        N
ANISOU 6386  N   ARG A 842    25940  6990 11899  -9317 -4120 -2458        N
ATOM   6387  CA  ARG A 842      11.830  10.010  19.649  1.00120.78        C
ANISOU 6387  CA  ARG A 842    26773  7279 11840  -9652 -4495 -2453        C
ATOM   6388  C   ARG A 842      12.471  10.903  20.686  1.00128.12        C
ANISOU 6388  C   ARG A 842    28521  7798 12361 -10375 -4913 -2624        C
ATOM   6389  O   ARG A 842      11.788  11.348  21.606  1.00131.15        O
ANISOU 6389  O   ARG A 842    29784  7886 12163 -10553 -4718 -2873        O
ATOM   6390  CB  ARG A 842      12.526   8.659  19.666  1.00119.11        C
ANISOU 6390  CB  ARG A 842    25889  7387 11981  -9638 -5005 -2150        C
ATOM   6391  CG  ARG A 842      11.815   7.610  18.862  1.00112.81        C
ANISOU 6391  CG  ARG A 842    24421  6947 11494  -9004 -4615 -2039        C
ATOM   6392  CD  ARG A 842      10.886   6.841  19.726  1.00112.10        C
ANISOU 6392  CD  ARG A 842    24682  6874 11035  -8932 -4487 -2064        C
ATOM   6393  NE  ARG A 842      10.836   5.469  19.255  1.00108.16        N
ANISOU 6393  NE  ARG A 842    23477  6680 10938  -8591 -4505 -1871        N
ATOM   6394  CZ  ARG A 842       9.929   4.999  18.403  1.00103.46        C
ANISOU 6394  CZ  ARG A 842    22437  6331 10542  -8083 -3974 -1923        C
ATOM   6395  NH1 ARG A 842       8.983   5.808  17.942  1.00101.95        N
ANISOU 6395  NH1 ARG A 842    22401  6135 10202  -7842 -3419 -2127        N
ATOM   6396  NH2 ARG A 842       9.962   3.719  18.021  1.00100.79        N
ANISOU 6396  NH2 ARG A 842    21516  6210 10569  -7845 -4016 -1787        N
ATOM   6397  N   TYR A 843      13.776  11.158  20.531  1.00244.79        N
ANISOU 6397  N   TYR A 843    43011 22546 27451 -10820 -5474 -2519        N
ATOM   6398  CA  TYR A 843      14.550  11.994  21.464  1.00252.75        C
ANISOU 6398  CA  TYR A 843    44716 23191 28128 -11633 -5994 -2694        C
ATOM   6399  C   TYR A 843      13.955  13.402  21.541  1.00255.93        C
ANISOU 6399  C   TYR A 843    45984 23106 28152 -11747 -5458 -3077        C
ATOM   6400  O   TYR A 843      14.584  14.351  22.013  1.00262.79        O
ANISOU 6400  O   TYR A 843    47428 23594 28827 -12411 -5743 -3295        O
ATOM   6401  CB  TYR A 843      16.053  12.000  21.108  1.00255.76        C
ANISOU 6401  CB  TYR A 843    44448 23668 29060 -12084 -6663 -2497        C
ATOM   6402  CG  TYR A 843      16.789  10.685  21.421  1.00255.28        C
ANISOU 6402  CG  TYR A 843    43742 23953 29301 -12162 -7360 -2154        C
ATOM   6403  CD1 TYR A 843      18.124  10.683  21.828  1.00261.23        C
ANISOU 6403  CD1 TYR A 843    44239 24716 30299 -12851 -8224 -2027        C
ATOM   6404  CD2 TYR A 843      16.140   9.447  21.321  1.00249.49        C
ANISOU 6404  CD2 TYR A 843    42651 23506 28639 -11578 -7166 -1964        C
ATOM   6405  CE1 TYR A 843      18.792   9.483  22.114  1.00261.23        C
ANISOU 6405  CE1 TYR A 843    43628 24996 30633 -12904 -8880 -1692        C
ATOM   6406  CE2 TYR A 843      16.802   8.245  21.610  1.00249.49        C
ANISOU 6406  CE2 TYR A 843    42114 23729 28952 -11642 -7779 -1654        C
ATOM   6407  CZ  TYR A 843      18.123   8.272  22.002  1.00255.28        C
ANISOU 6407  CZ  TYR A 843    42590 24457 29946 -12281 -8635 -1508        C
```

FIG. 13 Continued

```
ATOM   6408  OH  TYR A 843      18.776   7.094  22.277  1.00 255.65           O
ANISOU 6408  OH  TYR A 843    42074  24698  30362 -12330  -9257  -1182        O
ATOM   6409  N   ILE A 844      12.716  13.489  21.064  1.00 153.39           N
ANISOU 6409  N   ILE A 844    33067  10118  15097 -11101  -4684  -3165        N
ATOM   6410  CA  ILE A 844      11.896  14.683  21.095  1.00 155.61           C
ANISOU 6410  CA  ILE A 844    34144   9914  15067 -11025  -4044  -3510        C
ATOM   6411  C   ILE A 844      10.419  14.258  21.050  1.00 150.77           C
ANISOU 6411  C   ILE A 844    33583   9417  14286 -10356  -3379  -3558        C
ATOM   6412  O   ILE A 844      10.061  13.080  20.920  1.00 145.74           O
ANISOU 6412  O   ILE A 844    32352   9235  13787  -9993  -3407  -3335        O
ATOM   6413  CB  ILE A 844      12.212  15.616  19.911  1.00 155.23           C
ANISOU 6413  CB  ILE A 844    33818   9691  15472 -10909  -3751  -3516        C
ATOM   6414  CG1 ILE A 844      12.233  17.089  20.364  1.00 162.54           C
ANISOU 6414  CG1 ILE A 844    35795   9890  16074 -11377  -3537  -3904        C
ATOM   6415  CG2 ILE A 844      11.283  15.334  18.722  1.00 147.92           C
ANISOU 6415  CG2 ILE A 844    32277   9047  14879 -10073  -3132  -3383        C
ATOM   6416  CD1 ILE A 844      11.058  17.520  21.220  1.00 164.89           C
ANISOU 6416  CD1 ILE A 844    37101   9775  15776 -11248  -3012  -4251        C
TER    6417      ILE A 844
ATOM   6418  N   VAL B  12      13.903 -69.288  79.867  1.00 261.60           N
ANISOU 6418  N   VAL B  12    42558  23588  33251  -3398  -9221   4201        N
ATOM   6419  CA  VAL B  12      13.725 -70.718  80.079  1.00 264.76           C
ANISOU 6419  CA  VAL B  12    42776  23693  34127  -3552  -9709   4562        C
ATOM   6420  C   VAL B  12      13.494 -71.462  78.770  1.00 263.03           C
ANISOU 6420  C   VAL B  12    42040  23305  34594  -3540  -9925   4347        C
ATOM   6421  O   VAL B  12      12.650 -72.348  78.698  1.00 264.95           O
ANISOU 6421  O   VAL B  12    42054  23443  35170  -3647 -10013   4726        O
ATOM   6422  CB  VAL B  12      12.552 -71.014  81.033  1.00 268.29           C
ANISOU 6422  CB  VAL B  12    43377  24237  34324  -3676  -9457   5278        C
ATOM   6423  CG1 VAL B  12      12.884 -70.554  82.444  1.00 270.92           C
ANISOU 6423  CG1 VAL B  12    44234  24673  34031  -3707  -9378   5533        C
ATOM   6424  CG2 VAL B  12      11.278 -70.355  80.533  1.00 266.54           C
ANISOU 6424  CG2 VAL B  12    43030  24304  33940  -3622  -8822   5412        C
ATOM   6425  N   ASP B  13      14.234 -71.089  77.733  1.00 259.49           N
ANISOU 6425  N   ASP B  13    41407  22831  34354  -3404 -10001   3736        N
ATOM   6426  CA  ASP B  13      14.130 -71.756  76.437  1.00 257.77           C
ANISOU 6426  CA  ASP B  13    40714  22455  34773  -3371 -10227   3463        C
ATOM   6427  C   ASP B  13      15.179 -71.204  75.470  1.00 254.06           C
ANISOU 6427  C   ASP B  13    40137  21962  34433  -3198 -10305   2766        C
ATOM   6428  O   ASP B  13      16.052 -70.426  75.866  1.00 253.13           O
ANISOU 6428  O   ASP B  13    40300  21904  33971  -3123 -10251   2513        O
ATOM   6429  CB  ASP B  13      12.713 -71.629  75.849  1.00 257.00           C
ANISOU 6429  CB  ASP B  13    40377  22562  34707  -3360  -9786   3688        C
ATOM   6430  CG  ASP B  13      12.356 -72.776  74.896  1.00 257.27           C
ANISOU 6430  CG  ASP B  13    39937  22363  35451  -3408 -10141   3652        C
ATOM   6431  OD1 ASP B  13      13.107 -73.773  74.844  1.00 258.62           O
ANISOU 6431  OD1 ASP B  13    39982  22381  36083  -3476 -10727   3549        O
ATOM   6432  OD2 ASP B  13      11.317 -72.682  74.202  1.00 256.25           O
ANISOU 6432  OD2 ASP B  13    39558  22381  35425  -3378  -9837   3728        O
ATOM   6433  N   LEU B  14      15.083 -71.620  74.209  1.00 252.40           N
ANISOU 6433  N   LEU B  14    39517  21658  34725  -3131 -10432   2461        N
ATOM   6434  CA  LEU B  14      16.030 -71.238  73.161  1.00 249.02           C
ANISOU 6434  CA  LEU B  14    38932  21180  34503  -2957 -10527   1806        C
ATOM   6435  C   LEU B  14      15.689 -69.910  72.466  1.00 245.34           C
ANISOU 6435  C   LEU B  14    38465  21067  33685  -2765  -9912   1518        C
ATOM   6436  O   LEU B  14      14.571 -69.401  72.567  1.00 245.18           O
ANISOU 6436  O   LEU B  14    38477  21324  33357  -2767  -9421   1811        O
ATOM   6437  CB  LEU B  14      16.125 -72.366  72.123  1.00 248.93           C
ANISOU 6437  CB  LEU B  14    38485  20888  35208  -2967 -10978   1604        C
ATOM   6438  CG  LEU B  14      16.436 -73.765  72.673  1.00 252.52           C
ANISOU 6438  CG  LEU B  14    38876  20967  36102  -3154 -11601   1871        C
ATOM   6439  CD1 LEU B  14      15.673 -74.857  71.937  1.00 253.52           C
ANISOU 6439  CD1 LEU B  14    38588  20934  36804  -3226 -11822   1991        C
ATOM   6440  CD2 LEU B  14      17.933 -74.041  72.657  1.00 252.28           C
ANISOU 6440  CD2 LEU B  14    38889  20652  36316  -3123 -12069   1478        C
ATOM   6441  N   GLU B  15      16.666 -69.357  71.756  1.00 241.76           N
ANISOU 6441  N   GLU B  15    37968  20595  33297  -2594  -9935    951        N
ATOM   6442  CA  GLU B  15      16.472 -68.118  71.012  1.00 238.18           C
ANISOU 6442  CA  GLU B  15    37486  20449  32560  -2392  -9380    634        C
```

FIG. 13 Continued

```
ATOM   6443  C   GLU B  15      17.444 -68.053  69.837  1.00235.35           C
ANISOU 6443  C   GLU B  15    36893  19961  32567  -2210  -9569      7       C
ATOM   6444  O   GLU B  15      18.656 -68.156  70.015  1.00235.37           O
ANISOU 6444  O   GLU B  15    36990  19744  32698  -2189  -9915   -272       O
ATOM   6445  CB  GLU B  15      16.614 -66.900  71.926  1.00237.84           C
ANISOU 6445  CB  GLU B  15    37853  20649  31867  -2358  -8950    702       C
ATOM   6446  CG  GLU B  15      16.975 -65.619  71.202  1.00234.05           C
ANISOU 6446  CG  GLU B  15    37371  20390  31167  -2129  -8510    233       C
ATOM   6447  CD  GLU B  15      18.448 -65.281  71.323  1.00233.17           C
ANISOU 6447  CD  GLU B  15    37405  20111  31079  -2044  -8757   -203       C
ATOM   6448  OE1 GLU B  15      19.176 -65.410  70.319  1.00231.12           O
ANISOU 6448  OE1 GLU B  15    36903  19706  31207  -1909  -8956   -667       O
ATOM   6449  OE2 GLU B  15      18.878 -64.890  72.429  1.00234.66           O
ANISOU 6449  OE2 GLU B  15    37951  20308  30901  -2110  -8756    -79       O
ATOM   6450  N   LYS B  16      16.881 -67.870  68.644  1.00233.08           N
ANISOU 6450  N   LYS B  16    36304  19816  32441  -2074  -9330   -198       N
ATOM   6451  CA  LYS B  16      17.600 -67.895  67.363  1.00230.49           C
ANISOU 6451  CA  LYS B  16    35702  19383  32491  -1885  -9478   -767       C
ATOM   6452  C   LYS B  16      17.602 -69.310  66.775  1.00231.98           C
ANISOU 6452  C   LYS B  16    35565  19262  33315  -1966 -10035   -792       C
ATOM   6453  O   LYS B  16      18.447  69.670  65.957  1.00230.86           O
ANISOU 6453  O   LYS B  16    35232  18911  33572  -1860 -10349  -1229       O
ATOM   6454  CB  LYS B  16      19.009 -67.301  67.453  1.00229.04           C
ANISOU 6454  CB  LYS B  16    35689  19093  32243  -1766  -9567  -1195       C
ATOM   6455  CG  LYS B  16      19.029 -65.778  67.402  1.00226.34           C
ANISOU 6455  CG  LYS B  16    35522  19077  31401  -1591  -8951  -1377       C
ATOM   6456  CD  LYS B  16      18.149 -65.248  66.282  1.00223.81           C
ANISOU 6456  CD  LYS B  16    34952  19041  31046  -1425  -8486  -1492       C
ATOM   6457  CE  LYS B  16      18.625 -65.728  64.928  1.00222.15           C
ANISOU 6457  CE  LYS B  16    34391  18675  31342  -1269  -8742  -1947       C
ATOM   6458  NZ  LYS B  16      17.706 -65.308  63.843  1.00220.06           N
ANISOU 6458  NZ  LYS B  16    33877  18689  31048  -1113  -8329  -2029       N
ATOM   6459  N   ILE B  17      16.632 -70.098  67.227  1.00233.91           N
ANISOU 6459  N   ILE B  17    35751  19474  33652  -2155 -10141   -309       N
ATOM   6460  CA  ILE B  17      16.380 -71.443  66.736  1.00235.68           C
ANISOU 6460  CA  ILE B  17    35653  19430  34465  -2253 -10616   -252       C
ATOM   6461  C   ILE B  17      15.538 -71.239  65.449  1.00233.60           C
ANISOU 6461  C   ILE B  17    35067  19370  34321  -2108 -10336   -437       C
ATOM   6462  O   ILE B  17      15.777 -70.265  64.741  1.00230.51           O
ANISOU 6462  O   ILE B  17    34667  19188  33728  -1895  -9984   -808       O
ATOM   6463  CB  ILE B  17      15.700 -72.273  67.862  1.00239.55           C
ANISOU 6463  CB  ILE B  17    36240  19810  34969  -2511 -10804    373       C
ATOM   6464  CG1 ILE B  17      16.061 -73.765  67.750  1.00242.01           C
ANISOU 6464  CG1 ILE B  17    36323  19706  35923  -2644 -11475    394       C
ATOM   6465  CG2 ILE B  17      14.202 -71.943  67.968  1.00239.94           C
ANISOU 6465  CG2 ILE B  17    36259  20157  34752  -2555 -10328    794       C
ATOM   6466  CD1 ILE B  17      15.335 -74.672  68.718  1.00245.89           C
ANISOU 6466  CD1 ILE B  17    36847  20072  36508  -2884 -11667   1007       C
ATOM   6467  N   PRO B  18      14.607 -72.153  65.092  1.00268.07           N
ANISOU 6467  N   PRO B  18    39153  23665  39036  -2209 -10503   -209       N
ATOM   6468  CA  PRO B  18      13.816 -71.712  63.935  1.00265.89           C
ANISOU 6468  CA  PRO B  18    38623  23644  38759  -2048 -10158   -394       C
ATOM   6469  C   PRO B  18      13.016 -70.439  64.210  1.00264.37           C
ANISOU 6469  C   PRO B  18    38611  23869  37969  -1981  -9468   -189       C
ATOM   6470  O   PRO B  18      12.053 -70.457  64.978  1.00266.21           O
ANISOU 6470  O   PRO B  18    38940  24213  37995  -2130  -9265    323       O
ATOM   6471  CB  PRO B  18      12.865 -72.881  63.704  1.00268.42           C
ANISOU 6471  CB  PRO B  18    38644  23821  39520  -2197 -10441   -110       C
ATOM   6472  CG  PRO B  18      13.653 -74.058  64.111  1.00270.85           C
ANISOU 6472  CG  PRO B  18    38927  23710  40272  -2343 -11075    -99       C
ATOM   6473  CD  PRO B  18      14.509 -73.614  65.271  1.00271.24           C
ANISOU 6473  CD  PRO B  18    39370  23718  39973  -2399 -11070      6       C
ATOM   6474  N   ILE B  19      13.423 -69.355  63.555  1.00228.66           N
ANISOU 6474  N   ILE B  19    34122  19565  33195  -1751  -9107   -592       N
ATOM   6475  CA  ILE B  19      12.822 -68.033  63.711  1.00226.81           C
ANISOU 6475  CA  ILE B  19    34052  19726  32401  -1654  -8430   -481       C
ATOM   6476  C   ILE B  19      11.324 -67.990  63.407  1.00227.21           C
ANISOU 6476  C   ILE B  19    33921  20016  32392  -1684  -8100   -150       C
ATOM   6477  O   ILE B  19      10.555 -67.371  64.142  1.00227.68           O
```

FIG. 13 Continued

```
ANISOU 6477  O   ILE B  19    34168  20303  32038  -1752  -7668    243          O
ATOM   6478  CB  ILE B  19     13.556 -67.010  62.820  1.00223.18           C
ANISOU 6478  CB  ILE B  19    33575  19421  31801  -1376  -8151  -1030          C
ATOM   6479  CG1 ILE B  19     15.007 -66.853  63.282  1.00222.80           C
ANISOU 6479  CG1 ILE B  19    33751  19163  31739  -1348  -8391  -1313          C
ATOM   6480  CG2 ILE B  19     12.830 -65.685  62.811  1.00221.21           C
ANISOU 6480  CG2 ILE B  19    33433  19585  31031  -1262  -7439   -927          C
ATOM   6481  CD1 ILE B  19     15.174 -66.900  64.779  1.00225.14           C
ANISOU 6481  CD1 ILE B  19    34396  19376  31771  -1553  -8468   -926          C
ATOM   6482  N   GLU B  20     10.914 -68.657  62.331  1.00238.11           N
ANISOU 6482  N   GLU B  20    34937  21340  34194  -1633  -8310   -311          N
ATOM   6483  CA  GLU B  20      9.509 -68.685  61.923  1.00238.56           C
ANISOU 6483  CA  GLU B  20    34776  21605  34261  -1654  -8047    -34          C
ATOM   6484  C   GLU B  20      8.609 -69.216  63.035  1.00241.81           C
ANISOU 6484  C   GLU B  20    35281  21961  34636  -1912  -8062    607          C
ATOM   6485  O   GLU B  20      7.412 -69.428  62.835  1.00242.84           O
ANISOU 6485  O   GLU B  20    35221  22202  34846  -1971  -7914    907          O
ATOM   6486  CB  GLU B  20      9.324 -69.522  60.646  1.00238.57           C
ANISOU 6486  CB  GLU B  20    34368  21487  34789  -1580  -8397   -325          C
ATOM   6487  CG  GLU B  20      9.776 -68.834  59.350  1.00235.25           C
ANISOU 6487  CG  GLU B  20    33807  21237  34341  -1286  -8217   -894          C
ATOM   6488  CD  GLU B  20      8.798 -67.772  58.854  1.00233.33           C
ANISOU 6488  CD  GLU B  20    33506  21416  33734  -1142  -7591   -825          C
ATOM   6489  OE1 GLU B  20      7.575 -67.952  59.029  1.00234.82           O
ANISOU 6489  OE1 GLU B  20    33590  21719  33913  -1259  -7441   -415          O
ATOM   6490  OE2 GLU B  20      9.254 -66.758  58.279  1.00230.39           O
ANISOU 6490  OE2 GLU B  20    33181  21254  33103   -908  -7244  -1175          O
ATOM   6491  N   GLU B  21      9.190 -69.423  64.210  1.00233.41           N
ANISOU 6491  N   GLU B  21    34509  20724  33452  -2058  -8239    822          N
ATOM   6492  CA  GLU B  21      8.446 -69.958  65.337  1.00236.73           C
ANISOU 6492  CA  GLU B  21    35046  21070  33831  -2295  -8270   1437          C
ATOM   6493  C   GLU B  21      7.729 -68.887  66.153  1.00236.53           C
ANISOU 6493  C   GLU B  21    35303  21366  33201  -2311  -7640   1816          C
ATOM   6494  O   GLU B  21      8.329 -67.905  66.589  1.00234.97           O
ANISOU 6494  O   GLU B  21    35406  21313  32558  -2227  -7352   1685          O
ATOM   6495  CB  GLU B  21      9.365 -70.782  66.222  1.00239.08           C
ANISOU 6495  CB  GLU B  21    35514  21022  34302  -2448  -8788   1521          C
ATOM   6496  CG  GLU B  21      8.739 -72.056  66.717  1.00242.83           C
ANISOU 6496  CG  GLU B  21    35853  21247  35165  -2673  -9155   1979          C
ATOM   6497  CD  GLU B  21      9.771 -72.980  67.293  1.00244.86           C
ANISOU 6497  CD  GLU B  21    36197  21131  35709  -2790  -9744   1953          C
ATOM   6498  OE1 GLU B  21     10.969 -72.762  67.022  1.00243.13           O
ANISOU 6498  OE1 GLU B  21    36055  20820  35504  -2681  -9932   1495          O
ATOM   6499  OE2 GLU B  21      9.387 -73.918  68.016  1.00248.25           O
ANISOU 6499  OE2 GLU B  21    36609  21354  36359  -2988 -10011   2397          O
ATOM   6500  N   VAL B  22      6.436 -69.114  66.358  1.00238.67           N
ANISOU 6500  N   VAL B  22    35465  21731  33489  -2421  -7438   2289          N
ATOM   6501  CA  VAL B  22      5.554 -68.199  67.064  1.00238.80           C
ANISOU 6501  CA  VAL B  22    35700  22045  32987  -2445  -6823   2700          C
ATOM   6502  C   VAL B  22      5.073 -68.734  68.403  1.00242.50           C
ANISOU 6502  C   VAL B  22    36374  22395  33369  -2671  -6873   3320          C
ATOM   6503  O   VAL B  22      5.242 -68.100  69.443  1.00243.02           O
ANISOU 6503  O   VAL B  22    36818  22565  32953  -2707  -6601   3533          O
ATOM   6504  CB  VAL B  22      4.284 -67.977  66.243  1.00238.05           C
ANISOU 6504  CB  VAL B  22    35305  22176  32969  -2388  -6480   2813          C
ATOM   6505  CG1 VAL B  22      3.210 -67.332  67.103  1.00239.15           C
ANISOU 6505  CG1 VAL B  22    35636  22552  32678  -2467  -5915   3362          C
ATOM   6506  CG2 VAL B  22      4.590 -67.162  65.002  1.00234.27           C
ANISOU 6506  CG2 VAL B  22    34674  21910  32429  -2137  -6262   2265          C
ATOM   6507  N   PHE B  23      4.450 -69.905  68.347  1.00245.47           N
ANISOU 6507  N   PHE B  23    36490  22553  34223  -2817  -7215   3607          N
ATOM   6508  CA  PHE B  23      3.827 -70.539  69.507  1.00249.29           C
ANISOU 6508  CA  PHE B  23    37099  22909  34709  -3029  -7263   4243          C
ATOM   6509  C   PHE B  23      4.753 -70.708  70.720  1.00251.07           C
ANISOU 6509  C   PHE B  23    37708  22971  34715  -3124  -7490   4370          C
ATOM   6510  O   PHE B  23      4.811  69.839  71.588  1.00250.99           O
ANISOU 6510  O   PHE B  23    38073  23150  34142  -3113  -7105   4539          O
ATOM   6511  CB  PHE B  23      3.211 -71.891  69.105  1.00251.80           C
ANISOU 6511  CB  PHE B  23    37025  22958  35689  -3157  -7696   4435          C
```

FIG. 13 Continued

```
ATOM   6512  CG  PHE B  23       2.170 -71.796  68.009  1.00250.66           C
ANISOU 6512  CG  PHE B  23    36503  22970  35768  -3084  -7488   4380       C
ATOM   6513  CD1 PHE B  23       2.509 -71.350  66.738  1.00247.34           C
ANISOU 6513  CD1 PHE B  23    35883  22677  35418  -2889  -7469   3805       C
ATOM   6514  CD2 PHE B  23       0.857 -72.174  68.246  1.00253.08           C
ANISOU 6514  CD2 PHE B  23    36646  23289  36225  -3206  -7323   4907       C
ATOM   6515  CE1 PHE B  23       1.559 -71.270  65.731  1.00246.47           C
ANISOU 6515  CE1 PHE B  23    35430  22718  35499  -2815  -7297   3753       C
ATOM   6516  CE2 PHE B  23      -0.096 -72.097  67.242  1.00252.20           C
ANISOU 6516  CE2 PHE B  23    36179  23315  36329  -3141  -7155   4855       C
ATOM   6517  CZ  PHE B  23       0.257 -71.645  65.984  1.00248.90           C
ANISOU 6517  CZ  PHE B  23    35576  23037  35959  -2945  -7150   4274       C
ATOM   6518  N   GLN B  24       5.474 -71.824  70.774  1.00251.17           N
ANISOU 6518  N   GLN B  24    37625  22631  35175  -3214  -8119   4284       N
ATOM   6519  CA  GLN B  24       6.351 -72.130  71.908  1.00253.23           C
ANISOU 6519  CA  GLN B  24    38218  22707  35291  -3313  -8405   4424       C
ATOM   6520  C   GLN B  24       7.417 -71.065  72.178  1.00250.88           C
ANISOU 6520  C   GLN B  24    38270  22554  34497  -3186  -8239   4057       C
ATOM   6521  O   GLN B  24       7.902 -70.933  73.304  1.00252.54           O
ANISOU 6521  O   GLN B  24    38846  22731  34375  -3254  -8270   4256       O
ATOM   6522  CB  GLN B  24       6.996 -73.510  71.729  1.00255.11           C
ANISOU 6522  CB  GLN B  24    38239  22534  36159  -3412  -9126   4325       C
ATOM   6523  CG  GLN B  24       7.335 -73.876  70.281  1.00252.85           C
ANISOU 6523  CG  GLN B  24    37555  22139  36376  -3302  -9422   3771       C
ATOM   6524  CD  GLN B  24       6.170 -74.507  69.524  1.00253.69           C
ANISOU 6524  CD  GLN B  24    37245  22222  36925  -3343  -9432   3930       C
ATOM   6525  OE1 GLN B  24       5.380 -75.265  70.088  1.00256.94           O
ANISOU 6525  OE1 GLN B  24    37578  22504  37544  -3509  -9515   4447       O
ATOM   6526  NE2 GLN B  24       6.074 -74.205  68.232  1.00250.89           N
ANISOU 6526  NE2 GLN B  24    36617  21985  36726  -3187  -9358   3483       N
ATOM   6527  N   GLN B  25       7.777 -70.315  71.137  1.00247.81           N
ANISOU 6527  N   GLN B  25    37765  22321  34070  -2997  -8068   3523       N
ATOM   6528  CA  GLN B  25       8.760 -69.238  71.249  1.00245.30           C
ANISOU 6528  CA  GLN B  25    37732  22145  33326  -2856  -7876   3134       C
ATOM   6529  C   GLN B  25       8.184 -68.113  72.114  1.00245.31           C
ANISOU 6529  C   GLN B  25    38082  22466  32660  -2849  -7248   3448       C
ATOM   6530  O   GLN B  25       8.916 -67.441  72.848  1.00245.08           O
ANISOU 6530  O   GLN B  25    38413  22496  32212  -2820  -7148   3363       O
ATOM   6531  CB  GLN B  25       9.149 -68.717  69.859  1.00241.42           C
ANISOU 6531  CB  GLN B  25    36994  21753  32982  -2644  -7797   2525       C
ATOM   6532  CG  GLN B  25      10.326 -67.746  69.851  1.00238.85           C
ANISOU 6532  CG  GLN B  25    36905  21504  32342  -2490  -7690   2061       C
ATOM   6533  CD  GLN B  25      11.670 -68.439  69.759  1.00239.11           C
ANISOU 6533  CD  GLN B  25    36920  21200  32728  -2494  -8305   1706       C
ATOM   6534  OE1 GLN B  25      11.956 -69.135  68.785  1.00238.41           O
ANISOU 6534  OE1 GLN B  25    36510  20929  33146  -2447  -8665   1401       O
ATOM   6535  NE2 GLN B  25      12.512 -68.236  70.766  1.00240.17           N
ANISOU 6535  NE2 GLN B  25    37404  21253  32596  -2545  -8425   1736       N
ATOM   6536  N   LEU B  26       6.867 -67.924  72.012  1.00246.04           N
ANISOU 6536  N   LEU B  26    38057  22753  32672  -2874  -6832   3806       N
ATOM   6537  CA  LEU B  26       6.120 -66.953  72.816  1.00246.41           C
ANISOU 6537  CA  LEU B  26    38400  23096  32130  -2881  -6209   4174       C
ATOM   6538  C   LEU B  26       4.630 -67.270  72.718  1.00247.92           C
ANISOU 6538  C   LEU B  26    38374  23372  32453  -2964  -5949   4659       C
ATOM   6539  O   LEU B  26       3.943 -66.800  71.810  1.00245.79           O
ANISOU 6539  O   LEU B  26    37860  23301  32229  -2861  -5619   4544       O
ATOM   6540  CB  LEU B  26       6.387 -65.521  72.364  1.00242.73           C
ANISOU 6540  CB  LEU B  26    38044  22934  31246  -2683  -5705   3781       C
ATOM   6541  CG  LEU B  26       6.074 -64.461  73.421  1.00243.24           C
ANISOU 6541  CG  LEU B  26    38525  23253  30641  -2688  -5147   4065       C
ATOM   6542  CD1 LEU B  26       6.722 -63.144  73.041  1.00239.72           C
ANISOU 6542  CD1 LEU B  26    38211  23030  29843  -2494  -4786   3584       C
ATOM   6543  CD2 LEU B  26       4.575 -64.299  73.621  1.00244.45           C
ANISOU 6543  CD2 LEU B  26    38620  23602  30659  -2750  -4663   4590       C
ATOM   6544  N   LYS B  27       4.152 -68.058  73.680  1.00250.69           N
ANISOU 6544  N   LYS B  27    38818  23569  32863  -3145  -6096   5209       N
ATOM   6545  CA  LYS B  27       2.775 -68.558  73.735  1.00252.87           C
ANISOU 6545  CA  LYS B  27    38886  23855  33339  -3253  -5928   5736       C
ATOM   6546  C   LYS B  27       1.820 -67.875  72.754  1.00250.41           C
```

FIG. 13 Continued

```
ANISOU 6546  C   LYS B  27    38310  23812  33022  -3140  -5455   5653       C
ATOM   6547  O   LYS B  27      1.196 -66.870  73.083  1.00249.72            O
ANISOU 6547  O   LYS B  27    38404  24012  32466  -3094  -4851   5847       O
ATOM   6548  CB  LYS B  27      2.235 -68.466  75.172  1.00256.17            C
ANISOU 6548  CB  LYS B  27    39664  24321  33347  -3378  -5652   6365       C
ATOM   6549  CG  LYS B  27      3.097 -69.178  76.226  1.00259.08            C
ANISOU 6549  CG  LYS B  27    40305  24433  33699  -3492  -6116   6514       C
ATOM   6550  CD  LYS B  27      2.476 -70.484  76.710  1.00263.17            C
ANISOU 6550  CD  LYS B  27    40671  24684  34636  -3673  -6431   7057       C
ATOM   6551  CE  LYS B  27      1.395 -70.221  77.746  1.00265.92            C
ANISOU 6551  CE  LYS B  27    41249  25178  34612  -3752  -5944   7726       C
ATOM   6552  NZ  LYS B  27      0.809 -71.480  78.277  1.00270.11            N
ANISOU 6552  NZ  LYS B  27    41641  25440  35549  -3921  -6232   8282       N
ATOM   6553  N   CYS B  28      1.728 -68.443  71.552  1.00250.14            N
ANISOU 6553  N   CYS B  28    37849  23678  33515  -3096  -5746   5361       N
ATOM   6554  CA  CYS B  28      0.860 -67.953  70.479  1.00247.95            C
ANISOU 6554  CA  CYS B  28    37264  23628  33319  -2984  -5396   5245       C
ATOM   6555  C   CYS B  28      0.306 -66.553  70.711  1.00246.23            C
ANISOU 6555  C   CYS B  28    37261  23788  32506  -2887  -4650   5357       C
ATOM   6556  O   CYS B  28     -0.637 -66.366  71.481  1.00248.20            O
ANISOU 6556  O   CYS B  28    37639  24139  32528  -2979  -4273   5893       O
ATOM   6557  CB  CYS B  28     -0.291 -68.930  70.224  1.00250.46            C
ANISOU 6557  CB  CYS B  28    37221  23811  34131  -3109  -5538   5635       C
ATOM   6558  SG  CYS B  28     -1.394 -68.439  68.877  1.00248.17            S
ANISOU 6558  SG  CYS B  28    36521  23781  33990  -2979  -5173   5505       S
ATOM   6559  N   SER B  29      0.885 -65.575  70.026  1.00271.74            N
ANISOU 6559  N   SER B  29    40522  27222  35505  -2696  -4429   4854       N
ATOM   6560  CA  SER B  29      0.443 -64.191  70.145  1.00269.80            C
ANISOU 6560  CA  SER B  29    40460  27336  34717  -2585  -3719   4897       C
ATOM   6561  C   SER B  29      0.938 -63.379  68.954  1.00265.72            C
ANISOU 6561  C   SER B  29    39792  27003  34167  -2357  -3568   4298       C
ATOM   6562  O   SER B  29      1.956 -62.688  69.041  1.00263.77            O
ANISOU 6562  O   SER B  29    39771  26808  33642  -2248  -3516   3926       O
ATOM   6563  CB  SER B  29      0.958 -63.579  71.450  1.00270.72            C
ANISOU 6563  CB  SER B  29    41077  27502  34283  -2627  -3506   5055       C
ATOM   6564  OG  SER B  29      0.457 -64.275  72.579  1.00274.64            O
ANISOU 6564  OG  SER B  29    41732  27852  34766  -2822  -3597   5639       O
ATOM   6565  N   ARG B  30      0.213  63.467  67.841  1.00235.09            N
ANISOU 6565  N   ARG B  30    35526  23220  30579  -2281  -3501   4211       N
ATOM   6566  CA  ARG B  30      0.588 -62.750  66.627  1.00231.40            C
ANISOU 6566  CA  ARG B  30    34881  22936  30104  -2051  -3353   3668       C
ATOM   6567  C   ARG B  30      0.219 -61.282  66.720  1.00229.26            C
ANISOU 6567  C   ARG B  30    34782  23030  29296  -1924  -2614   3696       C
ATOM   6568  O   ARG B  30      0.451 -60.507  65.792  1.00226.16            O
ANISOU 6568  O   ARG B  30    34271  22834  28825  -1719  -2379   3294       O
ATOM   6569  CB  ARG B  30     -0.047 -63.384  65.390  1.00231.13            C
ANISOU 6569  CB  ARG B  30    34375  22880  30564  -2005  -3567   3555       C
ATOM   6570  CG  ARG B  30      0.517 -64.757  65.067  1.00232.65            C
ANISOU 6570  CG  ARG B  30    34368  22711  31319  -2087  -4318   3377       C
ATOM   6571  CD  ARG B  30      1.971 -64.875  65.528  1.00232.29            C
ANISOU 6571  CD  ARG B  30    34586  22466  31209  -2082  -4666   3065       C
ATOM   6572  NE  ARG B  30      2.906 -64.130  64.689  1.00228.80            N
ANISOU 6572  NE  ARG B  30    34137  22136  30659  -1852  -4596   2463       N
ATOM   6573  CZ  ARG B  30      4.158 -63.851  65.034  1.00227.80            C
ANISOU 6573  CZ  ARG B  30    34262  21915  30375  -1801  -4735   2154       C
ATOM   6574  NH1 ARG B  30      4.630 -64.246  66.209  1.00230.03            N
ANISOU 6574  NH1 ARG B  30    34833  22001  30567  -1965  -4964   2383       N
ATOM   6575  NH2 ARG B  30      4.935 -63.170  64.206  1.00224.67            N
ANISOU 6575  NH2 ARG B  30    33827  21620  29916  -1581  -4643   1621       N
ATOM   6576  N   GLU B  31     -0.354 -60.911  67.858  1.00230.66            N
ANISOU 6576  N   GLU B  31    35242  23293  29105  -2041  -2241   4180       N
ATOM   6577  CA  GLU B  31     -0.750 -59.540  68.110  1.00229.06            C
ANISOU 6577  CA  GLU B  31    35235  23420  28377  -1945  -1519   4264       C
ATOM   6578  C   GLU B  31     -0.420 -59.226  69.567  1.00230.86            C
ANISOU 6578  C   GLU B  31    35937  23619  28161  -2055  -1372   4531       C
ATOM   6579  O   GLU B  31      0.393 -58.347  69.858  1.00229.23            O
ANISOU 6579  O   GLU B  31    36005  23508  27585  -1959  -1175   4252       O
ATOM   6580  CB  GLU B  31     -2.245 -59.365  67.834  1.00229.63            C
ANISOU 6580  CB  GLU B  31    35082  23684  28481  -1968  -1092   4673       C
```

FIG. 13 Continued

```
ATOM   6581  CG  GLU B  31      -2.815 -60.321  66.773  1.00230.05           C
ANISOU 6581  CG  GLU B  31     34663  23632  29113  -1977  -1463   4639      C
ATOM   6582  CD  GLU B  31      -2.189 -60.158  65.388  1.00226.91           C
ANISOU 6582  CD  GLU B  31     34000  23291  28925  -1766  -1640   4020      C
ATOM   6583  OE1 GLU B  31      -1.998 -59.008  64.936  1.00223.99           O
ANISOU 6583  OE1 GLU B  31     33675  23187  28246  -1578  -1195   3748      O
ATOM   6584  OE2 GLU B  31      -1.896 -61.190  64.744  1.00227.47           O
ANISOU 6584  OE2 GLU B  31     33812  23138  29478  -1784  -2218   3809      O
ATOM   6585  N   GLY B  32      -1.039 -59.970  70.477  1.00233.95           N
ANISOU 6585  N   GLY B  32     36419  23869  28603  -2254  -1483   5068      N
ATOM   6586  CA  GLY B  32      -0.794 -59.814  71.899  1.00236.22           C
ANISOU 6586  CA  GLY B  32     37156  24115  28483  -2366  -1387   5370      C
ATOM   6587  C   GLY B  32      -2.068 -59.967  72.703  1.00239.22           C
ANISOU 6587  C   GLY B  32     37605  24544  28743  -2511  -1055   6053      C
ATOM   6588  O   GLY B  32      -2.887 -59.053  72.738  1.00238.46           O
ANISOU 6588  O   GLY B  32     37546  24714  28345  -2458   -428   6247      O
ATOM   6589  N   LEU B  33      -2.239 -61.121  73.348  1.00243.27           N
ANISOU 6589  N   LEU B  33     38127  24796  29508  -2688  -1461   6428      N
ATOM   6590  CA  LEU B  33      -3.426 -61.384  74.165  1.00246.53           C
ANISOU 6590  CA  LEU B  33     38602  25216  29850  -2830  -1181   7113      C
ATOM   6591  C   LEU B  33      -3.495 -60.412  75.347  1.00247.40           C
ANISOU 6591  C   LEU B  33     39196  25514  29292  -2833   -645   7366      C
ATOM   6592  O   LEU B  33      -3.015 -60.712  76.445  1.00249.89           O
ANISOU 6592  O   LEU B  33     39859  25701  29389  -2926   -825   7554      O
ATOM   6593  CB  LEU B  33      -3.447 -62.839  74.655  1.00250.17           C
ANISOU 6593  CB  LEU B  33     38992  25336  30726  -3010  -1759   7439      C
ATOM   6594  CG  LEU B  33      -3.664 -63.927  73.601  1.00250.18           C
ANISOU 6594  CG  LEU B  33     38494  25133  31432  -3041  -2256   7318      C
ATOM   6595  CD1 LEU B  33      -3.503 -65.296  74.220  1.00253.84           C
ANISOU 6595  CD1 LEU B  33     38941  25244  32260  -3216  -2826   7614      C
ATOM   6596  CD2 LEU B  33      -5.032 -63.791  72.964  1.00250.02           C
ANISOU 6596  CD2 LEU B  33     38136  25258  31603  -3032  -1886   7581      C
ATOM   6597  N   THR B  34      -4.113 -59.256  75.104  1.00280.75           N
ANISOU 6597  N   THR B  34     43436  30042  33196  -2728     15   7375      N
ATOM   6598  CA  THR B  34      -4.217 -58.181  76.088  1.00281.18           C
ANISOU 6598  CA  THR B  34     43925  30305  32605  -2706    594   7557      C
ATOM   6599  C   THR B  34      -2.853 -57.859  76.668  1.00280.72           C
ANISOU 6599  C   THR B  34     44245  30198  32217  -2667    373   7187      C
ATOM   6600  O   THR B  34      -2.357 -58.560  77.550  1.00283.46           O
ANISOU 6600  O   THR B  34     44828  30341  32534  -2779    -15   7348      O
ATOM   6601  CB  THR B  34      -5.191 -58.504  77.235  1.00285.21           C
ANISOU 6601  CB  THR B  34     44633  30784  32951  -2856    840   8276      C
ATOM   6602  OG1 THR B  34      -6.523 -58.611  76.719  1.00285.52           O
ANISOU 6602  OG1 THR B  34     44332  30898  33256  -2880   1145   8629      O
ATOM   6603  CG2 THR B  34      -5.158 -57.399  78.277  1.00285.75           C
ANISOU 6603  CG2 THR B  34     45189  31058  32324  -2824   1400   8408      C
ATOM   6604  N   THR B  35      -2.253 -56.790  76.165  1.00243.61           N
ANISOU 6604  N   THR B  35     39595  25684  27283  -2504    625   6696      N
ATOM   6605  CA  THR B  35      -0.943 -56.369  76.630  1.00242.91           C
ANISOU 6605  CA  THR B  35     39840  25558  26896  -2451    447   6298      C
ATOM   6606  C   THR B  35       0.946  56.267  78.157  1.00246.30           C
ANISOU 6606  C   THR B  35     40763  25978  26342  -2558    580   6687      C
ATOM   6607  O   THR B  35       0.107 -56.312  78.792  1.00247.08           O
ANISOU 6607  O   THR B  35     41162  25965  26750  -2571    268   6483      O
ATOM   6608  CB  THR B  35      -0.530 -55.026  75.986  1.00239.01           C
ANISOU 6608  CB  THR B  35     39351  25310  26152  -2255    874   5807      C
ATOM   6609  OG1 THR B  35      -0.850 -55.046  74.589  1.00236.21           O
ANISOU 6609  OG1 THR B  35     38531  25019  26197  -2148    884   5565      O
ATOM   6610  CG2 THR B  35       0.960 -54.784  76.154  1.00237.89           C
ANISOU 6610  CG2 THR B  35     39432  25070  25886  -2187    543   5292      C
ATOM   6611  N   GLN B  36      -2.140 -56.148  78.735  1.00247.36           N
ANISOU 6611  N   GLN B  36     40976  26224  26787  -2632   1039   7254      N
ATOM   6612  CA  GLN B  36      -2.295 -56.056  80.184  1.00250.89           C
ANISOU 6612  CA  GLN B  36     41889  26678  26759  -2726   1221   7681      C
ATOM   6613  C   GLN B  36      -2.290 -57.447  80.817  1.00254.68           C
ANISOU 6613  C   GLN B  36     42391  26870  27505  -2889    667   8061      C
ATOM   6614  O   GLN B  36      -1.723 -57.646  81.892  1.00257.27           O
ANISOU 6614  O   GLN B  36     43106  27107  27537  -2951    469   8177      O
ATOM   6615  CB  GLN B  36      -3.581 -55.305  80.546  1.00251.68           C
```

FIG. 13 Continued

```
ANISOU 6615  CB  GLN B  36     42072  27018  26537  -2724   1986   8138        C
ATOM   6616  CG  GLN B  36     -3.454 -54.391  81.761  1.00253.25              C
ANISOU 6616  CG  GLN B  36     42810  27371  26043  -2711   2424   8266        C
ATOM   6617  CD  GLN B  36     -3.029 -55.129  83.020  1.00257.33              C
ANISOU 6617  CD  GLN B  36     43703  27703  26368  -2832   2050   8553        C
ATOM   6618  OE1 GLN B  36     -3.414 -56.275  83.243  1.00260.02              O
ANISOU 6618  OE1 GLN B  36     43925  27843  27029  -2954   1708   8946        O
ATOM   6619  NE2 GLN B  36     -2.238 -54.466  83.856  1.00257.93              N
ANISOU 6619  NE2 GLN B  36     44235  27846  25922  -2793   2117   8361        N
ATOM   6620  N   GLU B  37     -2.925 -58.407  80.151  1.00254.89              N
ANISOU 6620  N   GLU B  37     41999  26753  28096  -2957    414   8255        N
ATOM   6621  CA  GLU B  37     -2.940 -59.780  80.641  1.00258.40              C
ANISOU 6621  CA  GLU B  37     42403  26904  28874  -3109   -125   8607        C
ATOM   6622  C   GLU B  37     -1.513 -60.285  80.727  1.00258.23              C
ANISOU 6622  C   GLU B  37     42490  26674  28953  -3113   -787   8191        C
ATOM   6623  O   GLU B  37     -1.023 -60.626  81.801  1.00261.12              O
ANISOU 6623  O   GLU B  37     43205  26926  29082  -3188  -1014   8375        O
ATOM   6624  CB  GLU B  37     -3.752 -60.688  79.714  1.00258.39              C
ANISOU 6624  CB  GLU B  37     41876  26773  29529  -3164   -325   8770        C
ATOM   6625  CG  GLU B  37     -5.258 -60.633  79.929  1.00260.23              C
ANISOU 6625  CG  GLU B  37     42007  27107  29761  -3222    189   9376        C
ATOM   6626  CD  GLU B  37      5.693  61.269  81.235  1.00264.97              C
ANISOU 6626  CD  GLU B  37     42879  27574  30222  -3361    182  10020        C
ATOM   6627  OE1 GLU B  37     -4.829 -61.492  82.108  1.00266.73              O
ANISOU 6627  OE1 GLU B  37     43458  27694  30193  -3396   -109   9996        O
ATOM   6628  OE2 GLU B  37     -6.901 -61.544  81.391  1.00267.03              O
ANISOU 6628  OE2 GLU B  37     42996  27834  30629  -3431    471  10559        O
ATOM   6629  N   GLY B  38     -0.844 -60.314  79.580  1.00254.12              N
ANISOU 6629  N   GLY B  38     41668  26107  28781  -3024  -1088   7628        N
ATOM   6630  CA  GLY B  38      0.530 -60.761  79.514  1.00253.60              C
ANISOU 6630  CA  GLY B  38     41656  25835  28865  -3015  -1709   7188        C
ATOM   6631  C   GLY B  38      1.437 -60.001  80.461  1.00253.98              C
ANISOU 6631  C   GLY B  38     42203  25960  28338  -2975  -1626   7018        C
ATOM   6632  O   GLY B  38      2.439 -60.540  80.916  1.00255.27              O
ANISOU 6632  O   GLY B  38     42529  25922  28540  -3020  -2147   6877        O
ATOM   6633  N   GLU B  39      1.095 -58.750  80.762  1.00270.46              N
ANISOU 6633  N   GLU B  39     44529  28332  29900  -2892   -979   7025        N
ATOM   6634  CA  GLU B  39      1.920 -57.944  81.664  1.00270.88              C
ANISOU 6634  CA  GLU B  39     45063  28473  29387  -2848   -867   6845        C
ATOM   6635  C   GLU B  39      1.959 -58.567  83.051  1.00275.48              C
ANISOU 6635  C   GLU B  39     46022  28930  29717  -2982  -1076   7306        C
ATOM   6636  O   GLU B  39      3.006 -59.040  83.501  1.00276.71              O
ANISOU 6636  O   GLU B  39     46353  28901  29883  -3016  -1604   7135        O
ATOM   6637  CB  GLU B  39      1.412 -56.497  81.760  1.00269.24              C
ANISOU 6637  CB  GLU B  39     45034  26595  28671  -2741    -88   6816        C
ATOM   6638  CG  GLU B  39      2.332 -55.564  82.567  1.00269.33              C
ANISOU 6638  CG  GLU B  39     45513  28700  28119  -2678     31   6536        C
ATOM   6639  CD  GLU B  39      1.688 -54.229  82.918  1.00268.71              C
ANISOU 6639  CD  GLU B  39     45667  28932  27500  -2601    826   6631        C
ATOM   6640  OE1 GLU B  39      0.444 -54.139  82.893  1.00269.36              O
ANISOU 6640  OE1 GLU B  39     45644  29143  27559  -2630   1286   7066        O
ATOM   6641  OE2 GLU B  39      2.429 -53.269  83.228  1.00267.68              O
ANISOU 6641  OE2 GLU B  39     45819  28908  26981  -2512    991   6273        O
ATOM   6642  N   ASP B  40      0.810 -58.560  83.722  1.00305.46              N
ANISOU 6642  N   ASP B  40     49940  32828  33291  -3050   -653   7902        N
ATOM   6643  CA  ASP B  40      0.699 -59.122  85.063  1.00310.10              C
ANISOU 6643  CA  ASP B  40     50891  33320  33611  -3164   -775   8408        C
ATOM   6644  C   ASP B  40      1.157 -60.577  85.077  1.00312.14              C
ANISOU 6644  C   ASP B  40     50981  33247  34372  -3277  -1525   8509        C
ATOM   6645  O   ASP B  40      1.861 -61.002  85.994  1.00314.89              O
ANISOU 6645  O   ASP B  40     51640  33464  34537  -3332  -1893   8590        O
ATOM   6646  CB  ASP B  40     -0.738 -59.015  85.589  1.00312.47              C
ANISOU 6646  CB  ASP B  40     51252  33754  33719  -3216   -200   9064        C
ATOM   6647  CG  ASP B  40     -1.031 -57.669  86.233  1.00312.38              C
ANISOU 6647  CG  ASP B  40     51634  34039  33017  -3136    497   9103        C
ATOM   6648  OD1 ASP B  40     -0.444 -56.656  85.801  1.00309.15              O
ANISOU 6648  OD1 ASP B  40     51274  33782  32406  -3018    683   8582        O
ATOM   6649  OD2 ASP B  40     -1.856 -57.625  87.172  1.00315.64              O
ANISOU 6649  OD2 ASP B  40     52304  34526  33098  -3188    870   9660        O
```

FIG. 13 Continued

```
ATOM   6650  N   ARG B  41       0.762 -61.334  84.057  1.00 278.11           N
ANISOU 6650  N   ARG B  41    46173  28800  30694   3308   1755   8496        N
ATOM   6651  CA  ARG B  41       1.132 -62.747  83.977  1.00 279.97           C
ANISOU 6651  CA  ARG B  41    46199  28708  31471  -3416  -2456   8587        C
ATOM   6652  C   ARG B  41       2.635 -62.940  83.749  1.00 278.57           C
ANISOU 6652  C   ARG B  41    46057  28366  31419  -3381  -3050   8018        C
ATOM   6653  O   ARG B  41       3.271 -63.726  84.450  1.00 281.33           O
ANISOU 6653  O   ARG B  41    46571  28505  31817  -3463  -3543   8138        O
ATOM   6654  CB  ARG B  41       0.302 -63.485  82.918  1.00 279.08           C
ANISOU 6654  CB  ARG B  41    45537  28489  32012  -3456  -2545   8696        C
ATOM   6655  CG  ARG B  41      -1.191 -63.544  83.230  1.00 281.24           C
ANISOU 6655  CG  ARG B  41    45746  28855  32256  -3518  -2055   9337        C
ATOM   6656  CD  ARG B  41      -1.446 -63.888  84.691  1.00 285.95           C
ANISOU 6656  CD  ARG B  41    46743  29402  32503  -3614  -1998   9933        C
ATOM   6657  NE  ARG B  41      -1.101 -65.269  85.009  1.00 288.95           N
ANISOU 6657  NE  ARG B  41    47031  29455  33302  -3734  -2643  10149        N
ATOM   6658  CZ  ARG B  41      -1.988 -66.251  85.122  1.00 291.80           C
ANISOU 6658  CZ  ARG B  41    47159  29646  34065  -3844  -2723  10682        C
ATOM   6659  NH1 ARG B  41      -3.279 -66.006  84.945  1.00 292.04           N
ANISOU 6659  NH1 ARG B  41    47026  29802  34135  -3851  -2205  11054        N
ATOM   6660  NH2 ARG B  41      -1.585 -67.480  85.417  1.00 294.48           N
ANISOU 6660  NH2 ARG B  41    47420  29683  34787  -3947  -3319  10850        N
ATOM   6661  N   ILE B  42       3.204 -62.233  82.774  1.00 280.11           N
ANISOU 6661  N   ILE B  42    46095  28654  31681  -3254  -3001   7413        N
ATOM   6662  CA  ILE B  42       4.644 -62.310  82.548  1.00 278.66           C
ANISOU 6662  CA  ILE B  42    45951  28321  31605  -3206  -3515   6859        C
ATOM   6663  C   ILE B  42       5.327 -61.561  83.678  1.00 280.00           C
ANISOU 6663  C   ILE B  42    46656  28594  31137  -3180  -3401   6808        C
ATOM   6664  O   ILE B  42       5.585 -60.364  83.570  1.00 277.63           O
ANISOU 6664  O   ILE B  42    46515  28510  30462  -3061  -3009   6475        O
ATOM   6665  CB  ILE B  42       5.069 -61.701  81.194  1.00 273.87           C
ANISOU 6665  CB  ILE B  42    45035  27790  31232  -3059  -3454   6228        C
ATOM   6666  CG1 ILE B  42       4.580 -62.576  80.039  1.00 272.74           C
ANISOU 6666  CG1 ILE B  42    44359  27507  31762  -3081  -3697   6205        C
ATOM   6667  CG2 ILE B  42       6.583 -61.558  81.122  1.00 272.49           C
ANISOU 6667  CG2 ILE B  42    44979  27490  31064  -2993  -3884   5665        C
ATOM   6668  CD1 ILE B  42       5.190 -63.965  80.025  1.00 274.63           C
ANISOU 6668  CD1 ILE B  42    44441  27390  32517  -3188  -4451   6217        C
ATOM   6669  N   GLN B  43       5.608 -62.276  84.763  1.00 268.09           N
ANISOU 6669  N   GLN B  43    45421  26929  29510  -3289  -3747   7143        N
ATOM   6670  CA  GLN B  43       6.242 -61.685  85.932  1.00 270.02           C
ANISOU 6670  CA  GLN B  43    46196  27258  29143  -3274  -3697   7137        C
ATOM   6671  C   GLN B  43       7.415 -60.829  85.503  1.00 266.79           C
ANISOU 6671  C   GLN B  43    45853  26893  28621  -3150  -3776   6445        C
ATOM   6672  O   GLN B  43       7.755 -59.849  86.164  1.00 266.97           O
ANISOU 6672  O   GLN B  43    46263  27088  28086   3088   3495   6315        O
ATOM   6673  CB  GLN B  43       6.709 -62.768  86.902  1.00 274.27           C
ANISOU 6673  CB  GLN B  43    46931  27555  29724  -3395  -4261   7454        C
ATOM   6674  CG  GLN B  43       5.581 -63.551  87.551  1.00 278.11           C
ANISOU 6674  CG  GLN B  43    47428  28002  30240  -3511  -4146   8192        C
ATOM   6675  CD  GLN B  43       4.701 -62.688  88.434  1.00 279.86           C
ANISOU 6675  CD  GLN B  43    48022  28503  29807  -3489  -3463   8586        C
ATOM   6676  OE1 GLN B  43       4.890 -61.474  88.526  1.00 278.06           O
ANISOU 6676  OE1 GLN B  43    48034  28509  29108  -3387  -3054   8298        O
ATOM   6677  NE2 GLN B  43       3.731 -63.314  89.070  1.00 283.47           N
ANISOU 6677  NE2 GLN B  43    48527  28930  30249  -3580  -3326   9254        N
ATOM   6678  N   ILE B  44       8.034 -61.208  84.391  1.00 302.34           N
ANISOU 6678  N   ILE B  44    49974  31232  33670  -3110  -4158   6000        N
ATOM   6679  CA  ILE B  44       9.141 -60.440  83.849  1.00 299.08           C
ANISOU 6679  CA  ILE B  44    49564  30837  33234  -2981  -4233   5334        C
ATOM   6680  C   ILE B  44       8.575 -59.180  83.188  1.00 295.63           C
ANISOU 6680  C   ILE B  44    49045  30698  32562  -2846  -3542   5126        C
ATOM   6681  O   ILE B  44       8.028 -59.241  82.085  1.00 293.06           O
ANISOU 6681  O   ILE B  44    48316  30409  32625  -2799  -3396   5038        O
ATOM   6682  CB  ILE B  44       9.960 -61.260  82.827  1.00 297.17           C
ANISOU 6682  CB  ILE B  44    48928  30321  33662  -2970  -4840   4933        C
ATOM   6683  CG1 ILE B  44       9.614 -62.750  82.917  1.00 299.94           C
ANISOU 6683  CG1 ILE B  44    49074  30415  34476  -3120  -5315   5340        C
ATOM   6684  CG2 ILE B  44      11.450 -61.042  83.047  1.00 296.72           C
```

FIG. 13 Continued

```
ANISOU 6684  CG2 ILE B  44     49061  30131  33547  -2920  -5247   4453          C
ATOM   6685  CD1 ILE B  44     10.320 -63.479 84.039  1.00303.80                  C
ANISOU 6685  CD1 ILE B  44     49862  30696  34870  -3229  -5828   5548          C
ATOM   6686  N   PHE B  45      8.695 -58.046 83.879  1.00266.08                  N
ANISOU 6686  N   PHE B  45     45687  27168  28242  -2783  -3120   5057          N
ATOM   6687  CA  PHE B  45      8.199 -56.762 83.382  1.00263.07                  C
ANISOU 6687  CA  PHE B  45     45272  27076  27605  -2654  -2431   4872          C
ATOM   6688  C   PHE B  45      8.444 -55.646 84.395  1.00264.15                  C
ANISOU 6688  C   PHE B  45     45902  27403  27059  -2609  -2055   4829          C
ATOM   6689  O   PHE B  45      8.290 -55.845 85.597  1.00267.91                  O
ANISOU 6689  O   PHE B  45     46755  27883  27156  -2700  -2079   5211          O
ATOM   6690  CB  PHE B  45      6.704 -56.847 83.059  1.00263.09                  C
ANISOU 6690  CB  PHE B  45     45059  27228  27676  -2687  -1963   5328          C
ATOM   6691  CG  PHE B  45      5.821 -56.925 84.275  1.00267.02                  C
ANISOU 6691  CG  PHE B  45     45893  27819  27744  -2791  -1673   5958          C
ATOM   6692  CD1 PHE B  45      5.176 -55.798 84.752  1.00267.06                  C
ANISOU 6692  CD1 PHE B  45     46159  28106  27206  -2737   -977   6102          C
ATOM   6693  CD2 PHE B  45      5.636 -58.124 84.940  1.00270.78                  C
ANISOU 6693  CD2 PHE B  45     46421  28096  28367  -2936  -2085   6414          C
ATOM   6694  CE1 PHE B  45      4.362 -55.870 85.872  1.00270.81                  C
ANISOU 6694  CE1 PHE B  45     46951  28663  27280  -2824   -694   6688          C
ATOM   6695  CE2 PHE B  45      4.824 -58.204 86.058  1.00274.54                  C
ANISOU 6695  CE2 PHE B  45     47208  28655  28449  -3019  -1804   7010          C
ATOM   6696  CZ  PHE B  45      4.187 -57.076 86.525  1.00274.57                  C
ANISOU 6696  CZ  PHE B  45     47481  28941  27901  -2961  -1106   7146          C
ATOM   6697  N   GLY B  46      8.822 -54.470 83.908  1.00252.08                  N
ANISOU 6697  N   GLY B  46     44369  26031  25377  -2464  -1701   4365          N
ATOM   6698  CA  GLY B  46      9.007 -54.253 82.489  1.00247.80                  C
ANISOU 6698  CA  GLY B  46     43387  25488  25278  -2345  -1669   3932          C
ATOM   6699  C   GLY B  46     10.466 -54.316 82.096  1.00246.20                  C
ANISOU 6699  C   GLY B  46     43127  25085  25333  -2276  -2182   3350          C
ATOM   6700  O   GLY B  46     11.323 -54.612 82.931  1.00248.53                  O
ANISOU 6700  O   GLY B  46     43709  25227  25405  -2335  -2606   3301          O
ATOM   6701  N   PRO B  47     10.755 -54.028 80.816  1.00242.54                  N
ANISOU 6701  N   PRO B  47     42291  24622  25241  -2142  -2140   2910          N
ATOM   6702  CA  PRO B  47     12.104 -54.031 80.240  1.00240.52                  C
ANISOU 6702  CA  PRO B  47     41916  24177  25294  -2050  -2569   2327          C
ATOM   6703  C   PRO B  47     12.947 -52.901 80.808  1.00240.20                  C
ANISOU 6703  C   PRO B  47     42209  24212  24842  -1963  -2388   1978          C
ATOM   6704  O   PRO B  47     13.892 -52.463 80.154  1.00237.61                  O
ANISOU 6704  O   PRO B  47     41751  23813  24718   1833   2491   1449          O
ATOM   6705  CB  PRO B  47     11.853 -53.770 78.750  1.00236.47                  C
ANISOU 6705  CB  PRO B  47     40943  23738  25166  -1906  -2345   2034          C
ATOM   6706  CG  PRO B  47     10.407 -54.041 78.541  1.00236.91                  C
ANISOU 6706  CG  PRO B  47     40831  23948  25237  -1966  -2000   2512          C
ATOM   6707  CD  PRO B  47      9.741 -53.665 79.815  1.00239.88                  C
ANISOU 6707  CD  PRO B  47     41616  24480  25050  -2063  -1645   2967          C
ATOM   6708  N   ASN B  48     12.593  52.432 82.002  1.00305.33                  N
ANISOU 6708  N   ASN B  48     50881  32603  32528  -2027  -2111   2273          N
ATOM   6709  CA  ASN B  48     13.310 -51.345 82.662  1.00305.52                  C
ANISOU 6709  CA  ASN B  48     51259  32709  32116  -1956  -1922   1974          C
ATOM   6710  C   ASN B  48     14.777 -51.663 82.957  1.00306.34                  C
ANISOU 6710  C   ASN B  48     51481  32550  32365  -1961  -2568   1598          C
ATOM   6711  O   ASN B  48     15.454 -52.332 82.174  1.00304.86                  O
ANISOU 6711  O   ASN B  48     50991  32138  32704  -1938  -3040   1332          O
ATOM   6712  CB  ASN B  48     12.594 -50.923 83.954  1.00308.81                  C
ANISOU 6712  CB  ASN B  48     52126  33316  31892  -2037  -1543   2408          C
ATOM   6713  CG  ASN B  48     11.333 -50.116 83.693  1.00307.46                  C
ANISOU 6713  CG  ASN B  48     51893  33444  31484  -1985   -757   2641          C
ATOM   6714  OD1 ASN B  48     10.774 -50.151 82.598  1.00304.66                  O
ANISOU 6714  OD1 ASN B  48     51137  33147  31471  -1925   -551   2616          O
ATOM   6715  ND2 ASN B  48     10.879 -49.381 84.704  1.00309.58                  N
ANISOU 6715  ND2 ASN B  48     52561  33904  31162  -2005   -315   2867          N
ATOM   6716  N   LYS B  49     15.264 -51.165 84.089  1.00245.24                  N
ANISOU 6716  N   LYS B  49     44186  24838  24157  -1987  -2583   1571          N
ATOM   6717  CA  LYS B  49     16.655 -51.360 84.473  1.00246.30                  C
ANISOU 6717  CA  LYS B  49     44467  24737  24379  -1991  -3172   1218          C
ATOM   6718  C   LYS B  49     16.814 -52.405 85.565  1.00250.73                  C
ANISOU 6718  C   LYS B  49     45303  25141  24822  -2157  -3714   1593          C
```

FIG. 13 Continued

```
ATOM   6719  O   LYS B  49      15.980 -52.506  86.464  1.00253.68           O
ANISOU 6719  O   LYS B  49    45957  25654  24777   2249   3501   2082       O
ATOM   6720  CB  LYS B  49      17.260 -50.037  84.944  1.00245.99           C
ANISOU 6720  CB  LYS B  49    44722  24814  23931  -1889  -2872    847       C
ATOM   6721  CG  LYS B  49      17.203 -48.931  83.905  1.00241.71           C
ANISOU 6721  CG  LYS B  49    43918  24417  23505  -1711  -2329    453       C
ATOM   6722  CD  LYS B  49      17.897 -49.344  82.623  1.00238.47           C
ANISOU 6722  CD  LYS B  49    43052  23803  23750  -1620  -2659     61       C
ATOM   6723  CE  LYS B  49      19.370 -49.621  82.866  1.00239.30           C
ANISOU 6723  CE  LYS B  49    43238  23623  24063  -1619  -3298   -327       C
ATOM   6724  NZ  LYS B  49      20.039 -50.211  81.676  1.00236.62           N
ANISOU 6724  NZ  LYS B  49    42465  23053  24386  -1546  -3679   -656       N
ATOM   6725  N   LEU B  50      17.895 -53.178  85.476  1.00256.71           N
ANISOU 6725  N   LEU B  50    45977  25606  25957  -2189  -4406   1370       N
ATOM   6726  CA  LEU B  50      18.208 -54.199  86.474  1.00260.90           C
ANISOU 6726  CA  LEU B  50    46748  25959  26423  -2337  -4985   1685       C
ATOM   6727  C   LEU B  50      18.760 -53.527  87.726  1.00263.79           C
ANISOU 6727  C   LEU B  50    47627  26392  26208  -2343  -4997   1622       C
ATOM   6728  O   LEU B  50      19.961 -53.572  87.998  1.00264.56           O
ANISOU 6728  O   LEU B  50    47830  26302  26388  -2333  -5477   1288       O
ATOM   6729  CB  LEU B  50      19.218 -55.210  85.923  1.00260.40           C
ANISOU 6729  CB  LEU B  50    46408  25553  26979  -2363  -5714   1443       C
ATOM   6730  CG  LEU B  50      19.346 -56.567  86.629  1.00264.24           C
ANISOU 6730  CG  LEU B  50    46985  25823  27591  -2526  -6335   1838       C
ATOM   6731  CD1 LEU B  50      19.928 -57.594  85.679  1.00262.70           C
ANISOU 6731  CD1 LEU B  50    46366  25326  28124  -2540  -6883   1649       C
ATOM   6732  CD2 LEU B  50      20.171 -56.498  87.912  1.00267.94           C
ANISOU 6732  CD2 LEU B  50    47913  26228  27664  -2576  -6689   1838       C
ATOM   6733  N   GLU B  51      17.862 -52.901  88.479  1.00327.92           N
ANISOU 6733  N   GLU B  51    56064  34783  33748  -2356  -4462   1945       N
ATOM   6734  CA  GLU B  51      18.202 -52.182  89.703  1.00330.88           C
ANISOU 6734  CA  GLU B  51    56955  35268  33496  -2354  -4381   1920       C
ATOM   6735  C   GLU B  51      16.906 -51.843  90.424  1.00332.96           C
ANISOU 6735  C   GLU B  51    57493  35811  33204  -2393  -3792   2434       C
ATOM   6736  O   GLU B  51      16.845 -51.843  91.654  1.00336.99           O
ANISOU 6736  O   GLU B  51    58454  36389  33198  -2452  -3837   2705       O
ATOM   6737  CB  GLU B  51      18.966 -50.889  89.382  1.00328.27           C
ANISOU 6737  CB  GLU B  51    56647  34994  33087  -2209  -4139   1305       C
ATOM   6738  CG  GLU B  51      20.488 -50.987  89.473  1.00328.59           C
ANISOU 6738  CG  GLU B  51    56722  34777  33352  -2186  -4767    829       C
ATOM   6739  CD  GLU B  51      21.040 -50.429  90.773  1.00332.18           C
ANISOU 6739  CD  GLU B  51    57701  35282  33231  -2199  -4865    760       C
ATOM   6740  OE1 GLU B  51      20.238 -49.985  91.621  1.00334.51           O
ANISOU 6740  OE1 GLU B  51    58348  35816  32935  -2225  -4444   1086       O
ATOM   6741  OE2 GLU B  51      22.277 -50.427  90.944  1.00332.76           O
ANISOU 6741  OE2 GLU B  51    57834  35155  33445  -2180  -5363    373       O
ATOM   6742  N   GLU B  52      15.867 -51.564  89.638  1.00261.59           N
ANISOU 6742  N   GLU B  52    48177  26933  24281  -2354  -3240   2572       N
ATOM   6743  CA  GLU B  52      14.566 -51.186  90.174  1.00263.09           C
ANISOU 6743  CA  GLU B  52    48571  27388  24005  -2380  -2614   3053       C
ATOM   6744  C   GLU B  52      14.682 -49.935  91.043  1.00264.42           C
ANISOU 6744  C   GLU B  52    49191  27762  23514  -2316  -2197   2903       C
ATOM   6745  O   GLU B  52      13.816 -49.676  91.878  1.00267.03           O
ANISOU 6745  O   GLU B  52    49839  28287  23334  -2351  -1788   3318       O
ATOM   6746  CB  GLU B  52      13.956 -52.333  90.988  1.00267.25           C
ANISOU 6746  CB  GLU B  52    49255  27856  24431  -2526  -2868   3695       C
ATOM   6747  CG  GLU B  52      13.951 -53.682  90.290  1.00266.68           C
ANISOU 6747  CG  GLU B  52    48775  27542  25011  -2606  -3375   3851       C
ATOM   6748  CD  GLU B  52      13.052 -53.714  89.072  1.00263.12           C
ANISOU 6748  CD  GLU B  52    47850  27156  24967  -2573  -3006   3906       C
ATOM   6749  OE1 GLU B  52      12.947 -52.685  88.374  1.00259.67           O
ANISOU 6749  OE1 GLU B  52    47276  26876  24512  -2454  -2533   3571       O
ATOM   6750  OE2 GLU B  52      12.453 -54.776  88.807  1.00263.86           O
ANISOU 6750  OE2 GLU B  52    47702  27143  25411  -2664  -3198   4285       O
ATOM   6751  N   LYS B  53      15.753 -49.164  90.850  1.00263.68           N
ANISOU 6751  N   LYS B  53    49125  27618  23414  -2219  -2298   2311       N
ATOM   6752  CA  LYS B  53      15.989 -47.975  91.664  1.00265.02           C
ANISOU 6752  CA  LYS B  53    49715  27955  23026  -2155  -1958   2105       C
ATOM   6753  C   LYS B  53      15.961 -48.410  93.121  1.00270.40           C
```

FIG. 13 Continued

```
ANISOU 6753  C   LYS B  53     50907  28650  23184  -2256  -2206   2488          C
ATOM   6754  O   LYS B  53     15.625 -47.626  94.005  1.00272.64               O
ANISOU 6754  O   LYS B  53     51601  29133  22856  -2235  -1807   2581          O
ATOM   6755  CB  LYS B  53     14.901 -46.927  91.408  1.00263.19               C
ANISOU 6755  CB  LYS B  53     49464  28014  22521  -2082  -1086   2204          C
ATOM   6756  CG  LYS B  53     15.059 -46.128  90.122  1.00258.10               C
ANISOU 6756  CG  LYS B  53     48410  27404  22254  -1946   -750   1737          C
ATOM   6757  CD  LYS B  53     15.487 -44.696  90.411  1.00257.51               C
ANISOU 6757  CD  LYS B  53     48567  27462  21814  -1833   -344   1312          C
ATOM   6758  CE  LYS B  53     14.421 -43.960  91.215  1.00259.55               C
ANISOU 6758  CE  LYS B  53     49172  28004  21440  -1841    337   1663          C
ATOM   6759  NZ  LYS B  53     14.791 -42.546  91.511  1.00259.11               N
ANISOU 6759  NZ  LYS B  53     49343  28079  21029  -1733    759   1250          N
ATOM   6760  N   LYS B  54     16.322 -49.673  93.344  1.00273.48               N
ANISOU 6760  N   LYS B  54     51262  28823  23826  -2358  -2868   2706          N
ATOM   6761  CA  LYS B  54     16.214 -50.336  94.649  1.00278.74               C
ANISOU 6761  CA  LYS B  54     52357  29477  24074  -2459  -3170   3150          C
ATOM   6762  C   LYS B  54     16.895 -49.616  95.830  1.00282.04               C
ANISOU 6762  C   LYS B  54     53317  29973  23871  -2428  -3229   2963          C
ATOM   6763  O   LYS B  54     17.646 -50.221  96.593  1.00285.38               O
ANISOU 6763  O   LYS B  54     53983  30254  24197  -2484  -3829   2995          O
ATOM   6764  CB  LYS B  54     16.785 -51.769  94.547  1.00279.96               C
ANISOU 6764  CB  LYS B  54     52324  29341  24706  -2558  -3946   3294          C
ATOM   6765  CG  LYS B  54     16.485 -52.667  95.745  1.00285.25               C
ANISOU 6765  CG  LYS B  54     53347  29993  25042  -2668  -4232   3874          C
ATOM   6766  CD  LYS B  54     15.057 -53.190  95.738  1.00286.07               C
ANISOU 6766  CD  LYS B  54     53358  30209  25127  -2731  -3837   4518          C
ATOM   6767  CE  LYS B  54     14.118 -52.267  96.487  1.00287.80               C
ANISOU 6767  CE  LYS B  54     53956  30734  24659  -2692  -3119   4782          C
ATOM   6768  NZ  LYS B  54     12.767 -52.870  96.621  1.00289.30               N
ANISOU 6768  NZ  LYS B  54     54089  31007  24824  -2760  -2786   5460          N
ATOM   6769  N   GLU B  55     16.606 -48.330  95.984  1.00279.90               N
ANISOU 6769  N   GLU B  55     53236  29929  23185  -2339  -2613   2766          N
ATOM   6770  CA  GLU B  55     17.087 -47.599  97.143  1.00283.30               C
ANISOU 6770  CA  GLU B  55     54203  30459  22980  -2308  -2606   2612          C
ATOM   6771  C   GLU B  55     16.475 -48.245  98.371  1.00288.54               C
ANISOU 6771  C   GLU B  55     55289  31205  23138  -2395  -2671   3231          C
ATOM   6772  O   GLU B  55     15.803 -49.273  98.275  1.00289.33               O
ANISOU 6772  O   GLU B  55     55234  31253  23446  -2478  -2769   3737          O
ATOM   6773  CB  GLU B  55     16.661 -46.132  97.092  1.00281.65               C
ANISOU 6773  CB  GLU B  55     54112  30496  22408  -2203  -1842   2372          C
ATOM   6774  CG  GLU B  55     17.787 -45.146  96.846  1.00279.76               C
ANISOU 6774  CG  GLU B  55     53867  30197  22234  -2103  -1921   1659          C
ATOM   6775  CD  GLU B  55     17.535 -43.819  97.530  1.00281.04               C
ANISOU 6775  CD  GLU B  55     54418  30596  21767  -2027  -1336   1511          C
ATOM   6776  OE1 GLU B  55     16.988 -43.831  98.651  1.00285.24               O
ANISOU 6776  OE1 GLU B  55     55409  31281  21689  -2068  -1183   1895          O
ATOM   6777  OE2 GLU B  55     17.882 -42.768  96.951  1.00277.96               O
ANISOU 6777  OE2 GLU B  55     53878  30237  21496  -1924  -1022   1015          O
ATOM   6778  N   SER B  56     16.711 -47.637  99.526  1.00346.80               N
ANISOU 6778  N   SER B  56     63203  38711  29856  -2368  -2611   3189          N
ATOM   6779  CA  SER B  56     16.148 -48.128 100.774  1.00352.12               C
ANISOU 6779  CA  SER B  56     64334  39488  29965  -2427  -2624   3763          C
ATOM   6780  C   SER B  56     14.764 -47.532 100.998  1.00352.48               C
ANISOU 6780  C   SER B  56     64524  39811  29591  -2402  -1780   4157          C
ATOM   6781  O   SER B  56     14.187 -47.686 102.076  1.00356.90               O
ANISOU 6781  O   SER B  56     65513  40504  29590   2425   1630   4619          O
ATOM   6782  CB  SER B  56     17.060 -47.769 101.948  1.00356.29               C
ANISOU 6782  CB  SER B  56     65397  40031  29948  -2401  -2976   3533          C
ATOM   6783  OG  SER B  56     18.372 -48.259 101.743  1.00355.97               O
ANISOU 6783  OG  SER B  56     65218  39728  30306  -2421  -3750   3150          O
ATOM   6784  N   LYS B  57     14.234 -46.855  99.978  1.00293.97               N
ANISOU 6784  N   LYS B  57     56755  32485  22457  -2350  -1226   3982          N
ATOM   6785  CA  LYS B  57     12.954 -46.160 100.099  1.00293.89               C
ANISOU 6785  CA  LYS B  57     56846  32734  22083  -2317   -383   4299          C
ATOM   6786  C   LYS B  57     13.022 -45.322 101.372  1.00297.95               C
ANISOU 6786  C   LYS B  57     57983  33433  21791  -2269   -143   4267          C
ATOM   6787  O   LYS B  57     12.011 -45.032 102.016  1.00300.32               O
ANISOU 6787  O   LYS B  57     58571  33938  21600  -2264    408   4690          O
```

FIG. 13 Continued

```
ATOM   6788  CB  LYS B  57       11.778 -47.141 100.126  1.00295.19           C
ANISOU 6788  CB  LYS B  57    56894  32916  22350  -2402   -241   5024        C
ATOM   6789  CG  LYS B  57       11.628 -47.966  98.852  1.00291.31           C
ANISOU 6789  CG  LYS B  57    55781  32249  22654  -2449   -454   5062        C
ATOM   6790  CD  LYS B  57       11.128 -47.130  97.685  1.00286.20           C
ANISOU 6790  CD  LYS B  57    54735  31708  22302  -2378    134   4809        C
ATOM   6791  CE  LYS B  57        9.627 -46.924  97.755  1.00286.60           C
ANISOU 6791  CE  LYS B  57    54790  31964  22140  -2387    868   5343        C
ATOM   6792  NZ  LYS B  57        9.097 -46.324  96.503  1.00281.56           N
ANISOU 6792  NZ  LYS B  57    53688  31404  21888  -2328   1367   5156        N
ATOM   6793  N   LEU B  58       14.253 -44.957 101.715  1.00259.22           N
ANISOU 6793  N   LEU B  58    44692  21428  32372 -12023   4749   2813        N
ATOM   6794  CA  LEU B  58       14.582 -44.164 102.895  1.00255.09           C
ANISOU 6794  CA  LEU B  58    43892  21426  31604 -11591   4761   3306        C
ATOM   6795  C   LEU B  58       14.017 -44.705 104.204  1.00260.43           C
ANISOU 6795  C   LEU B  58    45070  21739  32144 -11980   4862   4016        C
ATOM   6796  O   LEU B  58       13.215 -44.037 104.855  1.00257.96           O
ANISOU 6796  O   LEU B  58    44339  22097  31579 -12410   5051   4345        O
ATOM   6797  CB  LEU B  58       14.218 -42.680 102.710  1.00246.29           C
ANISOU 6797  CB  LEU B  58    41786  21505  30287 -11661   4848   3195        C
ATOM   6798  CG  LEU B  58       15.072 -41.631 103.446  1.00240.25           C
ANISOU 6798  CG  LEU B  58    40597  21357  29331 -10892   4766   3371        C
ATOM   6799  CD1 LEU B  58       15.059 -40.279 102.724  1.00232.04           C
ANISOU 6799  CD1 LEU B  58    38641  21292  28232 -10802   4750   3015        C
ATOM   6800  CD2 LEU B  58       14.632 -41.459 104.882  1.00241.39           C
ANISOU 6800  CD2 LEU B  58    40829  21672  29218 -11050   4889   3999        C
ATOM   6801  N   LEU B  59       14.410 -45.927 104.570  1.00256.25           N
ANISOU 6801  N   LEU B  59    45439  20145  31779 -11849   4737   4246        N
ATOM   6802  CA  LEU B  59       14.143 -46.411 105.919  1.00261.62           C
ANISOU 6802  CA  LEU B  59    46651  20476  32276 -12064   4777   5000        C
ATOM   6803  C   LEU B  59       15.017 -45.440 106.702  1.00255.78           C
ANISOU 6803  C   LEU B  59    45513  20396  31276 -11247   4687   5194        C
ATOM   6804  O   LEU B  59       14.959 -45.358 107.933  1.00257.50           O
ANISOU 6804  O   LEU B  59    45907  20735  31198 -11249   4720   5796        O
ATOM   6805  CB  LEU B  59       14.596 -47.862 106.121  1.00271.41           C
ANISOU 6805  CB  LEU B  59    48953  20384  33787 -11928   4573   5214        C
ATOM   6806  CG  LEU B  59       13.565 -48.992 105.977  1.00280.02           C
ANISOU 6806  CG  LEU B  59    50680  20672  35042 -12920   4668   5378        C
ATOM   6807  CD1 LEU B  59       14.236 -50.358 106.031  1.00289.49           C
ANISOU 6807  CD1 LEU B  59    52923  20472  36597 -12590   4391   5479        C
ATOM   6808  CD2 LEU B  59       12.487 -48.893 107.046  1.00282.28           C
ANISOU 6808  CD2 LEU B  59    50958  21319  34976 -13753   4919   6076        C
ATOM   6809  N   LYS B  60       15.837 -44.725 105.920  1.00205.18           N
ANISOU 6809  N   LYS B  60    38574  14416  24970 -10585   4567   4650        N
ATOM   6810  CA  LYS B  60       16.698 -43.616 106.331  1.00198.35           C
ANISOU 6810  CA  LYS B  60    37153  14302  23911  -9827   4466   4648        C
ATOM   6811  C   LYS B  60       17.955 -43.477 105.461  1.00195.67           C
ANISOU 6811  C   LYS B  60    36635  13907  23804  -8980   4247   4098        C
ATOM   6812  O   LYS B  60       18.547 -42.403 105.401  1.00188.92           O
ANISOU 6812  O   LYS B  60    35137  13810  22833  -8498   4188   3926        O
ATOM   6813  CB  LYS B  60       17.027 -43.619 107.831  1.00200.70           C
ANISOU 6813  CB  LYS B  60    37763  14580  23915  -9539   4394   5319        C
ATOM   6814  CG  LYS B  60       16.085 -42.737 108.673  1.00197.54           C
ANISOU 6814  CG  LYS B  60    36901  15044  23113 -10065   4652   5661        C
ATOM   6815  CD  LYS B  60       15.596 -41.472 107.915  1.00189.10           C
ANISOU 6815  CD  LYS B  60    34862  14954  22035 -10252   4801   5186        C
ATOM   6816  CE  LYS B  60       16.703 -40.436 107.642  1.00181.95           C
ANISOU 6816  CE  LYS B  60    33393  14604  21136  -9409   4599   4852        C
ATOM   6817  NZ  LYS B  60       16.213 -39.137 107.088  1.00174.37           N
ANISOU 6817  NZ  LYS B  60    31529  14581  20142  -9596   4709   4509        N
ATOM   6818  N   PHE B  61       18.358 -44.550 104.785  1.00263.63           N
ANISOU 6818  N   PHE B  61    45794  21633  32741  -8816   4136   3804        N
ATOM   6819  CA  PHE B  61       19.531 -44.481 103.917  1.00262.07           C
ANISOU 6819  CA  PHE B  61    45406  21409  32758  -8032   3975   3228        C
ATOM   6820  C   PHE B  61       19.446 -43.257 103.025  1.00253.54           C
ANISOU 6820  C   PHE B  61    43415  21358  31559  -8112   4078   2763        C
ATOM   6821  O   PHE B  61       18.368 -42.920 102.543  1.00251.19           O
ANISOU 6821  O   PHE B  61    42815  21442  31182  -8878   4257   2661        O
ATOM   6822  CB  PHE B  61       19.657 -45.734 103.056  1.00269.37           C
```

FIG. 13 Continued

```
ANISOU 6822  CB  PHE B  61    46951  21343  34053  -8055  3926  2811    C
ATOM   6823  CG  PHE B  61    20.790 -46.629 103.457  1.00275.99       C
ANISOU 6823  CG  PHE B  61    48406  21302  35154  -7207  3665  2890    C
ATOM   6824  CD1 PHE B  61    22.102 -46.200 103.329  1.00273.46       C
ANISOU 6824  CD1 PHE B  61    47724  21283  34894  -6233  3500  2623    C
ATOM   6825  CD2 PHE B  61    20.549 -47.902 103.954  1.00285.30       C
ANISOU 6825  CD2 PHE B  61    50514  21343  36545  -7387  3564  3243    C
ATOM   6826  CE1 PHE B  61    23.153 -47.020 103.696  1.00280.08       C
ANISOU 6826  CE1 PHE B  61    49074  21329  36013  -5403  3234  2686    C
ATOM   6827  CE2 PHE B  61    21.597 -48.732 104.324  1.00292.06       C
ANISOU 6827  CE2 PHE B  61    51942  21338  37690  -6559  3275  3335    C
ATOM   6828  CZ  PHE B  61    22.901 -48.290 104.195  1.00289.45       C
ANISOU 6828  CZ  PHE B  61    51201  21343  37432  -5541  3107  3044    C
ATOM   6829  N   LEU B  62    20.586 -42.601 102.808  1.00198.39       N
ANISOU 6829  N   LEU B  62    35991  14817  24571  -7335  3943  2507    N
ATOM   6830  CA  LEU B  62    20.654 -41.375 102.004  1.00190.56       C
ANISOU 6830  CA  LEU B  62    34141  14805  23457  -7353  3996  2124    C
ATOM   6831  C   LEU B  62    19.786 -40.277 102.612  1.00184.75       C
ANISOU 6831  C   LEU B  62    32893  14852  22452  -7820  4101  2482    C
ATOM   6832  O   LEU B  62    19.762 -39.147 102.129  1.00178.26       O
ANISOU 6832  O   LEU B  62    31358  14844  21530  -7854  4111  2277    O
ATOM   6833  CB  LEU B  62    20.290 -41.629 100.532  1.00191.16       C
ANISOU 6833  CB  LEU B  62    34119  14860  23654  -7766  4098  1510    C
ATOM   6834  CG  LEU B  62    21.350 -42.291  99.634  1.00195.02       C
ANISOU 6834  CG  LEU B  62    34804  14932  24361  -7182  4023   928    C
ATOM   6835  CD1 LEU B  62    20.787 -43.519  98.914  1.00202.13       C
ANISOU 6835  CD1 LEU B  62    36326  15005  25468  -7647  4100   597    C
ATOM   6836  CD2 LEU B  62    21.965 -41.305  98.636  1.00189.34       C
ANISOU 6836  CD2 LEU B  62    33327  15083  23529  -6938  4028   444    C
ATOM   6837  N   GLY B  63    19.058 -40.639 103.663  1.00178.01       N
ANISOU 6837  N   GLY B  63    32418  13730  21487  -8193  4180  3012    N
ATOM   6838  CA  GLY B  63    18.275 -39.698 104.437  1.00173.88       C
ANISOU 6838  CA  GLY B  63    31467  13898  20700  -8562  4303  3362    C
ATOM   6839  C   GLY B  63    19.230 -39.337 105.545  1.00173.02       C
ANISOU 6839  C   GLY B  63    31387  13925  20427  -7851  4136  3691    C
ATOM   6840  O   GLY B  63    18.832 -39.045 106.668  1.00173.16       O
ANISOU 6840  O   GLY B  63    31434  14170  20190  -7995  4203  4142    O
ATOM   6841  N   PHE B  64    20.512  39.377 105.192  1.00188.69       N
ANISOU 6841  N   PHE B  64    33350  15798  22548  -7086  3925  3434    N
ATOM   6842  CA  PHE B  64    21.604 -39.134 106.117  1.00188.64       C
ANISOU 6842  CA  PHE B  64    33374  15871  22431  -6327  3702  3689    C
ATOM   6843  C   PHE B  64    22.832 -38.595 105.408  1.00185.17       C
ANISOU 6843  C   PHE B  64    32463  15774  22120  -5634  3526  3250    C
ATOM   6844  O   PHE B  64    23.826 -38.277 106.052  1.00184.70       O
ANISOU 6844  O   PHE B  64    32305  15883  21990  -4981  3314  3393    O
ATOM   6845  CB  PHE B  64    22.004 -40.439 106.795  1.00196.89       C
ANISOU 6845  CB  PHE B  64    35274  15968  23566  -6044  3563  4039    C
ATOM   6846  CG  PHE B  64    21.112 -40.832 107.931  1.00200.79       C
ANISOU 6846  CG  PHE B  64    36240  16233  23817  -6565  3671  4656    C
ATOM   6847  CD1 PHE B  64    20.530 -39.869 108.741  1.00196.79       C
ANISOU 6847  CD1 PHE B  64    35344  16478  22951  -6860  3798  4933    C
ATOM   6848  CD2 PHE B  64    20.882 -42.169 108.216  1.00209.10       C
ANISOU 6848  CD2 PHE B  64    38139  16315  24995  -6754  3643  4959    C
ATOM   6849  CE1 PHE B  64    19.713 -40.232 109.800  1.00201.00       C
ANISOU 6849  CE1 PHE B  64    36288  16878  23207  -7365  3939  5487    C
ATOM   6850  CE2 PHE B  64    20.068 -42.544 109.278  1.00213.36       C
ANISOU 6850  CE2 PHE B  64    39123  16675  25268  -7293  3754  5574    C
ATOM   6851  CZ  PHE B  64    19.483 -41.575 110.072  1.00209.31       C
ANISOU 6851  CZ  PHE B  64    38181  16997  24349  -7605  3921  5835    C
ATOM   6852  N   MET B  65    22.775 -38.521 104.083  1.00209.45       N
ANISOU 6852  N   MET B  65    35250  18970  25360  -5801  3611  2722    N
ATOM   6853  CA  MET B  65    23.915 -38.050 103.299  1.00206.84       C
ANISOU 6853  CA  MET B  65    34455  19007  25127  -5220  3489  2279    C
ATOM   6854  C   MET B  65    24.445 -36.728 103.852  1.00200.89       C
ANISOU 6854  C   MET B  65    33079  19066  24182  -4905  3358  2420    C
ATOM   6855  O   MET B  65    24.070 -35.648 103.393  1.00195.06       O
ANISOU 6855  O   MET B  65    31739  19021  23352  -5222  3415  2279    O
ATOM   6856  CB  MET B  65    23.544 -37.900 101.814  1.00204.87       C
ANISOU 6856  CB  MET B  65    33887  18995  24960  -5633  3634  1737    C
```

FIG. 13 Continued

```
ATOM   6857  CG  MET B  65      23.266 -39.216 101.072  1.00211.31           C
ANISOU 6857  CG  MET B  65    35290  19012  25987  -5846   3733   1435       C
ATOM   6858  SD  MET B  65      24.615 -39.868 100.053  1.00215.50           S
ANISOU 6858  SD  MET B  65    35874  19256  26751  -5123   3671    792       S
ATOM   6859  CE  MET B  65      24.649 -38.684  98.709  1.00208.96           C
ANISOU 6859  CE  MET B  65    34186  19458  25751  -5398   3764    303       C
ATOM   6860  N   TRP B  66      25.324 -36.819 104.842  1.00183.87           N
ANISOU 6860  N   TRP B  66    31082  16802  21978  -4284   3150   2706       N
ATOM   6861  CA  TRP B  66      25.875 -35.619 105.440  1.00179.03           C
ANISOU 6861  CA  TRP B  66    29929  16913  21182  -3982   2995   2831       C
ATOM   6862  C   TRP B  66      27.027 -35.061 104.621  1.00176.58           C
ANISOU 6862  C   TRP B  66    29055  17048  20987  -3494   2870   2412       C
ATOM   6863  O   TRP B  66      27.350 -33.884 104.739  1.00171.59           O
ANISOU 6863  O   TRP B  66    27846  17114  20238  -3420   2773   2400       O
ATOM   6864  CB  TRP B  66      26.261 -35.849 106.901  1.00182.21           C
ANISOU 6864  CB  TRP B  66    30700  17117  21414  -3602   2804   3338       C
ATOM   6865  CG  TRP B  66      25.184 -35.407 107.850  1.00180.68           C
ANISOU 6865  CG  TRP B  66    30575  17149  20924  -4138   2932   3734       C
ATOM   6866  CD1 TRP B  66      24.623 -34.165 107.917  1.00174.74           C
ANISOU 6866  CD1 TRP B  66    29259  17121  20012  -4481   3021   3684       C
ATOM   6867  CD2 TRP B  66      24.540 -36.195 108.869  1.00185.78           C
ANISOU 6867  CD2 TRP B  66    31877  17313  21398  -4393   2996   4227       C
ATOM   6868  NE1 TRP B  66      23.671 -34.129 108.910  1.00175.84           N
ANISOU 6868  NE1 TRP B  66    29626  17294  19891  -4902   3164   4061       N
ATOM   6869  CE2 TRP B  66      23.600 -35.360 109.510  1.00182.55           C
ANISOU 6869  CE2 TRP B  66    31219  17443  20698  -4890   3163   4416       C
ATOM   6870  CE3 TRP B  66      24.667 -37.520 109.300  1.00193.29           C
ANISOU 6870  CE3 TRP B  66    33605  17421  22415  -4260   2921   4535       C
ATOM   6871  CZ2 TRP B  66      22.790 -35.808 110.559  1.00186.56           C
ANISOU 6871  CZ2 TRP B  66    32199  17752  20932  -5284   3299   4890       C
ATOM   6872  CZ3 TRP B  66      23.860 -37.961 110.346  1.00197.22           C
ANISOU 6872  CZ3 TRP B  66    34612  17676  22646  -4682   3020   5065       C
ATOM   6873  CH2 TRP B  66      22.936 -37.106 110.961  1.00193.82           C
ANISOU 6873  CH2 TRP B  66    33888  17875  21880  -5202   3227   5232       C
ATOM   6874  N   ASN B  67      27.637 -35.900 103.787  1.00156.44           N
ANISOU 6874  N   ASN B  67    26670  14103  18668  -3184   2883   2050       N
ATOM   6875  CA  ASN B  67      28.695 -35.448 102.878  1.00154.95           C
ANISOU 6875  CA  ASN B  67    25922  14380  18571  -2781   2828   1598       C
ATOM   6876  C   ASN B  67      29.815 -34.670 103.567  1.00153.22           C
ANISOU 6876  C   ASN B  67    25272  14664  18280  -2189   2568   1739       C
ATOM   6877  O   ASN B  67      29.585 -33.533 103.963  1.00147.94           O
ANISOU 6877  O   ASN B  67    24199  14587  17426  -2418   2511   1917       O
ATOM   6878  CB  ASN B  67      28.100 -34.523 101.793  1.00149.32           C
ANISOU 6878  CB  ASN B  67    24664  14301  17769  -3383   2991   1307       C
ATOM   6879  CG  ASN B  67      27.335 -35.278 100.700  1.00151.61           C
ANISOU 6879  CG  ASN B  67    25229  14229  18148  -3876   3220    971       C
ATOM   6880  OD1 ASN B  67      26.708 -36.307 100.966  1.00155.95           O
ANISOU 6880  OD1 ASN B  67    26411  14060  18783  -4062   3299   1088       O
ATOM   6881  ND2 ASN B  67      27.375 -34.752  99.462  1.00149.07           N
ANISOU 6881  ND2 ASN B  67    24439  14420  17782  -4133   3313    564       N
ATOM   6882  N   PRO B  68      31.032 -35.254 103.685  1.00158.22           N
ANISOU 6882  N   PRO B  68    25960  15076  19081  -1426   2395   1631       N
ATOM   6883  CA  PRO B  68      32.144 -34.531 104.324  1.00157.14           C
ANISOU 6883  CA  PRO B  68    25371  15452  18884   -870   2117   1753       C
ATOM   6884  C   PRO B  68      32.386 -33.068 103.915  1.00150.58           C
ANISOU 6884  C   PRO B  68    23742  15560  17913  -1084   2100   1607       C
ATOM   6885  O   PRO B  68      33.536 -32.624 103.852  1.00150.81           O
ANISOU 6885  O   PRO B  68    23282  16035  17984   -612   1929   1468       O
ATOM   6886  CB  PRO B  68      33.348 -35.440 104.061  1.00163.72           C
ANISOU 6886  CB  PRO B  68    26271  15943  19994    -77   2000   1489       C
ATOM   6887  CG  PRO B  68      32.756 -36.799 104.184  1.00169.52           C
ANISOU 6887  CG  PRO B  68    27828  15694  20886   -112   2076   1585       C
ATOM   6888  CD  PRO B  68      31.350 -36.691 103.568  1.00165.88           C
ANISOU 6888  CD  PRO B  68    27522  15192  20315  -1016   2388   1512       C
ATOM   6889  N   LEU B  69      31.298 -32.347 103.650  1.00145.40           N
ANISOU 6889  N   LEU B  69    22958  15172  17114  -1797   2257   1653       N
ATOM   6890  CA  LEU B  69      31.298 -30.907 103.444  1.00139.33           C
ANISOU 6890  CA  LEU B  69    21534  15182  16221  -2084   2201   1625       C
ATOM   6891  C   LEU B  69      30.810 -30.353 104.780  1.00137.29           C
```

FIG. 13 Continued

```
ANISOU 6891  C   LEU B  69    21402  14984  15778  -2188   2065   2064        C
ATOM   6892  O   LEU B  69       31.153 -29.244 105.180  1.00133.95           O
ANISOU 6892  O   LEU B  69    20539  15099  15256  -2156   1888   2139        O
ATOM   6893  CB  LEU B  69       30.341 -30.529 102.306  1.00135.84           C
ANISOU 6893  CB  LEU B  69    20908  14937  15767  -2781   2432   1404        C
ATOM   6894  CG  LEU B  69       30.785 -30.783 100.847  1.00137.15           C
ANISOU 6894  CG  LEU B  69    20828  15265  16019  -2806   2579    923        C
ATOM   6895  CD1 LEU B  69       29.674 -31.381  99.948  1.00137.79           C
ANISOU 6895  CD1 LEU B  69    21214  15029  16111  -3389   2834    736        C
ATOM   6896  CD2 LEU B  69       31.402 -29.522 100.203  1.00133.34           C
ANISOU 6896  CD2 LEU B  69    19595  15604  15464  -2899   2489    780        C
ATOM   6897  N   SER B  70       30.000 -31.179 105.447  1.00139.77           N
ANISOU 6897  N   SER B  70    22343  14724  16037  -2339   2161   2335        N
ATOM   6898  CA  SER B  70       29.447 -30.956 106.789  1.00139.59           C
ANISOU 6898  CA  SER B  70    22585  14665  15786  -2449   2095   2762        C
ATOM   6899  C   SER B  70       29.266 -32.315 107.464  1.00145.80           C
ANISOU 6899  C   SER B  70    24139  14695  16563  -2289   2113   3053        C
ATOM   6900  O   SER B  70       28.220 -32.616 108.045  1.00146.72           O
ANISOU 6900  O   SER B  70    24662  14551  16533  -2714   2263   3335        O
ATOM   6901  CB  SER B  70       28.117 -30.206 106.759  1.00135.18           C
ANISOU 6901  CB  SER B  70    21883  14360  15120  -3151   2290   2811        C
ATOM   6902  OG  SER B  70       28.308 -28.826 107.018  1.00130.64           O
ANISOU 6902  OG  SER B  70    20756  14428  14455  -3174   2143   2787        O
ATOM   6903  N   TRP B  71       30.300 -33.137 107.312  1.00150.41           N
ANISOU 6903  N   TRP B  71    24893  14930  17328  -1681   1961   2966        N
ATOM   6904  CA  TRP B  71       30.443 -34.461 107.906  1.00157.47           C
ANISOU 6904  CA  TRP B  71    26504  15040  18287  -1361   1876   3239        C
ATOM   6905  C   TRP B  71       31.569 -34.161 108.877  1.00159.19           C
ANISOU 6905  C   TRP B  71    26580  15508  18395   -713   1505   3468        C
ATOM   6906  O   TRP B  71       31.564 -34.574 110.034  1.00163.01           O
ANISOU 6906  O   TRP B  71    27528  15714  18695   -554   1329   3928        O
ATOM   6907  CB  TRP B  71       30.986 -35.435 106.841  1.00161.62           C
ANISOU 6907  CB  TRP B  71    27154  15086  19168  -1032   1931   2841        C
ATOM   6908  CG  TRP B  71       30.308 -36.800 106.626  1.00167.18           C
ANISOU 6908  CG  TRP B  71    28611  14868  20042  -1235   2085   2884        C
ATOM   6909  CD1 TRP B  71       29.020 -37.037 106.213  1.00166.09           C
ANISOU 6909  CD1 TRP B  71    28735  14496  19874  -1989   2376   2865        C
ATOM   6910  CD2 TRP B  71       30.931 -38.086 106.733  1.00175.13           C
ANISOU 6910  CD2 TRP B  71    30162  15060  21318   -668   1933   2910        C
ATOM   6911  NE1 TRP B  71       28.797 -38.390 106.105  1.00172.85           N
ANISOU 6911  NE1 TRP B  71    30298  14435  20941  -1971   2414   2896        N
ATOM   6912  CE2 TRP B  71       29.953 -39.054 106.418  1.00178.54           C
ANISOU 6912  CE2 TRP B  71    31223  14752  21861  -1151   2140   2924        C
ATOM   6913  CE3 TRP B  71       32.212 -38.512 107.088  1.00180.18           C
ANISOU 6913  CE3 TRP B  71    30812  15510  22139    209   1615   2931        C
ATOM   6914  CZ2 TRP B  71       30.219 -40.414 106.450  1.00186.82           C
ANISOU 6914  CZ2 TRP B  71    32948  14829  23205   -791   2036   2956        C
ATOM   6915  CZ3 TRP B  71       32.473 -39.860 107.117  1.00188.42           C
ANISOU 6915  CZ3 TRP B  71    32498  15605  23488    613   1507   2965        C
ATOM   6916  CH2 TRP B  71       31.482 -40.799 106.800  1.00191.70           C
ANISOU 6916  CH2 TRP B  71    33578  15240  24021    112   1716   2977        C
ATOM   6917  N   VAL B  72       32.535 -33.404 108.360  1.00226.71           N
ANISOU 6917  N   VAL B  72    34460  24639  27042   -382   1379   3144        N
ATOM   6918  CA  VAL B  72       33.731 -33.002 109.085  1.00228.14           C
ANISOU 6918  CA  VAL B  72    34348  25177  27160    231   1006   3266        C
ATOM   6919  C   VAL B  72       33.399 -32.023 110.199  1.00224.95           C
ANISOU 6919  C   VAL B  72    33851  25237  26382    -13    877   3590        C
ATOM   6920  O   VAL B  72       33.697 -32.266 111.366  1.00228.63           O
ANISOU 6920  O   VAL B  72    34635  25591  26643    278    615   3981        O
ATOM   6921  CB  VAL B  72       34.764 -32.338 108.131  1.00225.94           C
ANISOU 6921  CB  VAL B  72    33291  25488  27070    512    956   2802        C
ATOM   6922  CG1 VAL B  72       36.030 -31.961 108.885  1.00228.09           C
ANISOU 6922  CG1 VAL B  72    33223  26141  27298   1135    548   2924        C
ATOM   6923  CG2 VAL B  72       35.091 -33.258 106.960  1.00229.41           C
ANISOU 6923  CG2 VAL B  72    33771  25552  27842    743   1133   2389        C
ATOM   6924  N   MET B  73       32.773 -30.914 109.837  1.00149.79           N
ANISOU 6924  N   MET B  73    23906  16235  16770   -546   1047   3418        N
ATOM   6925  CA  MET B  73       32.472 -29.885 110.818  1.00146.87           C
ANISOU 6925  CA  MET B  73    23391  16334  16080   -762    939   3621        C
```

FIG. 13 Continued

```
ATOM   6926  C    MET B  73      31.088 -30.085 111.437  1.00 146.77           C
ANISOU 6926  C    MET B  73    23863  16077  15827   -1311   1187   3895       C
ATOM   6927  O    MET B  73      30.381 -29.157 111.855  1.00 143.19           O
ANISOU 6927  O    MET B  73    23225  16013  15166   -1711   1274   3914       O
ATOM   6928  CB   MET B  73      32.762 -28.521 110.221  1.00 141.19           C
ANISOU 6928  CB   MET B  73    21918  16304  15425    -920    897   3300       C
ATOM   6929  CG   MET B  73      34.002 -28.636 109.318  1.00 142.34           C
ANISOU 6929  CG   MET B  73    21632  16603  15847    -470    771   2998       C
ATOM   6930  SD   MET B  73      35.393 -27.527 109.659  1.00 141.60           S
ANISOU 6930  SD   MET B  73    20844  17236  15720     -77    364   2914       S
ATOM   6931  CE   MET B  73      36.799 -28.465 109.029  1.00 147.14           C
ANISOU 6931  CE   MET B  73    21368  17818  16721     652    240   2710       C
ATOM   6932  N    GLU B  74      30.730 -31.360 111.441  1.00 185.30           N
ANISOU 6932  N    GLU B  74    29359  20276  20770   -1314   1305   4084       N
ATOM   6933  CA   GLU B  74      29.616 -31.886 112.185  1.00 187.64           C
ANISOU 6933  CA   GLU B  74    30238  20234  20824   -1746   1499   4445       C
ATOM   6934  C    GLU B  74      30.384 -32.710 113.209  1.00 194.37           C
ANISOU 6934  C    GLU B  74    31596  20727  21530   -1213   1182   4862       C
ATOM   6935  O    GLU B  74      29.978 -32.836 114.360  1.00 197.20           O
ANISOU 6935  O    GLU B  74    32357  21059  21511   -1358   1148   5281       O
ATOM   6936  CB   GLU B  74      28.778 -32.836 111.333  1.00 189.05           C
ANISOU 6936  CB   GLU B  74    30773  19823  21236   -2132   1809   4364       C
ATOM   6937  CG   GLU B  74      29.056 -34.312 111.649  1.00 196.68           C
ANISOU 6937  CG   GLU B  74    32476  19965  22289   -1830   1707   4663       C
ATOM   6938  CD   GLU B  74      28.274 -35.294 110.794  1.00 198.80           C
ANISOU 6938  CD   GLU B  74    33133  19589  22812   -2221   1986   4546       C
ATOM   6939  OE1  GLU B  74      27.970 -36.401 111.295  1.00 204.98           O
ANISOU 6939  OE1  GLU B  74    34628  19678  23575   -2277   1982   4909       O
ATOM   6940  OE2  GLU B  74      27.972 -34.967 109.627  1.00 194.76           O
ANISOU 6940  OE2  GLU B  74    32236  19255  22509   -2492   2186   4107       O
ATOM   6941  N    MET B  75      31.516 -33.263 112.768  1.00 178.29           N
ANISOU 6941  N    MET B  75    29513  18439  19789    -585    941   4738       N
ATOM   6942  CA   MET B  75      32.364 -34.108 113.610  1.00 185.42           C
ANISOU 6942  CA   MET B  75    30858  18947  20647      23    572   5118       C
ATOM   6943  C    MET B  75      33.115 -33.303 114.665  1.00 185.43           C
ANISOU 6943  C    MET B  75    30595  19542  20317     344    205   5309       C
ATOM   6944  O    MET B  75      32.900 -33.492 115.866  1.00 189.05           O
ANISOU 6944  O    MET B  75    31502  19948  20379     295     64   5783       O
ATOM   6945  CB   MET B  75      33.362 -34.916 112.762  1.00 189.16           C
ANISOU 6945  CB   MET B  75    31282  18996  21593     654    429   4855       C
ATOM   6946  CG   MET B  75      32.853 -36.280 112.274  1.00 194.09           C
ANISOU 6946  CG   MET B  75    32563  18690  22495     568    606   4895       C
ATOM   6947  SD   MET B  75      34.155 -37.482 111.856  1.00 202.15           S
ANISOU 6947  SD   MET B  75    33758  19034  24015    1521    298   4757       S
ATOM   6948  CE   MET B  75      34.736 -36.877 110.273  1.00 197.19           C
ANISOU 6948  CE   MET B  75    32268  18926  23728    1653    507   3944       C
ATOM   6949  N    ALA B  76      33.994 -32.411 114.210  1.00 193.73           N
ANISOU 6949  N    ALA B  76    30924  21175  21508     633     48   4942       N
ATOM   6950  CA   ALA B  76      34.786 -31.572 115.105  1.00 193.70           C
ANISOU 6950  CA   ALA B  76    30593  21774  21229     922   -328   5048       C
ATOM   6951  C    ALA B  76      33.892 -30.631 115.915  1.00 190.19           C
ANISOU 6951  C    ALA B  76    30157  21779  20326     358   -199   5163       C
ATOM   6952  O    ALA B  76      34.372 -29.773 116.664  1.00 189.58           O
ANISOU 6952  O    ALA B  76    29804  22253  19975     471   -469   5187       O
ATOM   6953  CB   ALA B  76      35.836 -30.791 114.319  1.00 190.58           C
ANISOU 6953  CB   ALA B  76    29388  21909  21115    1239   -478   4602       C
ATOM   6954  N    ALA B  77      32.583 -30.810 115.758  1.00 178.94           N
ANISOU 6954  N    ALA B  77    29036  20123  18830    -248    215   5203       N
ATOM   6955  CA   ALA B  77      31.592 -30.017 116.478  1.00 178.33           C
ANISOU 6955  CA   ALA B  77    28719  20183  18095    -793    412   5272       C
ATOM   6956  C    ALA B  77      31.098 -30.700 117.764  1.00 182.20           C
ANISOU 6956  C    ALA B  77    30177  20694  18359    -924    403   5815       C
ATOM   6957  O    ALA B  77      30.732 -30.023 118.724  1.00 182.08           O
ANISOU 6957  O    ALA B  77    30165  21133  17886   -1153    410   5914       O
ATOM   6958  CB   ALA B  77      30.424 -29.674 115.564  1.00 171.09           C
ANISOU 6958  CB   ALA B  77    27854  19527  17626   -1405    869   4977       C
ATOM   6959  N    ILE B  78      31.069 -32.034 117.775  1.00 246.29           N
ANISOU 6959  N    ILE B  78    38909  28100  26568    -804    392   6159       N
ATOM   6960  CA   ILE B  78      30.667 -32.783 118.970  1.00 252.90           C
```

FIG. 13 Continued

```
ANISOU 6960  CA  ILE B  78    40481 28664 26946   -942   348  6756      C
ATOM   6961  C   ILE B  78    31.780  32.651 119.990  1.00257.10        C
ANISOU 6961  C   ILE B  78    41058 29462 27168    388   180  7031      C
ATOM   6962  O   ILE B  78    31.585 -32.845 121.193  1.00261.99        O
ANISOU 6962  O   ILE B  78    42141 30162 27241   -502  -292  7496      O
ATOM   6963  CB  ILE B  78    30.415 -34.273 118.672  1.00258.53        C
ANISOU 6963  CB  ILE B  78    41873 28455 27901   -946   413  7075      C
ATOM   6964  CG1 ILE B  78    29.253 -34.418 117.692  1.00254.85        C
ANISOU 6964  CG1 ILE B  78    41374 27752 27705  -1563   923  6804      C
ATOM   6965  CG2 ILE B  78    30.117 -35.034 119.957  1.00266.22        C
ANISOU 6965  CG2 ILE B  78    43626 29152 28374  -1083   302  7772      C
ATOM   6966  CD1 ILE B  78    28.067 -33.536 118.033  1.00250.78        C
ANISOU 6966  CD1 ILE B  78    40644 27804 26839  -2258  1311  6719      C
ATOM   6967  N   MET B  79    32.956 -32.312 119.473  1.00208.20        N
ANISOU 6967  N   MET B  79    34350 23445 21311    190  -504  6733      N
ATOM   6968  CA  MET B  79    34.138 -32.064 120.277  1.00211.68        C
ANISOU 6968  CA  MET B  79    34666 24222 21541    752 -1048  6900      C
ATOM   6969  C   MET B  79    33.889 -30.813 121.102  1.00208.75        C
ANISOU 6969  C   MET B  79    34017 24643 20655    439 -1053  6798      C
ATOM   6970  O   MET B  79    34.796 -30.274 121.731  1.00210.25        O
ANISOU 6970  O   MET B  79    33963 25291 20632    790 -1481  6811      O
ATOM   6971  CB  MET B  79    35.357 -31.883 119.369  1.00210.05        C
ANISOU 6971  CB  MET B  79    33840 24106 21865   1351 -1307  6510      C
ATOM   6972  CG  MET B  79    35.888 -33.191 118.768  1.00215.18        C
ANISOU 6972  CG  MET B  79    34781 23986 22992   1861 -1425  6615      C
ATOM   6973  SD  MET B  79    34.614 -34.339 118.185  1.00216.39        S
ANISOU 6973  SD  MET B  79    35624 23253 23342   1374  -934  6742      S
ATOM   6974  CE  MET B  79    35.600 -35.798 117.856  1.00224.74        C
ANISOU 6974  CE  MET B  79    37047 23438 24905   2185 -1284  6905      C
ATOM   6975  N   ALA B  80    32.643 -30.355 121.075  1.00175.26        N
ANISOU 6975  N   ALA B  80    29795 20558 16236   -223  -577  6661      N
ATOM   6976  CA  ALA B  80    32.215 -29.195 121.839  1.00172.90        C
ANISOU 6976  CA  ALA B  80    29271 20955 15467   -563  -501  6504      C
ATOM   6977  C   ALA B  80    32.040 -29.598 123.288  1.00179.82        C
ANISOU 6977  C   ALA B  80    30767 21917 15639   -647  -635  7034      C
ATOM   6978  O   ALA B  80    32.508 -28.912 124.189  1.00181.37        O
ANISOU 6978  O   ALA B  80    30853 22663 15396   -530  -926  7031      O
ATOM   6979  CB  ALA B  80    30.910 -28.650 121.283  1.00167.33        C
ANISOU 6979  CB  ALA B  80    28360 20355 14864  -1197    60  6174      C
ATOM   6980  N   ILE B  81    31.336 -30.703 123.505  1.00256.79        N
ANISOU 6980  N   ILE B  81    41180 31133 25257   -903  -419  7489      N
ATOM   6981  CA  ILE B  81    31.181 -31.244 124.847  1.00264.48        C
ANISOU 6981  CA  ILE B  81    42822 32129 25538  -1015  -554  8091      C
ATOM   6982  C   ILE B  81    32.314 -32.264 125.061  1.00271.14        C
ANISOU 6982  C   ILE B  81    44050 32471 26499   -369 -1122  8568      C
ATOM   6983  O   ILE B  81    32.140 -33.300 125.706  1.00278.48        O
ANISOU 6983  O   ILE B  81    45710 32955 27146   -424 -1219  9198      O
ATOM   6984  CB  ILE B  81    29.753 -31.821 125.103  1.00266.73        C
ANISOU 6984  CB  ILE B  81    43626 32180 25539  -1729   -13  8377      C
ATOM   6985  CG1 ILE B  81    28.691 -30.726 124.949  1.00260.71        C
ANISOU 6985  CG1 ILE B  81    42390 31991 24678  -2288   506  7866      C
ATOM   6986  CG2 ILE B  81    29.638 -32.410 126.497  1.00275.49        C
ANISOU 6986  CG2 ILE B  81    45452 33340 25879  -1882  -160  9056      C
ATOM   6987  CD1 ILE B  81    28.638 -29.733 126.103  1.00261.88        C
ANISOU 6987  CD1 ILE B  81    42413 32956 24135  -2412   463  7759      C
ATOM   6988  N   ALA B  82    33.479 -31.946 124.490  1.00224.00        N
ANISOU 6988  N   ALA B  82    37555 26581 20975    242 -1502  8263      N
ATOM   6989  CA  ALA B  82    34.692 -32.753 124.639  1.00230.19        C
ANISOU 6989  CA  ALA B  82    38525 26989 21948    967 -2089  8610      C
ATOM   6990  C   ALA B  82    35.925 -31.847 124.751  1.00228.70        C
ANISOU 6990  C   ALA B  82    37672 27428 21797   1474 -2567  8306      C
ATOM   6991  O   ALA B  82    37.061 -32.316 124.654  1.00232.67        O
ANISOU 6991  O   ALA B  82    38077 27735 22591   2148 -3055  8431      O
ATOM   6992  CB  ALA B  82    34.845 -33.730 123.479  1.00230.37        C
ANISOU 6992  CB  ALA B  82    38621 26197 22710   1253 -2003  8541      C
ATOM   6993  N   LEU B  83    35.684 -30.553 124.970  1.00274.33        N
ANISOU 6993  N   LEU B  83    42987 33950 27295   1143 -2432  7899      N
ATOM   6994  CA  LEU B  83    36.750 -29.552 125.085  1.00272.63        C
ANISOU 6994  CA  LEU B  83    42119 34376 27093   1492 -2854  7566      C
```

FIG. 13 Continued

```
ATOM   6995  C   LEU B  83      36.397 -28.364 126.002  1.00271.18           C
ANISOU 6995  C   LEU B  83    41800  34956  26279   1088  -2831   7373       C
ATOM   6996  O   LEU B  83      37.063 -27.327 125.952  1.00268.33           O
ANISOU 6996  O   LEU B  83    40839  35136  25979   1215  -3074   6970       O
ATOM   6997  CB  LEU B  83      37.139 -29.021 123.700  1.00265.69           C
ANISOU 6997  CB  LEU B  83    40485  33529  26934   1635  -2720   6970       C
ATOM   6998  CG  LEU B  83      37.774 -29.985 122.694  1.00267.09           C
ANISOU 6998  CG  LEU B  83    40594  33110  27776   2145  -2798   6979       C
ATOM   6999  CD1 LEU B  83      37.732 -29.389 121.294  1.00259.52           C
ANISOU 6999  CD1 LEU B  83    38971  32242  27393   2025  -2468   6370       C
ATOM   7000  CD2 LEU B  83      39.200 -30.338 123.095  1.00273.33           C
ANISOU 7000  CD2 LEU B  83    41247  33970  28638   2895  -3462   7196       C
ATOM   7001  N   ALA B  84      35.359 -28.517 126.827  1.00211.79           N
ANISOU 7001  N   ALA B  84    34829  27482  18160    589  -2531   7638       N
ATOM   7002  CA  ALA B  84      34.918 -27.464 127.754  1.00211.43           C
ANISOU 7002  CA  ALA B  84    34716  28149  17467    195  -2448   7423       C
ATOM   7003  C   ALA B  84      33.574 -27.801 128.400  1.00213.86           C
ANISOU 7003  C   ALA B  84    35606  28429  17224   -412  -1943   7680       C
ATOM   7004  O   ALA B  84      32.721 -26.929 128.567  1.00210.58           O
ANISOU 7004  O   ALA B  84    34996  28435  16579   -874  -1541   7285       O
ATOM   7005  CB  ALA B  84      34.833 -26.113 127.043  1.00203.34           C
ANISOU 7005  CB  ALA B  84    32929  27525  16807     37  -2263   6680       C
ATOM   7006  N   ASN B  85      33.384 -29.067 128.750  1.00261.05           N
ANISOU 7006  N   ASN B  85    42278  33898  23010   -414  -1965   8339       N
ATOM   7007  CA  ASN B  85      32.132 -29.522 129.349  1.00264.38           C
ANISOU 7007  CA  ASN B  85    43278  34270  22904  -1032  -1482   8664       C
ATOM   7008  C   ASN B  85      32.109 -29.492 130.885  1.00272.16           C
ANISOU 7008  C   ASN B  85    44749  35776  22881  -1214  -1675   9067       C
ATOM   7009  O   ASN B  85      32.751 -30.320 131.536  1.00279.67           O
ANISOU 7009  O   ASN B  85    46216  36516  23529   -931  -2150   9706       O
ATOM   7010  CB  ASN B  85      31.795 -30.933 128.847  1.00267.31           C
ANISOU 7010  CB  ASN B  85    44189  33754  23620  -1061  -1345   9174       C
ATOM   7011  CG  ASN B  85      32.936 -31.928 129.062  1.00274.00           C
ANISOU 7011  CG  ASN B  85    45417  34112  24577   -429  -1996   9740       C
ATOM   7012  OD1 ASN B  85      34.062 -31.538 129.288  1.00274.92           O
ANISOU 7012  OD1 ASN B  85    45229  34525  24702    108  -2550   9661       O
ATOM   7013  ND2 ASN B  85      32.620 -33.219 128.990  1.00279.18           N
ANISOU 7013  ND2 ASN B  85    46732  33997  25346   -492  -1948  10311       N
ATOM   7014  N   GLY B  86      31.371 -28.548 131.466  1.00215.07           N
ANISOU 7014  N   GLY B  86    37362  29230  15125  -1676  -1318   8693       N
ATOM   7015  CA  GLY B  86      31.237 -28.504 132.911  1.00222.79           C
ANISOU 7015  CA  GLY B  86    38808  30770  15072  -1925  -1416   9020       C
ATOM   7016  C   GLY B  86      30.479 -29.748 133.332  1.00229.49           C
ANISOU 7016  C   GLY B  86    40444  31209  15542  -2323  -1155   9769       C
ATOM   7017  O   GLY B  86      29.253 -29.785 133.252  1.00228.49           O
ANISOU 7017  O   GLY B  86    40395  31117  15304  -2913   -498   9683       O
ATOM   7018  N   ASP B  87      31.208 -30.772 133.766  1.00268.42           N
ANISOU 7018  N   ASP B  87    45947  35737  20306  -2006  -1687  10518       N
ATOM   7019  CA  ASP B  87      30.609 -32.054 134.147  1.00275.78           C
ANISOU 7019  CA  ASP B  87    47700  36154  20931  -2361  -1539  11331       C
ATOM   7020  C   ASP B  87      30.198 -32.124 135.629  1.00284.80           C
ANISOU 7020  C   ASP B  87    49427  37910  20873  -2842  -1502  11812       C
ATOM   7021  O   ASP B  87      30.904 -31.613 136.498  1.00288.42           O
ANISOU 7021  O   ASP B  87    49875  38980  20732  -2628  -1956  11818       O
ATOM   7022  CB  ASP B  87      31.569 -33.194 133.798  1.00279.76           C
ANISOU 7022  CB  ASP B  87    48562  35792  21943  -1756  -2144  11921       C
ATOM   7023  CG  ASP B  87      30.941 -34.560 133.972  1.00286.85           C
ANISOU 7023  CG  ASP B  87    50303  35961  22727  -2111  -1997  12731       C
ATOM   7024  OD1 ASP B  87      30.674 -34.961 135.126  1.00295.59           O
ANISOU 7024  OD1 ASP B  87    52060  37305  22946  -2477  -2070  13378       O
ATOM   7025  OD2 ASP B  87      30.725 -35.238 132.947  1.00284.12           O
ANISOU 7025  OD2 ASP B  87    49987  34799  23168  -2047  -1821  12723       O
ATOM   7026  N   GLY B  88      29.067 -32.773 135.913  1.00261.13           N
ANISOU 7026  N   GLY B  88    46937  34777  17503  -3522   -968  12221       N
ATOM   7027  CA  GLY B  88      28.556 -32.885 137.275  1.00270.17           C
ANISOU 7027  CA  GLY B  88    48645  36543  17466  -4083   -831  12690       C
ATOM   7028  C   GLY B  88      27.546 -31.803 137.642  1.00267.52           C
ANISOU 7028  C   GLY B  88    47899  37133  16612  -4652   -134  12007       C
ATOM   7029  O   GLY B  88      26.947 -31.839 138.724  1.00274.90           O
```

FIG. 13 Continued

```
ANISOU 7029  O   GLY B  88     49237  38678  16536  -5210    135  12290       O
ATOM   7030  N   ARG B  89     27.374 -30.839 136.732  1.00340.42             N
ANISOU 7030  N   ARG B  89     56324  46474  26545  -4498    148  11103       N
ATOM   7031  CA  ARG B  89     26.444 -29.709 136.887  1.00336.88             C
ANISOU 7031  CA  ARG B  89     55360  46809  25831  -4918    787  10321       C
ATOM   7032  C   ARG B  89     25.253 -29.812 135.924  1.00331.34             C
ANISOU 7032  C   ARG B  89     54357  45777  25760  -5336   1509  10032       C
ATOM   7033  O   ARG B  89     25.388 -30.344 134.820  1.00326.49             O
ANISOU 7033  O   ARG B  89     53653  44364  26036  -5120   1439  10106       O
ATOM   7034  CB  ARG B  89     27.176 -28.381 136.659  1.00330.33             C
ANISOU 7034  CB  ARG B  89     53812  46405  25292  -4423    490   9481       C
ATOM   7035  CG  ARG B  89     28.423 -28.201 137.512  1.00335.27             C
ANISOU 7035  CG  ARG B  89     54633  47372  25384  -3985   -278   9688       C
ATOM   7036  CD  ARG B  89     28.093 -27.678 138.902  1.00342.59             C
ANISOU 7036  CD  ARG B  89     55798  49267  25103  -4380   -140   9609       C
ATOM   7037  NE  ARG B  89     28.162 -26.221 138.964  1.00338.03             N
ANISOU 7037  NE  ARG B  89     54567  49344  24525  -4275    -73   8633       N
ATOM   7038  CZ  ARG B  89     29.219 -25.543 139.399  1.00338.90             C
ANISOU 7038  CZ  ARG B  89     54511  49835  24420  -3871   -694   8379       C
ATOM   7039  NH1 ARG B  89     30.298 -26.190 139.817  1.00344.14             N
ANISOU 7039  NH1 ARG B  89     55576  50339  24843   3511   1434   9038       N
ATOM   7040  NH2 ARG B  89     29.197 -24.217 139.421  1.00335.01             N
ANISOU 7040  NH2 ARG B  89     53448  49866  23975  -3828   -602   7468       N
ATOM   7041  N   PRO B  90     24.086 -29.279 136.331  1.00255.25             N
ANISOU 7041  N   PRO B  90     44528  36791  15663  -5927   2204   9662       N
ATOM   7042  CA  PRO B  90     22.856 -29.374 135.530  1.00251.22             C
ANISOU 7042  CA  PRO B  90     43713  36073  15665  -6391   2907   9412       C
ATOM   7043  C   PRO B  90     22.526 -28.267 134.506  1.00241.06             C
ANISOU 7043  C   PRO B  90     41526  34866  15199  -6213   3166   8459       C
ATOM   7044  O   PRO B  90     21.337 -28.103 134.232  1.00239.82             O
ANISOU 7044  O   PRO B  90     41076  34884  15160  -6694   3818   8172       O
ATOM   7045  CB  PRO B  90     21.744 -29.410 136.601  1.00259.15             C
ANISOU 7045  CB  PRO B  90     44966  37823  15678  -7142   3534   9544       C
ATOM   7046  CG  PRO B  90     22.455 -29.520 137.948  1.00267.93             C
ANISOU 7046  CG  PRO B  90     46649  39428  15724  -7083   3112   9999       C
ATOM   7047  CD  PRO B  90     23.791 -28.890 137.720  1.00263.09             C
ANISOU 7047  CD  PRO B  90     45764  38721  15478  -6291   2378   9676       C
ATOM   7048  N   PRO B  91     23.519 -27.531 133.959  1.00241.85             N
ANISOU 7048  N   PRO B  91     41186  34858  15847  -5574   2669   8006       N
ATOM   7049  CA  PRO B  91     23.154 -26.514 132.955  1.00232.79             C
ANISOU 7049  CA  PRO B  91     39227  33739  15484  -5463   2906   7177       C
ATOM   7050  C   PRO B  91     22.333 -27.053 131.774  1.00228.26             C
ANISOU 7050  C   PRO B  91     38481  32571  15678  -5727   3303   7205       C
ATOM   7051  O   PRO B  91     21.249 -27.607 131.962  1.00232.05             O
ANISOU 7051  O   PRO B  91     39164  33095  15909  -6312   3839   7448       O
ATOM   7052  CB  PRO B  91     24.515 -26.005 132.456  1.00227.58             C
ANISOU 7052  CB  PRO B  91     38279  32863  15329  -4763   2220   6941       C
ATOM   7053  CG  PRO B  91     25.430 -26.202 133.606  1.00234.56             C
ANISOU 7053  CG  PRO B  91     39645  34045  15431  -4550   1714   7344       C
ATOM   7054  CD  PRO B  91     24.945 -27.441 134.332  1.00243.11             C
ANISOU 7054  CD  PRO B  91     41507  35004  15860  -4980   1899   8172       C
ATOM   7055  N   ASP B  92     22.854 -26.875 130.562  1.00273.75             N
ANISOU 7055  N   ASP B  92     43853  37820  22342  -5328   3039   6948       N
ATOM   7056  CA  ASP B  92     22.165 -27.320 129.353  1.00269.16             C
ANISOU 7056  CA  ASP B  92     43074  36686  22509  -5545   3351   6913       C
ATOM   7057  C   ASP B  92     23.089 -28.122 128.425  1.00266.47             C
ANISOU 7057  C   ASP B  92     42919  35525  22803  -5126   2897   7227       C
ATOM   7058  O   ASP B  92     24.013 -27.579 127.812  1.00261.17             O
ANISOU 7058  O   ASP B  92     41872  34751  22609  -4606   2491   6906       O
ATOM   7059  CB  ASP B  92     21.569 -26.123 128.598  1.00261.96             C
ANISOU 7059  CB  ASP B  92     41344  36050  22139  -5573   3630   6112       C
ATOM   7060  CG  ASP B  92     20.533 -25.356 129.419  1.00264.99             C
ANISOU 7060  CG  ASP B  92     41484  37205  21997  -5969   4143   5724       C
ATOM   7061  OD1 ASP B  92     20.278 -25.727 130.586  1.00272.63             O
ANISOU 7061  OD1 ASP B  92     42906  38564  22118  -6259   4317   6055       O
ATOM   7062  OD2 ASP B  92     19.970 -24.373 128.891  1.00260.17             O
ANISOU 7062  OD2 ASP B  92     40216  36818  21820  -5986   4371   5079       O
ATOM   7063  N   TRP B  93     22.815 -29.419 128.329  1.00201.34             N
ANISOU 7063  N   TRP B  93     35247  26697  14556   5377   2985   7840       N
```

FIG. 13 Continued

```
ATOM   7064  CA   TRP B  93      23.581 -30.353 127.504  1.00200.40           C
ANISOU 7064  CA   TRP B  93    35393  25736  15015  -5010   2608   8157       C
ATOM   7065  C    TRP B  93      23.784 -29.784 126.092  1.00191.38           C
ANISOU 7065  C    TRP B  93    33585  24380  14753  -4736   2572   7564       C
ATOM   7066  O    TRP B  93      24.774 -30.087 125.420  1.00189.25           O
ANISOU 7066  O    TRP B  93    33297  23653  14958  -4226   2157   7585       O
ATOM   7067  CB   TRP B  93      22.813 -31.700 127.466  1.00205.89           C
ANISOU 7067  CB   TRP B  93    36717  25844  15669  -5519   2893   8757       C
ATOM   7068  CG   TRP B  93      23.517 -32.942 126.883  1.00208.08           C
ANISOU 7068  CG   TRP B  93    37499  25155  16406  -5200   2515   9221       C
ATOM   7069  CD1  TRP B  93      23.475 -33.380 125.584  1.00203.86           C
ANISOU 7069  CD1  TRP B  93    36824  23970  16664  -5127   2554   9033       C
ATOM   7070  CD2  TRP B  93      24.293 -33.919 127.604  1.00215.86           C
ANISOU 7070  CD2  TRP B  93    39228  25718  17072  -4934   2058   9938       C
ATOM   7071  NE1  TRP B  93      24.199 -34.544 125.449  1.00208.48           N
ANISOU 7071  NE1  TRP B  93    38000  23747  17467  -4796   2166   9526       N
ATOM   7072  CE2  TRP B  93      24.711 -34.894 126.671  1.00215.88           C
ANISOU 7072  CE2  TRP B  93    39480  24782  17761  -4655   1839  10104       C
ATOM   7073  CE3  TRP B  93      24.688 -34.051 128.939  1.00223.22           C
ANISOU 7073  CE3  TRP B  93    40635  26978  17201  -4889   1787  10447       C
ATOM   7074  CZ2  TRP B  93      25.503 -35.982 127.033  1.00223.06           C
ANISOU 7074  CZ2  TRP B  93    41082  25030  18639  -4294   1352  10754       C
ATOM   7075  CZ3  TRP B  93      25.473 -35.133 129.295  1.00230.24           C
ANISOU 7075  CZ3  TRP B  93    42219  27234  18029  -4561   1279  11146       C
ATOM   7076  CH2  TRP B  93      25.872 -36.083 128.346  1.00230.15           C
ANISOU 7076  CH2  TRP B  93    42430  26245  18774  -4246   1062  11292       C
ATOM   7077  N    GLN B  94      22.864 -28.903 125.700  1.00266.96           N
ANISOU 7077  N    GLN B  94    42585  34347  24501  -5064   2996   7026       N
ATOM   7078  CA   GLN B  94      22.722 -28.380 124.330  1.00259.03           C
ANISOU 7078  CA   GLN B  94    40963  33171  24284  -4991   3066   6507       C
ATOM   7079  C    GLN B  94      23.889 -27.788 123.524  1.00259.15           C
ANISOU 7079  C    GLN B  94    39787  32330  24067  -4387   2603   6161       C
ATOM   7080  O    GLN B  94      23.670 -26.875 122.726  1.00246.95           O
ANISOU 7080  O    GLN B  94    38381  31725  23723  -4395   2687   5640       O
ATOM   7081  CB   GLN B  94      21.506 -27.441 124.235  1.00256.18           C
ANISOU 7081  CB   GLN B  94    40056  33327  23953  -5430   3559   6017       C
ATOM   7082  CG   GLN B  94      21.501 -26.291 125.222  1.00257.04           C
ANISOU 7082  CG   GLN B  94    39895  34195  23574  -5361   3572   5674       C
ATOM   7083  CD   GLN B  94      20.167 -25.570 125.255  1.00256.25           C
ANISOU 7083  CD   GLN B  94    39337  34560  23467  -5814   4116   5250       C
ATOM   7084  OE1  GLN B  94      19.868 -24.834 126.193  1.00258.94           O
ANISOU 7084  OE1  GLN B  94    39549  35521  23315  -5885   4273   4998       O
ATOM   7085  NE2  GLN B  94      19.354 -25.786 124.228  1.00253.06           N
ANISOU 7085  NE2  GLN B  94    38669  33873  23610  -6115   4400   5147       N
ATOM   7086  N    ASP B  95      25.109 -28.280 123.700  1.00172.58           N
ANISOU 7086  N    ASP B  95    29875  21862  13837  -3880   2112   6450       N
ATOM   7087  CA   ASP B  95      26.164 -27.856 122.778  1.00167.40           C
ANISOU 7087  CA   ASP B  95    28775  21087  13741  -3365   1734   6133       C
ATOM   7088  C    ASP B  95      26.523 -28.987 121.804  1.00167.61           C
ANISOU 7088  C    ASP B  95    29044  20365  14277  -3185   1645   6344       C
ATOM   7089  O    ASP B  95      26.859 -28.732 120.644  1.00162.45           O
ANISOU 7089  O    ASP B  95    27960  19568  14197  -3008   1588   5995       O
ATOM   7090  CB   ASP B  95      27.387 -27.278 123.485  1.00168.62           C
ANISOU 7090  CB   ASP B  95    28827  21612  13628  -2856   1217   6105       C
ATOM   7091  CG   ASP B  95      28.005 -26.147 122.698  1.00162.04           C
ANISOU 7091  CG   ASP B  95    27271  21035  13261  -2589   1013   5550       C
ATOM   7092  OD1  ASP B  95      28.964 -25.518 123.180  1.00162.49           O
ANISOU 7092  OD1  ASP B  95    27139  21443  13158  -2232    600   5443       O
ATOM   7093  OD2  ASP B  95      27.507 -25.882 121.587  1.00156.75           O
ANISOU 7093  OD2  ASP B  95    26225  20225  13109  -2778   1256   5236       O
ATOM   7094  N    PHE B  96      26.450 -30.230 122.289  1.00212.13           N
ANISOU 7094  N    PHE B  96    35387  25526  19685  -3242   1630   6910       N
ATOM   7095  CA   PHE B  96      26.616 -31.407 121.442  1.00213.60           C
ANISOU 7095  CA   PHE B  96    35899  24918  20340  -3133   1596   7106       C
ATOM   7096  C    PHE B  96      25.354 -31.515 120.619  1.00210.61           C
ANISOU 7096  C    PHE B  96    35401  24377  20245  -3739   2110   6902       C
ATOM   7097  O    PHE B  96      25.413 -31.692 119.405  1.00206.98           O
ANISOU 7097  O    PHE B  96    34714  23580  20350  -3683   2152   6622       O
ATOM   7098  CB   PHE B  96      26.770 -32.684 122.262  1.00222.28           C
```

FIG. 13 Continued

```
ANISOU 7098  CB  PHE B  96    37838 25503 21114  -3090  1431  7804       C
ATOM   7099  CG  PHE B  96       26.110 -33.889 121.634  1.00 224.98     C
ANISOU 7099  CG  PHE B  96    38648 25059 21775  -3420  1676  8036       C
ATOM   7100  CD1 PHE B  96       26.796 -34.682 120.732  1.00 225.57     C
ANISOU 7100  CD1 PHE B  96    38848 24435 22423  -2998  1450  8003       C
ATOM   7101  CD2 PHE B  96       24.799 -34.225 121.947  1.00 227.45     C
ANISOU 7101  CD2 PHE B  96    39258 25347 21815  -4167  2140  8257       C
ATOM   7102  CE1 PHE B  96       25.167 -35.786 120.155  1.00 228.53     C
ANISOU 7102  CE1 PHE B  96    39682 24050 23099  -3316  1659  8170       C
ATOM   7103  CE2 PHE B  96       24.184 -35.324 121.373  1.00 230.33     C
ANISOU 7103  CE2 PHE B  96    40057 24978 22480  -4524  2346  8463       C
ATOM   7104  CZ  PHE B  96       24.878 -36.106 120.477  1.00 230.87     C
ANISOU 7104  CZ  PHE B  96    40292 24302 23124  -4099  2094  8414       C
ATOM   7105  N   VAL B  97       24.205 -31.433 121.293  1.00 205.41     N
ANISOU 7105  N   VAL B  97    34887 23992 19168  -4336  2504  7042       N
ATOM   7106  CA  VAL B  97       22.932 -31.413 120.589  1.00 202.82     C
ANISOU 7106  CA  VAL B  97    34349 23630 19084  -4947  2994  6826       C
ATOM   7107  C   VAL B  97       22.774 -30.028 119.970  1.00 195.22     C
ANISOU 7107  C   VAL B  97    32558 23223 18394  -4919  3070  6192       C
ATOM   7108  O   VAL B  97       21.786 -29.751 119.293  1.00 192.12     O
ANISOU 7108  O   VAL B  97    31827 22910 18261  -5352  3414  5922       O
ATOM   7109  CB  VAL B  97       21.707 -31.762 121.475  1.00 208.06     C
ANISOU 7109  CB  VAL B  97    35355 24462 19235  -5627  3429  7158       C
ATOM   7110  CG1 VAL B  97       21.977 -32.992 122.320  1.00 216.49     C
ANISOU 7110  CG1 VAL B  97    37280 25058 19916  -5644  3278  7866       C
ATOM   7111  CG2 VAL B  97       21.310 -30.586 122.335  1.00 207.10     C
ANISOU 7111  CG2 VAL B  97    34840 25199 18649  -5753  3601  6909       C
ATOM   7112  N   GLY B  98       23.749 -29.156 120.220  1.00 163.33     N
ANISOU 7112  N   GLY B  98    28198 19559 14301  -4421  2718  5975       N
ATOM   7113  CA  GLY B  98       23.761 -27.851 119.591  1.00 156.58     C
ANISOU 7113  CA  GLY B  98    26598 19139 13757  -4350  2703  5409       C
ATOM   7114  C   GLY B  98       23.982 -28.113 118.118  1.00 152.42     C
ANISOU 7114  C   GLY B  98    25841 18203 13868  -4270  2658  5203       C
ATOM   7115  O   GLY B  98       23.385 -27.484 117.247  1.00 147.64     O
ANISOU 7115  O   GLY B  98    24748 17740 13610  -4518  2836  4840       O
ATOM   7116  N   ILE B  99       24.833 -29.092 117.847  1.00 167.44     N
ANISOU 7116  N   ILE B  99    28118 19589 15914  -3918  2412  5442       N
ATOM   7117  CA  ILE B  99       25.164 -29.459 116.480  1.00 164.59     C
ANISOU 7117  CA  ILE B  99    27594 18835 16108  -3794  2366  5228       C
ATOM   7118  C   ILE B  99       24.295 -30.598 115.927  1.00 167.10     C
ANISOU 7118  C   ILE B  99    28323 18568 16599  -4222  2670  5389       C
ATOM   7119  O   ILE B  99       23.888 -30.548 114.770  1.00 163.62     O
ANISOU 7119  O   ILE B  99    27601 18021 16548  -4448  2824  5090       O
ATOM   7120  CB  ILE B  99       26.663 -29.791 116.341  1.00 165.91     C
ANISOU 7120  CB  ILE B  99    27814 18801 16421  -3105  1924  5270       C
ATOM   7121  CG1 ILE B  99       27.506 -28.735 117.068  1.00 164.62     C
ANISOU 7121  CG1 ILE B  99    27303 19225 16021  -2738  1597  5172       C
ATOM   7122  CG2 ILE B  99       27.057 -29.887 114.873  1.00 162.40     C
ANISOU 7122  CG2 ILE B  99    27042 18143 16521  -2969  1905  4918       C
ATOM   7123  CD1 ILE B  99       27.434 -27.334 116.456  1.00 157.99     C
ANISOU 7123  CD1 ILE B  99    25722 18910 15397  -2843  1615  4684       C
ATOM   7124  N   ILE B 100       24.009 -31.618 116.736  1.00 194.09     N
ANISOU 7124  N   ILE B 100    32418 21609 19720  -4370  2737  5869       N
ATOM   7125  CA  ILE B 100       23.142 -32.706 116.274  1.00 197.19     C
ANISOU 7125  CA  ILE B 100    33234 21417 20271  -4847  3018  6040       C
ATOM   7126  C   ILE B 100       21.760 -32.145 115.952  1.00 194.12     C
ANISOU 7126  C   ILE B 100    32465 21385 19905  -5527  3446  5814       C
ATOM   7127  O   ILE B 100       21.042 -32.701 115.126  1.00 194.22     O
ANISOU 7127  O   ILE B 100    32541 21052 20202  -5941  3665  5739       O
ATOM   7128  CB  ILE B 100       23.010 -33.877 117.291  1.00 205.45     C
ANISOU 7128  CB  ILE B 100    35112 21988 20963  -4968  3009  6668       C
ATOM   7129  CG1 ILE B 100       22.539 -35.156 116.588  1.00 209.14     C
ANISOU 7129  CG1 ILE B 100    36073 21640 21752  -5283  3149  6808       C
ATOM   7130  CG2 ILE B 100       22.024 -33.539 118.390  1.00 207.76     C
ANISOU 7130  CG2 ILE B 100    35475 22759 20704  -5497  3313  6908       C
ATOM   7131  CD1 ILE B 100       23.444 -35.632 115.461  1.00 208.04     C
ANISOU 7131  CD1 ILE B 100    35915 20979 22152  -4784  2902  6525       C
ATOM   7132  N   CYS B 101       21.393 -31.043 116.605  1.00 161.08     N
ANISOU 7132  N   CYS B 101    27873 17893 15437  -5629  3548  5682       N
```

FIG. 13 Continued

```
ATOM   7133  CA  CYS B 101      20.113 -30.397 116.338  1.00158.47           C
ANISOU 7133  CA  CYS B 101    27089  17957  15164  -6192   3926   5429       C
ATOM   7134  C   CYS B 101      20.198 -29.764 114.963  1.00152.05           C
ANISOU 7134  C   CYS B 101    25688  17205  14881  -6124   3850   4957       C
ATOM   7135  O   CYS B 101      19.330 -29.971 114.120  1.00151.01           O
ANISOU 7135  O   CYS B 101    25408  16946  15022  -6571   4074   4823       O
ATOM   7136  CB  CYS B 101      19.796 -29.336 117.388  1.00158.22           C
ANISOU 7136  CB  CYS B 101    26755  18635  14725  -6224   4028   5339       C
ATOM   7137  SG  CYS B 101      18.053 -29.245 117.824  1.00160.90           S
ANISOU 7137  SG  CYS B 101    26951  19337  14846  -7006   4602   5352       S
ATOM   7138  N   LEU B 102      21.264 -29.003 114.744  1.00145.94           N
ANISOU 7138  N   LEU B 102    24583  16642  14226  -5591   3515   4726       N
ATOM   7139  CA  LEU B 102      21.537 -28.394 113.450  1.00140.36           C
ANISOU 7139  CA  LEU B 102    23347  16010  13975  -5495   3392   4327       C
ATOM   7140  C   LEU B 102      21.387 -29.393 112.299  1.00141.00           C
ANISOU 7140  C   LEU B 102    23639  15550  14387  -5681   3468   4299       C
ATOM   7141  O   LEU B 102      20.940 -29.047 111.208  1.00137.52           O
ANISOU 7141  O   LEU B 102    22806  14255  13589  -5936   3540   4012       O
ATOM   7142  CB  LEU B 102      22.969 -27.870 113.455  1.00138.31           C
ANISOU 7142  CB  LEU B 102    22902  15896  13754  -4862   2988   4213       C
ATOM   7143  CG  LEU B 102      23.728 -27.918 112.132  1.00135.30           C
ANISOU 7143  CG  LEU B 102    22274  15351  13783  -4632   2809   3959       C
ATOM   7144  CD1 LEU B 102      23.480 -26.647 111.359  1.00129.66           C
ANISOU 7144  CD1 LEU B 102    20869  15085  13312  -4788   2782   3599       C
ATOM   7145  CD2 LEU B 102      25.219 -28.114 112.364  1.00136.70           C
ANISOU 7145  CD2 LEU B 102    22554  15454  13931  -3983   2449   4020       C
ATOM   7146  N   LEU B 103      21.751 -30.642 112.565  1.00144.67           N
ANISOU 7146  N   LEU B 103    24747  15446  14775  -5556   3433   4602       N
ATOM   7147  CA  LEU B 103      21.785 -31.682 111.541  1.00146.31           C
ANISOU 7147  CA  LEU B 103    25239  15055  15296  -5644   3463   4541       C
ATOM   7148  C   LEU B 103      20.606 -32.659 111.537  1.00150.54           C
ANISOU 7148  C   LEU B 103    26212  15173  15815  -6282   3777   4752       C
ATOM   7149  O   LEU B 103      20.737 -33.822 111.149  1.00154.55           O
ANISOU 7149  O   LEU B 103    27228  15017  16479  -6303   3767   4847       O
ATOM   7150  CB  LEU B 103      23.128 -32.404 111.616  1.00149.32           C
ANISOU 7150  CB  LEU B 103    25993  15007  15734  -4993   3155   4647       C
ATOM   7151  CG  LEU B 103      24.197 -31.310 111.644  1.00145.11           C
ANISOU 7151  CG  LEU B 103    24928  15005  15204  -4459   2865   4430       C
ATOM   7152  CD1 LEU B 103      25.582 -31.839 111.962  1.00148.40           C
ANISOU 7152  CD1 LEU B 103    25601  15158  15627  -3754   2524   4556       C
ATOM   7153  CD2 LEU B 103      24.183 -30.557 110.322  1.00139.49           C
ANISOU 7153  CD2 LEU B 103    23596  14591  14813  -4567   2886   3970       C
ATOM   7154  N   VAL B 104      19.457 -32.172 111.981  1.00171.42           N
ANISOU 7154  N   VAL B 104    28637  18209  18285  -6802   4053   4804       N
ATOM   7155  CA  VAL B 104      18.212 -32.925 111.904  1.00175.10           C
ANISOU 7155  CA  VAL B 104    29361  18418  18751  -7508   4380   4961       C
ATOM   7156  C   VAL B 104      17.232 -31.930 111.302  1.00170.55           C
ANISOU 7156  C   VAL B 104    28065  18402  18333  -7915   4562   4625       C
ATOM   7157  O   VAL B 104      16.024 -32.168 111.211  1.00172.50           O
ANISOU 7157  O   VAL B 104    28258  18689  18595  -8551   4854   4667       O
ATOM   7158  CB  VAL B 104      17.746 -33.492 113.263  1.00181.24           C
ANISOU 7158  CB  VAL B 104    30652  19120  19091  -7769   4560   5460       C
ATOM   7159  CG1 VAL B 104      16.319 -34.034 113.171  1.00184.67           C
ANISOU 7159  CG1 VAL B 104    31179  19465  19524  -8602   4944   5581       C
ATOM   7160  CG2 VAL B 104      18.689 -34.597 113.712  1.00186.52           C
ANISOU 7160  CG2 VAL B 104    32082  19113  19672  -7381   4320   5833       C
ATOM   7161  N   ILE B 105      17.792 -30.787 110.914  1.00160.10           N
ANISOU 7161  N   ILE B 105    26174  17516  17139  -7535   4359   4308       N
ATOM   7162  CA  ILE B 105      17.066 -29.805 110.134  1.00155.61           C
ANISOU 7162  CA  ILE B 105    24913  17401  16812  -7811   4419   3974       C
ATOM   7163  C   ILE B 105      17.620 -29.942 108.694  1.00152.77           C
ANISOU 7163  C   ILE B 105    24431  16817  16798  -7696   4221   3697       C
ATOM   7164  O   ILE B 105      16.921 -29.667 107.712  1.00150.75           O
ANISOU 7164  O   ILE B 105    23803  16698  16778  -8075   4273   3478       O
ATOM   7165  CB  ILE B 105      17.161 -28.377 110.734  1.00152.10           C
ANISOU 7165  CB  ILE B 105    23925  17595  16271  -7551   4338   3826       C
ATOM   7166  CG1 ILE B 105      16.887 -28.419 112.228  1.00155.97           C
ANISOU 7166  CG1 ILE B 105    24665  18269  16326  -7572   4518   4089       C
ATOM   7167  CG2 ILE B 105      16.095 -27.473 110.160  1.00149.32           C
```

FIG. 13 Continued

```
ANISOU  7167  CG2 ILE B 105     22916  17661  16159  -7926   4451   3566       C
ATOM    7168  CD1 ILE B 105     15.434 -28.648 112.554  1.00159.29             C
ANISOU  7168  CD1 ILE B 105     25025  18845  16654  -8216   4923   4178       C
ATOM    7169  N   ASN B 106     18.866 -30.405 108.570  1.00137.81             N
ANISOU  7169  N   ASN B 106     22847  14599  14914  -7180   3997   3706       N
ATOM    7170  CA  ASN B 106     19.430 -30.693 107.252  1.00136.37             C
ANISOU  7170  CA  ASN B 106     22610  14200  15004  -7070   3862   3428       C
ATOM    7171  C   ASN B 106     19.014 -32.068 106.763  1.00141.03             C
ANISOU  7171  C   ASN B 106     23743  14153  15691  -7408   4009   3469       C
ATOM    7172  O   ASN B 106     19.055 -32.339 105.584  1.00140.47             O
ANISOU  7172  O   ASN B 106     23606  13940  15828  -7534   3985   3189       O
ATOM    7173  CB  ASN B 106     20.939 -30.551 107.240  1.00135.29             C
ANISOU  7173  CB  ASN B 106     22474  14053  14875  -6367   3577   3350       C
ATOM    7174  CG  ASN B 106     21.368 -29.113 107.215  1.00130.09             C
ANISOU  7174  CG  ASN B 106     21177  14023  14229  -6135   3392   3187       C
ATOM    7175  OD1 ASN B 106     22.532 -28.813 106.985  1.00128.63             O
ANISOU  7175  OD1 ASN B 106     20836  13947  14090  -5655   3160   3067       O
ATOM    7176  ND2 ASN B 106     20.423 -28.203 107.450  1.00127.74             N
ANISOU  7176  ND2 ASN B 106     20486  14137  13912  -6478   3490   3171       N
ATOM    7177  N   SER B 107     18.642 -32.945 107.687  1.00147.42             N
ANISOU  7177  N   SER B 107     25117  14568  16330   7568   4150   3823       N
ATOM    7178  CA  SER B 107     18.044 -34.231 107.341  1.00152.62             C
ANISOU  7178  CA  SER B 107     26316  14586  17085  -8015   4305   3906       C
ATOM    7179  C   SER B 107     16.568 -33.910 107.113  1.00151.99             C
ANISOU  7179  C   SER B 107     25892  14831  17024  -8779   4560   3874       C
ATOM    7180  O   SER B 107     15.681 -34.756 107.288  1.00156.73             O
ANISOU  7180  O   SER B 107     26857  15092  17602  -9339   4769   4067       O
ATOM    7181  CB  SER B 107     18.213 -35.241 108.485  1.00158.94             C
ANISOU  7181  CB  SER B 107     27860  14846  17684  -7926   4328   4369       C
ATOM    7182  OG  SER B 107     17.275 -36.310 108.406  1.00164.36             O
ANISOU  7182  OG  SER B 107     29025  15009  18416  -8563   4535   4541       O
ATOM    7183  N   THR B 108     16.330 -32.653 106.735  1.00146.22             N
ANISOU  7183  N   THR B 108     24436  14765  16356  -8790   4521   3639       N
ATOM    7184  CA  THR B 108     14.993 -32.119 106.489  1.00145.19             C
ANISOU  7184  CA  THR B 108     23822  15053  16291  -9406   4707   3568       C
ATOM    7185  C   THR B 108     15.025 -31.209 105.267  1.00140.06             C
ANISOU  7185  C   THR B 108     22544  14794  15878  -9399   4531   3199       C
ATOM    7186  O   THR B 108     14.922 -31.666 104.133  1.00140.48             O
ANISOU  7186  O   THR B 108     22637  14641  16096  -9645   4485   2991       O
ATOM    7187  CB  THR B 108     14.460 -31.323 107.719  1.00144.90             C
ANISOU  7187  CB  THR B 108     23502  15525  16029  -9430   4860   3756       C
ATOM    7188  OG1 THR B 108     13.981 -32.236 108.716  1.00150.79             O
ANISOU  7188  OG1 THR B 108     24782  15984  16526  -9730   5105   4126       O
ATOM    7189  CG2 THR B 108     13.330 -30.372 107.328  1.00142.48             C
ANISOU  7189  CG2 THR B 108     22467  15789  15880  -9838   4959   3564       C
ATOM    7190  N   ILE B 109     15.206 -29.920 105.490  1.00166.39             N
ANISOU  7190  N   ILE B 109     25325  18680  19215  -9119   4410   3120       N
ATOM    7191  CA  ILE B 109     15.207 -28.988 104.382  1.00162.00             C
ANISOU  7191  CA  ILE B 109     24180  18496  18875  -9142   4213   2841       C
ATOM    7192  C   ILE B 109     16.269 -29.370 103.337  1.00161.03             C
ANISOU  7192  C   ILE B 109     24228  18133  18824  -8878   4019   2639       C
ATOM    7193  O   ILE B 109     16.524 -28.626 102.393  1.00157.65             O
ANISOU  7193  O   ILE B 109     23368  18015  18517  -8846   3827   2432       O
ATOM    7194  CB  ILE B 109     15.270 -27.524 104.886  1.00158.09             C
ANISOU  7194  CB  ILE B 109     23111  18558  18398  -8861   4088   2807       C
ATOM    7195  CG1 ILE B 109     13.902 -27.133 105.456  1.00159.54             C
ANISOU  7195  CG1 ILE B 109     22970  19047  18602  -9273   4309   2871       C
ATOM    7196  CG2 ILE B 109     15.673 -26.556 103.789  1.00153.73             C
ANISOU  7196  CG2 ILE B 109     22053  18307  18051  -8750   3796   2582       C
ATOM    7197  CD1 ILE B 109     12.726 -27.544 104.574  1.00161.39             C
ANISOU  7197  CD1 ILE B 109     23038  19266  19017  -9929   4417   2809       C
ATOM    7198  N   SER B 110     16.887 -30.537 103.516  1.00158.32             N
ANISOU  7198  N   SER B 110     24515  17235  18403  -8689   4069   2701       N
ATOM    7199  CA  SER B 110     17.801 -31.087 102.509  1.00158.77             C
ANISOU  7199  CA  SER B 110     24765  17021  18539  -8461   3947   2449       C
ATOM    7200  C   SER B 110     17.161 -32.319 101.855  1.00163.35             C
ANISOU  7200  C   SER B 110     25781  17091  19191  -8953   4096   2356       C
ATOM    7201  O   SER B 110     16.476 -32.201 100.845  1.00162.80             O
ANISOU  7201  O   SER B 110     25454  17192  19212  -9432   4100   2154       O
```

FIG. 13 Continued

```
ATOM   7202  CB  SER B 110      19.191 -31.408 103.091  1.00159.70           C
ANISOU 7202  CB  SER B 110    25209  16892  18578  -7744   3827   2509       C
ATOM   7203  OG  SER B 110      20.126 -31.795 102.087  1.00160.17           O
ANISOU 7203  OG  SER B 110    25332  16799  18727  -7468   3723   2203       O
ATOM   7204  N   PHE B 111      17.356 -33.492 102.450  1.00171.27           N
ANISOU 7204  N   PHE B 111    27460  17457  20158  -8859   4192   2518       N
ATOM   7205  CA  PHE B 111      16.804 -34.734 101.903  1.00176.47           C
ANISOU 7205  CA  PHE B 111    28617  17524  20911  -9320   4315   2428       C
ATOM   7206  C   PHE B 111      15.266 -34.728 101.911  1.00177.69           C
ANISOU 7206  C   PHE B 111    28612  17826  21076 -10133   4496   2546       C
ATOM   7207  O   PHE B 111      14.619 -35.785 101.919  1.00182.96           O
ANISOU 7207  O   PHE B 111    29755  17979  21785 -10605   4635   2622       O
ATOM   7208  CB  PHE B 111      17.373 -35.971 102.626  1.00182.20           C
ANISOU 7208  CB  PHE B 111    30135  17464  21629  -9016   4336   2631       C
ATOM   7209  CG  PHE B 111      18.824 -35.827 103.056  1.00181.25           C
ANISOU 7209  CG  PHE B 111    30089  17301  21475  -8151   4147   2647       C
ATOM   7210  CD1 PHE B 111      19.757 -35.196 102.235  1.00177.50           C
ANISOU 7210  CD1 PHE B 111    29190  17195  21056  -7724   3994   2291       C
ATOM   7211  CD2 PHE B 111      19.254 -36.339 104.280  1.00184.69           C
ANISOU 7211  CD2 PHE B 111    31012  17352  21809  -7796   4112   3038       C
ATOM   7212  CE1 PHE B 111      21.084 -35.066 102.636  1.00177.10           C
ANISOU 7212  CE1 PHE B 111    29151  17150  20988  -6953   3819   2301       C
ATOM   7213  CE2 PHE B 111      20.574 -36.217 104.681  1.00184.31           C
ANISOU 7213  CE2 PHE B 111    30998  17289  21740  -7006   3902   3060       C
ATOM   7214  CZ  PHE B 111      21.487 -35.579 103.861  1.00180.48           C
ANISOU 7214  CZ  PHE B 111    30042  17191  21341  -6581   3761   2678       C
ATOM   7215  N   ILE B 112      14.700 -33.520 101.951  1.00157.52           N
ANISOU 7215  N   ILE B 112    25376  15967  18507 -10279   4481   2565       N
ATOM   7216  CA  ILE B 112      13.261 -33.311 101.819  1.00158.29           C
ANISOU 7216  CA  ILE B 112    25135  16350  18659 -10996   4618   2613       C
ATOM   7217  C   ILE B 112      13.050 -32.681 100.446  1.00155.24           C
ANISOU 7217  C   ILE B 112    24224  16361  18399 -11212   4443   2284       C
ATOM   7218  O   ILE B 112      12.051 -32.959  99.777  1.00157.37           O
ANISOU 7218  O   ILE B 112    24377  16665  18753 -11852   4485   2191       O
ATOM   7219  CB  ILE B 112      12.665 -32.402 102.936  1.00156.58           C
ANISOU 7219  CB  ILE B 112    24504  16635  18355 -10997   4733   2869       C
ATOM   7220  CG1 ILE B 112      11.294 -32.918 103.406  1.00161.19           C
ANISOU 7220  CG1 ILE B 112    25136  17187  18920 -11706   5011   3069       C
ATOM   7221  CG2 ILE B 112      12.647 -30.924 102.516  1.00150.88           C
ANISOU 7221  CG2 ILE B 112    22999  16597  17734 -10821   4547   2703       C
ATOM   7222  CD1 ILE B 112      10.355 -33.348 102.299  1.00163.37           C
ANISOU 7222  CD1 ILE B 112    25285  17419  19370 -12402   5019   2883       C
ATOM   7223  N   GLU B 113      14.005 -31.843 100.025  1.00136.81           N
ANISOU 7223  N   GLU B 113    21580  14340  16061 -10708   4230   2129       N
ATOM   7224  CA  GLU B 113      13.970 -31.221  98.693  1.00134.21           C
ANISOU 7224  CA  GLU B 113    20793  14403  15799 -10882   4031   1856       C
ATOM   7225  C   GLU B 113      14.293 -32.290  97.633  1.00137.63           C
ANISOU 7225  C   GLU B 113    21662  14423  16209 -11052   4032   1550       C
ATOM   7226  O   GLU B 113      15.076 -32.079  96.710  1.00136.16           O
ANISOU 7226  O   GLU B 113    21370  14391  15975 -10842   3889   1285       O
ATOM   7227  CB  GLU B 113      14.904 -29.993  98.606  1.00128.98           C
ANISOU 7227  CB  GLU B 113    19682  14202  15122 -10344   3809   1821       C
ATOM   7228  CG  GLU B 113      14.422 -28.828  97.685  1.00125.75           C
ANISOU 7228  CG  GLU B 113    18585  14390  14805 -10613   3583   1743       C
ATOM   7229  CD  GLU B 113      13.664 -27.694  98.412  1.00123.35           C
ANISOU 7229  CD  GLU B 113    17750  14497  14635 -10637   3538   1949       C
ATOM   7230  OE1 GLU B 113      12.740 -27.970  99.206  1.00125.61           O
ANISOU 7230  OE1 GLU B 113    18071  14703  14952 -10883   3742   2096       O
ATOM   7231  OE2 GLU B 113      13.977 -26.512  98.165  1.00119.78           O
ANISOU 7231  OE2 GLU B 113    16818  14441  14253 -10427   3298   1950       O
ATOM   7232  N   GLU B 114      13.677 -33.454  97.824  1.00173.16           N
ANISOU 7232  N   GLU B 114    26667  18391  20734 -11451   4209   1585       N
ATOM   7233  CA  GLU B 114      13.781 -34.600  96.929  1.00177.72           C
ANISOU 7233  CA  GLU B 114    27734  18470  21320 -11698   4234   1274       C
ATOM   7234  C   GLU B 114      12.407 -35.263  96.834  1.00182.12           C
ANISOU 7234  C   GLU B 114    28420  18831  21945 -12520   4354   1332       C
ATOM   7235  O   GLU B 114      12.122 -35.986  95.884  1.00185.74           O
ANISOU 7235  O   GLU B 114    29111  19045  22418 -12950   4335   1036       O
ATOM   7236  CB  GLU B 114      14.840 -35.588  97.402  1.00180.92           C
```

FIG. 13 Continued

```
ANISOU  7236  CB   GLU B 114     28829  18185  21727 -11157   4298   1244       C
ATOM    7237  CG   GLU B 114      16.250 -35.117  97.127  1.00177.82           C
ANISOU  7237  CG   GLU B 114     28296  17987  21281 -10416   4164   1052       C
ATOM    7238  CD   GLU B 114      17.182 -36.261  96.809  1.00182.50           C
ANISOU  7238  CD   GLU B 114     29495  17926  21920 -10042   4191    760       C
ATOM    7239  OE1  GLU B 114      18.334 -35.986  96.410  1.00180.94           O
ANISOU  7239  OE1  GLU B 114     29156  17909  21684  -9478   4105    522       O
ATOM    7240  OE2  GLU B 114      16.759 -37.432  96.950  1.00188.19           O
ANISOU  7240  OE2  GLU B 114     30822  17949  22733 -10319   4295    758       O
ATOM    7241  N    ASN B 115      11.577 -35.042  97.849  1.00172.91           N
ANISOU  7241  N    ASN B 115     27107  17784  20807 -12748   4491   1696       N
ATOM    7242  CA   ASN B 115      10.164 -35.383  97.763  1.00176.53           C
ANISOU  7242  CA   ASN B 115     27458  18278  21336 -13572   4599   1776       C
ATOM    7243  C    ASN B 115       9.627 -34.061  97.206  1.00171.97           C
ANISOU  7243  C    ASN B 115     26014  18522  20805 -13699   4427   1723       C
ATOM    7244  O    ASN B 115       8.520 -33.966  96.667  1.00173.64           O
ANISOU  7244  O    ASN B 115     25864  19015  21097 -14340   4389   1680       O
ATOM    7245  CB   ASN B 115       9.575 -35.711  99.146  1.00179.34           C
ANISOU  7245  CB   ASN B 115     28011  18459  21672 -13734   4854   2193       C
ATOM    7246  CG   ASN B 115       8.567 -36.870  99.115  1.00186.31           C
ANISOU  7246  CG   ASN B 115     29290  18888  22612 -14543   5017   2258       C
ATOM    7247  OD1  ASN B 115       8.644 -37.764  98.267  1.00189.95           O
ANISOU  7247  OD1  ASN B 115     30179  18865  23129 -14818   4950   1991       O
ATOM    7248  ND2  ASN B 115       7.633 -36.862 100.062  1.00188.68           N
ANISOU  7248  ND2  ASN B 115     29451  19349  22889 -14939   5243   2598       N
ATOM    7249  N    ASN B 116      10.471 -33.042  97.349  1.00153.54           N
ANISOU  7249  N    ASN B 116     23359  16545  18435 -13062   4292   1737       N
ATOM    7250  CA   ASN B 116      10.245 -31.701  96.840  1.00149.04           C
ANISOU  7250  CA   ASN B 116     22027  16673  17927 -13028   4068   1706       C
ATOM    7251  C    ASN B 116      10.989 -31.583  95.502  1.00147.61           C
ANISOU  7251  C    ASN B 116     21824  16597  17665 -12936   3833   1392       C
ATOM    7252  O    ASN B 116      10.653 -30.755  94.660  1.00145.65           O
ANISOU  7252  O    ASN B 116     21043  16854  17444 -13140   3600   1329       O
ATOM    7253  CB   ASN B 116      10.780 -30.692  97.871  1.00144.73           C
ANISOU  7253  CB   ASN B 116     21210  16397  17383 -12406   4061   1912       C
ATOM    7254  CG   ASN B 116      10.297 -29.250  97.644  1.00140.98           C
ANISOU  7254  CG   ASN B 116     19933  16585  17050 -12402   3849   1950       C
ATOM    7255  OD1  ASN B 116       9.872 -28.579  98.591  1.00139.96           O
ANISOU  7255  OD1  ASN B 116     19483  16698  16997 -12266   3929   2122       O
ATOM    7256  ND2  ASN B 116      10.413 -28.756  96.411  1.00139.35           N
ANISOU  7256  ND2  ASN B 116     19419  16661  16866 -12522   3568   1786       N
ATOM    7257  N    ALA B 117      12.004 -32.417  95.298  1.00263.42           N
ANISOU  7257  N    ALA B 117     51978  30235  17876  -1184   6008    380       N
ATOM    7258  CA   ALA B 117      12.756 -32.369  94.045  1.00258.87           C
ANISOU  7258  CA   ALA B 117     50885  29504  17971  -1102   5789    -59       C
ATOM    7259  C    ALA B 117      12.200 -33.291  92.960  1.00255.74           C
ANISOU  7259  C    ALA B 117     50001  29073  18096  -1130   5698    257       C
ATOM    7260  O    ALA B 117      11.668 -32.828  91.952  1.00251.98           O
ANISOU  7260  O    ALA B 117     49129  28689  17922  -1050   6192    240       O
ATOM    7261  CB   ALA B 117      14.226 -32.670  94.283  1.00259.91           C
ANISOU  7261  CB   ALA B 117     51105  29391  18258  -1104   5005   -525       C
ATOM    7262  N    GLY B 118      12.331 -34.596  93.180  1.00258.98           N
ANISOU  7262  N    GLY B 118     50443  29349  18609  -1242   5058    540       N
ATOM    7263  CA   GLY B 118      11.904 -35.603  92.224  1.00256.50           C
ANISOU  7263  CA   GLY B 118     49688  28969  18803  -1281   4859    822       C
ATOM    7264  C    GLY B 118      10.560 -35.349  91.577  1.00254.28           C
ANISOU  7264  C    GLY B 118     49138  28889  18587  -1259   5565   1195       C
ATOM    7265  O    GLY B 118      10.289 -35.864  90.497  1.00251.14           O
ANISOU  7265  O    GLY B 118     48279  28450  18692  -1245   5505   1274       O
ATOM    7266  N    ASN B 119       9.710 -34.568  92.238  1.00254.92           N
ANISOU  7266  N    ASN B 119     49509  29185  18163  -1254   6227   1428       N
ATOM    7267  CA   ASN B 119       8.406 -34.239  91.680  1.00253.00           C
ANISOU  7267  CA   ASN B 119     49027  29140  17960  -1230   6942   1789       C
ATOM    7268  C    ASN B 119       8.558 -33.669  90.276  1.00247.84           C
ANISOU  7268  C    ASN B 119     47841  28495  17832  -1100   7194   1430       C
ATOM    7269  O    ASN B 119       7.709 -33.880  89.412  1.00245.37           O
ANISOU  7269  O    ASN B 119     47153  28263  17813  -1087   7480   1697       O
ATOM    7270  CB   ASN B 119       7.652 -33.265  92.586  1.00255.46           C
ANISOU  7270  CB   ASN B 119     49736  29669  17657  -1220   7653   1977       C
```

FIG. 13 Continued

```
ATOM   7271  CG  ASN B 119       6.958 -33.962  93.737  1.00260.12           C
ANISOU 7271  CG  ASN B 119    50748  30309  17779  -1345   7595   2556       C
ATOM   7272  OD1 ASN B 119       6.774 -35.178  93.722  1.00261.10           O
ANISOU 7272  OD1 ASN B 119    50791  30330  18085  -1442   7139   2912       O
ATOM   7273  ND2 ASN B 119       6.565 -33.192  94.742  1.00263.14           N
ANISOU 7273  ND2 ASN B 119    51579  30844  17558  -1338   8070   2657       N
ATOM   7274  N   ALA B 120       9.648 -32.944  90.052  1.00275.67           N
ANISOU 7274  N   ALA B 120    51331  31933  21478   -997   7086    826       N
ATOM   7275  CA  ALA B 120       9.932 -32.413  88.729  1.00270.93           C
ANISOU 7275  CA  ALA B 120    50233  31320  21387   -856   7282    452       C
ATOM   7276  C   ALA B 120      10.407 -33.566  87.865  1.00268.98           C
ANISOU 7276  C   ALA B 120    49616  30880  21706   -877   6621    412       C
ATOM   7277  O   ALA B 120      10.078 -33.644  86.681  1.00265.40           O
ANISOU 7277  O   ALA B 120    48697  30456  21688   -805   6778    411       O
ATOM   7278  CB  ALA B 120      10.993 -31.331  88.802  1.00270.24           C
ANISOU 7278  CB  ALA B 120    50228  31174  21277   -740   7342   -173       C
ATOM   7279  N   ALA B 121      11.168 -34.470  88.478  1.00242.27           N
ANISOU 7279  N   ALA B 121    46448  27302  18303   -974   5880    387       N
ATOM   7280  CA  ALA B 121      11.710 -35.637  87.789  1.00240.96           C
ANISOU 7280  CA  ALA B 121    45975  26922  18656  -1008   5187    343       C
ATOM   7281  C   ALA B 121      10.608 -36.435  87.100  1.00239.65           C
ANISOU 7281  C   ALA B 121    45488  26827  18742  -1059   5298    827       C
ATOM   7282  O   ALA B 121      10.875 -37.374  86.351  1.00238.13           O
ANISOU 7282  O   ALA B 121    44973  26481  19023  -1075   4815    815       O
ATOM   7283  CB  ALA B 121      12.482 -36.517  88.762  1.00244.68           C
ANISOU 7283  CB  ALA B 121    46792  27202  18974  -1128   4436    366       C
ATOM   7284  N   ALA B 122       9.366 -36.050  87.362  1.00240.58           N
ANISOU 7284  N   ALA B 122    45693  27170  18546  -1082   5937   1249       N
ATOM   7285  CA  ALA B 122       8.220 -36.702  86.754  1.00239.55           C
ANISOU 7285  CA  ALA B 122    45264  27122  18631  -1130   6112   1728       C
ATOM   7286  C   ALA B 122       8.091 -36.316  85.288  1.00234.81           C
ANISOU 7286  C   ALA B 122    44127  26575  18515   -991   6388   1498       C
ATOM   7287  O   ALA B 122       8.620 -36.995  84.411  1.00232.70           O
ANISOU 7287  O   ALA B 122    43519  26154  18743   -963   5917   1307       O
ATOM   7288  CB  ALA B 122       6.950 -36.340  87.507  1.00241.88           C
ANISOU 7288  CB  ALA B 122    45823  27637  18446  -1190   6739   2243       C
ATOM   7289  N   ALA B 123       7.396 -35.213  85.032  1.00232.62           N
ANISOU 7289  N   ALA B 123    43781  26518  18085   -898   7159   1517       N
ATOM   7290  CA  ALA B 123       7.175 -34.752  83.673  1.00228.30           C
ANISOU 7290  CA  ALA B 123    42740  26057  17948   -754   7499   1336       C
ATOM   7291  C   ALA B 123       8.452 -34.901  82.877  1.00225.81           C
ANISOU 7291  C   ALA B 123    42169  25544  18083   -652   6994    782       C
ATOM   7292  O   ALA B 123       8.429 -35.335  81.730  1.00222.98           O
ANISOU 7292  O   ALA B 123    41377  25149  18195   -587   6849    717       O
ATOM   7293  CB  ALA B 123       6.717 -33.309  83.670  1.00227.19           C
ANISOU 7293  CB  ALA B 123    42636  26137  17548   -642   8335   1248       C
ATOM   7294  N   LEU B 124       9.573 -34.572  83.505  1.00227.10           N
ANISOU 7294  N   LEU B 124    42609  25575  18106   -639   6708    388       N
ATOM   7295  CA  LEU B 124      10.866 -34.627  82.831  1.00224.96           C
ANISOU 7295  CA  LEU B 124    42121  25099  18255   -536   6246   -160       C
ATOM   7296  C   LEU B 124      11.458 -36.026  82.665  1.00225.57           C
ANISOU 7296  C   LEU B 124    42102  24932  18675   -626   5403   -144       C
ATOM   7297  O   LEU B 124      11.275 -36.672  81.629  1.00223.27           O
ANISOU 7297  O   LEU B 124    41410  24599  18823   -594   5232   -100       O
ATOM   7298  CB  LEU B 124      11.879 -33.738  83.551  1.00226.15           C
ANISOU 7298  CB  LEU B 124    42584  25179  18165   -487   6240   -606       C
ATOM   7299  CG  LEU B 124      11.537 -32.257  83.540  1.00225.01           C
ANISOU 7299  CG  LEU B 124    42470  25236  17788   -365   7047   -755       C
ATOM   7300  CD1 LEU B 124      12.814 -31.452  83.412  1.00223.90           C
ANISOU 7300  CD1 LEU B 124    42317  24959  17796   -234   6955  -1385       C
ATOM   7301  CD2 LEU B 124      10.606 -31.986  82.382  1.00221.60           C
ANISOU 7301  CD2 LEU B 124    41601  24985  17612   -264   7586   -588       C
ATOM   7302  N   MET B 125      12.180 -36.471  83.693  1.00278.82           N
ANISOU 7302  N   MET B 125    49216  31514  25211   -734   4880   -191       N
ATOM   7303  CA  MET B 125      12.890 -37.751  83.677  1.00279.80           C
ANISOU 7303  CA  MET B 125    49293  31380  25637   -824   4048   -210       C
ATOM   7304  C   MET B 125      11.994 -38.955  83.377  1.00280.18           C
ANISOU 7304  C   MET B 125    49157  31430  25869   -936   3853    293       C
ATOM   7305  O   MET B 125      12.440 -40.099  83.448  1.00281.39           O
```

FIG. 13 Continued

```
ANISOU 7305  O   MET B 125    49286  31376  26252   -1030   3181    355          O
ATOM   7306  CB  MET B 125      13.672 -37.963  84.986  1.00283.72           C
ANISOU 7306  CB  MET B 125    50269  31740  25794    -929   3583   -273          C
ATOM   7307  CG  MET B 125      15.073 -37.320  85.027  1.00283.16           C
ANISOU 7307  CG  MET B 125    50258  31507  25822    -830   3343   -894          C
ATOM   7308  SD  MET B 125      15.219 -35.716  85.863  1.00284.36           S
ANISOU 7308  SD  MET B 125    50782  31814  25446    -754   3934  -1161          S
ATOM   7309  CE  MET B 125      15.107 -34.563  84.495  1.00279.32           C
ANISOU 7309  CE  MET B 125    49677  31293  25159    -535   4602  -1508          C
ATOM   7310  N   ALA B 126      10.730 -38.690  83.057  1.00228.69           N
ANISOU 7310  N   ALA B 126    42501  25134  19258    -928   4442    653          N
ATOM   7311  CA  ALA B 126       9.790 -39.739  82.683  1.00228.88           C
ANISOU 7311  CA  ALA B 126    42307  25169  19488   -1023   4325   1125          C
ATOM   7312  C   ALA B 126       9.333 -39.563  81.239  1.00224.84           C
ANISOU 7312  C   ALA B 126    41279  24751  19400    -894   4620   1039          C
ATOM   7313  O   ALA B 126       8.780 -40.483  80.638  1.00224.32           O
ANISOU 7313  O   ALA B 126    40932  24651  19648    -944   4416   1298          O
ATOM   7314  CB  ALA B 126       8.598 -39.739  83.616  1.00231.86           C
ANISOU 7314  CB  ALA B 126    42976  25718  19403   -1142   4719   1702          C
ATOM   7315  N   GLY B 127       9.562 -38.371  80.695  1.00223.23           N
ANISOU 7315  N   GLY B 127    40952  24664  19201     725   5102    675          N
ATOM   7316  CA  GLY B 127       9.163 -38.054  79.337  1.00219.42           C
ANISOU 7316  CA  GLY B 127    39998  24296  19077    -577   5438    569          C
ATOM   7317  C   GLY B 127      10.193 -38.372  78.272  1.00216.69           C
ANISOU 7317  C   GLY B 127    39310  23766  19255    -454   4991     99          C
ATOM   7318  O   GLY B 127      10.255 -37.687  77.254  1.00213.43           O
ANISOU 7318  O   GLY B 127    38584  23445  19066    -275   5333   -172          O
ATOM   7319  N   LEU B 128      10.997 -39.408  78.488  1.00217.24           N
ANISOU 7319  N   LEU B 128    39434  23577  19529    -544   4241     10          N
ATOM   7320  CA  LEU B 128      12.015 -39.766  77.507  1.00214.85           C
ANISOU 7320  CA  LEU B 128    38819  23078  19736    -431   3792   -434          C
ATOM   7321  C   LEU B 128      12.368 -41.254  77.409  1.00216.03           C
ANISOU 7321  C   LEU B 128    38877  22980  20224    -550   3007   -344          C
ATOM   7322  O   LEU B 128      12.934 -41.680  76.403  1.00213.85           O
ANISOU 7322  O   LEU B 128    38269  22567  20416    -455   2686   -629          O
ATOM   7323  CB  LEU B 128      13.290 -38.936  77.707  1.00214.28           C
ANISOU 7323  CB  LEU B 128    38881  22893  19641    -320   3742   -972          C
ATOM   7324  CG  LEU B 128      13.717 -38.513  79.112  1.00217.43           C
ANISOU 7324  CG  LEU B 128    39779  23258  19578    -417   3704   -991          C
ATOM   7325  CD1 LEU B 128      15.226 -38.466  79.205  1.00217.43           C
ANISOU 7325  CD1 LEU B 128    39839  23001  19774    -362   3211  -1506          C
ATOM   7326  CD2 LEU B 128      13.124 -37.166  79.463  1.00217.22           C
ANISOU 7326  CD2 LEU B 128    39911  23486  19138    -350   4495   -958          C
ATOM   7327  N   ALA B 129      12.033 -42.045  78.425  1.00219.63           N
ANISOU 7327  N   ALA B 129    39619  23375  20456    -748   2710     55          N
ATOM   7328  CA  ALA B 129      12.372 -43.473  78.420  1.00221.06           C
ANISOU 7328  CA  ALA B 129    39728  23309  20955    -871   1960    162          C
ATOM   7329  C   ALA B 129      12.028 -44.127  77.088  1.00218.53           C
ANISOU 7329  C   ALA B 129    38922  22964  21146    -808   1840    155          C
ATOM   7330  O   ALA B 129      10.876 -44.466  76.848  1.00218.67           O
ANISOU 7330  O   ALA B 129    38797  23117  21172    -862   2063    556          O
ATOM   7331  CB  ALA B 129      11.681 -44.197  79.561  1.00224.98           C
ANISOU 7331  CB  ALA B 129    40534  23806  21140   -1080   1817    710          C
ATOM   7332  N   PRO B 130      13.056 -44.357  76.257  1.00216.73           N
ANISOU 7332  N   PRO B 130    38449  22548  21351    -697   1451   -299          N
ATOM   7333  CA  PRO B 130      13.101 -44.833  74.867  1.00213.95           C
ANISOU 7333  CA  PRO B 130    37633  22140  21519    -583   1292   -485          C
ATOM   7334  C   PRO B 130      11.849 -45.542  74.359  1.00213.97           C
ANISOU 7334  C   PRO B 130    37388  22251  21659    -649   1374    -61          C
ATOM   7335  O   PRO B 130      11.964 -46.534  73.643  1.00213.48           O
ANISOU 7335  O   PRO B 130    37049  22037  22028    -660    922    -97          O
ATOM   7336  CB  PRO B 130      14.284 -45.796  74.882  1.00214.78           C
ANISOU 7336  CB  PRO B 130    37725  21908  21974    -631    503   -736          C
ATOM   7337  CG  PRO B 130      15.218 -45.186  75.868  1.00216.21           C
ANISOU 7337  CG  PRO B 130    38277  22006  21869    -644    432   -960          C
ATOM   7338  CD  PRO B 130      14.388 -44.429  76.882  1.00218.02           C
ANISOU 7338  CD  PRO B 130    38848  22473  21516    -718    968   -627          C
ATOM   7339  N   LYS B 131      10.682 -45.004  74.698  1.00216.43           N
ANISOU 7339  N   LYS B 131    37788  22820  21624    -685   1955    317          N
```

FIG. 13 Continued

```
ATOM   7340  CA  LYS B 131       9.390 -45.559  74.303  1.00 216.66           C
ANISOU 7340  CA  LYS B 131    37599  22971  21750    -752   2106    756       C
ATOM   7341  C   LYS B 131       9.456 -46.264  72.938  1.00 214.44           C
ANISOU 7341  C   LYS B 131    36856  22607  22015    -661   1800    570       C
ATOM   7342  O   LYS B 131      10.134 -45.798  72.021  1.00 211.62           O
ANISOU 7342  O   LYS B 131    36284  22243  21878    -471   1841    117       O
ATOM   7343  CB  LYS B 131       8.339 -44.444  74.334  1.00 215.82           C
ANISOU 7343  CB  LYS B 131    37520  23189  21294    -690   2927    972       C
ATOM   7344  CG  LYS B 131       8.376 -43.641  75.648  1.00 217.92           C
ANISOU 7344  CG  LYS B 131    38253  23537  21009    -756   3252   1086       C
ATOM   7345  CD  LYS B 131       7.794 -42.229  75.518  1.00 216.24           C
ANISOU 7345  CD  LYS B 131    38052  23615  20494    -628   4082   1071       C
ATOM   7346  CE  LYS B 131       8.019 -41.396  76.793  1.00 218.29           C
ANISOU 7346  CE  LYS B 131    38785  23930  20226    -676   4363   1088       C
ATOM   7347  NZ  LYS B 131       7.383 -40.039  76.750  1.00 216.97           N
ANISOU 7347  NZ  LYS B 131    38643  24040  19755    -567   5192   1111       N
ATOM   7348  N   THR B 132       8.762 -47.395  72.821  1.00 242.19           N
ANISOU 7348  N   THR B 132    40220  26048  25751    -793   1492    921       N
ATOM   7349  CA  THR B 132       8.835 -48.237  71.622  1.00 240.67           C
ANISOU 7349  CA  THR B 132    39614  25744  26087    -732   1111    761       C
ATOM   7350  C   THR B 132       7.811 -47.959  70.535  1.00 238.56           C
ANISOU 7350  C   THR B 132    38985  25708  25948    -618   1536    851       C
ATOM   7351  O   THR B 132       8.143 -47.960  69.346  1.00 236.03           O
ANISOU 7351  O   THR B 132    38340  25383  25956    -451   1459    504       O
ATOM   7352  CB  THR B 132       8.677 -49.721  71.971  1.00 243.43           C
ANISOU 7352  CB  THR B 132    39946  25860  26688    -934    482   1060       C
ATOM   7353  OG1 THR B 132       9.721 -50.116  72.865  1.00 245.39           O
ANISOU 7353  OG1 THR B 132    40468  25865  26883   -1031     -4    950       O
ATOM   7354  CG2 THR B 132       8.727 -50.564  70.705  1.00 241.93           C
ANISOU 7354  CG2 THR B 132    39324  25556  27044    -866    104    875       C
ATOM   7355  N   LYS B 133       6.562 -47.760  70.935  1.00 211.79           N
ANISOU 7355  N   LYS B 133    35646  22514  22309    -706   1968   1327       N
ATOM   7356  CA  LYS B 133       5.511 -47.544  69.960  1.00 210.10           C
ANISOU 7356  CA  LYS B 133    35090  22521  22219    -613   2357   1459       C
ATOM   7357  C   LYS B 133       5.199 -48.867  69.246  1.00 210.67           C
ANISOU 7357  C   LYS B 133    34835  22440  22769    -677   1828   1551       C
ATOM   7358  O   LYS B 133       5.245 -48.961  68.015  1.00 208.44           O
ANISOU 7358  O   LYS B 133    34199  22191  22809     526   1765   1285       O
ATOM   7359  CB  LYS B 133       5.937 -46.449  68.981  1.00 206.52           C
ANISOU 7359  CB  LYS B 133    34455  22232  21782    -353   2750   1008       C
ATOM   7360  CG  LYS B 133       6.581 -45.235  69.672  1.00 205.99           C
ANISOU 7360  CG  LYS B 133    34708  22238  21323    -284   3137    801       C
ATOM   7361  CD  LYS B 133       7.159 -44.257  68.660  1.00 202.51           C
ANISOU 7361  CD  LYS B 133    34062  21910  20974     -18   3451    320       C
ATOM   7362  CE  LYS B 133       7.904 -43.115  69.326  1.00 202.10           C
ANISOU 7362  CE  LYS B 133    34308  21889  20594      50   3773     74       C
ATOM   7363  NZ  LYS B 133       8.654 -42.318  68.313  1.00 198.86           N
ANISOU 7363  NZ  LYS B 133    33678  21524  20357     312   3970   -431       N
ATOM   7364  N   VAL B 134       4.902 -49.882  70.060  1.00 214.78           N
ANISOU 7364  N   VAL B 134    35469  22788  23328    -897   1449   1929       N
ATOM   7365  CA  VAL B 134       4.552 -51.232  69.620  1.00 216.04           C
ANISOU 7365  CA  VAL B 134    35383  22770  23934   -1001    922   2088       C
ATOM   7366  C   VAL B 134       3.135 -51.299  69.054  1.00 215.98           C
ANISOU 7366  C   VAL B 134    35091  22953  24019   -1008   1254   2441       C
ATOM   7367  O   VAL B 134       2.378 -50.336  69.156  1.00 215.29           O
ANISOU 7367  O   VAL B 134    35051  23130  23621    -957   1897   2626       O
ATOM   7368  CB  VAL B 134       4.598 -52.197  70.804  1.00 219.73           C
ANISOU 7368  CB  VAL B 134    36109  23009  24371   -1238    492   2443       C
ATOM   7369  CG1 VAL B 134       5.812 -51.915  71.657  1.00 220.32           C
ANISOU 7369  CG1 VAL B 134    36550  22951  24211   -1251    297   2200       C
ATOM   7370  CG2 VAL B 134       3.341 -52.045  71.637  1.00 222.00           C
ANISOU 7370  CG2 VAL B 134    36550  23448  24352   -1374    921   3043       C
ATOM   7371  N   LEU B 135       2.773 -52.441  68.470  1.00 215.02           N
ANISOU 7371  N   LEU B 135    34671  22689  24339   -1074    811   2536       N
ATOM   7372  CA  LEU B 135       1.437 -52.622  67.896  1.00 215.21           C
ANISOU 7372  CA  LEU B 135    34396  22865  24510   -1088   1051   2865       C
ATOM   7373  C   LEU B 135       0.386 -52.996  68.937  1.00 218.48           C
ANISOU 7373  C   LEU B 135    34966  23274  24774   -1303   1190   3505       C
ATOM   7374  O   LEU B 135      -0.676 -53.524  68.603  1.00 219.53           O
```

FIG. 13 Continued

```
ANISOU 7374  O   LEU B 135     34845  23433  25133  -1371   1207   3834           O
ATOM   7375  CB  LEU B 135      1.450 -53.612  66.730  1.00214.66                  C
ANISOU 7375  CB  LEU B 135     33914  22662  24987  -1047    550   2664           C
ATOM   7376  CG  LEU B 135      1.653 -52.935  65.371  1.00211.17                  C
ANISOU 7376  CG  LEU B 135     33186  22403  24645   -788    762   2214           C
ATOM   7377  CD1 LEU B 135      2.392 -53.835  64.398  1.00210.43                  C
ANISOU 7377  CD1 LEU B 135     32825  22099  25029   -715    139   1803           C
ATOM   7378  CD2 LEU B 135      0.325 -52.484  64.790  1.00210.55                  C
ANISOU 7378  CD2 LEU B 135     32863  22605  24532   -732   1264   2482           C
ATOM   7379  N   ARG B 136      0.720 -52.727  70.197  1.00221.11                  N
ANISOU 7379  N   ARG B 136     35717  23564  24730  -1404   1278   3670           N
ATOM   7380  CA  ARG B 136     -0.189 -52.874  71.338  1.00224.27                  C
ANISOU 7380  CA  ARG B 136     36347  23984  24880  -1586   1507   4274           C
ATOM   7381  C   ARG B 136     -0.999 -54.178  71.417  1.00227.08                  C
ANISOU 7381  C   ARG B 136     36508  24163  25608  -1762   1142   4712           C
ATOM   7382  O   ARG B 136     -0.634 -55.105  72.140  1.00229.69                  O
ANISOU 7382  O   ARG B 136     36987  24245  26040  -1912    664   4869           O
ATOM   7383  CB  ARG B 136     -1.121 -51.642  71.410  1.00223.28                  C
ANISOU 7383  CB  ARG B 136     36275  24186  24375  -1512   2326   4487           C
ATOM   7384  CG  ARG B 136     -2.289 -51.735  72.403  1.00226.37                  C
ANISOU 7384  CG  ARG B 136     36836  24632  24544  -1677   2661   5148           C
ATOM   7385  CD  ARG B 136     -3.277 -50.568  72.259  1.00225.15                  C
ANISOU 7385  CD  ARG B 136     36650  24797  24099  -1591   3465   5340           C
ATOM   7386  NE  ARG B 136     -4.642 -50.980  72.585  1.00227.60                  N
ANISOU 7386  NE  ARG B 136     36871  25136  24472  -1725   3682   5955           N
ATOM   7387  CZ  ARG B 136     -5.146 -51.006  73.814  1.00230.65                  C
ANISOU 7387  CZ  ARG B 136     37578  25505  24555  -1866   3901   6440           C
ATOM   7388  NH1 ARG B 136     -4.404 -50.635  74.847  1.00231.68                  N
ANISOU 7388  NH1 ARG B 136     38153  25603  24274  -1693   3924   6375           N
ATOM   7389  NH2 ARG B 136     -6.394 -51.404  74.009  1.00232.81                  N
ANISOU 7389  NH2 ARG B 136     37725  25790  24940  -1976   4096   6991           N
ATOM   7390  N   ASP B 137     -2.095 -54.224  70.667  1.00226.42                  N
ANISOU 7390  N   ASP B 137     36086  24210  25735  -1738   1374   4909           N
ATOM   7391  CA  ASP B 137     -3.048 -55.326  70.688  1.00229.06                  C
ANISOU 7391  CA  ASP B 137     36198  24406  26427  -1895   1131   5356           C
ATOM   7392  C   ASP B 137     -4.331 -54.756  70.103  1.00228.19                  C
ANISOU 7392  C   ASP B 137     35836  24553  26312  -1836   1688   5598           C
ATOM   7393  O   ASP B 137     -4.911 -55.316  69.172  1.00227.92                  O
ANISOU 7393  O   ASP B 137     35403  24501  26696  -1822   1513   5607           O
ATOM   7394  CB  ASP B 137     -3.282 -55.798  72.127  1.00232.86                  C
ANISOU 7394  CB  ASP B 137     37020  24749  26709  -2096   1082   5866           C
ATOM   7395  CG  ASP B 137     -4.612 -56.556  72.311  1.00235.61                  C
ANISOU 7395  CG  ASP B 137     37183  25051  27289  -2242   1143   6462           C
ATOM   7396  OD1 ASP B 137     -5.070 -56.605  73.468  1.00238.56                  O
ANISOU 7396  OD1 ASP B 137     37834  25392  27418  -2375   1320   6951           O
ATOM   7397  OD2 ASP B 137     -5.199 -56.962  71.311  1.00234.97                  O
ANISOU 7397  OD2 ASP B 137     36679  24962  27636  -2218   1016   6443           O
ATOM   7398  N   GLY B 138     -4.749 -53.622  70.663  1.00234.23                  N
ANISOU 7398  N   GLY B 138     36841  25557  26598  -1799   2360   5783           N
ATOM   7399  CA  GLY B 138     -5.937 -52.911  70.228  1.00233.38                  C
ANISOU 7399  CA  GLY B 138     36543  25713  26418  -1738   2972   6028           C
ATOM   7400  C   GLY B 138     -5.644 -51.859  69.174  1.00229.47                  C
ANISOU 7400  C   GLY B 138     35885  25464  25841  -1505   3301   5562           C
ATOM   7401  O   GLY B 138     -6.408 -51.714  68.220  1.00228.25                  O
ANISOU 7401  O   GLY B 138     35377  25458  25889  -1421   3491   5584           O
ATOM   7402  N   LYS B 139     -4.541 -51.128  69.335  1.00221.82                  N
ANISOU 7402  N   LYS B 139     35164  24532  24586  -1395   3364   5144           N
ATOM   7403  CA  LYS B 139     -4.161 -50.094  68.365  1.00218.13                  C
ANISOU 7403  CA  LYS B 139     34556  24284  24040  -1159   3684   4686           C
ATOM   7404  C   LYS B 139     -2.653 -49.876  68.206  1.00216.22                  C
ANISOU 7404  C   LYS B 139     34451  23944  23759  -1043   3387   4100           C
ATOM   7405  O   LYS B 139     -1.927 -49.718  69.188  1.00217.21                  O
ANISOU 7405  O   LYS B 139     34949  23969  23610  -1106   3322   4055           O
ATOM   7406  CB  LYS B 139     -4.844 -48.758  68.681  1.00217.32                  C
ANISOU 7406  CB  LYS B 139     34588  24479  23504  -1092   4513   4889           C
ATOM   7407  CG  LYS B 139     -6.123 -48.505  67.885  1.00216.66                  C
ANISOU 7407  CG  LYS B 139     34147  24610  23562  -1037   4912   5141           C
ATOM   7408  CD  LYS B 139     -5.891 -48.608  66.376  1.00213.97                  C
ANISOU 7408  CD  LYS B 139     33392  24331  23577   -852   4696   4716           C
```

FIG. 13 Continued

```
ATOM   7409  CE   LYS B 139      -5.150 -47.398  65.826  1.00210.58           C
ANISOU 7409  CE   LYS B 139    32990  24096  22924   -615   5057   4241       C
ATOM   7410  NZ   LYS B 139      -4.848 -47.548  64.376  1.00208.16           N
ANISOU 7410  NZ   LYS B 139    32301  23839  22953   -423   4819   3820       N
ATOM   7411  N    TRP B 140      -2.219 -49.847  66.945  1.00220.60           N
ANISOU 7411  N    TRP B 140    34695  24534  24589   -863   3222   3654       N
ATOM   7412  CA   TRP B 140      -0.828 -49.626  66.536  1.00218.44           C
ANISOU 7412  CA   TRP B 140    34468  24175  24354   -716   2959   3064       C
ATOM   7413  C    TRP B 140      -0.131 -48.545  67.363  1.00217.79           C
ANISOU 7413  C    TRP B 140    34773  24163  23815   -671   3326   2922       C
ATOM   7414  O    TRP B 140       1.091 -48.565  67.526  1.00217.22           O
ANISOU 7414  O    TRP B 140    34859  23933  23742   -632   3010   2541       O
ATOM   7415  CB   TRP B 140      -0.816 -49.253  65.039  1.00215.36           C
ANISOU 7415  CB   TRP B 140    33695  23948  24185   -477   3068   2693       C
ATOM   7416  CG   TRP B 140       0.511 -48.787  64.436  1.00212.68           C
ANISOU 7416  CG   TRP B 140    33356  23575  23876   -271   2949   2079       C
ATOM   7417  CD1  TRP B 140       1.601 -49.565  64.140  1.00212.52           C
ANISOU 7417  CD1  TRP B 140    33301  23296  24151   -254   2313   1703       C
ATOM   7418  CD2  TRP B 140       0.849 -47.445  64.005  1.00209.81           C
ANISOU 7418  CD2  TRP B 140    33003  23442  23275    -45   3497   1780       C
ATOM   7419  NE1  TRP B 140       2.597 -48.785  63.580  1.00209.80           N
ANISOU 7419  NE1  TRP B 140    32953  23001  23761    -33   2434   1199       N
ATOM   7420  CE2  TRP B 140       2.164 -47.489  63.488  1.00208.12           C
ANISOU 7420  CE2  TRP B 140    32765  23084  23227     99   3153   1236       C
ATOM   7421  CE3  TRP B 140       0.175 -46.214  64.023  1.00208.62           C
ANISOU 7421  CE3  TRP B 140    32875  23592  22799     50   4250   1928       C
ATOM   7422  CZ2  TRP B 140       2.817 -46.345  62.994  1.00205.32           C
ANISOU 7422  CZ2  TRP B 140    32405  22875  22731    337   3542    843       C
ATOM   7423  CZ3  TRP B 140       0.829 -45.081  63.532  1.00205.81           C
ANISOU 7423  CZ3  TRP B 140    32514  23384  22302    283   4630   1533       C
ATOM   7424  CH2  TRP B 140       2.133 -45.158  63.027  1.00204.22           C
ANISOU 7424  CH2  TRP B 140    32285  23031  22279    425   4275   1001       C
ATOM   7425  N    SER B 141      -0.926 -47.622  67.901  1.00210.44           N
ANISOU 7425  N    SER B 141    33992  23457  22509   -683   3987   3235       N
ATOM   7426  CA   SER B 141      -0.422 -46.463  68.643  1.00209.83           C
ANISOU 7426  CA   SER B 141    34264  23484  21977   -630   4431   3115       C
ATOM   7427  C    SER B 141       0.756 -46.719  69.579  1.00211.12           C
ANISOU 7427  C    SER B 141    34791  23416  22010    713   4024   2924       C
ATOM   7428  O    SER B 141       0.921 -47.808  70.120  1.00213.55           O
ANISOU 7428  O    SER B 141    35190  23489  22461   -882   3485   3089       O
ATOM   7429  CB   SER B 141      -1.560 -45.753  69.387  1.00211.11           C
ANISOU 7429  CB   SER B 141    34592  23856  21765   -704   5101   3605       C
ATOM   7430  OG   SER B 141      -2.208 -44.817  68.539  1.00208.73           O
ANISOU 7430  OG   SER B 141    34042  23836  21432   -536   5687   3575       O
ATOM   7431  N    GLU B 142       1.566 -45.682  69.757  1.00208.79           N
ANISOU 7431  N    GLU B 142    34692  23190  21451   -588   4296   2577       N
ATOM   7432  CA   GLU B 142       2.761 -45.746  70.579  1.00209.75           C
ANISOU 7432  CA   GLU B 142    35150  23112  21434   -637   3952   2334       C
ATOM   7433  C    GLU B 142       2.448 -46.038  72.029  1.00213.30           C
ANISOU 7433  C    GLU B 142    35994  23490  21561   -852   3927   2765       C
ATOM   7434  O    GLU B 142       1.292 -46.014  72.444  1.00214.88           O
ANISOU 7434  O    GLU B 142    36230  23816  21598   -950   4278   3252       O
ATOM   7435  CB   GLU B 142       3.499 -44.415  70.521  1.00207.49           C
ANISOU 7435  CB   GLU B 142    34989  22948  20900   -458   4370   1927       C
ATOM   7436  CG   GLU B 142       2.847 -43.337  71.363  1.00208.25           C
ANISOU 7436  CG   GLU B 142    35360  23262  20505   -482   5068   2197       C
ATOM   7437  CD   GLU B 142       3.818 -42.254  71.781  1.00207.28           C
ANISOU 7437  CD   GLU B 142    35497  23158  20101   -376   5302   1812       C
ATOM   7438  OE1  GLU B 142       4.754 -41.959  71.006  1.00204.81           O
ANISOU 7438  OE1  GLU B 142    35025  22795  20000   -206   5175   1317       O
ATOM   7439  OE2  GLU B 142       3.644 -41.699  72.888  1.00209.09           O
ANISOU 7439  OE2  GLU B 142    36092  23448  19904   -461   5616   2006       O
ATOM   7440  N    GLN B 143       3.501 -46.292  72.796  1.00225.17           N
ANISOU 7440  N    GLN B 143    37795  24791  22969   -916   3517   2580       N
ATOM   7441  CA   GLN B 143       3.386 -46.540  74.228  1.00228.69           C
ANISOU 7441  CA   GLN B 143    38658  25161  23071  -1102   3454   2939       C
ATOM   7442  C    GLN B 143       4.762 -46.460  74.884  1.00229.29           C
ANISOU 7442  C    GLN B 143    39045  25058  23017  -1104   3083   2578       C
ATOM   7443  O    GLN B 143       5.785 -46.660  74.221  1.00227.51           O
```

FIG. 13 Continued

```
ANISOU 7443  O   GLN B 143    38665  24686  23094  -1009   2685   2117       O
ATOM   7444  CB  GLN B 143       2.743 -47.901  74.509  1.00231.49           C
ANISOU 7444  CB  GLN B 143    38943  25358  23653  -1293   3029   3394       C
ATOM   7445  CG  GLN B 143       1.225 -47.890  74.503  1.00232.43           C
ANISOU 7445  CG  GLN B 143    38939  25653  23720  -1356   3486   3928       C
ATOM   7446  CD  GLN B 143       0.650 -46.750  75.315  1.00233.11           C
ANISOU 7446  CD  GLN B 143    39330  25969  23270  -1351   4204   4162       C
ATOM   7447  OE1 GLN B 143       1.266 -46.278  76.268  1.00234.29           O
ANISOU 7447  OE1 GLN B 143    39877  26100  23042  -1372   4256   4076       O
ATOM   7448  NE2 GLN B 143      -0.537 -46.297  74.937  1.00232.46           N
ANISOU 7448  NE2 GLN B 143    39063  26103  23157  -1320   4760   4455       N
ATOM   7449  N   GLU B 144       4.781 -46.162  76.181  1.00223.12           N
ANISOU 7449  N   GLU B 144    38700  24288  21786  -1207   3217   2788       N
ATOM   7450  CA  GLU B 144       6.033 -46.053  76.924  1.00224.12           C
ANISOU 7450  CA  GLU B 144    39155  24255  21744  -1220   2875   2477       C
ATOM   7451  C   GLU B 144       6.786 -47.391  76.990  1.00225.59           C
ANISOU 7451  C   GLU B 144    39305  24130  22279  -1324   2040   2419       C
ATOM   7452  O   GLU B 144       6.194 -48.463  76.843  1.00226.89           O
ANISOU 7452  O   GLU B 144    39298  24201  22710  -1437   1748   2748       O
ATOM   7453  CB  GLU B 144       5.785 -45.481  78.330  1.00226.98           C
ANISOU 7453  CB  GLU B 144    40007  24714  21522  -1310   3205   2752       C
ATOM   7454  CG  GLU B 144       5.330 -44.012  78.352  1.00225.50           C
ANISOU 7454  CG  GLU B 144    39907  24806  20966  -1191   4015   2699       C
ATOM   7455  CD  GLU B 144       5.395 -43.379  79.741  1.00228.26           C
ANISOU 7455  CD  GLU B 144    40774  25220  20735  -1257   4272   2833       C
ATOM   7456  OE1 GLU B 144       4.928 -44.008  80.714  1.00231.75           O
ANISOU 7456  OE1 GLU B 144    41475  25616  20962  -1416   4143   3281       O
ATOM   7457  OE2 GLU B 144       5.906 -42.245  79.859  1.00227.06           O
ANISOU 7457  OE2 GLU B 144    40767  25162  20341  -1143   4612   2490       O
ATOM   7458  N   ALA B 145       8.094 -47.308  77.212  1.00223.88           N
ANISOU 7458  N   ALA B 145    39241  23747  22075  -1286   1664   1997       N
ATOM   7459  CA  ALA B 145       8.968 -48.475  77.278  1.00225.13           C
ANISOU 7459  CA  ALA B 145    39375  23598  22566  -1370    872   1882       C
ATOM   7460  C   ALA B 145       8.480 -49.529  78.270  1.00229.12           C
ANISOU 7460  C   ALA B 145    40083  23989  22983  -1584    551   2410       C
ATOM   7461  O   ALA B 145       8.980 -50.654  78.298  1.00230.44           O
ANISOU 7461  O   ALA B 145    40186  23903  23467  -1675    -97   2417       O
ATOM   7462  CB  ALA B 145      10.380 -48.037  77.632  1.00224.89           C
ANISOU 7462  CB  ALA B 145    39563  23432  22451  -1307    613   1405       C
ATOM   7463  N   ALA B 146       7.502 -49.156  79.083  1.00241.18           N
ANISOU 7463  N   ALA B 146    41852  25700  24085   1659   1020   2860       N
ATOM   7464  CA  ALA B 146       6.977 -50.047  80.107  1.00245.20           C
ANISOU 7464  CA  ALA B 146    42584  26123  24457  -1848    799   3401       C
ATOM   7465  C   ALA B 146       6.045 -51.120  79.553  1.00245.68           C
ANISOU 7465  C   ALA B 146    42299  26119  24927  -1935    638   3778       C
ATOM   7466  O   ALA B 146       6.374 -52.310  79.578  1.00247.19           O
ANISOU 7466  O   ALA B 146    42401  26066  25456  -2036     18   3855       O
ATOM   7467  CB  ALA B 146       6.273 -49.242  81.194  1.00247.32           C
ANISOU 7467  CB  ALA B 146    43249  26607  24115  -1885   1382   3748       C
ATOM   7468  N   ILE B 147       4.888 -50.687  79.053  1.00234.85           N
ANISOU 7468  N   ILE B 147    40729  24964  23540  -1896   1195   4007       N
ATOM   7469  CA  ILE B 147       3.859 -51.590  78.540  1.00235.42           C
ANISOU 7469  CA  ILE B 147    40468  25001  23979  -1975   1121   4391       C
ATOM   7470  C   ILE B 147       4.478 -52.719  77.729  1.00234.67           C
ANISOU 7470  C   ILE B 147    40043  24646  24476  -1990    419   4153       C
ATOM   7471  O   ILE B 147       3.862 -53.765  77.526  1.00236.08           O
ANISOU 7471  O   ILE B 147    39996  24704  24997  -2095    151   4471       O
ATOM   7472  CB  ILE B 147       2.834 -50.839  77.655  1.00232.85           C
ANISOU 7472  CB  ILE B 147    39854  24936  23683  -1869   1754   4444       C
ATOM   7473  CG1 ILE B 147       2.335 -49.572  78.354  1.00233.11           C
ANISOU 7473  CG1 ILE B 147    40199  25231  23142  -1828   2489   4595       C
ATOM   7474  CG2 ILE B 147       1.661 -51.740  77.307  1.00234.05           C
ANISOU 7474  CG2 ILE B 147    39706  25059  24165  -1969   1712   4908       C
ATOM   7475  CD1 ILE B 147       1.393 -49.834  79.512  1.00236.93           C
ANISOU 7475  CD1 ILE B 147    40963  25750  23310  -1981   2708   5232       C
ATOM   7476  N   LEU B 148       5.712 -52.494  77.287  1.00232.06           N
ANISOU 7476  N   LEU B 148    39685  24217  24269  -1883    128   3590       N
ATOM   7477  CA  LEU B 148       6.451 -53.443  76.463  1.00231.05           C
ANISOU 7477  CA  LEU B 148    39255  23840  24692  -1871   -518   3281       C
```

FIG. 13 Continued

```
ATOM   7478  C   LEU B 148       6.229 -54.886  76.892  1.00234.27           C
ANISOU 7478  C   LEU B 148    39627  24005  25381  -2057  -1069   3663       C
ATOM   7479  O   LEU B 148       5.393 -55.580  76.315  1.00234.45           O
ANISOU 7479  O   LEU B 148    39332  24003  25746  -2105  -1124   3905       O
ATOM   7480  CB  LEU B 148       7.946 -53.101  76.468  1.00229.78           C
ANISOU 7480  CB  LEU B 148    39231  23552  24524  -1779   -823   2727       C
ATOM   7481  CG  LEU B 148       8.811 -53.607  75.308  1.00227.38           C
ANISOU 7481  CG  LEU B 148    38576  23059  24760  -1681  -1298   2243       C
ATOM   7482  CD1 LEU B 148       8.184 -53.291  73.958  1.00224.23           C
ANISOU 7482  CD1 LEU B 148    37762  22824  24611  -1538   -972   2101       C
ATOM   7483  CD2 LEU B 148      10.209 -53.020  75.400  1.00226.12           C
ANISOU 7483  CD2 LEU B 148    38583  22809  24522  -1576  -1459   1719       C
ATOM   7484  N   VAL B 149       6.962 -55.328  77.910  1.00252.72           N
ANISOU 7484  N   VAL B 149    42283  26161  27578  -2160  -1471   3724       N
ATOM   7485  CA  VAL B 149       6.861 -56.705  78.391  1.00255.99           C
ANISOU 7485  CA  VAL B 149    42682  26325  28257  -2334  -2017   4083       C
ATOM   7486  C   VAL B 149       6.616 -57.687  77.246  1.00254.88           C
ANISOU 7486  C   VAL B 149    42053  26032  28759  -2342  -2373   4023       C
ATOM   7487  O   VAL B 149       5.488 -57.848  76.778  1.00254.73           O
ANISOU 7487  O   VAL B 149    41783  26115  28887  -2360  -2111   4307       O
ATOM   7488  CB  VAL B 149       5.772 -56.871  79.475  1.00259.53           C
ANISOU 7488  CB  VAL B 149    43373  26862  28375  -2473  -1728   4753       C
ATOM   7489  CG1 VAL B 149       4.457 -56.238  79.032  1.00258.28           C
ANISOU 7489  CG1 VAL B 149    43049  26971  28116  -2427  -1056   5000       C
ATOM   7490  CG2 VAL B 149       5.586 -58.347  79.824  1.00262.78           C
ANISOU 7490  CG2 VAL B 149    43695  27007  29141  -2642  -2279   5139       C
ATOM   7491  N   PRO B 150       7.684 -58.357  76.805  1.00239.20           N
ANISOU 7491  N   PRO B 150    39930  23792  27165  -2328  -2982   3649       N
ATOM   7492  CA  PRO B 150       7.717 -59.321  75.702  1.00238.16           C
ANISOU 7492  CA  PRO B 150    39352  23474  27664  -2323  -3410   3488       C
ATOM   7493  C   PRO B 150       6.420 -60.107  75.516  1.00239.79           C
ANISOU 7493  C   PRO B 150    39305  23677  28127  -2433  -3367   3975       C
ATOM   7494  O   PRO B 150       5.861 -60.644  76.474  1.00243.19           O
ANISOU 7494  O   PRO B 150    39905  24049  28445  -2589  -3405   4494       O
ATOM   7495  CB  PRO B 150       8.853 -60.248  76.112  1.00239.91           C
ANISOU 7495  CB  PRO B 150    39662  23367  28126  -2407  -4125   3353       C
ATOM   7496  CG  PRO B 150       9.815 -59.315  76.805  1.00239.53           C
ANISOU 7496  CG  PRO B 150    40001  23379  27631  -2341  -4018   3085       C
ATOM   7497  CD  PRO B 150       9.000 -58.226  77.454  1.00239.81           C
ANISOU 7497  CD  PRO B 150    40311  23728  27078  -2323  -3318   3358       C
ATOM   7498  N   GLY B 151       5.957 -60.159  74.269  1.00262.36           N
ANISOU 7498  N   GLY B 151    41754  26596  31334  -2343  -3286   3799       N
ATOM   7499  CA  GLY B 151       4.731 -60.848  73.911  1.00263.56           C
ANISOU 7499  CA  GLY B 151    41609  26748  31783  -2428  -3245   4194       C
ATOM   7500  C   GLY B 151       4.096 -60.243  72.672  1.00260.41           C
ANISOU 7500  C   GLY B 151    40876  26574  31494  -2276  -2856   3990       C
ATOM   7501  O   GLY B 151       3.931 -60.913  71.652  1.00259.60           O
ANISOU 7501  O   GLY B 151    40384  26373  31877  -2249  -3137   3839       O
ATOM   7502  N   ASP B 152       3.753 -58.960  72.772  1.00234.21           N
ANISOU 7502  N   ASP B 152    37714  23558  27715  -2171  -2207   3980       N
ATOM   7503  CA  ASP B 152       3.111 -58.211  71.693  1.00231.25           C
ANISOU 7503  CA  ASP B 152    37063  23440  27363  -2015  -1747   3820       C
ATOM   7504  C   ASP B 152       4.052 -57.920  70.527  1.00227.81           C
ANISOU 7504  C   ASP B 152    36417  22995  27144  -1820  -1911   3170       C
ATOM   7505  O   ASP B 152       5.229 -58.280  70.561  1.00227.64           O
ANISOU 7505  O   ASP B 152    36467  22760  27265  -1808  -2376   2832       O
ATOM   7506  CB  ASP B 152       2.558 -56.897  72.235  1.00230.64           C
ANISOU 7506  CB  ASP B 152    37243  23674  26716  -1962  -1001   4000       C
ATOM   7507  CG  ASP B 152       3.598 -56.106  73.000  1.00230.24           C
ANISOU 7507  CG  ASP B 152    37598  23643  26239  -1915   -916   3754       C
ATOM   7508  OD1 ASP B 152       4.802 -56.400  72.846  1.00229.56           O
ANISOU 7508  OD1 ASP B 152    37537  23365  26321  -1877  -1384   3345       O
ATOM   7509  OD2 ASP B 152       3.214 -55.193  73.758  1.00230.70           O
ANISOU 7509  OD2 ASP B 152    37948  23902  25805  -1916   -384   3964       O
ATOM   7510  N   ILE B 153       3.524 -57.257  69.502  1.00224.06           N
ANISOU 7510  N   ILE B 153    35684  22753  26694   1662   1515   3008       N
ATOM   7511  CA  ILE B 153       4.299 -56.937  68.305  1.00220.77           C
ANISOU 7511  CA  ILE B 153    35045  22358  26481  -1452  -1607   2415       C
ATOM   7512  C   ILE B 153       4.804 -55.490  68.298  1.00218.13           C
```

FIG. 13 Continued

```
ANISOU 7512  C   ILE B 153     34902  22250  25727  -1275  -1089   2112           C
ATOM   7513  O   ILE B 153       4.134 -54.589  68.796  1.00218.11           O
ANISOU 7513  O   ILE B 153     35068  22487  25316  -1272   -503   2367           O
ATOM   7514  CB  ILE B 153       3.491 -57.227  67.027  1.00219.55           C
ANISOU 7514  CB  ILE B 153     34443  22298  26680  -1367  -1577   2374           C
ATOM   7515  CG1 ILE B 153       3.386 -58.733  66.792  1.00221.71           C
ANISOU 7515  CG1 ILE B 153     34479  22280  27481  -1504  -2232   2476           C
ATOM   7516  CG2 ILE B 153       4.136 -56.564  65.823  1.00215.96           C
ANISOU 7516  CG2 ILE B 153     33799  21958  26300  -1111  -1471   1802           C
ATOM   7517  CD1 ILE B 153       2.636 -59.466  67.864  1.00225.38           C
ANISOU 7517  CD1 ILE B 153     35069  22628  27938  -1747  -2332   3073           C
ATOM   7518  N   VAL B 154       5.982 -55.277  67.718  1.00217.29           N
ANISOU 7518  N   VAL B 154     34757  22058  25745  -1123  -1300   1568           N
ATOM   7519  CA  VAL B 154       6.628 -53.963  67.708  1.00214.87           C
ANISOU 7519  CA  VAL B 154     34622  21919  25101   -949   -872   1235           C
ATOM   7520  C   VAL B 154       6.810 -53.304  66.336  1.00211.34           C
ANISOU 7520  C   VAL B 154     33877  21632  24791   -689   -629    797           C
ATOM   7521  O   VAL B 154       6.028 -53.535  65.415  1.00210.60           O
ANISOU 7521  O   VAL B 154     33458  21647  24912   -629   -554    852           O
ATOM   7522  CB  VAL B 154       8.001 -54.050  68.383  1.00215.44           C
ANISOU 7522  CB  VAL B 154     34972  21757  25129   -977  -1255    961           C
ATOM   7523  CG1 VAL B 154       7.906 -53.614  69.829  1.00217.61           C
ANISOU 7523  CG1 VAL B 154     35680  22075  24927  -1115  -1035   1282           C
ATOM   7524  CG2 VAL B 154       8.544 -55.471  68.283  1.00217.08           C
ANISOU 7524  CG2 VAL B 154     35059  21621  25799  -1089  -2024    906           C
ATOM   7525  N   SER B 155       7.851 -52.476  66.226  1.00207.77           N
ANISOU 7525  N   SER B 155     33541  21189  24211   -530   -507    369           N
ATOM   7526  CA  SER B 155       8.181 -51.758  64.995  1.00204.44           C
ANISOU 7526  CA  SER B 155     32873  20909  23894   -261   -254    -70           C
ATOM   7527  C   SER B 155       9.546 -51.087  65.109  1.00202.95           C
ANISOU 7527  C   SER B 155     32856  20627  23629   -131   -272   -529           C
ATOM   7528  O   SER B 155      10.325 -51.415  65.995  1.00204.56           O
ANISOU 7528  O   SER B 155     33318  20609  23795   -254   -625   -555           O
ATOM   7529  CB  SER B 155       7.128 -50.697  64.698  1.00203.01           C
ANISOU 7529  CB  SER B 155     32618  21094  23424   -158    486    114           C
ATOM   7530  OG  SER B 155       5.853 -51.281  64.514  1.00204.31           O
ANISOU 7530  OG  SER B 155     32595  21347  23689   -265    516    525           O
ATOM   7531  N   ILE B 156       9.831 -50.146  64.210  1.00200.62           N
ANISOU 7531  N   ILE B 156     32407  20497  23321    122    108   -884           N
ATOM   7532  CA  ILE B 156      11.099 -49.411  64.251  1.00199.09           C
ANISOU 7532  CA  ILE B 156     32346  20221  23077    267    148  -1327           C
ATOM   7533  C   ILE B 156      11.275 -48.354  63.136  1.00195.77           C
ANISOU 7533  C   ILE B 156     31708  20008  22667    570    630  -1685           C
ATOM   7534  O   ILE B 156      10.568 -48.366  62.131  1.00194.52           O
ANISOU 7534  O   ILE B 156     31252  20025  22632    690    814  -1664           O
ATOM   7535  CB  ILE B 156      12.304 -50.373  64.253  1.00199.87           C
ANISOU 7535  CB  ILE B 156     32452  19952  23539    225   -578  -1619           C
ATOM   7536  CG1 ILE B 156      13.357 -49.908  65.251  1.00200.53           C
ANISOU 7536  CG1 ILE B 156     32877  19887  23426    182   -652  -1778           C
ATOM   7537  CG2 ILE B 156      12.897 -50.494  62.869  1.00197.54           C
ANISOU 7537  CG2 ILE B 156     31827  19601  23628    461   -724  -2071           C
ATOM   7538  CD1 ILE B 156      14.638 -50.671  65.166  1.00200.93           C
ANISOU 7538  CD1 ILE B 156     32918  19587  23840    178  -1303  -2116           C
ATOM   7539  N   LYS B 157      12.226 -47.442  63.339  1.00194.17           N
ANISOU 7539  N   LYS B 157     31656  19781  22338    694    828  -2007           N
ATOM   7540  CA  LYS B 157      12.544 -46.376  62.389  1.00191.15           C
ANISOU 7540  CA  LYS B 157     31096  19567  21968    988   1293  -2360           C
ATOM   7541  C   LYS B 157      14.058 -46.262  62.310  1.00190.35           C
ANISOU 7541  C   LYS B 157     31047  19209  22067   1102   1005  -2842           C
ATOM   7542  O   LYS B 157      14.763 -47.239  62.534  1.00191.70           O
ANISOU 7542  O   LYS B 157     31262  19081  22493    993    374  -2941           O
ATOM   7543  CB  LYS B 157      11.980 -45.028  62.857  1.00190.44           C
ANISOU 7543  CB  LYS B 157     31157  19764  21437   1032   2041  -2202           C
ATOM   7544  CG  LYS B 157      10.452 -44.904  62.871  1.00190.92           C
ANISOU 7544  CG  LYS B 157     31149  20112  21281    955   2455  -1733           C
ATOM   7545  CD  LYS B 157      10.007 -43.430  62.926  1.00189.39           C
ANISOU 7545  CD  LYS B 157     31005  20221  20735   1087   3262  -1690           C
ATOM   7546  CE  LYS B 157       8.526 -43.252  63.300  1.00190.44           C
ANISOU 7546  CE  LYS B 157     31161  20608  20588    961   3688  -1167           C
```

FIG. 13 Continued

```
ATOM   7547  NZ  LYS B 157       7.570 -43.579  62.201  1.00189.54           N
ANISOU 7547  NZ  LYS B 157    30684  20672  20662   1048   3778  -1031       N
ATOM   7548  N   LEU B 158      14.557 -45.075  61.981  1.00188.42           N
ANISOU 7548  N   LEU B 158    30785  19073  21732   1323   1468  -3137       N
ATOM   7549  CA  LEU B 158      15.999 -44.839  61.970  1.00187.70           C
ANISOU 7549  CA  LEU B 158    30752  18739  21827   1437   1251  -3588       C
ATOM   7550  C   LEU B 158      16.411 -44.045  63.212  1.00188.69           C
ANISOU 7550  C   LEU B 158    31237  18836  21622   1339   1446  -3568       C
ATOM   7551  O   LEU B 158      17.359 -43.260  63.196  1.00187.57           O
ANISOU 7551  O   LEU B 158    31139  18617  21511   1486   1592  -3919       O
ATOM   7552  CB  LEU B 158      16.452 -44.161  60.670  1.00184.76           C
ANISOU 7552  CB  LEU B 158    30087  18450  21665   1773   1558  -3984       C
ATOM   7553  CG  LEU B 158      17.943 -43.830  60.493  1.00183.77           C
ANISOU 7553  CG  LEU B 158    29969  18076  21780   1934   1399  -4472       C
ATOM   7554  CD1 LEU B 158      18.487 -44.254  59.126  1.00182.13           C
ANISOU 7554  CD1 LEU B 158    29430  17770  22001   2171   1189  -4817       C
ATOM   7555  CD2 LEU B 158      18.200 -42.348  60.735  1.00182.42           C
ANISOU 7555  CD2 LEU B 158    29897  18049  21367   2079   2027  -4612       C
ATOM   7556  N   GLY B 159      15.685 -44.263  64.300  1.00191.06           N
ANISOU 7556  N   GLY B 159    31794  19194  21607   1091   1444  -3153       N
ATOM   7557  CA  GLY B 159      15.974 -43.575  65.538  1.00192.39           C
ANISOU 7557  CA  GLY B 159    32328  19351  21422    983   1613  -3102       C
ATOM   7558  C   GLY B 159      15.431 -44.316  66.738  1.00195.57           C
ANISOU 7558  C   GLY B 159    33016  19701  21592    684   1327  -2668       C
ATOM   7559  O   GLY B 159      15.765 -44.006  67.877  1.00197.31           O
ANISOU 7559  O   GLY B 159    33576  19861  21533    562   1311  -2616       O
ATOM   7560  N   ASP B 160      14.580 -45.299  66.493  1.00196.76           N
ANISOU 7560  N   ASP B 160    33029  19874  21857    568   1104  -2350       N
ATOM   7561  CA  ASP B 160      14.030 -46.068  67.596  1.00199.91           C
ANISOU 7561  CA  ASP B 160    33676  20213  22067    290    832  -1909       C
ATOM   7562  C   ASP B 160      15.033 -47.131  68.069  1.00201.81           C
ANISOU 7562  C   ASP B 160    34031  20094  22554    157     60  -2027       C
ATOM   7563  O   ASP B 160      14.879 -48.311  67.750  1.00202.71           O
ANISOU 7563  O   ASP B 160    33985  20060  22974     68   -419  -1914       O
ATOM   7564  CB  ASP B 160      12.710 -46.739  67.193  1.00200.40           C
ANISOU 7564  CB  ASP B 160    33537  20419  22186    208    882  -1501       C
ATOM   7565  CG  ASP B 160      11.765 -45.804  66.458  1.00198.23           C
ANISOU 7565  CG  ASP B 160    33065  20485  21769    368   1585  -1426       C
ATOM   7566  OD1 ASP B 160      12.236 -44.835  65.831  1.00195.75           O
ANISOU 7566  OD1 ASP B 160    32645  20267  21463    595   1944  -1775       O
ATOM   7567  OD2 ASP B 160      10.543 -46.060  66.494  1.00199.09           O
ANISOU 7567  OD2 ASP B 160    33110  20758  21778    271   1774  -1008       O
ATOM   7568  N   ILE B 161      16.058 -46.725  68.821  1.00202.88           N
ANISOU 7568  N   ILE B 161    34432  20080  22574    145    -70  -2254       N
ATOM   7569  CA  ILE B 161      17.013 -47.697  69.347  1.00204.88           C
ANISOU 7569  CA  ILE B 161    34810  19994  23043     12   -797  -2344       C
ATOM   7570  C   ILE B 161      16.157 -48.783  69.942  1.00207.62           C
ANISOU 7570  C   ILE B 161    35235  20315  23337   -228  -1089  -1845       C
ATOM   7571  O   ILE B 161      15.461 -48.553  70.925  1.00209.55           O
ANISOU 7571  O   ILE B 161    35750  20696  23172   -368   -851  -1471       O
ATOM   7572  CB  ILE B 161      17.900 -47.134  70.481  1.00206.36           C
ANISOU 7572  CB  ILE B 161    35371  20072  22964    -43   -863  -2482       C
ATOM   7573  CG1 ILE B 161      18.790 -45.996  69.978  1.00203.85           C
ANISOU 7573  CG1 ILE B 161    34985  19761  22708    192   -560  -2980       C
ATOM   7574  CG2 ILE B 161      18.742 -48.247  71.104  1.00208.84           C
ANISOU 7574  CG2 ILE B 161    35821  20048  23482   -206  -1636  -2493       C
ATOM   7575  CD1 ILE B 161      19.575 -45.294  71.075  1.00205.28           C
ANISOU 7575  CD1 ILE B 161    35525  19864  22606    150   -554  -3127       C
ATOM   7576  N   ILE B 162      16.187 -49.958  69.335  1.00206.86           N
ANISOU 7576  N   ILE B 162    34896  20040  23661   -269  -1585  -1835       N
ATOM   7577  CA  ILE B 162      15.373 -51.064  69.802  1.00209.46           C
ANISOU 7577  CA  ILE B 162    35250  20320  24013   -489  -1883  -1366       C
ATOM   7578  C   ILE B 162      15.062 -50.926  71.294  1.00212.43           C
ANISOU 7578  C   ILE B 162    36046  20741  23928   -683  -1810   -985       C
ATOM   7579  O   ILE B 162      15.897 -50.474  72.073  1.00213.27           O
ANISOU 7579  O   ILE B 162    36438  20762  23831   -696  -1883  -1147       O
ATOM   7580  CB  ILE B 162      16.074 -52.423  69.535  1.00210.52           C
ANISOU 7580  CB  ILE B 162    35239  20110  24638   -565  -2654  -1479       C
ATOM   7581  CG1 ILE B 162      15.910 -52.857  68.074  1.00208.31           C
```

FIG. 13 Continued

```
ANISOU 7581  CG1 ILE B 162     34524  19822  24804    -420  -2730  -1687       C
ATOM   7582  CG2 ILE B 162     15.551 -53.500 70.473  1.00214.03              C
ANISOU 7582  CG2 ILE B 162     35838  20440  25043    -827  -3030   -996       C
ATOM   7583  CD1 ILE B 162     17.083 -52.493 67.186  1.00205.80              C
ANISOU 7583  CD1 ILE B 162     34041  19380  24774    -196  -2819  -2261       C
ATOM   7584  N   PRO B 163     13.841 -51.290 71.688  1.00214.20              N
ANISOU 7584  N   PRO B 163     36306  21101  23979    -827  -1649   -476       N
ATOM   7585  CA  PRO B 163     13.396 -51.298 73.085  1.00217.36              C
ANISOU 7585  CA  PRO B 163     37093  21547  23948   -1015  -1580    -46       C
ATOM   7586  C   PRO B 163     14.150 -52.360 73.871  1.00220.26              C
ANISOU 7586  C   PRO B 163     37636  21603  24449   -1182  -2288     19       C
ATOM   7587  O   PRO B 163     14.679 -52.093 74.951  1.00222.18              O
ANISOU 7587  O   PRO B 163     38244  21796  24380   -1253  -2372     40       O
ATOM   7588  CB  PRO B 163     11.934 -51.726 72.981  1.00218.24              C
ANISOU 7588  CB  PRO B 163     37071  21819  24034   -1111  -1348    457       C
ATOM   7589  CG  PRO B 163     11.556 -51.514 71.565  1.00215.09              C
ANISOU 7589  CG  PRO B 163     36258  21544  23924    -939  -1111    252       C
ATOM   7590  CD  PRO B 163     12.770 -51.661 70.752  1.00213.13              C
ANISOU 7590  CD  PRO B 163     35826  21099  24056    -798  -1485   -289       C
ATOM   7591  N   ALA B 164     14.171 -53.565 73.306  1.00222.39              N
ANISOU 7591  N   ALA B 164     37638  21671  25191   -1239  -2792     53       N
ATOM   7592  CA  ALA B 164     14.841 -54.733 73.867  1.00225.02              C
ANISOU 7592  CA  ALA B 164     38058  21685  25755   -1393  -3504    123       C
ATOM   7593  C   ALA B 164     14.752 -55.852 72.833  1.00224.37              C
ANISOU 7593  C   ALA B 164     37569  21427  26253   -1394  -3917     67       C
ATOM   7594  O   ALA B 164     13.907 -55.804 71.947  1.00222.73              O
ANISOU 7594  O   ALA B 164     37075  21375  26175   -1323  -3635    120       O
ATOM   7595  CB  ALA B 164     14.194 -55.151 75.167  1.00228.76              C
ANISOU 7595  CB  ALA B 164     38845  22178  25896   -1603  -3540    677       C
ATOM   7596  N   ASP B 165     15.606 -56.861 72.955  1.00224.61              N
ANISOU 7596  N   ASP B 165     37574  21135  26631   -1475  -4587    -36       N
ATOM   7597  CA  ASP B 165     15.678 -57.947 71.972  1.00224.08              C
ANISOU 7597  CA  ASP B 165     37128  20865  27147   -1471  -5027   -149       C
ATOM   7598  C   ASP B 165     14.348 -58.398 71.336  1.00223.94              C
ANISOU 7598  C   ASP B 165     36825  20984  27279   -1501  -4840    160       C
ATOM   7599  O   ASP B 165     13.288 -58.379 71.970  1.00225.66              O
ANISOU 7599  O   ASP B 165     37164  21360  27218   -1619  -4563    638       O
ATOM   7600  CB  ASP B 165     16.428 -59.146 72.561  1.00226.85              C
ANISOU 7600  CB  ASP B 165     37552  20862  27780   -1631  -5756    -80       C
ATOM   7601  CG  ASP B 165     15.660 -59.824 73.673  1.00230.55              C
ANISOU 7601  CG  ASP B 165     38222  21317  28058   -1856  -5865    517       C
ATOM   7602  OD1 ASP B 165     14.545 -60.311 73.402  1.00231.14              O
ANISOU 7602  OD1 ASP B 165     38111  21471  28239   -1922  -5749    857       O
ATOM   7603  OD2 ASP B 165     16.173 -59.880 74.813  1.00232.98              O
ANISOU 7603  OD2 ASP B 165     38869  21531  28121   -1961  -6071    650       O
ATOM   7604  N   ALA B 166     14.436 -58.802 70.068  1.00222.84              N
ANISOU 7604  N   ALA B 166     36305  20774  27592   -1388  -5000   -128       N
ATOM   7605  CA  ALA B 166     13.296 -59.287 69.292  1.00222.58              C
ANISOU 7605  CA  ALA B 166     35952  20841  27778   -1396  -4896     80       C
ATOM   7606  C   ALA B 166     13.787 -60.087 68.087  1.00221.35              C
ANISOU 7606  C   ALA B 166     35425  20477  28201   -1307  -5335   -286       C
ATOM   7607  O   ALA B 166     14.908 -60.594 68.090  1.00221.66              O
ANISOU 7607  O   ALA B 166     35475  20236  28511   -1309  -5826   -564       O
ATOM   7608  CB  ALA B 166     12.418 -58.143 68.846  1.00220.37              C
ANISOU 7608  CB  ALA B 166     35619  20931  27179   -1260  -4175    112       C
ATOM   7609  N   ARG B 167     12.963 -60.180 67.047  1.00222.14              N
ANISOU 7609  N   ARG B 167     35199  20716  28487   -1222  -5156   -295       N
ATOM   7610  CA  ARG B 167     13.310 -61.016 65.898  1.00221.32              C
ANISOU 7610  CA  ARG B 167     34740  20422  28928   -1143  -5578   -614       C
ATOM   7611  C   ARG B 167     12.733 -60.599 64.533  1.00218.66              C
ANISOU 7611  C   ARG B 167     34076  20310  28695    -938  -5247   -835       C
ATOM   7612  O   ARG B 167     12.915 -61.318 63.551  1.00218.19              O
ANISOU 7612  O   ARG B 167     33717  20109  29074    -869  -5586  -1085       O
ATOM   7613  CB  ARG B 167     12.911 -62.462 66.198  1.00224.42              C
ANISOU 7613  CB  ARG B 167     35023  20565  29679   -1362  -6109   -284       C
ATOM   7614  CG  ARG B 167     11.556 -62.585 66.883  1.00226.54              C
ANISOU 7614  CG  ARG B 167     35355  20990  29728   -1531  -5849    313       C
ATOM   7615  CD  ARG B 167     10.408 -62.274 65.927  1.00225.04              C
ANISOU 7615  CD  ARG B 167     34879  21065  29560   -1430  -5449    368       C
```

FIG. 13 Continued

```
ATOM   7616  NE  ARG B 167      10.016 -63.441  65.140  1.00225.98           N
ANISOU 7616  NE  ARG B 167    34638  21016  30208   1475   5866    369       N
ATOM   7617  CZ  ARG B 167       8.844 -64.063  65.250  1.00228.00           C
ANISOU 7617  CZ  ARG B 167    34750  21292  30587  -1617  -5869    802       C
ATOM   7618  NH1 ARG B 167       7.932 -63.621  66.106  1.00229.24           N
ANISOU 7618  NH1 ARG B 167    35095  21638  30369  -1722  -5456   1284       N
ATOM   7619  NH2 ARG B 167       8.579 -65.124  64.497  1.00228.87           N
ANISOU 7619  NH2 ARG B 167    34523  21229  31207  -1649  -6279    750       N
ATOM   7620  N   LEU B 168      12.046 -59.457  64.480  1.00214.49           N
ANISOU 7620  N   LEU B 168    33605  20126  27765   -838  -4594   -741       N
ATOM   7621  CA  LEU B 168      11.429 -58.929  63.246  1.00212.01           C
ANISOU 7621  CA  LEU B 168    33001  20069  27485   -634  -4212   -912       C
ATOM   7622  C   LEU B 168      10.889 -59.967  62.250  1.00212.50           C
ANISOU 7622  C   LEU B 168    32685  20047  28007   -633  -4548   -933       C
ATOM   7623  O   LEU B 168      11.663 -60.583  61.520  1.00212.01           O
ANISOU 7623  O   LEU B 168    32448  19771  28336   -551  -4977  -1306       O
ATOM   7624  CB  LEU B 168      12.343 -57.908  62.546  1.00208.83           C
ANISOU 7624  CB  LEU B 168    32586  19758  27002   -363  -3948  -1431       C
ATOM   7625  CG  LEU B 168      13.809 -58.204  62.225  1.00208.09           C
ANISOU 7625  CG  LEU B 168    32481  19376  27207   -268  -4388  -1914       C
ATOM   7626  CD1 LEU B 168      14.357 -57.185  61.242  1.00204.80           C
ANISOU 7626  CD1 LEU B 168    31952  19112  26749     35  -4023  -2378       C
ATOM   7627  CD2 LEU B 168      14.611 -58.207  63.484  1.00209.66           C
ANISOU 7627  CD2 LEU B 168    33028  19379  27254   -415  -4605  -1850       C
ATOM   7628  N   LEU B 169       9.564 -60.125  62.192  1.00212.36           N
ANISOU 7628  N   LEU B 169    32538  20201  27949   -715  -4338   -546       N
ATOM   7629  CA  LEU B 169       8.949 -61.146  61.324  1.00213.23           C
ANISOU 7629  CA  LEU B 169    32289  20228  28500   -737  -4669   -528       C
ATOM   7630  C   LEU B 169       9.469 -61.151  59.885  1.00210.87           C
ANISOU 7630  C   LEU B 169    31709  19939  28474   -484  -4771  -1068       C
ATOM   7631  O   LEU B 169       9.959 -62.124  59.373  1.00211.63           O
ANISOU 7631  O   LEU B 169    31626  19769  29013   -494  -5319  -1294       O
ATOM   7632  CB  LEU B 169       7.407 -61.066  61.335  1.00214.15           C
ANISOU 7632  CB  LEU B 169    32285  20582  28500   -815  -4318    -73       C
ATOM   7633  CG  LEU B 169       6.599 -62.361  61.091  1.00216.65           C
ANISOU 7633  CG  LEU B 169    32329  20738  29251   -972  -4735    178       C
ATOM   7634  CD1 LEU B 169       5.096 -62.130  61.227  1.00217.57           C
ANISOU 7634  CD1 LEU B 169    32359  21096  29213  -1048  -4324    655       C
ATOM   7635  CD2 LEU B 169       6.905 -63.025  59.750  1.00215.82           C
ANISOU 7635  CD2 LEU B 169    31874  20520  29610   -832  -5126   -254       C
ATOM   7636  N   GLU B 170       9.358 -59.955  59.241  1.00253.77           N
ANISOU 7636  N   GLU B 170    37104  25676  33642   -254  -4234  -1269       N
ATOM   7637  CA  GLU B 170       9.794 -59.802  57.857  1.00251.50           C
ANISOU 7637  CA  GLU B 170    36560  25440  33559     15  -4252  -1763       C
ATOM   7638  C   GLU B 170       9.417 -58.439  57.305  1.00248.80           C
ANISOU 7638  C   GLU B 170    36191  25482  32861    247  -3562  -1855       C
ATOM   7639  O   GLU B 170       9.029 -57.538  58.048  1.00248.47           O
ANISOU 7639  O   GLU B 170    36359  25638  32408    206  -3075  -1595       O
ATOM   7640  CB  GLU B 170       9.166 -60.884  56.974  1.00252.71           C
ANISOU 7640  CB  GLU B 170    36368  25515  34135     -5  -4632  -1771       C
ATOM   7641  CG  GLU B 170       7.683 -61.107  57.238  1.00254.43           C
ANISOU 7641  CG  GLU B 170    36490  25889  34293   -165  -4463  -1264       C
ATOM   7642  CD  GLU B 170       6.965 -59.829  57.626  1.00253.19           C
ANISOU 7642  CD  GLU B 170    36477  26090  33632   -120  -3743  -1001       C
ATOM   7643  OE1 GLU B 170       6.781 -58.960  56.749  1.00250.82           O
ANISOU 7643  OE1 GLU B 170    36052  26068  33180    117  -3326  -1212       O
ATOM   7644  OE2 GLU B 170       6.588  59.690  58.809  1.00254.66           O
ANISOU 7644  OE2 GLU B 170    36906  26281  33573   -317  -3585   -582       O
ATOM   7645  N   GLY B 171       9.526 -58.306  55.987  1.00204.79           N
ANISOU 7645  N   GLY B 171    30354  20011  27448    496  -3522  -2225       N
ATOM   7646  CA  GLY B 171       9.151 -57.082  55.307  1.00202.27           C
ANISOU 7646  CA  GLY B 171    29960  20058  26837    741  -2890  -2327       C
ATOM   7647  C   GLY B 171      10.199 -56.630  54.309  1.00199.84           C
ANISOU 7647  C   GLY B 171    29560  19745  26623   1045  -2855  -2882       C
ATOM   7648  O   GLY B 171       9.943 -56.575  53.105  1.00198.71           O
ANISOU 7648  O   GLY B 171    29154  19753  26593   1261  -2780  -3103       O
ATOM   7649  N   ASP B 172      11.386 -56.317  54.824  1.00197.24           N
ANISOU 7649  N   ASP B 172    29451  19239  26254   1066  -2917  -3101       N
ATOM   7650  CA  ASP B 172      12.496 -55.835  54.013  1.00195.02           C
```

FIG. 13 Continued

```
ANISOU 7650  CA  ASP B 172    29112 18919 26067   1349  -2867  -3616       C
ATOM   7651  C   ASP B 172      13.687 -55.490  54.911  1.00194.82         C
ANISOU 7651  C   ASP B 172    29374 18679 25970   1299  -2933  -3749       C
ATOM   7652  O   ASP B 172      13.805 -54.348  55.375  1.00193.53         O
ANISOU 7652  O   ASP B 172    29390 18682 25461   1360  -2437  -3717       O
ATOM   7653  CB  ASP B 172      12.065 -54.595  53.229  1.00192.52         C
ANISOU 7653  CB  ASP B 172    28687 18987 25477   1624  -2195  -3708       C
ATOM   7654  CG  ASP B 172      12.917 -54.352  52.004  1.00190.53         C
ANISOU 7654  CG  ASP B 172    28258 18725 25410   1953  -2188  -4224       C
ATOM   7655  OD1 ASP B 172      12.942 -55.223  51.108  1.00191.07         O
ANISOU 7655  OD1 ASP B 172    28101 18693 25806   2025  -2581  -4422       O
ATOM   7656  OD2 ASP B 172      13.553 -53.282  51.933  1.00188.51         O
ANISOU 7656  OD2 ASP B 172    28089 18562 24976   2147  -1778  -4433       O
ATOM   7657  N   PRO B 173      14.577 -56.478  55.148  1.00195.53         N
ANISOU 7657  N   PRO B 173    29501 18394 26398   1191  -3552  -3905       N
ATOM   7658  CA  PRO B 173      15.777 -56.380  55.996  1.00195.80         C
ANISOU 7658  CA  PRO B 173    29788 18165 26441   1121  -3750  -4042       C
ATOM   7659  C   PRO B 173      16.383 -54.968  56.111  1.00193.54         C
ANISOU 7659  C   PRO B 173    29651 18027 25859   1311  -3217  -4241       C
ATOM   7660  O   PRO B 173      16.283 -54.163  55.183  1.00191.31         O
ANISOU 7660  O   PRO B 173    29216 17976 25497   1579  -2783  -4449       O
ATOM   7661  CB  PRO B 173      16.739 -57.348  55.312  1.00196.11         C
ANISOU 7661  CB  PRO B 173    29669 17874 26969   1191  -4333  -4421       C
ATOM   7662  CG  PRO B 173      15.813 -58.444  54.797  1.00197.68         C
ANISOU 7662  CG  PRO B 173    29632 18064 27413   1093  -4653  -4254       C
ATOM   7663  CD  PRO B 173      14.448 -57.825  54.557  1.00197.08         C
ANISOU 7663  CD  PRO B 173    29471 18386 27026   1127  -4131  -3964       C
ATOM   7664  N   LEU B 174      17.011 -54.678  57.249  1.00194.48         N
ANISOU 7664  N   LEU B 174    30065 18008 25822   1175  -3255  -4177       N
ATOM   7665  CA  LEU B 174      17.568 -53.344  57.480  1.00192.65         C
ANISOU 7665  CA  LEU B 174    29987 17897 25312   1329  -2762  -4348       C
ATOM   7666  C   LEU B 174      18.895 -53.278  58.250  1.00193.14         C
ANISOU 7666  C   LEU B 174    30278 17660 25447   1277  -3036  -4556       C
ATOM   7667  O   LEU B 174      19.350 -54.261  58.846  1.00195.21         O
ANISOU 7667  O   LEU B 174    30632 17621 25916   1079  -3611  -4498       O
ATOM   7668  CB  LEU B 174      16.542 -52.438  58.170  1.00192.61         C
ANISOU 7668  CB  LEU B 174    30144 18217 24823   1249  -2184  -3968       C
ATOM   7669  CG  LEU B 174      15.961 -52.818  59.539  1.00195.22         C
ANISOU 7669  CG  LEU B 174    30738 18513 24922    925  -2311  -3497       C
ATOM   7670  CD1 LEU B 174      16.652 -54.010  60.193  1.00197.59         C
ANISOU 7670  CD1 LEU B 174    31147 18432 25497    712  -3029  -3479       C
ATOM   7671  CD2 LEU B 174      15.945 -51.618  60.475  1.00194.88         C
ANISOU 7671  CD2 LEU B 174    30985 18635 24425    903  -1804  -3375       C
ATOM   7672  N   LYS B 175      19.491 -52.086  58.221  1.00192.17         N
ANISOU 7672  N   LYS B 175    30232 17625 25157   1463  -2606  -4794       N
ATOM   7673  CA  LYS B 175      20.765 -51.793  58.875  1.00192.36         C
ANISOU 7673  CA  LYS B 175    30457 17397 25232   1455  -2774  -5030       C
ATOM   7674  C   LYS B 175      20.576 -51.417  60.338  1.00193.99         C
ANISOU 7674  C   LYS B 175    31015 17637 25057   1224  -2680  -4720       C
ATOM   7675  O   LYS B 175      20.250 -50.277  60.659  1.00193.05         O
ANISOU 7675  O   LYS B 175    31017 17760 24572   1282  -2117  -4650       O
ATOM   7676  CB  LYS B 175      21.494 -50.676  58.117  1.00189.69         C
ANISOU 7676  CB  LYS B 175    30017 17129 24926   1776  -2347  -5440       C
ATOM   7677  CG  LYS B 175      22.148 -51.167  56.826  1.00188.51         C
ANISOU 7677  CG  LYS B 175    29577 16823 25224   2005  -2587  -5830       C
ATOM   7678  CD  LYS B 175      22.048 -50.171  55.677  1.00185.78         C
ANISOU 7678  CD  LYS B 175    29019 16733 24837   2349  -2006  -6067       C
ATOM   7679  CE  LYS B 175      22.415 -50.825  54.345  1.00185.00         C
ANISOU 7679  CE  LYS B 175    28624 16525 25144   2562  -2256  -6380       C
ATOM   7680  NZ  LYS B 175      22.017 -50.002  53.167  1.00182.69         N
ANISOU 7680  NZ  LYS B 175    28106 16538 24769   2885  -1695  -6524       N
ATOM   7681  N   VAL B 176      20.788 -52.395  61.214  1.00209.21         N
ANISOU 7681  N   VAL B 176    33102 19315 27072    967  -3235  -4537       N
ATOM   7682  CA  VAL B 176      20.612 -52.223  62.654  1.00211.27         C
ANISOU 7682  CA  VAL B 176    33713 19584 26977    731  -3231  -4217       C
ATOM   7683  C   VAL B 176      21.919 -51.926  63.383  1.00211.84         C
ANISOU 7683  C   VAL B 176    34008 19406 27074    716  -3453  -4465       C
ATOM   7684  O   VAL B 176      22.196 -52.514  64.425  1.00214.33         O
ANISOU 7684  O   VAL B 176    34553 19533 27350    492  -3867  -4286       O
```

FIG. 13 Continued

```
ATOM   7685  CB  VAL B 176      19.981 -53.482  63.279  1.00214.12           C
ANISOU 7685  CB  VAL B 176    34133  19835  27390    447  -3697  -3808       C
ATOM   7686  CG1 VAL B 176      18.470 -53.446  63.134  1.00214.22           C
ANISOU 7686  CG1 VAL B 176    34063  20157  27174    391  -3332  -3414       C
ATOM   7687  CG2 VAL B 176      20.559 -54.741  62.638  1.00214.70           C
ANISOU 7687  CG2 VAL B 176    33986  19594  27996    439  -4338  -3997       C
ATOM   7688  N   ASP B 177      22.705 -51.005  62.839  1.00239.87           N
ANISOU 7688  N   ASP B 177    37488  22959  30693    958  -3172  -4867       N
ATOM   7689  CA  ASP B 177      24.020 -50.672  63.388  1.00240.23           C
ANISOU 7689  CA  ASP B 177    37701  22751  30824    976  -3375  -5158       C
ATOM   7690  C   ASP B 177      24.107 -50.609  64.910  1.00242.78           C
ANISOU 7690  C   ASP B 177    38406  23019  30819    733  -3521  -4912       C
ATOM   7691  O   ASP B 177      23.792 -49.591  65.525  1.00242.66           O
ANISOU 7691  O   ASP B 177    38593  23214  30391    731  -3056  -4816       O
ATOM   7692  CB  ASP B 177      24.533 -49.363  62.787  1.00237.58           C
ANISOU 7692  CB  ASP B 177    37279  22524  30465   1261  -2845  -5522       C
ATOM   7693  CG  ASP B 177      24.764 -49.463  61.292  1.00235.27           C
ANISOU 7693  CG  ASP B 177    36624  22218  30549   1529  -2782  -5836       C
ATOM   7694  OD1 ASP B 177      24.331 -50.472  60.687  1.00235.61           O
ANISOU 7694  OD1 ASP B 177    36481  22226  30815   1494  -3080  -5747       O
ATOM   7695  OD2 ASP B 177      25.378 -48.534  60.722  1.00233.23           O
ANISOU 7695  OD2 ASP B 177    36268  21982  30367   1780  -2432  -6172       O
ATOM   7696  N   GLN B 178      24.555 -51.711  65.502  1.00200.45           N
ANISOU 7696  N   GLN B 178    33142  17372  25649    535  -4173  -4816       N
ATOM   7697  CA  GLN B 178      24.768 -51.788  66.938  1.00203.19           C
ANISOU 7697  CA  GLN B 178    33852  17630  25721    310  -4405  -4600       C
ATOM   7698  C   GLN B 178      26.142  51.199  67.195  1.00202.92           C
ANISOU 7698  C   GLN B 178    33921  17380  25800    405  -4520  -5001       C
ATOM   7699  O   GLN B 178      27.097 -51.928  67.460  1.00204.33           O
ANISOU 7699  O   GLN B 178    34128  17227  26282    330  -5106  -5132       O
ATOM   7700  CB  GLN B 178      24.732 -53.241  67.411  1.00205.93           C
ANISOU 7700  CB  GLN B 178    34235  17744  26266     73  -5072  -4337       C
ATOM   7701  CG  GLN B 178      24.076 -54.193  66.427  1.00205.38           C
ANISOU 7701  CG  GLN B 178    33847  17674  26516     84  -5226  -4244       C
ATOM   7702  CD  GLN B 178      23.228 -55.236  67.113  1.00208.15           C
ANISOU 7702  CD  GLN B 178    34287  18012  26789   -180  -5529  -3755       C
ATOM   7703  OE1 GLN B 178      22.638 -54.970  68.158  1.00209.86           O
ANISOU 7703  OE1 GLN B 178    34781  18377  26578   -333  -5357  -3402       O
ATOM   7704  NE2 GLN B 178      23.150 -56.426  66.525  1.00208.71           N
ANISOU 7704  NE2 GLN B 178    34121  17903  27278   -229  -5969  -3729       N
ATOM   7705  N   SER B 179      26.232 -49.875  67.106  1.00201.47           N
ANISOU 7705  N   SER B 179    33780  17378  25391    572  -3956  -5191       N
ATOM   7706  CA  SER B 179      27.496 -49.169  67.262  1.00201.00           C
ANISOU 7706  CA  SER B 179    33786  17130  25454    691  -3986  -5596       C
ATOM   7707  C   SER B 179      27.887 -48.903  68.719  1.00203.62           C
ANISOU 7707  C   SER B 179    34512  17391  25463    511  -4154  -5495       C
ATOM   7708  O   SER B 179      28.830 -48.163  68.980  1.00203.43           O
ANISOU 7708  O   SER B 179    34576  17248  25471    598  -4116  -5808       O
ATOM   7709  CB  SER B 179      27.446 -47.860  66.478  1.00198.00           C
ANISOU 7709  CB  SER B 179    33255  16964  25014    964  -3301  -5858       C
ATOM   7710  OG  SER B 179      26.739 -48.041  65.265  1.00195.91           O
ANISOU 7710  OG  SER B 179    32674  16864  24897   1109  -3056  -5839       O
ATOM   7711  N   ALA B 180      27.180 -49.519  69.663  1.00206.82           N
ANISOU 7711  N   ALA B 180    35151  17862  25571    264  -4350  -5062       N
ATOM   7712  CA  ALA B 180      27.465 -49.301  71.082  1.00209.61           C
ANISOU 7712  CA  ALA B 180    35901  18174  25567     92  -4507  -4933       C
ATOM   7713  C   ALA B 180      27.540 -50.589  71.904  1.00212.89           C
ANISOU 7713  C   ALA B 180    36477  18385  26025   -159  -5178  -4636       C
ATOM   7714  O   ALA B 180      28.625 -50.996  72.312  1.00214.36           O
ANISOU 7714  O   ALA B 180    36742  18269  26436   -211  -5705  -4814       O
ATOM   7715  CB  ALA B 180      26.449 -48.346  71.686  1.00209.79           C
ANISOU 7715  CB  ALA B 180    36149  18558  25004     61  -3888  -4672       C
ATOM   7716  N   LEU B 181      26.396 -51.223  72.147  1.00214.99           N
ANISOU 7716  N   LEU B 181    36783  18810  26095   -312  -5155  -4178       N
ATOM   7717  CA  LEU B 181      26.352 -52.460  72.931  1.00218.22           C
ANISOU 7717  CA  LEU B 181    37334  19043  26538   -551  -5751  -3845       C
ATOM   7718  C   LEU B 181      27.564 -53.360  72.665  1.00218.77           C
ANISOU 7718  C   LEU B 181    37263  18710  27150   -558  -6439  -4110       C
ATOM   7719  O   LEU B 181      28.200 -53.864  73.592  1.00221.53           O
```

FIG. 13 Continued

```
ANISOU 7719  O   LEU B 181     37831  18849  27489   -706  -6936  -4040           O
ATOM   7720  CB  LEU B 181     25.047 -53.217  72.653 1.00218.53                  C
ANISOU 7720  CB  LEU B 181     37243  19239  26549   -651  -5671  -3415           C
ATOM   7721  CG  LEU B 181     25.043 -54.753  72.620 1.00220.41                  C
ANISOU 7721  CG  LEU B 181     37359  19230  27155   -809  -6308  -3203           C
ATOM   7722  CD1 LEU B 181     25.506 -55.380  73.931 1.00224.15                  C
ANISOU 7722  CD1 LEU B 181     38152  19514  27500  -1021  -6828  -2979           C
ATOM   7723  CD2 LEU B 181     23.661 -55.265  72.256 1.00220.36                  C
ANISOU 7723  CD2 LEU B 181     37202  19420  27106   -876  -6104  -2808           C
ATOM   7724  N   THR B 182     27.873 -53.550  71.389 1.00214.65                  N
ANISOU 7724  N   THR B 182     36376  18086  27096   -390  -6455  -4411           N
ATOM   7725  CA  THR B 182     29.013 -54.339  70.945 1.00214.74                  C
ANISOU 7725  CA  THR B 182     36207  17718  27669   -361  -7040  -4703           C
ATOM   7726  C   THR B 182     29.374 -53.667  69.634 1.00211.18                  C
ANISOU 7726  C   THR B 182     35447  17289  27504    -82  -6692  -5139           C
ATOM   7727  O   THR B 182     29.424 -54.296  68.574 1.00209.81                  O
ANISOU 7727  O   THR B 182     34959  17008  27754     10  -6837  -5272           O
ATOM   7728  CB  THR B 182     28.635 -55.822  70.739 1.00216.17                  C
ANISOU 7728  CB  THR B 182     36232  17744  28158   -510  -7528  -4438           C
ATOM   7729  OG1 THR B 182     28.257 -56.396  71.997 1.00219.60                  O
ANISOU 7729  OG1 THR B 182     36962  18174  28302   -761  -7807  -4001           O
ATOM   7730  CG2 THR B 182     29.802 -56.613  70.171 1.00216.06                  C
ANISOU 7730  CG2 THR B 182     36004  17337  28754   -463  -8095  -4761           C
ATOM   7731  N   GLY B 183     29.600 -52.357  69.733 1.00220.57                  N
ANISOU 7731  N   GLY B 183     36737  18627  28444     58  -6214  -5353           N
ATOM   7732  CA  GLY B 183     29.791 -51.499  68.580 1.00217.21                  C
ANISOU 7732  CA  GLY B 183     36050  18289  28191    338  -5749  -5719           C
ATOM   7733  C   GLY B 183     31.154 -51.133  68.022 1.00215.84                  C
ANISOU 7733  C   GLY B 183     35727  17845  28438    534  -5867  -6227           C
ATOM   7734  O   GLY B 183     31.853 -50.259  68.541 1.00216.02                  O
ANISOU 7734  O   GLY B 183     35908  17819  28349    584  -5750  -6436           O
ATOM   7735  N   GLU B 184     31.513 -51.811  66.936 1.00204.31                  N
ANISOU 7735  N   GLU B 184     33949  16204  27474    651  -6093  -6425           N
ATOM   7736  CA  GLU B 184     32.676 -51.466  66.140 1.00202.58                  C
ANISOU 7736  CA  GLU B 184     33521  15753  27696    883  -6117  -6904           C
ATOM   7737  C   GLU B 184     32.074 -50.531  65.097 1.00199.44                  C
ANISOU 7737  C   GLU B 184     32917  15657  27206   1138  -5414  -7027           C
ATOM   7738  O   GLU B 184     30.950 -50.758  64.653 1.00198.73                  O
ANISOU 7738  O   GLU B 184     32730  15822  26957   1128  -5180  -6784           O
ATOM   7739  CB  GLU B 184     33.253 -52.713  65.471 1.00202.89                  C
ANISOU 7739  CB  GLU B 184     33328  15467  28295    883  -6688  -7025           C
ATOM   7740  CG  GLU B 184     32.911 -54.019  66.178 1.00205.73                  C
ANISOU 7740  CG  GLU B 184     33804  15707  28658    596  -7264  -6663           C
ATOM   7741  CD  GLU B 184     31.483 -54.477  65.911 1.00205.60                  C
ANISOU 7741  CD  GLU B 184     33722  15974  28423    514  -7076  -6294           C
ATOM   7742  OE1 GLU B 184     31.033 -55.452  66.551 1.00207.99                  O
ANISOU 7742  OE1 GLU B 184     34130  16223  28672    275  -7463  -5944           O
ATOM   7743  OE2 GLU B 184     30.809 -53.861  65.060 1.00203.20                  O
ANISOU 7743  OE2 GLU B 184     33254  15942  28012    691  -6539  -6345           O
ATOM   7744  N   SER B 185     32.795 -49.486  64.704 1.00197.77                  N
ANISOU 7744  N   SER B 185     32629  15417  27100   1366  -5074  -7390           N
ATOM   7745  CA  SER B 185     32.253 -48.492  63.772 1.00194.89                  C
ANISOU 7745  CA  SER B 185     32079  15348  26624   1620  -4367  -7499           C
ATOM   7746  C   SER B 185     31.733 -49.023  62.419 1.00193.06                  C
ANISOU 7746  C   SER B 185     31517  15205  26632   1777  -4277  -7522           C
ATOM   7747  O   SER B 185     31.822 -48.332  61.405 1.00190.62                  O
ANISOU 7747  O   SER B 185     30984  14998  26444   2055  -3838  -7766           O
ATOM   7748  CB  SER B 185     33.272 -47.370  63.542 1.00193.49                  C
ANISOU 7748  CB  SER B 185     31846  15061  26611   1851  -4075  -7910           C
ATOM   7749  OG  SER B 185     33.648 -46.764  64.766 1.00195.16                  O
ANISOU 7749  OG  SER B 185     32362  15231  26560   1719  -4097  -7896           O
ATOM   7750  N   LEU B 186     31.168 -50.227  62.401 1.00194.88                  N
ANISOU 7750  N   LEU B 186     31716  15406  26925   1605  -4678  -7268           N
ATOM   7751  CA  LEU B 186     30.651 -50.797  61.160 1.00193.47                  C
ANISOU 7751  CA  LEU B 186     31236  15306  26968   1737  -4641  -7291           C
ATOM   7752  C   LEU B 186     29.324 -51.533  61.343 1.00194.55                  C
ANISOU 7752  C   LEU B 186     31400  15656  26865   1538  -4704  -6857           C
ATOM   7753  O   LEU B 186     29.193 -52.369  62.239 1.00197.02                  O
ANISOU 7753  O   LEU B 186     31887  15845  27129   1268  -5157  -6590           O
```

FIG. 13 Continued

```
ATOM   7754  CB   LEU B 186      31.678 -51.742  60.530  1.00193.73           C
ANISOU 7754  CB   LEU B 186    31077  14952  27580   1803  -5188  -7576       C
ATOM   7755  CG   LEU B 186      32.984 -51.158  59.984  1.00192.37           C
ANISOU 7755  CG   LEU B 186    30779  14544  27768   2056  -5124  -8040       C
ATOM   7756  CD1  LEU B 186      33.762 -52.238  59.240  1.00192.66           C
ANISOU 7756  CD1  LEU B 186    30601  14233  28370   2116  -5646  -8267       C
ATOM   7757  CD2  LEU B 186      32.721 -49.964  59.080  1.00189.56           C
ANISOU 7757  CD2  LEU B 186    30261  14463  27299   2365   4403   8219       C
ATOM   7758  N    PRO B 187      28.344 -51.221  60.474  1.00192.36           N
ANISOU 7758  N    PRO B 187    30940  15695  26455   1680  -4245  -6783       N
ATOM   7759  CA   PRO B 187      26.980 -51.752  60.363  1.00192.86           C
ANISOU 7759  CA   PRO B 187    30956  16005  26317   1557  -4180  -6408       C
ATOM   7760  C    PRO B 187      26.835 -53.228  60.666  1.00195.22           C
ANISOU 7760  C    PRO B 187    31256  16087  26831   1316  -4840  -6198       C
ATOM   7761  O    PRO B 187      27.781 -53.884  61.084  1.00196.69           O
ANISOU 7761  O    PRO B 187    31509  15929  27296   1216  -5376  -6310       O
ATOM   7762  CB   PRO B 187      26.645 -51.500  58.897  1.00190.39           C
ANISOU 7762  CB   PRO B 187    30321  15870  26149   1843  -3830  -6605       C
ATOM   7763  CG   PRO B 187      27.325 -50.196  58.615  1.00188.34           C
ANISOU 7763  CG   PRO B 187    30048  15665  25848   2098  -3346  -6920       C
ATOM   7764  CD   PRO B 187      28.547 -50.111  59.526  1.00189.58           C
ANISOU 7764  CD   PRO B 187    30411  15498  26123   2006  -3672  -7085       C
ATOM   7765  N    VAL B 188      25.638 -53.746  60.436  1.00195.83           N
ANISOU 7765  N    VAL B 188    31246  16363  26799   1226  -4794  -5890       N
ATOM   7766  CA   VAL B 188      25.353 -55.135  60.739  1.00198.19           C
ANISOU 7766  CA   VAL B 188    31533  16478  27293    989  -5377  -5648       C
ATOM   7767  C    VAL B 188      24.229 -55.645  59.856  1.00197.74           C
ANISOU 7767  C    VAL B 188    31229  16614  27289   1021  -5286  -5497       C
ATOM   7768  O    VAL B 188      24.283 -56.772  59.371  1.00198.64           O
ANISOU 7768  O    VAL B 188    31167  16533  27774    976  -5750  -5534       O
ATOM   7769  CB   VAL B 188      24.947 -55.298  62.204  1.00200.73           C
ANISOU 7769  CB   VAL B 188    32175  16813  27280    691  -5505  -5229       C
ATOM   7770  CG1  VAL B 188      26.176 -55.368  63.092  1.00202.15           C
ANISOU 7770  CG1  VAL B 188    32572  16683  27554    599  -5894  -5367       C
ATOM   7771  CG2  VAL B 188      24.058 -54.150  62.619  1.00199.94           C
ANISOU 7771  CG2  VAL B 188    32228  17092  26647    705  -4847  -5007       C
ATOM   7772  N    THR B 189      23.213 -54.803  59.670  1.00200.69           N
ANISOU 7772  N    THR B 189    31590  17367  27295   1095  -4691  -5328       N
ATOM   7773  CA   THR B 189      22.063 -55.082  58.802  1.00200.08           C
ANISOU 7773  CA   THR B 189    31277  17527  27218   1151  -4513  -5185       C
ATOM   7774  C    THR B 189      21.709 -56.555  58.596  1.00202.00           C
ANISOU 7774  C    THR B 189    31373  17587  27793    989  -5085  -5043       C
ATOM   7775  O    THR B 189      22.505 -57.325  58.059  1.00202.23           O
ANISOU 7775  O    THR B 189    31259  17328  28252   1042  -5539  -5322       O
ATOM   7776  CB   THR B 189      22.246 -54.425  57.418  1.00197.27           C
ANISOU 7776  CB   THR B 189    30661  17316  26976   1499  -4142  -5560       C
ATOM   7777  OG1  THR B 189      21.657 -55.257  56.413  1.00197.32           O
ANISOU 7777  OG1  THR B 189    30390  17353  27228   1551  -4328  -5571       O
ATOM   7778  CG2  THR B 189      23.724 -54.237  57.098  1.00196.31           C
ANISOU 7778  CG2  THR B 189    30517  16917  27156   1674  -4308  -6021       C
ATOM   7779  N    LYS B 190      20.498 -56.945  58.981  1.00199.09           N
ANISOU 7779  N    LYS B 190    31022  17379  27246    801  -5049  -4612       N
ATOM   7780  CA   LYS B 190      20.108 -58.342  58.795  1.00201.06           C
ANISOU 7780  CA   LYS B 190    31115  17449  27830    643  -5581  -4463       C
ATOM   7781  C    LYS B 190      18.658 -58.638  58.427  1.00201.51           C
ANISOU 7781  C    LYS B 190    31009  17754  27803    586  -5413  -4144       C
ATOM   7782  O    LYS B 190      17.744 -57.843  58.668  1.00200.93           O
ANISOU 7782  O    LYS B 190    31007  18001  27338    585  -4896  -3887       O
ATOM   7783  CB   LYS B 190      20.506 -59.194  60.002  1.00203.91           C
ANISOU 7783  CB   LYS B 190    31688  17511  28276    355  -6108  -4233       C
ATOM   7784  CG   LYS B 190      21.788 -59.980  59.812  1.00204.49           C
ANISOU 7784  CG   LYS B 190    31703  17180  28813    368  -6693  -4563       C
ATOM   7785  CD   LYS B 190      21.579 -61.227  58.966  1.00205.34           C
ANISOU 7785  CD   LYS B 190    31520  17117  29383    353  -7137  -4628       C
ATOM   7786  CE   LYS B 190      21.329 -60.897  57.504  1.00202.99           C
ANISOU 7786  CE   LYS B 190    30935  17002  29191    637  -6853  -4938       C
ATOM   7787  NZ   LYS B 190      22.242 -59.850  56.975  1.00200.42           N
ANISOU 7787  NZ   LYS B 190    30616  16721  28815    917  -6524  -5356       N
ATOM   7788  N    HIS B 191      18.490 -59.816  57.830  1.00209.97           N
```

FIG. 13 Continued

```
ANISOU 7788  N   HIS B 191    31851  18653  29274    539  -5873  -4176           N
ATOM   7789  CA  HIS B 191     17.201 -60.360  57.437  1.00 210.87               C
ANISOU 7789  CA  HIS B 191    31771  18923  29425    465  -5859  -3899           C
ATOM   7790  C   HIS B 191     16.363 -60.523  58.697  1.00 213.09               C
ANISOU 7790  C   HIS B 191    32260  19260  29443    178  -5823  -3350           C
ATOM   7791  O   HIS B 191     16.862 -60.320  59.805  1.00 214.02               O
ANISOU 7791  O   HIS B 191    32665  19275  29379     45  -5871  -3222           O
ATOM   7792  CB  HIS B 191     17.386 -61.753  56.800  1.00 212.30               C
ANISOU 7792  CB  HIS B 191    31711  18816  30140    420  -6484  -4039           C
ATOM   7793  CG  HIS B 191     17.888 -61.744  55.382  1.00 210.45               C
ANISOU 7793  CG  HIS B 191    31218  18567  30175    708  -6510  -4532           C
ATOM   7794  ND1 HIS B 191     19.164 -61.348  55.039  1.00 208.89               N
ANISOU 7794  ND1 HIS B 191    31053  18223  30093    901  -6534  -4965           N
ATOM   7795  CD2 HIS B 191     17.300 -62.144  54.228  1.00 210.15               C
ANISOU 7795  CD2 HIS B 191    30887  18627  30333    835  -6546  -4659           C
ATOM   7796  CE1 HIS B 191     19.328 -61.473  53.734  1.00 207.65               C
ANISOU 7796  CE1 HIS B 191    30642  18086  30172   1143  -6550  -5327           C
ATOM   7797  NE2 HIS B 191     18.212 -61.954  53.218  1.00 208.41               N
ANISOU 7797  NE2 HIS B 191    30542  18334  30310   1109  -6565  -5158           N
ATOM   7798  N   PRO B 192     15.083 -60.863  58.528  1.00 206.37               N
ANISOU 7798  N   PRO B 192    31265  18574  28573     89  -5735  -3023           N
ATOM   7799  CA  PRO B 192     14.143 -61.163  59.620  1.00 208.73               C
ANISOU 7799  CA  PRO B 192    31716  18920  28672   -180  -5704  -2467           C
ATOM   7800  C   PRO B 192     14.614 -62.259  60.594  1.00 211.65               C
ANISOU 7800  C   PRO B 192    32224  18931  29263   -437  -6298  -2276           C
ATOM   7801  O   PRO B 192     14.058 -63.358  60.627  1.00 213.85               O
ANISOU 7801  O   PRO B 192    32360  19065  29829   -602  -6667  -2041           O
ATOM   7802  CB  PRO B 192     12.889 -61.611  58.868  1.00 209.17               C
ANISOU 7802  CB  PRO B 192    31480  19131  28864   -183  -5649  -2287           C
ATOM   7803  CG  PRO B 192     12.932 -60.808  57.608  1.00 206.22               C
ANISOU 7803  CG  PRO B 192    30915  18994  28446    125  -5283  -2668           C
ATOM   7804  CD  PRO B 192     14.385 -60.710  57.239  1.00 204.84               C
ANISOU 7804  CD  PRO B 192    30768  18611  28449    287  -5497  -3169           C
ATOM   7805  N   GLY B 193     15.612 -61.924  61.406  1.00 212.21               N
ANISOU 7805  N   GLY B 193    32571  18865  29193   -470  -6373  -2364           N
ATOM   7806  CA  GLY B 193     16.165 -62.815  62.409  1.00 214.91               C
ANISOU 7806  CA  GLY B 193    33082  18884  29690   -697  -6901  -2190           C
ATOM   7807  C   GLY B 193     17.360 -62.101  63.006  1.00 214.13               C
ANISOU 7807  C   GLY B 193    33258  18704  29399   -641  -6867  -2423           C
ATOM   7808  O   GLY B 193     18.435 -62.088  62.408  1.00 212.77               O
ANISOU 7808  O   GLY B 193    33004  18360  29480   -491  -7064  -2872           O
ATOM   7809  N   GLN B 194     17.180 -61.509  64.185  1.00 270.85               N
ANISOU 7809  N   GLN B 194    40767  26001  36142   -759  -6619  -2121           N
ATOM   7810  CA  GLN B 194     18.237 -60.697  64.787  1.00 270.15               C
ANISOU 7810  CA  GLN B 194    40952  25870  35823   -701  -6534  -2339           C
ATOM   7811  C   GLN B 194     18.219 -60.592  66.313  1.00 272.61               C
ANISOU 7811  C   GLN B 194    41643  26166  35770   -909  -6555  -1967           C
ATOM   7812  O   GLN B 194     17.165 -60.414  66.928  1.00 273.80               O
ANISOU 7812  O   GLN B 194    41917  26523  35591  -1026  -6257  -1532           O
ATOM   7813  CB  GLN B 194     18.190 -59.279  64.201  1.00 266.99               C
ANISOU 7813  CB  GLN B 194    40541  25775  35128   -456  -5887  -2596           C
ATOM   7814  CG  GLN B 194     19.144 -59.028  63.042  1.00 264.42               C
ANISOU 7814  CG  GLN B 194    40003  25358  35106   -199  -5930  -3160           C
ATOM   7815  CD  GLN B 194     20.425 -58.335  63.476  1.00 263.69               C
ANISOU 7815  CD  GLN B 194    40119  25138  34934   -118  -5936  -3471           C
ATOM   7816  OE1 GLN B 194     21.313 -58.080  62.663  1.00 261.78               O
ANISOU 7816  OE1 GLN B 194    39736  24794  34935     89  -5966  -3921           O
ATOM   7817  NE2 GLN B 194     20.522 -58.019  64.763  1.00 265.33               N
ANISOU 7817  NE2 GLN B 194    40664  25349  34801   -276  -5904  -3231           N
ATOM   7818  N   GLU B 195     19.409 -60.696  66.905  1.00 251.07               N
ANISOU 7818  N   GLU B 195    39100  23190  33105   -945  -6909  -2147           N
ATOM   7819  CA  GLU B 195     19.605 -60.507  68.340  1.00 253.37               C
ANISOU 7819  CA  GLU B 195    39778  23457  33033  -1110  -6954  -1872           C
ATOM   7820  C   GLU B 195     19.670 -59.014  68.608  1.00 251.61               C
ANISOU 7820  C   GLU B 195    39770  23504  32326   -980  -6359  -1996           C
ATOM   7821  O   GLU B 195     20.646 -58.504  69.162  1.00 251.68               O
ANISOU 7821  O   GLU B 195    40001  23420  32207   -953  -6424  -2205           O
ATOM   7822  CB  GLU B 195     20.896 -61.170  68.825  1.00 254.96               C
ANISOU 7822  CB  GLU B 195    40080  23287  33505  -1187  -7578  -2044           C
```

FIG. 13 Continued

```
ATOM   7823  CG  GLU B 195      20.817 -62.680  68.966  1.00257.59           C
ANISOU 7823  CG  GLU B 195    40289  23337  34246  -1373  -8189  -1811       C
ATOM   7824  CD  GLU B 195      21.952 -63.244  69.799  1.00259.81           C
ANISOU 7824  CD  GLU B 195    40757  23291  34667  -1490  -8752  -1849       C
ATOM   7825  OE1 GLU B 195      22.391 -62.561  70.749  1.00260.55           O
ANISOU 7825  OE1 GLU B 195    41181  23434  34380  -1517  -8648  -1819       O
ATOM   7826  OE2 GLU B 195      22.399 -64.373  69.509  1.00260.92           O
ANISOU 7826  OE2 GLU B 195    40713  23123  35301  -1555  -9303  -1910       O
ATOM   7827  N   VAL B 196      18.627 -58.322  68.173  1.00232.22           N
ANISOU 7827  N   VAL B 196    37230  21376  29629   -896  -5782  -1875       N
ATOM   7828  CA  VAL B 196      18.510 -56.886  68.332  1.00230.46           C
ANISOU 7828  CA  VAL B 196    37172  21437  28955   -767  -5150  -1963       C
ATOM   7829  C   VAL B 196      18.404 -56.482  69.803  1.00232.77           C
ANISOU 7829  C   VAL B 196    37885  21798  28761   -925  -5032  -1647       C
ATOM   7830  O   VAL B 196      17.466 -55.796  70.198  1.00232.86           O
ANISOU 7830  O   VAL B 196    38028  22092  28355   -946  -4515  -1362       O
ATOM   7831  CB  VAL B 196      17.290 -56.371  67.555  1.00228.62           C
ANISOU 7831  CB  VAL B 196    36735  21535  28595   -663  -4584  -1838       C
ATOM   7832  CG1 VAL B 196      17.679 -56.042  66.124  1.00225.42           C
ANISOU 7832  CG1 VAL B 196    36006  21158  28486   -404  -4464  -2307       C
ATOM   7833  CG2 VAL B 196      16.181 -57.416  67.576  1.00230.57           C
ANISOU 7833  CG2 VAL B 196    36847  21782  28977   -834  -4763  -1398       C
ATOM   7834  N   PHE B 197      19.361 -56.920  70.615  1.00238.25           N
ANISOU 7834  N   PHE B 197    38790  22229  29507  -1033  -5515  -1693       N
ATOM   7835  CA  PHE B 197      19.375 -56.570  72.031  1.00240.71           C
ANISOU 7835  CA  PHE B 197    39520  22588  29352  -1173  -5457  -1425       C
ATOM   7836  C   PHE B 197      19.086 -55.076  72.191  1.00239.05           C
ANISOU 7836  C   PHE B 197    39477  22691  28662  -1049  -4758  -1500       C
ATOM   7837  O   PHE B 197      19.543 -54.264  71.392  1.00236.15           O
ANISOU 7837  O   PHE B 197    38966  22386  28375   -843  -4487  -1913       O
ATOM   7838  CB  PHE B 197      20.731 -56.928  72.663  1.00242.29           C
ANISOU 7838  CB  PHE B 197    39897  22474  29687  -1229  -6020  -1638       C
ATOM   7839  CG  PHE B 197      20.820 -58.350  73.189  1.00245.43           C
ANISOU 7839  CG  PHE B 197    40310  22601  30341  -1436  -6668  -1349       C
ATOM   7840  CD1 PHE B 197      20.646 -59.438  72.344  1.00245.21           C
ANISOU 7840  CD1 PHE B 197    39938  22405  30824  -1456  -7014  -1345       C
ATOM   7841  CD2 PHE B 197      21.110 -58.592  74.529  1.00248.71           C
ANISOU 7841  CD2 PHE B 197    41084  22925  30490  -1603  -6938  -1092       C
ATOM   7842  CE1 PHE B 197      20.739 -60.733  72.832  1.00248.15           C
ANISOU 7842  CE1 PHE B 197    40312  22519  31455  -1645  -7599  -1079       C
ATOM   7843  CE2 PHE B 197      21.199 -59.883  75.021  1.00251.68           C
ANISOU 7843  CE2 PHE B 197    41468  23053  31105  -1785  -7520   -811       C
ATOM   7844  CZ  PHE B 197      21.017 -60.954  74.172  1.00251.37           C
ANISOU 7844  CZ  PHE B 197    41072  22840  31596  -1809  -7847   -804       C
ATOM   7845  N   SER B 198      18.326 -54.724  73.225  1.00222.51           N
ANISOU 7845  N   SER B 198    37682  20786  26077  -1170  -4459  -1096       N
ATOM   7846  CA  SER B 198      17.942 -53.336  73.477  1.00221.30           C
ANISOU 7846  CA  SER B 198    37706  20934  25443  -1074  -3776  -1116       C
ATOM   7847  C   SER B 198      19.059 -52.352  73.153  1.00219.06           C
ANISOU 7847  C   SER B 198    37437  20615  25183   -885  -3654  -1659       C
ATOM   7848  O   SER B 198      18.804 -51.221  72.744  1.00216.76           O
ANISOU 7848  O   SER B 198    37105  20556  24699   -728  -3068  -1816       O
ATOM   7849  CB  SER B 198      17.517 -53.151  74.931  1.00224.46           C
ANISOU 7849  CB  SER B 198    38534  21432  25317  -1241  -3659   -707       C
ATOM   7850  OG  SER B 198      18.647 -52.995  75.767  1.00225.97           O
ANISOU 7850  OG  SER B 198    39017  21452  25390  -1272  -3979   -909       O
ATOM   7851  N   GLY B 199      20.299 -52.777  73.358  1.00326.27           N
ANISOU 7851  N   GLY B 199    51067  33892  39007   -901  -4203  -1936       N
ATOM   7852  CA  GLY B 199      21.432 -51.940  73.026  1.00324.31           C
ANISOU 7852  CA  GLY B 199    50806  33564  38854   -723  -4144  -2459       C
ATOM   7853  C   GLY B 199      21.665 -51.960  71.527  1.00321.03           C
ANISOU 7853  C   GLY B 199    49968  33109  38900   -521  -4093  -2815       C
ATOM   7854  O   GLY B 199      22.562 -52.649  71.042  1.00320.77           O
ANISOU 7854  O   GLY B 199    49765  32791  39322   -488  -4592  -3083       O
ATOM   7855  N   SER B 200      20.853 -51.211  70.787  1.00211.27           N
ANISOU 7855  N   SER B 200    35898  19494  24883   -379  -3487  -2814       N
ATOM   7856  CA  SER B 200      21.007 -51.153  69.338  1.00208.20           C
ANISOU 7856  CA  SER B 200    35116  19105  24886   -164  -3386  -3143       C
ATOM   7857  C   SER B 200      20.423 -49.889  68.719  1.00205.47           C
```

FIG. 13 Continued

```
ANISOU 7857  C   SER B 200    34667 19087 24316     33 -2628 -3235           C
ATOM   7858  O   SER B 200    19.214 -49.664 68.733 1.00205.42               O
ANISOU 7858  O   SER B 200    34652 19353 24045     -4 -2213 -2899           O
ATOM   7859  CB  SER B 200    20.441 -52.408 68.667 1.00208.56               C
ANISOU 7859  CB  SER B 200    34887 19071 25285   -233 -3732 -2961           C
ATOM   7860  OG  SER B 200    19.291 -52.879 69.339 1.00210.73               O
ANISOU 7860  OG  SER B 200    35282 19476 25309   -434 -3686 -2433           O
ATOM   7861  N   THR B 201    21.317 -49.068 68.186 1.00202.43               N
ANISOU 7861  N   THR B 201    34196 18659 24057    246 -2454 -3689           N
ATOM   7862  CA  THR B 201    20.953 -47.835 67.520 1.00199.70               C
ANISOU 7862  CA  THR B 201    33728 18591 23560    464 -1752 -3836           C
ATOM   7863  C   THR B 201    20.807 -48.157 66.049 1.00197.34               C
ANISOU 7863  C   THR B 201    33019 18314 23646    650 -1731 -4015           C
ATOM   7864  O   THR B 201    21.719 -47.907 65.267 1.00195.50               O
ANISOU 7864  O   THR B 201    32607 17952 23723    853 -1773 -4440           O
ATOM   7865  CB  THR B 201    22.080 -46.808 67.661 1.00198.68               C
ANISOU 7865  CB  THR B 201    33695 18373 23421    614 -1596 -4257           C
ATOM   7866  OG1 THR B 201    22.890 -47.142 68.795 1.00201.26               O
ANISOU 7866  OG1 THR B 201    34323 18455 23692    444 -2070 -4268           O
ATOM   7867  CG2 THR B 201    21.515 -45.402 67.821 1.00197.46               C
ANISOU 7867  CG2 THR B 201    33634 18533 22857    715  -833 -4221           C
ATOM   7868  N   CYS B 202    19.662 -48.712 65.668 1.00198.09               N
ANISOU 7868  N   CYS B 202    32966 18570 23730    587 -1667 -3694           N
ATOM   7869  CA  CYS B 202    19.458 -49.127 64.284 1.00196.20               C
ANISOU 7869  CA  CYS B 202    32344 18356 23849    752 -1698 -3847           C
ATOM   7870  C   CYS B 202    19.475 -47.951 63.322 1.00193.11               C
ANISOU 7870  C   CYS B 202    31762 18183 23429   1047 -1092 -4128           C
ATOM   7871  O   CYS B 202    19.010 -46.866 63.649 1.00192.44               O
ANISOU 7871  O   CYS B 202    31793 18346 22978   1090  -512 -4029           O
ATOM   7872  CB  CYS B 202    18.151 -49.908 64.124 1.00197.21               C
ANISOU 7872  CB  CYS B 202    32354 18624 23951    618 -1732 -3427           C
ATOM   7873  SG  CYS B 202    16.805 -48.995 63.328 1.00195.05               S
ANISOU 7873  SG  CYS B 202    31882 18796 23433    776  -952 -3261           S
ATOM   7874  N   LYS B 203    20.032 -48.176 62.138 1.00192.11               N
ANISOU 7874  N   LYS B 203    31342 17956 23694   1255 -1227 -4478           N
ATOM   7875  CA  LYS B 203    20.061 -47.166 61.092 1.00189.22               C
ANISOU 7875  CA  LYS B 203    30759 17789 23348   1560  -681 -4745           C
ATOM   7876  C   LYS B 203    18.723 -47.181 60.340 1.00188.36               C
ANISOU 7876  C   LYS B 203    30433 17997 23138   1614  -336 -4493           C
ATOM   7877  O   LYS B 203    17.666 -46.992 60.949 1.00189.29               O
ANISOU 7877  O   LYS B 203    30675 18330 22916   1464   -63 -4096           O
ATOM   7878  CB  LYS B 203    21.251 -47.369 60.152 1.00187.87               C
ANISOU 7878  CB  LYS B 203    30377 17372 23632   1776  -960 -5224           C
ATOM   7879  CG  LYS B 203    22.587 -46.866 60.684 1.00187.89               C
ANISOU 7879  CG  LYS B 203    30544 17132 23712   1820 -1058 -5544           C
ATOM   7880  CD  LYS B 203    22.776 -45.410 60.325 1.00185.63               C
ANISOU 7880  CD  LYS B 203    30213 17034 23284   2071  -388 -5761           C
ATOM   7881  CE  LYS B 203    22.528 -45.190 58.839 1.00183.19               C
ANISOU 7881  CE  LYS B 203    29552 16889 23164   2365   -78 -5939           C
ATOM   7882  NZ  LYS B 203    22.061 -43.806 58.530 1.00181.23               N
ANISOU 7882  NZ  LYS B 203    29249 16963 22647   2564   704 -5945           N
ATOM   7883  N   GLN B 204    18.759 -47.414 59.029 1.00195.55               N
ANISOU 7883  N   GLN B 204    31024 18936 24342   1829  -352 -4717           N
ATOM   7884  CA  GLN B 204    17.534 -47.416 58.224 1.00194.74               C
ANISOU 7884  CA  GLN B 204    30693 19135 24165   1903   -43 -4513           C
ATOM   7885  C   GLN B 204    16.763 -48.736 58.222 1.00196.66               C
ANISOU 7885  C   GLN B 204    30857 19320 24544   1697  -508 -4221           C
ATOM   7886  O   GLN B 204    17.298 -49.788 58.568 1.00198.35               O
ANISOU 7886  O   GLN B 204    31127 19231 25008   1540 -1129 -4249           O
ATOM   7887  CB  GLN B 204    17.837 -47.019 56.784 1.00192.26               C
ANISOU 7887  CB  GLN B 204    30070 18913 24067   2246   186 -4872           C
ATOM   7888  CG  GLN B 204    18.621 -48.050 56.003 1.00192.39               C
ANISOU 7888  CG  GLN B 204    29904 18648 24546   2323  -397 -5180           C
ATOM   7889  CD  GLN B 204    20.102 -47.755 55.981 1.00191.64               C
ANISOU 7889  CD  GLN B 204    29857 18281 24675   2461  -536 -5603           C
ATOM   7890  OE1 GLN B 204    20.716 -47.708 54.915 1.00190.16               O
ANISOU 7890  OE1 GLN B 204    29454 18035 24764   2723  -537 -5956           O
ATOM   7891  NE2 GLN B 204    20.686 -47.543 57.155 1.00192.76               N
ANISOU 7891  NE2 GLN B 204    30283 18255 24702   2292  -649 -5570           N
```

FIG. 13 Continued

```
ATOM   7892  N    GLY B 205      15.501 -48.660  57.804  1.00188.04           N
ANISOU 7892  N    GLY B 205    29619  18518  23308   1705   -195  -3944       N
ATOM   7893  CA   GLY B 205      14.644 -49.825  57.705  1.00189.78           C
ANISOU 7893  CA   GLY B 205    29726  18714  23670   1530   -570  -3659       C
ATOM   7894  C    GLY B 205      13.452 -49.841  58.643  1.00191.52           C
ANISOU 7894  C    GLY B 205    30102  19095  23572   1284   -380  -3129       C
ATOM   7895  O    GLY B 205      13.609 -49.956  59.854  1.00193.29           O
ANISOU 7895  O    GLY B 205    30616  19194  23631   1067   -515  -2927       O
ATOM   7896  N    GLU B 206      12.256 -49.716  58.071  1.00189.52           N
ANISOU 7896  N    GLU B 206    29656  19120  23233   1327    -60  -2899       N
ATOM   7897  CA   GLU B 206      11.007 -49.784  58.832  1.00191.20           C
ANISOU 7897  CA   GLU B 206    29971  19492  23187   1107    138  -2373       C
ATOM   7898  C    GLU B 206      10.545 -51.248  58.842  1.00193.52           C
ANISOU 7898  C    GLU B 206    30154  19601  23775    905   -459  -2159       C
ATOM   7899  O    GLU B 206      10.093 -51.767  57.823  1.00193.19           O
ANISOU 7899  O    GLU B 206    29813  19611  23982    993   -595  -2219       O
ATOM   7900  CB   GLU B 206       9.931 -48.874  58.207  1.00189.65           C
ANISOU 7900  CB   GLU B 206    29606  19684  22768   1259    802  -2222       C
ATOM   7901  CG   GLU B 206      10.309 -47.384  58.034  1.00187.20           C
ANISOU 7901  CG   GLU B 206    29350  19579  22200   1489   1443  -2439       C
ATOM   7902  CD   GLU B 206       9.341 -46.624  57.120  1.00185.50           C
ANISOU 7902  CD   GLU B 206    28889  19730  21861   1685   2026  -2356       C
ATOM   7903  OE1  GLU B 206       9.800 -45.968  56.155  1.00183.21           O
ANISOU 7903  OE1  GLU B 206    28428  19547  21637   1973   2280  -2700       O
ATOM   7904  OE2  GLU B 206       8.119 -46.692  57.361  1.00186.54           O
ANISOU 7904  OE2  GLU B 206    28993  20041  21842   1555   2231  -1936       O
ATOM   7905  N    ILE B 207      10.638 -51.901  59.998  1.00197.22           N
ANISOU 7905  N    ILE B 207    30861  19860  24214    638   -806  -1903       N
ATOM   7906  CA   ILE B 207      10.404 -53.340  60.077  1.00199.57           C
ANISOU 7906  CA   ILE B 207    31064  19923  24839    443  -1427  -1734       C
ATOM   7907  C    ILE B 207       9.507 -53.823  61.208  1.00202.38           C
ANISOU 7907  C    ILE B 207    31594  20266  25037    152  -1475  -1180       C
ATOM   7908  O    ILE B 207       9.546 -53.291  62.313  1.00203.21           O
ANISOU 7908  O    ILE B 207    32012  20401  24796     42  -1249   -976       O
ATOM   7909  CB   ILE B 207      11.735 -54.060  60.290  1.00200.25           C
ANISOU 7909  CB   ILE B 207    31237  19638  25211    402  -2038  -2038       C
ATOM   7910  CG1  ILE B 207      12.873 -53.269  59.646  1.00197.63           C
ANISOU 7910  CG1  ILE B 207    30878  19297  24917    670  -1892  -2560       C
ATOM   7911  CG2  ILE B 207      11.656 -55.492  59.782  1.00201.75           C
ANISOU 7911  CG2  ILE B 207    31196  19597  25864    315  -2668  -2047       C
ATOM   7912  CD1  ILE B 207      12.795 -53.178  58.136  1.00195.52           C
ANISOU 7912  CD1  ILE B 207    30264  19153  24873    937  -1790  -2872       C
ATOM   7913  N    GLU B 208       8.728 -54.866  60.920  1.00203.55           N
ANISOU 7913  N    GLU B 208    31534  20351  25454     33  -1789   -949       N
ATOM   7914  CA   GLU B 208       7.846 -55.501  61.900  1.00206.49           C
ANISOU 7914  CA   GLU B 208    32022  20674  25759   -241  -1891   -408       C
ATOM   7915  C    GLU B 208       8.637 -56.500  62.739  1.00208.82           C
ANISOU 7915  C    GLU B 208    32497  20607  26239   -436  -2514   -378       C
ATOM   7916  O    GLU B 208       9.652 -57.011  62.285  1.00208.34           O
ANISOU 7916  O    GLU B 208    32356  20315  26490   -370  -2965   -761       O
ATOM   7917  CB   GLU B 208       6.683 -56.212  61.201  1.00207.35           C
ANISOU 7917  CB   GLU B 208    31806  20853  26126   -281  -1975   -180       C
ATOM   7918  CG   GLU B 208       5.745 -55.287  60.438  1.00205.45           C
ANISOU 7918  CG   GLU B 208    31382  20981  25700   -112  -1366   -132       C
ATOM   7919  CD   GLU B 208       4.952 -54.363  61.347  1.00205.82           C
ANISOU 7919  CD   GLU B 208    31657  21264  25280   -192   -754    283       C
ATOM   7920  OE1  GLU B 208       4.807 -54.674  62.548  1.00208.16           O
ANISOU 7920  OE1  GLU B 208    32211  21443  25436   -414   -843    638       O
ATOM   7921  OE2  GLU B 208       4.467 -53.323  60.855  1.00203.84           O
ANISOU 7921  OE2  GLU B 208    31329  21319  24803    -26   -176    259       O
ATOM   7922  N    ALA B 209       8.163 -56.795  63.948  1.00210.52           N
ANISOU 7922  N    ALA B 209    32948  20771  26270   -670  -2537     85       N
ATOM   7923  CA   ALA B 209       9.900 -57.677  64.848  1.00212.92           C
ANISOU 7923  CA   ALA B 209    33450  20748  26703   -856  -3095    152       C
ATOM   7924  C    ALA B 209       8.127 -58.086  66.096  1.00216.13           C
ANISOU 7924  C    ALA B 209    34073  21128  26918  -1109  -3089    740       C
ATOM   7925  O    ALA B 209       7.231 -57.377  66.545  1.00216.33           O
ANISOU 7925  O    ALA B 209    34216  21401  26577  -1136  -2558   1071       O
ATOM   7926  CB   ALA B 209      10.193 -57.001  65.266  1.00211.81           C
```

FIG. 13 Continued

```
ANISOU 7926  CB  ALA B 209    33573  20532  26373   -772  -3095   -195       C
ATOM   7927  N   VAL B 210      8.479 -59.239  66.654  1.00220.45           N
ANISOU 7927  N   VAL B 210    34671  21368  27722  -1289  -3676    877       N
ATOM   7928  CA  VAL B 210      7.903 -59.677  67.922  1.00223.76           C
ANISOU 7928  CA  VAL B 210    35327  21729  27963  -1524  -3714   1428       C
ATOM   7929  C   VAL B 210      8.992 -59.749  68.991  1.00225.17           C
ANISOU 7929  C   VAL B 210    35864  21711  27979  -1609  -4005   1375       C
ATOM   7930  O   VAL B 210      9.931 -60.542  68.892  1.00225.73           O
ANISOU 7930  O   VAL B 210    35888  21492  28387  -1637  -4581   1140       O
ATOM   7931  CB  VAL B 210      7.183 -61.031  67.814  1.00226.28           C
ANISOU 7931  CB  VAL B 210    35403  21862  28711  -1689  -4127   1754       C
ATOM   7932  CG1 VAL B 210      6.565 -61.409  69.157  1.00229.77           C
ANISOU 7932  CG1 VAL B 210    36101  22257  28945  -1916  -4108   2353       C
ATOM   7933  CG2 VAL B 210      6.115 -60.972  66.738  1.00225.03           C
ANISOU 7933  CG2 VAL B 210    34881  21893  28728  -1604  -3870   1789       C
ATOM   7934  N   VAL B 211      8.861 -58.908  70.009  1.00226.42           N
ANISOU 7934  N   VAL B 211    36380  22030  27620  -1646  -3603   1591       N
ATOM   7935  CA  VAL B 211      9.835 -58.848  71.087  1.00227.90           C
ANISOU 7935  CA  VAL B 211    36939  22069  27584  -1719  -3829   1553       C
ATOM   7936  C   VAL B 211     10.004 -60.196  71.767  1.00231.32           C
ANISOU 7936  C   VAL B 211    37419  22194  28280  -1926  -4447   1834       C
ATOM   7937  O   VAL B 211      9.104 -60.673  72.462  1.00234.02           O
ANISOU 7937  O   VAL B 211    37833  22546  28540  -2087  -4403   2360       O
ATOM   7938  CB  VAL B 211      9.435 -57.805  72.136  1.00228.63           C
ANISOU 7938  CB  VAL B 211    37411  22400  27057  -1746  -3275   1822       C
ATOM   7939  CG1 VAL B 211      9.776 -56.413  71.644  1.00225.31           C
ANISOU 7939  CG1 VAL B 211    37022  22212  26374  -1533  -2767   1425       C
ATOM   7940  CG2 VAL B 211      7.951 -57.916  72.446  1.00230.27           C
ANISOU 7940  CG2 VAL B 211    37589  22777  27127  -1854  -2916   2391       C
ATOM   7941  N   ILE B 212     11.162 -60.810  71.552  1.00255.84           N
ANISOU 7941  N   ILE B 212    40471  25018  31719  -1916  -5014   1489       N
ATOM   7942  CA  ILE B 212     11.473 -62.092  72.169  1.00259.02           C
ANISOU 7942  CA  ILE B 212    40910  25104  32402  -2101  -5636   1712       C
ATOM   7943  C   ILE B 212     12.140 -61.843  73.514  1.00261.10           C
ANISOU 7943  C   ILE B 212    41619  25311  32276  -2188  -5720   1833       C
ATOM   7944  O   ILE B 212     12.263 -60.696  73.944  1.00260.14           O
ANISOU 7944  O   ILE B 212    41764  25400  31675  -2111  -5284   1755       O
ATOM   7945  CB  ILE B 212     12.400 -62.958  71.277  1.00258.16           C
ANISOU 7945  CB  ILE B 212    40512  24696  32879  -2055  -6236   1291       C
ATOM   7946  CG1 ILE B 212     12.347 -64.433  71.701  1.00261.51           C
ANISOU 7946  CG1 ILE B 212    40860  24809  33692  -2256  -6833   1602       C
ATOM   7947  CG2 ILE B 212     13.825 -62.420  71.300  1.00256.63           C
ANISOU 7947  CG2 ILE B 212    40478  24405  32623  -1940  -6386    800       C
ATOM   7948  CD1 ILE B 212     13.386 -65.314  71.034  1.00261.13           C
ANISOU 7948  CD1 ILE B 212    40589  24432  34198  -2231  -7460   1208       C
ATOM   7949  N   ALA B 213     12.558 -62.921  74.171  1.00239.62           N
ANISOU 7949  N   ALA B 213    38973  22305  29765  -2346  -6285   2023       N
ATOM   7950  CA  ALA B 213     13.227 -62.855  75.469  1.00242.07           C
ANISOU 7950  CA  ALA B 213    39699  22532  29742  -2438  -6459   2156       C
ATOM   7951  C   ALA B 213     12.510 -61.930  76.443  1.00243.14           C
ANISOU 7951  C   ALA B 213    40192  22957  29232  -2464  -5886   2508       C
ATOM   7952  O   ALA B 213     11.423 -61.442  76.146  1.00242.20           O
ANISOU 7952  O   ALA B 213    39983  23084  28958  -2430  -5368   2703       O
ATOM   7953  CB  ALA B 213     14.677 -62.438  75.305  1.00240.39           C
ANISOU 7953  CB  ALA B 213    39574  22197  29568  -2326  -6701   1603       C
ATOM   7954  N   THR B 214     13.113 -61.714  77.611  1.00301.44           N
ANISOU 7954  N   THR B 214    47982  30306  36246  -2524  -5991   2593       N
ATOM   7955  CA  THR B 214     12.534 -60.831  78.619  1.00302.76           C
ANISOU 7955  CA  THR B 214    48531  30734  35769  -2544  -5471   2903       C
ATOM   7956  C   THR B 214     13.153 -59.434  78.526  1.00300.13           C
ANISOU 7956  C   THR B 214    48376  30586  35074  -2381  -5092   2458       C
ATOM   7957  O   THR B 214     14.305 -59.279  78.116  1.00298.44           O
ANISOU 7957  O   THR B 214    48114  30233  35047  -2290  -5374   1962       O
ATOM   7958  CB  THR B 214     12.689 -61.393  80.057  1.00307.15           C
ANISOU 7958  CB  THR B 214    49462  31173  36066  -2706  -5763   3321       C
ATOM   7959  OG1 THR B 214     13.824 -60.801  80.697  1.00307.41           O
ANISOU 7959  OG1 THR B 214    49829  31177  35794  -2662  -5895   3019       O
ATOM   7960  CG2 THR B 214     12.832 -62.914  80.047  1.00309.45           C
ANISOU 7960  CG2 THR B 214    49555  31143  36880  -2844  -6413   3526       C
```

FIG. 13 Continued

```
ATOM   7961  N   GLY B 215      12.381 -58.423  78.912  1.00242.23           N
ANISOU 7961  N   GLY B 215    41242  23554  27241  -2344  -4447   2642       N
ATOM   7962  CA  GLY B 215      12.833 -57.049  78.835  1.00239.85           C
ANISOU 7962  CA  GLY B 215    41097  23443  26590  -2191  -4022   2256       C
ATOM   7963  C   GLY B 215      14.235 -56.835  79.365  1.00240.36           C
ANISOU 7963  C   GLY B 215    41415  23349  26561  -2167  -4388   1890       C
ATOM   7964  O   GLY B 215      15.193 -56.767  78.597  1.00238.02           O
ANISOU 7964  O   GLY B 215    40929  22914  26593  -2059  -4635   1391       O
ATOM   7965  N   VAL B 216      14.360 -56.750  80.684  1.00248.68           N
ANISOU 7965  N   VAL B 216    42898  24415  27174  -2264  -4434   2144       N
ATOM   7966  CA  VAL B 216      15.649 -56.475  81.314  1.00249.56           C
ANISOU 7966  CA  VAL B 216    43290  24395  27137  -2247  -4764   1823       C
ATOM   7967  C   VAL B 216      16.719 -57.523  81.006  1.00249.91           C
ANISOU 7967  C   VAL B 216    43158  24085  27711  -2285  -5523   1591       C
ATOM   7968  O   VAL B 216      17.861 -57.389  81.440  1.00250.59           O
ANISOU 7968  O   VAL B 216    43432  24026  27756  -2271  -5862   1302       O
ATOM   7969  CB  VAL B 216      15.515 -56.320  82.846  1.00253.53           C
ANISOU 7969  CB  VAL B 216    44298  24975  27056  -2355  -4716   2190       C
ATOM   7970  CG1 VAL B 216      15.442 -57.682  83.516  1.00257.29           C
ANISOU 7970  CG1 VAL B 216    44833  25239  27685  -2529  -5262   2625       C
ATOM   7971  CG2 VAL B 216      16.679  55.514  83.404  1.00253.69           C
ANISOU 7971  CG2 VAL B 216    44627  24971  26791  -2287  -4811   1783       C
ATOM   7972  N   HIS B 217      16.356 -58.568  80.269  1.00245.15           N
ANISOU 7972  N   HIS B 217    42193  23337  27617  -2335  -5796   1715       N
ATOM   7973  CA  HIS B 217      17.323 -59.609  79.925  1.00245.50           C
ANISOU 7973  CA  HIS B 217    42044  23035  28199  -2373  -6506   1505       C
ATOM   7974  C   HIS B 217      17.954 -59.354  78.567  1.00241.52           C
ANISOU 7974  C   HIS B 217    41179  22456  28132  -2208  -6540    935       C
ATOM   7975  O   HIS B 217      17.609 -59.976  77.564  1.00240.06           O
ANISOU 7975  O   HIS B 217    40612  22198  28402  -2188  -6640    900       O
ATOM   7976  CB  HIS B 217      16.686 -60.991  80.009  1.00247.94           C
ANISOU 7976  CB  HIS B 217    42189  23185  28834  -2533  -6858   1963       C
ATOM   7977  CG  HIS B 217      16.329 -61.394  81.406  1.00252.29           C
ANISOU 7977  CG  HIS B 217    43104  23741  29013  -2691  -6952   2501       C
ATOM   7978  ND1 HIS B 217      16.087 -60.474  82.403  1.00253.65           N
ANISOU 7978  ND1 HIS B 217    43697  24147  28532  -2686  -6544   2664       N
ATOM   7979  CD2 HIS B 217      16.153 -62.613  81.969  1.00255.69           C
ANISOU 7979  CD2 HIS B 217    43543  23976  29632  -2851  -7390   2921       C
ATOM   7980  CE1 HIS B 217      15.790 -61.107  83.523  1.00257.74           C
ANISOU 7980  CE1 HIS B 217    44479  24618  28833  -2830  -6730   3160       C
ATOM   7981  NE2 HIS B 217      15.823 -62.406  83.286  1.00259.04           N
ANISOU 7981  NE2 HIS B 217    44396  24523  29505  -2932  -7239   3334       N
ATOM   7982  N   THR B 218      18.908 -58.433  78.573  1.00238.84           N
ANISOU 7982  N   THR B 218    40973  22129  27647  -2085  -6465    488       N
ATOM   7983  CA  THR B 218      19.598 -57.995  77.375  1.00235.11           C
ANISOU 7983  CA  THR B 218    40208  21602  27522  -1902  -6430    -74       C
ATOM   7984  C   THR B 218      20.765 -57.087  77.762  1.00234.59           C
ANISOU 7984  C   THR B 218    40378  21498  27259  -1808  -6442   -490       C
ATOM   7985  O   THR B 218      21.887 -57.265  77.280  1.00233.48           O
ANISOU 7985  O   THR B 218    40097  21118  27498  -1735  -6822   -908       O
ATOM   7986  CB  THR B 218      18.636 -57.260  76.454  1.00232.07           C
ANISOU 7986  CB  THR B 218    39600  21503  27075  -1772  -5789   -105       C
ATOM   7987  OG1 THR B 218      18.046 -58.205  75.551  1.00231.44           O
ANISOU 7987  OG1 THR B 218    39140  21346  27451  -1796  -5956     10       O
ATOM   7988  CG2 THR B 218      19.364 -56.177  75.672  1.00228.57           C
ANISOU 7988  CG2 THR B 218    39052  21118  26674  -1553  -5514   -669       C
ATOM   7989  N   PHE B 219      20.485 -56.101  78.615  1.00235.13           N
ANISOU 7989  N   PHE B 219    40795  21797  26748  -1806  -6014   -379       N
ATOM   7990  CA  PHE B 219      21.531 -55.282  79.224  1.00235.47           C
ANISOU 7990  CA  PHE B 219    41119  21801  26547  -1748  -6055   -711       C
ATOM   7991  C   PHE B 219      22.085 -56.173  80.337  1.00239.48           C
ANISOU 7991  C   PHE B 219    41892  22086  27013  -1920  -6677   -487       C
ATOM   7992  O   PHE B 219      23.128 -55.890  80.937  1.00240.63           O
ANISOU 7992  O   PHE B 219    42262  22104  27061  -1913  -6950   -732       O
ATOM   7993  CB  PHE B 219      20.965 -53.987  79.828  1.00235.44           C
ANISOU 7993  CB  PHE B 219    41414  22121  25921  -1701  -5394   -634       C
ATOM   7994  CG  PHE B 219      21.056 -52.773  78.924  1.00231.56           C
ANISOU 7994  CG  PHE B 219    40749  21791  25444  -1492  -4856  -1056       C
ATOM   7995  CD1 PHE B 219      22.284  52.232  78.581  1.00229.92           C
```

FIG. 13 Continued

```
ANISOU 7995  CD1 PHE B 219    40491  21434  25434  -1359  -4994  -1596        C
ATOM   7996  CD2 PHE B 219    19.905 -52.148  78.459  1.00229.73              C
ANISOU 7996  CD2 PHE B 219    40408  21858  25021  -1426  -4196   -894        C
ATOM   7997  CE1 PHE B 219    22.363 -51.110  77.768  1.00226.50              C
ANISOU 7997  CE1 PHE B 219    39895  21145  25020  -1159  -4481  -1964        C
ATOM   7998  CE2 PHE B 219    19.980 -51.025  77.646  1.00226.29              C
ANISOU 7998  CE2 PHE B 219    39812  21576  24594  -1228  -3690  -1260        C
ATOM   7999  CZ  PHE B 219    21.208 -50.507  77.301  1.00224.69              C
ANISOU 7999  CZ  PHE B 219    39557  21221  24594  -1092  -3827  -1793        C
ATOM   8000  N   PHE B 220    21.339 -57.245  80.612  1.00315.40              N
ANISOU 8000  N   PHE B 220    51474  31660  36703  -2073  -6885     -4        N
ATOM   8001  CA  PHE B 220    21.709 -58.269  81.587  1.00319.34              C
ANISOU 8001  CA  PHE B 220    52173  31945  37216  -2242  -7480    288        C
ATOM   8002  C   PHE B 220    22.357 -59.454  80.861  1.00318.95              C
ANISOU 8002  C   PHE B 220    51779  31555  37853  -2272  -8102    140        C
ATOM   8003  O   PHE B 220    22.886 -60.372  81.490  1.00321.86              O
ANISOU 8003  O   PHE B 220    52244  31687  38360  -2396  -8676    296        O
ATOM   8004  CB  PHE B 220    20.480 -58.718  82.386  1.00322.30              C
ANISOU 8004  CB  PHE B 220    52728  32475  37257  -2388  -7305    938        C
ATOM   8005  CG  PHE B 220    20.721 -59.914  83.269  1.00326.37              C
ANISOU 8005  CG  PHE B 220    53388  32768  37850   2559   7907   1298        C
ATOM   8006  CD1 PHE B 220    21.631 -59.856  84.315  1.00329.10              C
ANISOU 8006  CD1 PHE B 220    54092  33012  37940  -2604  -8259   1250        C
ATOM   8007  CD2 PHE B 220    20.022 -61.092  83.064  1.00327.61              C
ANISOU 8007  CD2 PHE B 220    53320  32818  38338  -2674  -8117   1694        C
ATOM   8008  CE1 PHE B 220    21.846 -60.954  85.131  1.00332.96              C
ANISOU 8008  CE1 PHE B 220    54713  33304  38492  -2754  -8807   1599        C
ATOM   8009  CE2 PHE B 220    20.233 -62.193  83.877  1.00331.43              C
ANISOU 8009  CE2 PHE B 220    53927  33094  38908  -2826  -8654   2044        C
ATOM   8010  CZ  PHE B 220    21.146 -62.123  84.911  1.00334.10              C
ANISOU 8010  CZ  PHE B 220    54625  33341  38977  -2864  -8996   2003        C
ATOM   8011  N   GLY B 221    22.293 -59.430  79.530  1.00293.64              N
ANISOU 8011  N   GLY B 221    48170  28330  35071  -2153  -7976   -154        N
ATOM   8012  CA  GLY B 221    22.941 -60.431  78.699  1.00292.86              C
ANISOU 8012  CA  GLY B 221    47723  27915  35635  -2151  -8511   -370        C
ATOM   8013  C   GLY B 221    24.380 -60.009  78.453  1.00291.49              C
ANISOU 8013  C   GLY B 221    47542  27548  35664  -2035  -8768   -926        C
ATOM   8014  O   GLY B 221    25.142 -60.685  77.760  1.00290.66              O
ANISOU 8014  O   GLY B 221    47169  27161  36107  -2006  -9206  -1194        O
ATOM   8015  N   LYS B 222    24.730 -58.862  79.031  1.00239.19              N
ANISOU 8015  N   LYS B 222    41213  21073  28594  -1967  -8474  -1096        N
ATOM   8016  CA  LYS B 222    26.063 -58.271  78.957  1.00238.16              C
ANISOU 8016  CA  LYS B 222    41125  20785  28579  -1855  -8650  -1610        C
ATOM   8017  C   LYS B 222    26.388 -57.653  80.319  1.00240.90              C
ANISOU 8017  C   LYS B 222    41943  21212  28375  -1916  -8644  -1523        C
ATOM   8018  O   LYS B 222    26.862 -56.516  80.407  1.00239.69              O
ANISOU 8018  O   LYS B 222    41924  21153  27993  -1799  -8359  -1854        O
ATOM   8019  CB  LYS B 222    26.128 -57.189  77.872  1.00233.97              C
ANISOU 8019  CB  LYS B 222    40376  20395  28126  -1633  -8136  -2050        C
ATOM   8020  CG  LYS B 222    26.262 -57.706  76.446  1.00231.13              C
ANISOU 8020  CG  LYS B 222    39553  19892  28373  -1525  -8241  -2307        C
ATOM   8021  CD  LYS B 222    24.949 -58.241  75.919  1.00230.63              C
ANISOU 8021  CD  LYS B 222    39283  19989  28357  -1571  -8017  -1956        C
ATOM   8022  CE  LYS B 222    25.142 -58.905  74.581  1.00228.40              C
ANISOU 8022  CE  LYS B 222    38560  19533  28687  -1479  -8219  -2206        C
ATOM   8023  NZ  LYS B 222    24.020 -59.827  74.288  1.00229.13              N
ANISOU 8023  NZ  LYS B 222    38468  19677  28914  -1585  -8247  -1812        N
ATOM   8024  N   ALA B 223    26.102 -58.403  81.379  1.00258.34              N
ANISOU 8024  N   ALA B 223    44401  23387  30368  -2097  -8949  -1068        N
ATOM   8025  CA  ALA B 223    26.345 -57.943  82.740  1.00261.49              C
ANISOU 8025  CA  ALA B 223    45271  23867  30215  -2165  -8984   -933        C
ATOM   8026  C   ALA B 223    27.833 -57.988  83.082  1.00262.58              C
ANISOU 8026  C   ALA B 223    45503  23723  30542  -2153  -9535  -1297        C
ATOM   8027  O   ALA B 223    28.487 -59.020  82.907  1.00263.47              O
ANISOU 8027  O   ALA B 223    45448  23529  31128  -2216 -10130  -1321        O
ATOM   8028  CB  ALA B 223    25.544  58.781  83.730  1.00265.37              C
ANISOU 8028  CB  ALA B 223    45988  24412  30429  -2349  -9131   -308        C
ATOM   8029  N   ALA B 224    28.361 -56.866  83.571  1.00250.43              N
ANISOU 8029  N   ALA B 224    44225  22280  28647   2074   9337   1579        N
```

FIG. 13 Continued

```
ATOM   8030  CA   ALA B 224      29.771 -56.770 83.940 1.00251.55           C
ANISOU 8030  CA   ALA B 224    44471  22167  28938  -2055  -9825  -1943     C
ATOM   8031  C    ALA B 224      30.043 -57.407 85.304 1.00256.37           C
ANISOU 8031  C    ALA B 224    45453  22693  29265  -2219 -10328  -1611     C
ATOM   8032  O    ALA B 224      30.059 -58.633 85.432 1.00258.28           O
ANISOU 8032  O    ALA B 224    45609  22745  29780  -2342 -10809  -1325     O
ATOM   8033  CB   ALA B 224      30.222 -55.316 83.926 1.00249.84           C
ANISOU 8033  CB   ALA B 224    44376  22077  28474  -1904  -9420  -2381     C
ATOM   8034  N    HIS B 225      30.249 -56.571 86.319 1.00272.41           N
ANISOU 8034  N    HIS B 225    47893  24866  30744  -2216 -10210  -1649     N
ATOM   8035  CA   HIS B 225      30.509 -57.039 87.683 1.00277.22           C
ANISOU 8035  CA   HIS B 225    48901  25431  30998  -2353 -10650  -1347     C
ATOM   8036  C    HIS B 225      30.201 -55.938 88.707 1.00279.09           C
ANISOU 8036  C    HIS B 225    49602  25959  30481  -2334 -10254  -1303     C
ATOM   8037  O    HIS B 225      29.880 -54.808 88.338 1.00276.55           O
ANISOU 8037  O    HIS B 225    49273  25845  29960  -2216  -9663  -1539     O
ATOM   8038  CB   HIS B 225      31.955 -57.539 87.840 1.00278.61           C
ANISOU 8038  CB   HIS B 225    49040  25244  31573  -2373 -11383  -1635     C
ATOM   8039  CG   HIS B 225      32.154 -58.981 87.464 1.00279.23           C
ANISOU 8039  CG   HIS B 225    48838  25036  32219  -2471 -11937  -1439     C
ATOM   8040  ND1  HIS B 225      31.937 -60.016 88.347 1.00283.23           N
ANISOU 8040  ND1  HIS B 225    49528  25483  32603  -2630 -12350   -948     N
ATOM   8041  CD2  HIS B 225      32.570 -59.552 86.308 1.00276.48           C
ANISOU 8041  CD2  HIS B 225    48042  24437  32570  -2427 -12143  -1676     C
ATOM   8042  CE1  HIS B 225      32.199 -61.166 87.747 1.00282.87           C
ANISOU 8042  CE1  HIS B 225    49148  25157  33172  -2687 -12786   -890     C
ATOM   8043  NE2  HIS B 225      32.585 -60.912 86.512 1.00278.82           N
ANISOU 8043  NE2  HIS B 225    48255  24525  33159  -2566 -12673  -1332     N
ATOM   8044  N    LEU B 226      30.300 -56.278 89.990 1.00268.93           N
ANISOU 8044  N    LEU B 226    48717  24687  28777  -2444 -10579   -999     N
ATOM   8045  CA   LEU B 226      29.983 -55.346 91.074 1.00271.36           C
ANISOU 8045  CA   LEU B 226    49506  25269  28330  -2436 -10249   -914     C
ATOM   8046  C    LEU B 226      30.995 -54.209 91.267 1.00270.98           C
ANISOU 8046  C    LEU B 226    49607  25191  28160  -2329 -10244  -1474     C
ATOM   8047  O    LEU B 226      31.486 -53.992 92.376 1.00274.63           O
ANISOU 8047  O    LEU B 226    50468  25665  28213  -2365 -10506  -1476     O
ATOM   8048  CB   LEU B 226      29.777 -56.101 92.394 1.00276.62           C
ANISOU 8048  CB   LEU B 226    50565  25961  28576  -2577 -10610   -401     C
ATOM   8049  CG   LEU B 226      28.648 -57.135 92.442 1.00277.78           C
ANISOU 8049  CG   LEU B 226    50642  26175  28728  -2688 -10551    225     C
ATOM   8050  CD1  LEU B 226      28.562 -57.774 93.821 1.00283.26           C
ANISOU 8050  CD1  LEU B 226    51758  26894  28975  -2806 -10906    704     C
ATOM   8051  CD2  LEU B 226      27.317 -56.510 92.057 1.00275.55           C
ANISOU 8051  CD2  LEU B 226    50317  26205  28174  -2642  -9758    413     C
ATOM   8052  N    VAL B 227      31.299 -53.496 90.183 1.00324.81           N
ANISOU 8052  N    VAL B 227    56101  31969  35343  -2193  -9948  -1942     N
ATOM   8053  CA   VAL B 227      32.187 -52.327 90.212 1.00323.92           C
ANISOU 8053  CA   VAL B 227    56070  31828  35178  -2073  -9854  -2496     C
ATOM   8054  C    VAL B 227      32.481 -51.829 88.793 1.00318.86           C
ANISOU 8054  C    VAL B 227    54965  31095  35092  -1920  -9569  -2950     C
ATOM   8055  O    VAL B 227      32.542 -52.621 87.851 1.00316.69           O
ANISOU 8055  O    VAL B 227    54301  30643  35384  -1918  -9756  -2946     O
ATOM   8056  CB   VAL B 227      33.518 -52.607 90.954 1.00327.12           C
ANISOU 8056  CB   VAL B 227    56657  31963  35670  -2117 -10584  -2708     C
ATOM   8057  CG1  VAL B 227      34.386 -53.576 90.162 1.00325.78           C
ANISOU 8057  CG1  VAL B 227    56089  31420  36274  -2128 -11158  -2870     C
ATOM   8058  CG2  VAL B 227      34.264 -51.304 91.226 1.00327.00           C
ANISOU 8058  CG2  VAL B 227    56812  31970  35464  -2006 -10431  -3217     C
ATOM   8059  N    ASP B 228      32.645 -50.515 88.643 1.00260.49           N
ANISOU 8059  N    ASP B 228    47616  23825  27533  -1788  -9107  -3336     N
ATOM   8060  CA   ASP B 228      32.976 -49.923 87.343 1.00255.86           C
ANISOU 8060  CA   ASP B 228    46611  23160  27443  -1622  -8804  -3784     C
ATOM   8061  C    ASP B 228      33.536 -48.501 87.468 1.00255.09           C
ANISOU 8061  C    ASP B 228    46628  23117  27179  -1489  -8480  -4262     C
ATOM   8062  O    ASP B 228      33.464 -47.887 88.537 1.00257.93           O
ANISOU 8062  O    ASP B 228    47401  23629  26973  -1524  -8386  -4224     O
ATOM   8063  CB   ASP B 228      31.790 -49.982 86.362 1.00252.48           C
ANISOU 8063  CB   ASP B 228    45893  22933  27104  -1577  -8243  -3568     C
ATOM   8064  CG   ASP B 228      30.547 -49.297 86.892 1.00253.09           C
```

FIG. 13 Continued

```
ANISOU 8064  CG  ASP B 228    46244  23396  26524  -1594  -7595  -3254       C
ATOM   8065  OD1 ASP B 228    29.453 -49.563 86.353 1.00251.41               O
ANISOU 8065  OD1 ASP B 228    45862  23354  26308  -1604  -7223  -2944       O
ATOM   8066  OD2 ASP B 228    30.658 -48.496 87.840 1.00255.33               O
ANISOU 8066  OD2 ASP B 228    46906  23806  26301  -1596  -7457  -3320       O
ATOM   8067  N   SER B 229    34.115 -48.001 86.377 1.00269.80               N
ANISOU 8067  N   SER B 229    48120  24842  29549  -1331  -8321  -4713       N
ATOM   8068  CA  SER B 229    34.702 -46.665 86.350 1.00268.75               C
ANISOU 8068  CA  SER B 229    48023  24722  29366  -1188  -8008  -5196       C
ATOM   8069  C   SER B 229    33.661 -45.630 86.744 1.00268.66               C
ANISOU 8069  C   SER B 229    48256  25091  28731  -1160  -7279  -5060       C
ATOM   8070  O   SER B 229    32.484 -45.776 86.412 1.00267.29               O
ANISOU 8070  O   SER B 229    48018  25157  28385  -1177  -6845  -4712       O
ATOM   8071  CB  SER B 229    35.253 -46.340 84.956 1.00264.38               C
ANISOU 8071  CB  SER B 229    46986  23999  29468  -1007  -7839  -5623       C
ATOM   8072  OG  SER B 229    36.446 -47.055 84.686 1.00264.71               O
ANISOU 8072  OG  SER B 229    46836  23656  30087  -1010  -8504  -5855       O
ATOM   8073  N   THR B 230    34.097 -44.591 87.452 1.00259.85               N
ANISOU 8073  N   THR B 230    47416  24024  27293  -1117  -7149  -5339       N
ATOM   8074  CA  THR B 230    33.199 -43.522 87.876 1.00259.97               C
ANISOU 8074  CA  THR B 230    47679  24383  26716  -1084  -6454  -5255       C
ATOM   8075  C   THR B 230    32.202 -43.191 86.765 1.00255.75               C
ANISOU 8075  C   THR B 230    46818  24055  26302   -982  -5758  -5159       C
ATOM   8076  O   THR B 230    32.557 -43.159 85.584 1.00252.17               O
ANISOU 8076  O   THR B 230    45937  23464  26411   -855  -5683  -5423       O
ATOM   8077  CB  THR B 230    33.986 -42.258 88.306 1.00260.73               C
ANISOU 8077  CB  THR B 230    47939  24443  26684    987   6324   5745       C
ATOM   8078  OG1 THR B 230    33.977 -42.149 89.736 1.00265.38               O
ANISOU 8078  OG1 THR B 230    49048  25129  26656  -1101  -6529  -5602       O
ATOM   8079  CG2 THR B 230    33.366 -41.208 87.717 1.00257.60               C
ANISOU 8079  CG2 THR B 230    47414  24279  26183   -838  -5477  -5909       C
ATOM   8080  N   ASN B 231    30.948 -42.975 87.150 1.00262.93               N
ANISOU 8080  N   ASN B 231    47931  25291  26680  -1034  -5260  -4765       N
ATOM   8081  CA  ASN B 231    29.890 -42.655 86.196 1.00259.31               C
ANISOU 8081  CA  ASN B 231    47195  25057  26273   -949  -4585  -4622       C
ATOM   8082  C   ASN B 231    30.215 -41.398 85.379 1.00255.86               C
ANISOU 8082  C   ASN B 231    46511  24642  26064   -745  -4062  -5099       C
ATOM   8083  O   ASN B 231    30.159 -41.414 84.143 1.00252.10               O
ANISOU 8083  O   ASN B 231    45608  24128  26050   -624  -3856  -5226       O
ATOM   8084  CB  ASN B 231    28.556 -42.493 86.933 1.00261.09               C
ANISOU 8084  CB  ASN B 231    47739  25625  25838  -1040  -4127  -4138       C
ATOM   8085  CG  ASN B 231    28.293 -43.621 87.920 1.00265.11               C
ANISOU 8085  CG  ASN B 231    48553  26115  26061  -1233  -4627  -3670       C
ATOM   8086  OD1 ASN B 231    28.757 -44.743 87.732 1.00265.61               O
ANISOU 8086  OD1 ASN B 231    48472  25947  26500  -1304  -5231  -3590       O
ATOM   8087  ND2 ASN B 231    27.547  43.323 88.979 1.00268.08               N
ANISOU 8087  ND2 ASN B 231    49352  26732  25774  -1312  -4365  -3352       N
ATOM   8088  N   GLN B 232    30.561 -40.321 86.085 1.00242.54               N
ANISOU 8088  N   GLN B 232    45095  23011  24048   -705  -3856  -5361       N
ATOM   8089  CA  GLN B 232    30.935 -39.049 85.478 1.00239.85               C
ANISOU 8089  CA  GLN B 232    44561  22677  23893   -516  -3368  -5824       C
ATOM   8090  C   GLN B 232    31.053 -38.019 86.598 1.00242.69               C
ANISOU 8090  C   GLN B 232    45341  23148  23721   -530  -3168  -5974       C
ATOM   8091  O   GLN B 232    30.678 -36.866 86.422 1.00241.20               O
ANISOU 8091  O   GLN B 232    45136  23138  23372   -419  -2511  -6127       O
ATOM   8092  CB  GLN B 232    29.885 -38.601 84.453 1.00235.99               C
ANISOU 8092  CB  GLN B 232    43773  22434  23458    403   2624   5694       C
ATOM   8093  CG  GLN B 232    30.440 -38.080 83.117 1.00231.79               C
ANISOU 8093  CG  GLN B 232    42765  21776  23530   -191  -2389  -6115       C
ATOM   8094  CD  GLN B 232    31.112 -36.715 83.219 1.00231.41               C
ANISOU 8094  CD  GLN B 232    42743  21690  23491    -50  -2066  -6596       C
ATOM   8095  OE1 GLN B 232    32.142 -36.563 83.876 1.00233.72               O
ANISOU 8095  OE1 GLN B 232    43211  21768  23822    -73  -2491  -6891       O
ATOM   8096  NE2 GLN B 232    30.541 -35.723 82.545 1.00228.52               N
ANISOU 8096  NE2 GLN B 232    42185  21525  23118    102  -1318  -6678       N
ATOM   8097  N   VAL B 233    31.580 -38.443 87.745 1.00246.57               N
ANISOU 8097  N   VAL B 233    46208  23534  23945   -662  -3740  -5932       N
ATOM   8098  CA  VAL B 233    31.678 -37.596 88.942 1.00249.98               C
ANISOU 8098  CA  VAL B 233    47096  24074  23812   -693  -3633  -6044       C
```

FIG. 13 Continued

```
ATOM   8099  C   VAL B 233      32.293 -36.194  88.771  1.00248.81           C
ANISOU 8099  C   VAL B 233    46881  23885  23772   -536  -3264  -6590       C
ATOM   8100  O   VAL B 233      32.415 -35.451  89.742  1.00251.69           O
ANISOU 8100  O   VAL B 233    47615  24327  23689   -555  -3178  -6725       O
ATOM   8101  CB  VAL B 233      32.430 -38.327  90.076  1.00254.61           C
ANISOU 8101  CB  VAL B 233    48038  24486  24215   -836  -4430  -6002       C
ATOM   8102  CG1 VAL B 233      31.823 -39.700  90.314  1.00256.07           C
ANISOU 8102  CG1 VAL B 233    48301  24708  24288   -991  -4787  -5447       C
ATOM   8103  CG2 VAL B 233      33.909 -38.441  89.751  1.00254.30           C
ANISOU 8103  CG2 VAL B 233    47785  24069  24768   -778  -5010  -6482       C
ATOM   8104  N   GLY B 234      32.657 -35.831  87.545  1.00219.51           N
ANISOU 8104  N   GLY B 234    30856  27107  25441  -4081   4993  -5034       N
ATOM   8105  CA  GLY B 234      33.291 -34.550  87.256  1.00215.62           C
ANISOU 8105  CA  GLY B 234    29586  27674  24668  -4217   4957  -4833       C
ATOM   8106  C   GLY B 234      32.559 -33.259  87.606  1.00207.28           C
ANISOU 8106  C   GLY B 234    28266  27009  23483  -4833   4687  -4105       C
ATOM   8107  O   GLY B 234      31.883 -33.164  88.633  1.00203.18           O
ANISOU 8107  O   GLY B 234    28030  25962  23208  -4854   4469  -3586       O
ATOM   8108  N   HIS B 235      32.722 -32.258  86.737  1.00175.25           N
ANISOU 8108  N   HIS B 235    23656  23895  19036  -5327   4707  -4080       N
ATOM   8109  CA  HIS B 235      32.146 -30.915  86.894  1.00168.19           C
ANISOU 8109  CA  HIS B 235    22430  23458  18017  -5908   4435  -3437       C
ATOM   8110  C   HIS B 235      30.629 -30.928  87.084  1.00164.67           C
ANISOU 8110  C   HIS B 235    22407  22534  17625  -6498   4276  -3101       C
ATOM   8111  O   HIS B 235      29.882 -30.732  86.133  1.00164.75           O
ANISOU 8111  O   HIS B 235    22419  22841  17339  -7194   4284  -3169       O
ATOM   8112  CB  HIS B 235      32.502 -30.065  85.662  1.00168.81           C
ANISOU 8112  CB  HIS B 235    21955  24567  17619  -6430   4509  -3553       C
ATOM   8113  CG  HIS B 235      31.939 -28.676  85.685  1.00162.59           C
ANISOU 8113  CG  HIS B 235    20830  24231  16715  -7042   4202  -2913       C
ATOM   8114  ND1 HIS B 235      32.686 -27.567  85.349  1.00161.44           N
ANISOU 8114  ND1 HIS B 235    20066  24915  16361  -7199   4123  -2708       N
ATOM   8115  CD2 HIS B 235      30.702 -28.214  85.989  1.00157.79           C
ANISOU 8115  CD2 HIS B 235    20408  23348  16196  -7530   3946  -2442       C
ATOM   8116  CE1 HIS B 235      31.936 -26.485  85.450  1.00156.23           C
ANISOU 8116  CE1 HIS B 235    19265  24408  15688  -7740   3806  -2133       C
ATOM   8117  NE2 HIS B 235      30.728 -26.850  85.838  1.00153.93           N
ANISOU 8117  NE2 HIS B 235    19433  23472  15582  -7922   3699  -1979       N
ATOM   8118  N   PHE B 236      30.175 -31.134  88.314  1.00182.14           N
ANISOU 8118  N   PHE B 236    24948  24061  20196  -6241   4124  -2726       N
ATOM   8119  CA  PHE B 236      28.748 -31.210  88.596  1.00179.43           C
ANISOU 8119  CA  PHE B 236    24975  23263  19935  -6763   4006  -2419       C
ATOM   8120  C   PHE B 236      28.545 -30.688  89.995  1.00174.56           C
ANISOU 8120  C   PHE B 236    24354  22368  19602  -6520   3785  -1838       C
ATOM   8121  O   PHE B 236      27.850 -29.697  90.221  1.00169.58           O
ANISOU 8121  O   PHE B 236    23488  21986  18958  -6931   3584  -1399       O
ATOM   8122  CB  PHE B 236      28.277 -32.669  88.556  1.00184.58           C
ANISOU 8122  CB  PHE B 236    26310  23099  20723  -6698   4182  -2793       C
ATOM   8123  CG  PHE B 236      28.269 -33.282  87.178  1.00189.97           C
ANISOU 8123  CG  PHE B 236    27095  23970  21114  -7015   4402  -3428       C
ATOM   8124  CD1 PHE B 236      27.073 -33.651  86.576  1.00191.06           C
ANISOU 8124  CD1 PHE B 236    27555  23911  21128  -7712   4404  -3523       C
ATOM   8125  CD2 PHE B 236      29.455 -33.508  86.493  1.00194.51           C
ANISOU 8125  CD2 PHE B 236    27432  24946  21526  -6621   4612  -3960       C
ATOM   8126  CE1 PHE B 236      27.060 -34.218  85.307  1.00196.47           C
ANISOU 8126  CE1 PHE B 236    28358  24790  21503  -8031   4594  -4140       C
ATOM   8127  CE2 PHE B 236      29.451 -34.070  85.221  1.00200.04           C
ANISOU 8127  CE2 PHE B 236    28231  25865  21910  -6919   4840  -4598       C
ATOM   8128  CZ  PHE B 236      28.251 -34.428  84.629  1.00201.01           C
ANISOU 8128  CZ  PHE B 236    28715  25775  21884  -7631   4822  -4692       C
ATOM   8129  N   GLN B 237      29.160 -31.410  90.927  1.00178.82           N
ANISOU 8129  N   GLN B 237    25175  22371  20398  -5828   3820  -1865       N
ATOM   8130  CA  GLN B 237      29.176 -31.088  92.342  1.00175.55           C
ANISOU 8130  CA  GLN B 237    24811  21676  20214  -5480   3632  -1375       C
ATOM   8131  C   GLN B 237      30.591 -30.635  92.679  1.00175.72           C
ANISOU 8131  C   GLN B 237    24400  22100  20267  -4853   3559  -1388       C
ATOM   8132  O   GLN B 237      30.786 -29.689  93.441  1.00171.59           O
ANISOU 8132  O   GLN B 237    23573  21837  19787  -4763   3348   -990       O
ATOM   8133  CB  GLN B 237      28.820 -32.325  93.160  1.00178.92           C
```

FIG. 13 Continued

```
ANISOU 8133  CB  GLN B 237    25927 21174 20881  -5189  3691 -1354       C
ATOM   8134  CG  GLN B 237      27.635 -33.115  92.609  1.00 181.18      C
ANISOU 8134  CG  GLN B 237    26689 21005 21145  -5763  3823 -1518       C
ATOM   8135  CD  GLN B 237      26.310 -32.700  93.221  1.00 177.12      C
ANISOU 8135  CD  GLN B 237    26281 20350 20667  -6302  3718 -1040       C
ATOM   8136  OE1 GLN B 237      26.200 -31.627  93.818  1.00 172.09      O
ANISOU 8136  OE1 GLN B 237    25278 20087 20021  -6344  3553  -639       O
ATOM   8137  NE2 GLN B 237      25.295 -33.556  93.086  1.00 179.81      N
ANISOU 8137  NE2 GLN B 237    27113 20147 21060  -6720  3816 -1105       N
ATOM   8138  N   LYS B 238      31.578 -31.321  92.102  1.00 163.84      N
ANISOU 8138  N   LYS B 238    22852 20653 18749  -4421  3735 -1881       N
ATOM   8139  CA  LYS B 238      32.983 -30.951  92.274  1.00 165.06      C
ANISOU 8139  CA  LYS B 238    22515 21272 18929  -3838  3693 -1965       C
ATOM   8140  C   LYS B 238      33.233 -29.645  91.534  1.00 161.75      C
ANISOU 8140  C   LYS B 238    21427 21794 18238  -4298  3640 -1881       C
ATOM   8141  O   LYS B 238      34.294 -29.396  90.959  1.00 164.24      O
ANISOU 8141  O   LYS B 238    21261 22716 18429  -4104  3732 -2149       O
ATOM   8142  CB  LYS B 238      33.928 -32.060  91.803  1.00 172.43      C
ANISOU 8142  CB  LYS B 238    23539 22035 19943  -3242  3919 -2565       C
ATOM   8143  CG  LYS B 238      34.056 -33.234  92.790  1.00 176.38      C
ANISOU 8143  CG  LYS B 238    24623 21597 20798  -2573  3869 -2552       C
ATOM   8144  CD  LYS B 238      34.414 -32.782  94.220  1.00 173.49      C
ANISOU 8144  CD  LYS B 238    24190 21121 20608  -2147  3567 -2002       C
ATOM   8145  CE  LYS B 238      34.553 -33.970  95.178  1.00 178.19      C
ANISOU 8145  CE  LYS B 238    25395 20788 21519  -1506  3484 -1935       C
ATOM   8146  NZ  LYS B 238      34.672 -33.548  96.601  1.00 175.37      N
ANISOU 8146  NZ  LYS B 238    25071 20309 21252  -1225  3179 -1348       N
ATOM   8147  N   VAL B 239      32.206 -28.817  91.580  1.00 174.93      N
ANISOU 8147  N   VAL B 239    23074 23560 19830  -4923  3483 -1484       N
ATOM   8148  CA  VAL B 239      32.200 -27.519  90.967  1.00 171.55      C
ANISOU 8148  CA  VAL B 239    22107 23888 19187  -5446  3357 -1284       C
ATOM   8149  C   VAL B 239      31.843 -26.571  92.097  1.00 166.12      C
ANISOU 8149  C   VAL B 239    21326 23113 18677  -5461  3052  -728       C
ATOM   8150  O   VAL B 239      32.388 -25.474  92.197  1.00 163.80      O
ANISOU 8150  O   VAL B 239    20548 23333 18353  -5511  2865  -505       O
ATOM   8151  CB  VAL B 239      31.140 -27.473  89.862  1.00 171.30      C
ANISOU 8151  CB  VAL B 239    22182 23988 18918  -6211  3426 -1364       C
ATOM   8152  CG1 VAL B 239      31.447 -28.510  88.826  1.00 177.28      C
ANISOU 8152  CG1 VAL B 239    23108 24768 19483  -6179  3741 -1975       C
ATOM   8153  CG2 VAL B 239      29.754 -27.720  90.442  1.00 168.67      C
ANISOU 8153  CG2 VAL B 239    22307 23029 18749  -6492  3337 -1094       C
ATOM   8154  N   LEU B 240      30.938 -27.027  92.959  1.00 129.35      N
ANISOU 8154  N   LEU B 240    17147 17799 14200  -5426  3012  -528       N
ATOM   8155  CA  LEU B 240      30.504 -26.264  94.124  1.00 124.93      C
ANISOU 8155  CA  LEU B 240    16569 17104 13794  -5411  2768   -62       C
ATOM   8156  C   LEU B 240      31.386 -26.577  95.332  1.00 126.12      C
ANISOU 8156  C   LEU B 240    16812 17007 14102  -4685  2689    19       C
ATOM   8157  O   LEU B 240      31.789 -25.684  96.087  1.00 123.54      O
ANISOU 8157  O   LEU B 240    16199 16914 13826  -4531  2461   286       O
ATOM   8158  CB  LEU B 240      29.017 -26.530  94.428  1.00 123.21      C
ANISOU 8158  CB  LEU B 240    16762 16405 13646  -5812  2786   125       C
ATOM   8159  CG  LEU B 240      28.411 -27.945  94.499  1.00 126.72      C
ANISOU 8159  CG  LEU B 240    17833 16167 14149  -5775  3003   -57       C
ATOM   8160  CD1 LEU B 240      28.465 -28.553  95.907  1.00 127.63      C
ANISOU 8160  CD1 LEU B 240    18363 15694 14435  -5285  2979   153       C
ATOM   8161  CD2 LEU B 240      26.967 -27.931  94.004  1.00 125.48      C
ANISOU 8161  CD2 LEU B 240    17819 15904 13953  -6477  3038    12       C
ATOM   8162  N   THR B 241      31.676 -27.860  95.513  1.00 181.30      N
ANISOU 8162  N   THR B 241    24219 23494 21171  -4242  2850  -215       N
ATOM   8163  CA  THR B 241      32.567 -28.272  96.573  1.00 183.52      C
ANISOU 8163  CA  THR B 241    24603 23529 21598  -3519  2746  -141       C
ATOM   8164  C   THR B 241      33.849 -27.550  96.262  1.00 183.93      C
ANISOU 8164  C   THR B 241    24014 24271 21599  -3273  2655  -256       C
ATOM   8165  O   THR B 241      34.642 -27.275  97.150  1.00 184.11      O
ANISOU 8165  O   THR B 241    23864 24383 21706  -2810  2456   -94       O
ATOM   8166  CB  THR B 241      32.795 -29.789  96.586  1.00 189.41      C
ANISOU 8166  CB  THR B 241    25863 23633 22470  -3062  2917  -423       C
ATOM   8167  OG1 THR B 241      31.657 -30.428  97.174  1.00 189.28      O
ANISOU 8167  OG1 THR B 241    26469 22928 22520  -3271  2952  -206       O
```

FIG. 13 Continued

```
ATOM   8168  CG2 THR B 241      34.021 -30.142  97.405  1.00192.82           C
ANISOU 8168  CG2 THR B 241    26239  23972  23050  -3635   2246   2776  -411  C
ATOM   8169  N   ALA B 242      34.034 -27.221  94.987  1.00133.33           N
ANISOU 8169  N   ALA B 242    17240  18393  15025  -3635   2793   -525        N
ATOM   8170  CA  ALA B 242      35.201 -26.461  94.568  1.00134.03           C
ANISOU 8170  CA  ALA B 242    16668  19229  15028  -3534   2736   -619        C
ATOM   8171  C   ALA B 242      35.347 -25.197  95.436  1.00129.65           C
ANISOU 8171  C   ALA B 242    15792  18945  14523  -3602   2402   -181        C
ATOM   8172  O   ALA B 242      36.464 -24.790  95.764  1.00130.88           O
ANISOU 8172  O   ALA B 242    15527  19485  14716  -3253   2267   -173        O
ATOM   8173  CB  ALA B 242      35.116 -26.117  93.086  1.00134.64           C
ANISOU 8173  CB  ALA B 242    16437  19875  14845  -4107   2915   -861        C
ATOM   8174  N   ILE B 243      34.222 -24.586  95.815  1.00167.09           N
ANISOU 8174  N   ILE B 243    20717  23488  19280  -4045   2266    152        N
ATOM   8175  CA  ILE B 243      34.247 -23.437  96.724  1.00163.37           C
ANISOU 8175  CA  ILE B 243    20020  23171  18881  -4088   1951    519        C
ATOM   8176  C   ILE B 243      34.291 -23.947  98.151  1.00163.86           C
ANISOU 8176  C   ILE B 243    20454  22738  19067  -3554   1846    676        C
ATOM   8177  O   ILE B 243      35.141 -23.543  98.946  1.00164.25           O
ANISOU 8177  O   ILE B 243    20280  22965  19161  -3183   1626    785        O
ATOM   8178  CB  ILE B 243      32.985 -22.558  96.628  1.00158.85           C
ANISOU 8178  CB  ILE B 243    19481  22564  18310  -4721   1841    786        C
ATOM   8179  CG1 ILE B 243      32.630 -22.231  95.180  1.00158.73           C
ANISOU 8179  CG1 ILE B 243    19245  22920  18146  -5325   1937    683        C
ATOM   8180  CG2 ILE B 243      33.147 -21.292  97.461  1.00155.81           C
ANISOU 8180  CG2 ILE B 243    18811  22373  18017  -4746   1510   1082        C
ATOM   8181  CD1 ILE B 243      31.492 -23.066  94.646  1.00159.20           C
ANISOU 8181  CD1 ILE B 243    19733  22599  18157  -5624   2153    564        C
ATOM   8182  N   GLY B 244      33.347 -24.834  98.464  1.00121.86           N
ANISOU 8182  N   GLY B 244    15709  16814  13778  -3567   1991    705        N
ATOM   8183  CA  GLY B 244      33.254 -25.437  99.779  1.00123.00           C
ANISOU 8183  CA  GLY B 244    16296  16450  13988  -3136   1917    896        C
ATOM   8184  C   GLY B 244      34.613 -25.891 100.270  1.00126.99           C
ANISOU 8184  C   GLY B 244    16697  17003  14551  -2425   1805    813        C
ATOM   8185  O   GLY B 244      34.874 -25.888 101.466  1.00127.50           O
ANISOU 8185  O   GLY B 244    16906  16909  14628  -2063   1602   1046        O
ATOM   8186  N   ASN B 245      35.479 -26.274  99.337  1.00197.70           N
ANISOU 8186  N   ASN B 245    25375  26217  23526  -2226   1934    469        N
ATOM   8187  CA  ASN B 245      36.832 -26.718  99.658  1.00202.30           C
ANISOU 8187  CA  ASN B 245    25752  26909  24201  -1517   1837    332        C
ATOM   8188  C   ASN B 245      37.745 -25.542  99.998  1.00200.84           C
ANISOU 8188  C   ASN B 245    24940  27380  23989  -1461   1561    457        C
ATOM   8189  O   ASN B 245      38.381 -25.536 101.053  1.00202.33           O
ANISOU 8189  O   ASN B 245    25112  27533  24231   -988   1304    627        O
ATOM   8190  CB  ASN B 245      37.422 -27.537  98.499  1.00207.04           C
ANISOU 8190  CB  ASN B 245    26227  27599  24838  -1319   2112   -150        C
ATOM   8191  CG  ASN B 245      38.562 -28.454  98.936  1.00213.26           C
ANISOU 8191  CG  ASN B 245    27015  28205  25809   -460   2051   -321        C
ATOM   8192  OD1 ASN B 245      38.920 -28.511 100.115  1.00214.10           O
ANISOU 8192  OD1 ASN B 245    27238  28111  25997    -21   1774    -38        O
ATOM   8193  ND2 ASN B 245      39.135 -29.180  97.977  1.00218.18           N
ANISOU 8193  ND2 ASN B 245    27499  28908  26490   -207   2301   -803        N
ATOM   8194  N   PHE B 246      37.814 -24.550  99.109  1.00162.37           N
ANISOU 8194  N   PHE B 246    19566  23102  19024  -1970   1588    393        N
ATOM   8195  CA  PHE B 246      38.667 -23.377  99.348  1.00161.34           C
ANISOU 8195  CA  PHE B 246    18833  23590  18881  -2013   1318    515        C
ATOM   8196  C   PHE B 246      37.889 -22.185  99.963  1.00156.04           C
ANISOU 8196  C   PHE B 246    18189  22917  18185  -2479   1073    864        C
ATOM   8197  O   PHE B 246      38.100 -21.007  99.634  1.00154.02           O
ANISOU 8197  O   PHE B 246    17478  23138  17905  -2881    917    950        O
ATOM   8198  CB  PHE B 246      39.527 -23.021  98.112  1.00163.52           C
ANISOU 8198  CB  PHE B 246    18475  24574  19082  -2199   1455    244        C
ATOM   8199  CG  PHE B 246      40.664 -24.022  97.825  1.00169.88           C
ANISOU 8199  CG  PHE B 246    19081  25511  19955  -1552   1618   -129        C
ATOM   8200  CD1 PHE B 246      41.694 -24.230  98.745  1.00173.18           C
ANISOU 8200  CD1 PHE B 246    19310  25978  20513   -886   1387    -97        C
ATOM   8201  CD2 PHE B 246      40.710 -24.736  96.625  1.00173.09           C
ANISOU 8201  CD2 PHE B 246    19463  26017  20287  -1601   1989   -536        C
ATOM   8202  CE1 PHE B 246      42.736 -25.140  98.480  1.00179.63           C
```

FIG. 13 Continued

```
ANISOU 8202  CE1 PHE B 246      19895  26910  21444   -238   1517   -456       C
ATOM   8203  CE2 PHE B 246      41.755 -25.647  96.357  1.00179.60             C
ANISOU 8203  CE2 PHE B 246      20075  26957  21207   -958   2153   -942       C
ATOM   8204  CZ  PHE B 246      42.764 -25.845  97.287  1.00182.87             C
ANISOU 8204  CZ  PHE B 246      20278  27395  21811   -258   1913   -895       C
ATOM   8205  N   CYS B 247      36.984 -22.554 100.869  1.00136.82             N
ANISOU 8205  N   CYS B 247      16309  19913  15762  -2409   1048   1051       N
ATOM   8206  CA  CYS B 247      36.192 -21.648 101.698  1.00132.82             C
ANISOU 8206  CA  CYS B 247      15920  19302  15242  -2701    847   1331       C
ATOM   8207  C   CYS B 247      36.250 -22.206 103.131  1.00134.47             C
ANISOU 8207  C   CYS B 247      16541  19128  15423  -2202    714   1496       C
ATOM   8208  O   CYS B 247      36.466 -21.465 104.100  1.00133.59             O
ANISOU 8208  O   CYS B 247      16336  19149  15273  -2127    433   1658       O
ATOM   8209  CB  CYS B 247      34.746 -21.583 101.214  1.00129.62             C
ANISOU 8209  CB  CYS B 247      15796  18623  14828  -3248   1032   1383       C
ATOM   8210  SG  CYS B 247      33.560 -21.174 102.522  1.00126.67             S
ANISOU 8210  SG  CYS B 247      15812  17871  14447  -3373    922   1657       S
ATOM   8211  N   ILE B 248      36.045 -23.521 103.246  1.00127.92             N
ANISOU 8211  N   ILE B 248      16195  17811  14598  -1889    904   1456       N
ATOM   8212  CA  ILE B 248      36.230 -24.232 104.505  1.00130.81             C
ANISOU 8212  CA  ILE B 248      16983  17800  14918  -1383    771   1643       C
ATOM   8213  C   ILE B 248      37.691 -24.057 104.865  1.00133.95             C
ANISOU 8213  C   ILE B 248      16964  18583  15349   -866    489   1604       C
ATOM   8214  O   ILE B 248      38.012 -23.730 105.993  1.00134.58             O
ANISOU 8214  O   ILE B 248      17075  18719  15338   -638    200   1805       O
ATOM   8215  CB  ILE B 248      35.942 -25.738 104.386  1.00134.53             C
ANISOU 8215  CB  ILE B 248      18016  17658  15443  -1116    998   1595       C
ATOM   8216  CG1 ILE B 248      34.706 -26.134 105.186  1.00133.66             C
ANISOU 8216  CG1 ILE B 248      18537  17020  15226  -1332   1087   1862       C
ATOM   8217  CG2 ILE B 248      37.093 -26.530 104.941  1.00140.06             C
ANISOU 8217  CG2 ILE B 248      18766  18241  16211   -370    818   1599       C
ATOM   8218  CD1 ILE B 248      34.542 -27.644 105.323  1.00138.40             C
ANISOU 8218  CD1 ILE B 248      19756  16943  15886  -1026   1228   1895       C
ATOM   8219  N   CYS B 249      38.586 -24.279 103.905  1.00136.38             N
ANISOU 8219  N   CYS B 249      16855  19196  15768   -690    575   1328       N
ATOM   8220  CA  CYS B 249      39.999 -24.079 104.150  1.00139.66             C
ANISOU 8220  CA  CYS B 249      16750  20078  16236   -243    316   1266       C
ATOM   8221  C   CYS B 249      40.226 -22.512 104.185  1.00136.21             C
ANISOU 8221  C   CYS B 249      15783  20226  15744   -672     91   1339       C
ATOM   8222  O   CYS B 249      41.019  21.947 103.421  1.00136.89             O
ANISOU 8222  O   CYS B 249      15256  20879  15878   -798     78   1175       O
ATOM   8223  CB  CYS B 249      40.907 -24.722 103.129  1.00144.10             C
ANISOU 8223  CB  CYS B 249      16971  20845  16934     90    507    909       C
ATOM   8224  SG  CYS B 249      42.656 -24.900 103.664  1.00150.37             S
ANISOU 8224  SG  CYS B 249      17224  22056  17852    880    187    836       S
ATOM   8225  N   SER B 250      39.466 -21.871 105.066  1.00129.59             N
ANISOU 8225  N   SER B 250      15210  19224  14803   -927    -68   1579       N
ATOM   8226  CA  SER B 250      39.592 -20.415 105.388  1.00126.88             C
ANISOU 8226  CA  SER B 250      14497  19282  14430  -1275   -345   1666       C
ATOM   8227  C   SER B 250      39.076 -20.357 106.823  1.00126.34             C
ANISOU 8227  C   SER B 250      14871  18917  14214  -1156   -545   1889       C
ATOM   8228  O   SER B 250      39.602 -19.603 107.647  1.00126.88             O
ANISOU 8228  O   SER B 250      14740  19251  14216  -1087   -887   1959       O
ATOM   8229  CB  SER B 250      38.812 -19.592 104.408  1.00122.59             C
ANISOU 8229  CB  SER B 250      13780  18865  13935  -1967   -200   1626       C
ATOM   8230  OG  SER B 250      39.604 -19.327 103.262  1.00123.80             O
ANISOU 8230  OG  SER B 250      13379  19509  14153  -2120   -135   1459       O
ATOM   8231  N   ILE B 251      38.047 -21.154 107.107  1.00181.37             N
ANISOU 8231  N   ILE B 251      22446  25354  21110  -1155   -318   1988       N
ATOM   8232  CA  ILE B 251      37.527 -21.326 108.454  1.00181.96             C
ANISOU 8232  CA  ILE B 251      23014  25137  20986  -1018   -430   2208       C
ATOM   8233  C   ILE B 251      38.725 -21.758 109.279  1.00186.82             C
ANISOU 8233  C   ILE B 251      23582  25872  21528   -405   -746   2294       C
ATOM   8234  O   ILE B 251      39.057 -21.140 110.291  1.00187.56             O
ANISOU 8234  O   ILE B 251      23622  26181  21462   -323  -1068   2396       O
ATOM   8235  CB  ILE B 251      36.485 -22.471 108.497  1.00182.46             C
ANISOU 8235  CB  ILE B 251      23724  24605  20997  -1033   -107   2312       C
ATOM   8236  CG1 ILE B 251      35.108 -21.982 108.053  1.00177.99             C
ANISOU 8236  CG1 ILE B 251      23260  23916  20453  -1647    149   2286       C
```

FIG. 13 Continued

```
ATOM   8237  CG2 ILE B 251      36.394 -23.072 109.886  1.00185.67           C
ANISOU 8237  CG2 ILE B 251    24652  24727  21166    702    241   2580       C
ATOM   8238  CD1 ILE B 251      34.431 -21.120 109.072  1.00176.12           C
ANISOU 8238  CD1 ILE B 251    23125  23738  20054  -1866     35   2397       C
ATOM   8239  N   ALA B 252      39.377 -22.823 108.810  1.00134.10           N
ANISOU 8239  N   ALA B 252    16913  19059  14980     33   -667   2228       N
ATOM   8240  CA  ALA B 252      40.568 -23.383 109.442  1.00139.63           C
ANISOU 8240  CA  ALA B 252    17525  19846  15682    695   -973   2299       C
ATOM   8241  C   ALA B 252      41.832 -22.590 109.115  1.00140.73           C
ANISOU 8241  C   ALA B 252    16881  20657  15935    791  -1227   2128       C
ATOM   8242  O   ALA B 252      42.922 -22.981 109.519  1.00145.66           O
ANISOU 8242  O   ALA B 252    17292  21450  16603   1345  -1499   2149       O
ATOM   8243  CB  ALA B 252      40.742 -24.861 109.057  1.00143.99           C
ANISOU 8243  CB  ALA B 252    18395  19926  16387   1170   -793   2265       C
ATOM   8244  N   ILE B 253      41.688 -21.489 108.375  1.00135.98           N
ANISOU 8244  N   ILE B 253    15841  20434  15391    242  -1154   1978       N
ATOM   8245  CA  ILE B 253      42.831 -20.641 108.028  1.00137.12           C
ANISOU 8245  CA  ILE B 253    15229  21239  15632    206  -1383   1842       C
ATOM   8246  C   ILE B 253      42.960 -19.477 108.997  1.00135.98           C
ANISOU 8246  C   ILE B 253    14954  21360  15354     -5  -1777   1959       C
ATOM   8247  O   ILE B 253      44.056 -18.984 109.263  1.00138.78           O
ANISOU 8247  O   ILE B 253    14803  22193  15733    139  -2111   1926       O
ATOM   8248  CB  ILE B 253      42.732 -20.072 106.602  1.00134.36           C
ANISOU 8248  CB  ILE B 253    14446  21190  15416   -312  -1116   1639       C
ATOM   8249  CG1 ILE B 253      44.115 -20.063 105.934  1.00138.46           C
ANISOU 8249  CG1 ILE B 253    14238  22304  16066    -89  -1169   1442       C
ATOM   8250  CG2 ILE B 253      42.104 -18.680 106.617  1.00129.64           C
ANISOU 8250  CG2 ILE B 253    13745  20730  14782   -978  -1225   1709       C
ATOM   8251  CD1 ILE B 253      45.158 -19.174 106.611  1.00140.59           C
ANISOU 8251  CD1 ILE B 253    13985  23105  16328    -38  -1621   1499       C
ATOM   8252  N   GLY B 254      41.828 -19.016 109.505  1.00132.62           N
ANISOU 8252  N   GLY B 254    14958  20640  14791   -365  -1734   2063       N
ATOM   8253  CA  GLY B 254      41.842 -17.947 110.478  1.00131.94           C
ANISOU 8253  CA  GLY B 254    14825  20743  14564   -553  -2085   2116       C
ATOM   8254  C   GLY B 254      42.073 -18.544 111.844  1.00135.73           C
ANISOU 8254  C   GLY B 254    15697  21091  14784    -72  -2336   2294       C
ATOM   8255  O   GLY B 254      42.717 -17.939 112.688  1.00137.90           O
ANISOU 8255  O   GLY B 254    15791  21678  14929     10  -2740   2313       O
ATOM   8256  N   MET B 255      41.558 -19.753 112.042  1.00138.66           N
ANISOU 8256  N   MET B 255    16620  20995  15071    222  -2115   2439       N
ATOM   8257  CA  MET B 255      41.674 -20.435 113.325  1.00142.78           C
ANISOU 8257  CA  MET B 255    17607  21332  15310    652  -2341   2683       C
ATOM   8258  C   MET B 255      43.098 -20.891 113.679  1.00148.69           C
ANISOU 8258  C   MET B 255    18048  22356  16091   1260  -2732   2745       C
ATOM   8259  O   MET B 255      43.452 -20.919 114.855  1.00152.23           O
ANISOU 8259  O   MET B 255    18677  22894  16269   1516  -3102   2929       O
ATOM   8260  CB  MET B 255      40.638 -21.564 113.451  1.00142.86           C
ANISOU 8260  CB  MET B 255    18336  20722  15223    711  -2001   2868       C
ATOM   8261  CG  MET B 255      40.865 -22.740 112.541  1.00144.80           C
ANISOU 8261  CG  MET B 255    18633  20654  15729   1027  -1763   2833       C
ATOM   8262  SD  MET B 255      41.466 -24.187 113.418  1.00152.27           S
ANISOU 8262  SD  MET B 255    20050  21222  16584   1785  -2001   3143       S
ATOM   8263  CE  MET B 255      42.054 -25.199 112.058  1.00154.67           C
ANISOU 8263  CE  MET B 255    20113  21323  17329   2168  -1760   2902       C
ATOM   8264  N   VAL B 256      43.917 -21.242 112.686  1.00154.20           N
ANISOU 8264  N   VAL B 256    18262  23227  17101   1495  -2660   2581       N
ATOM   8265  CA  VAL B 256      45.318 -21.555 112.990  1.00160.21           C
ANISOU 8265  CA  VAL B 256    18598  24335  17940   2077  -3050   2599       C
ATOM   8266  C   VAL B 256      45.999 -20.234 113.310  1.00159.89           C
ANISOU 8266  C   VAL B 256    17981  24929  17842   1800  -3424   2503       C
ATOM   8267  O   VAL B 256      47.161 -20.192 113.713  1.00164.73           O
ANISOU 8267  O   VAL B 256    18159  25955  18477   2165  -3830   2516       O
ATOM   8268  CB  VAL B 256      46.087 -22.278 111.851  1.00162.99           C
ANISOU 8268  CB  VAL B 256    18506  24773  18649   2445  -2857   2388       C
ATOM   8269  CG1 VAL B 256      45.301 -23.472 111.331  1.00162.78           C
ANISOU 8269  CG1 VAL B 256    19049  24078  18720   2593  -2438   2399       C
ATOM   8270  CG2 VAL B 256      46.446 -21.310 110.732  1.00160.13           C
ANISOU 8270  CG2 VAL B 256    17417  24954  18470   1982  -2707   2095       C
ATOM   8271  N   ILE B 257      45.259 -19.150 113.090  1.00162.98           N
```

FIG. 13 Continued

```
ANISOU 8271  N   ILE B 257     18357  25377  18192   1143  -3296   2399          N
ATOM   8272  CA  ILE B 257      45.720 -17.818 113.448  1.00162.54              C
ANISOU 8272  CA  ILE B 257     17870  25804  18086    791  -3652   2304          C
ATOM   8273  C   ILE B 257      45.047 -17.407 114.752  1.00162.05              C
ANISOU 8273  C   ILE B 257     18336  25577  17660    662  -3856   2419          C
ATOM   8274  O   ILE B 257      45.657 -16.749 115.581  1.00164.67              O
ANISOU 8274  O   ILE B 257     18481  26257  17828    662  -4300   2405          O
ATOM   8275  CB  ILE B 257      45.461 -16.781 112.342  1.00157.98              C
ANISOU 8275  CB  ILE B 257     16880  25409  17737    150  -3447   2106          C
ATOM   8276  CG1 ILE B 257      46.264 -17.146 111.094  1.00159.52              C
ANISOU 8276  CG1 ILE B 257     16491  25904  18216    258  -3258   1975          C
ATOM   8277  CG2 ILE B 257      45.842 -15.390 112.816  1.00157.96              C
ANISOU 8277  CG2 ILE B 257     16533  25787  17696   -245  -3848   2024          C
ATOM   8278  CD1 ILE B 257      47.729 -17.417 111.368  1.00165.75              C
ANISOU 8278  CD1 ILE B 257     16729  27183  19065    749  -3608   1956          C
ATOM   8279  N   GLU B 258      43.795 -17.807 114.947  1.00179.51              N
ANISOU 8279  N   GLU B 258     21195  27290  19721    538  -3526   2512          N
ATOM   8280  CA  GLU B 258      43.117 -17.508 116.201  1.00179.75              C
ANISOU 8280  CA  GLU B 258     21737  27204  19358    431  -3656   2601          C
ATOM   8281  C   GLU B 258      43.757 -18.332 117.305  1.00185.84              C
ANISOU 8281  C   GLU B 258     22776  28013  19820    984  -4002   2857          C
ATOM   8282  O   GLU B 258      44.031 -17.822 118.391  1.00188.52              O
ANISOU 8282  O   GLU B 258     23182  28615  19833    986  -4386   2880          O
ATOM   8283  CB  GLU B 258      41.628 -17.816 116.128  1.00176.02              C
ANISOU 8283  CB  GLU B 258     21851  26233  18797    171  -3186   2652          C
ATOM   8284  CG  GLU B 258      40.875 -17.547 117.422  1.00176.82              C
ANISOU 8284  CG  GLU B 258     22461  26267  18454     45  -3252   2713          C
ATOM   8285  CD  GLU B 258      39.573 -18.331 117.538  1.00175.40              C
ANISOU 8285  CD  GLU B 258     22915  25608  18121    -51  -2801   2869          C
ATOM   8286  OE1 GLU B 258      38.505 -17.699 117.699  1.00172.40              O
ANISOU 8286  OE1 GLU B 258     22699  25145  17660   -457  -2574   2733          O
ATOM   8287  OE2 GLU B 258      39.615 -19.579 117.470  1.00177.75              O
ANISOU 8287  OE2 GLU B 258     23534  25602  18401    278  -2680   3120          O
ATOM   8288  N   ILE B 259      43.993 -19.612 117.019  1.00156.28              N
ANISOU 8288  N   ILE B 259     19204  23992  16182   1453  -3887   3047          N
ATOM   8289  CA  ILE B 259      44.608 -20.515 117.990  1.00162.76              C
ANISOU 8289  CA  ILE B 259     20306  24774  16763   2030  -4243   3352          C
ATOM   8290  C   ILE B 259      46.079 -20.190 118.203  1.00167.39              C
ANISOU 8290  C   ILE B 259     20249  25923  17431   2359  -4779   3301          C
ATOM   8291  O   ILE B 259      46.465 -19.628 119.229  1.00170.19              O
ANISOU 8291  O   ILE B 259     20583  26619  17462   2343  -5222   3350          O
ATOM   8292  CB  ILE B 259      44.535 -21.988 117.535  1.00165.10              C
ANISOU 8292  CB  ILE B 259     20930  24553  17248   2486  -4009   3548          C
ATOM   8293  CG1 ILE B 259      43.105 -22.378 117.177  1.00160.79              C
ANISOU 8293  CG1 ILE B 259     20965  23454  16675   2125  -3460   3585          C
ATOM   8294  CG2 ILE B 259      45.097 -22.913 118.610  1.00172.39              C
ANISOU 8294  CG2 ILE B 259     22216  25363  17922   3079  -4426   3928          C
ATOM   8295  CD1 ILE B 259      43.009 -23.721 116.498  1.00162.65              C
ANISOU 8295  CD1 ILE B 259     21470  23152  17178   2476  -3192   3685          C
ATOM   8296  N   ILE B 260      46.884 -20.543 117.204  1.00172.48              N
ANISOU 8296  N   ILE B 260     20343  26692  18499   2637  -4723   3176          N
ATOM   8297  CA  ILE B 260      48.335 -20.392 117.255  1.00177.60              C
ANISOU 8297  CA  ILE B 260     20286  27896  19300   3004  -5183   3118          C
ATOM   8298  C   ILE B 260      48.828 -18.946 117.402  1.00176.46              C
ANISOU 8298  C   ILE B 260     19572  28363  19113   2539  -5485   2900          C
ATOM   8299  O   ILE B 260      50.030 -18.687 117.329  1.00180.48              O
ANISOU 8299  O   ILE B 260     19393  29403  19778   2730  -5842   2817          O
ATOM   8300  CB  ILE B 260      49.021 -21.103 116.082  1.00179.35              C
ANISOU 8300  CB  ILE B 260     20009  28143  19994   3388  -4965   2970          C
ATOM   8301  CG1 ILE B 260      48.355 -22.458 115.795  1.00179.87              C
ANISOU 8301  CG1 ILE B 260     20707  27493  20142   3740  -4607   3121          C
ATOM   8302  CG2 ILE B 260      50.508 -21.302 116.335  1.00186.60              C
ANISOU 8302  CG2 ILE B 260     20286  29564  21049   3960  -5468   2984          C
ATOM   8303  CD1 ILE B 260      48.594 -23.489 116.880  1.00186.36              C
ANISOU 8303  CD1 ILE B 260     22034  28000  20772   4369  -4974   3505          C
ATOM   8304  N   VAL B 261      47.906 -18.006 117.600  1.00165.93              N
ANISOU 8304  N   VAL B 261     18505  26944  17597   1928  -5348   2794          N
ATOM   8305  CA  VAL B 261      48.304 -16.635 117.937  1.00165.68              C
ANISOU 8305  CA  VAL B 261     18065  27389  17496   1489  -5698   2598          C
```

FIG. 13 Continued

```
ATOM   8306  C   VAL B 261      47.443 -16.087 119.081  1.00164.64           C
ANISOU 8306  C   VAL B 261    18535  27110  16912   1199  -5804   2612       C
ATOM   8307  O   VAL B 261      47.214 -14.881 119.203  1.00162.39           O
ANISOU 8307  O   VAL B 261    18123  26978  16600    689  -5896   2378       O
ATOM   8308  CB  VAL B 261      48.425 -15.668 116.718  1.00161.64           C
ANISOU 8308  CB  VAL B 261    16939  27103  17375    958  -5498   2323       C
ATOM   8309  CG1 VAL B 261      48.718 -16.446 115.430  1.00161.21           C
ANISOU 8309  CG1 VAL B 261    16551  27011  17692   1182  -5121   2298       C
ATOM   8310  CG2 VAL B 261      47.202 -14.779 116.577  1.00155.65           C
ANISOU 8310  CG2 VAL B 261    16515  26043  16581    333  -5225   2188       C
ATOM   8311  N   MET B 262      46.990 -17.009 119.928  1.00190.42           N
ANISOU 8311  N   MET B 262    22460  30074  19818   1537  -5794   2886       N
ATOM   8312  CA  MET B 262      46.284 -16.658 121.153  1.00191.11           C
ANISOU 8312  CA  MET B 262    23126  30110  19376   1342  -5908   2922       C
ATOM   8313  C   MET B 262      46.727 -17.532 122.333  1.00197.94           C
ANISOU 8313  C   MET B 262    24377  31037  19794   1844  -6303   3277       C
ATOM   8314  O   MET B 262      47.259 -17.016 123.314  1.00202.09           O
ANISOU 8314  O   MET B 262    24852  31968  19964   1836  -6801   3256       O
ATOM   8315  CB  MET B 262      44.766 -16.697 120.980  1.00185.86           C
ANISOU 8315  CB  MET B 262    23025  28959  18637    996  -5339   2889       C
ATOM   8316  CG  MET B 262      44.019 -16.112 122.175  1.00186.59           C
ANISOU 8316  CG  MET B 262    23602  29096  18198    718  -5405   2814       C
ATOM   8317  SD  MET B 262      44.867 -14.696 122.937  1.00189.62           S
ANISOU 8317  SD  MET B 262    23568  30074  18403    482  -6022   2493       S
ATOM   8318  CE  MET B 262      45.087 -13.650 121.503  1.00184.29           C
ANISOU 8318  CE  MET B 262    22162  29442  18417     67  -5893   2158       C
ATOM   8319  N   TYR B 263      46.525 -18.846 122.242  1.00178.28           N
ANISOU 8319  N   TYR B 263    22285  28137  17317   2268  -6116   3612       N
ATOM   8320  CA  TYR B 263      46.947 -19.739 123.323  1.00185.41           C
ANISOU 8320  CA  TYR B 263    23589  29038  17820   2760  -6524   4024       C
ATOM   8321  C   TYR B 263      48.364 -19.419 123.772  1.00191.22           C
ANISOU 8321  C   TYR B 263    23750  30366  18539   3060  -7211   4017       C
ATOM   8322  O   TYR B 263      48.643 -19.417 124.965  1.00196.56           O
ANISOU 8322  O   TYR B 263    24688  31291  18706   3174  -7680   4213       O
ATOM   8323  CB  TYR B 263      46.853 -21.212 122.915  1.00187.36           C
ANISOU 8323  CB  TYR B 263    24168  28740  18280   3256  -6314   4364       C
ATOM   8324  CG  TYR B 263      45.485 -21.823 123.104  1.00185.10           C
ANISOU 8324  CG  TYR B 263    24705  27880  17746   3039  -5829   4571       C
ATOM   8325  CD1 TYR B 263      44.365 -21.262 122.500  1.00178.00           C
ANISOU 8325  CD1 TYR B 263    23890  26794  16948   2476  -5267   4295       C
ATOM   8326  CD2 TYR B 263      45.314 -22.970 123.872  1.00190.58           C
ANISOU 8326  CD2 TYR B 263    26074  28217  18120   3382  -5950   5065       C
ATOM   8327  CE1 TYR B 263      43.110 -21.814 122.662  1.00176.32           C
ANISOU 8327  CE1 TYR B 263    24365  26107  16523   2250  -4818   4472       C
ATOM   8328  CE2 TYR B 263      44.062 -23.535 124.040  1.00189.01           C
ANISOU 8328  CE2 TYR B 263    26608  27516  17690   3121  -5495   5272       C
ATOM   8329  CZ  TYR B 263      42.963 -22.949 123.431  1.00181.81           C
ANISOU 8329  CZ  TYR B 263    25716  26478  16886   2550  -4918   4957       C
ATOM   8330  OH  TYR B 263      41.708 -23.494 123.587  1.00180.56           O
ANISOU 8330  OH  TYR B 263    26222  25872  16511   2261  -4457   5147       O
ATOM   8331  N   PRO B 264      49.268 -19.150 122.815  1.00220.01           N
ANISOU 8331  N   PRO B 264    26591  34284  22720   3165  -7276   3794       N
ATOM   8332  CA  PRO B 264      50.640 -18.814 123.196  1.00225.88           C
ANISOU 8332  CA  PRO B 264    26692  35647  23484   3417  -7928   3769       C
ATOM   8333  C   PRO B 264      50.774 -17.354 123.605  1.00224.68           C
ANISOU 8333  C   PRO B 264    26248  35981  23138   2837  -8192   3441       C
ATOM   8334  O   PRO B 264      51.449 -17.050 124.587  1.00230.23           O
ANISOU 8334  O   PRO B 264    26860  37121  23495   2915  -8790   3495       O
ATOM   8335  CB  PRO B 264      51.435 -19.044 121.901  1.00225.46           C
ANISOU 8335  CB  PRO B 264    25863  35713  24089   3664  -7779   3607       C
ATOM   8336  CG  PRO B 264      50.492 -19.700 120.945  1.00220.21           C
ANISOU 8336  CG  PRO B 264    25551  34430  23668   3633  -7091   3600       C
ATOM   8337  CD  PRO B 264      49.132 -19.267 121.357  1.00215.07           C
ANISOU 8337  CD  PRO B 264    25598  33447  22674   3094  -6770   3587       C
ATOM   8338  N   ILE B 265      50.127 -16.465 122.860  1.00185.69           N
ANISOU 8338  N   ILE B 265    21185  30942  18426   2257  -7778   3106       N
ATOM   8339  CA  ILE B 265      50.257 -15.028 123.093  1.00184.59           C
ANISOU 8339  CA  ILE B 265    20740  31175  18220   1685  -8015   2757       C
ATOM   8340  C   ILE B 265      49.693 -14.555 124.440  1.00186.42           C
```

FIG. 13 Continued

```
ANISOU 8340  C   ILE B 265    21572  31449  17810    1458  -8242   2718          C
ATOM   8341  O   ILE B 265      50.372 -14.615 125.468  1.00192.80           O
ANISOU 8341  O   ILE B 265    22404  32630  18221    1668  -8808   2837          O
ATOM   8342  CB  ILE B 265      49.620 -14.235 121.939  1.00177.32           C
ANISOU 8342  CB  ILE B 265    19602  30049  17723    1137  -7521   2455          C
ATOM   8343  CG1 ILE B 265      49.885 -14.943 120.608  1.00175.29           C
ANISOU 8343  CG1 ILE B 265    18955  29664  17983    1372  -7150   2522          C
ATOM   8344  CG2 ILE B 265      50.139 -12.806 121.919  1.00177.52           C
ANISOU 8344  CG2 ILE B 265    19098  30483  17867     613  -7856   2120          C
ATOM   8345  CD1 ILE B 265      51.336 -15.305 120.371  1.00180.92           C
ANISOU 8345  CD1 ILE B 265    18940  30866  18937    1800  -7526   2584          C
ATOM   8346  N   GLN B 266      48.452 -14.074 124.428  1.00181.63           N
ANISOU 8346  N   GLN B 266    21424  30494  17095    1029  -7803   2531          N
ATOM   8347  CA  GLN B 266      47.780 -13.632 125.651  1.00183.34           C
ANISOU 8347  CA  GLN B 266    22225  30746  16692     799  -7906   2427          C
ATOM   8348  C   GLN B 266      47.576 -14.823 126.586  1.00187.88           C
ANISOU 8348  C   GLN B 266    23445  31223  16719    1229  -7966   2868          C
ATOM   8349  O   GLN B 266      46.873 -14.731 127.590  1.00189.61           O
ANISOU 8349  O   GLN B 266    24257  31443  16343    1076  -7936   2863          O
ATOM   8350  CB  GLN B 266      46.451 -12.931 125.319  1.00177.06           C
ANISOU 8350  CB  GLN B 266    21718  29577  15980     303  -7362   2117          C
ATOM   8351  CG  GLN B 266      46.539 -11.400 125.341  1.00176.11           C
ANISOU 8351  CG  GLN B 266    21270  29653  15992    -215  -7574   1624          C
ATOM   8352  CD  GLN B 266      46.101 -10.747 124.038  1.00169.59           C
ANISOU 8352  CD  GLN B 266    20098  28530  15810    -583  -7192   1409          C
ATOM   8353  OE1 GLN B 266      46.085  -9.520 123.915  1.00168.59           O
ANISOU 8353  OE1 GLN B 266    19731  28445  15882   -1021  -7332   1042          O
ATOM   8354  NE2 GLN B 266      45.762 -11.565 123.055  1.00165.66           N
ANISOU 8354  NE2 GLN B 266    19587  27718  15637    -419  -6741   1642          N
ATOM   8355  N   ARG B 267      48.206 -15.938 126.221  1.00194.90           N
ANISOU 8355  N   ARG B 267    24204  32025  17824    1765  -8048   3246          N
ATOM   8356  CA  ARG B 267      48.160 -17.194 126.965  1.00199.97           C
ANISOU 8356  CA  ARG B 267    25419  32499  18061    2237  -8165   3751          C
ATOM   8357  C   ARG B 267      46.862 -17.374 127.755  1.00199.28           C
ANISOU 8357  C   ARG B 267    26189  32143  17386    1982  -7815   3854          C
ATOM   8358  O   ARG B 267      45.763 -17.124 127.245  1.00193.23           O
ANISOU 8358  O   ARG B 267    25624  31034  16762    1622  -7221   3656          O
ATOM   8359  CB  ARG B 267      49.391 -17.336 127.883  1.00208.41           C
ANISOU 8359  CB  ARG B 267    26282  34086  18817    2606  -8958   3959          C
ATOM   8360  CG  ARG B 267      49.971 -18.760 127.925  1.00213.78           C
ANISOU 8360  CG  ARG B 267    27074  34573  19580    3321  -9178   4497          C
ATOM   8361  CD  ARG B 267      51.012 -18.979 129.017  1.00222.98           C
ANISOU 8361  CD  ARG B 267    28176  36220  20327    3694  -9994   4785          C
ATOM   8362  NE  ARG B 267      51.520 -20.347 128.974  1.00228.27           N
ANISOU 8362  NE  ARG B 267    28949  36612  21169    4417 -10199   5301          N
ATOM   8363  CZ  ARG B 267      50.897 -21.390 129.512  1.00231.03           C
ANISOU 8363  CZ  ARG B 267    30113  36502  21168    4638 -10101   5793          C
ATOM   8364  NH1 ARG B 267      49.747 -21.224 130.143  1.00229.01           N
ANISOU 8364  NH1 ARG B 267    30597  36089  20327    4172  -9770   5831          N
ATOM   8365  NH2 ARG B 267      51.424 -22.600 129.421  1.00236.36           N
ANISOU 8365  NH2 ARG B 267    30852  36868  22086    5321 -10335   6244          N
ATOM   8366  N   ARG B 268      47.023 -17.839 128.994  1.00218.67           N
ANISOU 8366  N   ARG B 268    29120  34791  19174    2174  -8203   4186          N
ATOM   8367  CA  ARG B 268      45.938 -18.050 129.960  1.00220.13           C
ANISOU 8367  CA  ARG B 268    30123  34869  18649    1935  -7954   4334          C
ATOM   8368  C   ARG B 268      44.543 -18.203 129.323  1.00213.44           C
ANISOU 8368  C   ARG B 268    29615  33492  17989    1621  -7144   4242          C
ATOM   8369  O   ARG B 268      43.610 -17.451 129.622  1.00210.82           O
ANISOU 8369  O   ARG B 268    29493  33216  17392    1155  -6813   3902          O
ATOM   8370  CB  ARG B 268      45.955 -16.957 131.050  1.00223.23           C
ANISOU 8370  CB  ARG B 268    30586  35816  18415    1565  -8276   3986          C
ATOM   8371  CG  ARG B 268      47.348 -16.361 131.375  1.00228.00           C
ANISOU 8371  CG  ARG B 268    30608  36997  19025    1704  -9052   3851          C
ATOM   8372  CD  ARG B 268      48.069 -17.036 132.547  1.00237.38           C
ANISOU 8372  CD  ARG B 268    32092  38536  19564    2064  -9710   4325          C
ATOM   8373  NE  ARG B 268      49.273  16.296 132.935  1.00242.00           N
ANISOU 8373  NE  ARG B 268    32115  39738  20096    2086 -10444   4111          N
ATOM   8374  CZ  ARG B 268      50.039 -16.586 133.983  1.00250.64           C
ANISOU 8374  CZ  ARG B 268    33329  41282  20621    2327 -11144   4416          C
```

FIG. 13 Continued

```
ATOM   8375  NH1 ARG B 268      49.740 -17.609 134.769  1.00255.82           N
ANISOU 8375  NH1 ARG B 268    34683  41826  20691   2574 -11220   4990       N
ATOM   8376  NH2 ARG B 268      51.109 -15.849 134.247  1.00254.54           N
ANISOU 8376  NH2 ARG B 268    33246  42344  21124   2292 -11795   4171       N
ATOM   8377  N   LYS B 269      44.419 -19.192 128.445  1.00195.06           N
ANISOU 8377  N   LYS B 269    27322  30660  16131   1895  -6844   4524       N
ATOM   8378  CA  LYS B 269      43.164 -19.476 127.767  1.00189.27           C
ANISOU 8378  CA  LYS B 269    26885  29414  15614   1624  -6118   4485       C
ATOM   8379  C   LYS B 269      43.167 -20.935 127.327  1.00190.85           C
ANISOU 8379  C   LYS B 269    27387  29076  16051   2035  -5980   4982       C
ATOM   8380  O   LYS B 269      44.234 -21.524 127.149  1.00194.62           O
ANISOU 8380  O   LYS B 269    27613  29554  16778   2551  -6392   5209       O
ATOM   8381  CB  LYS B 269      43.001 -18.556 126.556  1.00181.70           C
ANISOU 8381  CB  LYS B 269    25323  28407  15309   1334  -5810   3977       C
ATOM   8382  CG  LYS B 269      42.572 -17.143 126.903  1.00179.37           C
ANISOU 8382  CG  LYS B 269    24883  28431  14838    839  -5780   3465       C
ATOM   8383  CD  LYS B 269      41.295 -17.173 127.724  1.00179.90           C
ANISOU 8383  CD  LYS B 269    25604  28420  14331    529  -5394   3468       C
ATOM   8384  CE  LYS B 269      40.395 -15.984 127.413  1.00174.68           C
ANISOU 8384  CE  LYS B 269    24770  27754  13846     40  -5026   2913       C
ATOM   8385  NZ  LYS B 269      38.980 -16.222 127.827  1.00174.06           N
ANISOU 8385  NZ  LYS B 269    25237  27494  13404   -235  -4466   2924       N
ATOM   8386  N   TYR B 270      41.982 -21.517 127.166  1.00197.01           N
ANISOU 8386  N   TYR B 270    28694  29393  16768   1810  -5416   5133       N
ATOM   8387  CA  TYR B 270      41.850 -22.903 126.715  1.00198.56           C
ANISOU 8387  CA  TYR B 270    29246  28983  17213   2129  -5242   5574       C
ATOM   8388  C   TYR B 270      40.395 -23.335 126.755  1.00196.44           C
ANISOU 8388  C   TYR B 270    29589  28310  16739   1713  -4621   5701       C
ATOM   8389  O   TYR B 270      39.695 -23.297 125.744  1.00190.47           O
ANISOU 8389  O   TYR B 270    28700  27237  16433   1477  -4113   5470       O
ATOM   8390  CB  TYR B 270      42.693 -23.839 127.581  1.00207.31           C
ANISOU 8390  CB  TYR B 270    30683  30084  18001   2652  -5820   6133       C
ATOM   8391  CG  TYR B 270      42.633 -25.303 127.185  1.00210.18           C
ANISOU 8391  CG  TYR B 270    31458  29748  18651   3035  -5720   6603       C
ATOM   8392  CD1 TYR B 270      43.741 -25.941 126.636  1.00213.20           C
ANISOU 8392  CD1 TYR B 270    31492  29956  19559   3680  -6078   6714       C
ATOM   8393  CD2 TYR B 270      41.475 -26.051 127.380  1.00210.54           C
ANISOU 8393  CD2 TYR B 270    32238  29306  18454   2749  -5274   6921       C
ATOM   8394  CE1 TYR B 270      43.695 -27.285 126.287  1.00216.55           C
ANISOU 8394  CE1 TYR B 270    32321  29677  20280   4065   6008   7103       C
ATOM   8395  CE2 TYR B 270      41.417 -27.390 127.032  1.00213.75           C
ANISOU 8395  CE2 TYR B 270    33065  29007  19143   3069  -5210   7346       C
ATOM   8396  CZ  TYR B 270      42.528 -28.006 126.488  1.00216.79           C
ANISOU 8396  CZ  TYR B 270    33129  29169  20071   3745  -5586   7425       C
ATOM   8397  OH  TYR B 270      42.464 -29.343 126.149  1.00220.60           O
ANISOU 8397  OH  TYR B 270    34062  28887  20870   4091  -5537   7808       O
ATOM   8398  N   ARG B 271      39.947 -23.756 127.932  1.00201.05           N
ANISOU 8398  N   ARG B 271    30832  28943  16615   1599  -4672   6087       N
ATOM   8399  CA  ARG B 271      38.558 -24.133 128.117  1.00200.11           C
ANISOU 8399  CA  ARG B 271    31282  28540  16211   1145  -4086   6226       C
ATOM   8400  C   ARG B 271      37.676 -22.957 127.678  1.00192.99           C
ANISOU 8400  C   ARG B 271    30025  27855  15446    630  -3608   5613       C
ATOM   8401  O   ARG B 271      36.533 -23.150 127.252  1.00189.62           O
ANISOU 8401  O   ARG B 271    29786  27128  15132    272   -301   5564       O
ATOM   8402  CB  ARG B 271      38.298 -24.509 129.580  1.00207.67           C
ANISOU 8402  CB  ARG B 271    32923  29719  16265   1027  -4251   6678       C
ATOM   8403  CG  ARG B 271      39.157 -23.732 130.583  1.00211.92           C
ANISOU 8403  CG  ARG B 271    33291  30947  16284   1143  -4842   6569       C
ATOM   8404  CD  ARG B 271      38.765 -24.005 132.037  1.00219.44           C
ANISOU 8404  CD  ARG B 271    34936  32203  16239    923  -4939   6966       C
ATOM   8405  NE  ARG B 271      38.960 -25.403 132.410  1.00226.29           N
ANISOU 8405  NE  ARG B 271    36421  32642  16917   1205  -5165   7756       N
ATOM   8406  CZ  ARG B 271      39.912 -25.835 133.228  1.00234.15           C
ANISOU 8406  CZ  ARG B 271    37626  33816  17523   1589  -5853   8221       C
ATOM   8407  NH1 ARG B 271      40.757 -24.972 133.771  1.00236.04           N
ANISOU 8407  NH1 ARG B 271    37490  34703  17492   1709  -6373   7952       N
ATOM   8408  NH2 ARG B 271      40.013 -27.128 133.506  1.00240.56           N
ANISOU 8408  NH2 ARG B 271    39033  34140  18229   1842  -6051   8964       N
ATOM   8409  N   ASP B 272      38.220 -21.742 127.777  1.00183.55           N
```

FIG. 13 Continued

```
ANISOU 8409  N   ASP B 272    28308 27163 14269   598 -3882  5152       N
ATOM   8410  CA  ASP B 272      37.515 -20.525 127.369  1.00177.49      C
ANISOU 8410  CA  ASP B 272    27166 26576 13695   168 -3533  4553       C
ATOM   8411  C   ASP B 272      37.837 -20.161 125.921  1.00170.98      C
ANISOU 8411  C   ASP B 272    25710 25546 13708   227 -3453  4249       C
ATOM   8412  O   ASP B 272      37.005 -19.591 125.225  1.00165.41      O
ANISOU 8412  O   ASP B 272    24801 24725 13324  -118 -3031  3913       O
ATOM   8413  CB  ASP B 272      37.879 -19.334 128.271  1.00179.60      C
ANISOU 8413  CB  ASP B 272    27248 27457 13536    46 -3879  4182       C
ATOM   8414  CG  ASP B 272      37.558 -19.573 129.737  1.00186.49      C
ANISOU 8414  CG  ASP B 272    28726 28644 13487   -63 -3953  4419       C
ATOM   8415  OD1 ASP B 272      36.638 -20.363 130.036  1.00188.22      O
ANISOU 8415  OD1 ASP B 272    29487 28642 13388  -239 -3546  4747       O
ATOM   8416  OD2 ASP B 272      38.228 -18.952 130.592  1.00190.54      O
ANISOU 8416  OD2 ASP B 272    29170 29656 13569   -12 -4421  4272       O
ATOM   8417  N   GLY B 273      39.055 -20.472 125.482  1.00171.60      N
ANISOU 8417  N   GLY B 273    25457 25620 14123   660 -3868  4368       N
ATOM   8418  CA  GLY B 273      39.494 -20.148 124.133  1.00166.43      C
ANISOU 8418  CA  GLY B 273    24178 24862 14197   716 -3815  4095       C
ATOM   8419  C   GLY B 273      38.812 -21.010 123.090  1.00163.07      C
ANISOU 8419  C   GLY B 273    23900 23876 14184   682 -3321  4215       C
ATOM   8420  O   GLY B 273      38.571 -20.580 121.957  1.00157.50      O
ANISOU 8420  O   GLY B 273    22794 23069 13981   485 -3055  3919       O
ATOM   8421  N   ILE B 274      38.510 -22.242 123.490  1.00167.75      N
ANISOU 8421  N   ILE B 274    25095 24099 14545   852 -3226  4668       N
ATOM   8422  CA  ILE B 274      37.821 -23.197 122.635  1.00165.78      C
ANISOU 8422  CA  ILE B 274    25098 23264 14627   804 -2779  4813       C
ATOM   8423  C   ILE B 274      36.453 -22.666 122.230  1.00160.30      C
ANISOU 8423  C   ILE B 274    24428 22490 13990   224 -2219  4547       C
ATOM   8424  O   ILE B 274      36.082 -22.722 121.064  1.00155.71      O
ANISOU 8424  O   ILE B 274    23620 21648 13895    83 -1903  4367       O
ATOM   8425  CB  ILE B 274      37.662 -24.563 123.340  1.00172.09      C
ANISOU 8425  CB  ILE B 274    26634 23657 15096  1018 -2815  5388       C
ATOM   8426  CG1 ILE B 274      38.972 -25.333 123.262  1.00176.99      C
ANISOU 8426  CG1 ILE B 274    27166 24148 15935  1682 -3303  5639       C
ATOM   8427  CG2 ILE B 274      36.554 -25.383 122.705  1.00170.16      C
ANISOU 8427  CG2 ILE B 274    26775 22829 15049   746 -2266  5506       C
ATOM   8428  CD1 ILE B 274      39.549 -25.356 121.870  1.00173.35      C
ANISOU 8428  CD1 ILE B 274    26126 23554 16185  1908 -3232  5329       C
ATOM   8429  N   ASP B 275      35.713 -22.137 123.198  1.00161.96      N
ANISOU 8429  N   ASP B 275    24887 22959 13691  -104 -2106  4502       N
ATOM   8430  CA  ASP B 275      34.378 -21.621 122.934  1.00157.72      C
ANISOU 8430  CA  ASP B 275    24347 22386 13194  -619 -1587  4240       C
ATOM   8431  C   ASP B 275      34.420 -20.603 121.800  1.00151.29      C
ANISOU 8431  C   ASP B 275    22873 21653 12958  -769 -1526  3771       C
ATOM   8432  O   ASP B 275      33.568 -20.634 120.921  1.00147.16      O
ANISOU 8432  O   ASP B 275    22266 20875 12774 -1049 -1123  3652       O
ATOM   8433  CB  ASP B 275      33.754 -21.038 124.226  1.00160.52      C
ANISOU 8433  CB  ASP B 275    24959 23126 12905  -887 -1524  4162       C
ATOM   8434  CG  ASP B 275      33.638 -22.072 125.330  1.00167.45      C
ANISOU 8434  CG  ASP B 275    26536 23951 13138  -818 -1560  4688       C
ATOM   8435  OD1 ASP B 275      33.705  23.286 125.040  1.00169.47      O
ANISOU 8435  OD1 ASP B 275    27139 23742 13512  -654 -1518  5119       O
ATOM   8436  OD2 ASP B 275      33.482 -21.678 126.506  1.00171.39      O
ANISOU 8436  OD2 ASP B 275    27259 24863 12999  -941 -1640  4675       O
ATOM   8437  N   ASN B 276      35.423 -19.725 121.805  1.00153.11      N
ANISOU 8437  N   ASN B 276    22638 22239 13297  -607 -1950  3536       N
ATOM   8438  CA  ASN B 276      35.579 -18.710 120.753  1.00147.78      C
ANISOU 8438  CA  ASN B 276    21338 21656 13155  -775 -1957  3142       C
ATOM   8439  C   ASN B 276      36.219 -19.285 119.496  1.00145.84      C
ANISOU 8439  C   ASN B 276    20804 21189 13420  -570 -1959  3213       C
ATOM   8440  O   ASN B 276      36.256 -18.648 118.442  1.00141.53      O
ANISOU 8440  O   ASN B 276    19788 20671 13317  -754 -1890  2960       O
ATOM   8441  CB  ASN B 276      36.416 -17.530 121.251  1.00148.76      C
ANISOU 8441  CB  ASN B 276    21082 22243 13198  -744 -2419  2866       C
ATOM   8442  CG  ASN B 276      35.728 -16.736 122.360  1.00150.37      C
ANISOU 8442  CG  ASN B 276    21494 22690 12950  -992 -2387  2643       C
ATOM   8443  OD1 ASN B 276      34.694 -17.142 122.904  1.00151.53      O
ANISOU 8443  OD1 ASN B 276    22083 22732 12760 -1153 -2028  2739       O
```

FIG. 13 Continued

```
ATOM   8444  ND2 ASN B 276      36.312 -15.594 122.702  1.00150.95           N
ANISOU 8444  ND2 ASN B 276    21237  23107  13011  -1040  -2758   2320       N
ATOM   8445  N   LEU B 277      36.745 -20.494 119.642  1.00194.37           N
ANISOU 8445  N   LEU B 277    27244  27122  19484   -180  -2053   3559       N
ATOM   8446  CA  LEU B 277      37.368 -21.220 118.552  1.00193.89           C
ANISOU 8446  CA  LEU B 277    26974  26831  19864     92  -2034   3609       C
ATOM   8447  C   LEU B 277      36.312 -22.079 117.872  1.00192.00           C
ANISOU 8447  C   LEU B 277    27087  26079  19783   -108  -1535   3705       C
ATOM   8448  O   LEU B 277      36.287 -22.198 116.651  1.00188.90           O
ANISOU 8448  O   LEU B 277    26425  25535  19812   -179  -1334   3547       O
ATOM   8449  CB  LEU B 277      38.473 -22.106 119.114  1.00200.02           C
ANISOU 8449  CB  LEU B 277    27898  27592  20507    672  -2429   3914       C
ATOM   8450  CG  LEU B 277      39.533 -22.680 118.180  1.00201.21           C
ANISOU 8450  CG  LEU B 277    27675  27673  21102   1105  -2560   3887       C
ATOM   8451  CD1 LEU B 277      40.517 -23.505 118.997  1.00208.30           C
ANISOU 8451  CD1 LEU B 277    28767  28559  21820   1706  -3005   4219       C
ATOM   8452  CD2 LEU B 277      38.904 -23.519 117.085  1.00199.05           C
ANISOU 8452  CD2 LEU B 277    27570  26894  21167   1029  -2105   3868       C
ATOM   8453  N   LEU B 278      35.447 -22.675 118.688  1.00146.37           N
ANISOU 8453  N   LEU B 278    21915  20067  13631   -234  -1342   3968       N
ATOM   8454  CA  LEU B 278      34.358 -23.531 118.233  1.00145.53           C
ANISOU 8454  CA  LEU B 278    22210  19474  13610   -486   -880   4099       C
ATOM   8455  C   LEU B 278      33.326 -22.716 117.469  1.00139.67           C
ANISOU 8455  C   LEU B 278    21175  18791  13100  -1005   -515   3774       C
ATOM   8456  O   LEU B 278      32.461 -23.264 116.781  1.00138.01           O
ANISOU 8456  O   LEU B 278    21130  18233  13074  -1265   -140   3792       O
ATOM   8457  CB  LEU B 278      33.695 -24.185 119.439  1.00150.11           C
ANISOU 8457  CB  LEU B 278    23466  19904  13664   -574   -786   4472       C
ATOM   8458  CG  LEU B 278      32.966 -25.517 119.279  1.00152.56           C
ANISOU 8458  CG  LEU B 278    24362  19621  13983   -675   -470   4801       C
ATOM   8459  CD1 LEU B 278      33.925 -26.650 118.903  1.00156.38           C
ANISOU 8459  CD1 LEU B 278    25014  19683  14721   -146   -709   5026       C
ATOM   8460  CD2 LEU B 278      32.243 -25.833 120.576  1.00156.97           C
ANISOU 8460  CD2 LEU B 278    25504  20200  13936   -897   -367   5145       C
ATOM   8461  N   VAL B 279      33.409 -21.398 117.616  1.00144.62           N
ANISOU 8461  N   VAL B 279    21377  19845  13726  -1159   -658   3480       N
ATOM   8462  CA  VAL B 279      32.540 -20.506 116.869  1.00139.49           C
ANISOU 8462  CA  VAL B 279    20392  19253  13356  -1597   -402   3172       C
ATOM   8463  C   VAL B 279      33.085 -20.404 115.460  1.00136.26           C
ANISOU 8463  C   VAL B 279    19529  18802  13440  -1574   -434   3019       C
ATOM   8464  O   VAL B 279      32.362 -20.635 114.496  1.00133.48           O
ANISOU 8464  O   VAL B 279    19143  18222  13350  -1843   -123   2960       O
ATOM   8465  CB  VAL B 279      32.450 -19.103 117.498  1.00138.47           C
ANISOU 8465  CB  VAL B 279    19982  19527  13103  -1756   -574   2892       C
ATOM   8466  CG1 VAL B 279      31.858 -19.185 118.906  1.00142.21           C
ANISOU 8466  CG1 VAL B 279    20900  20112  13021  -1808   -493   2991       C
ATOM   8467  CG2 VAL B 279      33.812 -18.414 117.506  1.00138.95           C
ANISOU 8467  CG2 VAL B 279    19628  19912  13255  -1497  -1059   2769       C
ATOM   8468  N   LEU B 280      34.370 -20.079 115.345  1.00130.16           N
ANISOU 8468  N   LEU B 280    18399  18291  12766  -1272   -808   2956       N
ATOM   8469  CA  LEU B 280      34.998 -20.005 114.041  1.00127.98           C
ANISOU 8469  CA  LEU B 280    17667  18061  12900  -1248   -829   2814       C
ATOM   8470  C   LEU B 280      34.526 -21.185 113.211  1.00127.92           C
ANISOU 8470  C   LEU B 280    17930  17624  13050  -1255   -480   2906       C
ATOM   8471  O   LEU B 280      33.917 -21.007 112.159  1.00124.47           O
ANISOU 8471  O   LEU B 280    17321  17107  12864  -1595   -230   2762       O
ATOM   8472  CB  LEU B 280      36.532 -20.037 114.153  1.00131.03           C
ANISOU 8472  CB  LEU B 280    17743  18728  13313   -802  -1234   2826       C
ATOM   8473  CG  LEU B 280      37.298 -18.725 113.920  1.00129.50           C
ANISOU 8473  CG  LEU B 280    16926  19006  13272   -924  -1547   2599       C
ATOM   8474  CD1 LEU B 280      37.295 -17.850 115.168  1.00130.74           C
ANISOU 8474  CD1 LEU B 280    17142  19404  13130   -977  -1834   2560       C
ATOM   8475  CD2 LEU B 280      38.729 -18.952 113.420  1.00131.95           C
ANISOU 8475  CD2 LEU B 280    16793  19580  13763   -566  -1798   2573       C
ATOM   8476  N   LEU B 281      34.777 -22.387 113.730  1.00131.84           N
ANISOU 8476  N   LEU B 281    18883  17825  13386   -894   -490   3156       N
ATOM   8477  CA  LEU B 281      34.497 -23.653 113.039  1.00133.18           C
ANISOU 8477  CA  LEU B 281    19377  17511  13714   -820   -218   3242       C
ATOM   8478  C   LEU B 281      33.024 -24.036 112.850  1.00131.50           C
```

FIG. 13 Continued

```
ANISOU 8478  C   LEU B 281    19549 16941 13474  -1284   203  3298       C
ATOM   8479  O   LEU B 281       32.726  25.206 112.630  1.00133.95      O
ANISOU 8479  O   LEU B 281    20285 16781 13828   1228   392  3438       O
ATOM   8480  CB  LEU B 281       35.246 -24.829 113.706  1.00139.26      C
ANISOU 8480  CB  LEU B 281    20550 18000 14362   -261  -416  3522       C
ATOM   8481  CG  LEU B 281       36.761 -24.831 113.986  1.00142.85      C
ANISOU 8481  CG  LEU B 281    20698 18726 14852    321  -857  3535       C
ATOM   8482  CD1 LEU B 281       37.266 -26.256 114.206  1.00148.93      C
ANISOU 8482  CD1 LEU B 281    21899 19025 15663    858  -954  3784       C
ATOM   8483  CD2 LEU B 281       37.573 -24.163 112.888  1.00140.35      C
ANISOU 8483  CD2 LEU B 281    19657 18802 14867    345  -917  3193       C
ATOM   8484  N   ILE B 282       32.105 -23.080 112.943  1.00129.33      N
ANISOU 8484  N   ILE B 282    19121 16868 13151  -1734   335  3183       N
ATOM   8485  CA  ILE B 282       30.693 -23.383 112.687  1.00127.91      C
ANISOU 8485  CA  ILE B 282    19198 16416 12983  -2195   733  3209       C
ATOM   8486  C   ILE B 282       29.884 -22.137 112.324  1.00123.36      C
ANISOU 8486  C   ILE B 282    18212 16122 12538  -2638   827  2973       C
ATOM   8487  O   ILE B 282       28.864 -22.216 111.648  1.00121.34      O
ANISOU 8487  O   ILE B 282    17948 15718 12438  -3029  1111  2911       O
ATOM   8488  CB  ILE B 282       30.025 -24.180 113.836  1.00131.88      C
ANISOU 8488  CB  ILE B 282    20330 16660 13119  -2229   878  3524       C
ATOM   8489  CG1 ILE B 282       28.744 -24.880 113.334  1.00131.56      C
ANISOU 8489  CG1 ILE B 282    20576 16247 13163  -2671  1299  3579       C
ATOM   8490  CG2 ILE B 282       29.796 -23.287 115.063  1.00132.34      C
ANISOU 8490  CG2 ILE B 282    20366 17096 12820  -2294   776  3531       C
ATOM   8491  CD1 ILE B 282       28.974 -26.051 112.348  1.00132.98      C
ANISOU 8491  CD1 ILE B 282    20967 15951 13607   2573  1397  3600       C
ATOM   8492  N   GLY B 283       30.343 -20.980 112.774  1.00119.89      N
ANISOU 8492  N   GLY B 283    17428 16068 12057  -2574   557  2839       N
ATOM   8493  CA  GLY B 283       29.716 -19.737 112.378  1.00116.14      C
ANISOU 8493  CA  GLY B 283    16540 15808 11779  -2931   572  2606       C
ATOM   8494  C   GLY B 283       30.263 -19.367 111.015  1.00113.35      C
ANISOU 8494  C   GLY B 283    15734 15545 11787  -3008   469  2466       C
ATOM   8495  O   GLY B 283       30.456 -18.182 110.710  1.00111.10      O
ANISOU 8495  O   GLY B 283    15014 15517 11682  -3149   267  2305       O
ATOM   8496  N   GLY B 284       30.523 -20.403 110.211  1.00115.93      N
ANISOU 8496  N   GLY B 284    16188 15652 12206  -2924   608  2527       N
ATOM   8497  CA  GLY B 284       31.080 -20.274 108.865  1.00114.22      C
ANISOU 8497  CA  GLY B 284    15590 15549 12259  -2993   572  2392       C
ATOM   8498  C   GLY B 284       31.043 -21.530 107.988  1.00115.54      C
ANISOU 8498  C   GLY B 284    15987 15413 12501  -2961   819  2396       C
ATOM   8499  O   GLY B 284       32.020 -21.867 107.310  1.00116.73      O
ANISOU 8499  O   GLY B 284    15954 15652 12745  -2729   754  2304       O
ATOM   8500  N   ILE B 285       29.910 -22.227 108.009  1.00115.92      N
ANISOU 8500  N   ILE B 285    16425 15111 12510  -3203  1112  2475       N
ATOM   8501  CA  ILE B 285       29.728 -23.429 107.198  1.00117.57      C
ANISOU 8501  CA  ILE B 285    16909 14963 12797  -3236  1352  2450       C
ATOM   8502  C   ILE B 285       28.440 -23.324 106.375  1.00115.17      C
ANISOU 8502  C   ILE B 285    16571 14575 12613  -3806  1600  2379       C
ATOM   8503  O   ILE B 285       27.321 -23.354 106.937  1.00115.05      O
ANISOU 8503  O   ILE B 285    16773 14417 12522  -4077  1760  2490       O
ATOM   8504  CB  ILE B 285       29.773 -24.749 108.028  1.00122.11      C
ANISOU 8504  CB  ILE B 285    18106 15078 13211  -2926  1435  2659       C
ATOM   8505  CG1 ILE B 285       31.184 -25.349 108.007  1.00125.46      C
ANISOU 8505  CG1 ILE B 285    18532 15467 13672  -2337  1240  2635       C
ATOM   8506  CG2 ILE B 285       28.807 -25.782 107.466  1.00123.34      C
ANISOU 8506  CG2 ILE B 285    18657 14775 13431  -3238  1757  2670       C
ATOM   8507  CD1 ILE B 285       32.294 -24.410 108.462  1.00124.95      C
ANISOU 8507  CD1 ILE B 285    18029 15883 13564  -2024   892  2606       C
ATOM   8508  N   PRO B 286       28.622 -23.173 105.034  1.00131.33      N
ANISOU 8508  N   PRO B 286    18307 16767 14826  -3999  1622  2191       N
ATOM   8509  CA  PRO B 286       27.671 -23.053 103.918  1.00129.42      C
ANISOU 8509  CA  PRO B 286    17935 16532 14707  -4526  1782  2090       C
ATOM   8510  C   PRO B 286       26.414 -23.936 104.006  1.00130.73      C
ANISOU 8510  C   PRO B 286    18531 16292 14849  -4834  2066  2162       C
ATOM   8511  O   PRO B 286       25.342 -23.419 103.681  1.00128.74      O
ANISOU 8511  O   PRO B 286    18110 16128 14679  -5285  2130  2163       O
ATOM   8512  CB  PRO B 286       28.537 -23.406 102.709  1.00130.35      C
ANISOU 8512  CB  PRO B 286    17878 16769 14878  -4449  1790  1886       C
```

FIG. 13 Continued

```
ATOM   8513  CG  PRO B 286      29.852 -22.793 103.051  1.00130.44           C
ANISOU 8513  CG  PRO B 286    17566  17120  14875  -4049   1531   1875       C
ATOM   8514  CD  PRO B 286      30.005  22.955 104.555  1.00131.87           C
ANISOU 8514  CD  PRO B 286    18037  17127  14939  -3677   1432   2062       C
ATOM   8515  N   ILE B 287      26.510 -25.208 104.400  1.00124.64           N
ANISOU 8515  N   ILE B 287    18277  15086  13992  -4612   2207   2225       N
ATOM   8516  CA  ILE B 287      25.378 -26.077 104.685  1.00126.67           C
ANISOU 8516  CA  ILE B 287    18991  14930  14208  -4926   2465   2351       C
ATOM   8517  C   ILE B 287      24.345 -26.210 103.549  1.00125.75           C
ANISOU 8517  C   ILE B 287    18790  14776  14215  -5500   2639   2214       C
ATOM   8518  O   ILE B 287      23.709 -27.259 103.368  1.00128.54           O
ANISOU 8518  O   ILE B 287    19551  14719  14570  -5731   2846   2226       O
ATOM   8519  CB  ILE B 287      24.646 -25.607 106.000  1.00126.40           C
ANISOU 8519  CB  ILE B 287    19033  14965  14027  -5011   2494   2577       C
ATOM   8520  CG1 ILE B 287      25.509 -25.878 107.232  1.00128.96           C
ANISOU 8520  CG1 ILE B 287    19643  15207  14147  -4497   2359   2764       C
ATOM   8521  CG2 ILE B 287      23.273 -26.273 106.149  1.00128.20           C
ANISOU 8521  CG2 ILE B 287    19579  14907  14226  -5484   2787   2691       C
ATOM   8522  CD1 ILE B 287      25.682 -27.346 107.507  1.00133.81           C
ANISOU 8522  CD1 ILE B 287    20881  15268  14691  -4317   2462   2923       C
ATOM   8523  N   ALA B 288      24.172 -25.122 102.809  1.00191.66           N
ANISOU 8523  N   ALA B 288    26612  23546  22664  -5750   2521   2104       N
ATOM   8524  CA  ALA B 288      23.235 -25.058 101.706  1.00190.75           C
ANISOU 8524  CA  ALA B 288    26333  23493  22651  -6296   2608   1996       C
ATOM   8525  C   ALA B 288      23.964 -25.212 100.374  1.00190.94           C
ANISOU 8525  C   ALA B 288    26203  23656  22689  -6309   2560   1760       C
ATOM   8526  O   ALA B 288      23.445 -25.835  99.454  1.00192.37           O
ANISOU 8526  O   ALA B 288    26508  23707  22877  -6660   2693   1619       O
ATOM   8527  CB  ALA B 288      22.471 -23.758 101.758  1.00187.57           C
ANISOU 8527  CB  ALA B 288    25464  23447  22357  -6582   2482   2062       C
ATOM   8528  N   MET B 289      25.167 -24.647 100.270  1.00120.25           N
ANISOU 8528  N   MET B 289    16968  15003  13719  -5954   2378   1700       N
ATOM   8529  CA  MET B 289      25.965 -24.813  99.058  1.00121.15           C
ANISOU 8529  CA  MET B 289    16911  15322  13799  -5943   2373   1458       C
ATOM   8530  C   MET B 289      25.920 -26.271  98.601  1.00125.16           C
ANISOU 8530  C   MET B 289    17889  15395  14270  -5918   2613   1255       C
ATOM   8531  O   MET B 289      26.146 -26.556  97.434  1.00126.49           O
ANISOU 8531  O   MET B 289    17980  15693  14388  -6080   2685    995       O
ATOM   8532  CB  MET B 289      27.397 -24.348  99.263  1.00121.05           C
ANISOU 8532  CB  MET B 289    16624  15609  13760   5464   2201   1422       C
ATOM   8533  CG  MET B 289      28.410 -25.221  98.578  1.00124.48           C
ANISOU 8533  CG  MET B 289    17135  16021  14141  -5163   2312   1146       C
ATOM   8534  SD  MET B 289      30.011 -24.410  98.413  1.00124.33           S
ANISOU 8534  SD  MET B 289    16565  16580  14096  -4791   2109   1069       S
ATOM   8535  CE  MET B 289      29.550 -23.004  97.389  1.00120.73           C
ANISOU 8535  CE  MET B 289    15576  16680  13617   5450   1963   1139       C
ATOM   8536  N   PRO B 290      25.673 -27.210  99.531  1.00192.26           N
ANISOU 8536  N   PRO B 290    26900  23369  22781  -5712   2730   1367       N
ATOM   8537  CA  PRO B 290      25.390 -28.570  99.068  1.00196.42           C
ANISOU 8537  CA  PRO B 290    27917  23391  23321  -5801   2941   1189       C
ATOM   8538  C   PRO B 290      23.941 -28.658  98.608  1.00195.95           C
ANISOU 8538  C   PRO B 290    27930  23245  23276   6488   3061   1212       C
ATOM   8539  O   PRO B 290      23.670 -29.286  97.589  1.00198.13           O
ANISOU 8539  O   PRO B 290    28338  23402  23540  -6784   3175    955       O
ATOM   8540  CB  PRO B 290      25.579 -29.426 100.324  1.00199.51           C
ANISOU 8540  CB  PRO B 290    28833  23245  23727  -5388   2972   1396       C
ATOM   8541  CG  PRO B 290      26.440 -28.627 101.212  1.00197.59           C
ANISOU 8541  CG  PRO B 290    28322  23310  23442  -4926   2763   1570       C
ATOM   8542  CD  PRO B 290      26.080 -27.196 100.946  1.00192.64           C
ANISOU 8542  CD  PRO B 290    27121  23267  22806  -5260   2641   1611       C
ATOM   8543  N   THR B 291      23.022 -28.038  99.344  1.00146.75           N
ANISOU 8543  N   THR B 291    21591  17100  17068  -6739   3034   1486       N
ATOM   8544  CA  THR B 291      21.611 -28.103  98.962  1.00146.75           C
ANISOU 8544  CA  THR B 291    21590  17059  17109  -7384   3138   1517       C
ATOM   8545  C   THR B 291      21.017 -26.692  98.216  1.00143.20           C
ANISOU 8545  C   THR B 291    20555  17147  16709  -7798   2984   1517       C
ATOM   8546  O   THR B 291      20.265 -27.085  97.272  1.00144.04           O
ANISOU 8546  O   THR B 291    20610  17296  16823  -8296   3018   1403       O
ATOM   8547  CB  THR B 291      20.687 -28.547 100.124  1.00148.34           C
```

FIG. 13 Continued

```
ANISOU 8547  CB   THR B 291    22125  16921  17316  -7521   3288   1783         C
ATOM   8548  OG1  THR B 291       21.250 -29.692 100.777  1.00152.27            O
ANISOU 8548  OG1  THR B 291    23210  16878  17767  -7158   3385   1839         O
ATOM   8549  CG2  THR B 291       19.305 -28.922  99.588  1.00149.78            C
ANISOU 8549  CG2  THR B 291    22351  17004  17553  -8205   3428   1760         C
ATOM   8550  N    VAL B 292       21.316 -25.658  98.605  1.00153.53            N
ANISOU 8550  N    VAL B 292    21435  18841  18060  -7619   2786   1648         N
ATOM   8551  CA   VAL B 292       20.766 -24.544  97.829  1.00150.94            C
ANISOU 8551  CA   VAL B 292    20586  18948  17818  -8004   2595   1670         C
ATOM   8552  C    VAL B 292       21.152 -24.686  96.369  1.00151.72            C
ANISOU 8552  C    VAL B 292    20578  19252  17819  -8233   2545   1459         C
ATOM   8553  O    VAL B 292       20.315 -24.976  95.515  1.00152.98            O
ANISOU 8553  O    VAL B 292    20738  19427  17963  -8729   2578   1381         O
ATOM   8554  CB   VAL B 292       21.291 -23.165  98.256  1.00147.69            C
ANISOU 8554  CB   VAL B 292    19739  18893  17485  -7751   2338   1796         C
ATOM   8555  CG1  VAL B 292       20.587 -22.672  99.506  1.00146.79            C
ANISOU 8555  CG1  VAL B 292    19579  18720  17475  -7675   2349   1968         C
ATOM   8556  CG2  VAL B 292       22.795 -23.197  98.403  1.00147.70            C
ANISOU 8556  CG2  VAL B 292    19773  18963  17385  -7248   2274   1723         C
ATOM   8557  N    LEU B 293       22.433 -24.477  96.094  1.00110.82            N
ANISOU 8557  N    LEU B 293    15286  14273  12548  -7886   2468   1356         N
ATOM   8558  CA   LEU B 293       22.946 -24.536  94.743  1.00111.98            C
ANISOU 8558  CA   LEU B 293    15290  14714  12542  -8076   2446   1138         C
ATOM   8559  C    LEU B 293       22.407 -25.728  93.969  1.00115.50            C
ANISOU 8559  C    LEU B 293    16099  14897  12887  -8398   2656    887         C
ATOM   8560  O    LEU B 293       22.271 -25.660  92.751  1.00116.52            O
ANISOU 8560  O    LEU B 293    16084  15318  12872  -8794   2619    734         O
ATOM   8561  CB   LEU B 293       24.461 -24.552  94.767  1.00112.59            C
ANISOU 8561  CB   LEU B 293    15301  14948  12529  -7569   2443   1006         C
ATOM   8562  CG   LEU B 293       25.011 -23.198  95.195  1.00109.40            C
ANISOU 8562  CG   LEU B 293    14447  14919  12200  -7408   2177   1227         C
ATOM   8563  CD1  LEU B 293       26.529 -23.246  95.296  1.00110.47            C
ANISOU 8563  CD1  LEU B 293    14479  15238  12256  -6910   2172   1101         C
ATOM   8564  CD2  LEU B 293       24.552 -22.142  94.199  1.00107.84            C
ANISOU 8564  CD2  LEU B 293    13826  15157  11990  -7936   1957   1341         C
ATOM   8565  N    SER B 294       22.107 -26.819  94.668  1.00142.74            N
ANISOU 8565  N    SER B 294    20044  17796  16396  -8256   2860    850         N
ATOM   8566  CA   SER B 294       21.499 -27.985  94.028  1.00146.59            C
ANISOU 8566  CA   SER B 294    20928  17941  16828  -8602   3045    612         C
ATOM   8567  C    SER B 294       20.057 -27.666  93.632  1.00145.96            C
ANISOU 8567  C    SER B 294    20683  17982  16794  -9276   2976    736         C
ATOM   8568  O    SER B 294       19.695 -27.740  92.459  1.00147.38            O
ANISOU 8568  O    SER B 294    20772  18376  16849  -9734   2937    557         O
ATOM   8569  CB   SER B 294       21.550 -29.212  94.961  1.00149.77            C
ANISOU 8569  CB   SER B 294    21932  17659  17315  -8293   3245    605         C
ATOM   8570  OG   SER B 294       20.627 -30.242  94.606  1.00153.42            O
ANISOU 8570  OG   SER B 294    22798  17705  17790  -8740   3398    474         O
ATOM   8571  N    VAL B 295       19.246 -27.285  94.615  1.00181.04            N
ANISOU 8571  N    VAL B 295    25053  22333  21400  -9332   2956   1032         N
ATOM   8572  CA   VAL B 295       17.824 -27.029  94.395  1.00181.04            C
ANISOU 8572  CA   VAL B 295    24858  22435  21496  -9921   2905   1154         C
ATOM   8573  C    VAL B 295       17.562 -25.914  93.397  1.00179.04            C
ANISOU 8573  C    VAL B 295    24057  22740  21231 -10251   2622   1202         C
ATOM   8574  O    VAL B 295       16.794 -26.084  92.461  1.00180.83            O
ANISOU 8574  O    VAL B 295    24211  23092  21405 -10788   2561   1121         O
ATOM   8575  CB   VAL B 295       17.089 -26.731  95.713  1.00179.91            C
ANISOU 8575  CB   VAL B 295    24667  22167  21524  -9852   2964   1436         C
ATOM   8576  CG1  VAL B 295       17.300 -27.876  96.697  1.00182.62            C
ANISOU 8576  CG1  VAL B 295    25599  21954  21835  -9594   3224   1456         C
ATOM   8577  CG2  VAL B 295       17.558 -25.410  96.301  1.00175.97            C
ANISOU 8577  CG2  VAL B 295    23746  22005  21110  -9481   2767   1615         C
ATOM   8578  N    THR B 296       18.193 -24.770  93.590  1.00135.04            N
ANISOU 8578  N    THR B 296    18111  17493  15706  -9958   2419   1351         N
ATOM   8579  CA   THR B 296       18.011 -23.695  92.644  1.00133.69            C
ANISOU 8579  CA   THR B 296    17458  17807  15532 -10227   2111   1451         C
ATOM   8580  C    THR B 296       18.333 -24.194  91.227  1.00136.25            C
ANISOU 8580  C    THR B 296    17870  18332  15567 -10600   2113   1204         C
ATOM   8581  O    THR B 296       17.880 -23.604  90.254  1.00136.56            O
ANISOU 8581  O    THR B 296    17604  18743  15540  11043   1874   1281         O
```

FIG. 13 Continued

```
ATOM   8582  CB  THR B 296      18.872 -22.458  93.030  1.00130.45           C
ANISOU 8582  CB  THR B 296    16700  17663  15202  -9890   1889   1627       C
ATOM   8583  OG1 THR B 296      19.024 -21.575  91.908  1.00130.08           O
ANISOU 8583  OG1 THR B 296    16278  18068  15078 -10193   1593   1713       O
ATOM   8584  CG2 THR B 296      20.247 -22.885  93.506  1.00130.36           C
ANISOU 8584  CG2 THR B 296    16931  17533  15067  -9343   2044   1491       C
ATOM   8585  N   MET B 297      19.074 -25.302  91.117  1.00121.99           N
ANISOU 8585  N   MET B 297    16491  16271  13588 -10385   2376    899       N
ATOM   8586  CA  MET B 297      19.553 -25.831  89.820  1.00125.06           C
ANISOU 8586  CA  MET B 297    16986  16865  13666 -10613   2434    568       C
ATOM   8587  C   MET B 297      18.858 -27.086  89.303  1.00129.30           C
ANISOU 8587  C   MET B 297    17943  17080  14107 -10994   2619    270       C
ATOM   8588  O   MET B 297      19.177 -27.578  88.221  1.00132.48           O
ANISOU 8588  O   MET B 297    18463  17642  14230 -11209   2682    -66       O
ATOM   8589  CB  MET B 297      21.034 -26.121  89.924  1.00125.62           C
ANISOU 8589  CB  MET B 297    17175  16938  13617 -10054   2586    351       C
ATOM   8590  CG  MET B 297      21.815 -26.097  88.662  1.00127.85           C
ANISOU 8590  CG  MET B 297    17327  17682  13566 -10191   2598     78       C
ATOM   8591  SD  MET B 297      23.461 -26.318  89.332  1.00127.92           S
ANISOU 8591  SD  MET B 297    17387  17618  13598  -9375   2768    -78       S
ATOM   8592  CE  MET B 297      24.498 -25.438  88.164  1.00128.42           C
ANISOU 8592  CE  MET B 297    16957  18507  13330  -9512   2669   -150       C
ATOM   8593  N   ALA B 298      17.977 -27.641  90.122  1.00122.21           N
ANISOU 8593  N   ALA B 298    14693  16657  13085  -6812  -1295   3848       N
ATOM   8594  CA  ALA B 298      17.101 -28.726  89.712  1.00121.92           C
ANISOU 8594  CA  ALA B 298    14797  18265  13261  -6547  -1643   3958       C
ATOM   8595  C   ALA B 298      15.722 -28.053  89.589  1.00119.95           C
ANISOU 8595  C   ALA B 298    14747  17743  13084  -6701  -1466   4030       C
ATOM   8596  O   ALA B 298      14.757 -28.583  88.989  1.00119.28           O
ANISOU 8596  O   ALA B 298    14819  17342  13160  -6517  -1644   4089       O
ATOM   8597  CB  ALA B 298      17.091 -29.833  90.750  1.00123.04           C
ANISOU 8597  CB  ALA B 298    14855  18401  13495  -6561  -1998   4143       C
ATOM   8598  N   ILE B 299      15.662 -26.860  90.182  1.00126.54           N
ANISOU 8598  N   ILE B 299    15566  18720  13795  -7048  -1101   4017       N
ATOM   8599  CA  ILE B 299      14.481 -26.016  90.150  1.00124.88           C
ANISOU 8599  CA  ILE B 299    15523  18301  13626  -7220   -855   4078       C
ATOM   8600  C   ILE B 299      14.611 -25.120  88.945  1.00124.36           C
ANISOU 8600  C   ILE B 299    15540  18215  13497  -7098   -545   3928       C
ATOM   8601  O   ILE B 299      13.654 -24.475  88.536  1.00123.15           O
ANISOU 8601  O   ILE B 299    15540  17863  13388  -7125   -349   3970       O
ATOM   8602  CB  ILE B 299      14.344 -25.162  91.420  1.00124.63           C
ANISOU 8602  CB  ILE B 299    15439  18418  13496  -7656   -595   4131       C
ATOM   8603  CG1 ILE B 299      12.864 -25.032  91.804  1.00123.28           C
ANISOU 8603  CG1 ILE B 299    15421  17972  13446  -7788   -583   4300       C
ATOM   8604  CG2 ILE B 299      15.035 -23.813  91.250  1.00124.73           C
ANISOU 8604  CG2 ILE B 299    15415  18637  13341  -7847   -132   3954       C
ATOM   8605  CD1 ILE B 299      12.187 -26.376  92.177  1.00123.44           C
ANISOU 8605  CD1 ILE B 299    15462  17804  13635  -7668  -1036   4490       C
ATOM   8606  N   GLY B 300      15.820 -25.065  88.398  1.00145.76           N
ANISOU 8606  N   GLY B 300    18135  21151  16095  -6962   -491   3766       N
ATOM   8607  CA  GLY B 300      16.058 -24.352  87.163  1.00145.57           C
ANISOU 8607  CA  GLY B 300    18176  21128  16007  -6801   -231   3629       C
ATOM   8608  C   GLY B 300      15.382 -25.206  86.115  1.00145.26           C
ANISOU 8608  C   GLY B 300    18260  20830  16101  -6428   -515   3655       C
ATOM   8609  O   GLY B 300      14.724 -24.703  85.211  1.00144.46           O
ANISOU 8609  O   GLY B 300    18295  20577  16015  -6317   -357   3650       O
ATOM   8610  N   SER B 301      15.524 -26.518  86.271  1.00128.25           N
ANISOU 8610  N   SER B 301    16056  18627  14046  -6240   -938   3689       N
ATOM   8611  CA  SER B 301      14.899 -27.488  85.378  1.00128.30           C
ANISOU 8611  CA  SER B 301    16173  18379  14195  -5905  -1251   3696       C
ATOM   8612  C   SER B 301      13.399 -27.284  85.216  1.00126.86           C
ANISOU 8612  C   SER B 301    16168  17909  14123  -5955  -1232   3822       C
ATOM   8613  O   SER B 301      12.882 -27.343  84.105  1.00126.62           O
ANISOU 8613  O   SER B 301    16244  17741  14123  -5721  -1256   3775       O
ATOM   8614  CB  SER B 301      15.136 -28.912  85.877  1.00129.53           C
ANISOU 8614  CB  SER B 301    16261  18478  14476   5772   1693   3752       C
ATOM   8615  OG  SER B 301      14.005 -29.732  85.612  1.00129.19           O
ANISOU 8615  OG  SER B 301    16360  18106  14620  -5641  -1974   3844       O
ATOM   8616  N   HIS B 302      12.688 -27.058  86.314  1.00112.21           N
```

FIG. 13 Continued

```
ANISOU 8616  N   HIS B 302     14334  15984  12317  -6253  -1192   3984       N
ATOM   8617  CA  HIS B 302      11.253 -26.919  86.176  1.00111.00           C
ANISOU 8617  CA  HIS B 302     14333  15573  12271  -6289  -1189   4112       C
ATOM   8618  C   HIS B 302      10.862 -25.728  85.321  1.00110.13           C
ANISOU 8618  C   HIS B 302     14317  15450  12076  -6270   -810   4070       C
ATOM   8619  O   HIS B 302      10.236 -25.902  84.288  1.00109.94           O
ANISOU 8619  O   HIS B 302     14390  15287  12096  -6034   -881   4058       O
ATOM   8620  CB  HIS B 302      10.517 -26.916  87.509  1.00110.40           C
ANISOU 8620  CB  HIS B 302     14258  15429  12262  -6605  -1216   4299       C
ATOM   8621  CG  HIS B 302       9.403 -27.912  87.553  1.00110.27           C
ANISOU 8621  CG  HIS B 302     14326  15141  12430  -6524  -1562   4438       C
ATOM   8622  ND1 HIS B 302       8.758 -28.344  86.413  1.00110.22           N
ANISOU 8622  ND1 HIS B 302     14425  14946  12509  -6253  -1713   4401       N
ATOM   8623  CD2 HIS B 302       8.837 -28.585  88.584  1.00110.37           C
ANISOU 8623  CD2 HIS B 302     14327  15053  12557  -6684  -1791   4611       C
ATOM   8624  CE1 HIS B 302       7.838 -29.234  86.740  1.00110.32           C
ANISOU 8624  CE1 HIS B 302     14488  14741  12686  -6262  -2017   4534       C
ATOM   8625  NE2 HIS B 302       7.866 -29.400  88.051  1.00110.39           N
ANISOU 8625  NE2 HIS B 302     14430  14791  12722  -6518  -2068   4672       N
ATOM   8626  N   ARG B 303      11.230 -24.521  85.716  1.00146.31           N
ANISOU 8626  N   ARG B 303     18873  20179  16538  -6512   -404   4047       N
ATOM   8627  CA  ARG B 303      10.857 -23.381  84.894  1.00145.71           C
ANISOU 8627  CA  ARG B 303     18897  20068  16398  -6479    -26   4031       C
ATOM   8628  C   ARG B 303      11.366 -23.528  83.449  1.00146.37           C
ANISOU 8628  C   ARG B 303     18989  20206  16420  -6126    -52   3895       C
ATOM   8629  O   ARG B 303      10.909 -22.825  82.545  1.00146.06           O
ANISOU 8629  O   ARG B 303     19041  20113  16341  -6010    178   3907       O
ATOM   8630  CB  ARG B 303      11.272 -22.056  85.545  1.00145.59           C
ANISOU 8630  CB  ARG B 303     18855  20187  16274  -6803    437   4006       C
ATOM   8631  CG  ARG B 303      12.237 -22.205  86.712  1.00146.30           C
ANISOU 8631  CG  ARG B 303     18792  20495  16301  -7058    403   3950       C
ATOM   8632  CD  ARG B 303      11.990 -21.159  87.817  1.00145.94           C
ANISOU 8632  CD  ARG B 303     18753  20484  16214  -7467    753   3994       C
ATOM   8633  NE  ARG B 303      12.177 -19.782  87.355  1.00145.98           N
ANISOU 8633  NE  ARG B 303     18820  20511  16136  -7562   1251   3917       N
ATOM   8634  CZ  ARG B 303      12.577 -18.781  88.135  1.00146.39           C
ANISOU 8634  CZ  ARG B 303     18836  20680  16104  -7909   1616   3851       C
ATOM   8635  NH1 ARG B 303      12.843 -19.012  89.417  1.00146.75           N
ANISOU 8635  NH1 ARG B 303     18771  20870  16116  -8193   1527   3849       N
ATOM   8636  NH2 ARG B 303      12.723 -17.556  87.632  1.00146.63           N
ANISOU 8636  NH2 ARG B 303     18940  20689  16084  -7976   2075   3786       N
ATOM   8637  N   LEU B 304      12.291 -24.460  83.227  1.00109.53           N
ANISOU 8637  N   LEU B 304     14223  15651  11742  -5941   -332   3775       N
ATOM   8638  CA  LEU B 304      12.803 -24.715  81.878  1.00110.36           C
ANISOU 8638  CA  LEU B 304     14325  15821  11784  -5593   -387   3630       C
ATOM   8639  C   LEU B 304      11.751 -25.444  81.067  1.00110.19           C
ANISOU 8639  C   LEU B 304     14416  15583  11867  -5339   -660   3668       C
ATOM   8640  O   LEU B 304      11.092 -24.882  80.200  1.00109.80           O
ANISOU 8640  O   LEU B 304     14459  15478  11780  -5228   -495   3695       O
ATOM   8641  CB  LEU B 304      14.038 -25.608  81.942  1.00111.75           C
ANISOU 8641  CB  LEU B 304     14359  16165  11935  -5456   -636   3493       C
ATOM   8642  CG  LEU B 304      15.110 -25.321  80.901  1.00112.80           C
ANISOU 8642  CG  LEU B 304     14423  16514  11920  -5240   -489   3314       C
ATOM   8643  CD1 LEU B 304      14.442 -24.697  79.706  1.00112.35           C
ANISOU 8643  CD1 LEU B 304     14491  16380  11817  -5075   -295   3316       C
ATOM   8644  CD2 LEU B 304      16.175 -24.387  81.463  1.00113.16           C
ANISOU 8644  CD2 LEU B 304     14345  16825  11825  -5490   -150   3257       C
ATOM   8645  N   SER B 305      11.627 -26.721  81.391  1.00110.81           N
ANISOU 8645  N   SER B 305     14478  15549  12077  -5254  -1080   3673       N
ATOM   8646  CA  SER B 305      10.679 -27.651  80.798  1.00111.00           C
ANISOU 8646  CA  SER B 305     14592  15354  12227  -5047  -1409   3690       C
ATOM   8647  C   SER B 305       9.200 -27.237  80.838  1.00109.81           C
ANISOU 8647  C   SER B 305     14557  15022  12142  -5159  -1336   3856       C
ATOM   8648  O   SER B 305       8.301 -28.078  80.732  1.00109.94           O
ANISOU 8648  O   SER B 305     14633  14847  12292  -5087  -1638   3906       O
ATOM   8649  CB  SER B 305      10.867 -29.003  81.477  1.00111.88           C
ANISOU 8649  CB  SER B 305     14661  15358  12492  -5025  -1826   3698       C
ATOM   8650  OG  SER B 305      11.528 -28.853  82.730  1.00111.84           O
ANISOU 8650  OG  SER B 305     14551  15473  12470  -5277  -1763   3766       O
```

FIG. 13 Continued

```
ATOM   8651  N   GLN B 306       8.954 -25.948  81.030  1.00145.58           N
ANISOU 8651  N   GLN B 306    19115  19614  16586  -5345   -931   3944       N
ATOM   8652  CA  GLN B 306       7.606 -25.410  80.943  1.00144.63           C
ANISOU 8652  CA  GLN B 306    19094  19353  16505  -5414   -807   4103       C
ATOM   8653  C   GLN B 306       7.600 -24.432  79.770  1.00144.69           C
ANISOU 8653  C   GLN B 306    19146  19457  16373  -5243   -483   4068       C
ATOM   8654  O   GLN B 306       6.550 -23.969  79.298  1.00144.27           O
ANISOU 8654  O   GLN B 306    19170  19326  16320  -5194   -370   4183       O
ATOM   8655  CB  GLN B 306       7.194 -24.744  82.255  1.00143.61           C
ANISOU 8655  CB  GLN B 306    18969  19184  16414  -5776   -600   4261       C
ATOM   8656  CG  GLN B 306       6.588 -25.724  83.251  1.00143.47           C
ANISOU 8656  CG  GLN B 306    18942  19018  16554  -5917   -943   4372       C
ATOM   8657  CD  GLN B 306       5.777 -25.041  84.330  1.00142.46           C
ANISOU 8657  CD  GLN B 306    18841  18827  16462  -6235   -740   4551       C
ATOM   8658  OE1 GLN B 306       4.847 -25.625  84.889  1.00142.21           O
ANISOU 8658  OE1 GLN B 306    18830  18648  16554  -6327   -961   4686       O
ATOM   8659  NE2 GLN B 306       6.126 -23.793  84.628  1.00142.05           N
ANISOU 8659  NE2 GLN B 306    18786  18883  16303  -6411   -309   4548       N
ATOM   8660  N   GLN B 307       8.817 -24.161  79.305  1.00159.36           N
ANISOU 8660  N   GLN B 307    20941  21500  18107  -5145   -342   3917       N
ATOM   8661  CA  GLN B 307       9.118 -23.270  78.194  1.00159.75           C
ANISOU 8661  CA  GLN B 307    21012  21681  18006  -4978    -26   3869       C
ATOM   8662  C   GLN B 307       9.047 -24.032  76.872  1.00160.75           C
ANISOU 8662  C   GLN B 307    21147  21840  18092  -4608   -285   3753       C
ATOM   8663  O   GLN B 307       8.819 -23.458  75.804  1.00161.11           O
ANISOU 8663  O   GLN B 307    21230  21960  18025  -4422    -99   3761       O
ATOM   8664  CB  GLN B 307      10.543 -22.767  78.394  1.00160.29           C
ANISOU 8664  CB  GLN B 307    20988  21952  17965  -5065    205   3746       C
ATOM   8665  CG  GLN B 307      10.807 -21.335  78.013  1.00160.32           C
ANISOU 8665  CG  GLN B 307    21019  22052  17845  -5133    714   3777       C
ATOM   8666  CD  GLN B 307      12.032 -20.808  78.721  1.00160.69           C
ANISOU 8666  CD  GLN B 307    20968  22261  17824  -5368    946   3685       C
ATOM   8667  OE1 GLN B 307      12.234 -21.071  79.910  1.00160.36           O
ANISOU 8667  OE1 GLN B 307    20871  22213  17844  -5618    852   3690       O
ATOM   8668  NE2 GLN B 307      12.865 -20.071  77.995  1.00161.53           N
ANISOU 8668  NE2 GLN B 307    21045  22536  17794  -5297   1247   3602       N
ATOM   8669  N   GLY B 308       9.281 -25.336  76.974  1.00111.13           N
ANISOU 8669  N   GLY B 308    14825  15503  11897  -4503   -708   3642       N
ATOM   8670  CA  GLY B 308       9.261 -26.251  75.849  1.00112.34           C
ANISOU 8670  CA  GLY B 308    14984  15667  12034  -4170  -1004   3492       C
ATOM   8671  C   GLY B 308      10.371 -27.281  75.977  1.00113.49           C
ANISOU 8671  C   GLY B 308    15046  15861  12214  -4059  -1281   3309       C
ATOM   8672  O   GLY B 308      10.178 -28.478  75.715  1.00114.43           O
ANISOU 8672  O   GLY B 308    15179  15862  12435  -3892  -1665   3212       O
ATOM   8673  N   ALA B 309      11.531 -26.787  76.413  1.00120.52           N
ANISOU 8673  N   ALA B 309    15846  16923  13023  -4161  -1070   3264       N
ATOM   8674  CA  ALA B 309      12.759 -27.566  76.535  1.00121.76           C
ANISOU 8674  CA  ALA B 309    15896  17190  13179  -4050  -1259   3101       C
ATOM   8675  C   ALA B 309      12.970 -28.356  77.855  1.00121.76           C
ANISOU 8675  C   ALA B 309    15842  17090  13331  -4228  -1509   3160       C
ATOM   8676  O   ALA B 309      12.978 -27.801  78.961  1.00120.83           O
ANISOU 8676  O   ALA B 309    15694  16989  13226  -4537  -1346   3290       O
ATOM   8677  CB  ALA B 309      13.966 -26.656  76.237  1.00122.19           C
ANISOU 8677  CB  ALA B 309    15854  17526  13046  -4051   -910   3014       C
ATOM   8678  N   ILE B 310      13.152 -29.663  77.705  1.00119.96           N
ANISOU 8678  N   ILE B 310    15602  16761  13215  -4023  -1899   3060       N
ATOM   8679  CA  ILE B 310      13.450 -30.568  78.801  1.00120.46           C
ANISOU 8679  CA  ILE B 310    15610  16735  13425  -4119  -2168   3114       C
ATOM   8680  C   ILE B 310      14.966 -30.516  79.048  1.00121.50           C
ANISOU 8680  C   ILE B 310    15582  17132  13451  -4082  -2088   3012       C
ATOM   8681  O   ILE B 310      15.645 -29.616  78.557  1.00121.47           O
ANISOU 8681  O   ILE B 310    15519  17365  13268  -4069  -1781   2930       O
ATOM   8682  CB  ILE B 310      12.992 -31.992  78.398  1.00121.75           C
ANISOU 8682  CB  ILE B 310    15842  16652  13765  -3883  -2602   3041       C
ATOM   8683  CG1 ILE B 310      11.477 -31.999  78.167  1.00120.84           C
ANISOU 8683  CG1 ILE B 310    15865  16309  13740  -3947  -2674   3141       C
ATOM   8684  CG2 ILE B 310      13.412 -33.045  79.419  1.00122.76           C
ANISOU 8684  CG2 ILE B 310    15911  16676  14055  -3921  -2896   3099       C
ATOM   8685  CD1 ILE B 310      10.858  33.372  78.008  1.00122.08           C
```

FIG. 13 Continued

```
ANISOU 8685  CD1 ILE B 310    16097  16187  14102  -3809  -3095   3097        C
ATOM   8686  N   THR B 311    15.497 -31.446  79.837  1.00118.95              N
ANISOU 8686  N   THR B 311    15179  16783  13234  -4076  -2349   3032        N
ATOM   8687  CA  THR B 311    16.948 -31.594  79.967  1.00120.36              C
ANISOU 8687  CA  THR B 311    15188  17226  13319  -3979  -2331   2925        C
ATOM   8688  C   THR B 311    17.291 -33.065  80.083  1.00122.26              C
ANISOU 8688  C   THR B 311    15400  17333  13720  -3739  -2738   2882        C
ATOM   8689  O   THR B 311    16.448 -33.895  80.462  1.00122.32              O
ANISOU 8689  O   THR B 311    15505  17047  13925  -3753  -3013   2984        O
ATOM   8690  CB  THR B 311    17.571 -30.891  81.182  1.00119.89              C
ANISOU 8690  CB  THR B 311    14991  17393  13169  -4307  -2122   3034        C
ATOM   8691  OG1 THR B 311    19.004 -30.918  81.056  1.00121.41              O
ANISOU 8691  OG1 THR B 311    15005  17893  13233  -4184  -2068   2901        O
ATOM   8692  CG2 THR B 311    17.167 -31.613  82.456  1.00119.91              C
ANISOU 8692  CG2 THR B 311    14986  17245  13331  -4479  -2372   3220        C
ATOM   8693  N   LYS B 312    18.535 -33.377  79.731  1.00127.33              N
ANISOU 8693  N   LYS B 312    15908  18189  14281  -3513  -2763   2732        N
ATOM   8694  CA  LYS B 312    19.032 -34.736  79.795  1.00129.50              C
ANISOU 8694  CA  LYS B 312    16142  18359  14703  -3245  -3115   2680        C
ATOM   8695  C   LYS B 312    19.944 -34.816  80.992  1.00130.23              C
ANISOU 8695  C   LYS B 312    16051  18662  14769  -3386  -3123   2799        C
ATOM   8696  O   LYS B 312    19.709 -35.579  81.921  1.00130.78              O
ANISOU 8696  O   LYS B 312    16118  18573  14998  -3452  -3360   2961        O
ATOM   8697  CB  LYS B 312    19.785 -35.104  78.513  1.00131.24              C
ANISOU 8697  CB  LYS B 312    16332  18681  14851  -2853  -3150   2421        C
ATOM   8698  CG  LYS B 312    20.277 -36.548  78.477  1.00133.79              C
ANISOU 8698  CG  LYS B 312    16631  18860  15344  -2537  -3506   2346        C
ATOM   8699  CD  LYS B 312    19.149 -37.535  78.750  1.00133.97              C
ANISOU 8699  CD  LYS B 312    16824  18446  15633  -2540  -3822   2439        C
ATOM   8700  CE  LYS B 312    18.640 -38.153  77.475  1.00134.98              C
ANISOU 8700  CE  LYS B 312    17097  18355  15832  -2251  -3976   2221        C
ATOM   8701  NZ  LYS B 312    19.772 -38.760  76.735  1.00137.46              N
ANISOU 8701  NZ  LYS B 312    17323  18798  16108  -1870  -4051   1991        N
ATOM   8702  N   ARG B 313    20.988 -34.007  80.973  1.00171.00              N
ANISOU 8702  N   ARG B 313    21050  24201  19721  -3441  -2858   2726        N
ATOM   8703  CA  ARG B 313    21.897 -33.962  82.096  1.00171.80              C
ANISOU 8703  CA  ARG B 313    20948  24571  19756  -3600  -2838   2827        C
ATOM   8704  C   ARG B 313    22.112 -32.484  82.355  1.00170.30              C
ANISOU 8704  C   ARG B 313    20688  24666  19353  -3938  -2425   2831        C
ATOM   8705  O   ARG B 313    23.167 -31.911  82.056  1.00171.04              O
ANISOU 8705  O   ARG B 313    20628  25098  19262  -3918  -2212   2706        O
ATOM   8706  CB  ARG B 313    23.178 -34.749  81.797  1.00174.43              C
ANISOU 8706  CB  ARG B 313    21113  25097  20065  -3261  -2990   2704        C
ATOM   8707  CG  ARG B 313    22.912 -36.264  81.588  1.00176.19              C
ANISOU 8707  CG  ARG B 313    21428  24980  20534  -2926  -3395   2703        C
ATOM   8708  CD  ARG B 313    24.184 -37.065  81.272  1.00179.05              C
ANISOU 8708  CD  ARG B 313    21627  25518  20885  -2557  -3537   2580        C
ATOM   8709  NE  ARG B 313    23.931 -38.408  80.733  1.00180.91              N
ANISOU 8709  NE  ARG B 313    21984  25401  21351  -2191  -3869   2507        N
ATOM   8710  CZ  ARG B 313    24.014 -38.734  79.442  1.00181.87              C
ANISOU 8710  CZ  ARG B 313    22185  25439  21478  -1863  -3904   2262        C
ATOM   8711  NH1 ARG B 313    24.332 -37.818  78.535  1.00181.09              N
ANISOU 8711  NH1 ARG B 313    22053  25591  21161  -1844  -3632   2086        N
ATOM   8712  NH2 ARG B 313    23.777 -39.979  79.053  1.00183.79              N
ANISOU 8712  NH2 ARG B 313    22542  25346  21944  -1558  -4205   2188        N
ATOM   8713  N   MET B 314    21.052 -31.897  82.913  1.00141.37              N
ANISOU 8713  N   MET B 314    17146  20839  15729  -4251  -2314   2975        N
ATOM   8714  CA  MET B 314    20.926 -30.466  83.188  1.00139.77              C
ANISOU 8714  CA  MET B 314    16938  20797  15372  -4603  -1911   2995        C
ATOM   8715  C   MET B 314    22.168 -29.785  83.758  1.00140.63              C
ANISOU 8715  C   MET B 314    16819  21330  15283  -4793  -1680   2945        C
ATOM   8716  O   MET B 314    22.272 -28.561  83.763  1.00139.76              O
ANISOU 8716  O   MET B 314    16696  21374  15031  -5047  -1308   2906        O
ATOM   8717  CB  MET B 314    19.707 -30.191  84.091  1.00138.03              C
ANISOU 8717  CB  MET B 314    16841  20355  15250  -4921  -1895   3193        C
ATOM   8718  CG  MET B 314    19.936  30.350  85.600  1.00138.40              C
ANISOU 8718  CG  MET B 314    16758  20530  15297  -5200  -1969   3352        C
ATOM   8719  SD  MET B 314    19.199 -31.833  86.309  1.00139.01              S
ANISOU 8719  SD  MET B 314    16900  20293  15624  -5105  -2441   3552        S
```

FIG. 13 Continued

```
ATOM   8720  CE   MET B 314      18.897 -31.318  88.002  1.00138.29           C
ANISOU 8720  CE   MET B 314    16731  20330  15482  -5583  -2338   3765       C
ATOM   8721  N    THR B 315      23.116 -30.566  84.239  1.00182.28           N
ANISOU 8721  N    THR B 315    21910  26799  20550  -4676  -1890   2948       N
ATOM   8722  CA   THR B 315      24.312 -29.948  84.758  1.00183.32           C
ANISOU 8722  CA   THR B 315    21803  27371  20481  -4857  -1684   2892       C
ATOM   8723  C    THR B 315      24.918 -29.052  83.673  1.00183.39           C
ANISOU 8723  C    THR B 315    21784  27570  20326  -4793  -1361   2694       C
ATOM   8724  O    THR B 315      25.575 -28.054  83.987  1.00183.54           O
ANISOU 8724  O    THR B 315    21671  27898  20169  -5066  -1047   2637       O
ATOM   8725  CB   THR B 315      25.313 -30.990  85.248  1.00185.72           C
ANISOU 8725  CB   THR B 315    21893  27881  20789  -4661  -1971   2918       C
ATOM   8726  OG1  THR B 315      24.609 -32.042  85.929  1.00185.84           O
ANISOU 8726  OG1  THR B 315    21988  27616  21007  -4605  -2317   3107       O
ATOM   8727  CG2  THR B 315      26.314 -30.342  86.200  1.00186.67           C
ANISOU 8727  CG2  THR B 315    21754  28467  20705  -4964  -1783   2922       C
ATOM   8728  N    ALA B 316      24.668 -29.397  82.405  1.00125.96           N
ANISOU 8728  N    ALA B 316    14637  20114  13108  -4450  -1432   2588       N
ATOM   8729  CA   ALA B 316      25.171 -28.614  81.267  1.00126.14           C
ANISOU 8729  CA   ALA B 316    14647  20302  12978  -4350  -1140   2416       C
ATOM   8730  C    ALA B 316      24.469 -27.257  81.140  1.00124.24           C
ANISOU 8730  C    ALA B 316    14542  19987  12675  -4653   -748   2448       C
ATOM   8731  O    ALA B 316      24.763 -26.480  80.229  1.00124.30           O
ANISOU 8731  O    ALA B 316    14560  20106  12561  -4608   -465   2340       O
ATOM   8732  CB   ALA B 316      25.063 -29.407  79.970  1.00126.87           C
ANISOU 8732  CB   ALA B 316    14833  20237  13136  -3894  -1340   2295       C
ATOM   8733  N    ILE B 317      23.547 -26.986  82.065  1.00126.99           N
ANISOU 8733  N    ILE B 317    14991  20148  13110  -4954   -727   2606       N
ATOM   8734  CA   ILE B 317      22.820 -25.720  82.101  1.00125.32           C
ANISOU 8734  CA   ILE B 317    14912  19840  12863  -5253   -355   2656       C
ATOM   8735  C    ILE B 317      23.742 -24.582  82.518  1.00125.91           C
ANISOU 8735  C    ILE B 317    14835  20248  12756  -5573     33   2581       C
ATOM   8736  O    ILE B 317      23.441 -23.412  82.305  1.00125.06           O
ANISOU 8736  O    ILE B 317    14821  20110  12596  -5781    414   2576       O
ATOM   8737  CB   ILE B 317      21.621 -25.774  83.054  1.00123.77           C
ANISOU 8737  CB   ILE B 317    14848  19373  12805  -5489   -441   2840       C
ATOM   8738  CG1  ILE B 317      20.649 -26.871  82.634  1.00123.30           C
ANISOU 8738  CG1  ILE B 317    14942  18972  12933  -5204   -813   2912       C
ATOM   8739  CG2  ILE B 317      20.905 -24.452  83.089  1.00122.28           C
ANISOU 8739  CG2  ILE B 317    14791  19086  12584  -5778    -37   2888       C
ATOM   8740  CD1  ILE B 317      20.887 -27.413  81.259  1.00124.15           C
ANISOU 8740  CD1  ILE B 317    15084  19048  13040  -4783   -940   2773       C
ATOM   8741  N    GLU B 318      24.867 -24.927  83.131  1.00225.39           N
ANISOU 8741  N    GLU B 318    27199  33173  25266  -5618    -59   2526       N
ATOM   8742  CA   GLU B 318      25.854 -23.920  83.468  1.00226.34           C
ANISOU 8742  CA   GLU B 318    27146  33652  25202  -5916    291   2426       C
ATOM   8743  C    GLU B 318      26.374 -23.428  82.132  1.00226.95           C
ANISOU 8743  C    GLU B 318    27227  33822  25180  -5712    517   2285       C
ATOM   8744  O    GLU B 318      26.977 -22.362  82.025  1.00227.51           O
ANISOU 8744  O    GLU B 318    27225  34105  25113  -5938    898   2197       O
ATOM   8745  CB   GLU B 318      26.998 -24.526  84.294  1.00228.28           C
ANISOU 8745  CB   GLU B 318    27109  34269  25358  -5948    101   2396       C
ATOM   8746  CG   GLU B 318      27.969 -23.499  84.918  1.00229.42           C
ANISOU 8746  CG   GLU B 318    27047  34818  25305  -6342    444   2296       C
ATOM   8747  CD   GLU B 318      29.224 -23.225  84.073  1.00231.22           C
ANISOU 8747  CD   GLU B 318    27095  35385  25373  -6204    605   2120       C
ATOM   8748  OE1  GLU B 318      29.711 -24.155  83.397  1.00232.29           O
ANISOU 8748  OE1  GLU B 318    27156  35580  25521  -5793    344   2079       O
ATOM   8749  OE2  GLU B 318      29.736 -22.082  84.101  1.00231.74           O
ANISOU 8749  OE2  GLU B 318    27090  35660  25301  -6513   1002   2017       O
ATOM   8750  N    GLU B 319      26.108 -24.217  81.100  1.00134.90           N
ANISOU 8750  N    GLU B 319    15660  22000  13596  -5288    284   2263       N
ATOM   8751  CA   GLU B 319      26.629 -23.929  79.778  1.00135.72           C
ANISOU 8751  CA   GLU B 319    15754  22218  13597  -5037    444   2131       C
ATOM   8752  C    GLU B 319      25.677 -23.122  78.892  1.00134.32           C
ANISOU 8752  C    GLU B 319    15809  21788  13439  -5022    703   2172       C
ATOM   8753  O    GLU B 319      26.124 -22.366  78.026  1.00134.94           O
ANISOU 8753  O    GLU B 319    15873  22004  13394  -4982   1004   2092       O
ATOM   8754  CB   GLU B 319      27.049 -25.237  79.098  1.00137.04           C
```

FIG. 13 Continued

```
ANISOU 8754  CB  GLU B 319    15858  22411  13800  -4567     62   2050       C
ATOM   8755  CG  GLU B 319    27.953 -26.153  79.960  1.00138.67             C
ANISOU 8755  CG  GLU B 319    15835  22848  14006  -4524   -223   2040       C
ATOM   8756  CD  GLU B 319    29.467 -25.903  79.774  1.00140.85             C
ANISOU 8756  CD  GLU B 319    15836  23593  14087  -4500    -75   1894       C
ATOM   8757  OE1 GLU B 319    29.905 -24.730  79.736  1.00140.94             O
ANISOU 8757  OE1 GLU B 319    15784  23815  13953  -4779    317   1839       O
ATOM   8758  OE2 GLU B 319    30.229 -26.892  79.683  1.00142.65             O
ANISOU 8758  OE2 GLU B 319    15906  23980  14313  -4202   -349   1836       O
ATOM   8759  N   MET B 320    24.373 -23.281  79.102  1.00137.98             N
ANISOU 8759  N   MET B 320    16475  21898  14053  -5048    590   2308       N
ATOM   8760  CA  MET B 320    23.393 -22.531  78.322  1.00136.75             C
ANISOU 8760  CA  MET B 320    16530  21510  13917  -5026    824   2375       C
ATOM   8761  C   MET B 320    23.511 -21.042  78.619  1.00136.49             C
ANISOU 8761  C   MET B 320    16511  21548  13800  -5402   1329   2400       C
ATOM   8762  O   MET B 320    22.975 -20.205  77.898  1.00135.97             O
ANISOU 8762  O   MET B 320    16588  21359  13716  -5391   1619   2450       O
ATOM   8763  CB  MET B 320    21.973 -23.011  78.613  1.00135.10             C
ANISOU 8763  CB  MET B 320    16511  20935  13886  -5007    596   2524       C
ATOM   8764  CG  MET B 320    21.769 -24.509  78.434  1.00135.48             C
ANISOU 8764  CG  MET B 320    16565  20863  14050  -4679     96   2503       C
ATOM   8765  SD  MET B 320    21.982 -25.120  76.746  1.00136.66             S
ANISOU 8765  SD  MET B 320    16740  21041  14144  -4171    -49   2351       S
ATOM   8766  CE  MET B 320    21.059 -23.906  75.797  1.00135.54             C
ANISOU 8766  CE  MET B 320    16782  20779  13939  -4194    329   2428       C
ATOM   8767  N   ALA B 321    24.208 -20.722  79.701  1.00122.85             N
ANISOU 8767  N   ALA B 321    14633  20022  12021  -5737   1435   2367       N
ATOM   8768  CA  ALA B 321    24.452 -19.340  80.085  1.00123.00             C
ANISOU 8768  CA  ALA B 321    14648  20125  11963  -6132   1917   2353       C
ATOM   8769  C   ALA B 321    25.802 -18.906  79.536  1.00124.92             C
ANISOU 8769  C   ALA B 321    14708  20721  12034  -6122   2140   2197       C
ATOM   8770  O   ALA B 321    26.065 -17.712  79.361  1.00125.42             O
ANISOU 8770  O   ALA B 321    14788  20841  12023  -6355   2585   2167       O
ATOM   8771  CB  ALA B 321    24.428 -19.207  81.585  1.00122.75             C
ANISOU 8771  CB  ALA B 321    14547  20135  11956  -6530   1917   2385       C
ATOM   8772  N   GLY B 322    26.660 -19.893  79.286  1.00184.60             N
ANISOU 8772  N   GLY B 322    22089  28515  19537  -5853   1832   2100       N
ATOM   8773  CA  GLY B 322    27.980 -19.661  78.726  1.00186.59             C
ANISOU 8773  CA  GLY B 322    22141  29135  19621  -5791   1985   1949       C
ATOM   8774  C   GLY B 322    27.946 -19.693  77.210  1.00186.94             C
ANISOU 8774  C   GLY B 322    22264  29144  19620  -5408   2030   1916       C
ATOM   8775  O   GLY B 322    28.839 -19.168  76.548  1.00188.43             O
ANISOU 8775  O   GLY B 322    22340  29588  19666  -5385   2278   1817       O
ATOM   8776  N   MET B 323    26.895 -20.314  76.679  1.00130.33             N
ANISOU 8776  N   MET B 323    15282  21670  12566  -5120   1787   1999       N
ATOM   8777  CA  MET B 323    26.653 -20.431  75.242  1.00130.57             C
ANISOU 8777  CA  MET B 323    15409  21646  12556  -4740   1786   1978       C
ATOM   8778  C   MET B 323    27.215 -19.298  74.393  1.00131.64             C
ANISOU 8778  C   MET B 323    15522  21958  12539  -4789   2240   1941       C
ATOM   8779  O   MET B 323    26.484 -18.417  73.952  1.00130.90             O
ANISOU 8779  O   MET B 323    15601  21678  12457  -4856   2534   2052       O
ATOM   8780  CB  MET B 323    25.146 -20.539  74.973  1.00128.74             C
ANISOU 8780  CB  MET B 323    15432  21024  12460  -4637   1687   2123       C
ATOM   8781  CG  MET B 323    24.667 -21.913  74.501  1.00128.61             C
ANISOU 8781  CG  MET B 323    15467  20870  12531  -4241   1208   2093       C
ATOM   8782  SD  MET B 323    24.555 -22.052  72.699  1.00129.51             S
ANISOU 8782  SD  MET B 323    15650  21024  12536  -3784   1211   2019       S
ATOM   8783  CE  MET B 323    25.840 -20.912  72.197  1.00131.17             C
ANISOU 8783  CE  MET B 323    15704  21603  12531  -3893   1685   1940       C
ATOM   8784  N   ASP B 324    28.509 -19.361  74.124  1.00130.51             N
ANISOU 8784  N   ASP B 324    15159  22177  12252  -4732   2290   1797       N
ATOM   8785  CA  ASP B 324    29.171 -18.364  73.301  1.00131.87             C
ANISOU 8785  CA  ASP B 324    15281  22552  12271  -4771   2708   1756       C
ATOM   8786  C   ASP B 324    28.369 -18.104  72.027  1.00131.44             C
ANISOU 8786  C   ASP B 324    15423  22319  12202  -4491   2811   1841       C
ATOM   8787  O   ASP B 324    27.822 -17.016  71.837  1.00130.95             O
ANISOU 8787  O   ASP B 324    15507  22100  12149  -4666   3184   1965       O
ATOM   8788  CB  ASP B 324    30.579 -18.849  72.955  1.00134.08             C
ANISOU 8788  CB  ASP B 324    15294  23251  12401  -4601   2620   1581       C
```

FIG. 13 Continued

```
ATOM   8789  CG   ASP B 324      31.476 -17.738  72.513  1.00135.74           C
ANISOU 8789  CG   ASP B 324    15393  23729  12452   -4784   3081   1531       C
ATOM   8790  OD1  ASP B 324      31.362 -17.320  71.347  1.00136.24           O
ANISOU 8790  OD1  ASP B 324    15538  23790  12437   -4587   3277   1558       O
ATOM   8791  OD2  ASP B 324      32.297 -17.287  73.333  1.00136.69           O
ANISOU 8791  OD2  ASP B 324    15339  24075  12521   -5131   3247   1466       O
ATOM   8792  N    VAL B 325      28.274 -19.124  71.180  1.00142.90           N
ANISOU 8792  N    VAL B 325    16874  23789  13631   -4052   2475   1775       N
ATOM   8793  CA   VAL B 325      27.580 -19.012  69.901  1.00142.83           C
ANISOU 8793  CA   VAL B 325    17019  23675  13575   -3747   2524   1833       C
ATOM   8794  C    VAL B 325      26.957 -20.330  69.455  1.00142.43           C
ANISOU 8794  C    VAL B 325    17035  23488  13592   -3355   2043   1781       C
ATOM   8795  O    VAL B 325      27.653 -21.290  69.140  1.00143.71           O
ANISOU 8795  O    VAL B 325    17064  23830  13707   -3083   1765   1618       O
ATOM   8796  CB   VAL B 325      28.533 -18.536  68.797  1.00144.90           C
ANISOU 8796  CB   VAL B 325    17163  24262  13632   -3592   2790   1753       C
ATOM   8797  CG1  VAL B 325      29.949 -19.007  69.087  1.00146.63           C
ANISOU 8797  CG1  VAL B 325    17111  24839  13761   -3588   2693   1569       C
ATOM   8798  CG2  VAL B 325      28.060 -19.033  67.438  1.00145.36           C
ANISOU 8798  CG2  VAL B 325    17306  24313  13612   -3141   2637   1736       C
ATOM   8799  N    LEU B 326      25.634 -20.370  69.425  1.00128.21           N
ANISOU 8799  N    LEU B 326    15440  21366  11905   -3330   1954   1915       N
ATOM   8800  CA   LEU B 326      24.936 -21.573  69.015  1.00127.90           C
ANISOU 8800  CA   LEU B 326    15481  21173  11943   -2998   1512   1863       C
ATOM   8801  C    LEU B 326      24.826 -21.623  67.512  1.00129.06           C
ANISOU 8801  C    LEU B 326    15663  21435  11940   -2630   1537   1809       C
ATOM   8802  O    LEU B 326      24.504 -20.619  66.874  1.00129.10           O
ANISOU 8802  O    LEU B 326    15745  21458  11848   -2660   1882   1931       O
ATOM   8803  CB   LEU B 326      23.534 -21.610  69.616  1.00125.84           C
ANISOU 8803  CB   LEU B 326    15411  20544  11860   -3136   1399   2028       C
ATOM   8804  CG   LEU B 326      22.655 -22.799  69.211  1.00125.54           C
ANISOU 8804  CG   LEU B 326    15473  20311  11917   -2837    957   1986       C
ATOM   8805  CD1  LEU B 326      21.778 -23.240  70.374  1.00123.84           C
ANISOU 8805  CD1  LEU B 326    15347  19791  11916   -3043    727   2094       C
ATOM   8806  CD2  LEU B 326      21.812 -22.497  67.979  1.00125.66           C
ANISOU 8806  CD2  LEU B 326    15616  20288  11842   -2607   1041   2044       C
ATOM   8807  N    CYS B 327      25.114 -22.788  66.945  1.00147.97           N
ANISOU 8807  N    CYS B 327    17999  23912  14312   -2280   1180   1627       N
ATOM   8808  CA   CYS B 327      24.930 -22.982  65.518  1.00149.20           C
ANISOU 8808  CA   CYS B 327    18189  24181  14320   -1912   1150   1549       C
ATOM   8809  C    CYS B 327      23.738 -23.914  65.309  1.00148.49           C
ANISOU 8809  C    CYS B 327    18250  23818  14350   -1722    768   1536       C
ATOM   8810  O    CYS B 327      23.586 -24.926  66.002  1.00148.09           O
ANISOU 8810  O    CYS B 327    18206  23591  14471   -1713    408   1468       O
ATOM   8811  CB   CYS B 327      26.205 -23.490  64.842  1.00151.52           C
ANISOU 8811  CB   CYS B 327    18296  24816  14460   -1641   1090   1325       C
ATOM   8812  SG   CYS B 327      26.782 -25.076  65.429  1.00152.34           S
ANISOU 8812  SG   CYS B 327    18292  24890  14702   -1463    594   1113       S
ATOM   8813  N    SER B 328      22.883 -23.547  64.361  1.00136.76           N
ANISOU 8813  N    SER B 328    16880  22307  12773   -1581    859   1615       N
ATOM   8814  CA   SER B 328      21.656 -24.283  64.113  1.00136.17           C
ANISOU 8814  CA   SER B 328    16946  21996  12794   -1435    538   1616       C
ATOM   8815  C    SER B 328      21.522 -24.922  62.742  1.00137.96           C
ANISOU 8815  C    SER B 328    17176  22372  12871   -1032    356   1442       C
ATOM   8816  O    SER B 328      22.187 -24.538  61.776  1.00139.57           O
ANISOU 8816  O    SER B 328    17297  22879  12855    -851    555   1375       O
ATOM   8817  CB   SER B 328      20.453 -23.369  64.325  1.00134.46           C
ANISOU 8817  CB   SER B 328    16879  21582  12627   -1643    751   1884       C
ATOM   8818  OG   SER B 328      19.349 -23.801  63.543  1.00134.61           O
ANISOU 8818  OG   SER B 328    17005  21517  12626   -1425    548   1887       O
ATOM   8819  N    ASP B 329      20.619 -25.899  62.691  1.00133.63           N
ANISOU 8819  N    ASP B 329    16724  21607  12444    -912    -22   1370       N
ATOM   8820  CA   ASP B 329      20.239 -26.587  61.473  1.00135.29           C
ANISOU 8820  CA   ASP B 329    16961  21909  12535    -564   -239   1194       C
ATOM   8821  C    ASP B 329      19.233 -25.740  60.734  1.00134.95           C
ANISOU 8821  C    ASP B 329    17007  21913  12356    -548    -31   1382       C
ATOM   8822  O    ASP B 329      18.435 -25.031  61.338  1.00133.15           O
ANISOU 8822  O    ASP B 329    16867  21502  12220    -796    124   1632       O
ATOM   8823  CB   ASP B 329      19.584 -27.920  61.806  1.00135.28           C
```

FIG. 13 Continued

```
ANISOU 8823  CB  ASP B 329     17037  21623  12741   -493   -711   1055       C
ATOM   8824  CG  ASP B 329      20.535 -28.879  62.451  1.00136.02            C
ANISOU 8824  CG  ASP B 329     17047  21661  12974   -451   -946    874       C
ATOM   8825  OD1 ASP B 329      20.066 -29.738  63.220  1.00135.43            O
ANISOU 8825  OD1 ASP B 329     17038  21286  13134   -527  -1257    658       O
ATOM   8826  OD2 ASP B 329      21.751 -28.770  62.192  1.00137.33            O
ANISOU 8826  OD2 ASP B 329     17073  22090  13014   -339   -815    760       O
ATOM   8827  N   LYS B 330      19.263 -25.839  59.417  1.00134.72            N
ANISOU 8827  N   LYS B 330     16948  22140  12099   -242    -32   1260       N
ATOM   8828  CA  LYS B 330      18.352 -25.095  58.567  1.00134.89            C
ANISOU 8828  CA  LYS B 330     17031  22267  11953   -171    152   1436       C
ATOM   8829  C   LYS B 330      16.886 -25.453  58.852  1.00133.70            C
ANISOU 8829  C   LYS B 330     17010  21842  11949   -247    -87   1531       C
ATOM   8830  O   LYS B 330      16.228 -24.787  59.644  1.00131.77            O
ANISOU 8830  O   LYS B 330     16840  21391  11835   -512     63   1788       O
ATOM   8831  CB  LYS B 330      18.697 -25.367  57.103  1.00137.52            C
ANISOU 8831  CB  LYS B 330     17291  22953  12005    197    122   1241       C
ATOM   8832  CG  LYS B 330      18.276 -24.314  56.115  1.00138.26            C
ANISOU 8832  CG  LYS B 330     17390  23298  11846    293    448   1447       C
ATOM   8833  CD  LYS B 330      18.153 -24.951  54.765  1.00140.76            C
ANISOU 8833  CD  LYS B 330     17664  23894  11925    656    256   1225       C
ATOM   8834  CE  LYS B 330      17.291 -26.201  54.873  1.00140.80            C
ANISOU 8834  CE  LYS B 330     17742  23679  12077    718   -223   1023       C
ATOM   8835  NZ  LYS B 330      15.986 -25.929  55.541  1.00138.77            N
ANISOU 8835  NZ  LYS B 330     17601  23132  11991    492   -262   1269       N
ATOM   8836  N   THR B 331      16.384 -26.512  58.226  1.00152.72            N
ANISOU 8836  N   THR B 331     19439  24247  14340     26    456   1312       N
ATOM   8837  CA  THR B 331      14.979 -26.294  58.372  1.00151.97            C
ANISOU 8837  CA  THR B 331     19450  23932  14362    -87   -695   1382       C
ATOM   8838  C   THR B 331      14.528 -27.169  59.817  1.00149.73            C
ANISOU 8838  C   THR B 331     19242  23253  14397   -397   -837   1494       C
ATOM   8839  O   THR B 331      15.358 -27.337  60.717  1.00149.00            O
ANISOU 8839  O   THR B 331     19117  23047  14449   -536   -836   1458       O
ATOM   8840  CB  THR B 331      14.667 -28.130  57.527  1.00154.08            C
ANISOU 8840  CB  THR B 331     19718  24249  14577    180  -1095   1066       C
ATOM   8841  OG1 THR B 331      15.605 -28.211  56.446  1.00156.39            O
ANISOU 8841  OG1 THR B 331     19912  24891  14618    470  -1025    855       O
ATOM   8842  CG2 THR B 331      13.235 -28.065  56.993  1.00154.26            C
ANISOU 8842  CG2 THR B 331     19802  24278  14531    209  -1191   1168       C
ATOM   8843  N   GLY B 332      13.208 -27.193  60.025  1.00131.53            N
ANISOU 8843  N   GLY B 332     17024  20767  12184   -503   -952   1638       N
ATOM   8844  CA  GLY B 332      12.609 -27.525  61.311  1.00129.62            C
ANISOU 8844  CA  GLY B 332     16856  20161  12232   -783  -1115   1745       C
ATOM   8845  C   GLY B 332      13.119 -26.774  62.525  1.00127.63            C
ANISOU 8845  C   GLY B 332     16602  19782  12111  -1080   -851   1942       C
ATOM   8846  O   GLY B 332      12.914 -27.196  63.664  1.00126.31            O
ANISOU 8846  O   GLY B 332     16473  19341  12179  -1300  -1011   1984       O
ATOM   8847  N   THR B 333      13.782 -25.653  62.284  1.00127.02            N
ANISOU 8847  N   THR B 333     16477  19911  11875  -1097   -440   2061       N
ATOM   8848  CA  THR B 333      14.337 -24.849  63.363  1.00125.46            C
ANISOU 8848  CA  THR B 333     16268  19627  11774  -1391   -151   2223       C
ATOM   8849  C   THR B 333      14.610 -23.446  62.823  1.00125.69            C
ANISOU 8849  C   THR B 333     16279  19868  11609  -1396    341   2405       C
ATOM   8850  O   THR B 333      13.708 -22.602  62.772  1.00124.97            O
ANISOU 8850  O   THR B 333     16260  19721  11501  -1475    562   2652       O
ATOM   8851  CB  THR B 333      15.625 -25.499  63.956  1.00125.83            C
ANISOU 8851  CB  THR B 333     16224  19685  11900  -1418   -279   2022       C
ATOM   8852  OG1 THR B 333      15.300 -26.775  64.516  1.00125.72            O
ANISOU 8852  OG1 THR B 333     16242  19435  12091  -1419   -718   1891       O
ATOM   8853  CG2 THR B 333      16.226 -24.639  65.051  1.00124.46            C
ANISOU 8853  CG2 THR B 333     16020  19470  11799  -1739     27   2172       C
ATOM   8854  N   LEU B 334      15.842 -23.207  62.394  1.00129.14            N
ANISOU 8854  N   LEU B 334     16618  20548  11902  -1300    516   2291       N
ATOM   8855  CA  LEU B 334      16.186 -21.927  61.818  1.00129.71            C
ANISOU 8855  CA  LEU B 334     16669  20825  11791  -1295    984   2455       C
ATOM   8856  C   LEU B 334      15.105 -21.575  60.792  1.00130.39            C
ANISOU 8856  C   LEU B 334     16816  20996  11731  -1099   1040   2600       C
ATOM   8857  O   LEU B 334      14.976 -20.424  60.383  1.00130.68            O
ANISOU 8857  O   LEU B 334     16873  21131  11649  -1110   1438   2825       O
```

FIG. 13 Continued

```
ATOM   8858  CB  LEU B 334      17.565 -21.998  61.159  1.00131.52           C
ANISOU 8858  CB  LEU B 334    16768  21362  11843  -1123   1073   2261       C
ATOM   8859  CG  LEU B 334      18.316 -20.699  60.867  1.00132.16           C
ANISOU 8859  CG  LEU B 334    16800  21641  11774  -1200   1583   2404       C
ATOM   8860  CD1 LEU B 334      18.795 -20.088  62.155  1.00130.74           C
ANISOU 8860  CD1 LEU B 334    16617  21300  11757  -1581   1806   2495       C
ATOM   8861  CD2 LEU B 334      19.490 -20.947  59.943  1.00134.34           C
ANISOU 8861  CD2 LEU B 334    16939  22264  11838   -952   1603   2197       C
ATOM   8862  N   THR B 335      14.316 -22.566  60.385  1.00129.86           N
ANISOU 8862  N   THR B 335    16775  20892  11675   -925    646   2478       N
ATOM   8863  CA  THR B 335      13.245 -22.328  59.428  1.00130.69           C
ANISOU 8863  CA  THR B 335    16916  21110  11629   -739    655   2602       C
ATOM   8864  C   THR B 335      12.019 -23.158  59.748  1.00129.97           C
ANISOU 8864  C   THR B 335    16891  20802  11689   -771    275   2582       C
ATOM   8865  O   THR B 335      12.078 -24.093  60.545  1.00129.18           O
ANISOU 8865  O   THR B 335    16808  20480  11796   -885    -40   2427       O
ATOM   8866  CB  THR B 335      13.682 -22.633  58.009  1.00133.18           C
ANISOU 8866  CB  THR B 335    17149  21787  11667   -386    601   2421       C
ATOM   8867  OG1 THR B 335      13.970 -24.026  57.896  1.00134.04           O
ANISOU 8867  OG1 THR B 335    17224  21880  11824   -250    157   2075       O
ATOM   8868  CG2 THR B 335      14.919 -21.854  57.674  1.00134.06           C
ANISOU 8868  CG2 THR B 335    17184  22128  11626   -355    971   2438       C
ATOM   8869  N   LEU B 336      10.919 -22.820  59.085  1.00131.00           N
ANISOU 8869  N   LEU B 336    17050  21017  11707   -661    308   2746       N
ATOM   8870  CA  LEU B 336       9.605 -23.394  59.368  1.00130.37           C
ANISOU 8870  CA  LEU B 336    17026  20754  11756   -719      9   2785       C
ATOM   8871  C   LEU B 336       9.343 -24.871  59.015  1.00131.54           C
ANISOU 8871  C   LEU B 336    17158  20887  11933   -578   -504   2464       C
ATOM   8872  O   LEU B 336       8.480 -25.512  59.615  1.00130.73           O
ANISOU 8872  O   LEU B 336    17106  20546  12019   -711   -784   2458       O
ATOM   8873  CB  LEU B 336       8.531 -22.510  58.726  1.00130.83           C
ANISOU 8873  CB  LEU B 336    17097  20951  11662   -631    226   3076       C
ATOM   8874  CG  LEU B 336       7.149 -22.493  59.380  1.00129.53           C
ANISOU 8874  CG  LEU B 336    16994  20558  11662   -798    124   3274       C
ATOM   8875  CD1 LEU B 336       6.427 -21.209  59.028  1.00129.67           C
ANISOU 8875  CD1 LEU B 336    17026  20682  11561   -759    514   3643       C
ATOM   8876  CD2 LEU B 336       6.318 -23.719  59.003  1.00130.48           C
ANISOU 8876  CD2 LEU B 336    17098  20688  11792   -697   -361   3071       C
ATOM   8877  N   ASN B 337      10.077 -25.416  58.057  1.00132.34           N
ANISOU 8877  N   ASN B 337    17193  21234  11857   -319   -620   2194       N
ATOM   8878  CA  ASN B 337       9.795 -26.770  57.599  1.00133.87           C
ANISOU 8878  CA  ASN B 337    17380  21421  12065   -169  -1079   1872       C
ATOM   8879  C   ASN B 337       8.356 -26.950  57.109  1.00134.52           C
ANISOU 8879  C   ASN B 337    17479  21545  12088   -125  -1256   1940       C
ATOM   8880  O   ASN B 337       7.575 -27.728  57.653  1.00134.03           O
ANISOU 8880  O   ASN B 337    17466  21235  12225   -256  -1568   1881       O
ATOM   8881  CB  ASN B 337      10.078 -27.823  58.658  1.00132.97           C
ANISOU 8881  CB  ASN B 337    17309  20960  12252   -331  -1392   1694       C
ATOM   8882  CG  ASN B 337       9.362 -29.129  58.356  1.00134.35           C
ANISOU 8882  CG  ASN B 337    17511  21031  12504   -249  -1854   1439       C
ATOM   8883  OD1 ASN B 337       9.387 -29.606  57.222  1.00136.69           O
ANISOU 8883  OD1 ASN B 337    17765  21566  12605      7  -1994   1204       O
ATOM   8884  ND2 ASN B 337       8.674 -29.682  59.352  1.00133.06           N
ANISOU 8884  ND2 ASN B 337    17418  20522  12618   -476  -2062   1486       N
ATOM   8885  N   LYS B 338       8.001 -26.195  56.089  1.00136.52           N
ANISOU 8885  N   LYS B 338     8400  25609  17862  -4284   1782  -3998       N
ATOM   8886  CA  LYS B 338       6.732  26.397  55.429  1.00136.25           C
ANISOU 8886  CA  LYS B 338     8564  25285  17915  -4618   1716  -3974       C
ATOM   8887  C   LYS B 338       6.972 -26.022  53.978  1.00135.71           C
ANISOU 8887  C   LYS B 338     8485  25197  17882  -4623   1707  -4048       C
ATOM   8888  O   LYS B 338       7.316 -24.878  53.653  1.00134.02           O
ANISOU 8888  O   LYS B 338     7882  25242  17798  -4660   1720  -4121       O
ATOM   8889  CB  LYS B 338       5.614 -25.578  56.060  1.00134.52           C
ANISOU 8889  CB  LYS B 338     8074  25139  17897  -4980   1690  -3953       C
ATOM   8890  CG  LYS B 338       4.210 -25.994  55.603  1.00134.58           C
ANISOU 8890  CG  LYS B 338     8332  24824  17977  -5332   1619  -3875       C
ATOM   8891  CD  LYS B 338       3.784 -27.318  56.220  1.00136.61           C
ANISOU 8891  CD  LYS B 338     8991  24825  18089  -5306   1577  -3744       C
ATOM   8892  CE  LYS B 338       2.277 -27.518  56.108  1.00136.41           C
```

FIG. 13 Continued

```
ANISOU 8892  CE  LYS B 338      9110  24551  18169  -5701   1497  -3624       C
ATOM   8893  NZ  LYS B 338       1.829 -28.861  56.587  1.00138.53            N
ANISOU 8893  NZ  LYS B 338      9792  24547  18295  -5695   1420  -3470       N
ATOM   8894  N   LEU B 339       6.827 -27.028  53.122  1.00160.80            N
ANISOU 8894  N   LEU B 339     12103  28061  20931  -4570   1672  -4025       N
ATOM   8895  CA  LEU B 339       7.080 -26.898  51.701  1.00160.74            C
ANISOU 8895  CA  LEU B 339     12169  27990  20914  -4534   1663  -4088       C
ATOM   8896  C   LEU B 339       5.801 -26.764  50.883  1.00159.85            C
ANISOU 8896  C   LEU B 339     12173  27614  20948  -4935   1588  -4075       C
ATOM   8897  O   LEU B 339       4.727 -27.250  51.278  1.00160.15            O
ANISOU 8897  O   LEU B 339     12416  27408  21023  -5185   1527  -3985       O
ATOM   8898  CB  LEU B 339       7.864 -28.110  51.216  1.00163.28            C
ANISOU 8898  CB  LEU B 339     12928  28137  20973  -4165   1671  -4078       C
ATOM   8899  CG  LEU B 339       8.796 -28.724  52.256  1.00164.76            C
ANISOU 8899  CG  LEU B 339     13171  28444  20987  -3814   1725  -4043       C
ATOM   8900  CD1 LEU B 339       8.455 -30.186  52.409  1.00167.10            C
ANISOU 8900  CD1 LEU B 339     14012  28374  21106  -3740   1660  -3972       C
ATOM   8901  CD2 LEU B 339      10.273 -28.516  51.912  1.00165.29            C
ANISOU 8901  CD2 LEU B 339     13088  28786  20930  -3407   1810  -4087       C
ATOM   8902  N   SER B 340       5.937 -26.090  49.742  1.00139.30            N
ANISOU 8902  N   SER B 340      9424  25073  18431  -4999   1588  -4152       N
ATOM   8903  CA  SER B 340       4.857 -25.948  48.771  1.00138.46            C
ANISOU 8903  CA  SER B 340      9435  24715  18460  -5359   1521  -4147       C
ATOM   8904  C   SER B 340       5.486 -25.407  47.496  1.00137.88            C
ANISOU 8904  C   SER B 340      9233  24754  18401  -5268   1538  -4241       C
ATOM   8905  O   SER B 340       6.280 -24.449  47.523  1.00136.68            O
ANISOU 8905  O   SER B 340      8652  24966  18313  -5154   1584  -4307       O
ATOM   8906  CB  SER B 340       3.711 -25.075  49.289  1.00136.34            C
ANISOU 8906  CB  SER B 340      8868  24493  18444  -5789   1494  -4118       C
ATOM   8907  OG  SER B 340       2.922 -25.788  50.229  1.00137.24            O
ANISOU 8907  OG  SER B 340      9200  24421  18525  -5906   1460  -3999       O
ATOM   8908  N   VAL B 341       5.146 -26.067  46.392  1.00127.74            N
ANISOU 8908  N   VAL B 341      8337  23153  17045  -5308   1489  -4236       N
ATOM   8909  CA  VAL B 341       5.751 -25.795  45.100  1.00127.70            C
ANISOU 8909  CA  VAL B 341      8304  23210  17005  -5180   1504  -4314       C
ATOM   8910  C   VAL B 341       4.789 -25.073  44.160  1.00125.79            C
ANISOU 8910  C   VAL B 341      7945  22857  16991  -5605   1450  -4340       C
ATOM   8911  O   VAL B 341       3.576 -25.183  44.297  1.00125.21            O
ANISOU 8911  O   VAL B 341      8001  22528  17044  -5971   1388  -4275       O
ATOM   8912  CB  VAL B 341       6.267 -27.118  44.457  1.00130.56            C
ANISOU 8912  CB  VAL B 341      9221  23308  17078  -4832   1491  -4303       C
ATOM   8913  CG1 VAL B 341       7.051 -26.850  43.191  1.00130.77            C
ANISOU 8913  CG1 VAL B 341      9198  23456  17033  -4625   1524  -4380       C
ATOM   8914  CG2 VAL B 341       7.121 -27.889  45.439  1.00132.46            C
ANISOU 8914  CG2 VAL B 341      9597  23628  17103  -4441   1538  -4269       C
ATOM   8915  N   ASP B 342       5.358 -24.319  43.224  1.00151.38            N
ANISOU 8915  N   ASP B 342     10923  26310  20287  -5555   1472  -4422       N
ATOM   8916  CA  ASP B 342       4.612 -23.570  42.214  1.00149.51            C
ANISOU 8916  CA  ASP B 342     10539  26004  20265  -5931   1425  -4460       C
ATOM   8917  C   ASP B 342       4.807 -24.167  40.798  1.00150.84            C
ANISOU 8917  C   ASP B 342     11065  25951  20296  -5811   1404  -4487       C
ATOM   8918  O   ASP B 342       5.426 -25.216  40.654  1.00153.33            O
ANISOU 8918  O   ASP B 342     11777  26137  20343  -5442   1420  -4473       O
ATOM   8919  CB  ASP B 342       4.987 -22.076  42.276  1.00147.03            C
ANISOU 8919  CB  ASP B 342      9581  26123  20163  -6036   1440  -4529       C
ATOM   8920  CG  ASP B 342       6.455 -21.831  42.681  1.00147.66            C
ANISOU 8920  CG  ASP B 342      9394  26602  20105  -5598   1500  -4552       C
ATOM   8921  OD1 ASP B 342       6.962 -20.713  42.447  1.00146.04            O
ANISOU 8921  OD1 ASP B 342      8712  26745  20032  -5621   1489  -4597       O
ATOM   8922  OD2 ASP B 342       7.110 -22.737  43.234  1.00149.75            O
ANISOU 8922  OD2 ASP B 342      9919  26841  20138  -5239   1547  -4512       O
ATOM   8923  N   LYS B 343       4.283 -23.519  39.758  1.00119.87            N
ANISOU 8923  N   LYS B 343      7016  21979  16549  -6113   1366  -4527       N
ATOM   8924  CA  LYS B 343       4.424 -24.052  38.392  1.00121.10            C
ANISOU 8924  CA  LYS B 343      7515  21921  16578  -6010   1344  -4555       C
ATOM   8925  C   LYS B 343       5.577 -23.513  37.566  1.00121.06            C
ANISOU 8925  C   LYS B 343      7234  22258  16505  -5724   1395  -4632       C
ATOM   8926  O   LYS B 343       5.396 -23.011  36.459  1.00120.04            O
ANISOU 8926  O   LYS B 343      7003  22126  16480  -5896   1370  -4677       O
```

FIG. 13 Continued

```
ATOM   8927  CB   LYS B 343       3.115 -23.951  37.627  1.00119.94           C
ANISOU 8927  CB   LYS B 343     7528  21426  16620  -6493   1261  -4531       C
ATOM   8928  CG   LYS B 343       2.509 -25.314  37.374  1.00122.22           C
ANISOU 8928  CG   LYS B 343     8500  21204  16736  -6483   1185  -4450       C
ATOM   8929  CD   LYS B 343       3.219 -26.408  38.186  1.00124.89           C
ANISOU 8929  CD   LYS B 343     9162  21506  16784  -6040   1206  -4415       C
ATOM   8930  CE   LYS B 343       2.947 -26.324  39.690  1.00124.37           C
ANISOU 8930  CE   LYS B 343     8914  21550  16789  -6120   1224  -4349       C
ATOM   8931  NZ   LYS B 343       1.554 -25.938  40.014  1.00122.61           N
ANISOU 8931  NZ   LYS B 343     8612  21153  16822  -6645   1162  -4266       N
ATOM   8932  N    ASN B 344       6.770 -23.689  38.109  1.00120.54           N
ANISOU 8932  N    ASN B 344     7070  22477  16251  -5279   1465  -4631       N
ATOM   8933  CA   ASN B 344       8.000 -23.177  37.534  1.00120.69           C
ANISOU 8933  CA   ASN B 344     6780  22889  16187  -4956   1518  -4666       C
ATOM   8934  C    ASN B 344       9.035 -24.295  37.521  1.00123.81           C
ANISOU 8934  C    ASN B 344     7549  23268  16226  -4396   1580  -4642       C
ATOM   8935  O    ASN B 344      10.236 -24.074  37.678  1.00124.45           O
ANISOU 8935  O    ASN B 344     7379  23720  16186  -4025   1646  -4626       O
ATOM   8936  CB   ASN B 344       8.496 -22.016  38.394  1.00118.77           C
ANISOU 8936  CB   ASN B 344     5915  23102  16111  -4990   1533  -4662       C
ATOM   8937  CG   ASN B 344       7.496 -21.629  39.492  1.00117.07           C
ANISOU 8937  CG   ASN B 344     5565  22800  16115  -5372   1495  -4648       C
ATOM   8938  OD1  ASN B 344       6.860 -22.493  40.093  1.00118.11           O
ANISOU 8938  OD1  ASN B 344     6080  22618  16179  -5422   1491  -4607       O
ATOM   8939  ND2  ASN B 344       7.371 -20.329  39.762  1.00114.54           N
ANISOU 8939  ND2  ASN B 344     4699  22772  16051  -5628   1458  -4675       N
ATOM   8940  N    LEU B 345       8.528 -25.510  37.365  1.00126.19           N
ANISOU 8940  N    LEU B 345     8459  23124  16362  -4348   1547  -4627       N
ATOM   8941  CA   LEU B 345       9.337 -26.711  37.330  1.00129.35           C
ANISOU 8941  CA   LEU B 345     9308  23423  16417  -3841   1584  -4611       C
ATOM   8942  C    LEU B 345       9.361 -27.262  35.914  1.00130.92           C
ANISOU 8942  C    LEU B 345     9896  23395  16452  -3706   1556  -4650       C
ATOM   8943  O    LEU B 345       8.310 -27.424  35.282  1.00130.46           O
ANISOU 8943  O    LEU B 345    10104  22972  16493  -4046   1468  -4661       O
ATOM   8944  CB   LEU B 345       8.715 -27.747  38.248  1.00130.65           C
ANISOU 8944  CB   LEU B 345     9913  23224  16503  -3883   1533  -4559       C
ATOM   8945  CG   LEU B 345       7.404 -28.253  37.663  1.00130.71           C
ANISOU 8945  CG   LEU B 345    10356  22728  16581  -4249   1414  -4544       C
ATOM   8946  CD1  LEU B 345       7.648 -29.621  37.048  1.00133.96           C
ANISOU 8946  CD1  LEU B 345    11436  22790  16673  -3905   1364  -4543       C
ATOM   8947  CD2  LEU B 345       6.306 -28.297  38.712  1.00129.64           C
ANISOU 8947  CD2  LEU B 345    10235  22399  16622  -4639   1351  -4471       C
ATOM   8948  N    VAL B 346      10.561 -27.553  35.420  1.00133.70           N
ANISOU 8948  N    VAL B 346    10288  23965  16549  -3202   1631  -4661       N
ATOM   8949  CA   VAL B 346      10.732 -28.096  34.073  1.00135.52           C
ANISOU 8949  CA   VAL B 346    10890  24020  16581  -2992   1615  -4701       C
ATOM   8950  C    VAL B 346      10.549 -29.625  34.056  1.00138.63           C
ANISOU 8950  C    VAL B 346    12039  23945  16692  -2748   1555  -4696       C
ATOM   8951  O    VAL B 346      10.418 -30.253  35.114  1.00139.43           O
ANISOU 8951  O    VAL B 346    12332  23904  16741  -2708   1534  -4654       O
ATOM   8952  CB   VAL B 346      12.078 -27.659  33.447  1.00136.23           C
ANISOU 8952  CB   VAL B 346    10659  24581  16521  -2561   1719  -4703       C
ATOM   8953  CG1  VAL B 346      11.974 -26.239  32.897  1.00133.32           C
ANISOU 8953  CG1  VAL B 346     9680  24540  16434  -2884   1716  -4718       C
ATOM   8954  CG2  VAL B 346      13.192 -27.745  34.471  1.00137.16           C
ANISOU 8954  CG2  VAL B 346    10569  25042  16504  -2167   1812  -4641       C
ATOM   8955  N    GLU B 347      10.545  30.217  32.863  1.00152.66           N
ANISOU 8955  N    GLU B 347    14241  25481  18282  -2581   1514  -4737       N
ATOM   8956  CA   GLU B 347      10.263 -31.643  32.714  1.00155.63           C
ANISOU 8956  CA   GLU B 347    15373  25363  18398  -2385   1416  -4736       C
ATOM   8957  C    GLU B 347      11.143 -32.283  31.637  1.00158.55           C
ANISOU 8957  C    GLU B 347    16084  25735  18421  -1850   1448  -4784       C
ATOM   8958  O    GLU B 347      10.815 -32.265  30.459  1.00158.78           O
ANISOU 8958  O    GLU B 347    16305  25595  18430  -1923   1399  -4828       O
ATOM   8959  CB   GLU B 347       8.764 -31.839  32.415  1.00154.71           C
ANISOU 8959  CB   GLU B 347    15583  24735  18463  -2918   1257  -4719       C
ATOM   8960  CG   GLU B 347       8.287 -31.510  30.972  1.00154.13           C
ANISOU 8960  CG   GLU B 347    15601  24508  18453  -3118   1207  -4767       C
ATOM   8961  CD   GLU B 347       8.453 -30.037  30.528  1.00151.12           C
```

FIG. 13 Continued

```
ANISOU 8961  CD   GLU B 347     14517  24570  18333  -3349   1301  -4802        C
ATOM   8962  OE1  GLU B 347       7.838 -29.665  29.497  1.00150.07             O
ANISOU 8962  OE1  GLU B 347     14407  24287  18326  -3641   1248  -4831        O
ATOM   8963  OE2  GLU B 347       9.188 -29.258  31.181  1.00149.85             O
ANISOU 8963  OE2  GLU B 347     13791  24893  18252  -3249   1412  -4794        O
ATOM   8964  N    VAL B 348      12.261 -32.867  32.048  1.00232.79             N
ANISOU 8964  N    VAL B 348     25576  35329  27545  -1303   1532  -4772        N
ATOM   8965  CA   VAL B 348      13.233 -33.397  31.086  1.00235.64             C
ANISOU 8965  CA   VAL B 348     26196  35777  27561   -736   1587  -4809        C
ATOM   8966  C    VAL B 348      12.801 -34.629  30.267  1.00238.57             C
ANISOU 8966  C    VAL B 348     27374  35598  27672   -574   1449  -4857        C
ATOM   8967  O    VAL B 348      13.484 -35.007  29.311  1.00240.88             O
ANISOU 8967  O    VAL B 348     27902  35938  27684   -133   1485  -4900        O
ATOM   8968  CB   VAL B 348      14.623 -33.614  31.740  1.00237.31             C
ANISOU 8968  CB   VAL B 348     26234  36389  27544   -175   1729  -4766        C
ATOM   8969  CG1  VAL B 348      15.505 -32.394  31.531  1.00235.65             C
ANISOU 8969  CG1  VAL B 348     25304  36800  27433    -67   1874  -4728        C
ATOM   8970  CG2  VAL B 348      14.465 -33.899  33.217  1.00236.86             C
ANISOU 8970  CG2  VAL B 348     26153  36274  27570   -283   1713  -4716        C
ATOM   8971  N    PHE B 349      11.678 -35.246  30.634  1.00170.22             N
ANISOU 8971  N    PHE B 349     19143  26431  19102   -921   1281  -4840        N
ATOM   8972  CA   PHE B 349      11.164 -36.409  29.902  1.00172.93             C
ANISOU 8972  CA   PHE B 349     20276  26208  19221   -822   1106  -4868        C
ATOM   8973  C    PHE B 349      10.307 -35.929  28.733  1.00171.57             C
ANISOU 8973  C    PHE B 349     20152  25828  19209  -1207   1029  -4898        C
ATOM   8974  O    PHE B 349      10.727 -35.047  27.981  1.00170.35             O
ANISOU 8974  O    PHE B 349     19584  26025  19117  -1181   1145  -4938        O
ATOM   8975  CB   PHE B 349      10.355 -37.321  30.836  1.00173.68             C
ANISOU 8975  CB   PHE B 349     20809  25848  19334  -1025    933  -4804        C
ATOM   8976  CG   PHE B 349      10.065 -38.695  30.268  1.00177.13             C
ANISOU 8976  CG   PHE B 349     22104  25720  19476   -804    731  -4819        C
ATOM   8977  CD1  PHE B 349      11.098 -39.530  29.866  1.00180.59             C
ANISOU 8977  CD1  PHE B 349     22920  26178  19517   -147    758  -4880        C
ATOM   8978  CD2  PHE B 349       8.760 -39.158  30.170  1.00177.00             C
ANISOU 8978  CD2  PHE B 349     22522  25151  19577  -1249    501  -4758        C
ATOM   8979  CE1  PHE B 349      10.831  40.788  29.360  1.00183.85             C
ANISOU 8979  CE1  PHE B 349     24141  26062  19654     66    550  -4899        C
ATOM   8980  CE2  PHE B 349       8.490 -40.412  29.667  1.00180.22             C
ANISOU 8980  CE2  PHE B 349     23731  25027  19717  -1055    283  -4759        C
ATOM   8981  CZ   PHE B 349       9.524 -41.229  29.262  1.00183.66             C
ANISOU 8981  CZ   PHE B 349     24552  25477  19755   -394    302  -4838        C
ATOM   8982  N    CYS B 350       9.115 -36.513  28.583  1.00162.73             N
ANISOU 8982  N    CYS B 350     19532  24142  18158  -1569    824  -4865        N
ATOM   8983  CA   CYS B 350       8.161 -36.090  27.556  1.00161.29             C
ANISOU 8983  CA   CYS B 350     19421  23705  18158  -2004    732  -4873        C
ATOM   8984  C    CYS B 350       6.888 -36.933  27.565  1.00162.05             C
ANISOU 8984  C    CYS B 350     20141  23137  18293  -2361    480  -4797        C
ATOM   8985  O    CYS B 350       6.798 -37.929  26.850  1.00164.92             O
ANISOU 8985  O    CYS B 350     21185  23081  18395  -2135    328  -4815        O
ATOM   8986  CB   CYS B 350       8.809 -36.143  26.175  1.00162.99             C
ANISOU 8986  CB   CYS B 350     19803  23991  18136  -1625    777  -4964        C
ATOM   8987  SG   CYS B 350       8.390 -34.741  25.142  1.00159.64             S
ANISOU 8987  SG   CYS B 350     18836  23792  18027  -2071    848  -4997        S
ATOM   8988  N    LYS B 351       5.918 -36.523  28.380  1.00152.68             N
ANISOU 8988  N    LYS B 351     18718  21865  17428  -2910    429  -4700        N
ATOM   8989  CA   LYS B 351       4.615 -37.198  28.490  1.00153.02             C
ANISOU 8989  CA   LYS B 351     19265  21317  17559  -3326    186  -4583        C
ATOM   8990  C    LYS B 351       3.964 -36.890  29.839  1.00150.94             C
ANISOU 8990  C    LYS B 351     18672  21115  17562  -3727    182  -4466        C
ATOM   8991  O    LYS B 351       4.621  36.960  30.882  1.00151.19             O
ANISOU 8991  O    LYS B 351     18477  21434  17535  -3485    279  -4469        O
ATOM   8992  CB   LYS B 351       4.738 -38.718  28.293  1.00157.09             C
ANISOU 8992  CB   LYS B 351     20619  21360  17707  -2943    -14  -4570        C
ATOM   8993  CG   LYS B 351       3.407 -39.481  28.197  1.00157.82             C
ANISOU 8993  CG   LYS B 351     21306  20798  17862  -3355   -310  -4428        C
ATOM   8994  CD   LYS B 351       2.790 -39.748  29.572  1.00157.18             C
ANISOU 8994  CD   LYS B 351     21164  20628  17927  -3638   -396  -4278        C
ATOM   8995  CE   LYS B 351       3.788 -40.394  30.528  1.00159.18             C
ANISOU 8995  CE   LYS B 351     21457  21083  17940  -3133   -337  -4315        C
```

FIG. 13 Continued

```
ATOM   8996  NZ  LYS B 351       3.269 -40.510  31.920  1.00158.25           N
ANISOU 8996  NZ  LYS B 351    21177  20967  17983  -3406   -386  -4178       N
ATOM   8997  N   GLY B 352       2.671 -36.563  29.812  1.00158.33           N
ANISOU 8997  N   GLY B 352    19590  21782  18785  -4332     68  -4356       N
ATOM   8998  CA  GLY B 352       1.944 -36.216  31.023  1.00156.31           C
ANISOU 8998  CA  GLY B 352    19015  21584  18791  -4740     62  -4233       C
ATOM   8999  C   GLY B 352       2.653 -35.081  31.735  1.00153.89           C
ANISOU 8999  C   GLY B 352    17926  21906  18640  -4687    308  -4310       C
ATOM   9000  O   GLY B 352       3.074 -35.226  32.882  1.00154.13           O
ANISOU 9000  O   GLY B 352    17788  22145  18631  -4522    368  -4288       O
ATOM   9001  N   VAL B 353       2.778 -33.947  31.049  1.00142.39           N
ANISOU 9001  N   VAL B 353    15995  20743  17363  -4836    435  -4393       N
ATOM   9002  CA  VAL B 353       3.557 -32.809  31.547  1.00140.21           C
ANISOU 9002  CA  VAL B 353    14977  21077  17220  -4755    647  -4471       C
ATOM   9003  C   VAL B 353       3.198 -32.382  32.984  1.00138.41           C
ANISOU 9003  C   VAL B 353    14355  21035  17199  -5004    687  -4393       C
ATOM   9004  O   VAL B 353       2.112 -32.675  33.475  1.00138.02           O
ANISOU 9004  O   VAL B 353    14487  20674  17280  -5381    565  -4269       O
ATOM   9005  CB  VAL B 353       3.507 -31.594  30.562  1.00137.69           C
ANISOU 9005  CB  VAL B 353    14203  20997  17116  -4993    731  -4548       C
ATOM   9006  CG1 VAL B 353       4.893 -30.966  30.418  1.00137.58           C
ANISOU 9006  CG1 VAL B 353    13731  21544  17000  -4564    911  -4658       C
ATOM   9007  CG2 VAL B 353       2.982 -32.019  29.180  1.00138.70           C
ANISOU 9007  CG2 VAL B 353    14819  20704  17178  -5096    607  -4556       C
ATOM   9008  N   GLU B 354       4.152 -31.735  33.651  1.00137.04           N
ANISOU 9008  N   GLU B 354    13663  21373  17035  -4765    852  -4455       N
ATOM   9009  CA  GLU B 354       3.999 -31.192  35.008  1.00135.28           C
ANISOU 9009  CA  GLU B 354    12999  21406  16996  -4942    914  -4405       C
ATOM   9010  C   GLU B 354       2.943 -31.834  35.909  1.00135.60           C
ANISOU 9010  C   GLU B 354    13319  21100  17101  -5236    785  -4265       C
ATOM   9011  O   GLU B 354       3.219 -32.815  36.606  1.00137.78           O
ANISOU 9011  O   GLU B 354    13927  21250  17175  -4971    738  -4218       O
ATOM   9012  CB  GLU B 354       3.774 -29.677  34.931  1.00131.79           C
ANISOU 9012  CB  GLU B 354    11874  21319  16882  -5298   1003  -4446       C
ATOM   9013  CG  GLU B 354       4.990 -28.910  34.407  1.00131.30           C
ANISOU 9013  CG  GLU B 354    11386  21730  16770  -4981   1138  -4559       C
ATOM   9014  CD  GLU B 354       4.636 -27.595  33.715  1.00128.32           C
ANISOU 9014  CD  GLU B 354    10513  21557  16686  -5356   1164  -4607       C
ATOM   9015  OE1 GLU B 354       3.546 -27.517  33.081  1.00127.34           O
ANISOU 9015  OE1 GLU B 354    10550  21110  16724  -5778   1073  -4578       O
ATOM   9016  OE2 GLU B 354       5.468 -26.653  33.797  1.00127.03           O
ANISOU 9016  OE2 GLU B 354     9802  21876  16586  -5225   1264  -4663       O
ATOM   9017  N   LYS B 355       1.743 -31.251  35.888  1.00151.23           N
ANISOU 9017  N   LYS B 355    15145  22947  19370  -5785    728  -4189       N
ATOM   9018  CA  LYS B 355       0.597 -31.690  36.705  1.00151.18           C
ANISOU 9018  CA  LYS B 355    15326  22647  19469  -6139    607  -4023       C
ATOM   9019  C   LYS B 355       0.541 -33.217  36.895  1.00154.48           C
ANISOU 9019  C   LYS B 355    16433  22648  19613  -5913    447  -3930       C
ATOM   9020  O   LYS B 355       0.184 -33.713  37.972  1.00155.08           O
ANISOU 9020  O   LYS B 355    16594  22649  19681  -5970    387  -3813       O
ATOM   9021  CB  LYS B 355      -0.739 -31.158  36.124  1.00149.18           C
ANISOU 9021  CB  LYS B 355    15034  22154  19496  -6726    524  -3936       C
ATOM   9022  CG  LYS B 355      -1.226 -29.776  36.641  1.00145.77           C
ANISOU 9022  CG  LYS B 355    13926  22059  19401  -7117    628  -3939       C
ATOM   9023  CD  LYS B 355      -2.201 -29.890  37.847  1.00145.26           C
ANISOU 9023  CD  LYS B 355    13814  21911  19468  -7426    573  -3767       C
ATOM   9024  CE  LYS B 355      -3.583 -30.500  37.489  1.00145.75           C
ANISOU 9024  CE  LYS B 355    14315  21456  19607  -7848    388  -3567       C
ATOM   9025  NZ  LYS B 355      -4.414 -30.871  38.684  1.00146.00           N
ANISOU 9025  NZ  LYS B 355    14384  21395  19695  -8060    317  -3368       N
ATOM   9026  N   ASP B 356       0.886 -33.961  35.849  1.00223.72           N
ANISOU 9026  N   ASP B 356    25697  31148  28157  -5655    367  -3980       N
ATOM   9027  CA  ASP B 356       0.921 -35.412  35.957  1.00227.02           C
ANISOU 9027  CA  ASP B 356    26790  31171  28297  -5401    196  -3908       C
ATOM   9028  C   ASP B 356       2.056 -35.798  36.896  1.00228.42           C
ANISOU 9028  C   ASP B 356    26885  31635  28270  -4916    296  -3968       C
ATOM   9029  O   ASP B 356       1.830 -36.176  38.045  1.00228.75           O
ANISOU 9029  O   ASP B 356    26925  31668  28321  -4964    255  -3868       O
ATOM   9030  CB  ASP B 356       1.141 -36.075  34.591  1.00229.17           C
```

FIG. 13 Continued

```
ANISOU 9030  CB  ASP B 356    27609  31116  28350  -5178    93  -3970    C
ATOM   9031  CG  ASP B 356   -0.136 -36.193  33.770  1.00 228.78          C
ANISOU 9031  CG  ASP B 356    27888  30597  28440  -5650   -93  -3854    C
ATOM   9032  OD1 ASP B 356   -0.967 -35.261  33.808  1.00 225.95          O
ANISOU 9032  OD1 ASP B 356    27138  30317  28396  -6140   -54  -3795    O
ATOM   9033  OD2 ASP B 356   -0.302 -37.218  33.072  1.00 231.35          O
ANISOU 9033  OD2 ASP B 356    28876  30469  28558  -5526  -285  -3818    O
ATOM   9034  N   GLN B 357    3.279 -35.658  36.399  1.00 182.93          N
ANISOU 9034  N   GLN B 357    21027  26148  22331  -4458   432  -4121    N
ATOM   9035  CA  GLN B 357    4.484 -36.051  37.124  1.00 184.48          C
ANISOU 9035  CA  GLN B 357    21172  26616  22307  -3948   535  -4179    C
ATOM   9036  C   GLN B 357    4.392 -35.991  38.648  1.00 183.70          C
ANISOU 9036  C   GLN B 357    20796  26696  22306  -4040   571  -4099    C
ATOM   9037  O   GLN B 357    4.783 -36.939  39.333  1.00 185.85          O
ANISOU 9037  O   GLN B 357    21361  26875  22379  -3759   517  -4065    O
ATOM   9038  CB  GLN B 357    5.686 -35.254  36.611  1.00 183.83          C
ANISOU 9038  CB  GLN B 357    20671  27005  22173  -3610   741  -4323    C
ATOM   9039  CG  GLN B 357    6.819 -35.052  37.608  1.00 183.90          C
ANISOU 9039  CG  GLN B 357    20308  27462  22103  -3250   903  -4356    C
ATOM   9040  CD  GLN B 357    6.909 -33.614  38.096  1.00 180.61          C
ANISOU 9040  CD  GLN B 357    19132  27519  21971  -3488  1054  -4376    C
ATOM   9041  OE1 GLN B 357    5.913 -33.030  38.542  1.00 178.38          O
ANISOU 9041  OE1 GLN B 357    18615  27200  21962  -3969  1018  -4317    O
ATOM   9042  NE2 GLN B 357    8.105 -33.033  38.008  1.00 180.37          N
ANISOU 9042  NE2 GLN B 357    18718  27941  21873  -3144  1213  -4450    N
ATOM   9043  N   VAL B 358    3.878 -34.889  39.183  1.00 141.36          N
ANISOU 9043  N   VAL B 358    14880  21587  17244  -4426   655  -4072    N
ATOM   9044  CA  VAL B 358    3.753 -34.775  40.628  1.00 140.58          C
ANISOU 9044  CA  VAL B 358    14507  21668  17240  -4519   691  -3997    C
ATOM   9045  C   VAL B 358    2.855 -35.889  41.161  1.00 142.25          C
ANISOU 9045  C   VAL B 358    15210  21442  17395  -4687   487  -3836    C
ATOM   9046  O   VAL B 358    3.329 -36.784  41.862  1.00 144.29          O
ANISOU 9046  O   VAL B 358    15716  21649  17458  -4396   445  -3807    O
ATOM   9047  CB  VAL B 358    3.213 -33.405  41.049  1.00 137.17          C
ANISOU 9047  CB  VAL B 358    13438  21540  17140  -4930   791  -3991    C
ATOM   9048  CG1 VAL B 358    4.325 -32.376  41.024  1.00 135.76          C
ANISOU 9048  CG1 VAL B 358    12710  21878  16994  -4692   984  -4126    C
ATOM   9049  CG2 VAL B 358    2.067 -32.992  40.142  1.00 135.74          C
ANISOU 9049  CG2 VAL B 358    13308  21106  17161  -5398   703  -3947    C
ATOM   9050  N   LEU B 359    1.572 -35.837  40.803  1.00 206.08          N
ANISOU 9050  N   LEU B 359    23436  29215  25651  -5158   351  -3718    N
ATOM   9051  CA  LEU B 359    0.588 -36.837  41.227  1.00 207.57          C
ANISOU 9051  CA  LEU B 359    24080  28976  25812  -5380   126  -3524    C
ATOM   9052  C   LEU B 359    1.101 -38.264  41.043  1.00 211.11          C
ANISOU 9052  C   LEU B 359    25177  29103  25931  -4981   -28  -3518    C
ATOM   9053  O   LEU B 359    0.931 -39.119  41.915  1.00 212.65          O
ANISOU 9053  O   LEU B 359    25612  29152  26035  -4942  -152  -3401    O
ATOM   9054  CB  LEU B 359   -0.730 -36.656  40.461  1.00 206.60          C
ANISOU 9054  CB  LEU B 359    24112  28511  25875  -5884   -14  -3401    C
ATOM   9055  CG  LEU B 359   -1.829 -35.753  41.042  1.00 203.86          C
ANISOU 9055  CG  LEU B 359    23326  28281  25852  -6414    18  -3275    C
ATOM   9056  CD1 LEU B 359   -2.660 -35.122  39.930  1.00 202.22          C
ANISOU 9056  CD1 LEU B 359    23090  27901  25841  -6811   -15  -3255    C
ATOM   9057  CD2 LEU B 359   -2.726 -36.510  42.024  1.00 204.88          C
ANISOU 9057  CD2 LEU B 359    23672  28182  25992  -6637  -153  -3035    C
ATOM   9058  N   LEU B 360    1.712 -38.526  39.896  1.00 201.76          N
ANISOU 9058  N   LEU B 360    24284  27808  24567  -4685   -32  -3643    N
ATOM   9059  CA  LEU B 360    2.300 -39.829  39.662  1.00 205.22          C
ANISOU 9059  CA  LEU B 360    25335  27965  24673  -4254  -169  -3664    C
ATOM   9060  C   LEU B 360    3.257 -40.030  40.821  1.00 205.84          C
ANISOU 9060  C   LEU B 360    25203  28367  24638  -3902   -48  -3705    C
ATOM   9061  O   LEU B 360    3.103 -40.947  41.632  1.00 207.50          O
ANISOU 9061  O   LEU B 360    25696  28396  24749  -3854  -189  -3599    O
ATOM   9062  CB  LEU B 360    3.086 -39.844  38.341  1.00 206.33          C
ANISOU 9062  CB  LEU B 360    25673  28095  24628  -3898  -114  -3829    C
ATOM   9063  CG  LEU B 360    2.386 -39.557  37.003  1.00 205.73          C
ANISOU 9063  CG  LEU B 360    25782  27749  24638  -4167  -196  -3833    C
ATOM   9064  CD1 LEU B 360    3.383 -39.124  35.935  1.00 205.92          C
ANISOU 9064  CD1 LEU B 360    25705  28001  24533  -3802   -36  -4021    C
```

FIG. 13 Continued

```
ATOM   9065  CD2 LEU B 360       1.575 -40.752  36.514  1.00208.22           C
ANISOU 9065  CD2 LEU B 360    26859  27436  24822  -4272   -511  -3704       C
ATOM   9066  N   PHE B 361       4.215 -39.111  40.904  1.00221.83           N
ANISOU 9066  N   PHE B 361    26704  30884  26699  -3684    206  -3845       N
ATOM   9067  CA  PHE B 361       5.275 -39.121  41.902  1.00222.16           C
ANISOU 9067  CA  PHE B 361    26476  31291  26643  -3328    356  -3897       C
ATOM   9068  C   PHE B 361       4.823 -39.330  43.343  1.00221.75           C
ANISOU 9068  C   PHE B 361    26294  31270  26689  -3523    313  -3769       C
ATOM   9069  O   PHE B 361       5.077 -40.380  43.927  1.00223.99           O
ANISOU 9069  O   PHE B 361    26924  31393  26788  -3301    208  -3720       O
ATOM   9070  CB  PHE B 361       6.068 -37.822  41.812  1.00219.86           C
ANISOU 9070  CB  PHE B 361    25536  31531  26470  -3233    614  -4019       C
ATOM   9071  CG  PHE B 361       6.871 -37.528  43.034  1.00219.29           C
ANISOU 9071  CG  PHE B 361    25053  31863  26402  -3037    766  -4030       C
ATOM   9072  CD1 PHE B 361       8.132 -38.072  43.194  1.00221.28           C
ANISOU 9072  CD1 PHE B 361    25412  32266  26398  -2502    846  -4094       C
ATOM   9073  CD2 PHE B 361       6.368 -36.712  44.030  1.00216.82           C
ANISOU 9073  CD2 PHE B 361    24257  31780  26346  -3378    828  -3973       C
ATOM   9074  CE1 PHE B 361       8.881 -37.803  44.326  1.00220.74           C
ANISOU 9074  CE1 PHE B 361    24970  32561  26340  -2332    982  -4092       C
ATOM   9075  CE2 PHE B 361       7.110 -36.446  45.164  1.00216.35           C
ANISOU 9075  CE2 PHE B 361    23838  32079  26287  -3197    959  -3981       C
ATOM   9076  CZ  PHE B 361       8.370 -36.985  45.312  1.00218.26           C
ANISOU 9076  CZ  PHE B 361    24184  32460  26283  -2683   1035  -4038       C
ATOM   9077  N   ALA B 362       4.168 -38.328  43.919  1.00147.64           N
ANISOU 9077  N   ALA B 362    16406  22102  17590  -3926    392  -3716       N
ATOM   9078  CA  ALA B 362       3.749 -38.406  45.318  1.00147.10           C
ANISOU 9078  CA  ALA B 362    16152  22119  17621  -4107    373  -3596       C
ATOM   9079  C   ALA B 362       2.985 -39.668  45.632  1.00149.34           C
ANISOU 9079  C   ALA B 362    16992  21948  17801  -4217    113  -3427       C
ATOM   9080  O   ALA B 362       3.063 -40.205  46.746  1.00150.13           O
ANISOU 9080  O   ALA B 362    17102  22088  17853  -4157     76  -3347       O
ATOM   9081  CB  ALA B 362       2.939 -37.182  45.714  1.00143.94           C
ANISOU 9081  CB  ALA B 362    15208  21945  17539  -4563    460  -3551       C
ATOM   9082  N   ALA B 363       2.252 -40.201  44.649  1.00150.61           N
ANISOU 9082  N   ALA B 363    17619  21677  17930  -4383    -82  -3362       N
ATOM   9083  CA  ALA B 363       1.502 -41.434  44.827  1.00152.89           C
ANISOU 9083  CA  ALA B 363    18474  21500  18118  -4499   -371  -3182       C
ATOM   9084  C   ALA B 363       2.452 -42.451  45.425  1.00155.43           C
ANISOU 9084  C   ALA B 363    19067  21815  18175  -4041   -410  -3220       C
ATOM   9085  O   ALA B 363       2.140 -43.122  46.415  1.00156.40           O
ANISOU 9085  O   ALA B 363    19302  21847  18275  -4109   -539  -3080       O
ATOM   9086  CB  ALA B 363       0.977 -41.927  43.485  1.00154.20           C
ANISOU 9086  CB  ALA B 363    19176  21205  18210  -4584   -568  -3156       C
ATOM   9087  N   MET B 364       3.631 -42.519  44.810  1.00248.19           N
ANISOU 9087  N   MET B 364    30892  33682  29726  -3573   -289  -3407       N
ATOM   9088  CA  MET B 364       4.699 -43.438  45.180  1.00250.70           C
ANISOU 9088  CA  MET B 364    31474  34010  29769  -3070   -298  -3474       C
ATOM   9089  C   MET B 364       5.765 -42.779  46.052  1.00249.44           C
ANISOU 9089  C   MET B 364    30762  34380  29631  -2818    -22  -3574       C
ATOM   9090  O   MET B 364       6.682 -43.444  46.525  1.00251.22           O
ANISOU 9090  O   MET B 364    31124  34672  29657  -2420      1  -3617       O
ATOM   9091  CB  MET B 364       5.364 -43.990  43.910  1.00252.96           C
ANISOU 9091  CB  MET B 364    32229  34091  29795  -2669   -343  -3603       C
ATOM   9092  CG  MET B 364       4.481 -44.912  43.073  1.00255.01           C
ANISOU 9092  CG  MET B 364    33170  33762  29959  -2818   -662  -3507       C
ATOM   9093  SD  MET B 364       5.132 -45.334  41.433  1.00257.30           S
ANISOU 9093  SD  MET B 364    33965  33826  29970  -2393   -698  -3671       S
ATOM   9094  CE  MET B 364       4.676 -43.670  40.509  1.00254.01           C
ANISOU 9094  CE  MET B 364    33079  33612  29821  -2741   -518  -3728       C
ATOM   9095  N   ALA B 365       5.648 -41.473  46.260  1.00155.96           N
ANISOU 9095  N   ALA B 365    18311  22911  17037  -3050    176  -3605       N
ATOM   9096  CA  ALA B 365       6.656 -40.731  47.015  1.00154.63           C
ANISOU 9096  CA  ALA B 365    17600  23248  17902  -2830    427  -3693       C
ATOM   9097  C   ALA B 365       6.485 -40.776  48.520  1.00154.02           C
ANISOU 9097  C   ALA B 365    17279  23325  17916  -2956    439  -3594       C
ATOM   9098  O   ALA B 365       7.239 -40.121  49.229  1.00152.78           O
ANISOU 9098  O   ALA B 365    16665  23578  17808  -2815    634  -3651       O
ATOM   9099  CB  ALA B 365       6.694 -39.294  46.562  1.00151.77           C
```

FIG. 13 Continued

```
ANISOU 9099  CB   ALA B 365     16693  23224  17749  -2993    615  -3776       C
ATOM   9100  N    SER B 366        5.499 -41.540  48.992  1.00153.10           N
ANISOU 9100  N    SER B 366     17466  22885  17821  -3223    223  -3435       N
ATOM   9101  CA   SER B 366        5.186 -41.658  50.424  1.00152.67           C
ANISOU 9101  CA   SER B 366     17207  22949  17851  -3380    208  -3315       C
ATOM   9102  C    SER B 366        3.778 -42.212  50.648  1.00153.12           C
ANISOU 9102  C    SER B 366     17531  22651  17996  -3806    -42  -3105       C
ATOM   9103  O    SER B 366        2.914 -42.087  49.778  1.00152.77           O
ANISOU 9103  O    SER B 366     17655  22355  18034  -4085   -152  -3050       O
ATOM   9104  CB   SER B 366        5.290 -40.289  51.103  1.00149.66           C
ANISOU 9104  CB   SER B 366     16127  23042  17695  -3530    441  -3358       C
ATOM   9105  OG   SER B 366        4.417 -40.174  52.215  1.00148.71           O
ANISOU 9105  OG   SER B 366     15806  22967  17731  -3869    391  -3209       O
ATOM   9106  N    ARG B 367        3.538 -42.834  51.801  1.00164.98           N
ANISOU 9106  N    ARG B 367     19074  24131  19482  -3864   -141  -2971       N
ATOM   9107  CA   ARG B 367        2.174 -43.238  52.108  1.00165.22           C
ANISOU 9107  CA   ARG B 367     19273  23888  19616  -4295   -369  -2737       C
ATOM   9108  C    ARG B 367        1.462 -41.949  52.454  1.00162.20           C
ANISOU 9108  C    ARG B 367     18324  23794  19510  -4671   -216  -2699       C
ATOM   9109  O    ARG B 367        1.986 -40.861  52.209  1.00160.21           O
ANISOU 9109  O    ARG B 367     17659  23863  19351  -4598     17  -2862       O
ATOM   9110  CB   ARG B 367        2.088 -44.222  53.277  1.00166.89           C
ANISOU 9110  CB   ARG B 367     19644  24026  19741  -4269   -523  -2588       C
ATOM   9111  CG   ARG B 367        2.594 -43.690  54.604  1.00165.55           C
ANISOU 9111  CG   ARG B 367     18960  24299  19643  -4196   -318  -2619       C
ATOM   9112  CD   ARG B 367        3.887 -44.384  54.974  1.00167.27           C
ANISOU 9112  CD   ARG B 367     19325  24586  19644  -3722   -272  -2735       C
ATOM   9113  NE   ARG B 367        4.596 -43.776  56.100  1.00165.90           N
ANISOU 9113  NE   ARG B 367     18653  24855  19528  -3595    -43  -2800       N
ATOM   9114  CZ   ARG B 367        4.187 -43.813  57.365  1.00165.47           C
ANISOU 9114  CZ   ARG B 367     18372  24941  19557  -3773    -60  -2669       C
ATOM   9115  NH1  ARG B 367        3.041 -44.407  57.683  1.00166.26           N
ANISOU 9115  NH1  ARG B 367     18672  24797  19701  -4099   -294  -2449       N
ATOM   9116  NH2  ARG B 367        4.923 -43.242  58.312  1.00164.29           N
ANISOU 9116  NH2  ARG B 367     17791  25184  19446  -3626    151  -2745       N
ATOM   9117  N    VAL B 368        0.279 -42.058  53.040  1.00150.83           N
ANISOU 9117  N    VAL B 368     16856  22253  18199  -5066   -354  -2475       N
ATOM   9118  CA   VAL B 368       -0.482 -40.869  53.401  1.00148.12           C
ANISOU 9118  CA   VAL B 368     15995  22174  18111  -5426   -221  -2423       C
ATOM   9119  C    VAL B 368       -0.003 -40.186  54.709  1.00146.68           C
ANISOU 9119  C    VAL B 368     15272  22461  18000  -5341    -11  -2477       C
ATOM   9120  O    VAL B 368        0.642 -39.113  54.696  1.00144.76           O
ANISOU 9120  O    VAL B 368     14600  22565  17837  -5227    223  -2657       O
ATOM   9121  CB   VAL B 368       -1.985 -41.203  53.459  1.00148.40           C
ANISOU 9121  CB   VAL B 368     16199  21931  18257  -5887   -446  -2138       C
ATOM   9122  CG1  VAL B 368       -2.537 -41.333  52.050  1.00148.74           C
ANISOU 9122  CG1  VAL B 368     16605  21597  18313  -6052   -584  -2113       C
ATOM   9123  CG2  VAL B 368       -2.218 -42.496  54.227  1.00150.87           C
ANISOU 9123  CG2  VAL B 368     16866  22026  18431  -5865   -685  -1938       C
ATOM   9124  N    GLU B 369       -0.297 -40.850  55.829  1.00162.37           N
ANISOU 9124  N    GLU B 369     17302  24444  19947  -5389   -114  -2313       N
ATOM   9125  CA   GLU B 369        0.038  40.373  57.191  1.00161.33           C
ANISOU 9125  CA   GLU B 369     16717  24705  19875  -5353     38  -2314       C
ATOM   9126  C    GLU B 369        1.374 -40.615  57.731  1.00162.01           C
ANISOU 9126  C    GLU B 369     16752  24997  19810  -4908    165  -2479       C
ATOM   9127  O    GLU B 369        2.164 -41.339  57.138  1.00163.69           O
ANISOU 9127  O    GLU B 369     17323  25029  19842  -4601    115  -2572       O
ATOM   9128  CB   GLU B 369       -1.022 -41.079  58.126  1.00162.40           C
ANISOU 9128  CB   GLU B 369     16951  24730  20024  -5608   -151  -2039       C
ATOM   9129  CG   GLU B 369       -0.768 -42.578  58.229  1.00165.32           C
ANISOU 9129  CG   GLU B 369     17847  24781  20186  -5434   -387  -1946       C
ATOM   9130  CD   GLU B 369       -1.992 -43.412  57.891  1.00166.83           C
ANISOU 9130  CD   GLU B 369     18443  24565  20379  -5758   -699  -1670       C
ATOM   9131  OE1  GLU B 369       -2.874 -42.921  57.155  1.00165.83           O
ANISOU 9131  OE1  GLU B 369     18307  24317  20385  -6061   -733  -1593       O
ATOM   9132  OE2  GLU B 369       -2.070 -44.568  58.351  1.00169.05           O
ANISOU 9132  OE2  GLU B 369     19058  24640  20533  -5716   -924  -1519       O
ATOM   9133  N    ASN B 370        1.673 -40.006  58.874  1.00155.11           N
ANISOU 9133  N    ASN B 370     15432  24498  19004  -4874    326  -2504       N
```

FIG. 13 Continued

```
ATOM   9134  CA  ASN B 370       2.928 -40.249  59.577  1.00155.73           C
ANISOU 9134  CA  ASN B 370    15435  24779  18955  -4493    437  -2619       C
ATOM   9135  C   ASN B 370       4.189 -39.826  58.839  1.00155.37           C
ANISOU 9135  C   ASN B 370    15333  24864  18835  -4138    602  -2846       C
ATOM   9136  O   ASN B 370       5.285 -40.153  59.287  1.00156.18           O
ANISOU 9136  O   ASN B 370    15437  25094  18810  -3797    680  -2925       O
ATOM   9137  CB  ASN B 370       3.072 -41.754  59.889  1.00158.50           C
ANISOU 9137  CB  ASN B 370    16264  24845  19115  -4350    232  -2511       C
ATOM   9138  CG  ASN B 370       2.603 -42.137  61.293  1.00158.89           C
ANISOU 9138  CG  ASN B 370    16189  24992  19189  -4492    164  -2336       C
ATOM   9139  OD1 ASN B 370       3.321 -42.812  62.044  1.00160.12           O
ANISOU 9139  OD1 ASN B 370    16422  25194  19223  -4257    154  -2343       O
ATOM   9140  ND2 ASN B 370       1.389 -41.729  61.641  1.00157.91           N
ANISOU 9140  ND2 ASN B 370    15877  24902  19219  -4876    113  -2167       N
ATOM   9141  N   GLN B 371       4.089 -39.110  57.728  1.00165.77           N
ANISOU 9141  N   GLN B 371    16590  26167  20230  -4205    658  -2940       N
ATOM   9142  CA  GLN B 371       5.326 -38.927  56.962  1.00165.96           C
ANISOU 9142  CA  GLN B 371    16629  26285  20144  -3832    782  -3127       C
ATOM   9143  C   GLN B 371       6.112 -37.624  57.070  1.00163.80           C
ANISOU 9143  C   GLN B 371    15825  26440  19972  -3716   1014  -3271       C
ATOM   9144  O   GLN B 371       5.601 -36.598  57.527  1.00161.68           O
ANISOU 9144  O   GLN B 371    15137  26400  19896  -3967   1090  -3261       O
ATOM   9145  CB  GLN B 371       5.132 -39.317  55.490  1.00166.95           C
ANISOU 9145  CB  GLN B 371    17162  26078  20195  -3819    674  -3161       C
ATOM   9146  CG  GLN B 371       6.365 -40.014  54.850  1.00168.93           C
ANISOU 9146  CG  GLN B 371    17731  26251  20204  -3345    693  -3281       C
ATOM   9147  CD  GLN B 371       6.452 -41.522  55.144  1.00171.83           C
ANISOU 9147  CD  GLN B 371    18625  26299  20362  -3176    502  -3197       C
ATOM   9148  OE1 GLN B 371       6.040 -42.349  54.321  1.00173.58           O
ANISOU 9148  OE1 GLN B 371    19346  26130  20476  -3189    310  -3156       O
ATOM   9149  NE2 GLN B 371       6.991 -41.877  56.314  1.00172.35           N
ANISOU 9149  NE2 GLN B 371    18588  26525  20373  -3020    542  -3169       N
ATOM   9150  N   ASP B 372       7.372 -37.716  56.632  1.00158.18           N
ANISOU 9150  N   ASP B 372    15156  25826  19117  -3319   1110  -3394       N
ATOM   9151  CA  ASP B 372       8.317 -36.607  56.600  1.00156.54           C
ANISOU 9151  CA  ASP B 372    14499  26010  18969  -3145   1305  -3517       C
ATOM   9152  C   ASP B 372       7.572 -35.398  56.070  1.00154.16           C
ANISOU 9152  C   ASP B 372    13873  25811  18888  -3476   1338  -3548       C
ATOM   9153  O   ASP B 372       6.641 -35.544  55.281  1.00154.18           O
ANISOU 9153  O   ASP B 372    14092  25546  18942  -3724   1230  -3511       O
ATOM   9154  CB  ASP B 372       9.497 -36.916  55.651  1.00157.86           C
ANISOU 9154  CB  ASP B 372    14854  26177  18950  -2730   1363  -3619       C
ATOM   9155  CG  ASP B 372      10.451 -38.016  56.177  1.00160.18           C
ANISOU 9155  CG  ASP B 372    15423  26423  19016  -2342   1359  -3605       C
ATOM   9156  OD1 ASP B 372      11.214 -37.773  57.148  1.00159.79           O
ANISOU 9156  OD1 ASP B 372    15095  26655  18964  -2181   1471  -3605       O
ATOM   9157  OD2 ASP B 372      10.476 -39.116  55.573  1.00162.45           O
ANISOU 9157  OD2 ASP B 372    16216  26386  19121  -2185   1240  -3597       O
ATOM   9158  N   ALA B 373       7.983 -34.204  56.488  1.00187.06           N
ANISOU 9158  N   ALA B 373    17529  30356  23188  -3482   1475  -3612       N
ATOM   9159  CA  ALA B 373       7.317 -32.982  56.044  1.00184.70           C
ANISOU 9159  CA  ALA B 373    16888  30181  23109   3791   1502   3650       C
ATOM   9160  C   ALA B 373       7.269 -32.911  54.524  1.00184.76           C
ANISOU 9160  C   ALA B 373    17069  30026  23105  -3800   1473  -3715       C
ATOM   9161  O   ALA B 373       6.280 -32.460  53.945  1.00183.58           O
ANISOU 9161  O   ALA B 373    16887  29760  23107  -4136   1419  -3702       O
ATOM   9162  CB  ALA B 373       8.003 -31.757  56.612  1.00182.82           C
ANISOU 9162  CB  ALA B 373    16111  30372  22981  -3721   1632  -3722       C
ATOM   9163  N   ILE B 374       8.339 -33.366  53.881  1.00140.02           N
ANISOU 9163  N   ILE B 374    11589  24355  17255  -3424   1510  -3780       N
ATOM   9164  CA  ILE B 374       8.389 -33.363  52.430  1.00140.32           C
ANISOU 9164  CA  ILE B 374    11812  24250  17253  -3383   1487  -3844       C
ATOM   9165  C   ILE B 374       7.273 -34.226  51.866  1.00141.46           C
ANISOU 9165  C   ILE B 374    12435  23940  17372  -3615   1322  -3771       C
ATOM   9166  O   ILE B 374       6.544 -33.801  50.977  1.00140.46           O
ANISOU 9166  O   ILE B 374    12316  23689  17365  -3879   1277  -3783       O
ATOM   9167  CB  ILE B 374       9.726 -33.893  51.900  1.00142.15           C
ANISOU 9167  CB  ILE B 374    12223  24538  17249  -2894   1549  -3905       C
ATOM   9168  CG1 ILE B 374      10.888 -32.980  52.323  1.00141.03           C
```

FIG. 13 Continued

```
ANISOU 9168  CG1 ILE B 374    11595  24856  17135  -2664   1702  -3951         C
ATOM   9169  CG2 ILE B 374       9.658 -34.045  50.391  1.00142.80             C
ANISOU 9169  CG2 ILE B 374    12568  24424  17264  -2853   1506  -3961         C
ATOM   9170  CD1 ILE B 374      11.152 -31.791  51.404  1.00139.26             C
ANISOU 9170  CD1 ILE B 374    11005  24874  17034  -2712   1763  -4025         C
ATOM   9171  N   ASP B 375       7.125 -35.427  52.414  1.00166.52             N
ANISOU 9171  N   ASP B 375    16004  26866  20399  -3533   1219  -3684         N
ATOM   9172  CA  ASP B 375       6.154 -36.406  51.920  1.00168.03             C
ANISOU 9172  CA  ASP B 375    16709  26598  20535  -3716   1025  -3589         C
ATOM   9173  C   ASP B 375       4.696 -36.098  52.252  1.00166.70             C
ANISOU 9173  C   ASP B 375    16454  26309  20576  -4218    932  -3462         C
ATOM   9174  O   ASP B 375       3.793 -36.868  51.914  1.00167.86             O
ANISOU 9174  O   ASP B 375    17005  26078  20698  -4417    753  -3346         O
ATOM   9175  CB  ASP B 375       6.539 -37.782  52.429  1.00170.74             C
ANISOU 9175  CB  ASP B 375    17490  26734  20651  -3451    925  -3531         C
ATOM   9176  CG  ASP B 375       8.016 -38.039  52.290  1.00172.00             C
ANISOU 9176  CG  ASP B 375    17682  27063  20608  -2943   1039  -3641         C
ATOM   9177  OD1 ASP B 375       8.606 -37.512  51.319  1.00171.59             O
ANISOU 9177  OD1 ASP B 375    17535  27130  20531  -2779   1132  -3748         O
ATOM   9178  OD2 ASP B 375       8.584 -38.745  53.150  1.00173.38             O
ANISOU 9178  OD2 ASP B 375    17961  27265  20652  -2712   1038  -3611         O
ATOM   9179  N   ALA B 376       4.478 -34.990  52.947  1.00146.84             N
ANISOU 9179  N   ALA B 376    13417  24118  18258  -4411   1044  -3471         N
ATOM   9180  CA  ALA B 376       3.135 -34.524  53.231  1.00145.40             C
ANISOU 9180  CA  ALA B 376    13083  23880  18282  -4872    985  -3356         C
ATOM   9181  C   ALA B 376       2.900 -33.418  52.228  1.00143.34             C
ANISOU 9181  C   ALA B 376    12567  23707  18191  -5058   1047  -3449         C
ATOM   9182  O   ALA B 376       1.781 -33.182  51.783  1.00142.49             O
ANISOU 9182  O   ALA B 376    12491  23422  18228  -5430    969  -3370         O
ATOM   9183  CB  ALA B 376       3.045 -33.993  54.637  1.00144.27             C
ANISOU 9183  CB  ALA B 376    12536  24043  18237  -4945   1066  -3315         C
ATOM   9184  N   ALA B 377       3.988 -32.744  51.872  1.00140.08             N
ANISOU 9184  N   ALA B 377    11890  23574  17759  -4796   1181  -3605         N
ATOM   9185  CA  ALA B 377       3.940 -31.679  50.886  1.00138.18             C
ANISOU 9185  CA  ALA B 377    11383  23451  17668  -4932   1237  -3705         C
ATOM   9186  C   ALA B 377       3.496 -32.244  49.535  1.00139.16             C
ANISOU 9186  C   ALA B 377    11937  23198  17738  -5014   1128  -3695         C
ATOM   9187  O   ALA B 377       2.514 -31.782  48.965  1.00137.86             O
ANISOU 9187  O   ALA B 377    11732  22905  17746  -5382   1077  -3659         O
ATOM   9188  CB  ALA B 377       5.296 -30.987  50.779  1.00137.57             C
ANISOU 9188  CB  ALA B 377    10973  23748  17550  -4596   1378  -3844         C
ATOM   9189  N   MET B 378       4.188 -33.265  49.042  1.00142.77             N
ANISOU 9189  N   MET B 378    12825  23467  17955  -4674   1085  -3719         N
ATOM   9190  CA  MET B 378       3.836 -33.844  47.754  1.00143.93             C
ANISOU 9190  CA  MET B 378    13417  23246  18025  -4711    972  -3717         C
ATOM   9191  C   MET B 378       2.360 -34.236  47.691  1.00143.97             C
ANISOU 9191  C   MET B 378    13687  22878  18137  -5149    802  -3557         C
ATOM   9192  O   MET B 378       1.640 -33.774  46.804  1.00142.82             O
ANISOU 9192  O   MET B 378    13536  22598  18133  -5443    764  -3550         O
ATOM   9193  CB  MET B 378       4.726 -35.036  47.421  1.00146.85             C
ANISOU 9193  CB  MET B 378    14267  23438  18092  -4261    926  -3750         C
ATOM   9194  CG  MET B 378       6.217 -34.808  47.653  1.00147.18             C
ANISOU 9194  CG  MET B 378    14072  23848  18001  -3799   1090  -3866         C
ATOM   9195  SD  MET B 378       7.016 -33.563  46.617  1.00145.46             S
ANISOU 9195  SD  MET B 378    13428  23983  17855  -3681   1244  -4013         S
ATOM   9196  CE  MET B 378       5.926 -33.625  45.193  1.00145.26             C
ANISOU 9196  CE  MET B 378    13718  23567  17907  -4011   1114  -4005         C
ATOM   9197  N   VAL B 379       1.899 -35.070  48.623  1.00150.62             N
ANISOU 9197  N   VAL B 379    14748  23560  18921  -5204    695  -3412         N
ATOM   9198  CA  VAL B 379       0.482 -35.461  48.646  1.00150.77             C
ANISOU 9198  CA  VAL B 379    15001  23245  19041  -5626    520  -3217         C
ATOM   9199  C   VAL B 379      -0.384 -34.234  48.846  1.00147.96             C
ANISOU 9199  C   VAL B 379    14162  23085  18971  -6041    596  -3182         C
ATOM   9200  O   VAL B 379      -1.572 -34.229  48.510  1.00147.51             O
ANISOU 9200  O   VAL B 379    14217  22784  19044  -6434    483  -3040         O
ATOM   9201  CB  VAL B 379       0.154 -36.453  49.765  1.00152.48             C
ANISOU 9201  CB  VAL B 379    15443  23330  19163  -5625    397  -3048         C
ATOM   9202  CG1 VAL B 379       0.834 -36.022  51.059  1.00151.73             C
ANISOU 9202  CG1 VAL B 379    14921  23652  19077  -5447    555  -3101         C
```

FIG. 13 Continued

```
ATOM   9203  CG2 VAL B 379      -1.376 -36.583  49.943  1.00152.16           C
ANISOU 9203  CG2 VAL B 379    15494  23046  19273  -6112    238  -2813       C
ATOM   9204  N   GLY B 380       0.214 -33.207  49.437  1.00172.25           N
ANISOU 9204  N   GLY B 380    16705  26600  22141  -5949    777  -3301       N
ATOM   9205  CA  GLY B 380      -0.450 -31.931  49.568  1.00169.54           C
ANISOU 9205  CA  GLY B 380    15877  26480  22060  -6291    857  -3307       C
ATOM   9206  C   GLY B 380      -0.430 -31.375  48.162  1.00168.51           C
ANISOU 9206  C   GLY B 380    15736  26281  22008  -6377    870  -3414       C
ATOM   9207  O   GLY B 380      -1.158 -31.858  47.298  1.00169.14           O
ANISOU 9207  O   GLY B 380    16177  25995  22094  -6579    743  -3331       O
ATOM   9208  N   MET B 381       0.431 -30.392  47.919  1.00148.99           N
ANISOU 9208  N   MET B 381    12862  24156  19591  -6218   1011  -3588       N
ATOM   9209  CA  MET B 381       0.570 -29.807  46.588  1.00147.97           C
ANISOU 9209  CA  MET B 381    12675  24012  19534  -6274   1031  -3698       C
ATOM   9210  C   MET B 381      -0.803 -29.571  45.960  1.00146.86           C
ANISOU 9210  C   MET B 381    12610  23602  19587  -6762    937  -3596       C
ATOM   9211  O   MET B 381      -1.797 -29.329  46.663  1.00145.96           O
ANISOU 9211  O   MET B 381    12358  23476  19622  -7086    909  -3469       O
ATOM   9212  CB  MET B 381       1.408 -30.729  45.692  1.00150.22           C
ANISOU 9212  CB  MET B 381    13403  24105  19569  -5907    997  -3761       C
ATOM   9213  CG  MET B 381       2.221 -30.006  44.625  1.00149.34           C
ANISOU 9213  CG  MET B 381    13083  24193  19467  -5749   1084  -3921       C
ATOM   9214  SD  MET B 381       3.674 -29.125  45.250  1.00148.42           S
ANISOU 9214  SD  MET B 381    12418  24647  19329  -5382   1257  -4052       S
ATOM   9215  CE  MET B 381       4.869 -30.451  45.378  1.00151.69           C
ANISOU 9215  CE  MET B 381    13266  24985  19383  -4810   1266  -4063       C
ATOM   9216  N   LEU B 382      -0.851 -29.617  44.631  1.00214.59           N
ANISOU 9216  N   LEU B 382    21396  31976  28164  -6812    894  -3645       N
ATOM   9217  CA  LEU B 382      -2.114 -29.514  43.913  1.00213.76           C
ANISOU 9217  CA  LEU B 382    21429  31565  28226  -7266    792  -3537       C
ATOM   9218  C   LEU B 382      -2.780 -30.876  44.045  1.00216.16           C
ANISOU 9218  C   LEU B 382    22320  31423  28389  -7319    619  -3345       C
ATOM   9219  O   LEU B 382      -3.903 -31.086  43.583  1.00216.07           O
ANISOU 9219  O   LEU B 382    22534  31084  28479  -7688    494  -3195       O
ATOM   9220  CB  LEU B 382      -1.886 -29.190  42.426  1.00213.24           C
ANISOU 9220  CB  LEU B 382    21425  31410  28185  -7280    793  -3652       C
ATOM   9221  CG  LEU B 382      -1.225 -27.883  41.955  1.00210.99           C
ANISOU 9221  CG  LEU B 382    20608  31521  28038  -7245    926  -3833       C
ATOM   9222  CD1 LEU B 382      -0.904 -27.959  40.464  1.00211.36           C
ANISOU 9222  CD1 LEU B 382    20861  31417  28027  -7175    902  -3922       C
ATOM   9223  CD2 LEU B 382      -2.086 -26.655  42.250  1.00208.11           C
ANISOU 9223  CD2 LEU B 382    19752  31334  27986  -7682    961  -3814       C
ATOM   9224  N   ALA B 383      -2.057 -31.797  44.680  1.00163.82           N
ANISOU 9224  N   ALA B 383    15934  24786  21524  -6948    600  -3342       N
ATOM   9225  CA  ALA B 383      -2.507 -33.173  44.832  1.00166.40           C
ANISOU 9225  CA  ALA B 383    16838  24702  21684  -6934    412  -3171       C
ATOM   9226  C   ALA B 383      -3.847 -33.236  45.521  1.00165.93           C
ANISOU 9226  C   ALA B 383    16762  24506  21779  -7362    311  -2935       C
ATOM   9227  O   ALA B 383      -3.929 -33.331  46.744  1.00166.08           O
ANISOU 9227  O   ALA B 383    16616  24693  21794  -7344    334  -2853       O
ATOM   9228  CB  ALA B 383      -1.470 -34.016  45.579  1.00168.54           C
ANISOU 9228  CB  ALA B 383    17278  25056  21702  -6470    426  -3216       C
ATOM   9229  N   ASP B 384      -4.894 -33.187  44.709  1.00155.08           N
ANISOU 9229  N   ASP B 384    15559  22829  20535  -7747    199  -2814       N
ATOM   9230  CA  ASP B 384      -6.254 -33.285  45.190  1.00154.78           C
ANISOU 9230  CA  ASP B 384    15542  22623  20643  -8181     85  -2551       C
ATOM   9231  C   ASP B 384      -6.269 -34.411  46.209  1.00157.11           C
ANISOU 9231  C   ASP B 384    16122  22810  20762  -8034    -38  -2390       C
ATOM   9232  O   ASP B 384      -5.496 -35.361  46.097  1.00159.33           O
ANISOU 9232  O   ASP B 384    16787  22945  20806  -7680   -112  -2447       O
ATOM   9233  CB  ASP B 384      -7.185 -33.622  44.030  1.00155.11           C
ANISOU 9233  CB  ASP B 384    15977  22211  20747  -8509    -88  -2412       C
ATOM   9234  CG  ASP B 384      -6.501 -33.502  42.669  1.00155.11           C
ANISOU 9234  CG  ASP B 384    16139  22110  20683  -8335    -60  -2618       C
ATOM   9235  OD1 ASP B 384      -5.580 -32.666  42.501  1.00153.73           O
ANISOU 9235  OD1 ASP B 384    15585  22294  20531  -8116    130  -2858       O
ATOM   9236  OD2 ASP B 384      -6.889 -34.258  41.754  1.00156.58           O
ANISOU 9236  OD2 ASP B 384    16644  21855  20792  -8417   -241  -2528       O
ATOM   9237  N   PRO B 385      -7.159 -34.313  47.196  1.00158.34           N
```

FIG. 13 Continued

```
ANISOU 9237  N   PRO B 385    16091  23041  21030   -8304     -66   -2182          N
ATOM   9238  CA  PRO B 385       7.321  35.242  48.318  1.00160.24           C
ANISOU 9238  CA  PRO B 385    16504  23236  21143   -8230    -179   -1997          C
ATOM   9239  C   PRO B 385      -6.583 -36.583  48.192  1.00163.17           C
ANISOU 9239  C   PRO B 385    17420  23342  21235   -7870    -330   -2015          C
ATOM   9240  O   PRO B 385      -5.371 -36.632  47.968  1.00163.62           O
ANISOU 9240  O   PRO B 385    17497  23524  21147   -7464    -227   -2252          O
ATOM   9241  CB  PRO B 385      -6.833 -35.473  48.322  1.00160.35           C
ANISOU 9241  CB  PRO B 385    16656  22981  21290   -8710    -356   -1666          C
ATOM   9242  CG  PRO B 385      -9.405 -34.129  47.839  1.00157.45           C
ANISOU 9242  CG  PRO B 385    15855  22781  21188   -9034    -211   -1719          C
ATOM   9243  CD  PRO B 385      -8.297 -33.385  47.104  1.00156.14           C
ANISOU 9243  CD  PRO B 385    15492  22815  21019   -8770     -32   -2062          C
ATOM   9244  N   LYS B 386      -7.324 -37.664  48.407  1.00181.48           N
ANISOU 9244  N   LYS B 386    20164  25314  23477   -6017    -581   -1746          N
ATOM   9245  CA  LYS B 386      -6.787 -39.011  48.282  1.00184.45           C
ANISOU 9245  CA  LYS B 386    21106  25383  23592   -7719    -775   -1729          C
ATOM   9246  C   LYS B 386      -7.117 -39.491  46.886  1.00185.48           C
ANISOU 9246  C   LYS B 386    21748  25047  23677   -7816    -960   -1697          C
ATOM   9247  O   LYS B 386      -7.611 -40.603  46.678  1.00187.78           O
ANISOU 9247  O   LYS B 386    22580  24913  23856   -7890   -1248   -1493          O
ATOM   9248  CB  LYS B 386      -7.370 -39.941  49.346  1.00186.23           C
ANISOU 9248  CB  LYS B 386    21506  25498  23753   -7817    -973   -1448          C
ATOM   9249  CG  LYS B 386      -7.021 -39.500  50.762  1.00185.32           C
ANISOU 9249  CG  LYS B 386    20898  25845  23671   -7705    -790   -1482          C
ATOM   9250  CD  LYS B 386      -5.557 -39.046  50.851  1.00184.68           C
ANISOU 9250  CD  LYS B 386    20578  26096  23498   -7254    -546   -1822          C
ATOM   9251  CE  LYS B 386      -5.345 -37.955  51.908  1.00182.49           C
ANISOU 9251  CE  LYS B 386    19648  26336  23354   -7250    -292   -1908          C
ATOM   9252  NZ  LYS B 386      -5.793 -38.365  53.274  1.00183.22           N
ANISOU 9252  NZ  LYS B 386    19637  26542  23436   -7331    -354   -1701          N
ATOM   9253  N   GLU B 387      -6.854 -38.603  45.934  1.00187.69           N
ANISOU 9253  N   GLU B 387    21842  25418  24055   -7827    -802   -1895          N
ATOM   9254  CA  GLU B 387      -7.137 -38.840  44.528  1.00188.24           C
ANISOU 9254  CA  GLU B 387    22324  25091  24106   -7930    -935   -1898          C
ATOM   9255  C   GLU B 387      -5.841 -39.068  43.734  1.00189.29           C
ANISOU 9255  C   GLU B 387    22669  25225  24028   -7448    -863   -2185          C
ATOM   9256  O   GLU B 387      -5.645 -38.551  42.629  1.00188.37           O
ANISOU 9256  O   GLU B 387    22543  25077  23952   -7447    -789   -2333          O
ATOM   9257  CB  GLU B 387      -8.005 -37.693  43.987  1.00185.47           C
ANISOU 9257  CB  GLU B 387    21621  24807  24042   -8371    -840   -1860          C
ATOM   9258  CG  GLU B 387      -9.449 -37.726  44.549  1.00185.08           C
ANISOU 9258  CG  GLU B 387    21523  24632  24168   -8866    -978   -1511          C
ATOM   9259  CD  GLU B 387      -9.919 -36.399  45.132  1.00182.09           C
ANISOU 9259  CD  GLU B 387    20468  24667  24052   -9136    -756   -1514          C
ATOM   9260  OE1 GLU B 387      -9.583 -35.337  44.571  1.00179.90           O
ANISOU 9260  OE1 GLU B 387    19840  24611  23902   -9143    -560   -1733          O
ATOM   9261  OE2 GLU B 387     -10.632 -36.422  46.157  1.00182.02           O
ANISOU 9261  OE2 GLU B 387    20278  24765  24117   -9336    -787   -1290          O
ATOM   9262  N   ALA B 388      -4.968 -39.867  44.343  1.00173.49           N
ANISOU 9262  N   ALA B 388    20850  23269  21797   -7038    -887   -2249          N
ATOM   9263  CA  ALA B 388      -3.676 -40.259  43.791  1.00174.99           C
ANISOU 9263  CA  ALA B 388    21267  23475  21744   -6521    -828   -2490          C
ATOM   9264  C   ALA B 388      -3.337 -41.649  44.343  1.00178.13           C
ANISOU 9264  C   ALA B 388    22154  23642  21886   -6238   -1032   -2409          C
ATOM   9265  O   ALA B 388      -2.172 -41.975  44.589  1.00179.30           O
ANISOU 9265  O   ALA B 388    22332  23954  21838   -5774    -939   -2579          O
ATOM   9266  CB  ALA B 388      -2.603 -39.253  44.182  1.00177.13           C
ANISOU 9266  CB  ALA B 388    20443  23791  21548   -6252    -507   -2732          C
ATOM   9267  N   ARG B 389      -4.382 -42.448  44.555  1.00219.58           N
ANISOU 9267  N   ARG B 389    27768  28515  27146   -6535   -1318   -2132          N
ATOM   9268  CA  ARG B 389      -4.265 -43.784  45.131  1.00222.53           C
ANISOU 9268  CA  ARG B 389    28607  28637  27308   -6350   -1564   -2007          C
ATOM   9269  C   ARG B 389      -3.928 -44.827  44.087  1.00225.38           C
ANISOU 9269  C   ARG B 389    29677  28542  27416   -6065   -1793   -2057          C
ATOM   9270  O   ARG B 389      -3.507 -45.933  44.417  1.00228.04           O
ANISOU 9270  O   ARG B 389    30424  28692  27529   -5805   -1974   -2033          O
ATOM   9271  CB  ARG B 389      -5.574 -44.151  45.820  1.00222.75           C
ANISOU 9271  CB  ARG B 389    28693  28477  27465   -6805   -1793   -1655          C
```

FIG. 13 Continued

```
ATOM   9272  CG   ARG B 389      -6.291 -42.950  46.392  1.00219.68           C
ANISOU 9272  CG   ARG B 389    27662  28438  27369   -7192  -1595  -1573       C
ATOM   9273  CD   ARG B 389      -5.507 -42.305  47.540  1.00218.27           C
ANISOU 9273  CD   ARG B 389    26908  28805  27220   -6975  -1309  -1726       C
ATOM   9274  NE   ARG B 389      -4.086 -42.083  47.246  1.00218.27           N
ANISOU 9274  NE   ARG B 389    26822  29034  27077   -6489  -1099  -2052       N
ATOM   9275  CZ   ARG B 389      -3.529 -40.896  47.008  1.00215.90           C
ANISOU 9275  CZ   ARG B 389    26036  29109  26888   -6413   -808  -2273       C
ATOM   9276  NH1  ARG B 389      -4.264 -39.791  47.016  1.00213.25           N
ANISOU 9276  NH1  ARG B 389    25256  28958  26812   -6786   -688  -2229       N
ATOM   9277  NH2  ARG B 389      -2.228 -40.813  46.754  1.00216.23           N
ANISOU 9277  NH2  ARG B 389    26038  29347  26781   -5959   -648  -2527       N
ATOM   9278  N    ALA B 390      -4.137 -44.470  42.826  1.00171.00           N
ANISOU 9278  N    ALA B 390    22938  21469  20566   -6178  -1794  -2127       N
ATOM   9279  CA   ALA B 390      -3.830 -45.349  41.703  1.00173.62           C
ANISOU 9279  CA   ALA B 390    23941  21369  20657   -5922  -1997  -2194       C
ATOM   9280  C    ALA B 390      -4.378 -46.760  41.882  1.00176.74           C
ANISOU 9280  C    ALA B 390    24998  21260  20894   -5966  -2409  -1957       C
ATOM   9281  O    ALA B 390      -3.655 -47.672  42.276  1.00179.13           O
ANISOU 9281  O    ALA B 390    25600  21501  20959   -5580  -2508  -2013       O
ATOM   9282  CB   ALA B 390      -2.324 -45.388  41.455  1.00174.51           C
ANISOU 9282  CB   ALA B 390    24044  21722  20540   -5317  -1797  -2504       C
ATOM   9283  N    GLY B 391      -5.661 -46.922  41.594  1.00164.90           N
ANISOU 9283  N    GLY B 391    23719  19401  19534   -6447  -2658  -1681       N
ATOM   9284  CA   GLY B 391      -6.305 -48.218  41.649  1.00167.83           C
ANISOU 9284  CA   GLY B 391    24737  19256  19776   -6549  -3094  -1416       C
ATOM   9285  C    GLY B 391      -5.645 -49.252  42.540  1.00170.32           C
ANISOU 9285  C    GLY B 391    25280  19567  19866   -6192  -3227  -1418       C
ATOM   9286  O    GLY B 391      -5.239 -48.959  43.666  1.00169.30           O
ANISOU 9286  O    GLY B 391    24684  19854  19786   -6106  -3031  -1456       O
ATOM   9287  N    ILE B 392      -5.537 -50.467  42.002  1.00270.03           N
ANISOU 9287  N    ILE B 392    38646  31709  32244   -5983  -3573  -1379       N
ATOM   9288  CA   ILE B 392      -5.009 -51.644  42.703  1.00272.90           C
ANISOU 9288  CA   ILE B 392    39365  31953  32372   -5660  -3788  -1355       C
ATOM   9289  C    ILE B 392      -3.501 -51.648  42.992  1.00273.36           C
ANISOU 9289  C    ILE B 392    39268  32363  32235   -5062  -3516  -1687       C
ATOM   9290  O    ILE B 392      -2.697 -51.129  42.212  1.00272.78           O
ANISOU 9290  O    ILE B 392    39114  32446  32086   -4756  -3267  -1964       O
ATOM   9291  CB   ILE B 392      -5.346 -52.938  41.919  1.00276.48           C
ANISOU 9291  CB   ILE B 392    40705  31741  32604    5603   4270   1224       C
ATOM   9292  CG1  ILE B 392      -6.791 -52.902  41.415  1.00276.09           C
ANISOU 9292  CG1  ILE B 392    40856  31308  32739   -6182  -4544   -897       C
ATOM   9293  CG2  ILE B 392      -5.092 -54.172  42.776  1.00279.34           C
ANISOU 9293  CG2  ILE B 392    41416  31946  32774   -5400  -4564  -1117       C
ATOM   9294  CD1  ILE B 392      -7.824 -52.964  42.517  1.00275.40           C
ANISOU 9294  CD1  ILE B 392    40511  31275  32853   -6654  -4693   -527       C
ATOM   9295  N    ARG B 393      -3.144 -52.262  44.120  1.00178.93           N
ANISOU 9295  N    ARG B 393    27272  20520  20192   -4909  -3579  -1636       N
ATOM   9296  CA   ARG B 393      -1.762 -52.412  44.570  1.00179.62           C
ANISOU 9296  CA   ARG B 393    27235  20918  20093   -4364  -3362  -1899       C
ATOM   9297  C    ARG B 393      -1.734 -52.654  46.074  1.00179.44           C
ANISOU 9297  C    ARG B 393    26906  21144  20127   -4421  -3360  -1774       C
ATOM   9298  O    ARG B 393      -2.553 -52.109  46.817  1.00177.43           O
ANISOU 9298  O    ARG B 393    26223  21075  20117   -4848  -3314  -1578       O
ATOM   9299  CB   ARG B 393      -0.919 -51.187  44.220  1.00177.10           C
ANISOU 9299  CB   ARG B 393    26375  21076  19840   -4154  -2895  -2188       C
ATOM   9300  CG   ARG B 393       1.137 -49.980  45.115  1.00173.59           C
ANISOU 9300  CG   ARG B 393    25126  21146  19684   -4442  -2577  -2163       C
ATOM   9301  CD   ARG B 393      -0.020 -49.825  46.146  1.00173.18           C
ANISOU 9301  CD   ARG B 393    24673  21555  19572   -4087  -2316  -2319       C
ATOM   9302  NE   ARG B 393      -0.253 -50.605  47.359  1.00174.36           N
ANISOU 9302  NE   ARG B 393    24881  21666  19702   -4159  -2503  -2135       N
ATOM   9303  CZ   ARG B 393      -0.607 -50.083  48.531  1.00172.44           C
ANISOU 9303  CZ   ARG B 393    24108  21754  19656   -4418  -2379  -2018       C
ATOM   9304  NH1  ARG B 393      -0.766 -48.770  48.655  1.00169.26           N
ANISOU 9304  NH1  ARG B 393    23089  21739  19484   -4624  -2072  -2074       N
ATOM   9305  NH2  ARG B 393      -0.793 -50.874  49.581  1.00173.76           N
ANISOU 9305  NH2  ARG B 393    24366  21870  19785   -4463  -2570  -1847       N
ATOM   9306  N    GLU B 394      -0.787 -53.475  46.514  1.00239.68           N
```

FIG. 13 Continued

```
ANISOU 9306  N   GLU B 394    34758  28783  27527  -3982  -3409  -1886         N
ATOM   9307  CA  GLU B 394    -0.627 -53.794  47.929  1.00239.75              C
ANISOU 9307  CA  GLU B 394    34510  29020  27562  -3985  -3411  -1790         C
ATOM   9308  C   GLU B 394     0.839 -54.097  48.197  1.00240.87              C
ANISOU 9308  C   GLU B 394    34652  29384  27485  -3400  -3227  -2055         C
ATOM   9309  O   GLU B 394     1.182 -54.778  49.165  1.00242.10              O
ANISOU 9309  O   GLU B 394    34837  29588  27560  -3269  -3320  -2006         O
ATOM   9310  CB  GLU B 394    -1.491 -54.995  48.323  1.00242.20              C
ANISOU 9310  CB  GLU B 394    35309  28893  27823  -4222  -3901  -1479         C
ATOM   9311  CG  GLU B 394    -2.992 -54.759  48.228  1.00241.21              C
ANISOU 9311  CG  GLU B 394    35158  28568  27923  -4828  -4105  -1154         C
ATOM   9312  CD  GLU B 394    -3.502 -53.779  49.268  1.00238.16              C
ANISOU 9312  CD  GLU B 394    34030  28643  27816  -5186  -3851  -1032         C
ATOM   9313  OE1 GLU B 394    -2.759 -53.483  50.229  1.00237.18              O
ANISOU 9313  OE1 GLU B 394    33471  28947  27702  -4985  -3591  -1159         O
ATOM   9314  OE2 GLU B 394    -4.650 -53.310  49.124  1.00236.80              O
ANISOU 9314  OE2 GLU B 394    33719  28403  27850  -5663  -3917   -803         O
ATOM   9315  N   VAL B 395     1.696 -53.585  47.319  1.00181.04              N
ANISOU 9315  N   VAL B 395    27033  21944  19810  -3053  -2969  -2323         N
ATOM   9316  CA  VAL B 395     3.134 -53.804  47.417  1.00182.14              C
ANISOU 9316  CA  VAL B 395    27171  22305  19730  -2470  -2771  -2572         C
ATOM   9317  C   VAL B 395     3.933 -52.569  47.873  1.00179.21              C
ANISOU 9317  C   VAL B 395    26050  22552  19491  -2353  -2291  -2744         C
ATOM   9318  O   VAL B 395     4.308 -51.718  47.064  1.00177.84              O
ANISOU 9318  O   VAL B 395    25665  22565  19343  -2245  -2043  -2906         O
ATOM   9319  CB  VAL B 395     3.668 -54.355  46.094  1.00184.64              C
ANISOU 9319  CB  VAL B 395    28080  22301  19771  -2066  -2876  -2736         C
ATOM   9320  CG1 VAL B 395     3.857 -55.863  46.198  1.00188.45              C
ANISOU 9320  CG1 VAL B 395    29256  22362  19984  -1802  -3258  -2686         C
ATOM   9321  CG2 VAL B 395     2.701 -54.054  44.973  1.00184.07              C
ANISOU 9321  CG2 VAL B 395    28215  21929  19795  -2394  -3001  -2662         C
ATOM   9322  N   HIS B 396     4.191 -52.508  49.182  1.00219.00              N
ANISOU 9322  N   HIS B 396    30704  27897  24608  -2374  -2184  -2697         N
ATOM   9323  CA  HIS B 396     4.908 -51.405  49.835  1.00216.32              C
ANISOU 9323  CA  HIS B 396    29654  28136  24402  -2291  -1770  -2823         C
ATOM   9324  C   HIS B 396     6.436 -51.520  49.773  1.00217.33              C
ANISOU 9324  C   HIS B 396    29761  28501  24315  -1700  -1550  -3050         C
ATOM   9325  O   HIS B 396     7.011 -52.510  50.230  1.00219.63              O
ANISOU 9325  O   HIS B 396    30353  28683  24414  -1405  -1674  -3057         O
ATOM   9326  CB  HIS B 396     4.510 -51.320  51.316  1.00215.10              C
ANISOU 9326  CB  HIS B 396    29112  28200  24418  -2570  -1763  -2662         C
ATOM   9327  CG  HIS B 396     3.175 -50.689  51.560  1.00213.01              C
ANISOU 9327  CG  HIS B 396    28573  27938  24425  -3145  -1815  -2461         C
ATOM   9328  ND1 HIS B 396     2.951 -49.340  51.392  1.00209.95              N
ANISOU 9328  ND1 HIS B 396    27647  27870  24256  -3358  -1539  -2517         N
ATOM   9329  CD2 HIS B 396     2.004 -51.218  51.986  1.00213.60              C
ANISOU 9329  CD2 HIS B 396    28822  27750  24586  -3546  -2115  -2192         C
ATOM   9330  CE1 HIS B 396     1.691 -49.068  51.688  1.00208.76              C
ANISOU 9330  CE1 HIS B 396    27362  27647  24310  -3857  -1655  -2300         C
ATOM   9331  NE2 HIS B 396     1.097 -50.189  52.052  1.00210.93              N
ANISOU 9331  NE2 HIS B 396    28056  27579  24510  -3981  -2000  -2090         N
ATOM   9332  N   PHE B 397     7.090 -50.488  49.245  1.00188.51              N
ANISOU 9332  N   PHE B 397    25729  25192  20704  -1537  -1226  -3219         N
ATOM   9333  CA  PHE B 397     8.552 -50.450  49.169  1.00189.25              C
ANISOU 9333  CA  PHE B 397    25726  25569  20610   -988   -987  -3408         C
ATOM   9334  C   PHE B 397     9.056 -49.013  49.283  1.00186.15              C
ANISOU 9334  C   PHE B 397    24621  25711  20395  -1004   -605  -3505         C
ATOM   9335  O   PHE B 397    10.064 -48.632  48.692  1.00186.25              O
ANISOU 9335  O   PHE B 397    24520  25953  20292   -627   -393  -3656         O
ATOM   9336  CB  PHE B 397     9.059 -51.122  47.893  1.00191.97              C
ANISOU 9336  CB  PHE B 397    26647  25626  20669   -576  -1088  -3530         C
ATOM   9337  CG  PHE B 397     8.539 -52.516  47.702  1.00195.13              C
ANISOU 9337  CG  PHE B 397    27783  25468  20889   -561  -1498  -3436         C
ATOM   9338  CD1 PHE B 397     9.266 -53.608  48.142  1.00197.84              C
ANISOU 9338  CD1 PHE B 397    28478  25698  20995   -175  -1618  -3464         C
ATOM   9339  CD2 PHE B 397     7.309 -52.734  47.101  1.00195.39              C
ANISOU 9339  CD2 PHE B 397    28158  25086  20997   -945  -1780  -3308         C
ATOM   9340  CE1 PHE B 397     8.780 -54.893  47.972  1.00200.82              C
ANISOU 9340  CE1 PHE B 397    29544  25553  21208   -166  -2027  -3374         C
```

FIG. 13 Continued

```
ATOM   9341  CE2 PHE B 397       6.819 -54.012  46.930  1.00198.37           C
ANISOU 9341  CE2 PHE B 397    29224  24938  21211   -943  -2189  -3202       C
ATOM   9342  CZ  PHE B 397       7.553 -55.095  47.365  1.00201.11           C
ANISOU 9342  CZ  PHE B 397    29924  25172  21318   -552  -2322  -3239       C
ATOM   9343  N   LEU B 398       8.353 -48.239  50.103  1.00168.86           N
ANISOU 9343  N   LEU B 398    21953  23726  18481  -1436   -534  -3402       N
ATOM   9344  CA  LEU B 398       8.664 -46.839  50.372  1.00165.76           C
ANISOU 9344  CA  LEU B 398    20865  23825  18291  -1526   -216  -3469       C
ATOM   9345  C   LEU B 398       9.999 -46.548  51.103  1.00165.43           C
ANISOU 9345  C   LEU B 398    20453  24217  18186  -1149     43  -3563       C
ATOM   9346  O   LEU B 398      10.305 -45.385  51.366  1.00162.95           O
ANISOU 9346  O   LEU B 398    19565  24312  18034  -1214    287  -3608       O
ATOM   9347  CB  LEU B 398       7.511 -46.228  51.184  1.00163.40           C
ANISOU 9347  CB  LEU B 398    20205  23600  18280  -2073   -243  -3320       C
ATOM   9348  CG  LEU B 398       6.155 -46.916  51.015  1.00164.34           C
ANISOU 9348  CG  LEU B 398    20739  23261  18444  -2458   -567  -3140       C
ATOM   9349  CD1 LEU B 398       5.362 -46.918  52.310  1.00163.38           C
ANISOU 9349  CD1 LEU B 398    20376  23209  18493  -2823   -639  -2955       C
ATOM   9350  CD2 LEU B 398       5.375 -46.271  49.900  1.00163.10           C
ANISOU 9350  CD2 LEU B 398    20592  22969  18411  -2738   -585  -3141       C
ATOM   9351  N   PRO B 399      10.788 -47.585  51.457  1.00198.00           N
ANISOU 9351  N   PRO B 399    24898  28253  22081   -767    -20  -3581       N
ATOM   9352  CA  PRO B 399      12.040 -47.317  52.170  1.00197.68           C
ANISOU 9352  CA  PRO B 399    24505  28616  21988   -427    223  -3647       C
ATOM   9353  C   PRO B 399      12.765 -45.986  51.917  1.00195.40           C
ANISOU 9353  C   PRO B 399    23645  28798  21801   -327    536  -3740       C
ATOM   9354  O   PRO B 399      13.085 -45.645  50.777  1.00195.58           O
ANISOU 9354  O   PRO B 399    23717  28845  21749   -154    608  -3830       O
ATOM   9355  CB  PRO B 399      12.916 -48.487  51.717  1.00201.03           C
ANISOU 9355  CB  PRO B 399    25463  28831  22088     84    136  -3714       C
ATOM   9356  CG  PRO B 399      11.933 -49.638  51.596  1.00203.08           C
ANISOU 9356  CG  PRO B 399    26325  28562  22276   -101   -227  -3620       C
ATOM   9357  CD  PRO B 399      10.548 -49.040  51.413  1.00201.10           C
ANISOU 9357  CD  PRO B 399    25950  28188  22272   -659   -327  -3521       C
ATOM   9358  N   PHE B 400      13.030 -45.258  53.001  1.00164.85           N
ANISOU 9358  N   PHE B 400    19242  25299  18095   -432    705  -3709       N
ATOM   9359  CA  PHE B 400      13.823 -44.038  52.930  1.00162.84           C
ANISOU 9359  CA  PHE B 400    18434  25506  17930   -318    978  -3776       C
ATOM   9360  C   PHE B 400      14.981 -44.098  53.913  1.00163.08           C
ANISOU 9360  C   PHE B 400    18227  25843  17894    -11   1134  -3770       C
ATOM   9361  O   PHE B 400      14.906 -44.794  54.920  1.00163.86           O
ANISOU 9361  O   PHE B 400    18435  25851  17971    -40   1051  -3704       O
ATOM   9362  CB  PHE B 400      13.002 -42.783  53.224  1.00159.63           C
ANISOU 9362  CB  PHE B 400    17522  25301  17829   -782   1047  -3746       C
ATOM   9363  CG  PHE B 400      13.857 -41.556  53.463  1.00157.55           C
ANISOU 9363  CG  PHE B 400    16657  25533  17671   -679   1298  -3792       C
ATOM   9364  CD1 PHE B 400      14.912 -41.252  52.616  1.00158.05           C
ANISOU 9364  CD1 PHE B 400    16651  25793  17606   -306   1437  -3869       C
ATOM   9365  CD2 PHE B 400      13.619 -40.719  54.528  1.00155.24           C
ANISOU 9365  CD2 PHE B 400    15879  25511  17596   -943   1381  -3746       C
ATOM   9366  CE1 PHE B 400      15.716  40.148  52.831  1.00156.27           C
ANISOU 9366  CE1 PHE B 400    15879  26021  17476   -214   1638  -3883       C
ATOM   9367  CE2 PHE B 400      14.416 -39.608  54.734  1.00153.48           C
ANISOU 9367  CE2 PHE B 400    15130  25720  17463   -846   1578  -3779       C
ATOM   9368  CZ  PHE B 400      15.464 -39.326  53.878  1.00153.98           C
ANISOU 9368  CZ  PHE B 400    15128  25972  17406   -489   1700  -3840       C
ATOM   9369  N   ASN B 401      16.039 -43.346  53.610  1.00177.82           N
ANISOU 9369  N   ASN B 401    19755  28076  19733    267   1352  -3825       N
ATOM   9370  CA  ASN B 401      17.249 -43.281  54.421  1.00177.98           C
ANISOU 9370  CA  ASN B 401    19515  28418  19690    579   1518  -3805       C
ATOM   9371  C   ASN B 401      18.335 -42.492  53.706  1.00177.58           C
ANISOU 9371  C   ASN B 401    19167  28723  19582    896   1722  -3847       C
ATOM   9372  O   ASN B 401      18.402 -42.510  52.476  1.00178.45           O
ANISOU 9372  O   ASN B 401    19472  28750  19582   1047   1712  -3907       O
ATOM   9373  CB  ASN B 401      17.787 -44.685  54.660  1.00180.99           C
ANISOU 9373  CB  ASN B 401    20382  28568  19818    926   1426  -3796       C
ATOM   9374  CG  ASN B 401      18.187 -45.380  53.368  1.00183.55           C
ANISOU 9374  CG  ASN B 401    21181  28681  19879   1301   1373  -3868       C
ATOM   9375  OD1 ASN B 401      19.355 -45.711  53.160  1.00185.21           O
```

FIG. 13 Continued

```
ANISOU 9375  OD1 ASN B 401      21462  29020  19801    1772   1483  -3889           O
ATOM   9376  ND2 ASN B 401      17.217 -45.589  52.487  1.00183.94           N
ANISOU 9376  ND2 ASN B 401      21558  28399  19931    1099   1204  -3899           N
ATOM   9377  N   PRO B 402      19.206 -41.808  54.466  1.00161.17           N
ANISOU 9377  N   PRO B 402      16621  27045  17572    1004   1897  -3803           N
ATOM   9378  CA  PRO B 402      20.313 -41.110  53.808  1.00161.03           C
ANISOU 9378  CA  PRO B 402      16318  27380  17485    1328   2074  -3807           C
ATOM   9379  C   PRO B 402      21.117 -42.104  52.977  1.00164.14           C
ANISOU 9379  C   PRO B 402      17159  27646  17562    1834   2077  -3836           C
ATOM   9380  O   PRO B 402      20.875 -43.305  53.073  1.00166.29           O
ANISOU 9380  O   PRO B 402      17935  27568  17680    1929   1940  -3855           O
ATOM   9381  CB  PRO B 402      21.146 -40.597  54.982  1.00159.91           C
ANISOU 9381  CB  PRO B 402      15732  27601  17425    1396   2213   3724           C
ATOM   9382  CG  PRO B 402      20.172 -40.442  56.083  1.00158.25           C
ANISOU 9382  CG  PRO B 402      15398  27301  17427     956   2130  -3703           C
ATOM   9383  CD  PRO B 402      19.186 -41.563  55.917  1.00159.80           C
ANISOU 9383  CD  PRO B 402      16138  27029  17550     819   1932  -3734           C
ATOM   9384  N   VAL B 403      22.045 -41.605  52.168  1.00202.06           N
ANISOU 9384  N   VAL B 403      21778  32732  22263    2155   2218  -3832           N
ATOM   9385  CA  VAL B 403      22.882 -42.442  51.299  1.00205.08           C
ANISOU 9385  CA  VAL B 403      22547  33048  22326    2680   2245  -3855           C
ATOM   9386  C   VAL B 403      22.089 -43.281  50.284  1.00206.91           C
ANISOU 9386  C   VAL B 403      23372  32827  22417    2678   2068  -3954           C
ATOM   9387  O   VAL B 403      22.677 -43.988  49.461  1.00209.56           O
ANISOU 9387  O   VAL B 403      24077  33071  22474    3112   2070  -3989           O
ATOM   9388  CB  VAL B 403      23.877 -43.332  52.091  1.00207.11           C
ANISOU 9388  CB  VAL B 403      22957  33342  22395    3066   2300  -3796           C
ATOM   9389  CG1 VAL B 403      24.448 -42.568  53.279  1.00205.13           C
ANISOU 9389  CG1 VAL B 403      22156  33465  22319    2974   2436  -3690           C
ATOM   9390  CG2 VAL B 403      23.219 -44.632  52.533  1.00208.85           C
ANISOU 9390  CG2 VAL B 403      23728  33099  22527    2999   2102  -3838           C
ATOM   9391  N   ASP B 404      20.762 -43.194  50.347  1.00192.91           N
ANISOU 9391  N   ASP B 404      21693  30774  20830    2195   1910  -3987           N
ATOM   9392  CA  ASP B 404      19.882 -43.856  49.383  1.00194.30           C
ANISOU 9392  CA  ASP B 404      22401  30511  20913    2114   1720  -4059           C
ATOM   9393  C   ASP B 404      19.011 -42.758  48.811  1.00191.69           C
ANISOU 9393  C   ASP B 404      21774  30234  20826    1690   1717  -4083           C
ATOM   9394  O   ASP B 404      18.733 -42.712  47.614  1.00192.23           O
ANISOU 9394  O   ASP B 404      22042  30168  20828    1717   1672  -4143           O
ATOM   9395  CB  ASP B 404      19.045 -44.947  50.043  1.00195.44           C
ANISOU 9395  CB  ASP B 404      22997  30218  21044    1920   1494  -4045           C
ATOM   9396  CG  ASP B 404      19.675  46.323  49.907  1.00199.00           C
ANISOU 9396  CG  ASP B 404      24013  30427  21172    2385   1406  -4068           C
ATOM   9397  OD1 ASP B 404      20.007 -46.715  48.764  1.00201.06           O
ANISOU 9397  OD1 ASP B 404      24619  30571  21205    2721   1387  -4134           O
ATOM   9398  OD2 ASP B 404      19.835 -47.012  50.940  1.00199.78           O
ANISOU 9398  OD2 ASP B 404      24213  30454  21241    2420   1352  -4021           O
ATOM   9399  N   LYS B 405      18.576 -41.881  49.703  1.00162.30           N
ANISOU 9399  N   LYS B 405      17576  26705  17385    1297   1761  -4035           N
ATOM   9400  CA  LYS B 405      17.953 -40.634  49.316  1.00159.49           C
ANISOU 9400  CA  LYS B 405      16810  26509  17282     920   1799  -4050           C
ATOM   9401  C   LYS B 405      16.645 -40.684  48.519  1.00159.07           C
ANISOU 9401  C   LYS B 405      17028  26092  17320     553   1633  -4091           C
ATOM   9402  O   LYS B 405      16.366 -39.754  47.771  1.00157.39           O
ANISOU 9402  O   LYS B 405      16555  26004  17241     373   1676  -4124           O
ATOM   9403  CB  LYS B 405      18.989 -39.825  48.540  1.00159.18           C
ANISOU 9403  CB  LYS B 405      16430  26865  17186    1218   1975  -4062           C
ATOM   9404  CG  LYS B 405      18.913 -38.345  48.767  1.00155.98           C
ANISOU 9404  CG  LYS B 405      15372  26834  17059     922   2074  -4037           C
ATOM   9405  CD  LYS B 405      20.300 -37.738  48.741  1.00155.96           C
ANISOU 9405  CD  LYS B 405      14968  27305  16985    1289   2253  -3980           C
ATOM   9406  CE  LYS B 405      21.128 -38.207  49.924  1.00156.85           C
ANISOU 9406  CE  LYS B 405      15038  27545  17012    1530   2322  -3903           C
ATOM   9407  NZ  LYS B 405      22.274 -37.292  50.178  1.00155.90           N
ANISOU 9407  NZ  LYS B 405      14382  27924  16927    1727   2481  -3810           N
ATOM   9408  N   ARG B 406      15.826 -41.720  48.677  1.00164.87           N
ANISOU 9408  N   ARG B 406      18264  26383  17996     418   1433  -4076           N
ATOM   9409  CA  ARG B 406      14.570 -41.748  47.926  1.00164.46           C
ANISOU 9409  CA  ARG B 406      18466  25981  18039      51   1266  -4088           C
```

FIG. 13 Continued

```
ATOM   9410  C   ARG B 406      13.524 -42.738  48.413  1.00165.51           C
ANISOU 9410  C   ARG B 406    19044  25666  18177   -208   1025  -4021       C
ATOM   9411  O   ARG B 406      13.834 -43.682  49.141  1.00167.30           O
ANISOU 9411  O   ARG B 406    19526  25776  18264    -22    955  -3984       O
ATOM   9412  CB  ARG B 406      14.843 -42.026  46.447  1.00166.18           C
ANISOU 9412  CB  ARG B 406    19028  26055  18057    327   1243  -4168       C
ATOM   9413  CG  ARG B 406      15.381 -43.424  46.180  1.00169.83           C
ANISOU 9413  CG  ARG B 406    20112  26233  18182    780   1138  -4192       C
ATOM   9414  CD  ARG B 406      15.366 -43.795  44.707  1.00171.67           C
ANISOU 9414  CD  ARG B 406    20778  26229  18221    990   1063  -4268       C
ATOM   9415  NE  ARG B 406      15.947 -45.118  44.516  1.00175.29           N
ANISOU 9415  NE  ARG B 406    21826  26433  18342   1461    962  -4297       N
ATOM   9416  CZ  ARG B 406      15.249 -46.245  44.540  1.00177.27           C
ANISOU 9416  CZ  ARG B 406    22676  26189  18490   1390    698  -4277       C
ATOM   9417  NH1 ARG B 406      13.941 -46.204  44.733  1.00175.98           N
ANISOU 9417  NH1 ARG B 406    22588  25740  18537    862    517  -4210       N
ATOM   9418  NH2 ARG B 406      15.857 -47.410  44.367  1.00180.61           N
ANISOU 9418  NH2 ARG B 406    23622  26403  18599   1849    604  -4312       N
ATOM   9419  N   THR B 407      12.283 -42.502  47.985  1.00159.97           N
ANISOU 9419  N   THR B 407    18424  24719  17639   -647    892  -3991       N
ATOM   9420  CA  THR B 407      11.147 -43.381  48.268  1.00160.95           C
ANISOU 9420  CA  THR B 407    18977  24395  17781   -944    633  -3895       C
ATOM   9421  C   THR B 407      11.039 -44.414  47.137  1.00163.79           C
ANISOU 9421  C   THR B 407    20020  24315  17900   -738    440  -3928       C
ATOM   9422  O   THR B 407      11.590 -44.198  46.058  1.00164.35           O
ANISOU 9422  O   THR B 407    20152  24444  17851   -475    524  -4028       O
ATOM   9423  CB  THR B 407       9.842 -42.575  48.379  1.00158.33           C
ANISOU 9423  CB  THR B 407    18377  24027  17752  -1530    586  -3820       C
ATOM   9424  OG1 THR B 407      10.123 -41.290  48.937  1.00155.50           O
ANISOU 9424  OG1 THR B 407    17343  24136  17603  -1649    807  -3844       O
ATOM   9425  CG2 THR B 407       8.850 -43.282  49.277  1.00158.80           C
ANISOU 9425  CG2 THR B 407    18649  23810  17877  -1845    378  -3671       C
ATOM   9426  N   ALA B 408      10.335 -45.526  47.360  1.00217.66           N
ANISOU 9426  N   ALA B 408    27356  30701  24644   -849    171  -3839       N
ATOM   9427  CA  ALA B 408      10.283 -46.580  46.335  1.00220.65           C
ANISOU 9427  CA  ALA B 408    28430  30638  24770   -620    -42  -3870       C
ATOM   9428  C   ALA B 408       9.026 -47.466  46.272  1.00221.92           C
ANISOU 9428  C   ALA B 408    29116  30261  24942   -956   -391  -3736       C
ATOM   9429  O   ALA B 408       9.129 -48.688  46.319  1.00224.79           O
ANISOU 9429  O   ALA B 408    30029  30294  25089   -741   -612  -3710       O
ATOM   9430  CB  ALA B 408      11.536 -47.446  46.408  1.00223.43           C
ANISOU 9430  CB  ALA B 408    29059  31023  24812    -25     -9  -3949       C
ATOM   9431  N   LEU B 409       7.855 -46.856  46.122  1.00168.21           N
ANISOU 9431  N   LEU B 409    22156  23366  18388  -1474   -453  -3643       N
ATOM   9432  CA  LEU B 409       6.587 -47.594  46.068  1.00169.19           C
ANISOU 9432  CA  LEU B 409    22730  23002  18554  -1843   -787  -3475       C
ATOM   9433  C   LEU B 409       6.571 -48.698  45.009  1.00172.43           C
ANISOU 9433  C   LEU B 409    23901  22918  18696  -1604  -1051  -3499       C
ATOM   9434  O   LEU B 409       7.533 -48.868  44.264  1.00173.91           O
ANISOU 9434  O   LEU B 409    24268  23152  18659  -1138   -957  -3659       O
ATOM   9435  CB  LEU B 409       5.423 -46.622  45.842  1.00166.40           C
ANISOU 9435  CB  LEU B 409    22061  22660  18502  -2402   -772  -3384       C
ATOM   9436  CG  LEU B 409       3.961 -47.056  46.021  1.00166.52           C
ANISOU 9436  CG  LEU B 409    22337  22282  18651  -2907  -1070  -3154       C
ATOM   9437  CD1 LEU B 409       3.371 -47.588  44.729  1.00168.13           C
ANISOU 9437  CD1 LEU B 409    23130  21995  18759  -2975  -1315  -3125       C
ATOM   9438  CD2 LEU B 409       3.781 -48.058  47.159  1.00168.16           C
ANISOU 9438  CD2 LEU B 409    22751  22351  18793  -2921  -1273  -3003       C
ATOM   9439  N   THR B 410       5.474 -49.455  44.973  1.00174.45           N
ANISOU 9439  N   THR B 410    24606  22706  18970  -1919  -1390  -3327       N
ATOM   9440  CA  THR B 410       5.270 -50.521  43.993  1.00177.54           C
ANISOU 9440  CA  THR B 410    25765  22567  19127  -1762  -1700  -3320       C
ATOM   9441  C   THR B 410       3.787 -50.885  43.850  1.00177.69           C
ANISOU 9441  C   THR B 410    26104  22129  19279  -2288  -2040  -3087       C
ATOM   9442  O   THR B 410       3.165 -51.371  44.795  1.00177.96           O
ANISOU 9442  O   THR B 410    26172  22051  19392  -2548  -2231  -2895       O
ATOM   9443  CB  THR B 410       6.071 -51.773  44.345  1.00180.86           C
ANISOU 9443  CB  THR B 410    26646  22828  19245  -1293  -1851  -3361       C
ATOM   9444  OG1 THR B 410       7.469 -51.465  44.331  1.00180.96           O
```

FIG. 13 Continued

```
ANISOU 9444  OG1 THR B 410     26404  23242  19112   -778  -1540  -3564       O
ATOM   9445  CG2 THR B 410      5.801 -52.857 43.334  1.00184.13             C
ANISOU 9445  CG2 THR B 410     27875  22671  19415  -1140  -2200  -3352       C
ATOM   9446  N   TYR B 411      3.241 -50.661 42.654  1.00176.32             N
ANISOU 9446  N   TYR B 411     26166  21700  19127  -2440  -2120  -3093       N
ATOM   9447  CA  TYR B 411      1.814 -50.865 42.365  1.00176.21             C
ANISOU 9447  CA  TYR B 411     26428  21262  19261  -2966  -2422  -2861       C
ATOM   9448  C   TYR B 411      1.595 -51.477 40.990  1.00178.50             C
ANISOU 9448  C   TYR B 411     27403  21053  19365  -2859  -2670  -2887       C
ATOM   9449  O   TYR B 411      2.476 -51.429 40.129  1.00179.46             O
ANISOU 9449  O   TYR B 411     27664  21230  19291  -2428  -2537  -3106       O
ATOM   9450  CB  TYR B 411      1.052 -49.534 42.425  1.00172.45             C
ANISOU 9450  CB  TYR B 411     25334  21056  19133  -3464  -2214  -2795       C
ATOM   9451  CG  TYR B 411      1.529 -48.517 41.407  1.00170.76             C
ANISOU 9451  CG  TYR B 411     24844  21078  18958  -3348  -1930  -3004       C
ATOM   9452  CD1 TYR B 411      0.639 -47.689 40.736  1.00168.57             C
ANISOU 9452  CD1 TYR B 411     24389  20747  18913  -3784  -1903  -2943       C
ATOM   9453  CD2 TYR B 411      2.884 -48.392 41.113  1.00171.41             C
ANISOU 9453  CD2 TYR B 411     24838  21448  18844  -2798  -1695  -3249       C
ATOM   9454  CE1 TYR B 411      1.098 -46.758 39.804  1.00167.02             C
ANISOU 9454  CE1 TYR B 411     23927  20780  18755  -3680  -1653  -3133       C
ATOM   9455  CE2 TYR B 411      3.346 -47.478 40.188  1.00169.99             C
ANISOU 9455  CE2 TYR B 411     24391  21505  18692  -2684  -1449  -3422       C
ATOM   9456  CZ  TYR B 411      2.459 -46.664 39.540  1.00167.78             C
ANISOU 9456  CZ  TYR B 411     23932  21170  18647  -3125  -1432  -3369       C
ATOM   9457  OH  TYR B 411      2.966 -45.770 38.628  1.00166.41             O
ANISOU 9457  OH  TYR B 411     23483  21247  18498   3001   1196   3541       O
ATOM   9458  N   ILE B 412      0.403 -52.030 40.784  1.00251.76             N
ANISOU 9458  N   ILE B 412     37101  29850  28706  -3258  -3035  -2649       N
ATOM   9459  CA  ILE B 412      0.064 -52.682 39.522  1.00254.08             C
ANISOU 9459  CA  ILE B 412     38102  29606  28830  -3205  -3327  -2638       C
ATOM   9460  C   ILE B 412     -1.308 -52.248 39.019  1.00252.50             C
ANISOU 9460  C   ILE B 412     37915  29142  28880  -3813  -3474  -2422       C
ATOM   9461  O   ILE B 412     -1.969 -51.408 39.624  1.00249.58             O
ANISOU 9461  O   ILE B 412     36989  29030  28812  -4256  -3330  -2292       O
ATOM   9462  CB  ILE B 412      0.093 -54.238 39.634  1.00258.13             C
ANISOU 9462  CB  ILE B 412     39389  29627  29062  -2972  -3761  -2546       C
ATOM   9463  CG1 ILE B 412     -1.313 -54.814 39.838  1.00258.78             C
ANISOU 9463  CG1 ILE B 412     39807  29244  29272  -3510  -4191  -2197       C
ATOM   9464  CG2 ILE B 412      1.032  54.688 40.746  1.00259.07             C
ANISOU 9464  CG2 ILE B 412     39355  30028  29052  -2605  -3669  -2625       C
ATOM   9465  CD1 ILE B 412     -1.402 -56.310 39.596  1.00262.93             C
ANISOU 9465  CD1 ILE B 412     41196  29188  29517  -3313  -4683  -2101       C
ATOM   9466  N   ASP B 413     -1.720 -52.834 37.902  1.00248.92             N
ANISOU 9466  N   ASP B 413     38114  28171  28294  -3820  -3764  -2382       N
ATOM   9467  CA  ASP B 413     -2.998 -52.533 37.281  1.00247.80             C
ANISOU 9467  CA  ASP B 413     38081  27709  28361  -4374  -3939  -2169       C
ATOM   9468  C   ASP B 413     -3.181 -53.481 36.102  1.00251.01             C
ANISOU 9468  C   ASP B 413     39352  27496  28523  -4228  -4309  -2154       C
ATOM   9469  O   ASP B 413     -4.295 -53.699 35.622  1.00251.29             O
ANISOU 9469  O   ASP B 413     39727  27092  28661  -4654  -4609  -1916       O
ATOM   9470  CB  ASP B 413     -3.019 -51.082 36.802  1.00244.19             C
ANISOU 9470  CB  ASP B 413     36997  27639  28145  -4568  -3547  -2298       C
ATOM   9471  CG  ASP B 413     -4.245 -50.758 35.974  1.00243.12             C
ANISOU 9471  CG  ASP B 413     37010  27157  28206  -5098  -3710  -2109       C
ATOM   9472  OD1 ASP B 413     -5.318 -51.341 36.238  1.00243.96             O
ANISOU 9472  OD1 ASP B 413     37423  26879  28393   5493   4057   1796       O
ATOM   9473  OD2 ASP B 413     -4.134 -49.917 35.058  1.00241.43             O
ANISOU 9473  OD2 ASP B 413     36599  27062  28072  -5126  -3495  -2260       O
ATOM   9474  N   GLY B 414     -2.070 -54.052 35.649  1.00232.66             N
ANISOU 9474  N   GLY B 414     37390  25141  25868  -3609  -4291  -2403       N
ATOM   9475  CA  GLY B 414     -2.076 -54.966 34.524  1.00235.99             C
ANISOU 9475  CA  GLY B 414     38652  25003  26012  -3370  -4623  -2435       C
ATOM   9476  C   GLY B 414     -0.844 -55.850 34.492  1.00239.29             C
ANISOU 9476  C   GLY B 414     39471  25406  26041  -2659  -4655  -2659       C
ATOM   9477  O   GLY B 414     -0.126 -55.965 35.486  1.00239.30             O
ANISOU 9477  O   GLY B 414     39175  25751  25996  -2411  -4503  -2728       O
ATOM   9478  N   SER B 415     -0.601 -56.464 33.337  1.00250.58             N
ANISOU 9478  N   SER B 415     41580  26439  27190  -2328  -4851  -2771       N
```

FIG. 13 Continued

```
ATOM   9479  CA  SER B 415       0.514 -57.392  33.144  1.00254.18           C
ANISOU 9479  CA  SER B 415    42526  26811  27241  -1625  -4925  -2979       C
ATOM   9480  C   SER B 415       1.817 -56.955  33.820  1.00253.26           C
ANISOU 9480  C   SER B 415    41837  27333  27060  -1172  -4486  -3210       C
ATOM   9481  O   SER B 415       2.097 -57.354  34.950  1.00253.61           O
ANISOU 9481  O   SER B 415    41735  27527  27099  -1103  -4505  -3159       O
ATOM   9482  CB  SER B 415       0.753 -57.633  31.649  1.00256.37           C
ANISOU 9482  CB  SER B 415    43387  26762  27259  -1300  -5017  -3139       C
ATOM   9483  OG  SER B 415      -0.385 -58.214  31.033  1.00257.79           O
ANISOU 9483  OG  SER B 415    44207  26288  27455  -1666  -5481  -2919       O
ATOM   9484  N   GLY B 416       2.614 -56.147  33.125  1.00198.93           N
ANISOU 9484  N   GLY B 416    34632  20825  20126   -868  -4102  -3450       N
ATOM   9485  CA  GLY B 416       3.873 -55.675  33.672  1.00198.07           C
ANISOU 9485  CA  GLY B 416    33973  21328  19955   -437  -3685  -3651       C
ATOM   9486  C   GLY B 416       3.657 -54.926  34.971  1.00194.67           C
ANISOU 9486  C   GLY B 416    32771  21338  19858   -822  -3461  -3541       C
ATOM   9487  O   GLY B 416       2.587 -54.349  35.192  1.00192.12           O
ANISOU 9487  O   GLY B 416    32164  20977  19854  -1431  -3498  -3357       O
ATOM   9488  N   ASN B 417       4.660 -54.954  35.846  1.00194.94           N
ANISOU 9488  N   ASN B 417    32476  21780  19811   -465  -3239  -3643       N
ATOM   9489  CA  ASN B 417       4.575 -54.236  37.115  1.00191.84           C
ANISOU 9489  CA  ASN B 417    31347  21835  19711   -774  -3010  -3559       C
ATOM   9490  C   ASN B 417       5.400 -52.958  37.155  1.00188.95           C
ANISOU 9490  C   ASN B 417    30203  22125  19465   -640  -2510  -3728       C
ATOM   9491  O   ASN B 417       6.575 -52.933  36.770  1.00190.11           O
ANISOU 9491  O   ASN B 417    30332  22521  19382    -86  -2301  -3925       O
ATOM   9492  CB  ASN B 417       4.901 -55.144  38.306  1.00193.54           C
ANISOU 9492  CB  ASN B 417    31686  22029  19821   -610  -3154  -3493       C
ATOM   9493  CG  ASN B 417       3.656 -55.580  39.057  1.00193.26           C
ANISOU 9493  CG  ASN B 417    31774  21675  19981  -1166  -3492  -3207       C
ATOM   9494  OD1 ASN B 417       3.723 -56.029  40.201  1.00193.58           O
ANISOU 9494  OD1 ASN B 417    31717  21792  20044  -1192  -3564  -3112       O
ATOM   9495  ND2 ASN B 417       2.506 -55.434  38.414  1.00192.64           N
ANISOU 9495  ND2 ASN B 417    31897  21249  20049  -1623  -3699  -3052       N
ATOM   9496  N   TRP B 418       4.751 -51.872  37.606  1.00183.80           N
ANISOU 9496  N   TRP B 418    28918  21744  19172  -1155  -2338  -3633       N
ATOM   9497  CA  TRP B 418       5.371 -50.557  37.732  1.00180.71           C
ANISOU 9497  CA  TRP B 418    27747  21965  18948  -1128  -1901  -3759       C
ATOM   9498  C   TRP B 418       5.661 -50.224  39.175  1.00178.99           C
ANISOU 9498  C   TRP B 418    26969  22157  18884  -1202  -1725  -3712       C
ATOM   9499  O   TRP B 418       4.827 -50.422  40.053  1.00178.30           O
ANISOU 9499  O   TRP B 418    26834  21945  18966  -1600  -1884  -3527       O
ATOM   9500  CB  TRP B 418       4.456 -49.460  37.168  1.00177.59           C
ANISOU 9500  CB  TRP B 418    27000  21614  18861  -1655  -1818  -3702       C
ATOM   9501  CG  TRP B 418       3.786 -49.828  35.929  1.00178.96           C
ANISOU 9501  CG  TRP B 418    27747  21291  18957  -1765  -2063  -3676       C
ATOM   9502  CD1 TRP B 418       4.273 -49.667  34.670  1.00179.82           C
ANISOU 9502  CD1 TRP B 418    28043  21379  18902  -1467  -1984  -3838       C
ATOM   9503  CD2 TRP B 418       2.491 -50.432  35.789  1.00179.71           C
ANISOU 9503  CD2 TRP B 418    28319  20831  19133  -2209  -2442  -3458       C
ATOM   9504  NE1 TRP B 418       3.368 -50.135  33.747  1.00181.05           N
ANISOU 9504  NE1 TRP B 418    28778  20986  19029  -1695  -2288  -3750       N
ATOM   9505  CE2 TRP B 418       2.263 -50.609  34.407  1.00181.01           C
ANISOU 9505  CE2 TRP B 418    28963  20637  19175  -2157  -2579  -3510       C
ATOM   9506  CE3 TRP B 418       1.505 -50.841  36.695  1.00179.49           C
ANISOU 9506  CE3 TRP B 418    28354  20579  19265  -2644  -2686  -3209       C
ATOM   9507  CZ2 TRP B 418       1.086 -51.176  33.907  1.00182.05           C
ANISOU 9507  CZ2 TRP B 418    29646  20180  19345  -2535  -2957  -3318       C
ATOM   9508  CZ3 TRP B 418       0.338 -51.403  36.197  1.00180.56           C
ANISOU 9508  CZ3 TRP B 418    29019  20147  19437  -3017  -3062  -3004       C
ATOM   9509  CH2 TRP B 418       0.140 -51.565  34.815  1.00181.81           C
ANISOU 9509  CH2 TRP B 418    29661  19940  19477  -2965  -3197  -3059       C
ATOM   9510  N   HIS B 419       6.859 -49.722  39.415  1.00179.65           N
ANISOU 9510  N   HIS B 419    26628  22734  18899   -810  -1400  -3868       N
ATOM   9511  CA  HIS B 419       7.187 -49.195  40.722  1.00177.62           C
ANISOU 9511  CA  HIS B 419    25759  22917  18810   -891  -1189  -3837       C
ATOM   9512  C   HIS B 419       8.160 -48.025  40.570  1.00175.53           C
ANISOU 9512  C   HIS B 419    24855  23235  18603   -676   -792  -3987       C
ATOM   9513  O   HIS B 419       9.371 -48.165  40.697  1.00176.69           O
```

FIG. 13 Continued

```
ANISOU 9513  O   HIS B 419    24929  23653  18553   -173   -624  -4098       O
ATOM   9514  CB  HIS B 419       7.527 -50.292  41.777  1.00179.82           C
ANISOU 9514  CB  HIS B 419    26303  23088  18933   -677  -1342  -3778       C
ATOM   9515  CG  HIS B 419       8.951 -50.774  41.806  1.00182.01           C
ANISOU 9515  CG  HIS B 419    26687  23557  18911    -20  -1208  -3930       C
ATOM   9516  ND1 HIS B 419       9.993 -50.016  42.295  1.00180.51           N
ANISOU 9516  ND1 HIS B 419    25907  23924  18753    223   -856  -4023       N
ATOM   9517  CD2 HIS B 419       9.481 -51.988  41.518  1.00185.68           C
ANISOU 9517  CD2 HIS B 419    27784  23722  19042    434  -1398  -3983       C
ATOM   9518  CE1 HIS B 419      11.113 -50.716  42.242  1.00183.12           C
ANISOU 9518  CE1 HIS B 419    26492  24301  18783    801   -817  -4122       C
ATOM   9519  NE2 HIS B 419      10.830 -51.917  41.773  1.00186.29           N
ANISOU 9519  NE2 HIS B 419    27636  24191  18956    947  -1138  -4109       N
ATOM   9520  N   ARG B 420       7.583 -46.872  40.230  1.00282.03           N
ANISOU 9520  N   ARG B 420    37900  36894  32363  -1072   -663  -3975       N
ATOM   9521  CA  ARG B 420       8.327 -45.631  40.055  1.00279.68           C
ANISOU 9521  CA  ARG B 420    36956  37138  32172   -969   -322  -4090       C
ATOM   9522  C   ARG B 420       8.448 -44.928  41.379  1.00277.23           C
ANISOU 9522  C   ARG B 420    36011  37240  32083  -1153   -145  -4040       C
ATOM   9523  O   ARG B 420       7.601 -45.089  42.246  1.00276.46           O
ANISOU 9523  O   ARG B 420    35887  37005  32147  -1527   -272  -3904       O
ATOM   9524  CB  ARG B 420       7.619 -44.703  39.067  1.00277.54           C
ANISOU 9524  CB  ARG B 420    36503  36848  32101  -1330   -287  -4103       C
ATOM   9525  CG  ARG B 420       7.851 -43.218  39.327  1.00273.95           C
ANISOU 9525  CG  ARG B 420    35244  36941  31918  -1516      4  -4145       C
ATOM   9526  CD  ARG B 420       8.018 -42.428  38.031  1.00273.02           C
ANISOU 9526  CD  ARG B 420    34973  36942  31822  -1491    120  -4248       C
ATOM   9527  NE  ARG B 420       6.847 -42.468  37.157  1.00272.70           N
ANISOU 9527  NE  ARG B 420    35245  36482  31887  -1891    -69  -4195       N
ATOM   9528  CZ  ARG B 420       6.163 -41.395  36.767  1.00269.79           C
ANISOU 9528  CZ  ARG B 420    34487  36216  31804  -2333     -2  -4181       C
ATOM   9529  NH1 ARG B 420       6.530 -40.184  37.168  1.00266.98           N
ANISOU 9529  NH1 ARG B 420    33416  36369  31655  -2427    238  -4224       N
ATOM   9530  NH2 ARG B 420       5.114 -41.533  35.966  1.00269.73           N
ANISOU 9530  NH2 ARG B 420    34814  35794  31877  -2682   -187  -4119       N
ATOM   9531  N   VAL B 421       9.498 -44.137  41.532  1.00226.35           N
ANISOU 9531  N   VAL B 421    29055  31303  25644   -888    140  -4136       N
ATOM   9532  CA  VAL B 421       9.717 -43.410  42.768  1.00224.06           C
ANISOU 9532  CA  VAL B 421    28154  31425  25552  -1027    315  -4098       C
ATOM   9533  C   VAL B 421      10.944 -42.557  42.627  1.00223.12           C
ANISOU 9533  C   VAL B 421    27543  31829  25404   -691    601  -4201       C
ATOM   9534  O   VAL B 421      11.779 -42.815  41.760  1.00224.93           O
ANISOU 9534  O   VAL B 421    27971  32095  25396   -254    658  -4290       O
ATOM   9535  CB  VAL B 421       9.951 -44.352  43.927  1.00225.68           C
ANISOU 9535  CB  VAL B 421    28552  31549  25646   -880    227  -4031       C
ATOM   9536  CG1 VAL B 421       8.643 -44.642  44.628  1.00225.01           C
ANISOU 9536  CG1 VAL B 421    28577  31173  25744  -1385     15  -3876       C
ATOM   9537  CG2 VAL B 421      10.647 -45.620  43.439  1.00229.43           C
ANISOU 9537  CG2 VAL B 421    29659  31756  25758   -365    106  -4088       C
ATOM   9538  N   SER B 422      11.083 -41.562  43.498  1.00160.01           N
ANISOU 9538  N   SER B 422    18915  24246  17637   -875    773  -4178       N
ATOM   9539  CA  SER B 422      12.195 -40.652  43.335  1.00158.95           C
ANISOU 9539  CA  SER B 422    18280  24614  17500   -602   1022  -4250       C
ATOM   9540  C   SER B 422      12.263 -39.518  44.332  1.00155.96           C
ANISOU 9540  C   SER B 422    17213  24658  17386   -843   1176  -4216       C
ATOM   9541  O   SER B 422      11.269 -38.875  44.629  1.00153.66           O
ANISOU 9541  O   SER B 422    16683  24342  17360  -1326   1137  -4173       O
ATOM   9542  CB  SER B 422      12.113 -40.056  41.938  1.00158.39           C
ANISOU 9542  CB  SER B 422    18178  24560  17444   -626   1055  -4322       C
ATOM   9543  OG  SER B 422      10.756 -39.881  41.550  1.00157.12           O
ANISOU 9543  OG  SER B 422    18141  24078  17479  -1136    903  -4285       O
ATOM   9544  N   LYS B 423      13.473 -39.255  44.801  1.00162.27           N
ANISOU 9544  N   LYS B 423    17700  25854  18103   -486   1351  -4230       N
ATOM   9545  CA  LYS B 423      13.737 -38.199  45.754  1.00159.72           C
ANISOU 9545  CA  LYS B 423    16738  25954  17996   -638   1495  -4198       C
ATOM   9546  C   LYS B 423      15.239 -37.899  45.715  1.00160.32           C
ANISOU 9546  C   LYS B 423    16535  26454  17926   -158   1681  -4215       C
ATOM   9547  O   LYS B 423      16.045 -38.817  45.727  1.00162.90           O
ANISOU 9547  O   LYS B 423    17179  26728  17986    281   1694  -4215       O
```

FIG. 13 Continued

```
ATOM   9548  CB  LYS B 423      13.345 -38.659  47.164  1.00159.64           C
ANISOU 9548  CB  LYS B 423    16753  25853  18051   -802   1433  -4122       C
ATOM   9549  CG  LYS B 423      12.173 -39.656  47.256  1.00160.82           C
ANISOU 9549  CG  LYS B 423    17425  25493  18186  -1062   1204  -4069       C
ATOM   9550  CD  LYS B 423      10.782 -38.990  47.206  1.00158.49           C
ANISOU 9550  CD  LYS B 423    16973  25072  18174  -1643   1120  -4024       C
ATOM   9551  CE  LYS B 423      10.350 -38.365  48.543  1.00156.32           C
ANISOU 9551  CE  LYS B 423    16256  25010  18131  -1959   1166  -3953       C
ATOM   9552  NZ  LYS B 423       8.929 -37.886  48.519  1.00154.47           N
ANISOU 9552  NZ  LYS B 423    15936  24613  18142  -2505   1067  -3890       N
ATOM   9553  N   GLY B 424      15.625 -36.627  45.660  1.00152.04           N
ANISOU 9553  N   GLY B 424    14899  25825  17045   -236   1814  -4215       N
ATOM   9554  CA  GLY B 424      17.038 -36.255  45.679  1.00152.47           C
ANISOU 9554  CA  GLY B 424    14638  26312  16983    188   1979  -4192       C
ATOM   9555  C   GLY B 424      17.676 -36.019  44.324  1.00153.34           C
ANISOU 9555  C   GLY B 424    14745  26567  16952    478   2042  -4229       C
ATOM   9556  O   GLY B 424      17.577 -36.850  43.429  1.00155.52           O
ANISOU 9556  O   GLY B 424    15517  26552  17021    671   1976  -4278       O
ATOM   9557  N   ALA B 425      18.359 -34.893  44.173  1.00150.68           N
ANISOU 9557  N   ALA B 425    13851  26685  16715    521   2161  -4195       N
ATOM   9558  CA  ALA B 425      18.937 -34.562  42.881  1.00151.32           C
ANISOU 9558  CA  ALA B 425    13865  26949  16682    768   2219  -4213       C
ATOM   9559  C   ALA B 425      19.891 -35.633  42.334  1.00154.83           C
ANISOU 9559  C   ALA B 425    14734  27345  16750   1365   2268  -4209       C
ATOM   9560  O   ALA B 425      19.438 -36.527  41.616  1.00156.74           O
ANISOU 9560  O   ALA B 425    15529  27199  16826   1447   2175  -4280       O
ATOM   9561  CB  ALA B 425      19.579 -33.176  42.899  1.00149.12           C
ANISOU 9561  CB  ALA B 425    12890  27196  16574    723   2317  -4149       C
ATOM   9562  N   PRO B 426      21.198 -35.581  42.697  1.00164.19           N
ANISOU 9562  N   PRO B 426    15684  28907  17793   1787   2403  -4118       N
ATOM   9563  CA  PRO B 426      22.142 -36.535  42.086  1.00167.61           C
ANISOU 9563  CA  PRO B 426    16497  29330  17856   2384   2463  -4108       C
ATOM   9564  C   PRO B 426      21.722 -37.984  42.251  1.00170.12           C
ANISOU 9564  C   PRO B 426    17518  29147  17974   2510   2351  -4177       C
ATOM   9565  O   PRO B 426      21.648 -38.725  41.275  1.00172.40           O
ANISOU 9565  O   PRO B 426    18288  29181  18035   2747   2295  -4245       O
ATOM   9566  CB  PRO B 426      23.455 -36.297  42.858  1.00167.94           C
ANISOU 9566  CB  PRO B 426    16165  29816  17830   2724   2610  -3972       C
ATOM   9567  CG  PRO B 426      23.318 -34.959  43.467  1.00164.60           C
ANISOU 9567  CG  PRO B 426    15093  29714  17734   2334   2631  -3910       C
ATOM   9568  CD  PRO B 426      21.847 -34.791  43.762  1.00162.52           C
ANISOU 9568  CD  PRO B 426    14918  29102  17730   1755   2494  -4010       C
ATOM   9569  N   GLU B 427      21.443 -38.373  43.489  1.00163.35           N
ANISOU 9569  N   GLU B 427    16715  28150  17200   2349   2306  -4154       N
ATOM   9570  CA  GLU B 427      21.071 -39.743  43.811  1.00165.66           C
ANISOU 9570  CA  GLU B 427    17637  27985  17320   2447   2179  -4198       C
ATOM   9571  C   GLU B 427      19.800 -40.210  43.110  1.00165.95           C
ANISOU 9571  C   GLU B 427    18148  27525  17382   2151   1986  -4288       C
ATOM   9572  O   GLU B 427      19.167 -41.168  43.546  1.00167.11           O
ANISOU 9572  O   GLU B 427    18749  27263  17482   2052   1831  -4305       O
ATOM   9573  CB  GLU B 427      20.948 -39.925  45.328  1.00164.78           C
ANISOU 9573  CB  GLU B 427    17413  27859  17338   2265   2163  -4142       C
ATOM   9574  CG  GLU B 427      22.282 -40.066  46.064  1.00165.80           C
ANISOU 9574  CG  GLU B 427    17343  28324  17331   2683   2314  -4051       C
ATOM   9575  CD  GLU B 427      23.053 -38.757  46.190  1.00163.74           C
ANISOU 9575  CD  GLU B 427    16389  28609  17214   2691   2478  -3960       C
ATOM   9576  OE1 GLU B 427      23.477  38.193  45.158  1.00163.78           O
ANISOU 9576  OE1 GLU B 427    16218  28845  17165   2851   2548  -3953       O
ATOM   9577  OE2 GLU B 427      23.253 -38.302  47.334  1.00162.16           O
ANISOU 9577  OE2 GLU B 427    15824  28611  17176   2543   2527  -3887       O
ATOM   9578  N   GLN B 428      19.430 -39.539  42.026  1.00163.29           N
ANISOU 9578  N   GLN B 428    17701  27220  17121   2001   1984  -4333       N
ATOM   9579  CA  GLN B 428      18.260 -39.947  41.271  1.00163.59           C
ANISOU 9579  CA  GLN B 428    18188  26789  17181   1724   1803  -4405       C
ATOM   9580  C   GLN B 428      18.552 -40.016  39.785  1.00165.16           C
ANISOU 9580  C   GLN B 428    18604  26967  17181   2009   1816  -4467       C
ATOM   9581  O   GLN B 428      17.741 -40.493  39.004  1.00166.02           O
ANISOU 9581  O   GLN B 428    19169  26666  17243   1879   1663  -4527       O
ATOM   9582  CB  GLN B 428      17.076 -39.033  41.544  1.00160.23           C
```

FIG. 13 Continued

```
ANISOU 9582  CB  GLN B 428    17437 26318 17126  1075  1742 -4397       C
ATOM   9583  CG  GLN B 428       15.780 -39.639  41.068  1.00160.68     C
ANISOU 9583  CG  GLN B 428    18005 25832 17215   750  1528 -4433       C
ATOM   9584  CD  GLN B 428       15.816 -41.159  41.102  1.00164.10     C
ANISOU 9584  CD  GLN B 428    19149 25845 17358  1050  1379 -4444       C
ATOM   9585  OE1 GLN B 428       16.117 -41.803  40.099  1.00166.59     O
ANISOU 9585  OE1 GLN B 428    19904 25980 17412  1394  1332 -4501       O
ATOM   9586  NE2 GLN B 428       15.522 -41.736  42.261  1.00164.31     N
ANISOU 9586  NE2 GLN B 428    19291 25718 17423   931  1295 -4388       N
ATOM   9587  N   ILE B 429       19.710 -39.505  39.397  1.00165.46     N
ANISOU 9587  N   ILE B 429    18301 27460 17106  2391  1997 -4437       N
ATOM   9588  CA  ILE B 429       20.169 -39.635  38.026  1.00167.35     C
ANISOU 9588  CA  ILE B 429    18739 27737 17110  2755  2031 -4483       C
ATOM   9589  C   ILE B 429       21.108 -40.836  38.044  1.00171.14     C
ANISOU 9589  C   ILE B 429    19677 28147 17200  3384  2054 -4483       C
ATOM   9590  O   ILE B 429       21.044 -41.728  37.193  1.00173.90     O
ANISOU 9590  O   ILE B 429    20611 28180 17281  3666  1961 -4556       O
ATOM   9591  CB  ILE B 429       20.960 -38.402  37.582  1.00165.79     C
ANISOU 9591  CB  ILE B 429    17886 28114 16993  2844  2210 -4424       C
ATOM   9592  CG1 ILE B 429       20.386 -37.140  36.212  1.00161.82     C
ANISOU 9592  CG1 ILE B 429    16768 27820 16898  2275  2222 -4386       C
ATOM   9593  CG2 ILE B 429       20.932 -38.271  36.080  1.00166.70     C
ANISOU 9593  CG2 ILE B 429    18143 28211 16983  2979  2205 -4482       C
ATOM   9594  CD1 ILE B 429       19.619 -36.290  37.243  1.00159.81     C
ANISOU 9594  CD1 ILE B 429    16333 27545 16841  1897  2175 -4438       C
ATOM   9595  N   LEU B 430       21.972 -40.644  39.053  1.00171.23     N
ANISOU 9595  N   LEU B 430    19423 28452 17186  3595  2173 -4398       N
ATOM   9596  CA  LEU B 430       22.938 -41.909  39.265  1.00174.57     C
ANISOU 9596  CA  LEU B 430    20200 28860 17268  4179  2214 -4380       C
ATOM   9597  C   LEU B 430       22.227 -43.251  39.477  1.00176.69     C
ANISOU 9597  C   LEU B 430    21199 28531 17402  4163  1998 -4458       C
ATOM   9598  O   LEU B 430       22.664 -44.267  38.944  1.00180.06     O
ANISOU 9598  O   LEU B 430    22159 28765 17492  4637  1952 -4505       O
ATOM   9599  CB  LEU B 430       23.848 -41.556  40.459  1.00173.69     C
ANISOU 9599  CB  LEU B 430    19611 29157 17226  4289  2369 -4258       C
ATOM   9600  CG  LEU B 430       25.151 -42.298  40.791  1.00176.53     C
ANISOU 9600  CG  LEU B 430    20097 29699 17279  4908  2486 -4189       C
ATOM   9601  CD1 LEU B 430       26.151  41.354  41.451  1.00174.94     C
ANISOU 9601  CD1 LEU B 430    19201 30075 17191  4985  2683 -4034       C
ATOM   9602  CD2 LEU B 430       24.890 -43.500  41.681  1.00178.11     C
ANISOU 9602  CD2 LEU B 430    20786 29500 17389  4937  2357 -4224       C
ATOM   9603  N   GLU B 431       21.122 -43.249  40.225  1.00176.23     N
ANISOU 9603  N   GLU B 431    21171 28185 17602  3625  1852 -4464       N
ATOM   9604  CA  GLU B 431       20.407 -44.491  40.546  1.00178.08     C
ANISOU 9604  CA  GLU B 431    22058 27866 17739  3560  1619 -4505       C
ATOM   9605  C   GLU B 431       19.551 -45.039  39.407  1.00179.53     C
ANISOU 9605  C   GLU B 431    22824 27572 17815  3489  1415 -4591       C
ATOM   9606  O   GLU B 431       18.431 -44.594  39.191  1.00177.51     O
ANISOU 9606  O   GLU B 431    22530 27117 17799  2976  1305 -4599       O
ATOM   9607  CB  GLU B 431       19.554 -44.343  41.821  1.00175.75     C
ANISOU 9607  CB  GLU B 431    21580 27452 17744  3027  1530 -4451       C
ATOM   9608  CG  GLU B 431       20.343 -44.314  43.151  1.00175.31     C
ANISOU 9608  CG  GLU B 431    21186 27699 17723  3151  1660 -4371       C
ATOM   9609  CD  GLU B 431       19.456 -44.412  44.408  1.00173.62     C
ANISOU 9609  CD  GLU B 431    20912 27303 17754  2671  1541 -4323       C
ATOM   9610  OE1 GLU B 431       19.008 -45.532  44.743  1.00175.46     O
ANISOU 9610  OE1 GLU B 431    21664 27124 17881  2667  1344 -4328       O
ATOM   9611  OE2 GLU B 431       19.230 -43.375  45.075  1.00170.56     O
ANISOU 9611  OE2 GLU B 431    19956 27194 17656  2311  1635 -4272       O
ATOM   9612  N   LEU B 432       20.092 -46.030  38.706  1.00221.71     N
ANISOU 9612  N   LEU B 432    28722 32728 22790  4016  1360 -4650       N
ATOM   9613  CA  LEU B 432       19.420 -46.710  37.592  1.00223.73     C
ANISOU 9613  CA  LEU B 432    29625 32503 22880  4047  1148 -4734       C
ATOM   9614  C   LEU B 432       18.759 -45.779  36.564  1.00221.72     C
ANISOU 9614  C   LEU B 432    29170 32273 22800  3715  1161 -4764       C
ATOM   9615  O   LEU B 432       18.308 -46.227  35.508  1.00223.36     O
ANISOU 9615  O   LEU B 432    29874 32131 22860  3773  1012 -4833       O
ATOM   9616  CB  LEU B 432       18.447 -47.798  38.091  1.00224.92     C
ANISOU 9616  CB  LEU B 432    30370 32060 23028  3804   839 -4732       C
```

FIG. 13 Continued

```
ATOM   9617  CG  LEU B 432      19.037 -49.188  38.401  1.00228.69           C
ANISOU 9617  CG  LEU B 432    31429  32295  23167   4299    719  -4755       C
ATOM   9618  CD1 LEU B 432      18.007 -50.130  39.029  1.00229.38           C
ANISOU 9618  CD1 LEU B 432    32007  31834  23312   3969    396  -4722       C
ATOM   9619  CD2 LEU B 432      19.653 -49.827  37.155  1.00232.25           C
ANISOU 9619  CD2 LEU B 432    32390  32631  23221   4892    698  -4851       C
ATOM   9620  N   ALA B 433      18.717 -44.487  36.859  1.00178.64           N
ANISOU 9620  N   ALA B 433    22998  27224  17652   3375   1329  -4714       N
ATOM   9621  CA  ALA B 433      18.159 -43.530  35.922  1.00176.55           C
ANISOU 9621  CA  ALA B 433    22483  27029  17570   3058   1353  -4740       C
ATOM   9622  C   ALA B 433      19.131 -43.399  34.768  1.00178.37           C
ANISOU 9622  C   ALA B 433    22709  27530  17532   3582   1494  -4783       C
ATOM   9623  O   ALA B 433      18.865 -42.717  33.777  1.00177.30           O
ANISOU 9623  O   ALA B 433    22424  27471  17472   3445   1522  -4814       O
ATOM   9624  CB  ALA B 433      17.961 -42.197  36.595  1.00172.54           C
ANISOU 9624  CB  ALA B 433    21204  26909  17444   2602   1487  -4676       C
ATOM   9625  N   LYS B 434      20.266 -44.070  34.917  1.00182.80           N
ANISOU 9625  N   LYS B 434    23431  28248  17778   4190   1584  -4775       N
ATOM   9626  CA  LYS B 434      21.318 -44.035  33.919  1.00184.95           C
ANISOU 9626  CA  LYS B 434    23699  28820  17752   4768   1734  -4792       C
ATOM   9627  C   LYS B 434      21.805 -42.606  33.817  1.00182.11           C
ANISOU 9627  C   LYS B 434    22525  29063  17607   4645   1954  -4715       C
ATOM   9628  O   LYS B 434      21.305 -41.819  33.011  1.00180.36           O
ANISOU 9628  O   LYS B 434    22093  28892  17542   4359   1952  -4741       O
ATOM   9629  CB  LYS B 434      20.807 -44.545  32.568  1.00186.97           C
ANISOU 9629  CB  LYS B 434    24542  28687  17813   4872   1583  -4896       C
ATOM   9630  CG  LYS B 434      20.235 -45.968  32.606  1.00189.87           C
ANISOU 9630  CG  LYS B 434    25762  28407  17972   4963   1313  -4964       C
ATOM   9631  CD  LYS B 434      21.292 -47.043  32.337  1.00194.21           C
ANISOU 9631  CD  LYS B 434    26789  28944  18059   5729   1334  -5003       C
ATOM   9632  CE  LYS B 434      21.415 -47.350  30.847  1.00196.83           C
ANISOU 9632  CE  LYS B 434    27556  29141  18089   6104   1294  -5093       C
ATOM   9633  NZ  LYS B 434      22.287 -48.530  30.572  1.00201.39           N
ANISOU 9633  NZ  LYS B 434    28712  29611  18196   6843   1267  -5144       N
ATOM   9634  N   ALA B 435      22.770 -42.278  34.667  1.00181.87           N
ANISOU 9634  N   ALA B 435    22039  29476  17589   4846   2128  -4613       N
ATOM   9635  CA  ALA B 435      23.342 -40.946  34.700  1.00179.35           C
ANISOU 9635  CA  ALA B 435    20932  29748  17463   4756   2317   4513       C
ATOM   9636  C   ALA B 435      23.876 -40.594  33.323  1.00180.53           C
ANISOU 9636  C   ALA B 435    21012  30154  17428   5087   2408  -4517       C
ATOM   9637  O   ALA B 435      25.037 -40.840  33.021  1.00182.94           O
ANISOU 9637  O   ALA B 435    21298  30773  17439   5676   2546  -4453       O
ATOM   9638  CB  ALA B 435      24.451 -40.878  35.739  1.00179.56           C
ANISOU 9638  CB  ALA B 435    20600  30177  17447   5042   2475  -4387       C
ATOM   9639  N   SER B 436      23.024 -40.020  32.485  1.00176.95           N
ANISOU 9639  N   SER B 436    20515  29573  17144   4708   2331  -4582       N
ATOM   9640  CA  SER B 436      23.429 -39.664  31.136  1.00177.93           C
ANISOU 9640  CA  SER B 436    20573  29922  17111   4976   2403  -4591       C
ATOM   9641  C   SER B 436      24.094 -38.293  31.078  1.00175.56           C
ANISOU 9641  C   SER B 436    19438  30272  16995   4909   2570  -4462       C
ATOM   9642  O   SER B 436      24.714 -37.856  32.039  1.00174.42           O
ANISOU 9642  O   SER B 436    18834  30480  16958   4920   2671  -4344       O
ATOM   9643  CB  SER B 436      22.235 -39.716  30.192  1.00177.40           C
ANISOU 9643  CB  SER B 436    20870  29407  17128   4614   2235  -4715       C
ATOM   9644  OG  SER B 436      22.682 -39.719  28.852  1.00179.34           O
ANISOU 9644  OG  SER B 436    21234  29783  17123   4993   2287  -4742       O
ATOM   9645  N   ASN B 437      23.942 -37.607  29.951  1.00176.06           N
ANISOU 9645  N   ASN B 437    19306  30485  17103   4820   2582  -4479       N
ATOM   9646  CA  ASN B 437      24.585 -36.314  29.759  1.00174.03           C
ANISOU 9646  CA  ASN B 437    18270  30850  17005   4772   2713  -4348       C
ATOM   9647  C   ASN B 437      23.709 -35.262  29.094  1.00170.92           C
ANISOU 9647  C   ASN B 437    17546  30462  16932   4211   2642  -4394       C
ATOM   9648  O   ASN B 437      23.463 -34.204  29.670  1.00167.56           O
ANISOU 9648  O   ASN B 437    16540  30265  16859   3758   2641  -4337       O
ATOM   9649  CB  ASN B 437      25.851 -36.485  28.919  1.00177.06           C
ANISOU 9649  CB  ASN B 437    18615  31645  17016   5465   2859  -4255       C
ATOM   9650  CG  ASN B 437      27.008 -37.035  29.716  1.00179.26           C
ANISOU 9650  CG  ASN B 437    18884  32168  17057   5988   2983  -4133       C
ATOM   9651  OD1 ASN B 437      27.125 -36.775  30.909  1.00177.59           O
```

FIG. 13 Continued

```
ANISOU 9651  OD1 ASN B 437    18377  32060  17039   5791   3002  -4058       O
ATOM   9652  ND2 ASN B 437    27.878 -37.792  29.058  1.00183.05             N
ANISOU 9652  ND2 ASN B 437    19688  32749  17115   6666   3070  -4108       N
ATOM   9653  N   ASP B 438    23.244 -35.560  27.883  1.00218.37             N
ANISOU 9653  N   ASP B 438    23941  36215  22816   4249   2576  -4499       N
ATOM   9654  CA  ASP B 438    22.461 -34.610  27.089  1.00215.69             C
ANISOU 9654  CA  ASP B 438    23320  35882  22752   3757   2514  -4543       C
ATOM   9655  C   ASP B 438    21.577 -33.708  27.945  1.00211.55             C
ANISOU 9655  C   ASP B 438    22369  35315  22694   3044   2442  -4542       C
ATOM   9656  O   ASP B 438    21.796 -32.500  28.010  1.00208.94             O
ANISOU 9656  O   ASP B 438    21351  35424  22612   2807   2490  -4458       O
ATOM   9657  CB  ASP B 438    21.636 -35.325  26.005  1.00217.25             C
ANISOU 9657  CB  ASP B 438    24186  35552  22808   3729   2388  -4692       C
ATOM   9658  CG  ASP B 438    20.483 -36.141  26.575  1.00217.14             C
ANISOU 9658  CG  ASP B 438    24753  34868  22881   3385   2214  -4796       C
ATOM   9659  OD1 ASP B 438    20.634 -36.706  27.678  1.00217.74             O
ANISOU 9659  OD1 ASP B 438    24967  34843  22923   3469   2208  -4771       O
ATOM   9660  OD2 ASP B 438    19.424 -36.223  25.913  1.00216.47             O
ANISOU 9660  OD2 ASP B 438    24986  34364  22902   3025   2075  -4890       O
ATOM   9661  N   LEU B 439    20.581 -34.298  28.596  1.00239.42             N
ANISOU 9661  N   LEU B 439    26310  38322  26336   2712   2317  -4627       N
ATOM   9662  CA  LEU B 439    19.696 -33.556  29.485  1.00235.78             C
ANISOU 9662  CA  LEU B 439    25502  37791  26292   2063   2249  -4625       C
ATOM   9663  C   LEU B 439    20.087 -33.855  30.937  1.00235.85             C
ANISOU 9663  C   LEU B 439    25436  37868  26310   2152   2289  -4559       C
ATOM   9664  O   LEU B 439    19.758 -33.109  31.860  1.00233.02             O
ANISOU 9664  O   LEU B 439    24644  37633  26260   1746   2281  -4520       O
ATOM   9665  CB  LEU B 439    18.218 -33.922  29.223  1.00234.94             C
ANISOU 9665  CB  LEU B 439    25860  37069  26337   1573   2074  -4738       C
ATOM   9666  CG  LEU B 439    17.556 -33.693  27.848  1.00234.59             C
ANISOU 9666  CG  LEU B 439    25971  36832  26330   1370   2001  -4814       C
ATOM   9667  CD1 LEU B 439    16.250 -34.479  27.727  1.00234.90             C
ANISOU 9667  CD1 LEU B 439    26657  36182  26413   1030   1815  -4898       C
ATOM   9668  CD2 LEU B 439    17.319 -32.212  27.564  1.00230.96             C
ANISOU 9668  CD2 LEU B 439    24798  36731  26227    921   2031  -4786       C
ATOM   9669  N   SER B 440    20.813 -34.951  31.122  1.00192.58             N
ANISOU 9669  N   SER B 440    20383  32311  20480   2699   2331  -4548       N
ATOM   9670  CA  SER B 440    21.201 -35.405  32.449  1.00193.05             C
ANISOU 9670  CA  SER B 440    20454  32387  20509   2823   2362  -4491       C
ATOM   9671  C   SER B 440    22.310 -34.556  33.090  1.00191.99             C
ANISOU 9671  C   SER B 440    19635  32872  20440   2987   2514  -4343       C
ATOM   9672  O   SER B 440    22.350 -34.385  34.310  1.00190.67             O
ANISOU 9672  O   SER B 440    19241  32777  20428   2826   2526  -4289       O
ATOM   9673  CB  SER B 440    21.607 -36.878  32.380  1.00197.06             C
ANISOU 9673  CB  SER B 440    21663  32592  20617   3357   2343  -4531       C
ATOM   9674  OG  SER B 440    20.681 -37.625  31.603  1.00198.33             O
ANISOU 9674  OG  SER B 440    22464  32204  20687   3253   2185  -4653       O
ATOM   9675  N   LYS B 441    23.212 -34.036  32.265  1.00178.83             N
ANISOU 9675  N   LYS B 441    17646  31652  18650   3310   2621  -4264       N
ATOM   9676  CA  LYS B 441    24.295 -33.192  32.742  1.00177.96             C
ANISOU 9676  CA  LYS B 441    16877  32147  18594   3472   2744  -4092       C
ATOM   9677  C   LYS B 441    23.815 -31.748  32.825  1.00174.04             C
ANISOU 9677  C   LYS B 441    15729  31896  18503   2910   2698  -4062       C
ATOM   9678  O   LYS B 441    24.477 -30.899  33.417  1.00172.60             O
ANISOU 9678  O   LYS B 441    14962  32163  18455   2890   2750  -3921       O
ATOM   9679  CB  LYS B 441    25.481 -33.295  31.790  1.00180.62             C
ANISOU 9679  CB  LYS B 441    17154  32870  18603   4081   2866  -3993       C
ATOM   9680  CG  LYS B 441    26.852 -33.213  32.457  1.00181.75             C
ANISOU 9680  CG  LYS B 441    16951  33501  18606   4522   3004  -3794       C
ATOM   9681  CD  LYS B 441    27.383 -31.777  32.565  1.00179.21             C
ANISOU 9681  CD  LYS B 441    15801  33765  18527   4339   3038  -3619       C
ATOM   9682  CE  LYS B 441    28.901 -31.749  32.838  1.00181.08             C
ANISOU 9682  CE  LYS B 441    15727  34531  18544   4889   3180  -3382       C
ATOM   9683  NZ  LYS B 441    29.419 -30.377  33.156  1.00178.57             N
ANISOU 9683  NZ  LYS B 441    14608  34759  18481   4682   3178  -3184       N
ATOM   9684  N   LYS B 442    22.659 -31.483  32.218  1.00191.44             N
ANISOU 9684  N   LYS B 442    18049  33791  20898   2455   2588  -4189       N
ATOM   9685  CA  LYS B 442    22.056 -30.145  32.213  1.00187.70             C
ANISOU 9685  CA  LYS B 442    17008  33491  20818   1887   2526  -4185       C
```

FIG. 13 Continued

```
ATOM   9686  C   LYS B 442      20.944 -29.993  33.257  1.00185.22           C
ANISOU 9686  C   LYS B 442    16709  32854  20811   1330   2428  -4256       C
ATOM   9687  O   LYS B 442      20.530 -28.877  33.573  1.00182.09           O
ANISOU 9687  O   LYS B 442    15808  32631  20747    880   2382  -4240       O
ATOM   9688  CB  LYS B 442      21.552 -29.765  30.806  1.00187.20           C
ANISOU 9688  CB  LYS B 442    16960  33372  20796   1724   2477  -4259       C
ATOM   9689  CG  LYS B 442      21.344 -28.251  30.556  1.00183.76           C
ANISOU 9689  CG  LYS B 442    15820  33290  20712   1281   2435  -4216       C
ATOM   9690  CD  LYS B 442      19.862 -27.846  30.401  1.00181.02           C
ANISOU 9690  CD  LYS B 442    15530  32558  20692    615   2307  -4349       C
ATOM   9691  CE  LYS B 442      19.346 -28.024  28.961  1.00181.66           C
ANISOU 9691  CE  LYS B 442    15905  32415  20703    566   2265  -4443       C
ATOM   9692  NZ  LYS B 442      17.934 -27.561  28.763  1.00178.90           N
ANISOU 9692  NZ  LYS B 442    15571  31718  20685    -94   2143  -4549       N
ATOM   9693  N   VAL B 443      20.445 -31.104  33.787  1.00154.04           N
ANISOU 9693  N   VAL B 443    13335  28444  16751   1358   2386  -4327       N
ATOM   9694  CA  VAL B 443      19.457 -30.990  34.849  1.00151.90           C
ANISOU 9694  CA  VAL B 443    13057  27908  16751    866   2301  -4366       C
ATOM   9695  C   VAL B 443      20.139 -30.409  36.084  1.00150.68           C
ANISOU 9695  C   VAL B 443    12407  28136  16710    890   2367  -4256       C
ATOM   9696  O   VAL B 443      19.472 -29.892  36.980  1.00148.28           O
ANISOU 9696  O   VAL B 443    11878  27781  16682    460   2313  -4264       O
ATOM   9697  CB  VAL B 443      18.769 -32.332  35.204  1.00153.78           C
ANISOU 9697  CB  VAL B 443    14010  27574  16846    881   2220  -4442       C
ATOM   9698  CG1 VAL B 443      17.386 -32.445  34.541  1.00152.87           C
ANISOU 9698  CG1 VAL B 443    14222  26988  16872    431   2081  -4544       C
ATOM   9699  CG2 VAL B 443      19.669 -33.498  34.847  1.00157.64           C
ANISOU 9699  CG2 VAL B 443    14973  28006  16918   1522   2276  -4435       C
ATOM   9700  N   LEU B 444      21.467 -30.494  36.129  1.00150.16           N
ANISOU 9700  N   LEU B 444    12177  28452  16424   1398   2480  -4142       N
ATOM   9701  CA  LEU B 444      22.223 -29.949  37.255  1.00149.19           C
ANISOU 9701  CA  LEU B 444    11589  28706  16391   1454   2538  -4013       C
ATOM   9702  C   LEU B 444      22.243 -28.416  37.203  1.00146.11           C
ANISOU 9702  C   LEU B 444    10488  28719  16306   1116   2505  -3949       C
ATOM   9703  O   LEU B 444      22.351 -27.753  38.241  1.00144.28           O
ANISOU 9703  O   LEU B 444     9866  28683  16272    925   2491  -3883       O
ATOM   9704  CB  LEU B 444      23.646 -30.524  37.305  1.00152.07           C
ANISOU 9704  CB  LEU B 444    12000  29354  16426   2100   2664  -3886       C
ATOM   9705  CG  LEU B 444      24.334 -30.649  38.679  1.00152.22           C
ANISOU 9705  CG  LEU B 444    11862  29538  16436   2247   2721  -3774       C
ATOM   9706  CD1 LEU B 444      25.497 -31.639  38.654  1.00155.69           C
ANISOU 9706  CD1 LEU B 444    12581  30075  16499   2896   2838  -3687       C
ATOM   9707  CD2 LEU B 444      24.798 -29.306  39.235  1.00149.69           C
ANISOU 9707  CD2 LEU B 444    10816  29695  16365   2054   2721  -3637       C
ATOM   9708  N   SER B 445      22.125 -27.861  35.995  1.00195.69           N
ANISOU 9708  N   SER B 445    15348  33848  21358   1042   2482  -3970       N
ATOM   9709  CA  SER B 445      22.081 -26.409  35.797  1.00182.80           C
ANISOU 9709  CA  SER B 445    14327  33844  21285    702   2423  -3918       C
ATOM   9710  C   SER B 445      20.731 -25.838  36.206  1.00179.78           C
ANISOU 9710  C   SER B 445    13865  33191  21253     61   2309  -4036       C
ATOM   9711  O   SER B 445      20.659 -24.760  36.795  1.00177.26           O
ANISOU 9711  O   SER B 445    13032  33116  21203   -243   2252  -3991       O
ATOM   9712  CB  SER B 445      22.357 -26.042  34.340  1.00183.26           C
ANISOU 9712  CB  SER B 445    14257  34105  21269    822   2429  -3904       C
ATOM   9713  OG  SER B 445      21.895 -24.730  34.056  1.00180.17           O
ANISOU 9713  OG  SER B 445    13340  33908  21207    358   2331  -3907       O
ATOM   9714  N   ILE B 446      19.665 -26.557  35.868  1.00141.16           N
ANISOU 9714  N   ILE B 446     9487  27795  16352   -137   2266  -4175       N
ATOM   9715  CA  ILE B 446      18.316 -26.145  36.240  1.00138.57           C
ANISOU 9715  CA  ILE B 446     9142  27174  16335   -733   2164  -4273       C
ATOM   9716  C   ILE B 446      18.183 -26.209  37.773  1.00137.83           C
ANISOU 9716  C   ILE B 446     8989  27041  16339   -846   2161  -4245       C
ATOM   9717  O   ILE B 446      17.388 -25.484  38.390  1.00135.27           O
ANISOU 9717  O   ILE B 446     8410  26681  16306  -1302   2091  -4276       O
ATOM   9718  CB  ILE B 446      17.231 -26.989  35.501  1.00139.41           C
ANISOU 9718  CB  ILE B 446     9849  26734  16387   -898   2108  -4396       C
ATOM   9719  CG1 ILE B 446      15.913 -26.213  35.383  1.00136.40           C
ANISOU 9719  CG1 ILE B 446     9304  26165  16356  -1538   2004  -4471       C
ATOM   9720  CG2 ILE B 446      17.040 -28.348  36.154  1.00141.68           C
```

FIG. 13 Continued

```
ANISOU 9720  CG2 ILE B 446    10741  26622  16468   -708   2112  -4419       C
ATOM   9721  CD1 ILE B 446     15.962 -25.045  34.401  1.00134.49           C
ANISOU 9721  CD1 ILE B 446     8588  26221  16293  -1733   1976  -4474       C
ATOM   9722  N   ILE B 447     18.993 -27.072  38.378  1.00170.74           N
ANISOU 9722  N   ILE B 447    13388  31230  20256   -412   2239  -4184       N
ATOM   9723  CA  ILE B 447     19.071 -27.176  39.825  1.00170.33           C
ANISOU 9723  CA  ILE B 447    13268  31190  20261   -445   2250  -4141       C
ATOM   9724  C   ILE B 447     19.543 -25.829  40.369  1.00168.00           C
ANISOU 9724  C   ILE B 447    12284  31357  20190   -591   2235  -4052       C
ATOM   9725  O   ILE B 447     19.365 -25.530  41.549  1.00166.74           O
ANISOU 9725  O   ILE B 447    11948  31228  20176   -771   2213  -4032       O
ATOM   9726  CB  ILE B 447     20.084 -28.272  40.242  1.00173.37           C
ANISOU 9726  CB  ILE B 447    13967  31588  20318    105   2346  -4072       C
ATOM   9727  CG1 ILE B 447     19.467 -29.661  40.105  1.00175.53           C
ANISOU 9727  CG1 ILE B 447    14953  31340  20401    188   2321  -4163       C
ATOM   9728  CG2 ILE B 447     20.548 -28.079  41.667  1.00172.76           C
ANISOU 9728  CG2 ILE B 447    13638  31698  20306    131   2375  -3986       C
ATOM   9729  CD1 ILE B 447     18.880 -30.187  41.379  1.00175.29           C
ANISOU 9729  CD1 ILE B 447    15122  31042  20438      4   2282  -4179       C
ATOM   9730  N   ASP B 448     20.117 -25.002  39.497  1.00159.30           N
ANISOU 9730  N   ASP B 448    10795  30612  19119   -524   2231  -3994       N
ATOM   9731  CA  ASP B 448     20.706 -23.737  39.935  1.00157.38           C
ANISOU 9731  CA  ASP B 448     9899  30834  19064   -616   2189  -3883       C
ATOM   9732  C   ASP B 448     20.013 -22.398  39.654  1.00154.24           C
ANISOU 9732  C   ASP B 448     9040  30559  19006  -1114   2067  -3927       C
ATOM   9733  O   ASP B 448     20.509 -21.364  40.092  1.00152.75           O
ANISOU 9733  O   ASP B 448     8328  30742  18970  -1187   2006  -3831       O
ATOM   9734  CB  ASP B 448     22.167 -23.687  39.539  1.00159.14           C
ANISOU 9734  CB  ASP B 448     9906  31488  19071   -119   2261  -3715       C
ATOM   9735  CG  ASP B 448     23.003 -24.565  40.415  1.00161.33           C
ANISOU 9735  CG  ASP B 448    10401  31781  19114    298   2361  -3625       C
ATOM   9736  OD1 ASP B 448     23.223 -25.735  40.040  1.00163.97           O
ANISOU 9736  OD1 ASP B 448    11228  31908  19167    651   2448  -3653       O
ATOM   9737  OD2 ASP B 448     23.391 -24.100  41.507  1.00160.39           O
ANISOU 9737  OD2 ASP B 448     9982  31859  19099    259   2342  -3533       O
ATOM   9738  N   LYS B 449     18.907 -22.397  38.912  1.00170.38           N
ANISOU 9738  N   LYS B 449    11271  32299  21167  -1452   2018  -4061       N
ATOM   9739  CA  LYS B 449     18.101 -21.179  38.784  1.00167.29           C
ANISOU 9739  CA  LYS B 449    10475  31969  21117  -1969   1899  -4117       C
ATOM   9740  C   LYS B 449     17.249 -21.228  40.038  1.00166.08           C
ANISOU 9740  C   LYS B 449    10409  31574  21119  -2269   1869  -4176       C
ATOM   9741  O   LYS B 449     16.810 -20.213  40.577  1.00163.66           O
ANISOU 9741  O   LYS B 449     9718  31385  21080  -2621   1779  -4191       O
ATOM   9742  CB  LYS B 449     17.222 -21.200  37.527  1.00166.76           C
ANISOU 9742  CB  LYS B 449    10591  31653  21118  -2224   1865  -4228       C
ATOM   9743  CG  LYS B 449     16.190 -20.058  37.430  1.00163.54           C
ANISOU 9743  CG  LYS B 449     9837  31224  21075  -2805   1744  -4304       C
ATOM   9744  CD  LYS B 449     16.660 -18.898  36.552  1.00162.15           C
ANISOU 9744  CD  LYS B 449     9127  31451  21033  -2880   1668  -4256       C
ATOM   9745  CE  LYS B 449     17.171 -17.728  37.367  1.00160.39           C
ANISOU 9745  CE  LYS B 449     8309  31637  20996  -2970   1575  -4168       C
ATOM   9746  NZ  LYS B 449     17.881 -16.740  36.506  1.00159.64           N
ANISOU 9746  NZ  LYS B 449     7708  31978  20972  -2941   1492  -4079       N
ATOM   9747  N   TYR B 450     17.045 -22.462  40.483  1.00132.80           N
ANISOU 9747  N   TYR B 450     6719  27025  16716  -2101   1940  -4203       N
ATOM   9748  CA  TYR B 450     16.338 -22.795  41.702  1.00132.34           C
ANISOU 9748  CA  TYR B 450     6828  26722  16734  -2295   1930  -4237       C
ATOM   9749  C   TYR B 450     17.035 -22.164  42.894  1.00131.57           C
ANISOU 9749  C   TYR B 450     6328  26959  16703  -2219   1925  -4148       C
ATOM   9750  O   TYR B 450     16.399 -21.583  43.769  1.00129.73           O
ANISOU 9750  O   TYR B 450     5901  26709  16680  -2540   1865  -4177       O
ATOM   9751  CB  TYR B 450     16.358 -24.313  41.847  1.00135.09           C
ANISOU 9751  CB  TYR B 450     7797  26726  16805  -2005   2002  -4247       C
ATOM   9752  CG  TYR B 450     15.403 -24.968  40.910  1.00135.68           C
ANISOU 9752  CG  TYR B 450     8325  26380  16847  -2168   1971  -4338       C
ATOM   9753  CD1 TYR B 450     15.185 -24.444  39.649  1.00134.88           C
ANISOU 9753  CD1 TYR B 450     8112  26315  16822  -2306   1937  -4380       C
ATOM   9754  CD2 TYR B 450     14.694 -26.089  41.288  1.00137.00           C
ANISOU 9754  CD2 TYR B 450     9028  26109  16916  -2203   1960  -4371       C
```

FIG. 13 Continued

```
ATOM   9755  CE1 TYR B 450      14.289 -25.021  38.785  1.00135.37           C
ANISOU 9755  CE1 TYR B 450    8598  25975  16862  -2473   1898  -4455        C
ATOM   9756  CE2 TYR B 450      13.792 -26.682  40.430  1.00137.57           C
ANISOU 9756  CE2 TYR B 450    9531  25776  16964  -2370   1906  -4435        C
ATOM   9757  CZ  TYR B 450      13.592 -26.143  39.180  1.00136.74           C
ANISOU 9757  CZ  TYR B 450    9319  25702  16935  -2505   1878  -4478        C
ATOM   9758  OH  TYR B 450      12.691 -26.735  38.326  1.00137.33           O
ANISOU 9758  OH  TYR B 450    9838  25356  16986  -2679   1817  -4534        O
ATOM   9759  N   ALA B 451      18.357 -22.294  42.899  1.00137.03           N
ANISOU 9759  N   ALA B 451    6907  27955  17204  -1780   1985  -4031        N
ATOM   9760  CA  ALA B 451      19.211 -21.774  43.950  1.00136.67           C
ANISOU 9760  CA  ALA B 451    6503  28242  17185  -1642   1980  -3915        C
ATOM   9761  C   ALA B 451      19.168 -20.251  44.043  1.00134.01           C
ANISOU 9761  C   ALA B 451    5566  28222  17129  -1945   1852  -3889        C
ATOM   9762  O   ALA B 451      19.400 -19.680  45.107  1.00133.03           O
ANISOU 9762  O   ALA B 451    5166  28269  17111  -2004   1802  -3834        O
ATOM   9763  CB  ALA B 451      20.643 -22.252  43.724  1.00139.04           C
ANISOU 9763  CB  ALA B 451    6816  28801  17211  -1100   2071  -3772        C
ATOM   9764  N   GLU B 452      18.896 -19.585  42.929  1.00140.62           N
ANISOU 9764  N   GLU B 452    6204  29140  18084  -2132   1786  -3926        N
ATOM   9765  CA  GLU B 452      18.809 -18.132  42.951  1.00138.08           C
ANISOU 9765  CA  GLU B 452    5321  29106  18038  -2438   1640  -3908        C
ATOM   9766  C   GLU B 452      17.576 -17.711  43.747  1.00136.00           C
ANISOU 9766  C   GLU B 452    5038  28616  18019  -2892   1569  -4029        C
ATOM   9767  O   GLU B 452      17.688 -17.087  44.803  1.00134.94           O
ANISOU 9767  O   GLU B 452    4639  28632  18001  -2976   1501  -3994        O
ATOM   9768  CB  GLU B 452      18.763 -17.568  41.535  1.00137.39           C
ANISOU 9768  CB  GLU B 452    5037  29143  18022  -2545   1583  -3923        C
ATOM   9769  CG  GLU B 452      20.068 -17.700  40.784  1.00139.21           C
ANISOU 9769  CG  GLU B 452    5150  29705  18037  -2106   1629  -3771        C
ATOM   9770  CD  GLU B 452      21.178 -16.901  41.420  1.00138.94           C
ANISOU 9770  CD  GLU B 452    4635  30125  18031  -1942   1551  -3586        C
ATOM   9771  OE1 GLU B 452      22.131 -16.538  40.697  1.00139.61           O
ANISOU 9771  OE1 GLU B 452    4437  30572  18038  -1711   1526  -3438        O
ATOM   9772  OE2 GLU B 452      21.099 -16.633  42.638  1.00138.12           O
ANISOU 9772  OE2 GLU B 452    4434  30019  18024  -2042   1507  -3575        O
ATOM   9773  N   ARG B 453      16.396 -18.062  43.244  1.00180.65           N
ANISOU 9773  N   ARG B 453   10985  33911  23745  -3178   1582  -4160        N
ATOM   9774  CA  ARG B 453      15.164 -17.809  43.980  1.00178.98           C
ANISOU 9774  CA  ARG B 453   10806  33461  23737  -3588   1534  -4259        C
ATOM   9775  C   ARG B 453      15.263 -18.735  45.186  1.00180.45           C
ANISOU 9775  C   ARG B 453   11303  33493  23768  -3391   1620  -4231        C
ATOM   9776  O   ARG B 453      14.425 -18.718  46.084  1.00179.61           O
ANISOU 9776  O   ARG B 453   11257  33215  23770  -3632   1603  -4280        O
ATOM   9777  CB  ARG B 453      13.936 -18.142  43.131  1.00178.49           C
ANISOU 9777  CB  ARG B 453   11038  33028  23752  -3902   1538  -4371        C
ATOM   9778  CG  ARG B 453      14.204 -18.274  41.619  1.00179.13           C
ANISOU 9778  CG  ARG B 453   11185  33121  23755  -3809   1552  -4377        C
ATOM   9779  CD  ARG B 453      13.848 -17.030  40.803  1.00176.76           C
ANISOU 9779  CD  ARG B 453   10454  32991  23714  -4156   1435  -4418        C
ATOM   9780  NE  ARG B 453      14.916 -16.037  40.798  1.00176.13           N
ANISOU 9780  NE  ARG B 453    9847  33391  23682  -4015   1355  -4324        N
ATOM   9781  CZ  ARG B 453      14.933 -14.968  41.583  1.00174.31           C
ANISOU 9781  CZ  ARG B 453    9186  33391  23653  -4199   1238  -4307        C
ATOM   9782  NH1 ARG B 453      13.935 -14.756  42.431  1.00173.60           N
ANISOU 9782  NH1 ARG B 453    9279  33032  23648  -4474   1200  -4389        N
ATOM   9783  NH2 ARG B 453      15.942 -14.112  41.521  1.00175.06           N
ANISOU 9783  NH2 ARG B 453    9100  33780  23637  -3998   1128  -4200        N
ATOM   9784  N   GLY B 454      16.317 -19.550  45.158  1.00129.17           N
ANISOU 9784  N   GLY B 454    4999  27072  17010  -2940   1713  -4144        N
ATOM   9785  CA  GLY B 454      16.693 -20.456  46.224  1.00130.83           C
ANISOU 9785  CA  GLY B 454    5477  27191  17043  -2680   1796  -4096        C
ATOM   9786  C   GLY B 454      15.627 -21.437  46.614  1.00131.45           C
ANISOU 9786  C   GLY B 454    6031  26829  17086  -2831   1835  -4175        C
ATOM   9787  O   GLY B 454      15.110 -21.348  47.718  1.00130.70           O
ANISOU 9787  O   GLY B 454    5911  26665  17085  -3002   1817  -4188        O
ATOM   9788  N   LEU B 455      15.288 -22.368  45.728  1.00137.69           N
ANISOU 9788  N   LEU B 455    7255  27324  17737  -2768   1877  -4218        N
ATOM   9789  CA  LEU B 455      14.240 -23.337  46.045  1.00138.40           C
```

FIG. 13 Continued

```
ANISOU 9789  CA  LEU B 455     7817  26976  17793  -2927   1884  -4270       C
ATOM   9790  C   LEU B 455    14.730 -24.751  46.374  1.00141.20             C
ANISOU 9790  C   LEU B 455     8650  27140  17859  -2549   1960  -4230       C
ATOM   9791  O   LEU B 455    15.928 -25.046  46.295  1.00142.75             O
ANISOU 9791  O   LEU B 455     8839  27539  17863  -2131   2026  -4166       O
ATOM   9792  CB  LEU B 455    13.146 -23.327  44.983  1.00137.66             C
ANISOU 9792  CB  LEU B 455     7899  26600  17805  -3254   1832  -4348       C
ATOM   9793  CG  LEU B 455    12.492 -21.941  44.864  1.00134.72             C
ANISOU 9793  CG  LEU B 455     7059  26382  17746  -3682   1749  -4393       C
ATOM   9794  CD1 LEU B 455    11.045 -22.040  44.367  1.00133.77             C
ANISOU 9794  CD1 LEU B 455     7156  25897  17772  -4111   1697  -4456       C
ATOM   9795  CD2 LEU B 455    12.532 -21.202  46.195  1.00133.34             C
ANISOU 9795  CD2 LEU B 455     6526  26427  17710  -3783   1723  -4369       C
ATOM   9796  N   ARG B 456    13.803 -25.615  46.771  1.00128.06             N
ANISOU 9796  N   ARG B 456     7393  25094  16169  -2700   1940  -4255       N
ATOM   9797  CA  ARG B 456    14.186 -26.949  47.213  1.00130.63             C
ANISOU 9797  CA  ARG B 456     8169  25223  16241  -2378   1985  -4218       C
ATOM   9798  C   ARG B 456    14.137 -27.968  46.077  1.00132.75             C
ANISOU 9798  C   ARG B 456     8941  25193  16304  -2199   1979  -4248       C
ATOM   9799  O   ARG B 456    13.071 -28.459  45.711  1.00132.90             O
ANISOU 9799  O   ARG B 456     9301  24840  16355  -2449   1907  -4283       O
ATOM   9800  CB  ARG B 456    13.353 -27.385  48.437  1.00130.46             C
ANISOU 9800  CB  ARG B 456     8300  24988  16281  -2594   1952  -4202       C
ATOM   9801  CG  ARG B 456    14.129 -28.284  49.444  1.00132.38             C
ANISOU 9801  CG  ARG B 456     8731  25245  16324  -2247   2008  -4140       C
ATOM   9802  CD  ARG B 456    13.880 -27.983  50.955  1.00131.32             C
ANISOU 9802  CD  ARG B 456     8377  25208  16309  -2402   2006  -4102       C
ATOM   9803  NE  ARG B 456    14.960 -28.459  51.842  1.00132.69             N
ANISOU 9803  NE  ARG B 456     8558  25536  16321  -2039   2076  -4037       N
ATOM   9804  CZ  ARG B 456    16.198 -28.826  51.469  1.00134.31             C
ANISOU 9804  CZ  ARG B 456     8817  25888  16327  -1609   2147  -4000       C
ATOM   9805  NH1 ARG B 456    16.598 -28.791  50.204  1.00134.93             N
ANISOU 9805  NH1 ARG B 456     8947  26002  16319  -1447   2163  -4021       N
ATOM   9806  NH2 ARG B 456    17.059 -29.239  52.385  1.00135.38             N
ANISOU 9806  NH2 ARG B 456     8952  26146  16342  -1330   2207  -3931       N
ATOM   9807  N   SER B 457    15.315 -28.294  45.548  1.00137.04             N
ANISOU 9807  N   SER B 457     9538  25905  16628  -1751   2050  -4221       N
ATOM   9808  CA  SER B 457    15.460 -29.175  44.385  1.00139.24             C
ANISOU 9808  CA  SER B 457    10266  25958  16681  -1505   2051  -4253       C
ATOM   9809  C   SER B 457    15.137 -30.648  44.639  1.00141.68             C
ANISOU 9809  C   SER B 457    11204  25845  16784  -1366   2013  -4258       C
ATOM   9810  O   SER B 457    15.957 -31.361  45.200  1.00143.54             O
ANISOU 9810  O   SER B 457    11592  26127  16819   -998   2067  -4214       O
ATOM   9811  CB  SER B 457    16.902 -29.089  43.884  1.00140.58             C
ANISOU 9811  CB  SER B 457    10278  26479  16656  -1021   2147  -4202       C
ATOM   9812  OG  SER B 457    17.594 -28.017  44.501  1.00138.95             O
ANISOU 9812  OG  SER B 457     9492  26718  16585  -1019   2187  -4133       O
ATOM   9813  N   LEU B 458    13.985 -31.127  44.182  1.00154.58             N
ANISOU 9813  N   LEU B 458    13212  27064  18458  -1648   1909  -4300       N
ATOM   9814  CA  LEU B 458    13.637 -32.534  44.386  1.00156.98             C
ANISOU 9814  CA  LEU B 458    14130  26947  18569  -1535   1835  -4290       C
ATOM   9815  C   LEU B 458    13.398 -33.271  43.070  1.00158.83             C
ANISOU 9815  C   LEU B 458    14865  26851  18632  -1423   1764  -4339       C
ATOM   9816  O   LEU B 458    12.420 -32.997  42.375  1.00157.74             O
ANISOU 9816  O   LEU B 458    14798  26501  18636  -1777   1682  -4367       O
ATOM   9817  CB  LEU B 458    12.388 -32.651  45.257  1.00155.86             C
ANISOU 9817  CB  LEU B 458    14062  26548  18610  -1978   1736  -4258       C
ATOM   9818  CG  LEU B 458    11.584 -33.950  45.115  1.00157.89             C
ANISOU 9818  CG  LEU B 458    14967  26285  18737  -2034   1592  -4237       C
ATOM   9819  CD1 LEU B 458    12.453 -35.166  45.418  1.00160.88             C
ANISOU 9819  CD1 LEU B 458    15743  26573  18812  -1556   1598  -4222       C
ATOM   9820  CD2 LEU B 458    10.315 -33.939  45.983  1.00156.60             C
ANISOU 9820  CD2 LEU B 458    14804  25921  18777  -2502   1494  -4172       C
ATOM   9821  N   ALA B 459    14.264 -34.228  42.747  1.00156.71             N
ANISOU 9821  N   ALA B 459    14964  26524  18054   -932   1790  -4344       N
ATOM   9822  CA  ALA B 459    14.161 -34.968  41.481  1.00158.81             C
ANISOU 9822  CA  ALA B 459    15736  26487  18117   -755   1721  -4396       C
ATOM   9823  C   ALA B 459    13.162 -36.127  41.482  1.00160.39             C
ANISOU 9823  C   ALA B 459    16575  26123  18242   -905   1540  -4391       C
```

FIG. 13 Continued

```
ATOM   9824  O   ALA B 459      12.795 -36.644  42.539  1.00160.62           O
ANISOU 9824  O   ALA B 459    16728  26003  18298  -1016   1477  -4338       O
ATOM   9825  CB  ALA B 459      15.528 -35.466  41.056  1.00161.35           C
ANISOU 9825  CB  ALA B 459    16182  27001  18124   -137   1823  -4402       C
ATOM   9826  N   VAL B 460      12.743 -36.538  40.285  1.00152.37           N
ANISOU 9826  N   VAL B 460    15968  24799  17128   -904   1445  -4437       N
ATOM   9827  CA  VAL B 460      11.806 -37.653  40.127  1.00154.09           C
ANISOU 9827  CA  VAL B 460    16834  24454  17259  -1038   1240  -4417       C
ATOM   9828  C   VAL B 460      12.025 -38.449  38.836  1.00156.81           C
ANISOU 9828  C   VAL B 460    17735  24519  17325   -715   1163  -4479       C
ATOM   9829  O   VAL B 460      11.919 -37.912  37.737  1.00156.15           O
ANISOU 9829  O   VAL B 460    17580  24469  17279   -777   1186  -4530       O
ATOM   9830  CB  VAL B 460      10.334 -37.204  40.247  1.00151.78           C
ANISOU 9830  CB  VAL B 460    16471  23927  17271  -1677   1121  -4367       C
ATOM   9831  CG1 VAL B 460      10.174 -35.762  39.608  1.00148.70           C
ANISOU 9831  CG1 VAL B 460    15494  23858  17146  -1968   1231  -4402       C
ATOM   9832  CG2 VAL B 460       9.420 -38.140  39.464  1.00153.51           C
ANISOU 9832  CG2 VAL B 460    17353  23578  17396  -1808    904  -4348       C
ATOM   9833  N   ALA B 461      12.328 -39.737  38.994  1.00221.12           N
ANISOU 9833  N   ALA B 461    26440  32386  25189   -368   1063  -4475       N
ATOM   9834  CA  ALA B 461      12.657 -40.628  37.876  1.00224.21           C
ANISOU 9834  CA  ALA B 461    27419  32507  25265     26    981  -4538       C
ATOM   9835  C   ALA B 461      11.473 -41.401  37.314  1.00225.32           C
ANISOU 9835  C   ALA B 461    28179  32044  25389   -245    718  -4519       C
ATOM   9836  O   ALA B 461      10.324 -41.041  37.554  1.00223.28           O
ANISOU 9836  O   ALA B 461    27829  31609  25359   -792    619  -4452       O
ATOM   9837  CB  ALA B 461      13.765 -41.596  38.277  1.00227.24           C
ANISOU 9837  CB  ALA B 461    28078  32939  25322    616   1016  -4552       C
ATOM   9838  N   ARG B 462      11.767 -42.463  36.563  1.00166.65           N
ANISOU 9838  N   ARG B 462    21386  24301  17635    148    598  -4567       N
ATOM   9839  CA  ARG B 462      10.721 -43.269  35.942  1.00168.09           C
ANISOU 9839  CA  ARG B 462    22220  23882  17766    -62    320  -4542       C
ATOM   9840  C   ARG B 462      10.351 -44.501  36.746  1.00170.21           C
ANISOU 9840  C   ARG B 462    23000  23751  17920    -51     89  -4464       C
ATOM   9841  O   ARG B 462      10.875 -44.729  37.836  1.00170.43           O
ANISOU 9841  O   ARG B 462    22865  23970  17921    102    155  -4435       O
ATOM   9842  CB  ARG B 462      11.117 -43.688  34.532  1.00170.54           C
ANISOU 9842  CB  ARG B 462    22977  24028  17794    321    281  -4640       C
ATOM   9843  CG  ARG B 462       9.956 -44.222  33.695  1.00171.41           C
ANISOU 9843  CG  ARG B 462    23675  23547  17907     22      4  -4611       C
ATOM   9844  CD  ARG B 462       9.045 -43.106  33.165  1.00168.12           C
ANISOU 9844  CD  ARG B 462    22886  23166  17826   -543     38  -4585       C
ATOM   9845  NE  ARG B 462       8.219 -43.557  32.040  1.00169.29           N
ANISOU 9845  NE  ARG B 462    23603  22804  17918   -704   -186  -4581       N
ATOM   9846  CZ  ARG B 462       6.928 -43.867  32.124  1.00168.83           C
ANISOU 9846  CZ  ARG B 462    23845  22280  18021  -1203   -430  -4459       C
ATOM   9847  NH1 ARG B 462       6.292 -43.766  33.282  1.00167.21           N
ANISOU 9847  NH1 ARG B 462    23412  22074  18045  -1589   -476  -4332       N
ATOM   9848  NH2 ARG B 462       6.271 -44.273  31.046  1.00170.03           N
ANISOU 9848  NH2 ARG B 462    24525  21974  18105  -1316   -634  -4450       N
ATOM   9849  N   GLN B 463       9.423 -45.279  36.197  1.00175.27           N
ANISOU 9849  N   GLN B 463    24258  23832  18503   -233   -195  -4418       N
ATOM   9850  CA  GLN B 463       8.977 -46.512  36.828  1.00177.50           C
ANISOU 9850  CA  GLN B 463    25091  23680  18672   -246   -471  -4326       C
ATOM   9851  C   GLN B 463       9.758 -47.722  36.359  1.00181.60           C
ANISOU 9851  C   GLN B 463    26260  23964  18778    360   -590  -4408       C
ATOM   9852  O   GLN B 463       9.796 -48.025  35.166  1.00183.38           O
ANISOU 9852  O   GLN B 463    26910  23955  18813    565   -675  -4481       O
ATOM   9853  CB  GLN B 463       7.473 -46.744  36.642  1.00176.97           C
ANISOU 9853  CB  GLN B 463    25344  23115  18783   -815   -758  -4187       C
ATOM   9854  CG  GLN B 463       6.821 -46.009  35.496  1.00175.39           C
ANISOU 9854  CG  GLN B 463    25086  22823  18730  -1122   -749  -4205       C
ATOM   9855  CD  GLN B 463       5.328 -45.879  35.716  1.00173.69           C
ANISOU 9855  CD  GLN B 463    24908  22285  18803  -1793   -950  -4027       C
ATOM   9856  OE1 GLN B 463       4.804 -46.333  36.737  1.00173.77           O
ANISOU 9856  OE1 GLN B 463    24971  22162  18892  -2013  -1091  -3885       O
ATOM   9857  NE2 GLN B 463       4.634 -45.255  34.769  1.00172.18           N
ANISOU 9857  NE2 GLN B 463    24674  21975  18769  -2126   -962  -4020       N
ATOM   9858  N   VAL B 464      10.352  48.418  37.327  1.00212.84           N
```

FIG. 13 Continued

```
ANISOU 9858  N    VAL B 464    30296  27977  22598    638   -604  -4392          N
ATOM   9859  CA   VAL B 464    11.159 -49.603  37.078  1.00216.79                C
ANISOU 9859  CA   VAL B 464    31384  28282  22704   1236   -713  -4466          C
ATOM   9860  C    VAL B 464    10.628 -50.433  35.913  1.00219.50                C
ANISOU 9860  C    VAL B 464    32500  28060  22838   1312  -1010  -4489          C
ATOM   9861  O    VAL B 464    11.353 -50.688  34.950  1.00221.70                O
ANISOU 9861  O    VAL B 464    33063  28341  22832   1801   -962  -4614          O
ATOM   9862  CB   VAL B 464    11.246 -50.492  38.341  1.00218.05                C
ANISOU 9862  CB   VAL B 464    31705  28333  22813   1288   -850  -4388          C
ATOM   9863  CG1  VAL B 464    11.886 -49.740  39.487  1.00215.70                C
ANISOU 9863  CG1  VAL B 464    30683  28587  22684   1276   -557  -4373          C
ATOM   9864  CG2  VAL B 464     9.868 -50.955  38.745  1.00217.75                C
ANISOU 9864  CG2  VAL B 464    31957  27831  22948    742  -1178  -4226          C
ATOM   9865  N    VAL B 465     9.358 -50.823  35.995  1.00187.79                N
ANISOU 9865  N    VAL B 465    28815  23573  18965    826  -1317  -4356          N
ATOM   9866  CA   VAL B 465     8.745 -51.671  34.990  1.00190.40                C
ANISOU 9866  CA   VAL B 465    29920  23309  19114    842  -1650  -4346          C
ATOM   9867  C    VAL B 465     9.786 -52.683  34.484  1.00194.51                C
ANISOU 9867  C    VAL B 465    31007  23709  19189   1569  -1712  -4483          C
ATOM   9868  O    VAL B 465    10.403 -52.483  33.437  1.00195.53                O
ANISOU 9868  O    VAL B 465    31220  23947  19126   1945  -1580  -4620          O
ATOM   9869  CB   VAL B 465     8.115 -50.835  33.850  1.00188.60                C
ANISOU 9869  CB   VAL B 465    29592  23029  19040    534  -1605  -4362          C
ATOM   9870  CG1  VAL B 465     7.084 -49.898  34.413  1.00184.73                C
ANISOU 9870  CG1  VAL B 465    28564  22647  18979   -167  -1556  -4221          C
ATOM   9871  CG2  VAL B 465     9.164 -50.032  33.116  1.00188.04                C
ANISOU 9871  CG2  VAL B 465    29139  23433  18872    926  -1258  -4533          C
ATOM   9872  N    PRO B 466    10.012 -53.761  35.260  1.00203.68                N
ANISOU 9872  N    PRO B 466    32537  24671  20182   1781  -1908  -4445          N
ATOM   9873  CA   PRO B 466    10.964 -54.823  34.913  1.00207.78                C
ANISOU 9873  CA   PRO B 466    33627  25047  20274   2471  -1998  -4566          C
ATOM   9874  C    PRO B 466    10.277 -55.916  34.118  1.00211.01                C
ANISOU 9874  C    PRO B 466    34940  24761  20472   2495  -2441  -4541          C
ATOM   9875  O    PRO B 466    10.401 -55.985  32.896  1.00212.59                O
ANISOU 9875  O    PRO B 466    35501  24800  20474   2749  -2472  -4643          O
ATOM   9876  CB   PRO B 466    11.364 -55.404  36.278  1.00208.35                C
ANISOU 9876  CB   PRO B 466    33611  25218  20333   2567  -2026  -4510          C
ATOM   9877  CG   PRO B 466    10.542 -54.667  37.312  1.00204.61                C
ANISOU 9877  CG   PRO B 466    32552  24912  20277   1910  -1970  -4352          C
ATOM   9878  CD   PRO B 466     9.425 -53.988  36.587  1.00202.53                C
ANISOU 9878  CD   PRO B 466    32231  24471  20250   1386  -2036  -4283          C
ATOM   9879  N    GLU B 467     9.544 -56.761  34.834  1.00204.01                N
ANISOU 9879  N    GLU B 467    34414  23468  19632   2223  -2795  -4393          N
ATOM   9880  CA   GLU B 467     8.817 -57.867  34.239  1.00207.12                C
ANISOU 9880  CA   GLU B 467    35683  23166  19845   2195  -3278  -4328          C
ATOM   9881  C    GLU B 467     7.605 -58.147  35.102  1.00206.00                C
ANISOU 9881  C    GLU B 467    35578  22721  19973   1561  -3585  -4083          C
ATOM   9882  O    GLU B 467     6.460 -58.038  34.656  1.00205.21                O
ANISOU 9882  O    GLU B 467    35666  22268  20039   1074  -3811  -3941          O
ATOM   9883  CB   GLU B 467     9.698 -59.116  34.202  1.00211.50                C
ANISOU 9883  CB   GLU B 467    36864  23517  19977   2861  -3454  -4439          C
ATOM   9884  CG   GLU B 467    10.847 -59.054  33.205  1.00213.47                C
ANISOU 9884  CG   GLU B 467    37240  23978  19892   3551  -3219  -4665          C
ATOM   9885  CD   GLU B 467    11.690 -60.320  33.201  1.00217.95                C
ANISOU 9885  CD   GLU B 467    38445  24333  20033   4219  -3404  -4769          C
ATOM   9886  OE1  GLU B 467    11.945  60.870  34.295  1.00218.49                O
ANISOU 9886  OE1  GLU B 467    38477  24437  20102   4264  -3476  -4716          O
ATOM   9887  OE2  GLU B 467    12.099 -60.762  32.103  1.00220.96                O
ANISOU 9887  OE2  GLU B 467    39364  24516  20075   4704  -3479  -4905          O
ATOM   9888  N    LYS B 468     7.875 -58.490  36.355  1.00206.13                N
ANISOU 9888  N    LYS B 468    35390  22897  20033   1569  -3585  -4020          N
ATOM   9889  CA   LYS B 468     6.825 -58.804  37.306  1.00205.25                C
ANISOU 9889  CA   LYS B 468    35273  22556  20158   1011  -3867  -3775          C
ATOM   9890  C    LYS B 468     7.178 -58.349  38.714  1.00202.88                C
ANISOU 9890  C    LYS B 468    34273  22751  20061    894   3605   3733          C
ATOM   9891  O    LYS B 468     8.226 -57.742  38.943  1.00201.76                O
ANISOU 9891  O    LYS B 468    33639  23129  19893   1222  -3204  -3889          O
ATOM   9892  CB   LYS B 468     6.520 -60.300  37.295  1.00209.26                C
ANISOU 9892  CB   LYS B 468    36643  22446  20419   1141  -4397  -3686          C
```

FIG. 13 Continued

```
ATOM   9893  CG  LYS B 468       5.422 -60.673  36.328  1.00210.49           C
ANISOU 9893  CG  LYS B 468    37412  22000  20565    841   4796   3560       C
ATOM   9894  CD  LYS B 468       4.171 -59.879  36.641  1.00207.02           C
ANISOU 9894  CD  LYS B 468    36541  21581  20536     79  -4799  -3327       C
ATOM   9895  CE  LYS B 468       3.805 -60.023  38.104  1.00205.80           C
ANISOU 9895  CE  LYS B 468    36038  21566  20590   -258  -4865  -3131       C
ATOM   9896  NZ  LYS B 468       2.613 -59.217  38.455  1.00202.45           N
ANISOU 9896  NZ  LYS B 468    35160  21206  20558   -973  -4843  -2899       N
ATOM   9897  N   THR B 469       6.291 -58.664  39.651  1.00245.51           N
ANISOU 9897  N   THR B 469    39644  27983  25656    425  -3849  -3506       N
ATOM   9898  CA  THR B 469       6.418 -58.238  41.041  1.00243.15           C
ANISOU 9898  CA  THR B 469    38696  28111  25580    226  -3644  -3432       C
ATOM   9899  C   THR B 469       7.583 -58.877  41.823  1.00244.92           C
ANISOU 9899  C   THR B 469    38930  28535  25595    730  -3565  -3541       C
ATOM   9900  O   THR B 469       8.224 -59.826  41.359  1.00248.37           O
ANISOU 9900  O   THR B 469    39952  28720  25698   1231  -3733  -3653       O
ATOM   9901  CB  THR B 469       5.090 -58.496  41.797  1.00242.34           C
ANISOU 9901  CB  THR B 469    38610  27746  25721   -407  -3964  -3134       C
ATOM   9902  OG1 THR B 469       4.009 -58.575  40.860  1.00242.71           O
ANISOU 9902  OG1 THR B 469    39065  27336  25819   -748  -4248  -3006       O
ATOM   9903  CG2 THR B 469       4.813 -57.384  42.797  1.00238.36           C
ANISOU 9903  CG2 THR B 469    37254  27742  25568   -816  -3647  -3050       C
ATOM   9904  N   LYS B 470       7.845 -58.321  43.007  1.00198.92           N
ANISOU 9904  N   LYS B 470    32446  23165  19969    592  -3306  -3506       N
ATOM   9905  CA  LYS B 470       8.856 -58.810  43.951  1.00199.98           C
ANISOU 9905  CA  LYS B 470    32478  23533  19973    967  -3209  -3573       C
ATOM   9906  C   LYS B 470      10.297 -58.769  43.447  1.00201.32           C
ANISOU 9906  C   LYS B 470    32650  23972  19871   1646  -2921  -3816       C
ATOM   9907  O   LYS B 470      11.088 -57.931  43.885  1.00199.24           O
ANISOU 9907  O   LYS B 470    31763  24246  19694   1779  -2515  -3900       O
ATOM   9908  CB  LYS B 470       8.504 -60.221  44.455  1.00203.03           C
ANISOU 9908  CB  LYS B 470    33470  23451  20219    964  -3683  -3442       C
ATOM   9909  CG  LYS B 470       7.158 -60.340  45.207  1.00201.84           C
ANISOU 9909  CG  LYS B 470    33256  23095  20337    304  -3973  -3157       C
ATOM   9910  CD  LYS B 470       5.977 -60.652  44.267  1.00202.86           C
ANISOU 9910  CD  LYS B 470    33917  22682  20478    -24  -4355  -3013       C
ATOM   9911  CE  LYS B 470       4.636 -60.660  44.999  1.00201.50           C
ANISOU 9911  CE  LYS B 470    33615  22361  20586   -692  -4612  -2699       C
ATOM   9912  NZ  LYS B 470       3.493 -60.795  44.054  1.00202.10           N
ANISOU 9912  NZ  LYS B 470    34131  21954  20704  -1042  -4937  -2542       N
ATOM   9913  N   GLU B 471      10.627 -59.679  42.532  1.00215.05           N
ANISOU 9913  N   GLU B 471    35096  25336  21275   2077  -3143  -3915       N
ATOM   9914  CA  GLU B 471      11.990 -59.783  42.013  1.00216.87           C
ANISOU 9914  CA  GLU B 471    35405  25791  21204   2770  -2904  -4129       C
ATOM   9915  C   GLU B 471      12.473 -58.498  41.346  1.00214.49           C
ANISOU 9915  C   GLU B 471    34563  25951  20980   2860  -2466  -4247       C
ATOM   9916  O   GLU B 471      11.765 -57.891  40.540  1.00213.14           O
ANISOU 9916  O   GLU B 471    34364  25685  20933   2569  -2471  -4230       O
ATOM   9917  CB  GLU B 471      12.166 -60.999  41.083  1.00221.32           C
ANISOU 9917  CB  GLU B 471    36871  25838  21381   3216  -3249  -4213       C
ATOM   9918  CG  GLU B 471      12.423 -62.325  41.824  1.00224.34           C
ANISOU 9918  CG  GLU B 471    37724  25940  21574   3439  -3567  -4178       C
ATOM   9919  CD  GLU B 471      13.433 -63.244  41.124  1.00228.48           C
ANISOU 9919  CD  GLU B 471    38861  26297  21656   4182  -3644  -4358       C
ATOM   9920  OE1 GLU B 471      14.545 -62.785  40.778  1.00228.52           O
ANISOU 9920  OE1 GLU B 471    38603  26710  21514   4662  -3264  -4516       O
ATOM   9921  OE2 GLU B 471      13.124  64.442  40.944  1.00231.82           O
ANISOU 9921  OE2 GLU B 471    40028  26183  21871   4295  -4098  -4330       O
ATOM   9922  N   SER B 472      13.700 -58.114  41.692  1.00204.45           N
ANISOU 9922  N   SER B 472    32870  25177  19633   3266  -2103  -4353       N
ATOM   9923  CA  SER B 472      14.326 -56.880  41.229  1.00202.18           C
ANISOU 9923  CA  SER B 472    31992  25407  19421   3385  -1673  -4445       C
ATOM   9924  C   SER B 472      14.176 -56.622  39.735  1.00202.95           C
ANISOU 9924  C   SER B 472    32361  25358  19392   3512  -1678  -4537       C
ATOM   9925  O   SER B 472      13.898 -57.535  38.959  1.00206.00           O
ANISOU 9925  O   SER B 472    33476  25256  19538   3692  -1987  -4570       O
ATOM   9926  CB  SER B 472      15.811 -56.874  41.592  1.00203.04           C
ANISOU 9926  CB  SER B 472    31843  25959  19344   3961  -1368  -4542       C
ATOM   9927  OG  SER B 472      16.588 -57.304  40.491  1.00206.08           O
```

FIG. 13 Continued

```
ANISOU 9927  OG  SER B 472     32653 26280 19366   4568 -1345 -4680       O
ATOM   9928  N   PRO B 473     14.357 -55.355  39.336  1.00 200.18        N
ANISOU 9928  N   PRO B 473     31418 25433 19208   3410 -1345 -4575       N
ATOM   9929  CA  PRO B 473     14.243 -54.924  37.953  1.00 200.38        C
ANISOU 9929  CA  PRO B 473     31578 25403 19155   3493 -1300 -4659       C
ATOM   9930  C   PRO B 473     15.610 -54.644  37.378  1.00 201.52        C
ANISOU 9930  C   PRO B 473     31553 25966 19050   4129  -985 -4794       C
ATOM   9931  O   PRO B 473     16.257 -55.529  36.826  1.00 205.14        O
ANISOU 9931  O   PRO B 473     32553 26253 19139   4692 -1075 -4885       O
ATOM   9932  CB  PRO B 473     13.519 -53.581  38.078  1.00 196.03        C
ANISOU 9932  CB  PRO B 473     30357 25115 19010   2892 -1124 -4587       C
ATOM   9933  CG  PRO B 473     13.635 -53.181  39.562  1.00 193.62        C
ANISOU 9933  CG  PRO B 473     29464 25154 18950   2649  -975 -4497       C
ATOM   9934  CD  PRO B 473     14.526 -54.193  40.217  1.00 196.38        C
ANISOU 9934  CD  PRO B 473     30083 25490 19041   3124 -1021 -4524       C
ATOM   9935  N   GLY B 474     16.051 -53.402  37.552  1.00 205.34        N
ANISOU 9935  N   GLY B 474     31269 27016 19736   4038  -623 -4792       N
ATOM   9936  CA  GLY B 474     17.273 -52.927  36.937  1.00 205.96        C
ANISOU 9936  CA  GLY B 474     31083 27550 19622   4570  -309 -4884       C
ATOM   9937  C   GLY B 474     16.915 -52.526  35.516  1.00 206.07        C
ANISOU 9937  C   GLY B 474     31258 27454 19586   4557  -323 -4950       C
ATOM   9938  O   GLY B 474     17.747 -52.015  34.766  1.00 206.41        O
ANISOU 9938  O   GLY B 474     31082 27857 19488   4935   -81 -5017       O
ATOM   9939  N   ALA B 475     15.651 -52.764  35.162  1.00 204.48        N
ANISOU 9939  N   ALA B 475     31434 26753 19504   4105  -615 -4915       N
ATOM   9940  CA  ALA B 475     15.100 -52.456  33.842  1.00 204.49        C
ANISOU 9940  CA  ALA B 475     31653 26554 19490   3997  -683 -4964       C
ATOM   9941  C   ALA B 475     15.268 -50.976  33.499  1.00 201.04        C
ANISOU 9941  C   ALA B 475     30453 26639 19294   3798  -354 -4972       C
ATOM   9942  O   ALA B 475     15.858 -50.223  34.268  1.00 198.86        O
ANISOU 9942  O   ALA B 475     29509 26873 19177   3779   -85 -4938       O
ATOM   9943  CB  ALA B 475     13.627 -52.862  33.788  1.00 204.15        C
ANISOU 9943  CB  ALA B 475     32039 25915 19613   3430 -1049 -4876       C
ATOM   9944  N   PRO B 476     14.756 -50.547  32.339  1.00 196.35        N
ANISOU 9944  N   PRO B 476     29955 25916 18732   3645  -386 -5011       N
ATOM   9945  CA  PRO B 476     14.947 -49.132  32.021  1.00 193.08        C
ANISOU 9945  CA  PRO B 476     28798 26013 18551   3457   -87 -5016       C
ATOM   9946  C   PRO B 476     14.436 -48.238  33.139  1.00 189.07        C
ANISOU 9946  C   PRO B 476     27621 25750 18466   2875    13 -4913       C
ATOM   9947  O   PRO B 476     13.477 -48.604  33.818  1.00 188.39        O
ANISOU 9947  O   PRO B 476     27712 25318 18551   2444  -202 -4828       O
ATOM   9948  CB  PRO B 476     14.074 -48.936  30.780  1.00 192.85        C
ANISOU 9948  CB  PRO B 476     29055 25655 18565   3194  -229 -5046       C
ATOM   9949  CG  PRO B 476     13.984 -50.273  30.163  1.00 197.02        C
ANISOU 9949  CG  PRO B 476     30495 25632 18732   3549  -520 -5100       C
ATOM   9950  CD  PRO B 476     13.997 -51.252  31.293  1.00 198.54        C
ANISOU 9950  CD  PRO B 476     30977 25604 18855   3614  -693 -5044       C
ATOM   9951  N   TRP B 477     15.089 -47.094  33.328  1.00 184.07        N
ANISOU 9951  N   TRP B 477     26236 25713 17987   2882   324 -4911       N
ATOM   9952  CA  TRP B 477     14.663 -46.070  34.284  1.00 180.11        C
ANISOU 9952  CA  TRP B 477     25046 25499 17888   2351   441 -4827       C
ATOM   9953  C   TRP B 477     14.809 -44.746  33.536  1.00 177.57        C
ANISOU 9953  C   TRP B 477     24147 25584 17737   2217   654 -4855       C
ATOM   9954  O   TRP B 477     15.909 -44.408  33.080  1.00 178.31        O
ANISOU 9954  O   TRP B 477     23997 26089 17662   2667   862 -4897       O
ATOM   9955  CB  TRP B 477     15.496 -46.119  35.567  1.00 179.94        C
ANISOU 9955  CB  TRP B 477     24684 25822 17862   2554   589 -4783       C
ATOM   9956  CG  TRP B 477     14.860 -46.951  36.659  1.00 180.41        C
ANISOU 9956  CG  TRP B 477     25040 25527 17980   2322   376 -4711       C
ATOM   9957  CD1 TRP B 477     14.028 -48.017  36.493  1.00 182.44        C
ANISOU 9957  CD1 TRP B 477     25993 25188 18137   2212    55 -4693       C
ATOM   9958  CD2 TRP B 477     15.019 -46.787  38.076  1.00 178.91        C
ANISOU 9958  CD2 TRP B 477     24457 25564 17955   2177   455 -4635       C
ATOM   9959  NE1 TRP B 477     13.654 -48.521  37.711  1.00 182.27        N
ANISOU 9959  NE1 TRP B 477     26018 25024 18213   2001   -70 -4603       N
ATOM   9960  CE2 TRP B 477     14.246 -47.784  38.699  1.00 180.11        C
ANISOU 9960  CE2 TRP B 477     25083 25248 18101   1978   178 -4573       C
ATOM   9961  CE3 TRP B 477     15.739 -45.896  38.874  1.00 176.72        C
ANISOU 9961  CE3 TRP B 477     23481 25837 17828   2194   720 -4604       C
```

FIG. 13 Continued

```
ATOM   9962  CZ2 TRP B 477      14.172 -47.914  40.079  1.00179.17           C
ANISOU 9962  CZ2 TRP B 477    24749  25209  18119   1801    173  -4489       C
ATOM   9963  CZ3 TRP B 477      15.664 -46.026  40.241  1.00175.81           C
ANISOU 9963  CZ3 TRP B 477    23174  25780  17846   2022    714  -4528       C
ATOM   9964  CH2 TRP B 477      14.885 -47.027  40.831  1.00177.01           C
ANISOU 9964  CH2 TRP B 477    23796  25473  17987   1829    449  -4474       C
ATOM   9965  N   GLU B 478      13.700 -44.010  33.407  1.00176.54           N
ANISOU 9965  N   GLU B 478    23798  25342  17939   1598    592   4819       N
ATOM   9966  CA  GLU B 478      13.628 -42.863  32.486  1.00174.34           C
ANISOU 9966  CA  GLU B 478    23094  25329  17820   1418    727  -4853       C
ATOM   9967  C   GLU B 478      13.833 -41.423  32.979  1.00170.58           C
ANISOU 9967  C   GLU B 478    21737  25408  17666   1135    954  -4818       C
ATOM   9968  O   GLU B 478      14.003 -40.529  32.149  1.00169.21           O
ANISOU 9968  O   GLU B 478    21215  25504  17572   1094   1071  -4851       O
ATOM   9969  CB  GLU B 478      12.326 -42.927  31.670  1.00173.79           C
ANISOU 9969  CB  GLU B 478    23387  24768  17877    962    512  -4852       C
ATOM   9970  CG  GLU B 478      11.874 -44.341  31.272  1.00177.27           C
ANISOU 9970  CG  GLU B 478    24731  24574  18050   1121    221  -4861       C
ATOM   9971  CD  GLU B 478      12.358 -44.785  29.898  1.00180.12           C
ANISOU 9971  CD  GLU B 478    25548  24810  18078   1587    196  -4963       C
ATOM   9972  OE1 GLU B 478      11.537 -44.789  28.952  1.00180.06           O
ANISOU 9972  OE1 GLU B 478    25851  24450  18114   1329     45  -4975       O
ATOM   9973  OE2 GLU B 478      13.550 -45.138  29.763  1.00182.48           O
ANISOU 9973  OE2 GLU B 478    25905  25362  18068   2214    325  -5026       O
ATOM   9974  N   PHE B 479      13.816 -41.185  34.288  1.00167.64           N
ANISOU 9974  N   PHE B 479    21013  25206  17475    944   1004  -4750       N
ATOM   9975  CA  PHE B 479      13.976 -39.820  34.812  1.00164.12           C
ANISOU 9975  CA  PHE B 479    19757  25265  17336    668   1190  -4714       C
ATOM   9976  C   PHE B 479      12.947 -38.917  34.143  1.00161.38           C
ANISOU 9976  C   PHE B 479    19194  24839  17285    120   1145  -4722       C
ATOM   9977  O   PHE B 479      12.891 -38.841  32.918  1.00162.00           O
ANISOU 9977  O   PHE B 479    19441  24831  17279    187   1126   4778       O
ATOM   9978  CB  PHE B 479      15.405 -39.286  34.566  1.00164.53           C
ANISOU 9978  CB  PHE B 479    19386  25885  17243   1157   1425  -4729       C
ATOM   9979  CG  PHE B 479      15.742 -37.986  35.310  1.00161.29           C
ANISOU 9979  CG  PHE B 479    18160  26007  17117    939   1595  -4673       C
ATOM   9980  CD1 PHE B 479      16.172 -38.006  36.633  1.00160.85           C
ANISOU 9980  CD1 PHE B 479    17860  26148  17108    989   1661  -4610       C
ATOM   9981  CD2 PHE B 479      15.674 -36.756  34.667  1.00158.82           C
ANISOU 9981  CD2 PHE B 479    17334  25999  17012    705   1676  -4681       C
ATOM   9982  CE1 PHE B 479      16.490 -36.827  37.303  1.00158.04           C
ANISOU 9982  CE1 PHE B 479    16789  26259  16999    803   1795  -4557       C
ATOM   9983  CE2 PHE B 479      16.000 -35.576  35.338  1.00156.01           C
ANISOU 9983  CE2 PHE B 479    16254  26117  16907    518   1802  -4628       C
ATOM   9984  CZ  PHE B 479      16.404 -35.614  36.651  1.00155.66           C
ANISOU 9984  CZ  PHE B 479    15999  26245  16901    572   1857  -4566       C
ATOM   9985  N   VAL B 480      12.122 -38.240  34.934  1.00159.58           N
ANISOU 9985  N   VAL B 480    18600  24636  17396   -419   1128  -4665       N
ATOM   9986  CA  VAL B 480      11.111 -37.374  34.345  1.00156.91           C
ANISOU 9986  CA  VAL B 480    18048  24220  17352   -958   1084  -4666       C
ATOM   9987  C   VAL B 480      11.415 -35.879  34.499  1.00153.64           C
ANISOU 9987  C   VAL B 480    16824  24346  17207  -1154   1262  -4669       C
ATOM   9988  O   VAL B 480      11.439 -35.140  33.514  1.00152.52           O
ANISOU 9988  O   VAL B 480    16456  24354  17142  -1234   1310  -4713       O
ATOM   9989  CB  VAL B 480       9.662 -37.763  34.789  1.00156.17           C
ANISOU 9989  CB  VAL B 480    18254  23641  17444  -1489    879  -4589       C
ATOM   9990  CG1 VAL B 480       9.688  38.664  36.005  1.00157.60           C
ANISOU 9990  CG1 VAL B 480    18677  23676  17530  -1383    804  -4522       C
ATOM   9991  CG2 VAL B 480       8.827 -36.530  35.065  1.00152.36           C
ANISOU 9991  CG2 VAL B 480    17211  23319  17362  -2080    919  -4552       C
ATOM   9992  N   GLY B 481      11.676 -35.434  35.719  1.00151.46           N
ANISOU 9992  N   GLY B 481    16117  24364  17068  -1221   1347  -4622       N
ATOM   9993  CA  GLY B 481      11.912 -34.023  35.935  1.00148.40           C
ANISOU 9993  CA  GLY B 481    14984  24460  16942  -1427   1480  -4618       C
ATOM   9994  C   GLY B 481      12.216 -33.691  37.373  1.00147.22           C
ANISOU 9994  C   GLY B 481    14446  24585  16906  -1461   1553  -4562       C
ATOM   9995  O   GLY B 481      12.422 -34.579  38.196  1.00148.93           O
ANISOU 9995  O   GLY B 481    14947  24668  16973  -1259   1527  -4528       O
ATOM   9996  N   LEU B 482      12.231 -32.404  37.686  1.00147.91           N
```

FIG. 13 Continued

```
ANISOU 9996  N   LEU B 482    13887 25051 17263  -1722  1631 -4552           N
ATOM   9997  CA  LEU B 482     12.581 -31.986  39.032  1.00146.73            C
ANISOU 9997  CA  LEU B 482    13338 25192 17222  -1742  1700 -4501           C
ATOM   9998  C   LEU B 482     11.723 -30.843  39.570  1.00143.33            C
ANISOU 9998  C   LEU B 482    12425 24876 17159  -2287  1682 -4489           C
ATOM   9999  O   LEU B 482     11.335 -29.935  38.834  1.00141.39            O
ANISOU 9999  O   LEU B 482    11897 24722 17103  -2567  1673 -4523           O
ATOM  10000  CB  LEU B 482     14.062  31.622  39.105  1.00147.34            C
ANISOU10000  CB  LEU B 482    13063 25759 17160  -1280  1846 -4481           C
ATOM  10001  CG  LEU B 482     14.586 -30.585  38.110  1.00146.16            C
ANISOU10001  CG  LEU B 482    12482 25976 17075  -1241  1910 -4498           C
ATOM  10002  CD1 LEU B 482     15.628 -29.710  38.791  1.00145.08            C
ANISOU10002  CD1 LEU B 482    11743 26380 16999  -1078  2016 -4431           C
ATOM  10003  CD2 LEU B 482     15.154 -31.235  36.840  1.00148.74            C
ANISOU10003  CD2 LEU B 482    13175 26231 17110   -830  1930 -4531           C
ATOM  10004  N   LEU B 483     11.453 -30.907  40.873  1.00138.11            N
ANISOU10004  N   LEU B 483    11672 24216 16586  -2421  1674 -4440           N
ATOM  10005  CA  LEU B 483     10.598 -29.958  41.564  1.00135.22            C
ANISOU10005  CA  LEU B 483    10904 23934 16540  -2906  1652 -4423           C
ATOM  10006  C   LEU B 483     11.336 -28.880  42.332  1.00133.46            C
ANISOU10006  C   LEU B 483    10056 24208 16445  -2860  1746 -4411           C
ATOM  10007  O   LEU B 483     12.388 -29.138  42.923  1.00134.66            O
ANISOU10007  O   LEU B 483    10146 24582 16437  -2479  1822 -4380           O
ATOM  10008  CB  LEU B 483      9.720 -30.701  42.563  1.00135.68            C
ANISOU10008  CB  LEU B 483    11260 23672 16621  -3109  1569 -4362           C
ATOM  10009  CG  LEU B 483      8.849 -31.789  41.975  1.00137.39            C
ANISOU10009  CG  LEU B 483    12107 23359 16734  -3214  1433 -4340           C
ATOM  10010  CD1 LEU B 483      7.667 -31.965  42.880  1.00136.58            C
ANISOU10010  CD1 LEU B 483    12077 23025 16791  -3618  1340 -4256           C
ATOM  10011  CD2 LEU B 483      8.397 -31.370  40.603  1.00136.61            C
ANISOU10011  CD2 LEU B 483    12042 23145 16717  -3407  1396 -4390           C
ATOM  10012  N   PRO B 484     10.772 -27.659  42.313  1.00153.49            N
ANISOU10012  N   PRO B 484    12136 26912 19273  -3257  1729 -4431           N
ATOM  10013  CA  PRO B 484     11.167 -26.495  43.112  1.00151.40            C
ANISOU10013  CA  PRO B 484    11269 27068 19190  -3336  1771 -4420           C
ATOM  10014  C   PRO B 484     10.326 -26.490  44.392  1.00150.45            C
ANISOU10014  C   PRO B 484    11117 26838 19209  -3622  1738 -4387           C
ATOM  10015  O   PRO B 484      9.176 -26.051  44.356  1.00148.76            O
ANISOU10015  O   PRO B 484    10840 26474 19210  -4060  1675 -4397           O
ATOM  10016  CB  PRO B 484     10.762 -25.307  42.224  1.00149.03            C
ANISOU10016  CB  PRO B 484    10592 26906 19126  -3659  1735 -4469           C
ATOM  10017  CG  PRO B 484     10.367 -25.897  40.891  1.00150.11            C
ANISOU10017  CG  PRO B 484    11134 26730 19171  -3676  1700 -4506           C
ATOM  10018  CD  PRO B 484      9.868 -27.263  41.226  1.00152.25            C
ANISOU10018  CD  PRO B 484    12010 26568 19270  -3611  1662 -4475           C
ATOM  10019  N   LEU B 485     10.882 -26.982  45.498  1.00129.17            N
ANISOU10019  N   LEU B 485     8467 24220 16391  -3378  1781 -4339           N
ATOM  10020  CA  LEU B 485     10.128 -27.075  46.744  1.00128.55            C
ANISOU10020  CA  LEU B 485     8383 24044 16415  -3613  1752 -4299           C
ATOM  10021  C   LEU B 485     10.417 -25.865  47.617  1.00126.45            C
ANISOU10021  C   LEU B 485     7544 24170 16332  -3705  1781 -4299           C
ATOM  10022  O   LEU B 485     11.572 -25.407  47.691  1.00126.47            O
ANISOU10022  O   LEU B 485     7259 24514 16279  -3423  1835 -4293           O
ATOM  10023  CB  LEU B 485     10.462 -28.366  47.494  1.00130.99            C
ANISOU10023  CB  LEU B 485     9101 24177 16493  -3326  1764 -4244           C
ATOM  10024  CG  LEU B 485     10.269 -29.723  46.808  1.00133.52            C
ANISOU10024  CG  LEU B 485    10048 24088 16593  -3176  1710 -4235           C
ATOM  10025  CD1 LEU B 485     11.076 -30.768  47.555  1.00135.86            C
ANISOU10025  CD1 LEU B 485    10612 24361 16647  -2779  1743 -4193           C
ATOM  10026  CD2 LEU B 485      8.800 -30.145  46.695  1.00133.32            C
ANISOU10026  CD2 LEU B 485    10335 23651 16669  -3583  1590 -4199           C
ATOM  10027  N   PHE B 486      9.367 -25.339  48.264  1.00145.28            N
ANISOU10027  N   PHE B 486     9765 26507 18927  -4096  1736 -4295           N
ATOM  10028  CA  PHE B 486      9.545 -24.158  49.105  1.00143.31            C
ANISOU10028  CA  PHE B 486     8993 26606 18852  -4199  1742 -4305           C
ATOM  10029  C   PHE B 486      9.352 -24.257  50.621  1.00143.28            C
ANISOU10029  C   PHE B 486     8928 26649 18863  -4223  1754 -4258           C
ATOM  10030  O   PHE B 486      8.338 -24.765  51.090  1.00143.50            O
ANISOU10030  O   PHE B 486     9180 26425 18919  -4441  1724 -4222           O
```

FIG. 13 Continued

```
ATOM  10031  CB   PHE B 486       8.804 -22.940  48.583  1.00140.79           C
ANISOU10031  CB   PHE B 486     8322  26371  18801  -4590   1685  -4360       C
ATOM  10032  CG   PHE B 486       9.403 -21.684  49.092  1.00139.11           C
ANISOU10032  CG   PHE B 486     7566  26566  18721  -4578   1673  -4381       C
ATOM  10033  CD1  PHE B 486      10.797 -21.615  49.271  1.00139.93           C
ANISOU10033  CD1  PHE B 486     7517  26960  18691  -4188   1713  -4350       C
ATOM  10034  CD2  PHE B 486       8.619 -20.603  49.441  1.00136.86           C
ANISOU10034  CD2  PHE B 486     6938  26378  18683  -4935   1613  -4416       C
ATOM  10035  CE1  PHE B 486      11.400 -20.484  49.769  1.00138.54           C
ANISOU10035  CE1  PHE B 486     6856  27152  18629  -4167   1677  -4346       C
ATOM  10036  CE2  PHE B 486       9.214 -19.455  49.940  1.00135.46           C
ANISOU10036  CE2  PHE B 486     6282  26569  18617  -4905   1575  -4433       C
ATOM  10037  CZ   PHE B 486      10.615 -19.399  50.108  1.00136.31           C
ANISOU10037  CZ   PHE B 486     6245  26953  18592  -4524   1599  -4393       C
ATOM  10038  N    ASP B 487      10.331 -23.686  51.348  1.00188.94           N
ANISOU10038  N    ASP B 487    14378  32774  24636  -4010   1787  -4249       N
ATOM  10039  CA   ASP B 487      10.414 -23.661  52.822  1.00188.91           C
ANISOU10039  CA   ASP B 487    14261  32885  24633  -3970   1805  -4208       C
ATOM  10040  C    ASP B 487      10.719 -22.245  53.348  1.00186.88           C
ANISOU10040  C    ASP B 487    13462  32992  24552  -4052   1772  -4233       C
ATOM  10041  O    ASP B 487      11.888 -21.824  53.371  1.00186.95           O
ANISOU10041  O    ASP B 487    13237  33282  24512  -3792   1784  -4213       O
ATOM  10042  CB   ASP B 487      11.521 -24.614  53.292  1.00191.08           C
ANISOU10042  CB   ASP B 487    14749  33186  24664  -3544   1873  -4151       C
ATOM  10043  CG   ASP B 487      11.333 -25.068  54.720  1.00191.61           C
ANISOU10043  CG   ASP B 487    14888  33222  24694  -3531   1889  -4100       C
ATOM  10044  OD1  ASP B 487      10.453 -24.516  55.402  1.00190.25           O
ANISOU10044  OD1  ASP B 487    14544  33063  24680  -3822   1853  -4107       O
ATOM  10045  OD2  ASP B 487      12.059 -25.982  55.159  1.00193.44           O
ANISOU10045  OD2  ASP B 487    15347  33418  24733  -3225   1938  -4051       O
ATOM  10046  N    PRO B 488       9.663 -21.528  53.800  1.00127.72           N
ANISOU10046  N    PRO B 488     5780  25490  17256  -4407   1721  -4263       N
ATOM  10047  CA   PRO B 488       9.618 -20.128  54.269  1.00125.64           C
ANISOU10047  CA   PRO B 488     5035  25513  17189  -4565   1658  -4303       C
ATOM  10048  C    PRO B 488      10.314 -19.887  55.617  1.00125.82           C
ANISOU10048  C    PRO B 488     4873  25767  17166  -4369   1666  -4265       C
ATOM  10049  O    PRO B 488      10.635 -20.852  56.306  1.00127.45           O
ANISOU10049  O    PRO B 488     5333  25886  17205  -4161   1731  -4208       O
ATOM  10050  CB   PRO B 488       8.110 -19.863  54.425  1.00124.46           C
ANISOU10050  CB   PRO B 488     4895  25189  17206  -4974   1622  -4328       C
ATOM  10051  CG   PRO B 488       7.401 -21.071  53.854  1.00125.81           C
ANISOU10051  CG   PRO B 488     5538  24983  17282  -5049   1654  -4290       C
ATOM  10052  CD   PRO B 488       8.356 -22.192  53.965  1.00128.03           C
ANISOU10052  CD   PRO B 488     6122  25204  17319  -4670   1714  -4241       C
ATOM  10053  N    PRO B 489      10.543 -18.617  56.004  1.00134.37           N
ANISOU10053  N    PRO B 489    17423  22303  11329   -164   1774   3675       N
ATOM  10054  CA   PRO B 489      11.155 -18.429  57.324  1.00132.32           C
ANISOU10054  CA   PRO B 489    17215  21729  11330   -496   1886   3658       C
ATOM  10055  C    PRO B 489      10.053 -18.442  58.393  1.00130.25           C
ANISOU10055  C    PRO B 489    17046  21123  11321   -732   1789   3808       C
ATOM  10056  O    PRO B 489       9.067 -17.743  58.168  1.00130.41           O
ANISOU10056  O    PRO B 489    17107  21139  11304   -691   1971   4095       O
ATOM  10057  CB   PRO B 489      11.736 -17.010  57.237  1.00132.77           C
ANISOU10057  CB   PRO B 489    17288  21835  11322   -566   2456   3914       C
ATOM  10058  CG   PRO B 489      11.154 -16.386  56.004  1.00134.76           C
ANISOU10058  CG   PRO B 489    17520  22362  11319   -283   2650   4144       C
ATOM  10059  CD   PRO B 489      10.164 -17.333  55.400  1.00135.41           C
ANISOU10059  CD   PRO B 489    17570  22573  11307    -68   2218   4040       C
ATOM  10060  N    ARG B 490      10.157 -19.189  59.497  1.00163.47           N
ANISOU10060  N    ARG B 490    21279  25065  15766   -957   1522   3645       N
ATOM  10061  CA   ARG B 490       9.102 -19.075  60.515  1.00161.62           C
ANISOU10061  CA   ARG B 490    21129  24521  15757  -1190   1481   3821       C
ATOM  10062  C    ARG B 490       9.162 -17.658  61.102  1.00160.81           C
ANISOU10062  C    ARG B 490    21094  24281  15726  -1400   2005   4116       C
ATOM  10063  O    ARG B 490      10.252 -17.131  61.320  1.00160.88           O
ANISOU10063  O    ARG B 490    21089  24310  15729  -1509   2278   4081       O
ATOM  10064  CB   ARG B 490       9.222 -20.130  61.610  1.00160.10           C
ANISOU10064  CB   ARG B 490    20950  24079  15802  -1396   1108   3610       C
ATOM  10065  CG   ARG B 490       7.972 -20.179  62.487  1.00158.53           C
```

FIG. 13 Continued

```
ANISOU10065  CG   ARG B 490   20824  23608  15803  -1591   1001   3779      C
ATOM  10066  CD   ARG B 490       8.162 -20.970  63.774  1.00156.92          C
ANISOU10066  CD   ARG B 490   20640  23131  15850  -1852    733   3642      C
ATOM  10067  NE   ARG B 490       8.041 -22.407  63.565  1.00157.50          N
ANISOU10067  NE   ARG B 490   20684  23197  15963  -1735    223   3378      N
ATOM  10068  CZ   ARG B 490       9.060 -23.198  63.247  1.00158.48          C
ANISOU10068  CZ   ARG B 490   20751  23423  16043  -1608     25   3094      C
ATOM  10069  NH1  ARG B 490      10.278 -22.686  63.100  1.00158.91          N
ANISOU10069  NH1  ARG B 490   20756  23622  15999  -1587    286   3043      N
ATOM  10070  NH2  ARG B 490       8.862 -24.499  63.073  1.00159.21          N
ANISOU10070  NH2  ARG B 490   20831  23467  16194  -1504   -426   2860      N
ATOM  10071  N    HIS B 491       8.013 -17.044  61.370  1.00126.55          N
ANISOU10071  N    HIS B 491   16823  19801  11459  -1463   2151   4396      N
ATOM  10072  CA   HIS B 491       7.993 -15.630  61.768  1.00126.26          C
ANISOU10072  CA   HIS B 491   16861  19635  11478  -1619   2686   4687      C
ATOM  10073  C    HIS B 491       8.945 -15.164  62.864  1.00125.10          C
ANISOU10073  C    HIS B 491   16749  19292  11492  -1950   2930   4632      C
ATOM  10074  O    HIS B 491       9.833 -14.334  62.614  1.00126.00          O
ANISOU10074  O    HIS B 491   16858  19487  11529  -1975   3312   4673      O
ATOM  10075  CB   HIS B 491       6.587 -15.199  62.137  1.00125.59          C
ANISOU10075  CB   HIS B 491   16845  19377  11497  -1669   2755   4966      C
ATOM  10076  CG   HIS B 491       6.188 -15.527  63.544  1.00123.45          C
ANISOU10076  CG   HIS B 491   16628  18788  11490  -1987   2607   4934      C
ATOM  10077  ND1  HIS B 491       5.812 -16.790  63.939  1.00122.56          N
ANISOU10077  ND1  HIS B 491   16485  18611  11472  -2027   2102   4739      N
ATOM  10078  CD2  HIS B 491       6.069 -14.739  64.642  1.00122.21          C
ANISOU10078  CD2  HIS B 491   16553  18364  11518  -2280   2909   5081      C
ATOM  10079  CE1  HIS B 491       5.483 -16.774  65.218  1.00120.82          C
ANISOU10079  CE1  HIS B 491   16320  18111  11475  -2326   2093   4783      C
ATOM  10080  NE2  HIS B 491       5.622 -15.540  65.666  1.00120.56          N
ANISOU10080  NE2  HIS B 491   16354  17960  11495  -2483   2576   4982      N
ATOM  10081  N    ASP B 492       8.738 -15.668  64.079  1.00123.21          N
ANISOU10081  N    ASP B 492   16538  18807  11469  -2214   2722   4548      N
ATOM  10082  CA   ASP B 492       9.581 -15.290  65.205  1.00122.17          C
ANISOU10082  CA   ASP B 492   16425  18510  11482  -2549   2919   4484      C
ATOM  10083  C    ASP B 492      11.052 -15.465  64.857  1.00123.10          C
ANISOU10083  C    ASP B 492   16454  18832  11488  -2513   2947   4259      C
ATOM  10084  O    ASP B 492      11.828 -14.526  64.996  1.00123.59          O
ANISOU10084  O    ASP B 492   16521  18906  11531  -2655   3356   4309      O
ATOM  10085  CB   ASP B 492       9.213 -16.051  66.494  1.00120.28          C
ANISOU10085  CB   ASP B 492   16203  18037  11462  -2802   2603   4392      C
ATOM  10086  CG   ASP B 492       8.684 -17.454  66.234  1.00120.15          C
ANISOU10086  CG   ASP B 492   16143  18055  11452  -2634   2042   4236      C
ATOM  10087  OD1  ASP B 492       8.296 -18.140  67.209  1.00118.81          O
ANISOU10087  OD1  ASP B 492   15989  17695  11460  -2817   1764   4182      O
ATOM  10088  OD2  ASP B 492       8.646 -17.871  65.065  1.00121.52          O
ANISOU10088  OD2  ASP B 492   16270  18445  11456  -2327   1886   4165      O
ATOM  10089  N    SER B 493      11.405 -16.655  64.368  1.00122.52          N
ANISOU10089  N    SER B 493   16296  18919  11337  -2316   2521   4014      N
ATOM  10090  CA   SER B 493      12.779 -17.002  63.983  1.00123.57          C
ANISOU10090  CA   SER B 493   16325  19271  11355  -2237   2484   3776      C
ATOM  10091  C    SER B 493      13.504 -15.876  63.237  1.00125.11          C
ANISOU10091  C    SER B 493   16500  19656  11381  -2175   2962   3882      C
ATOM  10092  O    SER B 493      14.738 -15.841  63.180  1.00125.86          O
ANISOU10092  O    SER B 493   16511  19903  11409  -2211   3059   3728      O
ATOM  10093  CB   SER B 493      12.813 -18.314  63.178  1.00124.48          C
ANISOU10093  CB   SER B 493   16369  19559  11369  -1933   2009   3538      C
ATOM  10094  OG   SER B 493      12.622 -18.097  61.794  1.00126.26          O
ANISOU10094  OG   SER B 493   16571  20040  11362  -1614   2087   3589      O
ATOM  10095  N    ALA B 494      12.739 -14.958  62.661  1.00125.86          N
ANISOU10095  N    ALA B 494   16667  19748  11407  -2078   3266   4157      N
ATOM  10096  CA   ALA B 494      13.333 -13.785  62.046  1.00127.41          C
ANISOU10096  CA   ALA B 494   16864  20073  11473  -2048   3767   4308      C
ATOM  10097  C    ALA B 494      13.947 -12.950  63.174  1.00126.63          C
ANISOU10097  C    ALA B 494   16806  19771  11538  -2442   4125   4338      C
ATOM  10098  O    ALA B 494      15.152 -12.677  63.223  1.00127.39          O
ANISOU10098  O    ALA B 494   16832  19984  11586  -2554   4311   4217      O
ATOM  10099  CB   ALA B 494      12.255 -12.998  61.336  1.00128.25          C
ANISOU10099  CB   ALA B 494   17048  20176  11505  -1870   4008   4631      C
```

FIG. 13 Continued

```
ATOM   10100  N   GLU B 495      13.069 -12.562  64.087  1.00169.79           N
ANISOU10100  N   GLU B 495    22378  24942  17193  -2657   4213   4494        N
ATOM   10101  CA  GLU B 495      13.425 -11.795  65.260  1.00169.02           C
ANISOU10101  CA  GLU B 495    22333  24621  17265  -3053   4532   4520        C
ATOM   10102  C   GLU B 495      14.437 -12.569  66.088  1.00168.22           C
ANISOU10102  C   GLU B 495    22130  24564  17220  -3258   4275   4223        C
ATOM   10103  O   GLU B 495      15.509 -12.077  66.389  1.00168.84           O
ANISOU10103  O   GLU B 495    22159  24706  17287  -3459   4531   4134        O
ATOM   10104  CB  GLU B 495      12.163 -11.550  66.100  1.00167.56           C
ANISOU10104  CB  GLU B 495    22266  24131  17267  -3204   4547   4700        C
ATOM   10105  CG  GLU B 495      11.018 -10.867  65.351  1.00168.35           C
ANISOU10105  CG  GLU B 495    22456  24186  17324  -2980   4761   5015        C
ATOM   10106  CD  GLU B 495      11.022  -9.356  65.525  1.00169.28           C
ANISOU10106  CD  GLU B 495    22681  24130  17506  -3141   5384   5252        C
ATOM   10107  OE1 GLU B 495      11.357  -8.640  64.550  1.00171.18           O
ANISOU10107  OE1 GLU B 495    22927  24506  17609  -2965   5709   5389        O
ATOM   10108  OE2 GLU B 495      10.698  -8.890  66.644  1.00168.25           O
ANISOU10108  OE2 GLU B 495    22635  23725  17567  -3445   5556   5299        O
ATOM   10109  N   THR B 496      14.079 -13.796  66.445  1.00130.79           N
ANISOU10109  N   THR B 496    17355  19798  12543  -3203   3766   4079        N
ATOM   10110  CA  THR B 496      14.912 -14.638  67.294  1.00130.07           C
ANISOU10110  CA  THR B 496    17167  19732  12520  -3373   3479   3827        C
ATOM   10111  C   THR B 496      16.391 -14.506  66.984  1.00131.44           C
ANISOU10111  C   THR B 496    17216  20156  12567  -3383   3622   3656        C
ATOM   10112  O   THR B 496      17.184 -14.182  67.868  1.00131.27           O
ANISOU10112  O   THR B 496    17146  20122  12607  -3688   3779   3574        O
ATOM   10113  CB  THR B 496      14.482 -16.124  67.222  1.00129.42           C
ANISOU10113  CB  THR B 496    17046  19659  12467  -3176   2888   3679        C
ATOM   10114  OG1 THR B 496      13.626 -16.430  68.330  1.00127.69           O
ANISOU10114  OG1 THR B 496    16894  19180  12444  -3386   2711   3741        O
ATOM   10115  CG2 THR B 496      15.685 -17.039  67.285  1.00129.95           C
ANISOU10115  CG2 THR B 496    16975  19909  12491  -3132   2617   3401        C
ATOM   10116  N   ILE B 497      16.769 -14.750  65.736  1.00124.23           N
ANISOU10116  N   ILE B 497    16241  19495  11466  -3056   3570   3598        N
ATOM   10117  CA  ILE B 497      18.174 -14.641  65.381  1.00125.70           C
ANISOU10117  CA  ILE B 497    16296  19946  11519  -3046   3705   3438        C
ATOM   10118  C   ILE B 497      18.621 -13.206  65.664  1.00126.35           C
ANISOU10118  C   ILE B 497    16414  19982  11613  -3330   4283   3577        C
ATOM   10119  O   ILE B 497      19.733 -12.953  66.136  1.00126.91           O
ANISOU10119  O   ILE B 497    16387  20158  11675  -3553   4440   3448        O
ATOM   10120  CB  ILE B 497      18.421 -15.045  63.918  1.00127.40           C
ANISOU10120  CB  ILE B 497    16445  20449  11513  -2635   3594   3373        C
ATOM   10121  CG1 ILE B 497      19.809 -14.586  63.461  1.00129.20           C
ANISOU10121  CG1 ILE B 497    16547  20954  11587  -2643   3870   3276        C
ATOM   10122  CG2 ILE B 497      17.314 -14.500  63.024  1.00127.85           C
ANISOU10122  CG2 ILE B 497    16614  20470  11494  -2424   3746   3622        C
ATOM   10123  CD1 ILE B 497      20.947 -15.251  64.191  1.00129.12           C
ANISOU10123  CD1 ILE B 497    16392  21053  11615  -2874   3675   3018        C
ATOM   10124  N   ARG B 498      17.717 -12.273  65.400  1.00167.99           N
ANISOU10124  N   ARG B 498    21826  25089  16913  -3325   4601   3842        N
ATOM   10125  CA  ARG B 498      17.964 -10.870  65.669  1.00168.76           C
ANISOU10125  CA  ARG B 498    21992  25074  17054  -3591   5174   3997        C
ATOM   10126  C   ARG B 498      18.368 -10.732  67.135  1.00168.67           C
ANISOU10126  C   ARG B 498    21842  24782  17084  -4029   5226   3881        C
ATOM   10127  O   ARG B 498      19.447 -10.237  67.446  1.00168.63           O
ANISOU10127  O   ARG B 498    21886  25005  17182  -4266   5483   3774        O
ATOM   10128  CB  ARG B 498      16.693 -10.062  65.350  1.00168.75           C
ANISOU10128  CB  ARG B 498    22158  24855  17104  -3505   5432   4314        C
ATOM   10129  CG  ARG B 498      16.697  -8.609  65.794  1.00169.45           C
ANISOU10129  CG  ARG B 498    22359  24726  17297  -3796   6027   4497        C
ATOM   10130  CD  ARG B 498      15.334  -7.947  65.567  1.00169.38           C
ANISOU10130  CD  ARG B 498    22512  24484  17359  -3680   6229   4816        C
ATOM   10131  NE  ARG B 498      15.125  -7.533  64.181  1.00171.22           N
ANISOU10131  NE  ARG B 498    22759  24876  17421  -3326   6410   5025        N
ATOM   10132  CZ  ARG B 498      15.703  -6.470  63.620  1.00173.31           C
ANISOU10132  CZ  ARG B 498    23048  25181  17620  -3342   6907   5160        C
ATOM   10133  NH1 ARG B 498      16.542  -5.714  64.321  1.00173.84           N
ANISOU10133  NH1 ARG B 498    23130  25136  17786  -3712   7275   5085        N
ATOM   10134  NH2 ARG B 498      15.453  -6.163  62.350  1.00175.05           N
```

FIG. 13 Continued

```
ANISOU10134  NH2 ARG B 498     23273  25567  17670  -2997   7040   5369        N
ATOM   10135  N   ARG B 499     17.509 -11.228  68.022  1.00148.80              N
ANISOU10135  N   ARG B 499     19514  22177  14848  -4132   4962   3892        N
ATOM   10136  CA  ARG B 499     17.692 -11.139  69.477  1.00147.70              C
ANISOU10136  CA  ARG B 499     19370  21886  14863  -4542   4982   3803        C
ATOM   10137  C   ARG B 499     18.981 -11.772  70.002  1.00147.94              C
ANISOU10137  C   ARG B 499     19221  22140  14850  -4685   4786   3533        C
ATOM   10138  O   ARG B 499     19.674 -11.190  70.840  1.00148.29              O
ANISOU10138  O   ARG B 499     19222  22186  14934  -5046   5038   3455        O
ATOM   10139  CB  ARG B 499     16.484 -11.772  70.176  1.00145.75              C
ANISOU10139  CB  ARG B 499     19203  21412  14763  -4552   4653   3869        C
ATOM   10140  CG  ARG B 499     16.509 -11.707  71.679  1.00144.61              C
ANISOU10140  CG  ARG B 499     19061  21114  14770  -4957   4658   3803        C
ATOM   10141  CD  ARG B 499     15.176 -12.170  72.253  1.00142.89              C
ANISOU10141  CD  ARG B 499     18940  20660  14692  -4952   4400   3919        C
ATOM   10142  NE  ARG B 499     14.050 -11.393  71.732  1.00142.99              N
ANISOU10142  NE  ARG B 499     19103  20489  14737  -4828   4664   4177        N
ATOM   10143  CZ  ARG B 499     12.837 -11.347  72.288  1.00141.81              C
ANISOU10143  CZ  ARG B 499     19056  20106  14719  -4886   4619   4328        C
ATOM   10144  NH1 ARG B 499     12.570 -12.032  73.400  1.00140.38              N
ANISOU10144  NH1 ARG B 499     18852  19835  14651  -5082   4322   4249        N
ATOM   10145  NH2 ARG B 499     11.889 -10.604  71.728  1.00142.21              N
ANISOU10145  NH2 ARG B 499     19227  20024  14783  -4742   4881   4573        N
ATOM   10146  N   ALA B 500     19.284 -12.970  69.513  1.00125.66              N
ANISOU10146  N   ALA B 500     16290  19509  11944  -4400   4337   3387        N
ATOM   10147  CA  ALA B 500     20.483 -13.689  69.916  1.00126.08              C
ANISOU10147  CA  ALA B 500     16161  19794  11951  -4467   4112   3144        C
ATOM   10148  C   ALA B 500     21.700 -12.792  69.855  1.00127.77              C
ANISOU10148  C   ALA B 500     16276  20203  12067  -4676   4528   3075        C
ATOM   10149  O   ALA B 500     22.490 -12.767  70.787  1.00127.90              O
ANISOU10149  O   ALA B 500     16182  20304  12110  -4970   4554   2941        O
ATOM   10150  CB  ALA B 500     20.693 -14.887  69.028  1.00126.54              C
ANISOU10150  CB  ALA B 500     16131  20042  11904  -4060   3683   3015        C
ATOM   10151  N   LEU B 501     21.847 -12.065  68.750  1.00139.50              N
ANISOU10151  N   LEU B 501     17793  21776  13434  -4511   4850   3172        N
ATOM   10152  CA  LEU B 501     22.988 -11.170  68.560  1.00141.39              C
ANISOU10152  CA  LEU B 501     17943  22201  13577  -4694   5274   3122        C
ATOM   10153  C   LEU B 501     22.992  -9.998  69.530  1.00141.45              C
ANISOU10153  C   LEU B 501     18027  22010  13707  -5159   5722   3184        C
ATOM   10154  O   LEU B 501     24.047  -9.446  69.827  1.00142.82              O
ANISOU10154  O   LEU B 501     18092  22336  13836  -5431   5993   3072        O
ATOM   10155  CB  LEU B 501     23.075 -10.663  67.114  1.00143.08              C
ANISOU10155  CB  LEU B 501     18182  22548  13635  -4401   5523   3242        C
ATOM   10156  CG  LEU B 501     23.905 -11.492  66.119  1.00144.33              C
ANISOU10156  CG  LEU B 501     18173  23068  13598  -4055   5267   3083        C
ATOM   10157  CD1 LEU B 501     23.321 -12.902  65.966  1.00143.07              C
ANISOU10157  CD1 LEU B 501     18005  22907  13448  -3735   4680   2991        C
ATOM   10158  CD2 LEU B 501     24.064 -10.798  64.747  1.00146.31              C
ANISOU10158  CD2 LEU B 501     18442  23473  13677  -3820   5595   3219        C
ATOM   10159  N   ASN B 502     21.822  -9.589  70.003  1.00181.55              N
ANISOU10159  N   ASN B 502     23288  26757  18936  -5257   5816   3355        N
ATOM   10160  CA  ASN B 502     21.798  -8.551  71.022  1.00181.65              C
ANISOU10160  CA  ASN B 502     23378  26566  19077  -5709   6219   3382        C
ATOM   10161  C   ASN B 502     22.064  -9.189  72.380  1.00180.48              C
ANISOU10161  C   ASN B 502     23130  26443  19001  -5994   5932   3199        C
ATOM   10162  O   ASN B 502     22.179  -8.503  73.396  1.00180.59              O
ANISOU10162  O   ASN B 502     23168  26345  19103  -6406   6196   3158        O
ATOM   10163  CB  ASN B 502     20.504  -7.731  71.004  1.00181.13              C
ANISOU10163  CB  ASN B 502     23542  26138  19141  -5712   6501   3642        C
ATOM   10164  CG  ASN B 502     20.700  -6.339  70.394  1.00183.18              C
ANISOU10164  CG  ASN B 502     23899  26313  19389  -5789   7116   3793        C
ATOM   10165  OD1 ASN B 502     21.680  -6.087  69.680  1.00184.97              O
ANISOU10165  OD1 ASN B 502     24026  26771  19482  -5740   7289   3737        O
ATOM   10166  ND2 ASN B 502     19.769  -5.428  70.663  1.00183.10              N
ANISOU10166  ND2 ASN B 502     24082  25964  19524  -5906   7459   3992        N
ATOM   10167  N   LEU B 503     22.161 -10.517  72.376  1.00126.10              N
ANISOU10167  N   LEU B 503     16130  19710  12073  -5766   5394   3089        N
ATOM   10168  CA  LEU B 503     22.515 -11.276  73.575  1.00125.25              C
ANISOU10168  CA  LEU B 503     15899  19677  12012  -5978   5073   2927        C
```

FIG. 13 Continued

```
ATOM  10169  C    LEU B 503      23.936 -11.880  73.525  1.00 126.51           C
ANISOU10169  C    LEU B 503    15813  20220  12035  -5957   4898   2706        C
ATOM  10170  O    LEU B 503      24.244 -12.828  74.260  1.00 125.95           O
ANISOU10170  O    LEU B 503    15616  20261  11978  -5987   4516   2586        O
ATOM  10171  CB   LEU B 503      21.461 -12.334  73.874  1.00 123.28           C
ANISOU10171  CB   LEU B 503    15717  19260  11863  -5789   4597   2989        C
ATOM  10172  CG   LEU B 503      20.269 -11.648  74.534  1.00 122.10           C
ANISOU10172  CG   LEU B 503    15758  18767  11867  -5997   4801   3161        C
ATOM  10173  CD1  LEU B 503      19.424 -12.620  75.337  1.00 120.25           C
ANISOU10173  CD1  LEU B 503    15550  18391  11749  -5985   4361   3185        C
ATOM  10174  CD2  LEU B 503      20.778 -10.536  75.426  1.00 122.93           C
ANISOU10174  CD2  LEU B 503    15859  18845  12003  -6468   5251   3107        C
ATOM  10175  N    GLY B 504      24.788 -11.309  72.664  1.00 127.81           N
ANISOU10175  N    GLY B 504    15907  20587  12069  -5903   5190   2669        N
ATOM  10176  CA   GLY B 504      26.174 -11.729  72.500  1.00 129.35           C
ANISOU10176  CA   GLY B 504    15859  21170  12118  -5877   5093   2471        C
ATOM  10177  C    GLY B 504      26.366 -13.060  71.793  1.00 129.26           C
ANISOU10177  C    GLY B 504    15746  21339  12027  -5426   4604   2390        C
ATOM  10178  O    GLY B 504      27.441 -13.348  71.285  1.00 130.82           O
ANISOU10178  O    GLY B 504    15761  21859  12084  -5298   4564   2254        O
ATOM  10179  N    VAL B 505      25.314 -13.870  71.763  1.00 133.02           N
ANISOU10179  N    VAL B 505    16341  21604  12598  -5190   4240   2467        N
ATOM  10180  CA   VAL B 505      25.358 -15.198  71.156  1.00 132.96           C
ANISOU10180  CA   VAL B 505    16265  21709  12545  -4771   3756   2379        C
ATOM  10181  C    VAL B 505      25.057 -15.204  69.638  1.00 133.67           C
ANISOU10181  C    VAL B 505    16425  21838  12525  -4366   3786   2438        C
ATOM  10182  O    VAL B 505      23.947 -14.842  69.211  1.00 132.85           O
ANISOU10182  O    VAL B 505    16506  21501  12469  -4272   3875   2613        O
ATOM  10183  CB   VAL B 505      24.402 -16.165  71.911  1.00 131.05           C
ANISOU10183  CB   VAL B 505    16103  21225  12463  -4734   3321   2414        C
ATOM  10184  CG1  VAL B 505      22.959 -15.679  71.820  1.00 129.59           C
ANISOU10184  CG1  VAL B 505    16153  20697  12388  -4742   3432   2623        C
ATOM  10185  CG2  VAL B 505      24.542 -17.589  71.396  1.00 131.28           C
ANISOU10185  CG2  VAL B 505    16058  21354  12470  -4334   2820   2295        C
ATOM  10186  N    ASN B 506      26.059 -15.617  68.845  1.00 142.56           N
ANISOU10186  N    ASN B 506    17390  23283  13494  -4127   3712   2291        N
ATOM  10187  CA   ASN B 506      25.966 -15.722  67.378  1.00 143.63           C
ANISOU10187  CA   ASN B 506    17551  23537  13485  -3728   3717   2308        C
ATOM  10188  C    ASN B 506      25.232 -16.986  66.951  1.00 142.88           C
ANISOU10188  C    ASN B 506    17511  23353  13424  -3354   3220   2259        C
ATOM  10189  O    ASN B 506      25.392 -18.041  67.558  1.00 142.40           O
ANISOU10189  O    ASN B 506    17379  23281  13445  -3314   2826   2130        O
ATOM  10190  CB   ASN B 506      27.357 -15.785  66.713  1.00 145.89           C
ANISOU10190  CB   ASN B 506    17625  24224  13581  -3601   3800   2145        C
ATOM  10191  CG   ASN B 506      28.317 -14.683  67.170  1.00 147.06           C
ANISOU10191  CG   ASN B 506    17668  24522  13684   3987   4254   2140        C
ATOM  10192  OD1  ASN B 506      29.287 -14.361  66.468  1.00 149.05           O
ANISOU10192  OD1  ASN B 506    17784  25075  13773  -3921   4461   2073        O
ATOM  10193  ND2  ASN B 506      28.073 -14.122  68.346  1.00 146.00           N
ANISOU10193  ND2  ASN B 506    17590  24194  13690  -4399   4408   2197        N
ATOM  10194  N    VAL B 507      24.430 -16.903  65.904  1.00 132.37           N
ANISOU10194  N    VAL B 507    16301  21963  12030  -3081   3234   2362        N
ATOM  10195  CA   VAL B 507      23.821 -18.118  65.400  1.00 132.08           C
ANISOU10195  CA   VAL B 507    16300  21878  12005  -2729   2768   2277        C
ATOM  10196  C    VAL B 507      24.482 -18.395  64.056  1.00 134.17           C
ANISOU10196  C    VAL B 507    16465  22462  12051  -2363   2752   2151        C
ATOM  10197  O    VAL B 507      24.884 -17.461  63.356  1.00 135.43           O
ANISOU10197  O    VAL B 507    16601  22797  12060  -2360   3139   2231        O
ATOM  10198  CB   VAL B 507      22.280 -18.025  65.327  1.00 130.59           C
ANISOU10198  CB   VAL B 507    16313  21390  11916  -2692   2704   2466        C
ATOM  10199  CG1  VAL B 507      21.672 -19.373  65.005  1.00 130.33           C
ANISOU10199  CG1  VAL B 507    16308  21288  11924  -2392   2190   2348        C
ATOM  10200  CG2  VAL B 507      21.735 -17.542  66.649  1.00 128.78           C
ANISOU10200  CG2  VAL B 507    16171  20878  11881  -3081   2811   2600        C
ATOM  10201  N    LYS B 508      24.625 -19.671  63.713  1.00 134.03           N
ANISOU10201  N    LYS B 508    16387  22520  12018  -2063   2319   1951        N
ATOM  10202  CA   LYS B 508      25.267 -20.064  62.461  1.00 136.17           C
ANISOU10202  CA   LYS B 508    16554  23104  12079  -1697   2266   1794        C
ATOM  10203  C    LYS B 508      24.436 -21.106  61.722  1.00 136.33           C
```

FIG. 13 Continued

```
ANISOU10203  C    LYS B 508    16656  23051  12091  -1342   1869   1698       C
ATOM  10204  O    LYS B 508    23.872  22.016  62.335  1.00135.23             O
ANISOU10204  O    LYS B 508    16577  22675  12129  -1341   1500   1639       O
ATOM  10205  CB   LYS B 508    26.660 -20.623  62.737  1.00137.48             C
ANISOU10205  CB   LYS B 508    16511  23520  12206  -1669   2162   1573       C
ATOM  10206  CG   LYS B 508    27.591 -19.646  63.397  1.00137.74             C
ANISOU10206  CG   LYS B 508    16430  23687  12220  -2019   2542   1630       C
ATOM  10207  CD   LYS B 508    28.885 -20.314  63.800  1.00139.00             C
ANISOU10207  CD   LYS B 508    16365  24093  12354  -1995   2383   1418       C
ATOM  10208  CE   LYS B 508    29.833 -19.308  64.428  1.00139.52             C
ANISOU10208  CE   LYS B 508    16298  24332  12380  -2366   2772   1460       C
ATOM  10209  NZ   LYS B 508    29.876 -18.042  63.649  1.00140.37             N
ANISOU10209  NZ   LYS B 508    16446  24542  12345  -2441   3256   1600       N
ATOM  10210  N    MET B 509    24.367 -20.983  60.403  1.00135.76             N
ANISOU10210  N    MET B 509    16582  23193  11809  -1047   1948   1679       N
ATOM  10211  CA   MET B 509    23.566 -21.902  59.614  1.00136.23             C
ANISOU10211  CA   MET B 509    16712  23218  11832   -721   1597   1572       C
ATOM  10212  C    MET B 509    24.252 -23.245  59.460  1.00137.55             C
ANISOU10212  C    MET B 509    16774  23485  12004   -468   1204   1255       C
ATOM  10213  O    MET B 509    25.469 -23.323  59.389  1.00138.91             O
ANISOU10213  O    MET B 509    16788  23903  12090   -415   1276   1117       O
ATOM  10214  CB   MET B 509    23.283 -21.303  58.241  1.00137.72             C
ANISOU10214  CB   MET B 509    16919  23643  11768   -488   1819   1658       C
ATOM  10215  CG   MET B 509    22.040 -21.849  57.567  1.00137.74             C
ANISOU10215  CG   MET B 509    17035  23557  11742   -262   1551   1655       C
ATOM  10216  SD   MET B 509    21.476 -20.768  56.246  1.00139.04             S
ANISOU10216  SD   MET B 509    17239  23958  11632    -96   1910   1891       S
ATOM  10217  CE   MET B 509    19.881 -21.503  55.926  1.00138.49             C
ANISOU10217  CE   MET B 509    17300  23712  11608     60   1531   1894       C
ATOM  10218  N    ILE B 510    23.462 -24.306  59.400  1.00146.37             N
ANISOU10218  N    ILE B 510    17977  24409  13226   -309    796   1138       N
ATOM  10219  CA   ILE B 510    24.014 -25.639  59.197  1.00147.88             C
ANISOU10219  CA   ILE B 510    18094  24651  13444    -42    417    830       C
ATOM  10220  C    ILE B 510    23.042 -26.541  58.441  1.00148.59             C
ANISOU10220  C    ILE B 510    18290  24641  13528    222     76    692       C
ATOM  10221  O    ILE B 510    22.126 -27.137  59.022  1.00147.35             O
ANISOU10221  O    ILE B 510    18250  24160  13578    137   -201    712       O
ATOM  10222  CB   ILE B 510    24.440 -26.288  60.519  1.00146.94             C
ANISOU10222  CB   ILE B 510    17936  24322  13571   -220    204    780       C
ATOM  10223  CG1  ILE B 510    25.866 -25.858  60.862  1.00147.73             C
ANISOU10223  CG1  ILE B 510    17849  24685  13597   -312    439    749       C
ATOM  10224  CG2  ILE B 510    24.375 -27.800  60.423  1.00148.06             C
ANISOU10224  CG2  ILE B 510    18092  24334  13830     42   -266    522       C
ATOM  10225  CD1  ILE B 510    26.537 -26.728  61.903  1.00147.76             C
ANISOU10225  CD1  ILE B 510    17761  24597  13784   -365    181    638       C
ATOM  10226  N    THR B 511    23.258  26.638  57.133  1.00144.27             N
ANISOU10226  N    THR B 511    17691  24391  12732    536    102    545       N
ATOM  10227  CA   THR B 511    22.386 -27.442  56.296  1.00145.36             C
ANISOU10227  CA   THR B 511    17913  24495  12822    789   -198    385       C
ATOM  10228  C    THR B 511    23.139 -28.084  55.134  1.00148.36             C
ANISOU10228  C    THR B 511    18187  25199  12985   1170   -296     72       C
ATOM  10229  O    THR B 511    24.015 -27.471  54.510  1.00149.68             O
ANISOU10229  O    THR B 511    18231  25717  12923   1269    -11     72       O
ATOM  10230  CB   THR B 511    21.182 -26.622  55.785  1.00144.60             C
ANISOU10230  CB   THR B 511    17921  24405  12616    736    -34    627       C
ATOM  10231  OG1  THR B 511    20.222 -27.495  55.185  1.00145.48             O
ANISOU10231  OG1  THR B 511    18113  24443  12721    924    376    469       O
ATOM  10232  CG2  THR B 511    21.617 -25.573  54.786  1.00145.91             C
ANISOU10232  CG2  THR B 511    18007  24957  12473    846    361    741       C
ATOM  10233  N    GLY B 512    22.798 -29.345  54.886  1.00148.61             N
ANISOU10233  N    GLY B 512    18267  25096  13101   1372   -698   -202       N
ATOM  10234  CA   GLY B 512    23.374 -30.123  53.812  1.00151.63             C
ANISOU10234  CA   GLY B 512    18572  25735  13306   1744   -843   -543       C
ATOM  10235  C    GLY B 512    22.654 -29.814  52.528  1.00152.96             C
ANISOU10235  C    GLY B 512    18768  26155  13195   1923   -783   -555       C
ATOM  10236  O    GLY B 512    22.029 -30.683  51.937  1.00154.40             O
ANISOU10236  O    GLY B 512    19011  26293  13359   2106  -1080   -786       O
ATOM  10237  N    ASP B 513    22.731 -28.551  52.126  1.00153.81             N
ANISOU10237  N    ASP B 513    18829  26524  13086   1856   -388   -296       N
```

FIG. 13 Continued

```
ATOM  10238  CA  ASP B 513      22.119 -28.041  50.903  1.00155.15           C
ANISOU10238  CA  ASP B 513    19003  26993  12953   2020   -258   -233       C
ATOM  10239  C   ASP B 513      23.128 -27.071  50.279  1.00156.35           C
ANISOU10239  C   ASP B 513    19016  27559  12832   2096    156   -129       C
ATOM  10240  O   ASP B 513      23.580 -26.137  50.932  1.00154.85           O
ANISOU10240  O   ASP B 513    18799  27336  12703   1857    472    125       O
ATOM  10241  CB  ASP B 513      20.817 -27.287  51.224  1.00153.01           C
ANISOU10241  CB  ASP B 513    18856  26534  12746   1793   -160    110       C
ATOM  10242  CG  ASP B 513      19.558 -28.051  50.836  1.00153.50           C
ANISOU10242  CG  ASP B 513    19017  26479  12827   1884   -508    -11       C
ATOM  10243  OD1 ASP B 513      18.504 -27.405  50.680  1.00152.65           O
ANISOU10243  OD1 ASP B 513    18974  26366  12663   1797   -408    246       O
ATOM  10244  OD2 ASP B 513      19.607 -29.283  50.690  1.00154.88           O
ANISOU10244  OD2 ASP B 513    19203  26567  13078   2039   -672   -359       O
ATOM  10245  N   GLN B 514      23.487 -27.302  49.022  1.00157.32           N
ANISOU10245  N   GLN B 514    19048  28073  12652   2418    157   -333       N
ATOM  10246  CA  GLN B 514      24.434 -26.454  48.299  1.00158.90           C
ANISOU10246  CA  GLN B 514    19106  28702  12565   2520    537   -249       C
ATOM  10247  C   GLN B 514      24.480 -25.009  48.823  1.00157.00           C
ANISOU10247  C   GLN B 514    18876  28429  12349   2221    982    179       C
ATOM  10248  O   GLN B 514      23.447 -24.383  49.020  1.00155.44           O
ANISOU10248  O   GLN B 514    18793  28064  12203   2062   1076    461       O
ATOM  10249  CB  GLN B 514      24.036 -26.460  46.825  1.00161.56           C
ANISOU10249  CB  GLN B 514    19409  29433  12541   2827    540   -336       C
ATOM  10250  CG  GLN B 514      23.309 -27.752  46.417  1.00162.81           C
ANISOU10250  CG  GLN B 514    19635  29501  12724   3027     78   -682       C
ATOM  10251  CD  GLN B 514      22.199 -27.525  45.411  1.00163.98           C
ANISOU10251  CD  GLN B 514    19822  29864  12618   3154     57   -606       C
ATOM  10252  OE1 GLN B 514      22.287 -26.661  44.540  1.00165.31           O
ANISOU10252  OE1 GLN B 514    19915  30422  12473   3262    359   -424       O
ATOM  10253  NE2 GLN B 514      21.119 -28.308  45.527  1.00163.67           N
ANISOU10253  NE2 GLN B 514    19893  29583  12710   3141   -300   -739       N
ATOM  10254  N   LEU B 515      25.679 -24.478  49.029  1.00157.99           N
ANISOU10254  N   LEU B 515    18877  28718  12436   2147   1265    221       N
ATOM  10255  CA  LEU B 515      25.846 -23.120  49.556  1.00156.52           C
ANISOU10255  CA  LEU B 515    18696  28488  12286   1841   1707    591       C
ATOM  10256  C   LEU B 515      25.012 -22.050  48.872  1.00156.69           C
ANISOU10256  C   LEU B 515    18788  28621  12127   1838   2005    924       C
ATOM  10257  O   LEU B 515      24.665 -21.047  49.480  1.00154.96           O
ANISOU10257  O   LEU B 515    18646  28206  12025   1559   2292   1251       O
ATOM  10258  CB  LEU B 515      27.321 -22.721  49.522  1.00157.84           C
ANISOU10258  CB  LEU B 515    18685  28937  12349   1823   1983    547       C
ATOM  10259  CG  LEU B 515      27.787 -21.376  48.942  1.00158.96           C
ANISOU10259  CG  LEU B 515    18756  29377  12265   1762   2501    821       C
ATOM  10260  CD1 LEU B 515      27.149 -20.157  49.602  1.00156.85           C
ANISOU10260  CD1 LEU B 515    18614  28844  12137   1415   2832   1223       C
ATOM  10261  CD2 LEU B 515      29.319 -21.292  49.032  1.00160.37           C
ANISOU10261  CD2 LEU B 515    18737  29819  12378   1743   2674    691       C
ATOM  10262  N   ALA B 516      24.692 -22.256  47.608  1.00157.97           N
ANISOU10262  N   ALA B 516    18919  29104  11999   2154   1944    844       N
ATOM  10263  CA  ALA B 516      23.921 -21.268  46.869  1.00158.55           C
ANISOU10263  CA  ALA B 516    19039  29334  11869   2195   2224   1174       C
ATOM  10264  C   ALA B 516      22.546 -20.983  47.473  1.00156.21           C
ANISOU10264  C   ALA B 516    18912  28672  11770   2007   2166   1425       C
ATOM  10265  O   ALA B 516      22.058 -19.861  47.385  1.00155.84           O
ANISOU10265  O   ALA B 516    18920  28617  11677   1904   2509   1800       O
ATOM  10266  CB  ALA B 516      23.786 -21.688  45.408  1.00161.62           C
ANISOU10266  CB  ALA B 516    19350  30163  11894   2584   2111   1008       C
ATOM  10267  N   ILE B 517      21.924 -21.988  48.085  1.00155.20           N
ANISOU10267  N   ILE B 517    18865  28238  11864   1966   1745   1230       N
ATOM  10268  CA  ILE B 517      20.578 -21.812  48.633  1.00153.13           C
ANISOU10268  CA  ILE B 517    18751  27650  11782   1800   1658   1447       C
ATOM  10269  C   ILE B 517      20.527 -21.222  50.035  1.00150.19           C
ANISOU10269  C   ILE B 517    18467  26865  11734   1413   1822   1670       C
ATOM  10270  O   ILE B 517      19.737 -20.325  50.314  1.00148.96           O
ANISOU10270  O   ILE B 517    18404  26556  11639   1253   2051   2010       O
ATOM  10271  CB  ILE B 517      19.765 -23.119  48.625  1.00153.09           C
ANISOU10271  CB  ILE B 517    18803  27498  11868   1912   1138   1163       C
ATOM  10272  CG1 ILE B 517      20.674 -24.311  48.888  1.00153.68           C
```

FIG. 13 Continued

```
ANISOU10272  CG1 ILE B 517     18818  27526  12048   1993    829    748       C
ATOM  10273  CG2 ILE B 517     19.009 -23.276  47.315  1.00155.42             C
ANISOU10273  CG2 ILE B 517     19073  28128  11852   2205   1038   1127       C
ATOM  10274  CD1 ILE B 517     21.076 -24.423  50.307  1.00151.24             C
ANISOU10274  CD1 ILE B 517     18548  26834  12082   1698    796    767       C
ATOM  10275  N   GLY B 518     21.354 -21.733  50.927  1.00150.50             N
ANISOU10275  N   GLY B 518     18473  26732  11977   1268   1703   1479       N
ATOM  10276  CA  GLY B 518     21.354 -21.214  52.271  1.00147.91             C
ANISOU10276  CA  GLY B 518     18215  26048  11937    895   1846   1664       C
ATOM  10277  C   GLY B 518     21.451 -19.712  52.185  1.00147.88             C
ANISOU10277  C   GLY B 518     18224  26113  11852    742   2380   2024       C
ATOM  10278  O   GLY B 518     20.727 -18.995  52.859  1.00146.11             O
ANISOU10278  O   GLY B 518     18112  25615  11787    503   2553   2298       O
ATOM  10279  N   LYS B 519     22.338 -19.240  51.320  1.00148.23             N
ANISOU10279  N   LYS B 519     18152  26523  11644    890   2649   2024       N
ATOM  10280  CA  LYS B 519     22.564 -17.813  51.164  1.00148.67             C
ANISOU10280  CA  LYS B 519     18213  26657  11618    754   3185   2359       C
ATOM  10281  C   LYS B 519     21.347 -17.088  50.599  1.00148.86             C
ANISOU10281  C   LYS B 519     18345  26668  11549    832   3353   2689       C
ATOM  10282  O   LYS B 519     21.426 -15.909  50.271  1.00149.73             O
ANISOU10282  O   LYS B 519     18467  26859  11563    782   3804   2992       O
ATOM  10283  CB  LYS B 519     23.812 -17.537  50.322  1.00151.24             C
ANISOU10283  CB  LYS B 519     18378  27400  11686    904   3424   2279       C
ATOM  10284  CG  LYS B 519     24.384 -16.140  50.506  1.00151.56             C
ANISOU10284  CG  LYS B 519     18410  27454  11723    663   3983   2570       C
ATOM  10285  CD  LYS B 519     25.612 -15.934  49.636  1.00154.29             C
ANISOU10285  CD  LYS B 519     18583  28235  11804    818   4200   2483       C
ATOM  10286  CE  LYS B 519     26.015 -14.466  49.559  1.00155.19             C
ANISOU10286  CE  LYS B 519     18701  28389  11875    617   4791   2816       C
ATOM  10287  NZ  LYS B 519     27.040 -14.218  48.492  1.00158.23             N
ANISOU10287  NZ  LYS B 519     18921  29244  11957    812   5018   2779       N
ATOM  10288  N   GLU B 520     20.234 -17.800  50.448  1.00149.94             N
ANISOU10288  N   GLU B 520     18549  26717  11706    966   2994   2633       N
ATOM  10289  CA  GLU B 520     18.979 -17.153  50.067  1.00149.94             C
ANISOU10289  CA  GLU B 520     18644  26682  11646   1021   3122   2959       C
ATOM  10290  C   GLU B 520     18.020 -17.223  51.244  1.00147.14             C
ANISOU10290  C   GLU B 520     18425  25873  11609    759   2986   3060       C
ATOM  10291  O   GLU B 520     17.426 -16.219  51.643  1.00146.22             O
ANISOU10291  O   GLU B 520     18404  25559  11593    590   3297   3401       O
ATOM  10292  CB  GLU B 520     18.338 -17.775  48.834  1.00151.97             C
ANISOU10292  CB  GLU B 520     18854  27261  11626   1377   2859   2858       C
ATOM  10293  CG  GLU B 520     16.941 -17.228  48.553  1.00151.88             C
ANISOU10293  CG  GLU B 520     18927  27209  11571   1438   2930   3188       C
ATOM  10294  CD  GLU B 520     16.906 -15.713  48.420  1.00152.38             C
ANISOU10294  CD  GLU B 520     19029  27282  11585   1363   3493   3639       C
ATOM  10295  OE1 GLU B 520     15.792 -15.151  48.383  1.00152.11             O
ANISOU10295  OE1 GLU B 520     19073  27154  11567   1371   3601   3951       O
ATOM  10296  OE2 GLU B 520     17.981 -15.081  48.351  1.00153.20             O
ANISOU10296  OE2 GLU B 520     19085  27484  11640   1297   3836   3685       O
ATOM  10297  N   THR B 521     17.862 -18.418  51.806  1.00145.83             N
ANISOU10297  N   THR B 521     18269  25534  11606    731   2526   2767       N
ATOM  10298  CA  THR B 521     17.066 -18.569  53.016  1.00143.18             C
ANISOU10298  CA  THR B 521     18050  24770  11582    463   2379   2839       C
ATOM  10299  C   THR B 521     18.033 -18.099  54.114  1.00141.80             C
ANISOU10299  C   THR B 521     17872  24400  11605    141   2614   2851       C
ATOM  10300  O   THR B 521     17.934 -18.470  55.276  1.00139.76             O
ANISOU10300  O   THR B 521     17664  23830  11610   -102   2449   2788       O
ATOM  10301  CB  THR B 521     16.523 -20.029  53.177  1.00142.70             C
ANISOU10301  CB  THR B 521     18001  24598  11621    550   1807   2535       C
ATOM  10302  OG1 THR B 521     15.145 -20.019  53.583  1.00141.30             O
ANISOU10302  OG1 THR B 521     17930  24178  11580    456   1684   2711       O
ATOM  10303  CG2 THR B 521     17.360 -20.845  54.136  1.00141.59             C
ANISOU10303  CG2 THR B 521     17835  24264  11697    396   1579   2263       C
ATOM  10304  N   GLY B 522     18.998 -17.283  53.690  1.00150.62             N
ANISOU10304  N   GLY B 522     18918  25737  12575    146   3002   2930       N
ATOM  10305  CA  GLY B 522     19.981  16.658  54.554  1.00149.90             C
ANISOU10305  CA  GLY B 522     18801  25535  12617   -158   3298   2958       C
ATOM  10306  C   GLY B 522     19.681 -15.171  54.625  1.00149.90             C
ANISOU10306  C   GLY B 522     18887  25436  12632   -330   3828   3341       C
```

FIG. 13 Continued

```
ATOM  10307  O    GLY B 522      19.333 -14.676  55.686  1.00148.08           O
ANISOU10307  O    GLY B 522    18753  24874  12635   -637   3966   3480       O
ATOM  10308  N    ARG B 523      19.802 -14.460  53.503  1.00143.24           N
ANISOU10308  N    ARG B 523    18011  24873  11541   -128   4134   3516       N
ATOM  10309  CA   ARG B 523      19.478 -13.027  53.446  1.00143.70           C
ANISOU10309  CA   ARG B 523    18158  24832  11608   -250   4662   3908       C
ATOM  10310  C    ARG B 523      17.983 -12.779  53.688  1.00142.46           C
ANISOU10310  C    ARG B 523    18145  24417  11568   -255   4629   4162       C
ATOM  10311  O    ARG B 523      17.512 -11.642  53.669  1.00142.83           O
ANISOU10311  O    ARG B 523    18284  24339  11646   -327   5040   4508       O
ATOM  10312  CB   ARG B 523      19.932 -12.389  52.117  1.00146.65           C
ANISOU10312  CB   ARG B 523    18456  25589  11675      2   4979   4055       C
ATOM  10313  CG   ARG B 523      19.987 -13.355  50.903  1.00148.45           C
ANISOU10313  CG   ARG B 523    18566  26229  11609    410   4632   3841       C
ATOM  10314  CD   ARG B 523      19.890 -12.682  49.506  1.00151.35           C
ANISOU10314  CD   ARG B 523    18888  26966  11651    708   4917   4084       C
ATOM  10315  NE   ARG B 523      21.096 -11.952  49.104  1.00153.28           N
ANISOU10315  NE   ARG B 523    19045  27430  11765    671   5324   4140       N
ATOM  10316  CZ   ARG B 523      21.400 -11.629  47.845  1.00156.15           C
ANISOU10316  CZ   ARG B 523    19318  28203  11808    947   5511   4246       C
ATOM  10317  NH1  ARG B 523      20.598 -11.985  46.849  1.00157.47           N
ANISOU10317  NH1  ARG B 523    19465  28627  11738   1289   5317   4296       N
ATOM  10318  NH2  ARG B 523      22.515 -10.958  47.574  1.00157.86           N
ANISOU10318  NH2  ARG B 523    19454  28595  11931    876   5891   4299       N
ATOM  10319  N    ARG B 524      17.239 -13.857  53.894  1.00143.45           N
ANISOU10319  N    ARG B 524    18283  24463  11757   -171   4142   3990       N
ATOM  10320  CA   ARG B 524      15.828 -13.764  54.221  1.00142.18           C
ANISOU10320  CA   ARG B 524    18238  24064  11719   -193   4055   4194       C
ATOM  10321  C    ARG B 524      15.668 -13.823  55.766  1.00139.45           C
ANISOU10321  C    ARG B 524    17979  23294  11711   -572   3998   4158       C
ATOM  10322  O    ARG B 524      14.571 -13.654  56.321  1.00138.07           O
ANISOU10322  O    ARG B 524    17908  22860  11693    672   3969   4331       O
ATOM  10323  CB   ARG B 524      15.071 -14.898  53.525  1.00142.65           C
ANISOU10323  CB   ARG B 524    18255  24300  11645    101   3564   4027       C
ATOM  10324  CG   ARG B 524      13.598 -14.618  53.262  1.00142.61           C
ANISOU10324  CG   ARG B 524    18322  24241  11623    208   3548   4302       C
ATOM  10325  CD   ARG B 524      12.925 -15.804  52.580  1.00143.31           C
ANISOU10325  CD   ARG B 524    18352  24527  11572    469   3043   4088       C
ATOM  10326  NE   ARG B 524      13.129 -15.793  51.133  1.00146.15           N
ANISOU10326  NE   ARG B 524    18610  25346  11576    818   3079   4080       N
ATOM  10327  CZ   ARG B 524      13.123 -16.872  50.352  1.00147.51           C
ANISOU10327  CZ   ARG B 524    18693  25791  11562   1062   2680   3778       C
ATOM  10328  NH1  ARG B 524      12.935 -18.079  50.869  1.00146.32           N
ANISOU10328  NH1  ARG B 524    18552  25476  11567   1000   2213   3458       N
ATOM  10329  NH2  ARG B 524      13.323 -16.742  49.047  1.00150.24           N
ANISOU10329  NH2  ARG B 524    18943  26577  11567   1368   2759   3793       N
ATOM  10330  N    LEU B 525      16.786 -14.040  56.457  1.00141.08           N
ANISOU10330  N    LEU B 525    18132  23455  12016   -782   3992   3939       N
ATOM  10331  CA   LEU B 525      16.798 -14.154  57.911  1.00138.77           C
ANISOU10331  CA   LEU B 525    17895  22821  12010  -1140   3926   3876       C
ATOM  10332  C    LEU B 525      17.880 -13.282  58.539  1.00138.87           C
ANISOU10332  C    LEU B 525    17889  22779  12097  -1445   4336   3895       C
ATOM  10333  O    LEU B 525      18.525 -13.684  59.497  1.00137.76           O
ANISOU10333  O    LEU B 525    17704  22540  12096  -1680   4209   3700       O
ATOM  10334  CB   LEU B 525      16.998 -15.610  58.326  1.00137.79           C
ANISOU10334  CB   LEU B 525    17708  22685  11962  -1110   3378   3535       C
ATOM  10335  CG   LEU B 525      15.726 -16.385  58.657  1.00136.38           C
ANISOU10335  CG   LEU B 525    17605  22303  11910  -1074   2985   3533       C
ATOM  10336  CD1  LEU B 525      14.585 -15.988  57.755  1.00137.26           C
ANISOU10336  CD1  LEU B 525    17769  22495  11886   -848   3058   3772       C
ATOM  10337  CD2  LEU B 525      15.981 -17.868  58.579  1.00136.44           C
ANISOU10337  CD2  LEU B 525    17540  22383  11919   -925   2456   3191       C
ATOM  10338  N    GLY B 526      18.084 -12.095  57.979  1.00137.65           N
ANISOU10338  N    GLY B 526    17759  22702  11840  -1439   4829   4134       N
ATOM  10339  CA   GLY B 526      19.021 -11.125  58.518  1.00138.08           C
ANISOU10339  CA   GLY B 526    17808  22689  11967  -1750   5276   4178       C
ATOM  10340  C    GLY B 526      20.501 -11.467  58.576  1.00138.89           C
ANISOU10340  C    GLY B 526    17752  23024  11996  -1826   5247   3903       C
ATOM  10341  O    GLY B 526      21.341 -10.571  58.494  1.00140.26           O
```

FIG. 13 Continued

```
ANISOU10341  O   GLY B 526    17891  23273  12128  -1980   5670   3967         O
ATOM  10342  N   MET B 527    20.824 -12.750  58.709  1.00136.83               N
ANISOU10342  N   MET B 527    17391  22875  11723  -1717   4760   3603         N
ATOM  10343  CA  MET B 527    22.210 -13.206  58.859  1.00137.56               C
ANISOU10343  CA  MET B 527    17317  23190  11760  -1773   4681   3328         C
ATOM  10344  C   MET B 527    23.202 -12.537  57.915  1.00140.10               C
ANISOU10344  C   MET B 527    17535  23835  11862  -1680   5042   3361         C
ATOM  10345  O   MET B 527    23.685 -13.162  56.974  1.00141.60               O
ANISOU10345  O   MET B 527    17608  24348  11844  -1371   4861   3208         O
ATOM  10346  CB  MET B 527    22.278 -14.725  58.703  1.00137.24               C
ANISOU10346  CB  MET B 527    17191  23269  11685  -1524   4106   3035         C
ATOM  10347  CG  MET B 527    21.779 -15.477  59.931  1.00134.89               C
ANISOU10347  CG  MET B 527    16947  22673  11634  -1710   3752   2937         C
ATOM  10348  SD  MET B 527    21.063 -17.104  59.592  1.00134.41               S
ANISOU10348  SD  MET B 527    16890  22602  11579  -1379   3103   2728         S
ATOM  10349  CE  MET B 527    21.030 -17.829  61.228  1.00132.13               C
ANISOU10349  CE  MET B 527    16615  22006  11583  -1683   2795   2608         C
ATOM  10350  N   GLY B 528    23.537 -11.282  58.215  1.00141.48               N
ANISOU10350  N   GLY B 528    17750  23916  12089  -1964   5555   3546         N
ATOM  10351  CA  GLY B 528    24.413 -10.460  57.389  1.00144.01               C
ANISOU10351  CA  GLY B 528    17992  24499  12227  -1930   5974   3630         C
ATOM  10352  C   GLY B 528    25.923 -10.460  57.627  1.00145.18               C
ANISOU10352  C   GLY B 528    17956  24885  12322  -2107   6080   3413         C
ATOM  10353  O   GLY B 528    26.515  -9.412  57.938  1.00146.14               O
ANISOU10353  O   GLY B 528    18075  24965  12488  -2412   6538   3511         O
ATOM  10354  N   THR B 529    26.547 -11.628  57.459  1.00221.52               N
ANISOU10354  N   THR B 529    27467  34806  21895  -1912   5667   3119         N
ATOM  10355  CA  THR B 529    28.005 -11.785  57.570  1.00222.89               C
ANISOU10355  CA  THR B 529    27430  35271  21985  -2009   5711   2897         C
ATOM  10356  C   THR B 529    28.557 -12.576  56.355  1.00224.79               C
ANISOU10356  C   THR B 529    27520  35928  21962  -1580   5490   2727         C
ATOM  10357  O   THR B 529    29.702 -12.384  55.938  1.00226.83               O
ANISOU10357  O   THR B 529    27608  36509  22067  -1572   5672   2637         O
ATOM  10358  CB  THR B 529    28.423 -12.442  58.917  1.00221.22               C
ANISOU10358  CB  THR B 529    27146  34945  21962  -2273   5435   2671         C
ATOM  10359  OG1 THR B 529    28.168 -11.534  59.995  1.00220.07               O
ANISOU10359  OG1 THR B 529    27108  34490  22020  -2713   5732   2809         O
ATOM  10360  CG2 THR B 529    29.896 -12.780  58.920  1.00222.84               C
ANISOU10360  CG2 THR B 529    27106  35509  22053  -2297   5411   2431         C
ATOM  10361  N   ASN B 530    27.713 -13.440  55.790  1.00148.29               N
ANISOU10361  N   ASN B 530    17893  26232  12220  -1233   5110   2681         N
ATOM  10362  CA  ASN B 530    28.013 -14.250  54.612  1.00150.08               C
ANISOU10362  CA  ASN B 530    18007  26818  12199   -803   4869   2510         C
ATOM  10363  C   ASN B 530    27.898 -13.419  53.367  1.00152.24               C
ANISOU10363  C   ASN B 530    18294  27315  12234   -614   5223   2736         C
ATOM  10364  O   ASN B 530    27.186 -13.794  52.443  1.00152.85               O
ANISOU10364  O   ASN B 530    18416  27500  12161   -279   5052   2766         O
ATOM  10365  CB  ASN B 530    26.956 -15.327  54.510  1.00148.77               C
ANISOU10365  CB  ASN B 530    17935  26508  12082   -553   4379   2411         C
ATOM  10366  CG  ASN B 530    25.559 -14.761  54.685  1.00147.25               C
ANISOU10366  CG  ASN B 530    17950  25992  12005   -633   4470   2698         C
ATOM  10367  OD1 ASN B 530    25.205 -13.761  54.053  1.00148.27               O
ANISOU10367  OD1 ASN B 530    18145  26162  12029   -605   4842   2976         O
ATOM  10368  ND2 ASN B 530    24.769 -15.374  55.569  1.00144.93               N
ANISOU10368  ND2 ASN B 530    17757  25376  11935   -734   4146   2649         N
ATOM  10369  N   MET B 531    28.568 -12.277  53.348  1.00190.18               N
ANISOU10369  N   MET B 531    23063  32190  17006   -839   5722   2904         N
ATOM  10370  CA  MET B 531    28.447 -11.365  52.220  1.00192.39               C
ANISOU10370  CA  MET B 531    23368  32655  17077   -687   6113   3174         C
ATOM  10371  C   MET B 531    29.546 -11.514  51.159  1.00195.29               C
ANISOU10371  C   MET B 531    23533  33521  17148   -449   6191   3048         C
ATOM  10372  O   MET B 531    29.265 -11.821  49.996  1.00196.83               O
ANISOU10372  O   MET B 531    23702  33985  17098    -71   6092   3063         O
ATOM  10373  CB  MET B 531    28.346  -9.923  52.729  1.00192.39               C
ANISOU10373  CB  MET B 531    23485  32389  17225  -1058   6661   3487         C
ATOM  10374  CG  MET B 531    27.384  -9.776  53.904  1.00189.59               C
ANISOU10374  CG  MET B 531    23313  31550  17173  -1327   6598   3576         C
ATOM  10375  SD  MET B 531    26.388  -8.276  53.842  1.00189.87               S
ANISOU10375  SD  MET B 531    23574  31257  17309  -1468   7134   4046         S
```

FIG. 13 Continued

```
ATOM   10376  CE   MET B 531      27.579  -7.095  53.194  1.00193.20           C
ANISOU10376  CE   MET B 531    23899  31927  17580  -1589   7746   4192        C
ATOM   10377  N    TYR B 532      30.790 -11.288  51.562  1.00285.47           N
ANISOU10377  N    TYR B 532    34800  45085  28581   -678   6372   2923        N
ATOM   10378  CA   TYR B 532      31.926 -11.409  50.654  1.00288.29           C
ANISOU10378  CA   TYR B 532    34944  45926  28668   -486   6464   2796        C
ATOM   10379  C    TYR B 532      32.504 -12.826  50.746  1.00288.11           C
ANISOU10379  C    TYR B 532    34761  46104  28603   -273   5960   2393        C
ATOM   10380  O    TYR B 532      32.357 -13.481  51.778  1.00285.93           O
ANISOU10380  O    TYR B 532    34511  45580  28548   -410   5649   2229        O
ATOM   10381  CB   TYR B 532      32.969 -10.341  50.994  1.00289.71           C
ANISOU10381  CB   TYR B 532    35029  46172  28873   -855   6963   2892        C
ATOM   10382  CG   TYR B 532      32.353  -8.982  51.259  1.00289.48           C
ANISOU10382  CG   TYR B 532    35193  45811  28986  -1145   7445   3263        C
ATOM   10383  CD1  TYR B 532      32.257  -8.031  50.250  1.00291.84           C
ANISOU10383  CD1  TYR B 532    35532  46240  29115  -1041   7871   3568        C
ATOM   10384  CD2  TYR B 532      31.851  -8.657  52.517  1.00287.09           C
ANISOU10384  CD2  TYR B 532    35034  45060  28987  -1512   7478   3314        C
ATOM   10385  CE1  TYR B 532      31.689  -6.793  50.488  1.00291.89           C
ANISOU10385  CE1  TYR B 532    35722  45914  29268  -1287   8326   3918        C
ATOM   10386  CE2  TYR B 532      31.281  -7.423  52.762  1.00287.08           C
ANISOU10386  CE2  TYR B 532    35215  44734  29126  -1766   7929   3639        C
ATOM   10387  CZ   TYR B 532      31.203  -6.496  51.745  1.00289.51           C
ANISOU10387  CZ   TYR B 532    35566  45154  29278  -1648   8355   3942        C
ATOM   10388  OH   TYR B 532      30.636  -5.266  51.988  1.00289.73           O
ANISOU10388  OH   TYR B 532    35786  44836  29464  -1884   8820   4277        O
ATOM   10389  N    PRO B 533      33.157 -13.309  49.671  1.00203.50           N
ANISOU10389  N    PRO B 533    23879  35835  17606     70   5884   2237        N
ATOM   10390  CA   PRO B 533      33.685 -14.680  49.690  1.00203.65           C
ANISOU10390  CA   PRO B 533    23754  36034  17588    312   5414   1850        C
ATOM   10391  C    PRO B 533      34.341 -15.063  51.020  1.00202.16           C
ANISOU10391  C    PRO B 533    23482  35690  17639     20   5266   1665        C
ATOM   10392  O    PRO B 533      33.981 -16.095  51.583  1.00200.51           O
ANISOU10392  O    PRO B 533    23312  35292  17580    101   4826   1471        O
ATOM   10393  CB   PRO B 533      34.726 -14.667  48.563  1.00207.00           C
ANISOU10393  CB   PRO B 533    23966  36993  17691    561   5571   1756        C
ATOM   10394  CG   PRO B 533      34.196 -13.672  47.589  1.00208.40           C
ANISOU10394  CG   PRO B 533    24235  37264  17684    639   5943   2086        C
ATOM   10395  CD   PRO B 533      33.471 -12.616  48.405  1.00206.44           C
ANISOU10395  CD   PRO B 533    24185  36572  17682    253   6238   2410        C
ATOM   10396  N    SER B 534      35.259 -14.232  51.514  1.00236.47           N
ANISOU10396  N    SER B 534    27715  40117  22017   -321   5633   1734        N
ATOM   10397  CA   SER B 534      36.010 -14.507  52.749  1.00235.53           C
ANISOU10397  CA   SER B 534    27476  39930  22083   -616   5532   1565        C
ATOM   10398  C    SER B 534      35.152 -14.603  54.016  1.00232.36           C
ANISOU10398  C    SER B 534    27252  39043  21990   -890   5357   1617        C
ATOM   10399  O    SER B 534      35.380 -15.470  54.867  1.00231.21           O
ANISOU10399  O    SER B 534    27042  38820  21986   -925   5011   1413        O
ATOM   10400  CB   SER B 534      37.110 -13.453  52.951  1.00237.25           C
ANISOU10400  CB   SER B 534    27538  40354  22253   -962   6012   1647        C
ATOM   10401  OG   SER B 534      38.045 -13.459  51.884  1.00240.30           O
ANISOU10401  OG   SER B 534    27722  41225  22356   -724   6150   1571        O
ATOM   10402  N    SER B 535      34.185 -13.697  54.139  1.00157.96           N
ANISOU10402  N    SER B 535    18045  29303  12668  -1076   5611   1902        N
ATOM   10403  CA   SER B 535      33.279 -13.663  55.287  1.00155.06           C
ANISOU10403  CA   SER B 535    17860  28473  12582  -1340   5494   1983        C
ATOM   10404  C    SER B 535      32.637 -15.016  55.593  1.00153.28           C
ANISOU10404  C    SER B 535    17689  28088  12463  -1108   4919   1795        C
ATOM   10405  O    SER B 535      33.321 -16.003  55.885  1.00153.55           O
ANISOU10405  O    SER B 535    17570  28268  12504   -999   4595   1531        O
ATOM   10406  CB   SER B 535      32.168 -12.618  55.078  1.00154.35           C
ANISOU10406  CB   SER B 535    18006  28092  12547  -1443   5815   2322        C
ATOM   10407  OG   SER B 535      32.458 -11.364  55.677  1.00154.56           O
ANISOU10407  OG   SER B 535    18066  27982  12679  -1878   6300   2500        O
ATOM   10408  N    ALA B 536      31.310 -15.043  55.501  1.00150.94           N
ANISOU10408  N    ALA B 536    17609  27492  12250  -1026   4805   1943        N
ATOM   10409  CA   ALA B 536      30.534 -16.195  55.934  1.00149.06           C
ANISOU10409  CA   ALA B 536    17457  27022  12158   -883   4296   1806        C
ATOM   10410  C    ALA B 536      29.779  17.012  54.898  1.00149.54           C
```

FIG. 13 Continued

```
ANISOU10410  C   ALA B 536    17582  27144  12091   -446   3979   1733         C
ATOM  10411  O   ALA B 536    29.631 -16.631  53.743  1.00151.19              O
ANISOU10411  O   ALA B 536    17797  27569  12080   -220   4152   1829         O
ATOM  10412  CB  ALA B 536    29.579 -15.765  57.018  1.00146.46              C
ANISOU10412  CB  ALA B 536    17312  26249  12086  -1210   4334   1987         C
ATOM  10413  N   LEU B 537    29.260 -18.129  55.391  1.00148.34              N
ANISOU10413  N   LEU B 537    17484  26786  12093   -353   3513   1568         N
ATOM  10414  CA  LEU B 537    28.512 -19.114  54.620  1.00148.66              C
ANISOU10414  CA  LEU B 537    17589  26834  12063     23   3132   1437         C
ATOM  10415  C   LEU B 537    29.382 -19.800  53.564  1.00151.37              C
ANISOU10415  C   LEU B 537    17763  27587  12162    396   3009   1177         C
ATOM  10416  O   LEU B 537    28.964 -19.992  52.430  1.00152.76              O
ANISOU10416  O   LEU B 537    17963  27941  12138    706   2951   1149         O
ATOM  10417  CB  LEU B 537    27.196 -18.543  54.052  1.00148.11              C
ANISOU10417  CB  LEU B 537    17699  26630  11946     80   3242   1691         C
ATOM  10418  CG  LEU B 537    26.051 -18.308  55.063  1.00145.34              C
ANISOU10418  CG  LEU B 537    17533  25830  11860   -190   3193   1882         C
ATOM  10419  CD1 LEU B 537    24.707 -18.106  54.390  1.00145.11              C
ANISOU10419  CD1 LEU B 537    17654  25713  11767    -34   3174   2069         C
ATOM  10420  CD2 LEU B 537    25.928 -19.436  56.058  1.00143.73              C
ANISOU10420  CD2 LEU B 537    17342  25378  11889   -253   2750   1678         C
ATOM  10421  N   LEU B 538    30.599 -20.168  53.949  1.00156.65              N
ANISOU10421  N   LEU B 538    18251  28428  12840    367   2972    984         N
ATOM  10422  CA  LEU B 538    31.481 -20.878  53.045  1.00159.28              C
ANISOU10422  CA  LEU B 538    18413  29145  12962    723   2846    718         C
ATOM  10423  C   LEU B 538    30.936 -22.288  52.874  1.00159.26              C
ANISOU10423  C   LEU B 538    18473  29011  13028   1026   2330    461         C
ATOM  10424  O   LEU B 538    30.486 -22.894  53.837  1.00157.39              O
ANISOU10424  O   LEU B 538    18321  28432  13048    905   2048    422         O
ATOM  10425  CB  LEU B 538    32.894 -20.969  53.628  1.00160.20              C
ANISOU10425  CB  LEU B 538    18311  29461  13097    608   2913    580         C
ATOM  10426  CG  LEU B 538    33.357 -20.181  54.859  1.00156.84              C
ANISOU10426  CG  LEU B 538    18094  29165  13091    145   3164    731         C
ATOM  10427  CD1 LEU B 538    34.729 -20.678  55.280  1.00160.23              C
ANISOU10427  CD1 LEU B 538    18023  29602  13257    151   3090    517         C
ATOM  10428  CD2 LEU B 538    33.385 -18.687  54.626  1.00159.09              C
ANISOU10428  CD2 LEU B 538    18154  29267  13028   -113   3696   1012         C
ATOM  10429  N   GLY B 539    30.957 -22.821  51.661  1.00158.86              N
ANISOU10429  N   GLY B 539    18383  29225  12751   1412   2209    281         N
ATOM  10430  CA  GLY B 539    30.548 -24.201  51.490  1.00159.26              C
ANISOU10430  CA  GLY B 539    18484  29154  12873   1694   1729     -6         C
ATOM  10431  C   GLY B 539    31.409 -24.991  52.455  1.00159.10              C
ANISOU10431  C   GLY B 539    18356  29041  13054   1647   1514   -195         C
ATOM  10432  O   GLY B 539    32.458 -24.510  52.862  1.00159.51              O
ANISOU10432  O   GLY B 539    18249  29274  13084   1495   1745   -156         O
ATOM  10433  N   THR B 540    30.993 -26.192  52.832  1.00159.06              N
ANISOU10433  N   THR B 540    18428  28765  13243   1771   1082   -392         N
ATOM  10434  CA  THR B 540    31.769 -26.984  53.795  1.00159.04              C
ANISOU10434  CA  THR B 540    18326  28657  13445   1743    867   -543         C
ATOM  10435  C   THR B 540    33.204 -27.302  53.399  1.00161.77              C
ANISOU10435  C   THR B 540    18431  29397  13636   1969    920   -759         C
ATOM  10436  O   THR B 540    34.096 -27.382  54.244  1.00161.75              O
ANISOU10436  O   THR B 540    18285  29433  13738   1843    935   -768         O
ATOM  10437  CB  THR B 540    31.128 -28.353  54.051  1.00158.90              C
ANISOU10437  CB  THR B 540    18429  28302  13642   1918    383   -751         C
ATOM  10438  OG1 THR B 540    30.308 -28.291  55.225  1.00156.03              O
ANISOU10438  OG1 THR B 540    18211  27514  13558   1599    277   -558         O
ATOM  10439  CG2 THR B 540    32.228 -29.411  54.252  1.00160.92              C
ANISOU10439  CG2 THR B 540    18527  28653  13962   2152    163  -1028         C
ATOM  10440  N   HIS B 541    33.407 -27.504  52.109  1.00171.47              N
ANISOU10440  N   HIS B 541    19607  30938  14607   2310    940   -935         N
ATOM  10441  CA  HIS B 541    34.677 -27.985  51.591  1.00174.43              C
ANISOU10441  CA  HIS B 541    19760  31691  14824   2597    942  -1185         C
ATOM  10442  C   HIS B 541    35.888 -27.065  51.697  1.00175.26              C
ANISOU10442  C   HIS B 541    19639  32169  14781   2441   1329  -1070         C
ATOM  10443  O   HIS B 541    37.026 -27.522  51.566  1.00177.49              O
ANISOU10443  O   HIS B 541    19712  32737  14988   2634   1307  -1265         O
ATOM  10444  CB  HIS B 541    34.480 -28.446  50.154  1.00176.97              C
ANISOU10444  CB  HIS B 541    20095  32250  14894   3001    860  -1414         C
```

FIG. 13 Continued

```
ATOM  10445  CG  HIS B 541       33.676 -29.700  50.044  1.00 177.23           C
ANISOU10445  CG  HIS B 541     20285  31975  15078   3226    419  -1658        C
ATOM  10446  ND1 HIS B 541       32.911 -30.179  51.087  1.00 174.90           N
ANISOU10446  ND1 HIS B 541     20150  31191  15112   3039    155  -1595        N
ATOM  10447  CD2 HIS B 541       33.509 -30.571  49.019  1.00 179.71           C
ANISOU10447  CD2 HIS B 541     20623  32396  15261   3607    203  -1970        C
ATOM  10448  CE1 HIS B 541       32.313 -31.295  50.710  1.00 175.95           C
ANISOU10448  CE1 HIS B 541     20400  31131  15322   3290   -203  -1853        C
ATOM  10449  NE2 HIS B 541       32.659 -31.555  49.460  1.00 178.89           N
ANISOU10449  NE2 HIS B 541     20696  31854  15420   3633   -182  -2096        N
ATOM  10450  N   LYS B 542       35.661 -25.776  51.912  1.00 251.68           N
ANISOU10450  N   LYS B 542     29354  41854  24420   2097   1691   -761        N
ATOM  10451  CA  LYS B 542       36.785 -24.866  52.083  1.00 252.52           C
ANISOU10451  CA  LYS B 542     29252  42287  24408   1896   2071   -650        C
ATOM  10452  C   LYS B 542       37.355 -25.070  53.490  1.00 251.34           C
ANISOU10452  C   LYS B 542     29008  41990  24500   1637   1981   -638        C
ATOM  10453  O   LYS B 542       37.939 -24.160  54.076  1.00 250.91           O
ANISOU10453  O   LYS B 542     28844  42048  24443   1300   2288   -474        O
ATOM  10454  CB  LYS B 542       36.358 -23.413  51.870  1.00 251.52           C
ANISOU10454  CB  LYS B 542     29206  42182  24178   1604   2507   -325        C
ATOM  10455  CG  LYS B 542       35.606 -23.152  50.567  1.00 252.45           C
ANISOU10455  CG  LYS B 542     29438  42414  24069   1837   2590   -275        C
ATOM  10456  CD  LYS B 542       36.532 -22.805  49.402  1.00 255.62           C
ANISOU10456  CD  LYS B 542     29647  43346  24131   2058   2854   -340        C
ATOM  10457  CE  LYS B 542       35.722 -22.377  48.175  1.00 256.49           C
ANISOU10457  CE  LYS B 542     29871  43580  24002   2243   2981   -227        C
ATOM  10458  NZ  LYS B 542       36.556 -22.118  46.967  1.00 259.77           N
ANISOU10458  NZ  LYS B 542     30104  44530  24067   2491   3214   -294        N
ATOM  10459  N   ASP B 543       37.179 -26.280  54.021  1.00 165.68           N
ANISOU10459  N   ASP B 543     18200  30895  13855   1794   1561   -815        N
ATOM  10460  CA  ASP B 543       37.629 -26.631  55.367  1.00 164.69           C
ANISOU10460  CA  ASP B 543     17992  30620  13964   1591   1418   -801        C
ATOM  10461  C   ASP B 543       38.005 -28.117  55.395  1.00 166.37           C
ANISOU10461  C   ASP B 543     18141  30795  14278   1969   1003  -1087        C
ATOM  10462  O   ASP B 543       37.607 -28.876  56.288  1.00 165.16           O
ANISOU10462  O   ASP B 543     18075  30293  14386   1933    694  -1099        O
ATOM  10463  CB  ASP B 543       36.537 -26.288  56.380  1.00 161.37           C
ANISOU10463  CB  ASP B 543     17786  29741  13786   1227   1372   -574        C
ATOM  10464  CG  ASP B 543       36.031 -24.855  56.222  1.00 159.95           C
ANISOU10464  CG  ASP B 543     17704  29556  13515    905   1783   -299        C
ATOM  10465  OD1 ASP B 543       36.829 -23.911  56.411  1.00 160.46           O
ANISOU10465  OD1 ASP B 543     17617  29871  13478    659   2141   -192        O
ATOM  10466  OD2 ASP B 543       34.841 -24.671  55.896  1.00 158.53           O
ANISOU10466  OD2 ASP B 543     17748  29123  13365    900   1757   -189        O
ATOM  10467  N   ALA B 544       38.769 -28.501  54.370  1.00 215.90           N
ANISOU10467  N   ALA B 544     24263  37433  20337   2339   1018  -1311        N
ATOM  10468  CA  ALA B 544       39.269 -29.860  54.163  1.00 218.25           C
ANISOU10468  CA  ALA B 544     24480  37760  20687   2760    683  -1613        C
ATOM  10469  C   ALA B 544       40.311 -29.931  53.021  1.00 221.73           C
ANISOU10469  C   ALA B 544     24702  38715  20830   3104    829  -1823        C
ATOM  10470  O   ALA B 544       41.130 -30.854  52.983  1.00 224.12           O
ANISOU10470  O   ALA B 544     24849  39156  21150   3415    649  -2052        O
ATOM  10471  CB  ALA B 544       38.112 -30.827  53.902  1.00 217.74           C
ANISOU10471  CB  ALA B 544     24672  37282  20776   2972    318  -1748        C
ATOM  10472  N   ASN B 545       40.290 -28.954  52.108  1.00 174.82           N
ANISOU10472  N   ASN B 545     18745  33061  14619   3055   1164  -1733        N
ATOM  10473  CA  ASN B 545       41.222 -28.947  50.968  1.00 178.17           C
ANISOU10473  CA  ASN B 545     18964  33996  14734   3369   1328  -1913        C
ATOM  10474  C   ASN B 545       41.553 -27.608  50.240  1.00 178.77           C
ANISOU10474  C   ASN B 545     18943  34468  14511   3207   1799  -1731        C
ATOM  10475  O   ASN B 545       42.710 -27.389  49.874  1.00 181.18           O
ANISOU10475  O   ASN B 545     18991  35229  14622   3296   2002  -1799        O
ATOM  10476  CB  ASN B 545       40.835 -30.042  49.944  1.00 180.21           C
ANISOU10476  CB  ASN B 545     19320  34226  14925   3849   1041  -2229        C
ATOM  10477  CG  ASN B 545       39.433 -29.852  49.356  1.00 178.73           C
ANISOU10477  CG  ASN B 545     19410  33790  14709   3827    990  -2164        C
ATOM  10478  OD1 ASN B 545       38.989 -28.729  49.122  1.00 177.39           O
ANISOU10478  OD1 ASN B 545     19302  33683  14414   3580   1283  -1907        O
ATOM  10479  ND2 ASN B 545       38.741 -30.963  49.101  1.00 179.22           N
```

FIG. 13 Continued

```
ANISOU10479 ND2 ASN B 545    19634  33576  14887   4093    622  -2400       N
ATOM  10480 N   LEU B 546    40.574 -26.718  50.052  1.00177.08              N
ANISOU10480 N   LEU B 546    18926  34088  14268   2970   1981  -1490       N
ATOM  10481 CA  LEU B 546    40.777 -25.497  49.237  1.00177.96              C
ANISOU10481 CA  LEU B 546    18975  34543  14097   2861   2425  -1306       C
ATOM  10482 C   LEU B 546    41.447 -24.227  49.824  1.00177.39              C
ANISOU10482 C   LEU B 546    18768  34629  14004   2426   2850  -1042       C
ATOM  10483 O   LEU B 546    42.616 -23.952  49.525  1.00179.75              O
ANISOU10483 O   LEU B 546    18809  35367  14121   2461   3070  -1095       O
ATOM  10484 CB  LEU B 546    39.473 -25.106  48.533  1.00176.82              C
ANISOU10484 CB  LEU B 546    19084  34222  13879   2878   2460  -1169       C
ATOM  10485 CG  LEU B 546    39.628 -24.105  47.382  1.00178.56              C
ANISOU10485 CG  LEU B 546    19246  34836  13763   2915   2860  -1024       C
ATOM  10486 CD1 LEU B 546    38.592 -24.345  46.287  1.00179.11              C
ANISOU10486 CD1 LEU B 546    19487  34894  13671   3193   2742  -1068       C
ATOM  10487 CD2 LEU B 546    39.572 -22.665  47.875  1.00176.97              C
ANISOU10487 CD2 LEU B 546    19071  34576  13593   2455   3287   -650       C
ATOM  10488 N   ALA B 547    40.699 -23.450  50.618  1.00174.17              N
ANISOU10488 N   ALA B 547    18531  33871  13775   2018   2976   -770       N
ATOM  10489 CA  ALA B 547    41.167 -22.147  51.149  1.00173.62              C
ANISOU10489 CA  ALA B 547    18378  33893  13698   1565   3409   -514       C
ATOM  10490 C   ALA B 547    42.159 -22.156  52.349  1.00173.52              C
ANISOU10490 C   ALA B 547    18156  33947  13826   1291   3421   -544       C
ATOM  10491 O   ALA B 547    42.011 -22.937  53.287  1.00172.17              O
ANISOU10491 O   ALA B 547    18014  33520  13885   1273   3092   -630       O
ATOM  10492 CB  ALA B 547    39.965 -21.238  51.442  1.00170.91              C
ANISOU10492 CB  ALA B 547    18302  33162  13473   1249   3579   -213       C
ATOM  10493 N   SER B 548    43.154 -21.264  52.313  1.00183.92              N
ANISOU10493 N   SER B 548    19261  35622  14999   1068   3807   -462       N
ATOM  10494 CA  SER B 548    44.195 -21.182  53.353  1.00184.34              C
ANISOU10494 CA  SER B 548    19073  35833  15134    796   3857   -496       C
ATOM  10495 C   SER B 548    43.744 -20.459  54.620  1.00181.63              C
ANISOU10495 C   SER B 548    18846  35143  15022    272   3973   -290       C
ATOM  10496 O   SER B 548    42.593 -20.594  55.016  1.00179.01              O
ANISOU10496 O   SER B 548    18778  34359  14877    210   3803   -199       O
ATOM  10497 CB  SER B 548    45.449 -20.501  52.809  1.00187.34              C
ANISOU10497 CB  SER B 548    19163  36755  15262    739   4234   -502       C
ATOM  10498 OG  SER B 548    45.293 -19.094  52.760  1.00186.93              O
ANISOU10498 OG  SER B 548    19180  36680  15165    337   4701   -241       O
ATOM  10499 N   ILE B 549    44.653 -19.712  55.259  1.00233.00              N
ANISOU10499 N   ILE B 549    25145  41874  21509   -108   4259   -231       N
ATOM  10500 CA  ILE B 549    44.329 -18.935  56.470  1.00230.82              C
ANISOU10500 CA  ILE B 549    24957  41312  21430   -642   4414    -57       C
ATOM  10501 C   ILE B 549    43.880 -19.859  57.608  1.00228.68              C
ANISOU10501 C   ILE B 549    24758  40719  21411   -652   3984   -123       C
ATOM  10502 O   ILE B 549    43.661 -21.048  57.374  1.00228.73              O
ANISOU10502 O   ILE B 549    24794  40656  21457   -241   3582   -278       O
ATOM  10503 CB  ILE B 549    43.267 -17.822  56.149  1.00229.20              C
ANISOU10503 CB  ILE B 549    25044  40787  21255   -870   4737    205       C
ATOM  10504 CG1 ILE B 549    43.951 -16.472  55.912  1.00230.93              C
ANISOU10504 CG1 ILE B 549    25148  41257  21338  -1218   5288    345       C
ATOM  10505 CG2 ILE B 549    42.197 -17.693  57.233  1.00225.91              C
ANISOU10505 CG2 ILE B 549    24874  39849  21112  -1164   4625    335       C
ATOM  10506 CD1 ILE B 549    44.428 -15.785  57.169  1.00230.48              C
ANISOU10506 CD1 ILE B 549    24991  41170  21411  -1766   5488    392       C
ATOM  10507 N   PRO B 550    43.792 -19.345  58.853  1.00188.90              N
ANISOU10507 N   PRO B 550    19735  35499  16539   1119   4068     16       N
ATOM  10508 CA  PRO B 550    43.275 -20.266  59.873  1.00186.92              C
ANISOU10508 CA  PRO B 550    19567  34935  16518  -1096   3646    -58       C
ATOM  10509 C   PRO B 550    41.888 -20.750  59.464  1.00184.81              C
ANISOU10509 C   PRO B 550    19628  34224  16367   -851   3404    -10       C
ATOM  10510 O   PRO B 550    41.013 -19.923  59.202  1.00183.37              O
ANISOU10510 O   PRO B 550    19673  33796  16205  -1018   3633    168       O
ATOM  10511 CB  PRO B 550    43.182 -19.391  61.124  1.00185.39              C
ANISOU10511 CB  PRO B 550    19393  34589  16459  -1674   3854     84       C
ATOM  10512 CG  PRO B 550    44.195 -18.330  60.920  1.00187.56              C
ANISOU10512 CG  PRO B 550    19453  35253  16558  -1960   4308    105       C
ATOM  10513 CD  PRO B 550    44.259 -18.075  59.440  1.00189.17              C
ANISOU10513 CD  PRO B 550    19682  35635  16560  -1659   4503    110       C
```

FIG. 13 Continued

```
ATOM   10514  N   VAL B 551      41.700 -22.063  59.370  1.00167.87           N
ANISOU10514  N   VAL B 551    17502  31986  14293   -452   2959   -168        N
ATOM   10515  CA  VAL B 551      40.402 -22.607  58.988  1.00166.12           C
ANISOU10515  CA  VAL B 551    17576  31360  14182   -223   2704   -150        C
ATOM   10516  C   VAL B 551      39.464 -22.529  60.183  1.00163.12           C
ANISOU10516  C   VAL B 551    17388  30529  14060   -547   2584      0        C
ATOM   10517  O   VAL B 551      38.258 -22.303  60.045  1.00161.13           O
ANISOU10517  O   VAL B 551    17404  29921  13897   -589   2574    127        O
ATOM   10518  CB  VAL B 551      40.513 -24.052  58.468  1.00167.49           C
ANISOU10518  CB  VAL B 551    17716  31565  14359    301   2279   -389        C
ATOM   10519  CG1 VAL B 551      40.309 -24.099  56.953  1.00168.99           C
ANISOU10519  CG1 VAL B 551    17967  31903  14339    669   2341   -475        C
ATOM   10520  CG2 VAL B 551      41.853 -24.658  58.873  1.00169.75           C
ANISOU10520  CG2 VAL B 551    17685  32204  14607    412   2170   -550        C
ATOM   10521  N   GLU B 552      40.032 -22.699  61.366  1.00196.07           N
ANISOU10521  N   GLU B 552    21411  34746  18342   -779   2500    -10        N
ATOM   10522  CA  GLU B 552      39.245 -22.591  62.577  1.00193.45           C
ANISOU10522  CA  GLU B 552    21231  34034  18236  -1112   2404    130        C
ATOM   10523  C   GLU B 552      38.813 -21.131  62.755  1.00192.13           C
ANISOU10523  C   GLU B 552    21185  33758  18058  -1561   2847    334        C
ATOM   10524  O   GLU B 552      37.900 -20.833  63.521  1.00189.78           O
ANISOU10524  O   GLU B 552    21077  33098  17932  -1831   2839    476        O
ATOM   10525  CB  GLU B 552      40.036 -23.114  63.781  1.00193.95           C
ANISOU10525  CB  GLU B 552    21075  34232  18386  -1245   2218     73        C
ATOM   10526  CG  GLU B 552      40.407 -24.604  63.683  1.00195.36           C
ANISOU10526  CG  GLU B 552    21152  34464  18614   -786   1773   -107        C
ATOM   10527  CD  GLU B 552      41.746 -24.859  62.993  1.00198.61           C
ANISOU10527  CD  GLU B 552    21265  35381  18818   -510   1833   -282        C
ATOM   10528  OE1 GLU B 552      41.753 -25.334  61.835  1.00199.96           O
ANISOU10528  OE1 GLU B 552    21465  35625  18887    -96   1760   -415        O
ATOM   10529  OE2 GLU B 552      42.795 -24.592  63.615  1.00199.96           O
ANISOU10529  OE2 GLU B 552    21161  35896  18918   -709   1951   -293        O
ATOM   10530  N   GLU B 553      39.466 -20.226  62.027  1.00156.58           N
ANISOU10530  N   GLU B 553    16574  29561  13357  -1631   3242    352        N
ATOM   10531  CA  GLU B 553      39.122 -18.805  62.077  1.00155.82           C
ANISOU10531  CA  GLU B 553    16595  29361  13250  -2032   3704    546        C
ATOM   10532  C   GLU B 553      37.805 -18.543  61.384  1.00154.26           C
ANISOU10532  C   GLU B 553    16703  28818  13090  -1905   3742    694        C
ATOM   10533  O   GLU B 553      36.818 -18.209  62.035  1.00151.96           O
ANISOU10533  O   GLU B 553    16622  28146  12972  -2139   3753    841        O
ATOM   10534  CB  GLU B 553      40.201 -17.938  61.421  1.00158.40           C
ANISOU10534  CB  GLU B 553    16720  30110  13356  -2125   4125    533        C
ATOM   10535  CG  GLU B 553      39.682 -16.622  60.802  1.00158.26           C
ANISOU10535  CG  GLU B 553    16878  29970  13283  -2318   4594    740        C
ATOM   10536  CD  GLU B 553      39.910 -15.406  61.683  1.00158.05           C
ANISOU10536  CD  GLU B 553    16839  29887  13326  -2893   5000    855        C
ATOM   10537  OE1 GLU B 553      39.950 -15.561  62.919  1.00156.92           O
ANISOU10537  OE1 GLU B 553    16657  29639  13328  -3175   4872    820        O
ATOM   10538  OE2 GLU B 553      40.049 -14.290  61.138  1.00159.20           O
ANISOU10538  OE2 GLU B 553    17014  30092  13381  -3066   5456    980        O
ATOM   10539  N   LEU B 554      37.787 -18.698  60.064  1.00155.55           N
ANISOU10539  N   LEU B 554    16880  29139  13082  -1532   3761    655        N
ATOM   10540  CA  LEU B 554      36.581 -18.422  59.306  1.00154.45           C
ANISOU10540  CA  LEU B 554    17003  28740  12940  -1392   3808    802        C
ATOM   10541  C   LEU B 554      35.374 -18.963  60.048  1.00151.71           C
ANISOU10541  C   LEU B 554    16875  27937  12830  -1428   3489    856        C
ATOM   10542  O   LEU B 554      34.354 -18.287  60.158  1.00150.04           O
ANISOU10542  O   LEU B 554    16880  27422  12706  -1600   3645   1057        O
ATOM   10543  CB  LEU B 554      36.658 -18.995  57.888  1.00156.28           C
ANISOU10543  CB  LEU B 554    17207  29206  12967   -896   3690    685        C
ATOM   10544  CG  LEU B 554      37.395 -18.129  56.859  1.00158.75           C
ANISOU10544  CG  LEU B 554    17396  29898  13022   -860   4109    735        C
ATOM   10545  CD1 LEU B 554      38.899 -18.464  56.825  1.00161.23           C
ANISOU10545  CD1 LEU B 554    17390  30668  13202   -791   4115    532        C
ATOM   10546  CD2 LEU B 554      36.758 -18.238  55.461  1.00159.60           C
ANISOU10546  CD2 LEU B 554    17621  30066  12955   -470   4096    764        C
ATOM   10547  N   ILE B 555      35.498 -20.166  60.593  1.00152.10           N
ANISOU10547  N   ILE B 555    16864  27936  12990  -1273   3053    689        N
ATOM   10548  CA  ILE B 555      34.392 -20.736  61.343  1.00149.66           C
```

FIG. 13 Continued

```
ANISOU10548  CA  ILE B 555    16750  27201  12912  -1317   2738    741         C
ATOM  10549  C   ILE B 555     33.717 -19.642  62.174  1.00147.62              C
ANISOU10549  C   ILE B 555    16641  26666  12783  -1777   3024    974         C
ATOM  10550  O   ILE B 555     32.569 -19.301  61.897  1.00146.22              O
ANISOU10550  O   ILE B 555    16687  26210  12658  -1775   3074   1128         O
ATOM  10551  CB  ILE B 555     34.835 -21.916  62.217  1.00149.67              C
ANISOU10551  CB  ILE B 555    16631  27188  13048  -1245   2329    581         C
ATOM  10552  CG1 ILE B 555     35.606 -22.923  61.370  1.00152.08              C
ANISOU10552  CG1 ILE B 555    16779  27781  13225   -786   2097    343         C
ATOM  10553  CG2 ILE B 555     33.631 -22.595  62.839  1.00147.40              C
ANISOU10553  CG2 ILE B 555    16556  26458  12991  -1244   1986    636         C
ATOM  10554  CD1 ILE B 555     34.779 -23.520  60.267  1.00152.26              C
ANISOU10554  CD1 ILE B 555    16967  27681  13205   -394   1897    274         C
ATOM  10555  N   GLU B 556     34.426 -19.055  63.144  1.00183.57              N
ANISOU10555  N   GLU B 556    21064  31311  17374  -2166   3231    996         N
ATOM  10556  CA  GLU B 556     33.804 -17.997  63.951  1.00181.87              C
ANISOU10556  CA  GLU B 556    20993  30825  17282  -2613   3522   1193         C
ATOM  10557  C   GLU B 556     33.546 -16.694  63.194  1.00182.36              C
ANISOU10557  C   GLU B 556    21165  30878  17246  -2724   4010   1369         C
ATOM  10558  O   GLU B 556     32.387 -16.350  62.964  1.00180.96              O
ANISOU10558  O   GLU B 556    21219  30398  17140  -2707   4068   1538         O
ATOM  10559  CB  GLU B 556     34.527 -17.689  65.279  1.00181.81              C
ANISOU10559  CB  GLU B 556    20834  30898  17348  -3042   3614   1162         C
ATOM  10560  CG  GLU B 556     33.506 -17.324  66.416  1.00179.31              C
ANISOU10560  CG  GLU B 556    20710  30175  17244  -3394   3625   1310         C
ATOM  10561  CD  GLU B 556     33.836 -16.065  67.249  1.00179.40              C
ANISOU10561  CD  GLU B 556    20693  30192  17280  -3930   4063   1385         C
ATOM  10562  OE1 GLU B 556     32.886 -15.350  67.657  1.00177.82              O
ANISOU10562  OE1 GLU B 556    20704  29654  17204  -4174   4251   1545         O
ATOM  10563  OE2 GLU B 556     35.026 -15.797  67.514  1.00181.18              O
ANISOU10563  OE2 GLU B 556    20683  30755  17402  -4114   4219   1275         O
ATOM  10564  N   LYS B 557     34.604 -15.969  62.821  1.00179.80              N
ANISOU10564  N   LYS B 557    20671  30881  16763  -2838   4365   1343         N
ATOM  10565  CA  LYS B 557     34.449 -14.662  62.155  1.00180.61              C
ANISOU10565  CA  LYS B 557    20871  30970  16783  -2974   4872   1530         C
ATOM  10566  C   LYS B 557     33.625 -14.715  60.871  1.00180.73              C
ANISOU10566  C   LYS B 557    21045  30925  16700  -2588   4858   1641         C
ATOM  10567  O   LYS B 557     33.926 -14.014  59.898  1.00182.53              O
ANISOU10567  O   LYS B 557    21251  31343  16760  -2508   5190   1728         O
ATOM  10568  CB  LYS B 557     35.804 -14.002  61.873  1.00183.25              C
ANISOU10568  CB  LYS B 557    20973  31704  16949  -3127   5228   1467         C
ATOM  10569  CG  LYS B 557     36.553 -13.534  63.112  1.00183.44              C
ANISOU10569  CG  LYS B 557    20855  31791  17053  -3614   5390   1405         C
ATOM  10570  CD  LYS B 557     37.853 -12.826  62.735  1.00186.30              C
ANISOU10570  CD  LYS B 557    20987  32558  17240  -3774   5767   1346         C
ATOM  10571  CE  LYS B 557     38.787 -12.668  63.935  1.00186.92              C
ANISOU10571  CE  LYS B 557    20849  32813  17358  -4197   5820   1216         C
ATOM  10572  NZ  LYS B 557     38.200 -11.818  65.011  1.00185.46              N
ANISOU10572  NZ  LYS B 557    20825  32285  17358  -4685   6050   1322         N
ATOM  10573  N   ALA B 558     32.569 -15.525  60.901  1.00147.05              N
ANISOU10573  N   ALA B 558    16934  26400  12538  -2368   4479   1645         N
ATOM  10574  CA  ALA B 558     31.710 -15.761  59.754  1.00147.13              C
ANISOU10574  CA  ALA B 558    17083  26366  12455  -1989   4382   1718         C
ATOM  10575  C   ALA B 558     30.264 -15.994  60.143  1.00144.70              C
ANISOU10575  C   ALA B 558    17009  25644  12326  -1988   4173   1842         C
ATOM  10576  O   ALA B 558     29.673 -15.235  60.904  1.00143.24              O
ANISOU10576  O   ALA B 558    16957  25172  12294  -2314   4381   2018         O
ATOM  10577  CB  ALA B 558     32.206 -16.970  58.995  1.00148.50              C
ANISOU10577  CB  ALA B 558    17119  26817  12489  -1552   4010   1477         C
ATOM  10578  N   ASP B 559     29.718 -17.063  59.569  1.00144.32              N
ANISOU10578  N   ASP B 559    17002  25582  12249  -1611   3765   1736         N
ATOM  10579  CA  ASP B 559     28.351 -17.526  59.784  1.00142.32              C
ANISOU10579  CA  ASP B 559    16947  24985  12144  -1542   3487   1812         C
ATOM  10580  C   ASP B 559     28.335 -19.028  59.500  1.00142.61              C
ANISOU10580  C   ASP B 559    16936  25073  12178  -1189   2960   1563         C
ATOM  10581  O   ASP B 559     29.402 -19.644  59.351  1.00144.13              O
ANISOU10581  O   ASP B 559    16946  25530  12288  -1045   2831   1345         O
ATOM  10582  CB  ASP B 559     27.357 -16.812  58.859  1.00142.45              C
ANISOU10582  CB  ASP B 559    17123  24935  12067  -1414   3706   2043         C
```

FIG. 13 Continued

```
ATOM   10583  CG  ASP B 559      26.493 -15.791  59.584  1.00140.75           C
ANISOU10583  CG  ASP B 559    17081  24380  12017   -1749   3992   2316       C
ATOM   10584  OD1 ASP B 559      26.399 -14.651  59.084  1.00141.63           O
ANISOU10584  OD1 ASP B 559    17247  24520  12044   -1815   4430   2533       O
ATOM   10585  OD2 ASP B 559      25.898 -16.130  60.634  1.00138.69           O
ANISOU10585  OD2 ASP B 559    16903  23823  11971   -1936   3787   2321       O
ATOM   10586  N   GLY B 560      27.131 -19.601  59.421  1.00173.69           N
ANISOU10586  N   GLY B 560    21032  28755  16207   -1053   2670   1593       N
ATOM   10587  CA  GLY B 560      26.940 -21.025  59.181  1.00173.99           C
ANISOU10587  CA  GLY B 560    21061  28770  16277    -742   2171   1361       C
ATOM   10588  C   GLY B 560      27.436 -21.524  57.839  1.00176.47           C
ANISOU10588  C   GLY B 560    21278  29423  16350    -331   2088   1171       C
ATOM   10589  O   GLY B 560      28.218 -20.845  57.180  1.00178.13           O
ANISOU10589  O   GLY B 560    21378  29945  16359    -291   2408   1193       O
ATOM   10590  N   PHE B 561      26.994 -22.708  57.420  1.00147.95           N
ANISOU10590  N   PHE B 561    17704  25755  12754     -32   1670    976       N
ATOM   10591  CA  PHE B 561      27.466 -23.231  56.144  1.00150.51           C
ANISOU10591  CA  PHE B 561    17935  26410  12843     365   1583    763       C
ATOM   10592  C   PHE B 561      26.681 -24.360  55.480  1.00151.18           C
ANISOU10592  C   PHE B 561    18105  26416  12920     687   1172    570       C
ATOM   10593  O   PHE B 561      25.691 -24.874  56.012  1.00149.61           O
ANISOU10593  O   PHE B 561    18046  25879  12919     618    903    593       O
ATOM   10594  CB  PHE B 561      28.934 -23.620  56.251  1.00152.18           C
ANISOU10594  CB  PHE B 561    17934  26887  13000     441   1576    554       C
ATOM   10595  CG  PHE B 561      29.408 -23.785  57.656  1.00150.82           C
ANISOU10595  CG  PHE B 561    17708  26541  13057     156   1505    561       C
ATOM   10596  CD1 PHE B 561      29.005 -24.865  58.410  1.00149.83           C
ANISOU10596  CD1 PHE B 561    17645  26122  13163     175   1093    455       C
ATOM   10597  CD2 PHE B 561      30.264 -22.852  58.219  1.00150.75           C
ANISOU10597  CD2 PHE B 561    17579  26675  13025    -140   1856    677       C
ATOM   10598  CE1 PHE B 561      29.447 -25.010  59.689  1.00148.79           C
ANISOU10598  CE1 PHE B 561    17450  25862  13219     -77   1030    480       C
ATOM   10599  CE2 PHE B 561      30.712 -22.992  59.500  1.00149.73           C
ANISOU10599  CE2 PHE B 561    17381  26430  13078    -406   1791    678       C
ATOM   10600  CZ  PHE B 561      30.302 -24.069  60.238  1.00148.72           C
ANISOU10600  CZ  PHE B 561    17311  26030  13166    -368   1376    589       C
ATOM   10601  N   ALA B 562      27.167 -24.721  54.292  1.00149.90           N
ANISOU10601  N   ALA B 562    17850  26589  12517    1034   1141    371       N
ATOM   10602  CA  ALA B 562      26.532 -25.706  53.421  1.00151.23           C
ANISOU10602  CA  ALA B 562    18079  26768  12612    1366    802    151       C
ATOM   10603  C   ALA B 562      27.357 -26.952  53.179  1.00153.31           C
ANISOU10603  C   ALA B 562    18236  27139  12874    1655    498   -221       C
ATOM   10604  O   ALA B 562      28.567 -26.982  53.398  1.00154.27           O
ANISOU10604  O   ALA B 562    18199  27446  12972    1672    592   -312       O
ATOM   10605  CB  ALA B 562      26.174 -25.078  52.091  1.00152.76           C
ANISOU10605  CB  ALA B 562    18276  27271  12495    1556   1015    231       C
ATOM   10606  N   GLY B 563      26.679 -27.954  52.639  1.00162.10           N
ANISOU10606  N   GLY B 563    19434  28159  13997    1897    149   -440       N
ATOM   10607  CA  GLY B 563      27.246 -29.270  52.473  1.00164.09           C
ANISOU10607  CA  GLY B 563    19629  28414  14303    2176   -185   -806       C
ATOM   10608  C   GLY B 563      26.913 -29.875  53.813  1.00162.07           C
ANISOU10608  C   GLY B 563    19462  27704  14411    1962   -443   -770       C
ATOM   10609  O   GLY B 563      25.936 -30.601  53.959  1.00161.55           O
ANISOU10609  O   GLY B 563    19542  27333  14508    1973   -750   -837       O
ATOM   10610  N   VAL B 564      27.717 -29.521  54.807  1.00167.16           N
ANISOU10610  N   VAL B 564    20013  28326  15175    1746   -303   -647       N
ATOM   10611  CA  VAL B 564      27.503 -29.937  56.186  1.00165.20           C
ANISOU10611  CA  VAL B 564    19825  27693  15251    1507   -496   -563       C
ATOM   10612  C   VAL B 564      27.083 -31.395  56.351  1.00165.98           C
ANISOU10612  C   VAL B 564    20016  27484  15565    1688   -958   -799       C
ATOM   10613  O   VAL B 564      26.186 -31.698  57.128  1.00164.20           O
ANISOU10613  O   VAL B 564    19930  26882  15577    1503  -1151   -694       O
ATOM   10614  CB  VAL B 564      26.463 -29.044  56.878  1.00162.22           C
ANISOU10614  CB  VAL B 564    19585  27070  14981    1137   -349   -231       C
ATOM   10615  CG1 VAL B 564      26.902 -28.755  58.301  1.00160.40           C
ANISOU10615  CG1 VAL B 564    19308  26685  14953     807   -277    -65       C
ATOM   10616  CG2 VAL B 564      26.284 -27.744  56.116  1.00162.09           C
ANISOU10616  CG2 VAL B 564    19564  27313  14711    1080     53    -34       C
ATOM   10617  N   PHE B 565      27.713 -32.296  55.611  1.00160.87           N
```

FIG. 13 Continued

```
ANISOU10617  N   PHE B 565    19295 26988 14839   2049 -1127 -1120       N
ATOM   10618  CA  PHE B 565      27.420 -33.709  55.776  1.00162.02      C
ANISOU10618  CA  PHE B 565    19529 26822 15209   2229 -1547 -1362       C
ATOM   10619  C   PHE B 565      27.790 -34.052  57.213  1.00160.72      C
ANISOU10619  C   PHE B 565    19340 26391 15337   2034 -1661 -1242       C
ATOM   10620  O   PHE B 565      28.745 -33.509  57.755  1.00160.36      O
ANISOU10620  O   PHE B 565    19138 26537 15255   1919 -1453 -1126       O
ATOM   10621  CB  PHE B 565      28.224 -34.544  54.778  1.00165.56      C
ANISOU10621  CB  PHE B 565    19882 27505 15519   2656 -1658 -1733       C
ATOM   10622  CG  PHE B 565      27.966 -34.177  53.343  1.00167.12      C
ANISOU10622  CG  PHE B 565    20077 28032 15388   2856 -1528 -1854       C
ATOM   10623  CD1 PHE B 565      28.549 -33.052  52.782  1.00167.25      C
ANISOU10623  CD1 PHE B 565    19961 28478 15110   2839 -1147 -1723       C
ATOM   10624  CD2 PHE B 565      27.123 -34.947  52.559  1.00168.60      C
ANISOU10624  CD2 PHE B 565    20392 28111 15558   3049 -1784 -2092       C
ATOM   10625  CE1 PHE B 565      28.307 -32.704  51.469  1.00168.83      C
ANISOU10625  CE1 PHE B 565    20151 29001 14995   3028 -1023 -1808       C
ATOM   10626  CE2 PHE B 565      26.876 -34.607  51.239  1.00170.21      C
ANISOU10626  CE2 PHE B 565    20579 28657 15435   3233 -1670 -2200       C
ATOM   10627  CZ  PHE B 565      27.471 -33.484  50.694  1.00170.31      C
ANISOU10627  CZ  PHE B 565    20455 29106 15148   3231 -1289 -2046       C
ATOM   10628  N   PRO B 566      27.022 -34.941  57.846  1.00153.97      N
ANISOU10628  N   PRO B 566    18631 25105 14768   1982 -1989 -1262       N
ATOM   10629  CA  PRO B 566      27.256 -35.298  59.249  1.00152.78      C
ANISOU10629  CA  PRO B 566    18466 24687 14897   1790 -2115 -1120       C
ATOM   10630  C   PRO B 566      28.710 -35.172  59.731  1.00153.68      C
ANISOU10630  C   PRO B 566    18357 25062 14971   1827 -1978 -1112       C
ATOM   10631  O   PRO B 566      28.991 -34.290  60.543  1.00151.79      O
ANISOU10631  O   PRO B 566    18039 24912 14723   1522 -1755  -864       O
ATOM   10632  CB  PRO B 566      26.784 -36.747  59.299  1.00154.31      C
ANISOU10632  CB  PRO B 566    18787 24503 15340   1982 -2530 -1333       C
ATOM   10633  CG  PRO B 566      25.617 -36.752  58.341  1.00154.39      C
ANISOU10633  CG  PRO B 566    18954 24450 15258   2030 -2598 -1429       C
ATOM   10634  CD  PRO B 566      25.906 -35.709  57.270  1.00154.70      C
ANISOU10634  CD  PRO B 566    18901 24948 14931   2103 -2268 -1429       C
ATOM   10635  N   GLU B 567      29.609 -36.016  59.232  1.00156.62      N
ANISOU10635  N   GLU B 567    18625 25570 15314   2189 -2100 -1385       N
ATOM   10636  CA  GLU B 567      31.005 -36.018  59.679  1.00157.85      C
ANISOU10636  CA  GLU B 567    18549 25989 15437   2259 -2001 -1391       C
ATOM   10637  C   GLU B 567      31.532 -34.609  59.903  1.00156.29      C
ANISOU10637  C   GLU B 567    18207 26141 15036   1975 -1602 -1166       C
ATOM   10638  O   GLU B 567      32.383 -34.371  60.763  1.00156.10      O
ANISOU10638  O   GLU B 567    18016 26253 15043   1835 -1509 -1050       O
ATOM   10639  CB  GLU B 567      31.894 -36.715  58.646  1.00161.43      C
ANISOU10639  CB  GLU B 567    18889 26693 15753   2713 -2054 -1725       C
ATOM   10640  CG  GLU B 567      31.162 -37.696  57.740  1.00163.22      C
ANISOU10640  CG  GLU B 567    19290 26696 16029   3004 -2321 -2011       C
ATOM   10641  CD  GLU B 567      31.246 -39.132  58.221  1.00165.07      C
ANISOU10641  CD  GLU B 567    19584 26565 16571   3216 -2682 -2172       C
ATOM   10642  OE1 GLU B 567      31.823 -39.373  59.306  1.00164.83      O
ANISOU10642  OE1 GLU B 567    19459 26450 16717   3139 -2739 -2029       O
ATOM   10643  OE2 GLU B 567      30.737 -40.019  57.502  1.00166.98      O
ANISOU10643  OE2 GLU B 567    19963 26608 16873   3460 -2904 -2443       O
ATOM   10644  N   HIS B 568      31.017 -33.685  59.103  1.00160.29      N
ANISOU10644  N   HIS B 568    18774 26796 15331   1895 -1363 -1108       N
ATOM   10645  CA  HIS B 568      31.411 -32.290  59.161  1.00159.04      C
ANISOU10645  CA  HIS B 568    18509 26941 14979   1629  -953  -900       C
ATOM   10646  C   HIS B 568      31.187 -31.727  60.553  1.00156.37      C
ANISOU10646  C   HIS B 568    18186 26415 14812   1198  -877  -615       C
ATOM   10647  O   HIS B 568      32.134 -31.307  61.216  1.00156.43      O
ANISOU10647  O   HIS B 568    18013 26631 14792   1042  -714  -535       O
ATOM   10648  CB  HIS B 568      30.606 -31.490  58.138  1.00158.44      C
ANISOU10648  CB  HIS B 568    18548 26952 14700   1614  -752  -844       C
ATOM   10649  CG  HIS B 568      30.654 -32.062  56.753  1.00161.07      C
ANISOU10649  CG  HIS B 568    18883 27463 14851   2024  -847 -1127       C
ATOM   10650  ND1 HIS B 568      30.462 -31.297  55.624  1.00161.63      N
ANISOU10650  ND1 HIS B 568    18956 27815 14639   2097  -600 -1114       N
ATOM   10651  CD2 HIS B 568      30.885 -33.323  56.315  1.00163.50      C
ANISOU10651  CD2 HIS B 568    19189 27716 15216   2384 -1153 -1436       C
```

FIG. 13 Continued

```
ATOM   10652  CE1 HIS B 568        30.567 -32.062  54.551  1.00164.24           C
ANISOU10652  CE1 HIS B 568     19280  28281  14844   2478   -758  -1410         C
ATOM   10653  NE2 HIS B 568        30.821 -33.296  54.943  1.00165.43           N
ANISOU10653  NE2 HIS B 568     19433  28221  15203   2656  -1090  -1621         N
ATOM   10654  N   LYS B 569        29.931 -31.736  60.992  1.00149.66           N
ANISOU10654  N   LYS B 569     17544  25190  14131   1005   -999   -474         N
ATOM   10655  CA  LYS B 569        29.553 -31.209  62.300  1.00147.07           C
ANISOU10655  CA  LYS B 569     17256  24659  13967    591   -936   -208         C
ATOM   10656  C   LYS B 569        30.579 -31.552  63.381  1.00147.61           C
ANISOU10656  C   LYS B 569     17145  24802  14140    513  -1001   -190         C
ATOM   10657  O   LYS B 569        31.300 -30.673  63.856  1.00147.20           O
ANISOU10657  O   LYS B 569     16942  24999  13988    274   -719    -73         O
ATOM   10658  CB  LYS B 569        28.168 -31.725  62.692  1.00145.43           C
ANISOU10658  CB  LYS B 569     17276  23997  13984    503  -1204   -132         C
ATOM   10659  CG  LYS B 569        27.015 -31.064  61.934  1.00144.23           C
ANISOU10659  CG  LYS B 569     17290  23779  13732    448  -1076    -48         C
ATOM   10660  CD  LYS B 569        25.714 -31.891  61.992  1.00143.58           C
ANISOU10660  CD  LYS B 569     17411  23294  13846    481  -1414    -69         C
ATOM   10661  CE  LYS B 569        24.527 -31.105  61.427  1.00142.16           C
ANISOU10661  CE  LYS B 569     17376  23069  13570    373  -1265     72         C
ATOM   10662  NZ  LYS B 569        23.381 -31.949  60.971  1.00142.51           N
ANISOU10662  NZ  LYS B 569     17582  22853  13711    511  -1582    -37         N
ATOM   10663  N   TYR B 570        30.645 -32.828  63.757  1.00175.70           N
ANISOU10663  N   TYR B 570     20714  28149  17896    714  -1367   -304         N
ATOM   10664  CA  TYR B 570        31.611 -33.305  64.744  1.00176.64           C
ANISOU10664  CA  TYR B 570     20652  28345  18116    700  -1469   -284         C
ATOM   10665  C   TYR B 570        32.845 -32.432  64.614  1.00177.53           C
ANISOU10665  C   TYR B 570     20518  28943  17991    634  -1134   -283         C
ATOM   10666  O   TYR B 570        33.328 -31.875  65.600  1.00176.71           O
ANISOU10666  O   TYR B 570     20285  28967  17891    331   -993   -126         O
ATOM   10667  CB  TYR B 570        31.934 -34.792  64.473  1.00179.28           C
ANISOU10667  CB  TYR B 570     20979  28553  18587   1124  -1829   -511         C
ATOM   10668  CG  TYR B 570        33.030 -35.482  65.309  1.00181.05           C
ANISOU10668  CG  TYR B 570     20999  28883  18909   1229  -1967   -516         C
ATOM   10669  CD1 TYR B 570        33.285 -35.122  66.637  1.00179.76           C
ANISOU10669  CD1 TYR B 570     20732  28748  18819    899  -1920   -284         C
ATOM   10670  CD2 TYR B 570        33.776 -36.546  64.768  1.00184.24           C
ANISOU10670  CD2 TYR B 570     21315  29354  19335   1677  -2156   -756         C
ATOM   10671  CE1 TYR B 570        34.279 -35.782  67.390  1.00181.62           C
ANISOU10671  CE1 TYR B 570     20765  29113  19131   1014  -2058   -273         C
ATOM   10672  CE2 TYR B 570        34.762 -37.204  65.513  1.00186.11           C
ANISOU10672  CE2 TYR B 570     21358  29691  19663   1806  -2285   -743         C
ATOM   10673  CZ  TYR B 570        35.006 -36.817  66.819  1.00184.78           C
ANISOU10673  CZ  TYR B 570     21077  29579  19554   1475  -2239   -492         C
ATOM   10674  OH  TYR B 570        35.968 -37.464  67.556  1.00186.80           O
ANISOU10674  OH  TYR B 570     21125  29965  19884   1611  -2371   -460         O
ATOM   10675  N   GLU B 571        33.313 -32.267  63.378  1.00151.48           N
ANISOU10675  N   GLU B 571     17155  25926  14473    896   -994   -459         N
ATOM   10676  CA  GLU B 571        34.518 -31.486  63.110  1.00152.72           C
ANISOU10676  CA  GLU B 571     17069  26566  14391    864   -672   -479         C
ATOM   10677  C   GLU B 571        34.311 -29.974  63.267  1.00150.71           C
ANISOU10677  C   GLU B 571     16826  26428  14008    448   -267   -269         C
ATOM   10678  O   GLU B 571        34.980 -29.340  64.083  1.00150.37           O
ANISOU10678  O   GLU B 571     16624  26573  13936    156    -76   -154         O
ATOM   10679  CB  GLU B 571        35.118 -31.835  61.732  1.00155.48           C
ANISOU10679  CB  GLU B 571     17337  27197  14543   1292   -652   -737         C
ATOM   10680  CG  GLU B 571        36.622 -31.495  61.560  1.00157.69           C
ANISOU10680  CG  GLU B 571     17309  27990  14617   1365   -430   -810         C
ATOM   10681  CD  GLU B 571        37.568 -32.597  62.037  1.00160.00           C
ANISOU10681  CD  GLU B 571     17417  28363  15013   1626   -686   -939         C
ATOM   10682  OE1 GLU B 571        38.132 -33.305  61.178  1.00162.72           O
ANISOU10682  OE1 GLU B 571     17681  28869  15275   2046   -782  -1177         O
ATOM   10683  OE2 GLU B 571        37.752 -32.756  63.263  1.00159.27           O
ANISOU10683  OE2 GLU B 571     17256  28183  15078   1423   -785   -800         O
ATOM   10684  N   ILE B 572        33.383  29.396  62.511  1.00150.69           N
ANISOU10684  N   ILE B 572     17008  26315  13931    416   -131   -216         N
ATOM   10685  CA  ILE B 572        33.186 -27.952  62.571  1.00149.12           C
ANISOU10685  CA  ILE B 572     16833  26208  13618     56    279    -13         C
ATOM   10686  C   ILE B 572        33.052 -27.462  63.997  1.00147.10           C
```

FIG. 13 Continued

```
ANISOU10686  C   ILE B 572    16575  25803  13513    -386    348    189        C
ATOM  10687  O   ILE B 572     33.307 -26.294  64.294  1.00146.39              O
ANISOU10687  O   ILE B 572    16431  25856  13336    -718    710    327        O
ATOM  10688  CB  ILE B 572     31.941 -27.516  61.833  1.00147.80              C
ANISOU10688  CB  ILE B 572    16900  25839  13419      60    351     71        C
ATOM  10689  CG1 ILE B 572     31.679 -28.449  60.657  1.00149.52              C
ANISOU10689  CG1 ILE B 572    17181  26058  13573     511    104   -153        C
ATOM  10690  CG2 ILE B 572     32.110 -26.092  61.385  1.00147.57              C
ANISOU10690  CG2 ILE B 572    16842  26037  13190    -145    822    216        C
ATOM  10691  CD1 ILE B 572     30.280 -28.341  60.098  1.00148.25              C
ANISOU10691  CD1 ILE B 572    17257  25642  13428     533     51    -84        C
ATOM  10692  N   VAL B 573     32.637 -28.365  64.875  1.00146.08              N
ANISOU10692  N   VAL B 573    16509  25380  13613    -391      5    204        N
ATOM  10693  CA  VAL B 573     32.460 -28.045  66.281  1.00144.29              C
ANISOU10693  CA  VAL B 573    16281  25009  13534    -790     22    388        C
ATOM  10694  C   VAL B 573     33.756 -28.224  67.061  1.00145.77              C
ANISOU10694  C   VAL B 573    16195  25497  13693    -855     18    350        C
ATOM  10695  O   VAL B 573     34.137 -27.363  67.846  1.00145.11              O
ANISOU10695  O   VAL B 573    16009  25560  13569   -1230    263    466        O
ATOM  10696  CB  VAL B 573     31.333 -28.894  66.899  1.00142.79              C
ANISOU10696  CB  VAL B 573    16289  24366  13600    -790   -336    455        C
ATOM  10697  CG1 VAL B 573     31.727 -29.390  68.278  1.00142.69              C
ANISOU10697  CG1 VAL B 573    16166  24308  13740    -956   -518    528        C
ATOM  10698  CG2 VAL B 573     30.019 -28.102  66.933  1.00140.26              C
ANISOU10698  CG2 VAL B 573    16199  23766  13326   -1047   -188    635        C
ATOM  10699  N   LYS B 574     34.428 -29.346  66.828  1.00158.48              N
ANISOU10699  N   LYS B 574    17684  27207  15324    -484   -257    181        N
ATOM  10700  CA  LYS B 574     35.704 -29.650  67.472  1.00160.34              C
ANISOU10700  CA  LYS B 574    17636  27762  15524    -469   -294    137        C
ATOM  10701  C   LYS B 574     36.669 -28.478  67.366  1.00161.04              C
ANISOU10701  C   LYS B 574    17514  28294  15381    -704    119    148        C
ATOM  10702  O   LYS B 574     37.495 -28.250  68.253  1.00161.67              O
ANISOU10702  O   LYS B 574    17375  28626  15428    -923    191    194        O
ATOM  10703  CB  LYS B 574     36.325 -30.887  66.820  1.00163.08              C
ANISOU10703  CB  LYS B 574    17889  28195  15878      44   -571    -77        C
ATOM  10704  CG  LYS B 574     37.743 -31.214  67.261  1.00165.53              C
ANISOU10704  CG  LYS B 574    17877  28901  16117     140   -591   -137        C
ATOM  10705  CD  LYS B 574     37.945 -32.718  67.222  1.00167.58              C
ANISOU10705  CD  LYS B 574    18121  29020  16533     585   -989   -264        C
ATOM  10706  CE  LYS B 574     36.799 -33.413  67.964  1.00165.86              C
ANISOU10706  CE  LYS B 574    18142  28279  16598     520  -1296   -144        C
ATOM  10707  NZ  LYS B 574     36.889 -34.899  67.958  1.00167.94              N
ANISOU10707  NZ  LYS B 574    18427  28329  17053     937  -1682   -253        N
ATOM  10708  N   LYS B 575     36.566 -27.749  66.260  1.00163.37              N
ANISOU10708  N   LYS B 575    17868  28697  15509    -655    390    106        N
ATOM  10709  CA  LYS B 575     37.395 -26.579  66.026  1.00164.16              C
ANISOU10709  CA  LYS B 575    17795  29184  15392    -881    813    123        C
ATOM  10710  C   LYS B 575     36.732 -25.391  66.710  1.00161.76              C
ANISOU10710  C   LYS B 575    17620  28712  15130   -1385   1099    327        C
ATOM  10711  O   LYS B 575     37.396 -24.568  67.346  1.00162.01              O
ANISOU10711  O   LYS B 575    17492  28977  15088   -1741   1366    381        O
ATOM  10712  CB  LYS B 575     37.554 -26.328  64.521  1.00165.53              C
ANISOU10712  CB  LYS B 575    17983  29544  15368    -595    986      9        C
ATOM  10713  CG  LYS B 575     37.916 -27.577  63.706  1.00167.76              C
ANISOU10713  CG  LYS B 575    18209  29903  15628     -55    679   -214        C
ATOM  10714  CD  LYS B 575     39.320 -28.091  64.033  1.00170.33              C
ANISOU10714  CD  LYS B 575    18214  30612  15891      83    070   -334        C
ATOM  10715  CE  LYS B 575     39.619 -29.423  63.345  1.00172.62              C
ANISOU10715  CE  LYS B 575    18468  30917  16202     631    282   -557        C
ATOM  10716  NZ  LYS B 575     38.964 -30.583  64.016  1.00171.93              N
ANISOU10716  NZ  LYS B 575    18524  30416  16387     763   -138   -554        N
ATOM  10717  N   LEU B 576     35.409 -25.321  66.588  1.00153.39              N
ANISOU10717  N   LEU B 576    16845  27245  14192   -1416   1040    429        N
ATOM  10718  CA  LEU B 576     34.651 -24.248  67.210  1.00151.13              C
ANISOU10718  CA  LEU B 576    16707  26750  13966   -1859   1300    625        C
ATOM  10719  C   LEU B 576     35.017 -24.120  68.681  1.00150.61              C
ANISOU10719  C   LEU B 576    16518  26719  13988   -2232   1288    696        C
ATOM  10720  O   LEU B 576     35.513 -23.074  69.116  1.00150.74              O
ANISOU10720  O   LEU B 576    16431  26925  13918   -2604   1635    748        O
```

FIG. 13 Continued

```
ATOM   10721  CB   LEU B 576      33.151 -24.472  67.044  1.00149.00           C
ANISOU10721  CB   LEU B 576    16739  26029  13847   -1799   1140    723       C
ATOM   10722  CG   LEU B 576      32.533 -23.637  65.927  1.00148.64           C
ANISOU10722  CG   LEU B 576    16849  25941  13685   -1749   1422    786       C
ATOM   10723  CD1  LEU B 576      31.235 -24.251  65.463  1.00147.43           C
ANISOU10723  CD1  LEU B 576    16937  25437  13642   -1526   1158    809       C
ATOM   10724  CD2  LEU B 576      32.318 -22.212  66.402  1.00147.42           C
ANISOU10724  CD2  LEU B 576    16750  25747  13516   -2202   1855    969       C
ATOM   10725  N    GLN B 577      34.784 -25.187  69.443  1.00143.10           N
ANISOU10725  N    GLN B 577    15574  25593  13204   -2136    895    697       N
ATOM   10726  CA   GLN B 577      35.138 -25.182  70.856  1.00142.84           C
ANISOU10726  CA   GLN B 577    15408  25624  13240   -2458    845    770       C
ATOM   10727  C    GLN B 577      36.618 -24.812  70.985  1.00145.14           C
ANISOU10727  C    GLN B 577    15374  26427  13345   -2552   1040    677       C
ATOM   10728  O    GLN B 577      36.996 -24.057  71.873  1.00145.02           O
ANISOU10728  O    GLN B 577    15242  26571  13288   -2969   1253    734       O
ATOM   10729  CB   GLN B 577      34.888 -26.549  71.513  1.00142.84           C
ANISOU10729  CB   GLN B 577    15420  25428  13427   -2250    371    778       C
ATOM   10730  CG   GLN B 577      33.789 -27.406  70.895  1.00141.94           C
ANISOU10730  CG   GLN B 577    15561  24906  13466   -1926     76    767       C
ATOM   10731  CD   GLN B 577      33.914 -28.881  71.284  1.00143.06           C
ANISOU10731  CD   GLN B 577    15661  24931  13765   -1623   -377    720       C
ATOM   10732  OE1  GLN B 577      33.772 -29.771  70.446  1.00144.10           O
ANISOU10732  OE1  GLN B 577    15864  24946  13943   -1214   -605    593       O
ATOM   10733  NE2  GLN B 577      34.196 -29.138  72.557  1.00143.07           N
ANISOU10733  NE2  GLN B 577    15543  24971  13848   -1824   -501    823       N
ATOM   10734  N    GLU B 578      37.448 -25.326  70.080  1.00148.00           N
ANISOU10734  N    GLU B 578    15584  27059  13589   -2171    977    522       N
ATOM   10735  CA   GLU B 578      38.888 -25.089  70.148  1.00150.47           C
ANISOU10735  CA   GLU B 578    15563  27888  13720   -2216   1132    426       C
ATOM   10736  C    GLU B 578      39.252 -23.600  70.139  1.00150.48           C
ANISOU10736  C    GLU B 578    15500  28105  13570   -2648   1627    462       C
ATOM   10737  O    GLU B 578      40.321 -23.216  70.613  1.00152.13           O
ANISOU10737  O    GLU B 578    15434  28714  13655   -2864   1784    418       O
ATOM   10738  CB   GLU B 578      39.628 -25.851  69.039  1.00152.91           C
ANISOU10738  CB   GLU B 578    15742  28434  13923   -1707   1005    250       C
ATOM   10739  CG   GLU B 578      41.136 -26.033  69.296  1.00155.77           C
ANISOU10739  CG   GLU B 578    15723  29325  14138   -1661   1025    150       C
ATOM   10740  CD   GLU B 578      41.897 -26.584  68.085  1.00158.34           C
ANISOU10740  CD   GLU B 578    15914  29919  14326   -1178    982    -32       C
ATOM   10741  OE1  GLU B 578      41.269 -27.225  67.210  1.00158.11           O
ANISOU10741  OE1  GLU B 578    16081  29635  14358    -803    804   -102       O
ATOM   10742  OE2  GLU B 578      43.130 -26.375  68.013  1.00160.73           O
ANISOU10742  OE2  GLU B 578    15907  30707  14454   -1180   1129   -113       O
ATOM   10743  N    ARG B 579      38.374 -22.765  69.595  1.00162.92           N
ANISOU10743  N    ARG B 579    17324  29422  15157   -2773   1879    545       N
ATOM   10744  CA   ARG B 579      38.600 -21.322  69.619  1.00162.94           C
ANISOU10744  CA   ARG B 579    17307  29551  15053   -3198   2369    600       C
ATOM   10745  C    ARG B 579      38.189 -20.777  70.979  1.00161.37           C
ANISOU10745  C    ARG B 579    17157  29189  14966   -3693   2451    711       C
ATOM   10746  O    ARG B 579      37.967 -19.573  71.142  1.00160.76           O
ANISOU10746  O    ARG B 579    17163  29047  14871   -4083   2842    783       O
ATOM   10747  CB   ARG B 579      37.791 -20.624  68.526  1.00162.02           C
ANISOU10747  CB   ARG B 579    17440  29209  14910   -3126   2620    672       C
ATOM   10748  CG   ARG B 579      38.602 -20.201  67.310  1.00164.23           C
ANISOU10748  CG   ARG B 579    17593  29830  14977   -2949   2882    588       C
ATOM   10749  CD   ARG B 579      39.465 -18.968  67.593  1.00165.54           C
ANISOU10749  CD   ARG B 579    17588  30290  15019   -3387   3343    598       C
ATOM   10750  NE   ARG B 579      38.711 -17.712  67.635  1.00164.19           N
ANISOU10750  NE   ARG B 579    17638  29848  14898   -3746   3738    754       N
ATOM   10751  CZ   ARG B 579      38.123 -17.144  66.583  1.00163.94           C
ANISOU10751  CZ   ARG B 579    17797  29667  14824   -3619   3965    849       C
ATOM   10752  NH1  ARG B 579      38.166 -17.724  65.389  1.00164.86           N
ANISOU10752  NH1  ARG B 579    17915  29888  14835   -3153   3829    790       N
ATOM   10753  NH2  ARG B 579      37.475 -15.997  66.727  1.00162.91           N
ANISOU10753  NH2  ARG B 579    17858  29285  14756   -3953   4333   1005       N
ATOM   10754  N    LYS B 580      38.100 -21.680  71.953  1.00145.71           N
ANISOU10754  N    LYS B 580    15122  27142  13099   -3668   2087    724       N
ATOM   10755  CA   LYS B 580      37.629 -21.359  73.304  1.00144.22           C
```

FIG. 13 Continued

```
ANISOU10755  CA  LYS B 580     14982  26794  13020  -4095   2093    828       C
ATOM  10756  C   LYS B 580       36.200 -20.803  73.223  1.00141.56           C
ANISOU10756  C   LYS B 580     14995  25969  12822  -4230   2213    968       C
ATOM  10757  O   LYS B 580       35.905 -19.697  73.684  1.00140.75           O
ANISOU10757  O   LYS B 580     14972  25780  12726  -4655   2553   1036       O
ATOM  10758  CB  LYS B 580       38.593 -20.416  74.057  1.00145.62           C
ANISOU10758  CB  LYS B 580     14918  27346  13064  -4571   2417    784       C
ATOM  10759  CG  LYS B 580       40.006 -20.985  74.362  1.00148.35           C
ANISOU10759  CG  LYS B 580     14880  28217  13270  -4481   2275    663       C
ATOM  10760  CD  LYS B 580       40.014 -22.491  74.642  1.00148.63           C
ANISOU10760  CD  LYS B 580     14852  28220  13399  -4074   1757    668       C
ATOM  10761  CE  LYS B 580       39.198 -22.879  75.868  1.00146.83           C
ANISOU10761  CE  LYS B 580     14740  27709  13340  -4257   1518    799       C
ATOM  10762  NZ  LYS B 580       38.869 -24.334  75.880  1.00146.73           N
ANISOU10762  NZ  LYS B 580     14776  27503  13472  -3809   1032    834       N
ATOM  10763  N   HIS B 581       35.319 -21.603  72.629  1.00146.54           N
ANISOU10763  N   HIS B 581     15826  26287  13565  -3857   1929   1003       N
ATOM  10764  CA  HIS B 581       33.936 -21.212  72.410  1.00144.23           C
ANISOU10764  CA  HIS B 581     15850  25555  13394  -3907   1999   1136       C
ATOM  10765  C   HIS B 581       32.922 -22.216  72.949  1.00142.54           C
ANISOU10765  C   HIS B 581     15796  24981  13380  -3776   1583   1214       C
ATOM  10766  O   HIS B 581       32.894 -23.376  72.536  1.00143.06           O
ANISOU10766  O   HIS B 581     15859  24999  13496  -3377   1217   1150       O
ATOM  10767  CB  HIS B 581       33.700 -20.986  70.917  1.00144.58           C
ANISOU10767  CB  HIS B 581     16013  25568  13355  -3599   2136   1114       C
ATOM  10768  CG  HIS B 581       34.135 -19.639  70.446  1.00145.41           C
ANISOU10768  CG  HIS B 581     16088  25845  13317  -3837   2646   1131       C
ATOM  10769  ND1 HIS B 581       35.427 -19.183  70.599  1.00147.46           N
ANISOU10769  ND1 HIS B 581     16085  26516  13428  -4016   2868   1032       N
ATOM  10770  CD2 HIS B 581       33.449 -18.638  69.847  1.00144.66           C
ANISOU10770  CD2 HIS B 581     16189  25563  13211  -3933   2988   1247       C
ATOM  10771  CE1 HIS B 581       35.520 -17.960  70.106  1.00147.94           C
ANISOU10771  CE1 HIS B 581     16191  26619  13401  -4225   3330   1080       C
ATOM  10772  NE2 HIS B 581       34.333 -17.606  69.644  1.00146.28           N
ANISOU10772  NE2 HIS B 581     16262  26043  13275  -4169   3414   1219       N
ATOM  10773  N   ILE B 582       32.098 -21.755  73.886  1.00135.89           N
ANISOU10773  N   ILE B 582     15091  23885  12656  -4123   1652   1348       N
ATOM  10774  CA  ILE B 582       31.021 -22.563  74.434  1.00134.18           C
ANISOU10774  CA  ILE B 582     15042  23308  12633  -4055   1303   1449       C
ATOM  10775  C   ILE B 582       29.998 -22.658  73.313  1.00133.18           C
ANISOU10775  C   ILE B 582     15156  22890  12555  -3770   1268   1485       C
ATOM  10776  O   ILE B 582       29.538 -21.633  72.832  1.00132.49           O
ANISOU10776  O   ILE B 582     15198  22716  12424  -3898   1608   1554       O
ATOM  10777  CB  ILE B 582       30.373 -21.894  75.694  1.00132.53           C
ANISOU10777  CB  ILE B 582     14916  22921  12516  -4527   1442   1585       C
ATOM  10778  CG1 ILE B 582       31.434 -21.578  76.776  1.00133.77           C
ANISOU10778  CG1 ILE B 582     14819  23427  12581  -4871   1550   1534       C
ATOM  10779  CG2 ILE B 582       29.232 -22.776  76.243  1.00130.85           C
ANISOU10779  CG2 ILE B 582     14872  22341  12504  -4447   1071   1701       C
ATOM  10780  CD1 ILE B 582       31.169 -20.332  77.635  1.00132.95           C
ANISOU10780  CD1 ILE B 582     14763  23281  12471  -5402   1926   1596       C
ATOM  10781  N   VAL B 583       29.640 -23.860  72.873  1.00150.60           N
ANISOU10781  N   VAL B 583     17422  24952  14849  -3386    872   1440       N
ATOM  10782  CA  VAL B 583       28.714 -23.953  71.742  1.00149.97           C
ANISOU10782  CA  VAL B 583     17548  24648  14785  -3114    837   1451       C
ATOM  10783  C   VAL B 583       27.812 -25.167  71.719  1.00149.31           C
ANISOU10783  C   VAL B 583     17604  24252  14876  -2861    396   1457       C
ATOM  10784  O   VAL B 583       28.267 -26.303  71.858  1.00150.48           O
ANISOU10784  O   VAL B 583     17659  24434  15083  -2629     57   1358       O
ATOM  10785  CB  VAL B 583       29.453 -23.960  70.390  1.00151.86           C
ANISOU10785  CB  VAL B 583     17700  25156  14846  -2782    931   1301       C
ATOM  10786  CG1 VAL B 583       28.497 -24.353  69.277  1.00151.51           C
ANISOU10786  CG1 VAL B 583     17848  24901  14818  -2455    791   1289       C
ATOM  10787  CG2 VAL B 583       30.080 -22.609  70.105  1.00152.46           C
ANISOU10787  CG2 VAL B 583     17697  25481  14749  -3015   1423   1322       C
ATOM  10788  N   GLY B 584       26.526 -24.906  71.516  1.00129.61           N
ANISOU10788  N   GLY B 584     15332  21450  12464  -2902    415   1576       N
ATOM  10789  CA  GLY B 584       25.542 -25.957  71.374  1.00129.03           C
ANISOU10789  CA  GLY B 584     15409  21068  12550  -2684     29   1580       C
```

FIG. 13 Continued

```
ATOM   10790  C    GLY B 584      25.091 -25.959  69.934  1.00129.53           C
ANISOU10790  C    GLY B 584    15577  21118  12520  -2372     50   1509        C
ATOM   10791  O    GLY B 584      25.087  24.907  69.291  1.00129.46           O
ANISOU10791  O    GLY B 584    15591  21230  12366  -2427    407   1555        O
ATOM   10792  N    MET B 585      24.738 -27.131  69.414  1.00139.02           N
ANISOU10792  N    MET B 585    16836  22184  13800  -2046   -321   1393        N
ATOM   10793  CA   MET B 585      24.232 -27.222  68.049  1.00139.66           C
ANISOU10793  CA   MET B 585    17017  22264  13784  -1747   -338   1308        C
ATOM   10794  C    MET B 585      23.140 -28.257  67.937  1.00139.34           C
ANISOU10794  C    MET B 585    17130  21902  13911  -1592   -722   1282        C
ATOM   10795  O    MET B 585      23.121 -29.241  68.668  1.00139.48           O
ANISOU10795  O    MET B 585    17145  21741  14110  -1581  -1042   1254        O
ATOM   10796  CB   MET B 585      25.323 -27.564  67.052  1.00142.05           C
ANISOU10796  CB   MET B 585    17177  22878  13916  -1413   -340   1087        C
ATOM   10797  CG   MET B 585      24.745 -28.040  65.738  1.00143.02           C
ANISOU10797  CG   MET B 585    17401  22973  13968  -1065   -481    958        C
ATOM   10798  SD   MET B 585      25.991 -28.702  64.636  1.00146.10           S
ANISOU10798  SD   MET B 585    17627  23701  14182   -637   -557    663        S
ATOM   10799  CE   MET B 585      27.152 -29.391  65.813  1.00146.88           C
ANISOU10799  CE   MET B 585    17543  23856  14409   -693   -723    609        C
ATOM   10800  N    THR B 586      22.238 -28.024  66.998  1.00134.83           N
ANISOU10800  N    THR B 586    16687  21270  13272  -1471   -684   1296        N
ATOM   10801  CA   THR B 586      21.103 -28.895  66.792  1.00134.63           C
ANISOU10801  CA   THR B 586    16808  20960  13385  -1350  -1019   1268        C
ATOM   10802  C    THR B 586      21.509 -30.262  66.263  1.00136.78           C
ANISOU10802  C    THR B 586    17050  21219  13703   -999  -1384   1005        C
ATOM   10803  O    THR B 586      22.637 -30.455  65.806  1.00138.55           O
ANISOU10803  O    THR B 586    17140  21695  13809   -795  -1350    836        O
ATOM   10804  CB   THR B 586      20.147 -28.263  65.784  1.00134.29           C
ANISOU10804  CB   THR B 586    16876  20936  13212  -1278   -867   1333        C
ATOM   10805  OG1  THR B 586      20.267 -26.835  65.848  1.00133.28           O
ANISOU10805  OG1  THR B 586    16731  20953  12957  -1494   -418   1520        O
ATOM   10806  CG2  THR B 586      18.711 -28.691  66.065  1.00133.11           C
ANISOU10806  CG2  THR B 586    16884  20459  13233  -1358  -1102   1430        C
ATOM   10807  N    GLY B 587      20.568 -31.199  66.322  1.00137.99           N
ANISOU10807  N    GLY B 587    17329  21071  14031   -936  -1724    967        N
ATOM   10808  CA   GLY B 587      20.748 -32.545  65.811  1.00140.17           C
ANISOU10808  CA   GLY B 587    17614  21259  14386   -616  -2082    711        C
ATOM   10809  C    GLY B 587      19.377 -33.122  65.514  1.00139.97           C
ANISOU10809  C    GLY B 587    17757  20947  14479   -591  -2334    696        C
ATOM   10810  O    GLY B 587      18.370 -32.561  65.940  1.00138.01           O
ANISOU10810  O    GLY B 587    17599  20557  14282   -841  -2258    910        O
ATOM   10811  N    ASP B 588      19.330 -34.230  64.781  1.00136.47           N
ANISOU10811  N    ASP B 588    17351  20424  14076   -297  -2626    435        N
ATOM   10812  CA   ASP B 588      18.064 -34.869  64.434  1.00136.74           C
ANISOU10812  CA   ASP B 588    17534  20199  14222   -270  -2891    376        C
ATOM   10813  C    ASP B 588      18.346 -36.252  63.835  1.00139.61           C
ANISOU10813  C    ASP B 588    17919  20455  14670     48  -3219     49        C
ATOM   10814  O    ASP B 588      17.686 -37.242  64.148  1.00140.22           O
ANISOU10814  O    ASP B 588    18103  20194  14981     33  -3532     -9        O
ATOM   10815  CB   ASP B 588      17.270 -34.056  63.426  1.00136.30           C
ANISOU10815  CB   ASP B 588    17521  20326  13940   -250  -2705    415        C
ATOM   10816  CG   ASP B 588      18.123 -33.570  62.263  1.00137.80           C
ANISOU10816  CG   ASP B 588    17608  20917  13832      6  -2483    263        C
ATOM   10817  OD1  ASP B 588      19.268 -33.129  62.507  1.00137.81           O
ANISOU10817  OD1  ASP B 588    17488  21119  13756      8   2277    284        O
ATOM   10818  OD2  ASP B 588      17.647 -33.616  61.105  1.00139.08           O
ANISOU10818  OD2  ASP B 588    17800  21217  13827    197  -2511    126        O
ATOM   10819  N    GLY B 589      19.345 -36.275  62.961  1.00155.57           N
ANISOU10819  N    GLY B 589    19840  22770  16501    333  -3129   -168        N
ATOM   10820  CA   GLY B 589      19.771 -37.481  62.288  1.00158.62           C
ANISOU10820  CA   GLY B 589    20233  23102  16935    670  -3389   -510        C
ATOM   10821  C    GLY B 589      20.504 -38.419  63.217  1.00159.58           C
ANISOU10821  C    GLY B 589    20321  23001  17310    714  -3588   -538        C
ATOM   10822  O    GLY B 589      21.038 -38.010  64.249  1.00158.14           O
ANISOU10822  O    GLY B 589    20056  22841  17187    530  -3471   -320        O
ATOM   10823  N    VAL B 590      20.523 -39.688  62.828  1.00149.80           N
ANISOU10823  N    VAL B 590    19147  21553  16217    966  -3887   -814        N
ATOM   10824  CA   VAL B 590      21.146 -40.748  63.599  1.00151.31           C
```

FIG. 13 Continued

```
ANISOU10824  CA   VAL B 590     19327  21490  16675    1065  -4109   -859        C
ATOM  10825  C    VAL B 590     22.666 -40.695  63.464  1.00152.81              C
ANISOU10825  C    VAL B 590     19333  21989  16738    1304  -3971   -958        C
ATOM  10826  O    VAL B 590     23.393 -40.972  64.416  1.00152.94              O
ANISOU10826  O    VAL B 590     19264  21949  16896    1291  -4007   -838        O
ATOM  10827  CB   VAL B 590     20.595 -42.111  63.163  1.00153.96              C
ANISOU10827  CB   VAL B 590     19810  21467  17222    1254  -4456  -1133        C
ATOM  10828  CG1  VAL B 590     21.211 -42.527  61.842  1.00157.02              C
ANISOU10828  CG1  VAL B 590     20160  22066  17435    1644  -4464  -1519        C
ATOM  10829  CG2  VAL B 590     20.832 -43.145  64.241  1.00154.93              C
ANISOU10829  CG2  VAL B 590     19969  21207  17691    1250  -4696  -1062        C
ATOM  10830  N    ASN B 591     23.146 -40.337  62.278  1.00152.06              N
ANISOU10830  N    ASN B 591     19164  22245  16365    1534  -3813  -1169        N
ATOM  10831  CA   ASN B 591     24.573 -40.145  62.091  1.00153.39              C
ANISOU10831  CA   ASN B 591     19140  22765  16378    1743  -3645  -1250        C
ATOM  10832  C    ASN B 591     24.968 -38.954  62.938  1.00150.69              C
ANISOU10832  C    ASN B 591     18674  22643  15940    1438  -3356   -926        C
ATOM  10833  O    ASN B 591     26.056 -38.906  63.488  1.00151.18              O
ANISOU10833  O    ASN B 591     18573  22871  15997    1470  -3277   -873        O
ATOM  10834  CB   ASN B 591     24.917 -39.827  60.632  1.00155.06              C
ANISOU10834  CB   ASN B 591     19293  23348  16275    2009  -3493  -1507        C
ATOM  10835  CG   ASN B 591     24.897 -41.049  59.736  1.00158.49              C
ANISOU10835  CG   ASN B 591     19804  23646  16769    2371  -3750  -1896        C
ATOM  10836  OD1  ASN B 591     25.676 -41.147  58.788  1.00160.81              O
ANISOU10836  OD1  ASN B 591     20001  24238  16864    2678  -3671  -2148        O
ATOM  10837  ND2  ASN B 591     23.999 -41.980  60.022  1.00158.98              N
ANISOU10837  ND2  ASN B 591     20042  23260  17105    2329  -4050  -1955        N
ATOM  10838  N    ASP B 592     24.056 -37.996  63.051  1.00151.07              N
ANISOU10838  N    ASP B 592     18795  22691  15913    1136  -3198   -713        N
ATOM  10839  CA   ASP B 592     24.327 -36.745  63.747  1.00148.58              C
ANISOU10839  CA   ASP B 592     18382  22581  15489     825  -2884   -426        C
ATOM  10840  C    ASP B 592     24.795 -36.861  65.189  1.00147.67              C
ANISOU10840  C    ASP B 592     18191  22356  15560     619  -2925   -223        C
ATOM  10841  O    ASP B 592     25.227 -35.876  65.785  1.00146.07              O
ANISOU10841  O    ASP B 592     17880  22363  15258     375  -2660    -27        O
ATOM  10842  CB   ASP B 592     23.109 -35.834  63.676  1.00146.06              C
ANISOU10842  CB   ASP B 592     18186  22200  15109     551  -2740   -231        C
ATOM  10843  CG   ASP B 592     23.032 -35.088  62.370  1.00146.51              C
ANISOU10843  CG   ASP B 592     18229  22570  14867     682  -2511   -322        C
ATOM  10844  OD1  ASP B 592     23.088 -33.841  62.404  1.00144.87              O
ANISOU10844  OD1  ASP B 592     17973  22576  14493     487  -2173   -125        O
ATOM  10845  OD2  ASP B 592     22.939 -35.747  61.309  1.00148.69              O
ANISOU10845  OD2  ASP B 592     18542  22883  15071     983  -2661   -591        O
ATOM  10846  N    ALA B 593     24.723 -38.055  65.754  1.00146.64              N
ANISOU10846  N    ALA B 593     18115  21907  15696     714  -3249   -268        N
ATOM  10847  CA   ALA B 593     25.110 -38.217  67.143  1.00145.96              C
ANISOU10847  CA   ALA B 593     17953  21725  15781     526  -3307    -54        C
ATOM  10848  C    ALA B 593     26.380 -37.432  67.500  1.00145.88              C
ANISOU10848  C    ALA B 593     17710  22132  15587     464  -3035     23        C
ATOM  10849  O    ALA B 593     26.309 -36.480  68.277  1.00143.66              O
ANISOU10849  O    ALA B 593     17381  21949  15253     117  -2826    256        O
ATOM  10850  CB   ALA B 593     25.251 -39.685  67.494  1.00148.28              C
ANISOU10850  CB   ALA B 593     18288  21702  16349     751  -3665   -153        C
ATOM  10851  N    PRO B 594     27.526 -37.794  66.889  1.00149.84              N
ANISOU10851  N    PRO B 594     18062  22892  15979     793  -3020   -187        N
ATOM  10852  CA   PRO B 594     28.863 -37.241  67.165  1.00150.46              C
ANISOU10852  CA   PRO B 594     17889  23390  15889     786  -2798   -154        C
ATOM  10853  C    PRO B 594     28.888 -35.755  67.466  1.00148.02              C
ANISOU10853  C    PRO B 594     17511  23342  15388     413  -2431     40        C
ATOM  10854  O    PRO B 594     29.583 -35.325  68.386  1.00147.59              O
ANISOU10854  O    PRO B 594     17293  23477  15307     207  -2309    187        O
ATOM  10855  CB   PRO B 594     29.613 -37.499  65.861  1.00153.07              C
ANISOU10855  CB   PRO B 594     18139  23980  16042    1187  -2754   -451        C
ATOM  10856  CG   PRO B 594     29.019 -38.747  65.351  1.00154.81              C
ANISOU10856  CG   PRO B 594     18529  23842  16450    1475  -3083   -653        C
ATOM  10857  CD   PRO B 594     27.559 -38.708  65.734  1.00152.49              C
ANISOU10857  CD   PRO B 594     18462  23159  16319    1203  -3198   -502        C
ATOM  10858  N    ALA B 595     28.153 -34.980  66.683  1.00221.60              N
ANISOU10858  N    ALA B 595     26947  32680  24572     330  -2248     38        N
```

FIG. 13 Continued

```
ATOM   10859  CA   ALA B 595      28.088 -33.552  66.912  1.00219.46           C
ANISOU10859  CA   ALA B 595    26639  32606  24139    -17  -1880    225        C
ATOM   10860  C    ALA B 595      27.541 -33.328  68.307  1.00217.26           C
ANISOU10860  C    ALA B 595    26408  32107  24033   -400  -1910    482        C
ATOM   10861  O    ALA B 595      28.246 -32.840  69.190  1.00216.88           O
ANISOU10861  O    ALA B 595    26207  32248  23951   -625  -1764    601        O
ATOM   10862  CB   ALA B 595      27.193 -32.899  65.886  1.00218.50           C
ANISOU10862  CB   ALA B 595    26666  32468  23887    -17  -1725    211        C
ATOM   10863  N    LEU B 596      26.288 -33.727  68.498  1.00139.98           N
ANISOU10863  N    LEU B 596    16826  21936  14426   -473  -2109    555        N
ATOM   10864  CA   LEU B 596      25.587 -33.551  69.765  1.00137.88           C
ANISOU10864  CA   LEU B 596    16629  21433  14326   -831  -2151    801        C
ATOM   10865  C    LEU B 596      26.421 -33.902  71.004  1.00138.42           C
ANISOU10865  C    LEU B 596    16536  21571  14486   -939  -2238    897        C
ATOM   10866  O    LEU B 596      26.574 -33.092  71.926  1.00137.00           O
ANISOU10866  O    LEU B 596    16281  21509  14266  -1283  -2041   1074        O
ATOM   10867  CB   LEU B 596      24.305 -34.372  69.745  1.00137.42           C
ANISOU10867  CB   LEU B 596    16784  20946  14482   -789  -2456    813        C
ATOM   10868  CG   LEU B 596      23.364 -33.979  68.605  1.00136.83           C
ANISOU10868  CG   LEU B 596    16859  20824  14307   -719  -2376    745        C
ATOM   10869  CD1  LEU B 596      22.154 -34.905  68.519  1.00136.84           C
ANISOU10869  CD1  LEU B 596    17050  20427  14515   -660  -2703    718        C
ATOM   10870  CD2  LEU B 596      22.917 -32.533  68.762  1.00134.47           C
ANISOU10870  CD2  LEU B 596    16582  20635  13873  -1043  -2010    946        C
ATOM   10871  N    LYS B 597      26.960 -35.111  71.027  1.00139.33           N
ANISOU10871  N    LYS B 597    16596  21621  14722   -641  -2528    779        N
ATOM   10872  CA   LYS B 597      27.781 -35.520  72.148  1.00140.24           C
ANISOU10872  CA   LYS B 597    16542  21827  14914   -695  -2628    881        C
ATOM   10873  C    LYS B 597      28.967 -34.559  72.293  1.00140.49           C
ANISOU10873  C    LYS B 597    16333  22341  14708   -821  -2309    886        C
ATOM   10874  O    LYS B 597      29.119 -33.915  73.323  1.00139.30           O
ANISOU10874  O    LYS B 597    16092  22308  14527  -1167  -2170   1063        O
ATOM   10875  CB   LYS B 597      28.235 -36.977  71.980  1.00143.08           C
ANISOU10875  CB   LYS B 597    16879  22047  15436   -292  -2968    741        C
ATOM   10876  CG   LYS B 597      28.311 -37.788  73.290  1.00143.65           C
ANISOU10876  CG   LYS B 597    16910  21941  15729   -359  -3218    925        C
ATOM   10877  CD   LYS B 597      28.129 -39.292  73.037  1.00146.01           C
ANISOU10877  CD   LYS B 597    17317  21884  16276      6  -3586    814        C
ATOM   10878  CE   LYS B 597      28.588 -40.149  74.210  1.00147.50           C
ANISOU10878  CE   LYS B 597    17405  21989  16650     39  -3809    985        C
ATOM   10879  NZ   LYS B 597      27.800 -39.903  75.439  1.00145.35           N
ANISOU10879  NZ   LYS B 597    17196  21542  16489   -357  -3845   1275        N
ATOM   10880  N    LYS B 598      29.780 -34.418  71.253  1.00151.72           N
ANISOU10880  N    LYS B 598    17647  24049  15948   -563  -2179    687        N
ATOM   10881  CA   LYS B 598      30.951 -33.551  71.374  1.00152.26           C
ANISOU10881  CA   LYS B 598    17473  24587  15794   -684  -1880    684        C
ATOM   10882  C    LYS B 598      30.619 -32.093  71.635  1.00149.91           C
ANISOU10882  C    LYS B 598    17197  24399  15364  -1115  -1511    822        C
ATOM   10883  O    LYS B 598      31.078 -31.537  72.625  1.00149.44           O
ANISOU10883  O    LYS B 598    16997  24521  15261  -1426  -1372    947        O
ATOM   10884  CB   LYS B 598      31.906 -33.669  70.177  1.00154.63           C
ANISOU10884  CB   LYS B 598    17642  25193  15915   -320  -1798    445        C
ATOM   10885  CG   LYS B 598      33.268 -32.944  70.385  1.00155.74           C
ANISOU10885  CG   LYS B 598    17489  25847  15839   -424  -1526    436        C
ATOM   10886  CD   LYS B 598      33.704 -32.978  71.855  1.00155.62           C
ANISOU10886  CD   LYS B 598    17315  25920  15892   -689  -1581    612        C
ATOM   10887  CE   LYS B 598      35.021 -32.266  72.106  1.00156.87           C
ANISOU10887  CE   LYS B 598    17169  26602  15832   -825  -1320    595        C
ATOM   10888  NZ   LYS B 598      36.179 -33.185  71.966  1.00160.02           N
ANISOU10888  NZ   LYS B 598    17337  27253  16208   -445  -1495    473        N
ATOM   10889  N    ALA B 599      29.849 -31.470  70.749  1.00202.21           N
ANISOU10889  N    ALA B 599    23989  30925  21917  -1131  -1344    798        N
ATOM   10890  CA   ALA B 599      29.500 -30.066  70.928  1.00200.20           C
ANISOU10890  CA   ALA B 599    23775  30741  21552  -1515   -970    936        C
ATOM   10891  C    ALA B 599      29.230 -29.812  72.403  1.00198.67           C
ANISOU10891  C    ALA B 599    23570  30445  21472  -1911   -972   1136        C
ATOM   10892  O    ALA B 599      28.667 -30.675  73.080  1.00198.31           O
ANISOU10892  O    ALA B 599    23604  30119  21625  -1897  -1282   1212        O
ATOM   10893  CB   ALA B 599      28.287 -29.711  70.096  1.00198.77           C
```

FIG. 13 Continued

```
ANISOU10893  CB  ALA B 599    23831  30318  21374  -1489   -906    958       C
ATOM  10894  N   ASP B 600    29.644  28.648  72.904  1.00137.55             N
ANISOU10894  N   ASP B 600    15727  22932  13603  -2269   -626   1216       N
ATOM  10895  CA  ASP B 600    29.454 -28.330  74.318  1.00136.31             C
ANISOU10895  CA  ASP B 600    15543  22726  13524  -2668   -599   1386       C
ATOM  10896  C   ASP B 600    28.082 -28.786  74.766  1.00134.50             C
ANISOU10896  C   ASP B 600    15542  22055  13506  -2730   -826   1522       C
ATOM  10897  O   ASP B 600    27.949 -29.712  75.579  1.00134.74             O
ANISOU10897  O   ASP B 600    15560  21942  13693  -2704  -1139   1589       O
ATOM  10898  CB  ASP B 600    29.605 -26.834  74.564  1.00135.36             C
ANISOU10898  CB  ASP B 600    15388  22781  13261  -3073   -145   1447       C
ATOM  10899  CG  ASP B 600    31.042 -26.409  74.608  1.00137.24             C
ANISOU10899  CG  ASP B 600    15353  23481  13312  -3135     59   1346       C
ATOM  10900  OD1 ASP B 600    31.324 -25.258  74.234  1.00137.19             O
ANISOU10900  OD1 ASP B 600    15321  23644  13159  -3329    451   1328       O
ATOM  10901  OD2 ASP B 600    31.895 -27.231  75.007  1.00138.96             O
ANISOU10901  OD2 ASP B 600    15373  23893  13530  -2986   -170   1291       O
ATOM  10902  N   ILE B 601    27.064 -28.134  74.219  1.00131.31             N
ANISOU10902  N   ILE B 601    15340  21448  13105  -2806   -662   1574       N
ATOM  10903  CA  ILE B 601    25.694 -28.507  74.500  1.00129.66             C
ANISOU10903  CA  ILE B 601    15347  20835  13081  -2855   -857   1697       C
ATOM  10904  C   ILE B 601    25.311 -29.607  73.514  1.00130.63             C
ANISOU10904  C   ILE B 601    15572  20774  13286  -2432  -1173   1570       C
ATOM  10905  O   ILE B 601    26.171 -30.380  73.081  1.00132.68             O
ANISOU10905  O   ILE B 601    15716  21177  13519  -2126  -1337   1413       O
ATOM  10906  CB  ILE B 601    24.728 -27.316  74.397  1.00127.61             C
ANISOU10906  CB  ILE B 601    15249  20447  12792   3122    539   1823       C
ATOM  10907  CG1 ILE B 601    25.467 -25.987  74.607  1.00127.59             C
ANISOU10907  CG1 ILE B 601    15131  20731  12618  -3415    -93   1837       C
ATOM  10908  CG2 ILE B 601    23.568 -27.493  75.372  1.00125.83             C
ANISOU10908  CG2 ILE B 601    15164  19895  12752  -3352   -684   2003       C
ATOM  10909  CD1 ILE B 601    26.331 -25.919  75.837  1.00128.12             C
ANISOU10909  CD1 ILE B 601    15005  21008  12666  -3683    -70   1859       C
ATOM  10910  N   GLY B 602    24.031 -29.678  73.154  1.00129.17             N
ANISOU10910  N   GLY B 602    15599  20284  13197  -2416  -1253   1629       N
ATOM  10911  CA  GLY B 602    23.559 -30.732  72.272  1.00130.18             C
ANISOU10911  CA  GLY B 602    15833  20219  13409  -2055  -1561   1496       C
ATOM  10912  C   GLY B 602    22.065 -30.698  72.059  1.00128.63             C
ANISOU10912  C   GLY B 602    15853  19706  13315  -2117  -1632   1591       C
ATOM  10913  O   GLY B 602    21.351 -31.669  72.295  1.00128.70             O
ANISOU10913  O   GLY B 602    15964  19422  13515  -2049  -1960   1602       O
ATOM  10914  N   ILE B 603    21.608 -29.549  71.600  1.00128.33             N
ANISOU10914  N   ILE B 603    15877  19736  13147  -2248  -1308   1666       N
ATOM  10915  CA  ILE B 603    20.206 -29.309  71.339  1.00126.91             C
ANISOU10915  CA  ILE B 603    15880  19315  13025  -2314  -1311   1776       C
ATOM  10916  C   ILE B 603    19.657 -30.266  70.281  1.00128.10             C
ANISOU10916  C   ILE B 603    16125  19338  13210  -1972  -1604   1617       C
ATOM  10917  O   ILE B 603    20.263 -30.444  69.222  1.00129.75             O
ANISOU10917  O   ILE B 603    16280  19741  13280  -1681  -1594   1427       O
ATOM  10918  CB  ILE B 603    20.036 -27.879  70.825  1.00126.00             C
ANISOU10918  CB  ILE B 603    15790  19353  12730  -2439   -874   1868       C
ATOM  10919  CG1 ILE B 603    21.348  27.093  70.991  1.00126.60             C
ANISOU10919  CG1 ILE B 603    15701  19750  12652  -2545   -558   1836       C
ATOM  10920  CG2 ILE B 603    18.854 -27.212  71.494  1.00123.90             C
ANISOU10920  CG2 ILE B 603    15653  18867  12557  -2741   -751   2098       C
ATOM  10921  CD1 ILE B 603    21.752 -26.821  72.415  1.00125.81             C
ANISOU10921  CD1 ILE B 603    15517  19660  12627  -2892   -487   1943       C
ATOM  10922  N   ALA B 604    18.500 -30.865  70.551  1.00125.64             N
ANISOU10922  N   ALA B 604    15948  18715  13076  -2018  -1857   1686       N
ATOM  10923  CA  ALA B 604    17.895 -31.782  69.589  1.00126.92             C
ANISOU10923  CA  ALA B 604    16202  18743  13278  -1732  -2141   1522       C
ATOM  10924  C   ALA B 604    16.378 -31.627  69.540  1.00125.59             C
ANISOU10924  C   ALA B 604    16184  18352  13184  -1858  -2192   1657       C
ATOM  10925  O   ALA B 604    15.673 -32.222  70.351  1.00124.97             O
ANISOU10925  O   ALA B 604    16175  17995  13314  -2005  -2420   1754       O
ATOM  10926  CB  ALA B 604    18.264 -33.210  69.932  1.00128.54             C
ANISOU10926  CB  ALA B 604    16393  18773  13674  -1572  -2529   1386       C
ATOM  10927  N   VAL B 605    15.877 -30.852  68.577  1.00126.72             N
ANISOU10927  N   VAL B 605    16368  18629  13151  -1792  -1983   1673       N
```

FIG. 13 Continued

```
ATOM   10928  CA   VAL B 605      14.438 -30.572  68.481  1.00125.56           C
ANISOU 10928  CA   VAL B 605     16341  18322  13044  -1904  -1992   1823      C
ATOM   10929  C    VAL B 605      13.588 -31.819  68.237  1.00126.57           C
ANISOU 10929  C    VAL B 605     16556  18206  13328  -1784  -2409   1704      C
ATOM   10930  O    VAL B 605      13.986 -32.706  67.496  1.00128.59           O
ANISOU 10930  O    VAL B 605     16799  18488  13570  -1510  -2628   1453      O
ATOM   10931  CB   VAL B 605      14.143 -29.527  67.398  1.00125.54           C
ANISOU 10931  CB   VAL B 605     16348  18548  12802  -1809  -1686   1867      C
ATOM   10932  CG1  VAL B 605      15.068 -29.742  66.217  1.00127.61           C
ANISOU 10932  CG1  VAL B 605     16534  19080  12873  -1480  -1672   1624      C
ATOM   10933  CG2  VAL B 605      12.671 -29.577  66.984  1.00125.19           C
ANISOU 10933  CG2  VAL B 605     16409  18376  12781  -1808  -1795   1951      C
ATOM   10934  N    ALA B 606      12.409 -31.865  68.852  1.00123.97           N
ANISOU 10934  N    ALA B 606     16314  17642  13147  -1996  -2506   1878      N
ATOM   10935  CA   ALA B 606      11.527 -33.030  68.762  1.00124.92           C
ANISOU 10935  CA   ALA B 606     16518  17503  13442  -1943  -2897   1787      C
ATOM   10936  C    ALA B 606      11.393 -33.603  67.366  1.00127.07           C
ANISOU 10936  C    ALA B 606     16807  17872  13601  -1629  -3057   1522      C
ATOM   10937  O    ALA B 606      11.678 -32.937  66.371  1.00127.55           O
ANISOU 10937  O    ALA B 606     16826  18218  13418  -1462  -2842   1460      O
ATOM   10938  CB   ALA B 606      10.150 -32.731  69.338  1.00123.31           C
ANISOU 10938  CB   ALA B 606     16392  17117  13343  -2201  -2905   2023      C
ATOM   10939  N    ASP B 607      10.928 -34.847  67.320  1.00149.38           N
ANISOU 10939  N    ASP B 607     19698  20454  16607  -1563  -3433   1370      N
ATOM   10940  CA   ASP B 607      10.836 -35.590  66.083  1.00151.82           C
ANISOU 10940  CA   ASP B 607     20028  20819  16839  -1277  -3633   1070      C
ATOM   10941  C    ASP B 607      12.271 -35.847  65.649  1.00153.38           C
ANISOU 10941  C    ASP B 607     20146  21189  16944  -1018  -3595    849      C
ATOM   10942  O    ASP B 607      12.522 -36.338  64.553  1.00155.59           O
ANISOU 10942  O    ASP B 607     20418  21590  17110   -739  -3696    570      O
ATOM   10943  CB   ASP B 607      10.063 -34.799  65.025  1.00151.75           C
ANISOU 10943  CB   ASP B 607     20017  21057  16583  -1211  -3469   1096      C
ATOM   10944  CG   ASP B 607       9.434 -35.696  63.963  1.00154.16           C
ANISOU 10944  CG   ASP B 607     20365  21351  16858  -1017  -3755    823      C
ATOM   10945  OD1  ASP B 607       9.628 -36.931  64.044  1.00155.93           O
ANISOU 10945  OD1  ASP B 607     20633  21345  17270   -936  -4068    598      O
ATOM   10946  OD2  ASP B 607       8.745 -35.169  63.052  1.00154.47           O
ANISOU 10946  OD2  ASP B 607     20392  21613  16688   -947  -3662    832      O
ATOM   10947  N    ALA B 608      13.210 -35.506  66.531  1.00149.51           N
ANISOU 10947  N    ALA B 608     19585  20728  16493  -1117  -3444    971      N
ATOM   10948  CA   ALA B 608      14.640 -35.695  66.275  1.00150.91           C
ANISOU 10948  CA   ALA B 608     19662  21089  16588   -896  -3389    796      C
ATOM   10949  C    ALA B 608      15.021 -37.161  66.349  1.00153.23           C
ANISOU 10949  C    ALA B 608     19983  21148  17090   -711  -3748    567      C
ATOM   10950  O    ALA B 608      16.205 -37.500  66.362  1.00154.54           O
ANISOU 10950  O    ALA B 608     20062  21410  17246   -533  -3749    440      O
ATOM   10951  CB   ALA B 608      15.471 -34.902  67.264  1.00149.25           C
ANISOU 10951  CB   ALA B 608     19357  20991  16362  -1088  -3132   1002      C
ATOM   10952  N    THR B 609      14.004 -38.017  66.396  1.00138.68           N
ANISOU 10952  N    THR B 609     18258  18996  15439   -754  -4041    520      N
ATOM   10953  CA   THR B 609      14.171 -39.460  66.506  1.00141.07           C
ANISOU 10953  CA   THR B 609     18618  18997  15984   -607  -4391    318      C
ATOM   10954  C    THR B 609      14.681 -39.812  67.889  1.00140.46           C
ANISOU 10954  C    THR B 609     18514  18720  16135   -751  -4459    507      C
ATOM   10955  O    THR B 609      15.418 -39.047  68.517  1.00138.98           O
ANISOU 10955  O    THR B 609     18220  18725  15861   -854  -4229    680      O
ATOM   10956  CB   THR B 609      15.136 -40.022  65.455  1.00143.89           C
ANISOU 10956  CB   THR B 609     18929  19512  16231   -224  -4441    -32      C
ATOM   10957  OG1  THR B 609      16.465 -39.881  65.914  1.00144.01           O
ANISOU 10957  OG1  THR B 609     18821  19677  16219   -135  -4313     -2      O
ATOM   10958  CG2  THR B 609      14.975 -39.292  64.135  1.00144.14           C
ANISOU 10958  CG2  THR B 609     18930  19896  15941    -83  -4256   -164      C
ATOM   10959  N    ASP B 610      14.282 -40.981  68.362  1.00157.16           N
ANISOU 10959  N    ASP B 610     20721  20452  18538   -765  -4774    473      N
ATOM   10960  CA   ASP B 610      14.653 -41.424  69.696  1.00156.87           C
ANISOU 10960  CA   ASP B 610     20666  20206  18733   -899  -4871    675      C
ATOM   10961  C    ASP B 610      16.111 -41.887  69.791  1.00158.71           C
ANISOU 10961  C    ASP B 610     20792  20534  18976   -641  -4881    560      C
ATOM   10962  O    ASP B 610      16.575 -42.278  70.857  1.00158.85           O
```

FIG. 13 Continued

```
ANISOU10962  O    ASP B 610      20768  20426  19161   -708  -4958    724          O
ATOM  10963  CB   ASP B 610       13.681 -42.508  70.168  1.00157.87              C
ANISOU10963  CB   ASP B 610      20932  19879  19174  -1008  -5195    705          C
ATOM  10964  CG   ASP B 610       12.228 -42.127  69.922  1.00156.49              C
ANISOU10964  CG   ASP B 610      20847  19638  18975  -1230  -5204    778          C
ATOM  10965  OD1  ASP B 610       11.817 -42.051  68.742  1.00157.35              O
ANISOU10965  OD1  ASP B 610      20988  19862  18935  -1095  -5204    557          O
ATOM  10966  OD2  ASP B 610       11.498 -41.895  70.908  1.00154.68              O
ANISOU10966  OD2  ASP B 610      20644  19264  18862  -1535  -5207   1061          O
ATOM  10967  N    ALA B 611       16.830 -41.839  68.673  1.00141.88              N
ANISOU10967  N    ALA B 611      18606  18649  16653   -340  -4800    287          N
ATOM  10968  CA   ALA B 611       18.234 -42.240  68.642  1.00143.82              C
ANISOU10968  CA   ALA B 611      18733  19029  16882    -66  -4793    160          C
ATOM  10969  C    ALA B 611       19.086 -41.044  68.955  1.00141.96              C
ANISOU10969  C    ALA B 611      18329  19200  16410   -163  -4463    317          C
ATOM  10970  O    ALA B 611       19.939 -41.079  69.833  1.00142.00              O
ANISOU10970  O    ALA B 611      18219  19269  16465   -192  -4433    451          O
ATOM  10971  CB   ALA B 611       18.603 -42.779  67.272  1.00146.60              C
ANISOU10971  CB   ALA B 611      19101  19464  17135    307  -4858   -226          C
ATOM  10972  N    ALA B 612       18.842 -39.978  68.210  1.00145.75              N
ANISOU10972  N    ALA B 612      18791  19961  16627   -215  -4211    302          N
ATOM  10973  CA   ALA B 612       19.583 -38.753  68.389  1.00144.12              C
ANISOU10973  CA   ALA B 612      18438  20133  16188   -326  -3865    436          C
ATOM  10974  C    ALA B 612       19.537 -38.321  69.849  1.00142.01              C
ANISOU10974  C    ALA B 612      18130  19803  16025   -671  -3795    757          C
ATOM  10975  O    ALA B 612       20.577 -38.080  70.467  1.00142.08              O
ANISOU10975  O    ALA B 612      17989  20007  15987    696   3681    830          O
ATOM  10976  CB   ALA B 612       19.025 -37.664  67.483  1.00142.76              C
ANISOU10976  CB   ALA B 612      18291  20188  15763   -382  -3611    434          C
ATOM  10977  N    ARG B 613       18.336 -38.249  70.411  1.00135.80              N
ANISOU10977  N    ARG B 613      17465  18762  15372   -937  -3868    941          N
ATOM  10978  CA   ARG B 613       18.192 -37.803  71.786  1.00133.82              C
ANISOU10978  CA   ARG B 613      17180  18459  15204  -1280  -3793   1242          C
ATOM  10979  C    ARG B 613       19.272 -38.399  72.684  1.00135.07              C
ANISOU10979  C    ARG B 613      17215  18637  15469  -1227  -3896   1288          C
ATOM  10980  O    ARG B 613       19.824 -37.712  73.533  1.00133.91              O
ANISOU10980  O    ARG B 613      16946  18689  15244  -1431  -3710   1459          O
ATOM  10981  CB   ARG B 613       16.817 -38.162  72.330  1.00132.79              C
ANISOU10981  CB   ARG B 613      17200  17972  15281  -1498  -3980   1396          C
ATOM  10982  CG   ARG B 613       15.668 -37.726  71.457  1.00131.90              C
ANISOU10982  CG   ARG B 613      17203  17830  15085  -1531  -3926   1354          C
ATOM  10983  CD   ARG B 613       14.434 -37.507  72.313  1.00129.95              C
ANISOU10983  CD   ARG B 613      17044  17359  14971  -1867  -3959   1610          C
ATOM  10984  NE   ARG B 613       13.192 -37.767  71.591  1.00130.14              N
ANISOU10984  NE   ARG B 613      17196  17218  15033  -1849  -4094   1541          N
ATOM  10985  CZ   ARG B 613       12.527 -36.858  70.885  1.00128.98              C
ANISOU10985  CZ   ARG B 613      17072  17232  14701  -1890  -3893   1564          C
ATOM  10986  NH1  ARG B 613       12.993 -35.616  70.794  1.00127.54              N
ANISOU10986  NH1  ARG B 613      16812  17349  14404  -1951  -3534   1654          N
ATOM  10987  NH2  ARG B 613       11.398 -37.190  70.265  1.00129.44              N
ANISOU10987  NH2  ARG B 613      17228  17157  14796  -1871  -4048   1500          N
ATOM  10988  N    GLY B 614       19.587  39.672  72.463  1.00138.17              N
ANISOU10988  N    GLY B 614      17634  18835  16030   -944  -4184   1128          N
ATOM  10989  CA   GLY B 614       20.549 -40.403  73.276  1.00139.83              C
ANISOU10989  CA   GLY B 614      17733  19029  16368   -843  -4320   1182          C
ATOM  10990  C    GLY B 614       21.926 -39.807  73.535  1.00140.06              C
ANISOU10990  C    GLY B 614      17539  19473  16203   -807  -4101   1199          C
ATOM  10991  O    GLY B 614       22.677 -40.327  74.361  1.00141.30              O
ANISOU10991  O    GLY B 614      17582  19651  16454   -762  -4204   1294          O
ATOM  10992  N    ALA B 615       22.268 -38.726  72.841  1.00146.43              N
ANISOU10992  N    ALA B 615      18275  20622  16741   -825  -3799   1118          N
ATOM  10993  CA   ALA B 615       23.569 -38.083  73.034  1.00146.73              C
ANISOU10993  CA   ALA B 615      18092  21077  16580   -820  -3566   1122          C
ATOM  10994  C    ALA B 615       23.408 -36.575  73.117  1.00144.17              C
ANISOU10994  C    ALA B 615      17732  21006  16040  -1140  -3197   1241          C
ATOM  10995  O    ALA B 615       24.394 -35.832  73.132  1.00144.25              O
ANISOU10995  O    ALA B 615      17570  21385  15855  -1180  -2946   1228          O
ATOM  10996  CB   ALA B 615       24.529 -38.449  71.910  1.00149.21              C
ANISOU10996  CB   ALA B 615      18320  21596  16776   -415  -3562    837          C
```

FIG. 13 Continued

```
ATOM  10997  N    SER B 616      22.150 -36.143  73.166  1.00140.68           N
ANISOU10997  N    SER B 616    17453  20356  15643  -1367  -3160   1356       N
ATOM  10998  CA   SER B 616      21.799 -34.733  73.249  1.00138.30           C
ANISOU10998  CA   SER B 616    17155  20220  15174  -1671  -2810   1486       C
ATOM  10999  C    SER B 616      21.983 -34.214  74.674  1.00136.96           C
ANISOU10999  C    SER B 616    16896  20116  15027  -2034  -2698   1719       C
ATOM  11000  O    SER B 616      21.664 -34.906  75.637  1.00136.98           O
ANISOU11000  O    SER B 616    16922  19903  15220  -2132  -2929   1853       O
ATOM  11001  CB   SER B 616      20.349 -34.545  72.811  1.00136.85           C
ANISOU11001  CB   SER B 616    17170  19784  15042  -1755  -2833   1533       C
ATOM  11002  OG   SER B 616      19.970 -35.550  71.885  1.00138.50           O
ANISOU11002  OG   SER B 616    17481  19806  15336  -1445  -3102   1336       O
ATOM  11003  N    ASP B 617      22.501 -32.996  74.806  1.00131.58           N
ANISOU11003  N    ASP B 617    16110  19735  14148  -2241  -2339   1765       N
ATOM  11004  CA   ASP B 617      22.727 -32.401  76.122  1.00130.48           C
ANISOU11004  CA   ASP B 617    15875  19703  13999  -2609  -2198   1954       C
ATOM  11005  C    ASP B 617      21.498 -31.610  76.607  1.00128.00           C
ANISOU11005  C    ASP B 617    15707  19202  13726  -2951  -2049   2140       C
ATOM  11006  O    ASP B 617      21.561 -30.908  77.607  1.00126.93           O
ANISOU11006  O    ASP B 617    15513  19158  13557  -3289  -1869   2282       O
ATOM  11007  CB   ASP B 617      24.014 -31.554  76.145  1.00131.10           C
ANISOU11007  CB   ASP B 617    15746  20210  13857  -2684  -1892   1893       C
ATOM  11008  CG   ASP B 617      25.284 -32.398  75.982  1.00133.68           C
ANISOU11008  CG   ASP B 617    15889  20746  14158  -2380  -2061   1751       C
ATOM  11009  OD1  ASP B 617      26.374 -31.818  75.784  1.00134.57           O
ANISOU11009  OD1  ASP B 617    15821  21227  14082  -2380  -1835   1666       O
ATOM  11010  OD2  ASP B 617      25.192 -33.641  76.051  1.00134.98           O
ANISOU11010  OD2  ASP B 617    16087  20702  14497  -2140  -2413   1726       O
ATOM  11011  N    ILE B 618      20.389 -31.742  75.881  1.00129.30           N
ANISOU11011  N    ILE B 618    16052  19118  13956  -2856  -2124   2128       N
ATOM  11012  CA   ILE B 618      19.090 -31.149  76.217  1.00127.19           C
ANISOU11012  CA   ILE B 618    15934  18644  13748  -3120  -2027   2302       C
ATOM  11013  C    ILE B 618      18.124 -32.023  75.438  1.00127.60           C
ANISOU11013  C    ILE B 618    16140  18415  13928  -2886  -2312   2235       C
ATOM  11014  O    ILE B 618      18.401 -33.201  75.267  1.00129.29           O
ANISOU11014  O    ILE B 618    16347  18522  14256  -2644  -2627   2122       O
ATOM  11015  CB   ILE B 618      18.946 -29.681  75.751  1.00125.91           C
ANISOU11015  CB   ILE B 618    15795  18644  13402  -3272  -1591   2334       C
ATOM  11016  CG1  ILE B 618      20.153 -28.842  76.178  1.00126.19           C
ANISOU11016  CG1  ILE B 618    15660  19008  13279  -3439  -1288   2317       C
ATOM  11017  CG2  ILE B 618      17.663 -29.078  76.279  1.00123.90           C
ANISOU11017  CG2  ILE B 618    15675  18179  13222  -3553  -1484   2533       C
ATOM  11018  CD1  ILE B 618      19.926 -27.369  76.072  1.00124.91           C
ANISOU11018  CD1  ILE B 618    15534  18940  12986  -3681   -844   2395       C
ATOM  11019  N    VAL B 619      17.014 -31.457  74.968  1.00133.67           N
ANISOU11019  N    VAL B 619    17042  19071  14677  -2957  -2199   2300       N
ATOM  11020  CA   VAL B 619      16.019 -32.145  74.115  1.00134.13           C
ANISOU11020  CA   VAL B 619    17236  18908  14819  -2757  -2436   2225       C
ATOM  11021  C    VAL B 619      14.699 -31.401  74.167  1.00132.28           C
ANISOU11021  C    VAL B 619    17120  18551  14594  -2965  -2294   2398       C
ATOM  11022  O    VAL B 619      14.040 -31.370  75.204  1.00131.07           O
ANISOU11022  O    VAL B 619    17004  18229  14567  -3229  -2334   2585       O
ATOM  11023  CB   VAL B 619      15.731 -33.632  74.484  1.00135.37           C
ANISOU11023  CB   VAL B 619    17441  18775  15217  -2652  -2878   2188       C
ATOM  11024  CG1  VAL B 619      14.259 -33.965  74.250  1.00134.82           C
ANISOU11024  CG1  VAL B 619    17527  18427  15272  -2694  -3049   2244       C
ATOM  11025  CG2  VAL B 619      16.592 -34.576  73.656  1.00137.83           C
ANISOU11025  CG2  VAL B 619    17707  19137  15524  -2278  -3076   1930       C
ATOM  11026  N    LEU B 620      14.299 -30.823  73.043  1.00124.85           N
ANISOU11026  N    LEU B 620    16228  17704  13505  -2832  -2133   2345       N
ATOM  11027  CA   LEU B 620      13.095 -30.012  73.012  1.00123.29           C
ANISOU11027  CA   LEU B 620    16126  17428  13291  -2998  -1959   2522       C
ATOM  11028  C    LEU B 620      11.853 -30.821  72.691  1.00123.56           C
ANISOU11028  C    LEU B 620    16268  17223  13454  -2925  -2267   2520       C
ATOM  11029  O    LEU B 620      11.939 -31.987  72.302  1.00125.13           O
ANISOU11029  O    LEU B 620    16482  17319  13744  -2721  -2600   2347       O
ATOM  11030  CB   LEU B 620      13.256 -28.848  72.016  1.00123.19           C
ANISOU11030  CB   LEU B 620    16104  17657  13045  -2909  -1586   2514       C
ATOM  11031  CG   LEU B 620      14.463  27.911  72.200  1.00123.12           C
```

FIG. 13 Continued

```
ANISOU11031 CG  LEU B 620      15989  17900  12890  -2996  -1230   2510       C
ATOM  11032 CD1 LEU B 620       15.781 -28.628  71.947  1.00 124.83           C
ANISOU11032 CD1 LEU B 620      16089  18277  13066  -2786  -1374   2294       C
ATOM  11033 CD2 LEU B 620       14.371 -26.683  71.312  1.00 122.94           C
ANISOU11033 CD2 LEU B 620      15985  18055  12671  -2952   -838   2563       C
ATOM  11034 N   THR B 621       10.704 -30.185  72.917  1.00 123.93           N
ANISOU11034 N   THR B 621      16387  17181  13520  -3110  -2144   2714       N
ATOM  11035 CA  THR B 621        9.392 -30.682  72.494  1.00 124.12           C
ANISOU11035 CA  THR B 621      16500  17036  13623  -3065  -2365   2736       C
ATOM  11036 C   THR B 621        8.730 -29.527  71.730  1.00 123.45           C
ANISOU11036 C   THR B 621      16443  17101  13361  -3041  -2053   2842       C
ATOM  11037 O   THR B 621        7.570 -29.618  71.287  1.00 123.50           O
ANISOU11037 O   THR B 621      16505  17041  13378  -3011  -2148   2897       O
ATOM  11038 CB  THR B 621        8.466 -31.140  73.654  1.00 123.18           C
ANISOU11038 CB  THR B 621      16433  16643  13728  -3328  -2556   2912       C
ATOM  11039 OG1 THR B 621        8.834 -30.478  74.874  1.00 121.75           O
ANISOU11039 OG1 THR B 621      16212  16473  13573  -3608  -2341   3085       O
ATOM  11040 CG2 THR B 621        8.514 -32.658  73.818  1.00 124.69           C
ANISOU11040 CG2 THR B 621      16644  16618  14115  -3235  -2997   2778       C
ATOM  11041 N   GLU B 622        9.493 -28.446  71.564  1.00 126.59           N
ANISOU11041 N   GLU B 622      16793  17711  13593  -3049  -1676   2876       N
ATOM  11042 CA  GLU B 622        8.993 -27.278  70.860  1.00 126.17           C
ANISOU11042 CA  GLU B 622      16766  17800  13374  -3015  -1336   3000       C
ATOM  11043 C   GLU B 622        9.896 -26.821  69.719  1.00 127.37           C
ANISOU11043 C   GLU B 622      16864  18229  13301  -2767  -1133   2867       C
ATOM  11044 O   GLU B 622       11.105 -26.696  69.868  1.00 127.70           O
ANISOU11044 O   GLU B 622      16836  18394  13292  -2762  -1021   2771       O
ATOM  11045 CB  GLU B 622        8.679 -26.146  71.839  1.00 124.41           C
ANISOU11045 CB  GLU B 622      16566  17519  13185  -3325   -993   3249       C
ATOM  11046 CG  GLU B 622        7.253 -26.217  72.416  1.00 123.39           C
ANISOU11046 CG  GLU B 622      16507  17181  13196  -3493  -1095   3439       C
ATOM  11047 CD  GLU B 622        6.841 -27.622  72.876  1.00 123.76           C
ANISOU11047 CD  GLU B 622      16567  17022  13435  -3515  -1568   3363       C
ATOM  11048 OE1 GLU B 622        7.496 -28.163  73.800  1.00 123.61           O
ANISOU11048 OE1 GLU B 622      16516  16916  13533  -3643  -1701   3323       O
ATOM  11049 OE2 GLU B 622        5.860 -28.183  72.320  1.00 124.37           O
ANISOU11049 OE2 GLU B 622      16681  17031  13544  -3408  -1801   3348       O
ATOM  11050 N   PRO B 623        9.275 -26.597  68.563  1.00 118.91           N
ANISOU11050 N   PRO B 623      15816  17278  12087  -2559  -1096   2866       N
ATOM  11051 CA  PRO B 623        9.766 -26.205  67.245  1.00 120.33           C
ANISOU11051 CA  PRO B 623      15955  17736  12027  -2283   -934   2766       C
ATOM  11052 C   PRO B 623       10.884 -25.171  67.145  1.00 120.33           C
ANISOU11052 C   PRO B 623      15899  17935  11884  -2302   -525   2796       C
ATOM  11053 O   PRO B 623       12.066 -25.474  67.323  1.00 120.85           O
ANISOU11053 O   PRO B 623      15895  18081  11943  -2280   -549   2638       O
ATOM  11054 CB  PRO B 623        8.504 -25.622  66.594  1.00 120.29           C
ANISOU11054 CB  PRO B 623      15999  17774  11933  -2224   -826   2943       C
ATOM  11055 CG  PRO B 623        7.401 -26.444  67.147  1.00 119.79           C
ANISOU11055 CG  PRO B 623      15985  17471  12059  -2336  -1165   2973       C
ATOM  11056 CD  PRO B 623        7.839 -26.925  68.517  1.00 118.67           C
ANISOU11056 CD  PRO B 623      15848  17102  12138  -2585  -1291   2966       C
ATOM  11057 N   GLY B 624       10.457 -23.951  66.829  1.00 154.32           N
ANISOU11057 N   GLY B 624      20235  22321  16078  -2337   -146   3008       N
ATOM  11058 CA  GLY B 624       11.310 -22.836  66.453  1.00 154.71           C
ANISOU11058 CA  GLY B 624      20247  22570  15966  -2325    288   3063       C
ATOM  11059 C   GLY B 624       12.540 -22.442  67.232  1.00 154.32           C
ANISOU11059 C   GLY B 624      20140  22549  15947  -2524    495   3020       C
ATOM  11060 O   GLY B 624       12.620 -22.616  68.444  1.00 153.14           O
ANISOU11060 O   GLY B 624      19993  22227  15965  -2785    430   3044       O
ATOM  11061 N   LEU B 625       13.504 -21.882  66.507  1.00 125.00           N
ANISOU11061 N   LEU B 625      16361  19080  12053  -2403    756   2960       N
ATOM  11062 CA  LEU B 625       14.722 -21.372  67.107  1.00 124.96           C
ANISOU11062 CA  LEU B 625      16281  19157  12040  -2591   1002   2918       C
ATOM  11063 C   LEU B 625       14.326 -20.349  68.159  1.00 123.46           C
ANISOU11063 C   LEU B 625      16158  18787  11963  -2947   1324   3137       C
ATOM  11064 O   LEU B 625       15.118 -19.975  69.017  1.00 123.10           O
ANISOU11064 O   LEU B 625      16063  18747  11963  -3199   1493   3114       O
ATOM  11065 CB  LEU B 625       15.609 -20.730  66.044  1.00 126.57           C
ANISOU11065 CB  LEU B 625      16418  19655  12020  -2413   1297   2872       C
```

FIG. 13 Continued

```
ATOM   11066  CG  LEU B 625      16.955 -20.207  66.542  1.00126.91           C
ANISOU11066  CG  LEU B 625    16360  19828  12030  -2599   1559   2806        C
ATOM   11067  CD1 LEU B 625      17.632 -21.249  67.404  1.00126.69           C
ANISOU11067  CD1 LEU B 625    16244  19770  12121  -2673   1222   2618        C
ATOM   11068  CD2 LEU B 625      17.860 -19.793  65.395  1.00128.79           C
ANISOU11068  CD2 LEU B 625    16514  20378  12041  -2384   1784   2731        C
ATOM   11069  N   SER B 626      13.077 -19.906  68.089  1.00183.95           N
ANISOU11069  N   SER B 626    23926  26300  19665  -2965   1407   3342        N
ATOM   11070  CA  SER B 626      12.546 -18.952  69.049  1.00182.65           C
ANISOU11070  CA  SER B 626    23840  25942  19617  -3280   1710   3552        C
ATOM   11071  C   SER B 626      12.467 -19.579  70.424  1.00181.32           C
ANISOU11071  C   SER B 626    23665  25589  19640  -3545   1469   3511        C
ATOM   11072  O   SER B 626      12.129 -18.914  71.397  1.00180.26           O
ANISOU11072  O   SER B 626    23581  25301  19609  -3838   1683   3646        O
ATOM   11073  CB  SER B 626      11.155 -18.476  68.629  1.00182.37           C
ANISOU11073  CB  SER B 626    23907  25799  19585  -3195   1806   3782        C
ATOM   11074  OG  SER B 626      10.658 -17.495  69.526  1.00181.32           O
ANISOU11074  OG  SER B 626    23854  25476  19565  -3483   2135   3983        O
ATOM   11075  N   VAL B 627      12.761 -20.869  70.501  1.00116.49           N
ANISOU11075  N   VAL B 627    15393  17392  11476  -3435   1026   3328        N
ATOM   11076  CA  VAL B 627      12.726 -21.558  71.779  1.00115.48           C
ANISOU11076  CA  VAL B 627    15250  17104  11524  -3661    772   3302        C
ATOM   11077  C   VAL B 627      14.115 -21.717  72.368  1.00115.93           C
ANISOU11077  C   VAL B 627    15187  17297  11565  -3780    784   3150        C
ATOM   11078  O   VAL B 627      14.327 -21.453  73.549  1.00115.15           O
ANISOU11078  O   VAL B 627    15066  17136  11549  -4087    873   3196        O
ATOM   11079  CB  VAL B 627      12.064 -22.916  71.656  1.00115.55           C
ANISOU11079  CB  VAL B 627    15277  16992  11634  -3495    269   3228        C
ATOM   11080  CG1 VAL B 627      11.733 -23.458  73.040  1.00114.41           C
ANISOU11080  CG1 VAL B 627    15142  16643  11687  -3759     57   3282        C
ATOM   11081  CG2 VAL B 627      10.804 -22.788  70.813  1.00115.58           C
ANISOU11081  CG2 VAL B 627    15368  16943  11605  -3328    248   3342        C
ATOM   11082  N   ILE B 628      15.060 -22.157  71.548  1.00118.47           N
ANISOU11082  N   ILE B 628    15420  17827  11767  -3533    694   2967        N
ATOM   11083  CA  ILE B 628      16.444 -22.275  71.990  1.00119.19           C
ANISOU11083  CA  ILE B 628    15373  18098  11818  -3614    722   2823        C
ATOM   11084  C   ILE B 628      16.943 -20.954  72.560  1.00118.89           C
ANISOU11084  C   ILE B 628    15312  18133  11730  -3929   1195   2908        C
ATOM   11085  O   ILE B 628      17.690 -20.929  73.540  1.00118.85           O
ANISOU11085  O   ILE B 628    15212  18190  11754  -4169   1225   2859        O
ATOM   11086  CB  ILE B 628      17.369 -22.643  70.831  1.00120.96           C
ANISOU11086  CB  ILE B 628    15505  18572  11884  -3289    667   2633        C
ATOM   11087  CG1 ILE B 628      17.323 -24.142  70.553  1.00121.70           C
ANISOU11087  CG1 ILE B 628    15579  18615  12047  -3019    167   2472        C
ATOM   11088  CG2 ILE B 628      18.794 -22.216  71.134  1.00121.82           C
ANISOU11088  CG2 ILE B 628    15466  18923  11898  -3411    886   2536        C
ATOM   11089  CD1 ILE B 628      18.305 -24.557  69.477  1.00123.63           C
ANISOU11089  CD1 ILE B 628    15724  19115  12136  -2696    108   2260        C
ATOM   11090  N   ILE B 629      16.538 -19.861  71.918  1.00118.65           N
ANISOU11090  N   ILE B 629    15363  18101  11618  -3923   1570   3033        N
ATOM   11091  CA  ILE B 629      16.891 -18.514  72.350  1.00118.61           C
ANISOU11091  CA  ILE B 629    15366  18120  11579  -4217   2065   3121        C
ATOM   11092  C   ILE B 629      16.173 -18.192  73.658  1.00117.13           C
ANISOU11092  C   ILE B 629    15252  17704  11549  -4563   2126   3249        C
ATOM   11093  O   ILE B 629      16.521 -17.251  74.368  1.00117.08           O
ANISOU11093  O   ILE B 629    15240  17694  11549  -4879   2477   3281        O
ATOM   11094  CB  ILE B 629      16.482 -17.482  71.296  1.00119.18           C
ANISOU11094  CB  ILE B 629    15530  18205  11549  -4088   2438   3258        C
ATOM   11095  CG1 ILE B 629      17.079 -16.098  71.607  1.00119.69           C
ANISOU11095  CG1 ILE B 629    15595  18307  11574  -4374   2980   3316        C
ATOM   11096  CG2 ILE B 629      14.950 -17.431  71.194  1.00118.14           C
ANISOU11096  CG2 ILE B 629    15544  17837  11505  -4024   2378   3452        C
ATOM   11097  CD1 ILE B 629      18.502 -15.910  71.165  1.00121.28           C
ANISOU11097  CD1 ILE B 629    15656  18795  11629  -4348   3132   3158        C
ATOM   11098  N   SER B 630      15.143 -18.960  73.967  1.00117.97           N
ANISOU11098  N   SER B 630    15425  17619  11779  -4512   1792   3316        N
ATOM   11099  CA  SER B 630      14.487 -18.787  75.243  1.00116.67           C
ANISOU11099  CA  SER B 630    15313  17260  11758  -4829   1808   3428        C
ATOM   11100  C   SER B 630      15.319 -19.521  76.275  1.00116.71           C
```

FIG. 13 Continued

```
ANISOU11100  C   SER B 630    15191  17350  11805  -4996   1568   3301        C
ATOM  11101  O   SER B 630    15.735 -18.945  77.279  1.00116.55              O
ANISOU11101  O   SER B 630    15127  17360  11795  -5328   1779   3301        O
ATOM  11102  CB  SER B 630    13.067 -19.328  75.200  1.00115.68              C
ANISOU11102  CB  SER B 630    15294  16914  11746  -4723   1548   3560        C
ATOM  11103  OG  SER B 630    12.230 -18.425  74.504  1.00115.63              O
ANISOU11103  OG  SER B 630    15398  16832  11704  -4640   1843   3723        O
ATOM  11104  N   ALA B 631    15.590 -20.790  75.995  1.00114.91              N
ANISOU11104  N   ALA B 631    14897  17171  11594  -4757   1134   3187        N
ATOM  11105  CA  ALA B 631    16.400 -21.627  76.878  1.00115.26              C
ANISOU11105  CA  ALA B 631    14809  17307  11679  -4849    865   3081        C
ATOM  11106  C   ALA B 631    17.813 -21.064  77.161  1.00116.30              C
ANISOU11106  C   ALA B 631    14789  17713  11685  -5009   1117   2962        C
ATOM  11107  O   ALA B 631    18.591 -21.633  77.933  1.00116.81              O
ANISOU11107  O   ALA B 631    14718  17906  11757  -5103    938   2883        O
ATOM  11108  CB  ALA B 631    16.461 -23.064  76.345  1.00115.96              C
ANISOU11108  CB  ALA B 631    14866  17380  11812  -4513    385   2975        C
ATOM  11109  N   VAL B 632    18.154 -19.960  76.518  1.00146.32              N
ANISOU11109  N   VAL B 632    18607  21620  15370  -5035   1532   2955        N
ATOM  11110  CA  VAL B 632    19.390 -19.295  76.861  1.00147.35              C
ANISOU11110  CA  VAL B 632    18599  21996  15390  -5248   1816   2852        C
ATOM  11111  C   VAL B 632    19.023 -18.159  77.806  1.00146.64              C
ANISOU11111  C   VAL B 632    18575  21799  15341  -5664   2191   2952        C
ATOM  11112  O   VAL B 632    19.801 -17.792  78.686  1.00147.16              O
ANISOU11112  O   VAL B 632    18527  22018  15368  -5969   2337   2879        O
ATOM  11113  CB  VAL B 632    20.094 -18.712  75.654  1.00148.65              C
ANISOU11113  CB  VAL B 632    18730  22348  15400  -5068   2082   2777        C
ATOM  11114  CG1 VAL B 632    19.293 -17.558  75.120  1.00148.23              C
ANISOU11114  CG1 VAL B 632    18842  22136  15343  -5108   2478   2928        C
ATOM  11115  CG2 VAL B 632    21.498 -18.241  76.040  1.00149.98              C
ANISOU11115  CG2 VAL B 632    18720  22810  15456  -5282   2306   2643        C
ATOM  11116  N   LEU B 633    17.831 -17.599  77.635  1.00125.14              N
ANISOU11116  N   LEU B 633    16030  18825  12693  -5678   2351   3114        N
ATOM  11117  CA  LEU B 633    17.418 -16.515  78.510  1.00124.62              C
ANISOU11117  CA  LEU B 633    16041  18629  12678  -6055   2721   3203        C
ATOM  11118  C   LEU B 633    16.749 -17.029  79.774  1.00123.44              C
ANISOU11118  C   LEU B 633    15906  18344  12654  -6262   2483   3269        C
ATOM  11119  O   LEU B 633    16.584 -16.281  80.724  1.00123.19              O
ANISOU11119  O   LEU B 633    15900  18253  12653  -6612   2742   3301        O
ATOM  11120  CB  LEU B 633    16.545 -15.499  77.783  1.00124.40              C
ANISOU11120  CB  LEU B 633    16187  18412  12668  -5991   3083   3358        C
ATOM  11121  CG  LEU B 633    16.931 -14.058  78.142  1.00125.15              C
ANISOU11121  CG  LEU B 633    16314  18502  12736  -6324   3646   3358        C
ATOM  11122  CD1 LEU B 633    16.642 -13.080  76.988  1.00125.87              C
ANISOU11122  CD1 LEU B 633    16525  18513  12785  -6157   4036   3473        C
ATOM  11123  CD2 LEU B 633    16.291 -13.600  79.470  1.00124.31              C
ANISOU11123  CD2 LEU B 633    16273  18217  12742  -6698   3781   3421        C
ATOM  11124  N   THR B 634    16.353 -18.299  79.781  1.00114.35              N
ANISOU11124  N   THR B 634    14740  17137  11573  -6051   2001   3285        N
ATOM  11125  CA  THR B 634    15.824 -18.913  80.998  1.00113.48              C
ANISOU11125  CA  THR B 634    14620  16923  11574  -6239   1740   3352        C
ATOM  11126  C   THR B 634    16.998 -19.084  81.926  1.00114.34              C
ANISOU11126  C   THR B 634    14549  17281  11616  -6466   1704   3228        C
ATOM  11127  O   THR B 634    16.937 -18.731  83.102  1.00114.10              O
ANISOU11127  O   THR B 634    14491  17261  11603  -6811   1810   3254        O
ATOM  11128  CB  THR B 634    15.236 -20.335  80.771  1.00113.05              C
ANISOU11128  CB  THR B 634    14581  16751  11621  -5956   1213   3390        C
ATOM  11129  OG1 THR B 634    14.134 -20.556  81.661  1.00111.89              O
ANISOU11129  OG1 THR B 634    14513  16395  11606  -6121   1085   3540        O
ATOM  11130  CG2 THR B 634    16.287 -21.419  81.024  1.00114.04              C
ANISOU11130  CG2 THR B 634    14542  17067  11723  -5859    868   3261        C
ATOM  11131  N   SER B 635    18.082 -19.614  81.376  1.00116.12              N
ANISOU11131  N   SER B 635    14638  17730  11751  -6266   1560   3089        N
ATOM  11132  CA  SER B 635    19.240 -19.907  82.179  1.00117.18              C
ANISOU11132  CA  SER B 635    14573  18141  11811  -6430   1479   2976        C
ATOM  11133  C   SER B 635    20.205 -18.753  82.270  1.00118.25              C
ANISOU11133  C   SER B 635    14618  18504  11807  -6690   1922   2863        C
ATOM  11134  O   SER B 635    21.112 -18.808  83.074  1.00119.21              O
ANISOU11134  O   SER B 635    14564  18878  11852  -6901   1912   2773        O
```

FIG. 13 Continued

```
ATOM   11135  CB   SER B 635      19.946 -21.175  81.708  1.00118.15           C
ANISOU11135  CB   SER B 635    14572  18401  11919  -6090   1069   2888        C
ATOM   11136  OG   SER B 635      20.641 -21.769  82.788  1.00118.89           O
ANISOU11136  OG   SER B 635    14492  18683  11997  -6238    862   2860        O
ATOM   11137  N    ARG B 636      20.051 -17.707  81.469  1.00130.28           N
ANISOU11137  N    ARG B 636    14720  22164  12619 -14098   -324   2632        N
ATOM   11138  CA   ARG B 636      20.950 -16.578  81.701  1.00128.74           C
ANISOU11138  CA   ARG B 636    14251  22134  12530 -13939   -519   2978        C
ATOM   11139  C    ARG B 636      20.492 -15.855  82.977  1.00124.55           C
ANISOU11139  C    ARG B 636    13575  21065  12682 -13504   -734   3244        C
ATOM   11140  O    ARG B 636      21.075 -14.834  83.401  1.00122.92           O
ANISOU11140  O    ARG B 636    13149  20849  12705 -13322   -951   3541        O
ATOM   11141  CB   ARG B 636      21.110 -15.648  80.491  1.00132.12           C
ANISOU11141  CB   ARG B 636    14442  23166  12592 -14563   -919   3404        C
ATOM   11142  CG   ARG B 636      22.434 -14.840  80.545  1.00131.88           C
ANISOU11142  CG   ARG B 636    14205  23426  12477 -14456   -937   3601        C
ATOM   11143  CD   ARG B 636      22.936 -14.372  79.174  1.00136.68           C
ANISOU11143  CD   ARG B 636    14678  24784  12469 -15121  -1102   3848        C
ATOM   11144  NE   ARG B 636      23.499 -15.465  78.388  1.00140.19           N
ANISOU11144  NE   ARG B 636    15307  25693  12266 -15275   -618   3312        N
ATOM   11145  CZ   ARG B 636      24.074 -15.320  77.198  1.00145.05           C
ANISOU11145  CZ   ARG B 636    15840  27055  12218 -15822   -597   3364        C
ATOM   11146  NH1  ARG B 636      24.181 -14.120  76.646  1.00146.97           N
ANISOU11146  NH1  ARG B 636    15838  27657  12349 -16308  -1058   3996        N
ATOM   11147  NH2  ARG B 636      24.552 -16.380  76.561  1.00148.52           N
ANISOU11147  NH2  ARG B 636    16452  27881  12100 -15891   -113   2777        N
ATOM   11148  N    ALA B 637      19.462 -16.448  83.594  1.00136.03           N
ANISOU11148  N    ALA B 637    15165  22084  14437 -13354   -640   3092        N
ATOM   11149  CA   ALA B 637      18.877 -15.983  84.855  1.00132.26           C
ANISOU11149  CA   ALA B 637    14636  21162  14619 -12936   -745   3231        C
ATOM   11150  C    ALA B 637      18.891 -17.065  85.962  1.00130.69           C
ANISOU11150  C    ALA B 637    14693  20459  14504 -12441   -263   2828        C
ATOM   11151  O    ALA B 637      19.327 -16.791  87.081  1.00127.88           O
ANISOU11151  O    ALA B 637    14329  19825  14433 -11933   -177   2828        O
ATOM   11152  CB   ALA B 637      17.461 -15.442  84.635  1.00133.76           C
ANISOU11152  CB   ALA B 637    14539  21228  15057 -13253  -1163   3534        C
ATOM   11153  N    ILE B 638      18.440 -18.286  85.666  1.00116.73           N
ANISOU11153  N    ILE B 638    13220  18609  12524 -12604     30   2497        N
ATOM   11154  CA   ILE B 638      18.451 -19.359  86.683  1.00115.59           C
ANISOU11154  CA   ILE B 638    13420  17997  12502 -12180    463   2164        C
ATOM   11155  C    ILE B 638      19.869 -19.631  87.258  1.00114.27           C
ANISOU11155  C    ILE B 638    13416  17763  12240 -11638    751   1965        C
ATOM   11156  O    ILE B 638      20.032 -19.854  88.463  1.00112.17           O
ANISOU11156  O    ILE B 638    13284  17114  12221 -11148    928   1909        O
ATOM   11157  CB   ILE B 638      17.767 -20.680  86.192  1.00118.66           C
ANISOU11157  CB   ILE B 638    14145  18261  12679  12500    713   1831        C
ATOM   11158  CG1  ILE B 638      16.799 -21.200  87.238  1.00117.80           C
ANISOU11158  CG1  ILE B 638    14173  17663  12922 -12353    868   1798        C
ATOM   11159  CG2  ILE B 638      18.780 -21.757  85.913  1.00120.53           C
ANISOU11159  CG2  ILE B 638    14756  18476  12563 -12324   1106   1395        C
ATOM   11160  CD1  ILE B 638      15.956 -20.128  87.834  1.00115.82           C
ANISOU11160  CD1  ILE B 638    13528  17381  13099 -12324    559   2160        C
ATOM   11161  N    PHE B 639      20.885 -19.603  86.400  1.00115.06           N
ANISOU11161  N    PHE B 639    13477  18276  11966 -11738    790   1863        N
ATOM   11162  CA   PHE B 639      22.269 -19.784  86.833  1.00114.49           C
ANISOU11162  CA   PHE B 639    13460  18234  11808 -11245   1025   1680        C
ATOM   11163  C    PHE B 639      22.676 -18.564  87.618  1.00111.39           C
ANISOU11163  C    PHE B 639    12763  17839  11720 -10973    761   2023        C
ATOM   11164  O    PHE B 639      23.520 -18.655  88.505  1.00109.96           O
ANISOU11164  O    PHE B 639    12630  17502  11645 -10454    908   1930        O
ATOM   11165  CB   PHE B 639      23.204 -20.004  85.626  1.00117.90           C
ANISOU11165  CB   PHE B 639    13847  19206  11742 -11478   1146   1468        C
ATOM   11166  CG   PHE B 639      24.585 -19.372  85.753  1.00117.44           C
ANISOU11166  CG   PHE B 639    13532  19476  11615 -11200   1143   1531        C
ATOM   11167  CD1  PHE B 639      25.663 -20.101  86.223  1.00118.12           C
ANISOU11167  CD1  PHE B 639    13746  19482  11654 -10661   1486   1182        C
ATOM   11168  CD2  PHE B 639      24.807 -18.069  85.334  1.00117.07           C
ANISOU11168  CD2  PHE B 639    13105  19829  11547 -11512    779   1946        C
ATOM   11169  CE1  PHE B 639      26.926 -19.523  86.306  1.00118.23           C
```

FIG. 13 Continued

```
ANISOU11169  CE1 PHE B 639     13463  19856  11603 -10440   1475   1233       C
ATOM   11170 CE2 PHE B 639     26.073 -17.489  85.419  1.00117.19             C
ANISOU11170  CE2 PHE B 639     12864  20172  11492 -11331    773   2012       C
ATOM   11171 CZ  PHE B 639     27.128 -18.216  85.901  1.00117.74             C
ANISOU11171  CZ  PHE B 639     13015  20210  11509 -10802   1129   1646       C
ATOM   11172 N   GLN B 640     22.057 -17.428  87.306  1.00112.35             N
ANISOU11172  N   GLN B 640     12581  18107  11999 -11318    341   2415       N
ATOM   11173 CA  GLN B 640     22.381  16.174  87.979  1.00110.02             C
ANISOU11173  CA  GLN B 640     12004  17772  12028 -11110     35   2734       C
ATOM   11174 C   GLN B 640     22.111 -16.159  89.503  1.00107.10             C
ANISOU11174  C   GLN B 640     11721  16905  12067 -10576    113   2696       C
ATOM   11175 O   GLN B 640     22.961 -15.699  90.274  1.00105.57             O
ANISOU11175  O   GLN B 640     11455  16662  11993 -10192     90   2720       O
ATOM   11176 CB  GLN B 640     21.736 -14.981  87.262  1.00110.88             C
ANISOU11176  CB  GLN B 640     11798  18079  12253 -11593   -470   3168       C
ATOM   11177 CG  GLN B 640     21.865 -13.643  87.990  1.00109.01             C
ANISOU11177  CG  GLN B 640     11297  17678  12444 -11392   -838   3488       C
ATOM   11178 CD  GLN B 640     23.267 -13.051  87.930  1.00109.17             C
ANISOU11178  CD  GLN B 640     11179  17973  12329 -11316   -895   3574       C
ATOM   11179 OE1 GLN B 640     23.466 -11.962  87.382  1.00110.46             O
ANISOU11179  OE1 GLN B 640     11096  18342  12532 -11642  -1292   3943       O
ATOM   11180 NE2 GLN B 640     24.249 -13.763  88.494  1.00108.36             N
ANISOU11180  NE2 GLN B 640     11222  17872  12079 -10899   -519   3255       N
ATOM   11181 N   ARG B 641     20.963 -16.655  89.961  1.00160.00             N
ANISOU11181  N   ARG B 641     18565  23275  18952 -10571    209   2631       N
ATOM   11182 CA  ARG B 641     20.745 -16.652  91.405  1.00157.85             C
ANISOU11182  CA  ARG B 641     18378  22606  18990 -10097    318   2589       C
ATOM   11183 C   ARG B 641     21.846 -17.458  92.053  1.00157.48             C
ANISOU11183  C   ARG B 641     18612  22449  18772  -9630    653   2340       C
ATOM   11184 O   ARG B 641     22.515 -16.980  92.967  1.00155.92             O
ANISOU11184  O   ARG B 641     18360  22176  18705  -9228    606   2376       O
ATOM   11185 CB  ARG B 641     19.375 -17.186  91.795  1.00158.21             C
ANISOU11185  CB  ARG B 641     18533  22370  19211 -10199    439   2540       C
ATOM   11186 CG  ARG B 641     18.899 -18.357  90.997  1.00160.57             C
ANISOU11186  CG  ARG B 641     19081  22681  19249 -10549    662   2351       C
ATOM   11187 CD  ARG B 641     17.437 -18.119  90.682  1.00161.69             C
ANISOU11187  CD  ARG B 641     19021  22820  19592 -10956    472   2492       C
ATOM   11188 NE  ARG B 641     17.203 -16.701  90.389  1.00161.19             N
ANISOU11188  NE  ARG B 641     18520  22952  19774 -11078      2   2815       N
ATOM   11189 CZ  ARG B 641     16.175 -16.231  89.681  1.00162.92             C
ANISOU11189  CZ  ARG B 641     18462  23312  20129 -11494   -319   3012       C
ATOM   11190 NH1 ARG B 641     15.270 -17.063  89.178  1.00165.14             N
ANISOU11190  NH1 ARG B 641     18834  23611  20300 -11866   -212   2904       N
ATOM   11191 NE2 ARG B 641     16.050 -14.926  89.469  1.00162.91             N
ANISOU11191  NE2 ARG B 641     18094  23415  20390 -11546   -779   3326       N
ATOM   11192 N   MET B 642     22.046 -18.672  91.550  1.00114.36             N
ANISOU11192  N   MET B 642     13448  16977  13027  -9684    961   2077       N
ATOM   11193 CA  MET B 642     23.117 -19.539  92.035  1.00114.95             C
ANISOU11193  CA  MET B 642     13792  16930  12952  -9219   1260   1825       C
ATOM   11194 C   MET B 642     24.423 -18.788  92.177  1.00114.18             C
ANISOU11194  C   MET B 642     13442  17117  12826  -8949   1125   1889       C
ATOM   11195 O   MET B 642     25.147 -18.988  93.144  1.00113.56             O
ANISOU11195  O   MET B 642     13465  16879  12805  -8448   1222   1819       O
ATOM   11196 CB  MET B 642     23.349 -20.701  91.087  1.00118.07             C
ANISOU11196  CB  MET B 642     14442  17387  13033  -9376   1529   1511       C
ATOM   11197 CG  MET B 642     22.271 -21.747  91.104  1.00119.56             C
ANISOU11197  CG  MET B 642     14987  17203  13237  -9567   1729   1370       C
ATOM   11198 SD  MET B 642     22.811 -23.118  90.072  1.00123.91             S
ANISOU11198  SD  MET B 642     15878  17774  13430  -9646   2047    910       S
ATOM   11199 CE  MET B 642     23.754 -22.213  88.828  1.00124.67             C
ANISOU11199  CE  MET B 642     15538  18609  13224  -9892   1872    933       C
ATOM   11200 N   LYS B 643     24.741 -17.953  91.192  1.00109.35             N
ANISOU11200  N   LYS B 643     12503  16944  12100  -9312    892   2037       N
ATOM   11201 CA  LYS B 643     25.919 -17.109  91.291  1.00108.99             C
ANISOU11201  CA  LYS B 643     12165  17198  12046  -9157    727   2146       C
ATOM   11202 C   LYS B 643     25.764 -16.208  92.509  1.00106.35             C
ANISOU11202  C   LYS B 643     11727  16606  12074  -8878    491   2346       C
ATOM   11203 O   LYS B 643     26.142 -16.586  93.616  1.00105.51             O
ANISOU11203  O   LYS B 643     11788  16254  12047  -8387    628   2227       O
```

FIG. 13 Continued

```
ATOM   11204  CB   LYS B 643      26.142 -16.266  90.026  1.00110.50           C
ANISOU11204  CB   LYS B 643    12031  17897  12057  -9699    480   2354        C
ATOM   11205  CG   LYS B 643      27.397 -16.647  89.213  1.00113.36           C
ANISOU11205  CG   LYS B 643    12289  18752  12029  -9729    684   2152        C
ATOM   11206  CD   LYS B 643      28.643 -15.735  89.480  1.00113.37           C
ANISOU11206  CD   LYS B 643    11943  19064  12067  -9591    517   2300        C
ATOM   11207  CE   LYS B 643      29.894 -16.173  88.660  1.00116.93           C
ANISOU11207  CE   LYS B 643    12227  20082  12119  -9617    775   2058        C
ATOM   11208  NZ   LYS B 643      30.898 -15.100  88.357  1.00118.20           N
ANISOU11208  NZ   LYS B 643    11955  20745  12210  -9836    560   2299        N
ATOM   11209  N    ASN B 644      25.174 -15.034  92.319  1.00186.60           N
ANISOU11209  N    ASN B 644    21635  26809  22457  -9185    122   2640        N
ATOM   11210  CA   ASN B 644      25.063 -14.063  93.405  1.00184.75           C
ANISOU11210  CA   ASN B 644    21278  26341  22577  -8933   -128   2781        C
ATOM   11211  C    ASN B 644      24.665 -14.642  94.765  1.00183.42           C
ANISOU11211  C    ASN B 644    21378  25773  22540  -8470     93   2611        C
ATOM   11212  O    ASN B 644      25.129 -14.162  95.798  1.00182.48           O
ANISOU11212  O    ASN B 644    21229  25545  22559  -8117      4   2604        O
ATOM   11213  CB   ASN B 644      24.177 -12.887  93.000  1.00184.74           C
ANISOU11213  CB   ASN B 644    21021  26313  22861  -9306   -541   3081        C
ATOM   11214  CG   ASN B 644      24.836 -11.999  91.948  1.00186.32           C
ANISOU11214  CG   ASN B 644    20940  26890  22964  -9716   -858   3345        C
ATOM   11215  OD1  ASN B 644      25.927 -11.463  92.157  1.00186.51           O
ANISOU11215  OD1  ASN B 644    20824  27069  22970  -9609   -964   3393        O
ATOM   11216  ND2  ASN B 644      24.170 -11.839  90.812  1.00187.92           N
ANISOU11216  ND2  ASN B 644    21054  27263  23082 -10222  -1024   3539        N
ATOM   11217  N    TYR B 645      23.826 -15.673  94.776  1.00126.91           N
ANISOU11217  N    TYR B 645    14494  18414  15313  -8504    375   2479        N
ATOM   11218  CA   TYR B 645      23.504 -16.318  96.044  1.00126.34           C
ANISOU11218  CA   TYR B 645    14711  17994  15299  -8114    615   2351        C
ATOM   11219  C    TYR B 645      24.724 -17.016  96.641  1.00126.82           C
ANISOU11219  C    TYR B 645    14985  18033  15167  -7653    806   2198        C
ATOM   11220  O    TYR B 645      24.955 -16.942  97.843  1.00126.23           O
ANISOU11220  O    TYR B 645    15015  17794  15154  -7265    819   2183        O
ATOM   11221  CB   TYR B 645      22.415 -17.367  95.925  1.00127.31           C
ANISOU11221  CB   TYR B 645    15105  17895  15373  -8293    890   2260        C
ATOM   11222  CG   TYR B 645      22.641 -18.399  96.994  1.00127.82           C
ANISOU11222  CG   TYR B 645    15569  17661  15335  -7884   1204   2121        C
ATOM   11223  CD1  TYR B 645      22.215 -18.175  98.294  1.00127.15           C
ANISOU11223  CD1  TYR B 645    15555  17375  15382  -7629   1238   2160        C
ATOM   11224  CD2  TYR B 645      23.353 -19.559  96.730  1.00129.50           C
ANISOU11224  CD2  TYR B 645    16090  17801  15313  -7729   1449   1950        C
ATOM   11225  CE1  TYR B 645      22.449 -19.094  99.291  1.00128.13           C
ANISOU11225  CE1  TYR B 645    16068  17245  15371  -7284   1493   2093        C
ATOM   11226  CE2  TYR B 645      23.597 -20.480  97.722  1.00130.53           C
ANISOU11226  CE2  TYR B 645    16608  17615  15373  -7340   1679   1878        C
ATOM   11227  CZ   TYR B 645      23.138 -20.243  99.001  1.00129.81           C
ANISOU11227  CZ   TYR B 645    16601  17341  15380  -7140   1691   1980        C
ATOM   11228  OH   TYR B 645      23.372 -21.151 100.002  1.00131.34           O
ANISOU11228  OH   TYR B 645    17207  17236  15462  -6790   1893   1965        O
ATOM   11229  N    THR B 646      25.469  17.749  95.819  1.00129.95           N
ANISOU11229  N    THR B 646    15453  18600  15322  -7679    961   2062        N
ATOM   11230  CA   THR B 646      26.680 -18.390  96.314  1.00131.06           C
ANISOU11230  CA   THR B 646    15735  18740  15323  -7199   1108   1909        C
ATOM   11231  C    THR B 646      27.522 -17.327  96.979  1.00129.98           C
ANISOU11231  C    THR B 646    15315  18779  15292  -6968    834   2022        C
ATOM   11232  O    THR B 646      27.711 -17.341  98.185  1.00129.55           O
ANISOU11232  O    THR B 646    15392  18534  15296  -6579    822   2024        O
ATOM   11233  CB   THR B 646      27.507 -19.078  95.193  1.00133.52           C
ANISOU11233  CB   THR B 646    16025  19318  15386  -7257   1274   1708        C
ATOM   11234  OG1  THR B 646      27.168 -20.465  95.148  1.00135.44           O
ANISOU11234  OG1  THR B 646    16694  19236  15532  -7152   1593   1496        O
ATOM   11235  CG2  THR B 646      29.017 -18.976  95.449  1.00134.63           C
ANISOU11235  CG2  THR B 646    15980  19718  15456  -6851   1241   1628        C
ATOM   11236  N    ILE B 647      27.985 -16.375  96.189  1.00104.42           N
ANISOU11236  N    ILE B 647    11699  15911  12066  -7258    596   2133        N
ATOM   11237  CA   ILE B 647      28.854 -15.330  96.683  1.00103.98           C
ANISOU11237  CA   ILE B 647    11353  16038  12116  -7122    309   2238        C
ATOM   11238  C    ILE B 647      28.482 -14.834  98.090  1.00102.50           C
```

FIG. 13 Continued

```
ANISOU11238  C   ILE B 647    11262  15547  12135  -6830    173   2280           C
ATOM  11239  O   ILE B 647    29.345 -14.714  98.967  1.00102.85                 O
ANISOU11239  O   ILE B 647    11291  15624  12165  -6458     98   2234           O
ATOM  11240  CB  ILE B 647    28.925 -14.198  95.659  1.00104.16                 C
ANISOU11240  CB  ILE B 647    10999  16385  12192  -7629     14   2447           C
ATOM  11241  CG1 ILE B 647    29.872 -14.607  94.519  1.00106.52                 C
ANISOU11241  CG1 ILE B 647    11135  17145  12194  -7800    156   2364           C
ATOM  11242  CG2 ILE B 647    29.368 -12.889  96.321  1.00103.53                 C
ANISOU11242  CG2 ILE B 647    10668  16324  12346  -7584   -364   2603           C
ATOM  11243  CD1 ILE B 647    29.769 -16.064  94.117  1.00107.94                 C
ANISOU11243  CD1 ILE B 647    11610  17265  12139  -7668    564   2088           C
ATOM  11244  N   TYR B 648    27.199 -14.568  98.313  1.00130.35                 N
ANISOU11244  N   TYR B 648    14671  18817  15839  -6998    147   2345           N
ATOM  11245  CA  TYR B 648    26.723 -14.157  99.639  1.00129.54                 C
ANISOU11245  CA  TYR B 648    14865  18458  15897  -6734     80   2327           C
ATOM  11246  C   TYR B 648    26.965 -15.273 100.651  1.00130.26                 C
ANISOU11246  C   TYR B 648    15335  18371  15789  -6295    365   2200           C
ATOM  11247  O   TYR B 648    27.607 -15.061 101.682  1.00130.60                 O
ANISOU11247  O   TYR B 648    15418  18411  15794  -5943    274   2164           O
ATOM  11248  CB  TYR B 648    25.234 -13.773  99.574  1.00128.87                 C
ANISOU11248  CB  TYR B 648    14750  18176  16040  -7001     53   2385           C
ATOM  11249  CG  TYR B 648    24.390 -14.071 100.815  1.00128.88                 C
ANISOU11249  CG  TYR B 648    14981  17909  16077  -6759    240   2287           C
ATOM  11250  CD1 TYR B 648    24.065 -13.065 101.726  1.00128.77                 C
ANISOU11250  CD1 TYR B 648    14838  17809  16278  -6620     51   2248           C
ATOM  11251  CD2 TYR B 648    23.883 -15.346 101.045  1.00129.56                 C
ANISOU11251  CD2 TYR B 648    15415  17833  15979  -6706    612   2226           C
ATOM  11252  CE1 TYR B 648    23.284 -13.330 102.835  1.00129.36                 C
ANISOU11252  CE1 TYR B 648    15099  17719  16333  -6431    262   2136           C
ATOM  11253  CE2 TYR B 648    23.111 -15.618 102.151  1.00130.13                 C
ANISOU11253  CE2 TYR B 648    15688  17715  16040  -6552    804   2171           C
ATOM  11254  CZ  TYR B 648    22.812 -14.608 103.042  1.00130.03                 C
ANISOU11254  CZ  TYR B 648    15515  17695  16196  -6416    645   2120           C
ATOM  11255  OH  TYR B 648    22.041 -14.885 104.150  1.00131.17                 O
ANISOU11255  OH  TYR B 648    15841  17722  16275  -6284    877   2041           O
ATOM  11256  N   ALA B 649    26.458 -16.463 100.329  1.00150.15                 N
ANISOU11256  N   ALA B 649    18146  20731  18174  -6344    681   2145           N
ATOM  11257  CA  ALA B 649    26.608 -17.649 101.169  1.00151.55                 C
ANISOU11257  CA  ALA B 649    18742  20668  18170  -5978    947   2074           C
ATOM  11258  C   ALA B 649    28.079 -17.869 101.543  1.00152.82                 C
ANISOU11258  C   ALA B 649    18897  20967  18199  -5545    872   2025           C
ATOM  11259  O   ALA B 649    28.401 -18.618 102.473  1.00154.33                 O
ANISOU11259  O   ALA B 649    19403  20975  18260  -5155    977   2014           O
ATOM  11260  CB  ALA B 649    26.023 -18.877 100.465  1.00152.76                 C
ANISOU11260  CB  ALA B 649    19185  20629  18229  -6163   1252   2012           C
ATOM  11261  N   VAL B 650    28.971 -17.220 100.801  1.00129.01                 N
ANISOU11261  N   VAL B 650    15508  18297  15213  -5633    678   2016           N
ATOM  11262  CA  VAL B 650    30.381 -17.266 101.130  1.00130.52                 C
ANISOU11262  CA  VAL B 650    15577  18701  15315  -5252    570   1966           C
ATOM  11263  C   VAL B 650    30.641 -16.106 102.054  1.00129.66                 C
ANISOU11263  C   VAL B 650    15276  18681  15308  -5164    252   2038           C
ATOM  11264  O   VAL B 650    31.221 -16.288 103.117  1.00130.82                 O
ANISOU11264  O   VAL B 650    15547  18794  15365  -4761    187   2020           O
ATOM  11265  CB  VAL B 650    31.294 -17.122  99.910  1.00131.56                 C
ANISOU11265  CB  VAL B 650    15349  19236  15402  -5416    537   1907           C
ATOM  11266  CG1 VAL B 650    32.660 -16.650 100.347  1.00132.88                 C
ANISOU11266  CG1 VAL B 650    15219  19714  15555  -5126    317   1896           C
ATOM  11267  CG2 VAL B 650    31.422 -18.444  99.185  1.00133.66                 C
ANISOU11267  CG2 VAL B 650    15828  19436  15521  -5326    863   1734           C
ATOM  11268  N   SER B 651    30.196 -14.914 101.656  1.00107.94                 N
ANISOU11268  N   SER B 651    12242  16021  12748  -5545     30   2118           N
ATOM  11269  CA  SER B 651    30.384 -13.709 102.480  1.00107.54                 C
ANISOU11269  CA  SER B 651    12015  16003  12841  -5500   -301   2145           C
ATOM  11270  C   SER B 651    29.855 -13.897 103.915  1.00107.69                 C
ANISOU11270  C   SER B 651    12355  15763  12800  -5186   -237   2081           C
ATOM  11271  O   SER B 651    30.270 -13.202 104.855  1.00108.28                 O
ANISOU11271  O   SER B 651    12373  15882  12888  -5005   -469   2034           O
ATOM  11272  CB  SER B 651    29.789 -12.479 101.792  1.00106.38                 C
ANISOU11272  CB  SER B 651    11580  15875  12965  -5959   -550   2251           C
```

FIG. 13 Continued

```
ATOM   11273  OG   SER B 651      30.711 -11.959 100.852  1.00107.14           O
ANISOU11273  OG   SER B 651    11330  16304  13074  -6206   -739   2343        O
ATOM   11274  N    ILE B 652      28.931 -14.843 104.053  1.00111.49           N
ANISOU11274  N    ILE B 652    13174  15997  13189  -5166     83   2075        N
ATOM   11275  CA   ILE B 652      28.477 -15.293 105.348  1.00112.41           C
ANISOU11275  CA   ILE B 652    13643  15913  13154  -4895    224   2046        C
ATOM   11276  C    ILE B 652      29.704 -15.824 106.056  1.00114.41           C
ANISOU11276  C    ILE B 652    14028  16259  13183  -4454    157   2046        C
ATOM   11277  O    ILE B 652      30.094 -15.321 107.111  1.00115.35           O
ANISOU11277  O    ILE B 652    14156  16452  13218  -4232    -36   2012        O
ATOM   11278  CB   ILE B 652      27.427 -16.416 105.206  1.00112.68           C
ANISOU11278  CB   ILE B 652    14024  15684  13105  -5002    602   2080        C
ATOM   11279  CG1  ILE B 652      26.068 -15.883 105.635  1.00112.05           C
ANISOU11279  CG1  ILE B 652    13934  15489  13150  -5217    674   2053        C
ATOM   11280  CG2  ILE B 652      27.780 -17.637 106.048  1.00115.00           C
ANISOU11280  CG2  ILE B 652    14764  15811  13121  -4637    792   2123        C
ATOM   11281  CD1  ILE B 652      25.899 -14.407 105.296  1.00110.67           C
ANISOU11281  CD1  ILE B 652    13332  15439  13279  -5419    360   2007        C
ATOM   11282  N    THR B 653      30.332 -16.822 105.442  1.00104.29           N
ANISOU11282  N    THR B 653    12627  14985  11812  -4320    294   2062        N
ATOM   11283  CA   THR B 653      31.513 -17.461 106.000  1.00106.85           C
ANISOU11283  CA   THR B 653    13252  15381  11966  -3853    224   2068        C
ATOM   11284  C    THR B 653      32.781 -16.620 105.824  1.00107.31           C
ANISOU11284  C    THR B 653    12850  15831  12090  -3776   -104   2024        C
ATOM   11285  O    THR B 653      33.885 -17.087 106.065  1.00109.74           O
ANISOU11285  O    THR B 653    13111  16282  12303  -3404   -191   2012        O
ATOM   11286  CB   THR B 653      31.675 -18.883 105.447  1.00108.68           C
ANISOU11286  CB   THR B 653    13750  15418  12125  -3687    495   2060        C
ATOM   11287  OG1  THR B 653      30.457 -19.618 105.672  1.00108.63           O
ANISOU11287  OG1  THR B 653    14179  15031  12064  -3826    778   2122        O
ATOM   11288  CG2  THR B 653      32.841 -19.582 106.125  1.00112.04           C
ANISOU11288  CG2  THR B 653    14293  15863  12415  -3132    391   2083        C
ATOM   11289  N    ILE B 654      32.615 -15.380 105.374  1.00110.12           N
ANISOU11289  N    ILE B 654    12853  16354  12633  -4144   -300   2012        N
ATOM   11290  CA   ILE B 654      33.729 -14.438 105.330  1.00110.88           C
ANISOU11290  CA   ILE B 654    12523  16804  12804  -4156   -643   1994        C
ATOM   11291  C    ILE B 654      33.437 -13.315 106.315  1.00110.46           C
ANISOU11291  C    ILE B 654    12451  16699  12820  -4207   -921   1963        C
ATOM   11292  O    ILE B 654      34.136 -12.300 106.355  1.00111.05           O
ANISOU11292  O    ILE B 654    12195  16991  13006  -4317  -1253   1942        O
ATOM   11293  CB   ILE B 654      34.073 -13.926 103.912  1.00110.29           C
ANISOU11293  CB   ILE B 654    12028  17003  12875  -4557   -690   2022        C
ATOM   11294  CG1  ILE B 654      34.766 -15.036 103.142  1.00112.06           C
ANISOU11294  CG1  ILE B 654    12216  17390  12972  -4382   -448   1965        C
ATOM   11295  CG2  ILE B 654      35.070 -12.758 103.961  1.00111.31           C
ANISOU11295  CG2  ILE B 654    11717  17467  13108  -4682  -1076   2041        C
ATOM   11296  CD1  ILE B 654      35.839 -15.712 103.962  1.00114.98           C
ANISOU11296  CD1  ILE B 654    12627  17853  13207  -3822   -500   1908        C
ATOM   11297  N    ARG B 655      32.378 -13.505 107.102  1.00120.01           N
ANISOU11297  N    ARG B 655    14016  17622  13961  -4148   -771   1938        N
ATOM   11298  CA   ARG B 655      32.102 -12.608 108.223  1.00120.50           C
ANISOU11298  CA   ARG B 655    14122  17641  14022  -4105   -979   1835        C
ATOM   11299  C    ARG B 655      32.985 -13.087 109.376  1.00123.24           C
ANISOU11299  C    ARG B 655    14652  18111  14063  -3669  -1087   1824        C
ATOM   11300  O    ARG B 655      33.521 -12.260 110.111  1.00124.61           O
ANISOU11300  O    ARG B 655    14702  18433  14211  -3605  -1406   1725        O
ATOM   11301  CB   ARG B 655      30.607 -12.542 108.600  1.00119.48           C
ANISOU11301  CB   ARG B 655    14231  17236  13930  -4233   -756   1778        C
ATOM   11302  CG   ARG B 655      30.203 -11.263 109.351  1.00119.93           C
ANISOU11302  CG   ARG B 655    14187  17258  14124  -4300   -991   1596        C
ATOM   11303  CD   ARG B 655      28.713 -11.044 109.332  1.00119.01           C
ANISOU11303  CD   ARG B 655    14133  16917  14167  -4487   -779   1521        C
ATOM   11304  NE   ARG B 655      27.991 -12.312 109.209  1.00118.65           N
ANISOU11304  NE   ARG B 655    14383  16758  13939  -4477   -356   1634        N
ATOM   11305  CZ   ARG B 655      26.655 -12.448 109.195  1.00118.29           C
ANISOU11305  CZ   ARG B 655    14413  16557  13973   4641     88   1599        C
ATOM   11306  NH1  ARG B 655      25.857 -11.393 109.312  1.00118.30           N
ANISOU11306  NH1  ARG B 655    14201  16496  14252  -4772   -189   1434        N
ATOM   11307  NH2  ARG B 655      26.099 -13.651 109.071  1.00118.41           N
```

FIG. 13 Continued

```
ANISOU11307  NH2 ARG B 655     14708  16466  13815  -4674    276   1720        N
ATOM   11308  N   ILE B 656     33.175 -14.412 109.484  1.00109.23              N
ANISOU11308  N   ILE B 656     13167  16263  12072  -3381   -859   1931        N
ATOM   11309  CA  ILE B 656     34.047 -15.017 110.513  1.00112.48              C
ANISOU11309  CA  ILE B 656     13772  16773  12193  -2931   -989   1983        C
ATOM   11310  C   ILE B 656     35.471 -14.493 110.575  1.00114.32              C
ANISOU11310  C   ILE B 656     13614  17369  12454  -2779  -1376   1945        C
ATOM   11311  O   ILE B 656     36.419  15.240 110.792  1.00117.04              O
ANISOU11311  O   ILE B 656     13966  17838  12667  -2404  -1456   2018        O
ATOM   11312  CB  ILE B 656     34.115 -16.565 110.494  1.00114.25              C
ANISOU11312  CB  ILE B 656     14365  16796  12250  -2623   -730   2134        C
ATOM   11313  CG1 ILE B 656     35.156 -17.051 109.468  1.00115.05              C
ANISOU11313  CG1 ILE B 656     14169  17051  12495  -2479   -749   2131        C
ATOM   11314  CG2 ILE B 656     32.729 -17.152 110.297  1.00112.76              C
ANISOU11314  CG2 ILE B 656     14536  16255  12054  -2845   -336   2184        C
ATOM   11315  CD1 ILE B 656     36.102 -18.145 109.963  1.00119.09              C
ANISOU11315  CD1 ILE B 656     14855  17550  12845  -1934   -817   2228        C
ATOM   11316  N   VAL B 657     35.620 -13.214 110.303  1.00122.95              N
ANISOU11316  N   VAL B 657     14337  18621  13757  -3087  -1626   1837        N
ATOM   11317  CA  VAL B 657     36.815 -12.536 110.718  1.00125.27              C
ANISOU11317  CA  VAL B 657     14310  19248  14039  -2999  -2038   1780        C
ATOM   11318  C   VAL B 657     36.238 -11.787 111.935  1.00125.89              C
ANISOU11318  C   VAL B 657     14620  19224  13988  -3023  -2195   1640        C
ATOM   11319  O   VAL B 657     36.894 -10.946 112.533  1.00127.83              O
ANISOU11319  O   VAL B 657     14685  19668  14214  -3034  -2569   1523        O
ATOM   11320  CB  VAL B 657     37.432 -11.629 109.622  1.00124.51              C
ANISOU11320  CB  VAL B 657     13667  19392  14249  -3367  -2227   1764        C
ATOM   11321  CG1 VAL B 657     38.570 -12.349 108.897  1.00126.29              C
ANISOU11321  CG1 VAL B 657     13584  19933  14466  -3185  -2189   1835        C
ATOM   11322  CG2 VAL B 657     36.372 -11.183 108.640  1.00121.21              C
ANISOU11322  CG2 VAL B 657     13224  18748  14083  -3804  -2040   1784        C
ATOM   11323  N   PHE B 658     34.994 -12.128 112.301  1.00184.65              N
ANISOU11323  N   PHE B 658     22456  26375  21327  -3043  -1889   1628        N
ATOM   11324  CA  PHE B 658     34.316 -11.518 113.459  1.00185.73              C
ANISOU11324  CA  PHE B 658     22828  26442  21300  -3051  -1944   1449        C
ATOM   11325  C   PHE B 658     34.810 -12.031 114.811  1.00189.48              C
ANISOU11325  C   PHE B 658     23615  27073  21308  -2688  -2062   1472        C
ATOM   11326  O   PHE B 658     35.388 -11.278 115.592  1.00191.86              O
ANISOU11326  O   PHE B 658     23828  27577  21492  -2645  -2415   1313        O
ATOM   11327  CB  PHE B 658     32.764 -11.565 113.375  1.00183.73              C
ANISOU11327  CB  PHE B 658     22800  25894  21115  -3244  -1568   1395        C
ATOM   11328  CG  PHE B 658     32.164 -12.843 112.760  1.00182.32              C
ANISOU11328  CG  PHE B 658     22855  25523  20895  -3229  -1145   1608        C
ATOM   11329  CD1 PHE B 658     31.208 -12.753 111.747  1.00179.44              C
ANISOU11329  CD1 PHE B 658     22385  24965  20830  -3542   -914   1618        C
ATOM   11330  CD2 PHE B 658     32.497 -14.109 113.217  1.00184.36              C
ANISOU11330  CD2 PHE B 658     23459  25763  20828  -2920  -1007   1798        C
ATOM   11331  CE1 PHE B 658     30.627 -13.896 111.178  1.00178.52              C
ANISOU11331  CE1 PHE B 658     22489  24664  20678  -3577   -545   1778        C
ATOM   11332  CE2 PHE B 658     31.904 -15.253 112.648  1.00183.54              C
ANISOU11332  CE2 PHE B 658     23601  25414  20722  -2942   -635   1967        C
ATOM   11333  CZ  PHE B 658     30.973  15.132 111.622  1.00180.56              C
ANISOU11333  CZ  PHE B 658     23101  24869  20634  -3287   -400   1937        C
ATOM   11334  N   GLY B 659     34.568 -13.308 115.080  1.00119.65              N
ANISOU11334  N   GLY B 659     15153  18116  12193  -2453  -1789   1682        N
ATOM   11335  CA  GLY B 659     35.032 -13.944 116.300  1.00123.73              C
ANISOU11335  CA  GLY B 659     16012  18759  12242   2107   1910   1795        C
ATOM   11336  C   GLY B 659     36.543 -14.058 116.300  1.00126.18              C
ANISOU11336  C   GLY B 659     16051  19349  12544  -1827  -2308   1877        C
ATOM   11337  O   GLY B 659     37.196 -14.066 117.345  1.00130.02              O
ANISOU11337  O   GLY B 659     16645  20060  12695  -1590  -2613   1898        O
ATOM   11338  N   PHE B 660     37.099 -14.168 115.104  1.00140.77              N
ANISOU11338  N   PHE B 660     17520  21221  14745  -1862  -2302   1919        N
ATOM   11339  CA  PHE B 660     38.536 -14.174 114.945  1.00143.20              C
ANISOU11339  CA  PHE B 660     17440  21855  15116  -1635  -2653   1954        C
ATOM   11340  C   PHE B 660     39.039 -12.761 115.270  1.00143.84              C
ANISOU11340  C   PHE B 660     17160  22220  15271  -1872  -3064   1733        C
ATOM   11341  O   PHE B 660     40.222 -12.560 115.532  1.00146.88              O
ANISOU11341  O   PHE B 660     17238  22947  15622  -1718  -3446   1728        O
```

FIG. 13 Continued

```
ATOM   11342  CB   PHE B 660      38.907 -14.585 113.518  1.00141.42           C
ANISOU 11342  CB   PHE B 660    16873  21628  15231  -1672  -2476   2004       C
ATOM   11343  CG   PHE B 660      40.331 -14.294 113.152  1.00143.69           C
ANISOU 11343  CG   PHE B 660    16598  22337  15661  -1564  -2804   1972       C
ATOM   11344  CD1  PHE B 660      41.244 -15.326 112.997  1.00146.84           C
ANISOU 11344  CD1  PHE B 660    16898  22856  16040  -1111  -2826   2086       C
ATOM   11345  CD2  PHE B 660      40.763 -12.986 112.959  1.00143.25           C
ANISOU 11345  CD2  PHE B 660    16094  22551  15784  -1920  -3099   1824       C
ATOM   11346  CE1  PHE B 660      42.571 -15.060 112.662  1.00149.53           C
ANISOU 11346  CE1  PHE B 660    16643  23651  16519  -1004  -3111   2034       C
ATOM   11347  CE2  PHE B 660      42.082 -12.710 112.631  1.00145.86           C
ANISOU 11347  CE2  PHE B 660    15866  23318  16236  -1875  -3392   1805       C
ATOM   11348  CZ   PHE B 660      42.989 -13.749 112.479  1.00148.99           C
ANISOU 11348  CZ   PHE B 660    16110  23904  16596  -1414  -3384   1902       C
ATOM   11349  N    MET B 661      38.138 -11.781 115.258  1.00149.01           N
ANISOU 11349  N    MET B 661    17842  22718  16055  -2245  -3003   1540       N
ATOM   11350  CA   MET B 661      38.516 -10.402 115.566  1.00150.00           C
ANISOU 11350  CA   MET B 661    17684  23011  16297  -2495  -3399   1301       C
ATOM   11351  C    MET B 661      38.401 -10.066 117.045  1.00153.30           C
ANISOU 11351  C    MET B 661    18414  23514  16318  -2375  -3605   1127       C
ATOM   11352  O    MET B 661      39.382  -9.724 117.700  1.00156.85           O
ANISOU 11352  O    MET B 661    18719  24271  16606  -2276  -4027   1060       O
ATOM   11353  CB   MET B 661      37.682  -9.413 114.755  1.00146.57           C
ANISOU 11353  CB   MET B 661    17089  22332  16270  -2941  -3298   1161       C
ATOM   11354  CG   MET B 661      38.300  -9.057 113.416  1.00145.02           C
ANISOU 11354  CG   MET B 661    16395  22241  16466  -3211  -3382   1259       C
ATOM   11355  SD   MET B 661      39.517  -7.732 113.471  1.00147.86           S
ANISOU 11355  SD   MET B 661    16255  22906  17018  -3480  -3964   1130       S
ATOM   11356  CE   MET B 661      38.428  -6.306 113.541  1.00146.55           C
ANISOU 11356  CE   MET B 661    16182  22340  17161  -3889  -4066    881       C
ATOM   11357  N    LEU B 662      37.193 -10.155 117.573  1.00135.74           N
ANISOU 11357  N    LEU B 662    16601  21059  13916  -2406  -3303   1036       N
ATOM   11358  CA   LEU B 662      36.990  -9.826 118.970  1.00139.28           C
ANISOU 11358  CA   LEU B 662    17362  21629  13931  -2324  -3440    830       C
ATOM   11359  C    LEU B 662      37.662 -10.832 119.892  1.00143.31           C
ANISOU 11359  C    LEU B 662    18155  22380  13917  -1942  -3565   1065       C
ATOM   11360  O    LEU B 662      37.053 -11.308 120.844  1.00145.48           O
ANISOU 11360  O    LEU B 662    18892  22654  13729   1829   3389   1095       O
ATOM   11361  CB   LEU B 662      35.505  -9.659 119.284  1.00138.07           C
ANISOU 11361  CB   LEU B 662    17522  21226  13711  -2464  -3042    650       C
ATOM   11362  CG   LEU B 662      35.049  -8.227 119.009  1.00136.91           C
ANISOU 11362  CG   LEU B 662    17119  20926  13974  -2778  -3165    271       C
ATOM   11363  CD1  LEU B 662      35.780  -7.259 119.943  1.00141.02           C
ANISOU 11363  CD1  LEU B 662    17579  21676  14328  -2791  -3648    -50       C
ATOM   11364  CD2  LEU B 662      35.297  -7.870 117.556  1.00133.24           C
ANISOU 11364  CD2  LEU B 662    16223  20303  14098  -3012  -3224    394       C
ATOM   11365  N    ILE B 663      38.913 -11.161 119.578  1.00157.71           N
ANISOU 11365  N    ILE B 663    19679  24423  15819  -1749  -3870   1246       N
ATOM   11366  CA   ILE B 663      39.753 -12.023 120.410  1.00162.33           C
ANISOU 11366  CA   ILE B 663    20442  25258  15979  -1346  -4116   1484       C
ATOM   11367  C    ILE B 663      41.174 -11.524 120.290  1.00164.77           C
ANISOU 11367  C    ILE B 663    20227  25938  16440  -1295  -4639   1437       C
ATOM   11368  O    ILE B 663      41.697 -10.897 121.213  1.00168.56           O
ANISOU 11368  O    ILE B 663    20680  26711  16655  -1312  -5058   1270       O
ATOM   11369  CB   ILE B 663      39.708 -13.510 120.007  1.00162.09           C
ANISOU 11369  CB   ILE B 663    20638  25026  15922  -1021  -3827   1873       C
ATOM   11370  CG1  ILE B 663      38.714 -14.264 120.887  1.00163.57           C
ANISOU 11370  CG1  ILE B 663    21487  25023  15638   -943  -3526   2028       C
ATOM   11371  CG2  ILE B 663      41.080 -14.168 120.197  1.00166.37           C
ANISOU 11371  CG2  ILE B 663    20991  25840  16380   -593  -4219   2102       C
ATOM   11372  CD1  ILE B 663      39.252 -14.575 122.275  1.00169.61           C
ANISOU 11372  CD1  ILE B 663    22569  26072  15804   -676  -3878   2167       C
ATOM   11373  N    ALA B 664      41.789 -11.782 119.140  1.00180.81           N
ANISOU 11373  N    ALA B 664    21822  27931  18887  -1262  -4604   1561       N
ATOM   11374  CA   ALA B 664      43.125 -11.288 118.888  1.00183.23           C
ANISOU 11374  CA   ALA B 664    21539  28694  19385  -1268  -5050   1515       C
ATOM   11375  C    ALA B 664      43.082  -9.779 119.110  1.00183.16           C
ANISOU 11375  C    ALA B 664    21339  28764  19491  -1724  -5330   1174       C
ATOM   11376  O    ALA B 664      44.113  -9.137 119.326  1.00186.40           O
```

FIG. 13 Continued

```
ANISOU11376  O    ALA B 664     21355  29529  19942  -1811  -5800   1072           O
ATOM   11377  CB   ALA B 664     43.556 -11.619 117.461  1.00180.83                C
ANISOU11377  CB   ALA B 664     20775  28400  19534  -1287  -4855   1627           C
ATOM   11378  N    LEU B 665     41.868  -9.227 119.085  1.00174.06                N
ANISOU11378  N    LEU B 665     20470  27260  18404  -2008  -5053    987           N
ATOM   11379  CA   LEU B 665     41.658  -7.787 119.215  1.00174.03                C
ANISOU11379  CA   LEU B 665     20337  27197  18592  -2426  -5282    635           C
ATOM   11380  C    LEU B 665     41.357  -7.334 120.638  1.00177.66                C
ANISOU11380  C    LEU B 665     21178  27723  18602  -2394  -5480    350           C
ATOM   11381  O    LEU B 665     42.243  -7.256 121.493  1.00182.36                O
ANISOU11381  O    LEU B 665     21732  28678  18879  -2270  -5911    303           O
ATOM   11382  CB   LEU B 665     40.516  -7.342 118.291  1.00169.10                C
ANISOU11382  CB   LEU B 665     19736  26142  18374  -2741  -4904    561           C
ATOM   11383  CG   LEU B 665     40.287  -5.853 118.018  1.00168.65                C
ANISOU11383  CG   LEU B 665     19469  25900  18710  -3193  -5126    260           C
ATOM   11384  CD1  LEU B 665     41.409  -5.246 117.178  1.00169.35                C
ANISOU11384  CD1  LEU B 665     18979  26194  19171  -3479  -5474    342           C
ATOM   11385  CD2  LEU B 665     38.953  -5.681 117.332  1.00164.41                C
ANISOU11385  CD2  LEU B 665     19077  24920  18473  -3371  -4717    229           C
ATOM   11386  N    ILE B 666     40.087  -7.031 120.871  1.00169.86                N
ANISOU11386  N    ILE B 666     20538  26417  17583  -2514  -5158    141           N
ATOM   11387  CA   ILE B 666     39.651  -6.533 122.159  1.00173.44                C
ANISOU11387  CA   ILE B 666     21353  26935  17611  -2515  -5262   -208           C
ATOM   11388  C    ILE B 666     39.367  -7.684 123.137  1.00175.87                C
ANISOU11388  C    ILE B 666     22162  27406  17255  -2171  -5057     -4           C
ATOM   11389  O    ILE B 666     40.248  -8.505 123.417  1.00178.39                O
ANISOU11389  O    ILE B 666     22483  27997  17299   1891   5265    309           O
ATOM   11390  CB   ILE B 666     38.437  -5.583 122.017  1.00171.44                C
ANISOU11390  CB   ILE B 666     21193  26300  17647  -2786  -5027   -590           C
ATOM   11391  CG1  ILE B 666     38.613  -4.645 120.823  1.00168.61                C
ANISOU11391  CG1  ILE B 666     20377  25688  17999  -3128  -5181   -639           C
ATOM   11392  CG2  ILE B 666     38.307  -4.728 123.249  1.00176.20                C
ANISOU11392  CG2  ILE B 666     22016  27018  17916  -2843  -5271  -1083           C
ATOM   11393  CD1  ILE B 666     39.550  -3.487 121.101  1.00172.27                C
ANISOU11393  CD1  ILE B 666     20568  26278  18609  -3367  -5773   -917           C
ATOM   11394  N    TRP B 667     38.136  -7.745 123.641  1.00170.21                N
ANISOU11394  N    TRP B 667     21852  26525  16294  -2198  -4656   -165           N
ATOM   11395  CA   TRP B 667     37.758  -8.734 124.654  1.00173.26                C
ANISOU11395  CA   TRP B 667     22758  27076  15996  -1963  -4446     24           C
ATOM   11396  C    TRP B 667     38.018 10.170 124.241  1.00172.16                 C
ANISOU11396  C    TRP B 667     22734  26886  15794  -1684  -4273    591           C
ATOM   11397  O    TRP B 667     38.296 -10.452 123.080  1.00168.39                O
ANISOU11397  O    TRP B 667     21942  26222  15817  -1671  -4201    792           O
ATOM   11398  CB   TRP B 667     36.306  -8.526 125.144  1.00173.19                C
ANISOU11398  CB   TRP B 667     23097  26925  15784  -2095  -3968   -261           C
ATOM   11399  CG   TRP B 667     35.150  9.332 124.483  1.00169.13                 C
ANISOU11399  CG   TRP B 667     22740  26086  15436  -2116  -3345    -17           C
ATOM   11400  CD1  TRP B 667     34.971 -10.692 124.494  1.00169.10                C
ANISOU11400  CD1  TRP B 667     23050  26044  15157  -1943  -3063    462           C
ATOM   11401  CD2  TRP B 667     33.990  -8.790 123.821  1.00165.46                C
ANISOU11401  CD2  TRP B 667     22145  25297  15425  -2335  -2965   -264           C
ATOM   11402  NE1  TRP B 667     33.801 -11.023 123.849  1.00165.47                N
ANISOU11402  NE1  TRP B 667     22647  25271  14951  -2080  -2530    516           N
ATOM   11403  CE2  TRP B 667     33.183  -9.877 123.432  1.00163.18                C
ANISOU11403  CE2  TRP B 667     22070  24830  15102  -2310  -2465     81           C
ATOM   11404  CE3  TRP B 667     33.573  -7.493 123.504  1.00164.32                C
ANISOU11404  CE3  TRP B 667     21719  24970  15745  -2545  -3036   -731           C
ATOM   11405  CZ2  TRP B 667     31.995  -9.706 122.750  1.00159.77                C
ANISOU11405  CZ2  TRP B 667     21543  24108  15055  -2495  -2042    -30           C
ATOM   11406  CZ3  TRP B 667     32.393  -7.328 122.829  1.00161.04                C
ANISOU11406  CZ3  TRP B 667     21217  24239  15730  -2686  -2628   -822           C
ATOM   11407  CH2  TRP B 667     31.617  -8.426 122.456  1.00158.74                C
ANISOU11407  CH2  TRP B 667     21105  23837  15370  -2666  -2136   -476           C
ATOM   11408  N    GLU B 668     37.948 -11.067 125.215  1.00155.37                N
ANISOU11408  N    GLU B 668     21075  24927  13034  -1468  -4225    840           N
ATOM   11409  CA   GLU B 668     38.171 -12.489 124.982  1.00155.58                C
ANISOU11409  CA   GLU B 668     21303  24844  12965  -1172  -4098   1386           C
ATOM   11410  C    GLU B 668     36.877 -13.232 124.630  1.00152.67                C
ANISOU11410  C    GLU B 668     21273  24112  12623  -1260  -3462   1554           C
```

FIG. 13 Continued

```
ATOM   11411  O    GLU B 668       36.243 -12.944 123.614  1.00147.62           O
ANISOU11411  O    GLU B 668    20406  23182  12503  -1460  -3149   1426         O
ATOM   11412  CB   GLU B 668       38.846 -13.128 126.201  1.00162.17           C
ANISOU11412  CB   GLU B 668    22487  26016  13116   -893  -4452   1656         C
ATOM   11413  CG   GLU B 668       40.297 -12.726 126.407  1.00165.46           C
ANISOU11413  CG   GLU B 668    22520  26796  13550   -731  -5120   1623         C
ATOM   11414  CD   GLU B 668       41.226 -13.428 125.447  1.00164.15           C
ANISOU11414  CD   GLU B 668    21983  26538  13848   -436  -5262   1955         C
ATOM   11415  OE1  GLU B 668       40.897 -13.503 124.245  1.00158.85           O
ANISOU11415  OE1  GLU B 668    21071  25548  13738   -525  -4922   1951         O
ATOM   11416  OE2  GLU B 668       42.289 -13.906 125.897  1.00168.88           O
ANISOU11416  OE2  GLU B 668    22516  27407  14243   -106  -5720   2206         O
ATOM   11417  N    PHE B 669       36.491 -14.185 125.477  1.00216.91           N
ANISOU11417  N    PHE B 669    29953  32278  20184  -1144  -3295   1863         N
ATOM   11418  CA   PHE B 669       35.296 -14.987 125.227  1.00215.10           C
ANISOU11418  CA   PHE B 669    30069  31726  19933  -1262  -2708   2068         C
ATOM   11419  C    PHE B 669       34.224 -14.188 124.492  1.00210.07           C
ANISOU11419  C    PHE B 669    29180  30889  19749  -1598  -2309   1681         C
ATOM   11420  O    PHE B 669       33.634 -13.264 125.044  1.00210.96           O
ANISOU11420  O    PHE B 669    29278  31166  19710  -1797  -2231   1263         O
ATOM   11421  CB   PHE B 669       34.751 -15.644 126.511  1.00220.62           C
ANISOU11421  CB   PHE B 669    31392  32592  19841  -1275  -2547   2293         C
ATOM   11422  CG   PHE B 669       34.867 -14.789 127.759  1.00225.31           C
ANISOU11422  CG   PHE B 669    32089  33667  19850  -1358  -2792   1954         C
ATOM   11423  CD1  PHE B 669       33.762 -14.119 128.264  1.00225.84           C
ANISOU11423  CD1  PHE B 669    32261  33869  19680  -1655  -2418   1540         C
ATOM   11424  CD2  PHE B 669       36.069 -14.691 128.451  1.00229.83           C
ANISOU11424  CD2  PHE B 669    32653  34582  20091  -1131  -3395   2031         C
ATOM   11425  CE1  PHE B 669       33.859 -13.352 129.416  1.00230.76           C
ANISOU11425  CE1  PHE B 669    32999  34943  19735  -1727  -2621   1169         C
ATOM   11426  CE2  PHE B 669       36.171 -13.920 129.605  1.00234.63           C
ANISOU11426  CE2  PHE B 669    33382  35649  20119  -1235  -3632   1691         C
ATOM   11427  CZ   PHE B 669       35.065 -13.251 130.086  1.00235.11           C
ANISOU11427  CZ   PHE B 669    33573  35825  19933  -1534  -3233   1242         C
ATOM   11428  N    ASP B 670       33.998 -14.542 123.230  1.00162.37           N
ANISOU11428  N    ASP B 670    22927  24494  14271  -1642  -2080   1806         N
ATOM   11429  CA   ASP B 670       33.005 -13.859 122.406  1.00157.71           C
ANISOU11429  CA   ASP B 670    22074  23692  14157  -1946  -1746   1509         C
ATOM   11430  C    ASP B 670       32.055 -14.825 121.686  1.00155.13           C
ANISOU11430  C    ASP B 670    21924  23014  14003  -2059  -1241   1770         C
ATOM   11431  O    ASP B 670       32.193 -16.043 121.795  1.00156.94           O
ANISOU11431  O    ASP B 670    22504  23113  14012  -1903  -1147   2179         O
ATOM   11432  CB   ASP B 670       33.645 -12.843 121.444  1.00154.21           C
ANISOU11432  CB   ASP B 670    21057  23223  14315  -2020  -2052   1266         C
ATOM   11433  CG   ASP B 670       34.487 -13.492 120.357  1.00151.95           C
ANISOU11433  CG   ASP B 670    20538  22805  14390  -1872  -2161   1563         C
ATOM   11434  OD1  ASP B 670       34.421 -14.730 120.196  1.00152.40           O
ANISOU11434  OD1  ASP B 670    20875  22692  14339  -1709  -1952   1917         O
ATOM   11435  OD2  ASP B 670       35.214 -12.750 119.657  1.00150.15           O
ANISOU11435  OD2  ASP B 670    19845  22645  14561  -1932  -2450   1427         O
ATOM   11436  N    PHE B 671       31.083 -14.266 120.970  1.00154.34           N
ANISOU11436  N    PHE B 671    21590  22744  14308  -2336   -948   1532         N
ATOM   11437  CA   PHE B 671       30.040 -15.066 120.347  1.00152.30           C
ANISOU11437  CA   PHE B 671    21476  22193  14196  -2512   -465   1720         C
ATOM   11438  C    PHE B 671       29.726 -16.192 121.309  1.00156.66           C
ANISOU11438  C    PHE B 671    22600  22770  14153  -2453   -242   2047         C
ATOM   11439  O    PHE B 671       29.877 -16.056 122.517  1.00161.01           O
ANISOU11439  O    PHE B 671    23398  23614  14163  -2379   -350   2011         O
ATOM   11440  CB   PHE B 671       30.480 -15.671 119.010  1.00148.79           C
ANISOU11440  CB   PHE B 671    20855  21469  14209  -2469   -480   1948         C
ATOM   11441  CG   PHE B 671       30.725 -14.663 117.906  1.00144.64           C
ANISOU11441  CG   PHE B 671    19782  20914  14259  -2603   -660   1708         C
ATOM   11442  CD1  PHE B 671       29.860 -13.593 117.696  1.00142.73           C
ANISOU11442  CD1  PHE B 671    19282  20656  14293  -2867   -569   1383         C
ATOM   11443  CD2  PHE B 671       31.812 -14.823 117.045  1.00143.18           C
ANISOU11443  CD2  PHE B 671    19337  20718  14348  -2467   -917   1827         C
ATOM   11444  CE1  PHE B 671       30.105 -12.688 116.664  1.00139.49           C
ANISOU11444  CE1  PHE B 671    18408  20184  14409  -3014   -778   1235         C
ATOM   11445  CE2  PHE B 671       32.054 -13.932 116.029  1.00139.97           C
```

FIG. 13 Continued

```
ANISOU11445  CE2 PHE B 671     18451  20317  14416  -2645  -1076   1663        C
ATOM   11446  CZ  PHE B 671     31.209 -12.865 115.832  1.00138.11              C
ANISOU11446  CZ  PHE B 671     18005  20029  14442  -2932  -1026   1396        C
ATOM   11447  N   SER B 672     29.321 -17.329 120.774  1.00140.09              N
ANISOU11447  N   SER B 672     20736  20359  12132  -2508     48   2385        N
ATOM   11448  CA  SER B 672     29.016 -18.439 121.641  1.00144.70              C
ANISOU11448  CA  SER B 672     21898  20905  12178  -2497    244   2758        C
ATOM   11449  C   SER B 672     28.846 -19.732 120.900  1.00144.17              C
ANISOU11449  C   SER B 672     22083  20395  12299  -2511    452   3141        C
ATOM   11450  O   SER B 672     29.042 -19.826 119.693  1.00140.27              O
ANISOU11450  O   SER B 672     21316  19654  12327  -2496    441   3102        O
ATOM   11451  CB  SER B 672     27.735 -18.170 122.429  1.00146.88              C
ANISOU11451  CB  SER B 672     22326  21384  12098  -2818    661   2597        C
ATOM   11452  OG  SER B 672     27.994 -17.379 123.568  1.00150.26              O
ANISOU11452  OG  SER B 672     22777  22242  12073  -2745    469   2346        O
ATOM   11453  N   ALA B 673     28.514 -20.745 121.683  1.00150.83              N
ANISOU11453  N   ALA B 673     23487  21148  12675  -2550    623   3519        N
ATOM   11454  CA  ALA B 673     28.150 -22.033 121.166  1.00151.58              C
ANISOU11454  CA  ALA B 673     23931  20773  12888  -2633    865   3889        C
ATOM   11455  C   ALA B 673     26.709 -21.803 120.794  1.00149.35              C
ANISOU11455  C   ALA B 673     23519  20473  12755  -3112   1368   3699        C
ATOM   11456  O   ALA B 673     26.404 -21.439 119.657  1.00144.54              O
ANISOU11456  O   ALA B 673     22510  19730  12680  -3239   1463   3464        O
ATOM   11457  CB  ALA B 673     28.255 -23.077 122.250  1.00158.16              C
ANISOU11457  CB  ALA B 673     25424  21530  13139  -2560    840   4381        C
ATOM   11458  N   PHE B 674     25.831 -21.941 121.784  1.00148.42              N
ANISOU11458  N   PHE B 674     23698  20556  12139  -3385   1677   3787        N
ATOM   11459  CA  PHE B 674     24.399 -21.756 121.577  1.00147.46              C
ANISOU11459  CA  PHE B 674     23429  20490  12111  -3846   2182   3611        C
ATOM   11460  C   PHE B 674     23.989 -20.381 121.023  1.00142.80              C
ANISOU11460  C   PHE B 674     22183  20130  11945  -3919   2205   3054        C
ATOM   11461  O   PHE B 674     22.798 -20.100 120.900  1.00142.41              O
ANISOU11461  O   PHE B 674     21932  20178  11998  -4256   2591   2860        O
ATOM   11462  CB  PHE B 674     23.621 -22.055 122.860  1.00153.43              C
ANISOU11462  CB  PHE B 674     24572  21540  12183  -4118   2510   3773        C
ATOM   11463  CG  PHE B 674     22.148 -22.285 122.634  1.00153.83              C
ANISOU11463  CG  PHE B 674     24555  21585  12307  -4623   3073   3734        C
ATOM   11464  CD1 PHE B 674     21.655 -23.567 122.432  1.00156.29              C
ANISOU11464  CD1 PHE B 674     25290  21517  12575  -4910   3328   4184        C
ATOM   11465  CD2 PHE B 674     21.254 -21.224 122.621  1.00152.27              C
ANISOU11465  CD2 PHE B 674     23856  21748  12253  -4810   3330   3239        C
ATOM   11466  CE1 PHE B 674     20.294 -23.787 122.221  1.00157.09              C
ANISOU11466  CE1 PHE B 674     25291  21647  12747  -5420   3839   4151        C
ATOM   11467  CE2 PHE B 674     19.896 -21.436 122.409  1.00153.12              C
ANISOU11467  CE2 PHE B 674     23832  21897  12451  -5264   3839   3195        C
ATOM   11468  CZ  PHE B 674     19.417 -22.719 122.210  1.00155.48              C
ANISOU11468  CZ  PHE B 674     24532  21865  12679  -5590   4097   3657        C
ATOM   11469  N   MET B 675     24.948 -19.515 120.703  1.00139.14              N
ANISOU11469  N   MET B 675     21375  19749  11742  -3619   1783   2806        N
ATOM   11470  CA  MET B 675     24.577 -18.228 120.119  1.00135.17              C
ANISOU11470  CA  MET B 675     20290  19376  11693  -3700   1757   2329        C
ATOM   11471  C   MET B 675     24.855 -18.116 118.628  1.00129.90              C
ANISOU11471  C   MET B 675     19266  18414  11676  -3700   1615   2296        C
ATOM   11472  O   MET B 675     24.087 -17.496 117.905  1.00127.00              O
ANISOU11472  O   MET B 675     18515  18020  11720  -3917   1749   2057        O
ATOM   11473  CB  MET B 675     25.144 -17.049 120.899  1.00136.26              C
ANISOU11473  CB  MET B 675     20241  19874  11658  -3498   1446   1975        C
ATOM   11474  CG  MET B 675     24.061 -16.194 121.565  1.00138.20              C
ANISOU11474  CG  MET B 675     20313  20426  11769  -3689   1737   1561        C
ATOM   11475  SD  MET B 675     22.420 -16.957 121.778  1.00140.83              S
ANISOU11475  SD  MET B 675     20810  20792  11905  -4104   2424   1679        S
ATOM   11476  CE  MET B 675     21.574 -16.359 120.309  1.00135.42              C
ANISOU11476  CE  MET B 675     19527  19863  12064  -4296   2533   1427        C
ATOM   11477  N   VAL B 676     25.946 -18.706 118.160  1.00128.13              N
ANISOU11477  N   VAL B 676     19149  17996  11539  -3453   1339   2530        N
ATOM   11478  CA  VAL B 676     26.201 -18.702 116.725  1.00123.81              C
ANISOU11478  CA  VAL B 676     18288  17216  11537  -3485   1255   2500        C
ATOM   11479  C   VAL B 676     25.281 -19.749 116.132  1.00123.78              C
ANISOU11479  C   VAL B 676     18508  16897  11628  -3768   1645   2702        C
```

FIG. 13 Continued

```
ATOM   11480  O    VAL B 676      24.741 -19.580 115.051  1.00120.59           O
ANISOU11480  O    VAL B 676    17818  16373  11629  -4004   1757   2592       O
ATOM   11481  CB   VAL B 676      27.680 -18.976 116.370  1.00123.52           C
ANISOU11481  CB   VAL B 676    18226  17128  11579  -3120    867   2624       C
ATOM   11482  CG1  VAL B 676      27.787 -20.034 115.281  1.00122.43           C
ANISOU11482  CG1  VAL B 676    18193  16630  11697  -3132    989   2816       C
ATOM   11483  CG2  VAL B 676      28.392 -17.667 115.968  1.00120.74           C
ANISOU11483  CG2  VAL B 676    17345  17010  11522  -3046    504   2329       C
ATOM   11484  N    LEU B 677      25.086 -20.828 116.871  1.00127.91           N
ANISOU11484  N    LEU B 677    19560  17286  11756  -3774   1830   3014       N
ATOM   11485  CA   LEU B 677      24.152 -21.860 116.466  1.00128.90           C
ANISOU11485  CA   LEU B 677    19956  17096  11926  -4099   2206   3220       C
ATOM   11486  C    LEU B 677      22.776 -21.211 116.282  1.00127.49           C
ANISOU11486  C    LEU B 677    19447  17089  11903  -4516   2532   2975       C
ATOM   11487  O    LEU B 677      22.130 -21.360 115.248  1.00125.14           O
ANISOU11487  O    LEU B 677    18957  16617  11973  -4790   2690   2922       O
ATOM   11488  CB   LEU B 677      24.091 -22.931 117.551  1.00134.55           C
ANISOU11488  CB   LEU B 677    21308  17694  12123  -4089   2335   3610       C
ATOM   11489  CG   LEU B 677      23.885 -24.398 117.185  1.00137.06           C
ANISOU11489  CG   LEU B 677    22113  17500  12464  -4218   2509   3975       C
ATOM   11490  CD1  LEU B 677      22.528 -24.599 116.543  1.00136.01           C
ANISOU11490  CD1  LEU B 677    21873  17254  12549  -4748   2925   3906       C
ATOM   11491  CD2  LEU B 677      25.010 -24.888 116.290  1.00135.62           C
ANISOU11491  CD2  LEU B 677    21937  16983  12608  -3851   2210   4013       C
ATOM   11492  N    ILE B 678      22.334 -20.472 117.290  1.00130.58           N
ANISOU11492  N    ILE B 678    19753  17848  12015  -4550   2622   2799       N
ATOM   11493  CA   ILE B 678      21.048 -19.790 117.208  1.00130.04           C
ANISOU11493  CA   ILE B 678    19314  17980  12114  -4874   2922   2519       C
ATOM   11494  C    ILE B 678      21.150 -18.525 116.363  1.00125.54           C
ANISOU11494  C    ILE B 678    18146  17482  12070  -4802   2669   2155       C
ATOM   11495  O    ILE B 678      20.610 -17.463 116.714  1.00125.74           O
ANISOU11495  O    ILE B 678    17828  17768  12182  -4822   2698   1813       O
ATOM   11496  CB   ILE B 678      20.484 -19.459 118.591  1.00134.49           C
ANISOU11496  CB   ILE B 678    19980  18937  12182  -4930   3154   2404       C
ATOM   11497  CG1  ILE B 678      20.605 -20.675 119.502  1.00139.53           C
ANISOU11497  CG1  ILE B 678    21268  19518  12229  -4985   3315   2841       C
ATOM   11498  CG2  ILE B 678      19.027 -19.038 118.484  1.00135.04           C
ANISOU11498  CG2  ILE B 678    19684  19195  12431  -5283   3553   2151       C
ATOM   11499  CD1  ILE B 678      20.023 -21.926 118.909  1.00140.36           C
ANISOU11499  CD1  ILE B 678    21657  19242  12432  -5314   3587   3193       C
ATOM   11500  N    ILE B 679      21.886 -18.646 115.262  1.00122.16           N
ANISOU11500  N    ILE B 679    17612  16817  11986  -4709   2408   2229       N
ATOM   11501  CA   ILE B 679      21.991 -17.578 114.279  1.00118.14           C
ANISOU11501  CA   ILE B 679    16575  16330  11983  -4719   2157   1982       C
ATOM   11502  C    ILE B 679      22.091 -18.198 112.898  1.00115.46           C
ANISOU11502  C    ILE B 679    16190  15719  11960  -4871   2143   2133       C
ATOM   11503  O    ILE B 679      21.456 -17.731 111.946  1.00113.12           O
ANISOU11503  O    ILE B 679    15529  15401  12052  -5114   2149   2020       O
ATOM   11504  CB   ILE B 679      23.170 -16.627 114.537  1.00117.16           C
ANISOU11504  CB   ILE B 679    16279  16357  11880  -4390   1718   1824       C
ATOM   11505  CG1  ILE B 679      22.939 -15.319 113.792  1.00114.28           C
ANISOU11505  CG1  ILE B 679    15373  16036  12013   4482   1505   1547       C
ATOM   11506  CG2  ILE B 679      24.474 -17.224 114.085  1.00116.24           C
ANISOU11506  CG2  ILE B 679    16313  16113  11742  -4159   1463   2036       C
ATOM   11507  CD1  ILE B 679      24.103 -14.402 113.858  1.00113.37           C
ANISOU11507  CD1  ILE B 679    15072  16020  11984  -4244   1055   1419       C
ATOM   11508  N    ALA B 680      22.874 -19.268 112.809  1.00119.38           N
ANISOU11508  N    ALA B 680    17068  16012  12280  -4719   2116   2381       N
ATOM   11509  CA   ALA B 680      23.033 -20.000 111.564  1.00117.75           C
ANISOU11509  CA   ALA B 680    16887  15541  12312  -4835   2135   2484       C
ATOM   11510  C    ALA B 680      21.903 -21.005 111.423  1.00119.61           C
ANISOU11510  C    ALA B 680    17392  15553  12502  -5198   2523   2624       C
ATOM   11511  O    ALA B 680      21.287 -21.092 110.379  1.00117.97           O
ANISOU11511  O    ALA B 680    16994  15252  12576  -5506   2613   2571       O
ATOM   11512  CB   ALA B 680      24.389 -20.680 111.489  1.00118.54           C
ANISOU11512  CB   ALA B 680    17234  15505  12302  -4468   1928   2626       C
ATOM   11513  N    ILE B 681      21.607 -21.768 112.461  1.00118.96           N
ANISOU11513  N    ILE B 681    17755  15395  12049  -5208   2743   2820       N
ATOM   11514  CA   ILE B 681      20.456 -22.638 112.348  1.00121.15           C
```

FIG. 13 Continued

```
ANISOU11514  CA   ILE B 681      18251  15483  12297  -5633   3118   2955       C
ATOM  11515  C    ILE B 681      19.271 -21.681 112.255  1.00119.96              C
ANISOU11515  C    ILE B 681      17605  15633  12341  -5939   3270   2718       C
ATOM  11516  O    ILE B 681      18.182 -22.037 111.806  1.00120.67              O
ANISOU11516  O    ILE B 681      17616  15665  12568  -6355   3531   2730       O
ATOM  11517  CB   ILE B 681      20.309 -23.593 113.553  1.00126.28              C
ANISOU11517  CB   ILE B 681      19482  16020  12477  -5650   3331   3259       C
ATOM  11518  CG1  ILE B 681      20.105 -25.053 113.088  1.00128.82              C
ANISOU11518  CG1  ILE B 681      20286  15846  12814  -5871   3502   3527       C
ATOM  11519  CG2  ILE B 681      19.211 -23.094 114.531  1.00128.62              C
ANISOU11519  CG2  ILE B 681      19654  16683  12534  -5908   3630   3186       C
ATOM  11520  CD1  ILE B 681      18.656 -25.452 112.803  1.00130.31              C
ANISOU11520  CD1  ILE B 681      20442  15985  13086  -6468   3884   3551       C
ATOM  11521  N    LEU B 682      19.482 -20.446 112.683  1.00127.82              N
ANISOU11521  N    LEU B 682      18248  16943  13376  -5725   3086   2485       N
ATOM  11522  CA   LEU B 682      18.430 -19.461 112.541  1.00127.04              C
ANISOU11522  CA   LEU B 682      17640  17087  13543  -5932   3176   2222       C
ATOM  11523  C    LEU B 682      18.154 -19.327 111.056  1.00123.83              C
ANISOU11523  C    LEU B 682      16903  16546  13602  -6157   3059   2180       C
ATOM  11524  O    LEU B 682      17.092 -19.756 110.591  1.00124.72              O
ANISOU11524  O    LEU B 682      16932  16613  13845   6542   3301   2214       O
ATOM  11525  CB   LEU B 682      18.855 -18.117 113.123  1.00126.25              C
ANISOU11525  CB   LEU B 682      17236  17255  13478  -5623   2922   1944       C
ATOM  11526  CG   LEU B 682      17.975 -16.888 112.890  1.00125.46              C
ANISOU11526  CG   LEU B 682      16560  17343  13766  -5717   2893   1621       C
ATOM  11527  CD1  LEU B 682      18.365 -16.172 111.593  1.00121.42              C
ANISOU11527  CD1  LEU B 682      15673  16710  13749  -5713   2513   1567       C
ATOM  11528  CD2  LEU B 682      16.491 -17.259 112.934  1.00127.96              C
ANISOU11528  CD2  LEU B 682      16746  17752  14123  -6089   3315   1602       C
ATOM  11529  N    ASN B 683      19.139 -18.778 110.327  1.00129.35              N
ANISOU11529  N    ASN B 683      17426  17210  14511  -5947   2686   2126       N
ATOM  11530  CA   ASN B 683      19.053 -18.492 108.874  1.00126.41              C
ANISOU11530  CA   ASN B 683      16723  16774  14533  -6150   2507   2092       C
ATOM  11531  C    ASN B 683      19.149 -19.653 107.854  1.00126.20              C
ANISOU11531  C    ASN B 683      16944  16494  14513  -6366   2600   2247       C
ATOM  11532  O    ASN B 683      19.331 -19.411 106.662  1.00124.01              O
ANISOU11532  O    ASN B 683      16429  16213  14475  -6496   2416   2214       O
ATOM  11533  CB   ASN B 683      20.023 -17.350 108.477  1.00123.66              C
ANISOU11533  CB   ASN B 683      16055  16538  14393  -5912   2079   1980       C
ATOM  11534  CG   ASN B 683      21.463 -17.831 108.177  1.00122.75              C
ANISOU11534  CG   ASN B 683      16165  16341  14135  -5659   1894   2087       C
ATOM  11535  OD1  ASN B 683      22.427 -17.090 108.402  1.00121.86              O
ANISOU11535  OD1  ASN B 683      15916  16353  14031  -5394   1600   2023       O
ATOM  11536  ND2  ASN B 683      21.607 -19.047 107.649  1.00123.43              N
ANISOU11536  ND2  ASN B 683      16565  16218  14115  -5744   2058   2223       N
ATOM  11537  N    ASP B 684      19.043 -20.899 108.312  1.00130.75              N
ANISOU11537  N    ASP B 684      18011  16851  14816  -6417   2870   2411       N
ATOM  11538  CA   ASP B 684      19.095 -22.045 107.407  1.00131.35              C
ANISOU11538  CA   ASP B 684      18369  16624  14913  -6615   2966   2509       C
ATOM  11539  C    ASP B 684      17.743 -22.178 106.724  1.00131.82              C
ANISOU11539  C    ASP B 684      18224  16692  15171  -7139   3149   2475       C
ATOM  11540  O    ASP B 684      17.613 -21.913 105.532  1.00129.91              O
ANISOU11540  O    ASP B 684      17700  16491  15170  -7344   3006   2389       O
ATOM  11541  CB   ASP B 684      19.446 -23.343 108.151  1.00134.89              C
ANISOU11541  CB   ASP B 684      19453  16753  15045  -6487   3149   2717       C
ATOM  11542  CG   ASP B 684      20.547 -24.151 107.453  1.00134.99              C
ANISOU11542  CG   ASP B 684      19748  16473  15067  -6255   3020   2741       C
ATOM  11543  OD1  ASP B 684      21.507 -23.530 106.924  1.00132.41              O
ANISOU11543  OD1  ASP B 684      19150  16309  14852  -5987   2749   2617       O
ATOM  11544  OD2  ASP B 684      20.458 -25.404 107.456  1.00138.15              O
ANISOU11544  OD2  ASP B 684      20638  16482  15373  -6340   3192   2875       O
ATOM  11545  N    GLY B 685      16.727 -22.573 107.477  1.00115.76              N
ANISOU11545  N    GLY B 685      16308  14661  13015  -7385   3458   2550       N
ATOM  11546  CA   GLY B 685      15.398 -22.686 106.912  1.00116.81              C
ANISOU11546  CA   GLY B 685      16189  14851  13343  -7897   3632   2515       C
ATOM  11547  C    GLY B 685      14.860 -21.362 106.393  1.00114.47              C
ANISOU11547  C    GLY B 685      15223  14879  13393  -7953   3429   2333       C
ATOM  11548  O    GLY B 685      13.650 -21.140 106.395  1.00116.05              O
ANISOU11548  O    GLY B 685      15095  15250  13750  -8267   3578   2279       O
```

FIG. 13 Continued

```
ATOM   11549  N    THR B 686      15.757 -20.484 105.951  1.00111.24           N
ANISOU11549  N    THR B 686     14596  14548  13120  -7655   3075   2250       N
ATOM   11550  CA   THR B 686      15.385 -19.166 105.442  1.00109.34           C
ANISOU11550  CA   THR B 686     13764  14544  13237  -7673   2804   2118       C
ATOM   11551  C    THR B 686      16.302 -18.703 104.300  1.00106.30           C
ANISOU11551  C    THR B 686     13242  14152  12996  -7607   2428   2124       C
ATOM   11552  O    THR B 686      16.237 -17.555 103.844  1.00104.80           O
ANISOU11552  O    THR B 686     12614  14110  13093  -7592   2123   2069       O
ATOM   11553  CB   THR B 686      15.369 -18.110 106.567  1.00109.67           C
ANISOU11553  CB   THR B 686     13587  14780  13303  -7345   2760   1976       C
ATOM   11554  OG1  THR B 686      16.650 -18.063 107.205  1.00108.74           O
ANISOU11554  OG1  THR B 686     13765  14614  12938  -6938   2642   1992       O
ATOM   11555  CG2  THR B 686      14.315 -18.459 107.593  1.00113.26           C
ANISOU11555  CG2  THR B 686     14077  15347  13610  -7476   3161   1939       C
ATOM   11556  N    ILE B 687      17.182 -19.591 103.860  1.00171.78           N
ANISOU11556  N    ILE B 687     21909  22271  21088  -7562   2448   2192       N
ATOM   11557  CA   ILE B 687      18.029 -19.291 102.719  1.00169.64           C
ANISOU11557  CA   ILE B 687     21509  22054  20894  -7557   2162   2186       C
ATOM   11558  C    ILE B 687      17.336 -19.968 101.563  1.00170.53           C
ANISOU11558  C    ILE B 687     21628  22113  21054  -8023   2239   2196       C
ATOM   11559  O    ILE B 687      17.463 -19.563 100.405  1.00169.42           O
ANISOU11559  O    ILE B 687     21240  22109  21022  -8223   2007   2192       O
ATOM   11560  CB   ILE B 687      19.447 -19.872 102.878  1.00169.41           C
ANISOU11560  CB   ILE B 687     21833  21913  20621  -7199   2149   2196       C
ATOM   11561  CG1  ILE B 687      20.432 -19.170 101.933  1.00167.33           C
ANISOU11561  CG1  ILE B 687     21298  21840  20440  -7136   1830   2168       C
ATOM   11562  CG2  ILE B 687      19.438 -21.380 102.647  1.00171.66           C
ANISOU11562  CG2  ILE B 687     22599  21905  20718  -7307   2422   2217       C
ATOM   11563  CD1  ILE B 687      20.785 -17.768 102.358  1.00165.71           C
ANISOU11563  CD1  ILE B 687     20734  21831  20396  -6940   1528   2162       C
ATOM   11564  N    MEI B 688      16.583 -21.005 101.912  1.00148.39           N
ANISOU11564  N    MEI B 688     19121  19119  18142  -8233   2560   2219       N
ATOM   11565  CA   MEI B 688      15.834 -21.778 100.943  1.00150.01           C
ANISOU11565  CA   MEI B 688     19386  19239  18373  -8718   2660   2205       C
ATOM   11566  C    MEI B 688      14.673 -20.982 100.376  1.00149.99           C
ANISOU11566  C    MEI B 688     18850  19487  18651  -9081   2511   2206       C
ATOM   11567  O    MEI B 688      13.638 -21.538  99.994  1.00152.21           O
ANISOU11567  O    MEI B 688     19105  19747  18983  -9521   2643   2208       O
ATOM   11568  CB   MEI B 688      15.356 -23.086 101.558  1.00153.29           C
ANISOU11568  CB   MEI B 688     20281  19348  18615  -8870   3027   2253       C
ATOM   11569  CG   MEI B 688      16.473 -24.095 101.692  1.00154.20           C
ANISOU11569  CG   MEI B 688     20958  19132  18499  -8582   3114   2254       C
ATOM   11570  SD   MEI B 688      17.409 -24.248 100.152  1.00153.01           S
ANISOU11570  SD   MEI B 688     20794  19003  18341  -8593   2907   2090       S
ATOM   11571  CE   MEI B 688      16.060 -24.473  98.995  1.00154.51           C
ANISOU11571  CE   MEI B 688     20786  19270  18653  -9308   2923   2030       C
ATOM   11572  N    THR B 689      14.855 -19.666 100.350  1.00166.34           N
ANISOU11572  N    THR B 689     20494  21779  20928  -8890   2208   2211       N
ATOM   11573  CA   THR B 689      13.887 -18.767  99.758  1.00166.56           C
ANISOU11573  CA   THR B 689     19985  22020  21279  -9151   1971   2234       C
ATOM   11574  C    THR B 689      14.450 -18.258  98.453  1.00165.03           C
ANISOU11574  C    THR B 689     19620  21955  21130  -9284   1601   2295       C
ATOM   11575  O    THR B 689      14.190 -17.123  98.059  1.00164.50           O
ANISOU11575  O    THR B 689     19117  22047  21339  -9313   1255   2366       O
ATOM   11576  CB   THR B 689      13.605 -17.572 100.646  1.00166.22           C
ANISOU11576  CB   THR B 689     19577  22089  21489  -8848   1856   2193       C
ATOM   11577  OG1  THR B 689      13.720 -17.973 102.013  1.00167.09           O
ANISOU11577  OG1  THR B 689     19970  22112  21404  -8574   2185   2127       O
ATOM   11578  CG2  THR B 689      12.204 -17.041 100.383  1.00168.22           C
ANISOU11578  CG2  THR B 689     19322  22502  22093  -9118   1771   2185       C
ATOM   11579  N    ILE B 690      15.274 -19.078  97.808  1.00141.35           N
ANISOU11579  N    ILE B 690     16971  18883  17853  -9345   1669   2267       N
ATOM   11580  CA   ILE B 690      15.767 -18.718  96.487  1.00140.68           C
ANISOU11580  CA   ILE B 690     16737  18989  17726  -9553   1374   2314       C
ATOM   11581  C    ILE B 690      15.029 -19.463  95.382  1.00142.87           C
ANISOU11581  C    ILE B 690     17056  19316  17912 -10089   1407   2285       C
ATOM   11582  O    ILE B 690      15.203 -20.666  95.137  1.00144.34           O
ANISOU11582  O    ILE B 690     17649  19339  17856 -10212   1667   2152       O
ATOM   11583  CB   ILE B 690      17.280 -18.791  96.343  1.00139.26           C
```

FIG. 13 Continued

```
ATOM   11583  CB  ILE B 690      16.764  -18.830  97.319  1.00134.82           C
ANISOU11583  CB  ILE B 690    17928  18580  17199  -9257   1348   2272         C
ATOM   11584  CG1 ILE B 690      17.928  -17.971  97.463  1.00137.48           C
ANISOU11584  CG1 ILE B 690    16456  18580  17199  -8772   1264   2302         C
ATOM   11585  CG2 ILE B 690      17.679  -18.270  94.967  1.00139.14           C
ANISOU11585  CG2 ILE B 690    16520  19102  17243  -9544   1046   2344         C
ATOM   11586  CD1 ILE B 690      17.204  -16.679  97.765  1.00137.01           C
ANISOU11586  CD1 ILE B 690    15956  18606  17494  -8773    992   2394         C
ATOM   11587  N   SER B 691      14.168  -18.671  94.766  1.00138.09           N
ANISOU11587  N   SER B 691    16012  18919  17539 -10390   1105   2409         N
ATOM   11588  CA  SER B 691      13.289  -19.016  93.678  1.00140.46           C
ANISOU11588  CA  SER B 691    16194  19358  17815 -10941   1000   2429         C
ATOM   11589  C   SER B 691      13.077  -17.591  93.214  1.00139.93           C
ANISOU11589  C   SER B 691    15614  19527  18026 -10973    517   2645         C
ATOM   11590  O   SER B 691      11.994  -17.199  92.802  1.00141.82           O
ANISOU11590  O   SER B 691    15488  19895  18500 -11265    290   2752         O
ATOM   11591  CB  SER B 691      11.979  -19.625  94.199  1.00142.82           C
ANISOU11591  CB  SER B 691    16458  19550  18256 -11164   1235   2377         C
ATOM   11592  OG  SER B 691      12.225  -20.792  94.969  1.00143.39           O
ANISOU11592  OG  SER B 691    17029  19323  18129 -11043   1675   2237         O
ATOM   11593  N   LYS B 692      14.144  -16.809  93.337  1.00163.11           N
ANISOU11593  N   LYS B 692    18522  22495  20959 -10653    345   2718         N
ATOM   11594  CA  LYS B 692      14.131  -15.386  93.041  1.00162.77           C
ANISOU11594  CA  LYS B 692    18057  22581  21206 -10623   -133   2946         C
ATOM   11595  C   LYS B 692      13.744  -14.988  91.616  1.00164.75           C
ANISOU11595  C   LYS B 692    18063  23099  21434 -11121   -541   3165         C
ATOM   11596  O   LYS B 692      13.452  -15.833  90.776  1.00166.46           O
ANISOU11596  O   LYS B 692    18423  23451  21373 -11530   -451   3108         O
ATOM   11597  CB  LYS B 692      15.497  -14.795  93.382  1.00160.48           C
ANISOU11597  CB  LYS B 692    17855  22273  20846 -10260   -210   2972         C
ATOM   11598  CG  LYS B 692      15.623  -14.422  94.827  1.00159.08           C
ANISOU11598  CG  LYS B 692    17685  21877  20883  -9754    -78   2864         C
ATOM   11599  CD  LYS B 692      14.448  -13.532  95.250  1.00160.37           C
ANISOU11599  CD  LYS B 692    17438  21976  21520  -9707   -289   2915         C
ATOM   11600  CE  LYS B 692      14.172  -12.399  94.254  1.00161.65           C
ANISOU11600  CE  LYS B 692    17209  22251  21958  -9950   -850   3187         C
ATOM   11601  NZ  LYS B 692      13.312  -11.329  94.838  1.00163.07           N
ANISOU11601  NZ  LYS B 692    16983  22296  22680  -9731  -1104   3201         N
ATOM   11602  N   ASP B 693      13.755  -13.682  91.365  1.00221.87           N
ANISOU11602  N   ASP B 693    24949  30393  28957 -11092  -1015   3422         N
ATOM   11603  CA  ASP B 693      13.451  -13.115  90.058  1.00224.17           C
ANISOU11603  CA  ASP B 693    24999  30937  29240 -11547  -1491   3719         C
ATOM   11604  C   ASP B 693      14.635  -12.225  89.742  1.00223.19           C
ANISOU11604  C   ASP B 693    24870  30891  29041 -11478  -1769   3925         C
ATOM   11605  O   ASP B 693      14.893  -11.265  90.460  1.00222.18           O
ANISOU11605  O   ASP B 693    24593  30564  29262 -11127  -1952   3998         O
ATOM   11606  CB  ASP B 693      12.171  -12.271  90.115  1.00226.46           C
ANISOU11606  CB  ASP B 693    24818  31166  30060 -11573  -1877   3896         C
ATOM   11607  CG  ASP B 693      10.954  -13.058  90.621  1.00227.77           C
ANISOU11607  CG  ASP B 693    24902  31278  30363 -11610  -1573   3679         C
ATOM   11608  OD1 ASP B 693       9.890  -12.441  90.871  1.00229.87           O
ANISOU11608  OD1 ASP B 693    24739  31502  31101 -11542  -1803   3747         O
ATOM   11609  OD2 ASP B 693      11.055  -14.294  90.769  1.00227.20           O
ANISOU11609  OD2 ASP B 693    25181  31199  29947 -11712  -1110   3439         O
ATOM   11610  N   ARG B 694      15.361  -12.533  88.676  1.00133.39           N
ANISOU11610  N   ARG B 694    13654  19822  17204 -11833  -1794   4000         N
ATOM   11611  CA  ARG B 694      16.585  -11.783  88.392  1.00132.81           C
ANISOU11611  CA  ARG B 694    13577  19882  17003 -11811  -1990   4186         C
ATOM   11612  C   ARG B 694      16.853  -11.389  86.914  1.00135.66           C
ANISOU11612  C   ARG B 694    13853  20653  17039 -12384  -2354   4516         C
ATOM   11613  O   ARG B 694      16.150  -11.806  85.985  1.00138.18           O
ANISOU11613  O   ARG B 694    14157  21200  17146 -12830  -2448   4577         O
ATOM   11614  CB  ARG B 694      17.801  -12.507  89.000  1.00130.41           C
ANISOU11614  CB  ARG B 694    13587  19559  16404 -11471  -1515   3876         C
ATOM   11615  CG  ARG B 694      17.674  -12.838  90.498  1.00128.00           C
ANISOU11615  CG  ARG B 694    13403  18879  16353 -10917  -1187   3605         C
ATOM   11616  CD  ARG B 694      19.036  -13.252  91.146  1.00126.03           C
ANISOU11616  CD  ARG B 694    13405  18610  15873 -10529   -866   3394         C
ATOM   11617  NE  ARG B 694      20.018  -12.147  91.246  1.00125.46           N
ANISOU11617  NE  ARG B 694    13163  18608  15900 -10413  -1159   3579         N
```

FIG. 13 Continued

```
ATOM  11618  CZ   ARG B 694      21.114 -12.135  92.020  1.00123.95           C
ANISOU11618  CZ   ARG B 694    13069  18374  15653 -10026  -1010   3447       C
ATOM  11619  NH1  ARG B 694      21.425 -13.166  92.803  1.00122.81           N
ANISOU11619  NH1  ARG B 694    13211  18100  15352  -9666   -580   3148       N
ATOM  11620  NH2  ARG B 694      21.901 -11.072  92.014  1.00124.02           N
ANISOU11620  NH2  ARG B 694    12889  18460  15774 -10018  -1326   3639       N
ATOM  11621  N    VAL B 695      17.899 -10.588  86.728  1.00112.74           N
ANISOU11621  N    VAL B 695    10899  17867  14071 -12396  -2556   4732       N
ATOM  11622  CA   VAL B 695      18.274 -10.004  85.432  1.00115.85           C
ANISOU11622  CA   VAL B 695    11195  18662  14161 -12947  -2934   5122       C
ATOM  11623  C    VAL B 695      18.560 -10.917  84.217  1.00118.16           C
ANISOU11623  C    VAL B 695    11662  19475  13758 -13443  -2717   5019       C
ATOM  11624  O    VAL B 695      18.028 -12.030  84.093  1.00118.31           O
ANISOU11624  O    VAL B 695    11857  19524  13573 -13498  -2391   4692       O
ATOM  11625  CB   VAL B 695      19.474  -9.023  85.600  1.00115.51           C
ANISOU11625  CB   VAL B 695    11076  18644  14170 -12866  -3123   5346       C
ATOM  11626  CG1  VAL B 695      18.992  -7.600  85.891  1.00116.57           C
ANISOU11626  CG1  VAL B 695    10953  18421  14917 -12803  -3728   5750       C
ATOM  11627  CG2  VAL B 695      20.416  -9.519  86.687  1.00112.13           C
ANISOU11627  CG2  VAL B 695    10808  18073  13724 -12333  -2648   4947       C
ATOM  11628  N    LYS B 696      19.412 -10.385  83.330  1.00203.43           N
ANISOU11628  N    LYS B 696    22410  30686  24198 -13826  -2911   5301       N
ATOM  11629  CA   LYS B 696      19.757 -10.981  82.032  1.00206.77           C
ANISOU11629  CA   LYS B 696    22945  31705  23912 -14377  -2786   5265       C
ATOM  11630  C    LYS B 696      21.120 -10.499  81.472  1.00208.50           C
ANISOU11630  C    LYS B 696    23114  32381  23727 -14616  -2783   5440       C
ATOM  11631  O    LYS B 696      21.191  -9.476  80.780  1.00211.45           O
ANISOU11631  O    LYS B 696    23321  32967  24053 -15056  -3271   5974       O
ATOM  11632  CB   LYS B 696      18.640 -10.663  81.013  1.00210.58           C
ANISOU11632  CB   LYS B 696    23314  32371  24326 -14944  -3277   5639       C
ATOM  11633  CG   LYS B 696      18.463  -9.157  80.694  1.00212.88           C
ANISOU11633  CG   LYS B 696    23342  32610  24932 -15188  -3993   6321       C
ATOM  11634  CD   LYS B 696      17.115  -8.822  80.036  1.00216.28           C
ANISOU11634  CD   LYS B 696    23616  33037  25522 -15553  -4539   6683       C
ATOM  11635  CE   LYS B 696      17.187  -8.798  78.512  1.00221.55           C
ANISOU11635  CE   LYS B 696    24319  34351  25507 -16329  -4804   7011       C
ATOM  11636  NZ   LYS B 696      16.776 -10.090  77.892  1.00222.90           N
ANISOU11636  NZ   LYS B 696    24679  34876  25134 -16608  -4446   6586       N
ATOM  11637  N    PRO B 697      22.204 -11.245  81.756  1.00127.48           N
ANISOU11637  N    PRO B 697    12981  22282  13175 -14430  -2242   5006       N
ATOM  11638  CA   PRO B 697      23.552 -10.854  81.282  1.00129.48           C
ANISOU11638  CA   PRO B 697    13123  23028  13044 -14543  -2173   5115       C
ATOM  11639  C    PRO B 697      23.889 -11.201  79.804  1.00134.50           C
ANISOU11639  C    PRO B 697    13783  24424  12898 -15205  -2078   5129       C
ATOM  11640  O    PRO B 697      23.191 -10.762  78.877  1.00137.78           O
ANISOU11640  O    PRO B 697    14157  25062  13130 -15780  -2490   5527       O
ATOM  11641  CB   PRO B 697      24.505 -11.591  82.251  1.00126.50           C
ANISOU11641  CB   PRO B 697    12837  22511  12717 -13907  -1631   4598       C
ATOM  11642  CG   PRO B 697      23.618 -12.192  83.339  1.00122.72           C
ANISOU11642  CG   PRO B 697    12539  21391  12700 -13376  -1487   4314       C
ATOM  11643  CD   PRO B 697      22.250 -12.345  82.739  1.00124.16           C
ANISOU11643  CD   PRO B 697    12773  21512  12888 -13746  -1717   4441       C
ATOM  11644  N    SER B 698      24.982 -11.956  79.622  1.00132.34           N
ANISOU11644  N    SER B 698    13555  24556  12173 -15100  -1548   4690       N
ATOM  11645  CA   SER B 698      25.484 -12.431  78.315  1.00137.48           C
ANISOU11645  CA   SER B 698    14225  25988  12024 -15639  -1313   4541       C
ATOM  11646  C    SER B 698      26.637 -13.484  78.411  1.00138.16           C
ANISOU11646  C    SER B 698    14363  26368  11766 -15273   -628   3871       C
ATOM  11647  O    SER B 698      26.453 -14.642  78.028  1.00139.75           O
ANISOU11647  O    SER B 698    14792  26670  11637 -15239   -243   3342       O
ATOM  11648  CB   SER B 698      25.837 -11.262  77.388  1.00141.66           C
ANISOU11648  CB   SER B 698    14527  27057  12242 -16336  -1741   5182       C
ATOM  11649  OG   SER B 698      26.438 -10.188  78.095  1.00139.84           O
ANISOU11649  OG   SER B 698    14080  26596  12458 -16159  -2003   5564       O
ATOM  11650  N    PRO B 699      27.833 -13.084  78.901  1.00231.60           N
ANISOU11650  N    PRO B 699    25972  38337  23690 -15002   -494   3879       N
ATOM  11651  CA   PRO B 699      28.886 -14.082  79.145  1.00232.25           C
ANISOU11651  CA   PRO B 699    26061  38613  23569 -14529    119   3235       C
ATOM  11652  C    PRO B 699      28.766 -14.609  80.586  1.00227.05           C
```

FIG. 13 Continued

```
ANISOU11652  C    PRO B 699     25566  37180  23523 -13698    271   2940        C
ATOM  11653  O    PRO B 699     28.720 -13.776  81.493  1.00223.58              O
ANISOU11653  O    PRO B 699     25016  36336  23597 -13466    -42   3282        O
ATOM  11654  CB   PRO B 699     30.182 -13.264  79.009  1.00234.46              C
ANISOU11654  CB   PRO B 699     25956  39438  23691 -14684    109   3471        C
ATOM  11655  CG   PRO B 699     29.764 -11.870  78.594  1.00235.36              C
ANISOU11655  CG   PRO B 699     25924  39626  23875 -15317   -515   4257        C
ATOM  11656  CD   PRO B 699     28.362 -11.721  79.060  1.00231.68              C
ANISOU11656  CD   PRO B 699     25688  38435  23906 -15206   -899   4467        C
ATOM  11657  N    THR B 700     28.767 -15.925  80.820  1.00195.81              N
ANISOU11657  N    THR B 700     21873  33015  19510 -13264    727   2329        N
ATOM  11658  CA   THR B 700     28.501 -16.435  82.180  1.00191.32              C
ANISOU11658  CA   THR B 700     21515  31682  19494 -12547    826   2129        C
ATOM  11659  C    THR B 700     29.414 -17.525  82.761  1.00191.77              C
ANISOU11659  C    THR B 700     21679  31621  19563 -11869   1320   1549        C
ATOM  11660  O    THR B 700     29.349 -18.687  82.360  1.00194.31              O
ANISOU11660  O    THR B 700     22256  31932  19639 -11775   1683   1049        O
ATOM  11661  CB   THR B 700     27.093 -17.012  82.247  1.00189.92              C
ANISOU11661  CB   THR B 700     21679  31009  19472 -12620    763   2065        C
ATOM  11662  OG1  THR B 700     27.074 -18.259  81.543  1.00193.42              O
ANISOU11662  OG1  THR B 700     22381  31604  19506 -12685   1162   1524        O
ATOM  11663  CG2  THR B 700     26.085 -16.051  81.623  1.00190.16              C
ANISOU11663  CG2  THR B 700     21600  31141  19512 -13256    253   2607        C
ATOM  11664  N    PRO B 701     30.261 -17.147  83.722  1.00191.48              N
ANISOU11664  N    PRO B 701     21452  31469  19832 -11386   1304   1615        N
ATOM  11665  CA   PRO B 701     31.125 -18.127  84.380  1.00192.10              C
ANISOU11665  CA   PRO B 701     21611  31391  19985 -10683   1699   1125        C
ATOM  11666  C    PRO B 701     31.220 -17.973  85.915  1.00187.86              C
ANISOU11666  C    PRO B 701     21133  30261  19983 -10055   1574   1238        C
ATOM  11667  O    PRO B 701     31.187 -16.849  86.419  1.00185.24              O
ANISOU11667  O    PRO B 701     20598  29875  19909 -10144   1211   1668        O
ATOM  11668  CB   PRO B 701     32.499 -17.793  83.778  1.00196.00              C
ANISOU11668  CB   PRO B 701     21667  32663  20143 -10781   1847   1043        C
ATOM  11669  CG   PRO B 701     32.325 -16.371  83.099  1.00196.24              C
ANISOU11669  CG   PRO B 701     21397  33135  20029 -11539   1428   1650        C
ATOM  11670  CD   PRO B 701     30.976 -15.879  83.545  1.00192.02              C
ANISOU11670  CD   PRO B 701     21099  31991  19869 -11684   1024   2042        C
ATOM  11671  N    ASP B 702     31.327 -19.086  86.644  1.00124.71              N
ANISOU11671  N    ASP B 702     13434  21811  12140  -9442   1853    859        N
ATOM  11672  CA   ASP B 702     31.600 -19.031  88.089  1.00121.70              C
ANISOU11672  CA   ASP B 702     13108  20962  12170  -8825   1767    937        C
ATOM  11673  C    ASP B 702     33.032 -19.537  88.439  1.00124.38              C
ANISOU11673  C    ASP B 702     13267  21510  12480  -8236   2003    617        C
ATOM  11674  O    ASP B 702     33.336 -20.716  88.229  1.00127.51              O
ANISOU11674  O    ASP B 702     13861  21824  12764  -7906   2347    165        O
ATOM  11675  CB   ASP B 702     30.489 -19.710  88.951  1.00119.07              C
ANISOU11675  CB   ASP B 702     13257  19866  12118  -8576   1790    913        C
ATOM  11676  CG   ASP B 702     30.149 -21.150  88.516  1.00121.93              C
ANISOU11676  CG   ASP B 702     14029  19977  12323  -8486   2149    471        C
ATOM  11677  OD1  ASP B 702     29.445 -21.865  89.283  1.00120.72              O
ANISOU11677  OD1  ASP B 702     14282  19198  12387  -8233   2218    420        O
ATOM  11678  OD2  ASP B 702     30.566 -21.561  87.413  1.00125.82              O
ANISOU11678  OD2  ASP B 702     14447  20893  12464  -8696   2363    168        O
ATOM  11679  N    SER B 703     33.906 -18.646  88.939  1.00121.51              N
ANISOU11679  N    SER B 703     12515  21415  12238  -8113   1799    837        N
ATOM  11680  CA   SER B 703     35.288 -19.000  89.362  1.00124.20              C
ANISOU11680  CA   SER B 703     12598  21997  12597  -7546   1956    581        C
ATOM  11681  C    SER B 703     35.966 -17.969  90.309  1.00122.33              C
ANISOU11681  C    SER B 703     12030  21840  12608  -7380   1626    893        C
ATOM  11682  O    SER B 703     36.066 -18.182  91.507  1.00120.64              O
ANISOU11682  O    SER B 703     11979  21195  12664  -6842   1537    900        O
ATOM  11683  CB   SER B 703     36.211 -19.381  88.165  1.00129.72              C
ANISOU11683  CB   SER B 703     12971  23417  12902  -7680   2285    221        C
ATOM  11684  OG   SER B 703     36.000 -18.588  87.005  1.00130.77              O
ANISOU11684  OG   SER B 703     12668  24111  12707  -8465   2209    435        O
ATOM  11685  N    TRP B 704     36.411  16.848  89.753  1.00151.72              N
ANISOU11685  N    TRP B 704     15314  26115  16217  -7884   1430   1161        N
ATOM  11686  CA   TRP B 704     37.105 -15.774  90.476  1.00150.79              C
ANISOU11686  CA   TRP B 704     14847  26137  16309  -7855   1095   1448        C
```

FIG. 13 Continued

```
ATOM   11687  C   TRP B 704      36.234 -14.932  91.412  1.00146.14           C
ANISOU11687  C   TRP B 704     14472  24988  16066  -7912    693   1810       C
ATOM   11688  O   TRP B 704      36.689 -13.935  91.972  1.00145.48           O
ANISOU11688  O   TRP B 704     14138  24971  16167  -7966    370   2049       O
ATOM   11689  CB  TRP B 704      37.793 -14.847  89.464  1.00153.83           C
ANISOU11689  CB  TRP B 704     14723  27281  16445  -8486   1016   1645       C
ATOM   11690  CG  TRP B 704      37.263 -14.975  88.020  1.00155.90           C
ANISOU11690  CG  TRP B 704     15028  27893  16312  -9109   1190   1640       C
ATOM   11691  CD1 TRP B 704      37.995 -14.880  86.859  1.00160.71           C
ANISOU11691  CD1 TRP B 704     15259  29305  16500  -9538   1394   1564       C
ATOM   11692  CD2 TRP B 704      35.903 -15.237  87.609  1.00153.75           C
ANISOU11692  CD2 TRP B 704     15190  27230  16000  -9383   1174   1704       C
ATOM   11693  NE1 TRP B 704      37.174 -15.056  85.765  1.00161.66           N
ANISOU11693  NE1 TRP B 704     15583  29547  16292 -10063   1488   1584       N
ATOM   11694  CE2 TRP B 704      35.892 -15.279  86.197  1.00157.42           C
ANISOU11694  CE2 TRP B 704     15534  28279  15999  -9974   1339   1671       C
ATOM   11695  CE3 TRP B 704      34.696 -15.435  88.299  1.00149.54           C
ANISOU11695  CE3 TRP B 704     15106  25954  15760  -9209   1038   1785       C
ATOM   11696  CZ2 TRP B 704      34.727 -15.511  85.470  1.00156.91           C
ANISOU11696  CZ2 TRP B 704     15793  28059  15768 -10382   1331   1720       C
ATOM   11697  CZ3 TRP B 704      33.544 -15.670  87.571  1.00149.08           C
ANISOU11697  CZ3 TRP B 704     15327  25750  15566  -9611   1052   1828       C
ATOM   11698  CH2 TRP B 704      33.568 -15.702  86.173  1.00152.68           C
ANISOU11698  CH2 TRP B 704     15664  26779  15570 -10188   1176   1800       C
ATOM   11699  N   LYS B 705      34.977 -15.322  91.553  1.00126.24           N
ANISOU11699  N   LYS B 705     12396  21936  13635  -7923    717   1825       N
ATOM   11700  CA  LYS B 705      34.049 -14.647  92.453  1.00122.35           C
ANISOU11700  CA  LYS B 705     12108  20910  13468  -7923    401   2091       C
ATOM   11701  C   LYS B 705      34.390 -14.930  93.920  1.00121.08           C
ANISOU11701  C   LYS B 705     12091  20390  13523  -7265    368   1988       C
ATOM   11702  O   LYS B 705      34.205 -14.076  94.789  1.00119.04           O
ANISOU11702  O   LYS B 705     11816  19905  13509  -7224     58   2181       O
ATOM   11703  CB  LYS B 705      32.624 -15.134  92.191  1.00120.55           C
ANISOU11703  CB  LYS B 705     12274  20273  13255  -8096    493   2089       C
ATOM   11704  CG  LYS B 705      32.354 -16.555  92.695  1.00120.61           C
ANISOU11704  CG  LYS B 705     12699  19886  13240  -7598    838   1763       C
ATOM   11705  CD  LYS B 705      33.243 -17.590  91.998  1.00124.45           C
ANISOU11705  CD  LYS B 705     13142  20700  13445  -7411   1198   1396       C
ATOM   11706  CE  LYS B 705      32.968 -19.010  92.483  1.00125.19           C
ANISOU11706  CE  LYS B 705     13697  20305  13563  -6920   1498   1089       C
ATOM   11707  NZ  LYS B 705      33.818 -20.019  91.787  1.00129.61           N
ANISOU11707  NZ  LYS B 705     14220  21128  13899  -6689   1840    676       N
ATOM   11708  N   LEU B 706      34.876 -16.143  94.185  1.00125.03           N
ANISOU11708  N   LEU B 706     12752  20828  13925  -6748    675   1674       N
ATOM   11709  CA  LEU B 706      35.228 -16.587  95.534  1.00124.66           C
ANISOU11709  CA  LEU B 706     12887  20454  14026  -6104    649   1591       C
ATOM   11710  C   LEU B 706      36.197 -15.602  96.199  1.00125.01           C
ANISOU11710  C   LEU B 706     12549  20765  14183  -6008    328   1727       C
ATOM   11711  O   LEU B 706      36.209 -15.470  97.422  1.00123.84           O
ANISOU11711  O   LEU B 706     12545  20328  14180  -5653    155   1776       O
ATOM   11712  CB  LEU B 706      35.831 -18.004  95.486  1.00127.87           C
ANISOU11712  CB  LEU B 706     13443  20829  14311  -5583    991   1247       C
ATOM   11713  CG  LEU B 706      35.624 -19.065  96.580  1.00128.01           C
ANISOU11713  CG  LEU B 706     13934  20281  14423  -4972   1093   1144       C
ATOM   11714  CD1 LEU B 706      35.858 -20.444  95.975  1.00131.58           C
ANISOU11714  CD1 LEU B 706     14584  20648  14763  -4693   1456    799       C
ATOM   11715  CD2 LEU B 706      36.506 -18.857  97.833  1.00128.69           C
ANISOU11715  CD2 LEU B 706     13907  20369  14618  -4455    861   1211       C
ATOM   11716  N   LYS B 707      37.012 -14.916  95.397  1.00177.99           N
ANISOU11716  N   LYS B 707     18776  28050  20801  -6362    246   1788       N
ATOM   11717  CA  LYS B 707      37.950 -13.923  95.935  1.00178.86           C
ANISOU11717  CA  LYS B 707     18490  28443  21025  -6371    -81   1926       C
ATOM   11718  C   LYS B 707      37.286 -12.559  96.142  1.00176.30           C
ANISOU11718  C   LYS B 707     18158  27920  20909  -6832   -476   2248       C
ATOM   11719  O   LYS B 707      37.651 -11.819  97.057  1.00176.00           O
ANISOU11719  O   LYS B 707     18019  27805  21048  -6722   -790   2333       O
ATOM   11720  CB  LYS B 707      39.209 -13.792  95.063  1.00183.03           C
ANISOU11720  CB  LYS B 707     18463  29710  21371  -6554      9   1853       C
ATOM   11721  CG  LYS B 707      39.878 -12.408  95.089  1.00184.03           C
```

FIG. 13 Continued

```
ANISOU11721  CG  LYS B 707    18136  30194  21593  -6979   -368   2119       C
ATOM  11722  CD  LYS B 707    40.546 -12.064  96.420  1.00184.17             C
ANISOU11722  CD  LYS B 707    18056  30110  21810  -6567   -663   2114       C
ATOM  11723  CE  LYS B 707    41.048 -10.623  96.400  1.00185.24             C
ANISOU11723  CE  LYS B 707    17803  30508  22070  -7088  -1070   2386       C
ATOM  11724  NZ  LYS B 707    41.570 -10.156  97.709  1.00185.38             N
ANISOU11724  NZ  LYS B 707    17765  30389  22283  -6773  -1415   2378       N
ATOM  11725  N   GLU B 708    36.309 -12.231  95.300  1.00111.21             N
ANISOU11725  N   GLU B 708    10023  19576  12655  -7334   -483   2412       N
ATOM  11726  CA  GLU B 708    35.604 -10.963  95.429  1.00109.38             C
ANISOU11726  CA  GLU B 708     9791  19094  12674  -7737   -876   2713       C
ATOM  11727  C   GLU B 708    34.864 -10.864  96.768  1.00106.61             C
ANISOU11727  C   GLU B 708     9772  18160  12575  -7355  -1010   2669       C
ATOM  11728  O   GLU B 708    34.307  -9.824  97.108  1.00105.44             O
ANISOU11728  O   GLU B 708     9633  17743  12688  -7558  -1340   2840       O
ATOM  11729  CB  GLU B 708    34.669 -10.772  94.236  1.00109.04             C
ANISOU11729  CB  GLU B 708     9806  19063  12562  -8298   -862   2898       C
ATOM  11730  CG  GLU B 708    33.256 -10.387  94.591  1.00106.18             C
ANISOU11730  CG  GLU B 708     9734  18143  12466  -8371  -1038   3028       C
ATOM  11731  CD  GLU B 708    32.448 -11.555  95.133  1.00104.25             C
ANISOU11731  CD  GLU B 708     9898  17521  12191  -7949   -715   2784       C
ATOM  11732  OE1 GLU B 708    32.968 -12.292  95.995  1.00104.27             O
ANISOU11732  OE1 GLU B 708    10029  17448  12141  -7421   -535   2560       O
ATOM  11733  OE2 GLU B 708    31.290 -11.734  94.699  1.00103.13             O
ANISOU11733  OE2 GLU B 708     9944  17159  12081  -8167   -664   2841       O
ATOM  11734  N   ILE B 709    34.889 -11.954  97.530  1.00165.66             N
ANISOU11734  N   ILE B 709    17525  25451  19967  -6797   -752   2433       N
ATOM  11735  CA  ILE B 709    34.197 -12.035  98.814  1.00163.66             C
ANISOU11735  CA  ILE B 709    17615  24711  19856  -6434   -803   2378       C
ATOM  11736  C   ILE B 709    34.900 -11.312  99.943  1.00164.27             C
ANISOU11736  C   ILE B 709    17572  24795  20049  -6199  -1115   2370       C
ATOM  11737  O   ILE B 709    34.254 -10.649 100.748  1.00162.94             O
ANISOU11737  O   ILE B 709    17546  24300  20063  -6179  -1317   2395       O
ATOM  11738  CB  ILE B 709    34.043 -13.481  99.275  1.00163.75             C
ANISOU11738  CB  ILE B 709    17995  24516  19705  -5947   -444   2180       C
ATOM  11739  CG1 ILE B 709    33.528 -14.360  98.133  1.00163.98             C
ANISOU11739  CG1 ILE B 709    18151  24565  19588  -6151   -114   2115       C
ATOM  11740  CG2 ILE B 709    33.136 -13.538 100.500  1.00161.97             C
ANISOU11740  CG2 ILE B 709    18143  23821  19577  -5694   -464   2169       C
ATOM  11741  CD1 ILE B 709    32.041 -14.269  97.911  1.00161.75             C
ANISOU11741  CD1 ILE B 709    18111  23939  19408  -6456    -78   2207       C
ATOM  11742  N   PHE B 710    36.214 -11.491 100.032  1.00158.46             N
ANISOU11742  N   PHE B 710    16567  24442  19199  -5999  -1142   2299       N
ATOM  11743  CA  PHE B 710    37.003 -10.802 101.037  1.00159.69             C
ANISOU11743  CA  PHE B 710    16560  24677  19438  -5820  -1472   2285       C
ATOM  11744  C   PHE B 710    36.465  -9.375 101.117  1.00158.67             C
ANISOU11744  C   PHE B 710    16363  24350  19575  -6247  -1842   2436       C
ATOM  11745  O   PHE B 710    36.228  -8.868 102.211  1.00158.25             O
ANISOU11745  O   PHE B 710    16462  24026  19641  -6071  -2060   2371       O
ATOM  11746  CB  PHE B 710    38.493 -10.818 100.640  1.00163.08             C
ANISOU11746  CB  PHE B 710    16513  25685  19764  -5809  -1517   2258       C
ATOM  11747  CG  PHE B 710    39.458 -10.292 101.712  1.00165.09             C
ANISOU11747  CG  PHE B 710    16570  26086  20071  -5578  -1857   2215       C
ATOM  11748  CD1 PHE B 710    39.905 -11.115 102.747  1.00166.28             C
ANISOU11748  CD1 PHE B 710    16879  26196  20102  -4957  -1819   2067       C
ATOM  11749  CD2 PHE B 710    39.963  -8.993 101.643  1.00166.43             C
ANISOU11749  CD2 PHE B 710    16391  26446  20400  -6009  -2241   2340       C
ATOM  11750  CE1 PHE B 710    40.800 -10.639 103.710  1.00168.57             C
ANISOU11750  CE1 PHE B 710    16976  26666  20409  -4767  -2165   2030       C
ATOM  11751  CE2 PHE B 710    40.858  -8.517 102.604  1.00168.71             C
ANISOU11751  CE2 PHE B 710    16491  26885  20727  -5838  -2573   2278       C
ATOM  11752  CZ  PHE B 710    41.273  -9.341 103.635  1.00169.73             C
ANISOU11752  CZ  PHE B 710    16766  27013  20711  -5215  -2535   2115       C
ATOM  11753  N   ALA B 711    36.234  -8.752  99.955  1.00113.84             N
ANISOU11753  N   ALA B 711    10484  18787  13983  -6802  -1915   2632       N
ATOM  11754  CA  ALA B 711    35.733  -7.365  99.866  1.00113.63             C
ANISOU11754  CA  ALA B 711    10385  18527  14262  -7237  -2311   2819       C
ATOM  11755  C   ALA B 711    34.212  -7.212 100.104  1.00111.12             C
ANISOU11755  C   ALA B 711    10400  17676  14143  -7228  -2304   2819       C
```

FIG. 13 Continued

```
ATOM   11756  O   ALA B 711       33.688  -6.106 100.272  1.00111.21           O
ANISOU11756  O   ALA B 711      10399  17387  14469  -7445  -2642   2909       O
ATOM   11757  CB  ALA B 711       36.148  -6.730  98.543  1.00115.53           C
ANISOU11757  CB  ALA B 711      10278  19115  14503  -7859  -2441   3090       C
ATOM   11758  N   THR B 712       33.508  -8.331 100.104  1.00139.85           N
ANISOU11758  N   THR B 712      14321  21196  17621  -6979  -1921   2708       N
ATOM   11759  CA  THR B 712       32.113  -8.314 100.459  1.00137.93           C
ANISOU11759  CA  THR B 712      14356  20512  17541  -6924  -1867   2672       C
ATOM   11760  C   THR B 712       32.093  -8.412 101.966  1.00137.77           C
ANISOU11760  C   THR B 712      14555  20278  17512  -6448  -1868   2451       C
ATOM   11761  O   THR B 712       31.830  -7.434 102.657  1.00138.16           O
ANISOU11761  O   THR B 712      14595  20103  17798  -6444  -2154   2396       O
ATOM   11762  CB  THR B 712       31.406  -9.535  99.915  1.00136.70           C
ANISOU11762  CB  THR B 712      14422  20328  17190  -6882  -1450   2635       C
ATOM   11763  OG1 THR B 712       31.932  -9.849  98.621  1.00137.72           O
ANISOU11763  OG1 THR B 712      14359  20830  17140  -7195  -1347   2744       O
ATOM   11764  CG2 THR B 712       29.897  -9.292  99.829  1.00135.30           C
ANISOU11764  CG2 THR B 712      14386  19793  17231  -7041  -1452   2682       C
ATOM   11765  N   GLY B 713       32.410  -9.602 102.466  1.00101.01           N
ANISOU11765  N   GLY B 713      10110  15697  12572  -6047  -1560   2321       N
ATOM   11766  CA  GLY B 713       32.439  -9.865 103.892  1.00101.39           C
ANISOU11766  CA  GLY B 713      10410  15600  12515  -5598  -1536   2150       C
ATOM   11767  C   GLY B 713       33.308  -8.971 104.771  1.00103.14           C
ANISOU11767  C   GLY B 713      10481  15920  12788  -5487  -1907   2070       C
ATOM   11768  O   GLY B 713       33.564  -9.323 105.915  1.00104.09           O
ANISOU11768  O   GLY B 713      10800  16024  12727  -5104  -1892   1937       O
ATOM   11769  N   VAL B 714       33.798  -7.844 104.255  1.00165.92           N
ANISOU11769  N   VAL B 714      18099  23982  20963  -5844  -2257   2164       N
ATOM   11770  CA  VAL B 714       34.570  -6.914 105.088  1.00168.00           C
ANISOU11770  CA  VAL B 714      18226  24298  21309  -5801  -2648   2068       C
ATOM   11771  C   VAL B 714       33.620  -5.966 105.781  1.00167.92           C
ANISOU11771  C   VAL B 714      18365  23881  21557  -5832  -2844   1930       C
ATOM   11772  O   VAL B 714       33.586  -5.894 107.000  1.00168.90           O
ANISOU11772  O   VAL B 714      18679  23913  21581  -5526  -2895   1706       O
ATOM   11773  CB  VAL B 714       35.581  -6.066 104.300  1.00169.87           C
ANISOU11773  CB  VAL B 714      18037  24818  21688  -6214  -2968   2231       C
ATOM   11774  CG1 VAL B 714       36.897  -6.807 104.152  1.00171.54           C
ANISOU11774  CG1 VAL B 714      18023  25524  21631  -6047  -2869   2241       C
ATOM   11775  CG2 VAL B 714       35.004  -5.634 102.958  1.00169.02           C
ANISOU11775  CG2 VAL B 714      17792  24647  21779  -6718  -2981   2475       C
ATOM   11776  N   VAL B 715       32.852  -5.216 105.002  1.00131.95           N
ANISOU11776  N   VAL B 715      13714  19090  17331  -6195  -2968   2052       N
ATOM   11777  CA  VAL B 715       31.846  -4.374 105.615  1.00132.32           C
ANISOU11777  CA  VAL B 715      13883  18720  17674  -6164  -3125   1882       C
ATOM   11778  C   VAL B 715       30.958  -5.334 106.423  1.00131.04           C
ANISOU11778  C   VAL B 715      14050  18462  17275  -5773  -2710   1691       C
ATOM   11779  O   VAL B 715       30.450  -4.992 107.489  1.00132.08           O
ANISOU11779  O   VAL B 715      14344  18407  17435  -5546  -2730   1424       O
ATOM   11780  CB  VAL B 715       31.100  -3.494 104.566  1.00132.30           C
ANISOU11780  CB  VAL B 715      13717  18455  18097  -6586  -3344   2088       C
ATOM   11781  CG1 VAL B 715       29.682  -3.166 104.999  1.00132.13           C
ANISOU11781  CG1 VAL B 715      13836  18023  18342  -6446  -3256   1909       C
ATOM   11782  CG2 VAL B 715       31.886  -2.214 104.319  1.00134.92           C
ANISOU11782  CG2 VAL B 715      13811  18734  18719  -6927  -3862   2197       C
ATOM   11783  N   LEU B 716       30.859  -6.574 105.957  1.00187.54           N
ANISOU11783  N   LEU B 716      21316  25777  24166  -5702  -2326   1813       N
ATOM   11784  CA  LEU B 716       30.041  -7.583 106.630  1.00186.73           C
ANISOU11784  CA  LEU B 716      21542  25581  23825  -5405  -1920   1697       C
ATOM   11785  C   LEU B 716       30.518  -7.970 108.039  1.00188.29           C
ANISOU11785  C   LEU B 716      21981  25866  23693  -4996  -1872   1509       C
ATOM   11786  O   LEU B 716       29.794  -7.793 109.016  1.00189.16           O
ANISOU11786  O   LEU B 716      22280  25831  23761  -4831  -1797   1303       O
ATOM   11787  CB  LEU B 716       29.898  -8.822 105.743  1.00185.15           C
ANISOU11787  CB  LEU B 716      21426  25483  23441  -5460  -1560   1872       C
ATOM   11788  CG  LEU B 716       28.825  -8.698 104.650  1.00183.77           C
ANISOU11788  CG  LEU B 716      21155  25162  23507  -5813  -1484   2002       C
ATOM   11789  CD1 LEU B 716       28.738  -7.277 104.107  1.00184.36           C
ANISOU11789  CD1 LEU B 716      20929  25136  23984  -6139  -1908   2084       C
ATOM   11790  CD2 LEU B 716       29.047  -9.697 103.520  1.00182.88           C
```

FIG. 13 Continued

```
ANISOU11790  CD2 LEU B 716     21043  25226  23216  -5967  -1242   2164          C
ATOM   11791  N   GLY B 717      31.726  -8.511 108.136  1.00128.49           N
ANISOU11791  N   GLY B 717     14387  18563  15871  -4832  -1916   1577          N
ATOM   11792  CA  GLY B 717      32.291  -8.908 109.417  1.00130.50           C
ANISOU11792  CA  GLY B 717     14859  18936  15788  -4450  -1934   1455          C
ATOM   11793  C   GLY B 717      33.572  -8.173 109.779  1.00132.70           C
ANISOU11793  C   GLY B 717     14901  19449  16069  -4427  -2360   1395          C
ATOM   11794  O   GLY B 717      34.305  -8.610 110.665  1.00134.74           O
ANISOU11794  O   GLY B 717     15278  19894  16022  -4115  -2426   1349          O
ATOM   11795  N   GLY B 718      33.830  -7.062 109.085  1.00108.33           N
ANISOU11795  N   GLY B 718     11482  16351  13329  -4783  -2671   1421          N
ATOM   11796  CA  GLY B 718      35.008  -6.226 109.287  1.00110.75           C
ANISOU11796  CA  GLY B 718     11513  16864  13703  -4882  -3106   1380          C
ATOM   11797  C   GLY B 718      34.557  -4.781 109.411  1.00111.68           C
ANISOU11797  C   GLY B 718     11549  16690  14194  -5159  -3445   1233          C
ATOM   11798  O   GLY B 718      35.278  -3.832 109.098  1.00113.39           O
ANISOU11798  O   GLY B 718     11485  16957  14639  -5453  -3833   1270          O
ATOM   11799  N   TYR B 719      33.316  -4.647 109.867  1.00165.30           N
ANISOU11799  N   TYR B 719     18586  23160  21060  -5062  -3285   1060          N
ATOM   11800  CA  TYR B 719      32.668  -3.381 110.140  1.00166.69           C
ANISOU11800  CA  TYR B 719     18744  22983  21610  -5204  -3552    840          C
ATOM   11801  C   TYR B 719      31.869  -3.663 111.397  1.00167.60           C
ANISOU11801  C   TYR B 719     19187  23011  21480  -4849  -3317    516          C
ATOM   11802  O   TYR B 719      31.731  -2.810 112.271  1.00170.28           O
ANISOU11802  O   TYR B 719     19594  23207  21899  -4778  -3536    177          O
ATOM   11803  CB  TYR B 719      31.734  -3.024 109.003  1.00164.92           C
ANISOU11803  CB  TYR B 719     18392  22478  21791  -5498  -3512   1019          C
ATOM   11804  CG  TYR B 719      31.223  -1.612 109.045  1.00167.00           C
ANISOU11804  CG  TYR B 719     18569  22330  22554  -5673  -3886    855          C
ATOM   11805  CD1 TYR B 719      29.972  -1.292 108.521  1.00166.29           C
ANISOU11805  CD1 TYR B 719     18455  21902  22826  -5758  -3820    879          C
ATOM   11806  CD2 TYR B 719      31.986  -0.596 109.606  1.00170.20           C
ANISOU11806  CD2 TYR B 719     18910  22660  23099  -5747  -4333    668          C
ATOM   11807  CE1 TYR B 719      29.499  -0.006 108.545  1.00168.81           C
ANISOU11807  CE1 TYR B 719     18692  21790  23659  -5866  -4192    729          C
ATOM   11808  CE2 TYR B 719      31.520   0.697 109.638  1.00172.72           C
ANISOU11808  CE2 TYR B 719     19181  22522  23922  -5891  -4701    499          C
ATOM   11809  CZ  TYR B 719      30.272   0.986 109.106  1.00172.07           C
ANISOU11809  CZ  TYR B 719     19080  22077  24221  -5926  -4629    531          C
ATOM   11810  OH  TYR B 719      29.793   2.275 109.131  1.00175.18           O
ANISOU11810  OH  TYR B 719     19424  21962  25176  -6018  -5025    359          O
ATOM   11811  N   GLN B 720      31.346  -4.887 111.471  1.00111.46           N
ANISOU11811  N   GLN B 720     12292  16000  14058  -4650  -2860    617          N
ATOM   11812  CA  GLN B 720      30.678  -5.382 112.667  1.00112.68           C
ANISOU11812  CA  GLN B 720     12779  16171  13863  -4344  -2573    385          C
ATOM   11813  C   GLN B 720      31.623  -5.222 113.852  1.00115.84           C
ANISOU11813  C   GLN B 720     13300  16801  13915  -4135  -2815    191          C
ATOM   11814  O   GLN B 720      31.201  -4.951 114.970  1.00118.36           O
ANISOU11814  O   GLN B 720     13825  17115  14033  -3970  -2782   -131          O
ATOM   11815  CB  GLN B 720      30.296  -6.849 112.492  1.00110.76           C
ANISOU11815  CB  GLN B 720     12759  16028  13304  -4214  -2101    618          C
ATOM   11816  CG  GLN B 720      29.295  -7.346 113.510  1.00112.04           C
ANISOU11816  CG  GLN B 720     13244  16168  13160  -4018  -1737    444          C
ATOM   11817  CD  GLN B 720      28.194  -8.184 112.884  1.00109.88           C
ANISOU11817  CD  GLN B 720     13048  15769  12933  -4114  -1297    614          C
ATOM   11818  OE1 GLN B 720      28.304  -8.624 111.737  1.00107.41           O
ANISOU11818  OE1 GLN B 720     12613  15414  12784  -4279  -1246    878          O
ATOM   11819  NE2 GLN B 720      27.124  -8.406 113.635  1.00111.25           N
ANISOU11819  NE2 GLN B 720     13413  15915  12942  -4038   -972    445          N
ATOM   11820  N   ALA B 721      32.913  -5.389 113.588  1.00119.88           N
ANISOU11820  N   ALA B 721     13656  17554  14340  -4153  -3061    376          N
ATOM   11821  CA  ALA B 721      33.934  -5.162 114.591  1.00123.23           C
ANISOU11821  CA  ALA B 721     14118  18229  14474  -4000  -3379    222          C
ATOM   11822  C   ALA B 721      33.712  -3.770 115.137  1.00125.82           C
ANISOU11822  C   ALA B 721     14403  18356  15045  -4130  -3710   -167          C
ATOM   11823  O   ALA B 721      33.923  -3.522 116.318  1.00129.15           O
ANISOU11823  O   ALA B 721     15006  18899  15164  -3968  -3852   -462          O
ATOM   11824  CB  ALA B 721      35.329  -5.276 113.984  1.00123.47           C
ANISOU11824  CB  ALA B 721     13835  18537  14539  -4084  -3653    462          C
```

FIG. 13 Continued

```
ATOM  11825  N   ILE B 722      33.270  -2.853 114.285  1.00133.01           N
ANISOU11825  N   ILE B 722    15094  18942  16500  -4425  -3850   -177       N
ATOM  11826  CA  ILE B 722      33.026  -1.496 114.759  1.00136.04           C
ANISOU11826  CA  ILE B 722    15453  19038  17197  -4531  -4192   -568       C
ATOM  11827  C   ILE B 722      31.691  -1.337 115.501  1.00137.14           C
ANISOU11827  C   ILE B 722    15828  18962  17317  -4325  -3911   -947       C
ATOM  11828  O   ILE B 722      30.977  -0.350 115.348  1.00138.35           O
ANISOU11828  O   ILE B 722    15900  18731  17937  -4417  -4043  -1189       O
ATOM  11829  CB  ILE B 722      33.295  -0.419 113.686  1.00136.00           C
ANISOU11829  CB  ILE B 722    15127  18747  17799  -4939  -4586   -427       C
ATOM  11830  CG1 ILE B 722      34.716  -0.597 113.166  1.00136.00           C
ANISOU11830  CG1 ILE B 722    14874  19088  17712  -5139  -4833   -113       C
ATOM  11831  CG2 ILE B 722      33.175   0.983 114.271  1.00140.08           C
ANISOU11831  CG2 ILE B 722    15659  18907  18656  -5026  -5002   -856       C
ATOM  11832  CD1 ILE B 722      35.738  -0.821 114.268  1.00138.93           C
ANISOU11832  CD1 ILE B 722    15321  19833  17635  -4939  -5012   -286       C
ATOM  11833  N   MET B 723      31.350  -2.352 116.281  1.00129.42           N
ANISOU11833  N   MET B 723    15130  18241  15803  -4047  -3513   -978       N
ATOM  11834  CA  MET B 723      30.276  -2.228 117.239  1.00131.73           C
ANISOU11834  CA  MET B 723    15644  18477  15930  -3851  -3240  -1389       C
ATOM  11835  C   MET B 723      31.004  -2.258 118.586  1.00135.72           C
ANISOU11835  C   MET B 723    16390  19311  15869  -3673  -3392  -1654       C
ATOM  11836  O   MET B 723      30.834  -1.370 119.413  1.00139.68           O
ANISOU11836  O   MET B 723    16961  19742  16369  -3626  -3563  -2152       O
ATOM  11837  CB  MET B 723      29.261  -3.361 117.099  1.00129.36           C
ANISOU11837  CB  MET B 723    15489  18246  15416  -3748  -2658  -1191       C
ATOM  11838  CG  MET B 723      28.260  -3.491 118.242  1.00132.38           C
ANISOU11838  CG  MET B 723    16115  18733  15449  -3549  -2288  -1572       C
ATOM  11839  SD  MET B 723      26.774  -2.481 118.106  1.00133.86           S
ANISOU11839  SD  MET B 723    16099  18559  16202  -3557  -2155  -2015       S
ATOM  11840  CE  MET B 723      27.287  -0.892 118.742  1.00138.56           C
ANISOU11840  CE  MET B 723    16630  18948  17068  -3528  -2704  -2590       C
ATOM  11841  N   THR B 724      31.862  -3.253 118.795  1.00132.62           N
ANISOU11841  N   THR B 724    16116  19271  15003  -3569  -3370  -1332       N
ATOM  11842  CA  THR B 724      32.591  -3.309 120.056  1.00136.83           C
ANISOU11842  CA  THR B 724    16870  20147  14970  -3408  -3569  -1531       C
ATOM  11843  C   THR B 724      33.190  -1.945 120.393  1.00140.31           C
ANISOU11843  C   THR B 724    17168  20491  15653  -3550  -4107  -1940       C
ATOM  11844  O   THR B 724      32.802  -1.367 121.403  1.00144.35           O
ANISOU11844  O   THR B 724    17867  21017  15965  -3470  -4134  -2440       O
ATOM  11845  CB  THR B 724      33.636  -4.463 120.139  1.00136.42           C
ANISOU11845  CB  THR B 724    16898  20460  14477  -3262  -3611  -1091       C
ATOM  11846  OG1 THR B 724      33.183  -5.439 121.084  1.00138.16           O
ANISOU11846  OG1 THR B 724    17521  20907  14065  -3030  -3260  -1042       O
ATOM  11847  CG2 THR B 724      35.000  -3.955 120.603  1.00139.74           C
ANISOU11847  CG2 THR B 724    17193  21132  14770  -3284  -4174  -1180       C
ATOM  11848  N   VAL B 725      34.075  -1.406 119.543  1.00141.83           N
ANISOU11848  N   VAL B 725    17034  20578  16277  -3788  -4515  -1756       N
ATOM  11849  CA  VAL B 725      34.722  -0.108 119.827  1.00145.62           C
ANISOU11849  CA  VAL B 725    17382  20932  17014  -3988  -5072  -2110       C
ATOM  11850  C   VAL B 725      33.720   1.046 119.965  1.00147.64           C
ANISOU11850  C   VAL B 725    17674  20712  17709  -4047  -5105  -2612       C
ATOM  11851  O   VAL B 725      34.096   2.221 119.949  1.00150.57           O
ANISOU11851  O   VAL B 725    17928  20810  18473  -4259  -5569  -2886       O
ATOM  11852  CB  VAL B 725      35.884   0.230 118.856  1.00144.60           C
ANISOU11852  CB  VAL B 725    16869  20816  17256  -4298  -5490  -1771       C
ATOM  11853  CG1 VAL B 725      36.555   1.544 119.236  1.00149.22           C
ANISOU11853  CG1 VAL B 725    17351  21263  18083  -4550  -6079  -2134       C
ATOM  11854  CG2 VAL B 725      36.901  -0.878 118.889  1.00143.86           C
ANISOU11854  CG2 VAL B 725    16716  21226  16717  -4157  -5470  -1383       C
ATOM  11855  N   ILE B 726      32.447   0.680 120.103  1.00195.33           N
ANISOU11855  N   ILE B 726    23868  26652  23697  -3855  -4611  -2731       N
ATOM  11856  CA  ILE B 726      31.363   1.608 120.400  1.00197.98           C
ANISOU11856  CA  ILE B 726    24240  26606  24376  -3796  -4549  -3268       C
ATOM  11857  C   ILE B 726      30.970   1.417 121.855  1.00202.30           C
ANISOU11857  C   ILE B 726    25114  27470  24281  -3534  -4304  -3763       C
ATOM  11858  O   ILE B 726      30.489   2.343 122.501  1.00206.79           O
ANISOU11858  O   ILE B 726    25748  27843  24978  -3463  -4387  -4387       O
ATOM  11859  CB  ILE B 726      30.095   1.300 119.576  1.00194.42           C
```

FIG. 13 Continued

```
ANISOU11859  CB   ILE B 726    23679  25900  24292  -3757  -4116  -3088        C
ATOM  11860  CG1  ILE B 726     30.410    1.245 118.077  1.00189.88           C
ANISOU11860  CG1  ILE B 726    22815  25113  24220  -4028  -4271  -2516        C
ATOM  11861  CG2  ILE B 726     28.956    2.295 119.908  1.00197.95           C
ANISOU11861  CG2  ILE B 726    24105  25958  25150  -3636  -4066  -3684        C
ATOM  11862  CD1  ILE B 726     29.187    0.987 117.194  1.00186.72           C
ANISOU11862  CD1  ILE B 726    22286  24466  24192  -4030  -3915  -2324        C
ATOM  11863  N    PHE B 727     31.163    0.195 122.352  1.00154.66           N
ANISOU11863  N    PHE B 727    19295  21920  17549  -3393  -3998  -3479        N
ATOM  11864  CA   PHE B 727     30.771   -0.177 123.717  1.00158.87           C
ANISOU11864  CA   PHE B 727    20175  22842  17348  -3184  -3710  -3834        C
ATOM  11865  C    PHE B 727     31.867   -0.207 124.793  1.00163.24           C
ANISOU11865  C    PHE B 727    20944  23820  17257  -3154  -4061  -3970        C
ATOM  11866  O    PHE B 727     31.808   -0.995 125.742  1.00165.59           O
ANISOU11866  O    PHE B 727    21556  24566  16795  -3008  -3817  -3946        O
ATOM  11867  CB   PHE B 727     29.978   -1.480 123.702  1.00156.29           C
ANISOU11867  CB   PHE B 727    20007  22739  16637  -3062  -3089  -3470        C
ATOM  11868  CG   PHE B 727     28.523   -1.275 123.425  1.00155.72           C
ANISOU11868  CG   PHE B 727    19832  22419  16916  -3023  -2645  -3703        C
ATOM  11869  CD1  PHE B 727     27.556   -1.794 124.273  1.00158.39           C
ANISOU11869  CD1  PHE B 727    20388  23052  16743  -2894  -2107  -3915        C
ATOM  11870  CD2  PHE B 727     28.124   -0.519 122.333  1.00153.20           C
ANISOU11870  CD2  PHE B 727    19176  21595  17437  -3131  -2787  -3712        C
ATOM  11871  CE1  PHE B 727     26.218   -1.589 124.017  1.00158.39           C
ANISOU11871  CE1  PHE B 727    20221  22870  17092  -2855  -1699  -4151        C
ATOM  11872  CE2  PHE B 727     26.789   -0.306 122.070  1.00153.18           C
ANISOU11872  CE2  PHE B 727    19031  21374  17797  -3069  -2425  -3926        C
ATOM  11873  CZ   PHE B 727     25.835   -0.849 122.909  1.00155.74           C
ANISOU11873  CZ   PHE B 727    19523  22018  17632  -2921  -1871  -4160        C
ATOM  11874  N    PHE B 728     32.849    0.672 124.630  1.00162.64           N
ANISOU11874  N    PHE B 728    20697  23605  17493  -3326  -4655  -4095        N
ATOM  11875  CA   PHE B 728     33.935    0.863 125.576  1.00167.36           C
ANISOU11875  CA   PHE B 728    21430  24569  17591  -3349  -5097  -4283        C
ATOM  11876  C    PHE B 728     34.070    2.381 125.653  1.00171.18           C
ANISOU11876  C    PHE B 728    21799  24661  18582  -3530  -5557  -4882        C
ATOM  11877  O    PHE B 728     34.144    2.963 126.734  1.00177.13           O
ANISOU11877  O    PHE B 728    22763  25553  18984  -3502  -5735  -5480        O
ATOM  11878  CB   PHE B 728     35.208    0.165 125.082  1.00164.88           C
ANISOU11878  CB   PHE B 728    20947  24513  17186  -3412  -5387  -3656        C
ATOM  11879  CG   PHE B 728     35.233   -1.323 125.373  1.00163.40           C
ANISOU11879  CG   PHE B 728    20978  24742  16364  -3178  -5034  -3168        C
ATOM  11880  CD1  PHE B 728     34.152   -2.131 125.047  1.00159.97           C
ANISOU11880  CD1  PHE B 728    20667  24211  15902  -3057  -4430  -2938        C
ATOM  11881  CD2  PHE B 728     36.331   -1.908 125.978  1.00165.98           C
ANISOU11881  CD2  PHE B 728    21390  25534  16143  -3088  -5337  -2930        C
ATOM  11882  CE1  PHE B 728     34.161   -3.485 125.323  1.00159.22           C
ANISOU11882  CE1  PHE B 728    20818  24425  15255  -2872  -4131  -2483        C
ATOM  11883  CE2  PHE B 728     36.346   -3.268 126.253  1.00165.30           C
ANISOU11883  CE2  PHE B 728    21539  25754  15513  -2855  -5055  -2459        C
ATOM  11884  CZ   PHE B 728     35.258   -4.053 125.925  1.00161.94           C
ANISOU11884  CZ   PHE B 728    21277  25177  15077  -2759  -4450  -2234        C
ATOM  11885  N    TRP B 729     34.060    3.002 124.477  1.00164.66           N
ANISOU11885  N    TRP B 729    20658  23325  18580  -3731  -5743  -4713        N
ATOM  11886  CA   TRP B 729     33.995    4.448 124.307  1.00167.87           C
ANISOU11886  CA   TRP B 729    20952  23184  19647  -3919  -6153  -5197        C
ATOM  11887  C    TRP B 729     32.590    4.669 123.732  1.00165.76           C
ANISOU11887  C    TRP B 729    20621  22452  19906  -3793  -5749  -5309        C
ATOM  11888  O    TRP B 729     32.299    4.235 122.617  1.00160.36           O
ANISOU11888  O    TRP B 729    19731  21606  19592  -3854  -5562  -4772        O
ATOM  11889  CB   TRP B 729     35.050    4.895 123.287  1.00166.05           C
ANISOU11889  CB   TRP B 729    20392  22742  19957  -4285  -6671  -4778        C
ATOM  11890  CG   TRP B 729     35.642    6.294 123.466  1.00171.38           C
ANISOU11890  CG   TRP B 729    21016  23044  21058  -4578  -7316  -5225        C
ATOM  11891  CD1  TRP B 729     36.563    6.682 124.405  1.00176.82           C
ANISOU11891  CD1  TRP B 729    21813  24002  21371  -4687  -7755  -5580        C
ATOM  11892  CD2  TRP B 729     35.394    7.459 122.648  1.00172.16           C
ANISOU11892  CD2  TRP B 729    20948  22417  22048  -4835  -7634  -5316        C
ATOM  11893  NE1  TRP B 729     36.881    8.014 124.239  1.00180.95           N
ANISOU11893  NE1  TRP B 729    22259  23993  22502  -5007  -8305  -5924        N
```

FIG. 13 Continued

```
ATOM  11894  CE2 TRP B 729      36.180   8.514 123.171 1.00178.28           C
ANISOU11894  CE2 TRP B 729    21765 23019 22956  -5099 -8247 -5752          C
ATOM  11895  CE3 TRP B 729      34.572   7.716 121.536 1.00168.77           C
ANISOU11895  CE3 TRP B 729    20355 21457 22314  -4879 -7490 -5059          C
ATOM  11896  CZ2 TRP B 729      36.169   9.803 122.621 1.00181.19           C
ANISOU11896  CZ2 TRP B 729    22043 22652 24150  -5406 -8713 -5925          C
ATOM  11897  CZ3 TRP B 729      34.563   9.002 120.989 1.00171.68           C
ANISOU11897  CZ3 TRP B 729    20624 21120 23487  -5165 -7969 -5204          C
ATOM  11898  CH2 TRP B 729      35.358  10.026 121.536 1.00177.87           C
ANISOU11898  CH2 TRP B 729    21479 21698 24407  -5426 -8570 -5628          C
ATOM  11899  N   ALA B 730      31.704   5.320 124.475 1.00169.51           N
ANISOU11899  N   ALA B 730    21251 22743 20411  -3608 -5809 -6018          N
ATOM  11900  CA  ALA B 730      30.341   5.500 123.980 1.00168.16           C
ANISOU11900  CA  ALA B 730    20967 22182 20743  -3444 -5223 -6145          C
ATOM  11901  C   ALA B 730      29.563   6.604 124.683 1.00174.66           C
ANISOU11901  C   ALA B 730    21872 22656 21836  -3262 -5253 -7037          C
ATOM  11902  O   ALA B 730      28.343   6.497 124.830 1.00175.36           O
ANISOU11902  O   ALA B 730    21934 22709 21984  -3004 -4770 -7316          O
ATOM  11903  CB  ALA B 730      29.577   4.196 124.074 1.00164.68           C
ANISOU11903  CB  ALA B 730    20603 22179 19788  -3243 -4535 -5832          C
ATOM  11904  N   ALA B 731      30.262   7.654 125.115 1.00275.41           N
ANISOU11904  N   ALA B 731    34711 35163 34768  -3397 -5816 -7508          N
ATOM  11905  CA  ALA B 731      29.629   8.783 125.802 1.00282.56           C
ANISOU11905  CA  ALA B 731    35715 35675 35969  -3216 -5909 -8438          C
ATOM  11906  C   ALA B 731      28.611   9.493 124.901 1.00282.13           C
ANISOU11906  C   ALA B 731    35413 34877 36907  -3105 -5897 -8510          C
ATOM  11907  O   ALA B 731      28.947  10.456 124.209 1.00283.18           O
ANISOU11907  O   ALA B 731    35431 34341 37823  -3313 -6451 -8460          O
ATOM  11908  CB  ALA B 731      30.684   9.766 126.306 1.00288.17           C
ANISOU11908  CB  ALA B 731    36565 36190 36738  -3451 -6592 -8865          C
ATOM  11909  N   HIS B 732      27.365   9.016 124.957 1.00231.14           N
ANISOU11909  N   HIS B 732    28872 28557 30394  -2789 -5278 -8627          N
ATOM  11910  CA  HIS B 732      26.231   9.477 124.134 1.00230.64           C
ANISOU11910  CA  HIS B 732    28526 27912 31194  -2616 -5170 -8652          C
ATOM  11911  C   HIS B 732      26.118   8.698 122.806 1.00222.56           C
ANISOU11911  C   HIS B 732    27260 26877 30427  -2795 -5046 -7690          C
ATOM  11912  O   HIS B 732      25.259   8.981 121.973 1.00221.46           O
ANISOU11912  O   HIS B 732    26864 26295 30985  -2709 -5008 -7556          O
ATOM  11913  CB  HIS B 732      26.126  11.027 124.023 1.00236.84           C
ANISOU11913  CB  HIS B 732    29270 27826 32894  -2571 -5738 -9241          C
ATOM  11914  CG  HIS B 732      26.624  11.617 122.733 1.00234.14           C
ANISOU11914  CG  HIS B 732    28760 26810 33392  -2908 -6340 -8634          C
ATOM  11915  ND1 HIS B 732      27.800  12.333 122.647 1.00236.17           N
ANISOU11915  ND1 HIS B 732    29133 26758 33842  -3277 -7014 -8578          N
ATOM  11916  CD2 HIS B 732      26.071  11.659 121.496 1.00230.44           C
ANISOU11916  CD2 HIS B 732    28016 25921 33618  -2957 -6386 -8079          C
ATOM  11917  CE1 HIS B 732      27.970  12.754 121.405 1.00233.69           C
ANISOU11917  CE1 HIS B 732    28630 25886 34276  -3561 -7421 -7976          C
ATOM  11918  NE2 HIS B 732      26.935  12.359 120.688 1.00230.19           N
ANISOU11918  NE2 HIS B 732    27960 25366 34137  -3367 -7061 -7663          N
ATOM  11919  N   LYS B 733      26.984   7.694 122.645 1.00172.03           N
ANISOU11919  N   LYS B 733    20941 20989 23432  -3025 -4984 -7047          N
ATOM  11920  CA  LYS B 733      26.922   6.764 121.517 1.00164.68           C
ANISOU11920  CA  LYS B 733    19830 20176 22566  -3179 -4781 -6190          C
ATOM  11921  C   LYS B 733      25.836   5.794 121.923 1.00163.58           C
ANISOU11921  C   LYS B 733    19707 20478 21967  -2912 -4045 -6250          C
ATOM  11922  O   LYS B 733      25.769   4.640 121.483 1.00158.32           O
ANISOU11922  O   LYS B 733    19023 20165 20967  -2983 -3690 -5655          O
ATOM  11923  CB  LYS B 733      28.252   6.032 121.336 1.00160.85           C
ANISOU11923  CB  LYS B 733    19428 20100 21587  -3457 -4958 -5595          C
ATOM  11924  CG  LYS B 733      29.358   6.865 120.691 1.00161.19           C
ANISOU11924  CG  LYS B 733    19367 19769 22109  -3817 -5654 -5370          C
ATOM  11925  CD  LYS B 733      29.120   7.019 119.195 1.00157.09           C
ANISOU11925  CD  LYS B 733    18585 18824 22297  -4040 -5788 -4778          C
ATOM  11926  CE  LYS B 733      30.305   7.674 118.502 1.00157.26           C
ANISOU11926  CE  LYS B 733    18473 18599 22678  -4478 -6421 -4431          C
ATOM  11927  NZ  LYS B 733      30.212   7.521 117.022 1.00152.67           N
ANISOU11927  NZ  LYS B 733    17637 17818 22552  -4747 -6470 -3720          N
ATOM  11928  N   THR B 734      25.001   6.314 122.812 1.00269.53           N
```

FIG. 13 Continued

```
ANISOU11928  N   THR B 734     33164  33871  35372  -2616  -3826  -7025       N
ATOM  11929  CA  THR B 734       23.892   5.621 123.415  1.00270.67           C
ANISOU11929  CA  THR B 734     33308  34453  35081  -2364  -3122  -7269       C
ATOM  11930  C   THR B 734       22.895   6.714 123.781  1.00277.20           C
ANISOU11930  C   THR B 734     33972  34891  36459  -2052  -3096  -8107       C
ATOM  11931  O   THR B 734       21.977   6.497 124.570  1.00280.96           O
ANISOU11931  O   THR B 734     34434  35727  36594  -1798  -2553  -8606       O
ATOM  11932  CB  THR B 734       24.334   4.918 124.706  1.00273.02           C
ANISOU11932  CB  THR B 734     33963  35465  34306  -2333  -2838  -7464       C
ATOM  11933  OG1 THR B 734       24.600   5.898 125.718  1.00280.19           O
ANISOU11933  OG1 THR B 734     35037  36312  35110  -2216  -3097  -8288       O
ATOM  11934  CG2 THR B 734       25.591   4.092 124.471  1.00268.25           C
ANISOU11934  CG2 THR B 734     33536  35152  33233  -2595  -3055  -6751       C
ATOM  11935  N   ASP B 735       23.097   7.900 123.207  1.00199.50           N
ANISOU11935  N   ASP B 735     24006  24312  27483  -2078  -3693  -8259       N
ATOM  11936  CA  ASP B 735       22.243   9.059 123.472  1.00206.38           C
ANISOU11936  CA  ASP B 735     24722  24669  29025  -1747  -3786  -9067       C
ATOM  11937  C   ASP B 735       20.820   8.915 122.929  1.00206.05           C
ANISOU11937  C   ASP B 735     24294  24517  29477  -1492  -3378  -9056       C
ATOM  11938  O   ASP B 735       20.168   9.909 122.623  1.00210.27           O
ANISOU11938  O   ASP B 735     24596  24425  30873  -1253  -3622  -9449       O
ATOM  11939  CB  ASP B 735       22.883  10.344 122.933  1.00208.76           C
ANISOU11939  CB  ASP B 735     25025  24126  30168  -1880  -4599  -9138       C
ATOM  11940  CG  ASP B 735       23.020  10.344 121.420  1.00203.02           C
ANISOU11940  CG  ASP B 735     24075  22950  30112  -2158  -4947  -8264       C
ATOM  11941  OD1 ASP B 735       23.494  11.363 120.874  1.00205.01           O
ANISOU11941  OD1 ASP B 735     24321  22500  31075  -2324  -5610  -8213       O
ATOM  11942  OD2 ASP B 735       22.662   9.329 120.780  1.00196.98           O
ANISOU11942  OD2 ASP B 735     23159  22537  29146  -2241  -4566  -7628       O
ATOM  11943  N   PHE B 736       20.352   7.678 122.800  1.00250.01           N
ANISOU11943  N   PHE B 736     29791  30674  34528  -1548  -2791  -8595       N
ATOM  11944  CA  PHE B 736       18.989   7.402 122.352  1.00249.84           C
ANISOU11944  CA  PHE B 736     29381  30676  34870  -1350  -2351  -8571       C
ATOM  11945  C   PHE B 736       18.012   7.757 123.474  1.00257.72           C
ANISOU11945  C   PHE B 736     30272  31923  35725   -937  -1885  -9545       C
ATOM  11946  O   PHE B 736       16.810   7.508 123.372  1.00259.11           O
ANISOU11946  O   PHE B 736     30095  32267  36089   -733  -1417  -9679       O
ATOM  11947  CB  PHE B 736       18.860   5.926 121.946  1.00243.06           C
ANISOU11947  CB  PHE B 736     28526  30388  33437  -1594  -1867  -7802       C
ATOM  11948  CG  PHE B 736       17.481   5.521 121.474  1.00242.74           C
ANISOU11948  CG  PHE B 736     28078  30448  33704  -1465  -1401  -7722       C
ATOM  11949  CD1 PHE B 736       16.794   4.494 122.106  1.00243.15           C
ANISOU11949  CD1 PHE B 736     28128  31201  33058  -1450   -662  -7768       C
ATOM  11950  CD2 PHE B 736       16.885   6.145 120.392  1.00242.40           C
ANISOU11950  CD2 PHE B 736     27654  29817  34632  -1397  -1724  -7558       C
ATOM  11951  CE1 PHE B 736       15.537   4.107 121.677  1.00243.23           C
ANISOU11951  CE1 PHE B 736     27730  31341  33347  -1378   -237  -7691       C
ATOM  11952  CE2 PHE B 736       15.625   5.762 119.959  1.00242.48           C
ANISOU11952  CE2 PHE B 736     27252  29958  34920  -1290  -1327  -7479       C
ATOM  11953  CZ  PHE B 736       14.953   4.743 120.603  1.00242.86           C
ANISOU11953  CZ  PHE B 736     27271  30726  34279  -1287   -575  -7561       C
ATOM  11954  N   PHE B 737       18.547   8.343 124.545  1.00193.66           N
ANISOU11954  N   PHE B 737     22448  23870  27265   -830  -2014 -10244       N
ATOM  11955  CA  PHE B 737       17.751   8.740 125.706  1.00202.11           C
ANISOU11955  CA  PHE B 737     23460  25225  28107   -449  -1579 -11268       C
ATOM  11956  C   PHE B 737       16.840   7.594 126.180  1.00201.82           C
ANISOU11956  C   PHE B 737     23298  26040  27346   -422   -703 -11213       C
ATOM  11957  O   PHE B 737       15.747   7.832 126.698  1.00207.99           O
ANISOU11957  O   PHE B 737     23789  27029  28208    -91   -234 -11903       O
ATOM  11958  CB  PHE B 737       16.937  10.018 125.416  1.00208.30           C
ANISOU11958  CB  PHE B 737     23879  25262  30001    -34  -1845 -11931       C
ATOM  11959  CG  PHE B 737       17.768  11.293 125.350  1.00211.74           C
ANISOU11959  CG  PHE B 737     24520  24882  31048    -22  -2657 -12267       C
ATOM  11960  CD1 PHE B 737       17.612  12.292 126.300  1.00221.07           C
ANISOU11960  CD1 PHE B 737     25785  25852  32361    322  -2733 -13372       C
ATOM  11961  CD2 PHE B 737       18.684  11.496 124.330  1.00206.22           C
ANISOU11961  CD2 PHE B 737     23926  23633  30798   -378  -3333 -11498       C
ATOM  11962  CE1 PHE B 737       18.362  13.457 126.236  1.00224.72           C
ANISOU11962  CE1 PHE B 737     26458  25514  33412    297  -3498 -13684       C
```

FIG. 13 Continued

```
ATOM   11963  CE2 PHE B 737      19.433  12.658 124.264  1.00209.87           C
ANISOU11963  CE2 PHE B 737    24573  23343  31824    -431  -4077 -11770       C
ATOM   11964  CZ  PHE B 737      19.271  13.636 125.216  1.00219.08           C
ANISOU11964  CZ  PHE B 737    25848  24249  33144     -99  -4176 -12856       C
ATOM   11965  N   SER B 738      17.298   6.356 125.994  1.00195.45           N
ANISOU11965  N   SER B 738    22700  25712  25850    -778   -489 -10393       N
ATOM   11966  CA  SER B 738      16.542   5.170 126.406  1.00194.94           C
ANISOU11966  CA  SER B 738    22587  26423  25057    -851    302 -10208       C
ATOM   11967  C   SER B 738      17.417   3.907 126.476  1.00188.98           C
ANISOU11967  C   SER B 738    22249  26136  23419   -1238    395  -9397       C
ATOM   11968  O   SER B 738      16.914   2.807 126.725  1.00187.93           O
ANISOU11968  O   SER B 738    22149  26586  22672   -1375    990  -9085       O
ATOM   11969  CB  SER B 738      15.349   4.941 125.470  1.00192.95           C
ANISOU11969  CB  SER B 738    21812  26030  25471    -779    573  -9939       C
ATOM   11970  OG  SER B 738      14.579   3.823 125.875  1.00193.15           O
ANISOU11970  OG  SER B 738    21772  26795  24819    -894   1341  -9781       O
ATOM   11971  N   ASP B 739      18.724   4.084 126.264  1.00186.57           N
ANISOU11971  N   ASP B 739    22248  25561  23080   -1411   -209  -9070       N
ATOM   11972  CA  ASP B 739      19.714   2.994 126.278  1.00181.34           C
ANISOU11972  CA  ASP B 739    21960  25255  21687   -1721   -244  -8318       C
ATOM   11973  C   ASP B 739      19.990   2.456 127.683  1.00185.82           C
ANISOU11973  C   ASP B 739    22931  26552  21119   -1746     93  -8585       C
ATOM   11974  O   ASP B 739      19.166   2.608 128.583  1.00192.22           O
ANISOU11974  O   ASP B 739    23699  27750  21586   -1581    569  -9240       O
ATOM   11975  CB  ASP B 739      21.035   3.476 125.666  1.00177.71           C
ANISOU11975  CB  ASP B 739    21626  24316  21579   -1876  -1011  -7979       C
ATOM   11976  CG  ASP B 739      21.768   4.455 126.563  1.00183.52           C
ANISOU11976  CG  ASP B 739    22587  24976  22164   -1791  -1425  -8662       C
ATOM   11977  OD1 ASP B 739      21.243   5.561 126.796  1.00189.06           O
ANISOU11977  OD1 ASP B 739    23127  25327  23382   -1553  -1532  -9421       O
ATOM   11978  OD2 ASP B 739      22.873   4.120 127.033  1.00182.96           O
ANISOU11978  OD2 ASP B 739    22850  25185  21476   -1955  -1664  -8454       O
ATOM   11979  N   THR B 740      21.138   1.799 127.855  1.00183.93           N
ANISOU11979  N   THR B 740    23066  26533  20285   -1955   -149  -8058       N
ATOM   11980  CA  THR B 740      21.594   1.352 129.178  1.00188.49           C
ANISOU11980  CA  THR B 740    24074  27772  19773   -1999     18  -8243       C
ATOM   11981  C   THR B 740      23.128   1.347 129.272  1.00186.69           C
ANISOU11981  C   THR B 740    24154  27509  19273   -2136   -615  -7924       C
ATOM   11982  O   THR B 740      23.824   1.683 128.309  1.00181.95           O
ANISOU11982  O   THR B 740    23413  26397  19323   -2214  -1139  -7572       O
ATOM   11983  CB  THR B 740      20.978  -0.009 129.655  1.00188.66           C
ANISOU11983  CB  THR B 740    24270  28451  18962   -2125    721  -7841       C
ATOM   11984  OG1 THR B 740      21.718  -1.116 129.130  1.00182.45           O
ANISOU11984  OG1 THR B 740    23695  27689  17940   -2331    592  -6902       O
ATOM   11985  CG2 THR B 740      19.518  -0.130 129.263  1.00189.01           C
ANISOU11985  CG2 THR B 740    23917  28491  19406   -2059   1307  -7970       C
ATOM   11986  N   PHE B 741      23.643   0.991 130.445  1.00193.64           N
ANISOU11986  N   PHE B 741    25429  28969  19176   -2180   -573  -8056       N
ATOM   11987  CA  PHE B 741      25.080   0.999 130.680  1.00193.21           C
ANISOU11987  CA  PHE B 741    25638  28970  18801   -2292  -1180  -7819       C
ATOM   11988  C   PHE B 741      25.791   0.554 129.408  1.00185.08           C
ANISOU11988  C   PHE B 741    24458  27546  18318   -2417  -1527  -6976       C
ATOM   11989  O   PHE B 741      26.364   1.372 128.687  1.00183.00           O
ANISOU11989  O   PHE B 741    23987  26769  18775   -2458  -2059  -7006       O
ATOM   11990  CB  PHE B 741      25.449   0.083 131.859  1.00197.00           C
ANISOU11990  CB  PHE B 741    26572  30209  18069   -2367   -984  -7648       C
ATOM   11991  CG  PHE B 741      25.149   0.670 133.234  1.00206.15           C
ANISOU11991  CG  PHE B 741    27945  31833  18548   -2296   -821  -8534       C
ATOM   11992  CD1 PHE B 741      24.225   0.066 134.078  1.00210.71           C
ANISOU11992  CD1 PHE B 741    28685  33021  18354   -2302   -128  -8692       C
ATOM   11993  CD2 PHE B 741      25.808   1.805 133.688  1.00210.68           C
ANISOU11993  CD2 PHE B 741    28568  32261  19220   -2258  -1355  -9210       C
ATOM   11994  CE1 PHE B 741      23.956   0.590 135.325  1.00219.59           C
ANISOU11994  CE1 PHE B 741    30000  34637  18797   -2254     55  -9528       C
ATOM   11995  CE2 PHE B 741      25.538   2.330 134.940  1.00219.52           C
ANISOU11995  CE2 PHE B 741    29899  33824  19683   -2198  -1198 -10071       C
ATOM   11996  CZ  PHE B 741      24.614   1.719 135.756  1.00223.96           C
ANISOU11996  CZ  PHE B 741    30609  35031  19454   -2188   -482 -10236       C
ATOM   11997  N   GLY B 742      25.711   0.743 129.126  1.00177.84           N
```

FIG. 13 Continued

```
ANISOU11997  N    GLY B 742     23647  26867  17056   -2494  -1202  -6241           N
ATOM   11998  CA   GLY B 742      26.311   -1.325 127.941  1.00170.58           C
ANISOU11998  CA   GLY B 742     22599  25647  16568   -2597  -1431  -5458           C
ATOM   11999  C    GLY B 742      27.784   -1.650 128.081  1.00169.81           C
ANISOU11999  C    GLY B 742     22687  25706  16126   -2659  -1950  -5061           C
ATOM   12000  O    GLY B 742      28.175   -2.809 128.020  1.00167.47           O
ANISOU12000  O    GLY B 742     22574  25642  15416   -2681  -1851  -4424           O
ATOM   12001  N    VAL B 743      28.592   -0.617 128.295  1.00182.89           N
ANISOU12001  N    VAL B 743     24290  27229  17969   -2682  -2516  -5459           N
ATOM   12002  CA   VAL B 743      30.052   -0.742 128.354  1.00182.61           C
ANISOU12002  CA   VAL B 743     24326  27330  17726   -2758  -3089  -5140           C
ATOM   12003  C    VAL B 743      30.570   -1.944 129.152  1.00184.25           C
ANISOU12003  C    VAL B 743     24898  28118  16991   -2708  -2999  -4703           C
ATOM   12004  O    VAL B 743      30.597   -3.074 128.655  1.00180.20           O
ANISOU12004  O    VAL B 743     24428  27648  16392   -2686  -2781  -4030           O
ATOM   12005  CB   VAL B 743      30.717    0.549 128.934  1.00187.84           C
ANISOU12005  CB   VAL B 743     24980  27920  18472   -2815  -3654  -5801           C
ATOM   12006  CG1  VAL B 743      32.168    0.672 128.475  1.00186.10           C
ANISOU12006  CG1  VAL B 743     24616  27645  18448   -2961  -4308  -5432           C
ATOM   12007  CG2  VAL B 743      29.934    1.786 128.540  1.00188.86           C
ANISOU12007  CG2  VAL B 743     24871  27498  19391   -2807  -3664  -6410           C
ATOM   12008  N    ARG B 744      30.965   -1.675 130.395  1.00178.58           N
ANISOU12008  N    ARG B 744     24458  27824  15571   -2692  -3191  -5105           N
ATOM   12009  CA   ARG B 744      31.592   -2.654 131.289  1.00181.66           C
ANISOU12009  CA   ARG B 744     25219  28784  15019   -2652  -3250  -4725           C
ATOM   12010  C    ARG B 744      31.264   -4.114 130.987  1.00178.20           C
ANISOU12010  C    ARG B 744     24941  28447  14320   -2596  -2820  -3961           C
ATOM   12011  O    ARG B 744      32.077   -4.850 130.428  1.00174.78           O
ANISOU12011  O    ARG B 744     24462  27958  13966   -2551  -3055  -3323           O
ATOM   12012  CB   ARG B 744      31.227   -2.361 132.752  1.00189.76           C
ANISOU12012  CB   ARG B 744     26598  30316  15186   -2651  -3109  -5333           C
ATOM   12013  CG   ARG B 744      30.889   -0.913 133.062  1.00193.80           C
ANISOU12013  CG   ARG B 744     26981  30641  16012   -2677  -3233  -6287           C
ATOM   12014  CD   ARG B 744      31.979    0.037 132.610  1.00193.13           C
ANISOU12014  CD   ARG B 744     26649  30214  16517   -2767  -3969  -6443           C
ATOM   12015  NE   ARG B 744      33.314   -0.508 132.829  1.00193.57           N
ANISOU12015  NE   ARG B 744     26796  30598  16154   -2809  -4481  -5940           N
ATOM   12016  CZ   ARG B 744      33.844   -0.730 134.026  1.00199.88           C
ANISOU12016  CZ   ARG B 744     27933  31985  16027   -2817  -4692  -6051           C
ATOM   12017  NH1  ARG B 744      33.146   -0.472 135.122  1.00206.29           N
ANISOU12017  NH1  ARG B 744     29051  33152  16176   -2811  -4394  -6659           N
ATOM   12018  NH2  ARG B 744      35.071   -1.218 134.126  1.00200.24           N
ANISOU12018  NH2  ARG B 744     27993  32296  15793   -2826  -5201  -5558           N
ATOM   12019  N    SER B 745      30.060   -4.516 131.364  1.00181.71           N
ANISOU12019  N    SER B 745     25561  29036  14444   -2605  -2184  -4060           N
ATOM   12020  CA   SER B 745      29.628   -5.894 131.231  1.00179.73           C
ANISOU12020  CA   SER B 745     25530  28888  13873   -2605  -1741  -3385           C
ATOM   12021  C    SER B 745      29.833   -6.486 129.869  1.00172.33           C
ANISOU12021  C    SER B 745     24351  27497  13631   -2585  -1763  -2779           C
ATOM   12022  O    SER B 745      29.436   -5.900 128.874  1.00167.95           O
ANISOU12022  O    SER B 745     23421  26512  13880   -2625  -1717  -2936           O
ATOM   12023  CB   SER B 745      28.138    6.004 131.540  1.00181.60           C
ANISOU12023  CB   SER B 745     25828  29241  13932   -2679  -1018  -3663           C
ATOM   12024  OG   SER B 745      27.751   -7.361 131.654  1.00181.38           O
ANISOU12024  OG   SER B 745     26101  29384  13432   -2741   -607  -3021           O
ATOM   12025  N    ILE B 746      30.459   -7.652 129.825  1.00170.97           N
ANISOU12025  N    ILE B 746     24401  27420  13140   -2518  -1848  -2090           N
ATOM   12026  CA   ILE B 746      30.483   -8.414 128.598  1.00164.72           C
ANISOU12026  CA   ILE B 746     23448  26239  12901   -2497  -1740  -1527           C
ATOM   12027  C    ILE B 746      29.146   -9.116 128.697  1.00164.90           C
ANISOU12027  C    ILE B 746     23666  26271  12717   -2607  -1050  -1410           C
ATOM   12028  O    ILE B 746      28.223   -8.598 129.316  1.00168.16           O
ANISOU12028  O    ILE B 746     24108  26874  12913   -2697   -712  -1899           O
ATOM   12029  CB   ILE B 746      31.659   -9.425 128.527  1.00164.54           C
ANISOU12029  CB   ILE B 746     23583  26282  12650   -2336  -2093   -875           C
ATOM   12030  CG1  ILE B 746      32.088   -9.862 129.928  1.00171.48           C
ANISOU12030  CG1  ILE B 746     24921  27663  12569   -2264  -2256   -771           C
ATOM   12031  CG2  ILE B 746      32.851   -8.824 127.792  1.00161.82           C
ANISOU12031  CG2  ILE B 746     22834  25785  12867   -2268  -2673   -890           C
```

FIG. 13 Continued

```
ATOM   12032  CD1 ILE B 746      33.532 -10.322 130.009  1.00172.77           C
ANISOU12032  CD1 ILE B 746    25107  27949  12589  -2056  -2854   -352        C
ATOM   12033  N   ARG B 747      29.029 -10.291 128.107  1.00160.62           N
ANISOU12033  N   ARG B 747    23248  25540  12240  -2609   -830   -794        N
ATOM   12034  CA  ARG B 747      27.784 -11.031 128.200  1.00161.22           C
ANISOU12034  CA  ARG B 747    23519  25630  12109  -2770   -188   -635        C
ATOM   12035  C   ARG B 747      26.594 -10.217 127.715  1.00159.25           C
ANISOU12035  C   ARG B 747    22896  25222  12388  -2904    185  -1135        C
ATOM   12036  O   ARG B 747      26.759  -9.222 127.007  1.00156.07           O
ANISOU12036  O   ARG B 747    22086  24555  12659  -2864    -74  -1471        O
ATOM   12037  CB  ARG B 747      27.584 -11.501 129.627  1.00168.34           C
ANISOU12037  CB  ARG B 747    24911  27035  12017  -2826     -4   -588        C
ATOM   12038  CG  ARG B 747      28.501 -12.637 129.975  1.00170.37           C
ANISOU12038  CG  ARG B 747    25587  27359  11786  -2708   -280     89        C
ATOM   12039  CD  ARG B 747      29.196 -12.395 131.294  1.00177.06           C
ANISOU12039  CD  ARG B 747    26736  28718  11823  -2637   -630    -37        C
ATOM   12040  NE  ARG B 747      30.187 -13.431 131.575  1.00179.26           N
ANISOU12040  NE  ARG B 747    27370  29028  11714  -2468  -1003    637        N
ATOM   12041  CZ  ARG B 747      30.073 -14.337 132.542  1.00185.19           C
ANISOU12041  CZ  ARG B 747    28667  30069  11629  -2533   -892   1068        C
ATOM   12042  NH1 ARG B 747      29.012 -14.338 133.340  1.00189.56           N
ANISOU12042  NH1 ARG B 747    29466  30970  11589  -2806   -375    883        N
ATOM   12043  NH2 ARG B 747      31.029 -15.240 132.718  1.00187.32           N
ANISOU12043  NH2 ARG B 747    29227  30294  11652  -2327  -1306   1692        N
ATOM   12044  N   ASP B 748      25.398 -10.640 128.108  1.00179.88           N
ANISOU12044  N   ASP B 748    25641  28008  14699  -3072    779  -1166        N
ATOM   12045  CA  ASP B 748      24.167 -10.031 127.611  1.00178.43           C
ANISOU12045  CA  ASP B 748    25069  27690  15036  -3181   1176  -1583        C
ATOM   12046  C   ASP B 748      24.079  -8.514 127.706  1.00179.46           C
ANISOU12046  C   ASP B 748    24838  27795  15554  -3072    967  -2345        C
ATOM   12047  O   ASP B 748      23.207  -7.905 127.095  1.00177.74           O
ANISOU12047  O   ASP B 748    24229  27356  15948  -3100   1163  -2669        O
ATOM   12048  CB  ASP B 748      22.952 -10.696 128.244  1.00182.50           C
ANISOU12048  CB  ASP B 748    25772  28529  15042  -3393   1849  -1543        C
ATOM   12049  CG  ASP B 748      22.857 -12.163 127.882  1.00180.93           C
ANISOU12049  CG  ASP B 748    25880  28188  14676  -3552   2071   -782        C
ATOM   12050  OD1 ASP B 748      23.307 -12.995 128.695  1.00184.77           O
ANISOU12050  OD1 ASP B 748    26862  28913  14429   3577   2049    384        O
ATOM   12051  OD2 ASP B 748      22.365 -12.484 126.775  1.00176.21           O
ANISOU12051  OD2 ASP B 748    25049  27218  14687  -3652   2229   -574        O
ATOM   12052  N   ASN B 749      24.977  -7.904 128.466  1.00239.90           N
ANISOU12052  N   ASN B 749    32624  35653  22875  -2949    542  -2633        N
ATOM   12053  CA  ASN B 749      25.009  -6.451 128.549  1.00241.33           C
ANISOU12053  CA  ASN B 749    32506  35731  23458  -2851    271  -3365        C
ATOM   12054  C   ASN B 749      25.883  -5.868 127.432  1.00235.93           C
ANISOU12054  C   ASN B 749    31514  34556  23574  -2800   -299  -3247        C
ATOM   12055  O   ASN B 749      25.868  -4.660 127.179  1.00236.09           O
ANISOU12055  O   ASN B 749    31240  34321  24145  -2756   -561  -3755        O
ATOM   12056  CB  ASN B 749      25.483  -6.002 129.936  1.00248.27           C
ANISOU12056  CB  ASN B 749    33674  37081  23577  -2793     94  -3811        C
ATOM   12057  CG  ASN B 749      25.387  -4.494 130.142  1.00251.03           C
ANISOU12057  CG  ASN B 749    33761  37309  24311  -2697   -135  -4668        C
ATOM   12058  OD1 ASN B 749      26.159  -3.723 129.570  1.00248.56           O
ANISOU12058  OD1 ASN B 749    33240  36627  24576  -2650   -683  -4770        O
ATOM   12059  ND2 ASN B 749      24.453  -4.072 130.986  1.00256.82           N
ANISOU12059  ND2 ASN B 749    34511  38358  24711  -2679    284  -5300        N
ATOM   12060  N   ASN B 750      26.629  -6.737 126.753  1.00156.90           N
ANISOU12060  N   ASN B 750    21573  24409  13635  -2816   -480  -2577        N
ATOM   12061  CA  ASN B 750      27.502  -6.304 125.668  1.00152.14           C
ANISOU12061  CA  ASN B 750    20669  23426  13713  -2808   -973  -2408        C
ATOM   12062  C   ASN B 750      27.849  -7.431 124.717  1.00147.22           C
ANISOU12062  C   ASN B 750    20061  22633  13243  -2834   -927  -1701        C
ATOM   12063  O   ASN B 750      27.567  -7.348 123.530  1.00142.54           O
ANISOU12063  O   ASN B 750    19172  21689  13298  -2920   -890  -1556        O
ATOM   12064  CB  ASN B 750      28.783  -5.664 126.213  1.00154.81           C
ANISOU12064  CB  ASN B 750    21047  23909  13866  -2737  -1580  -2597        C
ATOM   12065  CG  ASN B 750      29.694  -5.123 125.113  1.00150.65           C
ANISOU12065  CG  ASN B 750    20165  23038  14038  -2785  -2082  -2447        C
ATOM   12066  OD1 ASN B 750      29.615  -5.543 123.962  1.00145.58           O
```

FIG. 13 Continued

```
ANISOU12066  OD1 ASN B 750      19329  22123  13863  -2847  -1995  -2047           O
ATOM   12067 ND2 ASN B 750      30.572  -4.188 125.474 1.00 153.28                 N
ANISOU12067  ND2 ASN B 750      20416  23411  14414  -2794  -2609  -2774           N
ATOM   12068 N   HIS B 751      28.459  -8.490 125.227 1.00 190.47                 N
ANISOU12068  N   HIS B 751      25893  28351  18127  -2755   -945  -1268           N
ATOM   12069 CA  HIS B 751      28.860  -9.589 124.359 1.00 186.57                 C
ANISOU12069  CA  HIS B 751      25435  27665  17788  -2732   -923   -643           C
ATOM   12070 C   HIS B 751      27.669 -10.266 123.683 1.00 183.80                 C
ANISOU12070  C   HIS B 751      25077  27095  17663  -2881   -377   -439           C
ATOM   12071 O   HIS B 751      27.398 -10.026 122.507 1.00 179.29                 O
ANISOU12071  O   HIS B 751      24175  26204  17742  -2977   -357   -408           O
ATOM   12072 CB  HIS B 751      29.704 -10.600 125.127 1.00 189.80                 C
ANISOU12072  CB  HIS B 751      26251  28336  17527  -2573  -1073   -226           C
ATOM   12073 CG  HIS B 751      29.802 -11.934 124.460 1.00 187.33                 C
ANISOU12073  CG  HIS B 751      26095  27811  17269  -2528   -905    382           C
ATOM   12074 ND1 HIS B 751      28.825 -12.896 124.581 1.00 188.02                 N
ANISOU12074  ND1 HIS B 751      26487  27840  17111  -2643   -392    644           N
ATOM   12075 CD2 HIS B 751      30.763 -12.468 123.672 1.00 184.75                 C
ANISOU12075  CD2 HIS B 751      25661  27313  17221  -2385  -1176    749           C
ATOM   12076 CE1 HIS B 751      29.176 -13.967 123.893 1.00 185.93                 C
ANISOU12076  CE1 HIS B 751      26333  27321  16990  -2569   -378   1141           C
ATOM   12077 NE2 HIS B 751      30.348 -13.734 123.334 1.00 183.97                 N
ANISOU12077  NE2 HIS B 751      25831  27012  17056  -2388   -837   1195           N
ATOM   12078 N   GLU B 752      26.957 -11.106 124.424 1.00 145.03                 N
ANISOU12078  N   GLU B 752      20532  22376  12196  -2938     53   -284           N
ATOM   12079 CA  GLU B 752      25.791 -11.789 123.881 1.00 143.24                 C
ANISOU12079  CA  GLU B 752      20308  21980  12136  -3129    580    -94           C
ATOM   12080 C   GLU B 752      24.797 -10.727 123.423 1.00 141.80                 C
ANISOU12080  C   GLU B 752      19688  21686  12502  -3240    747   -589           C
ATOM   12081 O   GLU B 752      23.703 -11.025 122.955 1.00 140.62                 O
ANISOU12081  O   GLU B 752      19421  21431  12578  -3413   1163   -551           O
ATOM   12082 CB  GLU B 752      25.176 -12.738 124.922 1.00 148.12                 C
ANISOU12082  CB  GLU B 752      21393  22884  12003  -3229   1008    116           C
ATOM   12083 CG  GLU B 752      25.925 -14.075 125.075 1.00 149.16                 C
ANISOU12083  CG  GLU B 752      21979  22957  11736  -3147    904    763           C
ATOM   12084 CD  GLU B 752      25.642 -14.794 126.392 1.00 155.61                 C
ANISOU12084  CD  GLU B 752      23323  24130  11674  -3226   1147    969           C
ATOM   12085 OE1 GLU B 752      26.158 -15.912 126.594 1.00 157.40                 O
ANISOU12085  OE1 GLU B 752      23967  24273  11564  -3162   1060   1528           O
ATOM   12086 OE2 GLU B 752      24.916 -14.237 127.233 1.00 159.44                 O
ANISOU12086  OE2 GLU B 752      23806  24980  11792  -3350   1418    572           O
ATOM   12087 N   LEU B 753      25.207  -9.475 123.572 1.00 142.67                 N
ANISOU12087  N   LEU B 753      19555  21806  12847  -3138    383  -1054           N
ATOM   12088 CA  LEU B 753      24.416  -8.335 123.157 1.00 141.99                 C
ANISOU12088  CA  LEU B 753      19053  21547  13351  -3180    420  -1545           C
ATOM   12089 C   LEU B 753      24.473  -8.171 121.641 1.00 136.24                 C
ANISOU12089  C   LEU B 753      17972  20393  13402  -3268    242  -1319           C
ATOM   12090 O   LEU B 753      23.506  -8.452 120.954 1.00 134.27                 O
ANISOU12090  O   LEU B 753      17555  19992  13469  -3406    562  -1220           O
ATOM   12091 CB  LEU B 753      24.956  -7.082 123.849 1.00 145.24                 C
ANISOU12091  CB  LEU B 753      19388  22049  13748  -3047     26  -2100           C
ATOM   12092 CG  LEU B 753      24.246  -5.728 123.886 1.00 147.17                 C
ANISOU12092  CG  LEU B 753      19298  22150  14470  -3008     -2  -2768           C
ATOM   12093 CD1 LEU B 753      23.368  -5.616 125.122 1.00 153.26                 C
ANISOU12093  CD1 LEU B 753      20212  23314  14708  -2959    430  -3255           C
ATOM   12094 CD2 LEU B 753      25.271  -4.605 123.881 1.00 147.71                 C
ANISOU12094  CD2 LEU B 753      19250  22050  14822   2935    629   3059           C
ATOM   12095 N   MET B 754      25.611  -7.733 121.115 1.00 133.07                 N
ANISOU12095  N   MET B 754      17445  19837  13276  -3221   -272  -1226           N
ATOM   12096 CA  MET B 754      25.721  -7.484 119.680 1.00 128.25                 C
ANISOU12096  CA  MET B 754      16496  18878  13356  -3344   -461  -1022           C
ATOM   12097 C   MET B 754      26.199  -8.654 118.848 1.00 124.69                 C
ANISOU12097  C   MET B 754      16141  18361  12875  -3399   -402   -454           C
ATOM   12098 O   MET B 754      25.648  -8.916 117.785 1.00 121.46                 O
ANISOU12098  O   MET B 754      15556  17739  12853  -3557   -246   -261           O
ATOM   12099 CB  MET B 754      26.539  -6.229 119.391 1.00 128.07                 C
ANISOU12099  CB  MET B 754      16208  18697  13755  -3339  -1022  -1256           C
ATOM   12100 CG  MET B 754      25.732  -4.993 119.698 1.00 130.72                 C
ANISOU12100  CG  MET B 754      16343  18888  14435  -3322  -1053  -1819           C
```

FIG. 13 Continued

```
ATOM   12101  SD   MET B 754      23.946  -5.334 119.627  1.00131.17           S
ANISOU12101  SD   MET B 754    16308  18928  14604  -3361   -427  -1938        S
ATOM   12102  CE   MET B 754      23.293   3.840 120.380  1.00136.32           C
ANISOU12102  CE   MET B 754    16767  19498  15529  -3209   -521  -2732        C
ATOM   12103  N    GLY B 755      27.220  -9.356 119.320  1.00145.85           N
ANISOU12103  N    GLY B 755    19093  21221  15103  -3257   -543   -204        N
ATOM   12104  CA   GLY B 755      27.706 -10.524 118.616  1.00143.40           C
ANISOU12104  CA   GLY B 755    18897  20831  14755  -3246   -481    286        C
ATOM   12105  C    GLY B 755      26.595 -11.549 118.474  1.00143.02           C
ANISOU12105  C    GLY B 755    19057  20695  14588  -3367     47    494        C
ATOM   12106  O    GLY B 755      26.890 -12.735 118.307  1.00142.75           O
ANISOU12106  O    GLY B 755    19288  20609  14343  -3321    169    879        O
ATOM   12107  N    ALA B 756      25.334 -11.091 118.559  1.00123.59           N
ANISOU12107  N    ALA B 756    16466  18211  12282  -3518    343    227        N
ATOM   12108  CA   ALA B 756      24.131 -11.934 118.414  1.00123.69           C
ANISOU12108  CA   ALA B 756    16595  18172  12229  -3702    858    377        C
ATOM   12109  C    ALA B 756      22.915 -11.225 117.780  1.00122.44           C
ANISOU12109  C    ALA B 756    16037  17892  12593  -3890   1031    119        C
ATOM   12110  O    ALA B 756      21.827 -11.815 117.705  1.00123.07           O
ANISOU12110  O    ALA B 756    16143  17977  12640  -4071   1459    191        O
ATOM   12111  CB   ALA B 756      23.745 -12.581 119.744  1.00128.41           C
ANISOU12111  CB   ALA B 756    17606  19042  12141  -3676   1187    397        C
ATOM   12112  N    VAL B 757      23.102  -9.964 117.362  1.00121.94           N
ANISOU12112  N    VAL B 757    15605  17715  13013  -3852    676   -167        N
ATOM   12113  CA   VAL B 757      22.091  -9.191 116.601  1.00120.83           C
ANISOU12113  CA   VAL B 757    15043  17392  13475  -3990    709   -368        C
ATOM   12114  C    VAL B 757      22.678  -8.190 115.628  1.00118.22           C
ANISOU12114  C    VAL B 757    14383  16814  13723  -4019    211   -388        C
ATOM   12115  O    VAL B 757      22.033  -7.832 114.653  1.00116.48           O
ANISOU12115  O    VAL B 757    13854  16393  14010  -4177    175   -351        O
ATOM   12116  CB   VAL B 757      21.069  -8.412 117.440  1.00124.81           C
ANISOU12116  CB   VAL B 757    15390  18020  14010  -3915    910   -869        C
ATOM   12117  CG1  VAL B 757      19.641  -8.850 117.084  1.00125.16           C
ANISOU12117  CG1  VAL B 757    15254  18078  14224  -4100   1364   -844        C
ATOM   12118  CG2  VAL B 757      21.380  -8.523 118.908  1.00129.06           C
ANISOU12118  CG2  VAL B 757    16263  18884  13889  -3749   1028  -1085        C
ATOM   12119  N    TYR B 758      23.878  -7.702 115.884  1.00146.99           N
ANISOU12119  N    TYR B 758    18077  20481  17291  -3899   -193   -432        N
ATOM   12120  CA   TYR B 758      24.499  -6.876 114.871  1.00144.70           C
ANISOU12120  CA   TYR B 758    17492  19972  17516  -4005   -649   -359        C
ATOM   12121  C    TYR B 758      24.511  -7.799 113.664  1.00141.03           C
ANISOU12121  C    TYR B 758    16999  19443  17141  -4197   -520     89        C
ATOM   12122  O    TYR B 758      24.646  -7.373 112.528  1.00138.81           O
ANISOU12122  O    TYR B 758    16455  18999  17287  -4384   -757    241        O
ATOM   12123  CB   TYR B 758      25.920  -6.496 115.266  1.00145.49           C
ANISOU12123  CB   TYR B 758    17661  20171  17448  -3900  -1066   -381        C
ATOM   12124  CG   TYR B 758      26.565  -5.518 114.316  1.00144.05           C
ANISOU12124  CG   TYR B 758    17162  19786  17785  -4066  -1548   -322        C
ATOM   12125  CD1  TYR B 758      26.071  -5.341 113.031  1.00141.49           C
ANISOU12125  CD1  TYR B 758    16577  19243  17938  -4302  -1578   -112        C
ATOM   12126  CD2  TYR B 758      27.674  -4.778 114.698  1.00145.72           C
ANISOU12126  CD2  TYR B 758    17337  20044  17987   4029   1988    452        C
ATOM   12127  CE1  TYR B 758      26.654  -4.450 112.148  1.00140.72           C
ANISOU12127  CE1  TYR B 758    16213  18977  18278  -4507  -2022     -1        C
ATOM   12128  CE2  TYR B 758      28.271  -3.879 113.821  1.00144.94           C
ANISOU12128  CE2  TYR B 758    16951  19764  18356  -4247  -2428   -359        C
ATOM   12129  CZ   TYR B 758      27.757  -3.722 112.544  1.00142.47           C
ANISOU12129  CZ   TYR B 758    16404  19234  18495  -4491  -2437   -116        C
ATOM   12130  OH   TYR B 758      28.336  -2.837 111.659  1.00142.22           O
ANISOU12130  OH   TYR B 758    16109  19038  18890  -4758  -2875     31        O
ATOM   12131  N    LEU B 759      24.363  -9.088 113.946  1.00114.26           N
ANISOU12131  N    LEU B 759    13914  16182  13319  -4165   -142    295        N
ATOM   12132  CA   LEU B 759      24.321 -10.140 112.936  1.00111.57           C
ANISOU12132  CA   LEU B 759    13627  15770  12993  -4327     40    666        C
ATOM   12133  C    LEU B 759      22.908 -10.420 112.418  1.00111.07           C
ANISOU12133  C    LEU B 759    13452  15604  13144  -4547    376    685        C
ATOM   12134  O    LEU B 759      22.383 -11.526 112.568  1.00111.54           O
ANISOU12134  O    LEU B 759    13758  15692  12930  -4612    763    837        O
ATOM   12135  CB   LEU B 759      24.929 -11.427 113.490  1.00112.42           C
```

FIG. 13 Continued

```
ANISOU12135 CB  LEU B 759     14154  15994  12568  -4173    231    893       C
ATOM  12136 CG  LEU B 759     26.450 -11.453 113.597  1.00112.46             C
ANISOU12136 CG  LEU B 759     14210  16105  12413  -3976   -115    994       C
ATOM  12137 CD1 LEU B 759     26.969 -12.835 113.974  1.00113.61             C
ANISOU12137 CD1 LEU B 759     14755  16297  12116  -3799     59   1266       C
ATOM  12138 CD2 LEU B 759     27.018 -11.019 112.278  1.00109.65             C
ANISOU12138 CD2 LEU B 759     13515  15676  12472  -4136   -387   1102       C
ATOM  12139 N   GLN B 760     22.314  -9.395 111.821  1.00107.80             N
ANISOU12139 N   GLN B 760     12663  15059  13236  -4669    192    541       N
ATOM  12140 CA  GLN B 760     21.000  -9.441 111.208  1.00107.61             C
ANISOU12140 CA  GLN B 760     12420  14949  13520  -4878    402    547       C
ATOM  12141 C   GLN B 760     20.951  -8.122 110.481  1.00107.15             C
ANISOU12141 C   GLN B 760     11967  14707  14039  -4944    -31    459       C
ATOM  12142 O   GLN B 760     20.110  -7.256 110.732  1.00109.28             O
ANISOU12142 O   GLN B 760     11985  14889  14646  -4884    -80    183       O
ATOM  12143 CB  GLN B 760     19.900  -9.537 112.247  1.00110.86             C
ANISOU12143 CB  GLN B 760     12865  15487  13770  -4798    789    279       C
ATOM  12144 CG  GLN B 760     19.880 -10.854 113.005  1.00112.07             C
ANISOU12144 CG  GLN B 760     13446  15808  13326  -4791   1216    425       C
ATOM  12145 CD  GLN B 760     19.621 -12.055 112.117  1.00110.16             C
ANISOU12145 CD  GLN B 760     13334  15479  13041  -5050   1438    784       C
ATOM  12146 OE1 GLN B 760     18.593 -12.129 111.434  1.00109.90             O
ANISOU12146 OE1 GLN B 760     13064  15396  13296  -5291   1582    809       O
ATOM  12147 NE2 GLN B 760     20.542 -13.020 112.142  1.00109.34             N
ANISOU12147 NE2 GLN B 760     13609  15352  12585  -4992   1457   1044       N
ATOM  12148 N   VAL B 761     21.933  -7.991 109.603  1.00154.87             N
ANISOU12148 N   VAL B 761     17966  20696  20181   5059    355    701       N
ATOM  12149 CA  VAL B 761     22.202  -6.808 108.817  1.00154.52             C
ANISOU12149 CA  VAL B 761     17613  20476  20622  -5185   -833    734       C
ATOM  12150 C   VAL B 761     23.107  -7.353 107.756  1.00151.92             C
ANISOU12150 C   VAL B 761     17313  20227  20182  -5394   -934   1093       C
ATOM  12151 O   VAL B 761     22.858  -7.242 106.563  1.00150.72             O
ANISOU12151 O   VAL B 761     16968  20016  20282  -5677  -1060   1318       O
ATOM  12152 CB  VAL B 761     23.047  -5.811 109.618  1.00156.33             C
ANISOU12152 CB  VAL B 761     17849  20663  20886  -4988  -1177    490       C
ATOM  12153 CG1 VAL B 761     23.833  -4.890 108.681  1.00155.66             C
ANISOU12153 CG1 VAL B 761     17543  20435  21166  -5197  -1693    674       C
ATOM  12154 CG2 VAL B 761     22.174  -5.022 110.582  1.00159.65             C
ANISOU12154 CG2 VAL B 761     18190  20976  21494  -4775  -1142     52       C
ATOM  12155 N   SER B 762     24.181  -7.959 108.227  1.00153.12             N
ANISOU12155 N   SER B 762     17703  20546  19930  -5241   -879   1132       N
ATOM  12156 CA  SER B 762     25.115  -8.623 107.362  1.00151.32             C
ANISOU12156 CA  SER B 762     17507  20447  19539  -5364   -903   1406       C
ATOM  12157 C   SER B 762     24.454  -9.951 107.010  1.00150.36             C
ANISOU12157 C   SER B 762     17586  20342  19204  -5437   -469   1534       C
ATOM  12158 O   SER B 762     24.919 -10.675 106.138  1.00149.13             O
ANISOU12158 O   SER B 762     17468  20261  18934  -5565   -399   1728       O
ATOM  12159 CB  SER B 762     26.429  -8.835 108.106  1.00152.06             C
ANISOU12159 CB  SER B 762     17758  20713  19304  -5111   -958   1370       C
ATOM  12160 OG  SER B 762     27.531  -8.906 107.223  1.00151.14             O
ANISOU12160 OG  SER B 762     17500  20743  19183  -5235  -1185   1568       O
ATOM  12161 N   ILE B 763     23.360 -10.267 107.698  1.00165.04             N
ANISOU12161 N   ILE B 763     19565  22138  21005  -5374   -166   1402       N
ATOM  12162 CA  ILE B 763     22.621 -11.493 107.411  1.00164.73             C
ANISOU12162 CA  ILE B 763     19718  22080  20790  -5503    239   1521       C
ATOM  12163 C   ILE B 763     21.629 -11.277 106.273  1.00163.94             C
ANISOU12163 C   ILE B 763     19344  21905  21041  -5847    216   1609       C
ATOM  12164 O   ILE B 763     21.370 -12.186 105.490  1.00163.17             O
ANISOU12164 O   ILE B 763     19339  21805  20855  -6062    407   1765       O
ATOM  12165 CB  ILE B 763     21.853 -12.010 108.631  1.00166.85             C
ANISOU12165 CB  ILE B 763     20229  22365  20802  -5358    606   1382       C
ATOM  12166 CG1 ILE B 763     21.844 -13.548 108.656  1.00167.10             C
ANISOU12166 CG1 ILE B 763     20653  22372  20467  -5391    973   1566       C
ATOM  12167 CG2 ILE B 763     20.448 -11.420 108.665  1.00168.04             C
ANISOU12167 CG2 ILE B 763     20104  22477  21265  -5492    701   1220       C
ATOM  12168 CD1 ILE B 763     21.603 -14.229 107.314  1.00165.55             C
ANISOU12168 CD1 ILE B 763     20423  22088  20390  -5694   1049   1749       C
ATOM  12169 N   ILE B 764     21.041 -10.087 106.208  1.00119.56             N
ANISOU12169 N   ILE B 764     13395  16209  15825  -5890    -34   1497       N
```

FIG. 13 Continued

```
ATOM   12170  CA  ILE B 764      20.169  -9.754 105.090  1.00119.30           C
ANISOU12170  CA  ILE B 764    13062  16109  16158  -6203   -159   1619        C
ATOM   12171  C   ILE B 764      21.021  -9.041 104.036  1.00118.16           C
ANISOU12171  C   ILE B 764    12737  15961  16200  -6384   -598   1820        C
ATOM   12172  O   ILE B 764      20.749  -7.907 103.636  1.00119.00           O
ANISOU12172  O   ILE B 764    12550  15944  16721  -6479   -971   1848        O
ATOM   12173  CB  ILE B 764      18.914  -8.937 105.506  1.00121.52           C
ANISOU12173  CB  ILE B 764    13055  16291  16825  -6147   -188   1411        C
ATOM   12174  CG1 ILE B 764      17.983  -9.779 106.390  1.00123.08           C
ANISOU12174  CG1 ILE B 764    13396  16580  16791  -6073    316   1250        C
ATOM   12175  CG2 ILE B 764      18.143  -8.458 104.272  1.00121.66           C
ANISOU12175  CG2 ILE B 764    12724  16233  17270  -6452   -443   1586        C
ATOM   12176  CD1 ILE B 764      16.600  -9.183 106.599  1.00125.71           C
ANISOU12176  CD1 ILE B 764    13369  16893  17503  -6067    368   1048        C
ATOM   12177  N   SER B 765      22.093  -9.723 103.641  1.00125.56           N
ANISOU12177  N   SER B 765    13854  17035  16820  -6419   -549   1957        N
ATOM   12178  CA  SER B 765      23.010  -9.243 102.619  1.00124.87           C
ANISOU12178  CA  SER B 765    13605  17044  16797  -6634   -879   2159        C
ATOM   12179  C   SER B 765      22.593  -9.875 101.315  1.00124.26           C
ANISOU12179  C   SER B 765    13489  17056  16667  -7001   -784   2357        C
ATOM   12180  O   SER B 765      22.981  -9.415 100.241  1.00124.24           O
ANISOU12180  O   SER B 765    13302  17160  16744  -7298  -1053   2560        O
ATOM   12181  CB  SER B 765      24.455  -9.637 102.951  1.00124.46           C
ANISOU12181  CB  SER B 765    13713  17158  16420  -6438   -858   2148        C
ATOM   12182  OG  SER B 765      25.386  -9.041 102.061  1.00124.42           O
ANISOU12182  OG  SER B 765    13493  17301  16480  -6662  -1175   2322        O
ATOM   12183  N   GLN B 766      21.810 -10.947 101.419  1.00179.92           N
ANISOU12183  N   GLN B 766    20730  24079  23552  -7014   -399   2299        N
ATOM   12184  CA  GLN B 766      21.300 -11.629 100.244  1.00179.80           C
ANISOU12184  CA  GLN B 766    20710  24138  23468  -7379   -291   2434        C
ATOM   12185  C   GLN B 766      20.368 -10.671  99.522  1.00180.63           C
ANISOU12185  C   GLN B 766    20465  24200  23965  -7669   -616   2567        C
ATOM   12186  O   GLN B 766      20.337 -10.629  98.289  1.00180.83           O
ANISOU12186  O   GLN B 766    20369  24351  23986  -8037   -782   2766        O
ATOM   12187  CB  GLN B 766      20.556 -12.890 100.636  1.00180.19           C
ANISOU12187  CB  GLN B 766    21038  24111  23316  -7354    158   2332        C
ATOM   12188  CG  GLN B 766      19.153 -12.623 101.084  1.00181.35           C
ANISOU12188  CG  GLN B 766    21032  24155  23718  -7400    229   2260        C
ATOM   12189  CD  GLN B 766      18.468 -13.879 101.544  1.00182.24           C
ANISOU12189  CD  GLN B 766    21429  24209  23606  -7427    686   2185        C
ATOM   12190  OE1 GLN B 766      19.115 -14.812 102.022  1.00182.15           O
ANISOU12190  OE1 GLN B 766    21791  24152  23266  -7255    939   2154        O
ATOM   12191  NE2 GLN B 766      17.150 -13.919 101.402  1.00183.61           N
ANISOU12191  NE2 GLN B 766    21419  24373  23971  -7654    777   2173        N
ATOM   12192  N   ALA B 767      19.617  -9.892 100.299  1.00105.96           N
ANISOU12192  N   ALA B 767    10842  14576  14841  -7490   -719   2449        N
ATOM   12193  CA  ALA B 767      18.749  -8.862  99.738  1.00107.44           C
ANISOU12193  CA  ALA B 767    10668  14666  15489  -7671  -1089   2563        C
ATOM   12194  C   ALA B 767      19.615  -7.829  99.011  1.00107.59           C
ANISOU12194  C   ALA B 767    10535  14687  15659  -7830  -1580   2793        C
ATOM   12195  O   ALA B 767      19.115  -6.960  98.305  1.00109.14           O
ANISOU12195  O   ALA B 767    10464  14792  16210  -8043  -1978   2990        O
ATOM   12196  CB  ALA B 767      17.884  -8.206 100.842  1.00109.15           C
ANISOU12196  CB  ALA B 767    10726  14696  16049  -7357  -1081   2311        C
ATOM   12197  N   LEU B 768      20.926  -7.954  99.191  1.00147.75           N
ANISOU12197  N   LEU B 768    15786  19883  20468  -7738  -1557   2787        N
ATOM   12198  CA  LEU B 768      21.904  -7.033  98.612  1.00148.23           C
ANISOU12198  CA  LEU B 768    15712  19993  20616  -7915  -1975   3000        C
ATOM   12199  C   LEU B 768      22.816  -7.729  97.589  1.00147.51           C
ANISOU12199  C   LEU B 768    15696  20241  20110  -8205  -1871   3176        C
ATOM   12200  O   LEU B 768      23.650  -7.097  96.925  1.00148.29           O
ANISOU12200  O   LEU B 768    15663  20482  20200  -8451  -2167   3392        O
ATOM   12201  CB  LEU B 768      22.722  -6.383  99.730  1.00148.41           C
ANISOU12201  CB  LEU B 768    15777  19899  20714  -7576  -2095   2815        C
ATOM   12202  CG  LEU B 768      21.982  -5.438 100.699  1.00150.02           C
ANISOU12202  CG  LEU B 768    15878  19770  21353  -7297  -2272   2595        C
ATOM   12203  CD1 LEU B 768      20.466  -5.673 100.757  1.00150.78           C
ANISOU12203  CD1 LEU B 768    15878  19754  21658  -7260  -2102   2501        C
ATOM   12204  CD2 LEU B 768      22.588  -5.482 102.111  1.00149.91           C
```

FIG. 13 Continued

```
ANISOU12204 CD2 LEU B 768     16049  19733  21177  -6881  -2115   2269       C
ATOM   12205  N   ILE B 769      22.651  -9.046  97.497  1.00 155.75         N
ANISOU12205  N   ILE B 769     16954  21412  20811  -8178  -1433   3060      N
ATOM   12206  CA  ILE B 769      23.338  -9.864  96.507  1.00 155.65         C
ANISOU12206  CA  ILE B 769     17025  21709  20404  -8420  -1264   3137      C
ATOM   12207  C   ILE B 769      22.354 -10.058  95.339  1.00 156.58         C
ANISOU12207  C   ILE B 769     17061  21903  20529  -8861  -1316   3303      C
ATOM   12208  O   ILE B 769      22.003 -11.174  94.937  1.00 156.55         O
ANISOU12208  O   ILE B 769     17234  21984  20265  -8968   -994   3206      O
ATOM   12209  CB  ILE B 769      23.869 -11.192  97.121  1.00 154.76         C
ANISOU12209  CB  ILE B 769     17229  21636  19934  -8091   -795   2888      C
ATOM   12210  CG1 ILE B 769      25.305 -11.440  96.668  1.00 155.14         C
ANISOU12210  CG1 ILE B 769     17264  21992  19689  -8089   -762   2895      C
ATOM   12211  CG2 ILE B 769      22.936 -12.382  96.853  1.00 154.82         C
ANISOU12211  CG2 ILE B 769     17454  21579  19792  -8191   -440   2795      C
ATOM   12212  CD1 ILE B 769      26.172 -10.218  96.815  1.00 155.61         C
ANISOU12212  CD1 ILE B 769     17074  22140  19910  -8104  -1143   3023      C
ATOM   12213  N   PHE B 770      21.918  -8.922  94.806  1.00 119.96         N
ANISOU12213  N   PHE B 770     12159  17211  16210  -9124  -1768   3562      N
ATOM   12214  CA  PHE B 770      20.932  -8.859  93.744  1.00 121.47         C
ANISOU12214  CA  PHE B 770     12216  17466  16470  -9543  -1946   3775      C
ATOM   12215  C   PHE B 770      21.353  -7.733  92.802  1.00 123.40         C
ANISOU12215  C   PHE B 770     12240  17830  16816  -9926  -2457   4160      C
ATOM   12216  O   PHE B 770      20.699  -7.424  91.809  1.00 125.35         O
ANISOU12216  O   PHE B 770     12348  18159  17122 -10327  -2742   4438      O
ATOM   12217  CB  PHE B 770      19.571  -8.571  94.374  1.00 121.93         C
ANISOU12217  CB  PHE B 770     12155  17217  16955  -9371  -2007   3696      C
ATOM   12218  CG  PHE B 770      18.735  -9.800  94.608  1.00 121.42         C
ANISOU12218  CG  PHE B 770     12253  17155  16726  -9331  -1560   3474      C
ATOM   12219  CD1 PHE B 770      19.325 -11.036  94.818  1.00 120.11         C
ANISOU12219  CD1 PHE B 770     12411  17091  16135  -9227  -1099   3269      C
ATOM   12220  CD2 PHE B 770      17.345  -9.719  94.615  1.00 122.82         C
ANISOU12220  CD2 PHE B 770     12243  17221  17204  -9403  -1619   3477      C
ATOM   12221  CE1 PHE B 770      18.539 -12.168  95.017  1.00 120.22         C
ANISOU12221  CE1 PHE B 770     12609  17052  16018  -9242   -715   3094      C
ATOM   12222  CE2 PHE B 770      16.568 -10.843  94.819  1.00 122.85         C
ANISOU12222  CE2 PHE B 770     12381  17238  17057  -9435  -1214   3292      C
ATOM   12223  CZ  PHE B 770      17.167 -12.062  95.021  1.00 121.55         C
ANISOU12223  CZ  PHE B 770     12587  17133  16462  -9374   -767   3112      C
ATOM   12224  N   VAL B 771      22.483  -7.130  93.123  1.00 233.84         N
ANISOU12224  N   VAL B 771     26201  31842  30805  -9827  -2588   4197      N
ATOM   12225  CA  VAL B 771      22.980  -6.011  92.355  1.00 236.10         C
ANISOU12225  CA  VAL B 771     26298  32211  31197 -10208  -3076   4585      C
ATOM   12226  C   VAL B 771      24.047  -6.411  91.342  1.00 237.00         C
ANISOU12226  C   VAL B 771     26421  32841  30788 -10592  -2957   4720      C
ATOM   12227  O   VAL B 771      25.172  -6.749  91.707  1.00 236.17         O
ANISOU12227  O   VAL B 771     26364  32929  30442 -10416  -2715   4544      O
ATOM   12228  CB  VAL B 771      23.550  -4.965  93.302  1.00 236.25         C
ANISOU12228  CB  VAL B 771     26251  31935  31580  -9937  -3347   4556      C
ATOM   12229  CG1 VAL B 771      22.439  -4.412  94.166  1.00 236.42         C
ANISOU12229  CG1 VAL B 771     26220  31471  32139  -9599  -3509   4418      C
ATOM   12230  CG2 VAL B 771      24.608  -5.598  94.179  1.00 234.25         C
ANISOU12230  CG2 VAL B 771     26140  31812  31052  -9572  -2966   4230      C
ATOM   12231  N   THR B 772      23.687  -6.394  90.065  1.00 178.42         N
ANISOU12231  N   THR B 772     18935  25684  23173 -11114  -3121   5016      N
ATOM   12232  CA  THR B 772      24.673  -6.630  89.008  1.00 180.24         C
ANISOU12232  CA  THR B 772     19134  26468  22882 -11547  -3032   5160      C
ATOM   12233  C   THR B 772      25.155  -5.268  88.433  1.00 183.35         C
ANISOU12233  C   THR B 772     19327  26922  23415 -11991  -3583   5662      C
ATOM   12234  O   THR B 772      26.015  -5.207  87.533  1.00 185.73         O
ANISOU12234  O   THR B 772     19548  27719  23301 -12438  -3580   5865      O
ATOM   12235  CB  THR B 772      24.126  -7.572  87.912  1.00 181.38         C
ANISOU12235  CB  THR B 772     19366  26959  22589 -11902  -2817   5137      C
ATOM   12236  OG1 THR B 772      22.694  -7.582  87.970  1.00 181.18         O
ANISOU12236  OG1 THR B 772     19354  26614  22872 -11881  -2974   5177      O
ATOM   12237  CG2 THR B 772      24.643  -8.991  88.120  1.00 179.80         C
ANISOU12237  CG2 THR B 772     19368  26967  21981 -11624  -2191   4658      C
ATOM   12238  N   ARG B 773      24.573  -4.194  88.986  1.00 198.08         N
ANISOU12238  N   ARG B 773     21118  28266  25876 -11860  -4044   5842      N
```

FIG. 13 Continued

```
ATOM   12239  CA  ARG B 773      24.833  -2.771  88.656  1.00201.39           C
ANISOU12239  CA  ARG B 773    21392  28518  26609 -12208  -4661   6328        C
ATOM   12240  C   ARG B 773      23.664  -1.917  89.200  1.00202.02           C
ANISOU12240  C   ARG B 773    21426  27939  27395 -11958  -5106   6410        C
ATOM   12241  O   ARG B 773      23.607  -0.690  88.986  1.00205.27           O
ANISOU12241  O   ARG B 773    21745  28042  28207 -12180  -5695   6911        O
ATOM   12242  CB  ARG B 773      25.005  -2.544  87.153  1.00205.23           C
ANISOU12242  CB  ARG B 773    21809  29465  26704 -12948  -4899   6830        C
ATOM   12243  CG  ARG B 773      25.542  -1.187  86.799  1.00209.12           C
ANISOU12243  CG  ARG B 773    22188  29850  27419 -13373  -5479   7361        C
ATOM   12244  CD  ARG B 773      26.449  -1.303  85.607  1.00212.25           C
ANISOU12244  CD  ARG B 773    22521  30956  27167 -14041  -5407   7673        C
ATOM   12245  NE  ARG B 773      27.383  -2.412  85.760  1.00209.99           N
ANISOU12245  NE  ARG B 773    22238  31193  26354 -13860  -4738   7205        N
ATOM   12246  CZ  ARG B 773      27.141  -3.653  85.349  1.00208.62           C
ANISOU12246  CZ  ARG B 773    22157  31394  25715 -13802  -4250   6883        C
ATOM   12247  NH1 ARG B 773      25.989  -3.950  84.767  1.00209.08           N
ANISOU12247  NH1 ARG B 773    22304  31399  25739 -13951  -4350   6979        N
ATOM   12248  NH2 ARG B 773      28.047  -4.601  85.525  1.00207.23           N
ANISOU12248  NH2 ARG B 773    21980  31626  25132 -13587  -3683   6453        N
ATOM   12249  N   SER B 774      22.747   2.615  89.892  1.00171.57           N
ANISOU12249  N   SER B 774    17630  23879  23681 -11499  -4803   6018        N
ATOM   12250  CA  SER B 774      21.523  -2.078  90.508  1.00172.08           C
ANISOU12250  CA  SER B 774    17609  23402  24372 -11163  -5066   5950        C
ATOM   12251  C   SER B 774      21.702  -1.703  91.995  1.00170.48           C
ANISOU12251  C   SER B 774    17437  22777  24559 -10571  -4986   5552        C
ATOM   12252  O   SER B 774      22.798  -1.824  92.564  1.00168.94           O
ANISOU12252  O   SER B 774    17337  22692  24160 -10433  -4775   5364        O
ATOM   12253  CB  SER B 774      20.359  -3.092  90.350  1.00170.89           C
ANISOU12253  CB  SER B 774    17466  23358  24107 -11081  -4755   5756        C
ATOM   12254  OG  SER B 774      20.775  -4.438  90.553  1.00167.78           O
ANISOU12254  OG  SER B 774    17262  23301  23187 -10963  -4112   5391        O
ATOM   12255  N   ARG B 775      20.627  -1.198  92.600  1.00126.87           N
ANISOU12255  N   ARG B 775    11809  16796  19599 -10234  -5182   5422        N
ATOM   12256  CA  ARG B 775      20.594  -0.973  94.039  1.00125.71           C
ANISOU12256  CA  ARG B 775    11699  16299  19766  -9655  -5034   4963        C
ATOM   12257  C   ARG B 775      19.704  -2.089  94.592  1.00123.34           C
ANISOU12257  C   ARG B 775    11436  16104  19323   9333   4495   4575        C
ATOM   12258  O   ARG B 775      18.655  -2.391  94.024  1.00124.27           O
ANISOU12258  O   ARG B 775    11431  16272  19512  -9465  -4515   4680        O
ATOM   12259  CB  ARG B 775      20.015   0.400  94.384  1.00129.33           C
ANISOU12259  CB  ARG B 775    11999  16171  20970  -9474  -5604   5023        C
ATOM   12260  CG  ARG B 775      20.364   1.473  93.386  1.00133.11           C
ANISOU12260  CG  ARG B 775    12408  16501  21668  -9952  -6262   5596        C
ATOM   12261  CD  ARG B 775      21.854   1.645  93.285  1.00132.64           C
ANISOU12261  CD  ARG B 775    12474  16652  21269 -10234  -6271   5732        C
ATOM   12262  NE  ARG B 775      22.388   2.396  94.413  1.00133.22           N
ANISOU12262  NE  ARG B 775    12600  16330  21687  -9892  -6401   5435        N
ATOM   12263  CZ  ARG B 775      22.068   3.656  94.686  1.00137.09           C
ANISOU12263  CZ  ARG B 775    13031  16210  22848  -9789  -6959   5500        C
ATOM   12264  NH1 ARG B 775      21.196   4.299  93.923  1.00140.74           N
ANISOU12264  NH1 ARG B 775    13365  16375  23736  -9965  -7454   5884        N
ATOM   12265  NH2 ARG B 775      22.611   4.268  95.729  1.00137.78           N
ANISOU12265  NH2 ARG B 775    13193  15968  23189  -9497  -7046   5168        N
ATOM   12266  N   SER B 776      20.136  -2.738  95.666  1.00144.89           N
ANISOU12266  N   SER B 776    14339  18893  21820  -8958  -4026   4159        N
ATOM   12267  CA  SER B 776      19.316  -3.762  96.275  1.00143.22           C
ANISOU12267  CA  SER B 776    14191  18752  21474  -8684  -3522   3821        C
ATOM   12268  C   SER B 776      18.091  -2.978  96.686  1.00145.84           C
ANISOU12268  C   SER B 776    14277  18721  22416  -8448  -3770   3718        C
ATOM   12269  O   SER B 776      17.005  -3.525  96.884  1.00146.06           O
ANISOU12269  O   SER B 776    14208  18782  22505  -8336  -3515   3551        O
ATOM   12270  CB  SER B 776      20.019  -4.337  97.500  1.00140.91           C
ANISOU12270  CB  SER B 776    14133  18506  20901  -8291  -3089   3436        C
ATOM   12271  OG  SER B 776      21.421  -4.444  97.288  1.00139.78           O
ANISOU12271  OG  SER B 776    14122  18577  20411  -8418  -3088   3538        O
ATOM   12272  N   TRP B 777      18.314  -1.669  96.790  1.00210.66           N
ANISOU12272  N   TRP B 777    22371  26578  31091  -8387  -4286   3816        N
ATOM   12273  CA  TRP B 777      17.324  -0.662  97.144  1.00214.21           C
```

FIG. 13 Continued

```
ANISOU12273 CA  TRP B 777    22567  26596  32227  -8121  -4642   3716       C
ATOM  12274 C   TRP B 777      16.286   -0.464   96.032  1.00216.86         C
ANISOU12274 C   TRP B 777    22638  26911  32845  -8401  -4992   4083       C
ATOM  12275 O   TRP B 777      15.079   -0.542   96.269  1.00218.53         O
ANISOU12275 O   TRP B 777    22612  27050  33369  -8183  -4923   3904       O
ATOM  12276 CB  TRP B 777      18.075    0.646   97.426  1.00216.51         C
ANISOU12276 CB  TRP B 777    22880  26485  32899  -8051  -5143   3764       C
ATOM  12277 CG  TRP B 777      17.257    1.895   97.372  1.00221.32         C
ANISOU12277 CG  TRP B 777    23240  26567  34283  -7897  -5714   3820       C
ATOM  12278 CD1 TRP B 777      16.431    2.295   96.363  1.00224.36         C
ANISOU12278 CD1 TRP B 777    23394  26831  35021  -8122  -6149   4218       C
ATOM  12279 CD2 TRP B 777      17.220    2.937   98.357  1.00224.30         C
ANISOU12279 CD2 TRP B 777    23582  26442  35200  -7471  -5954   3460       C
ATOM  12280 NE1 TRP B 777      15.864    3.508   96.668  1.00229.12         N
ANISOU12280 NE1 TRP B 777    23808  26856  36392  -7822  -6650   4139       N
ATOM  12281 CE2 TRP B 777      16.333    3.926   97.885  1.00229.22         C
ANISOU12281 CE2 TRP B 777    23942  26612  36538  -7419  -6528   3649       C
ATOM  12282 CE3 TRP B 777      17.843    3.126   99.596  1.00223.75         C
ANISOU12282 CE3 TRP B 777    23682  26260  35073  -7123  -5756   2980       C
ATOM  12283 CZ2 TRP B 777      16.053    5.089   98.609  1.00233.68         C
ANISOU12283 CZ2 TRP B 777    24414  26578  37796  -7004  -6890   3336       C
ATOM  12284 CZ3 TRP B 777      17.562    4.282  100.315  1.00228.07         C
ANISOU12284 CZ3 TRP B 777    24146  26253  36257  -6752  -6105   2656       C
ATOM  12285 CH2 TRP B 777      16.676    5.249   99.817  1.00233.02         C
ANISOU12285 CH2 TRP B 777    24515  26396  37625  -6682  -6657   2818       C
ATOM  12286 N   SER B 778      16.780   -0.212   94.822  1.00145.65         N
ANISOU12286 N   SER B 778    13646  18003  23690  -8903  -5368   4602       N
ATOM  12287 CA  SER B 778      15.961    0.040   93.627  1.00148.68         C
ANISOU12287 CA  SER B 778    13816  18407  24269  -9257  -5799   5052       C
ATOM  12288 C   SER B 778      15.060   -1.126   93.213  1.00147.51         C
ANISOU12288 C   SER B 778    13588  18644  23815  -9392  -5423   4994       C
ATOM  12289 O   SER B 778      13.998   -0.944   92.607  1.00150.52         O
ANISOU12289 O   SER B 778    13702  18996  24494  -9503  -5724   5196       O
ATOM  12290 CB  SER B 778      16.888    0.376   92.456  1.00149.58         C
ANISOU12290 CB  SER B 778    14047  18688  24096  -9840  -6172   5612       C
ATOM  12291 OG  SER B 778      17.721   -0.733   92.136  1.00145.95         O
ANISOU12291 OG  SER B 778    13814  18756  22884 -10106  -5677   5576       O
ATOM  12292 N   PHE B 779      15.518   -2.329   93.521  1.00162.43         N
ANISOU12292 N   PHE B 779    15716  20882  25117  -9398  -4796   4731       N
ATOM  12293 CA  PHE B 779      14.791   -3.539   93.200  1.00161.32         C
ANISOU12293 CA  PHE B 779    15573  21078  24643  -9554  -4392   4635       C
ATOM  12294 C   PHE B 779      13.468   -3.542   93.949  1.00162.94         C
ANISOU12294 C   PHE B 779    15501  21118  25293  -9190  -4269   4329       C
ATOM  12295 O   PHE B 779      12.864   -4.588   94.146  1.00161.87         O
ANISOU12295 O   PHE B 779    15378  21205  24919  -9203  -3807   4110       O
ATOM  12296 CB  PHE B 779      15.631   -4.751   93.593  1.00157.27         C
ANISOU12296 CB  PHE B 779    15412  20847  23497  -9533  -3757   4369       C
ATOM  12297 CG  PHE B 779      16.328   -5.433   92.439  1.00156.38         C
ANISOU12297 CG  PHE B 779    15487  21128  22803 -10032  -3690   4618       C
ATOM  12298 CD1 PHE B 779      17.474   -4.880   91.871  1.00156.62         C
ANISOU12298 CD1 PHE B 779    15597  21253  22659 -10274  -3956   4899       C
ATOM  12299 CD2 PHE B 779      15.860   -6.641   91.946  1.00155.77         C
ANISOU12299 CD2 PHE B 779    15506  21342  22340 -10271  -3336   4537       C
ATOM  12300 CE1 PHE B 779      18.124   -5.514   90.819  1.00156.39         C
ANISOU12300 CE1 PHE B 779    15711  21650  22060 -10725  -3845   5076       C
ATOM  12301 CE2 PHE B 779      16.501   -7.279   90.901  1.00155.51         C
ANISOU12301 CE2 PHE B 779    15651  21678  21759 -10704  -3248   4688       C
ATOM  12302 CZ  PHE B 779      17.632   -6.717   90.334  1.00155.86         C
ANISOU12302 CZ  PHE B 779    15747  21862  21611 -10920  -3486   4946       C
ATOM  12303 N   VAL B 780      13.031   -2.361   94.376  1.00183.43         N
ANISOU12303 N   VAL B 780    17836  23315  28544  -8869  -4679   4297       N
ATOM  12304 CA  VAL B 780      11.765   -2.216   95.081  1.00185.97         C
ANISOU12304 CA  VAL B 780    17812  23497  29350  -8485  -4590   3976       C
ATOM  12305 C   VAL B 780      10.695   -3.098   94.440  1.00186.85         C
ANISOU12305 C   VAL B 780    17721  23943  29328  -8771  -4432   4055       C
ATOM  12306 O   VAL B 780      10.626   -3.214   93.218  1.00187.76         O
ANISOU12306 O   VAL B 780    17815  24238  29286  -9239  -4746   4475       O
ATOM  12307 CB  VAL B 780      11.288   -0.747   95.100  1.00190.79         C
ANISOU12307 CB  VAL B 780    18096  23633  30762  -8216  -5244   4069       C
```

FIG. 13 Continued

```
ATOM   12308  CG1 VAL B 780      12.183    0.096  96.000  1.00190.52           C
ANISOU12308  CG1 VAL B 780    18246  23223  30919  -7066  -5332   3844         C
ATOM   12309  CG2 VAL B 780      11.248   -0.176  93.685  1.00193.54           C
ANISOU12309  CG2 VAL B 780    18347  23939  31250  -8665  -5931   4701         C
ATOM   12310  N   GLU B 781       9.868    3.711  95.283  1.00164.41           N
ANISOU12310  N   GLU B 781    14733  21210  26527  -8521  -3946   3648         N
ATOM   12311  CA  GLU B 781       8.819   -4.664  94.875  1.00165.41           C
ANISOU12311  CA  GLU B 781    14665  21669  26516  -8794  -3703   3643         C
ATOM   12312  C   GLU B 781       9.391   -5.953  94.259  1.00161.94           C
ANISOU12312  C   GLU B 781    14634  21563  25334  -9269  -3347   3760         C
ATOM   12313  O   GLU B 781       8.750   -7.015  94.331  1.00161.82           O
ANISOU12313  O   GLU B 781    14617  21791  25078  -9440  -2924   3605         O
ATOM   12314  CB  GLU B 781       7.744   -4.037  93.965  1.00170.26           C
ANISOU12314  CB  GLU B 781    14785  22267  27640  -8941  -4295   3945         C
ATOM   12315  CG  GLU B 781       6.329   -4.612  94.180  1.00173.10           C
ANISOU12315  CG  GLU B 781    14715  22865  28189  -8929  -4035   3724         C
ATOM   12316  CD  GLU B 781       6.319   -6.107  94.462  1.00170.10           C
ANISOU12316  CD  GLU B 781    14616  22825  27188  -9188  -3321   3508         C
ATOM   12317  OE1 GLU B 781       6.401   -6.909  93.505  1.00169.12           O
ANISOU12317  OE1 GLU B 781    14678  22953  26628  -9710  -3315   3743         O
ATOM   12318  OE2 GLU B 781       6.224   -6.478  95.649  1.00169.19           O
ANISOU12318  OE2 GLU B 781    14556  22715  27014  -8880  -2774   3098         O
ATOM   12319  N   ARG B 782      10.581   -5.856  93.656  1.00241.36           N
ANISOU12319  N   ARG B 782    25028  31631  35047  -9487  -3515   4013         N
ATOM   12320  CA  ARG B 782      11.260   -7.031  93.096  1.00238.49           C
ANISOU12320  CA  ARG B 782    25060  31565  33990  -9870  -3168   4059         C
ATOM   12321  C   ARG B 782      11.828   -7.874  94.244  1.00235.19           C
ANISOU12321  C   ARG B 782    24988  31132  33242  -9576  -2521   3669         C
ATOM   12322  O   ARG B 782      11.243   -8.906  94.587  1.00234.98           O
ANISOU12322  O   ARG B 782    25030  31228  33024  -9624  -2064   3456         O
ATOM   12323  CB  ARG B 782      12.320   -6.650  92.053  1.00237.96           C
ANISOU12323  CB  ARG B 782    25177  31587  33651 -10208  -3533   4436         C
ATOM   12324  CG  ARG B 782      11.740   -6.358  90.677  1.00241.30           C
ANISOU12324  CG  ARG B 782    25382  32184  34117 -10694  -4050   4862         C
ATOM   12325  CD  ARG B 782      12.614   -6.925  89.578  1.00240.37           C
ANISOU12325  CD  ARG B 782    25566  32414  33350 -11201  -4019   5076         C
ATOM   12326  NE  ARG B 782      11.879   -7.071  88.328  1.00243.64           N
ANISOU12326  NE  ARG B 782    25825  33104  33644 -11721  -4352   5381         N
ATOM   12327  CZ  ARG B 782      12.322   -7.749  87.276  1.00243.84           C
ANISOU12327  CZ  ARG B 782    26075  33515  33058 -12227  -4283   5501         C
ATOM   12328  NH1 ARG B 782      13.502   -8.351  87.323  1.00241.00           N
ANISOU12328  NH1 ARG B 782    26077  33297  32194 -12243  -3876   5329         N
ATOM   12329  NH2 ARG B 782      11.585   -7.829  86.177  1.00247.35           N
ANISOU12329  NH2 ARG B 782    26367  34224  33390 -12707  -4625   5770         N
ATOM   12330  N   PRO B 783      12.978   -7.476  94.824  1.00110.20           N
ANISOU12330  N   PRO B 783     9388  15159  17324  -9306  -2496   3600         N
ATOM   12331  CA  PRO B 783      13.164   -8.252  96.040  1.00108.22           C
ANISOU12331  CA  PRO B 783     9384  14889  16844  -8987  -1916   3228         C
ATOM   12332  C   PRO B 783      11.886   -8.079  96.858  1.00110.66           C
ANISOU12332  C   PRO B 783     9372  15120  17553  -8738  -1781   2983         C
ATOM   12333  O   PRO B 783      11.514   -6.950  97.183  1.00112.86           O
ANISOU12333  O   PRO B 783     9335  15199  18346  -8468  -2111   2939         O
ATOM   12334  CB  PRO B 783      14.364   -7.557  96.700  1.00106.61           C
ANISOU12334  CB  PRO B 783     9347  14518  16641  -8665  -2016   3164         C
ATOM   12335  CG  PRO B 783      15.205   -7.121  95.542  1.00106.37           C
ANISOU12335  CG  PRO B 783     9352  14566  16496  -9000  -2423   3526         C
ATOM   12336  CD  PRO B 783      14.252   -6.900  94.365  1.00109.03           C
ANISOU12336  CD  PRO B 783     9404  14992  17031  -9395  -2787   3826         C
ATOM   12337  N   GLY B 784      11.189   -9.175  97.132  1.00110.84           N
ANISOU12337  N   GLY B 784     9453  15301  17360  -8850  -1315   2825         N
ATOM   12338  CA  GLY B 784       9.975   -9.095  97.913  1.00113.64           C
ANISOU12338  CA  GLY B 784     9468  15668  18041  -8659  -1118   2581         C
ATOM   12339  C   GLY B 784       9.209  -10.385  97.824  1.00114.36           C
ANISOU12339  C   GLY B 784     9621  15974  17857  -8985   -682   2527         C
ATOM   12340  O   GLY B 784       8.605  -10.838  98.801  1.00115.65           O
ANISOU12340  O   GLY B 784     9746  16200  17995  -8851   -240   2274         O
ATOM   12341  N   ALA B 785       9.248  -10.980  96.639  1.00225.41           N
ANISOU12341  N   ALA B 785    23793  30162  31690  -9452   -805   2764         N
ATOM   12342  CA  ALA B 785       8.542  -12.223  96.382  1.00226.53           C
```

FIG. 13 Continued

```
ANISOU12342 CA  ALA B 785    24020  30474  31577  -9845   -456   2727      C
ATOM  12343 C   ALA B 785      8.809 -13.241  97.484  1.00225.34           C
ANISOU12343 C   ALA B 785    24282  30272  31065  -9711    166   2495      C
ATOM  12344 O   ALA B 785      9.885 -13.836  97.526  1.00222.65           O
ANISOU12344 O   ALA B 785    24439  29840  30319  -9678    337   2502      O
ATOM  12345 CB  ALA B 785      8.945 -12.788  95.023  1.00225.80           C
ANISOU12345 CB  ALA B 785    24152  30490  31149 -10326   -636   2952      C
ATOM  12346 N   LEU B 786      7.832 -13.413  98.379  1.00116.97           N
ANISOU12346 N   LEU B 786    10330  16622  17493  -9628    491   2302      N
ATOM  12347 CA  LEU B 786      7.898 -14.396  99.466  1.00116.93           C
ANISOU12347 CA  LEU B 786    10695  16595  17139  -9568   1083   2131      C
ATOM  12348 C   LEU B 786      9.250 -14.382 100.188  1.00113.72           C
ANISOU12348 C   LEU B 786    10770  16009  16431  -9183   1195   2080      C
ATOM  12349 O   LEU B 786      9.554 -15.277 100.978  1.00113.48           O
ANISOU12349 O   LEU B 786    11160  15921  16036  -9137   1623   2009      O
ATOM  12350 CB  LEU B 786      7.581 -15.815  98.941  1.00117.80           C
ANISOU12350 CB  LEU B 786    11105  16738  16917 -10087   1363   2204      C
ATOM  12351 CG  LEU B 786      6.247 -16.236  98.260  1.00121.47           C
ANISOU12351 CG  LEU B 786    11199  17403  17551 -10600   1349   2246      C
ATOM  12352 CD1 LEU B 786      5.323 -17.109  99.149  1.00124.76           C
ANISOU12352 CD1 LEU B 786    11608  17919  17878 -10796   1888   2116      C
ATOM  12353 CD2 LEU B 786      5.468 -15.068  97.627  1.00123.49           C
ANISOU12353 CD2 LEU B 786    10761  17827  18331 -10585    847   2315      C
ATOM  12354 N   LEU B 787     10.059 -13.364  99.904  1.00152.80           N
ANISOU12354 N   LEU B 787    15653  20868  21536  -8930    780   2142      N
ATOM  12355 CA  LEU B 787     11.399 -13.256 100.469  1.00150.01           C
ANISOU12355 CA  LEU B 787    15690  20380  20927  -8592    806   2107      C
ATOM  12356 C   LEU B 787     11.449 -12.278 101.628  1.00150.70           C
ANISOU12356 C   LEU B 787    15611  20422  21226  -8123    786   1893      C
ATOM  12357 O   LEU B 787     12.043 -12.561 102.670  1.00150.05           O
ANISOU12357 O   LEU B 787    15850  20305  20855  -7856   1060   1760      O
ATOM  12358 CB  LEU B 787     12.395 -12.810  99.400  1.00147.73           C
ANISOU12358 CB  LEU B 787    15463  20050  20617  -8671    379   2312      C
ATOM  12359 CG  LEU B 787     13.826 -12.847  99.940  1.00145.19           C
ANISOU12359 CG  LEU B 787    15526  19637  20002  -8361    431   2275      C
ATOM  12360 CD1 LEU B 787     14.296 -14.300  99.991  1.00144.41           C
ANISOU12360 CD1 LEU B 787    15924  19519  19427  -8465    833   2269      C
ATOM  12361 CD2 LEU B 787     14.820 -11.949  99.154  1.00143.63           C
ANISOU12361 CD2 LEU B 787    15249  19432  19893  -8356    -41   2445      C
ATOM  12362 N   MET B 788     10.849 -11.109 101.421  1.00171.22           N
ANISOU12362 N   MET B 788    17717  23007  24333  -8019    425   1856      N
ATOM  12363 CA  MET B 788     10.781 -10.088 102.452  1.00172.74           C
ANISOU12363 CA  MET B 788    17706  23129  24799  -7570    372   1587      C
ATOM  12364 C   MET B 788     10.362 -10.774 103.734  1.00174.37           C
ANISOU12364 C   MET B 788    18055  23480  24719  -7441    953   1329      C
ATOM  12365 O   MET B 788     10.988 -10.627 104.785  1.00174.05           O
ANISOU12365 O   MET B 788    18256  23413  24461   7120   1109   1143      O
ATOM  12366 CB  MET B 788      9.719  -9.046 102.083  1.00176.05           C
ANISOU12366 CB  MET B 788    17512  23527  25852  -7515     23   1538      C
ATOM  12367 CG  MET B 788     10.211  -7.889 101.227  1.00175.58           C
ANISOU12367 CG  MET B 788    17292  23245  26175  -7476   -638   1744      C
ATOM  12368 SD  MET B 788     10.751  -6.458 102.191  1.00176.75           S
ANISOU12368 SD  MET B 788    17367  23113  26677  -6922   -907   1456      S
ATOM  12369 CE  MET B 788     12.242  -7.067 102.974  1.00172.91           C
ANISOU12369 CE  MET B 788    17503  22647  25544  -6809   -607   1395      C
ATOM  12370 N   ILE B 789      9.302 -11.561 103.603  1.00170.25           N
ANISOU12370 N   ILE B 789    17389  23135  24163  -7747   1261   1344      N
ATOM  12371 CA  ILE B 789      8.671 -12.265 104.706  1.00172.84           C
ANISOU12371 CA  ILE B 789    17786  23655  24231  -7749   1834   1151      C
ATOM  12372 C   ILE B 789      9.600 -13.117 105.572  1.00171.23           C
ANISOU12372 C   ILE B 789    18217  23409  23434  -7662   2185   1167      C
ATOM  12373 O   ILE B 789      9.544 -13.037 106.797  1.00173.16           O
ANISOU12373 O   ILE B 789    18535  23768  23490  -7420   2486    945      O
ATOM  12374 CB  ILE B 789      7.527 -13.133 104.169  1.00175.18           C
ANISOU12374 CB  ILE B 789    17883  24127  24550  -8228   2060   1257      C
ATOM  12375 CG1 ILE B 789      6.698 -12.324 103.162  1.00176.83           C
ANISOU12375 CG1 ILE B 789    17471  24378  25339  -8327   1619   1306      C
ATOM  12376 CG2 ILE B 789      6.676 -13.680 105.309  1.00179.04           C
ANISOU12376 CG2 ILE B 789    18308  24871  24849  -8272   2641   1057      C
```

FIG. 13 Continued

```
ATOM   12377  CD1  ILE B 789       6.478 -10.867 103.553  1.00178.75           C
ANISOU12377  CD1  ILE B 789    17244  24576  26096  -7856    139   1065        C
ATOM   12378  N    ALA B 790      10.449 -13.929 104.952  1.00134.10           N
ANISOU12378  N    ALA B 790    13966  18556  18429  -7846   2140   1418        N
ATOM   12379  CA   ALA B 790      11.342 -14.797 105.728  1.00133.11           C
ANISOU12379  CA   ALA B 790    14442  18355  17777  -7737   2428   1466        C
ATOM   12380  C    ALA B 790      12.707 -14.204 106.156  1.00130.64           C
ANISOU12380  C    ALA B 790    14367  17932  17338  -7320   2184   1425        C
ATOM   12381  O    ALA B 790      13.625 -14.935 106.520  1.00129.51           O
ANISOU12381  O    ALA B 790    14711  17702  16793  -7229   2306   1524        O
ATOM   12382  CB   ALA B 790      11.497 -16.167 105.062  1.00132.40           C
ANISOU12382  CB   ALA B 790    14758  18146  17403  -8109   2596   1701        C
ATOM   12383  N    PHE B 791      12.840 -12.886 106.087  1.00142.51           N
ANISOU12383  N    PHE B 791    15518  19420  19210  -7078    182   1288        N
ATOM   12384  CA   PHE B 791      13.983 -12.214 106.705  1.00141.21           C
ANISOU12384  CA   PHE B 791    15521  19183  18948  -6699   1602   1188        C
ATOM   12385  C    PHE B 791      13.529 -10.870 107.261  1.00143.38           C
ANISOU12385  C    PHE B 791    15390  19478  19612  -6418   1420    880        C
ATOM   12386  O    PHE B 791      14.204  -9.843 107.180  1.00142.52           O
ANISOU12386  O    PHE B 791    15185  19234  19733  -6205   1014    814        O
ATOM   12387  CB   PHE B 791      15.257 -12.191 105.852  1.00137.81           C
ANISOU12387  CB   PHE B 791    15280  18621  18461  -6713   1255   1405        C
ATOM   12388  CG   PHE B 791      16.391 -13.082 106.406  1.00136.70           C
ANISOU12388  CG   PHE B 791    15660  18463  17817  -6570   1434   1483        C
ATOM   12389  CD1  PHE B 791      16.174 -14.458 106.520  1.00137.34           C
ANISOU12389  CD1  PHE B 791    16104  18531  17548  -6736   1820   1607        C
ATOM   12390  CD2  PHE B 791      17.572 -12.545 106.843  1.00135.60           C
ANISOU12390  CD2  PHE B 791    15643  18304  17577  -6267   1192   1436        C
ATOM   12391  CE1  PHE B 791      17.175 -15.278 107.045  1.00137.00           C
ANISOU12391  CE1  PHE B 791    16540  18427  17087  -6558   1942   1697        C
ATOM   12392  CE2  PHE B 791      18.574 -13.360 107.359  1.00135.15           C
ANISOU12392  CE2  PHE B 791    16019  18246  17084  -6101   1319   1516        C
ATOM   12393  CZ   PHE B 791      18.375 -14.724 107.462  1.00135.90           C
ANISOU12393  CZ   PHE B 791    16478  18302  16857  -6223   1685   1653        C
ATOM   12394  N    LEU B 792      12.336 -10.974 107.839  1.00115.04           N
ANISOU12394  N    LEU B 792    11566  16063  16083  -6444   1760    682        N
ATOM   12395  CA   LEU B 792      11.586  -9.950 108.533  1.00118.60           C
ANISOU12395  CA   LEU B 792    11602  16596  16866  -6175   1761    300        C
ATOM   12396  C    LEU B 792      10.674 -10.836 109.366  1.00121.86           C
ANISOU12396  C    LEU B 792    12049  17307  16944  -6311   2371    192        C
ATOM   12397  O    LEU B 792       9.518 -10.513 109.644  1.00125.70           O
ANISOU12397  O    LEU B 792    12085  17985  17690  -6298   2563    -54        O
ATOM   12398  CB   LEU B 792      10.785  -9.088 107.564  1.00119.66           C
ANISOU12398  CB   LEU B 792    11169  16627  17670  -6230   1391    301        C
ATOM   12399  CG   LEU B 792      11.385  -7.751 107.087  1.00118.82           C
ANISOU12399  CG   LEU B 792    10891  16224  18030  -6006    770    282        C
ATOM   12400  CD1  LEU B 792      11.255  -6.690 108.166  1.00122.22           C
ANISOU12400  CD1  LEU B 792    11145  16614  18680  -5561    740   -192        C
ATOM   12401  CD2  LEU B 792      12.839  -7.822 106.583  1.00114.60           C
ANISOU12401  CD2  LEU B 792    10757  15521  17264  -6069    465    567        C
ATOM   12402  N    ILE B 793      11.232 -12.005 109.684  1.00121.47           N
ANISOU12402  N    ILE B 793    12537  17287  16329  -6466   2657    413        N
ATOM   12403  CA   ILE B 793      10.657 -13.026 110.559  1.00124.51           C
ANISOU12403  CA   ILE B 793    13141  17915  16254   6647   3233    416        C
ATOM   12404  C    ILE B 793      11.870 -13.502 111.353  1.00123.30           C
ANISOU12404  C    ILE B 793    13604  17704  15540  -6466   3285    515        C
ATOM   12405  O    ILE B 793      11.828 -13.634 112.576  1.00126.33           O
ANISOU12405  O    ILE B 793    14175  18304  15519  -6345   3598    362        O
ATOM   12406  CB   ILE B 793      10.002 -14.204 109.786  1.00124.55           C
ANISOU12406  CB   ILE B 793    13203  17911  16210  -7147   3453    720        C
ATOM   12407  CG1  ILE B 793       8.502 -13.957 109.608  1.00128.27           C
ANISOU12407  CG1  ILE B 793    13057  18625  17053  -7350   3629    557        C
ATOM   12408  CG2  ILE B 793      10.234 -15.534 110.493  1.00125.78           C
ANISOU12408  CG2  ILE B 793    13947  18093  15751  -7339   3880    928        C
ATOM   12409  CD1  ILE B 793       7.890 -13.104 110.685  1.00132.47           C
ANISOU12409  CD1  ILE B 793    13213  19446  17672  -7047   3833    126        C
ATOM   12410  N    ALA B 794      12.967 -13.730 110.642  1.00117.80           N
ANISOU12410  N    ALA B 794    13196  16748  14812  -6444   2961    766        N
ATOM   12411  CA   ALA B 794      14.240 -14.028 111.281  1.00116.64           C
```

FIG. 13 Continued

```
ANISOU12411 CA  ALA B 794    13552  16536  14228  -6207   2895    854       C
ATOM  12412 C   ALA B 794    14.862 -12.691 111.631  1.00116.14             C
ANISOU12412 C   ALA B 794    13296  16471  14360  -5833   2526    575       C
ATOM  12413 O   ALA B 794    16.083 -12.529 111.637  1.00113.99             O
ANISOU12413 O   ALA B 794    13254  16090  13968  -5640   2232    649       O
ATOM  12414 CB  ALA B 794    15.148 -14.804 110.362  1.00113.24             C
ANISOU12414 CB  ALA B 794    13441  15864  13721  -6314   2716   1188       C
ATOM  12415 N   GLN B 795    13.991 -11.722 111.877  1.00119.53             N
ANISOU12415 N   GLN B 795    13271  17009  15134  -5740   2528    239       N
ATOM  12416 CA  GLN B 795    14.410 -10.413 112.317  1.00120.21             C
ANISOU12416 CA  GLN B 795    13174  17057  15443  -5391   2204    -97       C
ATOM  12417 C   GLN B 795    13.541 -10.091 113.500  1.00125.16             C
ANISOU12417 C   GLN B 795    13642  17969  15942  -5249   2569   -512       C
ATOM  12418 O   GLN B 795    13.826  -9.201 114.299  1.00127.24             O
ANISOU12418 O   GLN B 795    13867  18280  16198  -4940   2452   -835       O
ATOM  12419 CB  GLN B 795    14.241  -9.379 111.227  1.00118.74             C
ANISOU12419 CB  GLN B 795    12540  16635  15940  -5388   1740   -120       C
ATOM  12420 CG  GLN B 795    15.253  -8.269 111.368  1.00117.95             C
ANISOU12420 CG  GLN B 795    12449  16353  16013  -5111   1263   -274       C
ATOM  12421 CD  GLN B 795    16.688  -8.783 111.317  1.00114.82             C
ANISOU12421 CD  GLN B 795    12491  15912  15223  -5107   1107     -4       C
ATOM  12422 OE1 GLN B 795    17.642  -8.006 111.437  1.00114.21             O
ANISOU12422 OE1 GLN B 795    12448  15723  15222  -4934    725    -85       O
ATOM  12423 NE2 GLN B 795    16.846 -10.094 111.125  1.00113.30             N
ANISOU12423 NE2 GLN B 795    12618  15795  14637  -5298   1388    311       N
ATOM  12424 N   LEU B 796    12.442 -10.821 113.581  1.00138.52             N
ANISOU12424 N   LEU B 796    15221  19873  17536  -5504   3024   -468       N
ATOM  12425 CA  LEU B 796    11.633 -10.784 114.767  1.00143.79             C
ANISOU12425 CA  LEU B 796    15787  20914  17933  -5441   3491   -816       C
ATOM  12426 C   LEU B 796    12.348 -11.772 115.649  1.00144.22             C
ANISOU12426 C   LEU B 796    16475  21102  17220  -5499   3745   -597       C
ATOM  12427 O   LEU B 796    13.104 -11.387 116.537  1.00145.26             O
ANISOU12427 O   LEU B 796    16856  21311  17023  -5230   3652   -782       O
ATOM  12428 CB  LEU B 796    10.207 -11.235 114.482  1.00146.56             C
ANISOU12428 CB  LEU B 796    15748  21477  18463  -5748   3883   -810       C
ATOM  12429 CG  LEU B 796     9.244 -10.051 114.450  1.00149.92             C
ANISOU12429 CG  LEU B 796    15482  21992  19490  -5525   3818  -1294       C
ATOM  12430 CD1 LEU B 796     8.292 -10.093 115.640  1.00156.35             C
ANISOU12430 CD1 LEU B 796    16091  23305  20011  -5500   4407  -1684       C
ATOM  12431 CD2 LEU B 796    10.018  -8.713 114.375  1.00148.57             C
ANISOU12431 CD2 LEU B 796    15226  21516  19707  -5097   3261  -1554       C
ATOM  12432 N   ILE B 797    12.174 -13.051 115.343  1.00136.55             N
ANISOU12432 N   ILE B 797    15786  20112  15984  -5854   4003   -178       N
ATOM  12433 CA  ILE B 797    12.789 -14.104 116.136  1.00137.60             C
ANISOU12433 CA  ILE B 797    16551  20314  15417  -5929   4226    105       C
ATOM  12434 C   ILE B 797    14.246 -13.790 116.524  1.00135.55             C
ANISOU12434 C   ILE B 797    16659  19927  14918  -5582   3839    122       C
ATOM  12435 O   ILE B 797    14.708 -14.187 117.587  1.00138.12             O
ANISOU12435 O   ILE B 797    17404  20428  14647  -5501   3981    172       O
ATOM  12436 CB  ILE B 797    12.660 -15.494 115.447  1.00136.28             C
ANISOU12436 CB  ILE B 797    16691  19949  15140  -6328   4389    600       C
ATOM  12437 CG1 ILE B 797    12.667 -16.618 116.491  1.00140.16             C
ANISOU12437 CG1 ILE B 797    17733  20596  14926  -6507   4797    853       C
ATOM  12438 CG2 ILE B 797    13.733 -15.686 114.385  1.00130.99             C
ANISOU12438 CG2 ILE B 797    16215  18873  14684  -6253   3939    870       C
ATOM  12439 CD1 ILE B 797    12.476 -18.000 115.924  1.00139.98             C
ANISOU12439 CD1 ILE B 797    18055  20325  14807  -6912   4971   1312       C
ATOM  12440 N   ALA B 798    14.966 -13.059 115.686  1.00129.80             N
ANISOU12440 N   ALA B 798    15759  18924  14635  -5399   3337     94       N
ATOM  12441 CA  ALA B 798    16.351 -12.736 116.020  1.00128.22             C
ANISOU12441 CA  ALA B 798    15841  18637  14238  -5104   2958    105       C
ATOM  12442 C   ALA B 798    16.476 -11.450 116.832  1.00130.57             C
ANISOU12442 C   ALA B 798    15938  19086  14586  -4798   2790   -392       C
ATOM  12443 O   ALA B 798    17.573 -10.879 116.944  1.00129.20             O
ANISOU12443 O   ALA B 798    15865  18816  14410  -4568   2379   -456       O
ATOM  12444 CB  ALA B 798    17.215 -12.680 114.769  1.00123.22             C
ANISOU12444 CB  ALA B 798    15170  17675  13974  -5101   2517    352       C
ATOM  12445 N   THR B 799    15.349 -11.001 117.386  1.00131.31             N
ANISOU12445 N   THR B 799    15730  19424  14738  -4803   3111   -770       N
```

FIG. 13 Continued

```
ATOM  12446  CA   THR B 799      15.315  -9.821 118.253  1.00134.75           C
ANISOU12446  CA   THR B 799    15982  20017  15200  4506   3027   1335        C
ATOM  12447  C    THR B 799      14.440  10.083 119.488  1.00140.79           C
ANISOU12447  C    THR B 799    16785  21258  15448 -4550   3601  -1616        C
ATOM  12448  O    THR B 799      14.767  -9.637 120.585  1.00144.35           O
ANISOU12448  O    THR B 799    17396  21955  15496 -4348   3626  -1962        O
ATOM  12449  CB   THR B 799      14.938  -8.531 117.497  1.00133.95           C
ANISOU12449  CB   THR B 799    15328  19655  15910 -4357   2679  -1660        C
ATOM  12450  OG1  THR B 799      15.899  -8.299 116.465  1.00128.96           O
ANISOU12450  OG1  THR B 799    14727  18644  15626 -4359   2147  -1363        O
ATOM  12451  CG2  THR B 799      14.970  -7.344 118.428  1.00138.07           C
ANISOU12451  CG2  THR B 799    15719  20274  16468 -4028   2574  -2282        C
ATOM  12452  N    LEU B 800      13.352 -10.835 119.308  1.00144.71           N
ANISOU12452  N    LEU B 800    17144  21918  15920 -4851   4064  -1461        N
ATOM  12453  CA   LEU B 800      12.531 -11.312 120.426  1.00150.71           C
ANISOU12453  CA   LEU B 800    17974  23185  16103 -5003   4674  -1612        C
ATOM  12454  C    LEU B 800      13.460 -12.108 121.333  1.00151.79           C
ANISOU12454  C    LEU B 800    18797  23460  15416 -5034   4719  -1308        C
ATOM  12455  O    LEU B 800      13.124 -12.434 122.476  1.00157.23           O
ANISOU12455  O    LEU B 800    19690  24598  15450 -5128   5138  -1410        O
ATOM  12456  CB   LEU B 800      11.452 -12.278 119.932  1.00151.42           C
ANISOU12456  CB   LEU B 800    17918  23363  16253 -5430   5105  -1301        C
ATOM  12457  CG   LEU B 800      10.196 -11.825 119.194  1.00152.26           C
ANISOU12457  CG   LEU B 800    17323  23495  17035 -5518   5228  -1533        C
ATOM  12458  CD1  LEU B 800       9.929 -12.750 118.015  1.00148.62           C
ANISOU12458  CD1  LEU B 800    16870  22763  16835 -5898   5202  -1010        C
ATOM  12459  CD2  LEU B 800       8.997 -11.783 120.136  1.00159.43           C
ANISOU12459  CD2  LEU B 800    17910  24982  17683 -5619   5849  -1920        C
ATOM  12460  N    ILE B 801      14.614 -12.460 120.768  1.00144.80           N
ANISOU12460  N    ILE B 801    18249  22200  14567 -4969   4282   -906        N
ATOM  12461  CA   ILE B 801      15.654 -13.227 121.440  1.00145.30           C
ANISOU12461  CA   ILE B 801    18945  22299  13965 -4940   4192   -550        C
ATOM  12462  C    ILE B 801      16.784 -12.279 121.745  1.00144.27           C
ANISOU12462  C    ILE B 801    18859  22109  13848 -4568   3685   -819        C
ATOM  12463  O    ILE B 801      17.455 -12.400 122.758  1.00147.16           O
ANISOU12463  O    ILE B 801    19611  22703  13600 -4455   3631   -818        O
ATOM  12464  CB   ILE B 801      16.188 -14.382 120.537  1.00141.13           C
ANISOU12464  CB   ILE B 801    18738  21379  13507 -5107   4057     84        C
ATOM  12465  CG1  ILE B 801      17.005 -15.387 121.350  1.00143.33           C
ANISOU12465  CG1  ILE B 801    19682  21714  13064 -5103   4063    499        C
ATOM  12466  CG2  ILE B 801      17.012 -13.844 119.373  1.00135.23           C
ANISOU12466  CG2  ILE B 801    17787  20224  13369 -4921   3513    115        C
ATOM  12467  CD1  ILE B 801      17.209 -16.699 120.637  1.00141.26           C
ANISOU12467  CD1  ILE B 801    19761  21089  12822 -5308   4085   1082        C
ATOM  12468  N    ALA B 802      16.977 -11.315 120.858  1.00159.11           N
ANISOU12468  N    ALA B 802    20337  23687  16431 -4410   3293  -1035        N
ATOM  12469  CA   ALA B 802      18.058 -10.361 121.000  1.00158.04           C
ANISOU12469  CA   ALA B 802    20203  23438  16406 -4114   2767  -1273        C
ATOM  12470  C    ALA B 802      17.745  -9.356 122.080  1.00163.19           C
ANISOU12470  C    ALA B 802    20729  24391  16885 -3924   2843  -1919        C
ATOM  12471  O    ALA B 802      18.440  -8.353 122.196  1.00163.09           O
ANISOU12471  O    ALA B 802    20639  24261  17069 -3696   2411  -2241        O
ATOM  12472  CB   ALA B 802      18.314  -9.657 119.693  1.00153.14           C
ANISOU12472  CB   ALA B 802    19211  22394  16583 -4071   2332  -1258        C
ATOM  12473  N    VAL B 803      16.683  -9.619 122.840  1.00149.89           N
ANISOU12473  N    VAL B 803    19010  23099  14843 -4039   3402  -2127        N
ATOM  12474  CA   VAL B 803      16.276  -8.790 123.977  1.00156.01           C
ANISOU12474  CA   VAL B 803    19681  24256  15338 -3872   3591  -2794        C
ATOM  12475  C    VAL B 803      14.912  -9.223 124.461  1.00160.83           C
ANISOU12475  C    VAL B 803    20123  25294  15689 -4078   4285  -2938        C
ATOM  12476  O    VAL B 803      14.455 -10.308 124.110  1.00159.76           O
ANISOU12476  O    VAL B 803    20088  25183  15429 -4389   4597  -2441        O
ATOM  12477  CB   VAL B 803      16.186  -7.309 123.635  1.00155.96           C
ANISOU12477  CB   VAL B 803    19212  23986  16060 -3589   3243  -3393        C
ATOM  12478  CG1  VAL B 803      17.496  -6.608 123.940  1.00155.34           C
ANISOU12478  CG1  VAL B 803    19361  23754  15908 -3371   2667  -3548        C
ATOM  12479  CG2  VAL B 803      15.738  -7.117 122.186  1.00151.13           C
ANISOU12479  CG2  VAL B 803    18167  22921  16337 -3650   3065  -3193        C
ATOM  12480  N    TYR B 804      14.268  -8.365 125.253  1.00166.08           N
```

FIG. 13 Continued

```
ANISOU12480  N   TYR B 804    20515  26297  16290  -3913   4526  -3644       N
ATOM  12481  CA  TYR B 804      12.939   -8.627 125.823  1.00171.94          C
ANISOU12481  CA  TYR B 804    21004  27554  16769  -4087   5228  -3903       C
ATOM  12482  C   TYR B 804      12.768  -10.036 126.410  1.00174.29          C
ANISOU12482  C   TYR B 804    21759  28248  16215  -4495   5706  -3349       C
ATOM  12483  O   TYR B 804      11.840  -10.294 127.175  1.00180.51          O
ANISOU12483  O   TYR B 804    22448  29593  16543  -4688   6314  -3555       O
ATOM  12484  CB  TYR B 804      11.831   -8.322 124.808  1.00170.54          C
ANISOU12484  CB  TYR B 804    20166  27173  17458  -4107   5348  -4021       C
ATOM  12485  CG  TYR B 804      10.573   -9.138 125.024  1.00174.57          C
ANISOU12485  CG  TYR B 804    20474  28148  17707  -4461   6055  -3915       C
ATOM  12486  CD1 TYR B 804       9.466   -8.599 125.670  1.00181.57          C
ANISOU12486  CD1 TYR B 804    20879  29528  18580  -4382   6551  -4571       C
ATOM  12487  CD2 TYR B 804      10.494  -10.457 124.585  1.00171.94          C
ANISOU12487  CD2 TYR B 804    20421  27763  17147  -4888   6234  -3176       C
ATOM  12488  CE1 TYR B 804       8.309   -9.355 125.871  1.00185.79          C
ANISOU12488  CE1 TYR B 804    21180  30547  18865  -4754   7221  -4465       C
ATOM  12489  CE2 TYR B 804       9.347  -11.219 124.779  1.00176.06          C
ANISOU12489  CE2 TYR B 804    20763  28701  17432  -5280   6871  -3053       C
ATOM  12490  CZ  TYR B 804       8.258  -10.666 125.420  1.00182.94          C
ANISOU12490  CZ  TYR B 804    21119  30112  18276  -5230   7369  -3683       C
ATOM  12491  OH  TYR B 804       7.126  -11.430 125.608  1.00187.45          O
ANISOU12491  OH  TYR B 804    21468  31148  18606  -5664   8015  -3548       O
ATOM  12492  N   ALA B 805      13.674  -12.169 126.060  1.00266.71          N
ANISOU12492  N   ALA B 805    33961  39662  27715  -4628   5425  -2650       N
ATOM  12493  CA  ALA B 805      13.619  -12.314 126.527  1.00268.87          C
ANISOU12493  CA  ALA B 805    34736  40166  27255  -5004   5776  -2042       C
ATOM  12494  C   ALA B 805      14.939  -13.019 126.245  1.00264.43          C
ANISOU12494  C   ALA B 805    34735  39212  26524  -4963   5291  -1414       C
ATOM  12495  O   ALA B 805      15.887  -12.405 125.747  1.00259.97          O
ANISOU12495  O   ALA B 805    34132  38283  26361  -4662   4722  -1488       O
ATOM  12496  CB  ALA B 805      12.465  -13.057 125.867  1.00268.66          C
ANISOU12496  CB  ALA B 805    34441  40127  27511  -5386   6224  -1761       C
ATOM  12497  N   ASN B 806      14.986  -14.309 126.574  1.00295.11          N
ANISOU12497  N   ASN B 806    39126  43173  29828  -5271   5517   -798       N
ATOM  12498  CA  ASN B 806      16.180  -15.132 126.406  1.00292.22          C
ANISOU12498  CA  ASN B 806    39318  42457  29256  -5216   5104   -177       C
ATOM  12499  C   ASN B 806      15.990  -16.495 127.073  1.00296.86          C
ANISOU12499  C   ASN B 806    40483  43216  29095  -5581   5450    429       C
ATOM  12500  O   ASN B 806      15.781  -16.567 128.287  1.00303.47          O
ANISOU12500  O   ASN B 806    41569  44586  29149  -5703   5734    353       O
ATOM  12501  CB  ASN B 806      17.394  -14.417 126.997  1.00292.39          C
ANISOU12501  CB  ASN B 806    39522  42545  29029  -4836   4594   -406       C
ATOM  12502  CG  ASN B 806      17.033  -13.538 128.189  1.00298.62          C
ANISOU12502  CG  ASN B 806    40209  43923  29331  -4760   4811  -1050       C
ATOM  12503  OD1 ASN B 806      17.271  -12.330 128.178  1.00297.86          O
ANISOU12503  OD1 ASN B 806    39786  43812  29574  -4467   4538  -1647       O
ATOM  12504  ND2 ASN B 806      16.450  -14.142 129.217  1.00305.33          N
ANISOU12504  ND2 ASN B 806    41348  45291  29373  -5046   5307   -942       N
ATOM  12505  N   TRP B 807      16.055  -17.574 126.293  1.00287.22          N
ANISOU12505  N   TRP B 807    39496  41542  28095  -5775   5422   1028       N
ATOM  12506  CA  TRP B 807      15.839  -18.910 126.861  1.00292.04          C
ANISOU12506  CA  TRP B 807    40687  42209  28066  -6155   5723   1651       C
ATOM  12507  C   TRP B 807      17.092  -19.704 127.260  1.00292.88          C
ANISOU12507  C   TRP B 807    41485  42075  27722  -5988   5302   2221       C
ATOM  12508  O   TRP B 807      16.988  -20.654 128.044  1.00298.59          O
ANISOU12508  O   TRP B 807    42752  42932  27765  -6267   5507   2707       O
ATOM  12509  CB  TRP B 807      14.848  -19.753 126.033  1.00291.19          C
ANISOU12509  CB  TRP B 807    40471  41838  28330  -6596   6094   1954       C
ATOM  12510  CG  TRP B 807      15.122  -19.857 124.558  1.00283.89          C
ANISOU12510  CG  TRP B 807    39332  40285  28247  -6483   5773   2052       C
ATOM  12511  CD1 TRP B 807      15.922  -19.047 123.805  1.00277.83          C
ANISOU12511  CD1 TRP B 807    38280  39245  28038  -6059   5273   1787       C
ATOM  12512  CD2 TRP B 807      14.551  -20.810 123.652  1.00282.48          C
ANISOU12512  CD2 TRP B 807    39195  39716  28418  -6849   5949   2421       C
ATOM  12513  NE1 TRP B 807      15.901  -19.451 122.491  1.00272.81          N
ANISOU12513  NE1 TRP B 807    37515  38107  28032  -6133   5140   1979       N
ATOM  12514  CE2 TRP B 807      15.065  -20.530 122.371  1.00275.50          C
ANISOU12514  CE2 TRP B 807    38056  38358  28263  -6603   5541   2345       C
```

FIG. 13 Continued

```
ATOM   12515  CE3 TRP B 807      13.661 -21.880 123.804  1.00286.90           C
ANISOU 12515  CE3 TRP B 807    39996  40287  28725  -7397   6407   2810       C
ATOM   12516  CZ2 TRP B 807      14.720 -21.280 121.249  1.00272.83           C
ANISOU 12516  CZ2 TRP B 807    37705  37577  28381  -6865   5577   2606       C
ATOM   12517  CZ3 TRP B 807      13.321 -22.623 122.689  1.00284.17           C
ANISOU 12517  CZ3 TRP B 807    39638  39454  28878  -7663   6422   3071       C
ATOM   12518  CH2 TRP B 807      13.849 -22.320 121.428  1.00277.19           C
ANISOU 12518  CH2 TRP B 807    38506  38121  28694  -7385   6010   2950       C
ATOM   12519  N   GLU B 808      18.259 -19.332 126.731  1.00227.77           N
ANISOU 12519  N   GLU B 808    33207  33485  19849  -5550   4712   2184       N
ATOM   12520  CA  GLU B 808      19.506 -19.989 127.147  1.00229.09           C
ANISOU 12520  CA  GLU B 808    33950  33472  19621  -5317   4267   2669       C
ATOM   12521  C   GLU B 808      20.158 -19.262 128.327  1.00232.96           C
ANISOU 12521  C   GLU B 808    34560  34462  19491  -5077   4029   2399       C
ATOM   12522  O   GLU B 808      20.164 -18.032 128.392  1.00231.51           O
ANISOU 12522  O   GLU B 808    33936  34527  19498  -4889   3939   1763       O
ATOM   12523  CB  GLU B 808      20.502 -20.162 125.990  1.00222.66           C
ANISOU 12523  CB  GLU B 808    33071  32060  19471  -4991   3764   2841       C
ATOM   12524  CG  GLU B 808      21.933 -20.573 126.421  1.00224.02           C
ANISOU 12524  CG  GLU B 808    33684  32110  19324  -4623   3217   3205       C
ATOM   12525  CD  GLU B 808      22.038 -21.995 126.979  1.00229.44           C
ANISOU 12525  CD  GLU B 808    35080  32617  19479  -4776   3276   3924       C
ATOM   12526  OE1 GLU B 808      21.002 -22.685 127.075  1.00232.35           O
ANISOU 12526  OE1 GLU B 808    35638  32964  19682  -5221   3761   4159       O
ATOM   12527  OE2 GLU B 808      23.164 -22.424 127.318  1.00231.22           O
ANISOU 12527  OE2 GLU B 808    35669  32712  19473  -4456   2814   4270       O
ATOM   12528  N   PHE B 809      20.694 -20.044 129.259  1.00185.47           N
ANISOU 12528  N   PHE B 809    29165  28572  12732  -5098   3905   2894       N
ATOM   12529  CA  PHE B 809      21.311 -19.515 130.465  1.00190.29           C
ANISOU 12529  CA  PHE B 809    29977  29699  12624  -4928   3668   2717       C
ATOM   12530  C   PHE B 809      22.817 -19.329 130.243  1.00187.33           C
ANISOU 12530  C   PHE B 809    29656  29069  12450  -4443   2932   2810       C
ATOM   12531  O   PHE B 809      23.530 -18.836 131.119  1.00190.68           O
ANISOU 12531  O   PHE B 809    30209  29870  12370  -4252   2601   2654       O
ATOM   12532  CB  PHE B 809      20.953 -20.406 131.667  1.00198.90           C
ANISOU 12532  CB  PHE B 809    31687  31165  12720  -5280   3962   3204       C
ATOM   12533  CG  PHE B 809      19.478 -20.798 131.709  1.00201.76           C
ANISOU 12533  CG  PHE B 809    31980  31715  12965  -5821   4709   3227       C
ATOM   12534  CD1 PHE B 809      18.501 -19.865 132.042  1.00203.47           C
ANISOU 12534  CD1 PHE B 809    31723  32486  13101  -5983   5185   2540       C
ATOM   12535  CD2 PHE B 809      19.074 -22.092 131.392  1.00203.13           C
ANISOU 12535  CD2 PHE B 809    32531  31496  13152  -6164   4924   3912       C
ATOM   12536  CE1 PHE B 809      17.159 -20.219 132.066  1.00206.50           C
ANISOU 12536  CE1 PHE B 809    31965  33094  13401  -6476   5873   2547       C
ATOM   12537  CE2 PHE B 809      17.730 -22.448 131.417  1.00206.09           C
ANISOU 12537  CE2 PHE B 809    32603  32067  13433  -6708   5598   3938       C
ATOM   12538  CZ  PHE B 809      16.776 -21.511 131.753  1.00207.75           C
ANISOU 12538  CZ  PHE B 809    32492  32895  13549  -6864   6079   3260       C
ATOM   12539  N   ALA B 810      23.279 -19.743 129.061  1.00175.98           N
ANISOU 12539  N   ALA B 810    28103  27023  11738  -4268   2691   3052       N
ATOM   12540  CA  ALA B 810      24.626 -19.455 128.591  1.00172.28           C
ANISOU 12540  CA  ALA B 810    27505  26313  11640  -3817   2049   3047       C
ATOM   12541  C   ALA B 810      24.427 -18.135 127.876  1.00166.76           C
ANISOU 12541  C   ALA B 810    26132  25638  11591  -3741   2031   2358       C
ATOM   12542  O   ALA B 810      25.142 -17.799 126.941  1.00161.48           O
ANISOU 12542  O   ALA B 810    25147  24659  11548  -3499   1670   2273       O
ATOM   12543  CB  ALA B 810      25.120 -20.517 127.634  1.00169.32           C
ANISOU 12543  CB  ALA B 810    27294  25314  11728  -3687   1874   3574       C
ATOM   12544  N   LYS B 811      23.389 -17.432 128.333  1.00226.60           N
ANISOU 12544  N   LYS B 811    33500  33593  19003  -3973   2451   1884       N
ATOM   12545  CA  LYS B 811      22.961 -16.118 127.857  1.00223.09           C
ANISOU 12545  CA  LYS B 811    32446  33204  19113  -3930   2494   1187       C
ATOM   12546  C   LYS B 811      21.718 -15.681 128.652  1.00227.82           C
ANISOU 12546  C   LYS B 811    32948  34287  19327  -4192   3054    758       C
ATOM   12547  O   LYS B 811      21.287 -16.380 129.566  1.00233.68           O
ANISOU 12547  O   LYS B 811    34096  35361  19330  -4429   3389   1019       O
ATOM   12548  CB  LYS B 811      22.627 -16.136 126.358  1.00216.25           C
ANISOU 12548  CB  LYS B 811    31180  31834  19153  -3968   2544   1210       C
ATOM   12549  CG  LYS B 811      21.135 -16.353 126.050  1.00216.50           C
```

FIG. 13 Continued

```
ANISOU12549  CG  LYS B 811    31024  31879  19358  -4328   3161   1134         C
ATOM  12550  CD  LYS B 811    20.791 -16.179 124.566  1.00210.05              C
ANISOU12550  CD  LYS B 811    29755  30620  19433  -4368   3150   1080         C
ATOM  12551  CE  LYS B 811    19.271 -16.107 124.334  1.00210.86              C
ANISOU12551  CE  LYS B 811    29541  30831  19745  -4698   3710    871         C
ATOM  12552  NZ  LYS B 811    18.488 -17.252 124.905  1.00215.63              N
ANISOU12552  NZ  LYS B 811    30527  31595  19809  -5069   4216   1259         N
ATOM  12553  N   ILE B 812    21.180 -14.514 128.293  1.00200.66              N
ANISOU12553  N   ILE B 812    28960  30883  16397  -4139   3134    105         N
ATOM  12554  CA  ILE B 812    19.948 -13.901 128.829  1.00204.64              C
ANISOU12554  CA  ILE B 812    29194  31803  16759  -4309   3660   -451         C
ATOM  12555  C   ILE B 812    20.012 -12.404 128.489  1.00202.32              C
ANISOU12555  C   ILE B 812    28368  31427  17080  -4048   3399  -1186         C
ATOM  12556  O   ILE B 812    20.316 -11.556 129.327  1.00206.06              O
ANISOU12556  O   ILE B 812    28846  32215  17234  -3893   3247  -1694         O
ATOM  12557  CB  ILE B 812    19.663 -14.169 130.343  1.00213.16              C
ANISOU12557  CB  ILE B 812    30676  33542  16773  -4481   3994   -497         C
ATOM  12558  CG1 ILE B 812    18.908 -15.491 130.530  1.00216.24              C
ANISOU12558  CG1 ILE B 812    31405  34024  16731  -4889   4507    105         C
ATOM  12559  CG2 ILE B 812    18.795 -13.068 130.943  1.00217.36              C
ANISOU12559  CG2 ILE B 812    30824  34539  17224  -4477   4348  -1335         C
ATOM  12560  CD1 ILE B 812    18.456 -15.755 131.961  1.00225.20              C
ANISOU12560  CD1 ILE B 812    32898  35863  16802  -5151   4921     82         C
ATOM  12561  N   ARG B 813    19.727 -12.102 127.230  1.00254.30              N
ANISOU12561  N   ARG B 813    34515  37558  24551  -4021   3323  -1223         N
ATOM  12562  CA  ARG B 813    19.860 -10.756 126.685  1.00251.54              C
ANISOU12562  CA  ARG B 813    33682  36981  24912  -3791   2988  -1782         C
ATOM  12563  C   ARG B 813    19.226  -9.638 127.501  1.00256.76              C
ANISOU12563  C   ARG B 813    34094  37991  25472  -3690   3176  -2584         C
ATOM  12564  O   ARG B 813    18.616  -9.876 128.540  1.00262.87              O
ANISOU12564  O   ARG B 813    35034  39278  25566  -3811   3631  -2762         O
ATOM  12565  CB  ARG B 813    19.313 -10.729 125.262  1.00245.83              C
ANISOU12565  CB  ARG B 813    32535  35802  25067  -3866   3011  -1653         C
ATOM  12566  CG  ARG B 813    19.554  -9.432 124.528  1.00242.65              C
ANISOU12566  CG  ARG B 813    31677  35065  25454  -3660   2580  -2074         C
ATOM  12567  CD  ARG B 813    21.017  -9.216 124.184  1.00239.24              C
ANISOU12567  CD  ARG B 813    31376  34378  25146  -3500   1943  -1874         C
ATOM  12568  NE  ARG B 813    21.153  -8.236 123.111  1.00235.18              N
ANISOU12568  NE  ARG B 813    30423  33446  25490  -3425   1564  -2058         N
ATOM  12569  CZ  ARG B 813    20.932  -6.934 123.262  1.00237.11              C
ANISOU12569  CZ  ARG B 813    30364  33619  26109  -3285   1386  -2660         C
ATOM  12570  NH1 ARG B 813    20.572  -6.455 124.442  1.00242.99              N
ANISOU12570  NH1 ARG B 813    31181  34711  26435  -3183   1579  -3201         N
ATOM  12571  NH2 ARG B 813    21.072  -6.110 122.233  1.00233.69              N
ANISOU12571  NH2 ARG B 813    29573  32760  26460  -3254   1009  -2726         N
ATOM  12572  N   GLY B 814    19.376  -8.412 127.006  1.00165.77              N
ANISOU12572  N   GLY B 814    22173  26175  14637  -3475   2821  -3073         N
ATOM  12573  CA  GLY B 814    18.838  -7.253 127.683  1.00170.84              C
ANISOU12573  CA  GLY B 814    22558  27036  15318  -3315   2928  -3904         C
ATOM  12574  C   GLY B 814    18.484  -6.024 126.857  1.00168.76              C
ANISOU12574  C   GLY B 814    21748  26330  16043  -3128   2683  -4386         C
ATOM  12575  O   GLY B 814    19.217  -5.611 125.956  1.00163.75              O
ANISOU12575  O   GLY B 814    21001  25209  16010  -3055   2148  -4211         O
ATOM  12576  N   ILE B 815    17.334  -5.445 127.209  1.00190.11              N
ANISOU12576  N   ILE B 815    24108  29233  18892  -3053   3090  -4999         N
ATOM  12577  CA  ILE B 815    16.795  -4.193 126.654  1.00190.40              C
ANISOU12577  CA  ILE B 815    23613  28894  19836  -2820   2912  -5580         C
ATOM  12578  C   ILE B 815    16.095  -4.285 125.298  1.00185.54              C
ANISOU12578  C   ILE B 815    22557  27863  20076  -2890   2920  -5264         C
ATOM  12579  O   ILE B 815    16.552  -3.723 124.303  1.00181.04              O
ANISOU12579  O   ILE B 815    21814  26746  20229  -2822   2397  -5125         O
ATOM  12580  CB  ILE B 815    17.817  -3.047 126.891  1.00190.32              C
ANISOU12580  CB  ILE B 815    23651  28525  20138  -2595   2238  -5949         C
ATOM  12581  CG1 ILE B 815    18.245  -2.794 128.139  1.00196.89              C
ANISOU12581  CG1 ILE B 815    24837  29838  20133  -2513   2288  -6454         C
ATOM  12582  CG2 ILE B 815    17.213   1.780 126.112  1.00191.32              C
ANISOU12582  CG2 ILE B 815    23264  28189  21238  -2358   2034  -6506         C
ATOM  12583  CD1 ILE B 815    17.098  -2.400 129.063  1.00204.71              C
ANISOU12583  CD1 ILE B 815    25633  31287  20861   2396   2866   7226         C
```

FIG. 13 Continued

```
ATOM   12584  N   GLY B 816      14.961  -4.982 125.297  1.00229.64           N
ANISOU12584  N   GLY B 816    27958  33755  25540  -3062   3520  -5158        N
ATOM   12585  CA  GLY B 816      14.149   5.192 124.111  1.00226.06           C
ANISOU12585  CA  GLY B 816    27079  33021  25793  -3176   3598  -4867        C
ATOM   12586  C   GLY B 816      13.525  -3.958 123.503  1.00227.03           C
ANISOU12586  C   GLY B 816    26617  32772  26870  -2906   3364  -5369        C
ATOM   12587  O   GLY B 816      12.714  -3.285 124.134  1.00233.20           O
ANISOU12587  O   GLY B 816    27083  33781  27742  -2689   3643  -6060        O
ATOM   12588  N   TRP B 817      13.896  -3.673 122.260  1.00197.46           N
ANISOU12588  N   TRP B 817    22726  28459  23839  -2919   2849  -5013        N
ATOM   12589  CA  TRP B 817      13.350  -2.535 121.532  1.00198.17           C
ANISOU12589  CA  TRP B 817    22290  28108  24898  -2689   2530  -5353        C
ATOM   12590  C   TRP B 817      14.039  -1.222 121.905  1.00200.66           C
ANISOU12590  C   TRP B 817    22651  28090  25500  -2371   2020  -5900        C
ATOM   12591  O   TRP B 817      13.947  -0.237 121.176  1.00200.42           O
ANISOU12591  O   TRP B 817    22308  27529  26312  -2204   1560  -6045        O
ATOM   12592  CB  TRP B 817      11.834  -2.449 121.748  1.00203.46           C
ANISOU12592  CB  TRP B 817    22437  29080  25787  -2598   3061  -5776        C
ATOM   12593  CG  TRP B 817      11.144  -3.765 121.538  1.00202.07           C
ANISOU12593  CG  TRP B 817    22242  29288  25247  -2969   3600  -5278        C
ATOM   12594  CD1 TRP B 817      10.891  -4.724 122.480  1.00204.99           C
ANISOU12594  CD1 TRP B 817    22875  30261  24750  -3185   4211  -5224        C
ATOM   12595  CD2 TRP B 817      10.632  -4.275 120.299  1.00197.88           C
ANISOU12595  CD2 TRP B 817    21440  28549  25196  -3212   3550  -4746        C
ATOM   12596  NE1 TRP B 817      10.250  -5.794 121.903  1.00202.91           N
ANISOU12596  NE1 TRP B 817    22523  30134  24438  -3553   4542  -4693        N
ATOM   12597  CE2 TRP B 817      10.077  -5.544 120.566  1.00198.50           C
ANISOU12597  CE2 TRP B 817    21633  29096  24693  -3571   4148  -4418        C
ATOM   12598  CE3 TRP B 817      10.585  -3.777 118.990  1.00194.12           C
ANISOU12598  CE3 TRP B 817    20651  27544  25562  -3190   3041  -4505        C
ATOM   12599  CZ2 TRP B 817       9.480  -6.324 119.569  1.00195.45           C
ANISOU12599  CZ2 TRP B 817    21052  28649  24562  -3902   4250  -3906        C
ATOM   12600  CZ3 TRP B 817       9.992  -4.553 118.001  1.00191.07           C
ANISOU12600  CZ3 TRP B 817    20066  27146  25385  -3511   3146  -3990        C
ATOM   12601  CH2 TRP B 817       9.448  -5.811 118.298  1.00191.73           C
ANISOU12601  CH2 TRP B 817    20265  27687  24896  -3859   3745  -3720        C
ATOM   12602  N   GLY B 818      14.734  -1.210 123.035  1.00167.96           N
ANISOU12602  N   GLY B 818    18917  24243  20656  -2313   2070  -6185        N
ATOM   12603  CA  GLY B 818      15.423  -0.010 123.473  1.00170.90           C
ANISOU12603  CA  GLY B 818    19377  24323  21234  -2056   1589  -6737        C
ATOM   12604  C   GLY B 818      16.878  -0.001 123.052  1.00165.81           C
ANISOU12604  C   GLY B 818    19087  23366  20549  -2200    983  -6268        C
ATOM   12605  O   GLY B 818      17.400   0.999 122.550  1.00165.20           O
ANISOU12605  O   GLY B 818    18919  22750  21100  -2110    390  -6383        O
ATOM   12606  N   TRP B 819      17.541  -1.124 123.285  1.00162.94           N
ANISOU12606  N   TRP B 819    19123  23347  19441  -2430   1131  -5736        N
ATOM   12607  CA  TRP B 819      18.923  -1.285 122.873  1.00158.26           C
ANISOU12607  CA  TRP B 819    18820  22547  18763  -2566    615  -5247        C
ATOM   12608  C   TRP B 819      19.014  -1.667 121.390  1.00151.57           C
ANISOU12608  C   TRP B 819    17793  21331  18464  -2764    407  -4563        C
ATOM   12609  O   TRP B 819      19.668  -0.989 120.585  1.00148.95           O
ANISOU12609  O   TRP B 819    17357  20551  18688   2797    149   4419        O
ATOM   12610  CB  TRP B 819      19.627  -2.329 123.740  1.00158.46           C
ANISOU12610  CB  TRP B 819    19337  23074  17795  -2679    815  -4963        C
ATOM   12611  CG  TRP B 819      20.769  -1.753 124.456  1.00160.72           C
ANISOU12611  CG  TRP B 819    19896  23393  17779  -2594    374  -5227        C
ATOM   12612  CD1 TRP B 819      21.151  -2.005 125.728  1.00165.17           C
ANISOU12612  CD1 TRP B 819    20828  24441  17489  -2559    504  -5455        C
ATOM   12613  CD2 TRP B 819      21.684  -0.792 123.939  1.00159.21           C
ANISOU12613  CD2 TRP B 819    19622  22741  18131  -2571   -300  -5288        C
ATOM   12614  NE1 TRP B 819      22.264  -1.266 126.038  1.00166.43           N
ANISOU12614  NE1 TRP B 819    21128  24475  17631  -2504    -65  -5676        N
ATOM   12615  CE2 TRP B 819      22.607  -0.512 124.951  1.00162.82           C
ANISOU12615  CE2 TRP B 819    20392  23431  18040  -2522   -556  -5578        C
ATOM   12616  CE3 TRP B 819      21.816  -0.149 122.711  1.00155.55           C
ANISOU12616  CE3 TRP B 819    18855  21707  18540  -2627   -724  -5096        C
ATOM   12617  CZ2 TRP B 819      23.640   0.385 124.779  1.00162.87           C
ANISOU12617  CZ2 TRP B 819    20395  23113  18374  -2537  -1208  -5703        C
ATOM   12618  CZ3 TRP B 819      22.835   0.736 122.541  1.00155.68           C
```

FIG. 13 Continued

```
ANISOU12618 CZ3 TRP B 819     18887  21399  18864   -2653  -1352  -5189          C
ATOM  12619 CH2 TRP B 819     23.734    1.003 123.567  1.00159.29                C
ANISOU12619 CH2 TRP B 819     19638  22089  18797   -2613  -1588  -5502          C
ATOM  12620 N   ALA B 820     18.359   -2.766 121.038  1.00150.02                N
ANISOU12620 N   ALA B 820     17576  21347  18078   -2934    859  -4142          N
ATOM  12621 CA  ALA B 820     18.321   -3.184 119.662  1.00144.39                C
ANISOU12621 CA  ALA B 820     16695  20342  17825   -3137    722  -3554          C
ATOM  12622 C   ALA B 820     17.839   -1.967 118.897  1.00145.00                C
ANISOU12622 C   ALA B 820     16328  19949  18818   -3030    362  -3810          C
ATOM  12623 O   ALA B 820     18.289   -1.703 117.793  1.00141.17                O
ANISOU12623 O   ALA B 820     15730  19089  18817   -3159    -68  -3441          O
ATOM  12624 CB  ALA B 820     17.366   -4.339 119.497  1.00143.62                C
ANISOU12624 CB  ALA B 820     16565  20517  17488   -3319   1297  -3253          C
ATOM  12625 N   GLY B 821     16.940   -1.208 119.518  1.00171.65                N
ANISOU12625 N   GLY B 821     19454  23351  22414   -2785    531  -4457          N
ATOM  12626 CA  GLY B 821     16.376   -0.012 118.918  1.00173.61                C
ANISOU12626 CA  GLY B 821     19275  23120  23569   -2612    188  -4762          C
ATOM  12627 C   GLY B 821     17.418    0.854 118.246  1.00171.45                C
ANISOU12627 C   GLY B 821     19055  22315  23773   -2657   -542  -4597          C
ATOM  12628 O   GLY B 821     17.156    1.451 117.203  1.00170.34                O
ANISOU12628 O   GLY B 821     18621  21722  24378   -2694   -911  -4414          O
ATOM  12629 N   VAL B 822     18.600    0.939 118.844  1.00148.01                N
ANISOU12629 N   VAL B 822     16451  19417  20368   -2680   -772  -4644          N
ATOM  12630 CA  VAL B 822     19.679    1.690 118.224  1.00146.17                C
ANISOU12630 CA  VAL B 822     16267  18742  20527   -2794  -1449  -4446          C
ATOM  12631 C   VAL B 822     20.435    0.791 117.278  1.00139.73                C
ANISOU12631 C   VAL B 822     15561  18000  19529   -3116  -1536  -3661          C
ATOM  12632 O   VAL B 822     21.036    1.267 116.326  1.00137.39                O
ANISOU12632 O   VAL B 822     15172  17350  19678   -3297  -2023  -3330          O
ATOM  12633 CB  VAL B 822     20.633    2.317 119.232  1.00149.63                C
ANISOU12633 CB  VAL B 822     16986  19201  20667   -2693  -1730  -4886          C
ATOM  12634 CG1 VAL B 822     21.858    2.851 118.522  1.00147.16                C
ANISOU12634 CG1 VAL B 822     16726  18526  20660   -2917  -2387  -4540          C
ATOM  12635 CG2 VAL B 822     19.924    3.439 119.964  1.00156.54                C
ANISOU12635 CG2 VAL B 822     17718  19859  21900   -2370  -1758  -5721          C
ATOM  12636 N   ILE B 823     20.397   -0.514 117.526  1.00194.85                N
ANISOU12636 N   ILE B 823     22741  25436  25857   -3198  -1061  -3367          N
ATOM  12637 CA  ILE B 823     21.024   -1.454 116.603  1.00189.23                C
ANISOU12637 CA  ILE B 823     22124  24786  24990   -3464  -1092  -2672          C
ATOM  12638 C   ILE B 823     20.335    1.363 115.237  1.00186.60                C
ANISOU12638 C   ILE B 823     21454  24160  25285   -3635  -1180  -2339          C
ATOM  12639 O   ILE B 823     20.997   -1.347 114.204  1.00183.16                O
ANISOU12639 O   ILE B 823     20973  23548  25071   -3859  -1515  -1896          O
ATOM  12640 CB  ILE B 823     21.022   -2.914 117.137  1.00187.95                C
ANISOU12640 CB  ILE B 823     22269  25093  24052   -3502   -567  -2424          C
ATOM  12641 CG1 ILE B 823     22.361   -3.591 116.829  1.00184.39                C
ANISOU12641 CG1 ILE B 823     22067  24733  23259   -3629   -775  -1946          C
ATOM  12642 CG2 ILE B 823     19.853   -3.723 116.564  1.00186.44                C
ANISOU12642 CG2 ILE B 823     21922  24974  23943   -3627   -116  -2188          C
ATOM  12643 CD1 ILE B 823     23.550   -2.657 116.938  1.00185.19                C
ANISOU12643 CD1 ILE B 823     22181  24687  23497   -3606  -1345  -2072          C
ATOM  12644 N   TRP B 824     19.007    1.280 115.243  1.00130.98                N
ANISOU12644 N   TRP B 824     14150  17104  18513   -3539   -887  -2563          N
ATOM  12645 CA  TRP B 824     18.247   -1.135 114.008  1.00129.38                C
ANISOU12645 CA  TRP B 824     13597  16646  18917   -3685  -1003  -2280          C
ATOM  12646 C   TRP B 824     18.402    0.245 113.366  1.00130.88                C
ANISOU12646 C   TRP B 824     13551  16305  19873    3660   1636   2348          C
ATOM  12647 O   TRP B 824     17.588    0.653 112.538  1.00131.47                O
ANISOU12647 O   TRP B 824     13292  16121  20541   -3694  -1791  -2243          O
ATOM  12648 CB  TRP B 824     16.779   -1.501 114.201  1.00131.71                C
ANISOU12648 CB  TRP B 824     13635  17129  19280   -3600   -511  -2481          C
ATOM  12649 CG  TRP B 824     16.517   -2.879 113.756  1.00128.22                C
ANISOU12649 CG  TRP B 824     13292  16981  18445   -3866   -104  -2019          C
ATOM  12650 CD1 TRP B 824     17.397   -3.698 113.123  1.00123.55                C
ANISOU12650 CD1 TRP B 824     12962  16433  17550   -4117   -172  -1494          C
ATOM  12651 CD2 TRP B 824     15.285   -3.605 113.854  1.00129.58                C
ANISOU12651 CD2 TRP B 824     13289  17425  18522   -3925    422  -2048          C
ATOM  12652 NE1 TRP B 824     16.799   -4.898 112.835  1.00121.94                N
ANISOU12652 NE1 TRP B 824     12803  16460  17070   -4319    265  -1210          N
```

FIG. 13 Continued

```
ATOM   12653  CE2 TRP B 824      15.502  -4.868 113.272  1.00125.52           C
ANISOU 12653  CE2 TRP B 824    12993  17060  17638  -4237    630  -1519       C
ATOM   12654  CE3 TRP B 824      14.026  -3.314 114.385  1.00134.33           C
ANISOU 12654  CE3 TRP B 824    13548  18172  19317  -3751    747  -2491       C
ATOM   12655  CZ2 TRP B 824      14.508  -5.842 113.204  1.00125.97           C
ANISOU 12655  CZ2 TRP B 824    12974  17372  17518  -4422   1125  -1395       C
ATOM   12656  CZ3 TRP B 824      13.035  -4.287 114.317  1.00134.74           C
ANISOU 12656  CZ3 TRP B 824    13475  18544  19178  -3941   1262  -2354       C
ATOM   12657  CH2 TRP B 824      13.285  -5.536 113.731  1.00130.54           C
ANISOU 12657  CH2 TRP B 824    13203  18120  18278  -4295   1433  -1797       C
ATOM   12658  N   LEU B 825      19.432   0.966 113.795  1.00133.01           N
ANISOU 12658  N   LEU B 825    14001  16409  20128  -3610  -2022  -2523       N
ATOM   12659  CA  LEU B 825      19.849   2.213 113.166  1.00134.36           C
ANISOU 12659  CA  LEU B 825    14040  16047  20965  -3677  -2683  -2489       C
ATOM   12660  C   LEU B 825      21.199   1.885 112.558  1.00130.26           C
ANISOU 12660  C   LEU B 825    13707  15602  20185  -4007  -2952  -1966       C
ATOM   12661  O   LEU B 825      21.444   2.065 111.362  1.00128.08           O
ANISOU 12661  O   LEU B 825    13299  15123  20242  -4296  -3279  -1485       O
ATOM   12662  CB  LEU B 825      19.991   3.320 114.202  1.00139.88           C
ANISOU 12662  CB  LEU B 825    14799  16501  21848  -3389  -2912  -3161       C
ATOM   12663  CG  LEU B 825      18.952   4.429 114.091  1.00144.87           C
ANISOU 12663  CG  LEU B 825    15113  16646  23286  -3136  -3130  -3558       C
ATOM   12664  CD1 LEU B 825      19.488   5.542 113.196  1.00145.73           C
ANISOU 12664  CD1 LEU B 825    15152  16124  24096  -3320  -3878  -3302       C
ATOM   12665  CD2 LEU B 825      17.619   3.875 113.582  1.00144.26           C
ANISOU 12665  CD2 LEU B 825    14710  16709  23393  -3081  -2752  -3425       C
ATOM   12666  N   TYR B 826      22.062   1.356 113.415  1.00129.22           N
ANISOU 12666  N   TYR B 826    13869  15815  19413  -3959  -2791  -2065       N
ATOM   12667  CA  TYR B 826      23.372   0.895 113.024  1.00125.88           C
ANISOU 12667  CA  TYR B 826    13600  15571  18658  -4205  -2965  -1635       C
ATOM   12668  C   TYR B 826      23.137  -0.327 112.178  1.00121.38           C
ANISOU 12668  C   TYR B 826    13015  15253  17851  -4381  -2619  -1128       C
ATOM   12669  O   TYR B 826      24.062  -0.943 111.659  1.00118.30           O
ANISOU 12669  O   TYR B 826    12710  15054  17186  -4575  -2660   -729       O
ATOM   12670  CB  TYR B 826      24.184   0.532 114.246  1.00127.07           C
ANISOU 12670  CB  TYR B 826    14049  16063  18168  -4048  -2845  -1890       C
ATOM   12671  CG  TYR B 826      25.649   0.467 113.973  1.00125.38           C
ANISOU 12671  CG  TYR B 826    13915  15962  17762  -4250  -3182  -1580       C
ATOM   12672  CD1 TYR B 826      26.338   1.578 113.530  1.00126.85           C
ANISOU 12672  CD1 TYR B 826    13971  15820  18405  -4448  -3759  -1553       C
ATOM   12673  CD2 TYR B 826      26.348  -0.706 114.165  1.00122.90           C
ANISOU 12673  CD2 TYR B 826    13790  16077  16829  -4245  -2933  -1310       C
ATOM   12674  CE1 TYR B 826      27.687   1.519 113.285  1.00125.80           C
ANISOU 12674  CE1 TYR B 826    13853  15855  18092  -4662  -4047  -1276       C
ATOM   12675  CE2 TYR B 826      27.696  -0.777 113.927  1.00121.91           C
ANISOU 12675  CE2 TYR B 826    13672  16101  16548  -4394  -3232  -1054       C
ATOM   12676  CZ  TYR B 826      28.363   0.334 113.486  1.00123.33           C
ANISOU 12676  CZ  TYR B 826    13677  16019  17162  -4615  -3773  -1043       C
ATOM   12677  OH  TYR B 826      29.716   0.250 113.252  1.00122.79           O
ANISOU 12677  OH  TYR B 826    13561  16166  16928  -4791  -4048   -792       O
ATOM   12678  N   SER B 827      21.872  -0.692 112.077  1.00124.09           N
ANISOU 12678  N   SER B 827    13235  15613  18300  -4305  -2260  -1189       N
ATOM   12679  CA  SER B 827      21.474  -1.764 111.206  1.00120.48           C
ANISOU 12679  CA  SER B 827    12744  15330  17703  -4504  -1960   -751       C
ATOM   12680  C   SER B 827      21.639  -1.157 109.802  1.00119.11           C
ANISOU 12680  C   SER B 827    12334  14868  18055  -4803  -2417   -361       C
ATOM   12681  O   SER B 827      22.590  -1.476 109.074  1.00116.41           O
ANISOU 12681  O   SER B 827    12050  14625  17556  -5053  -2571     31       O
ATOM   12682  CB  SER B 827      20.012  -2.164 111.490  1.00121.94           C
ANISOU 12682  CB  SER B 827    12803  15603  17926  -4380  -1504   -952       C
ATOM   12683  OG  SER B 827      19.823  -3.571 111.577  1.00119.72           O
ANISOU 12683  OG  SER B 827    12715  15664  17108  -4459   -997   -738       O
ATOM   12684  N   ILE B 828      20.747  -0.226 109.462  1.00122.16           N
ANISOU 12684  N   ILE B 828    12446  14905  19065  -4767  -2657   -484       N
ATOM   12685  CA  ILE B 828      20.697   0.368 108.130  1.00121.71           C
ANISOU 12685  CA  ILE B 828    12165  14561  19519  -5062  -3102    -79       C
ATOM   12686  C   ILE B 828      21.885   1.247 107.793  1.00122.29           C
ANISOU 12686  C   ILE B 828    12278  14412  19773  -5262  -3657     91       C
ATOM   12687  O   ILE B 828      22.308   1.311 106.648  1.00120.73           O
```

FIG. 13 Continued

```
ANISOU12687  O   ILE B 828    12001  14189  19683  -5626  -3924    572           O
ATOM  12688  CB  ILE B 828       19.426    1.201 107.947  1.00125.29             C
ANISOU12688  CB  ILE B 828    12309  14655  20641   4916   3275    263           C
ATOM  12689  CG1 ILE B 828       18.192    0.379 108.326  1.00125.47             C
ANISOU12689  CG1 ILE B 828    12224  14943  20507  -4740  -2710   -463           C
ATOM  12690  CG2 ILE B 828       19.346    1.704 106.520  1.00125.05             C
ANISOU12690  CG2 ILE B 828    12075  14360  21078  -5255  -3750    246           C
ATOM  12691  CD1 ILE B 828       18.108    0.945 107.622  1.00121.33             C
ANISOU12691  CD1 ILE B 828    11769  14779  19553  -5025  -2354    -41           C
ATOM  12692  N   VAL B 829       22.426    1.928 106.782  1.00121.32             N
ANISOU12692  N   VAL B 829    12275  14157  19663  -5063  -3830   -306           N
ATOM  12693  CA  VAL B 829       23.535    2.819 108.513  1.00122.56             C
ANISOU12693  CA  VAL B 829    12456  14088  20024  -5292  -4378   -165           C
ATOM  12694  C   VAL B 829       24.754    2.095 107.947  1.00118.98             C
ANISOU12694  C   VAL B 829    12085  14021  19101  -5610  -4349    276           C
ATOM  12695  O   VAL B 829       25.593    2.703 107.295  1.00119.57             O
ANISOU12695  O   VAL B 829    12092  13981  19357  -5940  -4779    571           O
ATOM  12696  CB  VAL B 829       23.951    3.548 109.779  1.00126.25             C
ANISOU12696  CB  VAL B 829    13069  14405  20497  -5032  -4532   -723           C
ATOM  12697  CG1 VAL B 829       22.735    4.208 110.430  1.00130.44             C
ANISOU12697  CG1 VAL B 829    13506  14601  21456  -4656  -4489  -1264           C
ATOM  12698  CG2 VAL B 829       24.620    2.576 110.732  1.00124.46             C
ANISOU12698  CG2 VAL B 829    13084  14692  19514  -4883  -4133   -886           C
ATOM  12699  N   THR B 830       24.858    0.799 108.219  1.00171.97             N
ANISOU12699  N   THR B 830    18934  21189  25218  -5507  -3840    312           N
ATOM  12700  CA  THR B 830       25.989    0.005 107.747  1.00169.06             C
ANISOU12700  CA  THR B 830    18628  21205  24403  -5720  -3761    664           C
ATOM  12701  C   THR B 830       25.681   -0.605 106.392  1.00166.33             C
ANISOU12701  C   THR B 830    18160  20976  24063  -6022  -3644   1130           C
ATOM  12702  O   THR B 830       26.564   -1.131 105.713  1.00164.46             O
ANISOU12702  O   THR B 830    17908  21028  23551  -6255  -3623   1446           O
ATOM  12703  CB  THR B 830       26.306   -1.163 108.708  1.00167.63             C
ANISOU12703  CB  THR B 830    18693  21419  23579  -5434  -3298    489           C
ATOM  12704  OG1 THR B 830       25.171   -2.035 108.796  1.00166.32             O
ANISOU12704  OG1 THR B 830    18599  21330  23270  -5290  -2617    446           O
ATOM  12705  CG2 THR B 830       26.651   -0.650 110.093  1.00170.65             C
ANISOU12705  CG2 THR B 830    19224  21774  23839  -5154  -3399     25           C
ATOM  12706  N   TYR B 831       24.415   -0.522 106.011  1.00169.39             N
ANISOU12706  N   TYR B 831    18437  21163  24760  -6011  -3570   1139           N
ATOM  12707  CA  TYR B 831       23.908   -1.156 104.805  1.00167.24             C
ANISOU12707  CA  TYR B 831    18063  21014  24467  -6285  -3433   1524           C
ATOM  12708  C   TYR B 831       24.258   -0.473 103.466  1.00167.82             C
ANISOU12708  C   TYR B 831    17950  20981  24832  -6742  -3891   1981           C
ATOM  12709  O   TYR B 831       24.278   -1.126 102.420  1.00165.94             O
ANISOU12709  O   TYR B 831    17670  20986  24395  -7036  -3773   2328           O
ATOM  12710  CB  TYR B 831       22.403   -1.329 104.963  1.00167.92             C
ANISOU12710  CB  TYR B 831    18065  20970  24767  -6109  -3195   1352           C
ATOM  12711  CG  TYR B 831       21.689   -1.554 103.678  1.00167.12             C
ANISOU12711  CG  TYR B 831    17788  20874  24834  -6420  -3239   1725           C
ATOM  12712  CD1 TYR B 831       21.041   -2.748 103.428  1.00165.08             C
ANISOU12712  CD1 TYR B 831    17579  20872  24272  -6457  -2781   1783           C
ATOM  12713  CD2 TYR B 831       21.661   -0.569 102.708  1.00168.89             C
ANISOU12713  CD2 TYR B 831    17817  20843  25512  -6710  -3767   2036           C
ATOM  12714  CE1 TYR B 831       20.377   -2.954 102.247  1.00164.74             C
ANISOU12714  CE1 TYR B 831    17376  20859  24359  -6769  -2845   2102           C
ATOM  12715  CE2 TYR B 831       21.016   -0.760 101.521  1.00168.63             C
ANISOU12715  CE2 TYR B 831    17630  20851  25591  -7019  -3847   2399           C
ATOM  12716  CZ  TYR B 831       20.369   -1.957 101.288  1.00166.50             C
ANISOU12716  CZ  TYR B 831    17393  20870  24598  -7046  -3383   2413           C
ATOM  12717  OH  TYR B 831       19.711   -2.156 100.092  1.00166.61             O
ANISOU12717  OH  TYR B 831    17254  20952  25097  -7383  -3485   2757           O
ATOM  12718  N   PHE B 832       24.517    0.832 103.496  1.00122.18             N
ANISOU12718  N   PHE B 832    12080  14836  19508  -6825  -4416   1981           N
ATOM  12719  CA  PHE B 832       24.869    1.583 102.283  1.00123.62             C
ANISOU12719  CA  PHE B 832    12111  14888  19970  -7305  -4900   2460           C
ATOM  12720  C   PHE B 832       26.347    1.509 101.909  1.00123.04             C
ANISOU12720  C   PHE B 832    12047  15138  19564  -7632  -5001   2708           C
ATOM  12721  O   PHE B 832       26.709    1.786 100.769  1.00123.75             O
ANISOU12721  O   PHE B 832    12017  15311  19690  -8103  -5254   3164           O
```

FIG. 13 Continued

```
ATOM  12722  CB   PHE B 832      24.431    3.049 102.378  1.00128.02           C
ANISOU12722  CB   PHE B 832    12577  14833  21234   -7293  -5471   2408       C
ATOM  12723  CG   PHE B 832      22.956    3.253 102.190  1.00129.47           C
ANISOU12723  CG   PHE B 832    12624  14714  21854   -7113  -5501   2354       C
ATOM  12724  CD1  PHE B 832      22.052    2.252 102.556  1.00127.26           C
ANISOU12724  CD1  PHE B 832    12342  14676  21334   -6826  -4961   2115       C
ATOM  12725  CD2  PHE B 832      22.469    4.448 101.677  1.00133.60           C
ANISOU12725  CD2  PHE B 832    13010  14703  23049   -7229  -6086   2544       C
ATOM  12726  CE1  PHE B 832      20.690    2.420 102.402  1.00129.01           C
ANISOU12726  CE1  PHE B 832    12375  14680  21962   -6664  -4975   2046       C
ATOM  12727  CE2  PHE B 832      21.103    4.630 101.519  1.00135.46           C
ANISOU12727  CE2  PHE B 832    13067  14680  23721   -7017  -6133   2480       C
ATOM  12728  CZ   PHE B 832      20.209    3.606 101.886  1.00133.10           C
ANISOU12728  CZ   PHE B 832    12715  14695  23162   -6734  -5561   2216       C
ATOM  12729  N    PRO B 833      27.219    1.197 102.875  1.00185.92           N
ANISOU12729  N    PRO B 833    20128  23307  27206   -7401  -4831   2416       N
ATOM  12730  CA   PRO B 833      28.588    0.970 102.411  1.00185.48           C
ANISOU12730  CA   PRO B 833    20006  23653  26814   -7707  -4872   2665       C
ATOM  12731  C    PRO B 833      28.635   -0.284 101.532  1.00182.45           C
ANISOU12731  C    PRO B 833    19605  23741  25979   -7837  -4447   2905       C
ATOM  12732  O    PRO B 833      29.699   -0.616 101.013  1.00182.24           O
ANISOU12732  O    PRO B 833    19482  24117  25642   -8075  -4403   3100       O
ATOM  12733  CB   PRO B 833      29.364    0.739 103.709  1.00185.52           C
ANISOU12733  CB   PRO B 833    20136  23804  26549   -7352  -4747   2272       C
ATOM  12734  CG   PRO B 833      28.604    1.493 104.730  1.00187.63           C
ANISOU12734  CG   PRO B 833    20511  23606  27175   -7031  -4899   1865       C
ATOM  12735  CD   PRO B 833      27.155    1.400 104.331  1.00187.02           C
ANISOU12735  CD   PRO B 833    20413  23284  27364   -6949  -4766   1891       C
ATOM  12736  N    LEU B 834      27.498   -0.967 101.378  1.00106.98           N
ANISOU12736  N    LEU B 834    10121  14139  16389   -7686  -4133   2860       N
ATOM  12737  CA   LEU B 834      27.420   -2.169 100.545  1.00104.57           C
ANISOU12737  CA   LEU B 834     9835  14215  15682   -7814  -3737   3037       C
ATOM  12738  C    LEU B 834      27.244   -1.866  99.071  1.00105.47           C
ANISOU12738  C    LEU B 834     9783  14403  15886   -8341  -3960   3483       C
ATOM  12739  O    LEU B 834      28.034   -2.308  98.228  1.00105.24           O
ANISOU12739  O    LEU B 834     9682  14786  15516   -8644  -3864   3706       O
ATOM  12740  CB   LEU B 834      26.288   -3.088 101.000  1.00102.70           C
ANISOU12740  CB   LEU B 834     9757  13918  15345   -7491  -3305   2807       C
ATOM  12741  CG   LEU B 834      26.877   -4.371 101.571  1.00100.73           C
ANISOU12741  CG   LEU B 834     9707  13984  14583   -7207  -2835   2624       C
ATOM  12742  CD1  LEU B 834      27.276   -4.127 103.019  1.00101.49           C
ANISOU12742  CD1  LEU B 834     9929  13985  14649   -6806  -2849   2287       C
ATOM  12743  CD2  LEU B 834      25.919   -5.544 101.422  1.00 99.00           C
ANISOU12743  CD2  LEU B 834     9637  13813  14164   -7120  -2382   2576       C
ATOM  12744  N    ASP B 835      26.189   -1.125  98.763  1.00118.42           N
ANISOU12744  N    ASP B 835    11354  15668  17972   -8440  -4256   3603       N
ATOM  12745  CA   ASP B 835      25.928   -0.778  97.387  1.00119.88           C
ANISOU12745  CA   ASP B 835    11401  15904  18245   -8951  -4532   4069       C
ATOM  12746  C    ASP B 835      27.124   -0.087  96.770  1.00122.07           C
ANISOU12746  C    ASP B 835    11564  16349  18466   -9402  -4870   4401       C
ATOM  12747  O    ASP B 835      27.625   -0.528  95.748  1.00122.08           O
ANISOU12747  O    ASP B 835    11496  16793  18094   -9796  -4764   4682       O
ATOM  12748  CB   ASP B 835      24.661    0.048  97.257  1.00122.02           C
ANISOU12748  CB   ASP B 835    11589  15690  19084   -8935  -4892   4155       C
ATOM  12749  CG   ASP B 835      23.419   -0.806  97.345  1.00120.30           C
ANISOU12749  CG   ASP B 835    11395  15488  18824   -8699  -4528   3974       C
ATOM  12750  OD1  ASP B 835      23.340   -1.640  98.278  1.00118.01           O
ANISOU12750  OD1  ASP B 835    11243  15297  18298   -8306  -4062   3583       O
ATOM  12751  OD2  ASP B 835      22.534   -0.650  96.470  1.00121.62           O
ANISOU12751  OD2  ASP B 835    11442  15588  19181   -8938  -4724   4248       O
ATOM  12752  N    VAL B 836      27.616    0.971  97.391  1.00131.77           N
ANISOU12752  N    VAL B 836    12769  17260  20038   -9371  -5256   4349       N
ATOM  12753  CA   VAL B 836      28.788    1.615  96.828  1.00134.30           C
ANISOU12753  CA   VAL B 836    12965  17768  20296   -9858  -5569   4680       C
ATOM  12754  C    VAL B 836      29.950    0.613  96.779  1.00132.46           C
ANISOU12754  C    VAL B 836    12682  18188  19458   -9867  -5131   4587       C
ATOM  12755  O    VAL B 836      30.949    0.843  96.094  1.00134.43           O
ANISOU12755  O    VAL B 836    12766  18798  19511  -10319  -5246   4873       O
ATOM  12756  CB   VAL B 836      29.197    2.894  97.596  1.00137.46           C
```

FIG. 13 Continued

```
ANISOU12756  CB   VAL B 836    13367  17692  21169  -9832  -6063   4591        C
ATOM  12757  CG1  VAL B 836     30.350   2.608  98.562  1.00136.67              C
ANISOU12757  CG1  VAL B 836    13274  17856  20797   9603   5875   4250        C
ATOM  12758  CG2  VAL B 836     29.571   4.003  96.618  1.00141.77              C
ANISOU12758  CG2  VAL B 836    13800  18098  21970 -10487  -6632   5145        C
ATOM  12759  N    PHE B 837     29.820  -0.503  97.495  1.00114.04              N
ANISOU12759  N    PHE B 837    10478  16011  16839  -9372  -4633   4195        N
ATOM  12760  CA   PHE B 837     30.896  -1.494  97.512  1.00112.79              C
ANISOU12760  CA   PHE B 837    10277  16414  16165  -9287  -4238   4077        C
ATOM  12761  C    PHE B 837     30.798  -2.540  96.411  1.00111.65              C
ANISOU12761  C    PHE B 837    10112  16709  15601  -9486  -3861   4216        C
ATOM  12762  O    PHE B 837     31.781  -2.782  95.718  1.00112.91              O
ANISOU12762  O    PHE B 837    10098  17366  15437  -9774  -3766   4356        O
ATOM  12763  CB   PHE B 837     31.134  -2.113  98.906  1.00110.97              C
ANISOU12763  CB   PHE B 837    10204  16150  15810  -8675  -3962   3618        C
ATOM  12764  CG   PHE B 837     32.263  -1.449  99.675  1.00112.98              C
ANISOU12764  CG   PHE B 837    10356  16443  16129  -8631  -4229   3508        C
ATOM  12765  CD1  PHE B 837     32.460  -1.705 101.025  1.00112.33              C
ANISOU12765  CD1  PHE B 837    10421  16276  15985  -8126  -4126   3121        C
ATOM  12766  CD2  PHE B 837     33.120  -0.550  99.035  1.00116.04              C
ANISOU12766  CD2  PHE B 837    10500  16972  16620  -9148  -4604   3812        C
ATOM  12767  CE1  PHE B 837     33.505  -1.088 101.721  1.00114.60              C
ANISOU12767  CE1  PHE B 837    10604  16626  16314  -8117  -4407   3011        C
ATOM  12768  CE2  PHE B 837     34.160   0.074  99.720  1.00118.34              C
ANISOU12768  CE2  PHE B 837    10675  17309  16982  -9164  -4873   3711        C
ATOM  12769  CZ   PHE B 837     34.354  -0.195 101.065  1.00117.58              C
ANISOU12769  CZ   PHE B 837    10716  17131  16827  -8639  -4785   3296        C
ATOM  12770  N    LYS B 838     29.637  -3.167  96.236  1.00106.23              N
ANISOU12770  N    LYS B 838     9583  15873  14908  -9351  -3638   4152        N
ATOM  12771  CA   LYS B 838     29.524  -4.112  95.131  1.00105.74              C
ANISOU12771  CA   LYS B 838     9520  16207  14449  -9592  -3319   4264        C
ATOM  12772  C    LYS B 838     30.140  -3.417  93.902  1.00108.84              C
ANISOU12772  C    LYS B 838     9682  16926  14746 -10246  -3610   4695        C
ATOM  12773  O    LYS B 838     31.060  -3.931  93.248  1.00109.85              O
ANISOU12773  O    LYS B 838     9683  17602  14454 -10456  -3380   4730        O
ATOM  12774  CB   LYS B 838     28.068  -4.537  94.880  1.00104.40              C
ANISOU12774  CB   LYS B 838     9496  15795  14377  -9551  -3208   4251        C
ATOM  12775  CG   LYS B 838     27.013  -3.570  95.378  1.00104.93              C
ANISOU12775  CG   LYS B 838     9565  15310  14994  -9453  -3577   4288        C
ATOM  12776  CD   LYS B 838     26.375   4.069  96.676  1.00102.82              C
ANISOU12776  CD   LYS B 838     9476  14759  14832  -8872  -3295   3869        C
ATOM  12777  CE   LYS B 838     24.879  -3.675  96.807  1.00103.25              C
ANISOU12777  CE   LYS B 838     9515  14409  15308  -8792  -3441   3856        C
ATOM  12778  NZ   LYS B 838     24.028  -4.546  97.689  1.00101.42              N
ANISOU12778  NZ   LYS B 838     9442  14069  15024  -8371  -3016   3500        N
ATOM  12779  N    PHE B 839     29.661  -2.205  93.646  1.00132.50              N
ANISOU12779  N    PHE B 839    12619  19575  18150 -10556  -4128   5019        N
ATOM  12780  CA   PHE B 839     30.082  -1.406  92.509  1.00136.11              C
ANISOU12780  CA   PHE B 839    12900  20252  18564 -11234  -4486   5516        C
ATOM  12781  C    PHE B 839     31.576  -1.161  92.577  1.00138.00              C
ANISOU12781  C    PHE B 839    12943  20886  18604 -11416  -4490   5544        C
ATOM  12782  O    PHE B 839     32.147  -0.532  91.694  1.00141.50              O
ANISOU12782  O    PHE B 839    13212  21608  18944 -12021  -4737   5952        O
ATOM  12783  CB   PHE B 839     29.323  -0.071  92.507  1.00138.46              C
ANISOU12783  CB   PHE B 839    13208  19947  19453 -11418  -5110   5829        C
ATOM  12784  CG   PHE B 839     27.813  -0.210  92.398  1.00137.41              C
ANISOU12784  CG   PHE B 839    13187  19449  19575 -11249  -5160   5823        C
ATOM  12785  CD1  PHE B 839     27.120  -1.181  93.127  1.00133.85              C
ANISOU12785  CD1  PHE B 839    12871  18911  19074 -10705  -4725   5375        C
ATOM  12786  CD2  PHE B 839     27.084   0.644  91.583  1.00140.55              C
ANISOU12786  CD2  PHE B 839    13538  19590  20273 -11647  -5667   6287        C
ATOM  12787  CE1  PHE B 839     25.728  -1.314  93.036  1.00133.35              C
ANISOU12787  CE1  PHE B 839    12854  18563  19251 -10579  -4757   5361        C
ATOM  12788  CE2  PHE B 839     25.694   0.519  91.483  1.00140.08              C
ANISOU12788  CE2  PHE B 839    13520  19232  20473 -11477  -5735   6276        C
ATOM  12789  CZ   PHE B 839     25.018  -0.461  92.219  1.00136.44              C
ANISOU12789  CZ   PHE B 839    13151  18733  19958 -10947  -5263   5794        C
ATOM  12790  N    ALA B 840     32.208  -1.645  93.640  1.00135.96              N
ANISOU12790  N    ALA B 840    12700  20671  18288 -10913  -4232   5130        N
```

FIG. 13 Continued

```
ATOM   12791  CA   ALA B 840      33.649  -1.468  93.830  1.00137.94           C
ANISOU 12791  CA   ALA B 840    12716  21323  18373 -11020  -4233   5105       C
ATOM   12792  C    ALA B 840      34.461  -2.621  93.246  1.00137.98           C
ANISOU 12792  C    ALA B 840    12570  22048  17808 -11018  -3719   4969       C
ATOM   12793  O    ALA B 840      35.383  -2.414  92.446  1.00141.22           O
ANISOU 12793  O    ALA B 840    12698  22999  17959 -11496  -3725   5191       O
ATOM   12794  CB   ALA B 840      33.971  -1.293  95.308  1.00136.79           C
ANISOU 12794  CB   ALA B 840    12639  20864  18472 -10490  -4303   4743       C
ATOM   12795  N    ILE B 841      34.131  -3.836  93.675  1.00145.97           N
ANISOU 12795  N    ILE B 841    13766  23060  18636 -10475  -3269   4590       N
ATOM   12796  CA   ILE B 841      34.789  -5.019  93.144  1.00146.31           C
ANISOU 12796  CA   ILE B 841    13711  23690  18190 -10385  -2771   4396       C
ATOM   12797  C    ILE B 841      34.400  -5.216  91.670  1.00147.88           C
ANISOU 12797  C    ILE B 841    13876  24228  18086 -10929  -2665   4643       C
ATOM   12798  O    ILE B 841      35.256  -5.552  90.838  1.00150.63           O
ANISOU 12798  O    ILE B 841    13981  25219  18033 -11211  -2437   4660       O
ATOM   12799  CB   ILE B 841      34.450  -6.295  93.959  1.00143.15           C
ANISOU 12799  CB   ILE B 841    13581  23108  17701  -9682  -2352   3958       C
ATOM   12800  CG1  ILE B 841      32.938  -6.494  94.048  1.00140.45           C
ANISOU 12800  CG1  ILE B 841    13572  22256  17535  -9581  -2339   3950       C
ATOM   12801  CG2  ILE B 841      35.049  -6.225  95.339  1.00142.47           C
ANISOU 12801  CG2  ILE B 841    13504  22851  17779  -9171  -2423   3720       C
ATOM   12802  CD1  ILE B 841      32.527  -7.463  95.104  1.00137.73           C
ANISOU 12802  CD1  ILE B 841    13520  21613  17197  -8939  -2035   3587       C
ATOM   12803  N    ARG B 842      33.114  -4.990  91.360  1.00121.21           N
ANISOU 12803  N    ARG B 842    10716  20451  14886 -11079  -2837   4819       N
ATOM   12804  CA   ARG B 842      32.582  -5.162  90.003  1.00122.83           C
ANISOU 12804  CA   ARG B 842    10931  20937  14801 -11600  -2796   5066       C
ATOM   12805  C    ARG B 842      33.213  -4.222  88.994  1.00127.23           C
ANISOU 12805  C    ARG B 842    11222  21908  15210 -12342  -3097   5537       C
ATOM   12806  O    ARG B 842      33.900  -4.675  88.074  1.00129.88           O
ANISOU 12806  O    ARG B 842    11383  22918  15047 -12669  -2816   5544       O
ATOM   12807  CB   ARG B 842      31.080  -4.963  89.990  1.00121.11           C
ANISOU 12807  CB   ARG B 842    10949  20182  14884 -11598  -3015   5192       C
ATOM   12808  CG   ARG B 842      30.356  -6.011  90.752  1.00117.50           C
ANISOU 12808  CG   ARG B 842    10751  19419  14473 -11004  -2658   4771       C
ATOM   12809  CD   ARG B 842      29.939  -7.143  89.863  1.00117.57           C
ANISOU 12809  CD   ARG B 842    10880  19730  14062 -11127  -2275   4639       C
ATOM   12810  NE   ARG B 842      28.666  -7.679  90.335  1.00114.94           N
ANISOU 12810  NE   ARG B 842    10802  18941  13929 -10823  -2175   4465       N
ATOM   12811  CZ   ARG B 842      28.546  -8.705  91.172  1.00112.57           C
ANISOU 12811  CZ   ARG B 842    10713  18457  13600 -10287  -1786   4065       C
ATOM   12812  NH1  ARG B 842      29.637  -9.322  91.617  1.00112.50           N
ANISOU 12812  NH1  ARG B 842    10697  18661  13387  -9948  -1487   3795       N
ATOM   12813  NH2  ARG B 842      27.336  -9.120  91.551  1.00110.76           N
ANISOU 12813  NH2  ARG B 842    10689  17845  13551 -10104  -1709   3955       N
ATOM   12814  N    TYR B 843      32.988  -2.917  89.178  1.00195.18           N
ANISOU 12814  N    TYR B 843    19803  30107  24249 -12610  -3662   5919       N
ATOM   12815  CA   TYR B 843      33.504  -1.880  88.271  1.00199.94           C
ANISOU 12815  CA   TYR B 843    20200  30993  24777 -13379  -4042   6464       C
ATOM   12816  C    TYR B 843      35.026  -1.956  88.175  1.00202.63           C
ANISOU 12816  C    TYR B 843    20208  31995  24787 -13554  -3821   6394       C
ATOM   12817  O    TYR B 843      35.699  -1.028  87.724  1.00206.83           O
ANISOU 12817  O    TYR B 843    20524  32755  25305 -14151  -4128   6805       O
ATOM   12818  CB   TYR B 843      32.998  -0.479  88.671  1.00201.10           C
ANISOU 12818  CB   TYR B 843    20422  30437  25552 -13533  -4719   6835       C
ATOM   12819  CG   TYR B 843      31.507  -0.235  88.370  1.00200.40           C
ANISOU 12819  CG   TYR B 843    20558  29829  25755 -13551  -5015   7046       C
ATOM   12820  CD1  TYR B 843      31.040   1.028  87.997  1.00203.82           C
ANISOU 12820  CD1  TYR B 843    21015  29836  26591 -13984  -5671   7587       C
ATOM   12821  CD2  TYR B 843      30.567  -1.275  88.445  1.00196.88           C
ANISOU 12821  CD2  TYR B 843    20286  29316  25202 -13144  -4660   6716       C
ATOM   12822  CE1  TYR B 843      29.673   1.250  87.719  1.00203.74           C
ANISOU 12822  CE1  TYR B 843    21158  29369  26885 -13958  -5971   7778       C
ATOM   12823  CE2  TYR B 843      29.201  -1.061  88.162  1.00196.70           C
ANISOU 12823  CE2  TYR B 843    20405  28876  25456 -13170  -4937   6902       C
ATOM   12824  CZ   TYR B 843      28.763   0.201  87.803  1.00200.14           C
ANISOU 12824  CZ   TYR B 843    20821  28920  26302 -13553  -5594   7426       C
ATOM   12825  OH   TYR B 843      27.427   0.417  87.537  1.00200.49           O
```

FIG. 13 Continued

```
ANISOU12825  OH   TYR B 843    20953  28565  26657 -13534  -5895   7604           O
ATOM  12826  N    ILE B 844       35.534  -3.104  88.608  1.00129.67              N
ANISOU12826  N    ILE B 844    10923  23051  15294 -13019  -3288   5873           N
ATOM  12827  CA   ILE B 844       36.938  -3.456  88.558  1.00132.14              C
ANISOU12827  CA   ILE B 844    10881  24047  15279 -13027  -2978   5684           C
ATOM  12828  C    ILE B 844       37.042  -4.985  88.564  1.00130.32              C
ANISOU12828  C    ILE B 844    10705  24118  14692 -12485  -2350   5145           C
ATOM  12829  O    ILE B 844       36.054  -5.723  88.681  1.00127.06              O
ANISOU12829  O    ILE B 844    10625  23350  14302 -12139  -2177   4938           O
ATOM  12830  CB   ILE B 844       37.722  -2.870  89.761  1.00131.97              C
ANISOU12830  CB   ILE B 844    10711  23801  15632 -12736  -3210   5578           C
ATOM  12831  CG1  ILE B 844       39.098  -2.335  89.319  1.00137.14              C
ANISOU12831  CG1  ILE B 844    10894  25137  16076 -13263  -3255   5779           C
ATOM  12832  CG2  ILE B 844       37.784  -3.875  90.931  1.00128.13              C
ANISOU12832  CG2  ILE B 844    10357  23106  15221 -11846  -2885   5012           C
ATOM  12833  CD1  ILE B 844       39.893  -3.270  88.458  1.00139.87              C
ANISOU12833  CD1  ILE B 844    10932  26384  15827 -13363  -2703   5580           C
TER   12834       ILE B 844
HETATM12835  MG    MG A1002      -11.127 -10.529  50.393  1.00 60.40             MG
HETATM12836  MG    MG B1004       21.352 -34.072  57.563  1.00 52.82             MG
HETATM12837  PG   ACP A1001       -7.414 -11.860  51.683  1.00152.85              P
HETATM12838  O1G  ACP A1001       -7.839 -13.238  51.429  1.00152.85              O
HETATM12839  O2G  ACP A1001       -6.193 -11.685  52.657  1.00152.85              O
HETATM12840  O3G  ACP A1001       -6.733 -11.382  50.280  1.00152.85              O
HETATM12841  PB   ACP A1001       -9.475 -11.075  53.577  1.00152.85              P
HETATM12842  O1B  ACP A1001      -10.538 -10.077  53.884  1.00152.85              O
HETATM12843  O2B  ACP A1001       -8.449 -11.106  54.813  1.00152.85              O
HETATM12844  C3B  ACP A1001       -8.582 -10.729  52.205  1.00152.85              C
HETATM12845  PA   ACP A1001      -10.475 -13.880  54.769  1.00152.85              P
HETATM12846  O1A  ACP A1001       -9.252 -14.382  55.343  1.00152.85              O
HETATM12847  O2A  ACP A1001      -11.220 -14.806  53.755  1.00152.85              O
HETATM12848  O3A  ACP A1001      -10.232 -12.541  53.805  1.00152.85              O
HETATM12849  O5'  ACP A1001      -11.587 -13.626  55.986  1.00152.85              O
HETATM12850  C5'  ACP A1001      -11.230 -12.943  57.244  1.00152.85              C
HETATM12851  C4'  ACP A1001      -11.237 -13.928  58.378  1.00152.85              C
HETATM12852  O4'  ACP A1001      -11.487 -15.205  57.717  1.00152.85              O
HETATM12853  C3'  ACP A1001       -9.849 -14.323  58.976  1.00152.85              C
HETATM12854  O3'  ACP A1001        9.192  13.739  59.964  1.00152.85              O
HETATM12855  C2'  ACP A1001      -10.183 -15.699  59.492  1.00152.85              C
HETATM12856  O2'  ACP A1001      -10.311 -15.683  60.885  1.00152.85              O
HETATM12857  C1'  ACP A1001      -11.482 -16.063  58.853  1.00152.85              C
HETATM12858  N9   ACP A1001      -11.485 -17.501  58.425  1.00152.85              N
HETATM12859  C8   ACP A1001      -10.404 -18.202  58.068  1.00152.85              C
HETATM12860  N7   ACP A1001      -10.742 -19.466  57.645  1.00152.85              N
HETATM12861  C5   ACP A1001      -12.108 -19.506  57.783  1.00152.85              C
HETATM12862  C6   ACP A1001      -13.045 -20.588  57.503  1.00152.85              C
HETATM12863  N6   ACP A1001      -12.595 -21.747  57.113  1.00152.85              N
HETATM12864  N1   ACP A1001      -14.379 -20.293  57.744  1.00152.85              N
HETATM12865  C2   ACP A1001      -14.724 -19.075  58.224  1.00152.85              C
HETATM12866  N3   ACP A1001      -13.965 -17.980  58.520  1.00152.85              N
HETATM12867  C4   ACP A1001      -12.605 -18.239  58.283  1.00152.85              C
HETATM12868  PG   ACP B1003       18.396 -30.016  57.374  1.00150.29              P
HETATM12869  O1G  ACP B1003       17.357 -31.094  57.375  1.00150.29              O
HETATM12870  O2G  ACP B1003       18.085 -28.819  56.375  1.00150.29              O
HETATM12871  O3G  ACP B1003       18.284 -29.203  58.745  1.00150.29              O
HETATM12872  PB   ACP B1003       20.044 -31.442  55.577  1.00150.29              P
HETATM12873  O1B  ACP B1003       21.357 -32.001  55.153  1.00150.29              O
HETATM12874  O2B  ACP B1003       19.480 -30.543  54.397  1.00150.29              O
HETATM12875  C3B  ACP B1003       20.030 -30.311  56.858  1.00150.29              C
HETATM12876  PA   ACP B1003       17.644 -33.467  54.762  1.00150.29              P
HETATM12877  O1A  ACP B1003       16.680 -32.447  54.377  1.00150.29              O
HETATM12878  O2A  ACP B1003       17.214 -34.406  55.917  1.00150.29              O
HETATM12879  O3A  ACP B1003       18.912 -32.679  55.496  1.00150.29              O
HETATM12880  O5'  ACP B1003       18.189 -34.549  53.611  1.00150.29              O
HETATM12881  C5'  ACP B1003       18.640 -33.631  52.514  1.00150.29              C
HETATM12882  C4'  ACP B1003       17.481 -33.414  51.474  1.00150.29              C
HETATM12883  O4'  ACP B1003       16.361 -34.349  51.537  1.00150.29              O
HETATM12884  C3'  ACP B1003       17.340 -33.094  49.898  1.00150.29              C
HETATM12885  O3'  ACP B1003       17.404 -31.694  49.857  1.00150.29              O
```

FIG. 13 Continued

```
HETATM12886  C2'  ACP B1003     15.928 -33.661  49.504  1.00150.29           C
HETATM12887  O2'  ACP B1003     16.247  33.876  48.157  1.00150.29           O
HETATM12888  C1'  ACP B1003     16.024 -34.944  50.265  1.00150.29           C
HETATM12889  N9   ACP B1003     14.626 -35.449  50.570  1.00150.29           N
HETATM12890  C8   ACP B1003     13.605 -34.639  50.802  1.00150.29           C
HETATM12891  N7   ACP B1003     12.457 -35.345  51.105  1.00150.29           N
HETATM12892  C5   ACP B1003     12.877 -36.659  51.015  1.00150.29           C
HETATM12893  C6   ACP B1003     12.209 -37.928  51.192  1.00150.29           C
HETATM12894  N6   ACP B1003     10.970 -37.874  51.536  1.00150.29           N
HETATM12895  N1   ACP B1003     13.006 -39.089  51.008  1.00150.29           N
HETATM12896  C2   ACP B1003     14.308 -38.970  50.681  1.00150.29           C
HETATM12897  N3   ACP B1003     15.046 -37.833  50.504  1.00150.29           N
HETATM12898  C4   ACP B1003     14.275 -36.713  50.681  1.00150.29           C
CONECT1283712838128391284012844
CONECT1283812837
CONECT1283912837
CONECT1284012837
CONECT1284112842128431284412848
CONECT1284212841
CONECT1284312841
CONECT1284412837112841
CONECT1284512846128471284812849
CONECT1284612845
CONECT1284712845
CONECT1284812841112845
CONECT1284912845128 50
CONECT1285012849128 51
CONECT1285112850128521285 3
CONECT1285212851128 57
CONECT1285312851128541285 5
CONECT1285412853
CONECT1285512853128561285 7
CONECT1285612855
CONECT1285712852128551285 8
CONECT1285812857128591286 7
CONECT1285912858128 60
CONECT1286012859128 61
CONECT1286112860128621286 7
CONECT1286212861128631286 4
CONECT1286312862
CONECT1286412862128 65
CONECT1286512864128 66
CONECT1286612865128 67
CONECT1286712858128611286 6
CONECT1286812869128701287112875
CONECT1286912868
CONECT1287012868
CONECT1287112868
CONECT1287212873128741287512879
CONECT1287312872
CONECT1287412872
CONECT1287512868128 72
CONECT1287612877128781287912880
CONECT1287712876
CONECT1287812876
CONECT1287912872128 76
CONECT1288012876128 81
CONECT1288112880128 82
CONECT1288212881128831288 4
CONECT1288312882128 88
CONECT1288412882128851288 6
CONECT1288512884
CONECT1288612884128871288 8
CONECT1288712886
CONECT1288812883128861288 9
CONECT1288912888128901289 8
CONECT1289012889128 91
CONECT1289112890128 92
CONECT1289212891128931289 8
```

FIG. 13 Continued

```
CONECT128931289212894128995
CONECT1289412893
CONECT128951289312896
CONECT128961289512897
CONECT128971289612898
CONECT128981288912892128997
MASTER      892    0    4   76   10    0    0   912896    2   62  138
END
```

CRYSTAL STRUCTURE OF A PLASMA MEMBRANE PROTON PUMP

This application is a National Stage Application of PCT/DK2008/050305, filed 12 Dec. 2008, which claims benefit of Serial No. PA 2007 01778, filed 12 Dec. 2007 in Denmark and U.S. Ser. No. 61/013,282, field 12 Dec. 2007 and which applications are incorporated herein by reference. To the extent appropriate, a claim of priority is made to each of the above disclosed applications.

All patent and non-patent references cited in the application, or in the present application, are also hereby incorporated by reference in their entirety.

FIELD OF INVENTION

The present invention relates to the three dimensional structure of a type III P-type ATPases illustrated by the atomic coordinates obtained from crystallization experiments and X-ray diffraction results of the *A. thaliana* plasma membrane proton pump (AHA2) SEQ ID NO: 1. The invention further relates to method for purifying $H^+$ pumps and methods of growing crystals of $H^+$ pumps. Based on the three dimensional structure, detailed information regarding specific functionalities of the pump is obtained. The invention further relates to methods for identification of modulators, specifically inhibitors of type III P-type ATPase's. The invention further includes computer implemented methods for identification of ATPase modulators, based on the structural information obtained from the above described experiments.

BACKGROUND OF INVENTION

A prerequisite of life is the ability to maintain electrochemical imbalances across biomembranes and in all eukaryotes the plasma membrane potential and secondary transport systems are energised by the activity of P-type ATPase membrane proteins: $H^+$-ATPase (the proton pump) in plants and fungi[1-3], and $Na^+,K^+$-ATPase (the sodium-potassium pump) in animals[4]. The name P-type derives from the fact these proteins exploit a phosphorylated reaction cycle intermediate of ATP hydrolysis[5]. The plasma membrane proton pumps are included in the type III P-type ATPase subfamily while $Na^+$, $K^+$-ATPase and $Ca^{2+}$-ATPase belong to the type II subgroup[6]. Electron microscopy has revealed the overall shape of proton pumps[7], however an atomic structure has been lacking. Further data have been obtained by comparison on the primary structure with structural data obtained for a $Ca^{2+}$ ATPase[42], but this has not provided significant insight into the specific function of H+ proton pumps.

Proton translocating ATPases are essential for plant and fungi. Inhibitors of $H^+$ ATPase therefore have applicability as herbicides and fungicides.

So far no selective H+-ATPase inhibitor has been identified. Vanadate is a potent inhibitor of plasma membrane H+-ATPases. Vanadate is a phosphate analogue that inhibits the pumps in its plus 5 valence state at low concentrations (µM range). Vanadate is however not selective for plasma membrane H+-ATPases as it inhibits all other P-type ATPases as well as many other enzymes which make use of ATP. For this reason there seem to be no therapeutic potential for vanadate.

Some specific inhibitors for other P-type ATPase have been identified, such as the cardiac glycosides which potently inhibit the Na+, K+ ATPase.

The H+/K+-ATPases mediates gastric acid secretion in animal cells when H+ is extruded in exchange for K+. Clinical blockage of H+/K+-ATPase pump activity is employed in the treatment of many human disease conditions such as dyspepsia, peptic ulcer disease, prevention of stress gastritis, gastrinomas and other conditions that cause hypersecretion of acid. Clinically used proton pump inhibitors are substituted pyridylmethylsulfinyl benzimidazole drugs. H+/K+-ATPase specific inhibitors Omeprazole, Lansoprazole, Esomeprazole and Pantoprazole are among the most selling drugs in the world. The inhibitors bind from the extracellular face of the enzyme to the transmembane domains of the protein. Hereby they restrain pump activity by blocking the ion transport pathway going trough transmembrane domains.

The Sarcoplasmic Endoplasmic Reticulum $Ca2_+$-ATPase (SERCA) transport cytosolic calcium into intracellular compartments. Selective and potent inhibitors are known for SERCA (Inesi et al., 2005), and might have a therapeutic potential in prostate cancer (Denmeade and Isaacs, 2005). A plant derived sesquiterpene lactone, thapsigargin is highly effective in blocking SERCA with a Kd in the sub-nanomolar range. Thaspsigargin binds in a cavity bordered by transmembrane helix (M) M3, M5 and M7, part of the $Ca2_+$ transport pathway, and blocks conformational transitions of the pumps. Other specific inhibitors are DBHQ (2,5-di(tert-butyl)hydroquinone), CPA (cyclopiazonic acid) and Br2-TITU (1,3-dibromo-2,4,6-tris (methyl-isothio-uronium)benzene). The DBHQ and CPA binding sites are close to the thapsigargin binding site, and the inhibitory mechanism is similar to that of thapsigargin. The binding site of TITU is not known.

Caloxins are specific inhibitors of plasma membrane $Ca2_+$-ATPases (PMCA), and inhibition is established when caloxins binds to small extracellular domains of the pump molecule. Caloxins are peptide inhibitors, and are highly selective towards PMCA's. PMCA's extrude calcium from the cells, and defects in the activity of these pumps have been demonstrated to be associated with hypertension and decreased sperm mobility. Caloxins could potentially be used as contraceptive agents or to modulate artery blood pressure.

The SERCA-type $Ca^{2+}$-ATPase of the malaria-inducing parasite *Plasmodium falciparum* has been pinpointed as the target of the widely used anti-malarial drug artemisinin. Mutational studies suggest that the binding site is near that of thapsigargin and that the inhibitory function is similar (review: Golenser J, Waknine J H, Krugliak M, Hunt N H, Grau G E., Current perspectives on the mechanism of action of artemisinins. Int J Parasitol. 2006 December; 36(14):1427-41)

As seen from the above specific inhibitors of different ATPases have various applications. Until now no specific inhibitors of the H+-ATPases are known. This may be accounted for by the lack of knowledge regarding the functionality of the H+ATPase. Several studies have aimed ad clarifying the overall structure of H+ ATPase based on structural data obtained from different ATPases, such as the SERCA ($Ca2_+$ pump) as mentioned above. The structural models have been useful for identifying areas of similarity but the areas which are different, and therefore expected to be responsible for the selectivity of the pumps can not be envisioned with a sufficient level of detail from these model structures. Thus so far no selective H+ pump inhibitors have been identified.

In order to solve this problem the availability of high quality structural data of a H+pump may be of great help.

The previous lack of structural data of sufficient quality can be attributed to the difficulties encountered when expressing, purifying and crystallizing trans-membrane proteins and in particular complex proteins as type III P-type ATPase's.

Inhibitors of fungi H+ ATPases may be used in the treatment of fungal infections.

Inhibitors of H+ ATPases further have applications in agricultural industry as weed killers (herbicides) and fungicides.

BRIEF DESCRIPTION OF THE DRAWINGS

FIG. 2a provides a view of the N-(red) and P-(blue) domains of the H+-ATPase with bound Mg-AMPPCP together with the experimental electron density map contoured at 1 σ. FIG. 2b provides a view of the transmembrane region with the experimental electron density map contoured at 1 σ. FIG. 2c shows AHA2 (orange) aligned to the $Ca^{2+}$-ATPase (blue, PDB code 1T5T) on transmembrane segments M4 and M5. FIG. 2d provides a structural comparison between AHA2 and sarcoplasmic reticulum SERCA1a $Ca^{2+}$-ATPase.

FIG. 3a shows distribution of charged residues (Arg/Lys, blue; Asp/Glu, red) in the transmembrane region of the pump shown together with the identified intramembranous cavity (blue mesh). FIG. 3b presents a side view of the cavity and the residues lining it. FIG. 3c provides a corresponding top view of the cavity and the residues lining it.

FIG. 5a shows examples of AHA2 crystals. FIG. 5b shows a diffraction-image from the dataset named 'Native 1' in Supplementary Table I. FIG. 5c shows that the asymmetric unit contains two ATPase molecules (blue and green respectively) which interact via their N-domains (shown in lighter colour).

FIG. 8a provides an overview of AHA2 with experimental electron density (contoured at 1 σ). FIG. 8b representes a close up of M7 and M10 shows the fit of experimental electron density (1 σ) to the residues. FIG. 8c shows a side view of experimental electron density (1 σ) around the transmembrane proton binding site. FIG. 8d shows a top view of experimental electron density (1 σ) around the transmembrane proton binding site. FIG. 8e shows electron density (1 σ) around the transmembrane proton binding site. FIG. 8f shows an experimental electron density map (grey mesh) and the $2F_o-F_c$ electron density map (orange mesh) of the Mg-AMPPCP.

FIG. 9 illustrates an alignment of H+ATPases from different plant and fungal species. FIG. 10A shows an overview of the plasma membrane proton pump (AHA2). FIG. 10B provides a view of the plasma membrane proton pump seen from the extracellular side of the protein. FIG. 10C represents a magnification of a portion of FIG. 10 B.

FIG. 11A provides an overview of the plasma membrane proton pump (AHA2). FIG. 11B shows the Pt ion coordinated by residues from M3, M4 and the P. FIG. 11C shows coordination of the Pt ion with Thr315(P domain), Ser294(M4) and Gln237(M3).

FIG. 13 illustrates data including atomic coordinates for the crystal structure of AHA2.

SUMMARY OF INVENTION

Figure 1:
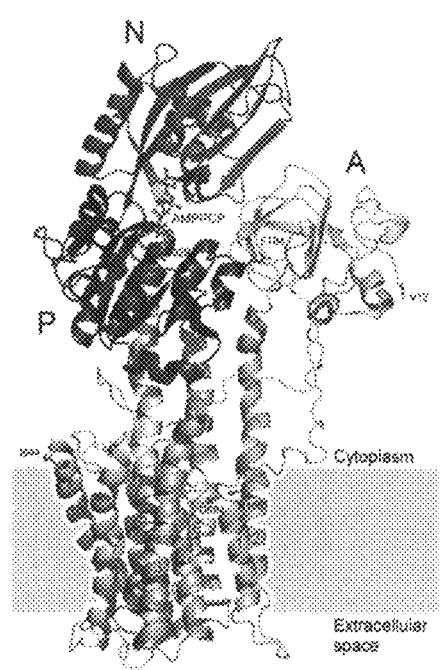
FIG. 1 illustrates an overall structure of a plasma membrane H+-ATPase including an active form of the proton pump without its auto inhibitory C-terminus in complex with Mg-AMPPCP.

The applicant has successfully achieved crystals of a plasma membrane $H^+$ ATPase and method for expressing, purifying and growing of crystals are disclosed herein. In further aspects the inventions relates to method of employing the structural information form identification of potential inhibitors of type III P-type ATPases.

The present invention provides a three dimensional structure of a P-type proton pump determined by X-ray crystallography with a resolution of 3.6 Å. Ten transmembrane helices and three cytoplasmic domains define the functional unit of ATP-coupled proton transport across the plasma membrane and the structure. Data are provided demonstrating a functional state not previously observed in type III P-type ATPases. The transmembrane domain reveals a large cavity likely to be filled with water and located near the middle of the membrane plane where it is lined by conserved hydrophilic and charged residues. Proton transport against a high membrane potential is explained by this structural arrangement. The structural data was obtained base on expression of the plasma membrane ATPase (AHA2) SEQ ID NO: 1 as described in details below which was purified from yeast (se below) and subjected to a method of growing proteins crystals as described here below.

An aspect of the invention relates to a crystal comprising a type III P-type ATPase, which is preferably a plant ATPase or fungal ATPase.

The crystal may comprise the ATPase as part of a complex with an organic compound such as ATP or ATP analogues such as AMPPCP. The ATPase crystal may further comprises one or more cations selected from the group of: $H^+$, $Mg^{2+}$, $Ho^{3+}$, $K^+$, $Pt^{4+}$ and $Ta^{2+}$. Preferably the crystal effectively diffracts x-rays for the determination of the atomic coordinates of the protein to a resolution better than 5 Å.

An aspect of the invention relates to a method of purification of a type III P-type ATPase which included solubilising the ATPase using dodecyl-maltoside (DDM). The method may further comprise dialysing against a composition comprising $C1_2E_8$ and/or Cymal-5 in order to optimise the purified protein composition for crystallization experiments. Both the ratio of DDM and the concentration of $C1_2E_8$ and/or Cymal-5 may be adjusted to improve the method.

A further aspect of the invention relates to a method of growing a crystal comprising a type III P-type ATPase according to the invention comprising the steps of:
  a. obtaining a composition comprising a type III P-type ATPase,
  b. subjecting said composition to a crystallization environment including PEG 400 and
  c. obtaining crystals comprising a type III P-type ATPase.

Preferably by vapour diffusion from hanging drops with a reservoir buffer containing PEG 400, wherein the concentration of PEG 400 is 25-40% (w/v), such as 27-35% (w/v) or 29-32% (w/v).

According to the invention a crystal may be used for determination of the three dimensional structure of a type III P-type ATPase.

The invention further relates to a computer-readable data storage medium comprising a data storage material encoded with at least a portion of the structure coordinates set forth in FIG. 13.

An aspect of the invention relates to the use of atomic coordinates as presented in FIG. 13 or atomic coordinates selected from a three-dimensional structure that deviates from the three-dimensional structure as presented in FIG. 13 by a root mean square deviation over protein backbone atoms of not more than 3 Å, in a method for identifying a potential inhibitor of a type III P-type ATPase.

Further methods as described herein are aspects of the invention, which based on the three dimensional structure of the *A. thaliana* AHA2 SEQ ID NO: 1. ATPase enables identification of potential inhibitors of type III P-type ATPase. Such methods implies in silico method steps such as generating the spatial structure of the proton transport pathway and potential inhibitors on a computer screen and selection of potential inhibitors.

Such methods are thus computer assisted methods (CAMs) or computer implemented methods (CIMs), based on the information derived from the three-dimensional structure disclosed herein. The methods use a programmed computer processor, a data storage system, a data input devise and a data output devise and comprise steps of inputting structure data into the programmed computer, and comparing, using said processor, the structure data to a computer data base of low molecular weight organic chemical structures stored in the data storage system; and selecting from said data base, using computer methods, a chemical structure having a portion that is structurally complementary to the structure data and being free of steric interference with the ATPase. The methods may use computer method for constructing a model of a chemical structure having a portion that is structurally complementary to the criteria data set and being free of steric interference with the ATPase A method for identifying a potential inhibitor capable of inhibiting the H+ translocating activity of a type III P-type ATPase, said method comprising the following steps:

a. selecting a potential inhibitor using atomic coordinates in conjunction with computer modelling, wherein said atomic coordinates are the atomic coordinates presented in FIG. 13 or wherein the atomic coordinates are selected from a three-dimensional structure that deviates from the three-dimensional structures presented in annexes 1 by a root mean square deviation over protein backbone atoms of not more than 3, by docking potential inhibitors into a set of binding interaction sites in a proton transfer pathway generated by computer modelling and selecting a potential inhibitor capable of binding to at least one amino acid in said proton transport pathway, b. providing said potential inhibitor and said ATPase, c. contacting the potential inhibitor with said ATPase and d. detecting inhibition of H+ translocating activity of said ATPase by the potential inhibitor.

Preferably docking of potential inhibitor molecules is performed by employing a three-dimensional structure defined by atomic coordinates of the three dimensional structure presented in FIG. 13 and such that said potential inhibitor is capable of binding to at least two amino acid or at least three amino acids in the proton transport pathway.

A method for identifying a potential inhibitor capable of inhibiting the H+ translocating activity of a type III P-type ATPase, said method comprising the following steps:

a. introducing into a computer information derived from atomic coordinates defining a conformation of the proton transport pathway, based on three-dimensional structure determination, whereby said program utilizes or displays on the computer screen the structure of said conformation, wherein the atomic coordinates are selected from the three-dimensional structure as presented in FIG. 13 or atomic coordinates selected from a three-dimensional structure that deviates from the three-dimensional structures as presented in FIG. 13 by a root mean square deviation over protein backbone atoms of not more than 3 Å, b. generating a three-dimensional representation of at least on of the three regions of the proton transport pathway of said ATPase by said computer program on a computer screen, c. superimposing a model of a potential inhibitor on the representation on at least one of the three regions of the proton transport pathway;

d. assessing the possibility of bonding and the absence of steric interference of the potential inhibitor with the proton transport pathway;

e. incorporation said potential compound in an activity assay of said ATPase and f. determining whether said potential compound inhibits H+ translocating activity of said ATPase.

As described herein the disclosed ATPase structure has revealed new detailed information regarding the proton transport pathway of type III P-type ATPase which may be used in any of the methods according to the invention. It is thus preferred, that the criteria data set, the structure data, the binding interaction sites or the atomic coordinates mentioned include amino acid residues including Pro68 to Asn85 (M1), Pro90 to Ala117 (M2), Asp272 to Met297 (M4), Arg636 to Leu665 (M5) and Ser672 to Thr689 (M6). In further embodiments; Asp684 (M6), Pro68 to Glu74 (M1) and Leu103 to Glu114 or Asp 684, Ile287 to Met297 (M4), Arg636 to Asn644 (M5) and Gly685 to Thr689 (M6) or Asp684, Asn 106, Glu74 to Asn85 (M1), Pro90 to Val104 (M2), Asp272 to Ile282 (M4), Ile656 to Leu665 (M5) and Ser672 to Asn683 (M6) are included SEQ ID NO: 1.

The potential inhibitor may be selected based on binding to at least 1, such as at least 2, or preferably such as at least 3 amino acids in the proton transport pathway.

Further aspects of the invention relates to methods of treatment using inhibitors identified according to the invention. Said inhibitors may be comprised by medicaments, which may be used for treatment of mycoses. Inhibitors may further be used as a fungicide or herbicide.

DETAILED DESCRIPTION OF THE INVENTION

The term "crystal" refers to an ordered state of matter. Proteins, by their nature are difficult to purify to homogeneity. Even highly purified proteins may be chronically heterogeneous due to modifications, structural flexibility, the binding of ligands or a host of other effects.

In addition, proteins are crystallized from generally complex solutions that may include not only the target molecule but also buffers, salts, precipitating agents, water and any number of small binding proteins. It is important to note that protein crystals are composed not only of protein, but also of a large percentage of solvents molecules, in particular water. These contents may vary from 30 to even 90%. Protein crystals may accumulate greater quantities and a diverse range of impurities which cannot be listed here or anticipated in detail. The skilled person knows that some crystals diffract better than others. Crystals vary in size from a barely observable 20 micron to 1 or more millimeters. Crystals useful for X-ray analysis are typically single, 0.05 mm or larger, and free of cracks and other defects.

The term "coordinate" as use herein, refers to the information of the three dimensional organization of the atoms contributing to a protein structure. The final map containing the atomic coordinates of the constituents of the crystal may be stored on a data carrier; typically the data is stored in PDB or CIF format which are known to the person skilled in the art. The PDB and CIF formats are organized according to the instructions and guidelines given by the Research Collaboratory for Structural Bioinformatics.

The term "root mean square deviation"(rmsd) is used as a mean of comparing two closely related structures and relates to a deviation in the distance between related atoms of the two structures after structurally minimizing this distance in an alignment. Related proteins with closely related structures are characterized by relatively low RMSD values whereas more changes results in an increase of the RMSD value.

The term "associating with" or "binding" refers to a condition of proximity between chemical entities or compounds, or portions thereof. The association may be non-covalent-wherein the juxtaposition is energetically favoured by hydrogen bonding or van der Waals or electrostatic interactions-or it may be covalent.

The term "binding pocket", as used herein, refers to a region of a molecule or molecular complex, that, as a result of its shape, favourably associates with another molecule, molecular complex, chemical entity or compound. As used herein, the pocket comprises at least a deep cavity and, optionally a shallow cavity.

As used herein the term "complex" refers to the combination of a molecule or a protein, conservative analogues or truncations thereof associated with a chemical entity.

H+ ATPase Crystal

An aspect of the invention relates to a crystal which comprises a type III P-type ATPase.

Depending on the resolution of a crystal structures different information can be obtained from the data. At a resolution of about 6 Å the overall shape of molecular parts is resolved, such as α-helices that are seen as rods with strong intensity. At a resolution of about 3.5 Å the main chain is visible (usually with some ambiguities). At a resolution of about 3 the side chains are partly resolved. At a resolution of about 2.5 the side chains are well resolved. The atoms are located within about 0.4 Å meaning that the lengths of hydrogen bonds calculated from a PDB file (for example, by RasMol) have at least this uncertainty. The normal limit of protein crystallography is around 1 Å or slightly less, where atoms are located at below ±0.1 Å[44].

The crystal of the invention preferably effectively diffracts x-rays for the determination of the atomic coordinates of the protein to a resolution better than 6 Å. More preferably the three dimensional structure determinations can be determined with a resolution better than 5 Å, such as better than 4 Å or most preferably about 3.5 Å or better using the crystals according to the invention. Most preferably the crystal effectively diffracts x-rays for the determination of the atomic coordinates of the protein to a resolution of 3.6 Å

The space group of crystals according to the invention is preferably $P2_12_12_1$ and the cell dimensions are preferably 85±4 Å, 144±4 Å, 312±4 Å. The cell dimensions can according to the application vary depending on the specific ATPase comprised by the crystal an even on the conformation of the ATPase comprised by the crystal.

Type III P-type ATPase

The family of Type III P-type ATPase includes a large number proton pumps from plant and fungi. An alignment of including 22 members of the family is disclosed herein (FIG. 9) which demonstrated the conservation of the molecules. AHA1, AHA2 SEQ ID NO: 1 and AHA6 from *A. thaliana*, PMA1 from *Candida albicans*, plasma membrane H+-ATPase from *Cryptococcus neoformans*, PMA1 from *Neurospora crassa* and PMA 1 from *Saccharomyces cerevisiae* is included in the scheme together with homologous genes from several other species.

In a preferred embodiment the invention relates a crystal comprising a type III P-type which is derived from a plant species. In a more preferred embodiment the ATPase is the AHA 2 ATPase identified by SEQ ID NO 1, which is the upper sequence of the alignment presented in FIG. 6.

The invention further encompasses type III P-type ATPase from different species such as yeast or other fungi. Such ATPase from other species can be interpreted as homologues of the AHA2 ATPase identified by SEQ ID NO 1. According to the inventions homologues of the AHA2 ATPase identified by SEQ ID NO 1 also covers sequences obtained by modifications of a type III P-type ATPase. The level of identity is preferably measured by comparison of the sequence with SEQ ID NO1.

A "predetermined sequence" is a defined sequence used as a basis for a sequence comparison; a predetermined sequence may be a subset of a larger sequence, for example, as a segment of a full-length sequence given in a sequence listing.

In further preferred embodiment of the ATPase is a homologue of AHA2 SEQ ID NO: 1. Homologues of polypeptides can be determined on the basis of their degree of identity with a predetermined amino acid sequence, said predetermined amino acid sequence for the present invention being SEQ ID NO: 1, when the homologue is a fragment, a fragment of the aforementioned amino acid sequences is used from determining their degree of identity (se below).

Accordingly, homologues preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence.

The percent identity is determined with the algorithms GAP, BESTFIT, or FASTA in the Wisconsin Genetics Software Package Release 7.0, using default gap weights.

The term "sequence identity" means that two polypeptide sequences are identical (i.e., on a residue-by-residue basis) over the window of comparison. The term "percentage of sequence identity" is calculated by comparing two optimally aligned sequences over the window of comparison, determining the number of positions at which the identical amino acid residues occurs in both sequences to yield the number of matched positions, dividing the number of matched positions by the total number of positions in the window of comparison (i.e., the window size), and multiplying the result by 100 to yield the percentage of sequence identity.

The invention relates to a crystal comprising any of the above mentioned ATPases of homologues thereof having, such as more than 85% preferably more than 90% of identity with *A. thaliana* protein AHA (SEQ ID NO 1). The level of identity should be calculated over the homologues sequences with may be such as a fragment of SEQ ID NO 1. The degree of identity may be calculated using suitable available programs, such as the program mentioned herein. The region of homology preferably covers at least 500 AA, such as 600 AA, more preferably 700 AA, most preferably at least 800 AA.

According to the invention the ATPase comprised by the crystal is not the necessarily a full-length protein. Truncated versions can readily be prepared by conventional methods of molecular biology (Sambrook and Russell, 2001). According to the invention it is preferred that the ATPase of the crystal comprise more than 75%, more preferred 80%, and mostly preferred more than 90% of the full length protein sequence, particularly the trans-membrane region should be included, such that the protein includes 5 or more of the trans-membrane helixes, preferably 7 or more, such as 8 or even more preferred 9 or mostly preferred 10 trans-membrane helixes. The trans-membrane helixes are comprised by SEQ ID NO 2-11 (see FIG. 6). Fragments of an ATPase can be joined by ordinary techniques known in the art.

Sequence identity is in one embodiment determined by utilising fragments of AHA2 (SEQ ID NO 1) comprising at least 400 amino acids. Fragments of an ATPase comprising such as most or all of the trans-membrane helixes are preferably used.

A homologue comprising fragments of AHA2 SEQ ID NO: 1 preferably includes least 25 contiguous amino acids of SEQ ID NO 1 and has an amino acid sequence which is at least 80%, such as 85%, for example 90%, such as 95%, for example 99% identical to the amino acid sequence of any of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, respectively. More preferable the homologue comprise a sequence with the aforementioned levels of identity to at least 6, further preferably at least 8, and more preferably at least 9 and mostly preferred all 10 trans-membrane sequences as identified by SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10.

Since two polypeptide sequences may each comprise (1) a portion of the complete polypeptide sequence that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window", as used herein, refers to a conceptual segment of at least 20 contiguous peptide positions wherein a polypeptide sequence may be compared to a predetermined sequence of at least 20 contiguous peptides and wherein the portion of the polypeptide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

In the example described herein the C-terminal regulatory region of 73 AA has been deleted, which with out being bound by the theory have stabilized the protein and thereby enable crystallization of the protein (se below). The ATPase of the examples thus comprise 875×100/948=92.3% of identity with the full length sequence (SEQ ID NO 1) and 100% identity with the ATPase fragment consisting of residue 1-875 if SEQ ID NO 1.

In a preferred embodiment the ATPase comprise a C-terminal truncation compared to the wild type sequence of the protein.

The a preferred embodiment the crystal includes a homologue of a type III P-type ATPase, such as the AHA 2 ATPase, wherein one ore more of the amino acids corresponding to Pro68, Leu69, Val72, Glu74, Ala76, Met79, Leu83, Asp92, Asp95, Ile99, Leu102, Val104, Asn106, Ser107, Ile109, Ser110, Phe111, Glu113, Glu114, Ile274, Leu278, Leu280, Ile282, Gly284, Ile285, Pro286, Ile287, Ala288, Met289, Val292, Ser294, Phe639, Gln640, Arg641, Met642, Tyr645, Tyr648, Ser651, Thr653, Ile654, Arg655, Ile656, Phe659, Leu661, Leu677, Ile678, Ile679, Ala680, Leu682, Asp684, Met688 and Thr689 are conserved or substituted by an amino acid residue with similar properties, e.g. the ATPase may comprise conserved amino acid substitutions (see below). Preferably more than 1, more than 2, more than 5 AA of the above mentioned AA are conserved or represented by a conserved amino acid substitution. Preferably the ATPase homologue comprised by the crystal comprise all of the above mentioned amino acids residues or alternatively the ATPase may comprise conserved amino acid substitutions for one or more of the mentioned amino acid residues.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, homologues are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)

iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphor-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a homologue or a fragment thereof according to the invention may comprise, within the same homologue of the sequence or fragments thereof, or among different variants of the sequence or fragments thereof, at least one substitution, such as a plurality of substitutions introduced independently of one another.

It is clear from the above outline that the same homologue or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

In addition to conservative substitutions introduced into any position of a preferred predetermined sequence, or a fragment thereof, it may also be desirable to introduce non-conservative substitutions in any one or more positions of such a sequence.

A non-conservative substitution leading to the formation of a functionally equivalent fragment of XXX would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Homologues obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take several of the foregoing characteristics into consideration are well known to those of skill in the art and include: arginine and lysine; glutamate and aspartate; serine and threonine; glutamine and asparagine; and valine, leucine and isoleucine.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554, 101).

ATPase Complex

In order to stabilize the protein one or more compounds may be added during purification of the ATPase (see below) enabling formation of an ATPase complex suited for crystallization. This may further enable fixing of the protein in a specific state which is needed to obtain detailed information regarding the functionality of the ATPase.

According to the invention the crystal may comprise one or more compounds for stabilising the protein, such as ATP, ATP analogues (such as AMPPCP), or ADP or ADP analogue, or other nucleotide analogues for which the ATPase has suitable affinity for use in structural determination. Such analogues may provide stability by fixing the protein in a specific state. In an embodiment the crystal comprises a non-hydrolysable ATP analogue preferably AMPPCP.

For various purposes different cations may be included in the crystal. Such cations may be included in the crystal by growing the crystal in the presence of said cations or by submerging the crystals in a solution comprising cations. Heavy atoms that bind to the protein are frequently included in protein structure determination projects to obtain phase information.

The crystal structure may further comprise cations such as a cations selected from the group of: $H^+, Mg^{2+}, Ho^{3+}, K^+, Pt^{4+}$ and $Ta^{2+}$.

The crystal structure may according to the invention further comprise remains from the buffer composition used during the crystallisation process, such as one or more compounds selected from the group of poly ethylene glycols (PEGs) comprising: PEG 100, PEG 200, PEG 400, PEG 600, PEG 800, PEG 1000, PEG 2000, PEG 3000, PEG 4000, PEG 5000, PEG 6000, PEG 7000 and PEG 8000.

HEPES, Mes, and MOPS are further standard buffers which according to the invention can be comprised by the crystal.

The crystal may further comprise such as one or more compounds selected from the group of salts ions comprising cations and an-ions: Mg, Ca, Na, Cl, Br, I, Rb, P, S, K, Mn, Zn, Cu, B, Mo, Se, Si and Co Preferably the crystal comprise: KCl, Mes, sucrose and PEG 400

Source

The protein material subjected to crystallization experiments according to the invention may be obtained from various sources, such as purified from plant, fungal or protest or archaebacterial material.

Alternatively the ATPase may be produced by recombinant method known by a person skilled in the art. Recombination methods enable expression of proteins at a high level wherefore proteins for crystallization experiment is preferably obtain using recombinant methods. The protein may be expressed in a host different from the organism from where the gene is derived. Heterogen expression is widely used in the art although complications may occur, particular when multi-domain proteins are expressed or where secondary modifications are involved. A suitable host providing both a high level of expression and enabling purification of high quality of protein is difficult to identify.

Heterogen expression has several advantages including the ability to manipulate the sequence of the protein to be expressed, as mentioned above a minor truncation of the C-terminus have been used by the applicant as described in the examples. Further advantages relate to the use of tags, which are usually attached to either of the terminals and provides easy purification of the expressed protein. Suitable tag and purification schemes for tagged proteins are well known in the art.

In an embodiment the ATPase comprise a C-terminal or N-terminal tag. In a preferred embodiment the ATPase comprise a MRGSH-6 tag attached to the C-terminal, which is designed to bind Ni-NTA resins.

Suitable host for heterogenic expression of proteins can be bacteria, fungi, yeast, plants and tissue culture cells.

According to the present invention the ATPase is preferably expressed in yeast, more preferably in *Saccharomyces cerevisiae*.

As described in the examples at crystal was prepared using material obtained by expression of the *A. thaliana* AHA2 ATPase SEQ ID NO: 1 in *Saccharomyces cerevisiae*.

Purification

Independent of the source of the ATPase the protein must be purified before crystallization. The purification may be performed by conventional methods known in the art, which may differ dependent on the source of ATPase. Particularly as mentioned above the method of purification may depend on the use of one or more particular tags.

Solubilization

ATPases of the invention are transmembrane proteins and thus comprises domains which are membrane integral as well as both intra and- extra cellular domains. Thus both hydrophilic and hydrophobic domains are present which complicates expression and purification of the protein. Detergents are usually required for solubilisation of membrane proteins, but such detergents often interfere with crystallization.

The applicant has success full established a procedure for expression, purification and crystallization of a P-type type IIIA ATPase.

The protein is expressed in *Saccharomyces cerivisiae* and the membrane fractions collected by a series of sequential centrifugation steps (se examples). The ATPase according to the invention is solubilised in a suitable detergent.

Preferred detergents include dodecyl-maltoside (DDM), 5-Cyclohexyl-1-pentyl-β-D-maltoside (Cymal-5) and Poly-oxyethylene(8)dodecyl ether ($C_{12}E_8$).

An aspect of the invention relates to a method of purification of a type III P-type ATPase comprising solubilising the ATPase using dodecyl-maltoside A method of purification of a type III P-type ATPase comprising the following steps:
 a. obtaining a compositions comprising a type III P-type ATPase,
 b. solubilising said ATPase using dodecyl-maltoside (DDM),
 c. purifying said ATPase.

DDM are preferably used in a ratio of DDM to protein of 3:1 w:w.

The purification of the ATPase may further include a step of dialysis as a pre-crystalization step. Compounds such as octa-ethyleneglycol mono-n-dodecylether ($C_{12}E_8$) and 5-cyclo-hexyl-1-pentyl-β-D-maltoside (Cymal-5) may be added to the dialysis buffer.

The method may further include a step of:
 d. dialysing against a dialysis composition comprising $C_{12}E_8$ and/or Cymal-5.

The concentrations of the compounds are preferably 0.09 mM of $C_{12}E_8$ and 2.4 mM of Cymal-5.

A detail method according to the application is described in the example section.

Method of Growing ATPase Crystal

Growing of a crystal comprising a type III P-type ATPase may according to the invention be performed by any suitable method known in the art, such as vapour diffusions methods and/or hanging drops systems known by the person skilled in the art.

As described above the crystal may contain one or more compounds/cations, such as ATP, ATP analogues and/or cations conveniently added after the purification process and before crystallization is initiated. Alternatively crystals made be submerged in a solution comprising the indication compounds/cations.

An aspect of the invention relates to a method of growing crystal comprising a type III P-type ATPase. Such method includes the steps of obtaining an ATPase composition of sufficient quality for growing of a crystal and growing of ATPase crystals. As described herein, both steps can be modulated to optimise the out come.

In an embodiment the invention relates to a method for growing a crystal comprising a type III P-type ATPase comprising the steps of:
  a) obtaining a composition comprising a type III P-type ATPase,
  b) growing type III P-type ATPase crystals and thereby
  c) obtaining a crystal comprising a type III P-type ATPase.

In a preferred embodiment the invention relates to a method for growing a crystal comprising a type III P-type ATPase comprising the steps of:
  a) obtaining a composition comprising a type III P-type ATPase comprising solubilising the ATPase in dodecyl-maltoside (DDM) or/and dialysing the composition against a composition comprising $C_{12}E_8$ and/or Cymal-5 and
  b) growing ATPase crystals and thereby
  c) obtaining a crystal comprising a type III P-type ATPase.

The method of growing crystals according to the invention preferably comprises using vapour diffusion in 4 µl hanging drops with a reservoir containing a suitable buffer. For growing of crystals a precipitant is included in the reservoir buffer.

In a preferred embodiment the hanging drop experiment is sealed by vacuum grease or other sealant with low permeability (as compared to immersion oil). Most preferably the hanging drop experiment is set up at 20° C. (for a maximum time of 10-15 minutes) and then incubated without disturbances at 4° C. In the optimal procedure for the hanging drop experiment is initiated by mixing 2 µl reservoir solution and 2 µl protein solution, incubating for one minute, spinning the mixture on a tabletop centrifuge for one minute and placing the supernatant in the hanging drop chamber.

Initiation of crystal formation, also known as nucleation can be performed by lowering the solubility of the ATPase. According to the invention PEG is included in the crystallization environment. PEG is preferably selected from the group of PEGs comprising: PEG 100, PEG 200, PEG 400, PEG 600, PEG 800, PEG 1000, PEG 2000, PEG 3000, PEG 4000, PEG 5000, PEG 6000, PEG 7000 and PEG 8000. Likewise PMEs and/or MMEs may be used.

In order to initiate crystallization of proteins various precipitating agents can be used. The precipitating agent is preferably included in the crystallization environment. The precipitating agent may be comprised by the buffer of the reservoir, when the crystals are grown by the vapour diffusion method.

Preferably, PEG 400 is used as precipitant.

In a preferred embodiment the method of growing a crystal comprising a type III P-type ATPase comprises the steps of:
  a. obtaining a composition comprising a type III P-type ATPase,
  b. growing ATPase crystals by vapour diffusion from hanging drops with a reservoir containing PEG 400 and thereby
  c. obtaining crystals comprising a type III P-type ATPase.

The concentration of the precipitating agent can be optimized. According to the invention a concentration of 25-40% (w/v) PEG 400 is preferred, more preferred is a concentration of 27-35% (w/v) and mostly preferred is a concentration of 29-32% (w/v) PEG 400.

In a most preferred embodiment the reservoir buffer comprise 29-32% (w/v) PEG 400, 100 mM KCl, 100 mM Mes pH 6.0 and 5% sucrose.

The crystal structure of H$^+$-ATPase (AHA2) SEQ ID NO: 1 from *A. thaliana* was obtained as described in Example 1 and summarized here below.

Figure 2:
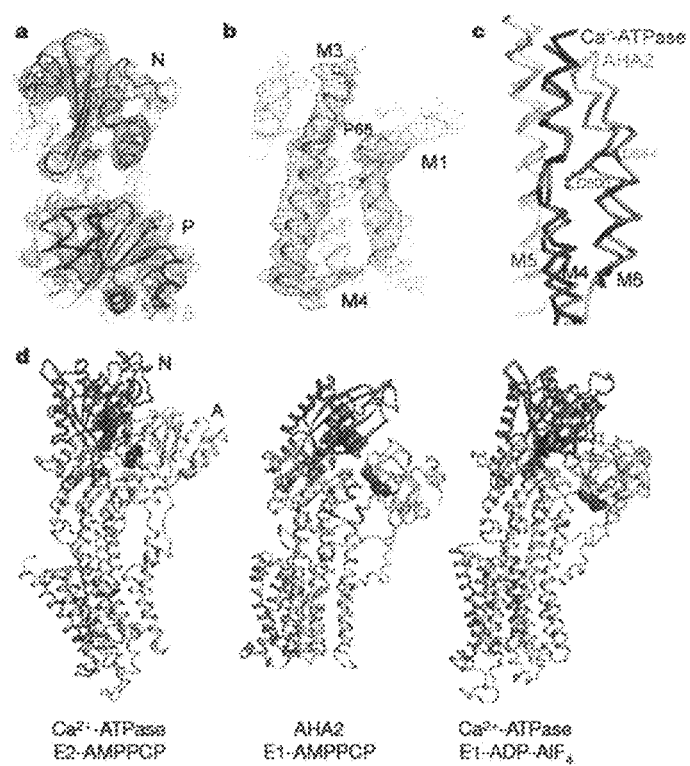
FIGS. 2a through d illustrate structural conservation of P-type ATPase architecture.
Figure 4:
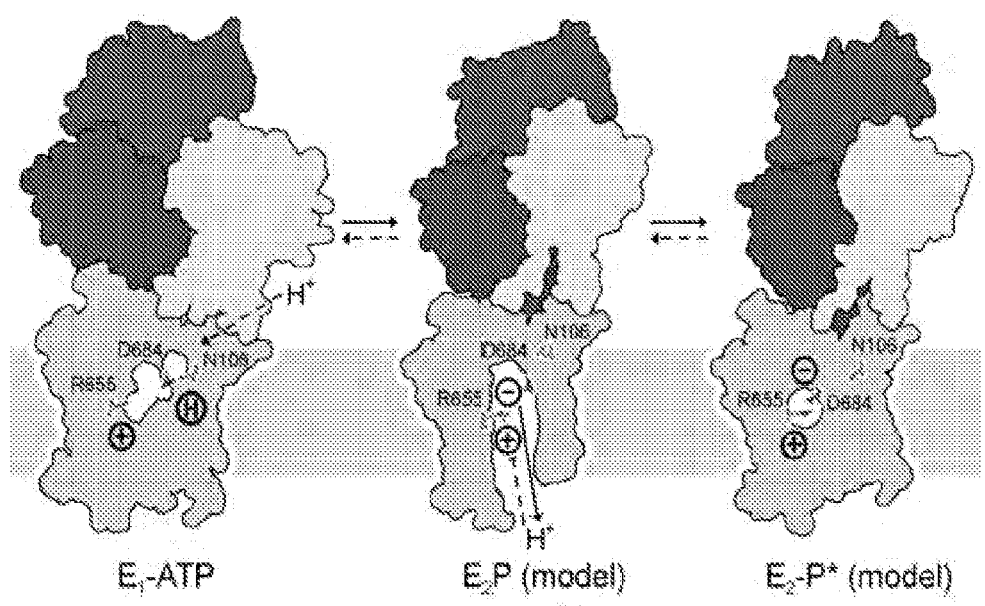
FIG. 4 illustrates a mechanism of proton transport by a plasma membrane H+-ATPase.

Expression and purification was based on a *Saccharomyces cerevisiae* expression system. Solubilisation and purification was performed with dodecyl-maltoside (DDM) as the detergent and the purified protein was dialysed against a buffer containing octaethylene glycol monododecyl ether ($C_{12}E_8$) and 5-cyclohexyl-1-pentyl-β-D-maltoside (CYMAL-5) detergents. Crystals were obtained using polyethylene glycol 400 as the precipitant. Crystals were cryoprotected by controlled dehydration procedure by vapour diffusion, which also improved diffraction properties. Crystallographic data were collected at the beam line X06SA of the Swiss Light Source (SLS). Phases were determined using derivative crystals with $HoCl_3$, $K_2PtCl_6$ and $Ta_6Br_{12}$, respectively. Heavy-atom derived phases were refined and extended at the maximum resolution of the native data by density modification, exploiting twofold rotational NCS, a solvent content of 75% and several data sets displaying low level of isomorphism for inter-crystal averaging. The experimental electron density was of high quality showing continuous backbone density, but lacking detail due to anisotropy and low resolution of the data (FIG. 2, Supplementary FIG. 4). Final refinement using data extending to 3.6 Å resolution produced a model with a crystallographic R-factor of 35.1% and a free R-factor of 36.5%. Details of the biochemical and crystallographic procedures as well as of data processing are given in the online PDF and in the full-text HMTL version of the paper online.

The Data are Summarized in Table 1

Those of skill in the art will understand that a set of structure coordinates for a protein or protein complex or a portion thereof, is a relative set of points that define a shape in three dimensions. Thus, it is possible that an entirely different set of coordinates could define a similar or identical shape. The variations in coordinates may be generated by mathematical manipulations of the structure coordinates. For example, the structure coordinates set forth in FIG. 13 could be manipulated by crystallographic permutations of the structure coordinates, fractionalization or matrix operations to sets of the structure coordinates or any combination of the above.

Coordinates Stored on Machine Readable Storage Medium

In a further aspect the invention provide a computer-readable data storage medium comprising a data storage material encoded with the structure coordinates, or at least a portion of the structure coordinates set forth in FIG. 13. Examples of such computer readable data storage media are well known to those skilled in the art and include, for example CD-ROM and diskette ("floppy disks"). Thus, in accordance with the present invention, the structure coordinates of an ATPase, and portions thereof can be stored in a machine-readable storage medium. Such data may be used for a variety of purposes, such as drug discovery and X-ray crystallographic analysis of protein crystal.

The storage medium may further be local to a computer or the storage medium may be located in a net-worked storage medium including the internet, to which remote accessibility is possible.

Use of Crystal

Provided that crystals of sufficient quality have been obtained, the crystals may according to the invention be used for X-ray diffraction experiments.

An aspect of the invention relates to the use of a crystal comprising a type III P-type ATPase for determination of the three dimensional structure of said ATPase.

Before data collection crystals may be treated by standard methods known in the art.

Crystals are according to the invention preferably dehydrated, by conventional methods such as using cryo-prolectants such as sucrose, glycol and salt etc. Dehydration may be performed by increasing the concentration of the precipitating agent, such as PEG 400, which according to the invention is preferably increased to 40% in the reservoir. Most preferably this increase is performed in a stepwise manner over two days, with an increase to 35% PEG 400 the first day and an increase to 40% PEG400 the second day.

Before data collection crystals may be treated by standard methods known in the art. Which include preparation of samples for heavy atom derivatization by dusting a dry powder of $Ta_6Br_{12}$ or Orange Pt directly to the drop until the crystal appears light green or faint orange, respectively.

The crystals are thereafter mounted in nylon loops and flashed cooled in liquid nitrogen.

Data collection and data processing can be performed by any suitable systems know by the person skilled in the art. Data may be collected using the Swiss Light Source X06SA beamline on a Mar225 CCD detector. Processing may be performed using XDS[31]. Data processing is further described in the examples.

Method Using Information Derived from a Three Dimensional Structure of an ATPase Three dimensional structures provide information regarding the spatial localization of the amide backbone and the side chains of the protein. Such information can not be derived from the primary amino acid sequence or from the knowledge of the secondary structure of the protein. The protein crystal diffraction pattern determines the level of details (resolution) that can be obtained. The quality of a three dimensional structure is evaluated by the resolution obtained, which is an expression for the minimum spacing observed in differentiation. As mentioned above the application relates to crystals of high quality e.g. crystals with a resolution of less than 6 Å preferably less than 4 Å, most preferably around 3.6 Å or less, which is required to have a sufficiently detailed model for selecting potential binding molecules e.g. modulators such as inhibitors of H+ATPase activity.

In order to employ virtual screening (by database docking programs such as Dock, FlexX, Gold) detailed information of the molecule is necessary. Based on the three dimensional structure disclosed herein the proton transport pathway trough the transmembrane part of the molecules was identified (see example and below).

The Proton Transport Pathway

The obtained structural information allows delineation of the proton transport pathway into a proton inlet channel, an active site, and a proton release pathway. These areas of the molecule are very conserved among plasma membrane H+-ATPases, and all three areas of the pump are targets for the design and generation of selective inhibitors of plasma membrane H+-ATPases. As catalytic transitions necessary for the pump molecule to perform proton transport involves the creation of a large aqueous vestibule between the transmembrane domains, these three areas of the molecule should be accessible for drugs from the extracellular side of the enzyme. This is extremely favorable with respect to drug design and drug administration in analogue with inhibitors for other P-type ATPases.

The proton transport pathway of plasma membrane H+-ATPases is structurally defined by transmembrane helices M1 (Pro68 to Asn85 in AHA2 SEQ ID NO: 1), M2 (Pro90 to Ala117 in AHA2 SEQ ID NO: 1), M4 (Asp272 to Met297 in AHA2 SEQ ID NO: 1 ), M5 (Arg636 to Leu665 in AHA2 SEQ ID NO: 1) and M6 (Ser672 to Thr689 in AHA2 SEQ ID NO: 1). Any ligand with the capacity to bind any of these transmembrane helices, either to a single of these transmembrane helices or to multiple of them, is a potential inhibitor capable of significantly restraining catalytic domain movements and proton pumping (se below). In particular, the plasma membrane H+-ATPase residues; Pro68, Leu69, Val72, Glu74, Ala76, Met79, Leu83, Asp92, Asp95, Ile99, Leu102, Val104, Asn106, Ser107, Ile109, Ser110, Phe111, Glu113, Glu114, Ile274, Asp275, Leu278, Leu280, Ile282, Gly284, Ile285, Pro286, Ile287, Ala288, Met289, Val292, Ser294, Phe639, Gln640, Arg641, Met642, Tyr645, Tyr648, Ser651, Thr653, Ile654, Arg655, Ile656, Phe659, Leu661, Leu677, Ile678, Ile679, Ala680, Leu682, Asp684, Met688 and Thr689 in AHA2 SEQ ID NO: 1 along the proton transport pathway, which are highly conserved are of particular interest as a compound targeting one or more of these residues, is a potential inhibitor of a type III P-type ATPase according to the invention (se below).

The proton inlet channel: The proton inlet channel is defined by M1 and M2 and creates a directional proton inlet pathway going directly to the central proton acceptor/donor (Asp684 in AHA2 SEQ ID NO: 1) on M6. With respect to the cytoplasmic located domains, it is the upper part of M1 (Pro68 to Glu74 in AHA2 SEQ ID NO: 1) and the upper part of M2 (Leu103 to Glu114 in AHA2 SEQ ID NO: 1) that define the proton inlet channel. Creation or identification of any kind of compound with selectivity for the proton inlet channel and the residues lining it will result in obstruction of proton pumping and enzyme conformational transitions and therefore have significant commercial potential. Several highly or completely conserved plasma membrane H+-ATPase residues (Pro68, Leu69, Val72, Glu74, Val104, Asn106, Ser107, Ile109, Ser110, Phe111, Glu113 and Glu114 in AHA2 SEQ ID NO: 1) forms part of the foundation of the proton inlet channel and are of particular interest with respect to drug design. Thus, any compound that targets any of these conserved residues of the proton inlet channel of plasma membrane H+-ATPases would possess broad-spectrum anti H+-ATPase activity.

The active site: The active site of plasma membrane H+-ATPases is defined by AA residues from M2, M4, M5 and M6. The active site consist of a central proton acceptor/donor (Asp684 in AHA2 SEQ ID NO: 1)), an asparagine residue on M2 (Asn106 in AHA2 SEQ ID NO: 1)), positively charged residues (Arg655 in AHA2 SEQ ID NO: 1)) and a centrally located water filled cavity. The cavity is lined by extremely conserved AA (Asn106, Ile282, Gly283, Gly284, Ile285, Pro286, Tyr645, Tyr648, Thr653, Arg655 and Asp684 in AHA2 SEQ ID NO: 1) and provides functionality to at least two features of efficient proton transport. The cavity serves as a proton dump during catalysis and makes the transport pathway of protons across the dielectric barrier of the membrane as short as achievable. Residues from the upper part of M4 (Ile287 to Met297 in AHA2 SEQ ID NO: 1)), M5 (Arg636 to Asn644 in AHA2 SEQ ID NO: 1)) and M6 (Gly685 to Thr689 in AHA2 SEQ ID NO: 1)) aids to define the structure and functionality of the pump molecule and the active proton binding site.

Accordingly, potential inhibitors interacting with any of the residues defining the active site are of special interest. Theses residues are highly conserved between species and necessary for proton transport, furthermore these residues are accessible for administered drugs from the extracellular milieu. Based on this it is with out being bound by the theory expected that any compound that interacts with at least a single of the residues that defines the active site will possess broad-spectrum anti-plasma membrane H+-ATPase activity and be of particular therapeutic and commercial value.

The proton release pathway. During proton transfer, the water molecules in the cavity may be the initial place for proton unloading after proton release from Asp684. The central proton acceptor/donor is together with Asn106 placed at the boundary of this cavity and provides a barrier between the proton inlet channel and the cavity. Hereby the water molecules in the cavity may serve as a delocalized proton binding site and thereby aid in the proton release from Asp684. Conformational changes results in the conjunction of the cavity with the extracellular basin which leads to proton release from the cavity. The merge of the cavity and the extracellular basin during proton release creates a large aqueous vestibule that traverses more than half of the membrane bilayer. This minimizes the effective distance of proton transport.

The creation of the large aqueous vestibule in essence means that administered drugs will have easy access to the proton release pathway and the centrally located cavity.

Residues from M1 (specifically Glu74 to Asn85 in AHA2 SEQ ID NO: 1), M2 (specifically Pro90 to Val104 in AHA2 SEQ ID NO: 1), M4 (specifically Asp272 to Ile282 in AHA2 SEQ ID NO: 1), M5 (specifically Ile656 to Leu665 in AHA2 SEQ ID NO: 1) and M6 (specifically Ser672 to Asn683 in AHA2 SEQ ID NO: 1) together defines the proton release pathway, and any compound either identified or constructed that can bind to either of these areas is with out bing bound by the theory expected to have an inhibitory effect upon H+-ATPase activity and are for this reason be of particular interest with respect to drug design. Many AA (Ala76, Met79, Leu83, Asp92, Asp95, Ile99, Leu102, Val104, Ile274, Asp275, Leu278, Leu280, Ile656, Phe659, Leu677, Ile678, Ile679, Ala680 and Leu682 in AHA2 SEQ ID NO: 1) in the proton release pathway are especially well conserved between species. This means that drugs that interact with one or more of these residues will exhibit broad spectrum anti-H+-ATPase activity.

Identification of Inhibitors

According to the invention various strategies can be followed to identify and generate selective inhibitors of plasma membrane H+-ATPases based on the structural information described herein.

Potential inhibitors that can bind to the conserved proton inlet channel, the active proton binding site and the proton release pathway can be identified for plant and fungal plasma membrane H+-ATPases trough virtual screening of chemical databases. Virtual screening are performed with different database docking programs (for instance Dock, FlexX, Gold, Flo, Fred, Glide, LigFit, MOE or MVP, but not limited to these) and used with different scoring functions (e.g. Warren et. al., 2005; Jain, 2006; Seifert et al., 2007). The scoring functions may include, but are not limited to force-field scoring functions (affinities estimated by summing Van der Waals and electrostatic interactions of all atoms in the complex between the type III P-type ATPase and the ligand), empirical scoring functions (counting the number of various interactions, for instance number of hydrogen bonds, hydrophobic-hydrophobic contacts and hydrophilic-hydrophobic contacts, between the type III P-type ATPase and the ligand), and knowledge based scoring functions (with basis on statistical findings of intermolecular contacts involving certain types of atoms or functional groups). Scoring functions involving terms from any of the two of the mentioned scoring functions may also be combined into a single function used in database virtual screening of chemical libraries.

Identified potential inhibitors are confirmed by in vitro and in vivo experiments before further developments. The binding of modulators may further be confirmed by x-ray experiments. Even when inhibitory activity is confirmed further drug development may be required before a compound suitable as a drug is identified.

As seen from the above and the examples the three dimensional structure described herein as identified the proton transport pathway and based on this knowledge potential inhibitors of a type III P-type ATPase can be identified. It is preferred that the structure used is based on the atomic coordinates presented in FIG. 13, but a structure that deviates from the three-dimensional structures as presented in FIG. 13 by a root mean square deviation over protein backbone atoms of not more than 3 Å may like wise be used. It is preferred that the deviate is less than 2 Å, more preferably less than 1 Å.

Such methods are preferable performed using computers, whereby the atomic coordinates are introduced into the computer, allowing generation of a model on the computer screen which allows visual selection of binding molecules.

Methods of Selecting or Identifying Potential Inhibitors

Preferably, potential inhibitors are selected by their potential of binding to the H+transport pathway. The pathway comprises the three regions described above. Compounds which bind to at least one of these regions can be expected to compete with binding of H+ and/or conformational transitions necessary for performing H+transport, thus functioning as competitive inhibitors of the ATPase. When selecting a potential inhibitor by computer modeling, the 3D structure of the ATPase is loaded from a data storage device into a computer memory and may be displayed (generated) on a computer screen using a suitable computer program. Preferably, only a subset of interest of the coordinates of the whole structure of the ATPase is loaded in the computer memory or displayed on the computer screen. This subset of interest may comprise the coordinates of H+ transport pathway residues. This subset may be called a criteria data set; this subset of atoms may be used for designing an inhibitor.

An aspect of the invention relates to a method of identifying a potential inhibitor of a type III P-type ATPase by determining binding interactions between the potential inhibitor and a set of binding interaction sites in the proton transport pathway of said ATPase comprising the steps of a. generating the special structure of the proton transport pathway on a computer screen using atomic coordinates as presented in FIG. 13 or atomic coordinates selected from a three-dimensional structure that deviates from the three-dimensional structures as presented in FIG. 13 by a root mean square deviation over protein backbone atoms of not more than 3 Å, b. generating the spatial structure of potential inhibitors on the computer screen, and c. selecting potential inhibitors that can bind to at least 1 amino acid residues of the set of binding interaction sites with out steric interference.

In an alternative aspect the potential inhibitors are identified using a computer, wherein the computer comprise programs and processor capable of utilizing the three dimensional structure information for selecting potential inhibitors bases on a criteria data set which defines target regions of the ATPase. Data base of potential inhibitors, such as data bases of low molecular weight organic chemical structures can be stored in the computer, e.g. in a storage system and used by the processor of the computer to identify potential inhibitors which in a region are structurally complementary to the criteria data set and being free of steric interference with the ATPase. Modulators being, in a region, complementary to the criteria data set, can be interpreted as inhibitors capable of accommodating a three-dimensional cavity defined by the criteria data set with out interfering with the structure of the target. Complementary indicates that the ATPase and the modulator interact with each other in an energy favourable way minimizing the availability of polar and charged residues (se below). The storage medium may be local to the computer as described above, or the storage medium may be remote such as a net-worked storage medium including the internet.

The low molecular weight organic chemical structures may include, but are not limited to, structures such as lipids, nucleic acids, peptides, proteins, antibodies and saccharides.

An alternative wording for binding interaction sites set of may be a criteria data set.

A further method according to the invention relates to a computer-assisted method for identifying potential inhibitors of a type III P-type ATPase using a programmed computer processor, a data storage system, a data input devise and a data output devise comprising the following steps:
   a. inputting into the programmed computer through said input device data comprising: a subset of the atoms of a type III P-type ATPase, thereby generating a criteria data set; wherein the atomic coordinates are selected from the three-dimensional structure as presented in FIG. 13 or atomic coordinates selected from a three-dimensional structure that deviates from the three-dimensional structures as presented in FIG. 13 by a root mean square deviation over protein backbone atoms of not more than 3 Å,
   b. comparing, using said processor, the criteria data set to a computer data base of low molecular weight organic chemical structures stored in the data storage system; and
   c. selecting from said data base, using computer methods, a chemical structure having a portion that is structurally complementary to the criteria data set and being free of steric interference with the ATPase.

The invention further relates to a computer-assisted method for identifying potential inhibitors of a type III P-type ATPase using a programmed computer processor, a data storage system, a data input devise and a data output devise comprising the following steps:
   a. inputting into the programmed computer through said input device data comprising: a subset of the atoms of a type III P-type ATPase, thereby generating a criteria data set; wherein the atomic coordinates are selected from the three-dimensional structure as presented in FIG. 13 or atomic coordinates selected from a three-dimensional structure that deviates from the three-dimensional structures as presented in FIG. 13 by a root mean square deviation over protein backbone atoms of not more than 3 Å,
   b. comparing, using said processor, the criteria data set to a computer data base of low molecular weight organic chemical structures stored in the data storage system; and
   c. constructing using computer methods a model for a chemical structure having a portion that is structurally complementary to the criteria data set and being free of steric interference with the ATPase.

According to the invention the criteria data set or the binding interaction site set may comprise amino acids forming the proton transport pathway of plasma membrane H+-ATPases of AHA2 SEQ ID NO: 1 e.g. the following amino acids of the transmembrane helices; Pro68 to Asn85 (M1), Pro90 to Ala117 (M2), Asp272 to Met297 (M4), Arg636 to Leu665 (M5) and Ser672 to Thr689 (M6).

It may preferably comprise at least some of the following amino acid residues: Pro68, Leu69, Val72, Glu74, Ala76, Met79, Leu83, Asp92, Asp95, Ile99, Leu102, Val104, Asn106, Ser107, Ile109, Ser110, Phe111, Glu113, Glu114, Ile274, Asp275 Leu278, Leu280, Ile282, Gly284, Ile285, Pro286, Ile287, Ala288, Met289, Val292, Ser294, Phe639, Gln640, Arg641, Met642, Tyr645, Tyr648, Ser651, Thr653, Ile654, Arg655, Ile656, Phe659, Leu661, Leu677, Ile678, Ile679, Ala680, Leu682, Asp684, Met688 and Thr689.

In a preferred embodiment the data criteria set includes residues from the proton inlet channel, e.g. one or more amino acids selected from any of the AA comprised by Asp684 (M6), Pro68 to Glu74 (M1) and Leu103 to Glu114 (M2), more preferred one or more of the specific residues Pro68, Leu69, Val72, Glu74, Val104, Asn106, Ser107, Ile109, Ser110, Phe111, Glu113 and Glu114 are included.

In a preferred embodiment the data criteria set includes residues from the active site, e.g. one or more amino acids selected from any of the AA comprised by Asp 684, Ile287 to Met297 (M4), Arg636 to Asn644 (M5) and Gly685 to Thr689 (M6), more preferred one or more of the specific residues Asp684, Asn106, Arg655, Asn106, Ile282, Gly283, Gly284, Ile285, Pro286, Tyr645, Tyr648, Thr653, Arg655 and Asp684 are included.

In a preferred embodiment the data criteria set includes residues from the proton release pathway, e.g. one or more amino acids selected from any of the AA comprised by Asn 683, Asn 106, Glu74 to Asn85 (M1), Pro90 to Val104 (M2), Asp272 to Ile282 (M4), Ile656 to Leu665 (M5) and Ser672 to Asn683 (M6) more preferred one or more of the specific residues Ala76, Met79, Leu83, Asp92, Asp95, Ile99, Leu102, Val104, Ile274, Leu278, Leu280, Ile656, Phe659, Leu677, Ile678, Ile679, Ala680 and Leu682 are included.

In the methods described herein the one or more amino acid residues comprised by the data cretera set may be at least one, or at least two, preferably at least 3, more preferably at least 4 or 5 or mostly preferred at least at least 6, 7 or 8 AA selected from the identified groups.

The residues lining the proton transport pathway are described above in relation to description of the proton transport pathway and the definition of criteria data sets are also applicable to further methods according to the invention.

A potential inhibitor may then be designed de novo in conjunction with computer modelling. Models of chemical structures or molecule fragments may be generated on a computer screen using information derived from known low-molecular weight organic chemical structures stored in a computer data base or are built using the general knowledge of an organic chemist regarding bonding types, conformations etc. Suitable computer programs may aid in this process in order to build chemical structures of realistic geometries. Chemical structures or molecule fragments may be selected and/or used to construct a potential inhibitor such that favourable interactions to said subset or criteria data set become possible. The more favourable interactions become possible, the stronger the potential inhibitor will bind to the ATPase. Preferably, favourable interactions to at least one amino acid residues should become possible. Such favourable interactions may occur with any atom of the amino acid residue e.g. atoms of the peptide back-bone or/and atoms of the side chains.

Favourable interactions are any non-covalent attractive forces which may exist between chemical structures such as hydrophobic or van-der-Waals interactions and polar interactions such as hydrogen bonding, salt-bridges etc. Unfavourable interactions such as hydrophobic-hydrophilic interactions should be avoided but may be accepted if they are weaker than the sum of the attractive forces. Steric interference such as clashes or overlaps of portions of the inhibitor being selected or constructed with protein moieties will prevent binding unless resolvable by conformational changes. The binding strength of a potential inhibitor thus created may be assessed by comparing favourable and unfavourable interactions on the computer screen or by using computational methods implemented in commercial computer programs.

Conformational freedom of the potential inhibitor and amino acid side chains of the ATPase should be taken into account. Accessible conformations of a potential inhibitor may be determined using known rules of molecular geometry, notably torsion angles, or computationally using computer programs having implemented procedures of molecular mechanics and/or dynamics or quantum mechanics or combinations thereof.

A potential inhibitor is at least partially complementary to at least a portion of the active site of the ATPase in terms of shape and in terms of hydrophilic or hydrophobic properties.

Databases of chemical structures (e. g. cambridge structural database or from Chemical Abstracts Service; for a review see: Rusinko (1993) Chem. Des. Auto. News 8,44-47) may be used to varying extents. In a totally automatic embodiment, all structures in a data base may be compared to the active site or to the binding pockets of the ATPase for complementarity and lack of steric interference computationally using the processor of the computer and a suitable computer program. In this case, computer modelling which comprises manual user interaction at a computer screen may not be necessary. Alternatively, molecular fragments may be selected from a data base and assembled or constructed on a computer screen e. g. manually. Also, the ratio of automation to manual interaction by a person skilled in the art in the process of selecting may vary a lot. As computer programs for drug design and docking of molecules to each other become better, the need for manual interaction decreases.

A preferred approach of selecting or identifying potential inhibitors of type III P-type ATPases makes use of the structure of the AHA2 SEQ ID NO: 1 of this invention. Analogously to the principles of drug design and computer modelling outlined above, chemical structures or fragments thereof may be selected or constructed based on non-covalent interactions with the potential inhibitor with the H+ transport pathway of an ATPase.

Potential inhibitors may be selected or designed such that they interfere with binding of and organic compound bound by the ATPase, such as ATP or an ATP analogues such as AAMPPCP present in the crystal structure or alternatively any cations associated with the ATPase such as in the structure (see section relating to the ATPase crystal). Such inhibitors may prevent binding of ATP or ATP analogues or cations the ATPase.

Programs usable for computer modelling include Quanta (Molecular Simulations, Inc.) and Sibyl (Tripos Associates). Other useful programs are Autodock (Scripps Research Institute, La Jolla, described in Goodsell and Olsen (1990) Proteins: Structure, Function and Genetics, 8, 195-201), Dock (University of California, San Francisco, described in: Kuntz et al. (1982) J. Mol. Biol. 161,269-288.

The present invention in an embodiment relates to a method for identifying a potential inhibitor capable of inhibiting the H+ translocating activity of a type III P-type ATPase, said method comprising the following steps:

a. selecting a potential inhibitor using atomic coordinates in conjunction with computer modelling, wherein said atomic coordinates are the atomic coordinates presented in FIG. 13 or wherein the atomic coordinates are selected from a three-dimensional structure that deviates from the three-dimensional structures presented in annexes 1 by a root mean square deviation over protein backbone atoms of not more than 3, by docking potential inhibitors into a set of binding interaction sites in a proton transfer pathway generated by computer modelling and selecting a potential inhibitor capable of binding to at least one amino acid in said proton transport pathway,
b. providing said potential inhibitor and said ATPase,
c. contacting the potential inhibitor with said ATPase and
d. detecting inhibition of H+ translocating activity of said ATPase by the potential inhibitor.

In a preferred embodiment docking of potential inhibitor molecules is performed by employing a three-dimensional structure defined by atomic coordinates of the three dimensional structure presented in FIG. 13 and such that said potential inhibitor is capable of binding to at least three amino acid in the proton transport pathway.

Any of the three regions of the proton transfer pathway, e.g. the inlet channel, the active proton binding site and the proton release pathway may be a target for inhibitor binding. Thus one or more of these regions may be of use for indentifying potential inhibitor molecules. The representation of any one of these regions can be superimposed with models of potentials molecules to indentify a potential molecule that bind at least 1 amino acid in any one of said regions. The evaluation may be performed by manual visualisation or by suitable programs capable of selecting binding molecules based on the representation and the structure of the potential inhibitors.

In an embodiment the invention relates to a method for identifying a potential inhibitor capable of inhibiting the H+ translocating activity of a type III P-type ATPase, said method comprising the following steps:

a. introducing into a computer information derived from atomic coordinates defining a conformation of the proton transport pathway, based on three-dimensional structure determination, whereby said program utilizes or displays on the computer screen the structure of said conformation, wherein the atomic coordinates are selected from the three-dimensional structure as presented in FIG. 13 or atomic coordinates selected from a three-dimensional structure that deviates from the three-dimensional structures as presented in FIG. 13 by a root mean square deviation over protein backbone atoms of not more than 3 Å,
b. generating a three-dimensional representation of at least one of the three regions of the proton transport pathway of said ATPase by said computer program on a computer screen,
c. superimposing a model of a potential inhibitor on the representation on at least one of the three regions of the proton transport pathway;
d. assessing the possibility of bonding and the absence of steric interference of the potential inhibitor with the proton transport pathway;

e. incorporation said potential compound in an activity assay of said ATPase and f. determining whether said potential compound inhibits H+ translocating activity of said ATPase.

As described above the data criteria sets described herein may be used for defining the group of residues for which the atomic coordinates are included.

As described above the most important residues lining the protein transport pathway include Pro68, Leu69, Val72, Glu74, Ala76, Met79, Leu83, Asp92, Asp95, Ile99, Leu102, Val104, Asn106, Ser107, Ile109, Ser110, Phe111, Glu113, Glu114, Ile274, Asp275, Leu278, Leu280, Ile282, Gly284, Ile285, Pro286, Ile287, Ala288, Met289, Val292, Ser294, Phe639, Gln640, Arg641, Met642, Tyr645, Tyr648, Ser651, Thr653, Ile654, Arg655, Ile656,Phe659, Leu661, Leu677, Ile678, Ile679, Ala680, Leu682, Asp684, Met688 and Thr689, thus information derived from the atomic coordinates of at least one of these residues are preferably used in any of the described methods for identifying a potential inhibitor.

More preferably information derived from at least 2, such as at least 3 amino acid residues in the proton transport pathway are used in the methods. In an even further preferred embodiment information regarding the special localisation for more than 3, such as more than 4, or more than 5 amino acids residues are used in the methods.

It is further preferred that the resolution of the atomic coordinates are determined to a resolution of at least 4 Å, more preferably at least 3, 5 Å or even more permeably at least 3 Å or mostly preferred at least 2.5 Å or better.

Potential inhibitors selected according to the invention preferably interacts with at least 1, more preferably at least 2, or further preferred as at least 3 amino acids in the proton transport pathway or mostly preferred at least 4 amino acids in the proton transport pathway.

H+ ATPase Specific Inhibitors

In order to identify inhibitors specific for the H+ ATPase, that is an inhibitor which do not inhibit different types of ATPases such as the $Na^+$, $K^+$ ATPase, the $Ca^{2+}$ ATPase or the $H^+$, $K^+$ ATPase, structural information regarding these ATPases may be used in the methods described herein. The specificity may following be tested in vivo or in vitro assays as described in relation to verification of potential inhibitors.

Specie Specific Inhibitors

It is possible to use sequence information, such as identities and sequence differences to AHA2 SEQ ID NO: 1 to develop inhibitors that are specific for different families, such as fungi, yeast or plant, or even different species with in a family. Eventually inhibitors for different genes from the same species may be identified.

The screening of different libraries can also be performed using different ATPase for selection of specific inhibitors.

A further aspect of the invention relates to a method for identifying a selective peptide inhibitor of a type III P-type ATPase comprising the following steps a. identification of a potential modulator of a type III P-type ATPase according to any of the claims, b. contacting the potential peptide modulator with said ATPase, c. contacting the potential peptide modulator with a different ATPase, d. detecting inhibition of ATPase activity of said ATPase by the potential modulator and e. detecting activity of said different ATPase in the presence of said potential modulator.

Based on the sequence of the *A. thaliana* ATPase gene (AHA2 SEQ ID NO: 1) use for the structure determination disclosed herein, it is possible to deduce alterations of the sequence which can provide resistance to a potential inhibitors. In continuations hereof it is further possible to construct ATPase mutants which are resistant to an inhibitor, and thereby generate transgenic plants resistant to an inhibitor identified according to the present invention.

Screening of Libraries

A part from the computer implemented methods potential inhibitors of the ATPase may be identified by screening of libraries, or combinations of computer implemented methods and screening procedures. This is performed in vitro using membrane localized as well as purified fungal and plant plasma membrane H+-ATPases. Production and purification of highly pure, active and homogenous plasma membrane H+-ATPases from both fungi and plant may be performed using suitable state of the art technology. For example may membranes harbouring H+-ATPases, or H+-ATPase proteins, suitable for biochemical experiments be purified from natural fungal or plant sources according to, or with modifications of, one of the following, but not limited to, already established protocols (Gupta et al., 1991; Monk et., al., 1991; Sampedro et al., 2007; Bowman et al., 1981; Guerra et al., 1995; Huang and Berry, 1990; Serrano, 1988; Serrano, 1984). Alternatively, plasma membrane H+-ATPases may be produced in a suitable heterologous or homologues host (for instance, but not limited to, of fungal, protest, archaebacterial or plant origin) for purification. State of the art techniques can be used to express type III P-type ATPases and established protocols can be used for the actual purification (see for instance this invention, Lanfermeier et al., 1998; Buch-Pedersen et al., 2000; Luo et al., 2002).

An aspect of the invention relates to a method of identifying potential inhibitors of a type III P-type ATPase including a step of screening of different types of libraries known in the art.

Different libraries may be screened according to the invention, preferably a library of small organic molecules are screened.

In a further preferred embodiment a library of potential peptide inhibitors are screened.

Compounds from the libraries are evaluated with respect to their effect upon plasma membrane H+-ATPase activity. The method maybe combined with the in silicon methods described above. Such library screening method may be used to improve the identified inhibitor, e.g. to find inhibitors with a higher specificity or specificity to particular ATPases, such as ATPase from specific species for which an inhibitor is desirable (se further below in relation to verification of inhibitors).

As discussed in the example the C-terminal regulatory R-domain is unique to the type III P-type H+ ATPase and a peptide molecule mimicking a selected region could be used as a starting point for developing of potential inhibitors and candidate peptide inhibitors may be screened in any of the methods described herein.

An aspect of the invention further relates to a method of producing an inhibitor of a type III P-type ATPase comprising the steps of:

a. identification of a potential modulator of a type III P-type ATPase according to the invention and b. producing said identified potential modulator.

Methods for Verification of Inhibitors

The antagonistic activity of identified inhibitors/regulators may be verified by state of the art techniques (se below). Thus, in vitro verification may include one or more of the following, but is not limited to tests of test of inhibition of ATP (or pNPP) hydrolytic activity, test of inhibition of proton transport, test of inhibitor binding, test of inhibition of phosphorylation from ATP and/or test of inhibition of conformational transitions.

The potency of an inhibitor directed against plasma membrane H+-ATPase can for instance be tested in an ATPase (or any hydrolysable compound) assay. In an ATPase assay, the adenosine triphosphate (ATP) hydrolytic activity of the H+-ATPase is determined. ATP hydrolysis and proton pumping by plasma membrane H+-ATPases are under normal circumstances strictly coupled and, therefore, ATP hydrolytic activity is a measure of the proton pumping capability of the pump. The ability of type III plasma membrane H+-ATPase preparations to split ATP can be tested, either in situ in isolated membranes, or in a detergent-solubilized purified form of the H+-ATPase. ATPase activity can be assayed by a variety of methods known by a skilled person in the art. Typically, one mayquantify the time dependent release of breakdown products resulting from ATP hydrolysis, namely inorganic phosphate (Pi) and adenosine diphosphate (ADP).

Time dependent release of Pi from ATP is a convenient assay for ATPase activity(se example 2). One assay known in the state of the art, benefits from the fact that Pi forms complexes with molybdate that are blue when reduced (Baginsky et al., 1967). Alternatively, ATPase activity can be determined by following the time-dependent release of ADP. One assay, known in the state of art, enzymatically couples ADP formation to NADH oxidation (se example 3).

Instead of testing the capacity to hydrolyze ATP, one can test the capability of the type III P-type ATPase to hydrolyze any other compound the ATPase molecule can hydrolyze instead of ATP. For instance, the capacity of the ATPase to hydrolyze small acylphosphates such as para-NitroPhenyl Phosphate (pNPP) can be tested in a manner similar to an ATPase assay (Chernoff and Li, 1983; Zhang and Dixon, 1994; Robinson et al., 1983) (example 4).

The potency of plasma membrane $H^+$-ATPase inhibitors can also be tested by assaying their effect on proton pumping by the $H^+$-ATPase. Proton pump assays require that the plasma membrane $H^+$-ATPase is embedded in the membrane of a lipid vesicle, either derived from the plasma membrane of natural host cells or a heterologous host expressing the $H^+$-ATPase gene, or, alternatively, detergent-solubilized purified $H^+$-ATPase is reconstituted into an artificial lipid vesicle (Perlin et al., 1984). In all cases, the ATP binding site has to face the extravesicular medium so that ATP supplied to the medium can initiate ATP dependent proton accumulation into the lipid vesicles (also called liposomes).

Proton pumping by the plasma membrane $H^+$-ATPase in a vesicle system can be followed by a number of methods known by a skilled person in the art. In one type of assay, proton accumulation within the lumen of vesicles is quantified indirectly by assaying the entrapment of membrane permeable dyes that become impermeable when protonated and hence cannot leave the vesicle again. Dyes used by experts in the art are often such molecules that change absorbance or fluorescence emission spectrum when they go from a monomeric to a dimeric state (Palmgren, 1991). The degree of such aggregation depends on the concentration of the dye within the vesicle lumen, which increases by increasing proton concentration. In one assay (Palmgren, 1991), 20 µM acridine orange is added to the assay medium described below (example 2) and proton accumulation inside vesicles is followed by measuring absorbance decrease of acridine orange at 495 nm, the optimum peak for absorption of the monomer of acridine orange.

Common to all P-type ATPases is the formation of a phosphorylated intermediate during the reaction cycle. The effect of potential ligands of type III P-type ATPases can be assayed by their effect upon the formation, the steady-state amount or the decay of the phosphorylated intermediate. The formation, the steady-state amount or decay of the phosphorylated intermediate can be investigated in various ways known in the state of the art such as one described by Buch-Pedersen et al. (example 5), In a comparable manner, the decay of the phosphorylated intermediate can be followed by stopping phosphorylation from [$^{32}$P]ATP with for instance cold ATP at different time points and the radioactivity (linear related to the amount of phosphorylated intermediate) measured as described. Testing the potential of ligands to interfere with conformational transitions of the type III P-type ATPase can be tested in this phosphorylation assay. When ligands blocks conformational transitions of the ATPase, particular conformational transitions will accumulate. Thus, if an identified ligand for instance blocks enzymatic transitions away from the phosphorylated state, but not phosphorylation, a high amount of the phosphorylated form of the ATPase will accumulate.

Inhibitor binding can also be assayed directly by using radiolabelled ligands. Radiolabelled ligand binding studies is widely used to characterize the biochemical and pharmacological properties of ligand-protein complexes. In this way identified type III P-type ATPase inhibitors can be tested by isotopically labelling the ligand, and its interaction with the type III P-type ATPase can be directly monitored. Such a technology is fairly straightforward for a skilled person, and can provide accurate measurements of binding constants between the ligand in question and the type III P-type ATPase.

In vivo verification may be shown by administration of potential inhibitors to diverse fungi and plants. In addition, in vivo effects of identified inhibitors may be shown in a yeast system where cell survival is tailored to be dependent upon the functionality of heterologous plasma membrane H+-ATPases. Recombinant methods may be employed for expression and testing the inhibitory activity on H+ pumps from different families and/or different species or even different genes from the same species.

The potential inhibitors can be synthesized according to the methods of organic chemistry. Preferably, compounds from a database have been selected without remodelling, and their synthesis may already be known.

In any event, the synthetic effort needed to find an inhibitor is greatly reduced by the achievements of this invention due to the pre-selection of promising inhibitors by the above methods. Binding of a potential inhibitor may be determined after contacting the potential inhibitor with the ATPase. This may be done crystallographically by soaking a crystal of the ATPase with the potential inhibitor or by co-crystallization and determining the crystal structure of the complex. Preferably, binding may be measured in solution according to methods known in the art. More preferably, inhibition of the catalytic activity of the ATPase by the inhibitor is determined e. g. using the assays described in the examples section.

Use of H+ ATPase Inhibitors
Agricultural Use

ATPase inhibitors have a plurality of potential uses, such as herbicides and weed killers based on the essentiality of H+ ATPases for plant and fungi.

An aspect of the present invention relates to the use of an ATPase inhibitor identified according to the methods described in the present application for use as an herbicide or weed killer.

An aspect of the present invention relates to the use of an ATPase inhibitor identified according to the methods described in the present application for use as a fungicide.

The inhibitor according to the invention may be used as a weed killer for any type of weed including any of the below mentioned sorts of weed.

*Azolla pinnata, Caulerpa taxifolia, Eichomia azurea, Hydrilla verticillata, Hygrophila, olysperma, Ipomoea aquatica Forsskal, Lagarosiphon major, Limnophila sessiliflora, Melaleuca quinquenervia, Monochoria hastate, Monochoria vaginalis, Ottelia alismoides, Sagittaria sagittifolia Linnaeus, Salvinia auriculata Aublet, Salvinia biloba Raddi, Salvinia herzogii de la Sota, Salvinia molesta, Solanum tampicense Dunal, Sparganium erectum, Linnaeus, Aeginetia* spp., *Alectra* spp., *Cuscuta* spp *Cuscuta americana, Cuscuta applanata, Cuscuta approximata, Cuscuta attenuate, Cuscuta boldinghii, Cuscuta brachycalyx, Cuscuta californica, Cuscuta campestris, Cuscuta cassytoides, Cuscuta ceanothii, Cuscuta cephalanthii, Cuscuta compacta, Cuscuta corylii, Cuscuta cuspidata, Cuscuta decipiens, Cuscuta, dentatasquamata, Cuscuta denticulata, Cuscuta epilinum, Cuscuta epithymum, Cuscuta erosa, Cuscuta europaea, Cuscuta exalta, Cuscuta fasciculate, Cuscuta glabrior, Cuscuta globulosa, Cuscuta glomerata, Cuscuta gronovii, Cuscuta harperi, Cuscuta howelliana, Cuscuta indecora, Cuscuta jepsonii, Cuscuta leptantha, Cuscuta mitriformis, Cuscuta nevadensis, Cuscuta obtusiflora, Cuscuta occidentalis, Cuscuta odontolepis, Cuscuta pentagona, Cuscuta planiflora, Cuscuta plattensis, Cuscuta polygonorum, Cuscuta rostrata, Cuscuta runyonii, Cuscuta salina, Cuscuta sandwichiana, Cuscuta squamata, Cuscuta suaveolens, Cuscuta suksdorfii, Cuscuta tuberculata, Cuscuta umbellata, Cuscuta umbrosa, Cuscuta vetchii, Cuscuta warneri, Orobanche* spp., *Orobanche bulbosa, Orobanche califomica, Orobanche cooperi, Orobanche corymbosa, Orobanche dugesii, Orobanche fasciculate, Orobanche ludoviciana, Orobanche multicaulis, Orobanche parishii, Orobanche pinorum, Orobanche uniflora, Orobanche valida, Orobanche vallicola, Striga* spp., *Ageratina adenophora, Altemanthera sessilis, Asphodelus fistulosus, Avena sterilis, Carthamus oxyacantha, Chrysopogon aciculatus, Commelina benghalensis, Crupina vulgaris, Digitaria scalarum, Digitaria velutina, Drymaria arenarioides, Emex australis, Emex spinosa, Galega officinalis, Heracleum mantegazzianum, Homeria* spp., *Imperata brasiliensis, Imperata cylindrica, Ischaemum rugosum, Leptochloa chinensis, Lycium ferocissimum, Melastoma malabathricum, Mikania cordata, Mikania micrantha, Mimosa invisa, Mimosa pigra, Nassella trichotoma, Opuntia aurantiaca, Oryza longistaminata, Oryza punctata, Oryza rufipogon Griffith, Paspalum scrobiculatum, Pennisetum clandestinum, Pennisetum macrourum, Pennisetum pedicellatum, Pennisetum polystachion, Prosopis alpataco, Prosopis argentina, Prosopis articulata, Prosopis burkartii, Prosopis caldenia, Prosopis calingastana, Prosopis campestris, Prosopis castellanosii, Prosopis denudans, Prosopis elata, Prosopis farcta, Prosopis ferox, Prosopis fiebrigii, Prosopis hassleri, Prosopis humilis, Prosopis pallida, Prosopis palmeri, Prosopis reptans, Prosopis rojasiana, Prosopis ruizlealii, Prosopis ruscifolia, Prosopis sericantha, Prosopis strombulifera, Prosopis torquata, Rottboellia cochinchinensis, Rubus fruticosus, Rubus moluccanus, Saccharum spontaneum, Salsola vermiculata, Senecio inaequidens, Senecio madagascariensis, Setaria pallide-fusca, Solanum torvum Swartz, Solanum viarum Dunal, Spermacoce alata, Tridax procumbens, Urochloa panicoides,*

By using a specific inhibitor in combination with transgenic crops resistant for said inhibitor highly effective condition for agricultural are established.

Method of Treatment

As H+ ATPases (type III P-type ATPases) are only expressed in plants and fungi, inhibitors specific for this family of ATPase are expected to be non-toxic to mammalian organisms.

Fungal infections of animals and humans are termed mycosis which refers to conditions in which fungi pass the resistance barriers of the human or animal body and establish infections.

Mycoses are classified according to the tissue levels initially colonized:

Superficial mycoses and cutaneous mycoses are restricted to the keratinized layers of the skin, hair, and nails. Only the latter may evoke an immune response, resulting in pathologic changes expressed in the deeper layers of the skin.

Subcutaneous mycoses affect the dermis, subcutaneous tissues, muscle, and fascia. The infections are chronic and difficult to treat and surgical interventions such as debridement may be required.

Systemic mycoses are caused by primary pathogens and originate primarily in the lungs and may there from spread to many organ systems. Systemic mycoses may further be caused by opportunistic pathogens that take advantage of individuals with immune deficiencies who would otherwise not be infected. Examples of immunocompromised conditions include AIDS, alteration of normal flora by antibiotics, immunosuppressive therapy, and metastatic cancer. Examples of opportunistic mycoses include candidiasis, cryptococcosis and aspergillosis.

Inhibitors identified according to the invention may be used as a medicament for treatment of mycoses, such as mycoses mentioned above.

The inhibitors identified according to the invention may be used as a medicament for treatment of infections caused by any type of fungi including the following fungi species:

*Absidia corymbifera, Ajellomyces capsulatus, Ajellomyces dermatitidis, Arthroderma benhamiae, Arthroderma fulvum, Arthroderma gypseum*

*Arthroderma incurvatum, Arthroderma otae*

*Arthroderma vanbreuseghemii, Aspergillus flavus, Aspergillus fumigatus, Aspergillus niger, Blastomyces dermatitidis, Candida albicans, Candida glabrata, Candida guilliermondii, Candida krusei, Candida lusitaniae, Candida parapsilosis, Candida Rugosa, Candida tropicalis, Candida pelliculosa, Cladophialophora carrionii, Coccidioides immitis, Cryptococcus neoformans, Cunninghamella bertholletiae, Epidermophyton floccosum, Exophiala dermatitidis, Filobasidiella neoformans, Fonsecaea pedrosoi, Fusarium solani, Fusarium oxysporum, Fusarium verticillioides, Fusarium proliferatum, Geotrichum candidum, Histoplasma capsulatum, Hortaea werneckii, Issatschenkia orientalis, Madurella grisae, Malassezia furfur, Malassezia globosa, Malassezia obtuse, Malassezia pachydermatis, Malassezia restricta, Malassezia slooffiae, Malassezia sympodialis, Microsporum canis, Microsporum fulvum, Microsporum gypseum, Mucor circinelloides, Nectria haematococca, Paecilomyces variotii, Paracoccidioides brasiliensis, Penicillium mameffei, Pichia anomala, Pichia guilliermondii, Pneumocystis carinii, Pseudallescheria boydii, Rhizomucor pusillus, Rhizomucor miehei, Rhizomucor variabilis, Rhizopus oryzae, Rhodotorula rubra, Scedosporium apiospermum, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin, Trichosporon mucoides*

The invention further relates to a method of treatment of mycoses comprising administrating a therapeutically effective amount of an inhibitor identified according to the invention to a subject in need. According to the invention individual in need may be a human or an animal suffering from a fungal infection.

The invention further relates to a method of reducing the risk of acquiring a fungal infection, comprising administrating a therapeutically effective amount of an inhibitor identified according to the invention to a subject in need. According to the invention a subject in need may be a human or an animal suffering from a fungal infection.

The inhibitors may be of particularly use in livestock e.g. in a domesticated animal intentionally reared in an agricultural setting to make produce such as food or fibre, or for its labor.

As livestock diseases compromise animal welfare, reduce productivity, and in rare cases can infect humans it is an advantage to reduce diseases in livestock including inhibiting development of diseases as well as spread of diseases. Treatment may thus reduces the risk of acquiring a fungal infection or reduce the severity of an acquired infection.

Medicament

Pharmaceutical compositions or medicaments containing a compound of the present invention may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications.

An aspect of the invention relates to a medicament comprising a modulator of a type III P-type ATPase identified according to the invention.

In an embodiment the medicament is for the treatment of mycoses as described above, more preferred for treatment of an infection caused by a fungi as identified above.

Administration Forms

The main routes of drug delivery, in the treatment method are intravenous, oral, and topical. Other drug-administration methods, such as subcutaneous injection or via inhalation, which are effective to deliver the drug to a target site or to introduce the drug into the bloodstream, are also contemplated.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

Compounds of the invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

The inhibitors may according to the invention be administered by any suitable route known in the art. Administration may be continuously, such as daily or weekly for treatment of a disease e.g. after confirmation that the subjected is infected, until the disease is treated or alternative administration may be prophylaxis e.g. administered continuously, such as daily or weekly for extended period to reduce the risk of acquiring an infection.

Formulations

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as herein defined, and a pharmaceutically acceptable carrier therefore.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, wetting agents, tablet disintegrating agents, or an encapsulating material.

Preferably, the composition may be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100 C for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations may typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations may typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compounds of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and may in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Passive Transdermal Drug Delivery

A variety of types of transdermal patches may find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention may utilize a hydrogel matrix patch. Typically, the hydrogel matrix may comprise alcohol, water, drug, and several hydrophilic polymers. This hydrogel matrix can be incorporated into a transdermal patch between the backing and the adhesive layer.

The liquid reservoir patch may also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%]).

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multi dose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound may generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier may form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compounds, where they can be prepared, are also intended to be covered by this invention. These salts may be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

DETAILED DESCRIPTION OF THE DRAWINGS

The patent or application file contains at least one drawing executed in color. Copies of this patent or patent publication with color drawing(s) will be provided by the Office upon request and payment of the necessary fee.

FIG. 1 Overall structure of the plasma membrane H+-ATPase. The structure represents an active form of the proton pump without its auto inhibitory C-terminus in complex with Mg-AMPPCP. The 10 transmembrane helices are coloured orange, green and brown as indicated; the nucleotide biding domain (N) is coloured red, the phosphorylation domain (P) blue, and the actuator domain (A) yellow. Mg-AMPPCP are found at the interface between the N- and P domain and are shown as ball-and-stick. Key residues mentioned in the text are shown as sticks. The grey box depicts the approximate location of the plasma membrane.

FIG. 2 Structural conservation of P-type ATPase architecture. a, View of the N-(red) and P-(blue) domains of the $H^+$-ATPase with bound Mg-AMPPCP together with the experimental electron density map contoured at $1\sigma$. The adenosine of the nucleotide is bound at the N-domain, whereas the tri-phosphate group and the magnesium ion extend towards the P-domain. b, View of the transmembrane region with the experimental electron density map contoured at $1\sigma$. M1 exhibits a ~90° kink perpendicular to the membrane face facilitated by Pro 68. c, AHA2 SEQ ID NO: 1 (orange) is aligned to the $Ca^{2+}$-ATPase (blue, PDB code 1T5T) on transmembrane segments M4 and M5. The bulge appearing at Asp 684 is clearly visible. d, Structural comparison between AHA2 SEQ ID NO: 1 and sarcoplasmic reticulum SERCA1a $Ca^{2+}$-ATPase indicates that the $H^+$-ATPase structure represents a novel $E_1$ intermediate. Middle, AHA2 $H^+$-ATPase SEQ ID NO: 1 with bound Mg-AMPPCP (this study). Left, an $E_2$ form of the $Ca^{2+}$-ATPase without bound calcium (PDB code 2C8K). Right, a $Ca^{2+}$ occluded $E_1$ form of the $Ca^{2+}$-ATPase[15,16] in the transition state of phosphoryl transfer (PDB code 1T5T). The structures are aligned on their P-domains. The N-domain is coloured red with the bound nucleotide in green. The A-domain is yellow, with the TGES motif required for de-phosphorylation indicated by magenta. The phosphorylation site is indicated in orange.

Figure 3:
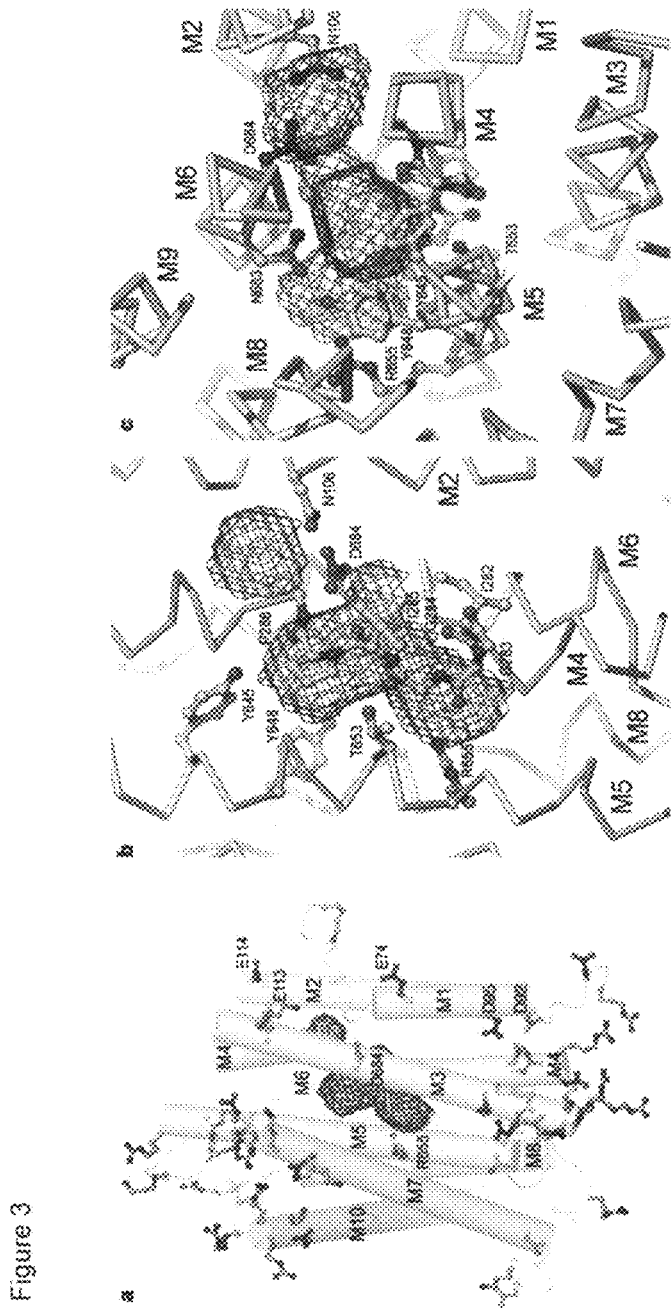
FIGS. 3a through c illustrate the intra-membranous buried cavity and proton binding site of the plasma membrane H+-ATPase.

FIG. 3 The intra-membranous buried cavity and proton binding site of the plasma membrane $H^+$-ATPase. a, Distribution of charged residues (Arg/Lys, blue; Asp/Glu, red) in the transmembrane region of the pump shown together with the identified intramembranous cavity (blue mesh). Among the charged residues in this region, Arg 655 and Asp 684 are the only two charged residues found in the transmembrane part (except Glu 74 of M1 that points towards the cytosolic interface). b, side view and c, top view of the cavity and the residues lining it. Polar and charged residues from M5 and M6 together with exposed backbone carbonyls and amide groups from M4 define the boundaries of the cavity. A small extension (~80 $Å^3$) of the cavity, placed over Asp 684 and Asn 106, is located along the expected proton entrance pathway and is likely to close as the phosphorylation site is fully assembled.

FIG. 4 Mechanism of proton transport by plasma membrane $H^+$-ATPase. $E_2$-model forms of the $H^+$-ATPase were made by structural alignment of our $E_1$-AMPPCP structure with the $E_2P$ structure of the $Ca^{2+}$-ATPase[26] and the $E_2$-P* transition state structure of the $Ca^{2+}$-ATPase (pdb code 1XP5). Asp 684 is the central proton donor/acceptor of the pump, and together with Arg 655 it lines a centrally located water filled cavity. In the $E_1$ conformation, hydrogen bonding between Asp 684 and Asn 106 gives preference to the protonated form of Asp 684 ($E_1$-ATP structure). Conformational movements in the membrane region, coupled to $E_1$-$E_2$ transitions, result in opening of the cavity towards the proton exit pathway ($E_2P$ model) and interrupt hydrogen bonding between Asn 106 and Asp 684. This result in proton release from Asp 684, now exposed to the extracellular environment. Placement of Arg 655 towards Asp 684 at the exit channel also stimulates proton release from Asp 684, and provides a positively charged plug in this area of the molecule that prevents protons from re-entering to Asp 684. At the same time Arg 655 functions as a built-in counterion that neutralises the negative charge on Asp 684 and promotes swift formation of the occluded $E_2$-$P^*$ transition state ($E_2P^*$ model), de-phosphorylation and transition to the $E_2$ form.

Figure 5:
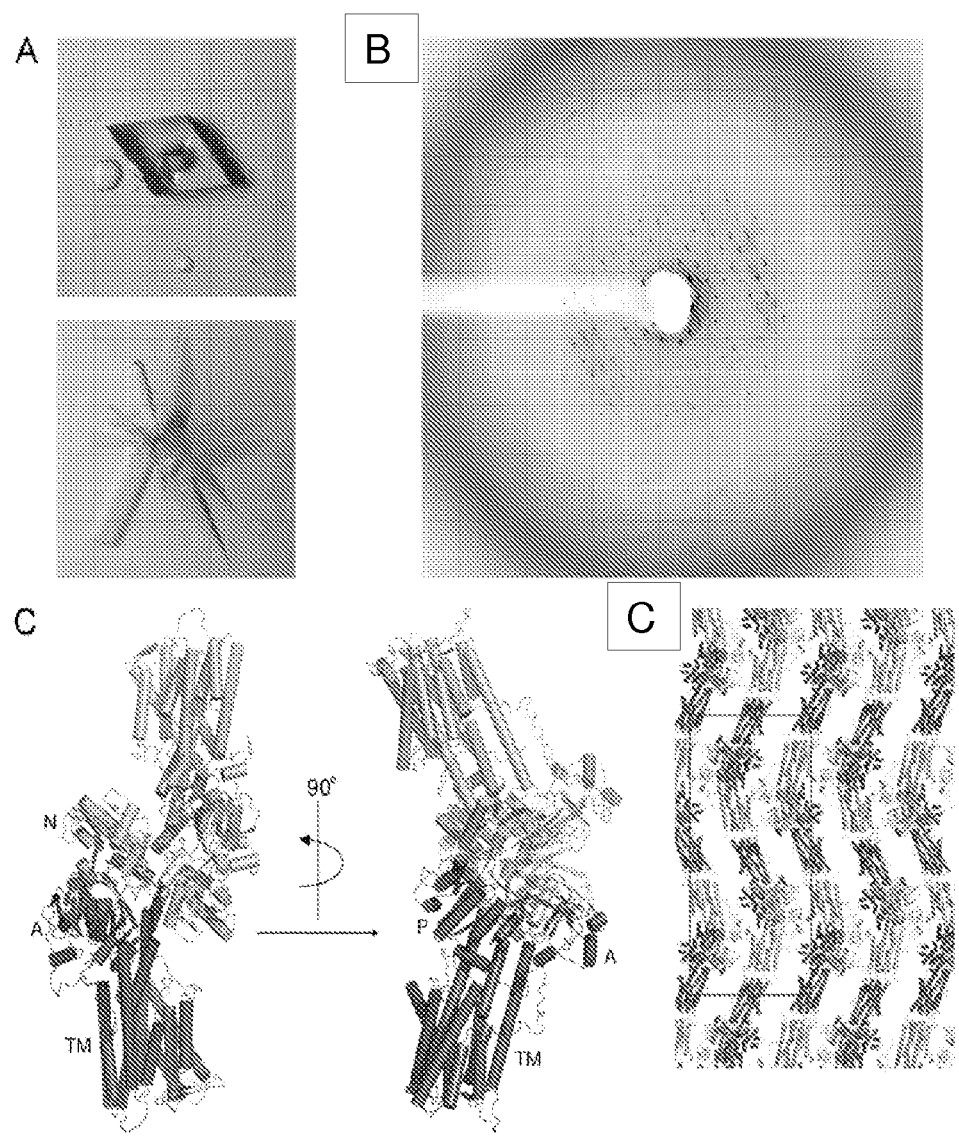
FIGS. 5a through c illustrate crystals, diffraction and crystal packing of the H+-ATPase.
FIG. 5d illustrates the b-c plane of the crystal lattice.

FIG. 5 Crystals, diffraction and crystal packing of the $H^+$-ATPase. a, Examples of AHA2 SEQ ID NO: 1 crystals. top, Crystals often show growth depletions in the center. This particular crystal is ~300 μm across. Bottom, Multiple crystals derivatised with $Ta_6Br_{12}$. These particular crystals were not used for data collection. The crystal-cluster is ~1 mm across. b, Diffraction-image from the dataset named 'Native 1' in Supplementary Table I. The anisotropy of the data is clearly visible, with reflections extending to 3.6 Å resolution only in some directions. c, The asymmetric unit contains two ATPase molecules (blue and green respectively) which interact via their N-domains (shown in lighter colour). d, The b-c plane of the crystal lattice. The red box shows the unit cell (a=85 Å, b=144 Å and c=312 Å).

Figure 6:
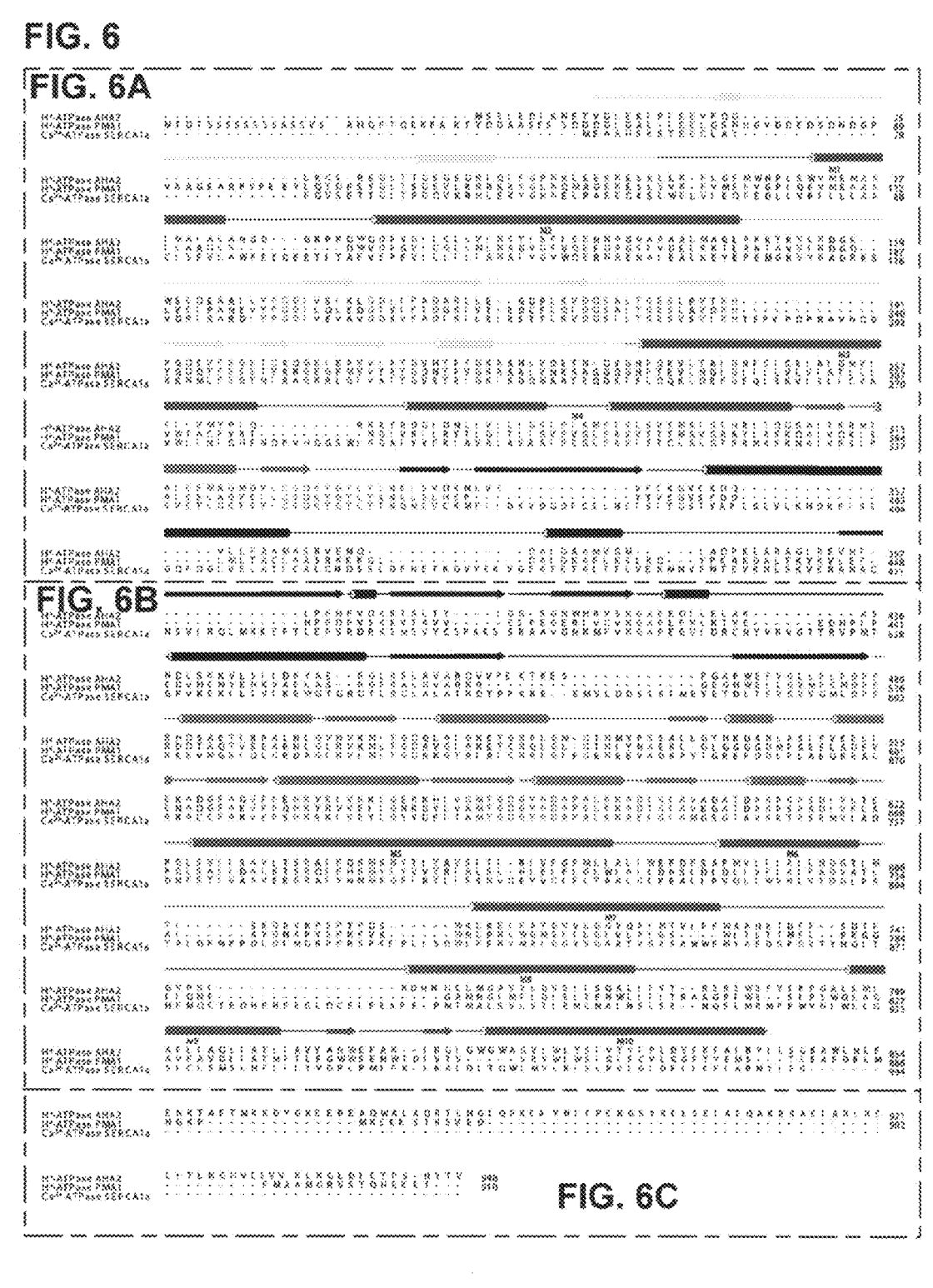
Figure 6A:
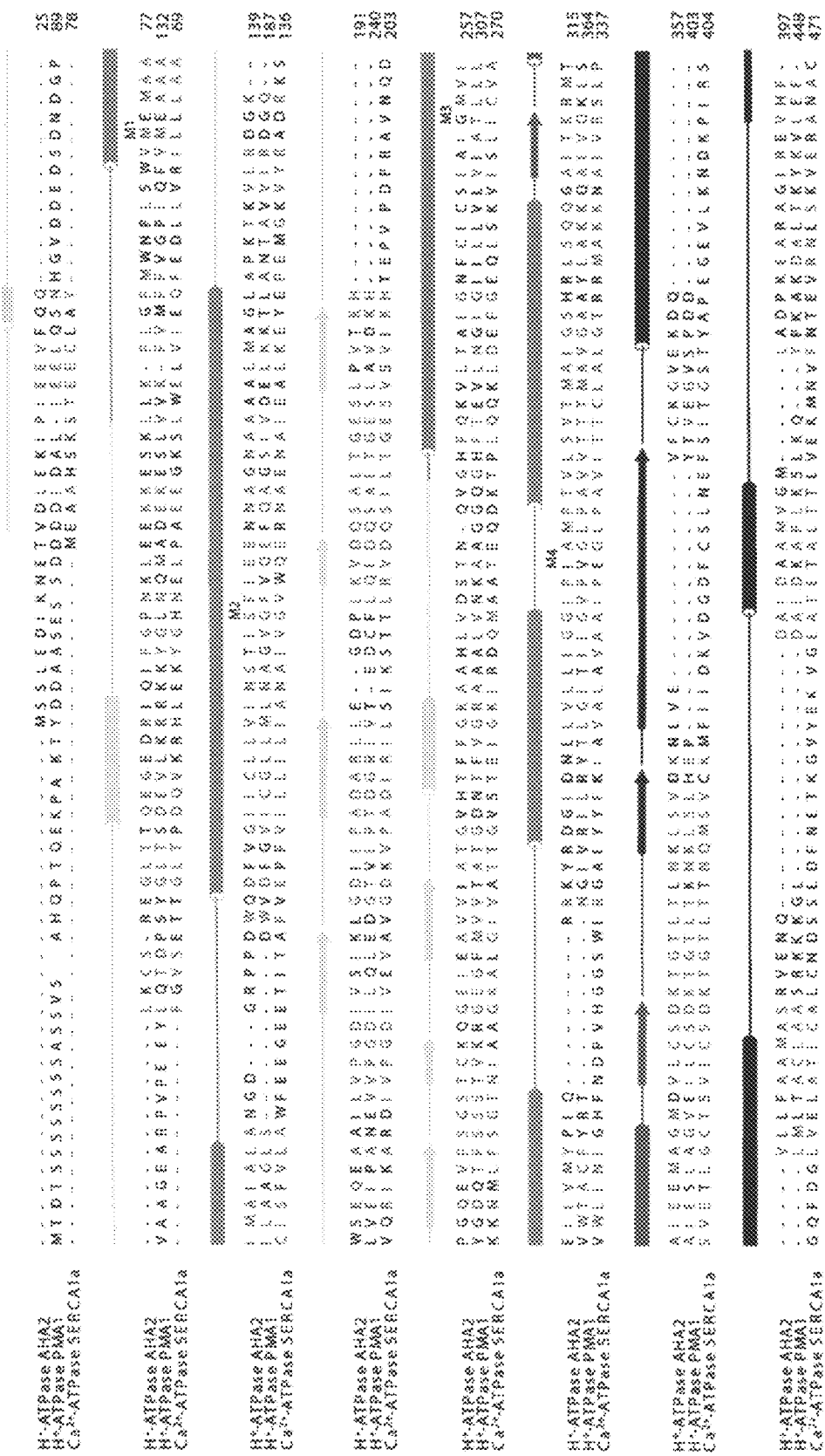
FIG. 6 illustrates a sequence Alignment of plant H+-ATPase, yeast H+-ATPase and rabbit $Ca^{2+}$-ATPase.
Figure 6B:
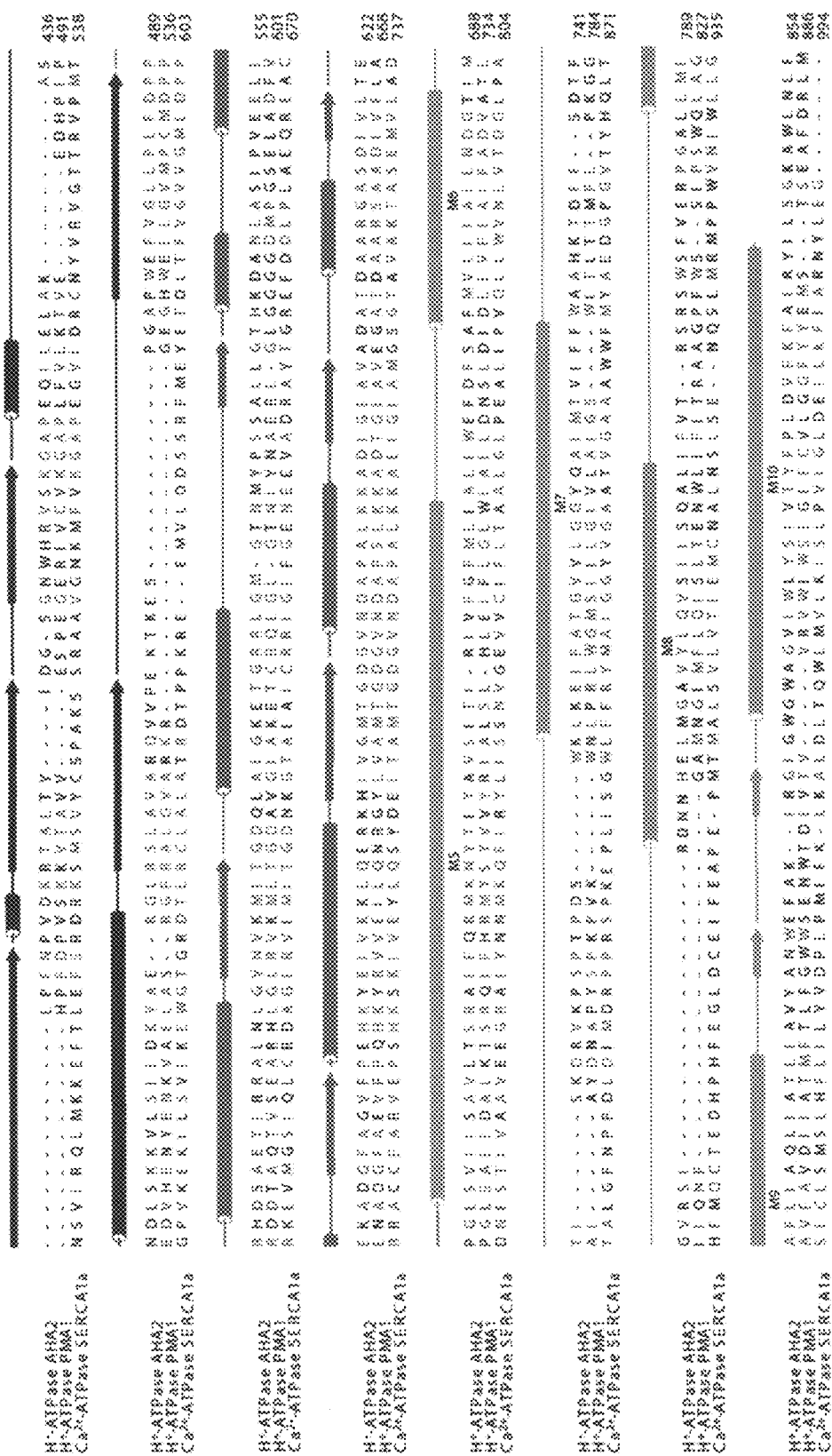

FIG. 6 Sequence Alignment of plant $H^+$-ATPase, yeast $H^+$-ATPase and rabbit $Ca^{2+}$-ATPase. Sequence alignment of plant $H^+$-ATPase AHA2 (accession number P19456, SEQ ID NO 1), yeast $H^+$-ATPase PMA1 (accession number P05030, SEQ ID NO 12) and rabbit $Ca^{2+}$-ATPase SERCA1a (accession number P04191, SEQ ID NO 13). The alignment was made with MUSCLE[43] using 68 different type IIa and Type IIIa ATPase sequences. Fully conserved residues are coloured red, semi-conserved green. Tubes (α-helix), arrows (β-strand) and lines (coil) represents secondary structural elements found in the A-domain (yellow), P-domain (blue), N-domain (red) and transmembrane domain (brown) of the AHA2 $H^+$-ATPase SEQ ID NO: 1.

Figure 7:
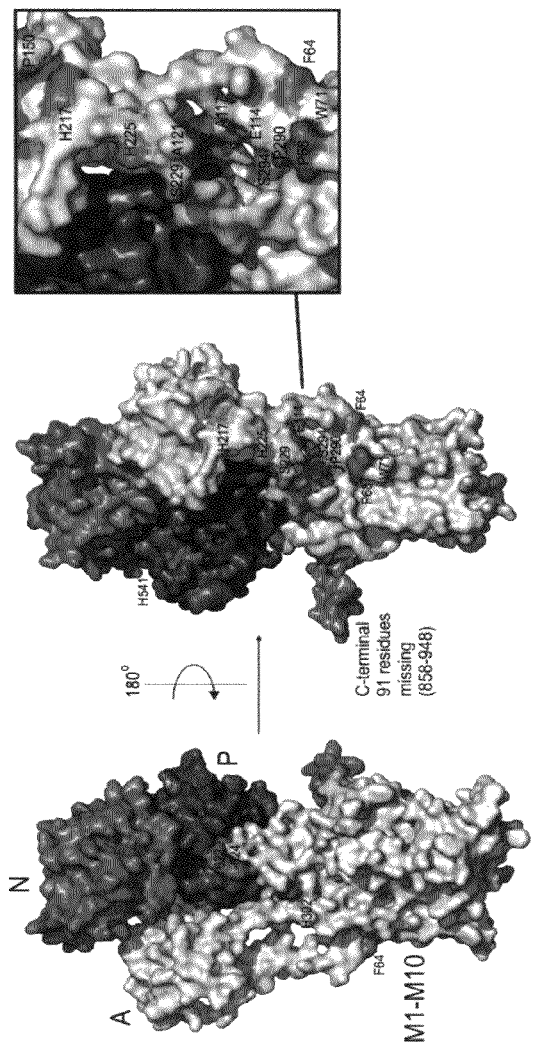
FIG. 7 illustrates placement of the R-domain in autoinhibition of H+-ATPase function.

FIG. 7 Autoinhibition of $H^+$-ATPase function—placement of the R-domain.

Residues that through mutagenesis have been suggested to interact with $H^+$-ATPase R-domains are indicated (in pink) on the AHA2 $H^+$-ATPase structure SEQ ID NO: 1. References and description of these regulatory residues are given in ref. 3. A 13 residue C-terminal extension (green) was introduced on basis of additional electron density (at 5.5 Å resolution) observed from crystals of the full-length version of the AHA2 SEQ ID NO: 1 protein. The insert shows the groove under the A domain between M1 and M2 where a large percentage (13 of 19 total) of the regulatory residues are found.

Figure 8:
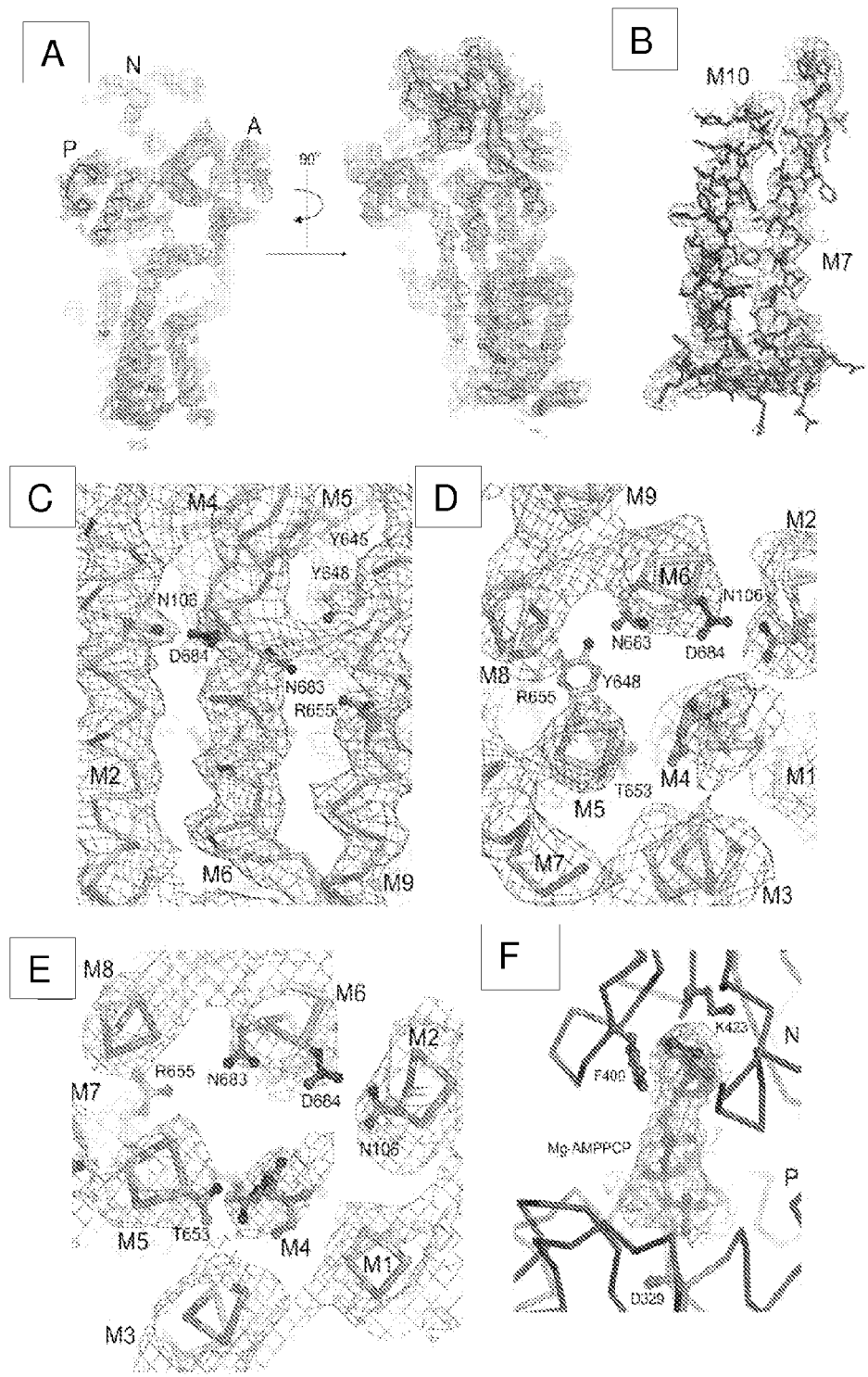
FIGS. 8a through f illustrate examples of experimental and model-based electron density maps.

FIG. 8 Examples of the experimental and model-based electron density maps.

a, Overview of AHA2 SEQ ID NO: 1 with experimental electron density (contoured at 1σ). b, Close up of M7 and M10 shows the fit of experimental electron density (1σ) to the residues. c, Side view and d, top view of experimental electron density (1σ) around the transmembrane proton binding site, showing the same residues as in FIG. 3b and FIG. 3c. e, Electron density (1σ) around the transmembrane proton binding site, emphasising the fit of the residues to the density. The map is a density modified map based on $F_{obs}$-coefficients and initial phases obtained by combining FOM-weighted experimental phases and $σ_A$-weighted model phases. f, Experimental electron density map (grey mesh) and the $2F_o$-$F_c$ electron density map (orange mesh) of the Mg-AMPPCP, both contoured at 1σ are shown, along with Phe 400, Lys 423 and Asp 329.

FIG. 9 Alignment of H+ ATPases from different plant and fungal species.

Sequence alignment of plasma membrane type III P-type H+-ATPases from different plant and fungal species. The areas of the pump molecules that defines the proton transport pathway (AHA2 (accession number P19456 SEQ ID NO: 1) numbering Pro68 to Asn85, Pro90 to Ala117, Asp272 to Met297, Arg636 to Leu665 and Ser672 to Thr689) are illustrated by blue background. Conservation of residues is indicated in the line below the alignment: "*" means that the residues in that column are identical in all sequences in the alignment, ":" means that conserved substitutions have been observed, "." means that semi-conserved substitutions are observed.

Figure 10:
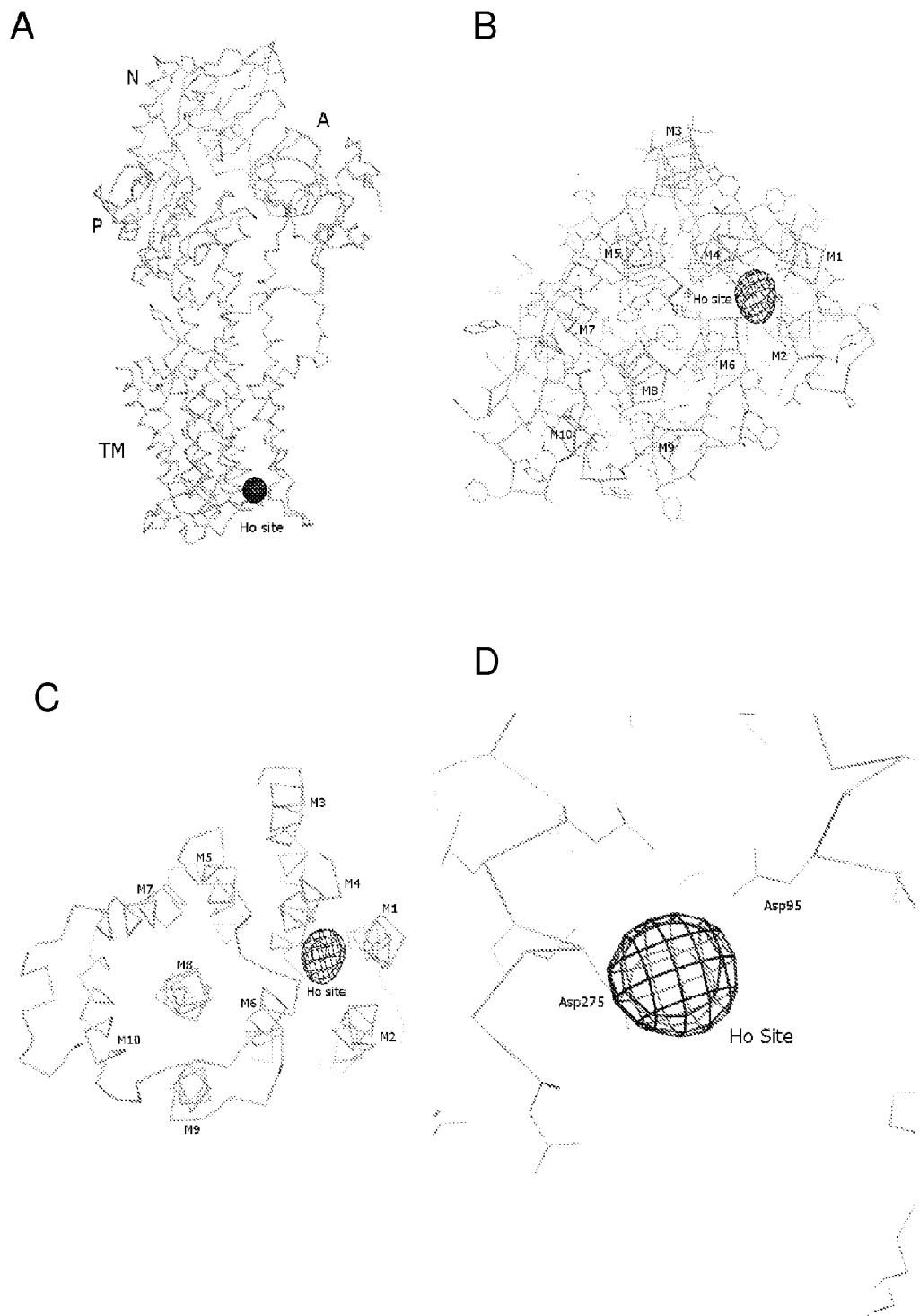
FIGS. 10A through C show holmium binding in a plasma membrane H+-ATPase.
FIG. 10D shows the Ho ion coordinated by Asp 275 (M4) and Asp 95 (M2).

FIG. 10 Holmium binding in plasma membrane H+-ATPase.

A) Overview of the plasma membrane proton pump (AHA2 SEQ ID NO: 1) shown as a main chain trace in grey. The four domains (A, P, N and TM) are clearly defined. In black is shown the location of the Ho-ion at the bottom of the trans-membrane (TM) domain. The binding site is located between M1, M2, M4 and M6, where the proton exit channel (proton release pathway) is located. B) View of the plasma membrane proton pump seen from the extracellular side of the protein focusing on the ten trans-membrane helices (M1-M10) of the trans-membrane domain, and showing all side chains. The Ho binding site is shown in black, between M1, M2, M4 and M6, in the middle of the closed proton exit channel. C) Zoome of B) of the plasma membrane proton pump seen from the extracellular side of the protein focusing on the ten trans-membrane helices (M1-M10) of the trans-membrane domain. The Ho binding site is shown in black, and is located between M1, M2, M4 and M6, in the middle of the closed proton exit channel. D) In the figure the Ho ion is coordinated by Asp 275 (M4) and Asp 95 (M2). With out being bound by the theory the Ho-ion 'lock's these trans-membrane helices in their current position and prevent opening of the proton pump, inhibiting proton transport by blocking the proton exit channel.

Figure 11:
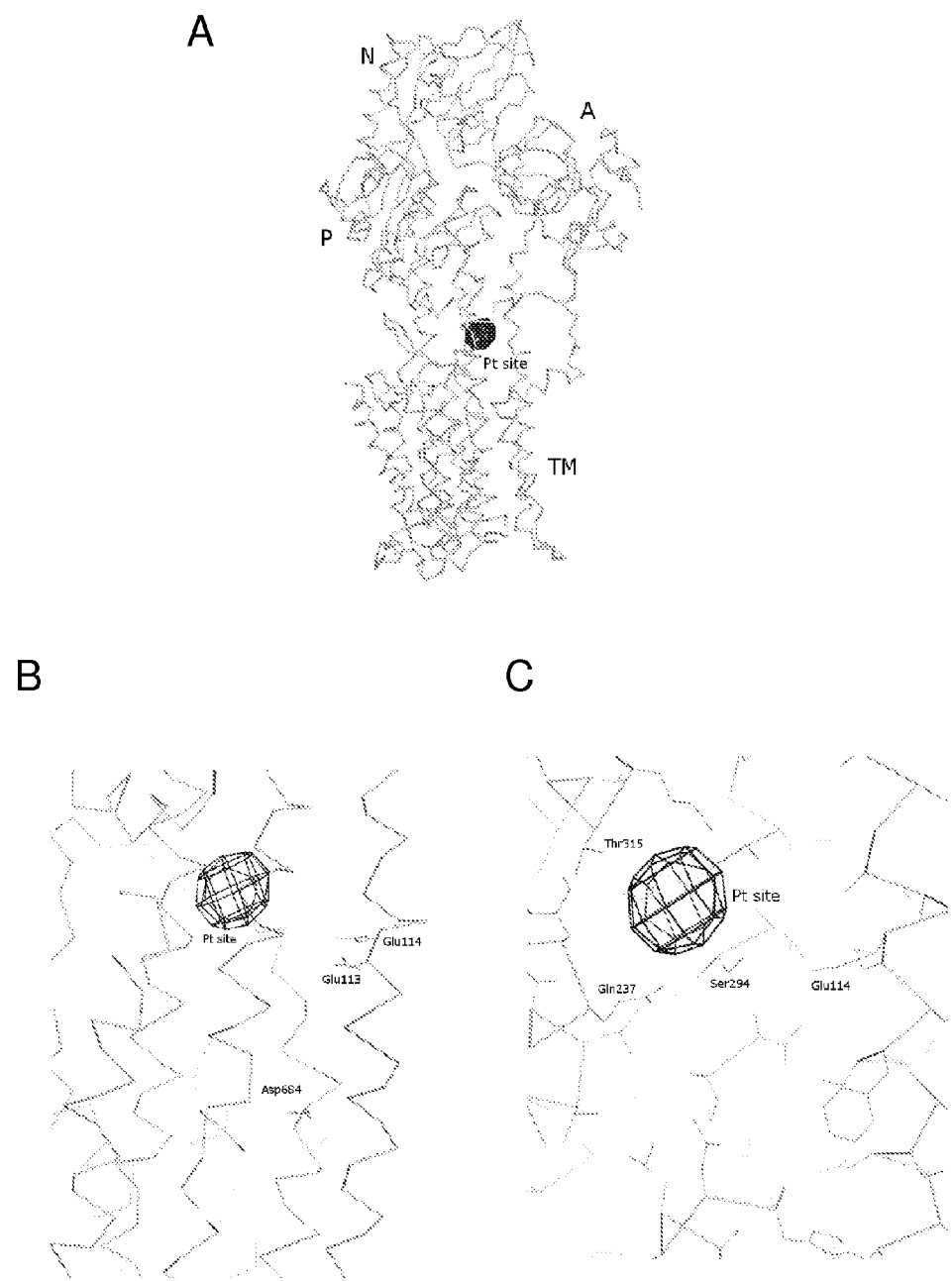
FIGS. 11A through C show a platin binding site in a plasma membrane H+-ATPase.

FIG. 11 Platin binding site in plasma membrane H+-ATPase.

A) Overview of the plasma membrane proton pump (AHA2 SEQ ID NO: 1) shown as a main chain trace in grey. The four domains (A, P, N and TM) are clearly defined. The location of the Pt-ion is shown in black at the top of the transmembrane (TM) domain. The Pt-ion is located above the kinked M1 helix and next to the M3 and M4 helices below the P domain, opposing the M2 helix. This location is just above the proposed entry channel (proton inlet channel) for the protons. B) In the figure the Pt ion is coordinated by residues from M3, M4 and the P domain and the Pt ion is further more located very close to Glu113 and Glu114 on M2. Glu114 and Glu113 are involved in proton loading to the transmembrane binding site at Asp684, and with out being bound by the theory the presence of a large positively charged ion, such as a platinum ion right next to this pathway, is expected to prevent proton loading into the trans-membrane binding site, thus effectively inhibiting the pump. C) The figure show coordination of the Pt ion with Thr315(P domain), Ser294 (M4) and Gln237(M3) and further as mentioned above the very close location of the Pt-ion to Glu114(M2).

Figure 12:
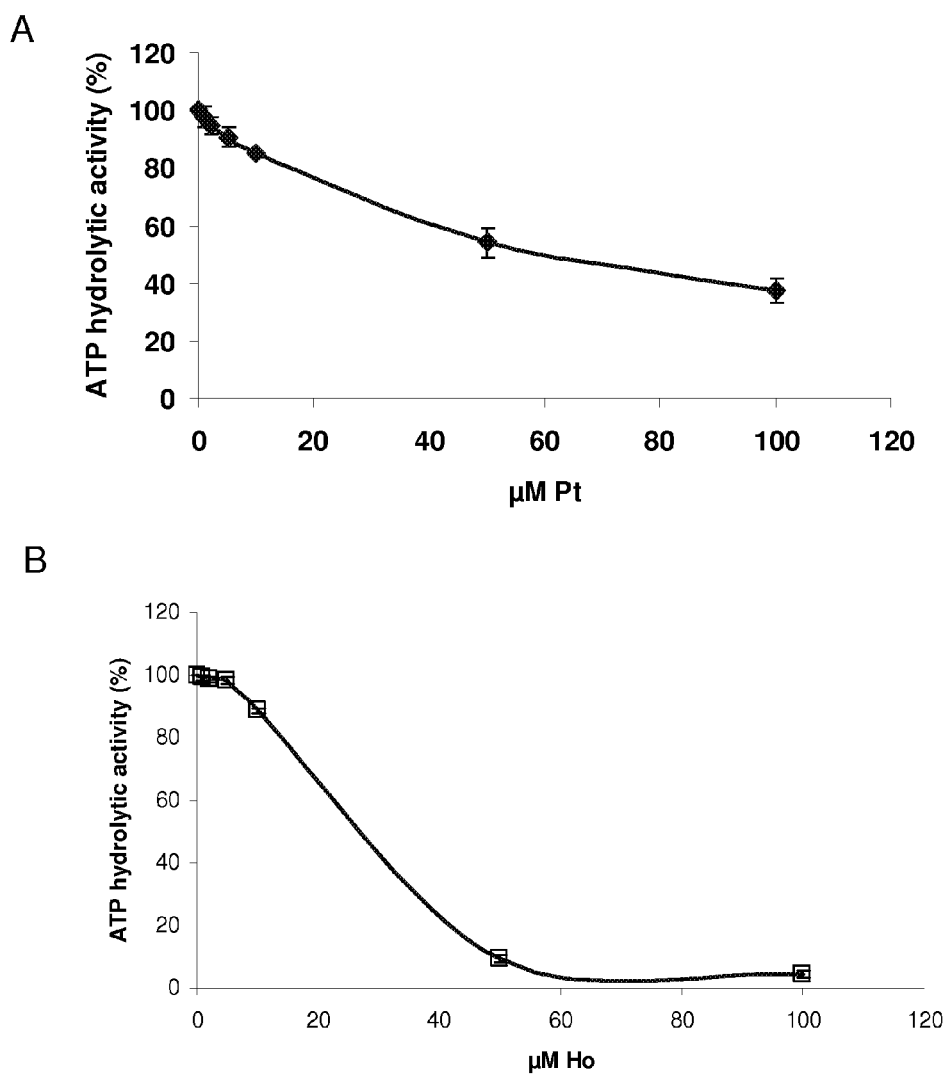
FIGS. 12A and B show inhibtion of H+ATPase activity by Pt and Ho, respectively.

FIG. 12 Inhibtion of H+ ATPase activtiy.

A) Pt inhibits ATP hydrolydic activity of plasma membrane $H^+$-ATPase. Activity is given as the percentage of the ATP hydrolytic activity in the absence of various concentrations of Pt (±StDev).B) Ho inhibits ATP hydrolydic activity of plasma membrane H$^+$-ATPase. Activity is given as the percentage of the ATP hydrolytic activity in the absence of various concentrations of Ho (±StDev).

Table 1. Summary of data collection, phasing and refinement statistics.

FIG. 13 Atomic coordinates

Data including atomic coordinates for the crystal structure of AHA2 SEQ ID NO: 1.

The data relates to amino acids 12-844 of the AHA2 SEQ ID NO: 1 gene. The structural data includes information on the two complexes of the asymmetric unit the peptides denoted A and B, respectively, which was used to interpret the data.

EXAMPLES

Example 1

The *Arabidopsis thaliana* auto-inhibited H$^+$-ATPase 2 (AHA2 SEQ ID NO: 1) is a well-characterised member of the plasmamembrane proton pump family[8]. As shown in FIG. 1, we have determined the structure of an active form of AHA2, devoid of a flexible, C-terminal regulatory domain (R domain)[3,9], in complex with adenosine 5'-(β,γ-methylene)-triphosphate (AMPPCP, a non-hydrolysable ATP analogue). Despite anisotropy of the data we successfully traced the structure and refined a model encompassing residues 12 to 844 and the bound nucleotide on the basis of experimental electron density maps calculated at 3.6 Å resolution (FIGS. 2a and 2b, Table I, FIG. 5).

The structure of AHA2 SEQ ID NO: 1 consists of four clearly defined domains: a transmembrane domain with 10 helices, M1 through M10, and three cytosolic domains, named after their counterparts in the Ca$^{2+}$-ATPase[10] as N (nucleotide binding; residues 338-488), P (phosphorylation; residues 308-337 and 489-625) and A (actuator; residues 12-57 and 129-233). AHA2 SEQ ID NO: 1 and the rabbit SERCA1a Ca$^{2+}$-ATPase share low sequence homology (20% identity, Supplementary FIG. 2), but a structural comparison shows the overall fold to be remarkably similar, supporting the assumption that the overall structure of P-type ATPases is conserved among different subfamilies (FIGS. 2c and 2d). However, the N domain of AHA2 SEQ ID NO: 1 is smaller than the N domains found in the type II subfamily. It has the same fold as the N domain of the *Archaeoglobus fulgidus* copper pump[11], although the loops connecting strand 3 to 4 and strand 5 to 6 are longer and resemble the loops found in the Ca$^{2+}$-ATPase[10] and Na$^+$,K$^+$-ATPase[12]. AMPPCP is bound with the adenosine part at the N-domain and the triphosphate group protruding towards the P-domain (FIG. 2a). The N domain is inserted into the P domain via a hinge (including the conserved sequence motif DPPR$^{490}$) and with bound nucleotide it can move towards the P domain to assemble the catalytic site, where Asp 329 will become phosphorylated once every pumping cycle. The A domain, which stimulates dephosphorylation of Asp 329, is situated on top of M2 which protrudes as a pole out of the membrane, and it is further connected to the M1 and M3 transmembrane segments via extended loops. Glu 184 in the conserved sequence TGES$^{185}$ involved in the A domain phosphatase functionality, is situated ~28 Å from Asp 329. This affirms that a large rotation of the A domain towards the P domain is required for dephosphorylation to occur, linking events at the phosphorylation site to conformational changes in the membrane. In the transmembrane domain, the M1 helix displays a prominent 90° kink (FIG. 2b) imposed by a proline residue, Pro 68, conserved in type III P-type ATPases[6]. A similar kink is seen in the Ca$^{2+}$-ATPase[13] and Na$^+$,K$^+$-ATPase[12], despite distinct motifs in the M1 primary structure for each type. M4 is unwound in the middle of the transmembrane segment, and M7 and M10 are tilted approximately 25° and 45°, respectively, relative to the plane of the membrane.

The overall arrangement of domains and transmembrane helices of AHA2 SEQ ID NO: 1 is similar, but not identical, to the occluded E$_1$ form of Ca$^{2+}$-ATPase trapped in the transition state of phosphoryl transfer[14,15] (FIGS. 2c and 2d). The A domain is moved away from the P domain allowing the N domain to approach as required for phosphorylation to occur, but closure of the active site at the interface between the N and P domains has not completed. Further comparison to the AMPPCP-bound E$_2$ form of Ca$^{2+}$-ATPase[16] (FIG. 2d) indicates that our AHA2 SEQ ID NO: 1 structure represents indeed a novel E$_1$ intermediate, which is compact, yet not completely occluded.

Autoinhibition by C-terminal regulatory R domains is characteristic of type III P-type H$^+$-ATPases. We have obtained crystals and collected a 5.5 Å resolution dataset of full-length AHA2 SEQ ID NO: 1 in a detergent-activated form. We observe additional electron density for approximately 13 residues (modelled as a helix) of the R domain extending from the M10 helix towards a large solvent channel in the crystal (Supplementary FIG. 3). However, we do not observe density for the bulk of the R domain (residue 858 to 948), indicating that it has no defined structure in the active form of the protein. If we plot residues that, when mutated, inhibit R domain interaction (shown by mutagenesis of plant and fungal P-type proton pumps[2,17,18]), a pattern emerges where the R domain may attain inhibition by winding around the body of the pump and interact with the A domain and the top of the M1 and M2 segments. In this position, the R domain potentially blocks entry of protons to the transmembrane binding site and restricts A-domain rotations that are essential for functional transitions in the pumping cycle. This is much like the fixation by thapsigargin of the transmembrane domain in Ca$^{2+}$-ATPase[14], and possibly similar to the effect of regulatory peptides like sarcolipin and phospholamban[19].

Asp 684, conserved in all plasma membrane H$^+$-ATPases, is the only acidic residue buried in the transmembrane domain of AHA2 SEQ ID NO: 1 (FIG. 3a). Mutational studies have shown this residue to be essential for proton transport and E$_1$-E$_2$ transitions and thus most likely to be the protonation site of P-type H$^+$-ATPases[9,20]. Asp 684 corresponds to the essential Ca$^{2+}$ coordinating residue Asp 800 in the Ca$^{2+}$-ATPase and it is situated in M6, next to a large cavity in the membrane (FIG. 2c, see below). Asp 684 is juxtaposed to the completely conserved Asn 106 of M2 (FIG. 3b, FIG. 3c), compatible with hydrogen bonding between the two. This feature suggests an elegant coupling mechanism of H$^+$-ATPase between formation of the phosphorylation site in the cytoplasmic domains and occlusion of the proton binding site with the protonated Asp 684 and Asn 106 pair buried between the M2, M4 and M6 segments. This will also readily explain the proton specificity of H$^+$-ATPase; the specificity arises at the protonated Asp 684-Asn 106 pair, serving as the "gate keeper" along the transport pathway.

Due to a conserved Pro 286 residue, M4 is unwound, which leads to exposure of backbone carbonyl and amide groups of residues 282 to 286 to a large cavity in the middle of the membrane (FIG. 3). The conserved residues Tyr 645, Tyr 648, Thr 653, Arg 655 (all in M5) and Asn 683 (in M6) expose their charged or polar side chains to this cavity. The corresponding residues in M5 of the yeast PMA1 H$^+$-ATPase (Tyr 691, Tyr 694, Ser 699 and His 701) have been shown to be essential for proton pumping[21]. The cavity is defined by M4, M5 and M6 (FIG. 3), and in dimensions it is substantially bigger than the Ca$^{2+}$ binding sites I and II of the Ca$^{2+}$-ATPase[10]. The enlargement is mainly due to M6, which is bulged at Asp 684 (FIG. 2c and Supplementary FIG. 4). The cavity is large enough (circa 380 Å$^3$) to accommodate about 12 water molecules. Proton access from the cytoplasm to the proton binding site appears nearly closed in our structure, but could occur through an entrance pathway located between M1, M2, and M4 (FIG. 3a). Several conserved H$^+$-ATPase residues are positioned in this area of the pump, e.g. Asn 106, Glu 113, Glu 114 (all in M2), and they could be involved in proton transfer to Asp 684 at the edge of the cavity.

Arg 655 of M5 is situated in the middle of the membrane domain, at the cavity opposite to the Asp 684 residue (FIG. 3). Arg 655 is important, but not indispensable, for proton transport[20]. The interaction of Arg 655 with the, presumably water filled, cavity is well-defined, even though the exact side chain structure is not at the given resolution. Due to the packing of nearby membrane residues Arg 655 is confined to side chain rotamer configurations pointing upwards, towards Asp 684 and in direct contact with the cavity. The cavity may aid in delocalisation of the buried positive charge on Arg 655 as the pump goes through phosphorylation and it may form the upper part of the proton exit pathway during subsequent proton release. The electrostatic field of Arg 655 is likely to influence Asp 684. A spatial arrangement of an arginine residue placed near an essential proton donor/acceptor is well-characterised in unrelated proton pumps like bacteriorhodopsin[22,23] and F-/V-type ATPases[24,25] as a means of stimulating proton release, and we find it likely that a similar role is achieved here. Arg 655 must be expected to impose an effect on Asp 684 in the E$_2$P state where the proton exit pathway opens to the extracellular environment. Also, the presence of similarly conserved positive-negative amino acid pair of M5/M6 in H$^+$, K$^+$-ATPases (e.g. Lys 800 and Asp 833 of human ATPase ATP12A) at equivalent positions hints to a conserved mechanism of proton transport in proton exporting P-type ATPases. Proton release from the pump might be aided by conserved acidic residues (e.g. Asp 92, Asp 95) found at the extracellular side (FIG. 3a).

Arg 655 may serve other important roles. The corresponding residue in Ca$^{2+}$-ATPase is Glu 771, which becomes exposed at the bottom of the Ca$^{2+}$ exit channel in the E$_2$P form[26]. Likewise, Arg 655 may become exposed in the proton exit pathway of AHA2 SEQ ID NO: 1. In this position it could serve as a positive plug, which prevents proton reflux to the transmembrane binding site (FIG. 4). A positive charge along the transport pathway may then explain how proton pumps are able to generate high membrane potentials. In plants, membrane potentials may exceed −200 mV[27] (negative on the inside) while the proton pumps from fungi generate the highest known membrane potentials (up to −300 mV[28]). In fungal H$^+$-ATPases, Arg 655 of AHA2 SEQ ID NO: 1 is replaced by a histidine (His 701 in yeast PMA1) while another arginine is found at the 649 position of the M5 helix, also facing the water-filled cavity. This arrangement of an arginine and a histidine positioned in tandem at the upper part of the proton exit pathway is indeed compatible with the even higher resistance to membrane potential attained. No countertransport during the E$_2$ to E$_1$ transition has been described for proton pumps. This is in contrast to other subfamilies of P-type ATPases. Arg 655 may act as a built-in counter ion during dephosphorylation and E$_2$ to E$_1$ transition, neutralising the deprotonated negatively charged Asp 684. Presence of Arg 655 as a constitutive counterion makes the transition from E$_2$-P to E$_2$ extremely favourable and minimizes exposure of Asp 684 to the extracellular side. This is consistent with the fact that proton pumps cannot be directly phosphorylated by inorganic phosphate, contrary to other P-type ATPase subfamilies[29]. The price of being able to sustain a high membrane potential may thus be the loss of countertransport. Indeed the apparent stoichiometry of P-type H$^+$-ATPase transport is one proton per ATP hydrolyzed[30].

The structure described here contributes to further understanding of structural/functional relationships found in plant and fungal P-type H$^+$-ATPases and furthermore provides a framework for new studies of members of this subfamily. Our observation of an Asp-Asn pair and an arginine residue lining a water-filled cavity in the membrane appears as key elements of proton transport by P-type H$^+$-ATPase and it represents a novel use of P-type ATPase architecture for active transport.

The structure is described in Pedersen B P, Buch-Pedersen M J, Morth J P, Palmgren M G, Nissen P. Nature. 2007 December 13; 450(7172)1111-4, where also the coloured figures are found.

Coordinates and structure factors have been deposited in the RCSB Protein Data Bank under accession number PDB ID: 3B8C.

Methods Summary

Methods

Sample Preparation.

A *S. cerevisiae* expression construct contained nucleotides coding for a C-terminal truncated version of the AHA2 SEQ ID NO: 1 protein lacking the 73 last residues[9]. The construct includes a MRGSH6 SEQ ID NO: 1 C-terminal tag. The construct of wild type protein contained nucleotides coding for amino acid 1 to 948 including the same tag. Transformed yeast were grown and harvested essentially as described[9]. Yeast were resuspended in 50 mM Mes-KOH, pH 6.5, 26% (v/v) glycerol, 50 mM KCl, 10 mM EDTA, 1 mM dithiothreitol (DTT), 1.2 mM ATP, 0.3 mM phenylmethylsulfonyl fluoride (PMSF) and 3 μg/ml pepstatin A before broken mechanically using glass beads at 4° C. After cell breakage, the homogenate was centrifuged 5 min at 1400×g. Centrifugation of the supernatant (15 min, 12000×g) was followed by sedimentation of microsomal membranes by ultracentrifugation at 50,000 rpm for 1 h (Beckman 70Ti rotor). An additional ultracentrifugation step at 50,000 rpm for 1 h (Beckman 70Ti rotor) after resuspension of the pellet in GMEKD$_{20}$ (50 mM Mes (pH 6.5), 20% (v/v) glycerol, 1 mM EDTA, 1 mM DTT, 50 mM KCl) supplemented with 0.2 mM PMSF and 2μg/ml pepstatin A, allowed harvesting and homogenization of the total membrane fraction in the same buffer. Membrane proteins were solubilized at 10 mg/ml using DDM at a detergent to protein ratio of 3:1 (w/w) in 50 mM Mes-KOH, pH 6.5, 20% (v/v) glycerol, 50 mM KCl, 0.7 mM DTT and 0.7 mM EDTA. Solubilisation was performed with gentle stiring for 30 min after which unsolubilised material was removed by ultracentrifugation for 1 h at 30,000 rpm (Beckman 70Ti rotor). Solubilised protein were diluted with 1 volume of 50 mM Mes (pH6.5), 20% (v/v) glycerol, 500 mM KCl, 20 mM imidazole, 0.15% (w/v) DDM including 6-8 ml Ni-NTA resin pre-equilibrated in the same buffer. PMSF and pepstatin A were added to final concentrations of 0.2 mM and 2 μg/ml, respectively, and following batch binding for 16 h the resin was washed with 30 volumes of wash buffer (50 mM Mes-KOH, pH 6.5, 20% (v/v) glycerol, 5 mM imidazole, 0.15% (w/v) DDM, 0.5 mM EDTA, 0.5 mM DTT, 0.2 mM PMSF, 2 μg/ml pepstatin) supplemented with 500 mM KCl, with 20 volumes of wash buffer with 250 mM KCl and 20 volumes of wash buffer with 50 mM KCl before bound protein was eluted with 50 mM Mes-KOH, pH 6.5, 20% (v/v) glycerol, 200 mM imidazole, 0.04% (w/v) DDM, 50 mM KCl 0.5 mM EDTA, 0.5 mM DTT, 0.2 mM PMSF and 2 g/ml pepstatin A. Eluted protein were dialysed against GMEKD$_{20}$ and concentrated to 20-30 mg/ml on spin columns. Before crystallization experiments, protein were dialysed overnight against 50 mM KCl, 50 mM Mes pH 6.5, 10% sucrose (w/v), 1 mM DTT, 0.09 mM (critical micelle concentration) octaethyleneglycol mono-n-dodecylether (C$_{12}$E$_8$) and 2.4 mM (critical micelle concentration) 5-cyclohexyl-1-pentyl-β-D-maltoside (Cymal-5). After dialysis, 5 mM AMPPCP and 15 mM MgCl$_2$ were added and a final ultracentrifugation spin (70,000 rpm, 15 min) was applied before the crystallisation setup.

Crystal Growth

Crystals were grown at 4° C. using the vapour diffusion method in 4 µl hanging drops with a reservoir containing 29-32% (w/v) PEG 400, 100 mM KCl, 100 mM Mes pH 6.0 and 5% sucrose. Crystals with a final size of around 100× 100×200 pm obtained after typically two weeks crystal growth, were dehydrated by increasing the PEG 400 concentration in the reservoir solution to 40%. Dehydrated crystals were mounted in nylon loops and flashcooled in liquid nitrogen. Data were collected at the Swiss Light Source X06SA beamline on a Mar225 CCD detector. Initial crystals displayed approximately 8 Å maximum resolution, but several lines of crystal improvement, such as dehydration and detergent mixtures, improved diffraction properties. Optimised crystals diffract anisotropically to at least 3.3 Å in the best direction, and about 4.5 Å in the worst direction. Heavy atom derivatives were obtained by adding HoCl$_3$, K$_2$PtCl$_6$ or Ta$_6$Br$_{12}$ to the crystals before or during dehydration, either directly as powder or as a concentrated, aqueous solution.

Data Processing

Datasets were processed using XDS[31]. The data quality was impaired by the strong anisotropy as also manifested by high R$_{sym}$ values in the higher resolution bins (Supplementary Table 1). Initial heavy atom positions were found using phases from a weak, low-resolution (d>8 Å) molecular replacement solution using PHASER[32] and a partial search model derived from Ca$^{2+}$-ATPase[15]. Phasing by multiple isomorphous replacement with anomalous scattering (MIRAS) was obtained by SHARP[33]. Several native data sets were used to yield optimal isomorphous pairing of individual derivative data sets. Heavy-atom derived phases were refined and extended at the maximum resolution of the native data by density modification using dmmulti[34], exploiting twofold rotational NCS, a solvent content of 75% and several data sets displaying low level of isomorphism for inter-crystal averaging. The resulting electron density map was of high quality providing a continuous trace of the main-chain, albeit with a limited level of detail due to the anisotropy of the data (FIG. 2, Supplementary FIG. 4). Refinement was focused on the fitting of a model with reasonable stereochemistry to the experimental map. Prior to refinement the data was anisotropically corrected using the Anisotropy Correction Server[35] (doe-mbi.ucla.edu/~sawaya/anisoscale/). The model was built using O (ref. 36) with a Ca$^{2+}$-ATPase structure[15] and the CopA N domain structure[11] as guides for chain tracing. Initial torsion-angle refinement, imposing strict noncrystallographic symmetry (NCS), was performed in CNS1.2[37] using only higher resolution reflections (5-3.6 Å) without bulk solvent correction. Iterative model building and refinement gradually improved the model and the fit to the experimental map. In later stages bulk solvent correction was applied using phenix.refine[38] along with tight NCS restraints and a use of all reflections in the 20-3.6 Å range. The final model yielded a crystallographic R-factor of 35.1% and a free R-factor of 36.5%. PROCHECK[39] evaluation of the ramachandran plot gave 51.8% in core regions, 38.4% in allowed regions, 8.9% in generously allowed regions and 1.0% in disallowed regions. Cavities in the model were located using Voidoo[40]. The full-length data was processed by XDS[31] and a molecular replacement solution was obtained using PHASER[32] and our model from the truncated form of AHA2 SEQ ID NO: 1. All figures were prepared using PyMol[41].

Example 2

ATPase Assay

The assay is typically carried out with 1 to 3 µg of membrane protein at 30 C. In one set-up (Regenberg et al., 1995), the assay medium (300 µL) contains 20 mM 2-(N-morpholino)ethane-sulfonic acid, 20 mM 3-(N-morpholino)propanesulfonic acid, 50 mM KNO$_3$, 5 mM NaN3, 3.5 mM sodium molybdate, 10 mM MgCl2, and 3 mM ATP. The pH is adjusted, typically to pH 6.5, with N-methyl-D-glucamine. After a suitable time period following addition of the plasma membrane H+-ATPase preparation to the assay medium, typically 20 min, the reaction is stopped by the addition of 300 µL of ice-cold stop solution made by mixing 10 mL of 102 mM ascorbic acid, 0.3 N HCl, and 0.065% sodium dodecyl sulphate with 1 mL of 57 mM NH4-heptamolybdate. The resulting solution is allowed to incubate or 10 min on ice to allow for formation of the Pi-molybdate comlex. Excess molybdate can subsequently be complexed by the addition of 450 µL of a solution containing 154 mM NaAsO$_2$, 68 mM Na$_3$-citrate, and 350 mM acetic acid. After 60 min at room temperature, the colour has become stabilized, and absorbance at 860 nM can be determined.

Example 3

ATPase Assay

The rate of ATP hydrolysis, is quantified from the rate of NADH oxidation measured at 340 nm after typically 30 s. To allow for this reaction to occur, one known solution (Palmgren, 1990), known in the state of art, is to add 0.3 mM NADH, 2.4 mM phosphoenolpyruvate (neutralized with KOH), 33 µg of pyruvate kinase, and 33 µg of lactate dehydrogenase to the assay medium described above.

Example 4

Reaction buffer (25 mM KCl, 25 mM HEPES pH 7.0, 15% Glycerol, 15 mM MgCl2, and 3× CMC DDM) is mixed with potential ligands/inhibitors together with the ATPase, and the reaction is initiated by the addition of para-NitroPhenyl Phosphate to a final concentration of 15 mM. The assay can for instance be performed on ATPases residing in isolated membranes or on detergent solubilized enzyme. After a certain time interval, the reaction is stopped by addition of NaOH (final concentration 0.66 M), and the amount of hydrolyzed pNPP can be monitored spectrophotometrically at 405-415 nm.

Example 5

Phosphorylation (by [−32P]ATP) is performed at 0° C. in a medium containing 20 mM MOPS, 1 mM MgSO4, pH 6.5, 1 µM [−32P]ATP, and enzymes (either in the membrane or in solubilized form). The reaction can be initiated by addition of [−32P]ATP and stopped at various time points by addition of 6 volumes of stop solution (1 mM ATP, 1 mM Pi, and 7.5% trichloroacetic acid). After centrifugation of the samples, the pellet is washed three times with stop solution. The radioactivity associated with the pellet gives a measure of the amount of phosphorylated protein. This can be measured by counting the amount of radioactivity associated with the pellet (after resuspension in for instance 2% SDS) by liquid scintillation counting.

Example 6

Holmium-ion Coordination in H+ ATPase

Crystals were grown as described above. HoCl3 (in the form of a salt) were added to the crystals in the drop and equilibrated overnight, during dehydration. Crystals were cooled and tested and data processed as described above. The Holmium data was collected at the wavelength 1.2782 Å. The Holmium sites were identified by the calculation of an anomalous difference Fourier map, using experimentally derived phases. The results are shown in FIG. 10.

Example 7

Platinum-ion Coordination in H+ ATPase

Crystals were grown as described above. K2PtCl6 (in the form of a salt) were added to the crystals in the drop and equilibrated overnight, during dehydration. Crystals were cooled and tested and data processed as described above. The Platinum data was collected at the wavelength 1.0716 Å. The Platinum sites were identified by the calculation of an anomalous difference Fourier map, using experimentally derived phases. The results are shown in FIG. 11.

Example 8

Inhibition of H+ ATPase by Platin and Holmium Ions

Assay conditions are 20 mM Mops, pH: 6.5, 50 mM KCl, 8 mM MgCl2 and 3 mM ATP. Production of Pi was measured by standard calorimetric tests. The results are shown in FIG. 12A and the activity is given as the percentage of the ATP hydrolytic activity in the absence of various concentrations of Pt (±StDev).

Assay conditions are 20 mM Mops, pH: 6.5, 50 mM KCl, 8 mM MgCl2 and 3 mM ATP. Production of Pi was measured by standard calorimetric tests. The results are shown in FIG. 12B and the activity is given as the percentage of the ATP hydrolytic activity in the absence of various concentrations of Ho (±StDev).

REFERENCES

1. Serrano R., Kielland-Brandt M. C. & Fink G. R. Yeast plasma membrane ATPase is essential for growth and has homology with (Na++K+), K+- and Ca2+-ATPases. Nature 319, 689-93 (1986).
2. Morsomme, P., Slayman, C. W. & Goffeau, A. Mutagenic study of the structure, function and biogenesis of the yeast plasma membrane H+-ATPase. Biochim. Biophys. Acta 1469, 133-157 (2000).
3. Palmgren, M. G. Plant plasma membrane H+-ATPases: Powerhouses for nutrient uptake. Annu. Rev. Plant Physiol. Plant Mol. Biol. 52, 817-845 (2001).
4. Skou, J. C. & Esmann, M. The Na,K-ATPase. J. Bioenerg. Biomembr. 24, 249-261 (1992).
5. Pedersen, P. & Carafoli, E. Ion motive ATPases. 1. Ubiquity, properties, and significance to cell function. Trends Biochem. Sci. 12, 146-150 (1987).
6. Axelsen, K. B. & Palmgren, M. G. Evolution of substrate specificities in the P-type ATPase superfamily. J. Mol. Evol. 46, 84-101 (1998).
7. Auer, M., Scarborough, G. A., Kuhlbrandt, W. Three-dimensional map of the plasma membrane H+-ATPase in the open conformation. Nature 392, 840-843 (1998).
8. Harper, J. F., Manney, L., DeWitt, N. D., Yoo, M. H. & Sussman, M. R. The *Arabidopsis thaliana* plasma membrane H+-ATPase multigene family. Genomic sequence and expression of a third isoform. J. Biol. Chem. 265, 13601-13608 (1990).
9. Buch-Pedersen, M. J., Venema, K., Serrano, R. & Palmgren, M. G. Abolishment of proton pumping and accumulation in the E1P conformational state of a plant plasma membrane H+-ATPase by substitution of a conserved aspartyl residue in transmembrane segment 6. J. Biol. Chem. 275, 39167-73 (2000).
10. Toyoshima, C., Nakasako, M., Nomura, H. & Ogawa, H. Crystal structure of the calcium pump of sarcoplasmic reticulum at 2.6 A resolution. Nature 405, 647-655 (2000).
11. Sazinsky, M. H., Mandal, A. K., Arguello, J. M. and Rosenzweig, A. C. Structure of the ATP binding domain from the Archaeoglobus fulgidus $Cu_+$-ATPase. J. Biol. Chem. 281, 11161-11166 (2006).
12. Morth, J. P. et al. Crystal structure of the sodium-potassium pump. Nature xxx (2007)
13. Toyoshima, C. & Nomura, H. Structural changes in the calcium pump accompanying the dissociation of calcium. Nature 418, 605-611 (2002).
14. Sorensen, T. L., Moller, J. V. & Nissen, P. Phosphoryl transfer and calcium ion occlusion in the calcium pump. Science 304, 1672-1675 (2004).
15. Toyoshima, C. & Mizutani, T. Crystal structure of the calcium pump with a bound ATP analogue. Nature 430, 529-535 (2004).
16. Jensen, A. M., Sorensen, T. L., Olesen, C., Møller, J. V., & Nissen, P. Modulatory and catalytic modes of ATP binding by the calcium pump. EMBO J, 25, 2305-2314 (2006).
17. Eraso, P. & Portillo, F. Molecular mechanism of regulation of yeast plasma membrane H+-ATPase by glucose. Interaction between domains and identification of new regulatory sites. J. Biol. Chem. 269, 10393-10399 (1994).
18. Morsomme, P., Dambly, S., Maudoux, O. & Boutry, M. Single point mutations distributed in 10 soluble and membrane regions of the *Nicotiana plumbaginifolia* plasma membrane PMA2 H+-ATPase activate the enzyme and modify the structure of the C-terminal region. J. Biol. Chem. 273, 34837-34842 (1998).
19. MacLennan, D. H., Abu-Abed, M. & Kang. C. Structure-function relationships in $Ca2_+$ cycling proteins. J. Mol. Cell. Cardiol. 34, 897-918 (2002).
20. Buch-Pedersen, M. J. & Palmgren, M. G. Conserved Asp684 in transmembrane segment M6 of the plant plasma membrane P-type proton pump AHA2 is a molecular determinant of proton translocation. J. Biol. Chem. 278, 17845-17851 (2003).
21. Dutra, M. B., Ambesi, A. & Slayman, C. W. Structure-function relationships in membrane segment 5 of the yeast Pma1 H+-ATPase. J. Biol. Chem. 273, 17411-17417 (1998).
22. Pebay-Peyroula, E., Rummel, G., Rosenbusch, J. P. & Landau, E. M. X-ray structure of bacteriorhodopsin at 2.5 angstroms from microcrystals grown in lipidic cubic phases. Science 277, 1676-1681 (1997).
23. Luecke, H., Richter, H. T. & Lanyi, J. K. Proton transfer pathways in bacteriorhodopsin at 2.3 angstrom resolution. Science 280, 1934-1937 (1998).

24. Hutcheon, M. L., Duncan, T. M., Ngai, H. & Cross, R. L. Energy-driven subunit rotation at the interface between subunit a and the c oligomer in the FO sector of *Escherichia coli* ATP synthase. Proc. Natl. Acad. Sci. USA 98, 8519-8524 (2001).
25. Fillingame, R. H. & Dmitriev, O. Y. Structural model of the transmembrane Fo rotary sector of H+-transporting ATP synthase derived by solution NMR and intersubunit cross-linking in situ. Biochim. Biophys. Acta 1565, 232-245 (2002).
26. Olesen, C. et al. The structural basis of calcium transport by the calcium pump. Nature. 2007 Dec. 13; 450 (7172):1036-42.
27. Hirsch, R. E., Lewis, B. D., Spalding, E. P. & Sussman, M. R. A role for the AKT1 potassium channel in plant nutrition. Science 280, 918-921 (1998).
28. Blatt, M. R., Rodriguez-Navarro, A. & Slayman, C. L. Potassium-proton symport in Neurospora: Kinetic control by pH and membrane potential. J. Membr. Biol. 98, 169-189 (1987).
29. Amory, A., Goffeau, A., McIntosh, D. B. & Boyer, P. D. Exchange of oxygen between phosphate and water catalyzed by the plasma membrane ATPase from the yeast *Schizosaccharomyces pombe*. J. Biol. Chem. 257, 12509-12516 (1982).
30. Briskin, D. P. & Reynolds-Niesman, I. Determination of H/ATP stoichiometry for the plasma membrane H-ATPase from red beet (*Beta vulgaris* L.) storage tissue. Plant Physiol. 95, 242-250 (1991).
31. Kabsch, W. Automatic processing of rotation diffraction data from crystals of initially unknown symmetry and cell constants. *J. Appl. Crystallogr.* 26, 795-800 (1993).
32. Storoni, L. C., McCoy, A. J. & Read, R. J. Likelihood-enhanced fast rotation functions. *Acta Crystallogr. D Biol. Crystallogr.* 60, 432-438 (2004).
33. de La Fortelle, E. & Bricogne, G. Maximum-likelihood heavy-atom parameter refinement for multiple isomorphous replacement and multiwavelength anomalous diffraction methods. *Macromol. Crystallogr., Pt A* 276, 472-494 (1997).
34. Cowtan, K. 'dm': An automated procedure for phase improvement by density modification. *Joint CCP4 and ESF-EACBM Newsletter on Protein Crystallography,* 31, 34-38 (1994).
35. Strong, M., Sawaya, M. R., Wang, S., Phillips, M., Cascio, D. & Eisenberg, D. Toward the structural genomics of complexes: Crystal structure of a PE/PPE protein complex from *Mycobacterium tuberculosis*. Proc. Natl. Acad. Sci. U.S.A 103, 8060-8065 (2006).
36. Jones, T. A., Zou, J. Y., Cowan, S. W. & Kjeldgaard, M. Improved methods for building protein models in electron-density maps and the location of errors in these models. *Acta Crystallogr. A* 47, 110-119 (1991).
37. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. & Warren, G. L. Crystallography & NMR system: A new software suite for macromolecular structure determination. *Acta Crystallogr. D Biol. Crystallogr.* 54, 905-921 (1998).
38. Afonine, P. V., Grosse-Kunstleve, R. W. & Adams, P. D. A robust bulk-solvent correction and anisotropic scaling procedure. *Acta Crystallogr. D Biol. Crystallogr.* 61, 850-855 (2005).
39. Laskowski, R. A., Macarthur, M. W., Moss, D. S. & Thornton, J. M. Procheck—a program to check the stereochemical quality of protein structures. *J. Appl. Crystallogr.* 26, 283-291 (1993).
40. Kleywegt, G. J. & Jones, T. A. Detection, delineation, measurement and display of cavities in macromolecular structures. *Acta Crystallogr. D Biol. Crystallog.* 50, 178-185 (1994).
41. DeLano, W. L. The PyMOL User's Manual. *DeLano Scientific*, Calif., USA, San Carlos (2002).
42. Kühlbrand, W. Zeelen, J. Dietrich, J. Structure, Mechanism, and regulation of the *Neurospora plasma* Membrane H+-ATPase. *Science*. 297, 1692-1696 (2002).
43. Edgar R. C., MUSCLE: multiple sequence alignment with high accuracy and high throughput, *Nucleic Acids Research* 32, 1792-97 (2004).
44. Freeman & Co., Enyzme Structure and Mechanism, 2nd edition, New York, 1985, p. 6.
45. Baginsky, E. S., Foa, P. P., and Zak, B. (1967). Determination of phosphate: Study of labile organic phosphate interference. *Clin. Chim. Acta* 15, 155-158.
46. Bagshaw, C. R. (2001) ATP analogues at a glance. *J. Cell Sci.* 114, 459-460.
47. Buch-Pedersen, M. J., Venema, K., Serrano, R., and Palmgren, M. G. (2006) Abolishment of proton pumping and accumulation in the E1P conformational state of a plant plasma membrane H+-ATPase by substitution of a conserved aspartyl residue in transmembrane segment 6. *J. Biol. Chem.* 275, 39167-73.
48. Bowman, B. J., Blasco, F., and Slayman, C. W. (1981) Purification and characterization of the plasma membrane ATPase of Neurospora crassa. *J. Biol. Chem.* 256, 12334-12349.
49. Chernoff, J., and Li, H. C. (1983) *Arch. Biochem. Biophys.* 226, 517-530.
50. Gupta, P., Mahanty, S. K., Ansari, S., and Prasdad, R. (1991) Isolation, purification and kinetic characterization of plasma membrane H+-ATPase of *Candida Albicans*. *Biochem. Int* 24, 907-915.
51. Guerra, G., Uribe, S., and Pardo, J. P. (1995) Reactivity of the H+-ATPase from *Kluyveromyces lactis* to sulfhydryl reagents. *Arch. Biochem. Biophys.* 321, 101-107.
52. Huang, L. S., and Berry, E. A. (1990) Purification and characterization of the proton translocating plasma membrane ATPase of red beet storage tissue. *Biochim. Biophys. Acta.* 1039, 241-252.
53. Jain, A. N. (2006) Scoring functions for protein-ligand docking. *Curr. Protein Pept. Sci.* 7, 407-420.
54. Lanfermeijer, F. C., Venema, K., and Palmgren, M. G. (1998) Purification of a histidine-tagged plant plasma membrane H+-ATPase expressed in yeast. *Protein Expr. Purif.* 12, 29-37.
55. Luo, S., Scott, D. A., and Docampo, R. (2002) Trypanosoma cruzi H+-ATPase 1 (TcHA1) and 2 (TcHA2) genes complement yeast mutants defective in H+ pumps and encode plasma membrane P-type H+-ATPases with different enzymatic properties. *J. Biol. Chem.* 277, 44497-44506.
56. Monk, B. C., Kurtz, M. B., Marrinan, J. A., and Perlin, D. S. (1991) Cloning and characterization of the plasma membrane H+-ATPase from *Candida Albicans*. *J. Bacteriol.* 173, 6826-6836.
57. Palmgren M G (1990) An H-ATPase assay: Proton pumping and ATPase activity determined simultaneously in the same sample. *Plant Physiol.* 94:882-886.
58. Palmgren M G (1991) Acridine orange as a probe for measuring pH gradients across membranes: mechanism and limitations. *Anal. Biochem.* 192:316-21.

59. Perlin D S, Kasamo K, Brooker R J, Slayman C W (1984) Electrogenic H⁺ translocation by the plasma membrane ATPase of Neurospora. Studies on plasma membrane vesicles and reconstituted enzyme. *J. Biol. Chem.* 259:7884-92.
60. Regenberg B, Villalba J M, Lanfermeijer F C, Palmgren M G (1995) C-terminal deletion analysis of plant plasma membrane H⁺-ATPase: yeast as a model system for solute transport across the plant plasma membrane. *Plant Cell* 7:1655-66.
61. Robinson, J. D., Levine, G. M., and Robinson, L. J. (1983) A model for the reaction pathways of the K+-dependent phosphatase activity of the (Na+/K+)-dependent ATPase. *Biochim. Biophys. Acta* 731, 406-414.
62. Sampedro, J. G., Ruiz-Granados, Y. G., Najera, H., Tellez-Valencia, A., and Uribe, S. (2007) Fluorescence quenching by nucleotides of the plasma membrane H+-ATPase from *Kluveromyces lactis. Biochemistry* 46, 5616-5622.
63. Seifert, M. H., Kraus, J., Kramer, B. (2007) Virtual high-throughput screening of molecular databases. *Curr. Opn. Drug Disc. Dev.* 10, 264-274.
64. Serrano, R. (1988) H+-ATPase from plasma membranes of *Saccharomyces cerevisiae* and *Avena sativa* roots: purification and reconstitution. *Methods Enzymol.* 157, 533-544.
65. Serrano, R. (1984) Purification of the proton pumping ATPase from plasma membranes. *Biochem. Biophys. Res. Commun.* 121, 735-740.
66. Warren G. L. et al. (2006) A critical assessment of docking programs and scoring functions. *J. Med. Chem.* 49, 5912-5931.
67. Zhang, Z. Y., and Dixon, J. E. (1994) *Adv. Enzymol. Relat. Areas Mol. Biol.* 68, 1-36.
68. Pedersen B P, Buch-Pedersen M J, Morth J P, Palmgren M G, Nissen P (2007). Crystal structure of the plasma membrane proton pump. *Nature.* December 13; 450(7172)1111-4.

The invention claimed is:

1. A method of identifying a potential inhibitor of a type III P-type ATPase by determining binding interactions between the potential inhibitor and a set of binding interaction sites in the proton transport pathway of said ATPase, the method comprising:
   obtaining a crystal of a type III P-type ATPase of an amino acid sequence of residues 1-875 of SEQ ID NO: 1 fused at its C-terminus to the amino acids of SEQ ID NO: 34, the crystal being of space group $P2_12_12_1$; with unit cell dimensions in which:
   a is 85±4Å, b is 144±4Å, c is 312±4Å, and α is 90°, β is 90°, γ is 90°;
   and determining the three-dimensional structure to obtain the atomic coordinates of this crystal as presented in FIG. 13 or atomic coordinates selected from a three-dimensional structure that deviates from the three-dimensional structure as presented in FIG. 13 by a root mean square deviation over protein backbone atoms of not more than 3 Å;
   generating the spatial structure of the proton transport pathway on a computer screen using atomic coordinates as presented in FIG. 13 or atomic coordinates selected from a three-dimensional structure that deviates from the three-dimensional structure as presented in FIG. 13 by a root mean square deviation over protein backbone atoms of not more than 3 Å,
   generating the spatial structure of potential inhibitors on the computer screen, and
   selecting as a potential inhibitor a compound that can bind to the proton transfer pathway without steric interference.

2. A computer-assisted method for identifying potential inhibitors of a type III P-type ATPase using a programmed computer processor, a data storage system, a data input devise and a data output devise, the method comprising:
   obtaining a crystal of a type III P-type ATPase of an amino acid sequence of residues 1-875 of SEQ ID NO: 1 fused at its C-terminus to the amino acids of SEQ ID NO: 34, the crystal being of space group $P2_12_12_1$; with unit cell dimensions in which: a is 85±4Å, b is 144±4Å, c is 312±4Å, and α is 90°, β is 90°, γ is 90°;
   and determining the three-dimensional structure to obtain the atomic coordinates of this crystal as presented in FIG. 13 or atomic coordinates selected from a three-dimensional structure that deviates from the three-dimensional structure as presented in FIG. 13 by a root mean square deviation over protein backbone atoms of not more than 3 Å;
   inputting into the programmed computer through said input device data comprising: a subset of the atoms of a type III P-type ATPase, thereby generating a criteria data set; wherein the atomic coordinates are selected from the three-dimensional structure as presented in FIG. 13 or atomic coordinates selected from a three-dimensional structure that deviates from the three-dimensional structures as presented in FIG. 13 by a root mean square deviation over protein backbone atoms of not more than 3 Å,
   comparing, using said processor, the criteria data set to a computer data base of low molecular weight organic chemical structures stored in the data storage system; and
   selecting from said data base, using computer methods, a chemical structure having a portion that is structurally complementary to the criteria data set and being free of steric interference with the ATPase.

3. The method according to claim 2, wherein information derived from the atomic coordinates of at least one of the following amino acid residues of SEQ ID NO:1 of the proton transport pathway: Pro68 to Asn85 (transmembrane helix M1), Pro90 to Ala117 (transmembrane helix M2), Asp272 to Met297 (transmembrane helix M4), Arg636 to Leu665 (transmembrane helix M5) and Ser672 to Thr689 (transmembrane helix M6) are used.

4. The method according to claim 2, wherein information derived from the atomic coordinates of at least one of the following amino acid residues of SEQ ID NO:1 of the proton inlet channel: Asp684 (transmembrane helix M6), Pro68 to Glu74 (transmembrane helix M1) and Leu103 to Glu114 are used.

5. The method according to claim 2, wherein information derived from the atomic coordinates of at least one of the following amino acid residues of SEQ ID NO:1 of the active site: Asp 684, Ile287 to Met297 (transmembrane helix M4), Arg636 to Asn644 (transmembrane helix M5) and Gly685 to Thr689 (transmembrane helix M6) are used.

6. The method according to claim 2, wherein information derived from the atomic coordinates of at least one of the following amino acid residues of SEQ ID NO:1 of the proton release pathway: Asn 683, Asn 106, Glu74 to Asn85 (transmembrane helix M1), Pro90 to Val104 (transmembrane helix M2), Asp272 to Ile282 (transmembrane helix M4), Ile656 to Leu665 (transmembrane helix M5) and Ser672 to Asn683 (transmembrane helix M6) are used.

7. A method for producing a potential modulator of a type III P-type ATPase comprising:
identification of a potential modulator of a type III P-type ATPase according to claim 2 and
producing said identified potential modulator.

8. The method of claim 2, wherein information derived from the atomic coordinates of at least one of the following amino acid residues of SEQ ID NO:1: Arg636 to Thr689 are used.

9. A method for identifying a potential inhibitor capable of inhibiting the H+ translocating activity of a type III P-type ATPase, said method comprising:
obtaining a crystal of a type III P-type ATPase of an amino acid sequence of residues 1-875 of SEQ ID NO: 1 fused at its C-terminus to the amino acids of SEQ ID NO: 34, the crystal being of space group $P2_12_12_1$; with unit cell dimensions in which: a is 85±4Å, b is 144±4Å, c is 312±4Å, and α is 90°, β is 90°, γ is 90°;
and determining the three-dimensional structure to obtain the atomic coordinates of this crystal as presented in FIG. 13 or atomic coordinates selected from a three-dimensional structure that deviates from the three-dimensional structure as presented in FIG. 13 by a root mean square deviation over protein backbone atoms of not more than 3 Å;
selecting a potential inhibitor using atomic coordinates in conjunction with computer modelling, wherein said atomic coordinates are the atomic coordinates presented in FIG. 13 or wherein the atomic coordinates are selected from a three-dimensional structure that deviates from the three-dimensional structures presented in FIG. 13 by a root mean square deviation over protein backbone atoms of not more than 3 Å, by docking potential inhibitors into a set of binding interaction sites in a proton transfer pathway generated by computer modeling and selecting a potential inhibitor capable of binding to said proton transport pathway,
providing said potential inhibitor and said ATPase,
contacting the potential inhibitor with said ATPase and
detecting inhibition of H+ translocating activity of said ATPase by the potential inhibitor.

10. A method for identifying a potential inhibitor capable of inhibiting the H+ translocating activity of a type III P-type ATPase, said method comprising:
obtaining a crystal of a type III P-type ATPase of an amino acid sequence of residues 1-875 of SEQ ID NO: 1 fused at its C-terminus to the amino acids of SEQ ID NO: 34, the crystal being of space group $P2_12_12_1$; with unit cell dimensions in which: a is 85±4Å, b is 144±4Å, c is 312±4Å, and α is 90°, β is 90°, γ is 90°;
and determining the three-dimensional structure to obtain the atomic coordinates of this crystal as presented in FIG. 13 or atomic coordinates selected from a three-dimensional structure that deviates from the three-dimensional structure as presented in FIG. 13 by a root mean square deviation over protein backbone atoms of not more than 3 Å;
introducing into a computer information derived from atomic coordinates defining a conformation of a proton transport pathway, the proton transfer pathway comprising three regions, an inlet channel, an active proton binding site, and a proton release pathway, based on three-dimensional structure determination, whereby said program utilizes or displays on the computer screen the structure of said conformation, wherein the atomic coordinates are selected from the three-dimensional structure as presented in FIG. 13 or atomic coordinates selected from a three-dimensional structure that deviates from the three-dimensional structures as presented in FIG. 13 by a root mean square deviation over protein backbone atoms of not more than 3 Å,
generating a three-dimensional representation of at least one of the three regions of the proton transport pathway of said ATPase by said computer program on a computer screen,
superimposing a model of a potential inhibitor on the representation on at least one of the three regions of the proton transport pathway; assessing the possibility of bonding and the absence of steric interference of the potential inhibitor with the proton transport pathway;
incorporation said potential compound in an activity assay of said ATPase and
determining whether said potential compound inhibits H+ translocating activity of said ATPase.

* * * * *

SEQUENCE LISTING

<160> NUMBER OF SEQ ID NOS: 34

<210> SEQ ID NO 1
<211> LENGTH: 948
<212> TYPE: PRT
<213> ORGANISM: Arabidopsis thaliana

<400> SEQUENCE: 1

```
Met Ser Ser Leu Glu Asp Ile Lys Asn Glu Thr Val Asp Leu Glu Lys
1               5                   10                  15

Ile Pro Ile Glu Glu Val Phe Gln Gln Leu Lys Cys Ser Arg Glu Gly
            20                  25                  30

Leu Thr Thr Gln Glu Gly Glu Asp Arg Ile Gln Ile Phe Gly Pro Asn
        35                  40                  45

Lys Leu Glu Glu Lys Lys Glu Ser Lys Leu Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Asp Gly Arg Pro Pro Asp Trp Gln Asp Phe
                85                  90                  95

Val Gly Ile Ile Cys Leu Leu Val Ile Asn Ser Thr Ile Ser Phe Ile
            100                 105                 110

Glu Glu Asn Asn Ala Gly Asn Ala Ala Ala Leu Met Ala Gly Leu
            115                 120                 125

Ala Pro Lys Thr Lys Val Leu Arg Asp Gly Lys Trp Ser Glu Gln Glu
        130                 135                 140

Ala Ala Ile Leu Val Pro Gly Asp Ile Val Ser Ile Lys Leu Gly Asp
145                 150                 155                 160

Ile Ile Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Lys His Pro
            180                 185                 190

Gly Gln Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
    210                 215                 220

His Leu Val Asp Ser Thr Asn Gln Val Gly His Phe Gln Lys Val Leu
```

```
            225                 230                 235                 240
Thr Ala Ile Gly Asn Phe Cys Ile Cys Ser Ile Ala Ile Gly Met Val
                245                 250                 255

Ile Glu Ile Ile Val Met Tyr Pro Ile Gln Arg Arg Lys Tyr Arg Asp
                260                 265                 270

Gly Ile Asp Asn Leu Leu Val Leu Ile Gly Gly Ile Pro Ile Ala
                275                 280                 285

Met Pro Thr Val Leu Ser Val Thr Met Ala Ile Gly Ser His Arg Leu
                290                 295                 300

Ser Gln Gln Gly Ala Ile Thr Lys Arg Met Thr Ala Ile Glu Glu Met
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Cys Lys Gly
                340                 345                 350

Val Glu Lys Asp Gln Val Leu Leu Phe Ala Ala Met Ala Ser Arg Val
                355                 360                 365

Glu Asn Gln Asp Ala Ile Asp Ala Ala Met Val Gly Met Leu Ala Asp
                370                 375                 380

Pro Lys Glu Ala Arg Ala Gly Ile Arg Glu Val His Phe Leu Pro Phe
385                 390                 395                 400

Asn Pro Val Asp Lys Arg Thr Ala Leu Thr Tyr Ile Asp Gly Ser Gly
                405                 410                 415

Asn Trp His Arg Val Ser Lys Gly Ala Pro Glu Gln Ile Leu Glu Leu
                420                 425                 430

Ala Lys Ala Ser Asn Asp Leu Ser Lys Lys Val Leu Ser Ile Ile Asp
                435                 440                 445

Lys Tyr Ala Glu Arg Gly Leu Arg Ser Leu Ala Val Ala Arg Gln Val
                450                 455                 460

Val Pro Glu Lys Thr Lys Glu Ser Pro Gly Ala Pro Trp Glu Phe Val
465                 470                 475                 480

Gly Leu Leu Pro Leu Phe Asp Pro Pro Arg His Asp Ser Ala Glu Thr
                485                 490                 495

Ile Arg Arg Ala Leu Asn Leu Gly Val Asn Val Lys Met Ile Thr Gly
                500                 505                 510

Asp Gln Leu Ala Ile Gly Lys Glu Thr Gly Arg Arg Leu Gly Met Gly
                515                 520                 525

Thr Asn Met Tyr Pro Ser Ser Ala Leu Leu Gly Thr His Lys Asp Ala
                530                 535                 540

Asn Leu Ala Ser Ile Pro Val Glu Glu Leu Ile Glu Lys Ala Asp Gly
545                 550                 555                 560

Phe Ala Gly Val Phe Pro Glu His Lys Tyr Glu Ile Val Lys Lys Leu
                565                 570                 575

Gln Glu Arg Lys His Ile Val Gly Met Thr Gly Asp Gly Val Asn Asp
                580                 585                 590

Ala Pro Ala Leu Lys Lys Ala Asp Ile Gly Ile Ala Val Ala Asp Ala
                595                 600                 605

Thr Asp Ala Ala Arg Gly Ala Ser Asp Ile Val Leu Thr Glu Pro Gly
                610                 615                 620

Leu Ser Val Ile Ile Ser Ala Val Leu Thr Ser Arg Ala Ile Phe Gln
625                 630                 635                 640

Arg Met Lys Asn Tyr Thr Ile Tyr Ala Val Ser Ile Thr Ile Arg Ile
                645                 650                 655
```

Val Phe Gly Phe Met Leu Ile Ala Leu Ile Trp Glu Phe Asp Phe Ser
            660                 665                 670

Ala Phe Met Val Leu Ile Ile Ala Ile Leu Asn Asp Gly Thr Ile Met
        675                 680                 685

Thr Ile Ser Lys Asp Arg Val Lys Pro Ser Pro Thr Pro Asp Ser Trp
690                 695                 700

Lys Leu Lys Glu Ile Phe Ala Thr Gly Val Val Leu Gly Gly Tyr Gln
705                 710                 715                 720

Ala Ile Met Thr Val Ile Phe Phe Trp Ala Ala His Lys Thr Asp Phe
                725                 730                 735

Phe Ser Asp Thr Phe Gly Val Arg Ser Ile Arg Asp Asn Asn His Glu
            740                 745                 750

Leu Met Gly Ala Val Tyr Leu Gln Val Ser Ile Ile Ser Gln Ala Leu
        755                 760                 765

Ile Phe Val Thr Arg Ser Arg Ser Trp Ser Phe Val Glu Arg Pro Gly
    770                 775                 780

Ala Leu Leu Met Ile Ala Phe Leu Ile Ala Gln Leu Ile Ala Thr Leu
785                 790                 795                 800

Ile Ala Val Tyr Ala Asn Trp Glu Phe Ala Lys Ile Arg Gly Ile Gly
                805                 810                 815

Trp Gly Trp Ala Gly Val Ile Trp Leu Tyr Ser Ile Val Thr Tyr Phe
            820                 825                 830

Pro Leu Asp Val Phe Lys Phe Ala Ile Arg Tyr Ile Leu Ser Gly Lys
        835                 840                 845

Ala Trp Leu Asn Leu Phe Glu Asn Lys Thr Ala Phe Thr Met Lys Lys
    850                 855                 860

Asp Tyr Gly Lys Glu Glu Arg Glu Ala Gln Trp Ala Leu Ala Gln Arg
865                 870                 875                 880

Thr Leu His Gly Leu Gln Pro Lys Glu Ala Val Asn Ile Phe Pro Glu
                885                 890                 895

Lys Gly Ser Tyr Arg Glu Leu Ser Glu Ile Ala Glu Gln Ala Lys Arg
            900                 905                 910

Arg Ala Glu Ile Ala Arg Leu Arg Glu Leu His Thr Leu Lys Gly His
        915                 920                 925

Val Glu Ser Val Val Lys Leu Lys Gly Leu Asp Ile Glu Thr Pro Ser
    930                 935                 940

His Tyr Thr Val
945

<210> SEQ ID NO 2
<211> LENGTH: 18
<212> TYPE: PRT
<213> ORGANISM: Arabidopsis thaliana

<400> SEQUENCE: 2

Trp Asn Pro Leu Ser Trp Val Met Glu Met Ala Ala Ile Met Ala Ile
1               5                   10                  15

Ala Leu

<210> SEQ ID NO 3
<211> LENGTH: 35
<212> TYPE: PRT
<213> ORGANISM: Arabidopsis thaliana

<400> SEQUENCE: 3

Gln Asp Phe Val Gly Ile Ile Cys Leu Leu Val Ile Asn Ser Thr Ile
1               5                   10                  15

```
Ser Phe Ile Glu Glu Asn Asn Ala Gly Asn Ala Ala Ala Leu Met
            20                  25                  30

Ala Gly Leu
        35

<210> SEQ ID NO 4
<211> LENGTH: 32
<212> TYPE: PRT
<213> ORGANISM: Arabidopsis thaliana

<400> SEQUENCE: 4

His Phe Gln Lys Val Leu Thr Ala Ile Gly Asn Phe Cys Ile Cys Ser
1               5                   10                  15

Ile Ala Ile Gly Met Val Ile Glu Ile Val Met Tyr Pro Ile Gln
            20                  25                  30

<210> SEQ ID NO 5
<211> LENGTH: 37
<212> TYPE: PRT
<213> ORGANISM: Arabidopsis thaliana

<400> SEQUENCE: 5

Arg Asp Gly Ile Asp Asn Leu Leu Val Leu Ile Gly Gly Ile Pro
1               5                   10                  15

Ile Ala Met Pro Thr Val Leu Ser Val Thr Met Ala Ile Gly Ser His
            20                  25                  30

Arg Leu Ser Gln Gln
        35

<210> SEQ ID NO 6
<211> LENGTH: 39
<212> TYPE: PRT
<213> ORGANISM: Arabidopsis thaliana

<400> SEQUENCE: 6

Leu Ser Val Ile Ile Ser Ala Val Leu Thr Ser Arg Ala Ile Phe Gln
1               5                   10                  15

Arg Met Lys Asn Tyr Thr Ile Tyr Ala Val Ser Ile Thr Ile Arg Ile
            20                  25                  30

Val Phe Gly Phe Met Leu Ile
        35

<210> SEQ ID NO 7
<211> LENGTH: 14
<212> TYPE: PRT
<213> ORGANISM: Arabidopsis thaliana

<400> SEQUENCE: 7

Ala Phe Met Val Leu Ile Ile Ala Ile Leu Asn Asp Gly Thr
1               5                   10

<210> SEQ ID NO 8
<211> LENGTH: 24
<212> TYPE: PRT
<213> ORGANISM: Arabidopsis thaliana

<400> SEQUENCE: 8

Lys Leu Lys Glu Ile Phe Ala Thr Gly Val Val Leu Gly Gly Tyr Gln
1               5                   10                  15

Ala Ile Met Thr Val Ile Phe Phe
            20
```

```
<210> SEQ ID NO 9
<211> LENGTH: 22
<212> TYPE: PRT
<213> ORGANISM: Arabidopsis thaliana

<400> SEQUENCE: 9

Arg Asp Asn Asn His Glu Leu Met Gly Ala Val Tyr Leu Gln Val Ser
1               5                   10                  15

Ile Ile Ser Gln Ala Leu
            20

<210> SEQ ID NO 10
<211> LENGTH: 15
<212> TYPE: PRT
<213> ORGANISM: Arabidopsis thaliana

<400> SEQUENCE: 10

Leu Leu Met Ile Ala Phe Leu Ile Ala Gln Leu Ile Ala Thr Leu
1               5                   10                  15

<210> SEQ ID NO 11
<211> LENGTH: 27
<212> TYPE: PRT
<213> ORGANISM: Arabidopsis thaliana

<400> SEQUENCE: 11

Trp Gly Trp Ala Gly Val Ile Trp Leu Tyr Ser Ile Val Thr Tyr Phe
1               5                   10                  15

Pro Leu Asp Val Phe Lys Phe Ala Ile Arg Tyr
            20                  25

<210> SEQ ID NO 12
<211> LENGTH: 918
<212> TYPE: PRT
<213> ORGANISM: Saccharomyces cerevisiae

<400> SEQUENCE: 12

Met Thr Asp Thr Ser Ser Ser Ser Ser Ser Ala Ser Ser Val
1               5                   10                  15

Ser Ala His Gln Pro Thr Gln Glu Lys Pro Ala Lys Thr Tyr Asp Asp
                20                  25                  30

Ala Ala Ser Glu Ser Ser Asp Asp Asp Ile Asp Ala Leu Ile Glu
            35                  40                  45

Glu Leu Gln Ser Asn His Gly Val Asp Glu Asp Ser Asp Asn Asp
    50                  55                  60

Gly Pro Val Ala Ala Gly Glu Ala Arg Pro Val Pro Glu Glu Tyr Leu
65                  70                  75                  80

Gln Thr Asp Pro Ser Tyr Gly Leu Thr Ser Asp Glu Val Leu Lys Arg
                85                  90                  95

Arg Lys Lys Tyr Gly Leu Asn Gln Met Ala Asp Glu Lys Glu Ser Leu
            100                 105                 110

Val Val Lys Phe Val Met Phe Phe Val Gly Pro Ile Gln Phe Val Met
        115                 120                 125

Glu Ala Ala Ala Ile Leu Ala Ala Gly Leu Ser Asp Trp Val Asp Phe
    130                 135                 140

Gly Val Ile Cys Gly Leu Leu Met Leu Asn Ala Gly Val Gly Phe Val
145                 150                 155                 160

Gln Glu Phe Gln Ala Gly Ser Ile Val Asp Glu Leu Lys Lys Thr Leu
                165                 170                 175
```

-continued

```
Ala Asn Thr Ala Val Val Ile Arg Asp Gly Gln Leu Val Glu Ile Pro
                180                 185                 190
Ala Asn Glu Val Val Pro Gly Asp Ile Leu Gln Leu Glu Asp Gly Thr
            195                 200                 205
Val Ile Pro Thr Asp Gly Arg Ile Val Thr Glu Asp Cys Phe Leu Gln
        210                 215                 220
Ile Asp Gln Ser Ala Ile Thr Gly Glu Ser Leu Ala Val Asp Lys His
225                 230                 235                 240
Tyr Gly Asp Gln Thr Phe Ser Ser Thr Val Lys Arg Gly Glu Gly
                245                 250                 255
Phe Met Val Val Thr Ala Thr Gly Asp Asn Thr Phe Val Gly Arg Ala
                260                 265                 270
Ala Ala Leu Val Asn Lys Ala Ala Gly Gly Gln Gly His Phe Thr Glu
            275                 280                 285
Val Leu Asn Gly Ile Gly Ile Ile Leu Leu Val Leu Val Ile Ala Thr
        290                 295                 300
Leu Leu Leu Val Trp Thr Ala Cys Phe Tyr Arg Thr Asn Gly Ile Val
305                 310                 315                 320
Arg Ile Leu Arg Tyr Thr Leu Gly Ile Thr Ile Ile Gly Val Pro Val
                325                 330                 335
Gly Leu Pro Ala Val Val Thr Thr Thr Met Ala Val Gly Ala Ala Tyr
                340                 345                 350
Leu Ala Lys Lys Gln Ala Ile Val Gln Lys Leu Ser Ala Ile Glu Ser
            355                 360                 365
Leu Ala Gly Val Glu Ile Leu Cys Ser Asp Lys Thr Gly Thr Leu Thr
        370                 375                 380
Lys Asn Lys Leu Ser Leu His Glu Pro Tyr Thr Val Glu Gly Val Ser
385                 390                 395                 400
Pro Asp Asp Leu Met Leu Thr Ala Cys Leu Ala Ala Ser Arg Lys Lys
                405                 410                 415
Lys Gly Leu Asp Ala Ile Asp Lys Ala Phe Leu Lys Ser Leu Lys Gln
                420                 425                 430
Tyr Pro Lys Ala Lys Asp Ala Leu Thr Lys Tyr Lys Val Leu Glu Phe
            435                 440                 445
His Pro Phe Asp Pro Val Ser Lys Lys Val Thr Ala Val Val Glu Ser
        450                 455                 460
Pro Glu Gly Glu Arg Ile Val Cys Val Lys Gly Ala Pro Leu Phe Val
465                 470                 475                 480
Leu Lys Thr Val Glu Glu Asp His Pro Ile Pro Glu Asp Val His Glu
                485                 490                 495
Asn Tyr Glu Asn Lys Val Ala Glu Leu Ala Ser Arg Gly Phe Arg Ala
            500                 505                 510
Leu Gly Val Ala Arg Lys Arg Gly Glu Gly His Trp Glu Ile Leu Gly
        515                 520                 525
Val Met Pro Cys Met Asp Pro Pro Arg Asp Asp Thr Ala Gln Thr Val
530                 535                 540
Ser Glu Ala Arg His Leu Gly Leu Arg Val Lys Met Leu Thr Gly Asp
545                 550                 555                 560
Ala Val Gly Ile Ala Lys Glu Thr Cys Arg Gln Leu Gly Leu Gly Thr
                565                 570                 575
Asn Ile Tyr Asn Ala Glu Arg Leu Gly Leu Gly Gly Gly Asp Met
            580                 585                 590
Pro Gly Ser Glu Leu Ala Asp Phe Val Glu Asn Ala Asp Gly Phe Ala
        595                 600                 605
```

Glu Val Phe Pro Gln His Lys Tyr Arg Val Val Glu Ile Leu Gln Asn
            610                 615                 620

Arg Gly Tyr Leu Val Ala Met Thr Gly Asp Gly Val Asn Asp Ala Pro
625                 630                 635                 640

Ser Leu Lys Lys Ala Asp Thr Gly Ile Ala Val Glu Gly Ala Thr Asp
            645                 650                 655

Ala Ala Arg Ser Ala Ala Asp Ile Val Phe Leu Ala Pro Gly Leu Ser
            660                 665                 670

Ala Ile Ile Asp Ala Leu Lys Thr Ser Arg Gln Ile Phe His Arg Met
            675                 680                 685

Tyr Ser Tyr Val Val Tyr Arg Ile Ala Leu Ser Leu His Leu Glu Ile
            690                 695                 700

Phe Leu Gly Leu Trp Ile Ala Ile Leu Asp Asn Ser Leu Asp Ile Asp
705                 710                 715                 720

Leu Ile Val Phe Ile Ala Ile Phe Ala Asp Val Ala Thr Leu Ala Ile
            725                 730                 735

Ala Tyr Asp Asn Ala Pro Tyr Ser Pro Lys Pro Val Lys Trp Asn Leu
            740                 745                 750

Pro Arg Leu Trp Gly Met Ser Ile Ile Leu Gly Ile Val Leu Ala Ile
            755                 760                 765

Gly Ser Trp Ile Thr Leu Thr Thr Met Phe Leu Pro Lys Gly Gly Ile
770                 775                 780

Ile Gln Asn Phe Gly Ala Met Asn Gly Ile Met Phe Leu Gln Ile Ser
785                 790                 795                 800

Leu Thr Glu Asn Trp Leu Ile Phe Ile Thr Arg Ala Ala Gly Pro Phe
            805                 810                 815

Trp Ser Ser Ile Pro Ser Trp Gln Leu Ala Gly Ala Val Phe Ala Val
            820                 825                 830

Asp Ile Ile Ala Thr Met Phe Thr Leu Phe Gly Trp Trp Ser Glu Asn
            835                 840                 845

Trp Thr Asp Ile Val Thr Val Val Arg Val Trp Ile Trp Ser Ile Gly
850                 855                 860

Ile Phe Cys Val Leu Gly Gly Phe Tyr Tyr Glu Met Ser Thr Ser Glu
865                 870                 875                 880

Ala Phe Asp Arg Leu Met Asn Gly Lys Pro Met Lys Glu Lys Lys Ser
            885                 890                 895

Thr Arg Ser Val Glu Asp Phe Met Ala Ala Met Gln Arg Val Ser Thr
            900                 905                 910

Gln His Glu Lys Glu Thr
            915

<210> SEQ ID NO 13
<211> LENGTH: 994
<212> TYPE: PRT
<213> ORGANISM: rabbit

<400> SEQUENCE: 13

Met Glu Ala Ala His Ser Lys Ser Thr Glu Cys Leu Ala Tyr Phe
1               5                   10                  15

Gly Val Ser Glu Thr Thr Gly Leu Thr Pro Asp Gln Val Lys Arg His
            20                  25                  30

Leu Glu Lys Tyr Gly His Asn Glu Leu Pro Ala Glu Glu Gly Lys Ser
        35                  40                  45

Leu Trp Glu Leu Val Ile Glu Gln Phe Glu Asp Leu Leu Val Arg Ile
    50                  55                  60

```
Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
            85                  90                  95

Ile Leu Ile Ala Asn Ala Ile Val Gly Val Trp Gln Glu Arg Asn Ala
        100                 105                 110

Glu Asn Ala Ile Glu Ala Leu Lys Glu Tyr Glu Pro Glu Met Gly Lys
    115                 120                 125

Val Tyr Arg Ala Asp Arg Lys Ser Val Gln Arg Ile Lys Ala Arg Asp
130                 135                 140

Ile Val Pro Gly Asp Ile Val Glu Val Ala Val Gly Asp Lys Val Pro
145                 150                 155                 160

Ala Asp Ile Arg Ile Leu Ser Ile Lys Ser Thr Thr Leu Arg Val Asp
                165                 170                 175

Gln Ser Ile Leu Thr Gly Glu Ser Val Ser Val Ile Lys His Thr Glu
            180                 185                 190

Pro Val Pro Asp Pro Arg Ala Val Asn Gln Asp Lys Lys Asn Met Leu
        195                 200                 205

Phe Ser Gly Thr Asn Ile Ala Ala Gly Lys Ala Leu Gly Ile Val Ala
    210                 215                 220

Thr Thr Gly Val Ser Thr Glu Ile Gly Lys Ile Arg Asp Gln Met Ala
225                 230                 235                 240

Ala Thr Glu Gln Asp Lys Thr Pro Leu Gln Gln Lys Leu Asp Glu Phe
                245                 250                 255

Gly Glu Gln Leu Ser Lys Val Ile Ser Leu Ile Cys Val Ala Val Trp
            260                 265                 270

Leu Ile Asn Ile Gly His Phe Asn Asp Pro Val His Gly Gly Ser Trp
        275                 280                 285

Ile Arg Gly Ala Ile Tyr Tyr Phe Lys Ile Ala Val Ala Leu Ala Val
290                 295                 300

Ala Ala Ile Pro Glu Gly Leu Pro Ala Val Ile Thr Thr Cys Leu Ala
305                 310                 315                 320

Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
            340                 345                 350

Thr Gly Thr Leu Thr Thr Asn Gln Met Ser Val Cys Lys Met Phe Ile
        355                 360                 365

Ile Asp Lys Val Asp Gly Asp Phe Cys Ser Leu Asn Glu Phe Ser Ile
370                 375                 380

Thr Gly Ser Thr Tyr Ala Pro Glu Gly Glu Val Leu Lys Asn Asp Lys
385                 390                 395                 400

Pro Ile Arg Ser Gly Gln Phe Asp Gly Leu Val Glu Leu Ala Thr Ile
                405                 410                 415

Cys Ala Leu Cys Asn Asp Ser Ser Leu Asp Phe Asn Glu Thr Lys Gly
            420                 425                 430

Val Tyr Glu Lys Val Gly Glu Ala Thr Glu Thr Ala Leu Thr Thr Leu
        435                 440                 445

Val Glu Lys Met Asn Val Phe Asn Thr Glu Val Arg Asn Leu Ser Lys
450                 455                 460

Val Glu Arg Ala Asn Ala Cys Asn Ser Val Ile Arg Gln Leu Met Lys
465                 470                 475                 480

Lys Glu Phe Thr Leu Glu Phe Ser Arg Asp Arg Lys Ser Met Ser Val
```

```
                    485             490             495
Tyr Cys Ser Pro Ala Lys Ser Ser Arg Ala Ala Val Gly Asn Lys Met
                500             505             510
Phe Val Lys Gly Ala Pro Glu Gly Val Ile Asp Arg Cys Asn Tyr Val
                515             520             525
Arg Val Gly Thr Thr Arg Val Pro Met Thr Gly Pro Val Lys Glu Lys
                530             535             540
Ile Leu Ser Val Ile Lys Glu Trp Gly Thr Gly Arg Asp Thr Leu Arg
545             550             555             560
Cys Leu Ala Leu Ala Thr Arg Asp Thr Pro Pro Lys Arg Glu Glu Met
                565             570             575
Val Leu Asp Asp Ser Ser Arg Phe Met Glu Tyr Glu Thr Asp Leu Thr
                580             585             590
Phe Val Gly Val Val Gly Met Leu Asp Pro Pro Arg Lys Glu Val Met
                595             600             605
Gly Ser Ile Gln Leu Cys Arg Asp Ala Gly Ile Arg Val Ile Met Ile
                610             615             620
Thr Gly Asp Asn Lys Gly Thr Ala Ile Ala Ile Cys Arg Arg Ile Gly
625             630             635             640
Ile Phe Gly Glu Asn Glu Glu Val Ala Asp Arg Ala Tyr Thr Gly Arg
                645             650             655
Glu Phe Asp Asp Leu Pro Leu Ala Glu Gln Arg Glu Ala Cys Arg Arg
                660             665             670
Ala Cys Cys Phe Ala Arg Val Glu Pro Ser His Lys Ser Lys Ile Val
                675             680             685
Glu Tyr Leu Gln Ser Tyr Asp Glu Ile Thr Ala Met Thr Gly Asp Gly
                690             695             700
Val Asn Asp Ala Pro Ala Leu Lys Lys Ala Glu Ile Gly Ile Ala Met
705             710             715             720
Gly Ser Gly Thr Ala Val Ala Lys Thr Ala Ser Glu Met Val Leu Ala
                725             730             735
Asp Asp Asn Phe Ser Thr Ile Val Ala Ala Val Glu Glu Gly Arg Ala
                740             745             750
Ile Tyr Asn Asn Met Lys Gln Phe Ile Arg Tyr Leu Ile Ser Ser Asn
                755             760             765
Val Gly Glu Val Val Cys Ile Phe Leu Thr Ala Ala Leu Gly Leu Pro
                770             775             780
Glu Ala Leu Ile Pro Val Gln Leu Leu Trp Val Asn Leu Val Thr Asp
785             790             795             800
Gly Leu Pro Ala Thr Ala Leu Gly Phe Asn Pro Pro Asp Leu Asp Ile
                805             810             815
Met Asp Arg Pro Pro Arg Ser Pro Lys Glu Pro Leu Ile Ser Gly Trp
                820             825             830
Leu Phe Phe Arg Tyr Met Ala Ile Gly Gly Tyr Val Gly Ala Ala Thr
                835             840             845
Val Gly Ala Ala Ala Trp Trp Phe Met Tyr Ala Glu Asp Gly Pro Gly
                850             855             860
Val Thr Tyr His Gln Leu Thr His Phe Met Gln Cys Thr Glu Asp His
865             870             875             880
Pro His Phe Glu Gly Leu Asp Cys Glu Ile Phe Glu Ala Pro Glu Pro
                885             890             895
Met Thr Met Ala Leu Ser Val Leu Val Thr Ile Glu Met Cys Asn Ala
                900             905             910
```

```
Leu Asn Ser Leu Ser Glu Asn Gln Ser Leu Met Arg Met Pro Pro Trp
            915                 920                 925

Val Asn Ile Trp Leu Leu Gly Ser Ile Cys Leu Ser Met Ser Leu His
        930                 935                 940

Phe Leu Ile Leu Tyr Val Asp Pro Leu Pro Met Ile Phe Lys Leu Lys
945                 950                 955                 960

Ala Leu Asp Leu Thr Gln Trp Leu Met Val Leu Lys Ile Ser Leu Pro
                965                 970                 975

Val Ile Gly Leu Asp Glu Ile Leu Lys Phe Ile Ala Arg Asn Tyr Leu
            980                 985                 990

Glu Gly

<210> SEQ ID NO 14
<211> LENGTH: 952
<212> TYPE: PRT
<213> ORGANISM: Solanum tuberosum

<400> SEQUENCE: 14

Met Ala Lys Ala Ile Ser Leu Glu Glu Ile Lys Asn Glu Thr Val Asp
1               5                   10                  15

Leu Glu Lys Ile Pro Ile Glu Glu Val Phe Glu Gln Leu Lys Cys Ser
            20                  25                  30

Arg Glu Gly Leu Thr Ser Asp Glu Gly Ala Asn Arg Leu Gln Ile Phe
        35                  40                  45

Gly Pro Asn Lys Leu Glu Glu Lys Lys Glu Ser Lys Ile Leu Lys Phe
    50                  55                  60

Leu Gly Phe Met Trp Asn Pro Leu Ser Trp Val Met Glu Ala Ala Ala
65                  70                  75                  80

Ile Met Ala Ile Ala Leu Ala Asn Gly Asn Gly Lys Pro Pro Asp Trp
                85                  90                  95

Gln Asp Phe Val Gly Ile Val Cys Leu Leu Val Ile Asn Ser Thr Ile
            100                 105                 110

Ser Phe Ile Glu Glu Asn Asn Ala Gly Asn Ala Ala Ala Ala Leu Met
        115                 120                 125

Ala Gly Leu Ala Pro Lys Thr Lys Val Leu Arg Asp Gly Arg Trp Ser
    130                 135                 140

Glu Gln Glu Ala Ala Ile Leu Val Pro Gly Asp Ile Ile Ser Val Lys
145                 150                 155                 160

Leu Gly Asp Ile Val Pro Ala Asp Ala Arg Leu Leu Glu Gly Asp Pro
                165                 170                 175

Leu Lys Ile Asp Gln Ser Ala Leu Thr Gly Glu Ser Leu Pro Val Thr
            180                 185                 190

Lys Asn Pro Gly Asp Glu Val Phe Ser Gly Ser Thr Cys Lys Gln Gly
        195                 200                 205

Glu Leu Glu Ala Val Val Ile Ala Thr Gly Val His Thr Phe Phe Gly
    210                 215                 220

Lys Ala Ala His Leu Val Asp Ser Thr Asn Asn Val Gly His Phe Gln
225                 230                 235                 240

Lys Val Leu Thr Ala Ile Gly Asn Phe Cys Ile Cys Ser Ile Ala Val
                245                 250                 255

Gly Met Leu Ile Glu Ile Val Met Tyr Pro Ile Gln His Arg Lys
            260                 265                 270

Tyr Arg Asp Gly Ile Asp Asn Leu Leu Val Leu Leu Ile Gly Gly Ile
        275                 280                 285

Pro Ile Ala Met Pro Thr Val Leu Ser Val Thr Met Ala Ile Gly Ser
```

-continued

```
               290                 295                 300
His Arg Leu Ser Gln Gln Gly Ala Ile Thr Lys Arg Met Thr Ala Ile
305                 310                 315                 320
Glu Glu Met Ala Gly Met Asp Val Leu Cys Ser Asp Lys Thr Gly Thr
                    325                 330                 335
Leu Thr Leu Asn Lys Leu Ser Val Asp Lys Thr Leu Val Glu Val Phe
                    340                 345                 350
Val Lys Gly Val Asp Lys Glu Tyr Val Leu Leu Pro Ala Arg Ala
                    355                 360                 365
Ser Arg Val Glu Asn Gln Asp Ala Ile Asp Ala Cys Met Val Gly Met
            370                 375                 380
Leu Ala Asp Pro Lys Glu Ala Arg Ala Gly Ile Arg Glu Val His Phe
385                 390                 395                 400
Leu Pro Phe Asn Pro Val Asp Lys Arg Thr Ala Leu Thr Tyr Ile Asp
                    405                 410                 415
Asn Asn Gly Asn Trp His Arg Ala Ser Lys Gly Ala Pro Glu Gln Ile
                    420                 425                 430
Leu Asp Leu Cys Asn Cys Lys Glu Asp Val Arg Arg Lys Val His Ser
            435                 440                 445
Met Ile Asp Lys Tyr Ala Glu Ala Gly Leu Arg Ser Leu Ala Val Ala
            450                 455                 460
Arg Gln Glu Val Pro Glu Lys Ser Lys Glu Ser Ala Gly Gly Pro Trp
465                 470                 475                 480
Gln Phe Val Gly Leu Leu Pro Leu Phe Asp Pro Pro Arg His Asp Ser
                    485                 490                 495
Ala Glu Thr Ile Arg Arg Ala Leu Asn Leu Gly Val Asn Val Lys Met
                    500                 505                 510
Ile Thr Gly Asp Gln Leu Ala Ile Ala Lys Glu Thr Gly Arg Arg Leu
            515                 520                 525
Gly Met Gly Thr Asn Met Tyr Pro Ser Ala Ser Leu Leu Gly Gln Asp
            530                 535                 540
Lys Asp Ser Ser Ile Ala Ser Leu Pro Val Glu Glu Leu Ile Glu Lys
545                 550                 555                 560
Ala Asp Gly Phe Ala Gly Val Phe Pro Glu His Lys Tyr Glu Ile Val
                    565                 570                 575
Lys Lys Leu Gln Glu Arg Lys His Ile Val Gly Met Thr Gly Asp Gly
                    580                 585                 590
Val Asn Asp Ala Pro Ala Leu Lys Lys Ala Asp Ile Gly Ile Ala Val
            595                 600                 605
Ala Asp Ala Thr Asp Ala Ala Arg Gly Ala Ser Asp Ile Val Leu Thr
            610                 615                 620
Glu Pro Gly Leu Ser Val Ile Ile Ser Ala Val Leu Thr Ser Arg Ala
625                 630                 635                 640
Ile Phe Gln Arg Met Lys Asn Tyr Thr Ile Tyr Ala Val Ser Ile Thr
                    645                 650                 655
Ile Arg Ile Val Phe Gly Phe Met Leu Ile Ala Leu Ile Trp Lys Tyr
                    660                 665                 670
Asp Phe Ser Ala Phe Met Val Leu Ile Ile Ala Ile Leu Asn Asp Gly
            675                 680                 685
Thr Ile Met Thr Ile Ser Lys Asp Arg Val Lys Pro Ser Pro Met Pro
            690                 695                 700
Asp Ser Trp Lys Leu Asn Glu Ile Phe Ala Thr Gly Val Val Leu Gly
705                 710                 715                 720
```

```
Gly Tyr Gln Ala Leu Met Thr Val Leu Phe Trp Ala Met His Asp
                    725                 730                 735

Thr Lys Phe Phe Ser Asp Lys Phe Gly Val Lys Asp Ile Arg Glu Ser
            740                 745                 750

Asp Glu Glu Met Met Ser Ala Leu Tyr Leu Gln Val Ser Ile Ile Ser
            755                 760                 765

Gln Ala Leu Ile Phe Val Thr Arg Ser Arg Ser Trp Ser Phe Val Glu
    770                 775                 780

Arg Pro Gly Ala Leu Leu Met Ile Ala Phe Leu Ile Ala Gln Leu Val
785                 790                 795                 800

Ala Thr Leu Ile Ala Val Tyr Ala Asp Trp Thr Phe Ala Arg Val Lys
                805                 810                 815

Gly Cys Gly Trp Gly Trp Ala Gly Val Ile Trp Ile Phe Ser Ile Val
            820                 825                 830

Thr Tyr Phe Pro Leu Asp Ile Met Lys Phe Ala Ile Arg Tyr Ile Leu
            835                 840                 845

Ser Gly Lys Ala Trp Asn Asn Leu Leu Asp Asn Lys Thr Ala Phe Thr
    850                 855                 860

Thr Lys Lys Asp Tyr Gly Lys Glu Glu Arg Glu Ala Gln Trp Ala Leu
865                 870                 875                 880

Ala Gln Arg Thr Leu His Gly Leu Gln Pro Pro Glu Ala Ser Asn Leu
                885                 890                 895

Phe Asn Glu Lys Asn Ser Tyr Arg Glu Leu Ser Glu Ile Ala Glu Gln
            900                 905                 910

Ala Lys Arg Arg Ala Glu Met Ala Arg Leu Arg Glu Leu His Thr Leu
            915                 920                 925

Lys Gly His Val Glu Ser Val Val Lys Leu Lys Gly Leu Asp Ile Glu
    930                 935                 940

Thr Ile Gln Gln His Tyr Thr Val
945                 950

<210> SEQ ID NO 15
<211> LENGTH: 952
<212> TYPE: PRT
<213> ORGANISM: Solanum lycopersicum

<400> SEQUENCE: 15

Met Ala Lys Ala Ile Ser Leu Glu Glu Ile Lys Asn Glu Thr Val Asp
1               5                   10                  15

Leu Glu Lys Ile Pro Ile Glu Val Phe Glu Gln Leu Lys Cys Ser
            20                  25                  30

Arg Glu Gly Leu Thr Ser Asp Glu Gly Ala Asn Arg Leu Gln Ile Phe
        35                  40                  45

Gly Pro Asn Lys Leu Glu Glu Lys Glu Ser Lys Ile Leu Lys Phe
    50                  55                  60

Leu Gly Phe Met Trp Asn Pro Leu Ser Trp Val Met Glu Met Ala Ala
65                  70                  75                  80

Ile Met Ala Ile Ala Leu Ala Asn Gly Asp Gly Lys Pro Pro Asp Trp
                85                  90                  95

Gln Asp Phe Val Gly Ile Val Cys Leu Leu Val Ile Asn Ser Thr Ile
            100                 105                 110

Ser Phe Ile Glu Glu Asn Asn Ala Gly Asn Ala Ala Ala Leu Met
        115                 120                 125

Ala Gly Leu Ala Pro Lys Thr Lys Val Leu Arg Asp Gly Arg Trp Ser
    130                 135                 140
```

-continued

```
Glu Gln Glu Ala Ala Ile Leu Val Pro Gly Asp Ile Ile Ser Val Lys
145                 150                 155                 160

Leu Gly Asp Ile Val Pro Ala Asp Ala Arg Leu Leu Glu Gly Asp Pro
                165                 170                 175

Leu Lys Ile Asp Gln Ser Ala Leu Thr Gly Glu Ser Leu Pro Val Thr
            180                 185                 190

Lys Asn Pro Gly Asp Glu Val Phe Ser Gly Ser Thr Cys Lys Gln Gly
        195                 200                 205

Glu Leu Glu Ala Val Val Ile Ala Thr Gly Val His Thr Phe Phe Gly
    210                 215                 220

Lys Ala Ala His Leu Val Asp Ser Thr Asn Asn Val Gly His Phe Gln
225                 230                 235                 240

Lys Val Leu Thr Ala Ile Gly Asn Phe Cys Ile Cys Ser Ile Ala Ile
                245                 250                 255

Gly Met Leu Val Glu Ile Ile Val Met Tyr Pro Ile Gln His Arg Lys
            260                 265                 270

Tyr Arg Asp Gly Ile Asp Asn Leu Leu Val Leu Ile Gly Gly Ile
        275                 280                 285

Pro Ile Ala Met Pro Thr Val Leu Ser Val Thr Met Ala Ile Gly Ser
    290                 295                 300

His Arg Leu Ser Gln Gln Gly Ala Ile Thr Lys Arg Met Thr Ala Ile
305                 310                 315                 320

Glu Glu Met Ala Gly Met Asp Val Leu Cys Ser Asp Lys Thr Gly Thr
                325                 330                 335

Leu Thr Leu Asn Lys Leu Ser Val Asp Arg Ser Leu Val Glu Val Phe
            340                 345                 350

Thr Lys Gly Val Asp Lys Glu Tyr Val Leu Leu Leu Ala Ala Arg Ala
        355                 360                 365

Ser Arg Val Glu Asn Gln Asp Ala Ile Asp Ala Cys Met Val Gly Met
    370                 375                 380

Leu Ala Asp Pro Lys Glu Ala Arg Ala Gly Ile Arg Glu Val His Phe
385                 390                 395                 400

Leu Pro Phe Asn Pro Val Asp Lys Arg Thr Ala Leu Thr Tyr Ile Asp
                405                 410                 415

Ser Asn Gly Asn Trp His Arg Ala Ser Lys Gly Ala Pro Glu Gln Ile
            420                 425                 430

Leu Asp Leu Cys Asn Cys Lys Glu Asp Val Arg Arg Lys Val His Ser
        435                 440                 445

Met Ile Asp Lys Tyr Ala Glu Arg Gly Leu Arg Ser Leu Ala Val Ala
    450                 455                 460

Arg Gln Glu Val Pro Glu Lys Ser Lys Glu Ser Thr Gly Gly Pro Trp
465                 470                 475                 480

Gln Phe Val Gly Leu Leu Pro Leu Phe Asp Pro Pro Arg His Asp Ser
                485                 490                 495

Ala Glu Thr Ile Arg Arg Ala Leu Asn Leu Gly Val Asn Val Lys Met
            500                 505                 510

Ile Thr Gly Asp Gln Leu Ala Ile Ala Lys Glu Thr Gly Arg Arg Leu
        515                 520                 525

Gly Met Gly Thr Asn Met Tyr Pro Ser Ala Ser Leu Leu Gly Gln Asp
    530                 535                 540

Lys Asp Ser Ser Ile Ala Ser Leu Pro Val Glu Glu Leu Ile Glu Lys
545                 550                 555                 560

Ala Asp Gly Phe Ala Gly Val Phe Pro Glu His Lys Tyr Glu Ile Val
                565                 570                 575
```

Lys Lys Leu Gln Glu Arg Lys His Ile Val Gly Met Thr Gly Asp Gly
                580                 585                 590

Val Asn Asp Ala Pro Ala Leu Lys Lys Ala Asp Ile Gly Ile Ala Val
            595                 600                 605

Ala Asp Ala Thr Asp Ala Ala Arg Gly Arg Ser Asp Ile Val Leu Thr
610                 615                 620

Glu Pro Gly Leu Ser Val Ile Ser Ala Val Leu Thr Ser Arg Ala
625                 630                 635                 640

Ile Phe Gln Arg Met Lys Asn Tyr Thr Ile Tyr Ala Val Ser Ile Thr
                645                 650                 655

Ile Arg Ile Val Phe Gly Phe Met Leu Ile Ala Leu Ile Trp Lys Tyr
            660                 665                 670

Asp Phe Ser Ala Phe Met Val Leu Ile Ile Ala Ile Leu Asn Asp Gly
        675                 680                 685

Thr Ile Met Thr Ile Ser Lys Asp Arg Val Lys Pro Ser Pro Met Pro
690                 695                 700

Asp Ser Trp Lys Leu Asn Glu Ile Phe Ala Thr Gly Val Val Leu Gly
705                 710                 715                 720

Gly Tyr Gln Ala Leu Met Thr Val Ile Phe Phe Trp Ala Met His Asp
                725                 730                 735

Thr Ser Phe Phe Thr Asp Lys Phe Gly Val Lys Asp Ile Arg Glu Ser
            740                 745                 750

Asp Glu Glu Met Met Ser Ala Leu Tyr Leu Gln Val Ser Ile Ile Ser
        755                 760                 765

Gln Ala Leu Ile Phe Val Thr Arg Ser Arg Ser Trp Ser Phe Val Glu
770                 775                 780

Arg Pro Gly Ala Leu Leu Met Ile Ala Phe Leu Ile Ala Gln Leu Val
785                 790                 795                 800

Ala Thr Leu Ile Ala Val Tyr Ala Asp Trp Thr Phe Ala Arg Val Lys
                805                 810                 815

Gly Cys Gly Trp Gly Trp Ala Gly Val Ile Trp Ile Phe Ser Ile Val
            820                 825                 830

Thr Tyr Phe Pro Leu Asp Ile Met Lys Phe Ala Ile Arg Tyr Ile Leu
        835                 840                 845

Ser Gly Lys Ala Trp Asn Asn Leu Leu Asp Asn Lys Thr Ala Phe Thr
850                 855                 860

Thr Lys Lys Asp Tyr Gly Lys Glu Arg Glu Ala Gln Trp Ala Leu
865                 870                 875                 880

Ala Gln Arg Thr Leu His Gly Leu Gln Pro Pro Glu Ala Ser Asn Leu
                885                 890                 895

Phe Asn Glu Lys Asn Ser Tyr Arg Glu Leu Ser Glu Ile Ala Glu Gln
            900                 905                 910

Ala Lys Arg Arg Ala Glu Met Ala Arg Leu Arg Glu Leu His Thr Leu
        915                 920                 925

Lys Gly His Val Glu Ser Val Val Lys Leu Lys Gly Leu Asp Ile Glu
930                 935                 940

Thr Ile Gln Gln His Tyr Thr Val
945                 950

<210> SEQ ID NO 16
<211> LENGTH: 956
<212> TYPE: PRT
<213> ORGANISM: Vicia Faba

<400> SEQUENCE: 16

```
Met Ala Ala Ile Ser Leu Glu Gln Ile Lys Asn Glu Ser Val Asp Leu
1               5                   10                  15

Glu Lys Ile Pro Ile Glu Val Phe Ala Gln Leu Lys Cys Thr Arg
            20                  25                  30

Glu Gly Leu Ser Ser Thr Glu Gly Ser Arg Ile Gln Ile Phe Gly
                35                  40                  45

Pro Asn Lys Leu Glu Glu Lys Lys Glu Ser Lys Phe Leu Lys Phe Leu
50                      55                  60

Gly Phe Met Trp Asn Pro Leu Ser Trp Val Met Glu Ala Ala Val
65              70                  75                      80

Met Ala Ile Ala Leu Ala Asn Gly Gly Gln Pro Pro Asp Trp Gln
                85                  90                  95

Asp Phe Val Gly Ile Val Cys Leu Leu Val Ile Asn Ser Thr Ile Ser
                100                 105                 110

Phe Ile Glu Glu Asn Asn Ala Gly Asn Ala Ala Ala Leu Met Ala
            115                 120                 125

Gly Leu Ala Pro Lys Thr Lys Val Leu Arg Asp Gly Lys Trp Ser Glu
130                 135                 140

Gln Glu Ala Ala Ile Leu Val Pro Gly Asp Ile Ile Ser Ile Lys Leu
145                 150                 155                 160

Gly Asp Ile Ile Pro Ala Asp Ala Arg Leu Leu Glu Gly Asp Pro Leu
                165                 170                 175

Lys Val Asp Gln Ala Ala Leu Thr Gly Glu Ser Leu Pro Val Thr Arg
                180                 185                 190

His Pro Gly Gln Glu Val Phe Ser Gly Ser Thr Cys Lys Gln Gly Glu
            195                 200                 205

Ile Glu Ala Val Val Ile Ala Thr Gly Val His Thr Phe Phe Gly Lys
210                 215                 220

Ala Ala His Leu Val Asp Asn Thr Asn Asn Val Gly His Phe Gln Met
225                 230                 235                 240

Val Leu Lys Ser Ile Gly Asn Phe Cys Ile Cys Ser Ile Ala Val Gly
                245                 250                 255

Met Leu Ala Glu Ile Ile Val Met Tyr Pro Ile Gln His Arg Lys Tyr
                260                 265                 270

Arg Asp Gly Ile Asp Asn Leu Leu Val Leu Leu Ile Gly Gly Ile Pro
                275                 280                 285

Ile Ala Met Pro Thr Val Leu Ser Val Thr Met Ala Ile Gly Ser His
                290                 295                 300

Lys Leu Ser Gln Gln Gly Ala Ile Thr Lys Arg Met Thr Ala Ile Glu
305                 310                 315                 320

Glu Met Ala Gly Met Asp Val Leu Cys Ser Asp Lys Thr Gly Thr Leu
                325                 330                 335

Thr Leu Asn Lys Leu Ser Val Asp Arg Asn Leu Ile Glu Val Phe Ile
                340                 345                 350

Lys Gly Met Asp Lys Glu His Val Ile Leu Leu Ala Ala Arg Ala Ala
                355                 360                 365

Arg Thr Glu Asn Gln Asp Ala Ile Asp Ala Ala Ile Val Gly Met Leu
            370                 375                 380

Ala Asp Pro Lys Glu Ala Arg Ala Glu Ile Thr Glu Val His Phe Leu
385                 390                 395                 400

Pro Phe Asn Pro Asn Asp Lys Arg Thr Ala Leu Thr Tyr Ile Asp Asn
                405                 410                 415

Lys Asp Gly Thr Trp His Arg Ala Ser Lys Gly Ala Pro Glu Gln Ile
```

```
                  420             425             430
Ile Glu Leu Cys Asn Met Arg Glu Asp Ala Gln Lys Lys Ile His Ser
            435                 440                 445
Met Ile Glu Lys Phe Ala Glu Arg Gly Leu Arg Ser Leu Gly Val Ala
            450                 455                 460
Arg Gln Glu Val Pro Glu Lys Thr Lys Glu Ser Ala Gly Ala Pro Trp
465                 470                 475                 480
Gln Phe Val Gly Leu Leu Ser Val Phe Asp Pro Pro Arg His Asp Ser
                    485                 490                 495
Ala Glu Thr Ile Arg Gln Ala Leu Asn Leu Gly Val Asn Val Lys Met
                500                 505                 510
Ile Thr Gly Asp Gln Leu Ala Ile Ala Lys Glu Thr Gly Arg Arg Leu
            515                 520                 525
Gly Met Gly Thr Asn Met Tyr Pro Ser Ala Thr Leu Leu Gly Leu Asp
            530                 535                 540
Lys Asp Ser Ser Val Ala Ser Met Pro Val Glu Glu Leu Ile Glu Lys
545                 550                 555                 560
Ala Asp Gly Phe Ala Gly Val Phe Pro Glu His Lys Tyr Glu Ile Val
                    565                 570                 575
Lys Lys Leu Gln Glu Arg Lys His Ile Cys Gly Met Thr Gly Asp Gly
                580                 585                 590
Val Asn Asp Ala Pro Ala Leu Lys Lys Ala Asp Ile Gly Ile Ala Val
                595                 600                 605
Ala Asp Ala Thr Asp Ala Ala Arg Gly Ala Ser Asp Ile Val Leu Thr
            610                 615                 620
Glu Pro Gly Leu Ser Val Ile Ile Ser Ala Val Leu Thr Ser Arg Ala
625                 630                 635                 640
Ile Phe Gln Arg Met Lys Asn Tyr Thr Ile Tyr Ala Val Ser Ile Thr
                    645                 650                 655
Ile Arg Ile Val Phe Gly Phe Met Phe Ile Ala Leu Ile Trp Lys Phe
                660                 665                 670
Asp Phe Ser Pro Phe Met Ile Leu Ile Ile Ala Ile Leu Asn Asp Gly
            675                 680                 685
Thr Ile Met Thr Ile Ser Lys Asp Arg Val Lys Pro Ser Pro Leu Pro
            690                 695                 700
Asp Ser Trp Lys Leu Lys Glu Ile Phe Ala Thr Gly Val Met Leu Gly
705                 710                 715                 720
Gly Tyr Gln Ala Leu Met Thr Val Ile Phe Phe Trp Ile Val Gln Gly
                    725                 730                 735
Thr Lys Phe Phe Pro Asp Arg Phe Gly Val Arg His Ile His Asp Asn
                740                 745                 750
Pro Asp Glu Leu Thr Ala Ala Leu Tyr Leu Gln Val Ser Ile Val Ser
            755                 760                 765
Gln Ala Leu Ile Phe Val Thr Arg Ser Arg Ser Gly Leu Met Leu Asn
            770                 775                 780
Ala Pro Gly Leu Leu Leu Leu Gly Ala Phe Leu Ile Ala Gln Leu Ile
785                 790                 795                 800
Ala Thr Leu Ile Ala Val Tyr Ala Asn Trp Ala Phe Ala Arg Ile Gln
                    805                 810                 815
Gly Ile Gly Trp Gly Trp Ala Gly Val Ile Trp Leu Tyr Ser Ile Ile
                820                 825                 830
Phe Tyr Ile Pro Leu Asp Ile Ile Lys Phe Ala Thr Arg Tyr Phe Leu
            835                 840                 845
```

```
Ser Gly Lys Ala Trp Ser Asn Leu Glu Asn Lys Thr Ala Phe Thr Thr
        850                 855                 860

Lys Lys Asp Tyr Gly Lys Gly Glu Arg Glu Ala Gln Trp Ala His Ala
865                 870                 875                 880

Gln Arg Thr Leu His Gly Leu Glu Pro Pro Glu Ser Ser Gly Ile Phe
                885                 890                 895

His Glu Lys Asn Ser Tyr Arg Glu Leu Ser Glu Ile Ala Glu Gln Ala
            900                 905                 910

Lys Arg Arg Ala Glu Val Ala Arg Leu Arg Glu Leu His Thr Leu Lys
        915                 920                 925

Gly His Val Glu Ser Val Val Lys Leu Lys Gly Leu Asp Ile Asp Thr
    930                 935                 940

Ile Gln Gln His Tyr Thr Val Tyr Lys Gly Asn Thr
945                 950                 955

<210> SEQ ID NO 17
<211> LENGTH: 948
<212> TYPE: PRT
<213> ORGANISM: Maize

<400> SEQUENCE: 17

Met Gly Gly Leu Glu Glu Ile Lys Asn Glu Ala Val Asp Leu Glu Asn
1               5                   10                  15

Ile Pro Ile Glu Glu Val Phe Glu Gln Leu Lys Cys Thr Arg Glu Gly
            20                  25                  30

Leu Ser Ser Ser Glu Gly Gln Gln Arg Leu Glu Ile Phe Gly Pro Asn
        35                  40                  45

Arg Leu Glu Glu Lys Lys Glu Ser Lys Val Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Ser Gly Gly Lys Pro Pro Asp Trp Gln Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Ala Leu Met Ala Asn Leu
        115                 120                 125

Ala Pro Lys Thr Lys Val Leu Arg Asp Gly Arg Trp Gly Glu Gln Glu
    130                 135                 140

Ala Ala Ile Leu Val Pro Gly Asp Ile Ile Ser Ile Lys Leu Gly Asp
145                 150                 155                 160

Ile Ile Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Lys Gly Pro
            180                 185                 190

Gly Asp Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
    210                 215                 220

His Leu Val Asp Ser Thr Asn Gln Val Gly His Phe Gln Gln Val Leu
225                 230                 235                 240

Thr Ala Ile Gly Asn Phe Cys Ile Cys Ser Ile Gly Val Gly Ile Leu
                245                 250                 255

Val Glu Ile Ile Val Met Phe Pro Ile Gln His Arg Arg Tyr Arg Ser
            260                 265                 270
```

-continued

```
Gly Ile Glu Asn Leu Leu Val Leu Ile Gly Gly Ile Pro Ile Ala
            275                 280                 285
Met Pro Thr Val Leu Ser Val Thr Met Pro Ile Gly Ser His Lys Leu
    290                 295                 300
Ser Gln Gln Gly Ala Ile Thr Lys Arg Met Thr Ala Ile Glu Glu Met
305                 310                 315                 320
Ala Gly Met Asp Val Leu Cys Ser Asp Lys Thr Gly Thr Leu Thr Leu
                325                 330                 335
Asn Lys Leu Ser Val Asp Lys Asn Leu Val Glu Val Phe Cys Lys Gly
            340                 345                 350
Val Asp Lys Asp His Val Leu Leu Ala Ala Arg Ala Ser Arg Thr
            355                 360                 365
Glu Asn Leu Asp Ala Ile Asp Ala Ala Met Val Gly Met Leu Ala Asp
    370                 375                 380
Pro Lys Glu Ala Arg Ala Gly Ile Arg Glu Ile His Phe Leu Pro Phe
385                 390                 395                 400
Asn Pro Val Asp Lys Arg Thr Ala Leu Thr Tyr Ile Asp Ala Asp Gly
                405                 410                 415
Asn Trp His Arg Val Ser Lys Gly Ala Pro Glu Gln Ile Leu Asp Leu
            420                 425                 430
Cys His Cys Lys Glu Asp Leu Arg Arg Lys Val His Ser Ile Ile Asp
            435                 440                 445
Lys Tyr Ala Glu Arg Gly Leu Arg Ser Leu Ala Val Ala Arg Gln Glu
    450                 455                 460
Val Pro Glu Lys Asn Lys Glu Ser Pro Gly Gly Pro Trp Gln Phe Val
465                 470                 475                 480
Gly Leu Leu Arg Val Phe Asp Pro Pro Arg His Asp Ser Ala Glu Thr
                485                 490                 495
Ile Arg Lys Ala Leu Val Leu Gly Val Asn Val Lys Met Ile Thr Gly
            500                 505                 510
Asp Gln Leu Ala Ile Gly Lys Glu Thr Gly Arg Arg Leu Gly Met Gly
    515                 520                 525
Thr Asn Met Tyr Pro Ser Ser Ala Leu Leu Gly Gln Asn Lys Asp Arg
530                 535                 540
Thr Leu Ser Ala Leu Pro Val Asp Glu Leu Ile Glu Lys Ala Asp Gly
545                 550                 555                 560
Phe Ala Gly Val Phe Pro Glu His Lys Tyr Glu Ile Val Lys Arg Leu
                565                 570                 575
Gln Glu Lys Lys His Ile Val Gly Met Thr Gly Asp Gly Val Asn Asp
            580                 585                 590
Ala Pro Ala Leu Lys Lys Ala Asp Ile Gly Ile Ala Val Ala Asp Ala
    595                 600                 605
Thr Asp Ala Ala Arg Ser Ala Ser Asp Ile Val Leu Thr Glu Pro Gly
610                 615                 620
Leu Ser Val Ile Ile Ser Ala Val Leu Thr Ser Arg Ala Ile Phe Gln
625                 630                 635                 640
Arg Met Lys Asn Tyr Thr Ile Tyr Ala Val Ser Ile Thr Ile Arg Ile
                645                 650                 655
Val Leu Gly Phe Met Leu Ile Ala Leu Ile Trp Gln Tyr Asp Phe Ser
            660                 665                 670
Pro Phe Met Val Leu Ile Ile Ala Ile Leu Asn Asp Gly Thr Ile Met
            675                 680                 685
Thr Ile Ser Lys Asp Arg Val Lys Pro Ser Pro Leu Pro Asp Ser Trp
    690                 695                 700
```

```
Lys Leu Lys Glu Ile Phe Ala Thr Gly Ile Val Leu Gly Gly Tyr Leu
705                 710                 715                 720

Ala Leu Met Thr Val Ile Phe Phe Trp Ala Met His Lys Thr Asp Phe
                725                 730                 735

Phe Ser Asp Lys Phe Gly Val Arg Ser Ile Arg Asp Ser Glu His Glu
            740                 745                 750

Met Met Ser Ala Leu Tyr Leu Gln Val Ser Ile Val Ser Gln Ala Leu
            755                 760                 765

Ile Phe Val Thr Arg Ser Arg Ser Trp Ser Phe Val Glu Arg Pro Gly
        770                 775                 780

Leu Leu Leu Val Thr Ala Phe Val Ala Gln Leu Val Ala Thr Leu Ile
785                 790                 795                 800

Ala Val Tyr Ala Asn Trp Arg Phe Ala Arg Ile Lys Gly Ile Gly Trp
                805                 810                 815

Gly Trp Ala Gly Val Val Trp Leu Tyr Ser Ile Val Phe Tyr Phe Pro
            820                 825                 830

Leu Asp Leu Leu Lys Phe Phe Ile Arg Phe Val Leu Ser Gly Arg Ala
            835                 840                 845

Trp Asp Asn Leu Leu Asp Thr Arg Ile Ala Phe Thr Arg Lys Lys Asp
            850                 855                 860

Leu Arg Lys Gly Glu Arg Glu Ala Gln Trp Ala Thr Ala Gln Arg Thr
865                 870                 875                 880

Leu His Gly Leu Gln Pro Pro Glu Ser Asn Thr Leu Phe Asn Asp Lys
                885                 890                 895

Ser Ser Tyr Arg Glu Leu Ser Glu Ile Ala Glu Gln Ala Lys Arg Arg
            900                 905                 910

Ala Glu Ile Ala Arg Leu Arg Glu Leu Asn Thr Leu Lys Gly His Val
            915                 920                 925

Glu Ser Val Ala Lys Leu Lys Gly Leu Asp Ile Asp Thr Ile Gln Gln
930                 935                 940

Asn Tyr Thr Val
945

<210> SEQ ID NO 18
<211> LENGTH: 949
<212> TYPE: PRT
<213> ORGANISM: Arabidopsis thaliana

<400> SEQUENCE: 18

Met Ala Ala Asp Ile Ser Trp Asp Glu Ile Lys Lys Glu Asn Val Asp
1               5                   10                  15

Leu Glu Lys Ile Pro Val Asp Glu Val Phe Gln Gln Leu Lys Cys Ser
            20                  25                  30

Arg Glu Gly Leu Ser Ser Glu Glu Gly Arg Asn Arg Leu Gln Ile Phe
        35                  40                  45

Gly Ala Asn Lys Leu Glu Glu Lys Val Glu Asn Lys Phe Leu Lys Phe
    50                  55                  60

Leu Gly Phe Met Trp Asn Pro Leu Ser Trp Val Met Glu Ala Ala Ala
65                  70                  75                  80

Ile Met Ala Ile Val Leu Ala Asn Gly Gly Arg Pro Pro Asp Trp
                85                  90                  95

Gln Asp Phe Val Gly Ile Thr Cys Leu Leu Ile Ile Asn Ser Thr Ile
            100                 105                 110

Ser Phe Ile Glu Glu Asn Asn Ala Gly Asn Ala Ala Ala Ala Leu Met
        115                 120                 125
```

```
Ala Asn Leu Ala Pro Lys Thr Lys Val Leu Arg Asp Gly Arg Trp Gly
    130                 135                 140

Glu Gln Glu Ala Ala Ile Leu Val Pro Gly Asp Leu Ile Ser Ile Lys
145                 150                 155                 160

Leu Gly Asp Ile Val Pro Ala Asp Ala Arg Leu Leu Glu Gly Asp Pro
                165                 170                 175

Leu Lys Ile Asp Gln Ser Ala Leu Thr Gly Glu Ser Leu Pro Ala Thr
                180                 185                 190

Lys His Gln Gly Asp Glu Val Phe Ser Gly Ser Thr Cys Lys Gln Gly
            195                 200                 205

Glu Ile Glu Ala Val Val Ile Ala Thr Gly Val His Thr Phe Phe Gly
    210                 215                 220

Lys Ala Ala His Leu Val Asp Ser Thr Asn Asn Val Gly His Phe Gln
225                 230                 235                 240

Lys Val Leu Thr Ala Ile Gly Asn Phe Cys Ile Cys Ser Ile Gly Ile
                245                 250                 255

Gly Met Leu Ile Glu Ile Ile Ile Met Tyr Pro Ile Gln His Arg Lys
                260                 265                 270

Tyr Arg Asp Gly Ile Asp Asn Leu Leu Val Leu Leu Ile Gly Gly Ile
            275                 280                 285

Pro Ile Ala Met Pro Thr Val Leu Ser Val Thr Met Ala Ile Gly Ser
    290                 295                 300

His Arg Leu Ser Gln Gln Gly Ala Ile Thr Lys Arg Met Thr Ala Ile
305                 310                 315                 320

Glu Glu Met Ala Gly Met Asp Val Leu Cys Ser Asp Lys Thr Gly Thr
                325                 330                 335

Leu Thr Leu Asn Lys Leu Thr Val Asp Lys Asn Leu Ile Glu Val Phe
                340                 345                 350

Ser Lys Asp Val Asp Lys Asp Tyr Val Ile Leu Leu Ser Ala Arg Ala
            355                 360                 365

Ser Arg Val Glu Asn Gln Asp Ala Ile Asp Thr Ser Ile Val Asn Met
    370                 375                 380

Leu Gly Asp Pro Lys Glu Ala Arg Ala Gly Ile Thr Glu Val His Phe
385                 390                 395                 400

Leu Pro Phe Asn Pro Val Glu Lys Arg Thr Ala Ile Thr Tyr Ile Asp
                405                 410                 415

Thr Asn Gly Glu Trp His Arg Cys Ser Lys Gly Ala Pro Glu Gln Ile
            420                 425                 430

Ile Glu Leu Cys Asp Leu Lys Gly Glu Thr Lys Arg Arg Ala His Glu
    435                 440                 445

Ile Ile Asp Lys Phe Ala Glu Arg Gly Leu Arg Ser Leu Gly Val Ala
    450                 455                 460

Arg Gln Arg Val Pro Glu Lys Asp Lys Glu Ser Ala Gly Thr Pro Trp
465                 470                 475                 480

Glu Phe Val Gly Leu Leu Pro Leu Phe Asp Pro Pro Arg His Asp Ser
                485                 490                 495

Ala Glu Thr Ile Arg Arg Ala Leu Asp Leu Gly Val Asn Val Lys Met
            500                 505                 510

Ile Thr Gly Asp Gln Leu Ala Ile Gly Lys Glu Thr Gly Arg Arg Leu
    515                 520                 525

Gly Met Gly Thr Asn Met Tyr Pro Ser Ser Ser Leu Leu Glu Asn Lys
530                 535                 540

Asp Asp Thr Thr Gly Gly Val Pro Val Asp Glu Leu Ile Glu Lys Ala
```

```
            545                 550                 555                 560
Asp Gly Phe Ala Gly Val Phe Pro Glu His Lys Tyr Glu Ile Val Arg
                565                 570                 575
Lys Leu Gln Glu Arg Lys His Ile Val Gly Met Thr Gly Asp Gly Val
                580                 585                 590
Asn Asp Ala Pro Ala Leu Lys Lys Ala Asp Ile Gly Ile Ala Val Asp
                595                 600                 605
Asp Ala Thr Asp Ala Ala Arg Ser Ala Ser Asp Ile Val Leu Thr Glu
            610                 615                 620
Pro Gly Leu Ser Val Ile Val Ser Ala Val Leu Thr Ser Arg Ala Ile
625                 630                 635                 640
Phe Gln Arg Met Lys Asn Tyr Thr Ile Tyr Ala Val Ser Ile Thr Ile
                645                 650                 655
Arg Ile Val Leu Gly Phe Met Leu Val Ala Leu Ile Trp Glu Phe Asp
            660                 665                 670
Phe Ser Pro Phe Met Val Leu Ile Ile Ala Ile Leu Asn Asp Gly Thr
            675                 680                 685
Ile Met Thr Ile Ser Lys Asp Arg Val Lys Pro Ser Pro Ile Pro Asp
690                 695                 700
Ser Trp Lys Leu Lys Glu Ile Phe Ala Thr Gly Val Val Leu Gly Thr
705                 710                 715                 720
Tyr Met Ala Leu Val Thr Val Val Phe Phe Trp Leu Ala His Asp Thr
                725                 730                 735
Thr Phe Phe Ser Asp Lys Phe Gly Val Arg Ser Leu Gln Gly Lys Asp
                740                 745                 750
Glu Glu Leu Ile Ala Val Leu Tyr Leu Gln Val Ser Ile Ile Ser Gln
            755                 760                 765
Ala Leu Ile Phe Val Thr Arg Ser Arg Ser Trp Ser Phe Val Glu Arg
            770                 775                 780
Pro Gly Leu Leu Leu Ile Ala Phe Phe Val Ala Gln Leu Ile Ala
785                 790                 795                 800
Thr Leu Ile Ala Thr Tyr Ala His Trp Glu Phe Ala Arg Ile Lys Gly
                805                 810                 815
Cys Gly Trp Gly Trp Cys Gly Val Ile Trp Ile Tyr Ser Ile Val Thr
                820                 825                 830
Tyr Ile Pro Leu Asp Ile Leu Lys Phe Ile Thr Arg Tyr Thr Leu Ser
            835                 840                 845
Gly Lys Ala Trp Asn Asn Met Ile Glu Asn Arg Thr Ala Phe Thr Thr
850                 855                 860
Lys Lys Asp Tyr Gly Arg Gly Glu Arg Glu Ala Gln Trp Ala Leu Ala
865                 870                 875                 880
Gln Arg Thr Leu His Gly Leu Lys Pro Pro Glu Ser Met Phe Glu Asp
                885                 890                 895
Thr Ala Thr Tyr Thr Glu Leu Ser Glu Ile Ala Glu Gln Ala Lys Lys
                900                 905                 910
Arg Ala Glu Val Ala Arg Leu Arg Glu Val His Thr Leu Lys Gly His
            915                 920                 925
Val Glu Ser Val Val Lys Leu Lys Gly Leu Asp Ile Asp Asn Leu Asn
            930                 935                 940
Gln His Tyr Thr Val
945

<210> SEQ ID NO 19
<211> LENGTH: 957
```

<212> TYPE: PRT
<213> ORGANISM: Nicotiana plumbaginifolia

<400> SEQUENCE: 19

```
Met Gly Glu Glu Lys Pro Glu Val Leu Asp Ala Val Leu Lys Glu Ala
1               5                   10                  15

Val Asp Leu Glu Asn Ile Pro Ile Glu Glu Val Phe Glu Asn Leu Arg
            20                  25                  30

Cys Thr Lys Glu Gly Leu Thr Ala Thr Ala Ala Gln Arg Leu Ala
        35                  40                  45

Ile Phe Gly Tyr Asn Lys Leu Glu Glu Lys Lys Asp Ser Lys Leu Leu
    50                  55                  60

Lys Phe Leu Gly Phe Met Trp Asn Pro Leu Ser Trp Val Met Glu Ala
65                  70                  75                  80

Ala Ala Ile Met Ala Ile Ala Leu Ala Asn Gly Gly Lys Pro Pro
                85                  90                  95

Asp Trp Gln Asp Phe Val Gly Ile Ile Thr Leu Leu Ile Ile Asn Ser
            100                 105                 110

Thr Ile Ser Phe Ile Glu Glu Asn Asn Ala Gly Asn Ala Ala Ala
        115                 120                 125

Leu Met Ala Arg Leu Ala Pro Lys Ala Lys Val Leu Arg Asp Gly Arg
130                 135                 140

Trp Lys Glu Glu Asp Ala Ala Val Leu Val Pro Gly Asp Ile Ile Ser
145                 150                 155                 160

Ile Lys Leu Gly Asp Ile Ile Pro Ala Asp Ala Arg Leu Leu Glu Gly
                165                 170                 175

Asp Pro Leu Lys Ile Asp Gln Ser Ala Leu Thr Gly Glu Ser Leu Pro
            180                 185                 190

Val Thr Lys Gly Pro Gly Asp Gly Val Tyr Ser Gly Ser Thr Cys Lys
        195                 200                 205

Gln Gly Glu Ile Glu Ala Ile Val Ile Ala Thr Gly Val His Thr Phe
210                 215                 220

Phe Gly Lys Ala Ala His Leu Val Asp Ser Thr Asn Gln Val Gly His
225                 230                 235                 240

Phe Gln Lys Val Leu Thr Ala Ile Gly Asn Phe Cys Ile Cys Ser Ile
                245                 250                 255

Ala Val Gly Met Ile Ile Glu Ile Ile Val Met Tyr Pro Ile Gln His
            260                 265                 270

Arg Ala Tyr Arg Pro Gly Ile Asp Asn Leu Leu Val Leu Leu Ile Gly
        275                 280                 285

Gly Ile Pro Ile Ala Met Pro Thr Val Leu Ser Val Thr Met Ala Ile
290                 295                 300

Gly Ser His Arg Leu Ala Gln Gln Gly Ala Ile Thr Lys Arg Met Thr
305                 310                 315                 320

Ala Ile Glu Glu Met Ala Gly Met Asp Val Leu Cys Ser Asp Lys Thr
                325                 330                 335

Gly Thr Leu Thr Leu Asn Lys Leu Thr Val Asp Lys Asn Leu Ile Glu
            340                 345                 350

Val Phe Ala Lys Gly Val Asp Ala Asp Met Val Val Leu Met Ala Ala
        355                 360                 365

Arg Ala Ser Arg Thr Glu Asn Gln Asp Ala Ile Asp Ala Ala Ile Val
370                 375                 380

Gly Met Leu Ala Asp Pro Lys Glu Ala Arg Ala Gly Ile Arg Glu Ile
385                 390                 395                 400
```

-continued

His Phe Leu Pro Phe Asn Pro Thr Asp Lys Arg Thr Ala Leu Thr Tyr
            405                 410                 415

Leu Asp Gly Glu Gly Lys Met His Arg Val Ser Lys Gly Ala Pro Glu
        420                 425                 430

Gln Ile Leu Asn Leu Ala His Asn Lys Ser Asp Ile Glu Arg Arg Val
            435                 440                 445

His Ala Val Ile Asp Lys Phe Ala Glu Arg Gly Leu Arg Ser Leu Gly
    450                 455                 460

Val Ala Tyr Gln Glu Val Pro Glu Gly Arg Lys Glu Ser Ala Gly Gly
465                 470                 475                 480

Pro Trp Gln Phe Ile Gly Leu Leu Pro Leu Phe Asp Pro Pro Arg His
                485                 490                 495

Asp Ser Ala Glu Thr Ile Arg Arg Ala Leu Asn Leu Gly Val Asn Val
            500                 505                 510

Lys Met Val Thr Gly Asp Gln Leu Ala Ile Gly Lys Glu Thr Gly Arg
        515                 520                 525

Arg Leu Gly Met Gly Thr Asn Met Tyr Pro Ser Ser Ala Leu Leu Gly
    530                 535                 540

Gln Thr Lys Asp Glu Ser Ile Ser Ala Leu Pro Ile Asp Glu Leu Ile
545                 550                 555                 560

Glu Lys Ala Asp Gly Phe Ala Gly Val Phe Pro Glu His Lys Tyr Glu
                565                 570                 575

Ile Val Lys Arg Leu Gln Ala Arg Lys His Ile Cys Gly Met Thr Gly
            580                 585                 590

Asp Gly Val Asn Asp Ala Pro Ala Leu Lys Lys Ala Asp Ile Gly Ile
        595                 600                 605

Ala Val Asp Asp Ala Thr Asp Ala Ala Arg Ser Ala Ser Asp Ile Val
    610                 615                 620

Leu Thr Glu Pro Gly Leu Ser Val Ile Ile Ser Ala Val Leu Thr Ser
625                 630                 635                 640

Arg Ala Ile Phe Gln Arg Met Lys Asn Tyr Thr Ile Tyr Ala Val Ser
                645                 650                 655

Ile Thr Ile Arg Ile Val Leu Gly Phe Met Leu Leu Ala Leu Ile Trp
            660                 665                 670

Lys Phe Asp Phe Pro Pro Phe Met Val Leu Ile Ile Ala Ile Leu Asn
        675                 680                 685

Asp Gly Thr Ile Met Thr Ile Ser Lys Asp Arg Val Lys Pro Ser Pro
    690                 695                 700

Leu Pro Asp Ser Trp Lys Leu Ala Glu Ile Phe Thr Thr Gly Ile Val
705                 710                 715                 720

Leu Gly Gly Tyr Leu Ala Met Met Thr Val Ile Phe Phe Trp Ala Ala
                725                 730                 735

Tyr Lys Thr Asn Phe Phe Pro His Val Phe Gly Val Ser Thr Leu Glu
            740                 745                 750

Lys Thr Ala Thr Asp Phe Arg Lys Leu Ala Ser Ala Ile Tyr Leu
        755                 760                 765

Gln Val Ser Ile Ile Ser Gln Ala Leu Ile Phe Val Thr Arg Ser Arg
770                 775                 780

Ser Trp Ser Phe Val Glu Arg Pro Gly Phe Leu Leu Val Ile Ala Phe
785                 790                 795                 800

Val Ile Ala Gln Leu Val Ala Thr Leu Ile Ala Val Tyr Ala Asn Trp
                805                 810                 815

Ser Phe Ala Ala Ile Glu Gly Ile Gly Trp Gly Trp Ala Gly Val Ile
            820                 825                 830

```
Trp Ile Tyr Asn Leu Val Phe Tyr Ile Pro Leu Asp Ile Ile Lys Phe
            835                 840                 845

Phe Ile Arg Tyr Ala Leu Ser Gly Arg Ala Trp Asp Leu Val Phe Glu
850                 855                 860

Arg Arg Ile Ala Phe Thr Arg Lys Lys Asp Phe Gly Lys Glu Gln Arg
865                 870                 875                 880

Glu Leu Gln Trp Ala His Ala Gln Arg Thr Leu His Gly Leu Gln Val
            885                 890                 895

Pro Asp Thr Lys Leu Phe Ser Glu Ala Thr Asn Phe Asn Glu Leu Asn
            900                 905                 910

Gln Leu Ala Glu Glu Ala Lys Arg Arg Ala Glu Ile Ala Arg Leu Arg
            915                 920                 925

Glu Leu His Thr Leu Lys Gly His Val Glu Ser Val Val Lys Leu Lys
            930                 935                 940

Gly Leu Asp Ile Glu Thr Ile Gln Gln Ala Tyr Thr Val
945                 950                 955

<210> SEQ ID NO 20
<211> LENGTH: 956
<212> TYPE: PRT
<213> ORGANISM: Nicotiana plumbaginifolia

<400> SEQUENCE: 20

Met Gly Glu Lys Pro Glu Val Leu Asp Ala Val Leu Lys Glu Thr Val
1               5                   10                  15

Asp Leu Glu Asn Ile Pro Ile Glu Glu Val Phe Glu Asn Leu Arg Cys
            20                  25                  30

Thr Lys Glu Gly Leu Ser Gly Pro Ala Ala Gln Glu Arg Leu Ala Ile
            35                  40                  45

Phe Gly Tyr Asn Lys Leu Glu Glu Lys Glu Ser Lys Phe Leu Lys
        50                  55                  60

Phe Leu Gly Phe Met Trp Asn Pro Leu Ser Trp Val Met Glu Ala Ala
65              70                  75                  80

Ala Ile Met Ala Ile Ala Leu Ala Asn Gly Gly Gly Lys Pro Pro Asp
            85                  90                  95

Trp Gln Asp Phe Val Gly Ile Ile Thr Leu Leu Val Ile Asn Ser Thr
            100                 105                 110

Ile Ser Phe Ile Glu Glu Asn Asn Ala Gly Asn Ala Ala Ala Ala Leu
        115                 120                 125

Met Ala Arg Leu Ala Pro Lys Ala Lys Val Leu Arg Asp Gly Lys Trp
130                 135                 140

Asp Glu Gln Asp Ala Ala Ile Leu Val Pro Gly Asp Ile Ile Ser Ile
145                 150                 155                 160

Lys Leu Gly Asp Ile Ile Pro Ala Asp Ala Arg Leu Leu Glu Gly Asp
            165                 170                 175

Pro Leu Lys Ile Asp Gln Ser Ala Leu Thr Gly Glu Ser Leu Pro Val
            180                 185                 190

Thr Lys Gly Pro Gly Asp Gly Val Tyr Ser Gly Ser Thr Cys Lys Gln
        195                 200                 205

Gly Glu Ile Glu Ala Val Val Ile Ala Thr Gly Val His Thr Phe Phe
    210                 215                 220

Gly Lys Ala Ala His Leu Val Asp Ser Thr Asn Gln Val Gly His Phe
225                 230                 235                 240

Gln Lys Val Leu Thr Ala Ile Gly Asn Phe Cys Ile Cys Ser Ile Ala
            245                 250                 255
```

```
Val Gly Met Ile Ile Glu Ile Ile Val Met Tyr Pro Ile Gln His Arg
            260                 265                 270

Lys Tyr Arg Pro Gly Ile Asp Asn Leu Leu Val Leu Leu Ile Gly Gly
        275                 280                 285

Ile Pro Ile Ala Met Pro Thr Val Leu Ser Val Thr Met Ala Ile Gly
    290                 295                 300

Ser His Arg Leu Ala Gln Gln Gly Ala Ile Thr Lys Arg Met Thr Ala
305                 310                 315                 320

Ile Glu Glu Met Ala Gly Met Asp Val Leu Cys Ser Asp Lys Thr Gly
                325                 330                 335

Thr Leu Thr Leu Asn Lys Leu Thr Val Asp Lys Asn Leu Val Glu Val
            340                 345                 350

Phe Ala Lys Gly Val Asp Ala Asp Thr Val Val Leu Met Ala Ala Arg
        355                 360                 365

Ala Ser Arg Thr Glu Asn Gln Asp Ala Ile Asp Thr Ala Ile Val Gly
    370                 375                 380

Met Leu Ser Asp Pro Lys Glu Ala Arg Ala Gly Ile Arg Glu Ile His
385                 390                 395                 400

Phe Leu Pro Phe Asn Pro Thr Asp Lys Arg Thr Ala Leu Thr Tyr Leu
                405                 410                 415

Asp Gly Glu Gly Lys Met His Arg Val Ser Lys Gly Ala Pro Glu Gln
            420                 425                 430

Ile Leu Asn Leu Ala His Asn Lys Ser Asp Ile Glu Arg Arg Val His
        435                 440                 445

Ser Val Ile Asp Lys Phe Ala Glu Arg Gly Leu Arg Ser Leu Gly Val
    450                 455                 460

Ala Tyr Gln Glu Val Pro Glu Gly Arg Lys Ser Thr Gly Gly Pro
465                 470                 475                 480

Trp Gln Phe Ile Gly Leu Leu Pro Leu Phe Asp Pro Pro Arg His Asp
                485                 490                 495

Ser Ala Glu Thr Ile Arg Arg Ala Leu Asn Leu Gly Val Asn Val Lys
            500                 505                 510

Met Ile Thr Gly Asp Gln Leu Ala Ile Gly Lys Glu Thr Gly Arg Arg
        515                 520                 525

Leu Gly Met Gly Thr Asn Met Tyr Pro Ser Ser Ala Leu Leu Gly Gln
    530                 535                 540

Thr Lys Asp Glu Ser Ile Ala Ser Leu Pro Ile Asp Glu Leu Ile Glu
545                 550                 555                 560

Lys Ala Asp Gly Phe Ala Gly Val Phe Pro Glu His Lys Tyr Glu Ile
                565                 570                 575

Val Lys Arg Leu Gln Ala Arg Lys His Ile Cys Gly Met Thr Gly Asp
            580                 585                 590

Gly Val Asn Asp Ala Pro Ala Leu Lys Lys Ala Asp Ile Gly Ile Ala
        595                 600                 605

Val Asp Asp Ala Thr Asp Ala Ala Arg Ser Ala Ser Asp Ile Val Leu
    610                 615                 620

Thr Glu Pro Gly Leu Ser Val Ile Ile Ser Ala Val Leu Thr Ser Arg
625                 630                 635                 640

Ala Ile Phe Gln Arg Met Lys Asn Tyr Thr Ile Tyr Ala Val Ser Ile
                645                 650                 655

Thr Ile Arg Ile Val Leu Gly Phe Met Leu Leu Ala Leu Ile Trp Lys
            660                 665                 670

Phe Asp Phe Pro Pro Phe Met Val Leu Ile Ile Ala Ile Leu Asn Asp
```

```
                    675                 680                 685
Gly Thr Ile Met Thr Ile Ser Lys Asp Arg Val Lys Pro Ser Pro Leu
            690                 695                 700
Pro Asp Ser Trp Lys Leu Ala Glu Ile Phe Thr Thr Gly Val Val Leu
705                 710                 715                 720
Gly Gly Tyr Leu Ala Met Met Thr Val Ile Phe Phe Trp Ala Ala Tyr
                725                 730                 735
Glu Thr Asp Phe Phe Pro Arg Val Phe Gly Val Ser Thr Leu Gln Lys
                740                 745                 750
Thr Ala Thr Asp Asp Phe Arg Lys Leu Ala Ser Ala Ile Tyr Leu Gln
            755                 760                 765
Val Ser Thr Ile Ser Gln Ala Leu Ile Phe Val Thr Arg Ser Arg Ser
        770                 775                 780
Trp Ser Phe Val Glu Arg Pro Gly Leu Leu Leu Val Val Ala Phe Leu
785                 790                 795                 800
Ile Ala Gln Leu Val Ala Thr Leu Ile Ala Val Tyr Ala Asn Trp Ala
                805                 810                 815
Phe Ala Ala Ile Glu Gly Ile Gly Trp Gly Trp Ala Gly Val Ile Trp
            820                 825                 830
Leu Tyr Asn Leu Val Phe Tyr Phe Pro Leu Asp Ile Ile Lys Phe Leu
        835                 840                 845
Ile Arg Tyr Ala Leu Ser Gly Arg Ala Trp Asp Leu Val Leu Glu Gln
    850                 855                 860
Arg Ile Ala Phe Thr Arg Lys Lys Asp Phe Gly Lys Glu Gln Arg Glu
865                 870                 875                 880
Leu Gln Trp Ala His Ala Gln Arg Thr Leu His Gly Leu Gln Val Pro
                885                 890                 895
Asp Thr Lys Leu Phe Ser Glu Ala Thr Asn Phe Asn Glu Leu Asn Gln
            900                 905                 910
Leu Ala Glu Glu Ala Lys Arg Arg Ala Glu Ile Ala Arg Gln Arg Glu
        915                 920                 925
Leu His Thr Leu Lys Gly His Val Glu Ser Val Val Lys Leu Lys Gly
    930                 935                 940
Leu Asp Ile Glu Thr Ile Gln Gln Ser Tyr Thr Val
945                 950                 955

<210> SEQ ID NO 21
<211> LENGTH: 957
<212> TYPE: PRT
<213> ORGANISM: Oryza sativa

<400> SEQUENCE: 21

Met Ala Glu Lys Gly Asp Asn Leu Glu Ala Val Leu Asn Glu Ser Val
1               5                   10                  15
Asp Leu Glu Asn Ile Pro Leu Glu Glu Val Phe Glu His Leu Arg Cys
            20                  25                  30
Asn Arg Glu Gly Leu Thr Ser Ala Asn Ala Glu Gln Arg Leu Asn Leu
        35                  40                  45
Phe Gly Leu Asn Arg Leu Glu Glu Lys Lys Glu Ser Lys Phe Leu Lys
    50                  55                  60
Phe Leu Gly Phe Met Trp Asn Pro Leu Ser Trp Val Met Glu Ala Ala
65                  70                  75                  80
Ala Ile Met Ala Ile Val Leu Ala Asn Gly Gly Gly Lys Pro Pro Asp
                85                  90                  95
Trp Gln Asp Phe Val Gly Ile Ile Thr Leu Leu Ile Ile Asn Ser Thr
```

```
               100                 105                 110
Ile Ser Phe Ile Glu Glu Asn Asn Ala Gly Asn Ala Ala Ala Leu
        115                 120                 125

Met Ala Arg Leu Ala Pro Lys Ala Lys Val Leu Arg Asn Gly Arg Trp
    130                 135                 140

Ser Glu Glu Glu Ala Ala Ile Leu Val Pro Gly Asp Ile Ile Ser Val
145                 150                 155                 160

Lys Arg Gly Asp Ile Ile Pro Ala Asp Ala Arg Leu Leu Glu Gly Asp
                165                 170                 175

Pro Leu Lys Ile Asp Gln Ser Ala Leu Thr Gly Glu Ser Leu Pro Val
        180                 185                 190

Thr Lys Gly Pro Gly Asp Gly Val Tyr Ser Gly Ser Thr Cys Lys Gln
    195                 200                 205

Gly Glu Ile Glu Ala Val Val Ile Ala Thr Gly Val His Thr Phe Phe
210                 215                 220

Gly Lys Ala Ala His Leu Val Asp Ser Thr Asn Gln Val Gly His Phe
225                 230                 235                 240

Gln Lys Val Leu Thr Ala Ile Gly Asn Phe Cys Ile Cys Ser Ile Ala
                245                 250                 255

Ile Gly Met Val Val Glu Ile Ile Val Met Tyr Pro Ile Gln His Arg
            260                 265                 270

Asp Tyr Arg Pro Gly Ile Asp Asn Leu Leu Val Leu Leu Ile Gly Gly
        275                 280                 285

Ile Pro Ile Ala Met Pro Thr Val Leu Ser Val Thr Met Ala Ile Gly
        290                 295                 300

Ser His Arg Leu Ala Gln Gln Gly Ala Ile Thr Lys Arg Met Thr Ala
305                 310                 315                 320

Ile Glu Glu Met Ala Gly Met Asp Val Leu Cys Ser Asp Lys Thr Gly
                325                 330                 335

Thr Leu Thr Leu Asn Lys Leu Thr Val Asp Lys Ser Leu Ile Glu Val
            340                 345                 350

Phe Gln Arg Gly Val Asp Gln Asp Thr Val Ile Leu Met Ala Ala Arg
        355                 360                 365

Ala Ser Arg Thr Glu Asn Gln Asp Ala Ile Asp Ala Thr Ile Val Gly
    370                 375                 380

Met Leu Ala Asp Pro Lys Glu Ala Arg Ala Gly Ile Gln Glu Val His
385                 390                 395                 400

Phe Leu Pro Phe Asn Pro Thr Asp Lys Arg Thr Ala Leu Thr Tyr Ile
                405                 410                 415

Asp Gly Glu Gly Lys Met His Arg Val Ser Lys Gly Ala Pro Glu Gln
            420                 425                 430

Ile Leu Asn Leu Ala His Asn Lys Thr Glu Ile Glu Arg Arg Val Arg
        435                 440                 445

Ala Val Ile Asp Lys Phe Ala Glu Arg Gly Leu Arg Ser Leu Ala Val
    450                 455                 460

Gln Tyr His Gln Val Pro Asp Gly Arg Lys Glu Ser Pro Gly Gly Pro
465                 470                 475                 480

Trp Gln Phe Val Gly Leu Leu Pro Leu Phe Asp Pro Pro Arg His Asp
                485                 490                 495

Ser Ala Glu Thr Ile Arg Arg Ala Leu Asn Leu Gly Val Asn Val Lys
            500                 505                 510

Met Ile Thr Gly Asp Gln Leu Ala Ile Gly Lys Glu Thr Ala Arg Arg
        515                 520                 525
```

-continued

Leu Gly Met Gly Thr Asn Met Tyr Pro Ser Ser Ala Leu Leu Gly Gln
530                 535                 540

Asp Lys Asp Glu Ser Ile Val Ala Leu Pro Val Asp Glu Leu Ile Glu
545                 550                 555                 560

Lys Ala Asp Gly Phe Ala Gly Val Phe Pro Glu His Lys Tyr Glu Ile
                565                 570                 575

Val Lys Arg Leu Gln Ala Arg Lys His Ile Cys Gly Met Thr Gly Asp
            580                 585                 590

Gly Val Asn Asp Ala Pro Ala Leu Lys Lys Ala Asp Ile Gly Ile Ala
        595                 600                 605

Val Asp Asp Ser Thr Asp Ala Ala Arg Ser Ala Ser Asp Ile Val Leu
610                 615                 620

Thr Glu Pro Gly Leu Ser Val Ile Ile Ser Ala Val Leu Thr Ser Arg
625                 630                 635                 640

Ala Ile Phe Gln Arg Met Lys Asn Tyr Thr Ile Tyr Ala Val Ser Ile
                645                 650                 655

Thr Ile Arg Ile Val Leu Gly Phe Met Leu Leu Ala Leu Ile Trp Lys
            660                 665                 670

Phe Asp Phe Pro Pro Phe Met Val Leu Ile Ile Ala Ile Leu Asn Asp
        675                 680                 685

Gly Thr Ile Met Thr Ile Ser Lys Asp Arg Val Lys Pro Ser Pro Gln
690                 695                 700

Pro Asp Ser Trp Lys Leu Ser Glu Ile Phe Ala Thr Gly Val Val Leu
705                 710                 715                 720

Gly Ser Tyr Leu Ala Met Met Thr Val Ile Phe Phe Trp Val Ala Tyr
                725                 730                 735

Lys Thr Asp Phe Phe Pro Arg Val Phe His Val Glu Ser Leu Gln Lys
            740                 745                 750

Thr Ala Gln Asp Asp Phe Gln Lys Leu Ala Ser Ala Val Tyr Leu Gln
        755                 760                 765

Val Ser Thr Ile Ser Gln Ala Leu Ile Phe Val Thr Arg Ser Arg Ser
770                 775                 780

Trp Ser Phe Val Glu Arg Pro Gly Phe Leu Leu Val Phe Ala Phe Phe
785                 790                 795                 800

Val Ala Gln Leu Ile Ala Thr Leu Ile Ala Val Tyr Ala Asn Trp Gly
                805                 810                 815

Phe Ala Ser Ile Lys Gly Ile Gly Trp Gly Trp Ala Gly Val Ile Trp
            820                 825                 830

Leu Tyr Asn Ile Val Phe Tyr Leu Pro Leu Asp Ile Ile Lys Phe Leu
        835                 840                 845

Ile Arg Tyr Ala Leu Ser Gly Arg Ala Trp Asp Leu Val Leu Glu Gln
850                 855                 860

Arg Ile Ala Phe Thr Arg Lys Lys Asp Phe Gly Thr Gln Glu Asn Gln
865                 870                 875                 880

Leu Lys Trp Ala Thr Ala Gln Arg Thr Ile His Gly Leu Gln Pro Ala
                885                 890                 895

Ala Thr Ala Ala Val Phe Arg Asp Met Thr Ser Tyr Asn Asp Leu Asn
            900                 905                 910

Gln Leu Ala Glu Glu Ala Arg Arg Arg Ala Glu Ile Ala Arg Leu Arg
        915                 920                 925

Glu Leu Thr Thr Leu Lys Gly Arg Met Glu Ser Val Val Lys Gln Lys
930                 935                 940

Gly Leu Asp Leu Glu Thr Ile Gln Gln Ser Tyr Thr Val
945                 950                 955

<210> SEQ ID NO 22
<211> LENGTH: 997
<212> TYPE: PRT
<213> ORGANISM: Cryptococcus neoformans

<400> SEQUENCE: 22

```
Met Ser Asp His Glu Lys Val Gly His Thr Glu Ile Pro Thr Lys
1               5                   10                  15

Glu Ser Ser Leu Glu Asn Lys Val Gln Gly Glu Val Pro Ala Ala
                20                  25                  30

Ala Ala Ala Asp Glu Glu Pro Arg Lys Lys Arg Glu Tyr Lys Glu Met
            35                  40                  45

Glu His Lys Thr Glu Gly Asp Leu His Ala Lys Val Asp Met Asn Thr
        50                  55                  60

Ile Gln Phe Thr Ala Ala Asp Leu Tyr Asp Lys Asp Lys Val Asp Ile
65                  70                  75                  80

Glu His Val Val Met Glu Val Tyr Gln Leu Leu Gln Cys Thr Asp
                85                  90                  95

Ala Gly Leu Thr Glu Ala Glu Ala Thr Asp Arg Ile Gly Ile Phe Gly
            100                 105                 110

Pro Asn Lys Leu Glu Glu Lys Ser Glu Asn Val Leu Leu Gln Phe Leu
            115                 120                 125

Ser Phe Met Trp Asn Pro Leu Ser Trp Val Met Glu Gly Ala Ala Leu
130                 135                 140

Val Ala Ile Ala Leu Ser Asn Gly Gly Gly Thr Pro Pro Asp Trp Gln
145                 150                 155                 160

Asp Phe Val Gly Ile Ile Leu Leu Leu Phe Val Asn Ser Thr Ile Gly
                165                 170                 175

Phe Val Glu Glu Arg Asn Ala Gly Asn Ala Val Lys Ala Leu Met Asp
            180                 185                 190

Ser Leu Ala Pro Lys Ala Arg Val Lys Arg Asp Gly Gln Trp Lys Glu
        195                 200                 205

Ile Glu Ser Ser Glu Leu Val Pro Gly Asp Leu Ile Ala Phe Lys His
    210                 215                 220

Gly Asp Val Cys Pro Ser Asp Cys Arg Leu Val Glu Ala Ile Asp Val
225                 230                 235                 240

Ser Met Asp Gln Ala Ala Leu Thr Gly Glu Ser Leu Pro Val Gly Lys
                245                 250                 255

His Glu Gly Asp Glu Cys Phe Ser Gly Ser Thr Cys Lys Gln Gly Glu
            260                 265                 270

Ala Glu Gly Ile Val Ile Ala Thr Gly Pro Asn Thr Phe Phe Gly Arg
        275                 280                 285

Ala Ala Thr Leu Val Gly Gln Asp Asn Asp Gln Val Gly His Leu Gln
    290                 295                 300

Gln Val Leu Ala Arg Ile Gly Thr Phe Cys Leu Val Ser Ile Gly Ile
305                 310                 315                 320

Phe Val Leu Leu Glu Ile Leu Ile Leu Tyr Ala Asp Phe Arg Tyr Pro
                325                 330                 335

Tyr Arg Arg Gly Leu Asp Asn Ile Leu Val Leu Leu Ile Gly Gly Ile
            340                 345                 350

Pro Ile Ala Met Pro Thr Val Leu Ser Val Thr Leu Ala Val Gly Ala
        355                 360                 365

Gln Gln Leu Ala Lys His Lys Ala Ile Val Thr Arg Ile Thr Ala Ile
    370                 375                 380
```

```
-continued

Glu Glu Leu Ala Gly Val Thr Ile Leu Cys Ser Asp Lys Thr Gly Thr
385                 390                 395                 400

Leu Thr Thr Asn Lys Leu Thr Ile Asp Lys Glu Asn Val Lys Cys Tyr
            405                 410                 415

Ser Lys Trp Asp Val Glu Gly Val Cys Leu Leu Ala Ala Tyr Ala Ser
            420                 425                 430

Arg Thr Glu Asn Gln Asp Ala Ile Asp Gly Cys Val Val Gly Thr Leu
            435                 440                 445

Pro Asp Pro Gln Gln Ala Arg Ala Gly Ile Lys Leu Leu Asp Phe Lys
450                 455                 460

Pro Phe Asn Pro Val Asp Lys Arg Thr Glu Ile Thr Tyr Arg Asp Glu
465                 470                 475                 480

Met Asp Gly Gly Lys Leu Lys Arg Ala Thr Lys Gly Met Thr Gly Ile
                485                 490                 495

Ile Ile Glu Ile Cys Thr Arg Asn Lys Thr Asn Glu Leu Glu Asp Gln
                500                 505                 510

Leu Glu Ala Asp Val Glu Glu Phe Ala Arg Arg Gly Leu Arg Ala Leu
            515                 520                 525

Ala Val Ala Phe Glu Asp Val Ala Gly Asp Asp Pro Ser Ala Glu Gly
            530                 535                 540

Asn Gly Phe Glu Leu Val Gly Leu Leu Ser Ile Phe Asp Pro Pro Arg
545                 550                 555                 560

Ser Asp Thr Lys Lys Thr Ile Asp Asp Ala Met Ala Leu Gly Val Lys
                565                 570                 575

Val Lys Met Val Thr Gly Asp Gln Leu Ala Ile Ala Lys Glu Thr Gly
            580                 585                 590

Arg Arg Leu Gly Leu Gly Asp His Met Tyr Pro Ala Lys Val Leu Lys
            595                 600                 605

Glu Gly Pro Glu Ala Gly Ser Lys His Ala Asn Leu Asp Glu Met Ile
            610                 615                 620

Met Asp Ala Asp Gly Phe Ala Gly Val Phe Pro Glu His Lys Phe Glu
625                 630                 635                 640

Ile Val Lys Arg Ile Gln Asn Leu Gly His Leu Cys Ala Met Thr Gly
                645                 650                 655

Asp Gly Ala Asn Asp Ala Pro Ala Leu Ser Arg Ala Asn Val Gly Ile
                660                 665                 670

Ala Val Glu Gly Ala Thr Asp Ala Ala Arg Gly Ala Ala Asp Ile Val
            675                 680                 685

Leu Thr Glu Pro Gly Leu Ser Thr Ile Val His Ala Ile Tyr Gly Ser
690                 695                 700

Arg Val Ile Phe Gln Arg Met Arg Asn Tyr Ala Ile Tyr Ala Cys Ala
705                 710                 715                 720

Val Thr Ile Arg Ile Val Leu Cys Phe Ala Ile Met Ala Phe Ala Trp
            725                 730                 735

Arg Phe Asp Phe Pro Pro Phe Met Val Leu Ile Ile Ala Val Leu Asn
            740                 745                 750

Asp Gly Thr Ile Met Thr Leu Ser Leu Asp Arg Val Leu Pro Ser Thr
            755                 760                 765

Thr Pro Asp Ser Trp Asp Leu Ala Glu Val Phe Ser Phe Gly Val Ala
            770                 775                 780

Tyr Gly Val Tyr Leu Ser Ala Ser Thr Ile Ala Leu Tyr Ala Thr Met
785                 790                 795                 800

Glu Asn Thr Thr Phe Phe Glu Asp Arg Phe Gly Val Glu Pro Leu Lys
```

```
                805                 810                 815
Gly Asn Ser Tyr Gly Gly His Met Val Ile Tyr Leu Gln Val Ala Ile
            820                 825                 830

Ile Ser Gln Ala Leu Ile Phe Val Thr Arg Ser His Gly Pro Ser Trp
            835                 840                 845

Thr Glu Arg Pro Ser Val Ala Leu Met Leu Ala Phe Cys Leu Ala Gln
850                 855                 860

Leu Val Ser Ser Ile Ile Ala Ala Tyr Ala Asp Trp Ser Phe Ser Gln
865                 870                 875                 880

Val His Ser Val Ser Gly Gly Trp Ile Gly Ile Val Trp Ile Trp Asn
                885                 890                 895

Ile Val Trp Tyr Phe Pro Leu Asp Gly Ile Lys Phe Ile Met Lys Lys
            900                 905                 910

Thr Val Ile Ala Ala Leu Gln Arg Arg Lys Ala Arg Lys Ala Gly Pro
            915                 920                 925

Ala Val Ala Asp Ala Ala Leu His Arg Ala Pro Ser Arg His Glu Ser
            930                 935                 940

Leu Tyr Ser Asn Arg Thr Asn Phe Leu Thr Arg Ala Ala Asn Arg Leu
945                 950                 955                 960

Arg Gly Gly Ala Lys Ile Ser Met Ser Gln Asn Glu Leu Gln Arg Phe
                965                 970                 975

Ser Ser Ile Gln Ala Gln Gln Ser Gly Ala Ala Leu Thr Arg Ala His
            980                 985                 990

Ser Arg Pro Ala Ala
        995

<210> SEQ ID NO 23
<211> LENGTH: 962
<212> TYPE: PRT
<213> ORGANISM: Uromyces fabae

<400> SEQUENCE: 23

Met Ser Leu Lys Glu Gly Ser Asp Pro Val His Lys Lys Asn Phe Asp
1               5                   10                  15

Lys Thr Phe Glu Asp Glu Ile Lys Gly Thr Ser Ala Leu Val Asp Ile
            20                  25                  30

Gly Thr Ile Gln Leu Thr Ala Glu Asp Leu Tyr Asp Lys Asp Lys Val
        35                  40                  45

Asp Leu Glu Gln Val His Leu Glu Asp Val Trp Lys Leu Leu Gln Thr
    50                  55                  60

Thr Glu Glu Gly Leu Thr Ala Glu Val Gln Arg Arg Leu Glu Ile
65                  70                  75                  80

Phe Gly Pro Asn Lys Leu Glu Ser Lys Glu Val Asn Pro Leu Leu Leu
                85                  90                  95

Phe Leu Ser Phe Met Trp Asn Pro Leu Ser Trp Val Met Glu Gly Ala
            100                 105                 110

Ala Ile Val Ala Ile Gly Leu Ser Asn Gly Gln Gly Arg Pro Pro Asp
        115                 120                 125

Trp Gln Asp Phe Leu Gly Ile Met Leu Leu Leu Phe Ile Asn Ala Gly
    130                 135                 140

Ile Gly Phe Tyr Glu Glu Arg Ser Ala Gly Asn Ala Val Lys Ala Leu
145                 150                 155                 160

Met Asp Ser Leu Ala Pro Lys Ala Lys Val Arg Arg Ala Gly Val Trp
                165                 170                 175

Ser Glu Ile Asp Ser Ala Asp Leu Val Pro Gly Asp Ile Val Ala Phe
```

```
                180             185             190
Lys Ile Gly Asp Val Val Pro Ser Asp Cys Arg Leu Tyr Asp Ala Ile
            195                 200             205
Asn Val Ser Ile Asp Gln Ala Ala Leu Thr Gly Glu Ser Leu Pro Ser
        210                 215                 220
Thr Lys His Val Gly Asp Gln Cys Phe Ser Gly Ser Thr Cys Lys Gln
225                 230                 235                 240
Gly Glu Ala Glu Gly Val Val Ile Ala Thr Gly Pro Asn Thr Phe Phe
                245                 250                 255
Gly Arg Ala Ala Thr Leu Val Gly Ala Asp Asn Asp Ser Thr Gly His
                260                 265                 270
Met Gln Ala Val Leu Ala Lys Ile Gly Thr Phe Cys Leu Val Ser Ile
            275                 280                 285
Gly Ile Phe Val Val Leu Glu Ile Ile Leu Tyr Gly Gly Phe Arg
        290                 295                 300
Tyr Gln Tyr Arg Arg Gly Ile Asp Asn Ile Leu Val Leu Leu Ile Gly
305                 310                 315                 320
Gly Ile Pro Ile Ala Met Pro Thr Val Leu Ser Val Thr Leu Ala Val
                325                 330                 335
Gly Ala Gln Gln Leu Ala Lys Tyr Lys Ala Ile Val Thr Arg Ile Thr
                340                 345                 350
Ala Ile Glu Glu Leu Ala Gly Val Thr Ile Leu Cys Ser Asp Lys Thr
                355                 360                 365
Gly Thr Leu Thr Thr Asn Lys Leu Thr Ile Asp Lys Ser Thr Val Lys
        370                 375                 380
Thr Tyr Ala Asp Phe Ser Ala Asp Glu Val Cys Val Leu Ala Ala Tyr
385                 390                 395                 400
Ala Ser Arg Thr Glu Asn Gln Asp Ala Ile Asp Thr Cys Val Val Gly
                405                 410                 415
Asn Val Gly Ala Asp Val Ala Arg Arg Gly Ile Gln Leu Leu Asp Phe
                420                 425                 430
Lys Pro Phe Asn Pro Val Asp Lys Arg Thr Glu Ile Thr Tyr Ile Asp
            435                 440                 445
Thr Glu Ser Gly Gln Met Arg Arg Val Thr Lys Gly Met Thr Gly Val
        450                 455                 460
Ile Ile Glu Leu Cys Thr His Asn Lys Thr Glu Ala Leu Glu Gln Arg
465                 470                 475                 480
Leu Glu Ser Asp Val Glu Glu Phe Ala Arg Arg Gly Leu Arg Ala Leu
                485                 490                 495
Ala Val Ala Tyr Glu Asp Val Pro Asn Ala Gln Val Asp Ala Pro Gly
                500                 505                 510
Ser Gly Phe Glu Leu Ile Gly Leu Leu Ser Ile Phe Asp Pro Pro Arg
        515                 520                 525
Asp Asp Thr Lys Gln Thr Ile Asp Ala Gln Ala Leu Gly Val Lys
            530                 535                 540
Val Lys Met Val Thr Gly Asp Gln Leu Ala Ile Ala Lys Glu Thr Gly
545                 550                 555                 560
Arg Arg Leu Gly Met Gly Asp His Met Tyr Pro Ser Lys Val Leu Lys
                565                 570                 575
Asp Gly Pro Glu Pro Gly Lys Phe Ser Ser Leu Asp Glu Met Ile
            580                 585                 590
Leu Asp Ala Asp Gly Phe Ala Gly Val Phe Pro Glu His Lys Tyr Glu
        595                 600                 605
```

```
Ile Val Lys Arg Leu Gln Gly Leu Gly His Leu Cys Ala Met Thr Gly
            610                 615                 620

Asp Gly Ala Asn Asp Ala Pro Ala Leu Ala Arg Ala Asn Val Gly Ile
625                 630                 635                 640

Ala Val Glu Gly Ala Thr Asp Ala Ala Arg Gly Ala Ala Asp Ile Val
                645                 650                 655

Leu Thr Glu Pro Gly Leu Ser Thr Ile Val His Ala Ile Arg Gln Ser
            660                 665                 670

Arg Ile Val Phe Gln Arg Met Arg Asn Tyr Ser Ile Tyr Ala Cys Ala
        675                 680                 685

Val Thr Ile Arg Ile Val Val Gly Phe Ala Val Met Ala Phe Ala Phe
    690                 695                 700

Lys Phe Asp Phe Pro Pro Phe Met Val Leu Val Ile Ala Leu Leu Asn
705                 710                 715                 720

Asp Gly Thr Ile Met Thr Leu Ser Leu Asp Arg Val Leu Pro Ser Ser
                725                 730                 735

Asn Pro Asp His Trp Asp Leu Thr Glu Ile Phe Thr Tyr Ala Ile Gly
            740                 745                 750

Tyr Gly Leu Cys Leu Ala Leu Ser Thr Ile Val Leu Leu Ala Val Ile
        755                 760                 765

Ile His Thr Gln Phe Phe Glu Asp Arg Phe Gly Val Gln Pro Leu Lys
    770                 775                 780

Asp Ala Asn Asp Pro His Val His Met Ile Ile Tyr Leu Gln Val Ala
785                 790                 795                 800

Ile Ile Ser Gln Ala Leu Ile Phe Val Thr Arg Ser His Gly Trp Phe
                805                 810                 815

Phe Met Glu Arg Pro Ser Val Ala Leu Phe Gly Ala Phe Val Ile Ala
            820                 825                 830

Gln Leu Ile Ser Ser Leu Ile Ala Ala Tyr Gly Asp Trp Ala Phe Thr
        835                 840                 845

Asp Val Arg Gly Ile Ser Ala Thr Trp Ile Ala Ile Val Trp Ile Trp
    850                 855                 860

Asn Val Ile Trp Phe Leu Pro Leu Asp Leu Val Lys Phe Gly Met Arg
865                 870                 875                 880

Ala Val Ile Arg Met Phe Lys Pro Pro Val Ala Leu Asn Lys Pro Ile
                885                 890                 895

Pro Ala Asn Gln Leu Thr Arg Thr Thr Ser Arg Pro Ala Ser Ile Asn
            900                 905                 910

Glu Ser Leu Tyr Ser Asn Arg Ala Ser Phe Ile Gln Arg Ala Ser Arg
        915                 920                 925

Arg Ser Val Leu Gly Gly Arg Val His Ala Asp Asp Arg Glu Leu Arg
    930                 935                 940

Arg Phe Ser Ser Ala Gln Ala Val Ser Ser Gly Ala Ala Leu Ser Arg
945                 950                 955                 960

Ala Gln

<210> SEQ ID NO 24
<211> LENGTH: 918
<212> TYPE: PRT
<213> ORGANISM: S. serevisiae

<400> SEQUENCE: 24

Met Thr Asp Thr Ser Ser Ser Ser Ser Ser Ser Ala Ser Ser Val
1               5                   10                  15

Ser Ala His Gln Pro Thr Gln Glu Lys Pro Ala Lys Thr Tyr Asp Asp
```

```
                  20                  25                  30
Ala Ala Ser Glu Ser Asp Asp Asp Ile Asp Ala Leu Ile Glu
            35                  40                  45
Glu Leu Gln Ser Asn His Gly Val Asp Asp Glu Asp Asn Asp
        50                  55                  60
Gly Pro Val Ala Ala Gly Glu Ala Arg Pro Val Pro Glu Glu Tyr Leu
65                  70                  75                  80
Gln Thr Asp Pro Ser Tyr Gly Leu Thr Ser Asp Glu Val Leu Lys Arg
                85                  90                  95
Arg Lys Lys Tyr Gly Leu Asn Gln Met Ala Asp Glu Lys Glu Ser Leu
            100                 105                 110
Val Val Lys Phe Val Met Phe Phe Val Gly Pro Ile Gln Phe Val Met
        115                 120                 125
Glu Ala Ala Ala Ile Leu Ala Ala Gly Leu Ser Asp Trp Val Asp Phe
130                 135                 140
Gly Val Ile Cys Gly Leu Leu Met Leu Asn Ala Gly Val Gly Phe Val
145                 150                 155                 160
Gln Glu Phe Gln Ala Gly Ser Ile Val Asp Glu Leu Lys Lys Thr Leu
                165                 170                 175
Ala Asn Thr Ala Val Val Ile Arg Asp Gly Gln Leu Val Glu Ile Pro
            180                 185                 190
Ala Asn Glu Val Val Pro Gly Asp Ile Leu Gln Leu Glu Asp Gly Thr
        195                 200                 205
Val Ile Pro Thr Asp Gly Arg Ile Val Thr Glu Asp Cys Phe Leu Gln
210                 215                 220
Ile Asp Gln Ser Ala Ile Thr Gly Glu Ser Leu Ala Val Asp Lys His
225                 230                 235                 240
Tyr Gly Asp Gln Thr Phe Ser Ser Ser Thr Val Lys Arg Gly Glu Gly
                245                 250                 255
Phe Met Val Val Thr Ala Thr Gly Asp Asn Thr Phe Val Gly Arg Ala
            260                 265                 270
Ala Ala Leu Val Asn Lys Ala Ala Gly Gly Gln Gly His Phe Thr Glu
        275                 280                 285
Val Leu Asn Gly Ile Gly Ile Ile Leu Leu Val Leu Val Ile Ala Thr
290                 295                 300
Leu Leu Leu Val Trp Thr Ala Cys Phe Tyr Arg Thr Asn Gly Ile Val
305                 310                 315                 320
Arg Ile Leu Arg Tyr Thr Leu Gly Ile Thr Ile Ile Gly Val Pro Val
                325                 330                 335
Gly Leu Pro Ala Val Val Thr Thr Thr Met Ala Val Gly Ala Ala Tyr
            340                 345                 350
Leu Ala Lys Lys Gln Ala Ile Val Gln Lys Leu Ser Ala Ile Glu Ser
        355                 360                 365
Leu Ala Gly Val Glu Ile Leu Cys Ser Asp Lys Thr Gly Thr Leu Thr
370                 375                 380
Lys Asn Lys Leu Ser Leu His Glu Pro Tyr Thr Val Glu Gly Val Ser
385                 390                 395                 400
Pro Asp Asp Leu Met Leu Thr Ala Cys Leu Ala Ala Ser Arg Lys Lys
                405                 410                 415
Lys Gly Leu Asp Ala Ile Asp Lys Ala Phe Leu Lys Ser Leu Lys Gln
            420                 425                 430
Tyr Pro Lys Ala Lys Asp Ala Leu Thr Lys Tyr Lys Val Leu Glu Phe
        435                 440                 445
```

-continued

His Pro Phe Asp Pro Val Ser Lys Lys Val Thr Ala Val Val Glu Ser
450                     455                 460

Pro Glu Gly Glu Arg Ile Val Cys Val Lys Gly Ala Pro Leu Phe Val
465                 470                 475                 480

Leu Lys Thr Val Glu Glu Asp His Pro Ile Pro Glu Asp Val His Glu
                485                 490                 495

Asn Tyr Glu Asn Lys Val Ala Glu Leu Ala Ser Arg Gly Phe Arg Ala
            500                 505                 510

Leu Gly Val Ala Arg Lys Arg Gly Glu Gly His Trp Glu Ile Leu Gly
        515                 520                 525

Val Met Pro Cys Met Asp Pro Arg Asp Asp Thr Ala Gln Thr Val
    530                 535                 540

Ser Glu Ala Arg His Leu Gly Leu Arg Val Lys Met Leu Thr Gly Asp
545                 550                 555                 560

Ala Val Gly Ile Ala Lys Glu Thr Cys Arg Gln Leu Gly Leu Gly Thr
                565                 570                 575

Asn Ile Tyr Asn Ala Glu Arg Leu Gly Leu Gly Gly Gly Asp Met
            580                 585                 590

Pro Gly Ser Glu Leu Ala Asp Phe Val Glu Asn Ala Asp Gly Phe Ala
        595                 600                 605

Glu Val Phe Pro Gln His Lys Tyr Arg Val Val Glu Ile Leu Gln Asn
    610                 615                 620

Arg Gly Tyr Leu Val Ala Met Thr Gly Asp Gly Val Asn Asp Ala Pro
625                 630                 635                 640

Ser Leu Lys Lys Ala Asp Thr Gly Ile Ala Val Glu Gly Ala Thr Asp
                645                 650                 655

Ala Ala Arg Ser Ala Ala Asp Ile Val Phe Leu Ala Pro Gly Leu Ser
            660                 665                 670

Ala Ile Ile Asp Ala Leu Lys Thr Ser Arg Gln Ile Phe His Arg Met
        675                 680                 685

Tyr Ser Tyr Val Val Tyr Arg Ile Ala Leu Ser Leu His Leu Glu Ile
    690                 695                 700

Phe Leu Gly Leu Trp Ile Ala Ile Leu Asp Asn Ser Leu Asp Ile Asp
705                 710                 715                 720

Leu Ile Val Phe Ile Ala Ile Phe Ala Asp Val Ala Thr Leu Ala Ile
                725                 730                 735

Ala Tyr Asp Asn Ala Pro Tyr Ser Pro Lys Pro Val Lys Trp Asn Leu
            740                 745                 750

Pro Arg Leu Trp Gly Met Ser Ile Leu Gly Ile Val Leu Ala Ile
        755                 760                 765

Gly Ser Trp Ile Thr Leu Thr Thr Met Phe Leu Pro Lys Gly Gly Ile
770                 775                 780

Ile Gln Asn Phe Gly Ala Met Asn Gly Ile Met Phe Leu Gln Ile Ser
785                 790                 795                 800

Leu Thr Glu Asn Trp Leu Ile Phe Ile Thr Arg Ala Ala Gly Pro Phe
                805                 810                 815

Trp Ser Ser Ile Pro Ser Trp Gln Leu Ala Gly Ala Val Phe Ala Val
            820                 825                 830

Asp Ile Ile Ala Thr Met Phe Thr Leu Phe Gly Trp Trp Ser Glu Asn
        835                 840                 845

Trp Thr Asp Ile Val Thr Val Arg Val Trp Ile Trp Ser Ile Gly
    850                 855                 860

Ile Phe Cys Val Leu Gly Gly Phe Tyr Tyr Glu Met Ser Thr Ser Glu
865                 870                 875                 880

```
Ala Phe Asp Arg Leu Met Asn Gly Lys Pro Met Lys Glu Lys Ser
                885                 890                 895

Thr Arg Ser Val Glu Asp Phe Met Ala Ala Met Gln Arg Val Ser Thr
            900                 905                 910

Gln His Glu Lys Glu Thr
            915

<210> SEQ ID NO 25
<211> LENGTH: 920
<212> TYPE: PRT
<213> ORGANISM: Candida mogii

<400> SEQUENCE: 25

Met Ser Asp Glu Arg Ile Thr Glu Lys Pro Pro His Gln Gln Pro Glu
1               5                   10                  15

Ser Glu Gly Glu Pro Val Pro Glu Glu Val Glu Glu Glu Thr Glu
            20                  25                  30

Glu Glu Val Pro Asp Glu Gln Ser Glu Asp Asp Ile Asp Gly
            35                  40                  45

Leu Ile Asp Glu Leu Gln Ser Gln Glu Ala His Glu Glu Ala Glu Glu
50                  55                  60

Asp Asp Gly Pro Ala Ala Ala Gly Glu Ala Arg Lys Ile Pro Glu Glu
65                  70                  75                  80

Leu Leu Gln Thr Asp Pro Ser Val Gly Leu Ser Ser Asp Glu Val Val
                85                  90                  95

Asn Arg Arg Lys Lys Tyr Gly Leu Asn Gln Met Arg Glu Glu Ser Glu
                100                 105                 110

Asn Leu Leu Val Lys Phe Leu Met Phe Phe Ile Gly Pro Ile Gln Phe
            115                 120                 125

Val Met Glu Ala Ala Ala Val Leu Ala Ala Gly Leu Glu Asp Trp Val
            130                 135                 140

Asp Phe Gly Val Ile Cys Gly Leu Leu Phe Leu Asn Ala Gly Val Gly
145                 150                 155                 160

Phe Ile Gln Glu Phe Gln Ala Gly Ser Ile Val Glu Glu Leu Lys Lys
                165                 170                 175

Thr Leu Ala Asn Thr Ala Thr Val Ile Arg Asp Gly Ser Val Gln Glu
            180                 185                 190

Ala Pro Ala Asn Glu Ile Val Pro Gly Asp Ile Leu Lys Leu Glu Asp
            195                 200                 205

Gly Thr Val Ile Pro Ala Asp Gly Arg Leu Val Thr Glu Glu Cys Phe
210                 215                 220

Leu Gln Val Asp Gln Ser Ser Ile Thr Gly Glu Ser Leu Ala Val Asp
225                 230                 235                 240

Lys His Tyr Gly Asp Glu Val Phe Ser Ser Thr Val Lys Arg Gly
                245                 250                 255

Glu Gly Phe Met Ile Val Thr Ala Thr Gly Asp Asn Thr Phe Val Gly
            260                 265                 270

Arg Ala Ala Ser Leu Val Asn Ala Ala Gly Gly Gln Gly His Phe
            275                 280                 285

Thr Glu Val Leu Asn Gly Ile Gly Val Ile Leu Leu Val Leu Val Val
            290                 295                 300

Ile Thr Leu Leu Leu Ile Trp Thr Ala Cys Phe Tyr Arg Thr Val Arg
305                 310                 315                 320

Ile Val Pro Ile Leu Arg Tyr Thr Leu Gly Ile Thr Ile Val Gly Val
                325                 330                 335
```

```
Pro Val Gly Leu Pro Ala Val Val Thr Thr Thr Met Ala Gly Gly Ala
                340                 345                 350

Ala Tyr Leu Ala Lys Lys Gln Ala Ile Val Gln Lys Leu Ser Ala Ile
                355                 360                 365

Glu Ser Leu Ala Gly Val Glu Ile Leu Cys Ser Asp Lys Thr Gly Thr
            370                 375                 380

Leu Thr Lys Asn Lys Leu Ser Leu His Glu Pro Tyr Thr Val Glu Gly
385                 390                 395                 400

Val Ser Ser Asp Asp Leu Met Leu Thr Ala Cys Leu Ala Ala Ser Arg
                405                 410                 415

Lys Lys Lys Gly Leu Asp Ala Ile Asp Lys Ala Phe Leu Lys Ser Leu
                420                 425                 430

Ala Gln Tyr Pro Lys Ala Lys Gly Ala Leu Thr Lys Tyr Lys Val Leu
                435                 440                 445

Glu Phe His Pro Phe Asp Pro Val Ser Lys Lys Val Thr Ala Val Val
                450                 455                 460

Glu Ser Pro Glu Gly Glu Arg Ile Ile Cys Val Lys Gly Ala Pro Leu
465                 470                 475                 480

Phe Val Leu Lys Thr Val Glu Glu Asp His Pro Ile Pro Glu Asp Val
                485                 490                 495

His Glu Asn Tyr Glu Asn Lys Val Ala Glu Leu Ala Ser Arg Gly Phe
                500                 505                 510

Arg Ala Leu Gly Val Ala Arg Lys Arg Gly Glu Gly His Trp Glu Ile
                515                 520                 525

Leu Gly Val Met Pro Cys Met Asp Pro Pro Arg Asp Asp Thr Ala Ala
530                 535                 540

Thr Val Asn Glu Ala Lys Arg Leu Gly Leu Ser Val Lys Met Leu Thr
545                 550                 555                 560

Gly Asp Ala Val Gly Ile Ala Lys Glu Thr Cys Arg Gln Leu Gly Leu
                565                 570                 575

Gly Thr Asn Ile Tyr Asp Ala Glu Arg Leu Gly Leu Gly Gly Gly Gly
                580                 585                 590

Ser Met Pro Gly Ser Glu Met Tyr Asp Phe Val Glu Asn Ala Asp Gly
                595                 600                 605

Phe Ala Glu Val Phe Pro Gln His Lys Phe Ala Val Val Asp Ile Leu
                610                 615                 620

Gln Gln Arg Gly Tyr Leu Val Ala Met Thr Gly Asp Gly Val Asn Asp
625                 630                 635                 640

Ala Pro Ser Leu Lys Lys Ala Asp Thr Gly Ile Ala Val Glu Gly Ala
                645                 650                 655

Thr Asp Ala Ala Arg Ser Ala Ala Asp Ile Val Phe Leu Ala Pro Gly
                660                 665                 670

Leu Ser Ala Ile Ile Asp Ala Leu Lys Thr Ser Arg Gln Ile Phe His
                675                 680                 685

Arg Met Tyr Ala Tyr Val Val Tyr Arg Ile Ala Leu Ser Leu His Leu
                690                 695                 700

Glu Ile Phe Leu Gly Leu Trp Ile Ala Ile Leu Asn His Ser Leu Asp
705                 710                 715                 720

Ile Asp Leu Ile Val Phe Ile Ala Ile Phe Ala Asp Val Ala Thr Leu
                725                 730                 735

Ala Ile Ala Tyr Asp Asn Ala Pro Phe Ser Pro Ser Pro Val Lys Trp
                740                 745                 750

Asn Leu Pro Arg Leu Trp Gly Met Ser Ile Met Met Gly Ile Ile Leu
```

```
                755                 760                 765
Ala Ala Gly Thr Trp Ile Thr Leu Thr Thr Met Phe Leu Pro Lys Gly
770                 775                 780
Gly Ile Ile Gln Asn Phe Gly Ser Ile Asp Gly Ile Leu Phe Leu Glu
785                 790                 795                 800
Ile Ser Leu Thr Glu Asn Trp Leu Ile Phe Ile Thr Arg Ala Val Gly
                805                 810                 815
Pro Phe Trp Ser Ser Ile Pro Ser Trp Gln Leu Ala Gly Ala Val Phe
            820                 825                 830
Val Val Asp Val Val Ala Thr Met Phe Thr Leu Phe Gly Trp Trp Ser
            835                 840                 845
Gln Asn Trp Thr Asp Ile Val Thr Val Val Arg Ile Tyr Ile Trp Ser
    850                 855                 860
Ile Gly Ile Phe Cys Cys Leu Gly Gly Ala Tyr Tyr Leu Met Ser Glu
865                 870                 875                 880
Ser Glu Thr Phe Asp Arg Leu Met Asn Gly Lys Pro Leu Lys Glu Asn
                885                 890                 895
Lys Ser Thr Arg Ser Val Glu Asp Phe Leu Ala Ser Met Arg Arg Val
            900                 905                 910
Ser Thr Gln His Glu Lys Gly Asn
        915                 920

<210> SEQ ID NO 26
<211> LENGTH: 436
<212> TYPE: PRT
<213> ORGANISM: Candida glabrata

<400> SEQUENCE: 26

Ala Arg Asp Met Thr Lys Gln Ala Leu Pro Ala Val Ser Glu Val Thr
1               5                   10                  15
Lys Asp Thr Leu Glu Glu Phe Lys Thr Ala Asp Lys Val Val Leu Val
            20                  25                  30
Ala Tyr Phe Ala Ala Asp Asp Lys Ala Ser Asn Glu Thr Phe Thr Ser
        35                  40                  45
Val Ala Asn Gly Leu Arg Asp Asn Phe Leu Phe Gly Ala Thr Asn Asp
    50                  55                  60
Ala Ala Leu Ala Lys Ala Glu Gly Val Lys Gln Pro Gly Leu Val Cys
65                  70                  75                  80
Thr Ser Pro Ser Thr Thr Ala Arg Thr Ser Ser Pro Arg Pro Ser Met
                85                  90                  95
Arg Thr Tyr Pro Arg Leu Arg Lys Val Ala Ser Thr Pro Leu Ile Gly
            100                 105                 110
Glu Val Gly Pro Glu Thr Tyr Ala Gly Tyr Met Ala Ala Gly Ile Pro
        115                 120                 125
Leu Ala Tyr Ile Phe Ala Glu Thr Pro Glu Glu Arg Glu Glu Phe Ala
    130                 135                 140
Lys Glu Leu Lys Pro Leu Ala Leu Lys His Lys Gly Glu Ile Asn Phe
145                 150                 155                 160
Ala Thr Ile Asp Ala Lys Ser Phe Gly Gln His Ala Gly Asn Leu Asn
                165                 170                 175
Leu Lys Val Gly Thr Trp Pro Ala Phe Ala Ile Gln Arg Thr Glu Lys
            180                 185                 190
Asn Glu Lys Phe Pro Thr Asn Gln Glu Ala Lys Ile Thr Glu Lys Glu
        195                 200                 205
Ile Gly Lys Phe Val Asp Asp Phe Leu Ala Gly Lys Ile Asp Pro Ser
```

```
                210                 215                 220
Ile Lys Ser Glu Pro Ile Pro Glu Ser Asn Asp Gly Pro Val Thr Val
225                 230                 235                 240

Val Val Ala His Asn Tyr Lys Asp Val Val Ile Asp Asn Asp Lys Asp
                245                 250                 255

Val Leu Val Glu Phe Tyr Ala Pro Trp Cys Gly His Cys Lys Ala Leu
                260                 265                 270

Ala Pro Lys Tyr Glu Glu Leu Gly Gln Leu Tyr Ala Ser Asp Glu Leu
                275                 280                 285

Ser Lys Leu Val Thr Ile Ala Lys Val Asp Ala Thr Leu Asn Asp Val
290                 295                 300

Pro Asp Glu Ile Gln Gly Phe Leu Pro Ser Ser Leu Phe Pro Leu Ala
305                 310                 315                 320

Arg Arg Met Pro Gln Ser Thr Thr Leu Val Pro His Cys Arg Gly Ser
                325                 330                 335

Arg Pro Val His Arg Arg Glu Arg Leu Thr Gln Ala Ser Ala Ser Val
                340                 345                 350

Gly Glu Ala Val Glu Asp Ala Thr Glu Ser Ala Lys Ala Ser Ala Ser
                355                 360                 365

Ser Ala Thr Asp Ser Ala Ala Ser Ala Val Ser Glu Gly Thr Glu Thr
                370                 375                 380

Val Lys Ser Gly Ala Ser Val Ala Ser Asp Ser Ala Ser Ser Ala Ala
385                 390                 395                 400

Ser Glu Ala Thr Lys Ser Val Lys Ser Ala Ala Ser Glu Val Thr Asn
                405                 410                 415

Ser Ala Ser Ser Ala Ala Ser Glu Ala Ser Ala Ser Ala Ser Ser Val
                420                 425                 430

Lys Asp Glu Leu
        435

<210> SEQ ID NO 27
<211> LENGTH: 899
<212> TYPE: PRT
<213> ORGANISM: Kluyveromyces lactis

<400> SEQUENCE: 27

Met Ser Ala Ala Thr Glu Pro Thr Lys Glu Lys Pro Val Asn Asn Gln
1               5                   10                  15

Asp Ser Asp Asp Glu Asp Glu Asp Ile Asp Gln Leu Ile Glu Asp Leu
                20                  25                  30

Gln Ser His His Gly Leu Asp Asp Glu Ser Glu Asp Asp Glu His Val
                35                  40                  45

Ala Ala Gly Ser Ala Arg Pro Val Pro Glu Glu Leu Leu Gln Thr Asp
        50                  55                  60

Pro Ser Tyr Gly Leu Thr Ser Asp Glu Val Thr Lys Arg Arg Lys Lys
65              70                  75                  80

Tyr Gly Leu Asn Gln Met Ser Glu Glu Thr Glu Asn Leu Phe Val Lys
                85                  90                  95

Phe Leu Met Phe Phe Ile Gly Pro Ile Gln Phe Val Met Glu Ala Ala
                100                 105                 110

Ala Ile Leu Ala Ala Gly Leu Glu Asp Trp Val Asp Phe Gly Val Ile
        115                 120                 125

Cys Gly Leu Leu Phe Leu Asn Ala Ala Val Gly Phe Ile Gln Glu Tyr
        130                 135                 140

Gln Ala Gly Ser Ile Val Asp Glu Leu Lys Lys Thr Leu Ala Asn Ser
```

```
            145                 150                 155                 160
Ala Val Val Ile Arg Asp Gly Asn Leu Val Glu Val Pro Ser Asn Glu
                165                 170                 175
Val Val Pro Gly Asp Ile Leu Gln Leu Glu Asp Gly Val Val Ile Pro
                180                 185                 190
Ala Asp Gly Arg Leu Val Thr Glu Asp Cys Phe Ile Gln Ile Asp Gln
                195                 200                 205
Ser Ala Ile Thr Gly Glu Ser Leu Ala Val Asp Lys Arg Phe Gly Asp
                210                 215                 220
Ser Thr Phe Ser Ser Ser Thr Val Lys Arg Gly Glu Ala Phe Met Ile
225                 230                 235                 240
Val Thr Ala Thr Gly Asp Ser Thr Phe Val Gly Arg Ala Ala Ala Leu
                245                 250                 255
Val Asn Lys Ala Ala Ala Gly Ser Gly His Phe Thr Glu Val Leu Asn
                260                 265                 270
Gly Ile Gly Thr Ile Leu Leu Ile Leu Val Ile Val Thr Leu Leu Leu
                275                 280                 285
Val Trp Val Ala Ser Phe Tyr Arg Thr Asn Lys Ile Val Arg Ile Leu
290                 295                 300
Arg Tyr Thr Leu Ala Ile Thr Ile Val Gly Val Pro Val Gly Leu Pro
305                 310                 315                 320
Ala Val Val Thr Thr Thr Met Ala Val Gly Ala Ala Tyr Leu Ala Lys
                325                 330                 335
Lys Gln Ala Ile Val Gln Lys Leu Ser Ala Ile Glu Ser Leu Ala Gly
                340                 345                 350
Val Glu Ile Leu Cys Ser Asp Lys Thr Gly Thr Leu Thr Lys Asn Lys
                355                 360                 365
Leu Ser Leu His Glu Pro Tyr Thr Val Glu Gly Val Asp Pro Asp Asp
                370                 375                 380
Leu Met Leu Thr Ala Cys Leu Ala Ala Ser Arg Lys Lys Lys Gly Leu
385                 390                 395                 400
Asp Ala Ile Asp Lys Ala Phe Leu Lys Ser Leu Ile Ser Tyr Pro Arg
                405                 410                 415
Ala Lys Ala Ala Leu Thr Lys Tyr Lys Leu Leu Glu Phe His Pro Phe
                420                 425                 430
Asp Pro Val Ser Lys Lys Val Thr Ala Ile Val Glu Ser Pro Glu Gly
                435                 440                 445
Glu Arg Ile Ile Cys Val Lys Gly Ala Pro Leu Phe Val Leu Lys Thr
                450                 455                 460
Val Glu Glu Glu His Pro Ile Pro Glu Asp Val Arg Glu Asn Tyr Glu
465                 470                 475                 480
Asn Lys Val Ala Glu Leu Ala Ser Arg Gly Phe Arg Ala Leu Gly Val
                485                 490                 495
Ala Arg Lys Arg Gly Glu Gly His Trp Glu Ile Leu Gly Val Met Pro
                500                 505                 510
Cys Met Asp Pro Pro Arg Asp Asp Thr Ala Gln Thr Val Asn Glu Ala
                515                 520                 525
Arg His Leu Gly Leu Arg Val Lys Met Leu Thr Gly Asp Ala Val Gly
                530                 535                 540
Ile Ala Lys Glu Thr Cys Arg Gln Leu Gly Leu Gly Thr Asn Ile Tyr
545                 550                 555                 560
Asn Ala Glu Arg Leu Gly Leu Gly Gly Gly Asp Met Pro Gly Ser
                565                 570                 575
```

```
Glu Leu Ala Asp Phe Val Glu Asn Ala Asp Gly Phe Ala Glu Val Phe
            580                 585                 590

Pro Gln His Lys Tyr Asn Val Glu Ile Leu Gln Gln Arg Gly Tyr
            595                 600                 605

Leu Val Ala Met Thr Gly Asp Gly Val Asn Asp Ala Pro Ser Leu Lys
            610                 615                 620

Lys Ala Asp Thr Gly Ile Ala Val Glu Gly Ala Thr Asp Ala Ala Arg
625                 630                 635                 640

Ser Ala Ala Asp Ile Val Phe Leu Ala Pro Gly Leu Ser Ala Ile Ile
                645                 650                 655

Asp Ala Leu Lys Thr Ser Arg Gln Ile Phe His Arg Met Tyr Ser Tyr
            660                 665                 670

Val Val Tyr Arg Ile Ala Leu Ser Leu His Leu Glu Ile Phe Leu Gly
            675                 680                 685

Leu Trp Ile Ala Ile Leu Asn Arg Ser Leu Asn Ile Asp Leu Val Val
            690                 695                 700

Phe Ile Ala Ile Phe Ala Asp Val Ala Thr Leu Ala Ile Ala Tyr Asp
705                 710                 715                 720

Asn Ala Pro Tyr Ser Pro Lys Pro Val Lys Trp Asn Leu Arg Arg Leu
                725                 730                 735

Trp Gly Met Ser Val Ile Leu Gly Ile Ile Leu Ala Ile Gly Thr Trp
            740                 745                 750

Ile Thr Leu Thr Thr Met Phe Val Pro Lys Gly Gly Ile Ile Gln Asn
            755                 760                 765

Phe Gly Ser Ile Asp Gly Val Leu Phe Leu Gln Ile Ser Leu Thr Glu
            770                 775                 780

Asn Trp Leu Ile Phe Ile Thr Arg Ala Ala Gly Pro Phe Trp Ser Ser
785                 790                 795                 800

Ile Pro Ser Trp Gln Leu Ser Gly Ala Val Leu Ile Val Asp Ile Ile
                805                 810                 815

Ala Thr Met Phe Cys Leu Phe Gly Trp Trp Ser Gln Asn Trp Asn Asp
            820                 825                 830

Ile Val Thr Val Val Arg Val Trp Ile Phe Ser Phe Gly Val Phe Cys
            835                 840                 845

Val Met Gly Gly Ala Tyr Tyr Met Met Ser Glu Ser Glu Ala Phe Asp
            850                 855                 860

Arg Phe Met Asn Gly Lys Ser Arg Arg Asp Lys Pro Ser Gly Arg Ser
865                 870                 875                 880

Val Glu Asp Phe Leu Met Ala Met Gln Arg Val Ser Thr Gln His Glu
                885                 890                 895

Lys Glu Asn

<210> SEQ ID NO 28
<211> LENGTH: 895
<212> TYPE: PRT
<213> ORGANISM: Candida albicans

<400> SEQUENCE: 28

Met Ser Ala Thr Glu Pro Thr Asn Glu Lys Val Asp Lys Ile Val Ser
1               5                   10                  15

Asp Asp Glu Asp Glu Asp Ile Asp Gln Leu Val Ala Asp Leu Gln Ser
            20                  25                  30

Asn Pro Gly Ala Gly Asp Glu Glu Glu Glu Asn Asp Ser Ser
            35                  40                  45

Phe Lys Ala Val Pro Glu Glu Leu Leu Gln Thr Asp Pro Arg Val Gly
```

-continued

```
            50                  55                  60
Leu Thr Asp Asp Glu Val Thr Lys Arg Arg Lys Arg Tyr Gly Leu Asn
 65                  70                  75                  80

Gln Met Ala Glu Glu Glu Asn Leu Val Leu Lys Phe Val Met Phe
                 85                  90                  95

Phe Val Gly Pro Ile Gln Phe Val Met Glu Ala Ala Val Leu Ala
                100                 105                 110

Ala Gly Leu Glu Asp Trp Val Asp Phe Gly Val Ile Cys Ala Leu Leu
                115                 120                 125

Leu Leu Asn Ala Phe Val Gly Phe Ile Gln Glu Tyr Gln Ala Gly Ser
            130                 135                 140

Ile Val Asp Glu Leu Lys Lys Thr Leu Ala Asn Ser Ala Leu Val Val
145                 150                 155                 160

Arg Asn Gly Gln Leu Val Glu Ile Pro Ala Asn Glu Val Val Pro Gly
                165                 170                 175

Asp Ile Leu Gln Leu Glu Asp Gly Thr Val Ile Pro Thr Asp Gly Arg
                180                 185                 190

Ile Val Ser Glu Asp Cys Leu Leu Gln Val Asp Gln Ser Ala Ile Thr
                195                 200                 205

Gly Glu Ser Leu Ala Val Asp Lys Arg Ser Gly Asp Ser Cys Tyr Ser
            210                 215                 220

Ser Ser Thr Val Lys Thr Gly Glu Ala Phe Met Ile Val Thr Ala Thr
225                 230                 235                 240

Gly Asp Ser Thr Phe Val Gly Arg Ala Ala Leu Val Asn Lys Ala
                245                 250                 255

Ser Ala Gly Thr Gly His Phe Thr Glu Val Leu Asn Gly Ile Gly Thr
                260                 265                 270

Thr Leu Leu Val Phe Val Ile Val Thr Leu Leu Val Val Trp Val Ala
            275                 280                 285

Cys Phe Tyr Arg Thr Val Arg Ile Val Pro Ile Leu Arg Tyr Thr Leu
                290                 295                 300

Ala Ile Thr Ile Ile Gly Val Pro Val Gly Leu Pro Ala Val Val Thr
305                 310                 315                 320

Thr Thr Met Ala Val Gly Ala Ala Tyr Leu Ala Lys Lys Gln Ala Ile
                325                 330                 335

Val Gln Lys Leu Ser Ala Ile Glu Ser Leu Ala Gly Val Glu Ile Leu
                340                 345                 350

Cys Ser Asp Lys Thr Gly Thr Leu Thr Lys Asn Lys Leu Ser Leu His
            355                 360                 365

Glu Pro Tyr Thr Val Glu Gly Val Glu Pro Asp Asp Leu Met Leu Thr
                370                 375                 380

Ala Cys Leu Ala Ala Ser Arg Lys Lys Lys Gly Leu Asp Ala Ile Asp
385                 390                 395                 400

Lys Ala Phe Leu Lys Ser Leu Ile Asn Tyr Pro Arg Ala Lys Ala Ala
                405                 410                 415

Leu Pro Lys Tyr Lys Val Ile Glu Phe Gln Pro Phe Asp Pro Val Ser
                420                 425                 430

Lys Lys Val Thr Ala Ile Val Glu Ser Pro Glu Gly Glu Arg Ile Ile
            435                 440                 445

Cys Val Lys Gly Ala Pro Leu Phe Val Leu Lys Thr Val Glu Asp Asp
                450                 455                 460

His Pro Ile Pro Glu Asp Val His Glu Asn Tyr Gln Asn Thr Val Ala
465                 470                 475                 480
```

```
Glu Phe Ala Ser Arg Gly Phe Arg Ser Leu Gly Val Ala Arg Lys Arg
            485                 490                 495

Gly Glu Gly His Trp Glu Ile Leu Gly Ile Met Pro Cys Met Asp Pro
        500                 505                 510

Pro Arg Asp Asp Thr Ala Ala Thr Val Asn Glu Ala Arg Arg Leu Gly
        515                 520                 525

Leu Arg Val Lys Met Leu Thr Gly Asp Ala Val Gly Ile Ala Lys Glu
    530                 535                 540

Thr Cys Arg Gln Leu Gly Leu Gly Thr Asn Ile Tyr Asp Ala Asp Arg
545                 550                 555                 560

Leu Gly Leu Ser Gly Gly Asp Met Ala Gly Ser Glu Ile Ala Asp
                565                 570                 575

Phe Val Glu Asn Ala Asp Gly Phe Ala Glu Gly Phe Pro Thr Asn Lys
                580                 585                 590

Tyr Asn Ala Val Glu Ile Leu Gln Ser Arg Gly Tyr Leu Val Ala Met
            595                 600                 605

Thr Gly Asp Gly Val Asn Asp Ala Pro Ser Leu Lys Lys Ala Asp Thr
        610                 615                 620

Gly Ile Ala Val Glu Gly Ala Thr Asp Ala Ala Arg Ser Ala Ala Asp
625                 630                 635                 640

Ile Val Phe Leu Ala Pro Gly Leu Ser Ala Ile Ile Asp Ala Leu Lys
                645                 650                 655

Thr Ser Arg Gln Ile Phe His Arg Met Tyr Ser Tyr Val Val Tyr Arg
            660                 665                 670

Ile Ala Leu Ser Leu His Leu Glu Leu Phe Leu Gly Leu Trp Ile Ala
        675                 680                 685

Ile Leu Asn Arg Ser Leu Asp Ile Asn Leu Ile Val Phe Ile Ala Ile
    690                 695                 700

Phe Ala Asp Val Ala Thr Leu Ala Ile Ala Tyr Asp Asn Ala Pro Tyr
705                 710                 715                 720

Asp Pro Lys Pro Val Lys Trp Asn Leu Pro Arg Leu Trp Gly Met Ser
                725                 730                 735

Ile Val Leu Gly Ile Ile Leu Ala Ile Gly Thr Trp Ile Thr Leu Thr
            740                 745                 750

Thr Met Leu Leu Pro Lys Gly Gly Ile Ile Gln Asn Phe Gly Gly Leu
        755                 760                 765

Asp Gly Ile Leu Phe Leu Gln Ile Ser Leu Thr Glu Asn Trp Leu Ile
    770                 775                 780

Phe Val Thr Arg Ala Gln Gly Pro Phe Trp Ser Ser Ile Pro Ser Trp
785                 790                 795                 800

Gln Leu Ser Gly Ala Val Leu Ile Val Asp Ile Ile Ala Thr Cys Phe
                805                 810                 815

Thr Leu Phe Gly Trp Trp Ser Gln Asn Trp Thr Asp Ile Val Thr Val
            820                 825                 830

Val Arg Thr Trp Ile Trp Ser Phe Gly Val Phe Cys Val Met Gly Gly
        835                 840                 845

Ala Tyr Tyr Leu Met Ser Thr Ser Glu Ala Phe Asp Asn Phe Cys Asn
    850                 855                 860

Gly Arg Lys Pro Gln Gln His Thr Asp Lys Arg Ser Leu Glu Asp Phe
865                 870                 875                 880

Leu Val Ser Met Gln Arg Val Ser Thr Gln His Glu Lys Ser Thr
                885                 890                 895

<210> SEQ ID NO 29
```

```
<211> LENGTH: 920
<212> TYPE: PRT
<213> ORGANISM: Neurospora crassa

<400> SEQUENCE: 29

Met Ala Asp His Ser Ala Ser Gly Ala Pro Ala Leu Ser Thr Asn Ile
1               5                   10                  15

Glu Ser Gly Lys Phe Asp Glu Lys Ala Glu Ala Ala Tyr Gln
            20                  25                  30

Pro Lys Pro Lys Val Glu Asp Asp Glu Asp Glu Asp Ile Asp Ala Leu
        35                  40                  45

Ile Glu Asp Leu Glu Ser His Asp Gly His Asp Ala Glu Glu Glu Glu
50                  55                  60

Glu Glu Ala Thr Pro Gly Gly Arg Val Val Pro Glu Asp Met Leu
65                  70                  75                  80

Gln Thr Asp Thr Arg Val Gly Leu Thr Ser Glu Glu Val Val Gln Arg
                85                  90                  95

Arg Arg Lys Tyr Gly Leu Asn Gln Met Lys Glu Glu Lys Glu Asn His
            100                 105                 110

Phe Leu Lys Phe Leu Gly Phe Phe Val Gly Pro Ile Gln Phe Val Met
        115                 120                 125

Glu Gly Ala Ala Val Leu Ala Ala Gly Leu Glu Asp Trp Val Asp Phe
130                 135                 140

Gly Val Ile Cys Gly Leu Leu Leu Leu Asn Ala Val Val Gly Phe Val
145                 150                 155                 160

Gln Glu Phe Gln Ala Gly Ser Ile Val Asp Leu Lys Lys Thr Leu
                165                 170                 175

Ala Leu Lys Ala Val Val Leu Arg Asp Gly Thr Leu Lys Glu Ile Glu
            180                 185                 190

Ala Pro Glu Val Val Pro Gly Asp Ile Leu Gln Val Glu Glu Gly Thr
        195                 200                 205

Ile Ile Pro Ala Asp Gly Arg Ile Val Thr Asp Asp Ala Phe Leu Gln
210                 215                 220

Val Asp Gln Ser Ala Leu Thr Gly Glu Ser Leu Ala Val Asp Lys His
225                 230                 235                 240

Lys Gly Asp Gln Val Phe Ala Ser Ser Ala Val Lys Arg Gly Glu Ala
                245                 250                 255

Phe Val Val Ile Thr Ala Thr Gly Asp Asn Thr Phe Val Gly Arg Ala
            260                 265                 270

Ala Ala Leu Val Asn Ala Ala Ser Gly Gly Ser Gly His Phe Thr Glu
        275                 280                 285

Val Leu Asn Gly Ile Gly Thr Ile Leu Leu Ile Leu Val Ile Phe Thr
290                 295                 300

Leu Leu Ile Val Trp Val Ser Ser Phe Tyr Arg Ser Asn Pro Ile Val
305                 310                 315                 320

Gln Ile Leu Glu Phe Thr Leu Ala Ile Thr Ile Gly Val Pro Val
                325                 330                 335

Gly Leu Pro Ala Val Val Thr Thr Thr Met Ala Val Gly Ala Ala Tyr
            340                 345                 350

Leu Ala Lys Lys Lys Ala Ile Val Gln Lys Leu Ser Ala Ile Glu Ser
        355                 360                 365

Leu Ala Gly Val Glu Ile Leu Cys Ser Asp Lys Thr Gly Thr Leu Thr
370                 375                 380

Lys Asn Lys Leu Ser Leu His Asp Pro Tyr Thr Val Ala Gly Val Asp
385                 390                 395                 400
```

```
Pro Glu Asp Leu Met Leu Thr Ala Cys Leu Ala Ala Ser Arg Lys Lys
                405                 410                 415

Lys Gly Ile Asp Ala Ile Asp Lys Ala Phe Leu Lys Ser Leu Lys Tyr
            420                 425                 430

Tyr Pro Arg Ala Lys Ser Val Leu Ser Lys Tyr Lys Val Leu Gln Phe
        435                 440                 445

His Pro Phe Asp Pro Val Ser Lys Lys Val Val Ala Val Val Glu Ser
    450                 455                 460

Pro Gln Gly Glu Arg Ile Thr Cys Val Lys Gly Ala Pro Leu Phe Val
465                 470                 475                 480

Leu Lys Thr Val Glu Glu Asp His Pro Ile Pro Glu Glu Val Asp Gln
                485                 490                 495

Ala Tyr Lys Asn Lys Val Ala Glu Phe Ala Thr Arg Gly Phe Arg Ser
            500                 505                 510

Leu Gly Val Ala Arg Lys Arg Gly Glu Gly Ser Trp Glu Ile Leu Gly
        515                 520                 525

Ile Met Pro Cys Met Asp Pro Pro Arg His Asp Thr Tyr Lys Thr Val
    530                 535                 540

Cys Glu Ala Lys Thr Leu Gly Leu Ser Ile Lys Met Leu Thr Gly Asp
545                 550                 555                 560

Ala Val Gly Ile Ala Arg Glu Thr Ser Arg Gln Leu Gly Leu Gly Thr
                565                 570                 575

Asn Ile Tyr Asn Ala Glu Arg Leu Gly Leu Gly Gly Gly Asp Met
            580                 585                 590

Pro Gly Ser Glu Val Tyr Asp Phe Val Glu Ala Ala Asp Gly Phe Ala
        595                 600                 605

Glu Val Phe Pro Gln His Lys Tyr Asn Val Val Glu Ile Leu Gln Gln
    610                 615                 620

Arg Gly Tyr Leu Val Ala Met Thr Gly Asp Gly Val Asn Asp Ala Pro
625                 630                 635                 640

Ser Leu Lys Lys Ala Asp Thr Gly Ile Ala Val Glu Gly Ser Ser Asp
                645                 650                 655

Ala Ala Arg Ser Ala Ala Asp Ile Val Phe Leu Ala Pro Gly Leu Gly
            660                 665                 670

Ala Ile Ile Asp Ala Leu Lys Thr Ser Arg Gln Ile Phe His Arg Met
        675                 680                 685

Tyr Ala Tyr Val Val Tyr Arg Ile Ala Leu Ser Ile His Leu Glu Ile
    690                 695                 700

Phe Leu Gly Leu Trp Ile Ala Ile Leu Asn Arg Ser Leu Asn Ile Glu
705                 710                 715                 720

Leu Val Val Phe Ile Ala Ile Phe Ala Asp Val Ala Thr Leu Ala Ile
                725                 730                 735

Ala Tyr Asp Asn Ala Pro Tyr Ser Gln Thr Pro Val Lys Trp Asn Leu
            740                 745                 750

Pro Lys Leu Trp Gly Met Ser Val Leu Leu Gly Val Val Leu Ala Val
        755                 760                 765

Gly Thr Trp Ile Thr Val Thr Thr Met Tyr Ala Gln Gly Glu Asn Gly
    770                 775                 780

Gly Ile Val Gln Asn Phe Gly Asn Met Asp Glu Val Leu Phe Leu Gln
785                 790                 795                 800

Ile Ser Leu Thr Glu Asn Trp Leu Ile Phe Ile Thr Arg Ala Asn Gly
                805                 810                 815

Pro Phe Trp Ser Ser Ile Pro Ser Trp Gln Leu Ser Gly Ala Ile Phe
```

```
                  820                 825                 830
Leu Val Asp Ile Leu Ala Thr Cys Phe Thr Ile Trp Gly Trp Phe Glu
        835                 840                 845

His Ser Asp Thr Ser Ile Val Ala Val Val Arg Ile Trp Ile Phe Ser
    850                 855                 860

Phe Gly Ile Phe Cys Ile Met Gly Val Tyr Tyr Ile Leu Gln Asp
865                 870                 875                 880

Ser Val Gly Phe Asp Asn Leu Met His Gly Lys Ser Pro Lys Gly Asn
                885                 890                 895

Gln Lys Gln Arg Ser Leu Glu Asp Phe Val Val Ser Leu Gln Arg Val
                900                 905                 910

Ser Thr Gln His Glu Lys Ser Gln
        915                 920

<210> SEQ ID NO 30
<211> LENGTH: 916
<212> TYPE: PRT
<213> ORGANISM: Ajellomyces capsulata

<400> SEQUENCE: 30

Met Ala His Ser Ala Ala Ser Gly Ala Ala Ser Ala Ala His Phe Glu
1               5                   10                  15

Lys Lys Thr Pro Glu Val Ala His Glu Glu Lys Lys Pro Pro Leu Pro
            20                  25                  30

Glu Glu Glu Asp Glu Asp Glu Asp Met Asp Ala Leu Ile Glu Glu Leu
        35                  40                  45

Glu Ser Gln Asp Gly His Ile Asp Ile Glu Asp Glu Asp Gly Glu
    50                  55                  60

Pro Gly Gly Ala Arg Pro Val Pro Asp Glu Leu Leu Thr Thr Asp Thr
65                  70                  75                  80

Arg His Gly Leu Thr Asp Ala Glu Val Val Ala Arg Arg Lys Lys Tyr
                85                  90                  95

Gly Leu Asn Gln Met Lys Glu Glu Lys Glu Asn Leu Val Leu Lys Phe
            100                 105                 110

Leu Ser Tyr Phe Val Gly Pro Ile Gln Phe Val Met Glu Ala Ala Ala
        115                 120                 125

Ile Leu Ala Ala Gly Leu Glu Asp Trp Val Asp Phe Gly Val Ile Cys
    130                 135                 140

Ala Leu Leu Leu Leu Asn Ala Cys Val Gly Phe Val Gln Glu Phe Gln
145                 150                 155                 160

Ala Gly Ser Ile Val Asp Glu Leu Lys Lys Thr Leu Ala Leu Lys Ala
                165                 170                 175

Val Val Leu Arg Asn Gly Arg Leu Thr Glu Val Glu Ala Pro Glu Val
            180                 185                 190

Val Pro Gly Asp Ile Leu Gln Val Glu Glu Gly Thr Ile Ile Pro Ala
        195                 200                 205

Asp Gly Arg Ile Val Thr Glu Glu Ala Phe Leu Gln Val Asp Gln Ser
    210                 215                 220

Ala Ile Thr Gly Glu Ser Leu Ala Val Asp Lys His Lys Gly Asp Thr
225                 230                 235                 240

Cys Tyr Ala Ser Ser Ala Val Lys Arg Gly Glu Ala Phe Met Val Ile
                245                 250                 255

Thr Ala Thr Gly Asp Asn Thr Phe Val Gly Arg Gly Pro Ala Leu Val
            260                 265                 270

Asn Ala Ala Ser Ala Gly Thr Gly His Phe Thr Glu Val Leu Asn Gly
```

```
              275                 280                 285
Ile Gly Thr Val Leu Leu Ile Leu Val Ile Leu Thr Leu Leu Val Val
290                 295                 300
Trp Val Ser Ser Phe Tyr Arg Ser Asn Ser Ile Val Thr Ile Leu Glu
305                 310                 315                 320
Phe Thr Leu Ala Ile Thr Ile Gly Val Pro Val Gly Leu Pro Ala
                325                 330                 335
Val Val Thr Thr Thr Met Ala Val Gly Ala Ala Tyr Leu Ala Lys Lys
                340                 345                 350
Lys Ala Ile Val Gln Lys Leu Ser Ala Ile Glu Ser Leu Ala Gly Val
                355                 360                 365
Glu Ile Leu Cys Ser Asp Lys Thr Gly Thr Leu Thr Lys Asn Lys Leu
370                 375                 380
Ser Leu Ala Glu Pro Tyr Cys Val Ser Gly Val Asp Pro Glu Asp Leu
385                 390                 395                 400
Met Leu Thr Ala Cys Leu Ala Ala Ser Arg Lys Lys Lys Gly Ile Asp
                405                 410                 415
Ala Ile Asp Lys Ala Phe Leu Lys Ser Leu Arg Tyr Tyr Pro Arg Ala
                420                 425                 430
Lys Ser Val Leu Thr Gln Tyr Lys Val Leu Glu Phe His Pro Phe Asp
                435                 440                 445
Pro Val Ser Lys Lys Val Ser Ala Val Val Leu Ser Pro Gln Gly Glu
                450                 455                 460
Arg Ile Thr Cys Val Lys Gly Ala Pro Leu Ser Val Leu Lys Thr Val
465                 470                 475                 480
Glu Glu Asp His Pro Ile Pro Asp Val Asp Ser Ala Tyr Lys Asn
                485                 490                 495
Lys Val Ala Glu Phe Ala Thr Arg Gly Phe Arg Ser Leu Gly Val Ala
                500                 505                 510
Arg Lys Arg Gly Glu Gly Ser Trp Glu Ile Leu Gly Ile Met Pro Cys
                515                 520                 525
Ser Asp Pro Pro Arg His Asp Thr Ala Lys Thr Ile Asn Glu Ala Lys
530                 535                 540
Thr Leu Gly Leu Ser Ile Lys Met Leu Thr Gly Asp Ala Val Gly Ile
545                 550                 555                 560
Ala Arg Glu Thr Ser Arg Gln Leu Gly Leu Gly Thr Asn Val Tyr Asn
                565                 570                 575
Ala Glu Arg Leu Gly Leu Gly Gly Gly Thr Met Pro Gly Ser Glu
                580                 585                 590
Val Tyr Asp Phe Val Glu Ala Ala Asp Gly Phe Ala Glu Val Phe Pro
                595                 600                 605
Gln His Lys Tyr Asn Val Val Glu Ile Leu Gln Gln Arg Gly Tyr Leu
                610                 615                 620
Val Ala Met Thr Gly Asp Gly Val Asn Asp Ala Pro Ser Leu Lys Lys
625                 630                 635                 640
Ala Asp Thr Gly Ile Ala Val Glu Gly Ala Ser Asp Ala Ala Arg Ser
                645                 650                 655
Ala Ala Asp Ile Val Phe Leu Ala Pro Gly Leu Ser Ala Ile Ile Asp
                660                 665                 670
Ala Leu Lys Thr Ser Arg Gln Ile Phe His Arg Met Tyr Ala Tyr Val
                675                 680                 685
Val Tyr Arg Ile Ala Leu Ser Leu His Leu Glu Ile Phe Leu Gly Leu
                690                 695                 700
```

-continued

```
Trp Ile Ala Ile Leu Asn Thr Ser Leu Asn Leu Gln Leu Val Val Phe
705                 710                 715                 720

Ile Ala Ile Phe Ala Asp Ile Ala Thr Leu Ala Ile Ala Tyr Asp Asn
                725                 730                 735

Ala Pro Phe Ser Lys Thr Pro Val Lys Trp Asn Leu Pro Lys Leu Trp
            740                 745                 750

Gly Met Ser Val Leu Leu Gly Ile Val Leu Ala Val Gly Thr Trp Ile
        755                 760                 765

Thr Leu Thr Thr Met Leu Val Gly Ser Glu Asn Gly Gly Ile Val Gln
    770                 775                 780

Asn Phe Gly Arg Thr His Pro Val Leu Phe Leu Glu Ile Ser Leu Thr
785                 790                 795                 800

Glu Asn Trp Leu Ile Phe Ile Thr Arg Ala Asn Gly Pro Phe Trp Ser
                805                 810                 815

Ser Ile Pro Ser Trp Gln Leu Ser Gly Ala Ile Leu Leu Val Asp Ile
            820                 825                 830

Ile Ala Thr Leu Phe Thr Ile Phe Gly Trp Phe Val Gly Gly Gln Thr
        835                 840                 845

Ser Ile Val Ala Val Val Arg Ile Trp Val Phe Ser Phe Gly Cys Phe
    850                 855                 860

Cys Val Leu Gly Gly Leu Tyr Tyr Leu Leu Gln Gly Ser Ala Gly Phe
865                 870                 875                 880

Asp Asn Met Met His Gly Lys Ser Pro Lys Lys Asn Gln Lys Gln Arg
                885                 890                 895

Ser Leu Glu Asp Phe Val Val Ser Leu Gln Arg Val Ser Thr Gln His
            900                 905                 910

Glu Lys Ser Ser
        915

<210> SEQ ID NO 31
<211> LENGTH: 927
<212> TYPE: PRT
<213> ORGANISM: Pneumocystis carinii

<400> SEQUENCE: 31

Met Ser Glu Glu Gly Lys Ala Leu Ile His Glu Thr Val Tyr Tyr Lys
1               5                   10                  15

His Thr Ser Thr Phe Glu Ile Ser Glu Thr Thr Lys Asp Leu Glu Lys
                20                  25                  30

Gly Gly Glu Glu Glu Cys Leu Leu Asp Asp Glu Asp Asn Asp Ile Glu
            35                  40                  45

Ala Leu Ile Asp Glu Leu Glu Ser Gln Gly Gly Asp Gln Glu Asp Asn
        50                  55                  60

Ile Glu Asp Thr Glu Phe Gln Ser Gln Arg Gln Val Pro Glu Glu Leu
65                  70                  75                  80

Leu Ala Thr Asp Thr Arg Ile Gly Leu Thr Ser Gln Glu Val Val Asn
                85                  90                  95

Arg Arg Lys Lys Tyr Gly Leu Asn Lys Met Lys Glu Glu Lys Glu Asn
                100                 105                 110

Met Ile Ile Lys Phe Leu Met Tyr Phe Val Gly Pro Ile Gln Phe Val
            115                 120                 125

Met Glu Ala Ala Ala Ile Leu Ala Ala Ser Leu Gln Asp Trp Val Asp
        130                 135                 140

Phe Gly Val Ile Cys Ala Leu Leu Leu Leu Asn Ala Val Gly Phe
145                 150                 155                 160
```

```
Ile Gln Glu Phe Gln Ala Gly Ser Ile Val Asp Glu Leu Lys Lys Thr
                165                 170                 175
Leu Ala Leu Lys Ala Thr Val Leu Arg Asp Gly Arg Leu Ile Asp Ile
            180                 185                 190
Glu Ala Glu Glu Val Val Pro Gly Asp Ile Leu Gln Leu Glu Glu Gly
        195                 200                 205
Ser Ile Val Pro Ala Asp Gly Arg Ile Val Thr Glu Glu Ala Tyr Ile
    210                 215                 220
Gln Val Asp Gln Ser Ser Ile Thr Gly Glu Ser Leu Ala Val Asp Lys
225                 230                 235                 240
His Lys Gly Asp Asn Ile Tyr Ser Ser Val Val Lys Arg Gly Glu
                245                 250                 255
Thr Phe Met Val Val Thr Ala Thr Gly Asp Gly Thr Phe Val Gly His
            260                 265                 270
Ala Ala Ser Leu Val Asn Lys Ala Ser Cys Gly Thr Gly His Phe Thr
        275                 280                 285
Asp Val Leu Asn Arg Ile Gly Thr Ile Leu Leu Val Leu Val Val Phe
    290                 295                 300
Thr Leu Phe Val Val Tyr Ile Ser Ala Phe Tyr Arg Ser Ser Thr Thr
305                 310                 315                 320
Ile Thr Ile Leu Lys Tyr Thr Leu Ala Ile Thr Ile Ile Gly Val Pro
                325                 330                 335
Val Gly Leu Pro Ala Val Val Thr Thr Thr Met Ala Val Gly Ala Ala
            340                 345                 350
Tyr Leu Ala Lys Lys Ala Ile Val Gln Lys Leu Ser Ala Ile Glu
        355                 360                 365
Ser Leu Ala Gly Val Glu Ile Leu Cys Ser Asp Lys Thr Gly Thr Leu
    370                 375                 380
Thr Lys Asn Asp Leu Ser Leu Ala Glu Pro Tyr Thr Val Glu Gly Ile
385                 390                 395                 400
Ser Cys Asp Glu Leu Met Leu Thr Ala Cys Leu Ala Ala Ser Arg Lys
                405                 410                 415
Lys Lys Gly Leu Asp Ala Ile Asp Lys Ala Phe Leu Lys Ala Leu Arg
            420                 425                 430
Asn Tyr Pro Val Val Arg Ser Ala Ile Ser Lys Tyr Asn Leu Val Glu
        435                 440                 445
Phe His Pro Phe Asp Pro Val Ser Lys Lys Val Thr Ala Ile Val Glu
    450                 455                 460
Ser Pro Ser Gly Glu Arg Ile Ala Cys Val Lys Gly Ala Pro Leu Phe
465                 470                 475                 480
Val Leu Arg Thr Val Glu Glu Asp Gln Pro Val Pro Glu Asp Ile Gln
                485                 490                 495
Asn Ala Tyr Lys Asp Lys Val Ala Glu Phe Ala Ser Arg Gly Tyr Arg
            500                 505                 510
Ser Leu Gly Ile Ala Arg Lys Thr Gly Asn Ser Asn Trp Glu Ile Leu
        515                 520                 525
Gly Ile Met Pro Cys Ser Asp Pro Arg Cys Asp Thr Ala Arg Thr
    530                 535                 540
Ile Ser Glu Ala Ile Arg Leu Gly Leu Arg Ile Lys Met Leu Thr Gly
545                 550                 555                 560
Asp Ala Val Gly Ile Ala Lys Glu Thr Ala Arg Gln Leu Gly Met Gly
                565                 570                 575
Thr Asn Val Tyr Asn Ala Glu Arg Leu Gly Leu Gly Gly Gly Asp
            580                 585                 590
```

Met Pro Gly Ser Glu Val Tyr Asp Phe Val Glu Ala Ala Asp Gly Phe
            595                 600                 605

Ala Glu Val Phe Pro Gln His Lys Tyr Asn Val Val Glu Ile Leu Gln
    610                 615                 620

Gln Arg Gly Tyr Leu Val Ala Met Thr Gly Asp Gly Val Asn Asp Ala
625                 630                 635                 640

Pro Ser Leu Lys Lys Ala Asp Thr Gly Ile Ala Val Glu Gly Ala Ser
                645                 650                 655

Asp Ala Ala Arg Ser Ala Ala Asp Ile Val Phe Leu Ala Pro Gly Leu
            660                 665                 670

Ser Ala Ile Ile Asp Ala Leu Lys Thr Ser Arg Gln Ile Phe His Arg
        675                 680                 685

Met Tyr Ala Tyr Val Val Tyr Arg Ile Ala Leu Ser Leu His Leu Glu
    690                 695                 700

Ile Phe Leu Gly Leu Trp Ile Val Ile Phe Asn His Leu Met Ile Leu
705                 710                 715                 720

Glu Leu Val Val Phe Ile Ala Ile Phe Ala Asp Ile Ala Thr Leu Ala
                725                 730                 735

Ile Ala Tyr Asp Asn Ala Pro Tyr Ser Leu Leu Pro Thr Lys Trp Asn
            740                 745                 750

Leu Pro Lys Leu Trp Gly Ile Ser Leu Leu Leu Gly Ala Ala Leu Ala
        755                 760                 765

Ile Gly Ser Trp Ile Ala Leu Thr Thr Ile Tyr Ile Asn Asp Asn Thr
    770                 775                 780

Phe Gly Ile Val Gln Gly Tyr Gly Asn Val Asp Ala Val Met Phe Leu
785                 790                 795                 800

Glu Ile Ser Leu Thr Glu Asn Trp Leu Ile Phe Ile Thr Arg Ala Asn
                805                 810                 815

Gly Pro Phe Trp Ser Ser Leu Pro Ser Trp Gln Leu Phe Gly Ala Val
            820                 825                 830

Phe Leu Val Asp Val Ile Ala Thr Ile Phe Cys Ile Phe Gly Trp Phe
        835                 840                 845

Thr Gly Thr Lys Glu His Gly Leu Glu Arg Thr Ser Ile Ile Thr Val
    850                 855                 860

Val Arg Val Trp Leu Phe Ser Leu Gly Val Phe Cys Ile Met Ala Gly
865                 870                 875                 880

Ile Tyr Tyr Leu Leu Ser Asp Ser Val Ala Phe Asp Asn Ile Met His
                885                 890                 895

Gly Lys Ser Val Lys Lys Asn Ser Lys Gln Arg Ser Leu Glu Asp Phe
            900                 905                 910

Val Val Ala Leu Gln Arg Met Ser Thr Lys His Glu Lys Gly Glu
        915                 920                 925

<210> SEQ ID NO 32
<211> LENGTH: 440
<212> TYPE: PRT
<213> ORGANISM: Aspergillus

<400> SEQUENCE: 32

Met Arg Ala Leu Phe Leu Leu Ala Leu Gly Ser Ile Pro Ala Leu Val
1               5                   10                  15

Ser Gly Gln Leu Ser Gly Ser Val Gly Pro Leu Thr Ser Ala Ser Thr
            20                  25                  30

Lys Gly Ala Thr Lys Thr Cys Asn Ile Leu Ser Tyr Gly Ala Val Ala
        35                  40                  45

Asp Asn Ser Thr Asp Val Gly Pro Ala Ile Thr Ser Ala Trp Ala Ala
 50                  55                  60

Cys Lys Ser Gly Gly Leu Val Tyr Ile Pro Ser Gly Asn Tyr Ala Leu
 65                  70                  75                  80

Asn Thr Trp Val Thr Leu Thr Gly Gly Ser Ala Thr Ala Ile Gln Leu
                 85                  90                  95

Asp Gly Ile Ile Tyr Arg Thr Gly Thr Ala Ser Gly Asn Met Ile Ala
            100                 105                 110

Val Thr Asp Thr Thr Asp Phe Glu Leu Phe Ser Ser Thr Ser Lys Gly
        115                 120                 125

Ala Val Gln Gly Phe Gly Tyr Val Tyr His Ala Glu Gly Thr Tyr Gly
    130                 135                 140

Ala Arg Ile Leu Arg Leu Thr Asp Val Thr His Phe Ser Val His Asp
145                 150                 155                 160

Val Ile Leu Val Asp Ala Pro Ala Phe His Phe Thr Met Asp Thr Cys
                165                 170                 175

Ser Asp Gly Glu Val Tyr Asn Met Ala Ile Arg Gly Gly Asn Glu Gly
            180                 185                 190

Gly Leu Asp Gly Ile Asp Val Trp Gly Ser Asn Ile Trp Val His Asp
        195                 200                 205

Val Glu Val Thr Asn Lys Asp Glu Cys Val Thr Val Lys Ser Pro Ala
210                 215                 220

Asn Asn Ile Leu Val Glu Ser Ile Tyr Cys Asn Trp Ser Gly Gly Cys
225                 230                 235                 240

Ala Met Gly Ser Leu Gly Ala Asp Thr Asp Val Thr Asp Ile Val Tyr
                245                 250                 255

Arg Asn Val Tyr Thr Trp Ser Ser Asn Gln Met Tyr Met Ile Lys Ser
            260                 265                 270

Asn Gly Gly Ser Gly Thr Val Ser Asn Val Leu Leu Glu Asn Phe Ile
        275                 280                 285

Gly His Gly Asn Ala Tyr Ser Leu Asp Ile Asp Gly Tyr Trp Ser Ser
290                 295                 300

Met Thr Ala Val Ala Gly Asp Gly Val Gln Leu Asn Asn Ile Thr Val
305                 310                 315                 320

Lys Asn Trp Lys Gly Thr Glu Ala Asn Gly Ala Thr Arg Pro Pro Ile
                325                 330                 335

Arg Val Val Cys Ser Asp Thr Ala Pro Cys Thr Asp Leu Thr Leu Glu
            340                 345                 350

Asp Ile Ala Ile Trp Thr Glu Ser Gly Ser Ser Glu Leu Tyr Leu Cys
        355                 360                 365

Arg Ser Ala Tyr Gly Ser Gly Tyr Cys Leu Lys Asp Ser Ser Ser His
370                 375                 380

Thr Ser Tyr Thr Thr Thr Ser Thr Val Thr Ala Ala Pro Ser Gly Tyr
385                 390                 395                 400

Ser Ala Thr Thr Met Ala Ala Asp Leu Ala Thr Ala Phe Gly Leu Thr
                405                 410                 415

Ala Ser Ile Pro Ile Pro Thr Ile Pro Thr Ser Phe Tyr Pro Gly Leu
            420                 425                 430

Thr Pro Tyr Ser Ala Leu Ala Gly
        435                 440

<210> SEQ ID NO 33
<211> LENGTH: 919
<212> TYPE: PRT

<213> ORGANISM: Schizosaccharomyces pombe

<400> SEQUENCE: 33

| Met | Ala | Asp | Asn | Ala | Gly | Glu | Tyr | His | Asp | Ala | Glu | Lys | His | Ala | Pro |
|---|---|---|---|---|---|---|---|---|---|---|---|---|---|---|---|
| 1 | | | | 5 | | | | | 10 | | | | | 15 | |
| Glu | Gln | Gln | Ala | Pro | Pro | Gln | Gln | Pro | Ala | His | Ala | Ala | Ala | Pro | |
| | | | 20 | | | | | 25 | | | | | 30 | | |
| Ala | Gln | Asp | Asp | Glu | Pro | Asp | Asp | Ile | Asp | Ala | Leu | Ile | Glu | Glu | |
| | | 35 | | | | | 40 | | | | | 45 | | | |
| Leu | Phe | Ser | Glu | Asp | Val | Gln | Glu | Glu | Gln | Glu | Asp | Asn | Asp | Asp | Ala |
| | 50 | | | | | 55 | | | | | 60 | | | | |
| Pro | Ala | Ala | Gly | Glu | Ala | Lys | Ala | Val | Pro | Glu | Glu | Leu | Leu | Gln | Thr |
| 65 | | | | | 70 | | | | 75 | | | | | | 80 |
| Asp | Met | Asn | Thr | Gly | Leu | Thr | Met | Ser | Glu | Val | Glu | Glu | Arg | Arg | Lys |
| | | | | 85 | | | | | 90 | | | | | 95 | |
| Lys | Tyr | Gly | Leu | Asn | Gln | Met | Lys | Glu | Glu | Leu | Glu | Asn | Pro | Phe | Leu |
| | | | 100 | | | | | 105 | | | | | 110 | | |
| Lys | Phe | Ile | Met | Phe | Phe | Val | Gly | Pro | Ile | Gln | Phe | Val | Met | Glu | Met |
| | | 115 | | | | | 120 | | | | | 125 | | | |
| Ala | Ala | Ala | Leu | Ala | Ala | Gly | Leu | Arg | Asp | Trp | Val | Asp | Phe | Gly | Val |
| | 130 | | | | | 135 | | | | | 140 | | | | |
| Ile | Cys | Ala | Leu | Leu | Met | Leu | Asn | Ala | Val | Val | Gly | Phe | Val | Gln | Glu |
| 145 | | | | | 150 | | | | | 155 | | | | | 160 |
| Tyr | Gln | Ala | Gly | Ser | Ile | Val | Asp | Glu | Leu | Lys | Lys | Ser | Leu | Ala | Leu |
| | | | | 165 | | | | | 170 | | | | | 175 | |
| Lys | Ala | Val | Val | Ile | Arg | Glu | Gly | Gln | Val | His | Glu | Leu | Glu | Ala | Asn |
| | | | 180 | | | | | 185 | | | | | 190 | | |
| Glu | Val | Val | Pro | Gly | Asp | Ile | Leu | Lys | Leu | Asp | Glu | Gly | Thr | Ile | Ile |
| | | 195 | | | | | 200 | | | | | 205 | | | |
| Cys | Ala | Asp | Gly | Arg | Val | Val | Thr | Pro | Asp | Val | His | Leu | Gln | Val | Asp |
| | 210 | | | | | 215 | | | | | 220 | | | | |
| Gln | Ser | Ala | Ile | Thr | Gly | Glu | Ser | Leu | Ala | Val | Asp | Lys | His | Tyr | Gly |
| 225 | | | | | 230 | | | | | 235 | | | | | 240 |
| Asp | Pro | Thr | Phe | Ala | Ser | Ser | Gly | Val | Lys | Arg | Gly | Glu | Gly | Leu | Met |
| | | | | 245 | | | | | 250 | | | | | 255 | |
| Val | Val | Thr | Ala | Thr | Gly | Asp | Ser | Thr | Phe | Val | Gly | Arg | Ala | Ala | Ser |
| | | | 260 | | | | | 265 | | | | | 270 | | |
| Leu | Val | Asn | Ala | Ala | Gly | Gly | Thr | Gly | His | Phe | Thr | Glu | Val | Leu | |
| | | 275 | | | | | 280 | | | | | 285 | | | |
| Asn | Gly | Ile | Gly | Thr | Ile | Leu | Leu | Val | Leu | Val | Leu | Leu | Thr | Leu | Phe |
| | 290 | | | | | 295 | | | | | 300 | | | | |
| Cys | Ile | Tyr | Thr | Ala | Ala | Phe | Tyr | Arg | Ser | Val | Arg | Leu | Ala | Arg | Leu |
| 305 | | | | | 310 | | | | | 315 | | | | | 320 |
| Leu | Glu | Tyr | Thr | Leu | Ala | Ile | Thr | Ile | Ile | Gly | Val | Pro | Val | Gly | Leu |
| | | | | 325 | | | | | 330 | | | | | 335 | |
| Pro | Ala | Val | Val | Thr | Thr | Thr | Met | Ala | Val | Gly | Ala | Ala | Tyr | Leu | Ala |
| | | | 340 | | | | | 345 | | | | | 350 | | |
| Glu | Lys | Gln | Ala | Ile | Val | Gln | Lys | Leu | Ser | Ala | Ile | Glu | Ser | Leu | Ala |
| | | 355 | | | | | 360 | | | | | 365 | | | |
| Gly | Val | Glu | Val | Leu | Cys | Ser | Asp | Lys | Thr | Gly | Thr | Leu | Thr | Lys | Asn |
| | 370 | | | | | 375 | | | | | 380 | | | | |
| Lys | Leu | Ser | Leu | Gly | Glu | Pro | Phe | Thr | Val | Ser | Gly | Val | Ser | Gly | Asp |
| 385 | | | | | 390 | | | | | 395 | | | | | 400 |
| Asp | Leu | Val | Leu | Thr | Ala | Cys | Leu | Ala | Ala | Ser | Arg | Lys | Arg | Lys | Gly |

```
                405                 410                 415
Leu Asp Ala Ile Asp Lys Ala Phe Leu Lys Ala Leu Lys Asn Tyr Pro
            420                 425                 430

Gly Pro Arg Ser Met Leu Thr Lys Tyr Lys Val Ile Glu Phe Gln Pro
            435                 440                 445

Phe Asp Pro Val Ser Lys Lys Val Thr Ala Tyr Val Gln Ala Pro Asp
450                 455                 460

Gly Thr Arg Ile Thr Cys Val Lys Gly Ala Pro Leu Trp Val Leu Lys
465                 470                 475                 480

Thr Val Glu Glu Asp His Pro Ile Pro Glu Asp Val Leu Ser Ala Tyr
                485                 490                 495

Lys Asp Lys Val Gly Asp Leu Ala Ser Arg Gly Tyr Arg Ser Leu Gly
            500                 505                 510

Val Ala Arg Lys Ile Glu Gly Gln His Trp Glu Ile Met Gly Ile Met
            515                 520                 525

Pro Cys Ser Asp Pro Pro Arg His Asp Thr Ala Arg Thr Ile Ser Glu
            530                 535                 540

Ala Lys Arg Leu Gly Leu Arg Val Lys Met Leu Thr Gly Asp Ala Val
545                 550                 555                 560

Asp Ile Ala Lys Glu Thr Ala Arg Gln Leu Gly Met Gly Thr Asn Ile
                565                 570                 575

Tyr Asn Ala Glu Arg Leu Gly Leu Thr Gly Gly Asn Met Pro Gly
            580                 585                 590

Ser Glu Val Tyr Asp Phe Val Glu Ala Asp Gly Phe Gly Glu Val
            595                 600                 605

Phe Pro Gln His Lys Tyr Ala Val Asp Ile Leu Gln Gln Arg Gly
            610                 615                 620

Tyr Leu Val Ala Met Thr Gly Asp Gly Val Asn Asp Ala Pro Ser Leu
625                 630                 635                 640

Lys Lys Ala Asp Thr Gly Ile Ala Val Glu Gly Ala Thr Asp Ala Ala
                645                 650                 655

Arg Ser Ala Ala Asp Ile Val Phe Leu Ala Pro Gly Leu Ser Ala Ile
            660                 665                 670

Ile Asp Ala Leu Lys Thr Ser Arg Gln Ile Phe His Arg Met Tyr Ser
            675                 680                 685

Tyr Val Val Tyr Arg Ile Ala Leu Ser Leu His Leu Glu Ile Phe Leu
            690                 695                 700

Gly Leu Trp Leu Ile Ile Arg Asn Gln Leu Leu Asn Leu Glu Leu Val
705                 710                 715                 720

Val Phe Ile Ala Ile Phe Ala Asp Val Ala Thr Leu Ala Ile Ala Tyr
                725                 730                 735

Asp Asn Ala Pro Tyr Ser Met Lys Pro Val Lys Trp Asn Leu Pro Arg
            740                 745                 750

Leu Trp Gly Leu Ser Thr Val Ile Gly Ile Val Leu Ala Ile Gly Thr
            755                 760                 765

Trp Ile Thr Asn Thr Thr Met Ile Ala Gln Gly Gln Asn Arg Gly Ile
            770                 775                 780

Val Gln Asn Phe Gly Val Gln Asp Glu Val Leu Phe Leu Glu Ile Ser
785                 790                 795                 800

Leu Thr Glu Asn Trp Leu Ile Phe Val Thr Arg Cys Asn Gly Pro Phe
                805                 810                 815

Trp Ser Ser Ile Pro Ser Trp Gln Leu Ser Gly Ala Val Leu Ala Val
            820                 825                 830
```

```
-continued

Asp Ile Leu Ala Thr Met Phe Cys Ile Phe Gly Trp Phe Lys Gly Gly
            835                 840                 845

His Gln Thr Ser Ile Val Ala Val Leu Arg Ile Trp Met Tyr Ser Phe
        850                 855                 860

Gly Ile Phe Cys Ile Met Ala Gly Thr Tyr Tyr Ile Leu Ser Glu Ser
865                 870                 875                 880

Ala Gly Phe Asp Arg Met Met Asn Gly Lys Pro Lys Glu Ser Arg Asn
                885                 890                 895

Gln Arg Ser Ile Glu Asp Leu Val Val Ala Leu Gln Arg Thr Ser Thr
            900                 905                 910

Arg His Glu Lys Gly Asp Ala
        915

<210> SEQ ID NO 34
<211> LENGTH: 10
<212> TYPE: PRT
<213> ORGANISM: Artificial Sequence
<220> FEATURE:
<223> OTHER INFORMATION: affinity tag for protein purification

<400> SEQUENCE: 34

Met Arg Gly Ser His His His His His His
1               5                   10
```